(12) United States Patent  
Su et al.

(10) Patent No.: US 10,647,747 B2
(45) Date of Patent: *May 12, 2020

(54) CYCLOSPORIN DERIVATIVES AND USES THEREOF

(71) Applicant: S&T Global Inc., Woburn, MA (US)

(72) Inventors: Zhuang Su, Andover, MA (US); Zhengyu Long, Bolton, MA (US); Zhennian Huang, Newton, MA (US); Suizhou Yang, Dracut, MA (US)

(73) Assignee: S&T GLOBAL INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/843,729

(22) Filed: Dec. 15, 2017

(65) Prior Publication Data

US 2018/0105558 A1  Apr. 19, 2018

Related U.S. Application Data

(63) Continuation of application No. 13/840,088, filed on Mar. 15, 2013, now Pat. No. 9,890,198, which is a continuation-in-part of application No. PCT/US2011/063295, filed on Dec. 5, 2011.

(60) Provisional application No. 61/684,928, filed on Aug. 20, 2012, provisional application No. 61/655,236, filed on Jun. 4, 2012, provisional application No. 61/419,326, filed on Dec. 3, 2010.

(51) Int. Cl.
*A61K 38/12* (2006.01)
*C07K 7/64* (2006.01)

(52) U.S. Cl.
CPC .................. *C07K 7/645* (2013.01)

(58) Field of Classification Search
None
See application file for complete search history.

(56) References Cited

U.S. PATENT DOCUMENTS

| | | | |
|---|---|---|---|
| 3,869,448 A | 3/1975 | Earley et al. |
| 4,108,985 A | 8/1978 | Ruegger et al. |
| 4,703,033 A | 10/1987 | Seebach |
| 5,242,812 A | 9/1993 | Even-Chen |
| 5,767,069 A | 6/1998 | Ko et al. |
| 5,965,527 A | 10/1999 | Barriere et al. |
| 5,981,479 A | 11/1999 | Ko et al. |
| 5,994,299 A | 11/1999 | Barriere et al. |
| 6,100,065 A | 8/2000 | Thoma |
| 6,583,265 B1 | 6/2003 | Ellmerer-Muller et al. |
| 6,927,208 B1 | 8/2005 | Wenger et al. |
| 7,439,227 B2 | 10/2008 | Scalfaro et al. |
| 7,511,013 B2 | 3/2009 | Molino et al. |
| 7,696,166 B2 | 4/2010 | Molino |
| 7,718,767 B2 | 5/2010 | Fliri et al. |
| 9,200,038 B2 | 12/2015 | Hegmans et al. |
| 9,890,198 B2 * | 2/2018 | Su .................. C07K 7/645 |
| 2006/0069015 A1 | 3/2006 | Molino et al. |
| 2006/0160727 A1 | 7/2006 | Fliri et al. |
| 2010/0167996 A1 | 7/2010 | Fliri et al. |
| 2010/0173836 A1 | 7/2010 | Li et al. |
| 2010/0173837 A1 | 7/2010 | Hopkins |
| 2010/0196316 A1* | 8/2010 | Or ........................ A61K 38/13 424/85.4 |
| 2011/0165194 A1 | 7/2011 | Yum et al. |
| 2012/0088734 A1* | 4/2012 | Frydrych ............... C07K 1/113 514/18.7 |
| 2013/0190223 A1 | 7/2013 | Hegmans et al. |
| 2013/0210704 A1 | 8/2013 | Su et al. |
| 2013/0324480 A1 | 12/2013 | Pettit et al. |
| 2014/0134132 A1 | 5/2014 | Fu et al. |
| 2014/0142033 A1 | 5/2014 | Hegmans et al. |
| 2015/0313959 A1 | 11/2015 | Kissel et al. |
| 2016/0002299 A1 | 1/2016 | Towers et al. |
| 2016/0039880 A1 | 2/2016 | Pettit et al. |
| 2016/0289271 A1 | 10/2016 | Pettit et al. |

FOREIGN PATENT DOCUMENTS

| | | |
|---|---|---|
| CN | 101068829 A | 11/2007 |
| CN | 103153330 A | 6/2013 |
| JP | 61-212599 A | 9/1986 |
| JP | 2000-502320 A | 2/2000 |
| RU | 2011127080 A | 2/2013 |

(Continued)

OTHER PUBLICATIONS

Baugh, J.M. et al., "Host-Targeting Agents in the Treatment of Hepatitis C: A Beginning and an End?", Antiviral Res., 100(2):555-561, Nov. 2013 (16 pages)—Author Manuscript.

(Continued)

*Primary Examiner* — Karlheinz R. Skowronek
(74) *Attorney, Agent, or Firm* — Wilmer Cutler Pickering Hale and Dorr LLP

(57) ABSTRACT

The present invention relates to a compound of the Formula (I):

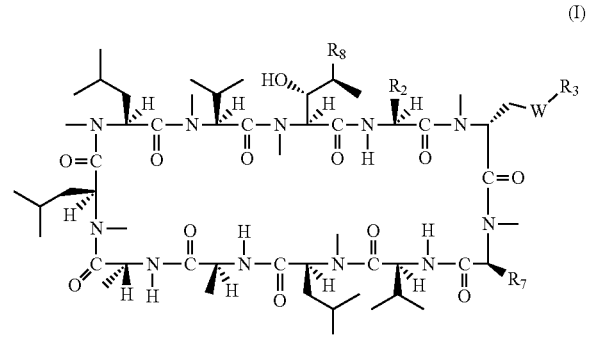

or pharmaceutically acceptable salt thereof, wherein the symbols are as defined in the specification; a pharmaceutical composition comprising the same, a method for treating or preventing viral infections, inflammation, dry eye, central nervous disorders, cardiovascular diseases, cancer, obesity, diabetes, muscular dystrophy, and hair loss.

34 Claims, No Drawings

(56) References Cited

FOREIGN PATENT DOCUMENTS

| | | |
|---|---|---|
| WO | WO-2000001715 A1 | 1/2000 |
| WO | WO-2006038088 A1 | 4/2006 |
| WO | WO-2006038119 A1 | 4/2006 |
| WO | WO-2006039164 A2 | 4/2006 |
| WO | WO-2006039668 A2 | 4/2006 |
| WO | WO-2007015824 A2 | 2/2007 |
| WO | WO-2008143996 A1 | 11/2008 |
| WO | WO-2010088573 A1 | 8/2010 |
| WO | WO-2012009715 A2 | 1/2012 |
| WO | WO-2012021796 A2 | 2/2012 |
| WO | WO-2012051194 A1 | 4/2012 |
| WO | WO-2012075494 A1 | 6/2012 |
| WO | WO-2012079172 | 6/2012 |
| WO | WO-2014091239 A1 | 6/2014 |
| WO | WO-2014145686 A2 | 9/2014 |
| WO | WO-2015193673 A1 | 12/2015 |

OTHER PUBLICATIONS

European Extended Search Report issued in EP14762728.5, dated Sep. 12, 2016 (8 pages).

Fu, J. et al., "Potent Nonimmunosuppressive Cyclophilin Inhibitors With Improved Pharmaceutical Properties and Decreased Transporter Inhibition", J. Medicinal Chemistry, 57(20):8503-8516, Oct. 13, 2014 (14 Pages).

Gaither, L.A. et al., "Multiple cyclophilins involved in different cellular pathways mediate HCV replication", Virology, 397:43-55, 2010, available online Nov. 24, 2009 (13 pages).

Gallay, P.A. et al., "Characterization of the Anti-HCV Activities of the New Cyclophilin Inhibitor STG-175", PLoS ONE, 11(4):e0152036, Apr. 22, 2016 (23 pages).

Gallay, P.A. et al., "The Novel Cyclophilin Inhibitor CPI-431-32 Concurrently Blocks HCV and HIV-1 Infections via a Similar Mechanism of Action", PLoS One, 10(8):e0134707, Aug. 11, 2015 (18 pages).

International Search Report and Written Opinion issued by the U.S. Patent and Trademark Office as International Searching Authority in International Application No. PCT/US17/32811, dated Sep. 27, 2017 (11 pages).

Luly, J. et al., Presentation of Enanta Pharmaceuticals Inc. at J.P. Morgan Healthcare Conference, Jan. 13, 2016 (6 pages).

Owens, C. et al., "Poster Presentations: THU-250: EDP-494 Is a Potent Pan-Genotypic Cyclophilin Inhibitor for HCV Infection, Including DAA Resistance Associated Variants (RAVS)", Abstracts of the International Liver Congress™ 2016—51st annual meeting of the European Association for the Study of the Liver, Apr. 13-17, 2016, Barcelona, Spain, Journal of Hepatology, 64(Supp. 2):S414, 2016 (3 pages).

Berge, S.M. et al., "Pharmaceutical Salts", Journal of Pharmaceutical Sciences, vol. 66, No. 1, pp. 1-19 (Jan. 1977), 19 pages.

Bouchard, M.J. et al., "Activation and Inhibition of Cellular Calcium and Tyrosine Kinase Signaling Pathways Identify Targets of the HBx Protein Involved in Hepatitis B Virus Replication", Journal of Virology, vol. 77, No. 14, pp. 7713-7719, (Jul. 2003), 8 pages.

Bout, D. et al., "Antischistosomal Effect of Cyclosporin A: Cure and Prevention of Mouse and Rat Schistosomiasis Mansoni", Infection and Immunity, 52(3):823-827, Jun. 1986, 5 pages.

Carry, J., et al., "Semisynthetic Di- and Tri-Functionalized Non-Immunosuppressive Cyclosporin A Derivatives as Potential Anti-HIV 1 Drugs," *Synlett*, vol. 2, pp. 0316-0320 (2004), 5 pages.

Castro, A.P.V. et al., "Redistribution of Cyclophilin A to Viral Factories during Vaccinia Virus Infection and Its Incorporation into Mature Particles", Journal of Virology, vol. 77, No. 16, pp. 9052-9068, (Aug. 2003). 18 pages.

Chen, Z. et al., "Function of HAb18G/CD147 in Invasion of Host Cells by Severe Acute Respiratory Syndrome Coronavirus", The Journal of Infectious Diseases, vol. 191, Issue 5, pp. 755-760 (Mar. 1, 2005), 6 pages.

Chokshi, S. et al., "1104: Characterization of Antiviral Activities of Cyclophilin Inhibitors DEB025 (Alisporivir) and NIM811 on Hepatitis B Virus (HBV) Replication and HBSAG Secretiona In Vitro", 07a: Viral Hepatitis B&D: Experimental, Journal of Hepataology, vol. 54, pp. S437-S438 (2011), 2 pages.

Cruz, et al., "Immunosuppressive and Nonimmunosuppressive Cyclosporine Analogs are Toxic to the Opportunistic Fungal Pathogen *Cryptococcus neoformans* via Cyclophilin-Dependent Inhibition of Calcineurin", Antimicrobial Agents and Chemotherapy, 44(1):143-149, Jan. 2000, 8 pages.

Edman, P., "Preparation of Phenyl Thiohydantoins from Some Natural Amino Acids", ACTA Chemica Scandinavica, vol. 4, pp. 277-282 (1950), 6 pages.

Edman, P., et al. "A Protein Sequenator", European J. Biochem., 1, 80-91 (1967), 12 pages.

Zenke, G. et al., "Molecular mechanisms of Immunosuppression by Cyclosporins", Annals of the New York Academy of Sciences, vol. 685, pp. 330-335 (Jun. 1993), 6 pages.

Evers, et al., "Synthesis of Non-Immunosuppressive Cyclophilin-Binding Cyclosporin A Derivatives as Potential Anti HIV-1 Drugs", Bioorganic & Medicinal Chemistry Letters, vol. 13, pp. 4415-4419 (2003), 5 pages.

Extended European Search Report issued by the European Patent Office for European Patent Application No. 11845460.2 dated Apr. 30, 2014 (11 pgs.).

Fliri, H. et al., "Cyclosporins. Structure-Activity Relationships", Annals New York Academy of Sciences, vol. 696, pp. 47-53 (Nov. 1993), 7 pages.

Franke, E.K. et al., "Specific incorporation of cyclophilin A into HIV-1 virions", Nature, vol. 372, pp. 359-362 (Nov. 24, 1994), 4 pages.

Gilden, "Sandoz Axes Cyclosporin Research", GMHC Treatment Issues, vol. 9, No. 12, pp. 1 and 7 (Dec. 1995), 2 pages.

Hopkins, S. et al., "SCY-635, a Novel Nonimmunosuppressive Analog of Cyclosporine That Exhibits Potent Inhibition of Hepatitis C Virus RNA Replication In Vitro", Antimicrobial Agents and Chemotherapy, vol. 54, No. 2, pp. 660-672 (Feb. 2010), 14 pages.

Hopkins, S. et al., "SCYNEXIS' SCY-635 Demonstrates Impressive Barrier to Resistance in HCV Treatment", 45th Annual Meeting of the European Association for the Study of the Liver (EASL), Vienna, Austria, (Apr. 15, 2010), 2 pages.

Inoue, K. et al., "Combined interferon α2b and cyclosporin A in the treatment of chronic hepatitis C: controlled trial", Journal of Gastroenterology, vol. 38, No. 6, pp. 567-572 (Jun. 2003), 6 pages.

Inoue, K. et al., "IFN combined Cyclosporin A therapy", Nippon Rinsho, vol. 59, No. 7, pp. 1326-1330 (Jul. 2001), 5 pages.

International Search Report and Written Opinion issued by the U.S. Patent and Trademark Office as International Searching Authority for International Application No. PCT/US11/047571 dated Feb. 29, 2012 (13 pgs.).

International Search Report and Written Opinion issued by the U.S. Patent and Trademark Office as International Searching Authority for International Application No. PCT/US11/063295 dated Apr. 23, 2012 (10 pgs.).

International Search Report and Written Opinion issued by the U.S. Patent and Trademark Office as International Searching Authority for International Application No. PCT/US12/51572 dated Oct. 16, 2012 (11 pgs.).

International Search Report and Written Opinion issued by the U.S. Patent and Trademark Office as the International Searching Authority for International Application No. PCT/US11/44362 dated Feb. 2, 2012 (10 pages).

International Search Report and Written Opinion issued by the U.S. Patent and Trademark Office as the International Searching Authority for International Application No. PCT/US14/030491 dated Nov. 5, 2014 (11 pages).

Kirkland, T.N. et al., "Cyclosporin A inhibits Coccidioides immitis In vitro and in vivo", Antimicrobial Agents and Chemotherapy, 24(6):921-924, Dec. 1983, 5 pages.

Klatzmann, D. et al., "Functional inhibition by cyclosporin A of the lymphocyte receptor for the AIDS virus (HIV)", C.R. Acad. Sci. III, vol. 303, No. 9, pp. 343-348 (1986) (abstract included), 6 pages.

(56) References Cited

OTHER PUBLICATIONS

Krieger, N. et al., "Enhancement of Hepatitis C Virus RNA Replication by Cell Culture-Adaptive Mutations", Journal of Virology, vol. 75, No. 10, pp. 4614-4624, (May 2001), 12 pages.
Kuhnt, M. et al., "Microbial Biotransformation Products of Cyclosporin A," The Journal of Antibiotics, vol. 49, No. 8, pp. 781-787 (1996), 7 pages.
Lill, J. et al., "Cyclosporine-drug interactions and the influence of patient age", Am. J. Health-Syst. Pharm., vol. 57, pp. 1579-1584 (Sep. 1, 2000) 6 pages.
Liu, X. et al., "Cyclophilin A interacts with influenza A virus M1 protein and impairs the early stage of the viral replication", Cellular Microbiology, vol. 11, No. 5, pp. 730-741 (Feb. 6, 2009), 12 pages.
Luban, Jeremy, "Absconding with the Chaperone: Essential Cyclophilin-Gag Interaction in HIV-1 Virions", Cell, vol. 87, pp. 1157-1159 (Dec. 27, 1996), 3 pages.
Luban,J. et al., "Human immunodeficiency virus type 1 Gag protein binds to cyclophilins A and B," Cell, vol. 73, Issue 6, pp. p1067-p1078 (Jun. 18, 1993).
Mody, C. et al., "Cyclosporin A inhibits the growth of Cryptococcus neoformans in a murine model", Infection and Immunity, 56(1):7-12, Jan. 1988, 7 pages.
Moussaif, M. et al., "Cyclosporin C is the main antifungal compound produced by Acremonium luzulae", Applied and Environmental Microbiology, 63(5):1739-1743, May 1997, 6 pages.
Nickell,S.P. et al., "Inhibition by cyclosporin A of rodent malaria in vivo and human malaria in vitro", Infection and Immunity, 37(3):1093-1100, Sep. 1982, 9 pages.
Papageorgiou, C. et al., "Calcineurin Has a Very Tight-Binding Pocket for the Side Chain of Residue 4 of Cyclosporin", Bioorganic & Medicinal Chemistry Letters, vol. 4, No. 2, pp. 267-272 (Jan. 1994), 6 pages.
Papageorgiou, C. et al., "Improved Binding Affinity for Cyclophilin A by a Cyclosporin Derivative Singly Modified at Its effector Domain", Journal of Medicinal Chemistry, vol. 37, No. 22, pp. 3674-3676 (1994).
Papageorgiou, C., et al., "Anti HIV-1 Activity of a Hydrophilic Cyclosporin Derivative with Improved Binding Affinity to Cyclophilin A", Bioorganic & Medicinal Chemistry Letters, 6(1):23-26, 1996; including Corrected Figure, Bioorganic & Medicinal Chemistry Letters, Additions and Corrections, 6(4):497, 1996 (5 pages).
Perkins,M. et al., "Cyclosporin Analogs Inhibit In Vitro Growth of *Cryptosporidium parvum*", Antimicrobial Agents and Chemotherapy, 42(4):843-848, Apr. 1998, 7 pages.
Pietschmann, T. et al., "Persistent and Transient Replication of Full-Length Hepatitis C Virus Genomes in Cell Culture", Journal of Virology, vol. 76, No. 8, pp. 4008-4021, (Apr. 2002), 15 pages.
Roilides, E. et al., "In vitro and ex vivo effects of cyclosporin A on phagocytic host defenses against Aspergillus fumigatus", Antimicrobial Agents and Chemotherapy, 38(12):2883-2888, Dec. 1994, 7 pages.

Rosenwirth, B. et al., "Inhibition of human immunodeficiency virus type 1 replication by SDZ NIM 811, a nonimmunosuppressive cyclosporine analog", Antimicrobial Agents and Chemotherapy, 38(8):1763-1772, Aug. 1994, 11 pages.
Seebach, D. et al., "Modification of Cyclosporin A (CS): Generation of an Enolate at the Sarcosine Residue and Reactions with Electrophiles", Helvetica Chimica Acta, vol. 76, Issue 4, pp. 1564-1590 (Jun. 30, 1993), 27 pages.
Silverman, J.A. et al., "Characterization of anti-Toxoplasma activity of SDZ 215-918, a cyclosporin derivative lacking Immunosuppressive and peptidyl-prolyl=isomerase-inhibiting activity: possible role of a P glycoprotein in Toxoplasma physiology", Antimicrobial Agents and Chemotherapy, 41(9):1859-1866, Sep. 1997, 9 pages.
Takahashi,T. et al., "Cyclosporin A Promotes Hair Epithelial Cell Proliferation and Modulates Protein Kinase C Expression and Translocation in Hair Epithelial Cells", The Journal of Investigative Dermatology, 117(3):605-611, Sep. 2001, 7 pages.
Tang, Hengli, "Cyclophilin Inhibitors as a Novel HCV Therapy", Viruses, vol. 2, No. 8, pp. 1621-1634 (Aug. 5, 2010), 14 pages.
Taylor, M. et al., "Cyclosporin A Prolongs Human Hair Growth In Vitro", The Journal of Investigative Dermatology, 100(3):237-239, Mar. 1993, 4 pages.
Thali, M. et al., "Functional association of cyclophilin A with HIV-1 virions", Nature, vol. 372, pp. 363-365 (1994), Nov. 1994, 3 pages.
Tian, X. et al., "Hepatitis B Virus (HBV) Surface Antigen Interacts with and Promotes Cyclophilin A Secretion: Possible Link to Pathogenesis of HBV Infection", Journal of Virology, vol. 84, No. 7, pp. 3373-3381, (Apr. 2010), 10 pages.
Wainberg, M.A. et al., "The effect of cyclosporine A on infection of susceptible cells by human immunodeficiency virus type 1", Blood, vol. 72, No. 6, pp. 1904-1910, (Dec. 1988) 8 pages.
Watashi, K. et al., "Chemical genetics approach to hepatitis C virus replication: cyclophilin as a target for anti-hepatitis C virus strategy", Reviews in Medical Virology, vol. 17, Issue 4, pp. 245-252 (Jul./Aug. 2007), 8 pages.
Watashi, K. et al., "Cyclosporin A Supresses Replication of Hepatitis C Virus Genome in Cultured Hepatocytes", Hepatology, vol. 38, No. 5, pp. 1282-1288 (2003), 7 pages.
Xia, et al., "Inhibitory effect of cyclosporine A on hepatitis B virus replication in vitro and its possible mechanisms," Hepatobiliary Pancreat Dis Int, vol. 4, pp. 18-22 (2005), 5 pages.
Yau, W.L. et al., "Cyclosporin A Treatment of *Leishmania donovani* Reveals Stage-Specific Functions of Cyclophilins in Parasite Proliferation and Viability", PLOS Neglected Tropical Diseases, 4(6):e729, Jun. 2010, 16 pages.
European Partial Supplementary Search Report issued in EP17799977.8, dated Dec. 20, 2019 (14 pages).
Sweeney, Z.K. et al., "From Chemical Tools to Clinical Medicines: Nonimmunosuppressive Cyclophilin Inhibitors Derived from the Cyclosporin and Sanglifehrin Scaffolds", Journal of Medicinal Chemistry, 57:7145-7159, 2014 (15 pages).

\* cited by examiner

CYCLOSPORIN DERIVATIVES AND USES THEREOF

CROSS REFERENCE TO RELATED APPLICATIONS

This patent application is a continuation of U.S. application Ser. No. 13/840,088 filed Mar. 15, 2013, which is a continuation-in-part of International Application No. PCT/US2011/063295, filed Dec. 5, 2011, which claims priority to U.S. Application Ser. Nos. 61/419,326, filed Dec. 3, 2010; U.S. application Ser. No. 13/840,088 also claims priority to U.S. Application Ser. No. 61/655,236, filed Jun. 4, 2012; and U.S. Application Ser. No. 61/684,928, filed Aug. 20, 2012; and the entire contents of each of the foregoing applications are hereby incorporated by reference herein.

FIELD OF THE INVENTION

The invention relates to novel cyclosporine derivatives, their pharmaceutical compositions comprising the same, and methods for treating or preventing viral infections, inflammation, dry eye, central nervous disorders, cardiovascular diseases, cancer, obesity, diabetes, muscular dystrophy, and hair loss.

BACKGROUND OF THE INVENTION

Cyclosporins in nature are poly-N-methyl, cyclic undecapeptides, isolated from fungi. Cyclosporin A has an immunosuppressive activity and has been used for almost 30 years to prevent rejection in kidney, heart and liver transplant recipients. It possesses anti-inflammatory properties and has been used for treating severe rheumatoid arthritis, severe psoriasis, Behget's uveitis, and dry eye disease. In addition, it is useful for treating severe ulcerative colitis, Crohn's disease, alopecia areata, aplastic anemia, HSV-1 stromal keratitis, systemic lupus erythematosus, and severe lupus nephritis. However, its strong immunosuppressive activity limits its applications in many diseases.

The anti-HIV activity of cyclosporin A was first discovered in 1986 and has been continually studied since then (Klatzmann, D., et al., 1986, *C R Acad. Sci. III*, 303(9):343-8; Wainberg, M. A., et al., 1988, *Blood*, 72, 1904-10; Luban, J., et al., 1993, *Cell*, 73, 1067-1078; each of which is incorporated herein by reference). Its non-immunosuppressive derivative, NIM-811, was reported to have potent anti HIV activity due to its ability to inhibit cyclophilin A (Franke, E. K., et al., 1994, *Nature*, 372, 359-362; Thali, M., et al., 1994, *Nature*, 372, 363-365; Gamble, T. R., et al., 1996, *Cell*, 87, 1157-1159; Rosenwirth B., et al., 1994, *Antimicrob. Agents Chemother.*, 38, 1763-1772; each of which is incorporated herein by reference).

Cyclosporin A and its non-immunosuppressive derivatives, as such as NIM-811 (N-MeIle-4-Cyclosporin), Debio-025, and SCY-635, bind and inhibit cyclophilins; cyclophilins interact with HCV protein NS5A and NS5B and stimulate its RNA-binding activity. As a result, these compounds have an effective anti-HCV activity (Watashi, K., et al., 2007, *Rev. Med. Virol.*, 17:245-252.37; Inoue, K., et al., 2001, *Nippon Rinsho.*, 59, 1326-30; Inoue, K., et al., 2003, *J. Gastroenterol.*, 38, 567-72; Watashi, K., et al., 2003, *Hepatology*, 38, 1282-8; Gaither, L. A., et al., 2010, *Virology*, 397, 43-55; each of which is incorporated herein by reference). Currently, NIM-811, Debio-025, and SCY-635 are undergoing clinical trials for treating HCV.

NIM-811 and Debio-025 have a chemical structure similar to cyclosporine A and possess a poor pharmacokinetic profile. In addition, they are metabolized by P450 for inducing drug interactions (Lill, J., et al., 2000, *Am J Health-Syst Pharm* 57, 1579; incorporated herein by reference).

SCY-635 has an improved pharmacokinetic profile and low blood serum binding. In addition, it has a low potential for drug-drug interactions. SCY-635's in vitro anti-HCV activity ($EC_{50}$) was reported to be 0.10 µM (Hopkins, S. et al., 2010, *Antimicrob. Agents Chemother.*, 54, 660-672, incorporated herein by reference). However, SCY-635 is not chemically stable, as it is easily converted to its diastereoisomer by epimerization. Its diastereoisomer is expected to have poor binding activity with cyclophilins, and as a result, its anti-viral activity in vivo may be affected (See, e.g., WO2012/009715, WO2012/021796, and WO2012/075494, each of which incorporated herein by reference in its entirety).

Cyclosporin A and its non-immunosuppressive derivatives were also found to possess anti-HBV activity through the inhibition of cyclophilins (Chokshi, S., et al., 2012, Gut 61:A11; Chokshi, S., et al., 2012, Poster Presentations, 47th Annual Meeting of the European Association for the Study of the Liver (EASL 2012), Barcelona, Spain; Chokshi, S., et al., 2011, Abstract 190 (Poster Presentations), 46th Annual Meeting of the European Association for the Study of the Liver (EASL 2011), Berlin, March 30-April 3; Tian, X. C., et al., 2010, *J. Virol.*, 84, 3373-3381; Xia, W. L., et al., 2004, *Hepatobiliary Pancreat Dis Int.*, 4, 18-22; Michael, J., et al., 2003, *J. Virol.*, 77, 7713-7719; each of which is incorporated herein by reference).

Furthermore, cyclophilins were reported to regulate the life cycle and pathogenesis of several viruses, including severe acute respiratory syndrome coronavirus, vaccinia virus, and herpes simplex virus (Castro, A. P., et al., 2003, *J. Virol.*, 77, 9052-9068; Chen, Z., L., et al., 2005, *J. Infect. Dis.* 191(5):755-760; Arai, C., et al., *Nihon Rinsho Meneki Gakkai Kaishi.*, 35(1), 87-91; Labetoulle, M., 2012, *J Fr Ophtalmol.*, 35(4), 292-307; De Clercq, E., 2008, *Expert Opin Emerg Drugs.*, 13(3):393-416; Vahlne, A., 1992, *Arch Virol.*, 122(1-2):61-75; each of which is incorporated herein by reference). Cyclosporin A and its non-immunosuppressive derivatives also possess such anti viral-activities.

N-MeVal-4-Cyclosporin (SDZ 220-384), another non-immunosuppressive cyclosporine derivative, was reported to have similar biological activities to that of NIM-811 (Fliri, H., et al., 1993, *Ann. N Y Acad Sci.* 696, 47-53; Zenke, G., et al., 1993, *Ann N Y Acad Sci.* 23; 685:330-5).

Hepatitis C virus (HCV) is a small (55-65 nm in size), enveloped, positive sense single strand RNA virus in the Flaviviridae family. HCV has a high rate of replication and an exceptionally high mutation rate. About 80% of people infected with HCV develop chronic, persistent infection. More than 4 million Americans have been infected with HCV and more than 200 million people are estimated to be infected chronically worldwide. About 35,000 new cases of hepatitis C are estimated to occur in the United States each year. HCV infection is responsible for about 50% of all chronic liver disease, 30% of all liver transplants, and 30% of all cirrhosis, end-stage liver disease, and liver cancer in the U.S. The peg-interferon and ribavirin combination is the standard treatment for chronic hepatitis C, but it has low efficacy against HCV infection. Recently, the FDA has approved Vertex's Incivek (telaprevir) and Merck's Victrelis (boceprevir) as an add-on to the current interferon/ribavirin therapy for treating HCV. Both drugs are HCV protease inhibitors that target the virus to prevent its replication. However, due to HCV's fast mutation rate, drug resistance can be developed in a short period of time. Thus, there exists a need for an effective therapeutic for HCV treatment.

Hepatitis B virus (HBV) is a 42 nm partially double stranded DNA virus composed of a 27 nm nucleocapsid core (HBcAg) that is surrounded by an outer lipoprotein envelope containing the surface antigen (HBsAg). More than 2 billion people have been infected, and there are 350 million chronic carriers of the virus. The disease has caused epidemics in parts of Asia and Africa. Chronic hepatitis B will cause liver cirrhosis and liver cancer, a fatal disease with a very poor response to current chemotherapies. The infection is preventable by vaccination, and HBV load and replication can be reduced by current antiviral drugs, such as lamivudine (Epivir), adefovir (Hepsera), tenofovir (Viread), telbivudine (Tyzeka), entecavir (Baraclude), and the two immune system modulators interferon alpha-2a and PEGylated interferon alpha-2a (Pegasys). However, none of the available drugs can clear the infection. There remains a need for an effective therapeutic to treat HBV infection.

The non-immunosuppressive cyclosporin derivatives bind to cyclophilins, a family of host proteins that catalyze cis-trans peptidyl-prolyl isomerization in protein folding and regulation, which are crucial for the processing and maturation of the viral proteins for viral replication. HIV and HCV are viruses with a high mutation rate. All current anti-viral drugs target the virus itself; when the virus mutates, it leads to the development of drug resistance. Instead of directly targeting the virus, targeting host cofactors (cyclophilins) will be slow down the development of drug resistance due to a higher genetic barrier (Rosenwirth, B., et al., 1994, *Antimicrob. Agents Chemother.*, 38, 1763-1772; Tang, H. L. et al., 2010, *Viruses*, 2, 1621-1634; Hopkins, S. et al., 2010, Oral Presentation, Scynexis's SCY-635 Demonstrates Impressive Barrier to Resistance in HCV Treatment, the 45th Annual Meeting of the European Association for the Study of the Liver (EASL 2010), Vienna, Austria, April 14-18; each of which is incorporated herein by reference). Cyclosporine derivatives affect a new target, cyclophilins, and therefore represent a new mechanism of action against viruses.

There are 17 cyclophilins in the human genome, but the functions of these cyclophilin isoforms are still unclear (Davis, T. L., et al., 2010, *PLoS Biol.* 8(7):e1000439; incorporated herein by reference). Cyclophilin A, B, C, D, and other such isoforms play an important role in the pathophysiology of a number of serious diseases, such as cancer (Campa, M J., et al., 2003, Cancer Res., 63(7), 1652-6; Li, M., et al., 2006, *Cancer,* 106: 2284-94; Yang, H., et al., 2007, *Biochem Biophys Res Commun.*, 361(3):763-7; Obchoei, S., et al., 2009, *Med Sci Monit.*, 15(11), RA221-32; Andersson, Y., et al., 2009, *Br J Cancer,* 101, 1307-1315; Lee, J., 2010, *Arch Pharm Res.*, 33(2), 181-7; Lee, J., et al., 2010, J Exp Clin Cancer Res., 29:97; Obchoei, S., 2011, *Molecular Cancer,* 10:102; Takahashi, M., et al., 2012, *Oncol Rep.*, 27(1):198-203; Qian, Z., et al., 2010, *BMC Cancer,* 12:442; each of which is incorporated herein by reference), inflammations (the result of interactions between a secreted extracellular cyclophilin and CD-147, a surface protein; Yurchenko V., 2005, *Immunology,* 117(3):301-9; Yurchenko, V., 2010, *Clin Exp Immunol.*, 160(3):305-17; Malesević, M., 2010, *Angew Chem Int Ed Engl.*, 49(1):213-5; each of which is incorporated herein by reference), rheumatoid arthritis (Wells, G., et al., 2000, Cochrane Database Syst Rev., (2):CD001083; Kim, H., et al., 2005, *Clin Immunol.*, 116(3):217-24; Yang, Y., *Rheumatology (Oxford)*, 47(9):1299-310; Yurchenko, V., et al., 2006, *Immunology,* 117(3):301-9; Damsker, J. M., 2009, Immunology, 126(1): 55-62; Wang, L., et al., 2010, *J Clin Immunol.*, 30(1):24-33; Billich A., et al., 1997, *J Exp Med.*, 185:975-80; De Ceuninck F., et al., 2003, *Arthritis Rheum.*, 48:2197-206; each of which is incorporated herein by reference), respiratory inflammation (Foda, H. D., et al., 2001, *Am J Respir Cell Mol Biol.*, 25:717-24; Hasaneen, N. A., et al., *FASEB J.*, 19:1507-9.Yurchenko, V., et al., 2006, *Immunology,* 117(3): 301-9; Gwinn, W. M., 2006, *J Immunol.*, 177(7):4870-9; Onoue, S., 2009, *J Control Release.*, 138(1):16-23; Balsley, M. A., et al., 2010, *J Immunol.*, 185(12):7663-70; Balsley, M., et al., 2010, *Am. J. Respir. Crit. Care Med.*, 181(1): A6821; Stemmy, E. J., et al., 2011, J. Asthma, 48(10):986-993; Stemmy, E. J., et al., 2011, *Am J Respir Cell Mol Biol.*, 45(5):991-8; Amin, K., 2012, *Respir. Med.*, 106(1):9-14; Onoue, S., 2012, *Eur J Pharm Biopharm.*, 80(1):54-60; each of which is incorporated herein by reference), lupus (Caccavo, D., et al., 1997, Arthritis & Rheumatism, 40(1):27-35; Dostál, C., et al., 1998, *Lupus,* 7(1):1 29-36; Tam, L S., et al., 1998, *Q J Med.*, 91(8):573-580; Fu, L W., et al., 1998, Rheumatology 37 (2): 217-221; Hallegua, D., et al., 2009, *Lupus,* 9: 241-251; each of which is incorporated herein by reference), psoriasis (Ellis, C. N., 1991, *N Engl J Med.*, 324, 277-284; Lebwohl, M., et al., 1998, J Am Acad Dermatol., 39(3):464-75; Rosmarin, D M., et al., 2010, J Am Acad Dermatol., 62(5):838-53; each of which is incorporated herein by reference), atopic dermatitis (Naeyaert, J. M., et al., 1999, *Dermatology,* 198:145-152; Pacor, M L., et al., 2001, *Recenti Prog Med.*, 92(6):390-1; Ricci, G., et al., 2009, *Drugs,* 69(3):297-306; Simon, D., 2011, *Curr Probl Dermatol.*, 41:156-64; each of which is incorporated herein by reference), dry eye disease (Pflugfelder, S. C., 2004, *Am J Ophthalmol.*, 137(2), 337-42; Kymionis, G. D., et al 2008, *Clin Ophthalmol.*, 2, 829-836; Kunert, K. S., et al., 2002, *Arch Ophthalmol.*, 120, 330-7; Yavuz, B., et al., 2012, *Scientific World Journal.* 2012:194848.; each of which is incorporated herein by reference), severe Graves' ophthalmopathy (Prummel, M. F., 1989, *N Engl J Med.*, 321(20), 1353-9; incorporated herein by reference), endogenous uveitis (Nussenblatt, R. B., et al., 1991, *Am J Ophthalmol.*, 112(2), 138-46; which is incorporated herein by reference), Wegener's granulomatosis (Georganas, C., et al., 1996, *Clin Rheumatol.*, 15(2), 189-92; incorporated herein by reference), vernal keratoconjutivitis (Pucci, N., et al., 2002, *Ann Allergy Asthma Immunol.*, 89, 298-303; incorporated herein by reference), atopic keratoconjutivitis (Akpek, E. K., et al., 2004, *Ophthalmology,* 111, 476-82; incorporated herein by reference), ligneous conjutivitis (Rubin, B. I., et al., 1991, *Am J Ophthalmol.*, 112, 95-96; incorporated herein by reference), conjutival linchen planus (Levell, N. J., et al., 1992, *Br J Dermatol.*, 127, 66-7; incorporated herein by reference), and superior limbic keratoconjutivitis (Perry, H. D., et al., 2003, *Ophthalmology,* 110, 1578-81; incorporated herein by reference), inflammatory bowel disease-Crohn's Disease and Ulcerative Colitis (Sandborn, W. J., 1995, *Inflamm Bowel Dis.* 1:48-63; Shibolet, O., et al., 2005, *Cochrane Database Syst Rev.*, (1):CD004277; Rufo, P. A., et al., 2006, *Paediatr Drugs,* 8(5):279-302; Reindl, W., et al., 2007, *Gut.*, 56(7):1019; Hart, A. L., et al., 2010, *Aliment Pharmacol Ther* 32(5):615-27; Cheifetz, A. S., et al., 2011, *J Clin Gastroenterol.*, 45(2):107-12; Sharkey, L., 2011, *J Crohns Colitis.*, 5(2):91-4; Fabro, M., et al., 2011, *Curr Drug Targets.*, 12(10):1448-53; Van Assche, G., et al., 2011, *Gut.*, 60(1):130-3; each of which is incorporated herein by reference), NSAID-induced enteropathy (LoGuidice, A., at al., 2010, *Toxicol. Sci.*, 118, 276-285; which is incorporated herein by reference), cardiovascular diseases (including vascular stenosis, atherosclerosis, abdominal aortic aneurysms, aortic rupture, cardiac hypertrophy, pulmonary arterial hypertension, myocarditis and myocardial fibrosis, and ischaemic heart diseases; Jin, Z. G., et al., 2000, Circ Res., 87(9):789-96; Yurchenko, V., et al., 2005, Immunology, 117, 301-309; Suzuki, J., et al., 2006, Circ Res., 98(6):811-7; Satoh, K., et al., 2008, Circulation., 117(24):3088-98; Nishihara, M., et al., 2008, J Mol Cell Cardiol., 44(2):441-442; Satoh, K., et al., 2010, Circ J., 74(11):2249-56; Satoh, K., et al., 2010, Antioxid Redox Signal., 12(5):675-82; Hausenloy, D. J., et al., 2012, Br J Pharmacol. 165(5):1235-45; Coppinger, J. A., et al., 2004, Blood, 103(6):2096-104; Satoh, K., et al., 2010, Antioxid Redox Signal., 1:12(5), 675-682; Nigro, P., et al., 2010, J Exp Med., 208(1):53-66; Wang, W. L., et al., 2011, Med Hypotheses, 77(5):734-8; Hattori, F., 2012, J Mol Cell Cardiol., 53(1):1-2; Seizer P., 2012, J Mol Cell Cardiol., 53(1):6-14; each of which is incorporated herein by reference), and ischaemic brain diseases (Boulos, S., et al., 2007, Neurobiol Dis., 25:54-64; incorporated herein by reference).

Due to cyclophilin inhibition, cyclosporin derivatives also possess the following biological activities: anti-fungal (Kirkland, T. N., et al., 1983, Antimicrob Agents Chemother., 24(6): 921-924; Mody, C. H., et al., 1988, Infect Immun., 56(1): 7-12; Roilides, E., et al., 1994, Antimicrob Agents Chemother., 38(12): 2883-2888; Moussaïf, M., et al., 1997, Appl Environ Microbiol., 63(5):1739-43; Cruz, M. C., et al., 2000, Antimicrob Agents Chemother., 44(1):143-9; each of which is incorporated herein by reference), anti-malarial (Nickell, S. P., et al., 1982, Infect Immun., 37(3):1093-100; Murphy, J. R., et al, 1988, Antimicrob Agents Chemother., 32(4):462-6; Marín-Menéndez, A., et al., 2012, Mol Biochem Parasitol., 184(1):44-7; each of which is incorporated herein by reference), and anti-parasitic (including Leishmania donovani, Cryptosporidium parvum, Hymenolepis nana, Toxoplasma, Trypanosoma cruzi, and Schistosome; Chappell, L. H., et al., 1992, Parasitology, 105 Suppl:S25-40; Bell, A., et al., 1996, Gen Pharmacol., 27(6):963-71; Yau, W. L., et al., 2010, PLoS Negl Trop Dis., 4(6):e729; Yurchenko, V., et al., 2008, Int J Parasitol., 38(6):633-9; Perkins, M. E., et al., 1998, Antimicrob Agents Chemother., 42(4): 843-8; Matsuzawa, K., et al., 1998, Int J Parasitol., 28(4): 579-88; Silverman, J. A., et al., 1997, Antimicrob Agents Chemother., 41(9):1859-66; Búa, J., et al., 2008, Parasitology, 135(2):217-28; Búa, J., et al., 2004, Bioorg Med Chem Lett., 14(18):4633-7; Bout, D. T, et al., 1984, Am J Trop Med Hyg., 33(1):185-6; Bout, D., et al., 1986, Infect Immun., 52(3):823-7; Munro, G. H., et al., 1991, Parasitology, 102 Pt 1:57-63; each of which is incorporated herein by reference). In addition, cyclosporin derivatives can promote hair growth (Watanabe, S., et al., 1991, J Dermatol., (12):714-9; Paus R., et al., 1994, J Invest Dermatol., 103:2, 143-7; Hozumi, Y., et al., 1994, J Dermatol Sci., 7 Suppl:, S33-8; Takahashi, T., et al., 2001, J Invest Dermatol., 117(3):605-11; Taylor M., et al., 1993, J Invest Dermatol., 100:3, 237-9; Gafter-Gvili, A., et al., 2004, Arch Dermatol Res., 296(6):265-9; each of which is incorporated herein by reference).

Recent research for Alzheimer's disease indicated that Cyclophilin A is a key target for treating APOE4-mediated neurovascular injury and the resulting neuronal dysfunction and degeneration (Bell, R. D., et al., 2012, Nature, 485 (7399):512-6; Bell, R. D., et al., 2009, Acta Neuropathol., 118(1):103-13; each of which is incorporated herein by reference).

Due to the function of extracellular cyclophilins, it is necessary to emphasize that the special target of a secreted extracellular cyclophilin using a cell-impermeable derivative of cyclosporine will be very effective in reducing inflammation for diseases such as respiratory inflammation and cardiovascular diseases (Yurchenko V., 2005, Immunology, 117(3):301-9; Yurchenko, V., 2010, Clin Exp Immunol., 160(3):305-17; Malesević, M., 2010, Angew Chem Int Ed Engl., 49(1):213-5; Balsley, M. A., et al., 2010, J Immunol., 185(12):7663-70; Balsley, M., et al., 2010, Am. J. Respir. Crit. Care Med., 181(1): A6821; Satoh, K., et al., 2010, Circ J., 74(11):2249-56; each of which is incorporated herein by reference).

Cyclophilin D (CypD) is very important for mitochondrial related neuro and cardiovascular functions because it is an integral part of the mitochondrial permeability transition pore (mPTP). Unregulated opening of the mPTP can lead to mitochondrial swelling and cell death. Thus, the CypD-mediated mPTP is directly linked to a new pharmacologic treatment strategy for many neuro and cardiovascular diseases, such as Alzheimer's disease, Parkinson's disease, Huntington's disease, ALS, aging, heart failure, traumatic brain injury, spinal cord injury, epilepticus, stroke, ischemia-reperfusion injury in the brain, heart, kidney, and particularly in myocardial infarction. The CypD-mediated mPTP is also linked to a new treatment strategy for cancer, obesity, diabetes, and muscular dystrophy (Henry-Mowatt, J., 2004, Oncogene, 23, 2850-60; Galluzzi, L., 2006, Oncogene, 25, 4812-4830; Hirai, K., et al., 2001, J Neurosci., 21, 3017-3023; Friberg, H., et al., 2002, Biochimie, 84, 241-250; Waldmeier, P. C., et al., 2003, Curr Med Chem., 10, 1485-506; Hansson, M. J., et al., 2004, J Bioenerg Biomembr., 36, 407-13; Sullivan, P. G., et al., 2005, J Neurosci Res., 79, 231-9; Baines, C. P., et al, 2005, Nature 434, 658-662; Shanmuganathan, S., et al, 2005, Am J Physiol Heart Circ Physiol., 289, H237-H242; McBride, H. M., et al., 2006, Curr Biol., 16, R551-560; Mandemakers, W., et al., 2007, J Cell Sci., 120, 1707-1716; Kroemer, G., et al., 2007, Physiol Rev., 87, 99-163; Ibarra, A., et al., 2007, Brain Res., 1149, 200-209; Michelakis, E. D., et al, 2008, Circulation, 117, 2431-2434; Du, H., et al 2008, Nature Medicine, 14, 1097-1105; Piot C., et al., 2008, N Engl J Med., 359, 473-81; Hatton, J., et al., 2008, J Neurosurg., 109, 699-707; Tatsuta, T., et al., 2008, EMBO J, 27, 306-314; Reutenauer, J., et al., 2008, Br J Pharmacol., 155, 574-84; Mazzeo, A. T., et al., 2009, Exp Neurol., 218, 363-370; Galluzzi, L., et al, 2009, Nature Rev Neurosci., 10, 481-494; Halestrap, A. P., et al., 2009, Biochim Biophys Acta., 1787, 1402-15; Arnett, A. L. H., et al., 2009, Curr. Opin. Genet. Dev., 19, 290-297; Tiepolo, T., et al., 2009, Br J Pharmacol., 157, 1045-1052; Wissing, E. R., et al., 2010, Neuromuscul Disord., 20, 753-60; Halestrap, A. P., et al., 2010, Biochem Soc Trans., 38, 841-860; Cernak, I., et al., 2010, J Cereb Blood Flow Metab., 30, 255-66; Elrod, J. W., et al., 2010, J Clin Invest., 120, 3680-3687; Duchen, M. R., et al., 2010, Essays Biochem., 47, 115-37; Schapira, A. H. V., et al., 2011, Parkinson's Disease, Volume 2011, 1-7 Article ID 159160; Osman, M. M., et al., 2011, Neuropeptides, 45, 359-368; Devalaraja-Narashimha K., et al., 2011, FEBS Lett., 585, 677-82; Fujimoto, K., et al., 2010, Proc Natl Acad Sci U S A. 107, 10214-9; Irwin, W. A., et al., 2003, Nat Genet., 35, 267-271; Angelin, A., et al., 2007, Proc Natl Acad Sci U S A, 104, 991-6; Merlini, L., et al., 2008, Proc Natl Acad Sci U S A, 105, 5225-9; Millay, D. P., 2008, Nat Med., 14, 442-7; each of which is incorporated herein by reference). Cyclosporine A and its derivatives can block CypD to prevent mitochondrial swelling and cell death, and therefore could be useful for treatment of the aforementioned diseases, for example, as a neuro and cardiovascular protective agent or as a novel mitochondrial medicine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

SUMMARY OF THE INVENTION

In one aspect, the present invention provides a compound of Formula (I):

$R_7$ is

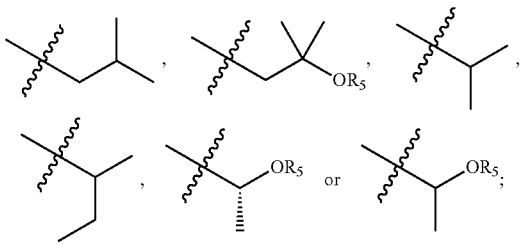

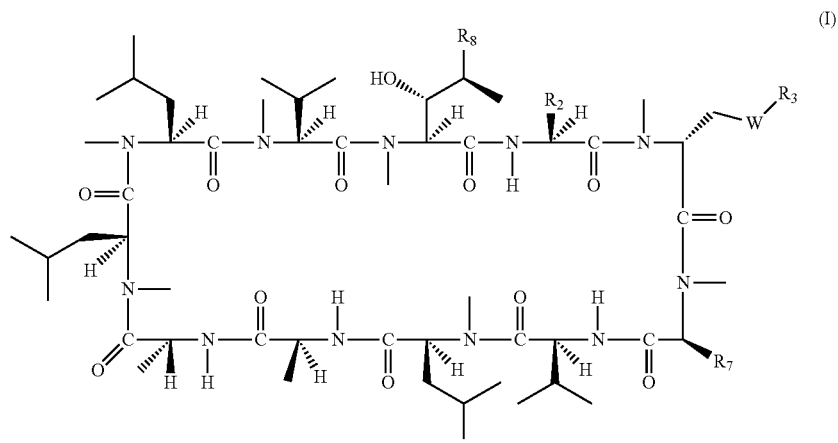

(I)

or pharmaceutically acceptable salt thereof, wherein:
$R_8$ is n-butyl, (E)-but-2-enyl, or

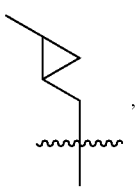 [SMILES: *CC1CC1C]

—$(CH_2)_4$—$SR_9$, —$(CH_2)_4$—$(C=O)OR_9$, or —$(CH_2)_3$—$(C=O)OR_9$;
each occurrence of $R_9$ is independently hydrogen or $(C_1$-$C_6)$alkyl;
$R_2$ is ethyl, 1-hydroxyethyl, isopropyl or n-propyl;
W is O, S, $CH_2$ or $NR_1$;
$R_1$ is H, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle or substituted heterocycle; or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
$R_3$ is H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl;

and
each $R_5$ is independently H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl.

In another aspect, the present invention provides a compound of Formula (I) as shown above, or pharmaceutically acceptable salt thereof, wherein:
$R_8$ is n-butyl, (E)-but-2-enyl, or

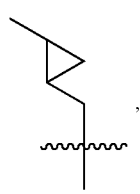 [SMILES: *CC1CC1C]

—$(CH_2)_4$—$SR_9$, —$(CH_2)_4$—$(C=O)OR_9$, or —$(CH_2)_3$—$(C=O)OR_9$;
each occurrence of $R_9$ is independently hydrogen or $(C_1$-$C_6)$alkyl;
$R_2$ is ethyl, 1-hydroxyethyl, isopropyl or n-propyl;
W is O, S, $CH_2$, or $NR_1$;
$R_1$ is hydrogen;
  $(C_1$-$C_6)$alkyl, optionally substituted by one or more groups $R_D$ which may be the same or different;
  $(C_2$-$C_6)$alkenyl or $(C_2$-$C_6)$alkynyl;
  $(C_3$-$C_7)$cycloalkyl optionally substituted with $(C_1$-$C_6)$ alkyl;
  phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of ($C_1$-$C_6$)alkyl, phenyl and benzyl;

$R_3$ is:
H;
($C_1$-$C_6$)alkyl, optionally substituted by one or more groups $R_4$ which may be the same or different;
($C_2$-$C_6$)alkenyl, optionally substituted by one or more groups which may be the same or different selected from halogen, hydroxy, amino, monoalkylamino and dialkylamino;
($C_2$-$C_6$)alkynyl, optionally substituted by one or one or more groups which may be the same or different selected from halogen, hydroxy, amino, monoalkylamino and dialkylamino;
($C_3$-$C_7$)cycloalkyl, optionally substituted by one or more groups which may be the same or different selected from halogen, hydroxy, amino, monoalkylamino and dialkylamino;
phenyl or $CH_2$-phenyl, optionally substituted by one or more groups which may be the same or different selected from halogen, hydroxy, ($C_1$-$C_6$)alkyl;

$R_7$ is

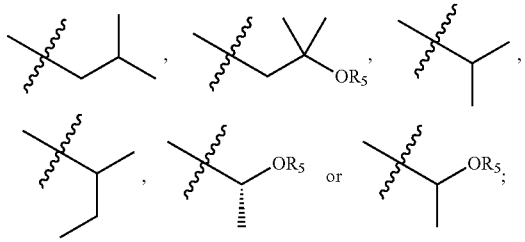

$R_5$ is:
H;
($C_1$-$C_6$)alkyl, optionally substituted by one or more groups $R_6$ which may be the same or different;
($C_2$-$C_6$)alkenyl, optionally substituted by one or more groups which may be the same or different selected from hydroxy, ($C_1$-$C_6$)alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
($C_2$-$C_6$)alkynyl, optionally substituted by one or one or more groups which may be the same or different selected from halogen, hydroxy, amino, monoalkylamino and dialkylamino;
($C_3$-$C_7$)cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, —$NR_AR_B$, —$NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:
hydrogen;
($C_1$-$C_6$)alkyl, optionally substituted by one or more groups $R_D$ which may be the same or different;
($C_2$-$C_6$)alkenyl or ($C_2$-$C_6$)alkynyl;
($C_3$-$C_7$)cycloalkyl optionally substituted with ($C_1$-$C_6$) alkyl;
phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;
or a heterocyclic ring which may be saturated or unsaturated containing five or six ring atoms and from one to three heteroatoms which may be the same or different selected from nitrogen, sulfur and oxygen;
or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or ($C_1$-$C_6$)alkyl;
p is an integer of 0, 1, 2, 3, 4, or 5; and
m is an integer of 1, 2, 3, 4 or 5.

In another aspect, the present invention provides a compound of Formula (I) as shown above, or pharmaceutically acceptable salt thereof, wherein:
$R_8$ is n-butyl, (E)-but-2-enyl, or

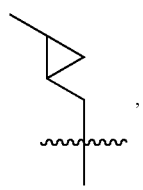

—$(CH_2)_4$—$SR_9$, —$(CH_2)_4$—$C(=O)OR_9$, or —$(CH_2)_3$—$C(=O)OR_9$;

each occurrence of $R_9$ is independently hydrogen or $(C_1-C_6)$alkyl;

$R_2$ is ethyl, 1-hydroxyethyl, isopropyl or n-propyl;

W is O, S, $CH_2$, or $NR_1$;

$R_1$ is hydrogen;
 $(C_1-C_6)$alkyl, optionally substituted by one or more groups $R_D$ which may be the same or different;
 $(C_2-C_6)$alkenyl or $(C_2-C_6)$alkynyl;
 $(C_3-C_7)$cycloalkyl optionally substituted with $(C_1-C_6)$alkyl;
 phenyl optionally substituted with from one to five groups which may be the same or different selected from halogen, —O$(C_1-C_6)$alkyl, —C(=O)O$(C_1-C_6)$alkyl, amino, alkylamino and dialkylamino;
 or a heterocyclic ring which may be saturated or unsaturated containing five or six ring atoms and from one to three heteroatoms which may be the same or different selected from nitrogen, sulfur and oxygen;
 or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1-C_6)$alkyl, phenyl and benzyl;

$R_3$ is:
 H;
 $(C_7-C_{12})$alkyl, optionally substituted by one or more groups $R_4$ which may be the same or different;
 $(C_7-C_{12})$alkenyl, optionally substituted by one or more groups which may be the same or different selected from halogen, hydroxy, amino, monoalkylamino and dialkylamino; or
 $(C_7-C_{12})$alkynyl, optionally substituted by one or one or more groups which may be the same or different selected from halogen, hydroxy, amino, monoalkylamino and dialkylamino;

$R_7$ is

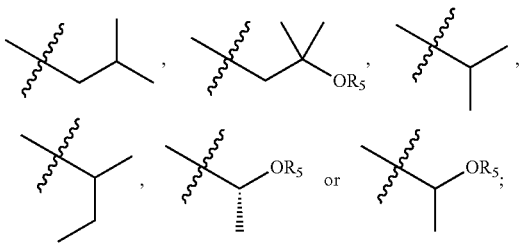

$R_5$ is:
 H;
 $(C_1-C_6)$alkyl, optionally substituted by one or more groups $R_6$ which may be the same or different;
 $(C_2-C_6)$alkenyl, optionally substituted by one or more groups which may be the same or different selected from hydroxy, $(C_1-C_6)$alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

$(C_2-C_6)$alkynyl, optionally substituted by one or one or more groups which may be the same or different selected from halogen, hydroxy, amino, monoalkylamino and dialkylamino;
 $(C_3-C_7)$cycloalkyl, optionally substituted by one or more groups which may be the same or different selected from halogen, hydroxy, amino, monoalkylamino and dialkylamino;
 phenyl or $CH_2$-phenyl, optionally substituted by one or more groups which may be the same or different selected from halogen, hydroxy, $(C_1-C_6)$alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, $(C_3-C_7)$cycloalkyl, aryl (e.g., phenyl), $O(CH_2)_mOR_A$, $O(CH_2)_mO(CH_2)_mOR_A$, $C(=O)(C_1-C_6)$alkyl, $C(=O)OR_A$, $C(=O)NR_AR_B$, —$NR_AR_B$, —$NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1-C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, $(C_1-C_6)$alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:
 hydrogen;
 $(C_1-C_6)$alkyl, optionally substituted by one or more groups $R_D$ which may be the same or different;
 $(C_2-C_6)$alkenyl or $(C_2-C_6)$alkynyl;
 $(C_3-C_7)$cycloalkyl optionally substituted with $(C_1-C_6)$alkyl;
 phenyl optionally substituted with from one to five groups which may be the same or different selected from halogen, —O$(C_1-C_6)$alkyl, —C(=O)O$(C_1-C_6)$alkyl, amino, alkylamino and dialkylamino;
 or a heterocyclic ring which may be saturated or unsaturated containing five or six ring atoms and from one to three heteroatoms which may be the same or different selected from nitrogen, sulfur and oxygen;
 or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or $(C_1-C_6)$alkyl;

p is an integer of 0, 1, 2, 3, 4, or 5; and m is an integer of 1, 2, 3, 4 or 5.

In another aspect, the present invention provides a compound of Formulae (II) through (VI):

(II)
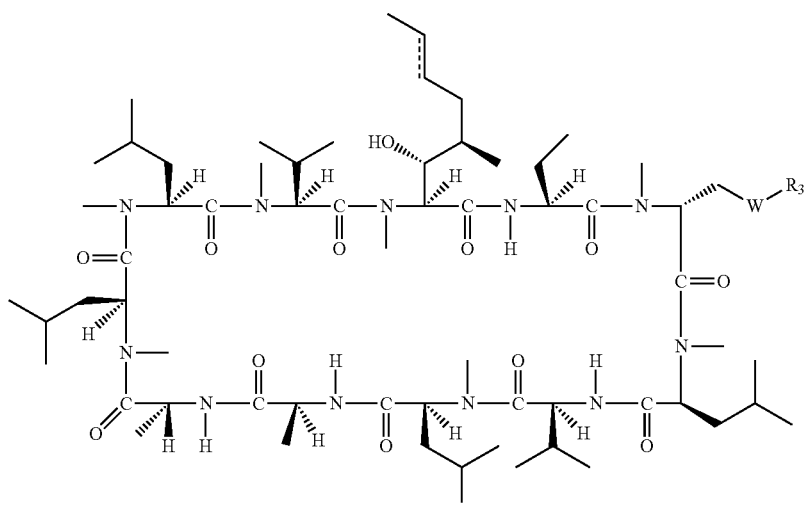
(III)
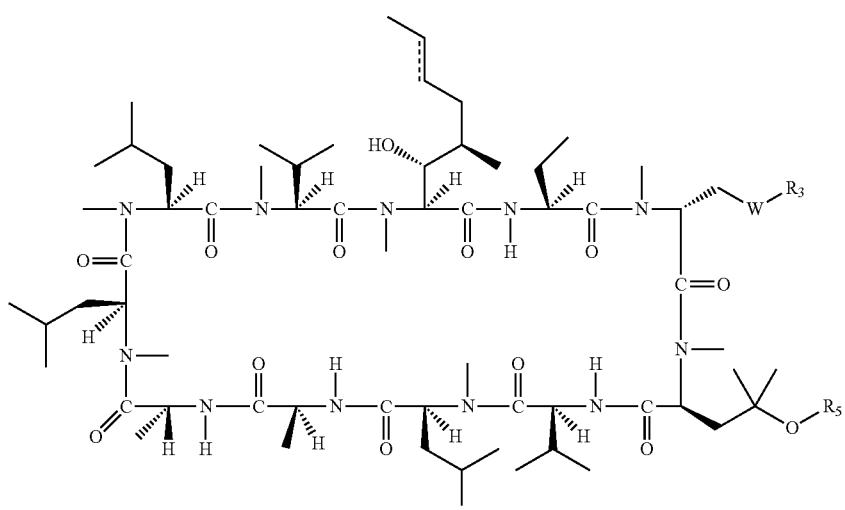
(IV)
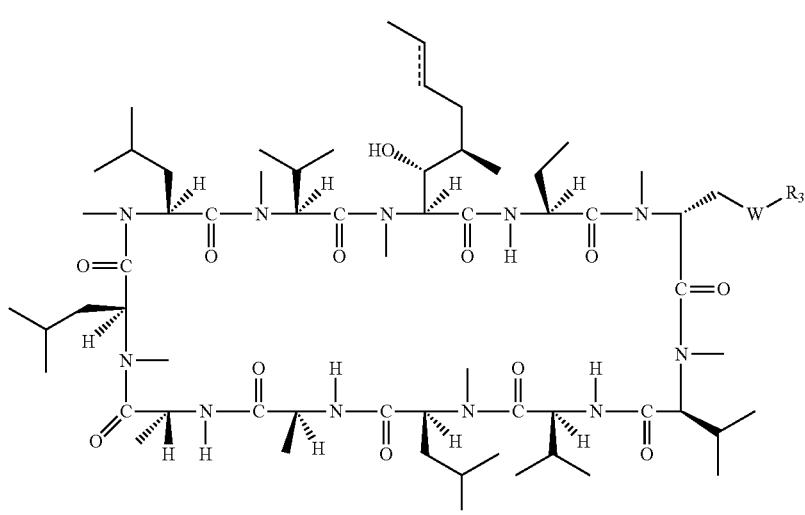

(V)

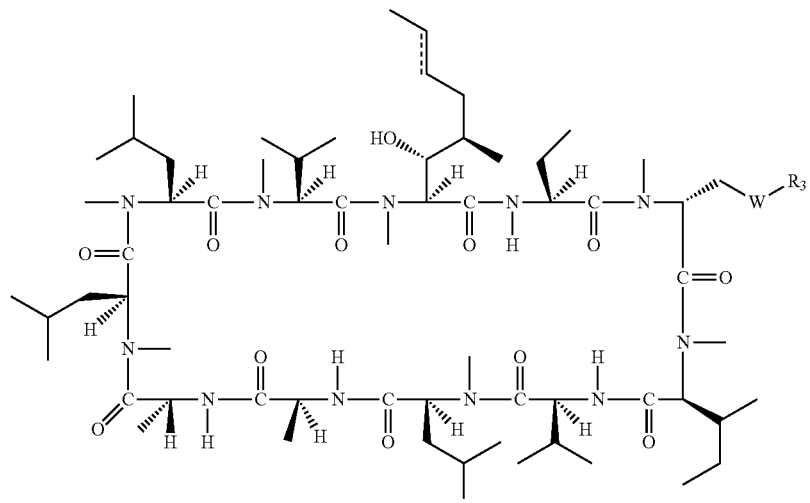

(VI)

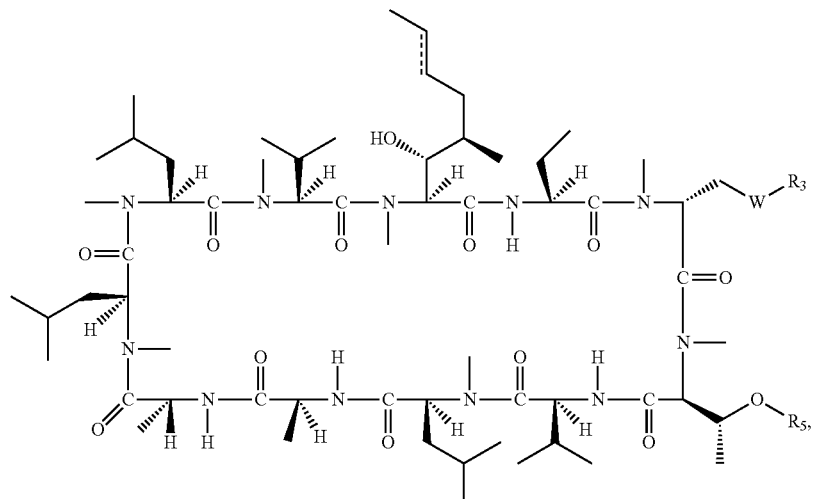

or pharmaceutically acceptable salt thereof, wherein:

| represents a single bond or double bond;

each W is independently O, S, $CH_2$, or $NR_1$;

each $R_1$ is independently H, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle or substituted heterocycle; or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and each occurrence of $R_3$ and $R_5$ is independently H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl.

In another aspect, the present invention provides a compound of Formulae (II) through (VI):as shown above, or pharmaceutically acceptable salt thereof, wherein:

each W is independently O, S, $CH_2$ or $NR_1$;

each $R_1$ is independently hydrogen;

$(C_1-C_6)$alkyl, optionally substituted by one or more groups $R_D$ which may be the same or different;

$(C_2-C_6)$alkenyl or $(C_2-C_6)$alkynyl;

$(C_3-C_7)$cycloalkyl optionally substituted with $(C_1-C_6)$ alkyl;

phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1-C_6)$alkyl, phenyl and benzyl;

each $R_3$ is independently:
- H;
- $(C_1$-$C_6)$alkyl, optionally substituted by one or more groups $R_4$ which may be the same or different;
- $(C_2$-$C_6)$alkenyl, optionally substituted by one or more groups which may be the same or different selected from halogen, hydroxy, $(C_1$-$C_6)$alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
- $(C_2$-$C_6)$alkynyl, optionally substituted by one or one or more groups which may be the same or different selected from halogen, hydroxy, amino, monoalkylamino and dialkylamino;
- $(C_3$-$C_7)$cycloalkyl, optionally substituted by one or more groups which may be the same or different selected from halogen, hydroxy, amino, monoalkylamino and dialkylamino;
- phenyl or $CH_2$-phenyl, optionally substituted by one or more groups which may be the same or different selected from halogen, hydroxy, $(C_1$-$C_6)$alkyl;

each $R_5$ is independently:
- H;
- $(C_1$-$C_6)$alkyl, optionally substituted by one or more groups $R_6$ which may be the same or different;
- $(C_2$-$C_6)$alkenyl, optionally substituted by one or more groups which may be the same or different selected from halogen, hydroxy, $(C_1$-$C_6)$alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
- $(C_2$-$C_6)$alkynyl, optionally substituted by one or one or more groups which may be the same or different selected from halogen, hydroxy, amino, monoalkylamino and dialkylamino;
- $(C_3$-$C_7)$cycloalkyl, optionally substituted by one or more groups which may be the same or different selected from halogen, hydroxy, amino, monoalkylamino and dialkylamino;
- phenyl or $CH_2$-phenyl, optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, $-NR_AR_B$, $-NR_CCH_2(CH_2)_pNR_AR_B$, $NR_C[CH_2(CH_2)_pNR_AI_mCH_2(CH_2)_pNR_AR_B$, $O[CH_2(CH_2)_pO]_mCH_2(CH_2)_pOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:
- hydrogen;
- $(C_1$-$C_6)$alkyl, optionally substituted by one or more groups $R_D$ which may be the same or different;
- $(C_2$-$C_6)$alkenyl or $(C_2$-$C_6)$alkynyl;
- $(C_3$-$C_7)$cycloalkyl optionally substituted with $(C_1$-$C_6)$alkyl;
- phenyl optionally substituted with from one to five groups which may be the same or different selected from halogen, $-O(C_1$-$C_6)$alkyl, $-C(=O)O(C_1$-$C_6)$alkyl, amino, alkylamino and dialkylamino;
- or a heterocyclic ring which may be saturated or unsaturated containing five or six ring atoms and from one to three heteroatoms which may be the same or different selected from nitrogen, sulfur and oxygen;
- or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
- or $R_A$ and $R_B$, together with the nitrogen atom to which they are attached, form $-N=CH-NR_FR_{F'}$, $-N=CMe-NR_FR_{F'}$, or $-NR_FC(=NH)NR_FR_{F'}$;

each occurrence of $R_C$ is independently hydrogen or $(C_1$-$C_6)$alkyl;

each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl;

each occurrence of $R_F$ and $R_{F'}$ is independently hydrogen, $(C_1$-$C_6)$alkyl, phenyl, benzyl, or $R_F$ and $R_{F'}$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

p is an integer of 0, 1, 2, 3, 4, 5, or 6;
m is an integer of 1, 2, 3, 4, 5, or 6; and
n is an integer of 1, 2, 3, 4, 5 or 6.

In another aspect, the present invention provides a compound of Formulae (II) through (VI) as shown above, or pharmaceutically acceptable salt thereof, wherein:
each W is independently O, S, $CH_2$ or $NR_1$;
each $R_1$ is independently hydrogen;
- $(C_1$-$C_6)$alkyl, optionally substituted by one or more groups $R_D$ which may be the same or different;
- $(C_2$-$C_6)$alkenyl or $(C_2$-$C_6)$alkynyl;
- $(C_3$-$C_7)$cycloalkyl optionally substituted with $(C_1$-$C_6)$alkyl;
- phenyl optionally substituted with from one to five groups which may be the same or different selected from halogen, $-O(C_1$-$C_6)$alkyl, $-C(=O)O(C_1$-$C_6)$alkyl, amino, alkylamino and dialkylamino;
- or a heterocyclic ring which may be saturated or unsaturated containing five or six ring atoms and from one to three heteroatoms which may be the same or different selected from nitrogen, sulfur and oxygen;
- or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1$-$C_6)$alkyl, phenyl and benzyl;

each R$_3$ is independently:
  H;
  (C$_7$-C$_{12}$)alkyl, optionally substituted by one or more groups R$_4$ which may be the same or different;
  (C$_7$-C$_{12}$)alkenyl, optionally substituted by one or more groups which may be the same or different selected from halogen, hydroxy, (C$_1$-C$_6$)alkyl, aryl (e.g., phenyl), (CH$_2$)$_p$OR$_A$, (CH$_2$)$_m$OH, (CH$_2$)$_m$O(CH$_2$)$_m$OH, (CH$_2$)$_m$NR$_A$R$_B$, (CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(=O)NR$_A$R$_B$, (CH$_2$)$_p$C(=O)OR$_A$; or
  (C$_7$-C$_{12}$)alkynyl, optionally substituted by one or one or more groups which may be the same or different selected from halogen, hydroxy, amino, monoalkylamino and dialkylamino;
each R$_5$ is independently:
  H;
  (C$_1$-C$_6$)alkyl, optionally substituted by one or more groups R$_6$ which may be the same or different;
  (C$_2$-C$_6$)alkenyl, optionally substituted by one or more groups which may be the same or different selected from halogen, hydroxy, (C$_1$-C$_6$)alkyl, aryl (e.g., phenyl), (CH$_2$)$_p$OR$_A$, (CH$_2$)$_m$OH, (CH$_2$)$_m$O(CH$_2$)$_m$OH, (CH$_2$)$_m$NR$_A$R$_B$, (CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(=O)NR$_A$R$_B$, (CH$_2$)$_p$C(=O)OR$_A$;
  (C$_2$-C$_6$)alkynyl, optionally substituted by one or one or more groups which may be the same or different selected from halogen, hydroxy, amino, monoalkylamino and dialkylamino;
  (C$_3$-C$_7$)cycloalkyl, optionally substituted by one or more groups which may be the same or different selected from halogen, hydroxy, amino, monoalkylamino and dialkylamino; or
  phenyl or CH$_2$-phenyl, optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$, (CH$_2$)$_p$C(=O)OR$_A$;
each occurrence of R$_4$ is independently halogen, hydroxy, (C$_3$-C$_7$)cycloalkyl, aryl (e.g., phenyl), O(CH$_2$)$_m$OR$_A$, O(CH$_2$)$_m$O(CH$_2$)$_m$OR$_A$, C(=O)(C$_1$-C$_6$)alkyl, C(=O)OR$_A$, C(=O)NR$_A$R$_B$, —NR$_A$R$_B$, —NR$_C$CH$_2$(CH$_2$)$_p$NR$_A$R$_B$, NR$_C$[CH$_2$(CH$_2$)$_p$NR$_A$]$_m$CH$_2$(CH$_2$)$_n$NR$_A$R$_B$, O[CH$_2$(CH$_2$)$_p$O]$_m$CH$_2$(CH$_2$)$_n$OR$_A$, OCH$_2$(CH$_2$)$_p$NR$_A$R$_B$, or O[CH$_2$(CH$_2$)$_p$O]$_m$CH$_2$(CH$_2$)$_n$NR$_A$R$_B$;
each occurrence of R$_6$ is independently halogen, hydroxy, aryl (e.g., phenyl), S(C$_1$-C$_6$)alkyl, SR$_A$, OR$_A$, O(CH$_2$)$_m$OR$_A$, O(CH$_2$)$_m$O(CH$_2$)$_m$OR$_A$, C(=O)OR$_A$, C(=O)NR$_A$R$_B$, NR$_A$R$_B$, O(CH$_2$)$_m$NR$_A$R$_B$, O(CH$_2$)$_m$O(CH$_2$)$_m$NR$_A$R$_B$, NR$_C$(CH$_2$)$_m$NR$_A$R$_B$, or NR$_C$(CH$_2$)$_m$NR$_C$(CH$_2$)$_m$NR$_A$R$_B$, wherein said aryl or phenyl is optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$ and (CH$_2$)$_p$C(=O)OR$_A$;
each occurrence of R$_A$ and R$_B$ is independently:
  hydrogen;
  (C$_1$-C$_6$)alkyl, optionally substituted by one or more groups R$_D$ which may be the same or different;
  (C$_2$-C$_6$)alkenyl or (C$_2$-C$_6$)alkynyl;
  (C$_3$-C$_7$)cycloalkyl optionally substituted with (C$_1$-C$_6$)alkyl;
  phenyl optionally substituted with from one to five groups which may be the same or different selected from halogen, —O(C$_1$-C$_6$)alkyl, —C(=O)O(C$_1$-C$_6$)alkyl, amino, alkylamino and dialkylamino;
  or a heterocyclic ring which may be saturated or unsaturated containing five or six ring atoms and from one to three heteroatoms which may be the same or different selected from nitrogen, sulfur and oxygen;
  or R$_A$ and R$_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
  or R$_A$ and R$_B$, together with the nitrogen atom to which they are attached, form —N=CH—NR$_F$R$_{F'}$, —N=CMe-NR$_F$R$_{F'}$, or —NR$_F$C(=NH)NR$_F$R$_{F'}$;
each occurrence of R$_C$ is independently hydrogen or (C$_1$-C$_6$)alkyl;
each occurrence of R$_D$ is independently halogen, hydroxy, O(C$_1$-C$_4$)alkyl, C(=O)(C$_1$-C$_4$)alkyl, or C(=O)O(C$_1$-C$_4$)alkyl;
each occurrence of R$_F$ and R$_{F'}$ is independently hydrogen, (C$_1$-C$_6$)alkyl, phenyl, benzyl, or R$_F$ and R$_{F'}$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
p is an integer of 0, 1, 2, 3, 4, 5, or 6;
m is an integer of 1, 2, 3, 4, 5, or 6; and
n is an integer of 1, 2, 3, 4, 5 or 6.

In yet another aspect, the present invention provides a pharmaceutical composition comprising at least one compound as described herein and a pharmaceutically-acceptable carrier.

In a further aspect, the present invention provides a method for treating or preventing a viral infection in a mammalian species in need thereof, the method comprising administering to the mammalian species a therapeutically effective amount of at least one compound as described herein.

In another aspect, the present invention provides a method for treating or preventing hepatitis C virus infection in a mammalian species in need thereof, the method comprising administering to the mammalian species a therapeutically effective amount of at least one compound as described herein.

In yet another aspect, the present invention provides a method for inhibiting a cyclophilin in a subject in need thereof, which comprises administrating to said subject an effective cyclophilin-inhibiting amount of at least one compound as described herein.

In yet another aspect, the present invention provides a method for treating or preventing diseases that are mediated by cyclophilins in a mammalian species in need thereof, the method comprising administering to the mammalian species a therapeutically effective amount of at least one compound as described herein.

In yet another aspect, the present invention provides a method for treating or preventing diseases in a mammalian species in need thereof, the method comprising administering to the mammalian species a therapeutically effective amount of at least one compound as described herein, wherein the diseases are selected from inflammation, respiratory inflammation, rheumatoid arthritis, and dry eye.

In yet another aspect, the present invention provides a method for treating or preventing diseases in a mammalian species in need thereof, the method comprising administering to the mammalian species a therapeutically effective amount of at least one compound as described herein, wherein the diseases are selected from neurodegenerative diseases such as Alzheimer's disease, Parkinson's disease, Huntington's Diseases, and ALS; traumatic brain injury; stroke; and ischemia-reperfusion injury in the brain, heart, and kidney.

In yet another aspect, the present invention provides a method for treating or preventing diseases in a mammalian species in need thereof, the method comprising administering to the mammalian species a therapeutically effective amount of at least one compound as described herein, wherein the diseases are selected from cardiovascular diseases, vascular stenosis, atherosclerosis, abdominal aortic aneurysms, cardiac hypertrophy, aortic rupture, pulmonary arterial hypertension, myocarditis and myocardial fibrosis, and ischaemic heart diseases.

In yet another aspect, the present invention provides a method for treating or preventing diseases or conditions in a mammalian species in need thereof, the method comprising administering to the mammalian species a therapeutically effective amount of at least one compound as described herein, wherein the diseases or conditions are selected from cancer, obesity, diabetes, muscular dystrophy, and hair loss.

In yet another aspect, the present invention provides a method for treating or preventing diseases or conditions in a mammalian species in need thereof, the method comprising administering to the mammalian species a therapeutically effective amount of at least one compound as described herein, wherein the diseases or conditions are selected from allergic conjunctivitis, atopic and vernal keratoconjunctivitis, atopic keratoconjunctivitis, anterior uveitis, Behcet's disease, blepharitis, chronic ocular surface inflammation caused by viral infection, corneal transplant rejection, corneal sensitivity impaired due to surgery on the cornea or other surface of the eye, meibomian gland disease, ptyregia, ocular symptoms of graft versus host disease, ocular allergy, ocular cicatricial pemphigoid, Steven Johnson syndrome, vernal keratoconjunctivitis, uveitis, herpes simplex keratitis, ocular rosacea, and Pinguecula.

DETAILED DESCRIPTION OF THE INVENTION

Definitions

The following are definitions of terms used in the present specification. The initial definition provided for a group or term herein applies to that group or term throughout the present specification individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$(C_1-C_4)$ alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "$(C_1-C_6)$alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "$(C_1-C_4)$alkyl."

"Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplaries of such groups include ethenyl or allyl. The term "$C_2-C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "alkynyl" refers to a straight or branched chain hydrocarbon radical containing from 2 to 12 carbon atoms and at least one carbon to carbon triple bond. An exemplary of such groups includes ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_c$ is independently alkyl, cycloalkyl, alkenyl, cycloalkenyl, alkynyl, heterocycle, or aryl. The exemplary substitutents can themselves be optionally substituted.

The term "cycloalkyl" refers to a fully saturated cyclic hydrocarbon group containing from 1 to 4 rings and 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substitutents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplaries of such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cyclolakyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolalkenyl, aryl or substituted aryl, heterocylyl or substituted heterocyclyl, as defined herein. R and R' may be the same or different in an dialkyamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of a compound of the present invention may be formed, for example, by reacting a compound I with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

Compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the present invention, or a salt and/or solvate thereof. Solvates of the compounds of the present invention include, for example, hydrates.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% pure ("substantially pure" compound I), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, or an enantiomer, diastereomer, tautomer, or pharmaceutically acceptable salt or solvate thereof, which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Compounds

The novel cyclosporin derivatives of the present invention are potent inhibitors of cyclophilins and are useful for inhibiting viruses such as HCV, HBV, and HIV.

In one aspect, the present invention provides a compound Formula (I):

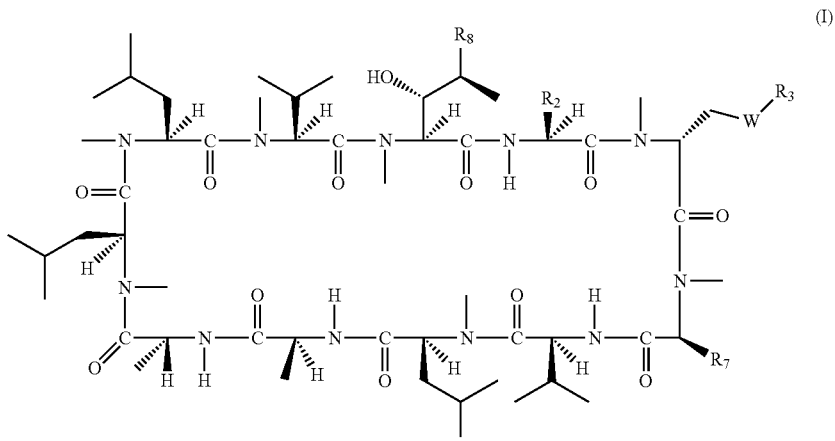

or pharmaceutically acceptable salt thereof, wherein:

$R_8$ is n-butyl, (E)-but-2-enyl, or

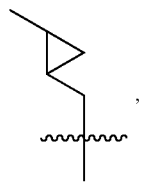 [SMILES: *CC1CC1C]

$(CH_2)_4$—$SR_9$, —$(CH_2)_4$—(C=O)$OR_9$, or —$(CH_2)_3$—(C=O)$OR_9$;

each occurrence of $R_9$ is independently hydrogen or ($C_1$-$C_6$)alkyl;

$R_2$ is ethyl, 1-hydroxyethyl, isopropyl or n-propyl;

W is O, S, $CH_2$ or $NR_1$;

$R_1$ is hydrogen;
 ($C_1$-$C_6$)alkyl, optionally substituted by one or more groups $R_D$ which may be the same or different;
 ($C_2$-$C_6$)alkenyl or ($C_2$-$C_6$)alkynyl;
 ($C_3$-$C_7$)cycloalkyl optionally substituted with ($C_1$-$C_6$) alkyl;
 phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;
 or a heterocyclic ring which may be saturated or unsaturated containing five or six ring atoms and from one to three heteroatoms which may be the same or different selected from nitrogen, sulfur and oxygen;
 or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of ($C_1$-$C_6$)alkyl, phenyl and benzyl;

R$_3$ is:
- H;
- (C$_1$-C$_6$)alkyl, optionally substituted by one or more groups R$_4$ which may be the same or different;
- (C$_2$-C$_6$)alkenyl, optionally substituted by one or more groups which may be the same or different selected from halogen, hydroxy, amino, monoalkylamino and dialkylamino;
- (C$_2$-C$_6$)alkynyl, optionally substituted by one or one or more groups which may be the same or different selected from halogen, hydroxy, amino, monoalkylamino and dialkylamino;
- (C$_3$-C$_7$)cycloalkyl, optionally substituted by one or more groups which may be the same or different selected from halogen, hydroxy, amino, monoalkylamino and dialkylamino;
- phenyl or CH$_2$-phenyl, optionally substituted by one or more groups which may be the same or different selected from halogen, hydroxy, (C$_1$-C$_6$)alkyl;

R$_7$ is

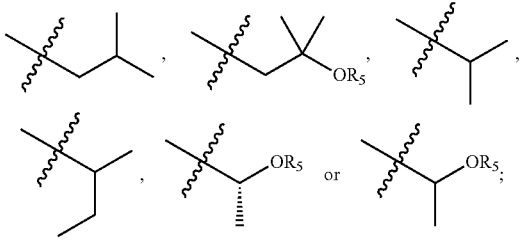

R$_5$ is:
- H;
- (C$_1$-C$_6$)alkyl, optionally substituted by one or more groups R$_6$ which may be the same or different;
- (C$_2$-C$_6$)alkenyl, optionally substituted by one or more groups which may be the same or different selected from hydroxy, (C$_1$-C$_6$)alkyl, aryl (e.g., phenyl), (CH$_2$)$_p$OR$_A$, O(CH$_2$)$_m$OH, O(CH$_2$)$_m$O(CH$_2$)$_m$OH, O(CH$_2$)$_m$NR$_A$R$_B$, O(CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(=O)NR$_A$R$_B$, (CH$_2$)$_p$C(=O)OR$_A$;
- (C$_2$-C$_6$)alkynyl, optionally substituted by one or one or more groups which may be the same or different selected from halogen, hydroxy, amino, monoalkylamino and dialkylamino;
- (C$_3$-C$_7$)cycloalkyl, optionally substituted by one or more groups which may be the same or different selected from halogen, hydroxy, amino, monoalkylamino and dialkylamino;
- phenyl or CH$_2$-phenyl, optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$, (CH$_2$)$_p$C(=O)OR$_A$;

each occurrence of R$_4$ is independently halogen, hydroxy, aryl (e.g., phenyl), O(CH$_2$)$_m$OR$_A$, O(CH$_2$)$_m$O(CH$_2$)$_m$OR$_A$, C(=O)(C$_1$-C$_6$)alkyl, C(=O)OR$_A$, C(=O)NR$_A$R$_B$, —NR$_A$R$_B$, —NR$_C$CH$_2$(CH$_2$)$_p$NR$_A$R$_B$, NR$_C$[CH$_2$(CH$_2$)$_p$NR$_A$]$_m$CH$_2$(CH$_2$)$_n$NR$_A$R$_B$, O[CH$_2$(CH$_2$)$_p$O]$_m$CH$_2$(CH$_2$)$_n$OR$_A$, OCH$_2$(CH$_2$)$_p$NR$_A$R$_B$, or O[CH$_2$(CH$_2$)$_p$O]$_m$CH$_2$(CH$_2$)$_n$NR$_A$R$_B$;

each occurrence of R$_6$ is independently halogen, hydroxy, aryl (e.g., phenyl), S(C$_1$-C$_6$)alkyl, SR$_A$, OR$_A$, O(CH$_2$)$_m$OR$_A$, O(CH$_2$)$_m$O(CH$_2$)$_m$OR$_A$, C(=O)OR$_A$, C(=O)NR$_A$R$_B$, NR$_A$R$_B$, O(CH$_2$)$_m$NR$_A$R$_B$, O(CH$_2$)$_m$O(CH$_2$)$_m$NR$_A$R$_B$, NR$_C$(CH$_2$)$_m$NR$_A$R$_B$, or NR$_C$(CH$_2$)$_m$NR$_C$(CH$_2$)$_m$NR$_A$R$_B$, wherein said aryl or phenyl is optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$ and (CH$_2$)$_p$C(=O)OR$_A$;

each occurrence of R$_A$ and R$_B$ is independently:
- hydrogen;
- (C$_1$-C$_6$)alkyl, optionally substituted by one or more groups R$_D$ which may be the same or different;
- (C$_2$-C$_6$)alkenyl or (C$_2$-C$_6$)alkynyl;
- (C$_3$-C$_7$)cycloalkyl optionally substituted with (C$_1$-C$_6$)alkyl;
- phenyl optionally substituted with from one to five groups which may be the same or different selected from halogen, —O(C$_1$-C$_6$)alkyl, —C(=O)O(C$_1$-C$_6$)alkyl, amino, alkylamino and dialkylamino;
- or a heterocyclic ring which may be saturated or unsaturated containing five or six ring atoms and from one to three heteroatoms which may be the same or different selected from nitrogen, sulfur and oxygen;
- or R$_A$ and R$_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of R$_C$ is independently hydrogen or (C$_1$-C$_6$)alkyl;

p is an integer of 0, 1, 2, 3, 4, or 5; and m is an integer of 1, 2, 3, 4 or 5.

In one aspect, the present invention provides a compound Formula (I):

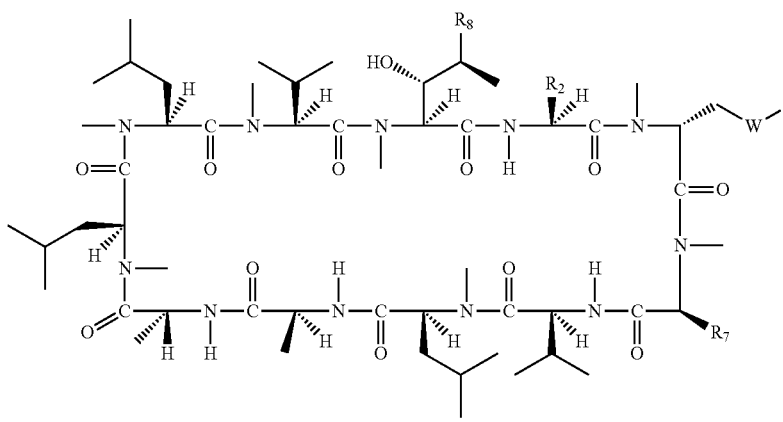

(I)

or pharmaceutically acceptable salt thereof, wherein:

$R_8$ is n-butyl, (E)-but-2-enyl, or

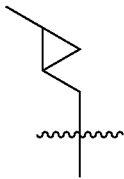

,

—(CH$_2$)$_4$—SR$_9$, —(CH$_2$)$_4$—(C═O)OR$_9$, or —(CH$_2$)$_3$—(C═O)OR$_9$;

each occurrence of $R_9$ is independently hydrogen or (C$_1$-C$_6$)alkyl;

$R_2$ is ethyl, 1-hydroxyethyl, isopropyl or n-propyl;

W is O, S, CH$_2$ or NR$_1$;

$R_1$ is hydrogen;
 (C$_1$-C$_6$)alkyl, optionally substituted by one or more groups $R_D$ which may be the same or different;
 (C$_2$-C$_6$)alkenyl or (C$_2$-C$_6$)alkynyl;
 (C$_3$-C$_7$)cycloalkyl optionally substituted with (C$_1$-C$_6$)alkyl;
 phenyl optionally substituted with from one to five groups which may be the same or different selected from halogen, —O(C$_1$-C$_6$)alkyl, —C(═O)O(C$_1$-C$_6$)alkyl, amino, alkylamino and dialkylamino;
 or a heterocyclic ring which may be saturated or unsaturated containing five or six ring atoms and from one to three heteroatoms which may be the same or different selected from nitrogen, sulfur and oxygen;
 or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of (C$_1$-C$_6$)alkyl, phenyl and benzyl;

$R_3$ is:
 H;
 (C$_7$-C$_{12}$)alkyl, optionally substituted by one or more groups $R_4$ which may be the same or different;
 (C$_7$-C$_{12}$)alkenyl, optionally substituted by one or more groups which may be the same or different selected from halogen, hydroxy, amino, monoalkylamino and dialkylamino; or
 (C$_7$-C$_{12}$)alkynyl, optionally substituted by one or one or more groups which may be the same or different selected from halogen, hydroxy, amino, monoalkylamino and dialkylamino;

$R_7$ is

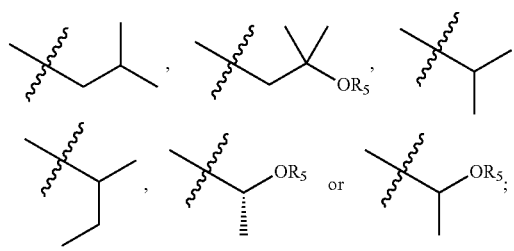

$R_5$ is:
 H;
 (C$_1$-C$_6$)alkyl, optionally substituted by one or more groups $R_6$ which may be the same or different;
 (C$_2$-C$_6$)alkenyl, optionally substituted by one or more groups which may be the same or different selected from hydroxy, (C$_1$-C$_6$)alkyl, aryl (e.g., phenyl), (CH$_2$)$_p$OR$_A$, O(CH$_2$)$_m$OH, O(CH$_2$)$_m$O(CH$_2$)$_m$OH, O(CH$_2$)$_m$NR$_A$R$_B$, O(CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(═O)NR$_A$R$_B$, (CH$_2$)$_p$C(═O)OR$_A$;
 (C$_2$-C$_6$)alkynyl, optionally substituted by one or one or more groups which may be the same or different selected from halogen, hydroxy, amino, monoalkylamino and dialkylamino;
 (C$_3$-C$_7$)cycloalkyl, optionally substituted by one or more groups which may be the same or different selected from halogen, hydroxy, amino, monoalkylamino and dialkylamino;
 phenyl or CH$_2$-phenyl, optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(═O)NR$_A$R$_B$, (CH$_2$)$_p$C(═O)OR$_A$;

each occurrence of $R_4$ is independently halogen, hydroxy, (C$_3$-C$_7$)cycloalkyl, aryl (e.g., phenyl), O(CH$_2$)$_m$OR$_A$, O(CH$_2$)$_m$O(CH$_2$)$_m$OR$_A$, C(═O)(C$_1$-C$_6$)alkyl, C(═O)OR$_A$, C(═O)NR$_A$R$_B$, —NR$_A$R$_B$, —NR$_C$CH$_2$(CH$_2$)$_p$NR$_A$R$_B$, NR$_C$[CH$_2$(CH$_2$)$_p$NR$_A$]$_m$CH$_2$(CH$_2$)$_n$NR$_A$R$_B$, O[CH$_2$(CH$_2$)$_p$O]$_m$CH$_2$(CH$_2$)$_n$OR$_A$, OCH$_2$(CH$_2$)$_p$NR$_A$R$_B$, or O[CH$_2$(CH$_2$)$_p$O]$_m$CH$_2$(CH$_2$)$_n$NR$_A$R$_B$;

each occurrence of $R_6$ is independently halogen, hydroxy, aryl (e.g., phenyl), S(C$_1$-C$_6$)alkyl, SR$_A$, OR$_A$, O(CH$_2$)$_m$OR$_A$, O(CH$_2$)$_m$O(CH$_2$)$_m$OR$_A$, C(═O)OR$_A$, C(═O)NR$_A$R$_B$, NR$_A$R$_B$, O(CH$_2$)$_m$NR$_A$R$_B$, O(CH$_2$)$_m$O(CH$_2$)$_m$NR$_A$R$_B$, NR$_C$(CH$_2$)$_m$NR$_A$R$_B$, or NR$_C$(CH$_2$)$_m$NR$_C$(CH$_2$)$_m$NR$_A$R$_B$, wherein said aryl or phenyl is optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(═O)NR$_A$R$_B$ and (CH$_2$)$_p$C(═O)OR$_A$;

each occurrence of $R_A$ and $R_B$ is independently:
 hydrogen;
 (C$_1$-C$_6$)alkyl, optionally substituted by one or more groups $R_D$ which may be the same or different;
 (C$_2$-C$_6$)alkenyl or (C$_2$-C$_6$)alkynyl;
 (C$_3$-C$_7$)cycloalkyl optionally substituted with (C$_1$-C$_6$)alkyl;
 phenyl optionally substituted with from one to five groups which may be the same or different selected from halogen, —O(C$_1$-C$_6$)alkyl, —C(═O)O(C$_1$-C$_6$)alkyl, amino, alkylamino and dialkylamino;
 or a heterocyclic ring which may be saturated or unsaturated containing five or six ring atoms and from one to three heteroatoms which may be the same or different selected from nitrogen, sulfur and oxygen;
 or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or $(C_1-C_6)$alkyl;

p is an integer of 0, 1, 2, 3, 4, or 5; and m is an integer of 1, 2, 3, 4 or 5.

In certain embodiments, $R_3$ is $(C_7-C_{10})$alkyl. In certain other embodiments, $R_3$ is $(C_7-C_8)$alkyl. In yet other embodiments, $R_3$ is $(C_7-C_{12})$ linear alkyl. In yet other embodiments, $R_3$ is $(C_7-C_{10})$ linear alkyl. In yet other embodiments, $R_3$ is $(C_7-C_8)$ linear alkyl.

In certain embodiments, $R_4$ is hydroxyl. In certain other embodiments, $R_4$ is $C(=O)OR_4$.

In certain embodiments, $R_8$ is n-butyl. In certain other embodiments, $R_8$ is (E)-but-2-enyl. In certain other embodiments, $R_8$ is

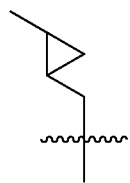

In yet other embodiments, $R_8$ is $-(CH_2)_4-SR_9$. In yet other embodiments, $R_8$ is $-(CH_2)_4-(C=O)OR_9$. In yet other embodiments, $R_8$ is $-(CH_2)_3-(C=O)OR_9$. In certain embodiments, each occurrence of $R_9$ is independently hydrogen. In certain other embodiments, each occurrence of $R_9$ is independently $(C_1-C_6)$alkyl. In certain embodiments, $R_2$ is ethyl.

In certain embodiments, the compound of Formula I has the structure of Formulae (II) through (VI):

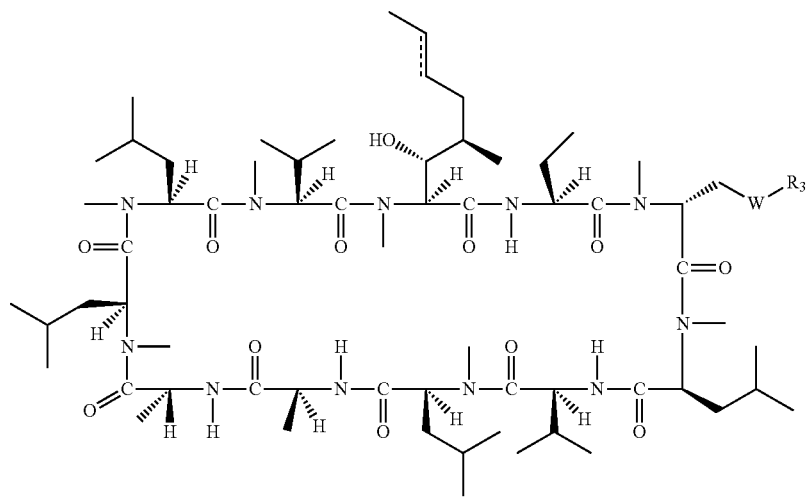

(II)

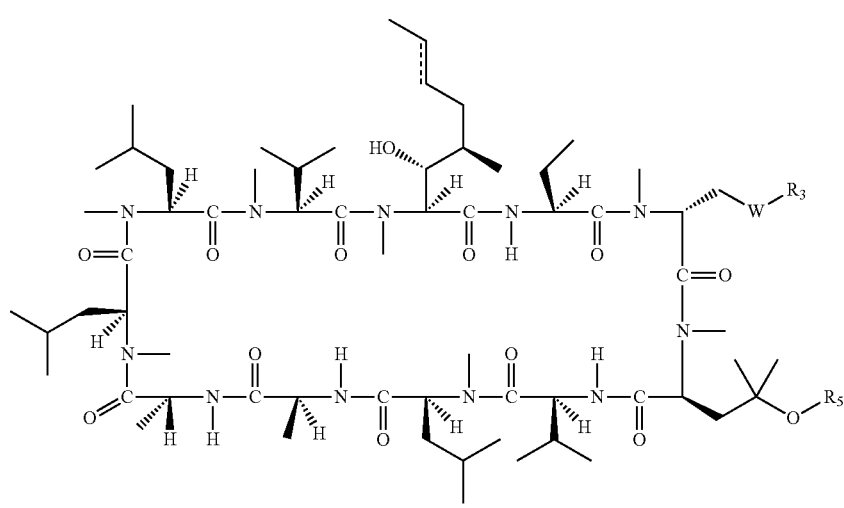

(III)

(IV)
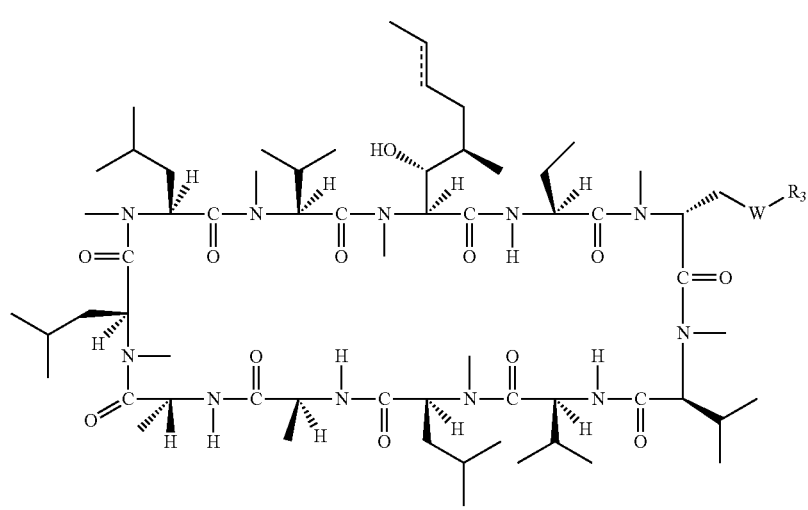
(V)
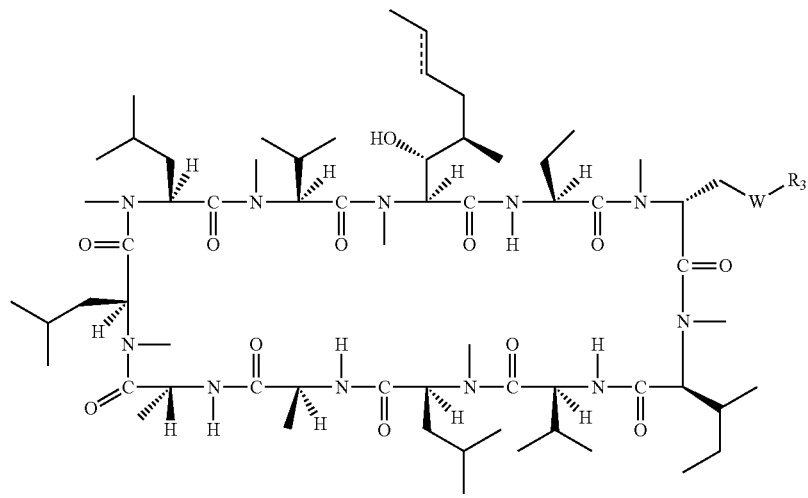
(VI)
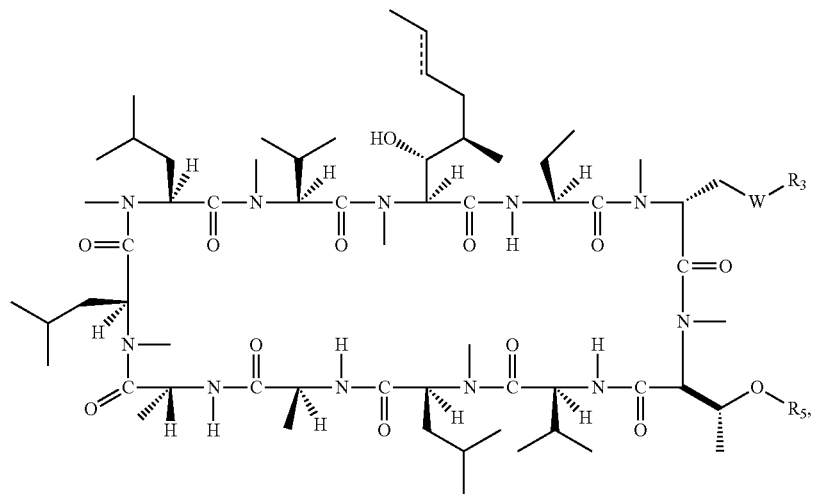
or pharmaceutically acceptable salt thereof, wherein:
┃ represents a single bond or double bond;
each W is independently O, S, $CH_2$, or $NR_1$;
each $R_1$ is independently hydrogen;
$(C_1-C_6)$alkyl, optionally substituted by one or more groups $R_D$ which may be the same or different;

($C_2$-$C_6$)alkenyl or ($C_2$-$C_6$)alkynyl;

($C_3$-$C_7$)cycloalkyl optionally substituted with ($C_1$-$C_6$) alkyl;

phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of ($C_1$-$C_6$)alkyl, phenyl and benzyl;

each $R_3$ is independently:

H;

($C_1$-$C_6$)alkyl, optionally substituted by one or more groups $R_4$ which may be the same or different;

($C_2$-$C_6$)alkenyl, optionally substituted by one or more groups which may be the same or different selected from halogen, hydroxy, ($C_1$-$C_6$)alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

($C_2$-$C_6$)alkynyl, optionally substituted by one or one or more groups which may be the same or different selected from halogen, hydroxy, amino, monoalkylamino and dialkylamino;

($C_3$-$C_7$)cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, ($C_1$-$C_6$)alkyl;

each $R_5$ is independently:

H;

($C_1$-$C_6$)alkyl, optionally substituted by one or more groups $R_6$ which may be the same or different;

($C_2$-$C_6$)alkenyl, optionally substituted by one or more groups which may be the same or different selected from halogen, hydroxy, ($C_1$-$C_6$)alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

($C_2$-$C_6$)alkynyl, optionally substituted by one or one or more groups which may be the same or different selected from halogen, hydroxy, amino, monoalkylamino and dialkylamino;

($C_3$-$C_7$)cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, —$NR_AR_B$, —$NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:

hydrogen;

($C_1$-$C_6$)alkyl, optionally substituted by one or more groups $R_D$ which may be the same or different;

($C_2$-$C_6$)alkenyl or ($C_2$-$C_6$)alkynyl;

($C_3$-$C_7$)cycloalkyl optionally substituted with ($C_1$-$C_6$) alkyl;

phenyl optionally substituted with from one to five groups which may be the same or different selected from halogen, —O($C_1$-$C_6$)alkyl, —C(=O)O($C_1$-$C_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

or $R_A$ and $R_B$, together with the nitrogen atom to which they are attached, form —N=CH—$NR_FR_{F'}$, —N=CMe-$NR_FR_{F'}$, or —$NR_FC(=NH)NR_FR_{F'}$;

each occurrence of $R_C$ is independently hydrogen or ($C_1$-$C_6$)alkyl;

each occurrence of $R_D$ is independently halogen, hydroxy, $O(C_1$-$C_4)$alkyl, $C(=O)(C_1$-$C_4)$alkyl, $C(=O)O(C_1$-$C_4)$ alkyl;

each occurrence of $R_F$ and $R_{F'}$ is independently hydrogen, ($C_1$-$C_6$)alkyl, phenyl, benzyl, or $R_F$ and $R_{F'}$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

p is an integer of 0, 1, 2, 3, 4, 5, or 6;

m is an integer of 1, 2, 3, 4, 5, or 6; and n is an integer of 1, 2, 3, 4, 5 or 6.

In certain embodiments, the compound of Formula I has the structure of Formulae (II) through (VI):
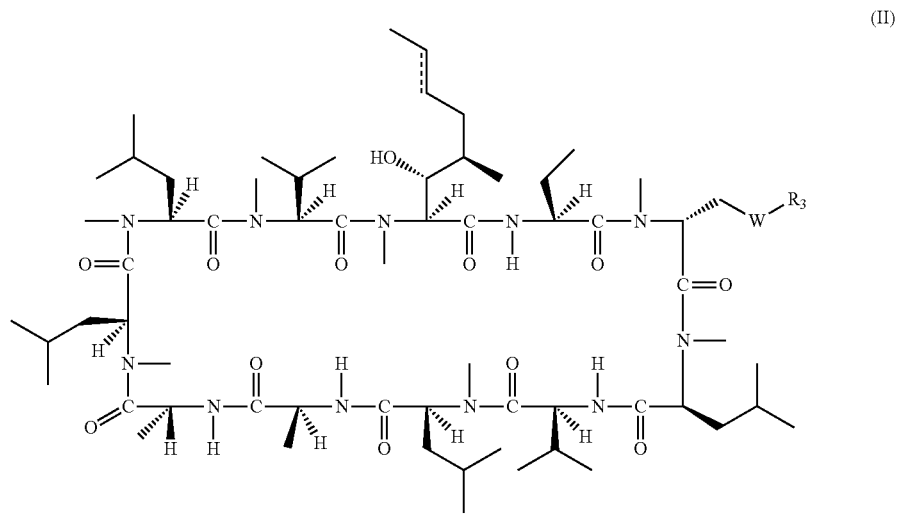
(II)
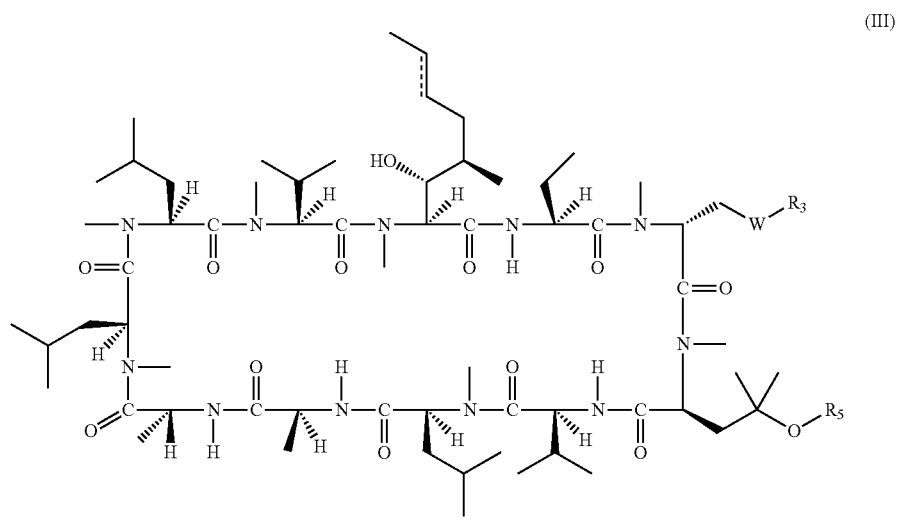
(III)
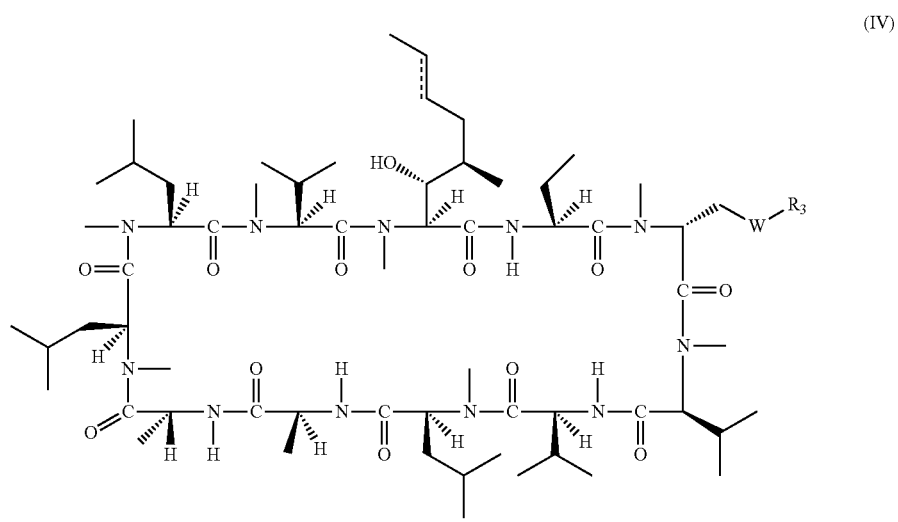
(IV)

(V)

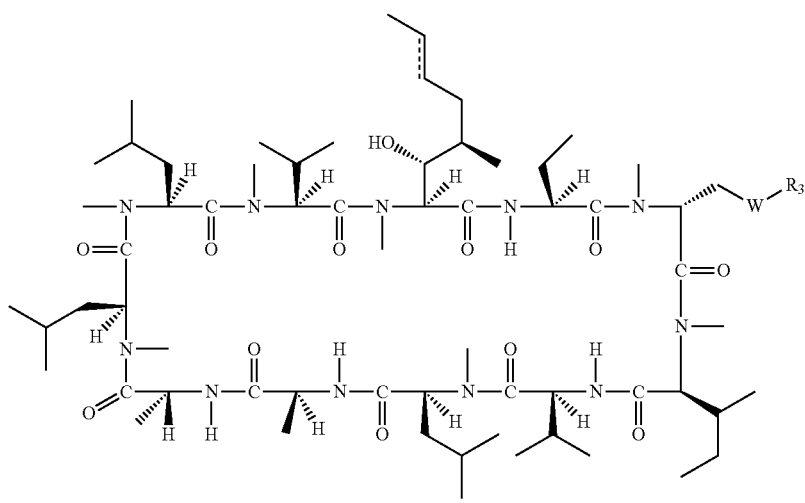

(VI)

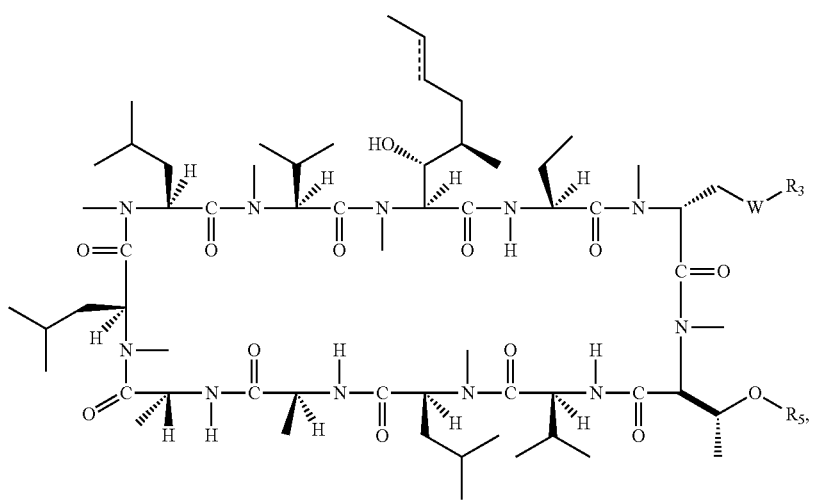

or pharmaceutically acceptable salt thereof, wherein:
| represents a single bond or double bond;
each W is independently O, S, $CH_2$, or $NR_1$;
each $R_1$ is independently hydrogen;
- $(C_1-C_6)$alkyl, optionally substituted by one or more groups $R_D$ which may be the same or different;
- $(C_2-C_6)$alkenyl or $(C_2-C_6)$alkynyl;
- $(C_3-C_7)$cycloalkyl optionally substituted with $(C_1-C_6)$alkyl;
- phenyl optionally substituted with from one to five groups which may be the same or different selected from halogen, —O$(C_1-C_6)$alkyl, —C(=O)O$(C_1-C_6)$alkyl, amino, alkylamino and dialkylamino;
- or a heterocyclic ring which may be saturated or unsaturated containing five or six ring atoms and from one to three heteroatoms which may be the same or different selected from nitrogen, sulfur and oxygen;
- or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1-C_6)$alkyl, phenyl and benzyl;

each $R_3$ is independently:
- H;
- $(C_7-C_{12})$alkyl, optionally substituted by one or more groups $R_4$ which may be the same or different;
- $(C_7-C_{12})$alkenyl, optionally substituted by one or more groups which may be the same or different selected from halogen, hydroxy, $(C_1-C_6)$alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_m NR_C(CH_2)_mNR_AR_B$, $(CH_2)_pC(=O)NR_AR_B$, $(CH_2)_pC(=O)OR_A$; or
- $(C_7-C_{12})$alkynyl, optionally substituted by one or one or more groups which may be the same or different selected from halogen, hydroxy, amino, monoalkylamino and dialkylamino;

each $R_5$ is independently:
- H;
- $(C_1-C_6)$alkyl, optionally substituted by one or more groups $R_6$ which may be the same or different;
- $(C_2-C_6)$alkenyl, optionally substituted by one or more groups which may be the same or different selected from halogen, hydroxy, $(C_1-C_6)$alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

$(C_2$-$C_6)$alkynyl, optionally substituted by one or one or more groups which may be the same or different selected from halogen, hydroxy, amino, monoalkylamino and dialkylamino;

$(C_3$-$C_7)$cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, $(C_3$-$C_7)$cycloalkyl, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, —$NR_AR_B$, —$NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:
hydrogen;
$(C_1$-$C_6)$alkyl, optionally substituted by one or more groups $R_D$ which may be the same or different;
$(C_2$-$C_6)$alkenyl or $(C_2$-$C_6)$alkynyl;
$(C_3$-$C_7)$cycloalkyl optionally substituted with $(C_1$-$C_6)$alkyl;
phenyl optionally substituted with from one to five groups which may be the same or different selected from halogen, —$O(C_1$-$C_6)$alkyl, —$C(=O)O(C_1$-$C_6)$alkyl, amino, alkylamino and dialkylamino;
or a heterocyclic ring which may be saturated or unsaturated containing five or six ring atoms and from one to three heteroatoms which may be the same or different selected from nitrogen, sulfur and oxygen;
or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
or $R_A$ and $R_B$, together with the nitrogen atom to which they are attached, form —N=CH—$NR_FR_{F'}$, —N=CMe-$NR_FR_{F'}$, or —$NR_FC(=NH)NR_FR_{F'}$;

each occurrence of $R_C$ is independently hydrogen or $(C_1$-$C_6)$alkyl;

each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl;

each occurrence of $R_F$ and $R_{F'}$ is independently hydrogen, $(C_1$-$C_6)$alkyl, phenyl, benzyl, or $R_F$ and $R_{F'}$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

p is an integer of 0, 1, 2, 3, 4, 5, or 6;
m is an integer of 1, 2, 3, 4, 5, or 6; and
n is an integer of 1, 2, 3, 4, 5 or 6.

In certain embodiments, $R_3$ is $(C_7$-$C_{10})$alkyl. In certain other embodiments, $R_3$ is $(C_7$-$C_8)$alkyl. In yet other embodiments, $R_3$ is $(C_7$-$C_{12})$ linear alkyl. In yet other embodiments, $R_3$ is $(C_7$-$C_{10})$ linear alkyl. In yet other embodiments, $R_3$ is $(C_7$-$C_8)$ linear alkyl.

In certain embodiments, $R_4$ is hydroxyl. In certain other embodiments, $R_4$ is $C(=O)OR_A$.

In certain embodiments, W is O. In certain other embodiments, W is S. In yet other embodiments, W is NH. In yet other embodiments, W is $CH_2$, yet other embodiments, W is $NR_1$. In yet other embodiments, W is N—$(C_1$-$C_4)$alkyl.

In certain embodiments, m is 1. In certain other embodiments, m is 2. In yet other embodiments, m is 3. In yet other embodiments, m is 4 or 5.

In certain embodiments, p is 0. In certain other embodiments, p is 1. In yet other embodiments, m is 2. In yet other embodiments, m is 3, 4 or 5.

In certain embodiments, $R_3$ is H, methyl, ethyl, n-propyl, propyl, n-butyl, i-butyl, t-butyl, $CH_2CMe_3$, phenyl, $CH_2$-phenyl,

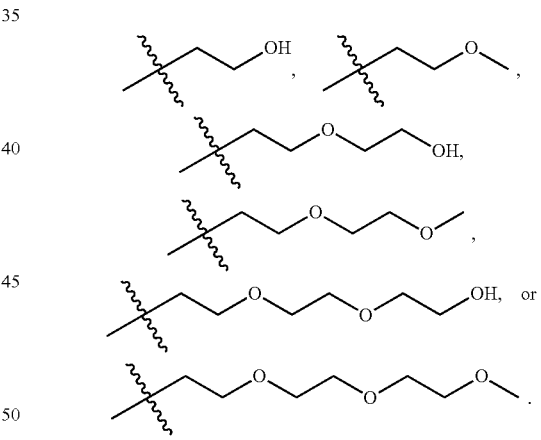

In certain embodiments, $R_3$ is —$(CH_2)_nNR_AR_B$, wherein n is an integer of 2, 3, 4, 5 or 6, or integer of 7, 8, 9, 10, 11 or 12; and wherein each occurrence of $R_A$ and $R_B$ is independently hydrogen; $(C_1$-$C_4)$alkyl, optionally substituted by one or more groups $R_D$ which may be the same or different, in which each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1$-$C_4)$alkyl, phenyl and benzyl.

In certain embodiments, $R_3$ is —$(CH_2)_nNR_AR_B$, wherein n is an integer of 2, 3, 4, 5 or 6, or integer of 7, 8, 9, 10, 11 or 12; and wherein $R_A$ and $R_B$, together with the nitrogen atom to which they are attached, form a saturated or unsaturated heterocyclic ring containing from three to seven ring atoms, which ring may optionally contain another heteroatom selected from nitrogen, oxygen and sulfur and may be optionally substituted by from one to four groups which may be the same or different selected from $(C_1-C_4)$alkyl, phenyl and benzyl.

In certain embodiments, n is 2. In certain other embodiments, n is 3. In yet other embodiments, n is 4, 5, or 6. In yet other embodiments, n is 7 or 8. In yet other embodiments, n is 9 or 10. In yet other embodiments, n is 11 or 12.

In certain embodiments, $R_3$ is —$(CH_2)_nNR_AR_B$, wherein n is an integer of 7, 8, 9, 10, 11 or 12; and wherein each occurrence of $R_A$ and $R_B$ is independently hydrogen; $(C_1-C_4)$alkyl, optionally substituted by one or more groups $R_D$ which may be the same or different, in which each occurrence of $R_D$ is independently halogen, hydroxy, $O(C_1-C_4)$alkyl, $C(=O)(C_1-C_4)$alkyl, $C(=O)O(C_1-C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1-C_4)$alkyl, phenyl and benzyl.

In certain embodiments, n is 7. In certain other embodiments, n is 8. In yet other embodiments, n is 9, 10, 11 or 12.

In certain embodiments, $R_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is $(C_1-C_4)$alkyl.

In certain embodiments, $R_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is $(C_1-C_4)$alkyl, wherein $R_3$ is dimethylaminoethyl, diethylaminoethyl, methylethylaminoethyl, methyl-iso-butylaminoethyl, ethyl-iso-butylaminoethyl, methyl-tert-butylaminoethyl, or ethyl-tert-butylaminoethyl.

In certain embodiments, $R_3$ is

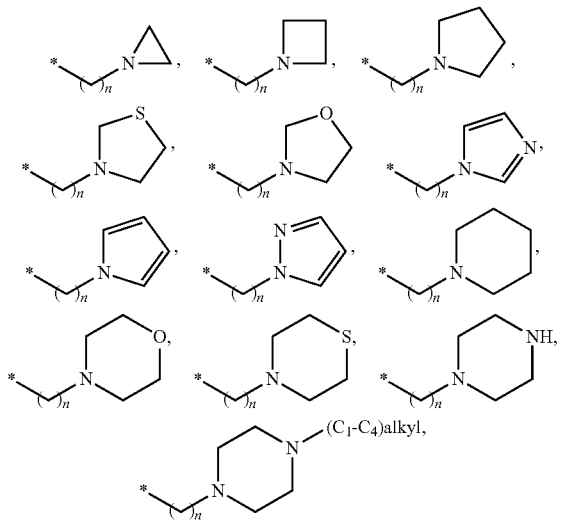

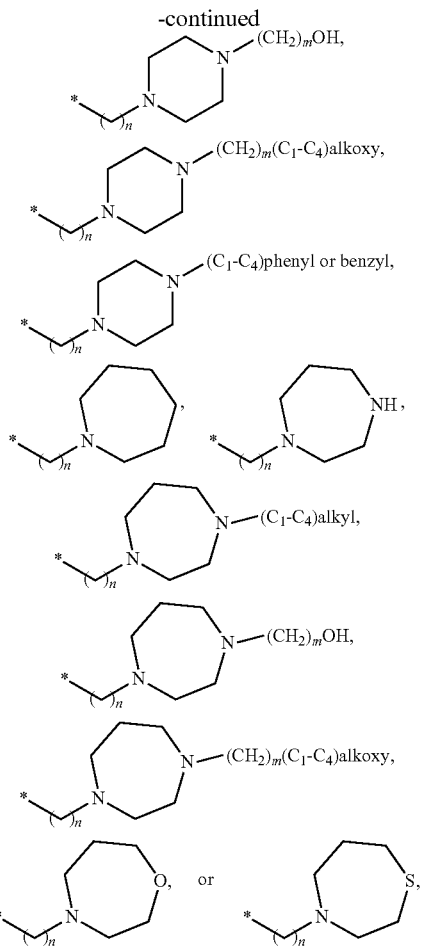

in which n is an integer of 2, 3, 4, 5, or 6, and m is an integer of 2, 3, or 4. In certain embodiments, n is 2. In certain other embodiments, n is 3. In yet other embodiments, n is 4, or 5, or 6. In certain embodiments, m is 2. In certain other embodiments, m is 3. In certain other embodiments, m is 4. In certain embodiments, n is 7. In certain other embodiments, n is 8. In yet other embodiments, n is 9, 10, 11 or 12.

In certain embodiments, W is $NR_1$, and $R_1$ and $R_3$ together with the nitrogen atom to which they are attached, form a heterocycle selected from

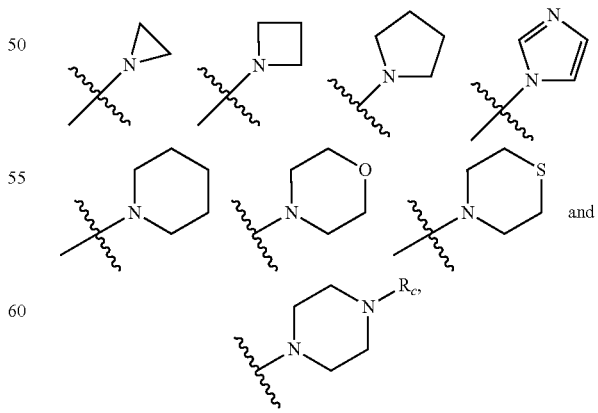

in which $R_C$ is H, Me, Et, n-Pr, i-Pr, n-Bu, i-Bu, t-Bu, $CH_2CMe_3$, Ph, $CH_2Ph$, $CH_2CH_2OH$, or $CH_2CH_2O(C_1-C_4)$alkyl.

In certain embodiments, $R_5$ is H, $(C_1-C_6)$alkyl, $(C_2-C_6)$alkenyl, phenyl, benzyl, $CH_2$—S—$(C_1-C_6)$alky, $CH_2$—O—$(C_1-C_6)$alkyl, $(C_2-C_6)OR_A$, $(C_1-C_6)$-monoalkyl amine, $(C_1-C_6)$-dialkyl amine, or $(C_1-C_6)$-cyclic amine, in which said phenyl or benzyl is optionally substituted by one to three substitutents selected from $(C_1-C_4)$alkyl, $(C_1-C_4)$alkoxy, and halogen; and $R_A$ is H, $(C_1-C_6)$alkyl, phenyl, $CH_2$-phenyl, $(C_1-C_6)$alkylOH, $(CH_2)_pO(CH_2)_mOH$, $(CH_2)_pO(CH_2)_mO(CH_2)_mOH$, $(C_1-C_6)$alkylO$(C_1-C_4)$alkyl, $(CH_2)_pO(CH_2)_mO(C_1-C_4)$alkyl, or $(CH_2)_pO(CH_2)_mO(CH_2)_mO(C_1-C_4)$alkyl; p is an integer of 0, 1, 2, 3, 4, or 5; and m is an integer of 1, 2, 3, 4 or 5.

In certain embodiments, $R_5$ is H. In certain other embodiments, $R_5$ is methyl. In yet other embodiments, $R_5$ is $CH_2$—S—$(C_1-C_6)$alky, e.g., $CH_2$—S—$CH_3$. In yet other embodiments, $R_5$ is $CH_2$—O—$(C_1-C_6)$alkyl, e.g., $CH_2$—O—$CH_2$—$CH_3$. In yet other embodiments, $R_5$ is $(C_2-C_6)$alkenyl, e.g., $CH_2$—CH=$CH_2$. In yet other embodiments, $R_5$ is benzyl. In yet other embodiments, $R_5$ is $(C_2-C_6)$OH. In yet other embodiments, $R_5$ is $(C_1-C_6)$-monoalkyl amine, e.g., $CH_2$—NH-Me. In yet other embodiments, $R_5$ is $(C_1-C_6)$-dialkyl amine, e.g., $CH_2$—$CH_2$—$N(Et)_2$. In yet other embodiments, $R_5$ is $(C_1-C_6)$-cyclic amine, e.g., $CH_2$—$CH_2$-morpholine.

In certain embodiments, each occurrence $R_A$ and $R_B$ is independently H, $(C_1-C_6)$alkyl, phenyl, $CH_2$-phenyl, $(C_1-C_6)$alkylOH, $(CH_2)_pO(CH_2)_mOH$, or $(CH_2)_pO(CH_2)_mO(CH_2)_mOH$, $(C_1-C_6)$alkylO$(C_1-C_4)$alkyl, $(CH_2)_pO(CH_2)_mO(C_1-C_4)$alkyl, or $(CH_2)_pO(CH_2)_mO(CH_2)_mO(C_1-C_4)$alkyl. In certain other embodiments, $R_A$ and $R_B$, together with the nitrogen atom to which they are attached, form a heterocycle selected from

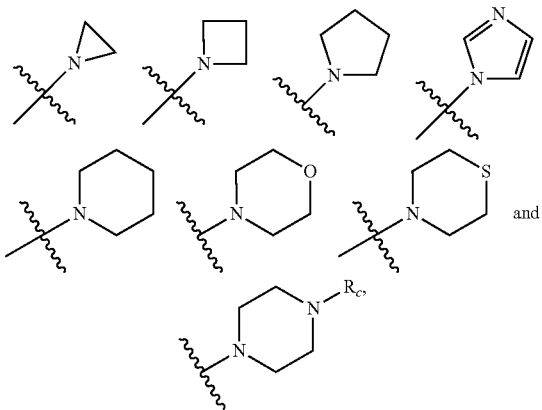

in which $R_C$ is H, Me, Et, n-Pr, i-Pr, n-Bu, i-Bu, t-Bu, $CH_2CMe_3$, Ph, $CH_2$Ph, $CH_2CH_2OH$, or $CH_2CH_2O(C_1-C_4)$alkyl.

In certain embodiments, wherein ∥ represents a single bond. In certain other embodiments, wherein ∥ represents a double bond.

In another aspect, the present invention provides a compound of Formulae (IIa)-(VIa):

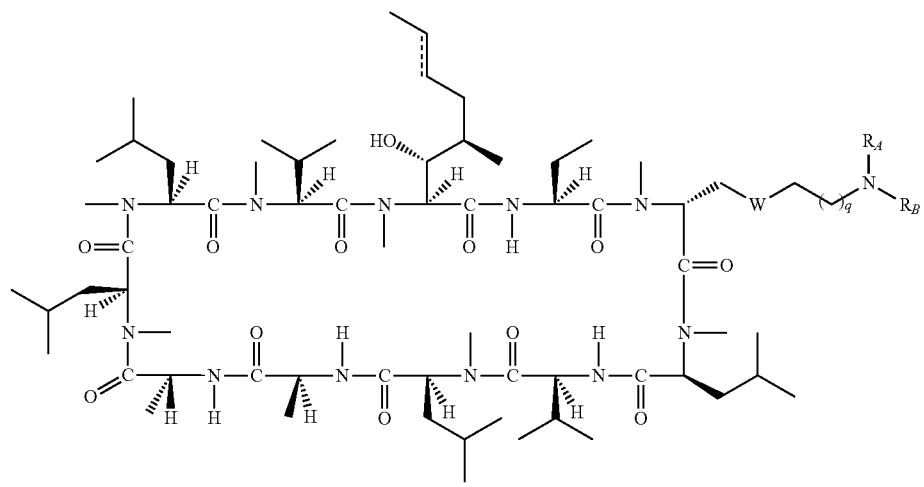

(IIa)

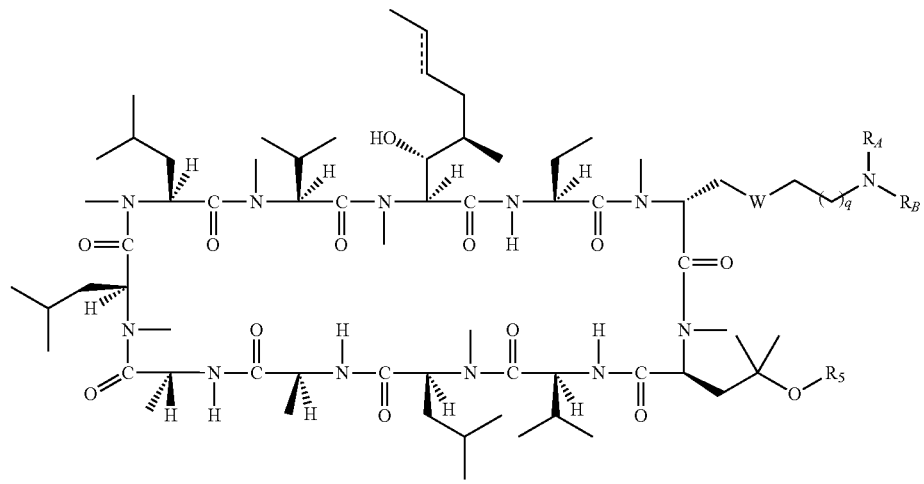

(IIIa)

(IVa)

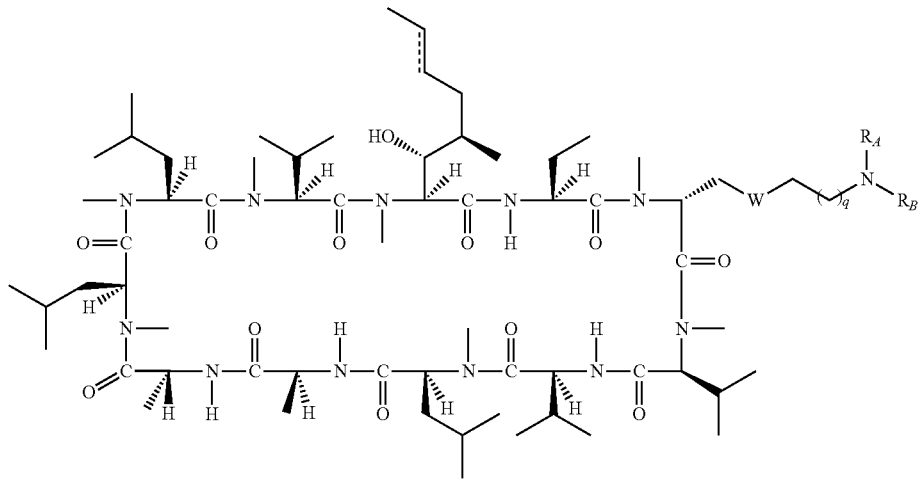

(Va)

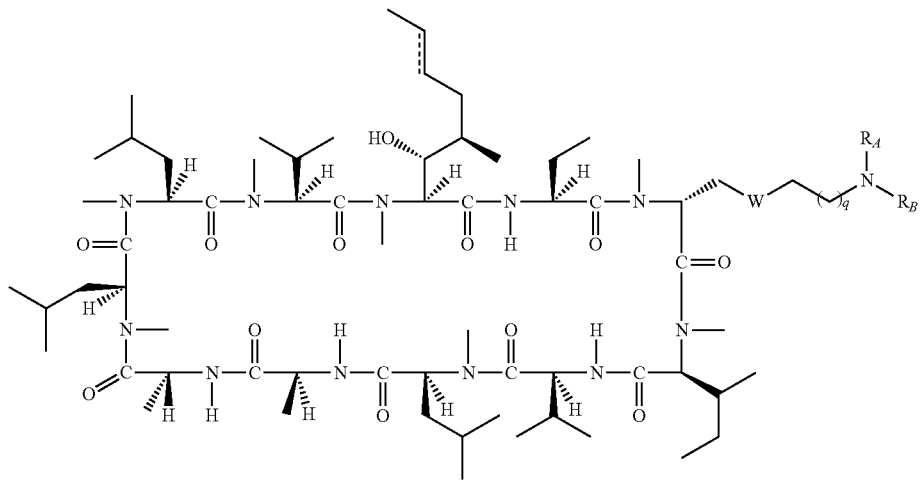

(VIa)

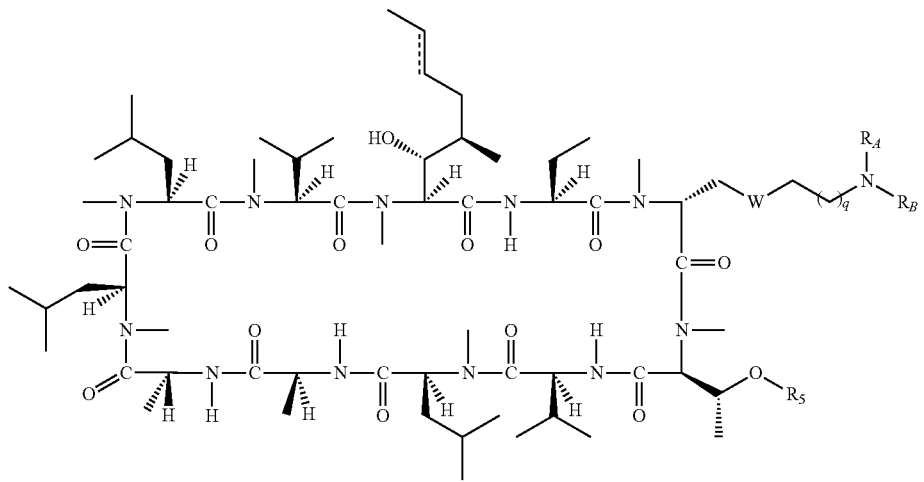

or a pharmaceutically acceptable salt thereof, wherein:
| represents a single bond or double bond;
each W is independently O, S, $CH_2$, or $NR_1$;
each $R_1$ is independently hydrogen;
  $(C_1-C_6)$alkyl, optionally substituted by one or more groups $R_D$ which may be the same or different;
  $(C_2-C_6)$alkenyl or $(C_2-C_6)$alkynyl;
  $(C_3-C_7)$cycloalkyl optionally substituted with $(C_1-C_6)$alkyl;
  phenyl optionally substituted with from one to five groups which may be the same or different selected from halogen, —O$(C_1-C_6)$alkyl, —C(=O)O$(C_1-C_6)$alkyl, amino, alkylamino and dialkylamino;
or a heterocyclic ring which may be saturated or unsaturated containing five or six ring atoms and from one to three heteroatoms which may be the same or different selected from nitrogen, sulfur and oxygen;

each $R_5$ is independently:

H;

($C_1$-$C_6$)alkyl, optionally substituted by one or more groups $R_6$ which may be the same or different;

($C_2$-$C_6$)alkenyl, optionally substituted by one or more groups which may be the same or different selected from halogen, hydroxy, ($C_1$-$C_6$)alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

($C_2$-$C_6$)alkynyl, optionally substituted by one or one or more groups which may be the same or different selected from halogen, hydroxy, amino, monoalkylamino and dialkylamino;

($C_3$-$C_7$)cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:

hydrogen;

($C_1$-$C_6$)alkyl, optionally substituted by one or more groups $R_D$ which may be the same or different;

($C_2$-$C_6$)alkenyl or ($C_2$-$C_6$)alkynyl;

($C_3$-$C_7$)cycloalkyl optionally substituted with ($C_1$-$C_6$) alkyl;

phenyl optionally substituted with from one to five groups which may be the same or different selected from halogen, —$O(C_1$-$C_6)$alkyl, —$C(=O)O(C_1$-$C_6)$alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or ($C_1$-$C_6$)alkyl;

each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl;

each p is independently an integer of 0, 1, 2, 3, 4, or 5; and each of m, n and q is independently an integer of 1, 2, 3, 4 or 5.

In another aspect, the present invention provides a compound of Formulae (IIa)-(VIa):

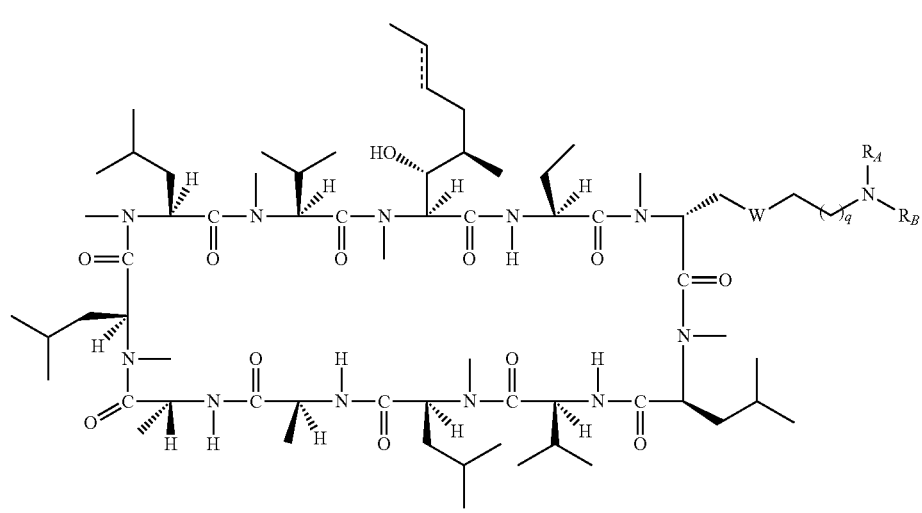

(IIa)

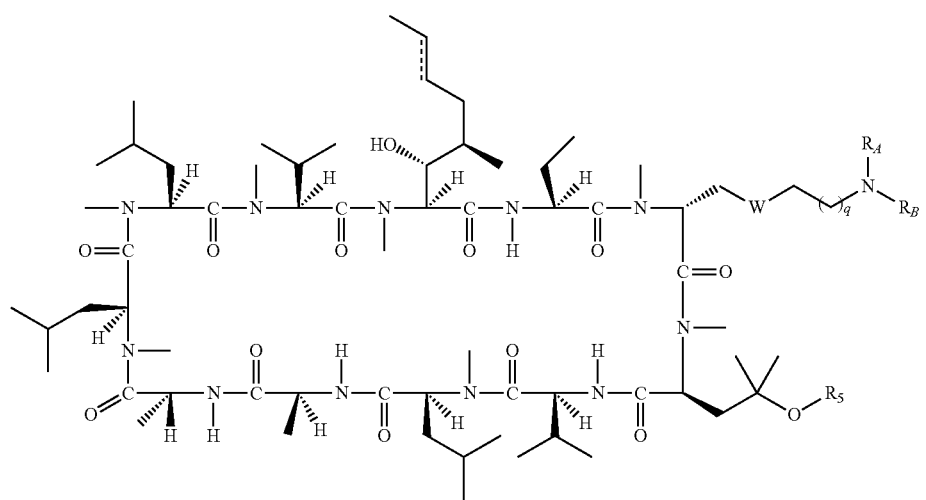
(IIIa)
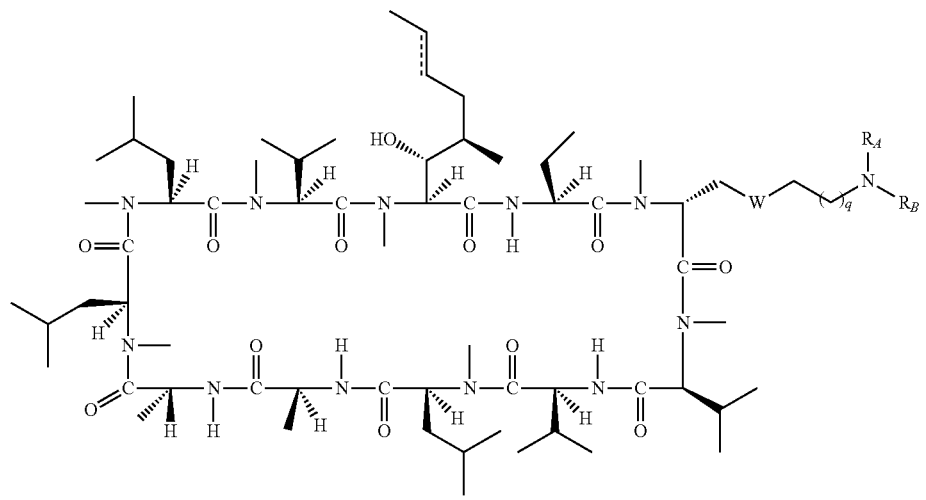
(IVa)
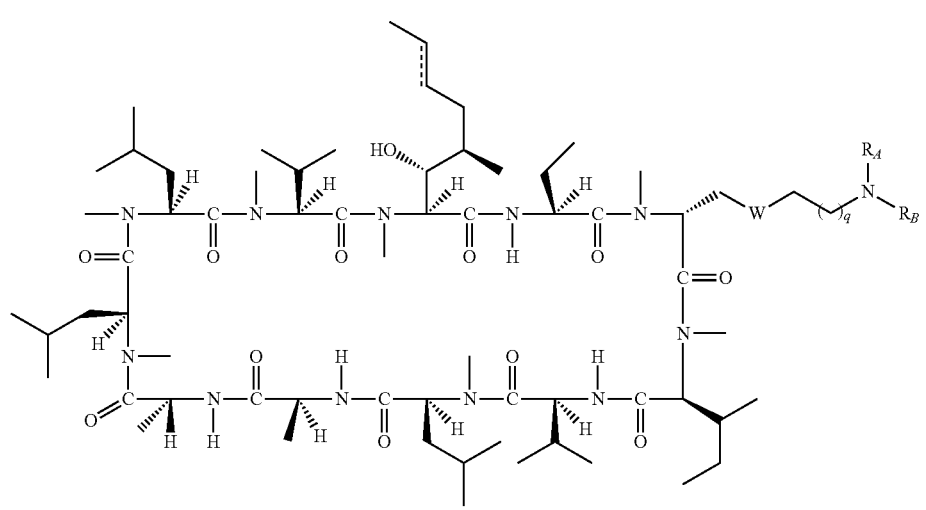
(Va)

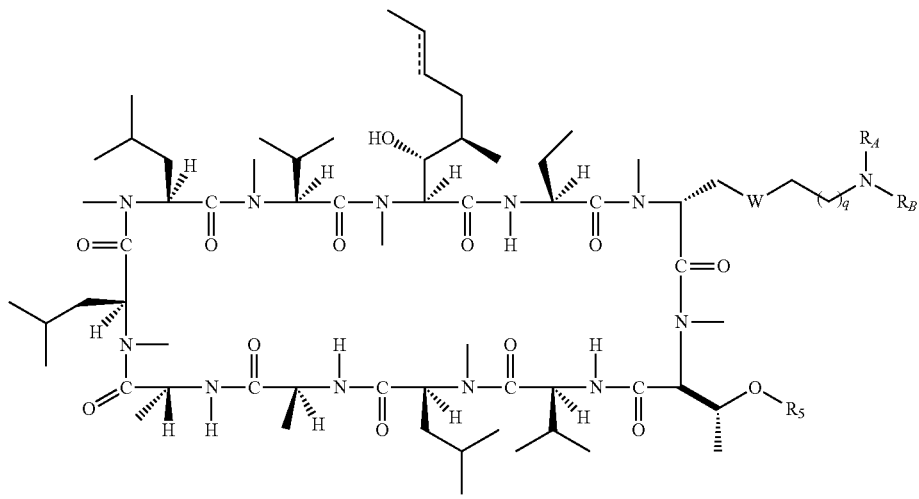

(VIa)

or a pharmaceutically acceptable salt thereof, wherein:
| represents a single bond or double bond;
each W is independently O, S, $CH_2$, or $NR_1$;
each $R_1$ is independently hydrogen;
  $(C_1-C_6)$alkyl, optionally substituted by one or more groups $R_D$ which may be the same or different;
  $(C_2-C_6)$alkenyl or $(C_2-C_6)$alkynyl;
  $(C_3-C_7)$cycloalkyl optionally substituted with $(C_1-C_6)$alkyl;
  phenyl optionally substituted with from one to five groups which may be the same or different selected from halogen, $-O(C_1-C_6)$alkyl, $-C(=O)O(C_1-C_6)$alkyl, amino, alkylamino and dialkylamino;
  or a heterocyclic ring which may be saturated or unsaturated containing five or six ring atoms and from one to three heteroatoms which may be the same or different selected from nitrogen, sulfur and oxygen;
each $R_5$ is independently:
  H;
  $(C_1-C_6)$alkyl, optionally substituted by one or more groups $R_6$ which may be the same or different;
  $(C_2-C_6)$alkenyl, optionally substituted by one or more groups which may be the same or different selected from halogen, hydroxy, $(C_1-C_6)$alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
  $(C_2-C_6)$alkynyl, optionally substituted by one or one or more groups which may be the same or different selected from halogen, hydroxy, amino, monoalkylamino and dialkylamino;
  $(C_3-C_7)$cycloalkyl, optionally substituted by one or more groups which may be the same or different selected from halogen, hydroxy, amino, monoalkylamino and dialkylamino;
  phenyl or $CH_2$-phenyl, optionally substituted by one or more groups which may be the same or different selected from halogen, hydroxy, $(C_1-C_6)$alkyl, $(CH_2)_pOR_A$, $(CH_2)_pNR_AR_B$, $(CH_2)_pC(=O)NR_AR_B$, $(CH_2)_pC(=O)OR_A$;
each occurrence of $R_6$ is independently halogen, hydroxy, aryl (e.g., phenyl), $S(C_1-C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, $(C_1-C_6)$alkyl, $(CH_2)_pOR_A$, $(CH_2)_pNR_AR_B$, $(CH_2)_pC(=O)NR_AR_B$ and $(CH_2)_pC(=O)OR_A$;
each occurrence of $R_A$ and $R_B$ is independently:
  hydrogen;
  $(C_1-C_6)$alkyl, optionally substituted by one or more groups $R_D$ which may be the same or different;
  $(C_2-C_6)$alkenyl or $(C_2-C_6)$alkynyl;
  $(C_3-C_7)$cycloalkyl optionally substituted with $(C_1-C_6)$alkyl;
  phenyl optionally substituted with from one to five groups which may be the same or different selected from halogen, $-O(C_1-C_6)$alkyl, $-C(=O)O(C_1-C_6)$alkyl, amino, alkylamino and dialkylamino;
  or a heterocyclic ring which may be saturated or unsaturated containing five or six ring atoms and from one to three heteroatoms which may be the same or different selected from nitrogen, sulfur and oxygen;
  or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
each occurrence of $R_C$ is independently hydrogen or $(C_1-C_6)$alkyl;
each occurrence of $R_D$ is independently halogen, hydroxy, $O(C_1-C_4)$alkyl, $C(=O)(C_1-C_4)$alkyl, $C(=O)O(C_1-C_4)$alkyl;
each p is independently an integer of 0, 1, 2, 3, 4, or 5;
each of m and n is independently an integer of 1, 2, 3, 4 or 5; and
q is independently an integer of 6, 7, 8, 9, 10 or 11.

In another aspect, the present invention provides a compound of Formulae (IIb)-(VIb):
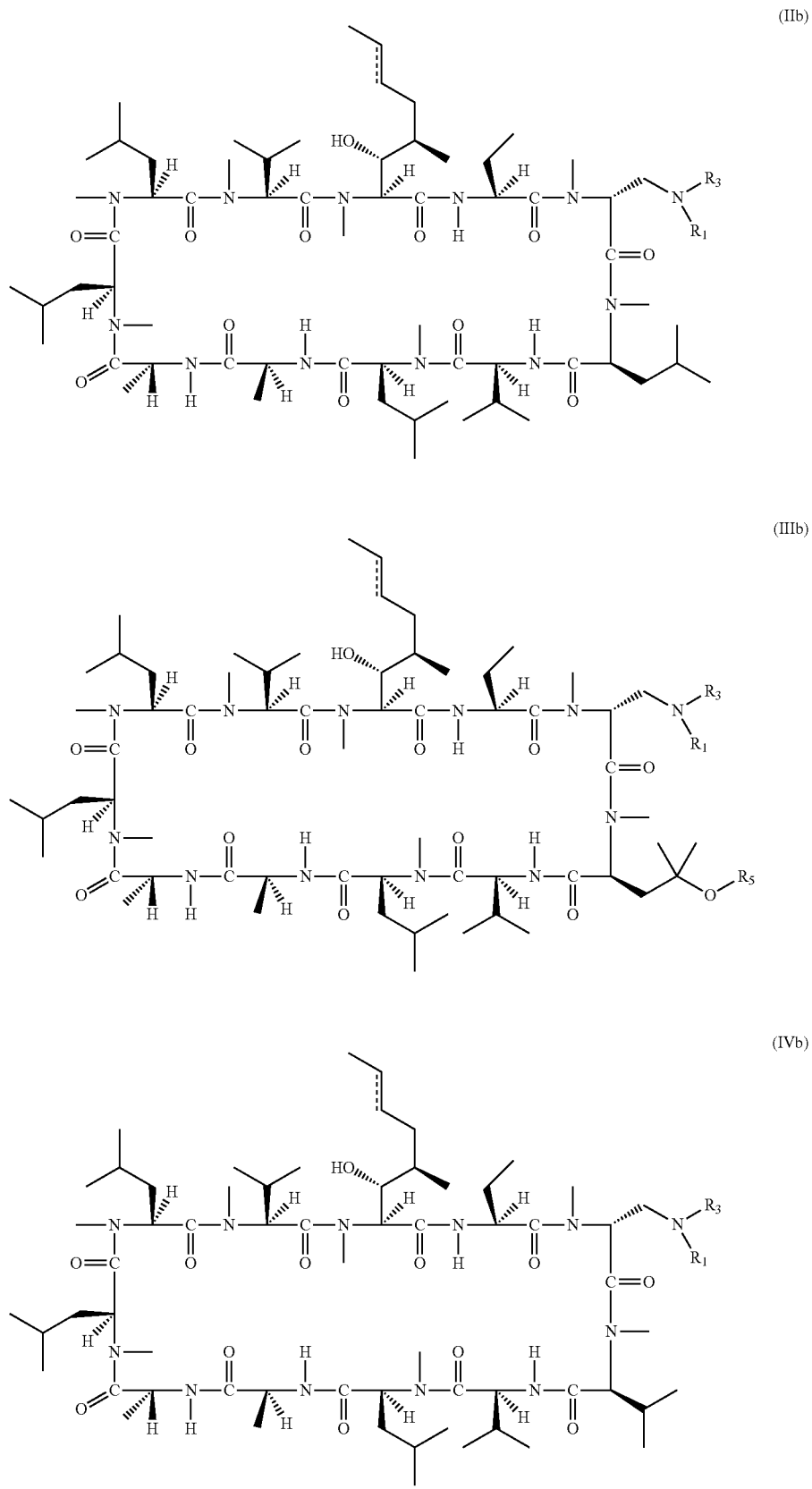

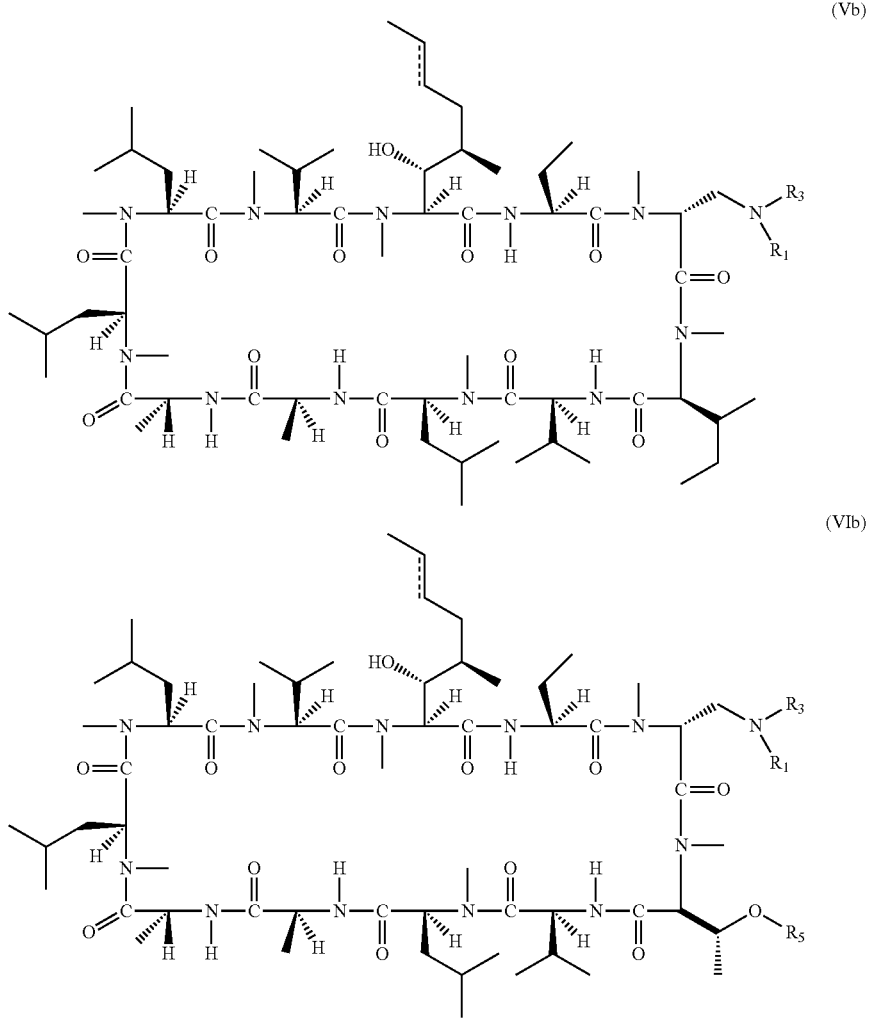

(Vb)

(VIb)

or a pharmaceutically acceptable salt thereof, wherein:

| represents a single bond or double bond;

each $R_1$ is independently hydrogen;

(C$_1$-C$_6$)alkyl, optionally substituted by one or more groups $R_D$ which may be the same or different;

(C$_2$-C$_6$)alkenyl or (C$_2$-C$_6$)alkynyl;

(C$_3$-C$_7$)cycloalkyl optionally substituted with (C$_1$-C$_6$) alkyl;

phenyl optionally substituted with from one to five groups which may be the same or different selected from halogen, —O(C$_1$-C$_6$)alkyl, —C(═O)O(C$_1$-C$_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of (C$_1$-C$_6$)alkyl, phenyl and benzyl;

each $R_3$ is independently:

H;

(C$_1$-C$_6$)alkyl, optionally substituted by one or more groups $R_4$ which may be the same or different;

(C$_2$-C$_6$)alkenyl, optionally substituted by one or more groups which may be the same or different selected from halogen, hydroxy, (C$_1$-C$_6$)alkyl, aryl (e.g., phenyl), (CH$_2$)$_p$OR$_A$, (CH$_2$)$_m$OH, (CH$_2$)$_m$O(CH$_2$)$_m$OH, (CH$_2$)$_m$NR$_A$R$_B$, (CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(═O)NR$_A$R$_B$, (CH$_2$)$_p$C(═O)OR$_A$;

(C$_2$-C$_6$)alkynyl, optionally substituted by one or one or more groups which may be the same or different selected from halogen, hydroxy, amino, monoalkylamino and dialkylamino;

(C$_3$-C$_7$)cycloalkyl, optionally substituted by one or more groups which may be the same or different selected from halogen, hydroxy, amino, monoalkylamino and dialkylamino;

phenyl or CH$_2$-phenyl, optionally substituted by one or more groups which may be the same or different selected from halogen, hydroxy, (C$_1$-C$_6$)alkyl;

each $R_5$ is independently:

H;

(C$_1$-C$_6$)alkyl, optionally substituted by one or more groups $R_6$ which may be the same or different;

($C_2$-$C_6$)alkenyl, optionally substituted by one or more groups which may be the same or different selected from halogen, hydroxy, ($C_1$-$C_6$)alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;

($C_2$-$C_6$)alkynyl, optionally substituted by one or one or more groups which may be the same or different selected from halogen, hydroxy, amino, monoalkylamino and dialkylamino;

($C_3$-$C_7$)cycloalkyl, optionally substituted by one or more groups which may be the same or different selected from halogen, hydroxy, amino, monoalkylamino and dialkylamino;

phenyl or $CH_2$-phenyl, optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, $—NR_AR_B$, $—NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_pO]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, ($C_1$-$C_6$)alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:

hydrogen;

($C_1$-$C_6$)alkyl, optionally substituted by one or more groups $R_D$ which may be the same or different;

($C_2$-$C_6$)alkenyl or ($C_2$-$C_6$)alkynyl;

($C_3$-$C_7$)cycloalkyl optionally substituted with ($C_1$-$C_6$)alkyl;

phenyl optionally substituted with from one to five groups which may be the same or different selected from halogen, $—O(C_1$-$C_6)$alkyl, $—C(=O)O(C_1$-$C_6)$alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or ($C_1$-$C_6$)alkyl;

each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl;

each p is independently an integer of 0, 1, 2, 3, 4, or 5; and each of m, n and q is independently an integer of 1, 2, 3, 4 or 5.

In another aspect, the present invention provides a compound of Formulae (IIb)-(VIb):

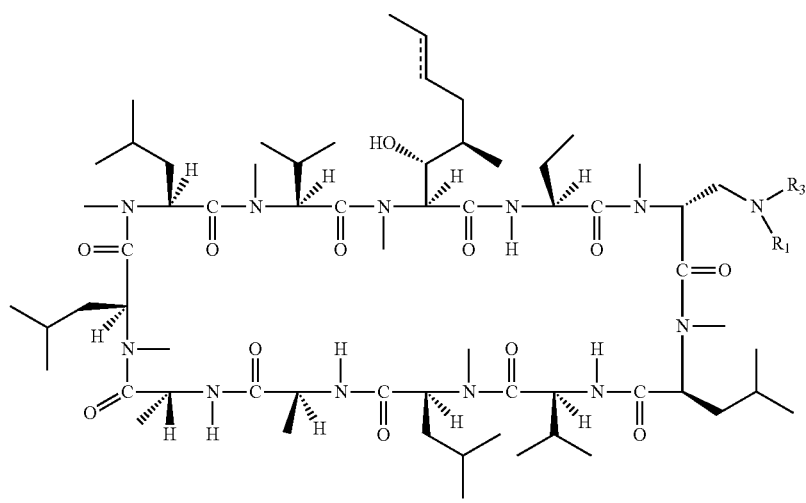

(IIb)

-continued
(IIIb)
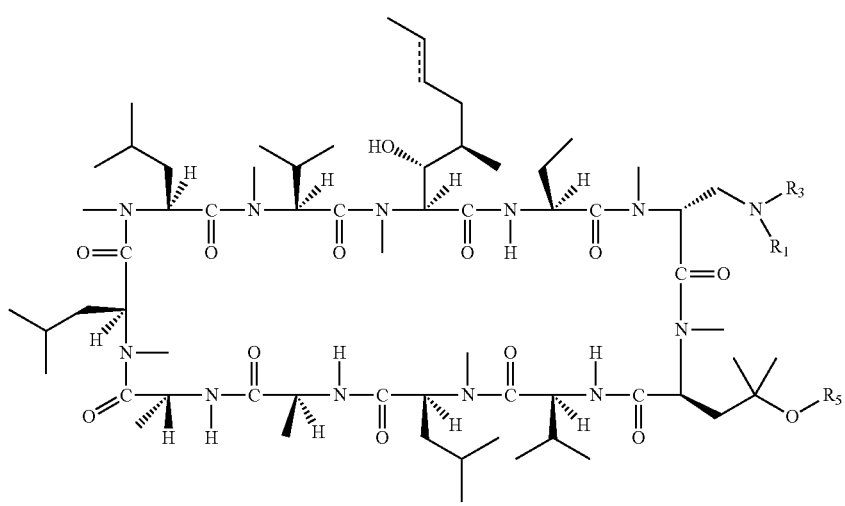
(IVb)
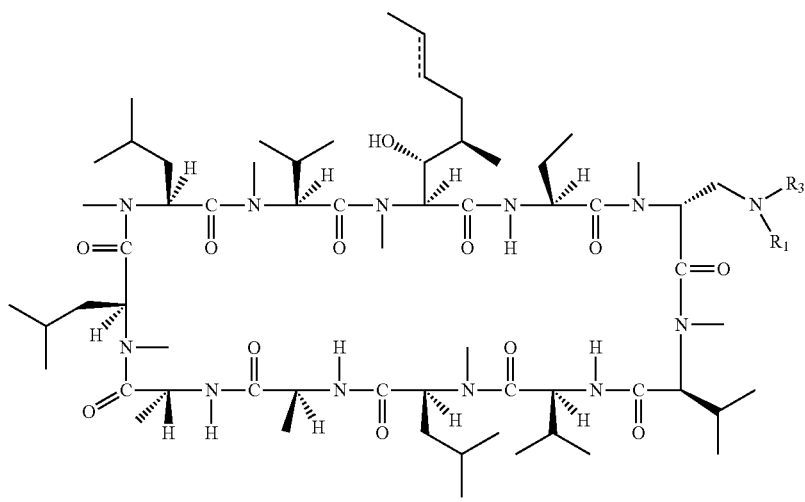
(Vb)
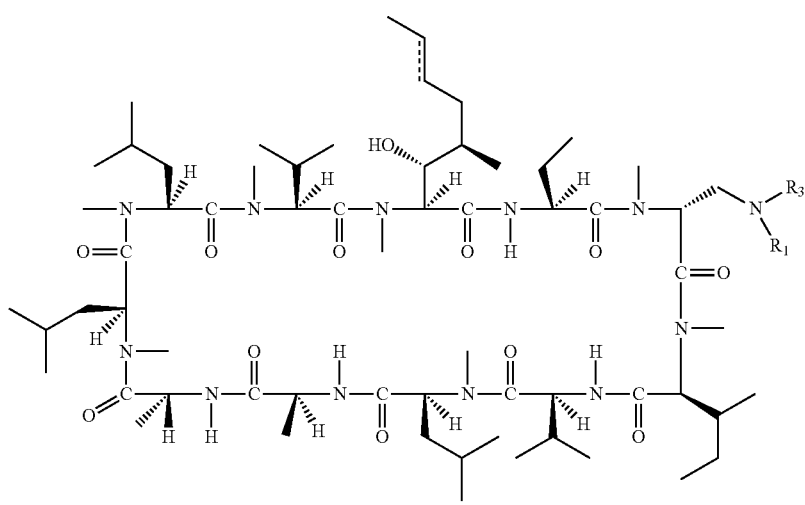

-continued (VIb)

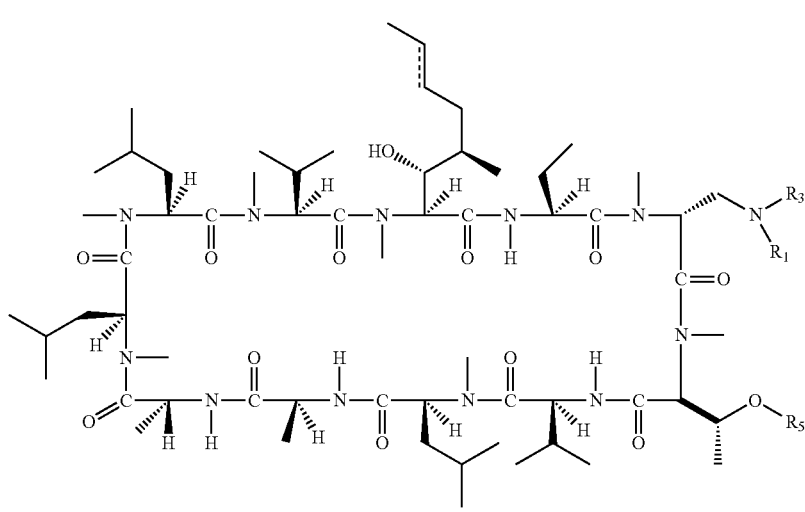

or a pharmaceutically acceptable salt thereof, wherein:
| represents a single bond or double bond;
each $R_1$ is independently hydrogen;
- $(C_1$-$C_6)$alkyl, optionally substituted by one or more groups $R_D$ which may be the same or different;
- $(C_2$-$C_6)$alkenyl or $(C_2$-$C_6)$alkynyl;
- $(C_3$-$C_7)$cycloalkyl optionally substituted with $(C_1$-$C_6)$ alkyl;
- phenyl optionally substituted with from one to five groups which may be the same or different selected from halogen, —O$(C_1$-$C_6)$alkyl, —C(=O)O$(C_1$-$C_6)$alkyl, amino, alkylamino and dialkylamino;
- or a heterocyclic ring which may be saturated or unsaturated containing five or six ring atoms and from one to three heteroatoms which may be the same or different selected from nitrogen, sulfur and oxygen;
- or $R_1$ and $R_3$ together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1$-$C_6)$alkyl, phenyl and benzyl;

each $R_3$ is independently:
- H;
- $(C_7$-$C_{12})$alkyl, optionally substituted by one or more groups $R_4$ which may be the same or different;
- $(C_7$-$C_{12})$alkenyl, optionally substituted by one or more groups which may be the same or different selected from halogen, hydroxy, $(C_1$-$C_6)$alkyl, aryl (e.g., phenyl), $(CH_2)_pOR_A$, $(CH_2)_mOH$, $(CH_2)_mO(CH_2)_mOH$, $(CH_2)_mNR_AR_B$, $(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$; or
- $(C_7$-$C_{12})$alkynyl, optionally substituted by one or one or more groups which may be the same or different selected from halogen, hydroxy, amino, monoalkylamino and dialkylamino;

each $R_5$ is independently:
- H;
- $(C_1$-$C_6)$alkyl, optionally substituted by one or more groups $R_6$ which may be the same or different;
- $(C_2$-$C_6)$alkenyl, optionally substituted by one or more groups which may be the same or different selected from halogen, hydroxy, $(C_1$-$C_6)$alkyl, aryl (e.g., phenyl), $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
- $(C_2$-$C_6)$alkynyl, optionally substituted by one or one or more groups which may be the same or different selected from halogen, hydroxy, amino, monoalkylamino and dialkylamino;
- $(C_3$-$C_7)$cycloalkyl, optionally substituted by one or more groups which may be the same or different selected from halogen, hydroxy, amino, monoalkylamino and dialkylamino;
- phenyl or $CH_2$-phenyl, optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$, $(CH_2)_pC(=O)OR_A$;

each occurrence of $R_4$ is independently halogen, hydroxy, $(C_3$-$C_7)$cycloalkyl, aryl (e.g., phenyl), $O(CH_2)_mOR_A$, $O(CH_2)_mO(CH_2)_mOR_A$, $C(=O)(C_1$-$C_6)$alkyl, $C(=O)OR_A$, $C(=O)NR_AR_B$, —$NR_AR_B$, —$NR_CCH_2(CH_2)_pNR_AR_B$, $NR_C[CH_2(CH_2)_pNR_A]_mCH_2(CH_2)_nNR_AR_B$, $O[CH_2(CH_2)_pO]_mCH_2(CH_2)_nOR_A$, $OCH_2(CH_2)_pNR_AR_B$, or $O[CH_2(CH_2)_p]_mCH_2(CH_2)_nNR_AR_B$;

each occurrence of $R_6$ is independently halogen, hydroxy, aryl (e.g., phenyl), $S(C_1$-$C_6)$alkyl, $SR_A$, $OR_A$, $O(CH_2)_mOR_A$, $O(CH_2)_mO(CH_2)_mOR_A$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, $(C_1$-$C_6)$alkyl, $(CH_2)_pOR_A$, $(CH_2)_pNR_AR_B$, $(CH_2)_pC(=O)NR_AR_B$ and $(CH_2)_pC(=O)OR_A$;

each occurrence of $R_A$ and $R_B$ is independently:
hydrogen;
$(C_1\text{-}C_6)$alkyl, optionally substituted by one or more groups $R_D$ which may be the same or different;
$(C_2\text{-}C_6)$alkenyl or $(C_2\text{-}C_6)$alkynyl;
$(C_3\text{-}C_7)$cycloalkyl optionally substituted with $(C_1\text{-}C_6)$ alkyl;
phenyl optionally substituted with from one to five groups which may be the same or different selected from halogen, —O$(C_1\text{-}C_6)$alkyl, —C(=O)O$(C_1\text{-}C_6)$alkyl, amino, alkylamino and dialkylamino;
or a heterocyclic ring which may be saturated or unsaturated containing five or six ring atoms and from one to three heteroatoms which may be the same or different selected from nitrogen, sulfur and oxygen;
or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or $(C_1\text{-}C_6)$alkyl;

each occurrence of $R_D$ is independently halogen, hydroxy, O$(C_1\text{-}C_4)$alkyl, C(=O)$(C_1\text{-}C_4)$alkyl, C(=O)O$(C_1\text{-}C_4)$ alkyl;

each p is independently an integer of 0, 1, 2, 3, 4, or 5; and
each of m and n is independently an integer of 1, 2, 3, 4 or 5.

In certain embodiments, $R_3$ is $(C_7\text{-}C_{10})$alkyl. In certain other embodiments, $R_3$ is $(C_7\text{-}C_8)$alkyl. In yet other embodiments, $R_3$ is $(C_7\text{-}C_{12})$ linear alkyl. In yet other embodiments, $R_3$ is $(C_7\text{-}C_{10})$ linear alkyl. In yet other embodiments, $R_3$ is $(C_7\text{-}C_8)$ linear alkyl.

In certain embodiments, $R_4$ is hydroxyl. In certain other embodiments, $R_4$ is C(=O)OR$_A$.

In certain embodiments, the compound of Formula I has the structure of Formulae (II) through (VI):

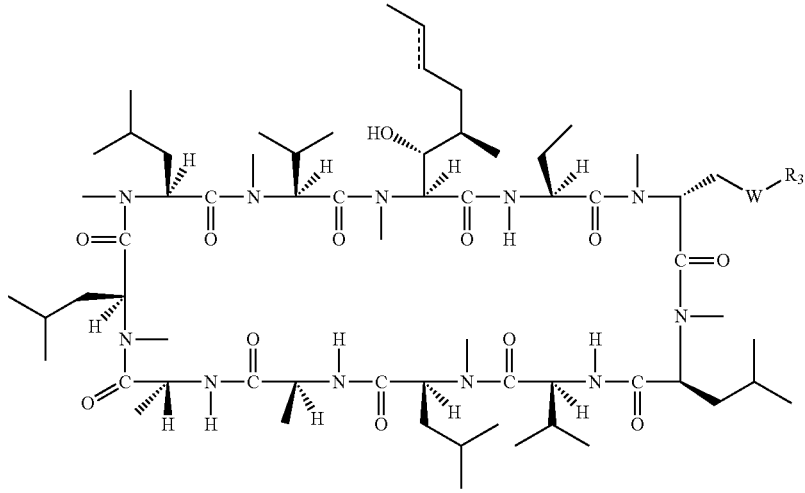

(II)

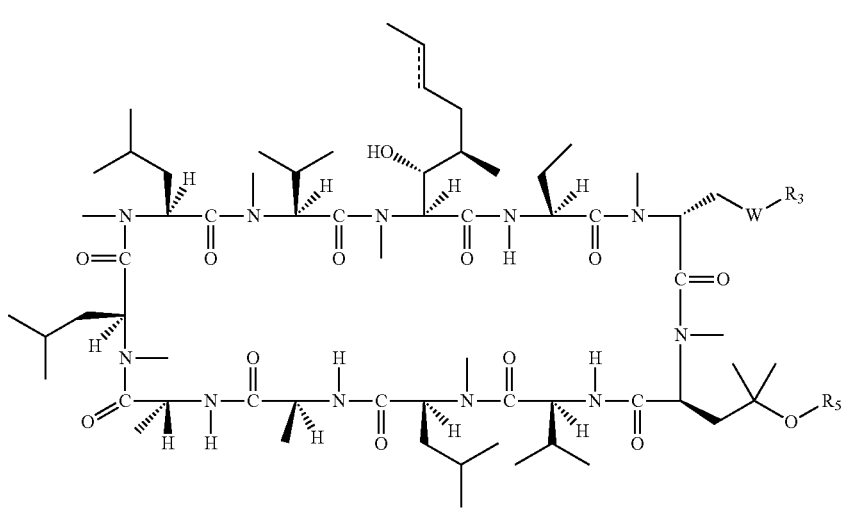

(III)

(IV)
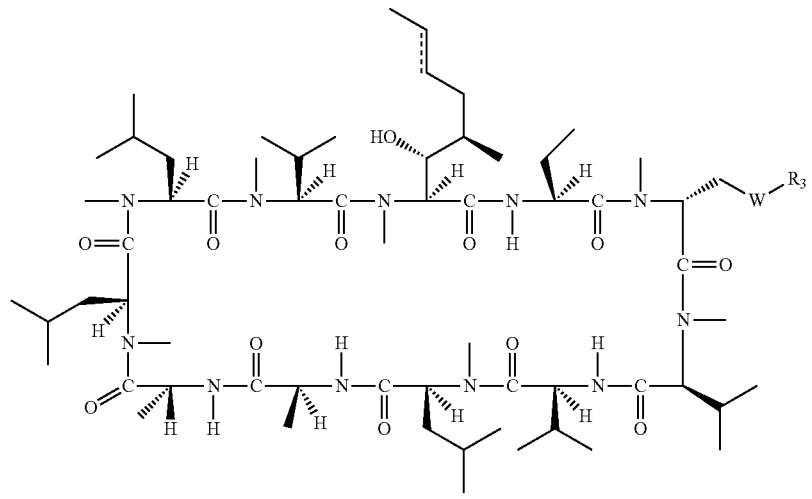
(V)
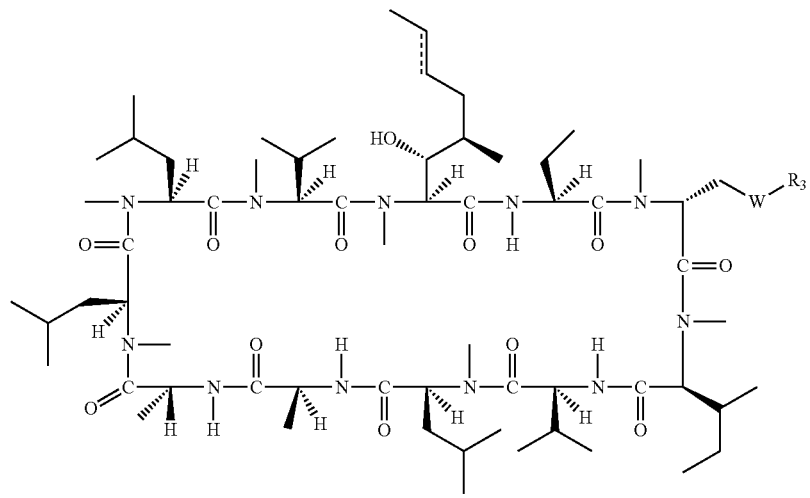
(VI)
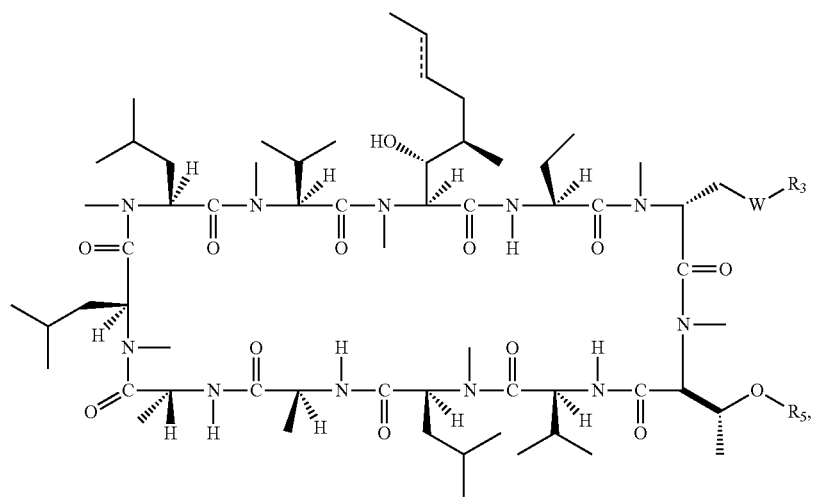
or a pharmaceutically acceptable salt thereof, wherein:
| represents a single bond or double bond;
each W is independently O, S, $CH_2$, or $NR_1$;
each $R_1$ is independently hydrogen;
$(C_1-C_6)$alkyl, optionally substituted by one or more groups $R_D$ which may be the same or different;
$(C_2-C_6)$alkenyl or $(C_2-C_6)$alkynyl;
$(C_3-C_7)$cycloalkyl optionally substituted with $(C_1-C_6)$alkyl;

phenyl optionally substituted with from one to five groups which may be the same or different selected from halogen, —O(C$_1$-C$_6$)alkyl, —C(=O)O(C$_1$-C$_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

each R$_3$ is independently

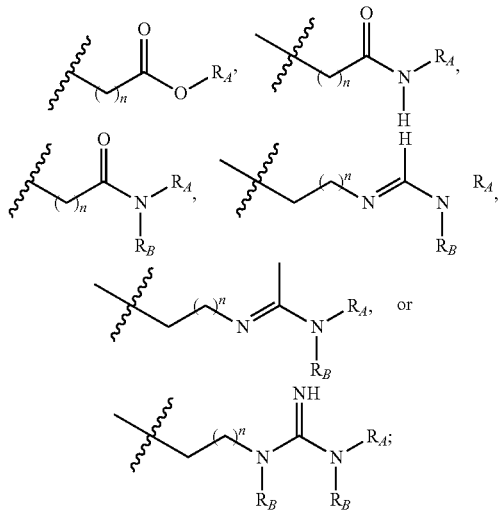

each R$_5$ is independently:

H;

(C$_1$-C$_6$)alkyl, optionally substituted by one or more groups R$_6$ which may be the same or different;

(C$_2$-C$_6$)alkenyl, optionally substituted by one or more groups which may be the same or different selected from halogen, hydroxy, (C$_1$-C$_6$)alkyl, aryl (e.g., phenyl), (CH$_2$)$_p$OR$_A$, O(CH$_2$)$_m$OH, O(CH$_2$)$_m$O(CH$_2$)$_m$OH, O(CH$_2$)$_m$NR$_A$R$_B$, O(CH$_2$)$_m$O(CH$_2$)$_m$NR$_A$R$_B$, (CH$_2$)$_p$NR$_A$R$_B$, (CH$_2$)$_p$NR$_C$(CH$_2$)$_m$NR$_A$R$_B$, (CH$_2$)$_p$NR$_C$(CH$_2$)$_m$NR$_C$(CH$_2$)$_m$NR$_A$R$_B$, (CH$_2$)$_p$C(=O)NR$_A$R$_B$, (CH$_2$)$_p$C(=O)OR$_A$;

(C$_2$-C$_6$)alkynyl, optionally substituted by one or one or more groups which may be the same or different selected from halogen, hydroxy, amino, monoalkylamino and dialkylamino;

(C$_3$-C$_7$)cycloalkyl, optionally substituted by one or more groups which may be the same or different selected from halogen, hydroxy, amino, monoalkylamino and dialkylamino;

phenyl or CH$_2$-phenyl, optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$, (CH$_2$)$_p$C(=O)OR$_A$;

each occurrence of R$_6$ is independently halogen, hydroxy, aryl (e.g., phenyl), S(C$_1$-C$_6$)alkyl, SR$_A$, OR$_A$, O(CH$_2$)$_m$OR$_A$, O(CH$_2$)$_m$O(CH$_2$)$_m$OR$_A$, C(=O)OR$_A$, C(=O)NR$_A$R$_B$, NR$_A$R$_B$, O(CH$_2$)$_m$NR$_A$R$_B$, O(CH$_2$)$_m$O(CH$_2$)$_m$NR$_A$R$_B$, NR$_C$(CH$_2$)$_m$NR$_A$R$_B$, or NR$_C$(CH$_2$)$_m$NR$_C$(CH$_2$)$_m$NR$_A$R$_B$, wherein said aryl or phenyl is optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$ and (CH$_2$)$_p$C(=O)OR$_A$;

each occurrence of R$_A$ and R$_B$ is independently:

hydrogen;

(C$_1$-C$_6$)alkyl, optionally substituted by one or more groups R$_D$ which may be the same or different;

(C$_2$-C$_6$)alkenyl or (C$_2$-C$_6$)alkynyl;

(C$_3$-C$_7$)cycloalkyl optionally substituted with (C$_1$-C$_6$)alkyl;

phenyl optionally substituted with from one to five groups which may be the same or different selected from halogen, —O(C$_1$-C$_6$)alkyl, —C(=O)O(C$_1$-C$_6$)alkyl, amino, alkylamino and dialkylamino;

or a heterocyclic ring which may be saturated or unsaturated containing five or six ring atoms and from one to three heteroatoms which may be the same or different selected from nitrogen, sulfur and oxygen;

or R$_A$ and R$_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of R$_C$ is independently hydrogen or (C$_1$-C$_6$)alkyl;

each occurrence of R$_D$ is independently halogen, hydroxy, O(C$_1$-C$_4$)alkyl, C(=O)(C$_1$-C$_4$)alkyl, C(=O)O(C$_1$-C$_4$)alkyl;

each p is independently an integer of 0, 1, 2, 3, 4, or 5; and each of m, n and q is independently an integer of 1, 2, 3, 4 or 5, or n is independently an integer of 6, 7, 8, 9, 10 or 11.

In certain embodiments, q is 1. In certain other embodiments, q is 2. In certain other embodiments, n is independently an integer of 6, 7, 8, 9, 10 or 11.

In certain embodiments, W is S. In certain other embodiments, W is O. In yet other embodiments, W is NH. In yet other embodiments, W is N—(C$_1$-C$_4$)alkyl.

In certain embodiments, R$_1$ is hydrogen. In certain other embodiments, R$_1$ is (C$_1$-C$_6$)alkyl. In certain embodiments, R$_3$ is (C$_1$-C$_6$)alkyl. In certain other embodiments, R$_3$ is NR$_C$CH$_2$(CH$_2$)$_p$NR$_A$R$_B$.

In certain embodiments, R$_1$ and R$_3$ together with the nitrogen atom to which they are attached, form a heterocycle selected from

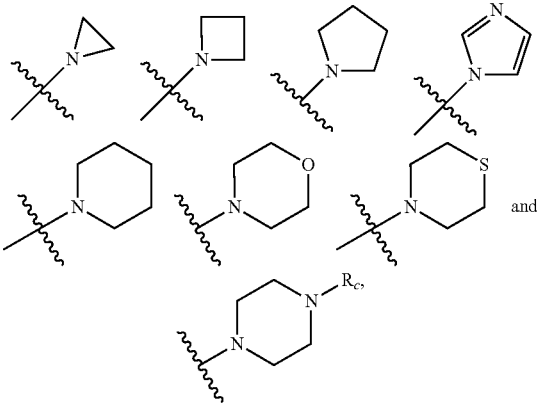

in which R$_C$ is H, Me, Et, n-Pr, i-Pr, n-Bu, i-Bu, t-Bu, CH$_2$CMe$_3$, Ph, CH$_2$Ph, CH$_2$CH$_2$OH, or CH$_2$CH$_2$O(C$_1$-C$_4$) alkyl.

In certain embodiments, $R_5$ is H, $(C_1-C_6)$alkyl, $(C_2-C_6)$alkenyl, phenyl, benzyl, $CH_2-S-(C_1-C_6)$alkyl, $CH_2-O-(C_1-C_6)$alkyl, $(C_2-C_6)OR_A$, $(C_1-C_6)$-monoalkyl amine, $(C_1-C_6)$-dialkyl amine, or $(C_1-C_6)$-cyclic amine, in which said phenyl or benzyl is optionally substituted by one to three substitutents selected from $(C_1-C_4)$alkyl, $(C_1-C_4)$ alkoxy, and halogen; and $R_A$ is H, $(C_1-C_6)$alkyl, phenyl, $CH_2$-phenyl, $(C_1-C_6)$alkylOH, $(CH_2)_pO(CH_2)_mOH$, $(CH_2)_pO(CH_2)_mO(CH_2)_mOH$, $(C_1-C_6)$alkylO$(C_1-C_4)$alkyl, $(CH_2)_pO(CH_2)_mO(C_1-C_4)$alkyl, or $(CH_2)_pO(CH_2)_mO(CH_2)_mO(C_1-C_4)$alkyl; p is an integer of 0, 1, 2, 3, 4, or 5; and m is an integer of 1, 2, 3, 4 or 5.

In certain other embodiments, $R_5$ is H, $(C_1-C_4)$alkyl, $(C_2-C_4)$alkenyl, phenyl, benzyl, $CH_2-S-(C_1-C_4)$alkyl, $CH_2-O-(C_1-C_4)$alkyl, $(CH_2)_2OH$, or $(CH_2)_2O(C_1-C_4)$ alkyl. In certain embodiments, $R_5$ is H. In certain other embodiments, $R_5$ is methyl.

In certain embodiments, each occurrence $R_A$ and $R_B$ is independently H, $(C_1-C_6)$alkyl, phenyl, $CH_2$-phenyl, $(C_1-C_6)$alkylOH, $(CH_2)_pO(CH_2)_mOH$, or $(CH_2)_pO(CH_2)_mO(CH_2)_mOH$, $(C_1-C_6)$alkylO$(C_1-C_4)$alkyl, $(CH_2)_pO(CH_2)_mO(C_1-C_4)$alkyl, or $(CH_2)_pO(CH_2)_mO(CH_2)_mO(C_1-C_4)$alkyl. In certain other embodiments, each occurrence $R_A$ and $R_B$ is independently H or $(C_1-C_6)$alkyl. In yet other embodiments, $R_A$ and $R_B$, together with the nitrogen atom to which they are attached, form a heterocycle selected from

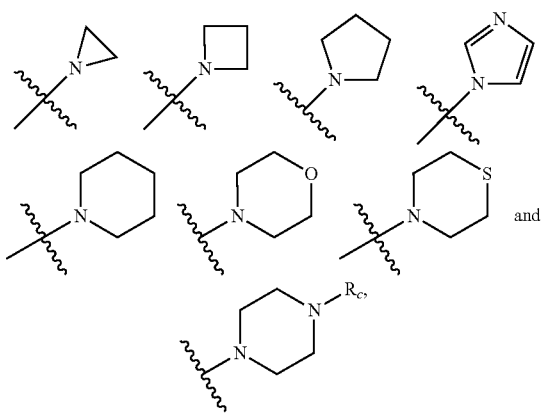

in which $R_C$ is H, Me, Et, n-Pr, i-Pr, n-Bu, i-Bu, t-Bu, $CH_2CMe_3$, Ph, $CH_2Ph$, or $CH_2CH_2OH$ and $CH_2CH_2OR_d$.

In one aspect, the present invention provides a compound selected from the following:

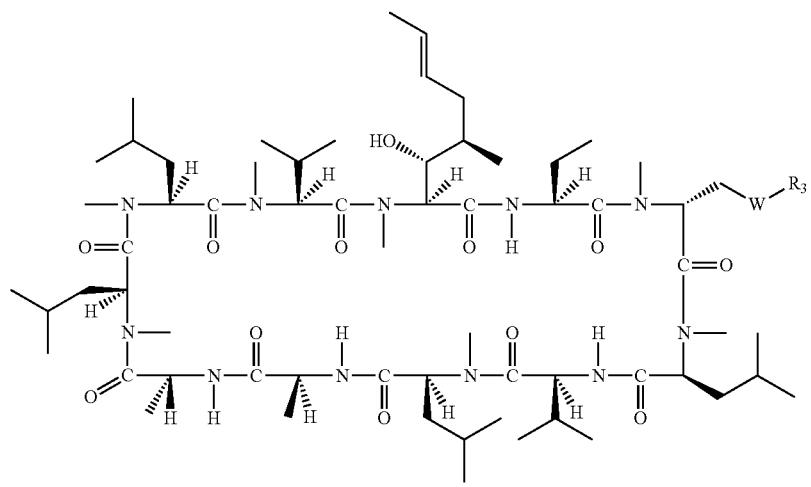

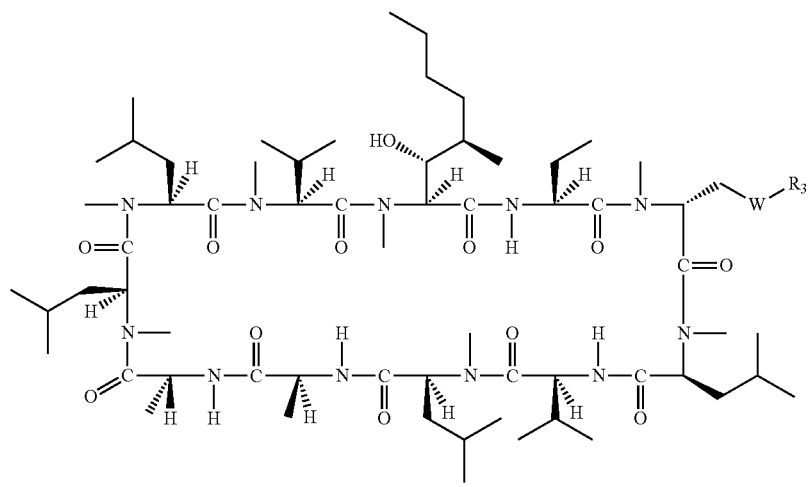

W = O, S, N—H, and N—$R_a$
$R_3$ = H, Me, Et, n-Pr, i-Pr, n-Bu, i-Bu, t-Bu, $CH_2CMe_3$, Ph, $CH_2Ph$ -continued
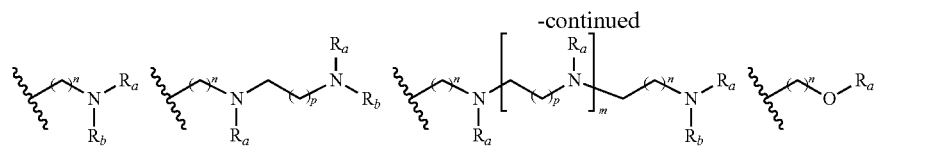
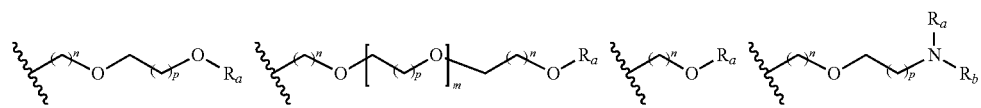
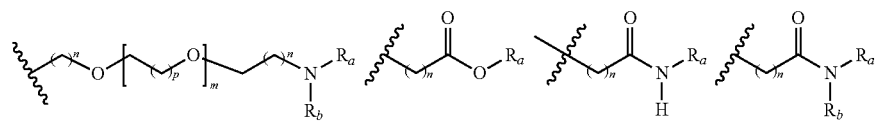
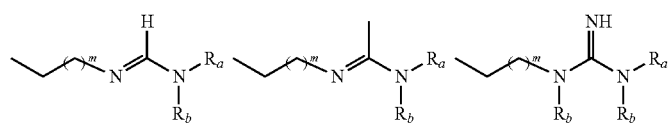
n = 2, 3, 4, 5, 6    n = 7, 8, 9, 10, 11, or 12,
m = 1, 2, 3, 4, 5, 6;  or  m = 7, 8, 9, 10, 11, or 12,
p = 1, 2, 3, 4, 5, 6    p = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
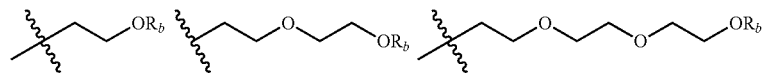
$R_b$ = H, Me, Et, n-Pr, i-Pr, n-Bu, i-Bu, t-Bu, $CH_2CMe_3$, Ph, $CH_2Ph$
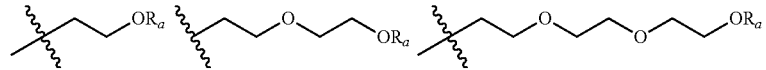
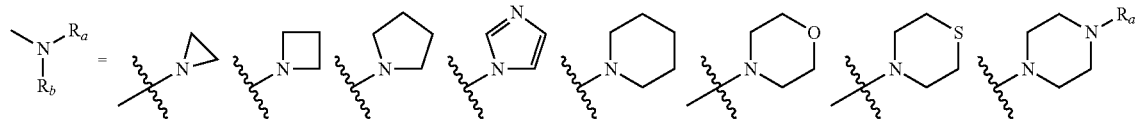
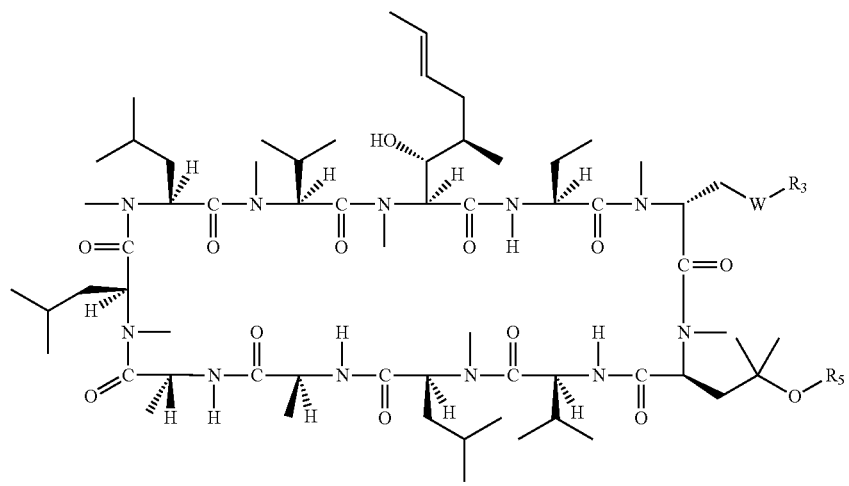

-continued
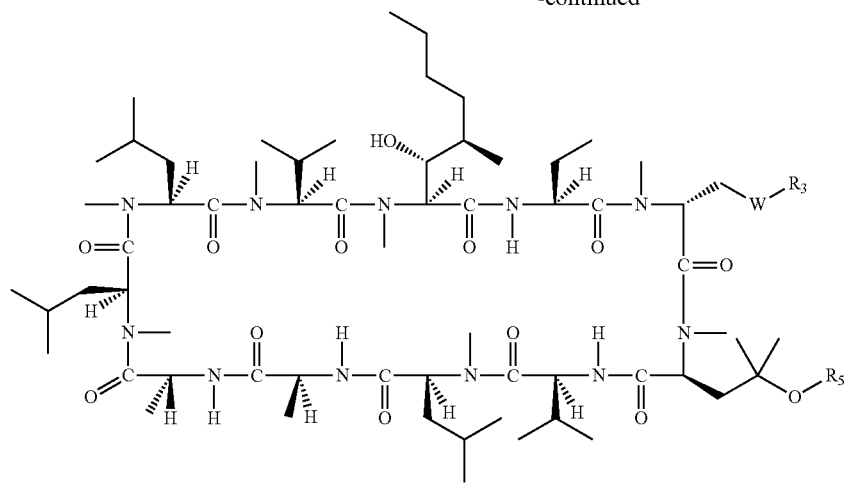
W = O, S, N—H, and N—R$_a$
R$_3$ = H, Me, Et, n-Pr, i-Pr, n-Bu, i-Bu, t-Bu, CH$_2$CMe$_3$, Ph, CH$_2$Ph
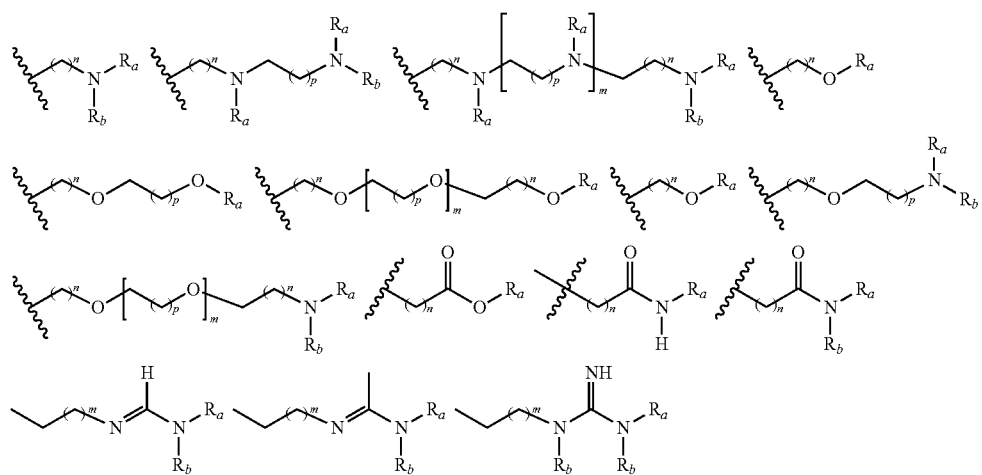
n = 2, 3, 4, 5, 6    n = 7, 8, 9, 10, 11, or 12,
m = 1, 2, 3, 4, 5, 6   or   m = 7, 8, 9, 10, 11, or 12,
p = 1, 2, 3, 4, 5, 6    p = 7, 8, 9, 10, 11, or 12
R$_a$ = H, Me, Et, n-Pr, i-Pr, n-Bu, i-Bu, t-Bu, CH$_2$CMe$_3$, Ph, CH$_2$Ph
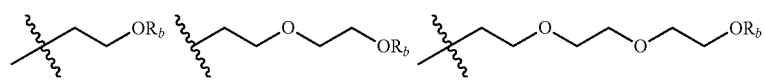
R$_b$ = H, Me, Et, n-Pr, i-Pr, n-Bu, i-Bu, t-Bu, CH$_2$CMe$_3$, Ph, CH$_2$Ph
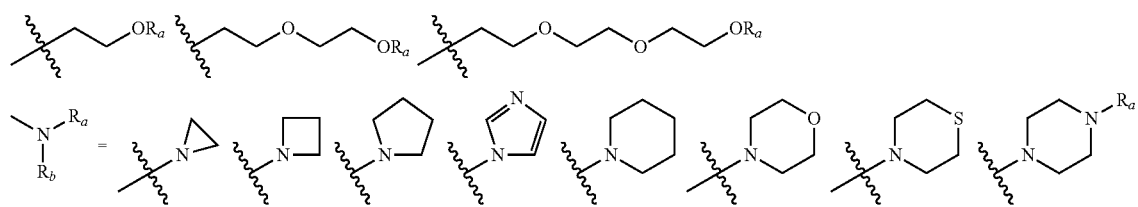
R$_5$ = H, Me, Et, n-Pr, i-Pr, n-Bu, i-Bu, t-Bu, CH$_2$CMe$_3$, Ph, CH$_2$Ph
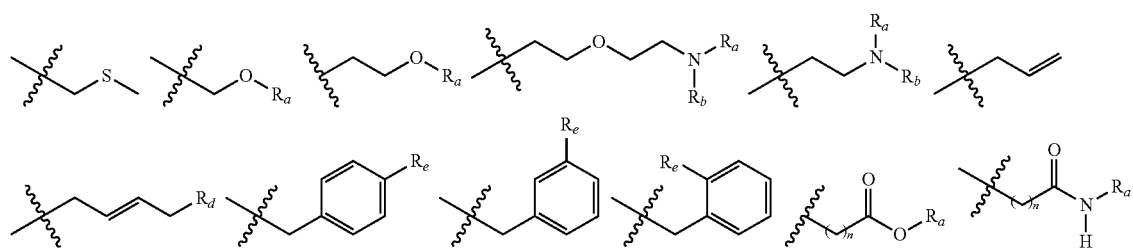

-continued
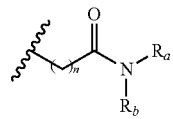
$R_d$ = $R_a$, $OR_a$, $R_3$
$R_e$ = H, Me, Et, $OR_a$, $R_3$, $CH_2OR_a$, $CH_2CH_2OR_a$
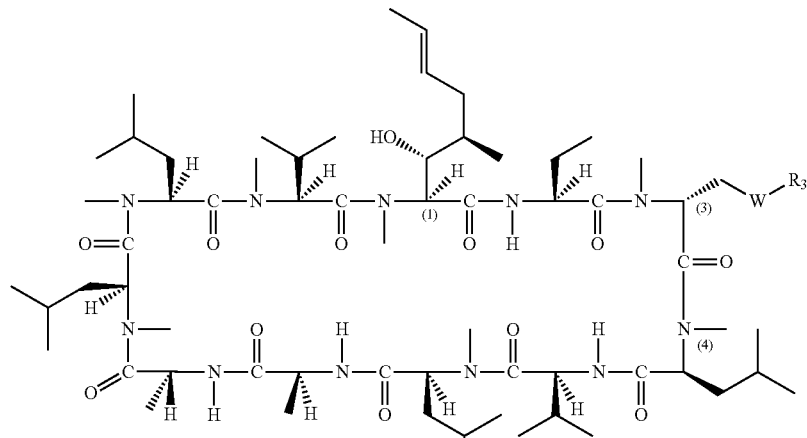
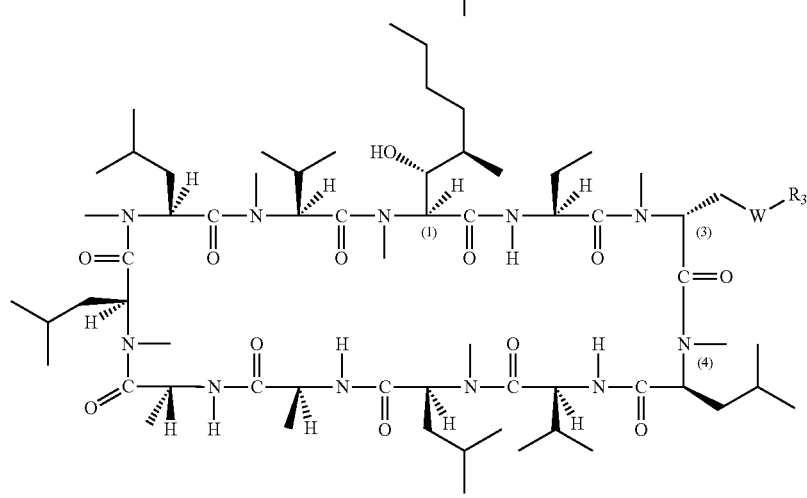
W = O, S, N—H, and N—$R_a$
$R_a$ = H, Me, Et, n-Pr, i-Pr, n-Bu, i-Bu, t-Bu, $CH_2CMe_3$, Ph, $CH_2Ph$
$R_b$ = H, Me, Et, n-Pr, i-Pr, n-Bu, i-Bu, t-Bu, $CH_2CMe_3$, Ph, $CH_2Ph$
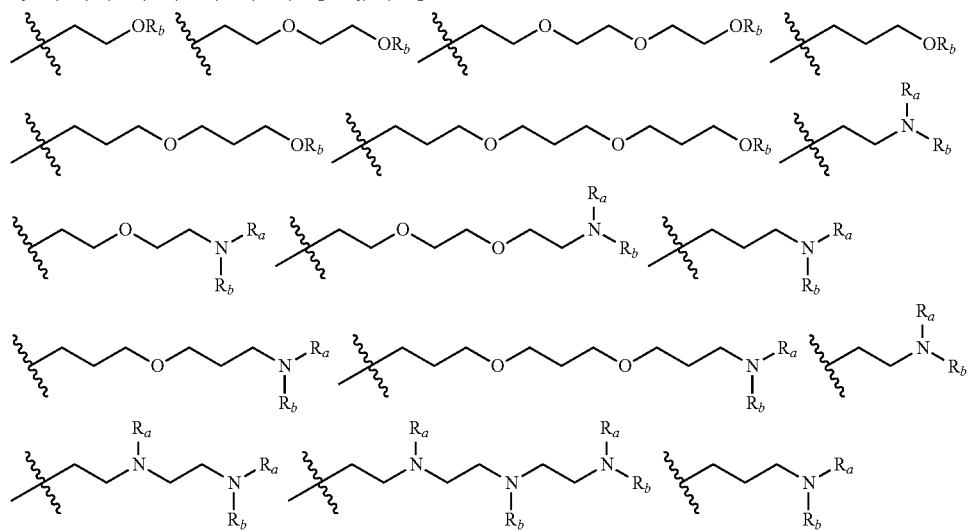

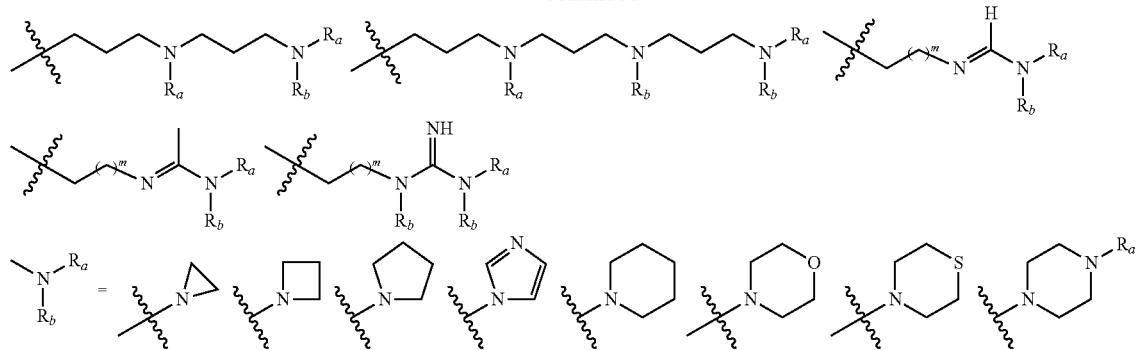
m = 1, 2, 3, 4, 5, 6
or m = 7, 8, 9, 10, 11, or 12
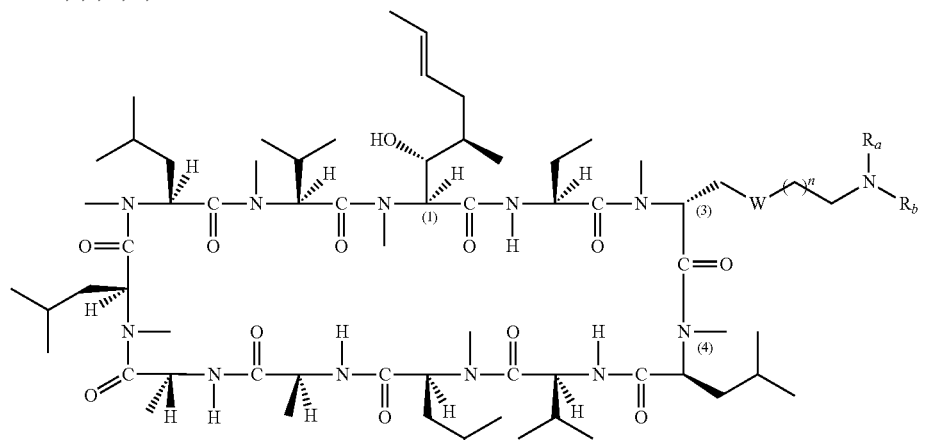
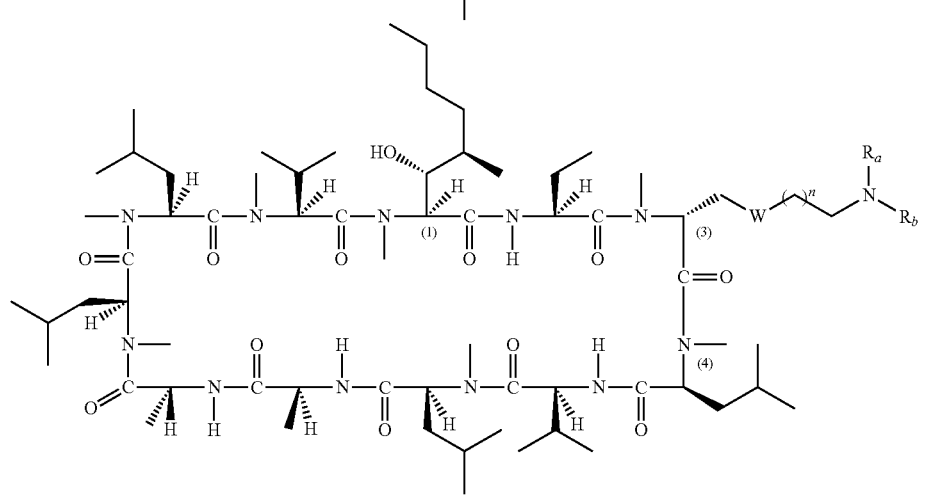
W = O, S, N—H, and N—R$_a$
n = 1, 2, 3, 4, 5, 6 or n = 7, 8, 9, 10, 11, or 12
R$_a$ = H, Me, Et, n-Pr, i-Pr, n-Bu, i-Bu, t-Bu, CH$_2$CMe$_3$, Ph, CH$_2$Ph
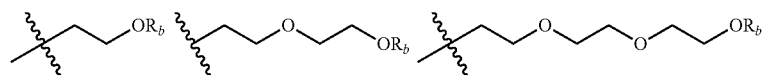
R$_b$ = H, Me, Et, n-Pr, i-Pr, n-Bu, i-Bu, t-Bu, CH$_2$CMe$_3$, Ph, CH$_2$Ph
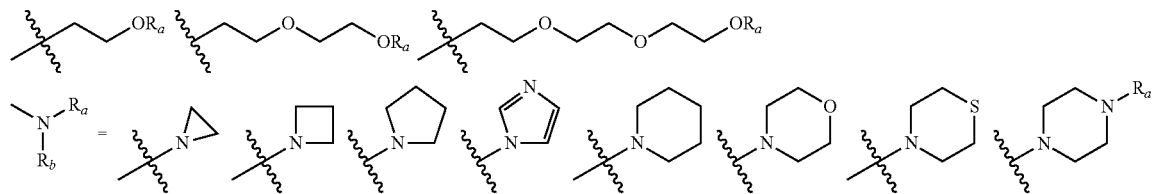

-continued
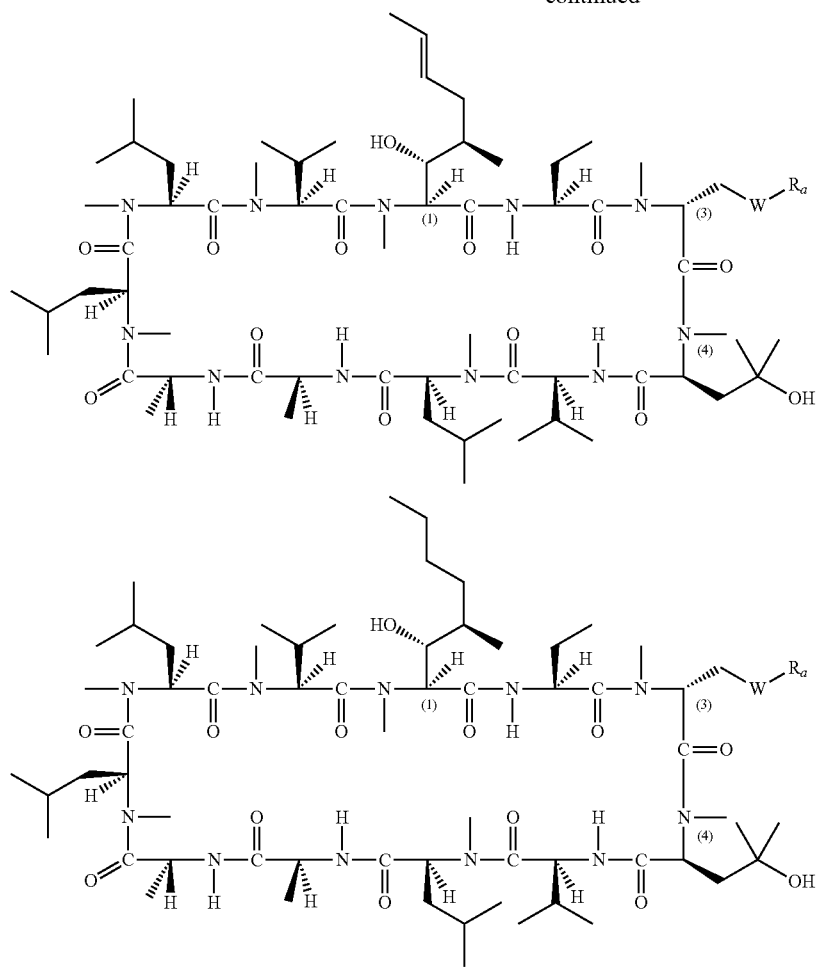
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
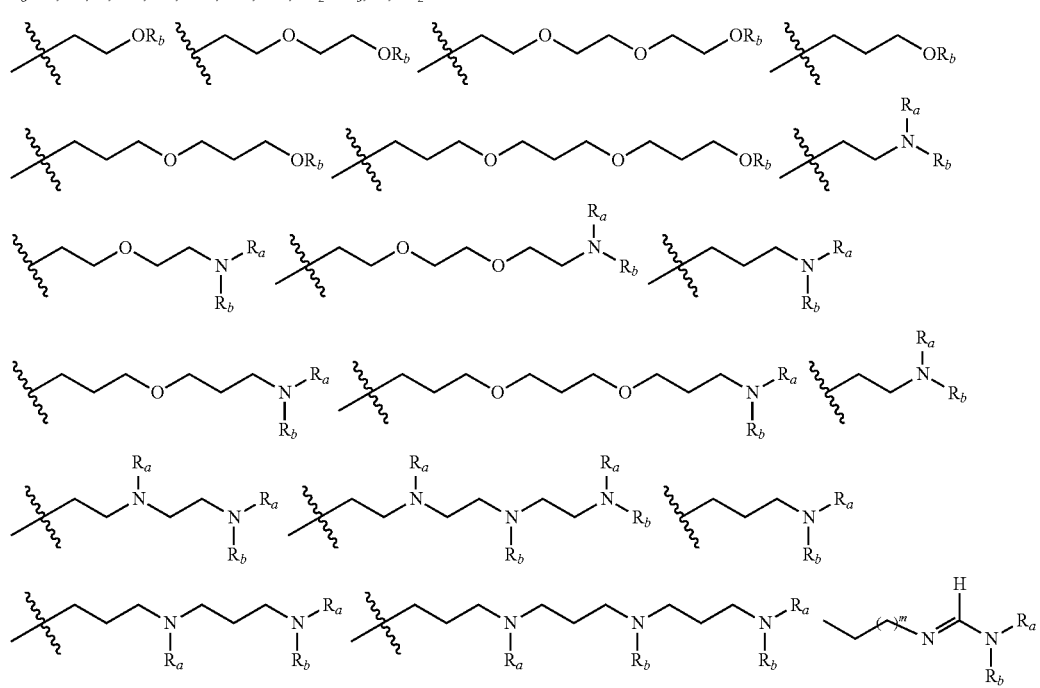

-continued
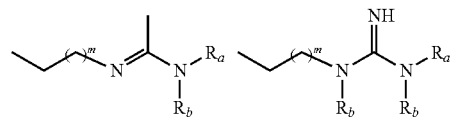
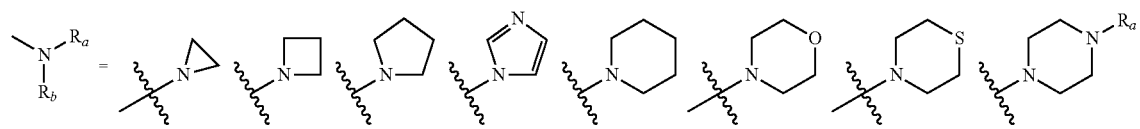
m = 1, 2, 3, 4, 5, 6
or m = 7, 8, 9, 10, 11, or 12
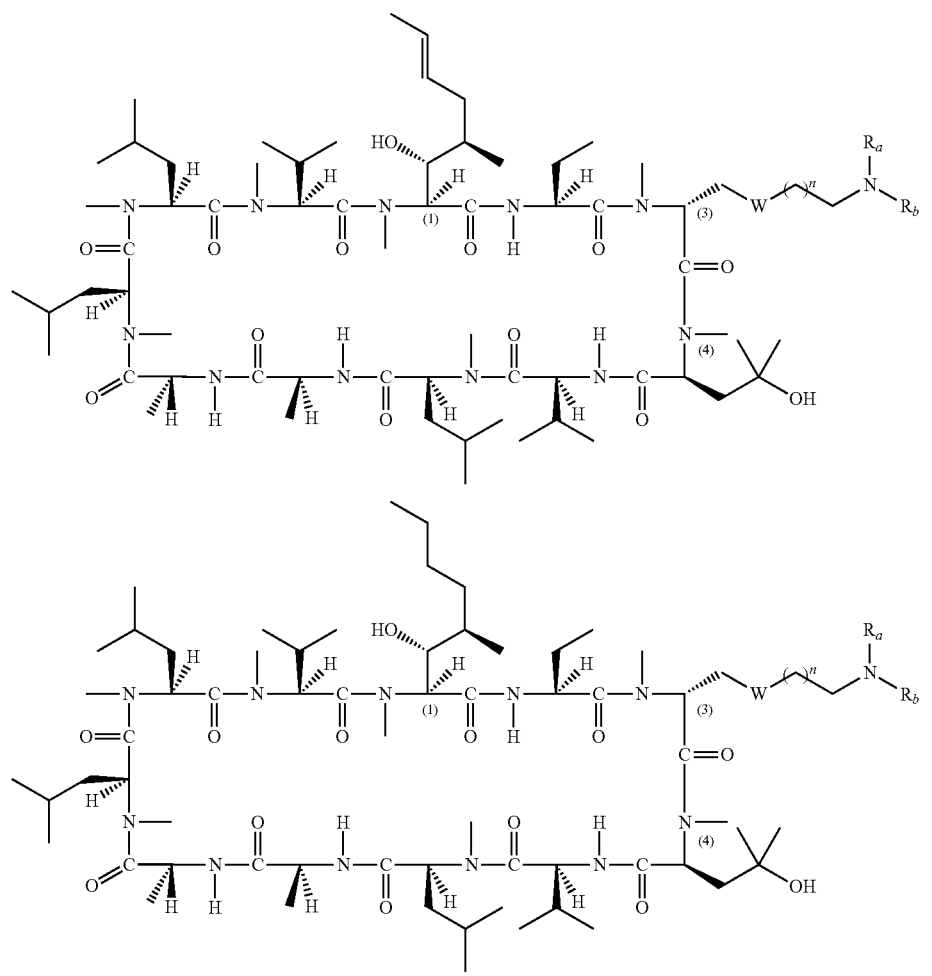
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
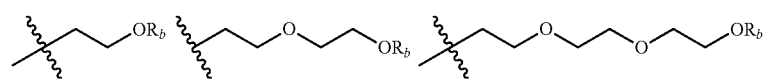
$R_b$ = H, Me, Et, n-Pr, i-Pr, n-Bu, i-Bu, t-Bu, $CH_2CMe_3$, Ph, $CH_2Ph$
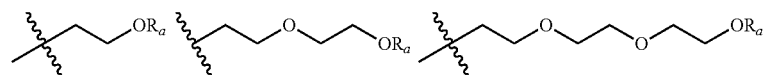
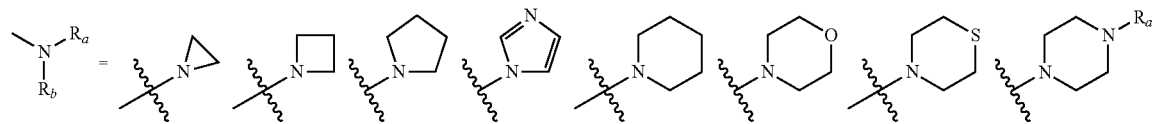

-continued
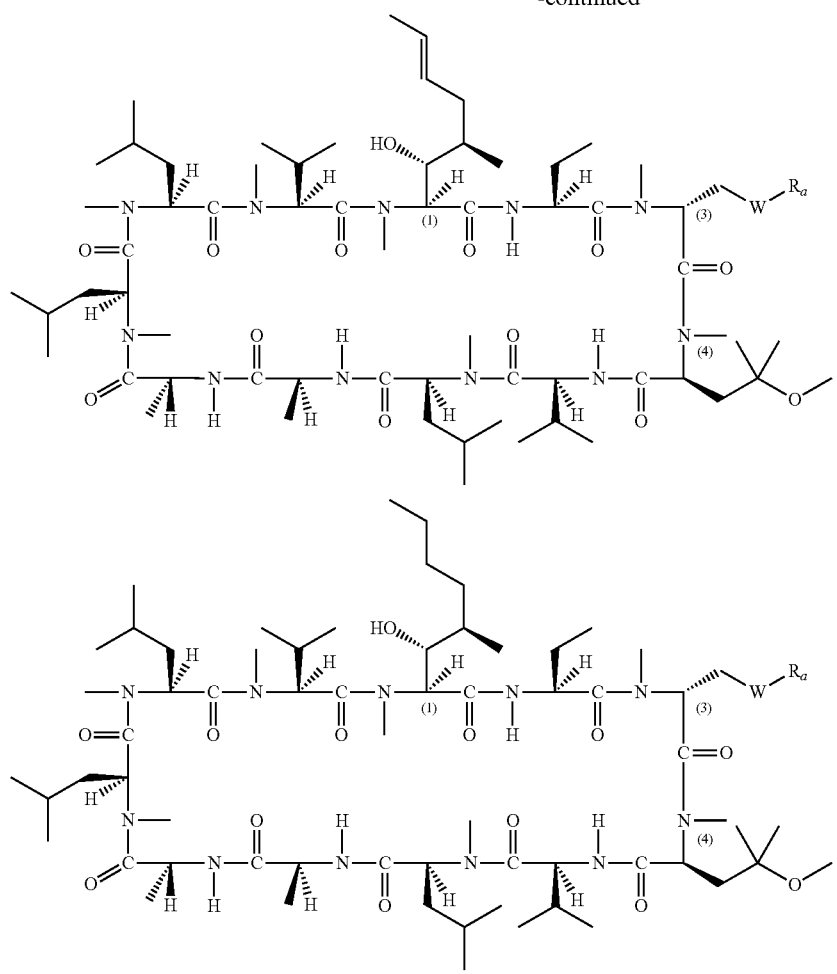
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
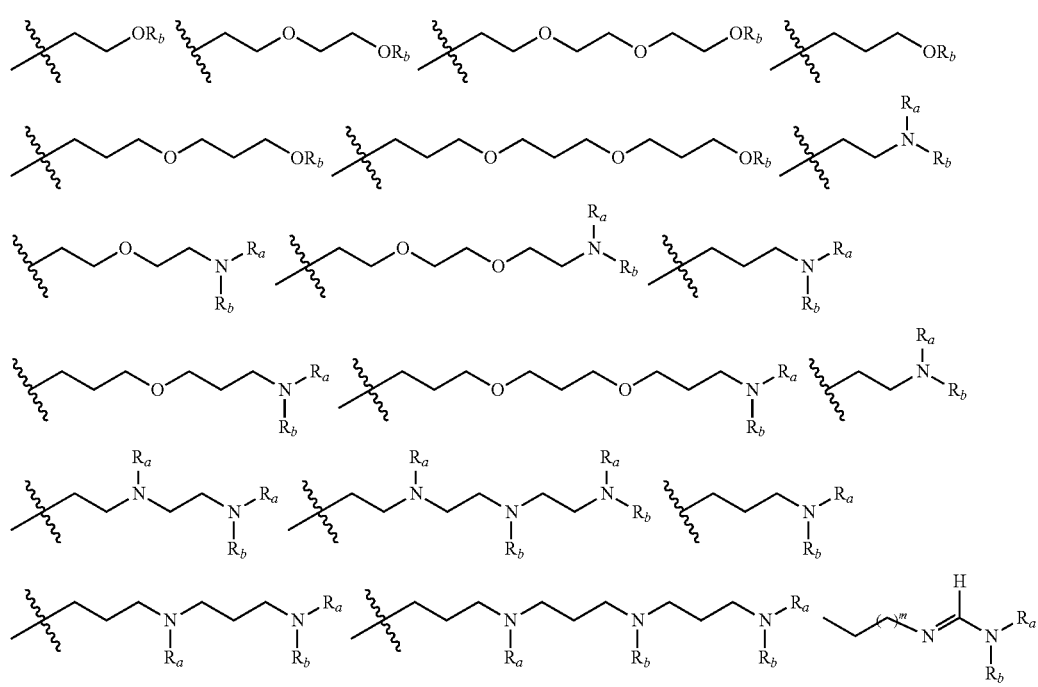

-continued
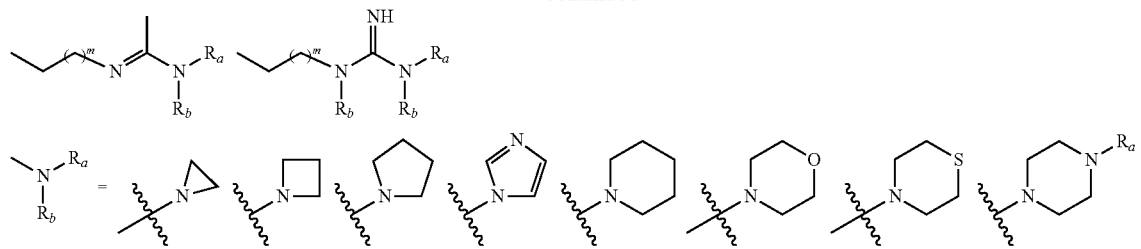
m = 1, 2, 3, 4, 5, 6
or m = 7, 8, 9, 10, 11, or 12
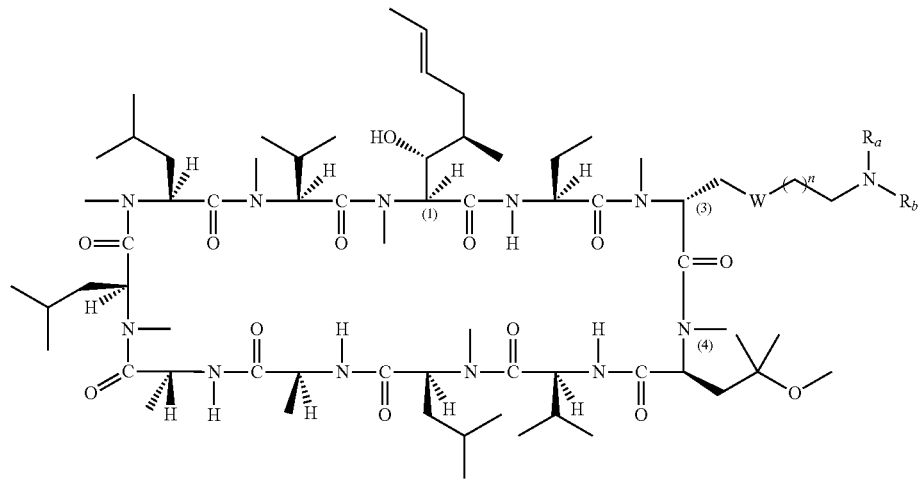
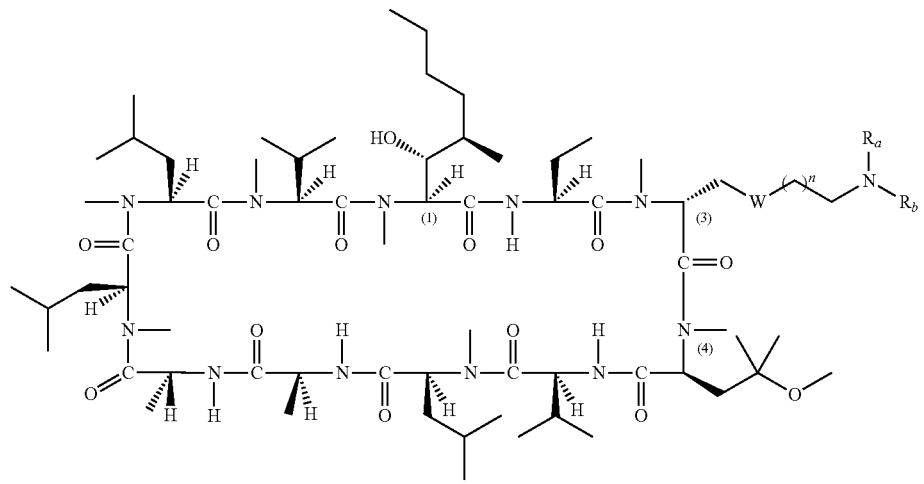
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
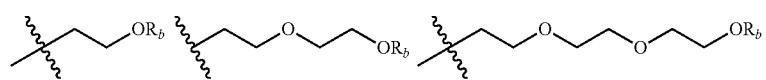
$R_b$ = H, Me, Et, n-Pr, i-Pr, n-Bu, i-Bu, t-Bu, $CH_2CMe_3$, Ph, $CH_2Ph$
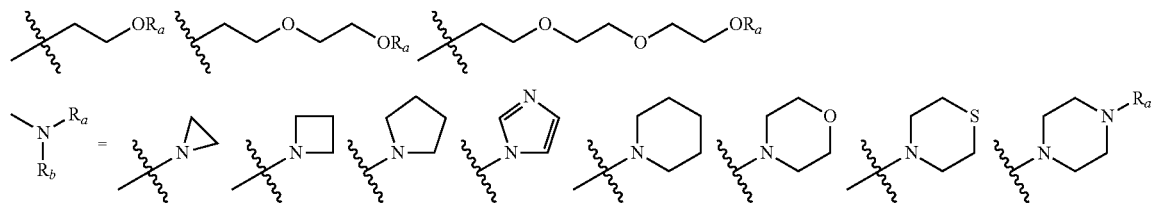

-continued
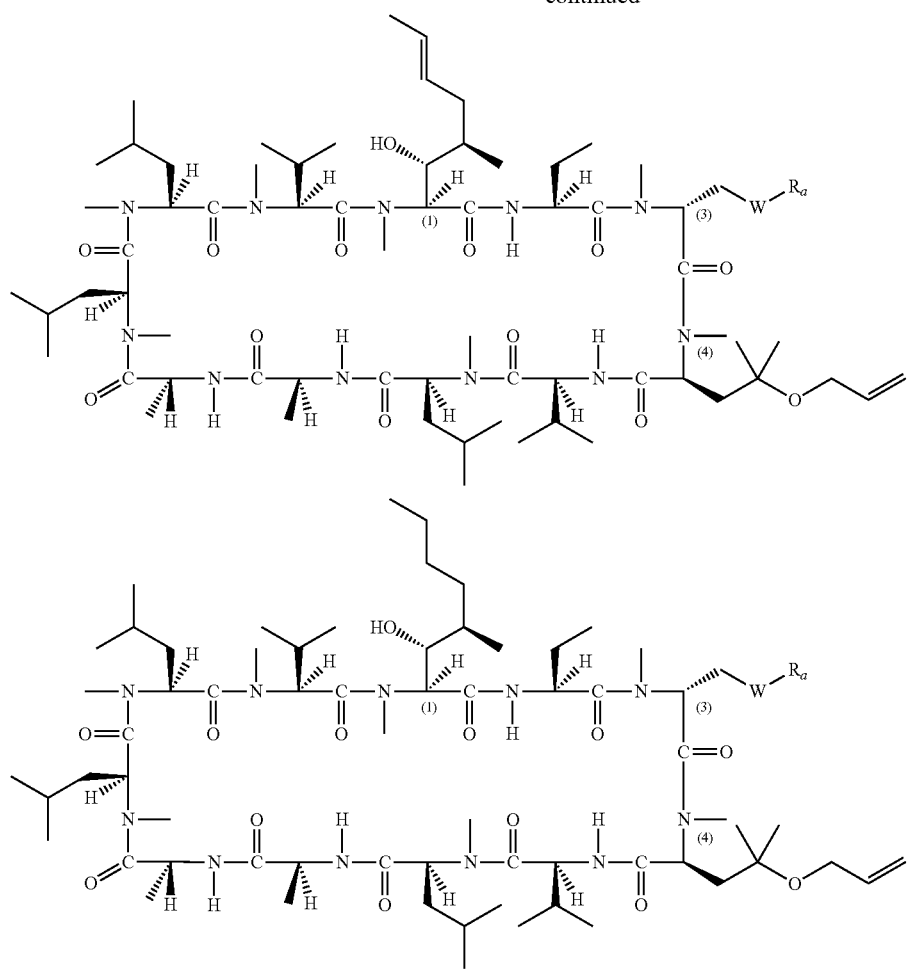
W = O, S, N—H, and N—$R_a$
$R_a$ = H, Me, Et, n-Pr, i-Pr, n-Bu, i-Bu, t-Bu, CH$_2$CMe$_3$, Ph, CH$_2$Ph
$R_b$ = H, Me, Et, n-Pr, i-Pr, n-Bu, i-Bu, t-Bu, CH$_2$CMe$_3$, Ph, CH$_2$Ph
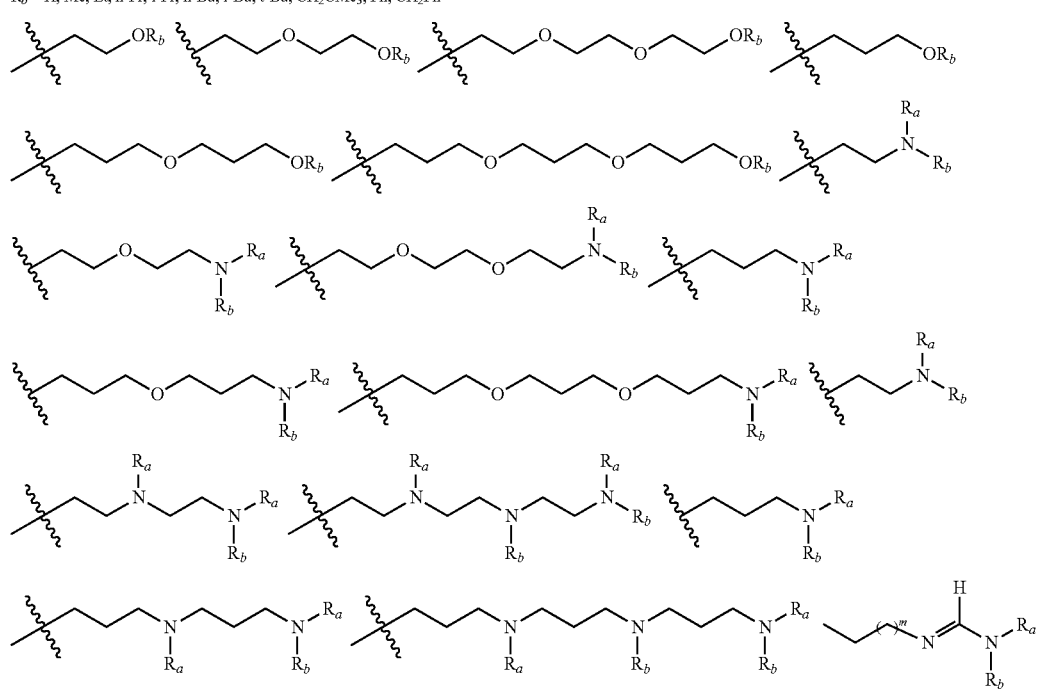

-continued
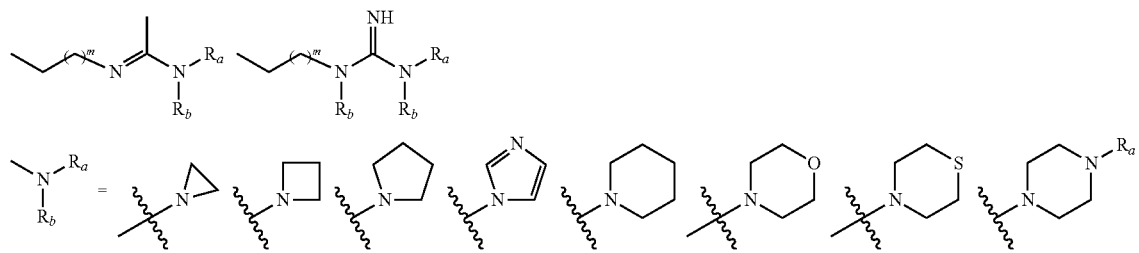
m = 1, 2, 3, 4, 5, 6
or m = 7, 8, 9, 10, 11, or 12
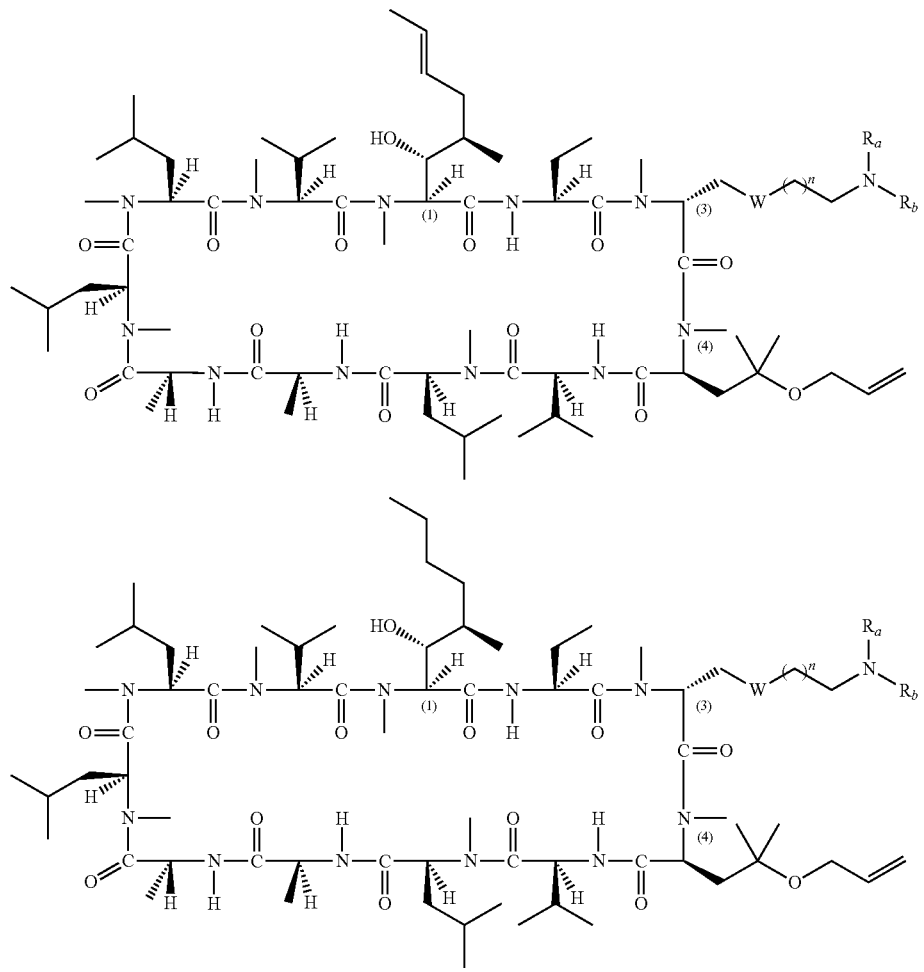
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, CH$_2$CMe$_3$, Ph, CH$_2$Ph
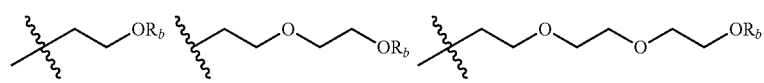
$R_b$ = H, Me, Et, n-Pr, i-Pr, n-Bu, i-Bu, t-Bu, CH$_2$CMe$_3$, Ph, CH$_2$Ph
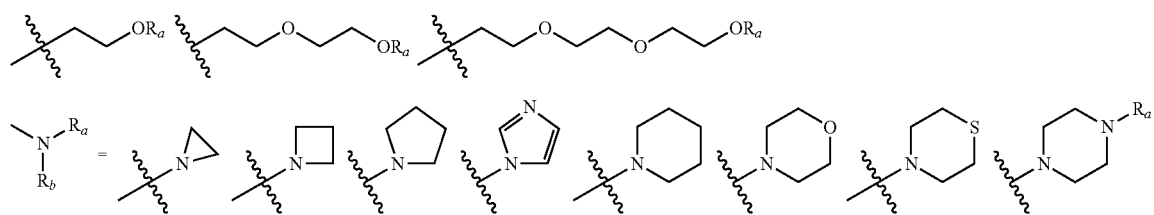

-continued
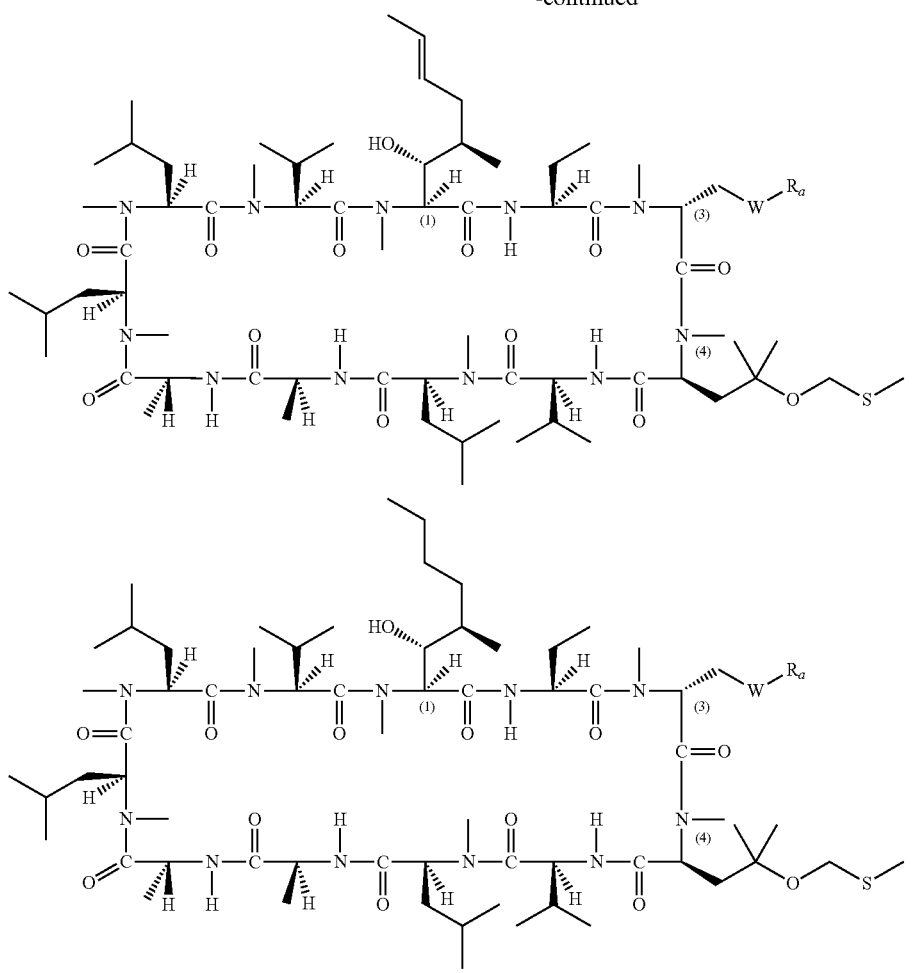
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
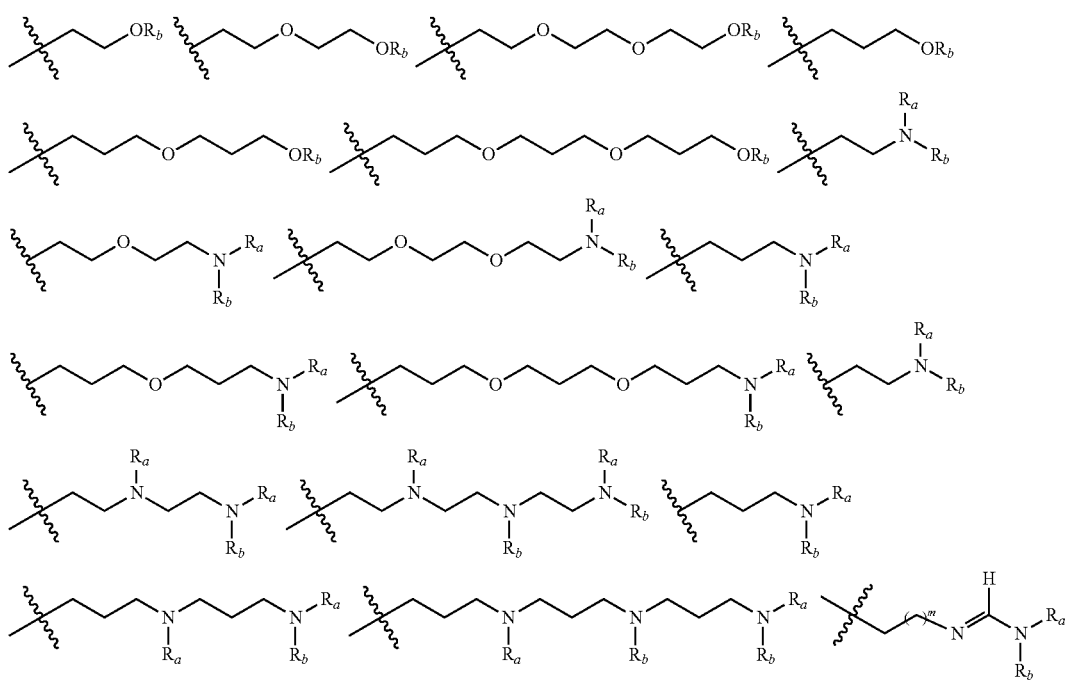

-continued
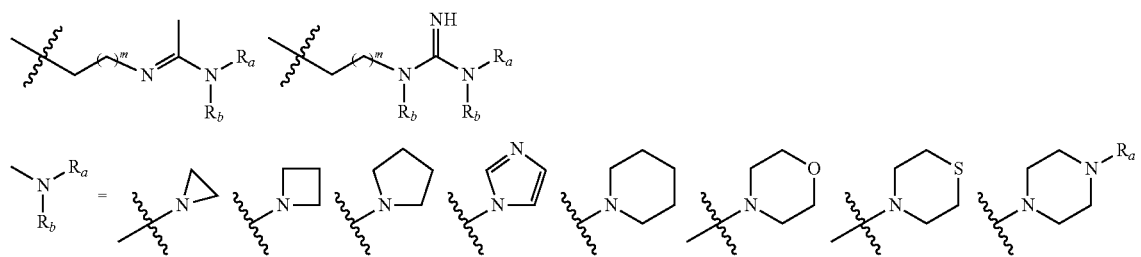
m = 1, 2, 3, 4, 5, 6
or m = 7, 8, 9, 10, 11, or 12
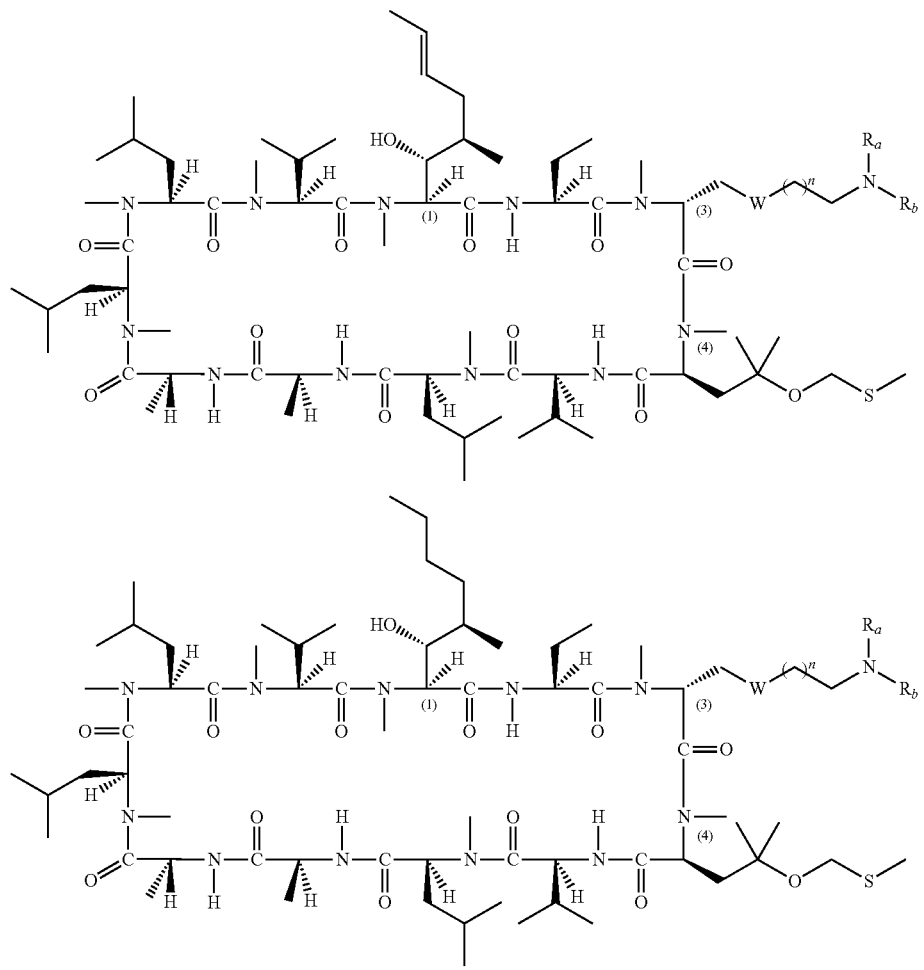
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
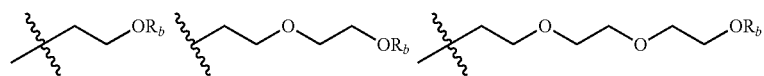
$R_b$ = H, Me, Et, n-Pr, i-Pr, n-Bu, i-Bu, t-Bu, $CH_2CMe_3$, Ph, $CH_2Ph$
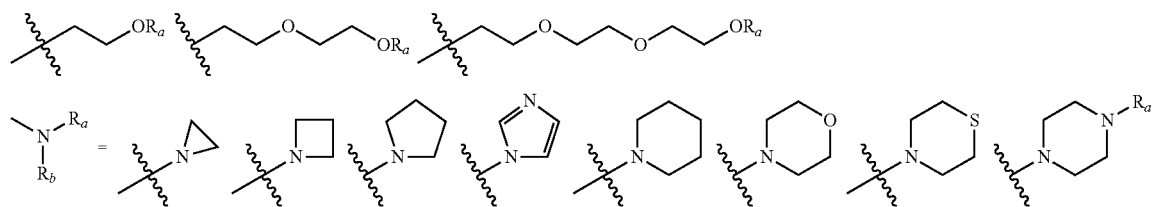

-continued
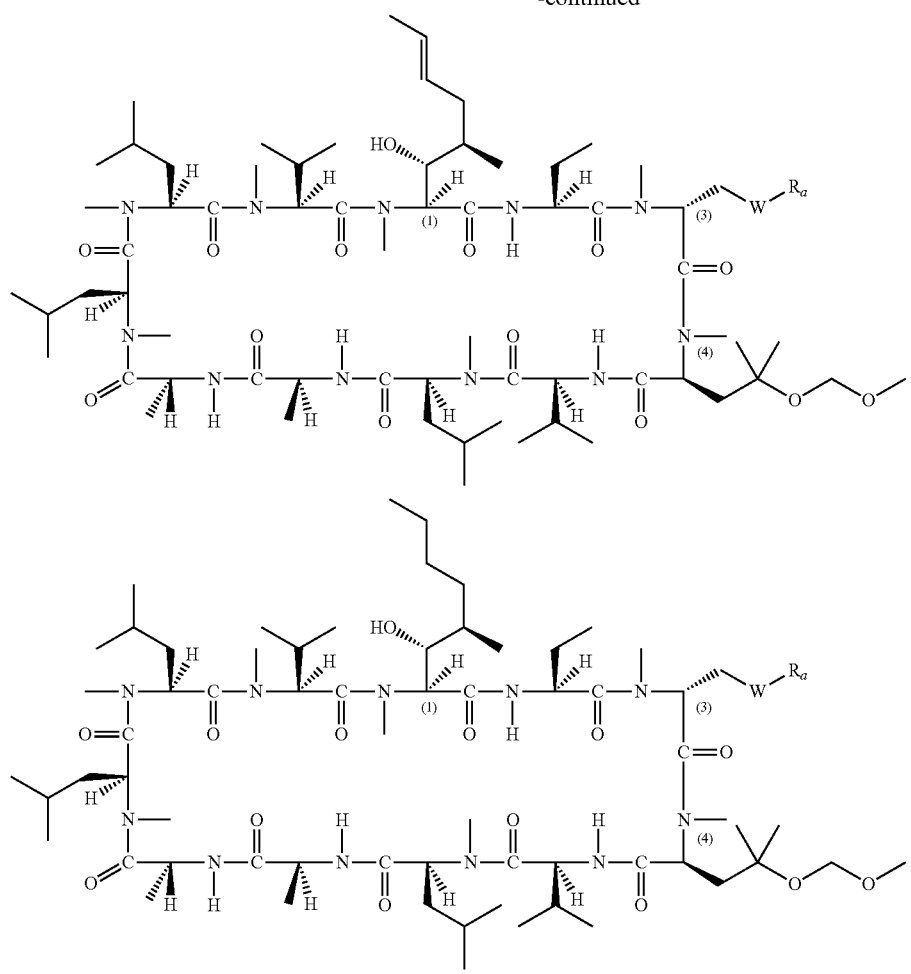
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
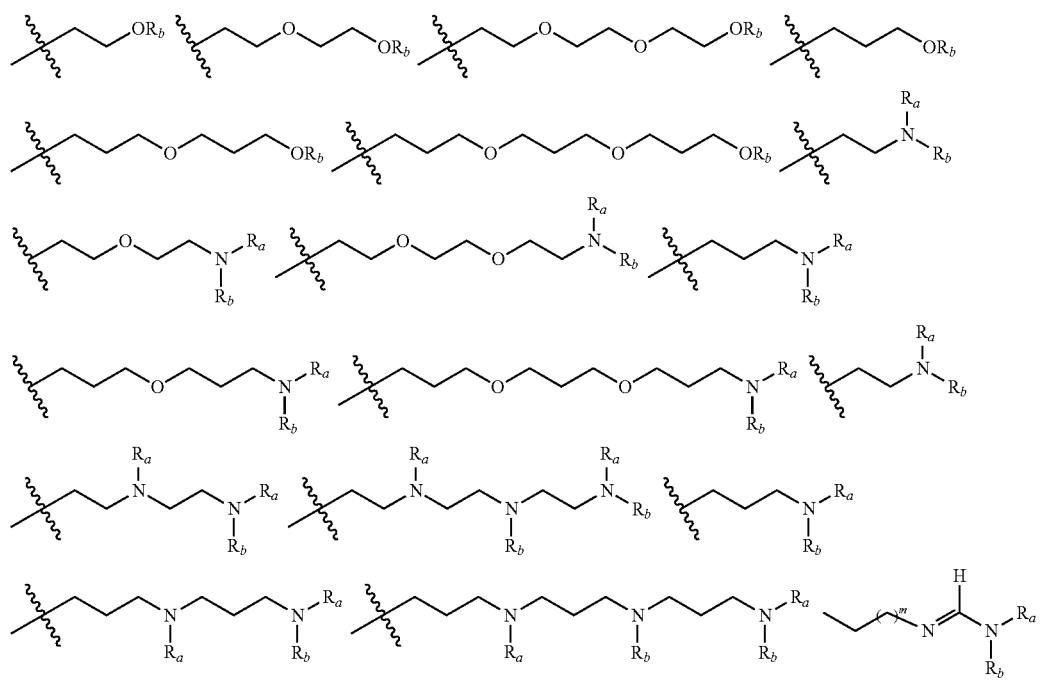

-continued
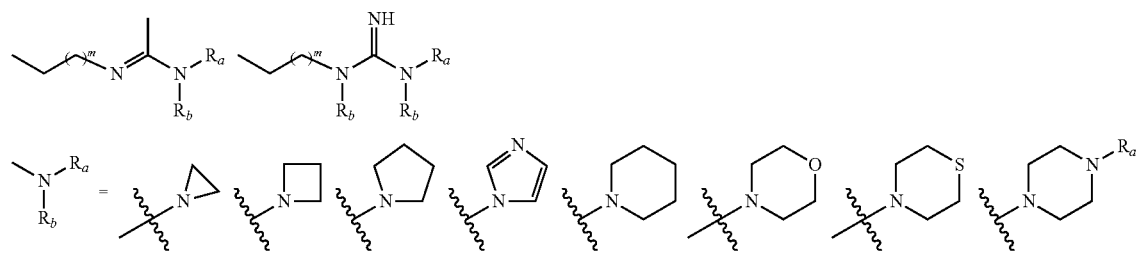
m = 1, 2, 3, 4, 5, 6
or m = 7, 8, 9, 10, 11, or 12
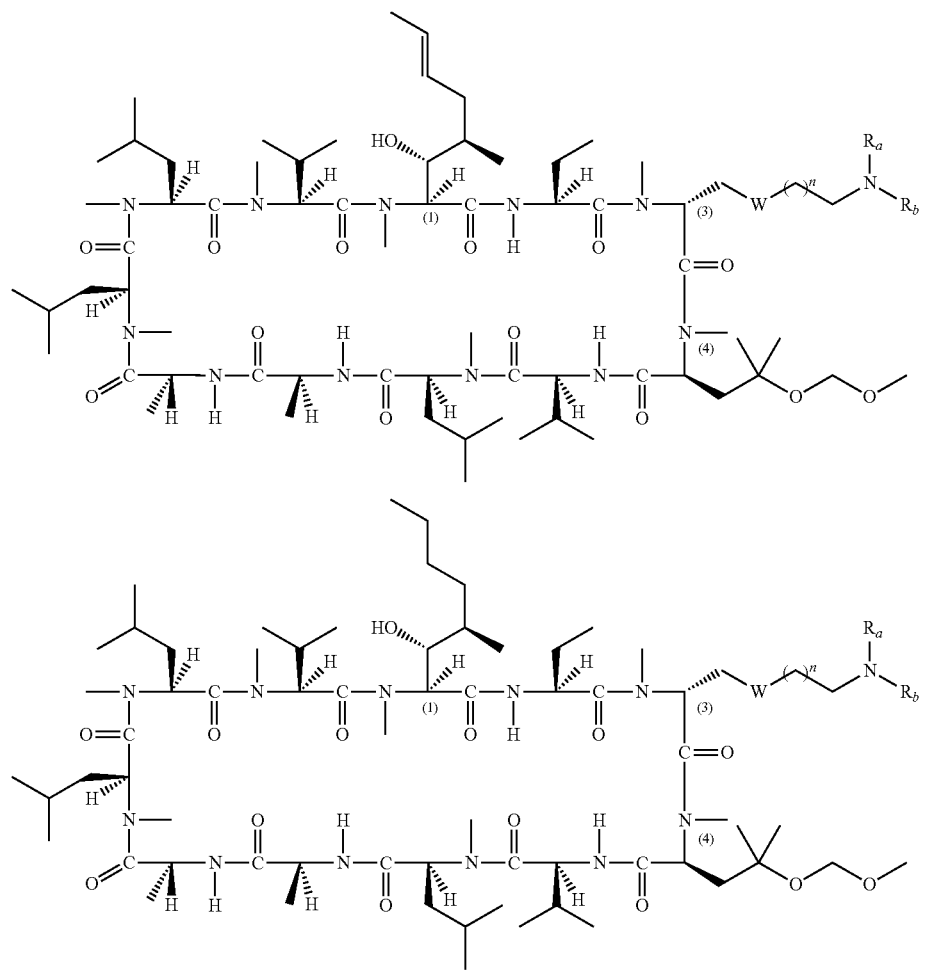
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
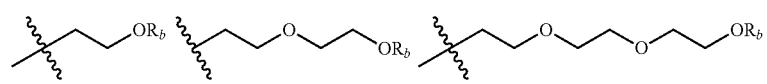
$R_b$ = H, Me, Et, n-Pr, i-Pr, n-Bu, i-Bu, t-Bu, $CH_2CMe_3$, Ph, $CH_2Ph$
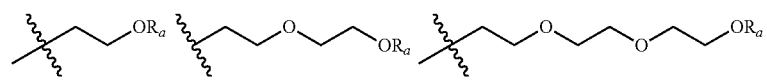
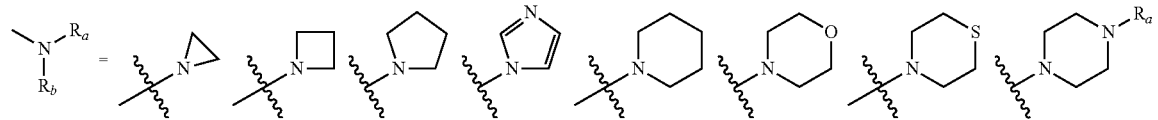

-continued
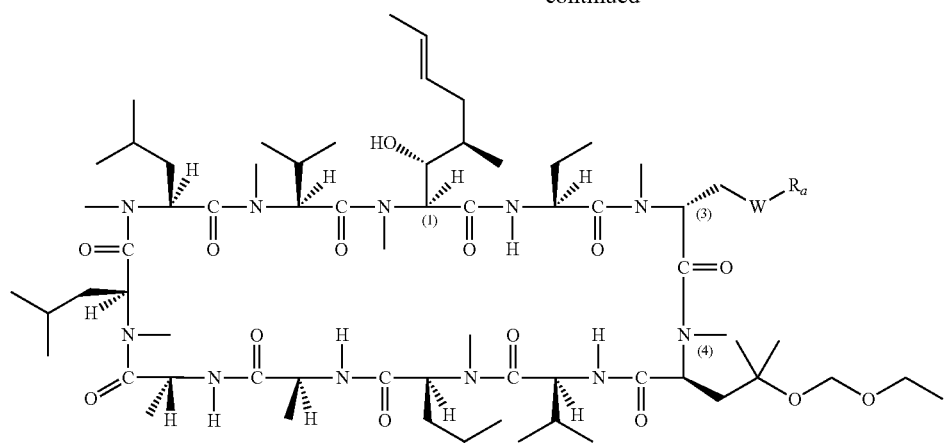
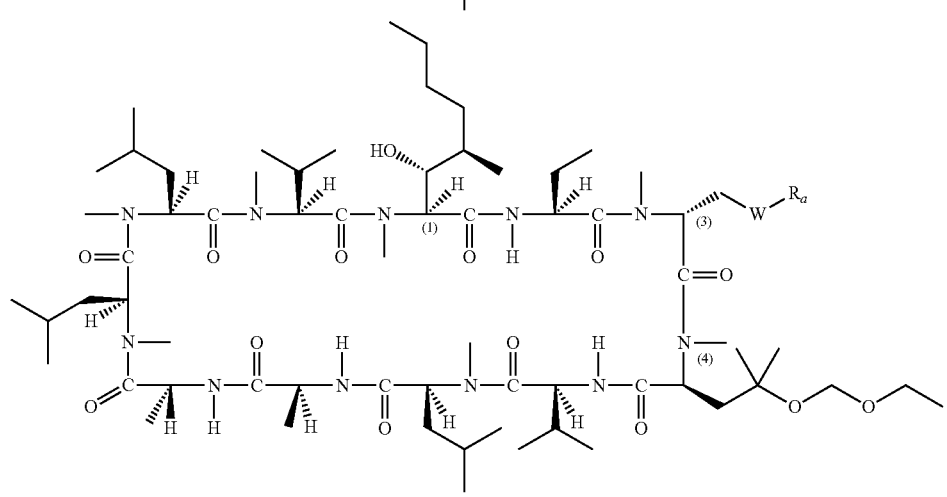
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
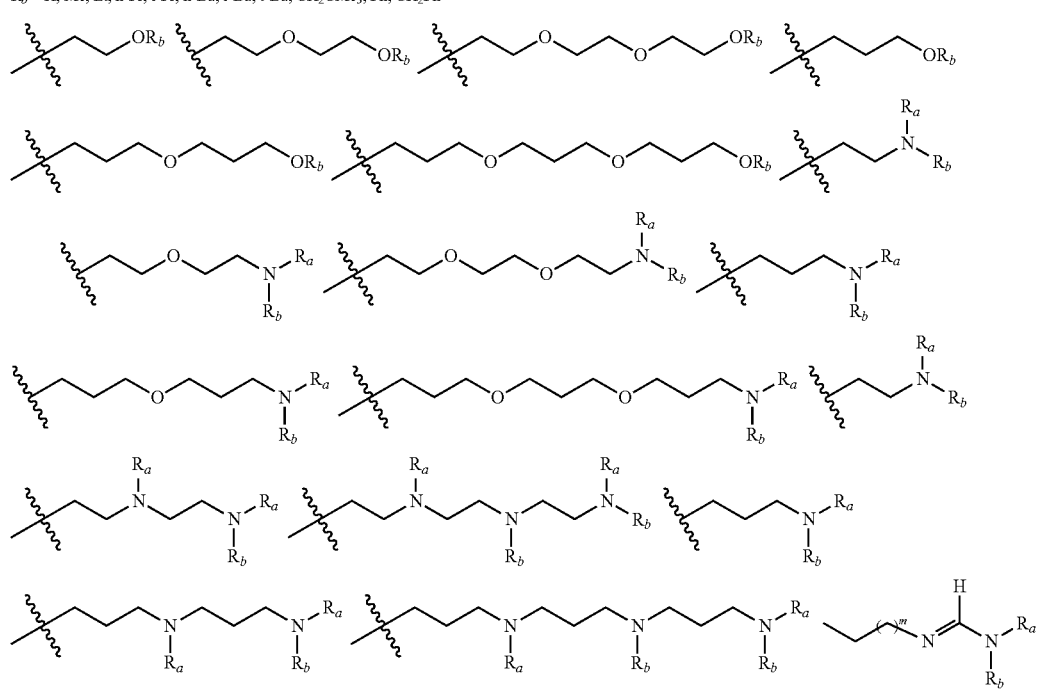

-continued
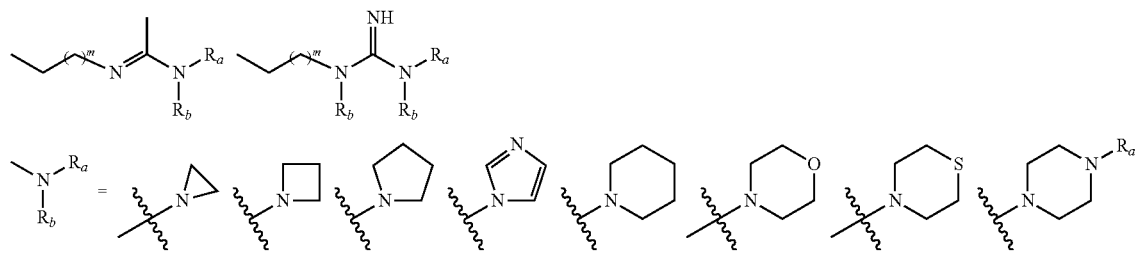
m = 1, 2, 3, 4, 5, 6
or m = 7, 8, 9, 10, 11, or 12
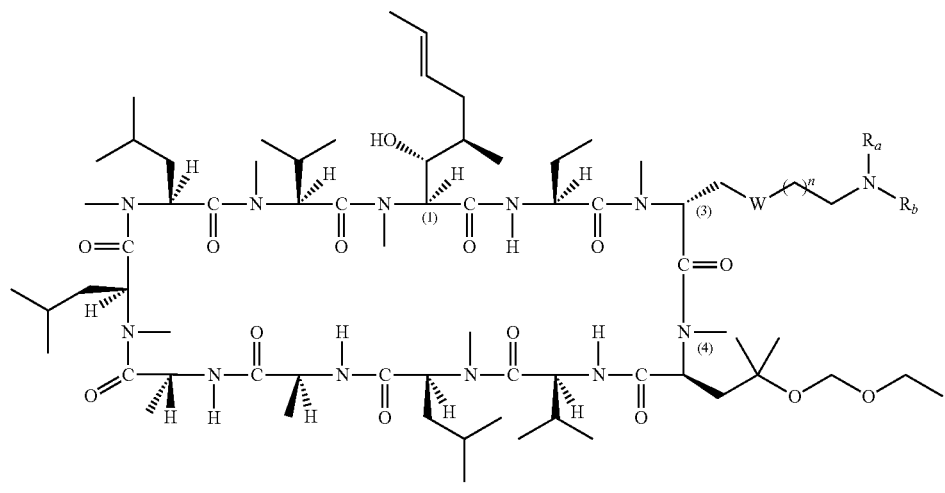
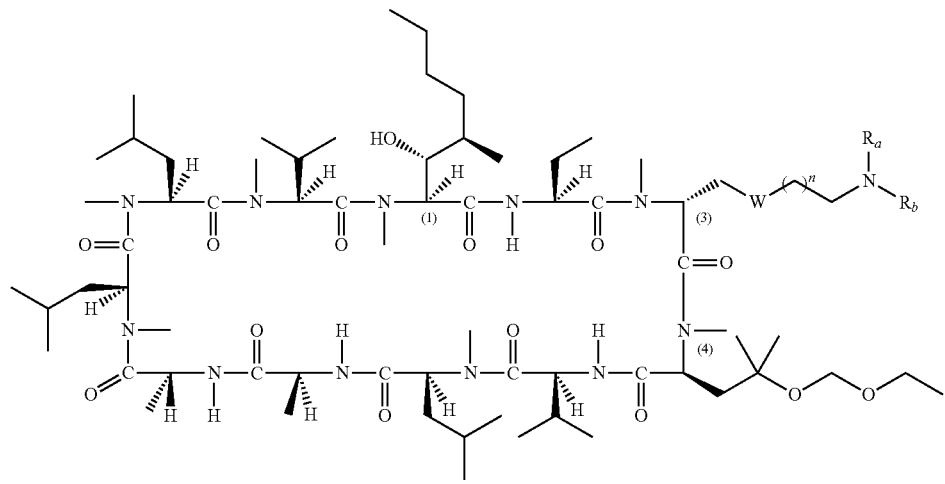
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, CH$_2$CMe$_3$, Ph, CH$_2$Ph
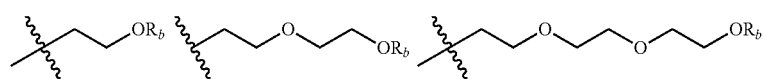
$R_b$ = H, Me, Et, n-Pr, i-Pr, n-Bu, i-Bu, t-Bu, CH$_2$CMe$_3$, Ph, CH$_2$Ph
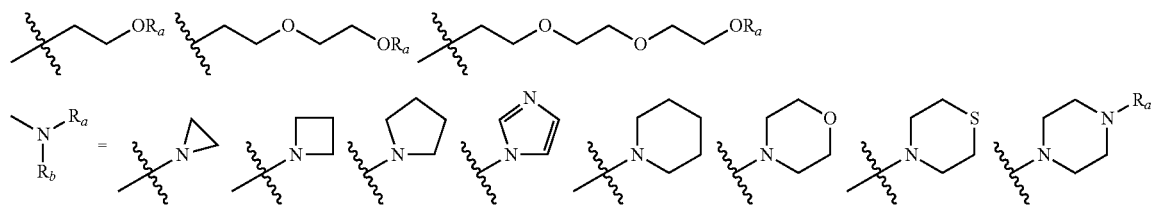

-continued
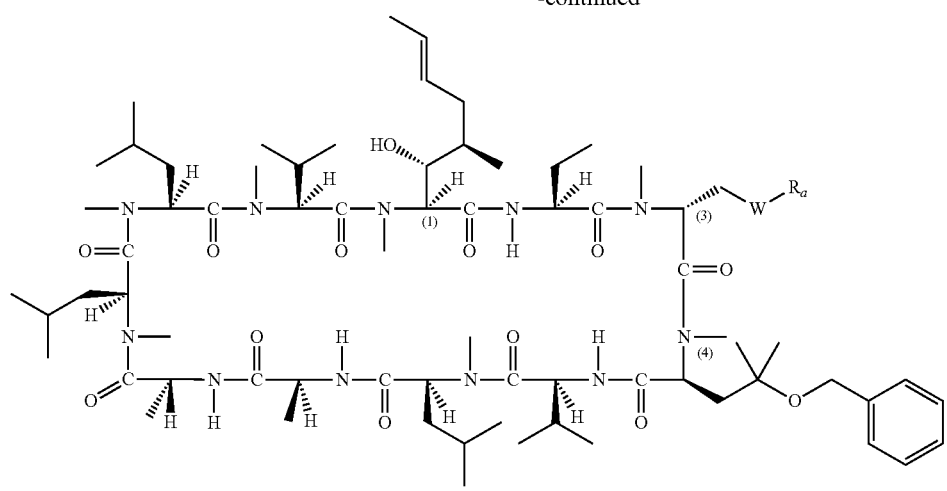
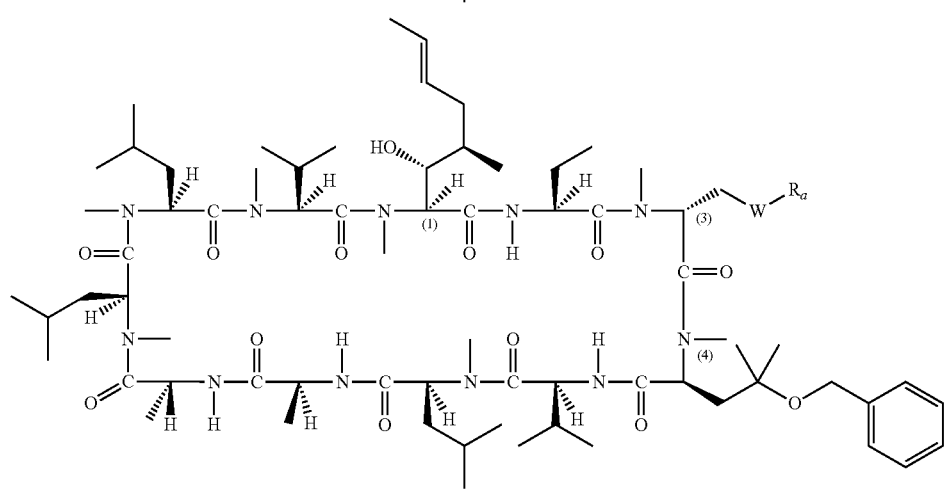
W = O, S, N—H, and N—$R_a$
$R_a$ = H, Me, Et, n-Pr, i-Pr, n-Bu, i-Bu, t-Bu, $CH_2CMe_3$, Ph, $CH_2Ph$
$R_b$ = H, Me, Et, n-Pr, i-Pr, n-Bu, i-Bu, t-Bu, $CH_2CMe_3$, Ph, $CH_2Ph$
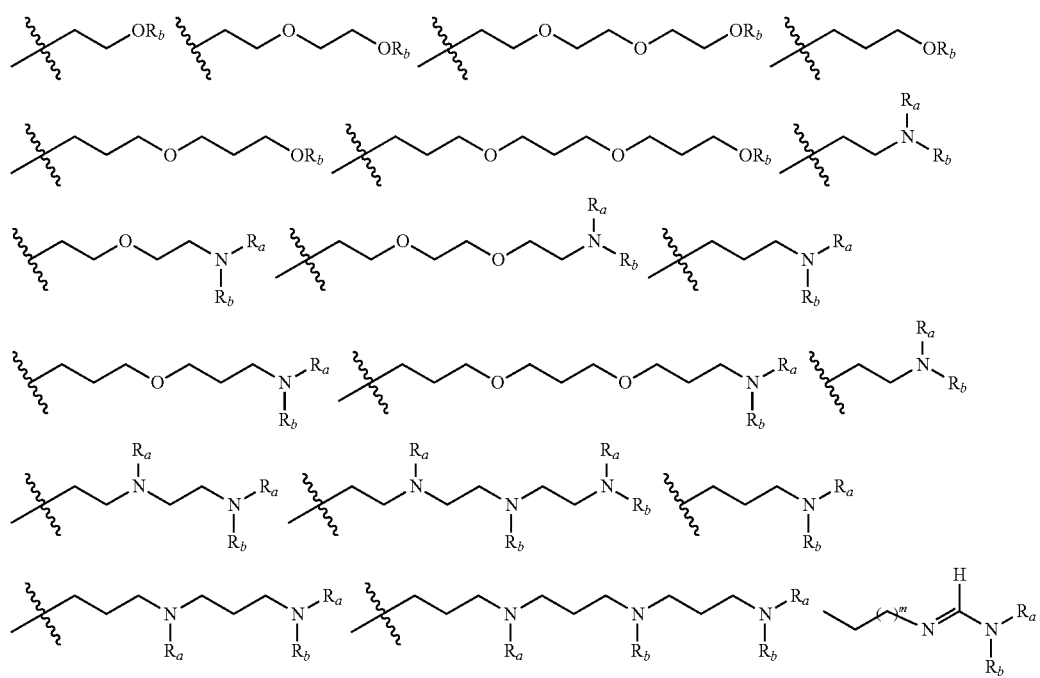

-continued
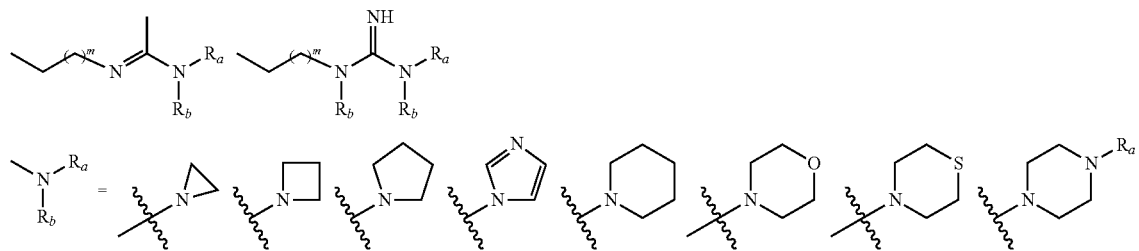
m = 1, 2, 3, 4, 5, 6
or m = 7, 8, 9, 10, 11, or 12
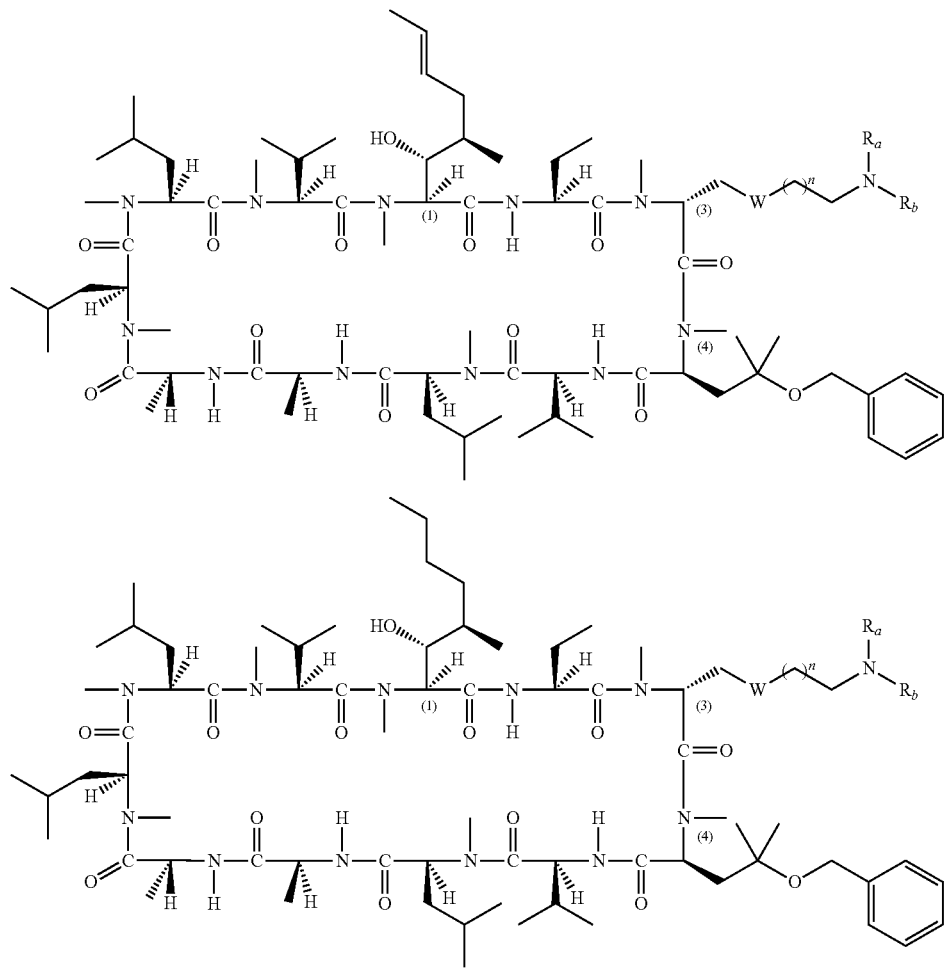
W = O, S, N—H, and N—R$_a$
n = 1, 2, 3, 4, 5, 6 or n = 7, 8, 9, 10, 11, or 12
R$_a$ = H, Me, Et, n-Pr, i-Pr, n-Bu, i-Bu, t-Bu, CH$_2$CMe$_3$, Ph, CH$_2$Ph
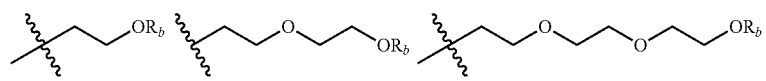
R$_b$ = H, Me, Et, n-Pr, i-Pr, n-Bu, i-Bu, t-Bu, CH$_2$CMe$_3$, Ph, CH$_2$Ph
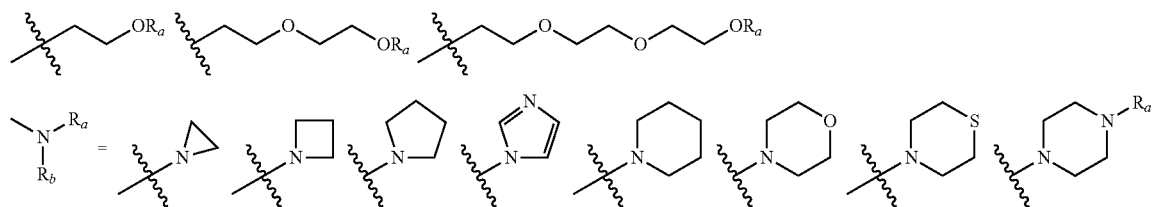

-continued
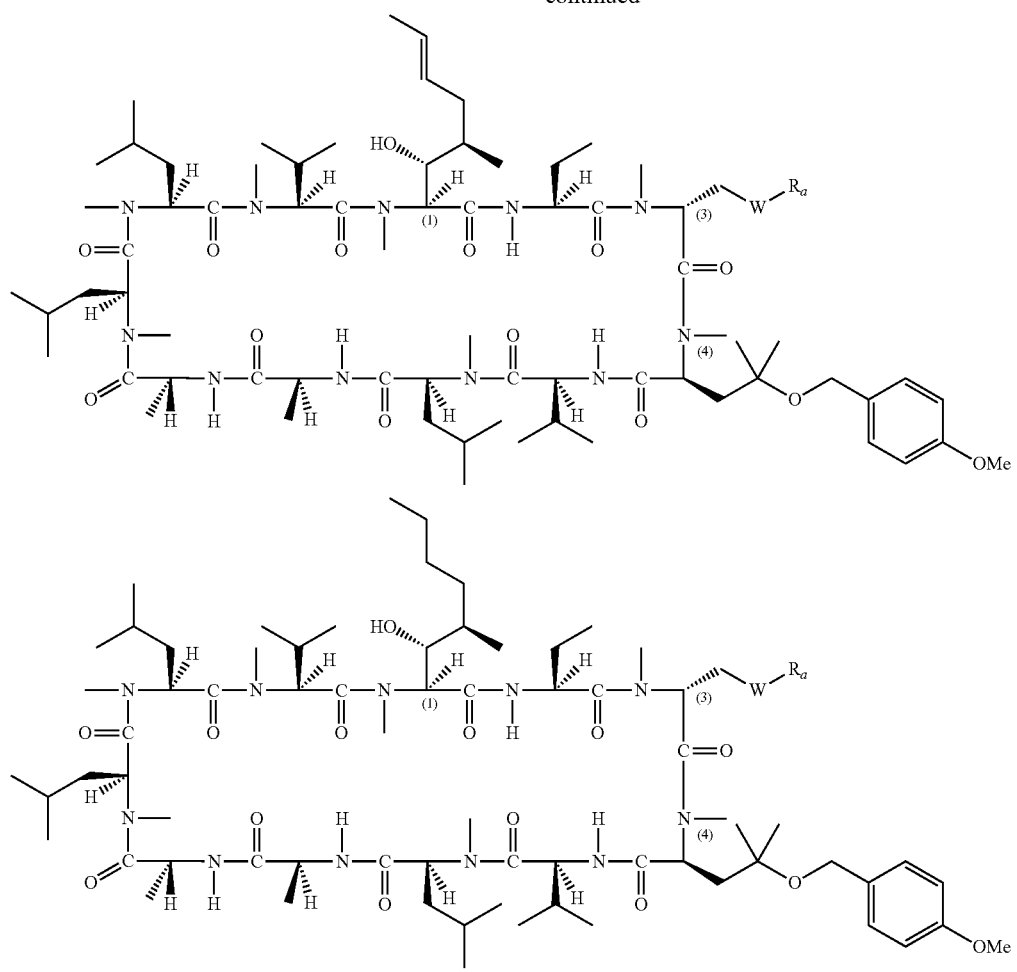
W = O, S, N—H, and N—$R_a$
$R_a$ = H, Me, Et, n-Pr, i-Pr, n-Bu, i-Bu, t-Bu, $CH_2CMe_3$, Ph, $CH_2Ph$
$R_b$ = H, Me, Et, n-Pr, i-Pr, n-Bu, i-Bu, t-Bu, $CH_2CMe_3$, Ph, $CH_2Ph$
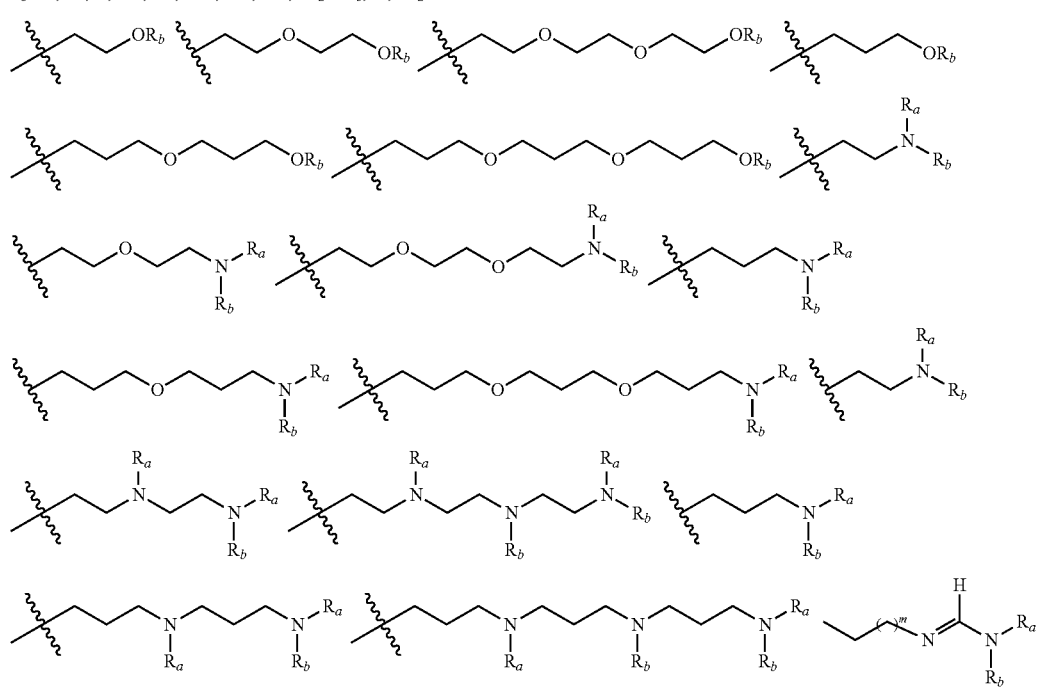

-continued
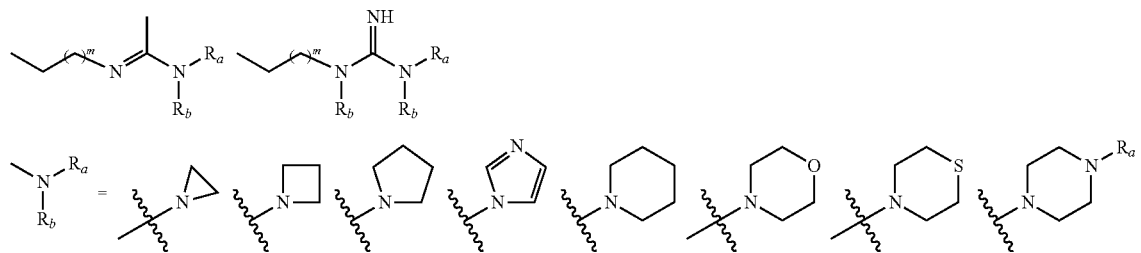
m = 1, 2, 3, 4, 5, 6
or m = 7, 8, 9, 10, 11, or 12
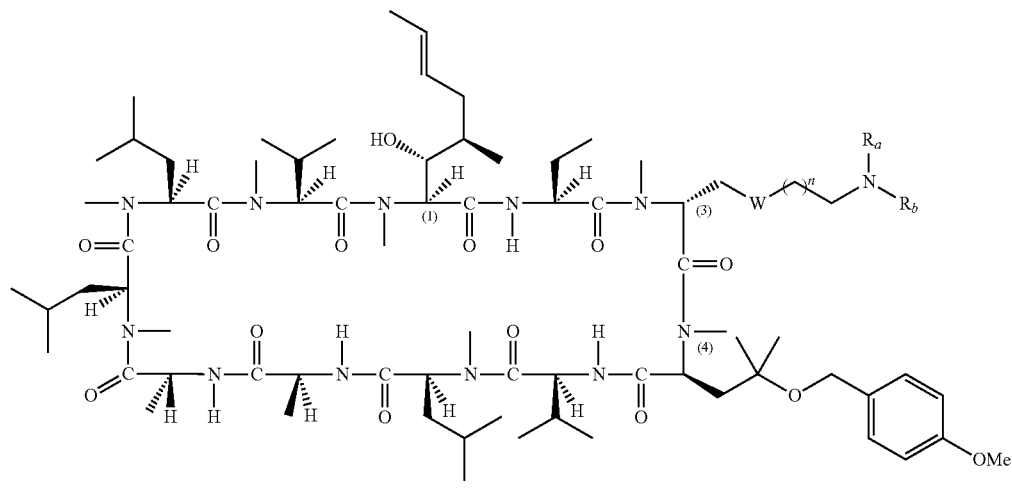
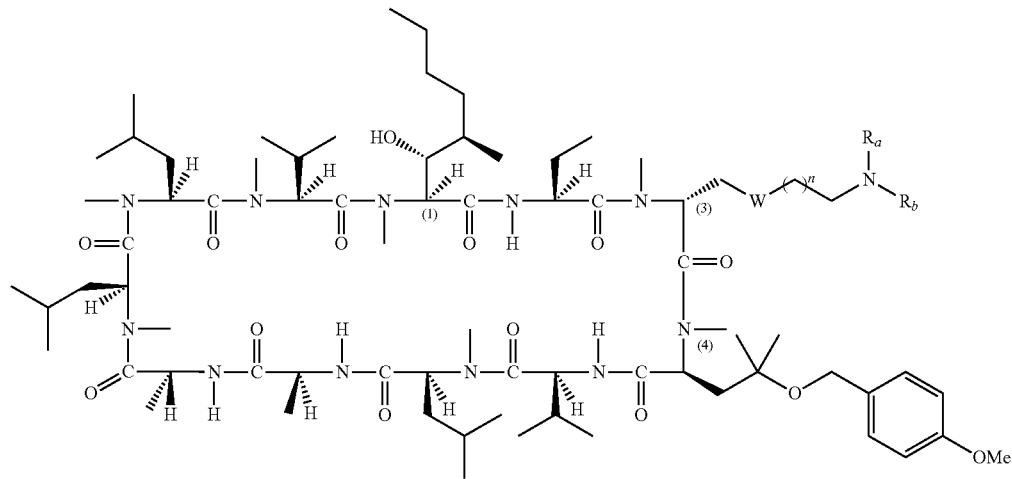
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
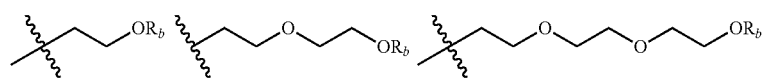
$R_b$ = H, Me, Et, n-Pr, i-Pr, n-Bu, i-Bu, t-Bu, $CH_2CMe_3$, Ph, $CH_2Ph$
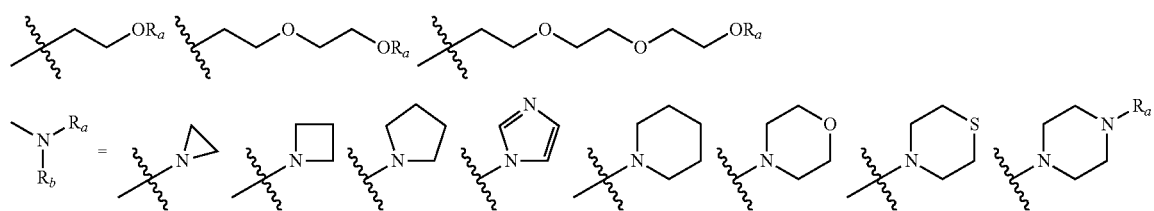

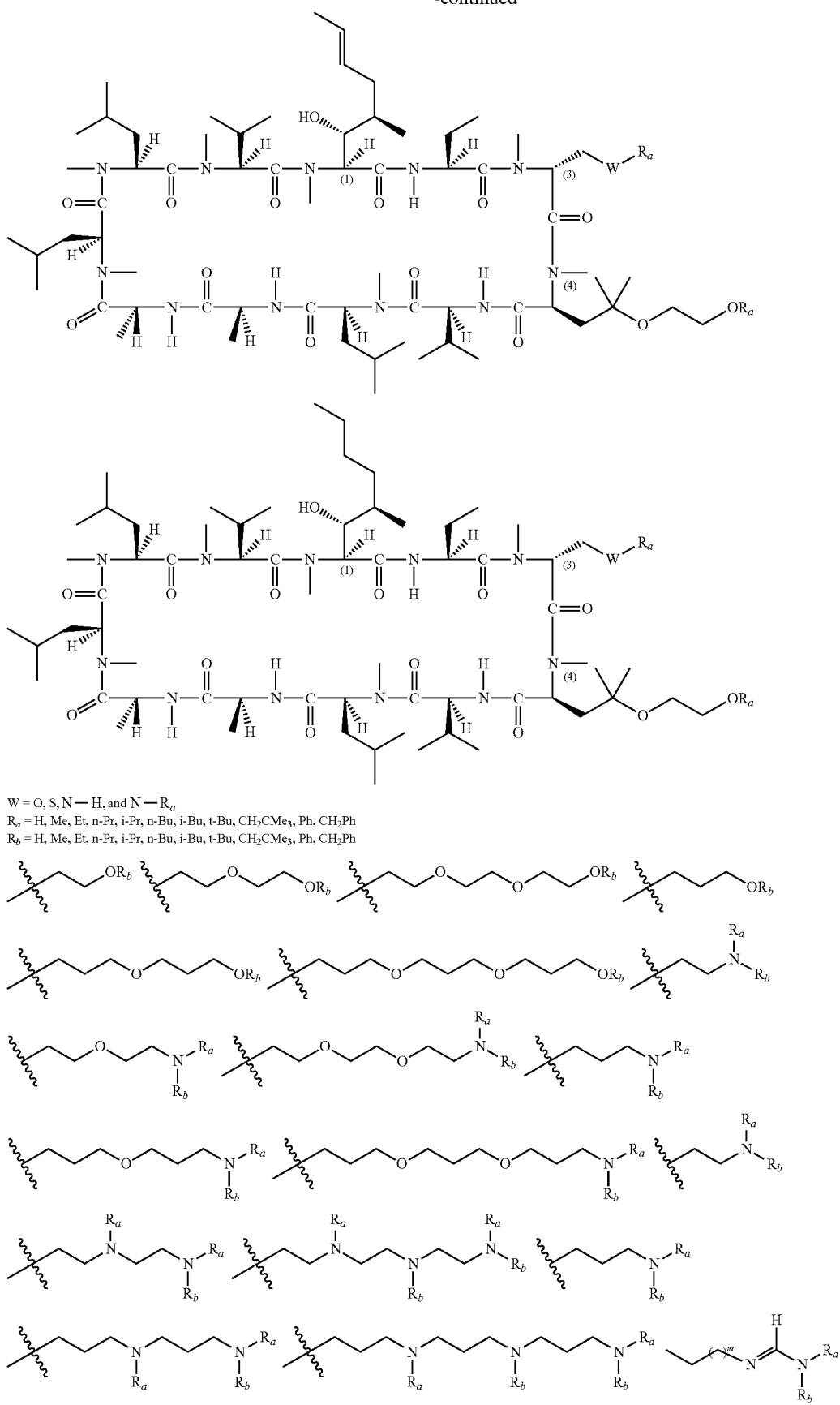

-continued
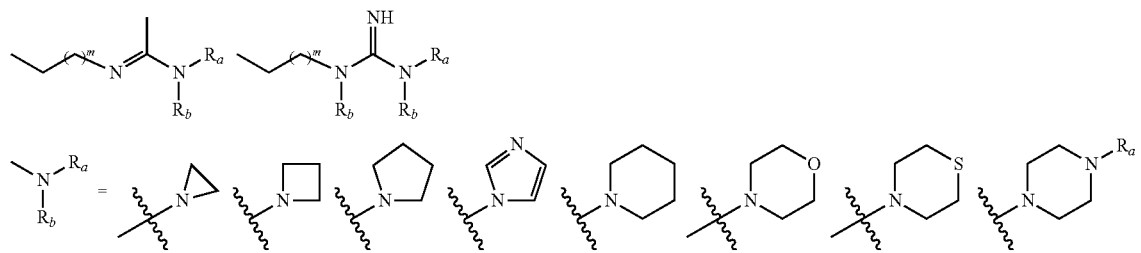
m = 1, 2, 3, 4, 5, 6
or m = 7, 8, 9, 10, 11, or 12
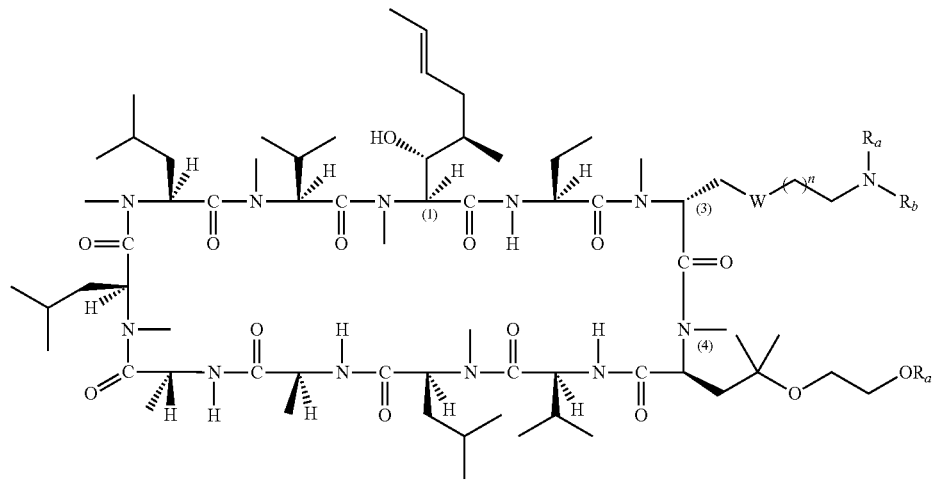
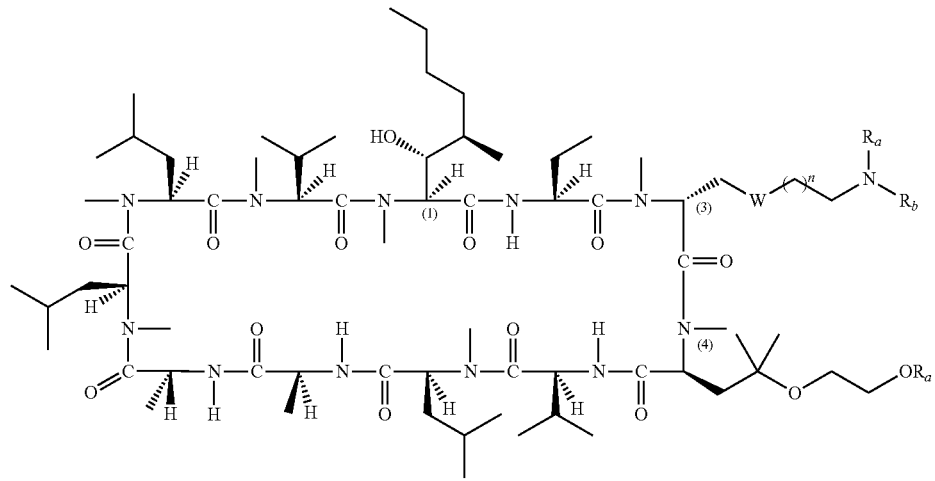
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
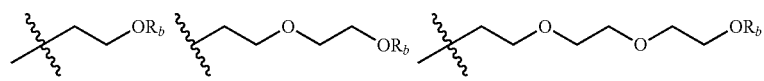
$R_b$ = H, Me, Et, n-Pr, i-Pr, n-Bu, i-Bu, t-Bu, $CH_2CMe_3$, Ph, $CH_2Ph$
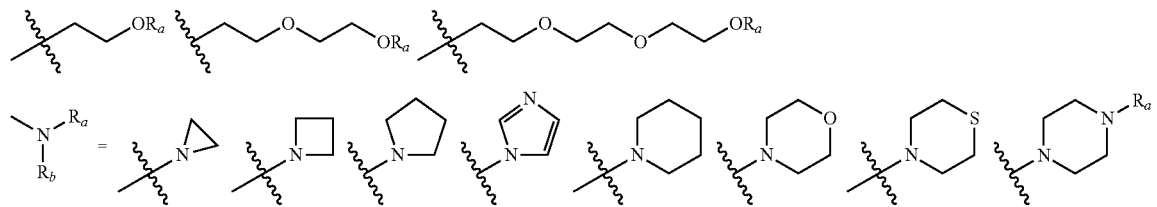

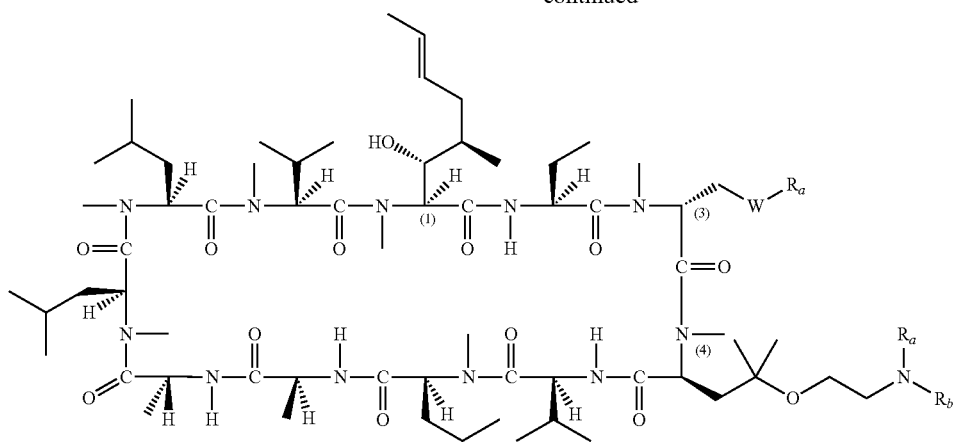
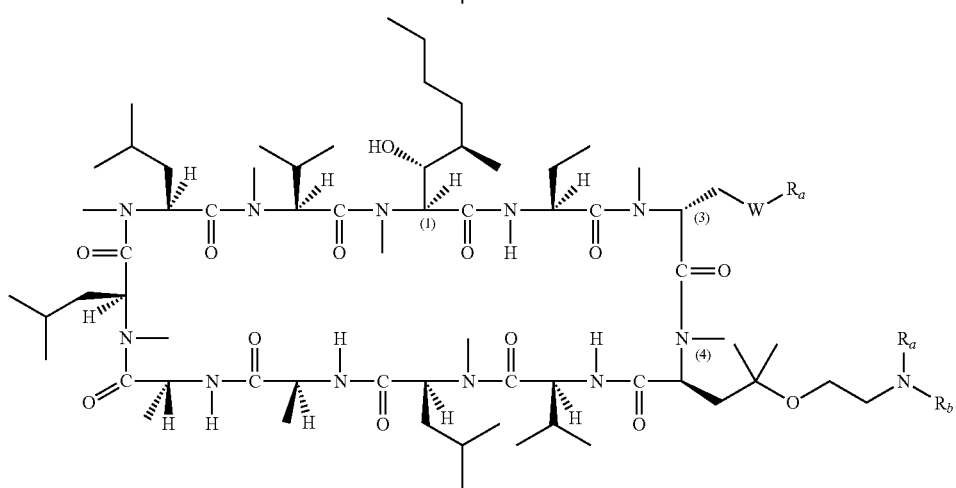
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
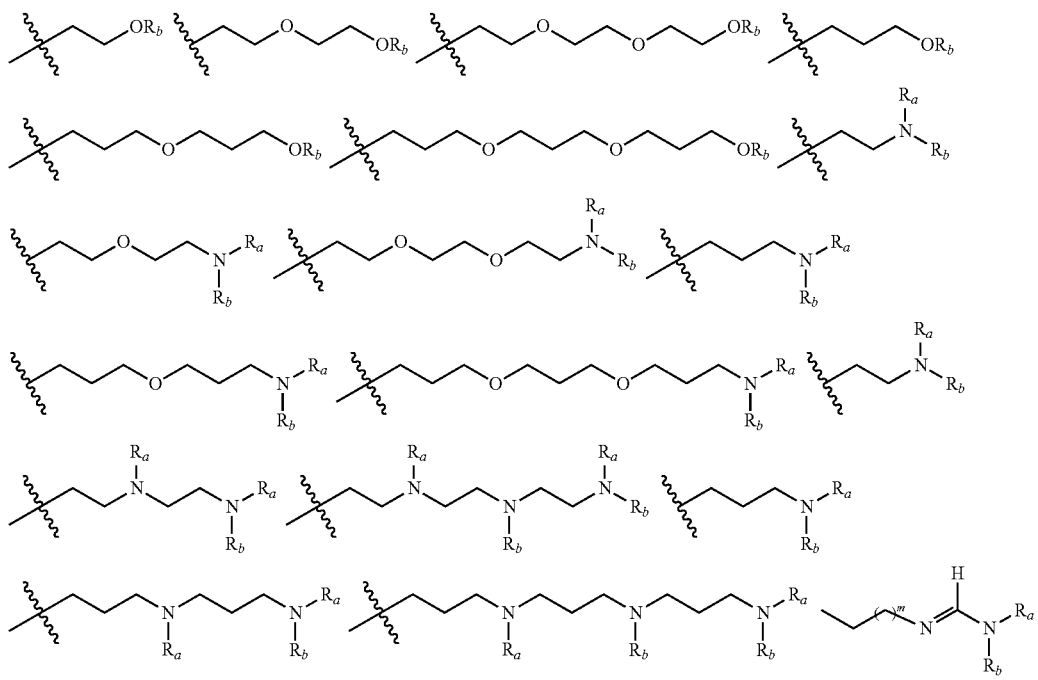

-continued
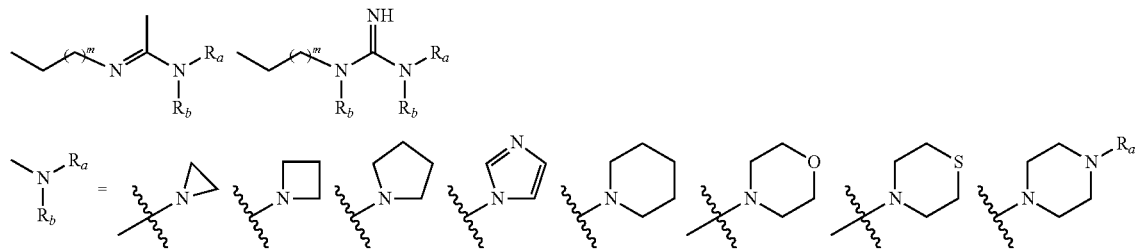
m = 1, 2, 3, 4, 5, 6
or m = 7, 8, 9, 10, 11, or 12
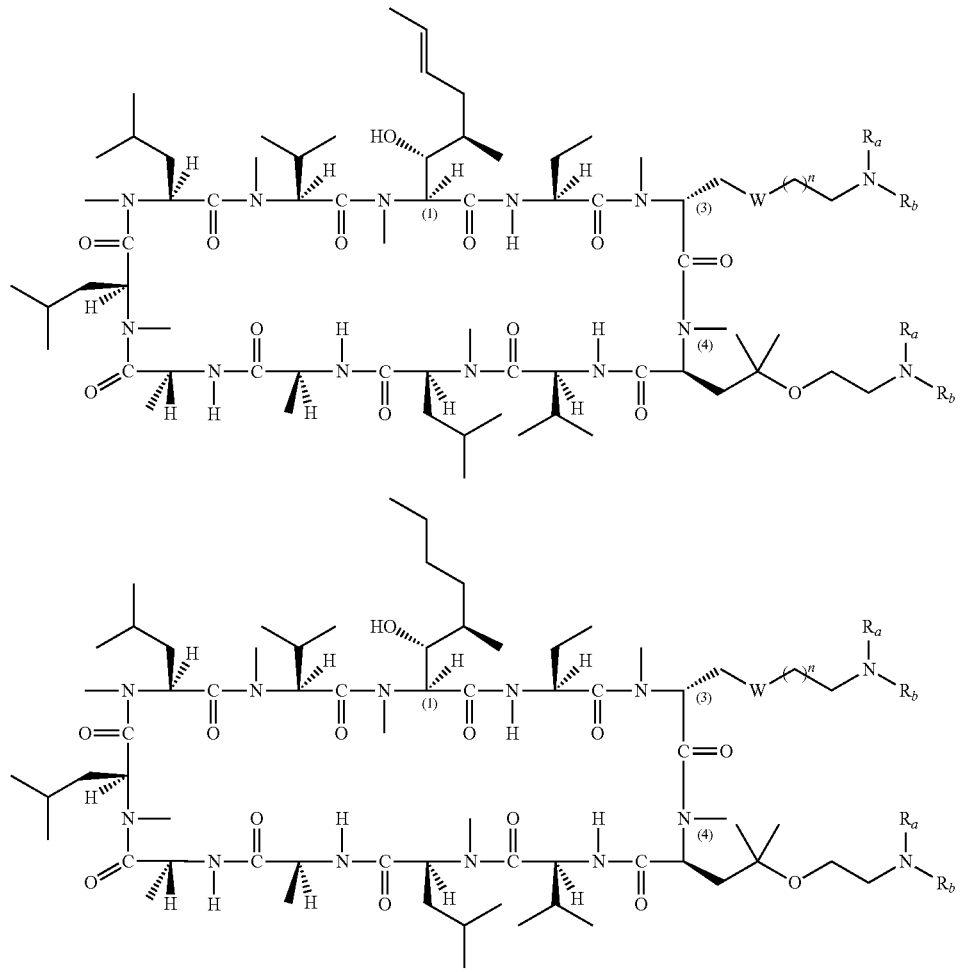
W = O, S, N—H, and N—$R_a$
n = 1, 2, 3, 4, 5, 6 or n = 7, 8, 9, 10, 11, or 12
$R_a$ = H, Me, Et, n-Pr, i-Pr, n-Bu, i-Bu, t-Bu, $CH_2CMe_3$, Ph, $CH_2Ph$
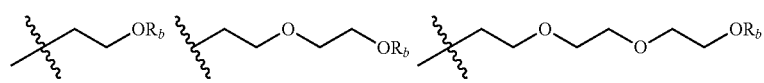
$R_b$ = H, Me, Et, n-Pr, i-Pr, n-Bu, i-Bu, t-Bu, $CH_2CMe_3$, Ph, $CH_2Ph$
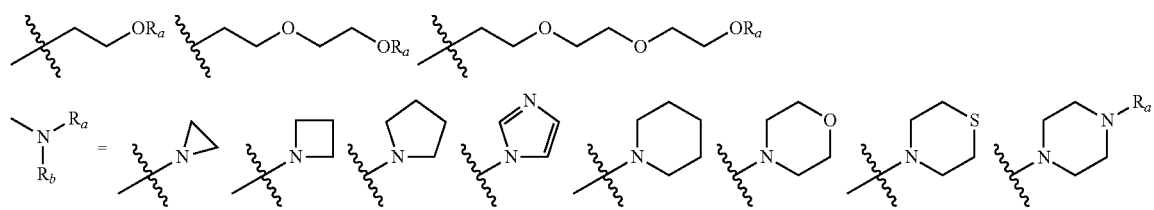

-continued
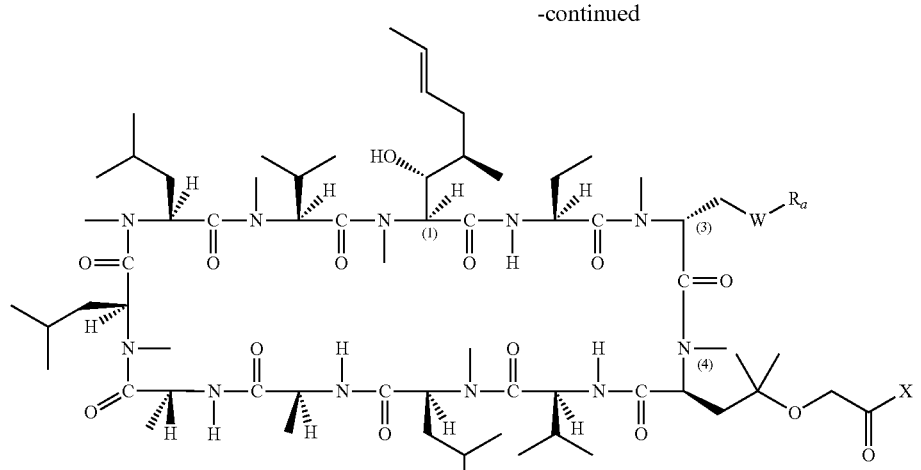
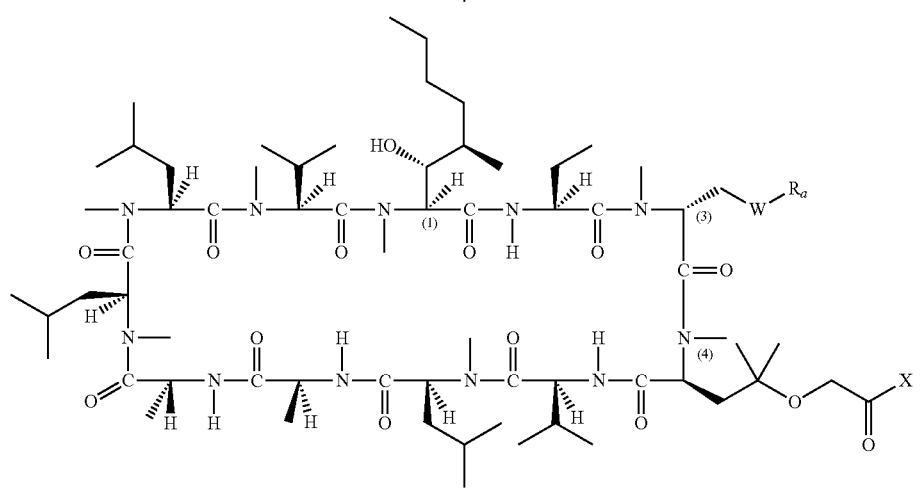
X = OH, OR$_a$, NR$_a$R$_b$
W = O, S, N—H, and N—R$_a$
R$_a$ = H, Me, Et, n-Pr, i-Pr, n-Bu, i-Bu, t-Bu, CH$_2$CMe$_3$, Ph, CH$_2$Ph
R$_b$ = H, Me, Et, n-Pr, i-Pr, n-Bu, i-Bu, t-Bu, CH$_2$CMe$_3$, Ph, CH$_2$Ph
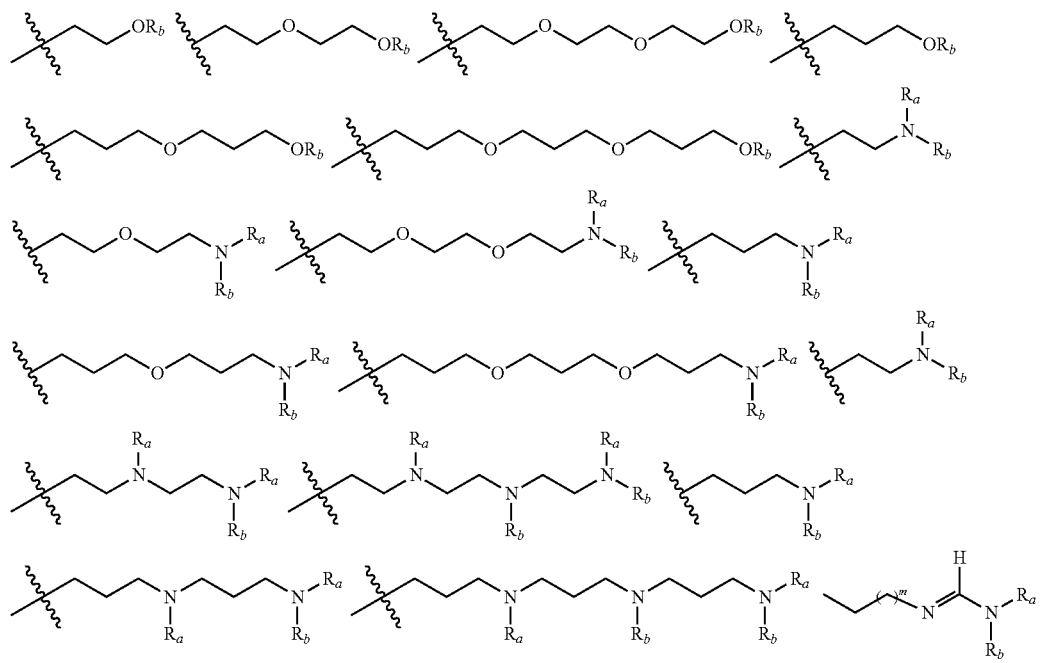

-continued

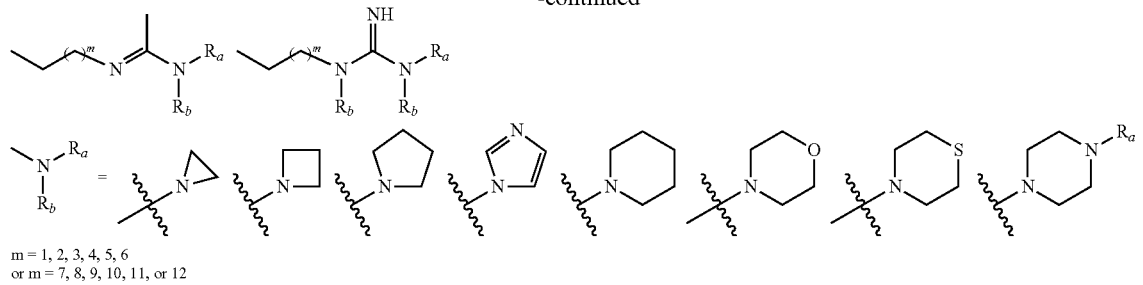

m = 1, 2, 3, 4, 5, 6
or m = 7, 8, 9, 10, 11, or 12

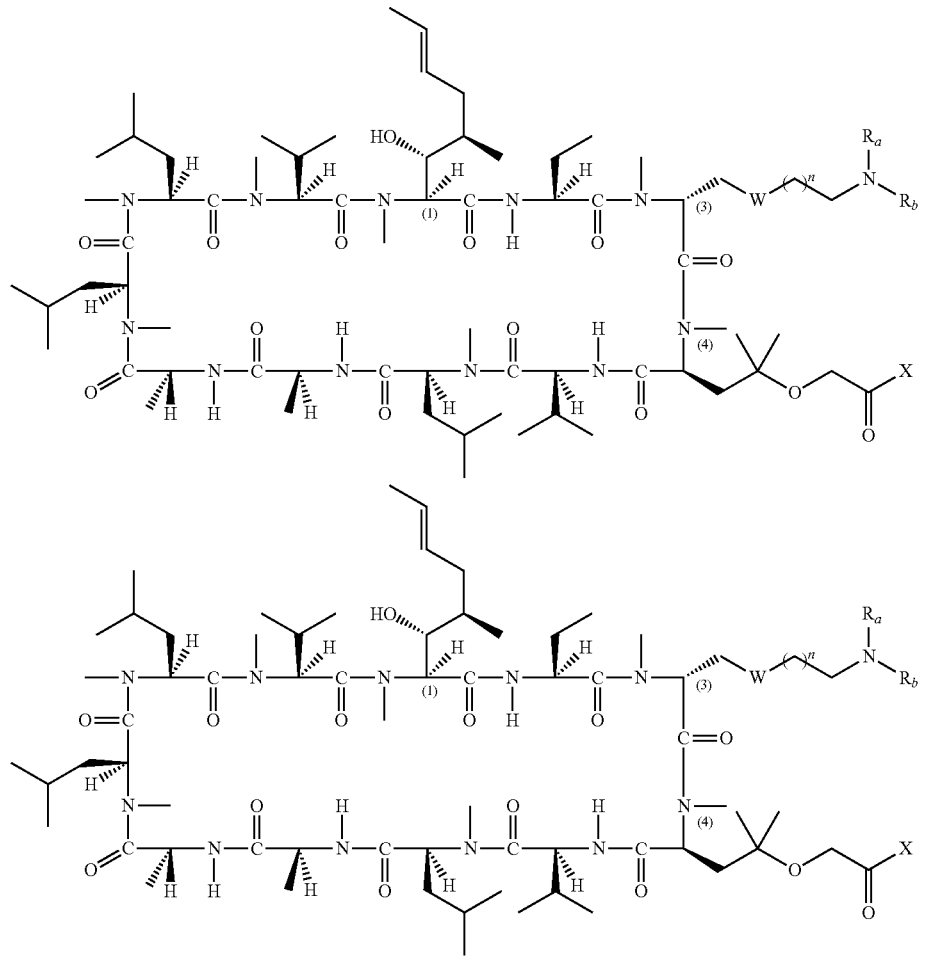

X = OH, OR$_a$, NR$_a$R$_b$
W = O, S, N—H, and N—R$_a$
n = 1, 2, 3, 4, 5, 6 or n = 7, 8, 9, 10, 11, or 12
R$_a$ = H, Me, Et, n-Pr, i-Pr, n-Bu, i-Bu, t-Bu, CH$_2$CMe$_3$, Ph, CH$_2$Ph

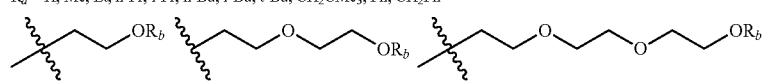

R$_b$ = H, Me, Et, n-Pr, i-Pr, n-Bu, i-Bu, t-Bu, CH$_2$CMe$_3$, Ph, CH$_2$Ph

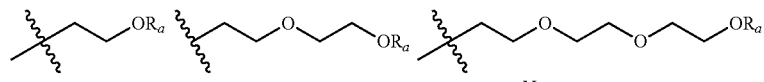

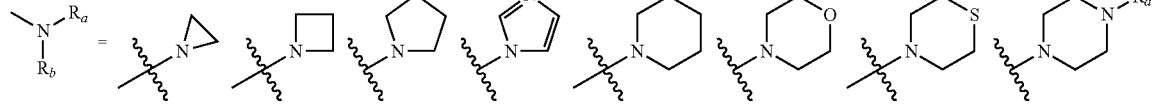

or a pharmaceutically acceptable salt thereof.

In a further aspect, the present invention provides a compound as described in the Examples.

In certain embodiments, the compounds are selected from:

[(R)-(2-(N,N-Dimethylamino)ethoxy)methyl-Sar]-3-cyclosporin,

[(R)-(2-(N,N-Diethylamino)ethoxy)methyl-Sar]-3-cyclosporin,
[(R)-(2-(N-Morpholino)ethoxy)methyl-Sar]-3-cyclosporin,
[(R)-(2-(N-Pyrrolidinyl)ethoxy)methyl-Sar]-3-cyclosporin,
[(R)-(2-(N-Piperidinyl)ethoxy)methyl-Sar]-3-cyclosporin,
[(R)-(3-(N,N-Dimethylamino)propoxy)methyl-Sar]-3-cyclosporin,
[(R)-(3-(N,N-Diethylamino)propoxy)methyl-Sar]-3-cyclosporin,
[(R)-(3-(N-Morpholino)propoxy)methyl-Sar]-3-cyclosporin,
[(R)-(3-(N-Pyrrolidinyl)propoxy)methyl-Sar]-3-cyclosporin,
[(R)-(3-(N-Piperidinyl)propoxy)methyl-Sar]-3-cyclosporin,
[(R)-(Carboxymethoxy)methyl-Sar]-3-cyclosporin,
[(R)-(Carboxymethoxy)methyl-Sar]-3-cyclosporin sodium salt,
[(R)-(Carboxymethoxy)methyl-Sar]-3-cyclosporin potassium salt,
[(R)-(Methoxycarboxymethoxy)methyl-Sar]-3-cyclosporin,
[(R)-(Carboxyethoxy)methyl-Sar]-3-cyclosporin,
[(R)-(Carboxyethoxy)methyl-Sar]-3-cyclosporin sodium salt,
[(R)-(Carboxyethoxy)methyl-Sar]-3-cyclosporin potassium salt,
[(R)-(Methoxycarboxyethoxy)methyl-Sar]-3-cyclosporin,
[(R)-(Carboxypropoxy)methyl-Sar]-3-cyclosporin,
[(R)-(Carboxypropoxy)methyl-Sar]-3-cyclosporin sodium salt,
[(R)-(Carboxypropoxy)methyl-Sar]-3-cyclosporin potassium salt,
[(R)-(Methoxycarboxypropoxy)methyl-Sar]-3-cyclosporin,
[(R)-(Carboxypentyloxy)methyl-Sar]-3-cyclosporin,
[(R)-(Carboxypentyloxy)methyl-Sar]-3-cyclosporin sodium salt,
[(R)-(Carboxypentyloxy)methyl-Sar]-3-cyclosporin potassium salt,
[(R)-(Methoxycarboxypentyloxy)methyl-Sar]-3-cyclosporin,
[(R)-[([HO-Gly-(D-Glu)$_6$]carbamoyl)methoxy]methyl-Sar]-3-cyclosporin,1
[(R)-[([HO-Gly-(D-Glu)$_6$]carbamoyl)ethoxy]methyl-Sar]-3-cyclosporin,
[(R)-[([HO-Gly-(D-Glu)$_6$]carbamoyl)propoxy]methyl-Sar]-3-cyclosporin,
[(R)-((2-[([HO-Gly-(D-Glu)$_6$]carbamoyl)methoxy]ethoxy)methyl-Sar]-3-cyclosporin,
[(R)-((3-[([HO-Gly-(D-Glu)$_6$]carbamoyl)methoxy]propoxy)methyl-Sar]-3-cyclosporin,
[(R)-((4-[([HO-Gly-(D-Glu)$_6$]carbamoyl)methoxy]butoxy)methyl-Sar]-3-cyclosporin,
[(R)-((5-[([HO-Gly-(D-Glu)$_6$]carbamoyl)methoxy]pentyloxy)methyl-Sar]-3-cyclosporin,
[(R)-((6-[([HO-Gly-(D-Glu)$_6$]carbamoyl)methoxy]hexyloxy)methyl-Sar]-3-cyclosporin,
[(S)-(2-(N-Neopentylamino)ethylthio)methyl-Sar]-3-[(γ-hydroxy)-N-MeLeu]-4-cyclosporin,
[(S)-(2-(N-Neopentylamino)ethylthio)methyl-Sar]-3-[(γ-methoxy)-N-MeLeu]-4-cyclosporin,
[(S)-(2-(N-Methyl-N-Neopentylamino)ethylthio)methyl-Sar]-3-[(γ-hydroxy)-N-MeLeu]-4-cyclosporin,
[(S)-(2-(N-Methyl-N-Neopentylamino)ethylthio)methyl-Sar]-3-[(γ-methoxy)-N-MeLeu]-4-cyclosporin,
[(S)-(2-(N-Ethyl-N-Neopentylamino)ethylthio)methyl-Sar]-3-[(γ-hydroxy)-N-MeLeu]-4cyclosporin,
[(S)-(2-(N-Ethyl-N-Neopentylamino)ethylthio)methyl-Sar]-3-[(γ-methoxy)-N-MeLeu]-4-cyclosporin,
[(S)-(3-(N-Neopentylamino)propylthio)methyl-Sar]-3-[(γ-hydroxy)-N-MeLeu]-4-cyclosporin,
[(S)-(3-(N-Neopentylamino)propylthio)methyl-Sar]-3-[(γ-methoxy)-N-MeLeu]-4-cyclosporin,
[(S)-(3-(N-Methyl-N-Neopentylamino)propylthio)methyl-Sar]-3-[(γ-hydroxy)-N-MeLeu]-4-cyclosporin,
[(S)-(3-(N-Methyl-N-Neopentylamino)propylthio)methyl-Sar]-3-[(γ-methoxy)-N-MeLeu]-4-cyclosporin,
[(S)-(3-(N-Ethyl-N-Neopentylamino)propylthio)methyl-Sar]-3-[(γ-hydroxy)-N-MeLeu]-4-cyclosporin,
[(S)-(3-(N-Ethyl-N-Neopentylamino)propylthio)methyl-Sar]-3-[(γ-methoxy)-N-MeLeu]-4-cyclosporin,
[(S)-(4-(N-Neopentylamino)butylthio)methyl-Sar]-3-[(γ-hydroxy)-N-MeLeu]-4-cyclosporin,
[(S)-(4-(N-Neopentylamino)butylthio)methyl-Sar]-3-[(γ-methoxy)-N-MeLeu]-4-cyclosporin,
[(S)-(4-(N-Methyl-N-Neopentylamino)butylthio)methyl-Sar]-3-[(γ-hydroxy)-N-MeLeu]-4-cyclosporin,
[(S)-(4-(N-Methyl-N-Neopentylamino)butylthio)methyl-Sar]-3-[(γ-methoxy)-N-MeLeu]-4-cyclosporin,
[(S)-(4-(N-Ethyl-N-Neopentylamino)butylthio)methyl-Sar]-3-[(γ-hydroxy)-N-MeLeu]-4-cyclosporin,
[(S)-(4-(N-Ethyl-N-Neopentylamino)butylthio)methyl-Sar]-3-[(γ-methoxy)-N-MeLeu]-4-cyclosporin,
[(R)-(2-(N-Neopentylamino)ethoxy)methyl-Sar]-3-[(γ-hydroxy)-N-MeLeu]-4-cyclosporin,
[(R)-(2-(N-Neopentylamino)ethoxy)methyl-Sar]-3-[(γ-methoxy)-N-MeLeu]-4-cyclosporin,
[(R)-(2-(N-Methyl-N-Neopentylamino)ethoxy)methyl-Sar]-3-[(γ-hydroxy)-N-MeLeu]-4-cyclosporin,
[(R)-(2-(N-Methyl-N-Neopentylamino)ethoxy)methyl-Sar]-3-[(γ-methoxy)-N-MeLeu]-4-cyclosporin,
[(R)-(2-(N-Ethyl-N-Neopentylamino)ethoxy)methyl-Sar]-3-[(γ-hydroxy)-N-MeLeu]-4-cyclosporin,
[(R)-(2-(N-Ethyl-N-Neopentylamino)ethoxy)methyl-Sar]-3-[(γ-methoxy)-N-MeLeu]-4-cyclosporin,
[(R)-(3-(N-Neopentylamino)propoxy)methyl-Sar]-3-[(γ-hydroxy)-N-MeLeu]-4-cyclosporin,
[(R)-(3-(N-Neopentylamino)propoxy)methyl-Sar]-3-[(γ-methoxy)-N-MeLeu]-4-cyclosporin,
[(R)-(3-(N-Methyl-N-Neopentylamino)propoxy)methyl-Sar]-3-[(γ-hydroxy)-N-MeLeu]-4-cyclosporin,
[(R)-(3-(N-Methyl-N-Neopentylamino)propoxy)methyl-Sar]-3-[(γ-methoxy)-N-MeLeu]-4-cyclosporin,
[(R)-(3-(N-Ethyl-N-Neopentylamino)propoxy)methyl-Sar]-3-[(γ-hydroxy)-N-MeLeu]-4-cyclosporin,
[(R)-(3-(N-Ethyl-N-Neopentylamino)propoxy)methyl-Sar]-3-[(γ-methoxy)-N-MeLeu]-4-cyclosporin,
[(R)-(4-(N-Neopentylamino)butoxy)methyl-Sar]-3-[(γ-hydroxy)-N-MeLeu]-4-cyclosporin,
[(R)-(4-(N-Neopentylamino)butoxy)methyl-Sar]-3-[(γ-methoxy)-N-MeLeu]-4-cyclosporin,
[(R)-(4-(N-Methyl-N-Neopentylamino)butoxy)methyl-Sar]-3-[(γ-hydroxy)-N-MeLeu]-4-cyclosporin
[(R)-(4-(N-Methyl-N-Neopentylamino)butoxy)methyl-Sar]-3-[(γ-methoxy)-N-MeLeu]-4-cyclosporin,
[(R)-(4-(N-Ethyl-N-Neopentylamino)butoxy)methyl-Sar]-3-[(γ-hydroxy)-N-MeLeu]-4-cyclosporin,
[(R)-(4-(N-Ethyl-N-Neopentylamino)butoxy)methyl-Sar]-3-[(γ-methoxy)-N-MeLeu]-4-cyclosporin,
[(S)-(2-(N-Morpholino)ethylthio)methyl-Sar]-3-[(γ-hydroxy)-N-MeLeu]-4-cyclosporin,
[(S)-(2-(N-Morpholino)ethylthio)methyl-Sar]-3-[(γ-methoxy)-N-MeLeu]-4-cyclosporin,
[(S)-(2-(N-Thiomorpholino)ethylthio)methyl-Sar]-3-[(γ-hydroxy)-N-MeLeu]-4-cyclosporin,

[(S)-(2-(N-Thiomorpholino)ethylthio)methyl-Sar]-3-[(γ-methoxy)-N-MeLeu]-4-cyclosporin,
[(S)-(3-(N-Morpholino)propylthio)methyl-Sar]-3-[(γ-hydroxy)-N-MeLeu]-4-cyclosporin,
[(S)-(3-(N-Morpholino)propylthio)methyl-Sar]-3-[(γ-methoxy)-N-MeLeu]-4-cyclosporin,
[(S)-(3-(N-Thiomorpholino)propylthio)methyl-Sar]-3-[(γ-hydroxy)-N-MeLeu]-4-cyclosporin,
[(S)-(3-(N-Thiomorpholino)propylthio)methyl-Sar]-3-[(γ-methoxy)-N-MeLeu]-4-cyclosporin,
[(S)-(4-(N-Morpholino)butylthio)methyl-Sar]-3-[(γ-hydroxy)-N-MeLeu]-4-cyclosporin,
[(S)-(4-(N-Morpholino)butylthio)methyl-Sar]-3-[(γ-methoxy)-N-MeLeu]-4-cyclosporin,
[(S)-(4-(N-Thiomorpholino)butylthio)methyl-Sar]-3-[(γ-hydroxy)-N-MeLeu]-4-cyclosporin,
[(S)-(4-(N-Thiomorpholino)butylthio)methyl-Sar]-3-[(γ-methoxy)-N-MeLeu]-4-cyclosporin,
[(R)-(2-(N-Morpholino)ethoxy)methyl-Sar]-3-[(γ-hydroxy)-N-MeLeu]-4-cyclosporin,
[(R)-(2-(N-Morpholino)ethoxy)methyl-Sar]-3-[(γ-methoxy)-N-MeLeu]-4-cyclosporin,
[(R)-(2-(N-Thiomorpholino)ethoxy)methyl-Sar]-3-[(γ-hydroxy)-N-MeLeu]-4-cyclosporin,
[(R)-(2-(N-Thiomorpholino)ethoxy)methyl-Sar]-3-[(γ-methoxy)-N-MeLeu]-4-cyclosporin,
[(R)-(3-(N-Morpholino)propoxy)methyl-Sar]-3-[(γ-hydroxy)-N-MeLeu]-4-cyclosporin,
[(R)-(3-(N-Morpholino)propoxy)methyl-Sar]-3-[(γ-methoxy)-N-MeLeu]-4-cyclosporin,
[(R)-(3-(N-Morpholino)propoxy)methyl-Sar]-3-[(γ-allyloxy)-N-MeLeu]-4-cyclosporin,
[(R)-(3-(N-Thiomorpholino)propoxy)methyl-Sar]-3-[(γ-hydroxy)-N-MeLeu]-4-cyclosporin,
[(R)-(3-(N-Thiomorpholino)propoxy)methyl-Sar]-3-[(γ-methoxy)-N-MeLeu]-4-cyclosporin,
[(R)-(3-(N-Thiomorpholino)propoxy)methyl-Sar]-3-[(γ-allyloxy)-N-MeLeu]-4-cyclosporin,
[(R)-(4-(N-Morpholino)butoxy)methyl-Sar]-3-[(γ-hydroxy)-N-MeLeu]-4-cyclosporin,
[(R)-(4-(N-Morpholino)butoxy)methyl-Sar]-3-[(γ-methoxy)-N-MeLeu]-4-cyclosporin,
[(R)-(4-(N-Morpholino)butoxy)methyl-Sar]-3-[(γ-allyloxy)-N-MeLeu]-4-cyclosporin,
[(R)-(4-(N-Thiomorpholino)butoxy)methyl-Sar]-3-[(γ-hydroxy)-N-MeLeu]-4-cyclosporin,
[(R)-(4-(N-Thiomorpholino)butoxy)methyl-Sar]-3-[(γ-methoxy)-N-MeLeu]-4-cyclosporin,
[(R)-(4-(N-Thiomorpholino)butoxy)methyl-Sar]-3-[(γ-allyloxy)-N-MeLeu]-4-cyclosporin,
[(S)-(2-(4-Ethyl-N-piperazinyl)ethylthio)methyl-Sar]-3-[(γ-hydroxy)-N-MeLeu]-4-cyclosporin,
[(S)-(2-(4-Ethyl-N-piperazinyl)ethylthio)methyl-Sar]-3-[(γ-methoxy)-N-MeLeu]-4-cyclosporin,
[(S)-(3-(4-Methyl-N-piperazinyl)propylthio)methyl-Sar]-3-[(γ-hydroxy)-N-MeLeu]-4-cyclosporin,
[(S)-(3-(4-Methyl-N-piperazinyl)propylthio)methyl-Sar]-3-[(γ-methoxy)-N-MeLeu]-4-cyclosporin,
[(S)-(3-(4-Ethyl-N-piperazinyl)propylthio)methyl-Sar]-3-[(γ-hydroxy)-N-MeLeu]-4-cyclosporin,
[(S)-(3-(4-Ethyl-N-piperazinyl)propylthio)methyl-Sar]-3-[(γ-methoxy)-N-MeLeu]-4-cyclosporin,
[(S)-(3-(4-Propyl-N-piperazinyl)propylthio)methyl-Sar]-3-[(γ-hydroxy)-N-MeLeu]-4-cyclosporin,
[(S)-(3-(4-Propyl-N-piperazinyl)propylthio)methyl-Sar]-3-[(γ-methoxy)-N-MeLeu]-4-cyclosporin,
[(R)-(3-(4-Propyl-N-piperazinyl)propoxy)methyl-Sar]-3-[(γ-hydroxy)-N-MeLeu]-4-cyclosporin,
[(R)-(3-(4-Propyl-N-piperazinyl)propoxy)methyl-Sar]-3-[(γ-methoxy)-N-MeLeu]-4-cyclosporin,
[(S)-(3-(4-Isopropyl-N-piperazinyl)propylthio)methyl-Sar]-3-[(γ-hydroxy)-N-MeLeu]-4-cyclosporin,
[(S)-(3-(4-Isopropyl-N-piperazinyl)propylthio)methyl-Sar]-3-[(γ-methoxy)-N-MeLeu]-4-cyclosporin,
[(R)-(3-(4-Isopropyl-N-piperazinyl)propoxy)methyl-Sar]-3-[(γ-hydroxy)-N-MeLeu]-4-cyclosporin,
[(R)-(3-(4-Isopropyl-N-piperazinyl)propoxy)methyl-Sar]-3-[(γ-methoxy)-N-MeLeu]-4-cyclosporin,
[(S)-(3-(4-Isobutyl-N-piperazinyl)propylthio)methyl-Sar]-3-[(γ-hydroxy)-N-MeLeu]-4-cyclosporin,
[(S)-(3-(4-Isobutyl-N-piperazinyl)propylthio)methyl-Sar]-3-[(γ-methoxy)-N-MeLeu]-4-cyclosporin,
[(R)-(3-(4-Isobutyl-N-piperazinyl)propoxy)methyl-Sar]-3-[(γ-hydroxy)-N-MeLeu]-4-cyclosporin,
[(R)-(3-(4-Isobutyl-N-piperazinyl)propoxy)methyl-Sar]-3-[(γ-methoxy)-N-MeLeu]-4-cyclosporin,
[(S)-(3-(4-Neopentyl-N-piperazinyl)propylthio)methyl-Sar]-3-[(γ-hydroxy)-N-MeLeu]-4-cyclosporin,
[(S)-(3-(4-Neopentyl-N-piperazinyl)propylthio)methyl-Sar]-3-[(γ-methoxy)-N-MeLeu]-4-cyclosporin,
[(R)-(3-(4-Neopentyl-N-piperazinyl)propoxy)methyl-Sar]-3-[(γ-hydroxy)-N-MeLeu]-4-cyclosporin,
[(R)-(3-(4-Neopentyl-N-piperazinyl)propoxy)methyl-Sar]-3-[(γ-methoxy)-N-MeLeu]-4-cyclosporin,
[(S)-(2-(N,N-Diethylamino)ethylthio)methyl-Sar]-3-[(γ-hydroxy)-N-MeLeu]-4-cyclosporin,
[(S)-(2-(N,N-Diethylamino)ethylthio)methyl-Sar]-3-[(γ-methoxy)-N-MeLeu]-4-cyclosporin,
[(S)-(3-(N,N-Diethylamino)propylthio)methyl-Sar]-3-[(γ-hydroxy)-N-MeLeu]-4-cyclosporin,
[(S)-(3-(N,N-Diethylamino)propylthio)methyl-Sar]-3-[(γ-methoxy)-N-MeLeu]-4-cyclosporin,
[(S)-(4-(N,N-Diethylamino)butylthio)methyl-Sar]-3-[(γ-hydroxy)-N-MeLeu]-4-cyclosporin,
[(S)-(4-(N,N-Diethylamino)butylthio)methyl-Sar]-3-[(γ-methoxy)-N-MeLeu]-4-cyclosporin,
[(R)-(2-(N,N-Diethylamino)ethoxy)methyl-Sar]-3-[(γ-hydroxy)-N-MeLeu]-4-cyclosporin,
[(R)-(2-(N,N-Diethylamino)ethoxy)methyl-Sar]-3-[(γ-methoxy)-N-MeLeu]-4-cyclosporin,
[(R)-(3-(N,N-Diethylamino)propoxy)methyl-Sar]-3-[(γ-hydroxy)-N-MeLeu]-4-cyclosporin,
[(R)-(3-(N,N-Diethylamino)propoxy)methyl-Sar]-3-[(γ-methoxy)-N-MeLeu]-4-cyclosporin,
[(R)-(4-(N,N-Diethylamino)butoxy)methyl-Sar]-3-[(γ-hydroxy)-N-MeLeu]-4-cyclosporin,
[(R)-(4-(N,N-Diethylamino)butoxy)methyl-Sar]-3-[(γ-methoxy)-N-MeLeu]-4-cyclosporin,
[(S)-(3-(N,N-Diisobutylamino)propylthio)methyl-Sar]-3-[(γ-hydroxy)-N-MeLeu]-4-cyclosporin,
[(S)-(3-(N,N-Diisobutylamino)propylthio)methyl-Sar]-3-[(γ-Methoxy)-N-MeLeu]-4-cyclosporin,
[(S)-(4-(N,N-Diisobutylamino)butylthio)methyl-Sar]-3-[(γ-hydroxy)-N-MeLeu]-4-cyclosporin,
[(S)-(4-(N,N-Diisobutylamino)butylthio)methyl-Sar]-3-[(γ-methoxy)-N-MeLeu]-4-cyclosporin,
[(R)-(3-(N,N-Diisobutylamino)propoxy)methyl-Sar]-3-[(γ-hydroxy)-N-MeLeu]-4-cyclosporin,
[(R)-(3-(N,N-Diisobutylamino)propoxy)methyl-Sar]-3-[(γ-Methoxy)-N-MeLeu]-4-cyclosporin,
[(R)-(4-(N,N-Diisobutylamino)butoxy)methyl-Sar]-3-[(γ-hydroxy)-N-MeLeu]-4-cyclosporin,

[(R)-(4-(N,N-Diisobutylamino)butoxy)methyl-Sar]-3-[(γ-methoxy)-N-MeLeu]-4-cyclosporin,
[(R)-(4-(2-(N,N-Diethylamino)ethoxy)butylthio)methyl-Sar]-3-[(γ-hydroxy)-N-MeLeu]-4-cyclosporin,
[(R)-(4-(2-(N,N-Diethylamino)ethoxy)butylthio)methyl-Sar]-3-[(γ-methoxy)-N-MeLeu]-4-cyclosporin,
[(S)-(3-Hydroxylpropylthio)methyl-Sar]-3-[(γ-hydroxy)-N-MeLeu]-4-cyclosporin,
[(S)-(3-Methoxypropylthio)methyl-Sar]-3-[(γ-hydroxy)-N-MeLeu]-4-cyclosporin,
[(S)-(3-Hydroxyl-3,3-dimethylpropylthio)methyl-Sar]-3-[(γ-hydroxy)-N-MeLeu]-4-cyclosporin,
[(S)-(3-Hydroxylpropylthio)methyl-Sar]-3-[(γ-methoxy)-N-MeLeu]-4-cyclosporin,
[(S)-(3-Methoxypropylthio)methyl-Sar]-3-[(γ-methoxy)-N-MeLeu]-4-cyclosporin,
[(S)-(3-Hydroxyl-3,3-dimethylpropylthio)methyl-Sar]-3-[(γ-methoxy)-N-MeLeu]-4-cyclosporin,
[(S)-(4-Hydroxylbutylthio)methyl-Sar]-3-[(γ-hydroxy)-N-MeLeu]-4-cyclosporin,
[(S)-(4-Methoxybutylthio)methyl-Sar]-3-[(γ-hydroxy)-N-MeLeu]-4-cyclosporin,
[(S)-(4-Hydroxyl-4,4-dimethylbutylthio)methyl-Sar]-3-[(γ-hydroxy)-N-MeLeu]-4-cyclosporin,
[(S)-(4-Hydroxylbutylthio)methyl-Sar]-3-[(γ-methoxy)-N-MeLeu]-4-cyclosporin,
[(S)-(4-Methoxybutylthio)methyl-Sar]-3-[(γ-methoxy)-N-MeLeu]-4-cyclosporin,
[(S)-(4-Hydroxyl-4,4-dimethylbutylthio)methyl-Sar]-3-[(γ-methoxy)-N-MeLeu]-4-cyclosporin,
[(S)-(5-Hydroxylpentylthio)methyl-Sar]-3-[(γ-hydroxy)-N-MeLeu]-4-cyclosporin,
[(S)-(5-Methoxypentylthio)methyl-Sar]-3-[(γ-hydroxy)-N-MeLeu]-4-cyclosporin,
[(S)-(5-Hydroxyl-5,5-dimethylpentylthio)methyl-Sar]-3-[(γ-hydroxy)-N-MeLeu]-4-cyclosporin,
[(S)-(5-Hydroxylpentylthio)methyl-Sar]-3-[(γ-methoxy)-N-MeLeu]-4-cyclosporin,
[(S)-(5-Methoxypentylthio)methyl-Sar]-3-[(γ-methoxy)-N-MeLeu]-4-cyclosporin,
[(S)-(5-Hydroxyl-5,5-dimethylpentylthio)methyl-Sar]-3-[(γ-methoxy)-N-MeLeu]-4-cyclosporin,
[(S)-(3-(N-Piperidinyl)propylthio)methyl-Sar]-3-[(γ-hydroxy)-N-MeLeu]-4-cyclosporin,
[(S)-(3-(N-Piperidinyl)propylthio)methyl-Sar]-3-[(γ-methox)-N-MeLeu]-4-cyclosporin,
[(R)-(3-(N-Piperidinyl)propoxy)methyl-Sar]-3-[(γ-hydroxy)-N-MeLeu]-4-cyclosporin,
[(R)-(3-(N-Piperidinyl)propoxy)methyl-Sar]-3-[(γ-methox)-N-MeLeu]-4-cyclosporin,
[(S)-(4-(N-Piperidinyl)butylthio)methyl-Sar]-3-[(γ-hydroxy)-N-MeLeu]-4-cyclosporin,
[(S)-(4-(N-Piperidinyl)butylthio)methyl-Sar]-3-[(γ-methox)-N-MeLeu]-4-cyclosporin,
[(R)-(4-(N-Piperidinyl)butoxy)methyl-Sar]-3-[(γ-hydroxy)-N-MeLeu]-4-cyclosporin, and
[(R)-(4-(N-Piperidinyl)butoxy)methyl-Sar]-3-[(γ-methox)-N-MeLeu]-4-cyclosporin,
[(S)-(5-Carboxyheptylthio)methyl-Sar]-3-cyclosporin
[(S)-(5-Carboxyheptylthio)methyl-Sar]-3-cyclosporin-potassium salt
[(S)-(5-(Ethoxycarbonyl)heptylthio)methyl-Sar]-3-cyclosporin
[(S)-((7,7'-Dicarboxy)heptylthio)methyl-Sar]-3-cyclosporin
[(S)-((7,7'-Dicarboxy)heptylthio)methyl-Sar]-3-cyclosporin-dipotassium salt
[(S)-((7,7'-Dicarboxy)heptylthio)methyl-Sar]-3-cyclosporin-disodium salt
[(S)-(7,7'-Diethoxycarbonyl)heptylthio)methyl-Sar]-3-cyclosporin
[(S)—(((R)-3-Hydroxymethyl-6-(imidazol-1-yl)hexyl)thio)methyl-Sar]-3-cyclosporin
[(S)—(((S)-3-Hydroxymethyl-6-(imidazo-1-yl)hexyl)thio)methyl-Sar]-3-cyclosporin
[(S)—(((R)-3-Hydroxymethyl-6-morpholinohexyl)thio)methyl-Sar]-3-cyclosporin
[(S)—(((S)-3-Hydroxymethyl-6-morpholinohexyl)thio)methyl-Sar]-3-cyclosporin
[(S)—(((R)-3-Hydroxymethyl-6-(4-ethylpiperazin-1-yl)hexyl)thio)methyl-Sar]-3-cyclosporin
[(S)—(((S)-3-Hydroxymethyl-6-(4-isopropylpiperazin-1-yl)hexyl)thio)methyl-Sar]-3-cyclosporin
[(S)—(((S)-4-Hydroxy-7-(imidazol-1-yl)heptyl)thio)methyl-Sar]-3-cyclosporin
[(S)—(((R)-4-Hydroxy-7-(imidazo-1-yl)heptyl)thio)methyl-Sar]-3-cyclosporin
[(S)—(((S)-4-Hydroxy-7-morpholinoheptyl)thio)methyl-Sar]-3-cyclosporin
[(S)—(((R)-4-Hydroxy-7-morpholinoheptyl)thio)methyl-Sar]-3-cyclosporin
[(S)—(((S)-4-Hydroxy-7-(4-ethylpiperazin-1-yl) heptyl)thio)methyl-Sar]-3-cyclosporin
[(S)—(((R)-4-Hydroxy-7-(4-ethylpiperazin-1-yl) heptyl)thio)methyl-Sar]-3-cyclosporin
[(R)-(5-Carboxyheptyloxy)methyl-Sar]-3-cyclosporin
[(R)-(5-Carboxyheptyloxy)methyl-Sar]-3-cyclosporin-potassium salt
[(R)-((7,7'-Dicarboxy)heptyloxy)methyl-Sar]-3-cyclosporin
[(R)-((7,7'-Dicarboxy)heptyloxy)methyl-Sar]-3-cyclosporin-dipotassium salt
[(R)-(7,7'-Diethoxycarbonyl)heptyloxy)methyl-Sar]-3-cyclosporin
[(R)—(((S)-4-Hydroxy-7-(imidazol-1-yl)heptyl)oxy)methyl-Sar]-3-cyclosporin
[(R)—(((R)-4-Hydroxy-7-(imidazo-1-yl)heptyl)oxy)methyl-Sar]-3-cyclosporin
[(R)—(((S)-4-Hydroxy-7-morpholinoheptyl)oxy)methyl-Sar]-3-cyclosporin
[(R)—(((R)-4-Hydroxy-7-morpholinoheptyl)oxy)methyl-Sar]-3-cyclosporin
[(R)—(((S)-4-Hydroxy-7-(4-ethylpiperazin-1-yl)heptylcyclos)oxy)methyl-Sar]-3-cyclosporin
[(R)—(((R)-4-Hydroxy-7-(4-ethylpiperazin-1-yl) heptyl)oxy)methyl-Sar]-3-cyclosporin
[(S)-(7,7'-Di(carboxy)heptylthio)methyl-Sar]-3-[(γ-hydroxy)-N-MeLeu]-4-cyclosporin
[(S)-(7,7'-Di(carboxy)heptylthio)methyl-Sar]-3-[(γ-hydroxy)-N-MeLeu]-4-cyclosporin-dipotassium salt
[(S)-(7,7'-Di(ethoxycarbonyl)heptylthio)methyl-Sar]-3-[(γ-hydroxy)-N-MeLeu]-4-cyclosporin
[(S)—(((S)-4-Hydroxy-7-(imidazol-1-yl)heptyl)thio)methyl-Sar]-3-[(γ-hydroxy)-N-MeLeu]-4-cyclosporin
[(S)—(((R)-4-Hydroxy-7-(imidazo-1-yl)heptyl)thio)methyl-Sar]-3-[(γ-hydroxy)-N-MeLeu]-4-cyclosporin
[(S)—(((S)-4-Hydroxy-7-morpholinoheptyl)thio)methyl-Sar]-3-[(γ-hydroxy)-N-MeLeu]-4-cyclosporin
[(S)—(((R)-4-Hydroxy-7-morpholinoheptyl)thio)methyl-Sar]-3-[(γ-hydroxy)-N-MeLeu]-4-cyclosporin
[(S)—(((S)-4-Hydroxy-7-(4-ethylpiperazin-1-yl) heptyl)thio)methyl-Sar]-3-[(γ-hydroxy)-N-MeLeu]-4-cyclosporin

[(S)—(((R)-4-Hydroxy-7-(4-ethylpiperazin-1-yl) heptyl)thio)methyl-Sar]-3-[(γ-hydroxy)-N-MeLeu]-4-cyclosporin
[(S)—(((R)-3-Hydroxymethyl-6-(imidazol-1-yl)hexyl)thio)methyl-Sar]-3-[(γ-hydroxy)-N-MeLeu]-4-cyclosporin
[(S)—(((S)-3-Hydroxymethyl-6-(imidazo-1-yl)hexyl)thio)methyl-Sar]-3-[(γ-hydroxy)-N-MeLeu]-4-cyclosporin
[(S)—(((R)-3-Hydroxymethyl-6-morpholinohexyl)thio)methyl-Sar]-3-[(γ-hydroxy)-N-MeLeu]-4-cyclosporin
[(S)—(((S)-3-Hydroxymethyl-6-morpholinohexyl)thio)methyl-Sar]-3-[(γ-hydroxy)-N-MeLeu]-4-cyclosporin
[(S)—(((R)-3-Hydroxymethyl-6-(4-ethylpiperazin-1-yl)hexyl)thio)methyl-Sar]-3-[(γ-hydroxy)-N-MeLeu]-4-cyclosporin
[(S)—(((S)-3-Hydroxymethyl-6-(4-isopropylpiperazin-1-yl)hexyl)thio)methyl-Sar]-3-[(γ-hydroxy)-N-MeLeu]-4-cyclosporin
[(R)-(7,7'-Di(carboxy)heptyloxy)methyl-Sar]-3-[(γ-hydroxy)-N-MeLeu]-4-cyclosporin
[(R)-(7,7'-Di(carboxy)heptyloxy)methyl-Sar]-3-[(γ-hydroxy)-N-MeLeu]-4-cyclosporin-dipotassium salt
[(R)-(7,7'-Di(ethoxycarbonyl)heptyloxy)methyl-Sar]-3-[(γ-hydroxy)-N-MeLeu]-4-cyclosporin
[(S)—(((S)-4-Hydroxy-7-(imidazol-1-yl)heptyl)thio)methyl-Sar]-3-[(γ-hydroxy)-N-MeLeu]-4-cyclosporin
[(S)—(((R)-4-Hydroxy-7-(imidazo-1-yl)heptyl)thio)methyl-Sar]-3-[(γ-hydroxy)-N-MeLeu]-4-cyclosporin
[(S)—(((S)-4-Hydroxy-7-morpholinoheptyl)thio)methyl-Sar]-3-[(γ-hydroxy)-N-MeLeu]-4-cyclosporin
[(S)—(((R)-4-Hydroxy-7-morpholinoheptyl)thio)methyl-Sar]-3-[(γ-hydroxy)-N-MeLeu]-4-cyclosporin
[(S)—(((S)-4-Hydroxy-7-(4-ethylpiperazin-1-yl) heptyl)thio)methyl-Sar]-3-[(γ-hydroxy)-N-MeLeu]-4-cyclosporin
[(S)—(((R)-4-Hydroxy-7-(4-ethylpiperazin-1-yl) heptyl)thio)methyl-Sar]-3-[(γ-hydroxy)-N-MeLeu]-4-cyclosporin
[(S)—(((R)-3-Hydroxymethyl-6-(imidazol-1-yl)hexyl)thio)methyl-Sar]-3-[(γ-hydroxy)-N-MeLeu]-4-cyclosporin
[(S)—(((S)-3-Hydroxymethyl-6-(imidazo-1-yl)hexyl)thio)methyl-Sar]-3-[(γ-hydroxy)-N-MeLeu]-4-cyclosporin
[(S)—(((R)-3-Hydroxymethyl-6-morpholinohexyl)thio)methyl-Sar]-3-[(γ-hydroxy)-N-MeLeu]-4-cyclosporin
[(S)—(((S)-3-Hydroxymethyl-6-morpholinohexyl)thio)methyl-Sar]-3-[(γ-hydroxy)-N-MeLeu]-4-cyclosporin
[(S)—(((R)-3-Hydroxymethyl-6-(4-ethylpiperazin-1-yl)hexyl)thio)methyl-Sar]-3-[(γ-hydroxy)-N-MeLeu]-4-cyclosporin, and
[(S)—(((S)-3-Hydroxymethyl-6-(4-isopropylpiperazin-1-yl)hexyl)thio)methyl-Sar]-3-[(γ-hydroxy)-N-MeLeu]-4-cyclosporin, or a pharmaceutically acceptable salt thereof.

In another aspect, the present invention provides a pharmaceutical composition comprising at least one compound described herein and a pharmaceutically-acceptable carrier or diluent.

In a further aspect, the present invention provides a method for treating or preventing a viral infection in a mammalian species in need thereof, the method comprising administering to the mammalian species a therapeutically effective amount of at least one compound described herein. In certain embodiments, the viral infection is HIV infection. In certain other embodiments, the viral infection is HBV infection. In yet other embodiments, the viral infection is HCV infection. In yet other embodiments, the viral infection is influenza A virus infection, severe acute respiratory syndrome coronavirus infection or vaccinia virus infection.

In another aspect, the present invention provides a method for treating or preventing hepatitis C virus infection in a mammalian species in need thereof, the method comprising administering to the mammalian species a therapeutically effective amount of at least one compound described herein.

In yet another aspect, the present invention provides a method for inhibiting a cyclophilin in a subject in need thereof, which comprises administrating to said subject an effective cyclophilin-inhibiting amount of at least one compound as described herein.

In yet another aspect, the present invention provides a method for treating or preventing diseases that are mediated by cyclophilins in a mammalian species in need thereof, the method comprising administering to the mammalian species a therapeutically effective amount of at least one compound as described herein.

In yet another aspect, the present invention provides a method for treating or preventing diseases in a mammalian species in need thereof, the method comprising administering to the mammalian species a therapeutically effective amount of at least one compound as described herein, wherein the diseases are selected from inflammation, respiratory inflammation, rheumatoid arthritis, and dry eye.

In yet another aspect, the present invention provides a method for treating or preventing diseases in a mammalian species in need thereof, the method comprising administering to the mammalian species a therapeutically effective amount of at least one compound as described herein, wherein the diseases are selected from neurodegenerative diseases such as Alzheimer's disease, Parkinson's disease, Huntington's Diseases, and ALS; traumatic brain injury; stroke; and ischemia-reperfusion injury in the brain, heart, and kidney.

In yet another aspect, the present invention provides a method for treating or preventing diseases in a mammalian species in need thereof, the method comprising administering to the mammalian species a therapeutically effective amount of at least one compound as described herein, wherein the diseases are selected from cardiovascular diseases, vascular stenosis, atherosclerosis, abdominal aortic aneurysms, cardiac hypertrophy, aortic rupture, pulmonary arterial hypertension, myocarditis and myocardial fibrosis, and ischaemic heart diseases.

In yet another aspect, the present invention provides a method for treating or preventing diseases or conditions in a mammalian species in need thereof, the method comprising administering to the mammalian species a therapeutically effective amount of at least one compound as described herein, wherein the diseases or conditions are selected from cancer, obesity, diabetes, muscular dystrophy, and hair loss.

In yet another aspect, the present invention provides a method for treating or preventing diseases or conditions in a mammalian species in need thereof, the method comprising administering to the mammalian species a therapeutically effective amount of at least one compound as described herein, wherein the diseases or conditions are selected from allergic conjunctivitis, atopic and vernal keratoconjunctivitis, atopic keratoconjunctivitis, anterior uveitis, Behcet's disease, blepharitis, chronic ocular surface inflammation caused by viral infection, corneal transplant rejection, corneal sensitivity impaired due to surgery on the cornea or other surface of the eye, meibomian gland disease, ptyregia, ocular symptoms of graft versus host disease, ocular allergy, ocular cicatricial pemphigoid, Steven Johnson syndrome, vernal keratoconjunctivitis, uveitis, herpes simplex keratitis, ocular rosacea, and Pinguecula.

Methods of Preparation

In certain embodiments, the compound of formulae (I) and (II) can be prepared by treating cyclosporin A or an analog thereof with a base (e.g., LDA) to form a sarcosine enolate at 3-position, and then $CO_2$ gas is introduced to yield carboxylic acid-3-cyclosporin, after formation of its corresponding methyl ester and reduction of the methyl ester side chain to alcohol, its mesylate, tosylate or chloride can be formed by treatment with MSCl or TsCl in dichloromethane solution, and they can be converted to the methylene on the sarcosine by treatment with a base (e.g., NaH), when sulfur nuclectrophile is used for 1,4-addition reaction on the methylene group, the methylene sulfur side chain with S-conformation can be formed on the sarcosine of position 3 as novel cyclosporine derivatives. For example:

Scheme 1

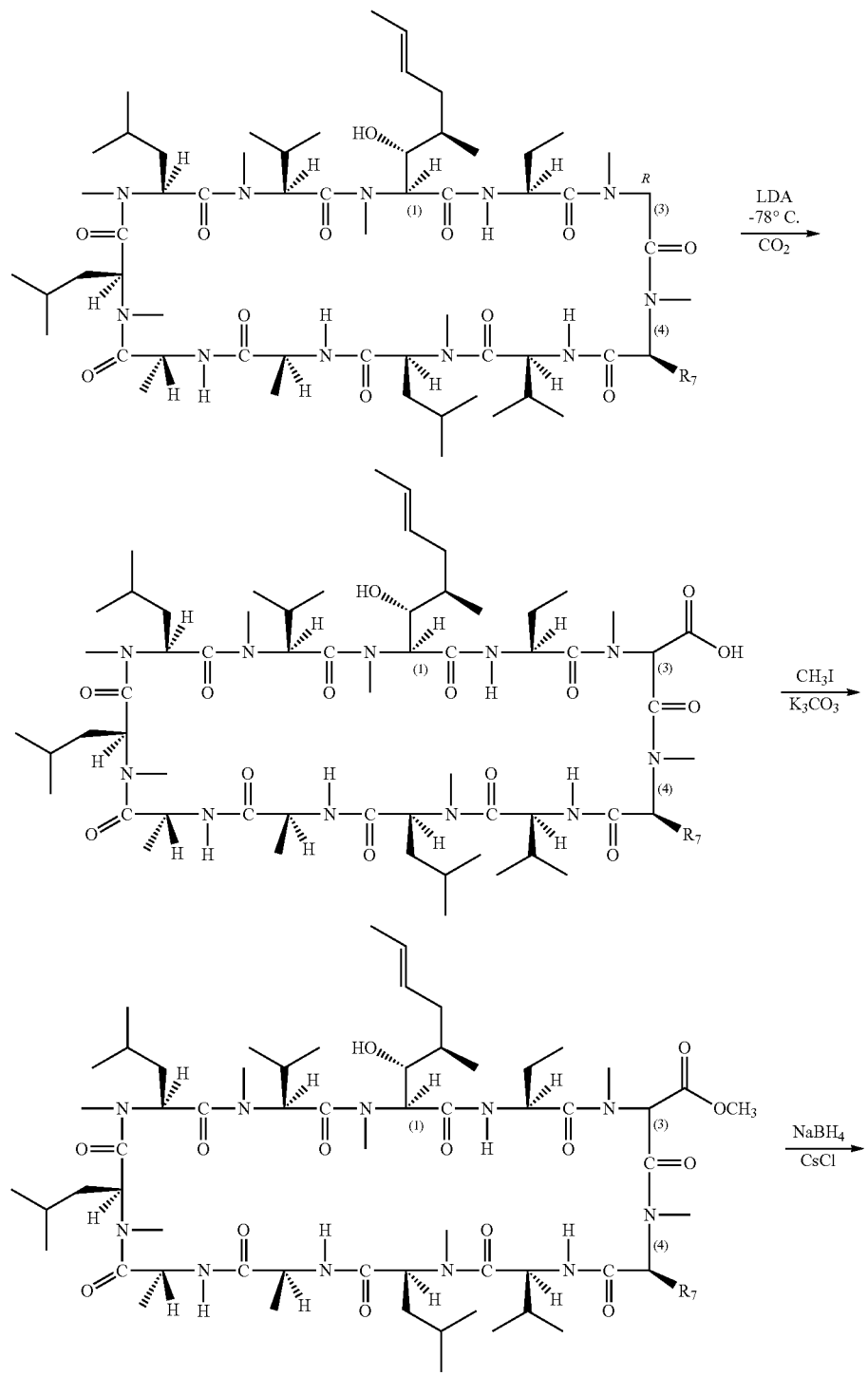

-continued
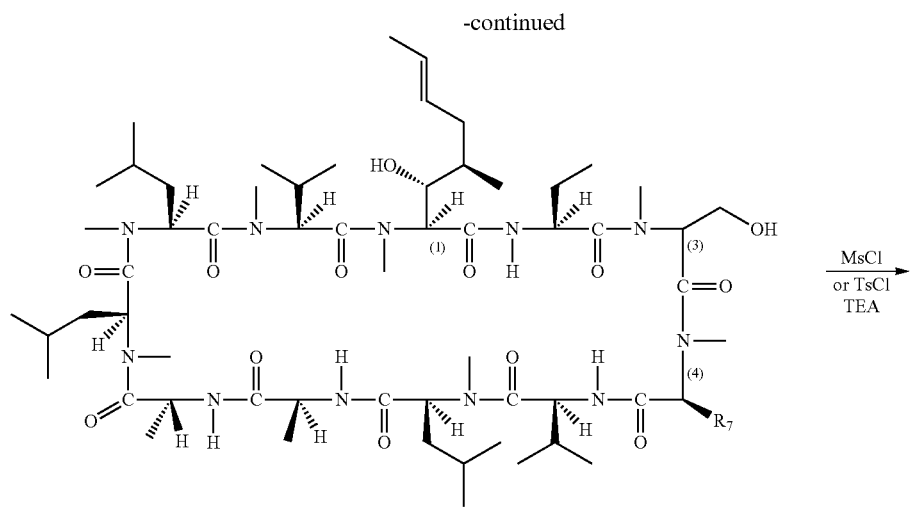
$\xrightarrow{\substack{\text{MsCl} \\ \text{or TsCl} \\ \text{TEA}}}$
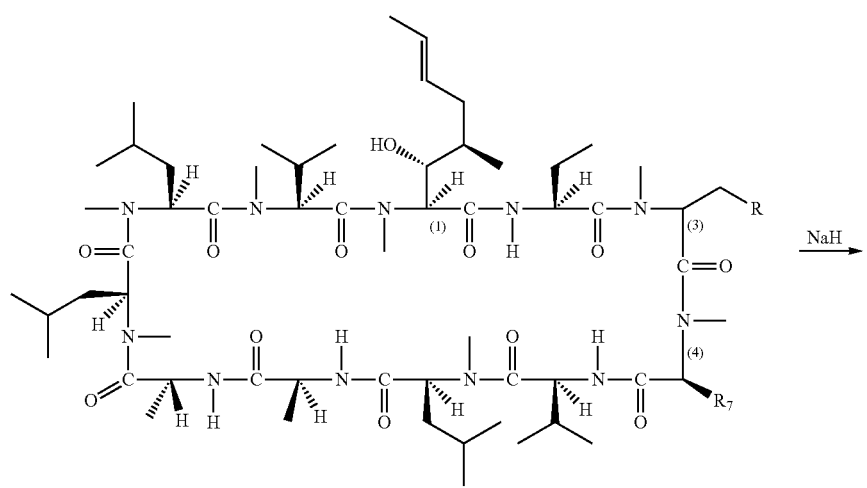
R = OMs, OTs, or Cl
$\xrightarrow{\text{NaH}}$
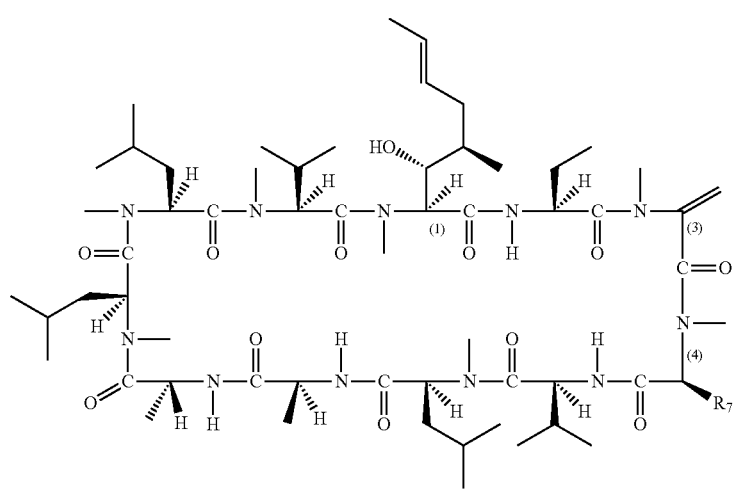

-continued
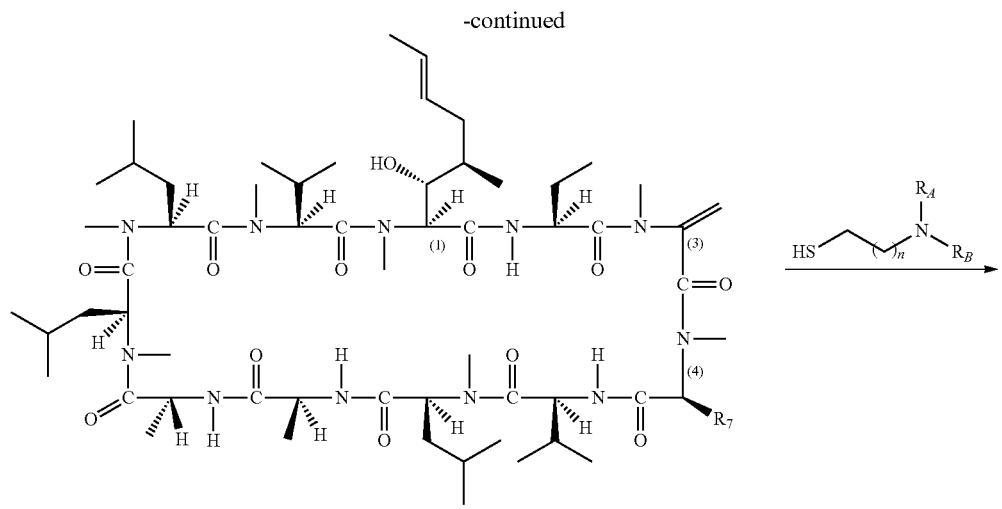
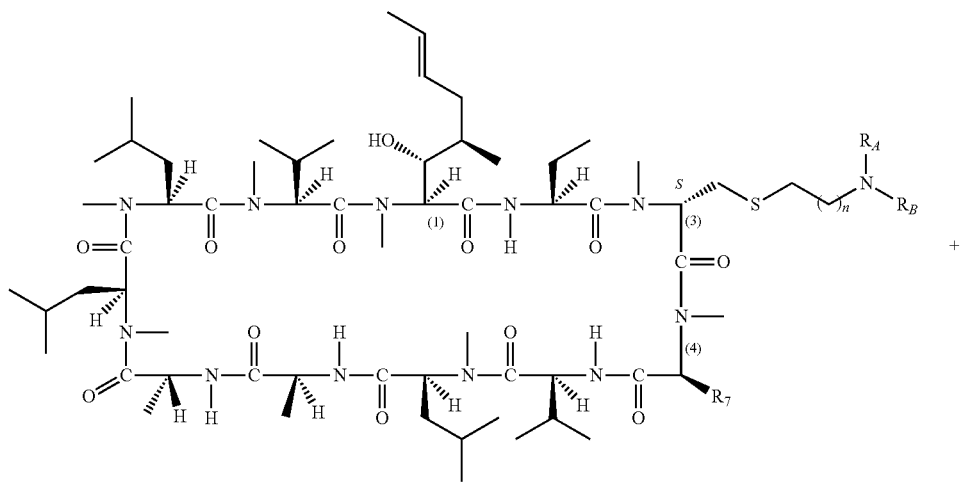
The desired compound
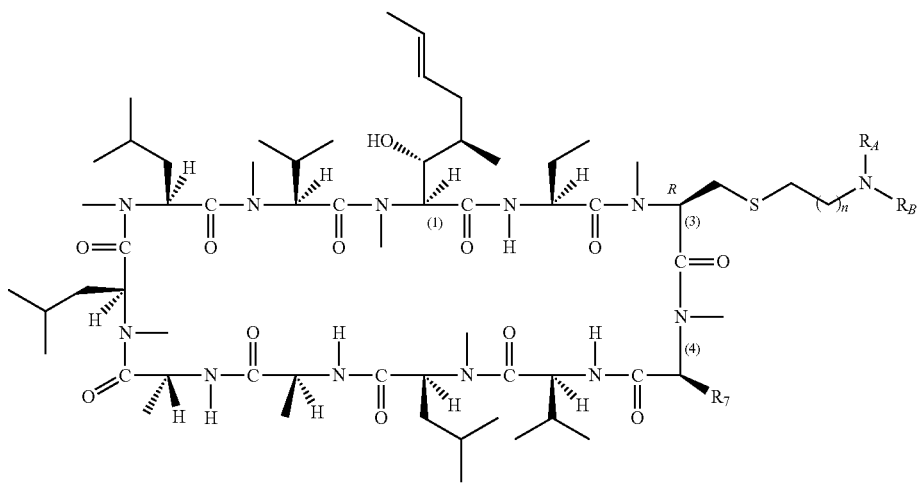
[α-Methylene-Sar]-3-cyclosporin can also be prepared using a method analogous to the procedure described in Reference Example 2 or WO2012/051194A1 (which is incorporated herein by reference).

In certain embodiments, the above resulting methylene-3-cyclosporin can be converted to its methylene amine side chain to form novel cyclosporine derivatives. For example:
Scheme 2
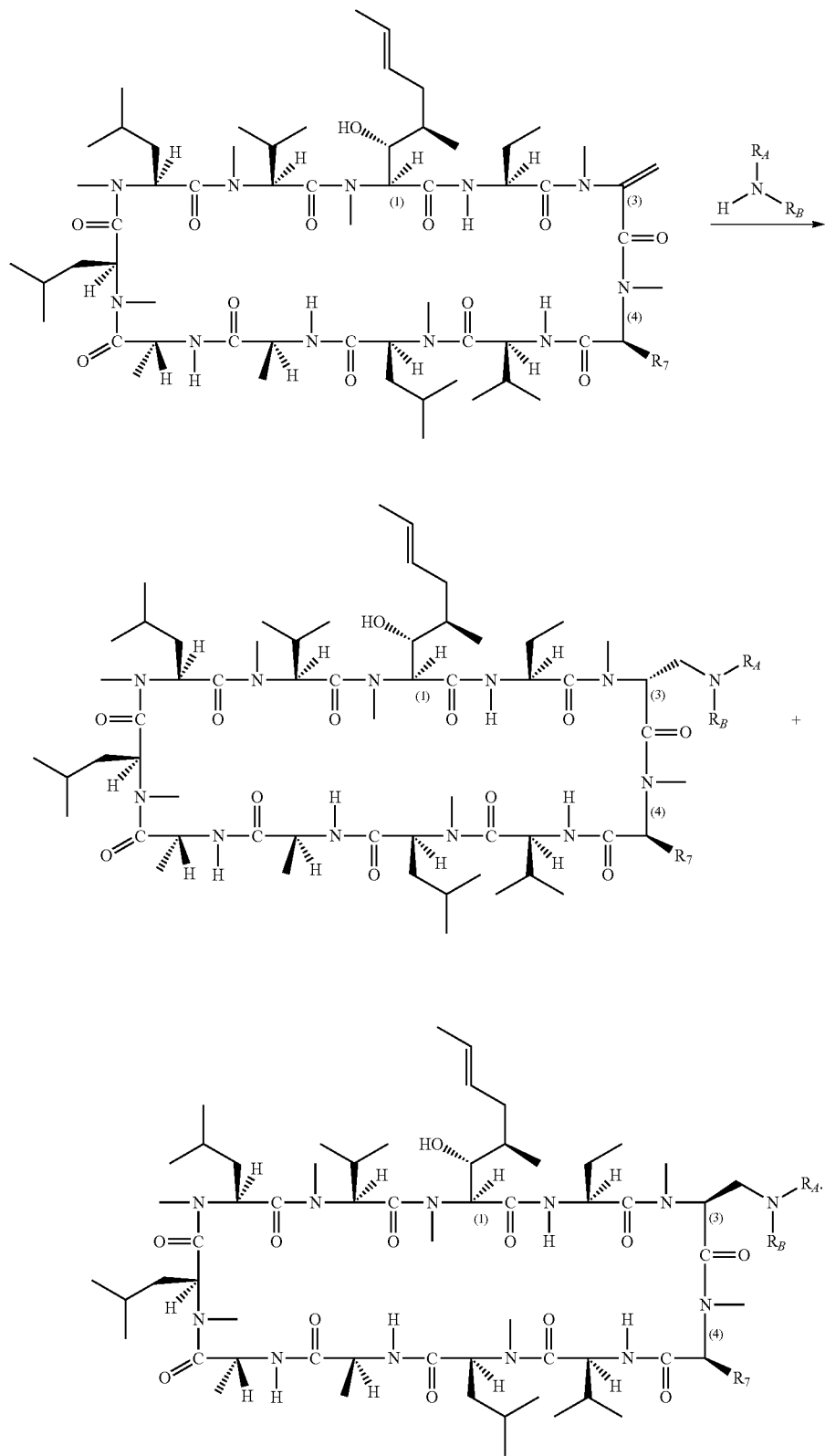

Therefore, the following derivatives can be prepared by this procedure.
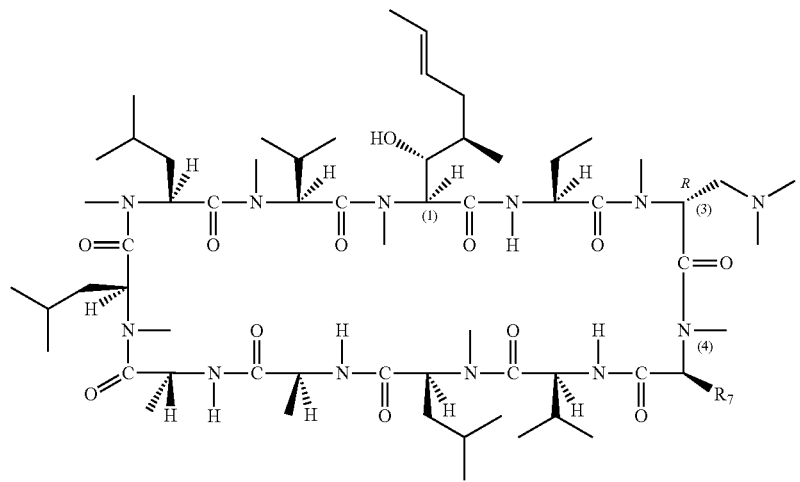
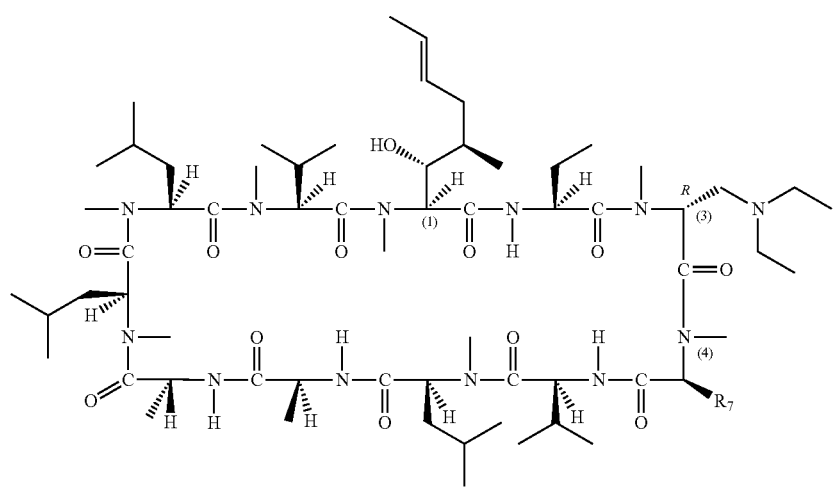
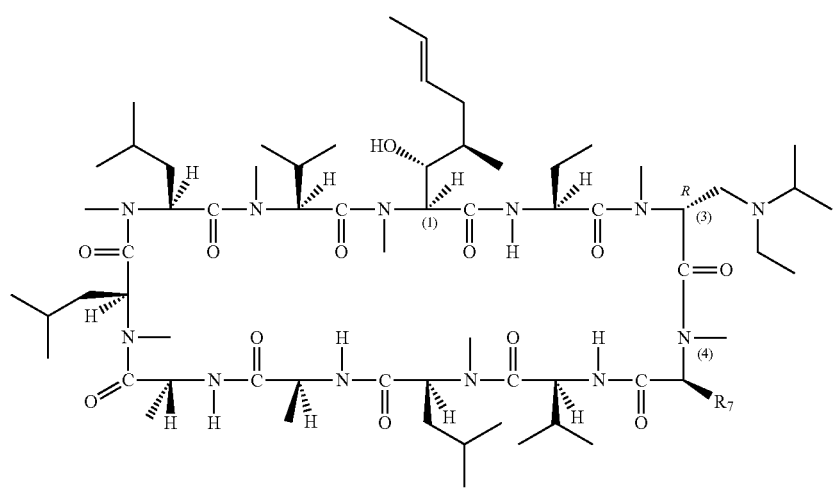

-continued
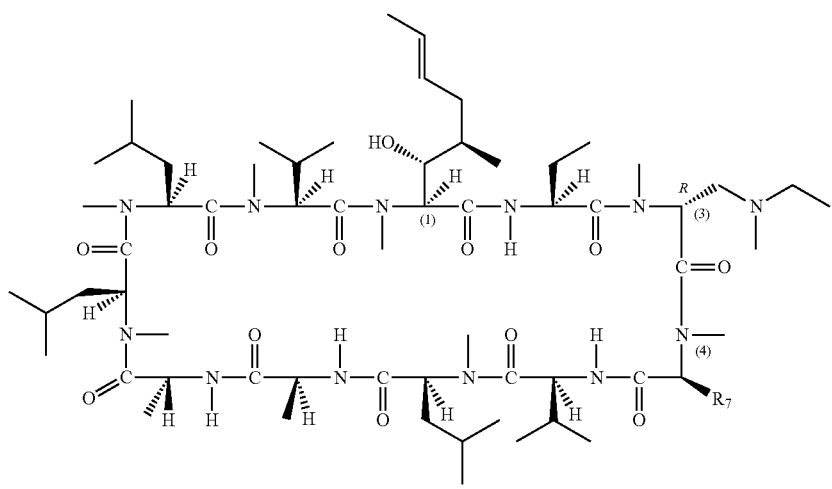
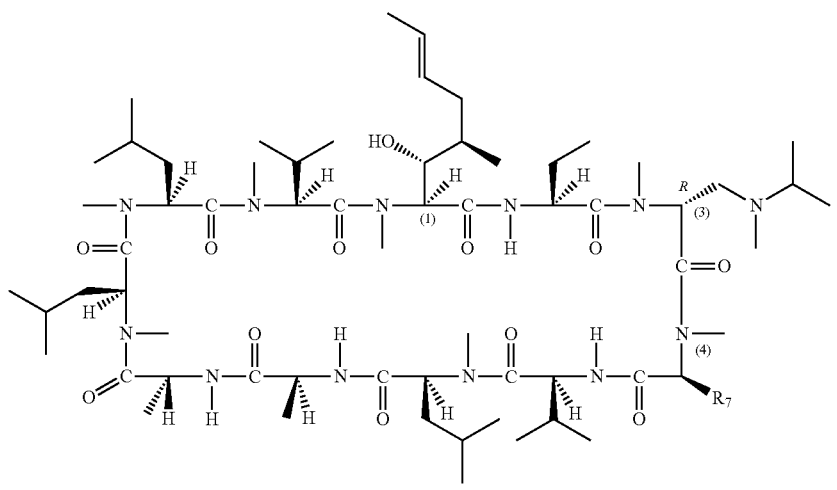
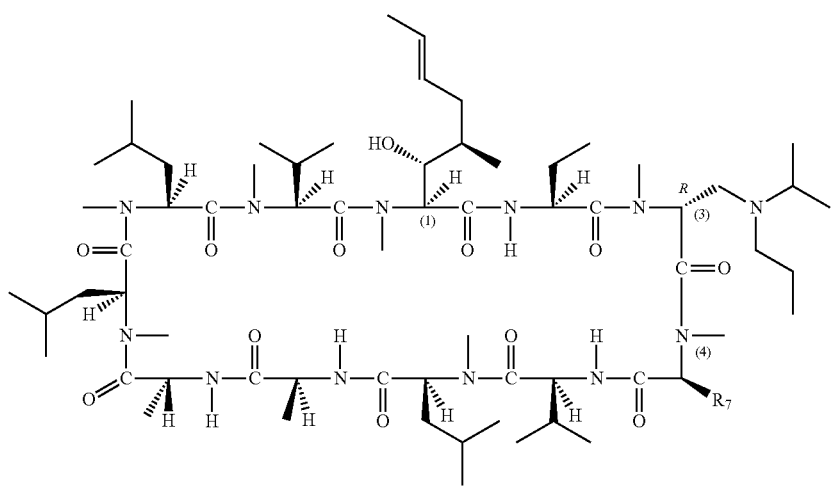

-continued
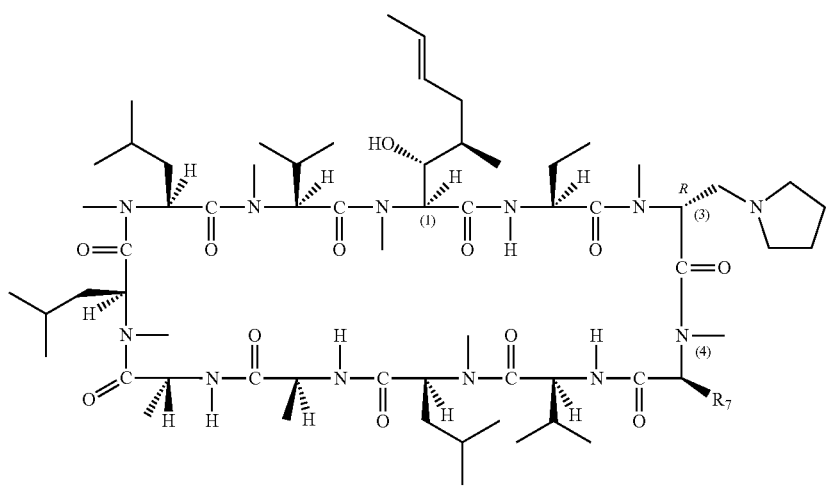
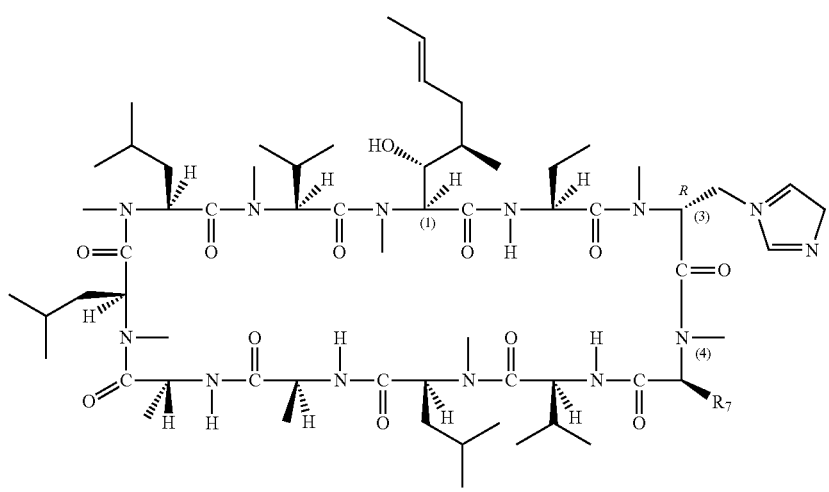
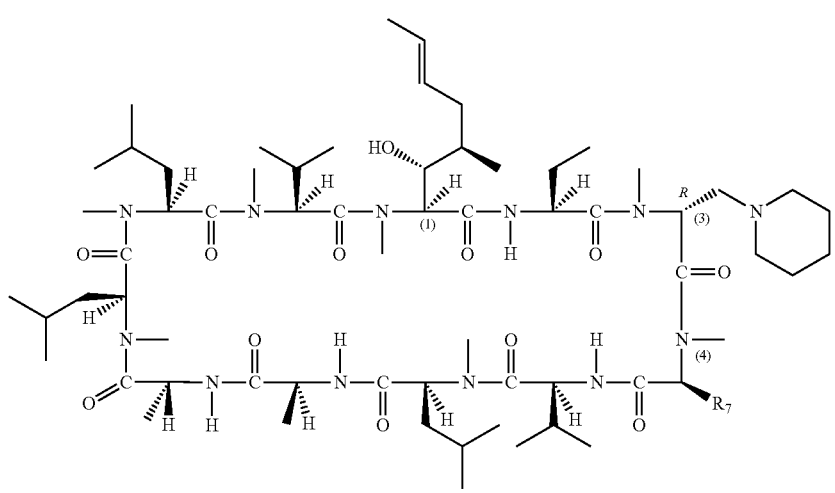

-continued
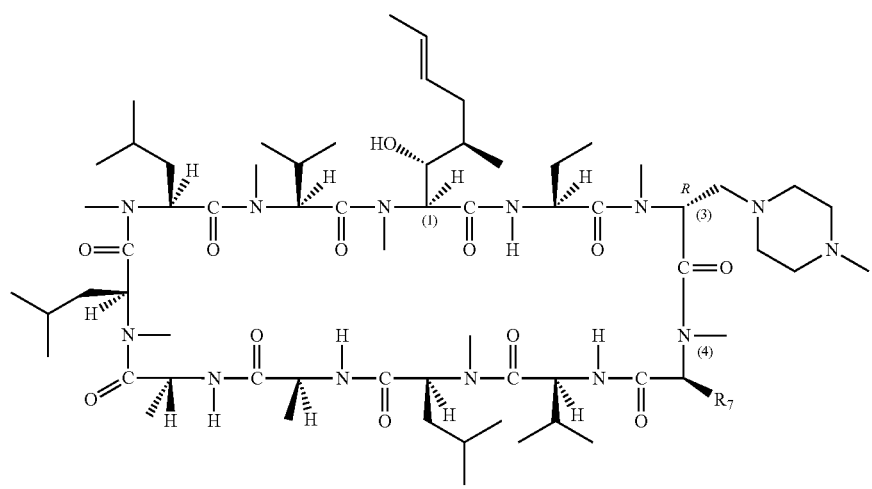
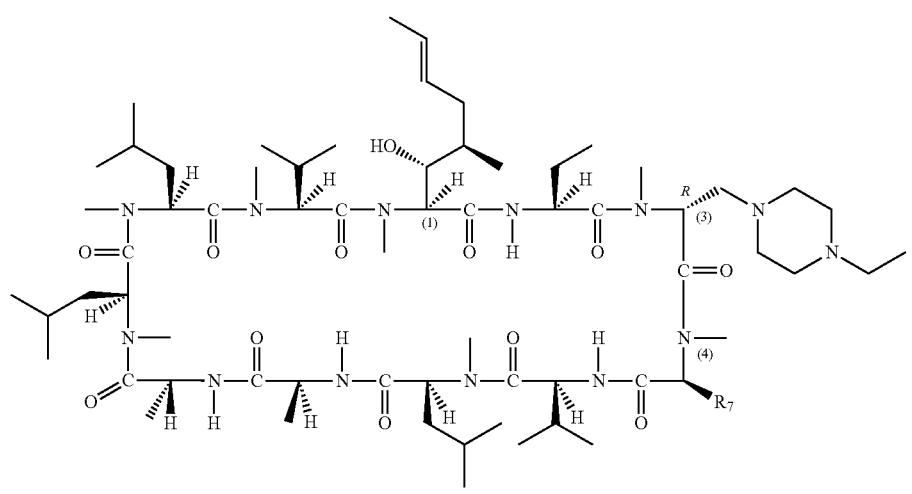
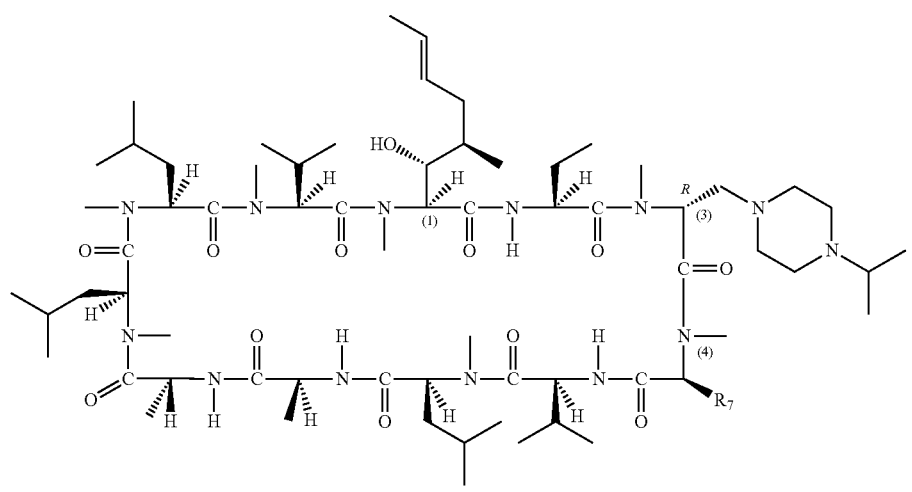

-continued
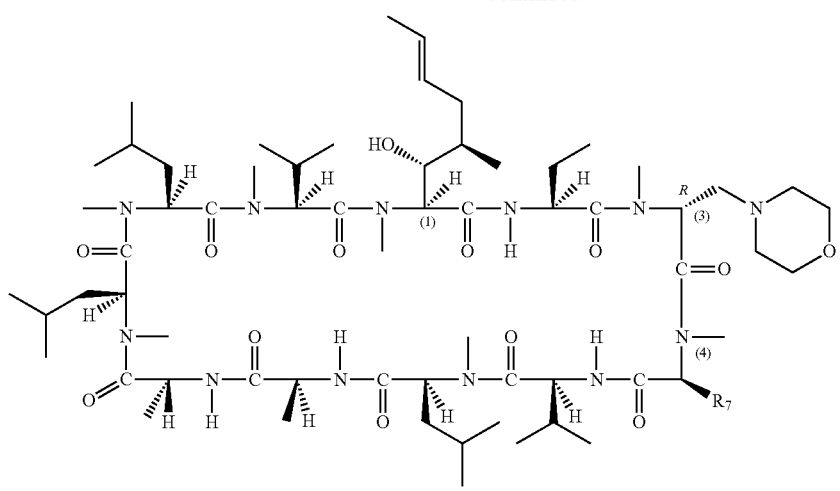
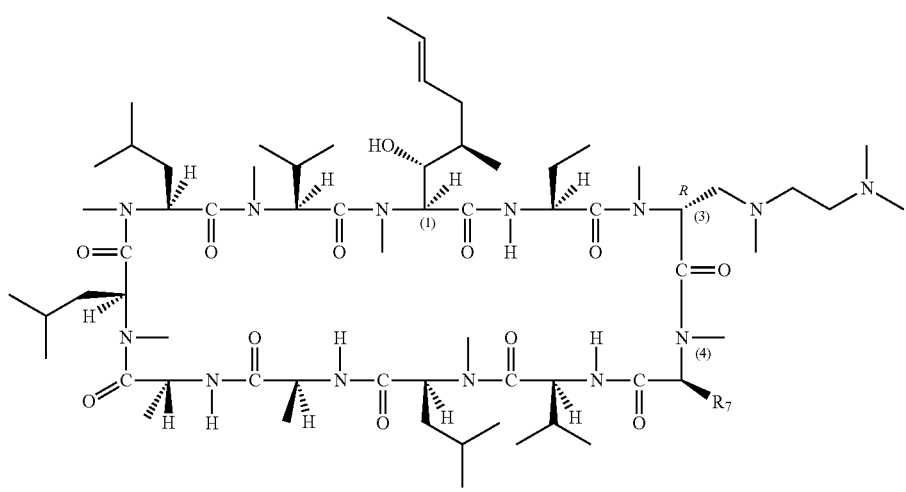
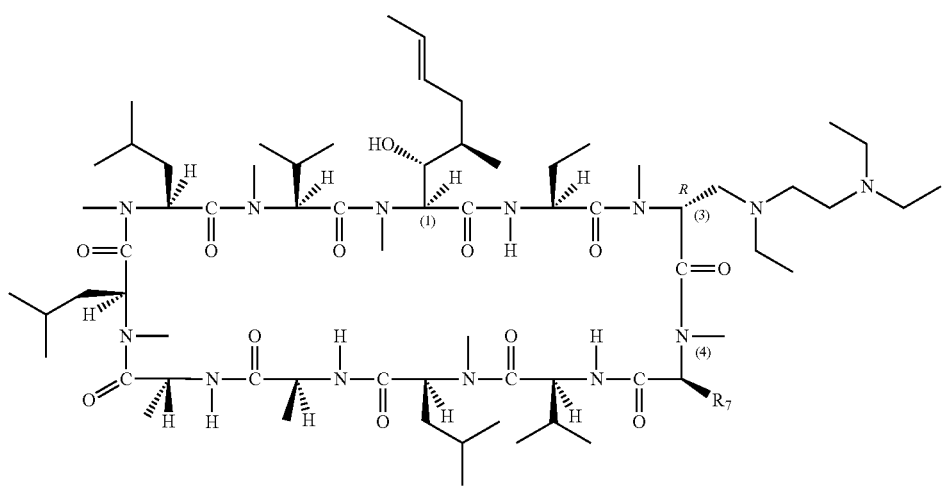

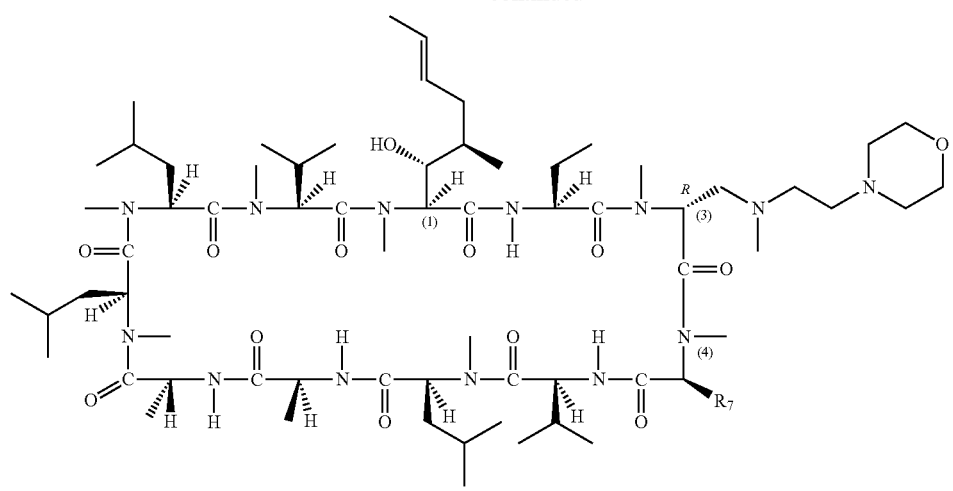
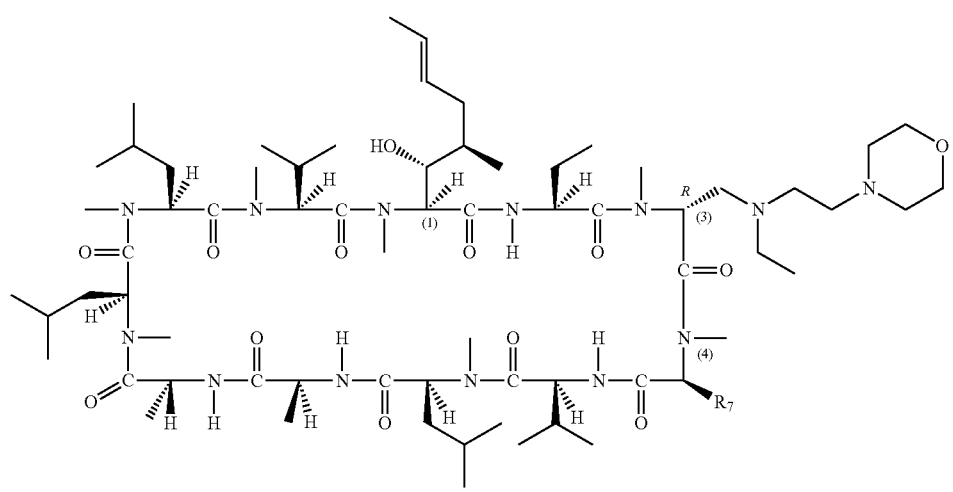
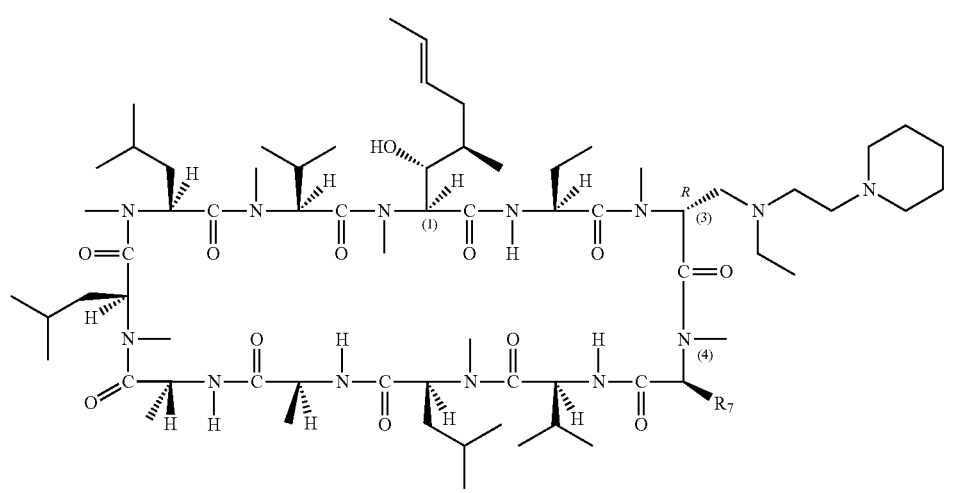

-continued
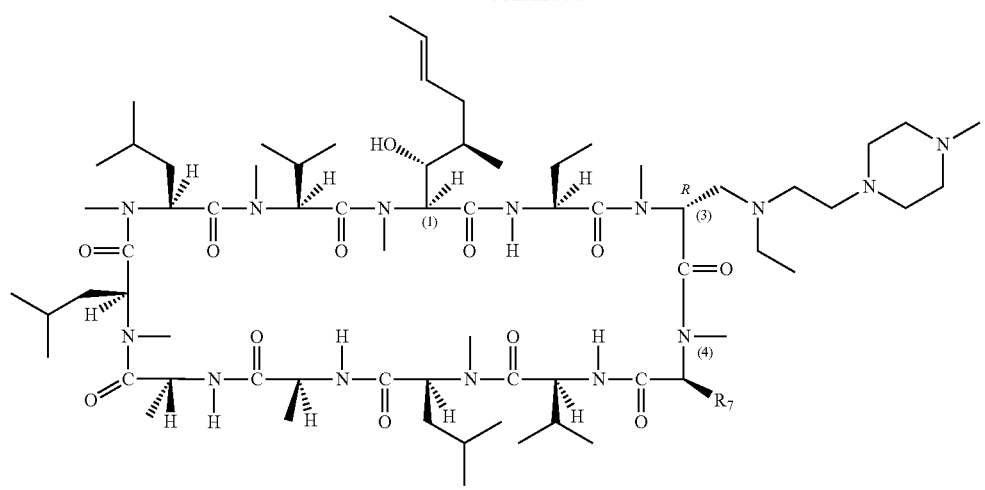
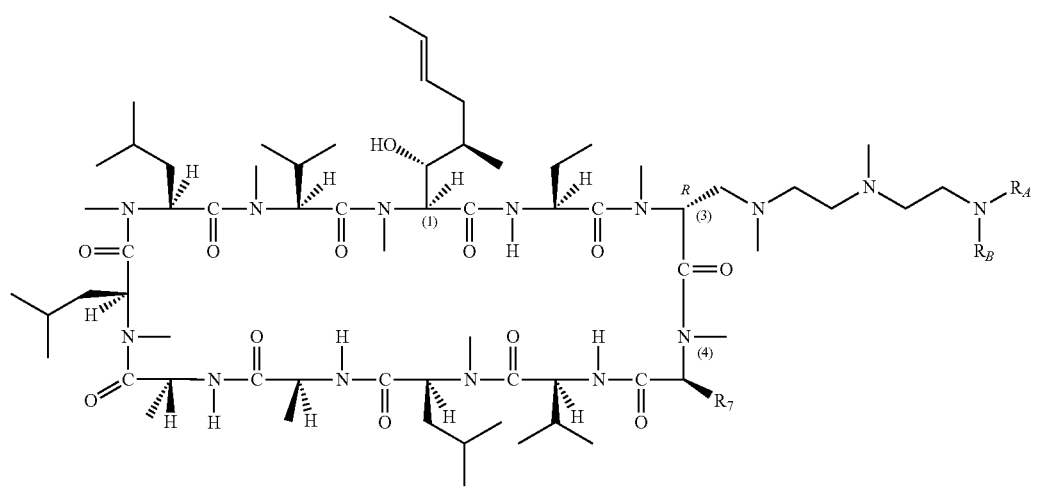
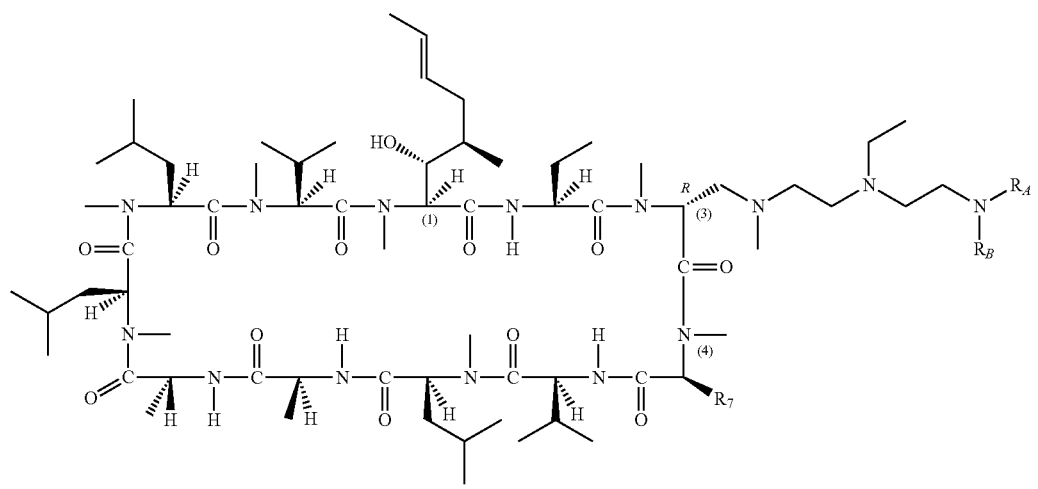

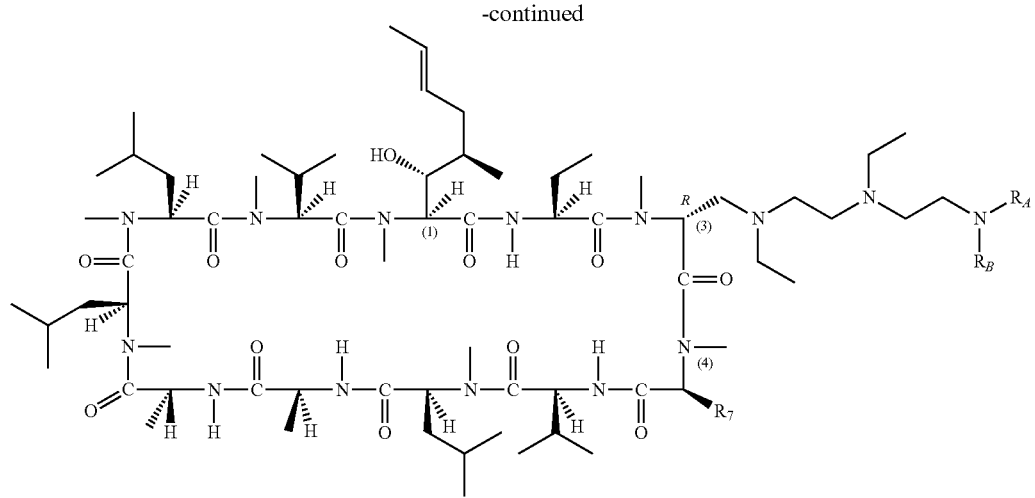
In certain embodiments, the above resulting alcohol can be converted to its methylene oxygen ether side chain to form novel cyclosporine derivatives too. For example:
Scheme 4
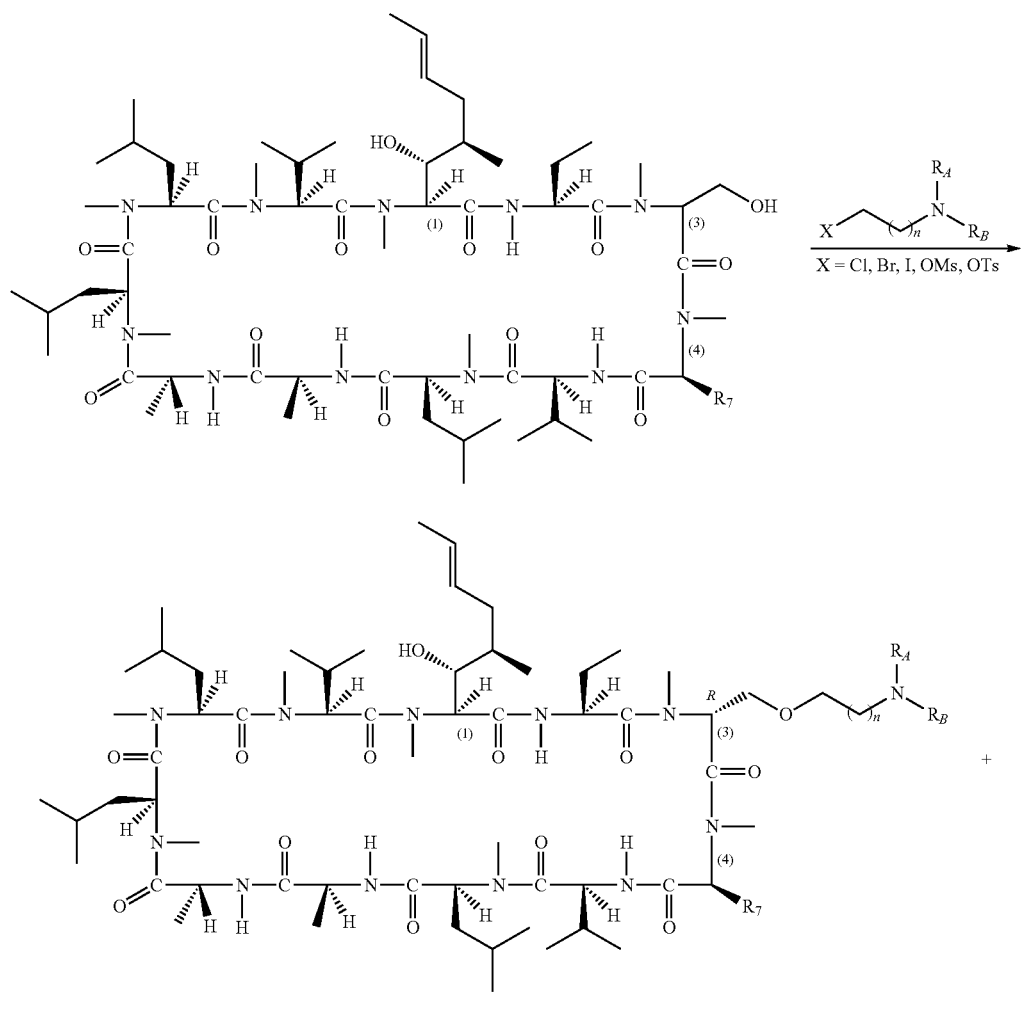
The desired compound -continued

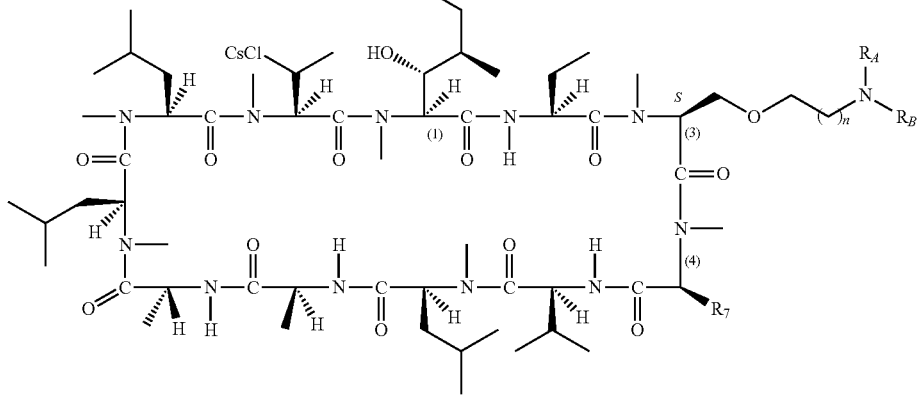

In Schemes 1-4 above, the symbols have the same meaning as defined in the claims and throughout the specification, unless otherwise noted.

In certain other embodiments, the compound of formula (IIa) or (IIIa) can be obtained according to the procedures described herein.

Pharmaceutical Compositions

This invention also provides a pharmaceutical composition comprising at least one of the compounds as described herein or a pharmaceutically-acceptable salt or solvate thereof, and a pharmaceutically-acceptable carrier.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present pharmaceutical agents may be provided in the form of pharmaceutically-acceptable salts. The term "pharmaceutically-acceptable salt", in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples are embedding compositions, which can be used include polymeric substances and waxes. The active ingredient can also be in micro-encapsulated form, if apbutriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the buter medium. Absorption enhancers can also be used to increase the flux of the pharmaceutical agents of the invention across the skin. The rate of such flux can be controlled, by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-HCV agent), or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Equivalents

The representative examples which follow are intended to help illustrate the invention, and are not intended to, nor should they be construed to, limit the scope of the invention.

EXAMPLES

Example 1

[α-Methoxycarbonyl-Sar]-3-cyclosporin

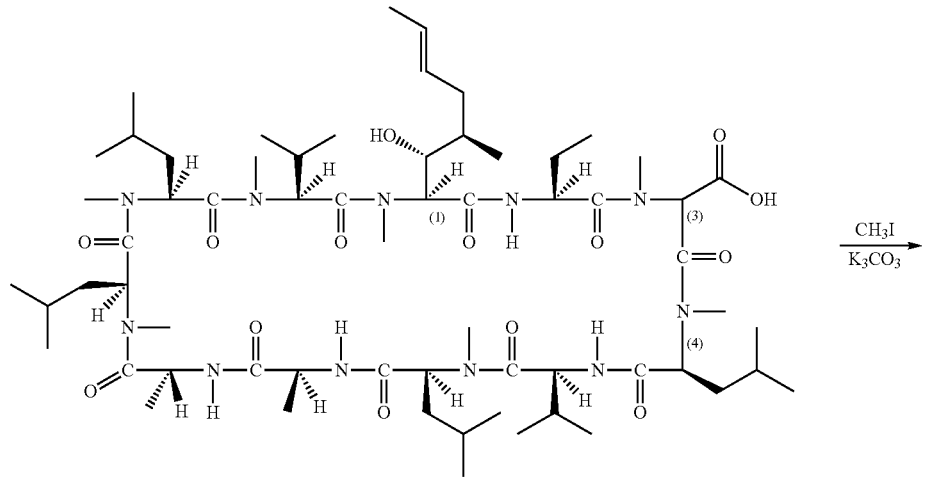

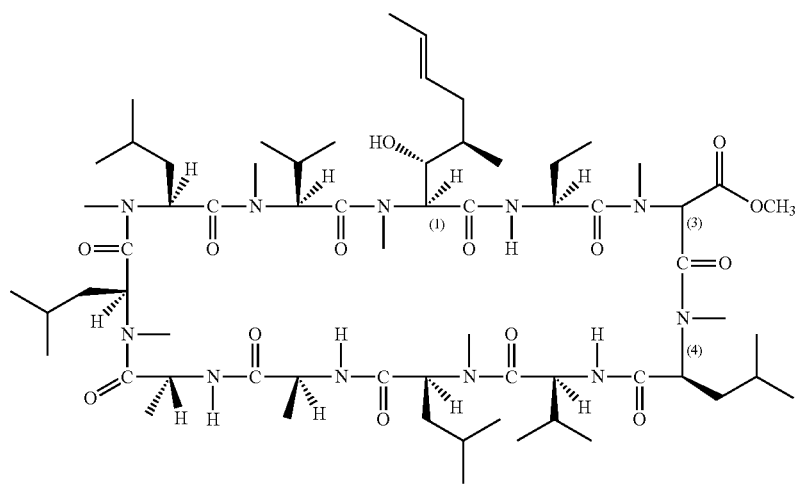

[α-Carboxy-sar]-3-cyclosporin (5.00 g, 4.01 mmol) was dissolved in N,N-dimethylformamide (30 ml). Iodomethane (2.85 g, 20.10 mmol) and potassium carbonate (1.38 g, 10.00 mmol) were added. The mixture was stirred at room temperature for 2 hours. Then ethyl acetate (60 ml) and water (60 ml) were added and the mixture was separated. The ethyl acetate layer was washed with brine, dried over magnesium sulfate and evaporated under reduced pressure to give 5.32 g of crude product, which was directly used for the next step without purification (yield: ~100%) [Molecular Formula: $C_{64}H_{113}N_{11}O_{14}$; Exact Mass: 1259.85; MS (m/z): 1260.7 (M+1)$^+$, 1282.7 (M+Na)$^+$; TLC $R_f$: 0.55 (dichloromethane/methanol=9/1)].

Example 2

[(R)-α-Hydroxymethyl-Sar]-3-cyclosporin

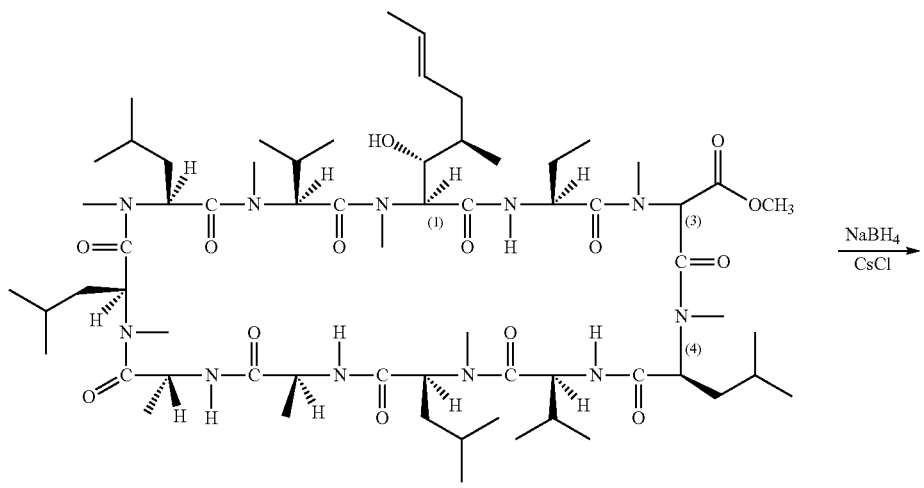

C₆₄H₁₁₃N₁₁O₁₄
Exact Mass: 1259.85
Mol. Wt.: 1260.67

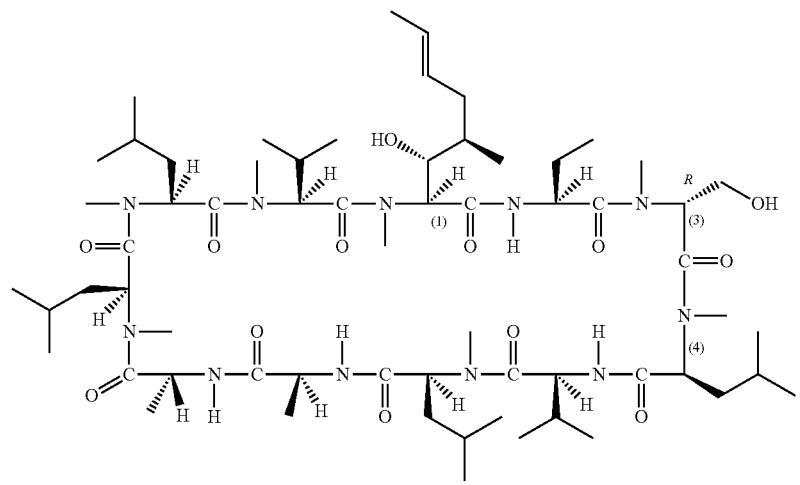

C₆₃H₁₁₃N₁₁O₁₃
Exact Mass: 1231.85
Mol. Wt.: 1232.66

[α-Methoxycarbonyl-Sar]-3-cyclosporin (2.00 g, 1.59 mmol) was dissolved in tetrahydrofuran (30 ml). Cesium chloride (1.33 g, 7.90 mmol) and sodium borohydride (0.60 g, 15.89 mmol) were added in portions. Then methanol (30 ml) was added dropwise to the mixture over 2 hours. After addition, the mixture was stirred at room temperature overnight. Most of solvent was then evaporated under reduced pressure. Ethyl acetate (50 ml) and water (50 ml) were added. The ethyl acetate layer was separated and washed with brine, dried over magnesium sulfate and evaporated under reduced pressure to give 1.99 g of crude product, which was purified by on silica gel column with dichloromethane/methanol (from 100:0 to 95:5) to give the 1.50 g of pure product (yield: 76%) [Molecular Formula: $C_{63}H_{113}N_{11}O_{13}$; Exact Mass: 1231.85; MS (m/z): 1232.7 (M+1)⁺, 1254.7 (M+Na)⁺].

Example 3

[α-Methylmethanesulfonate-Sar]-3-cyclosporin

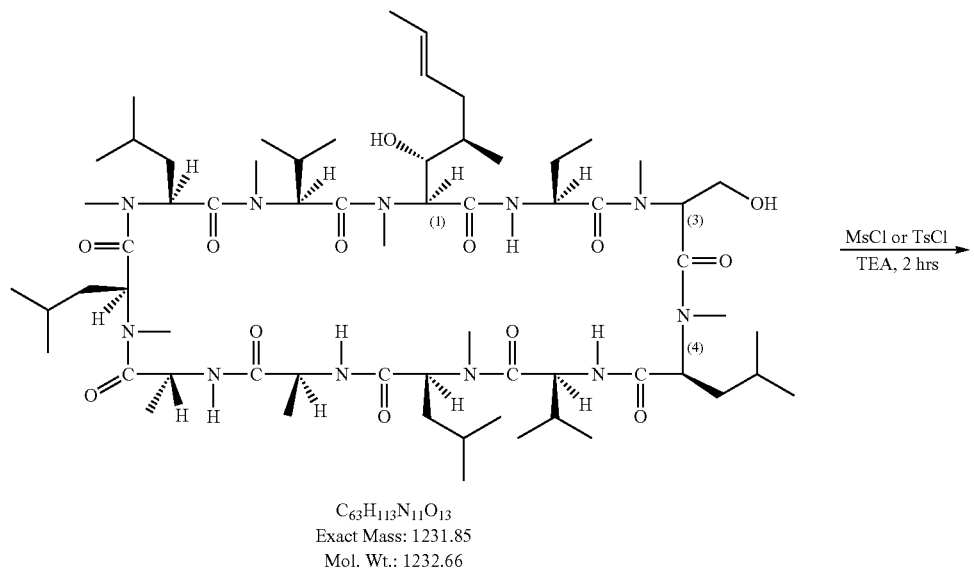

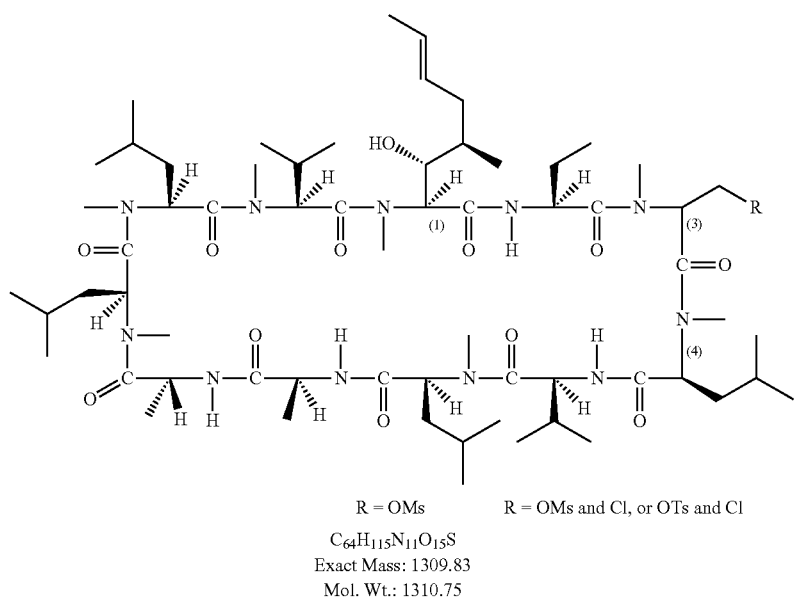

To a solution of [α-hydroxymethyl-Sar]-3-cyclosporin (30 mg, 0.024 mmol) in dichloromethane (2 ml) at 0° C. were added triethylamine (52.8 μl, 0.38 mmol), and methanesulfonyl chloride (23 mg, 0.20 mmol). The mixture was stirred at room temperature for two hours. Then reaction mixture was washed with brine, dried over magnesium sulfate and evaporated under reduced pressure to give 33 mg of crude product, which was directly used in next step reaction without further purification [Molecular Formula: $C_{64}H_{115}N_{11}O_{15}S$; Exact Mass: 1309.83; MS (m/z): 1310.7 $(M+1)^-$].

Example 4

[α-Chloromethyl-Sar]-3-cyclosporin

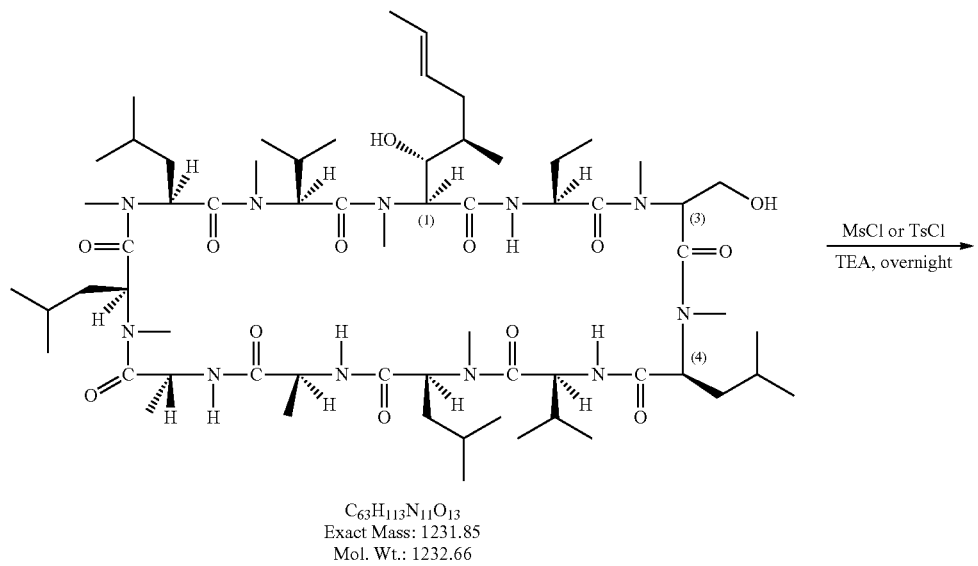

C63H113N11O13
Exact Mass: 1231.85
Mol. Wt.: 1232.66

MsCl or TsCl
TEA, overnight

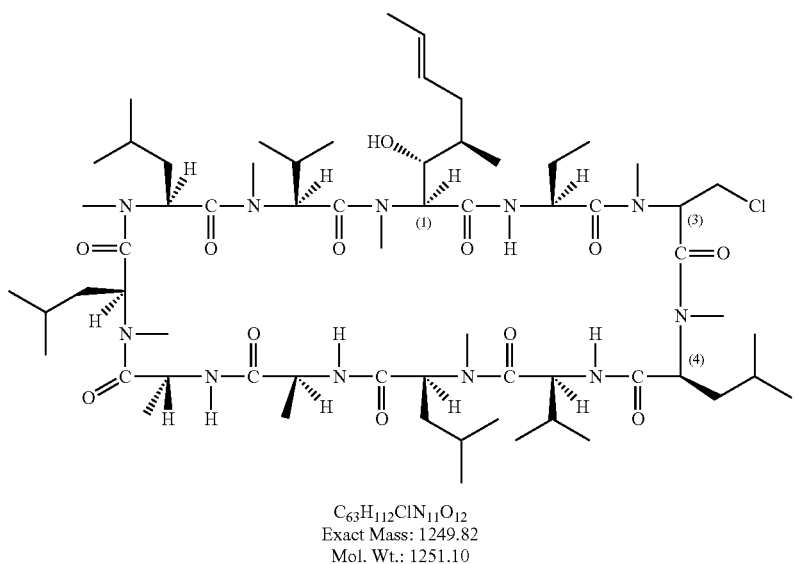

C63H112ClN11O12
Exact Mass: 1249.82
Mol. Wt.: 1251.10

To a solution of [α-hydroxymethyl-Sar]-3-cyclosporin (30 mg, 0.024 mmol) in dichloromethane (2 ml) at 0° C. were added triethylamine (52.8 µL, 0.384 mmol, 16 equivalents) and methanesulfonyl chloride (23 mg, 0.20 mmol). The mixture was stirred at room temperature overnight. Then the reaction mixture was washed with brine, dried over magnesium sulfate and evaporated under reduced pressure to give 30 mg of crude product, which was directly used in next step reaction without further purification [Molecular Formula: $C_{63}H_{112}ClN_{11}O_{12}$; Exact Mass: 1249.82; MS (m/z): 1250.7 (M+1)$^-$, 1272.9 (M+Na)$^+$].

Example 5

[α-Methylene-Sar]-3-cyclosporin*

$C_{64}H_{115}N_{11}O_{15}S$
Exact Mass: 1309.83
Mol. Wt.: 1310.75

R = OMs

R = OMs, or OTs, and Cl $C_{63}H_{111}N_{11}O_{12}$
Exact Mass: 1213.84
Mol. Wt.: 1214.65

To a solution of either [α-methanesulfonatemethyl-Sar]-3-cyclosporin (33 mg, 0.025 mmol) or [α-chloromethyl-Sar]-3-cyclosporin (30 mg, 0.025 mmol) in tetrahydrofuran (3 ml) was added sodium hydride (15.3 mg, 60% in oil, 0.38 mmol, 10 equivalents) at 0° C. The mixture was stirred at 0° C. for one hour and then warmed up to room temperature for 30 minutes. After removal of solvent, the residue was dissolved in dichloromethane (20 ml). The dichloromethane layer was washed with 1 N hydrochloric acid, saturated sodium bicarbonate solution and brine, dried over magnesium sulfate and evaporated under reduced pressure. The residue was purified by chromatography on silica gel using dichloromethylene/methanol (20/1) to give 16 mg of product (yield: 54%) [Molecular Formula: $C_{63}H_{111}N_{11}O_{12}$; Exact Mass: 1213.84; MS (m/z): 1214.7 $(M+1)^+$, 1236.7 $(M+Na)^+$; TLC $R_f$: 0.55 (ethyl acetate/methanol=20/1); HPLC RT: 7.0 min (C8 reverse phase column: 150 mm; acetonitrile/water (0.05% trifluoroacetic acid); operation temperature: 64° C.; detector: 210 nm)].

[α-Methylene-Sar]-3-cyclosporin can also be prepared by a method analogous to the procedure described in WO2012/051194A1 (which is incorporated herein by reference).

Example 6
[(S)-(2-(N,N-Dimethylamino)ethylthio)methyl-Sar]-3-cyclosporin (Isomer B) and [(R)-(2-(N,N-Dimethylamino)ethylthio)methyl-Sar]-3-cyclosporin (Isomer A)
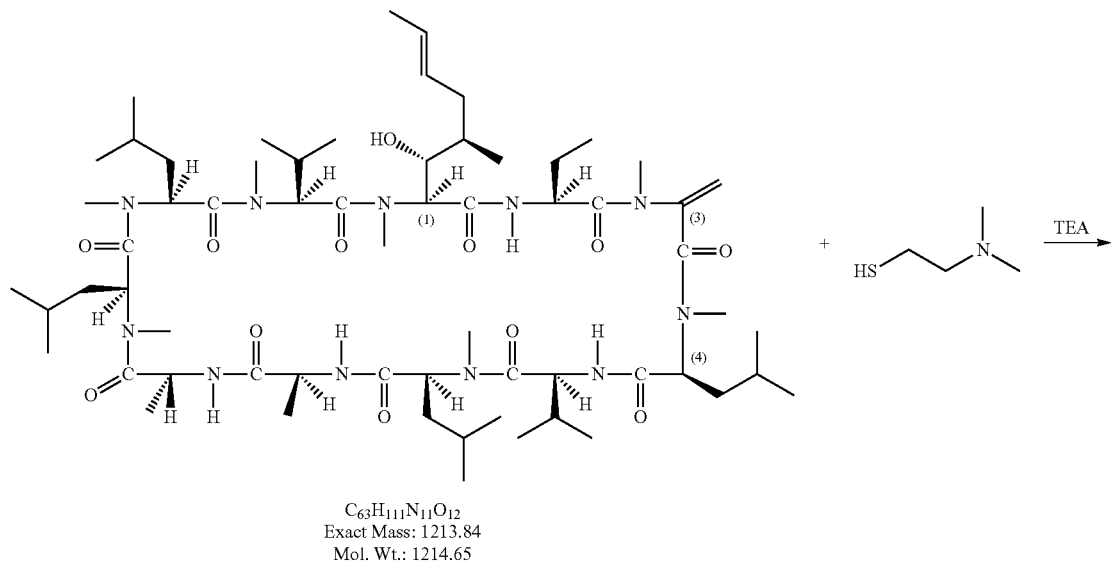
$C_{63}H_{111}N_{11}O_{12}$
Exact Mass: 1213.84
Mol. Wt.: 1214.65
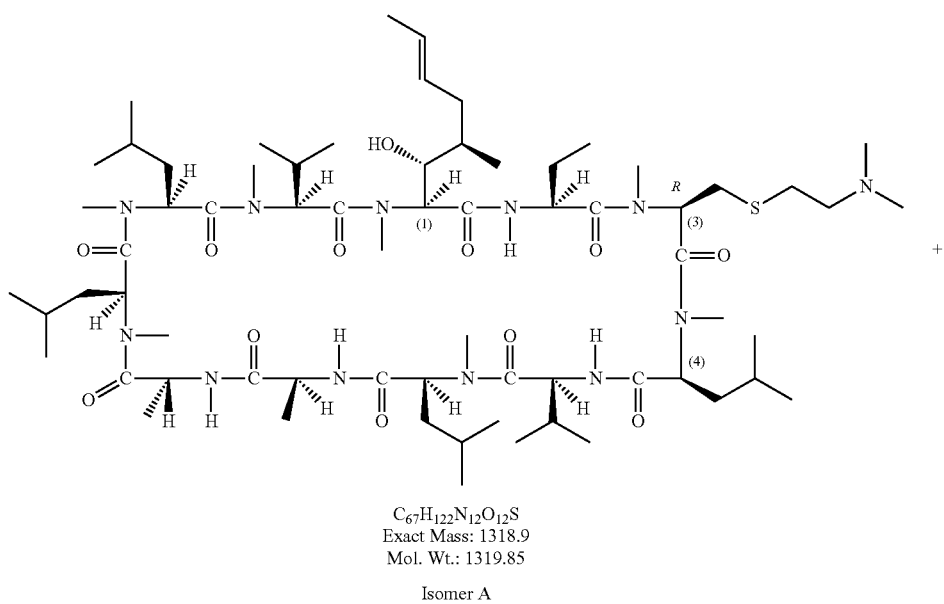
$C_{67}H_{122}N_{12}O_{12}S$
Exact Mass: 1318.9
Mol. Wt.: 1319.85
Isomer A

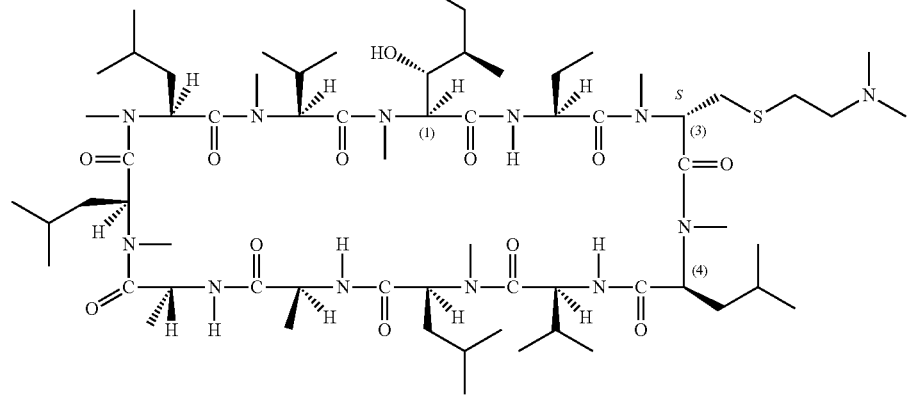

$C_{67}H_{122}N_{12}O_{12}S$
Exact Mass: 1318.9
Mol. Wt.: 1319.85

Isomer B

To a solution of [α-methylene-Sar]-3-cyclosporine (0.60 g, 0.50 mmol) and 2-(dimethylamino)ethanethiol (0.63 g, 6.00 mmol) in methanol (20 ml) was added triethylamine (0.82 ml, 6.0 mmol). The reaction mixture was stirred overnight at room temperature. After removal of solvent, the residue was subjected to chromatography using dichloromethane/methanol as eluent to give 0.35 g of (R)-2-(N,N-dimethylamino)ethylthiomethyl-Sar]-3-cyclosporin (isomer A) and 0.20 g of [(S)-2-(N,N-dimethylamino) ethylthiomethyl-Sar]-3-cyclosporin (isomer B) [Molecular Formula: $C_{67}H_{122}N_{12}O_{12}S$; Exact Mass: 1218.9; MS (m/z): 1319.80 (M+1)$^+$; TLC $R_f$: 0.20 (ethyl acetate/methanol=5/1); HPLC RT: 12.55 min (isomer A) and 13.22 min (isomer B) (C8 reverse phase column: 250 mm; acetonitrile/water (0.05% trifluoroacetic acid); operation temperature: 64° C.; detector: 210 nm)].

Example 7

[(S)-(2-(N,N-Diethylamino)ethylthio)methyl-Sar]-3-cyclosporin (Isomer B) and [(R)-(2-(N,N-Diethylamino)ethylthio)methyl-Sar]-3-cyclosporin (Isomer A)

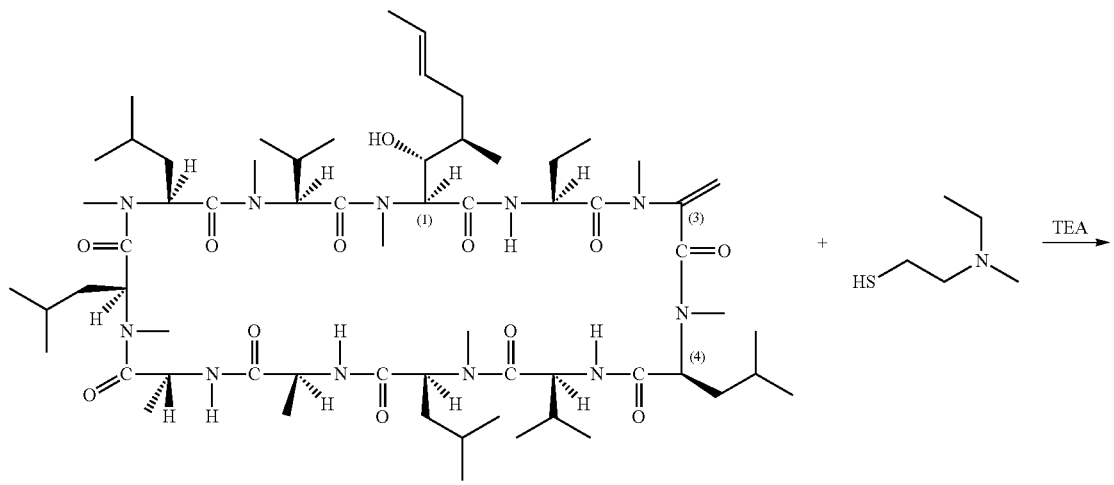

$C_{63}H_{111}N_{11}O_{12}$
Exact Mass: 1213.84
Mol. Wt.: 1214.65

-continued

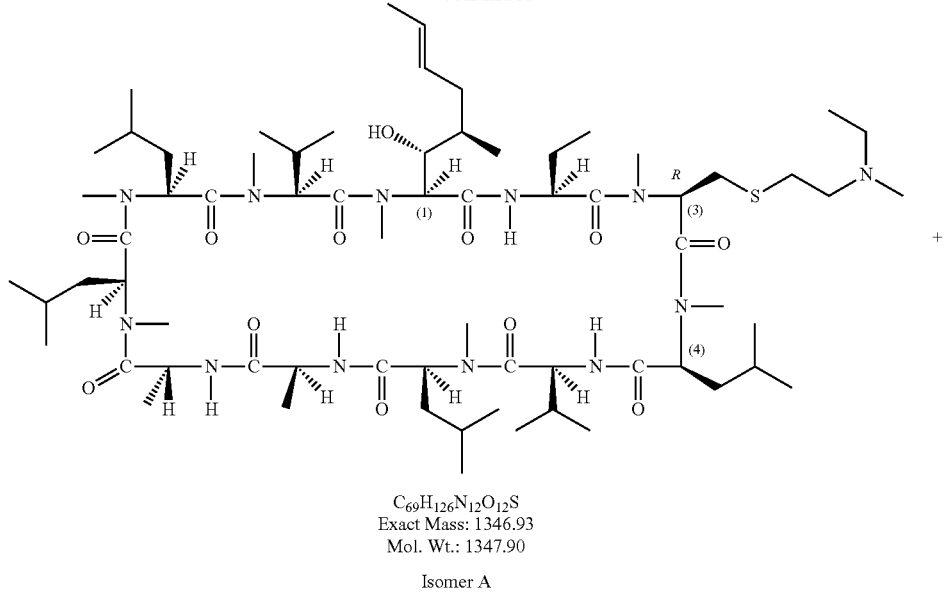

C$_{69}$H$_{126}$N$_{12}$O$_{12}$S
Exact Mass: 1346.93
Mol. Wt.: 1347.90

Isomer A

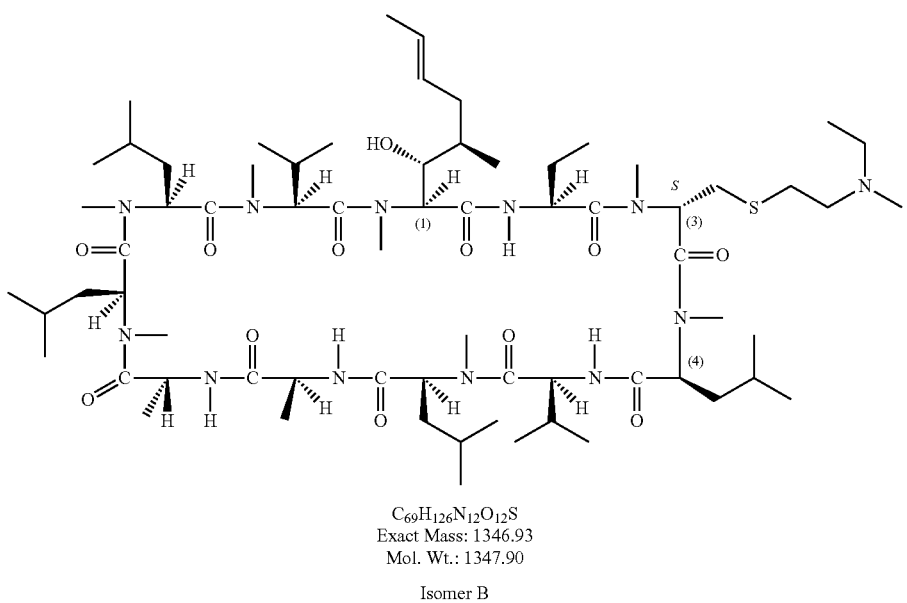

C$_{69}$H$_{126}$N$_{12}$O$_{12}$S
Exact Mass: 1346.93
Mol. Wt.: 1347.90

Isomer B

To a solution of [α-methylene-Sar]-3-cyclosporin (0.31 g, 0.25 mmol) and 2-diethylaminoethanethiol (0.40 g, 3.00 mmol) in methanol (10 ml) was added triethylamine (0.41 ml, 3.00 mmol, 12 equivalents). The reaction mixture was stirred overnight at room temperature. After removal of solvent, the residue was subjected to chromatography using dichloromethane/methanol as eluent to yield 0.20 g of [(R)-2-(N,N-Diethylamino)ethylthiomethyl-Sar]-3-cyclosporin (isomer A) and 0.08 g of [(S)-2-(N,N-Diethylamino)ethylthiomethyl-Sar]-3-cyclosporin (isomer B) [Molecular Formula: C$_{69}$H$_{126}$N$_{12}$O$_{12}$S; Exact Mass: 1346.93; MS (m/z): 1347.80 (M+1)$^+$; TLC R$_f$: 0.23 (ethyl acetate/methanol=5/1); HPLC RT: 13.37 min (isomer A) and 13.91 min (isomer B) (C8 reverse phase column: 250 mm; acetonitrile/water (0.05% trifluoroacetic acid); operation temperature: 64° C.; detector: 210 nm)].

Example 8

[(R)-(2-(N,N-Diethylamino)ethoxy)methyl-Sar]-3-cyclosporin

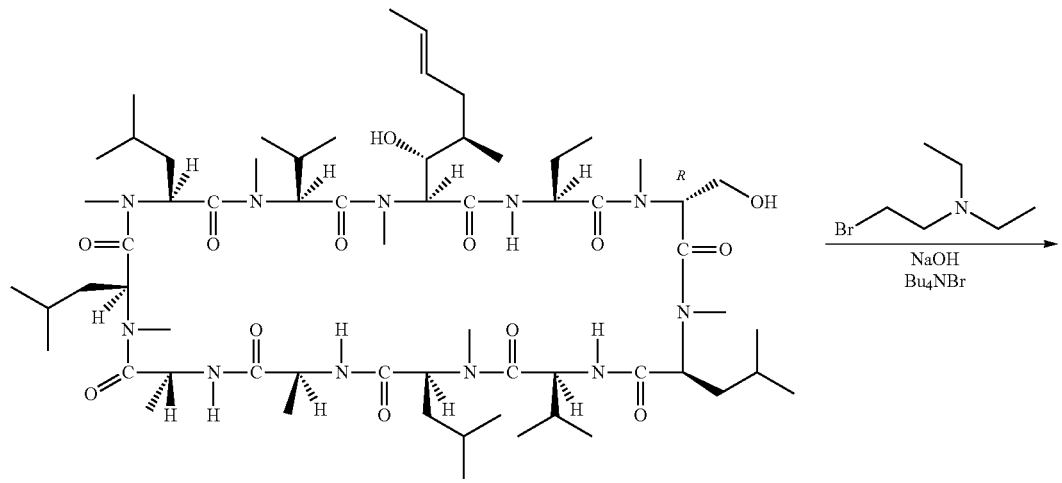

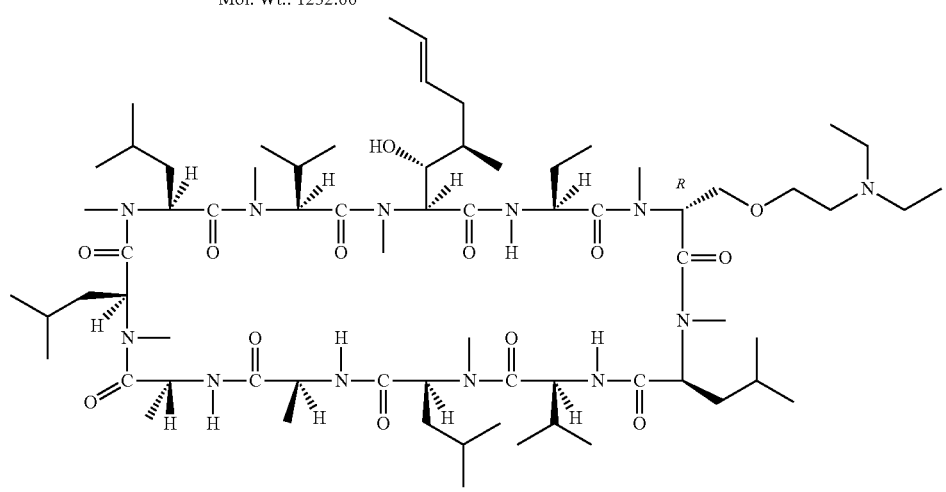

To a solution of [(R)-α-hydroxymethyl-Sar]-3-cyclosporin (0.36 g, 0.29 mmol) in benzene (30 ml) were added a solution of sodium hydroxide (1.20 g, 30 mmol) in water (2 ml), 2-bromo-N,N-diethylethylamine hydrobromide (3.80 g, 14.56 mmol) and tetra-n-butylammonium bromide(0.20 g, 0.62 mmol). The reaction mixture was stirred at 30° C. for 20 hours. After diluted with ice water, the mixture was separated. The aqueous layer was extracted with dichloromethane (30 ml). The combined organic layers were washed with brine, dried over magnesium sulfate and evaporated under reduced pressure. The residue was purified by chromatography (dichloromethane/methanol=96/4) to give 210 mg of product [Molecular Formula: $C_{69}H_{126}N_{12}O_{13}$; Exact Mass: 1330.96; MS (m/z): 1331.71 (M+1)$^+$; TLC $R_f$: 0.38 (dichloromethane/methanol=95/5); HPLC RT: 14.12 min (C8 reverse phase column: 250 mm; acetonitrile/0.077% ammonium acetate in water; operation temperature: 64° C.; detector: 210 nm)].

Example 9

[(R)-(tert-Butoxycarbonylmethoxy)methyl-Sar]-3-cyclosporin

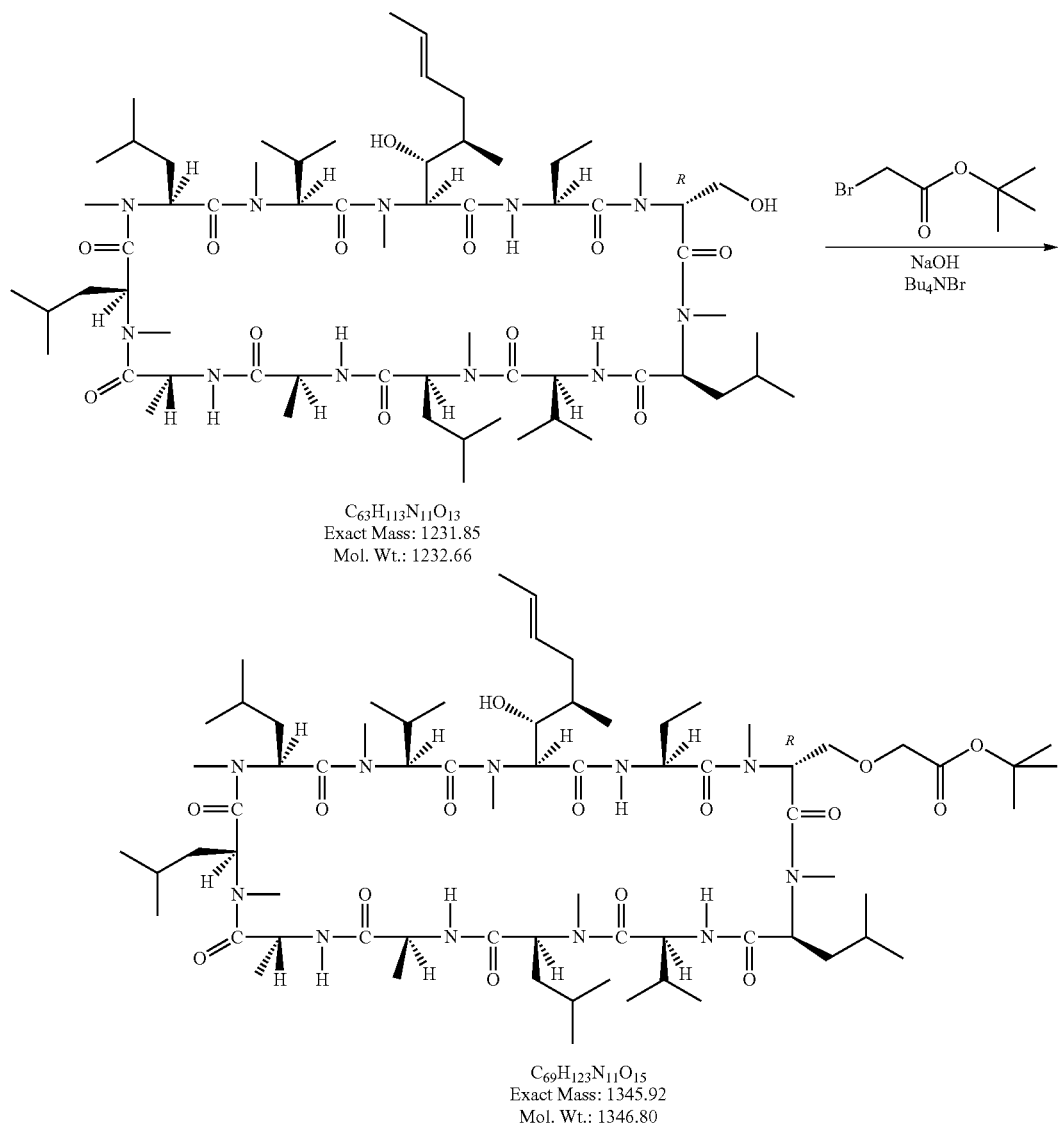

To a solution of [(R)-α-hydroxymethyl-Sar]-3-cyclosporin (0.50 g, 0.41 mmol) in benzene (30 ml) were added a solution of sodium hydroxide (1.00 g, 25.00 mmol) in water (1 ml), t-butyl bromoacetate (3.20 g, 16.41 mmol) and tetra-n-butylammonium bromide (0.40 g, 1.24 mmol). The mixture was stirred at room temperature for 10 hours. After diluted with ice water, the mixture was separated. The aqueous layer was extracted with dichloromethane (30 ml). The combined organic layers were washed with brine, dried over magnesium sulfate and evaporated under reduced pressure. The residue was purified by chromatography (hexane/acetone=2/1) to give 0.41 g product [Molecular Formula: $C_{69}H_{123}N_{11}O_{15}$; Exact Mass: 1345.92; MS (m/z): 1346.61 (M+1)$^+$; TLC $R_f$: 0.60 (dichloromethane/methanol=95/5); HPLC RT: 18.29 min (C8 reverse phase column: 250 mm; acetonitrile/0.077% ammonium acetate in water; operation temperature: 64° C.; detector: 210 nm)].

Example 10

[(R)-(Ethoxycarbonylmethoxy)methyl-Sar]-3-cyclosporin

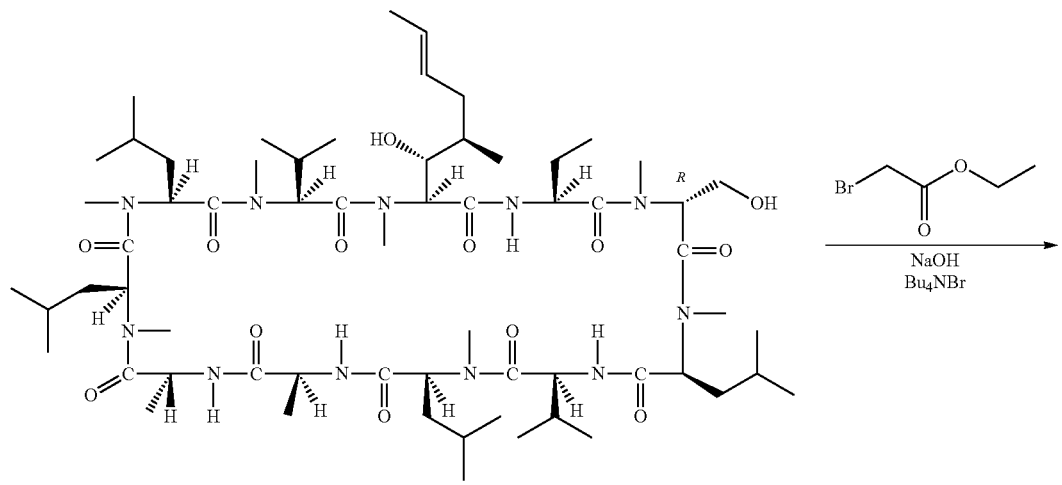

C$_{63}$H$_{113}$N$_{11}$O$_{13}$
Exact Mass: 1231.85
Mol. Wt.: 1232.66

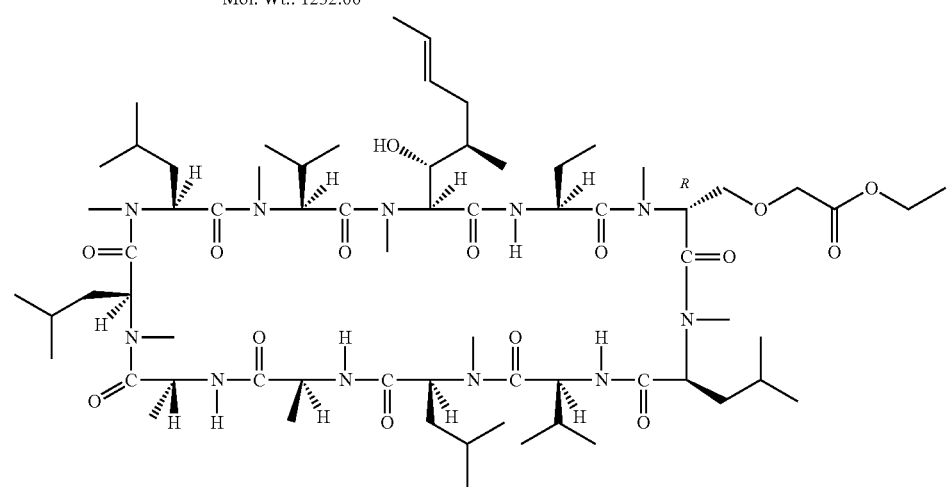

C$_{67}$H$_{119}$N$_{11}$O$_{15}$
Exact Mass: 1317.89
Mol. Wt.: 1318.75

To a solution of [(R)-α-hydroxymethyl-Sar]-3-cyclosporin (0.35 g, 0.28 mmol) in benzene (15 ml) were added a solution of sodium hydroxide (0.60 g, 15.00 mmol) in water (1 ml), ethyl bromoacetate (1.60 g, 9.58 mmol) and tetra-n-butylammonium bromide (0.20 g, 0.62 mmol). The mixture was stirred at room temperature for 10 hours. After diluted with ice water, the mixture was separated. The aqueous layer was extracted with dichloromethane (15 ml). The combined organic layers were washed with brine, dried over magnesium sulfate and evaporated under reduced pressure. The residue was purified by chromatography (hexane/acetone=2/1) to give 0.31 g of product [Molecular Formula: C$_{67}$H$_{119}$N$_{11}$O$_{15}$; Exact Mass: 1317.89; MS (m/z): 1318.46 (M+1)$^+$; TLC R$_f$: 0.55 (dichloromethane/methanol=95/5); HPLC RT: 17.40 min (C8 reverse phase column: 250 mm; acetonitrile/0.077% ammonium acetate in water; operation temperature: 64° C.; detector: 210 nm)].

Example 11

[(R)-(Carboxymethoxy)methyl-Sar]-3-cyclosporin

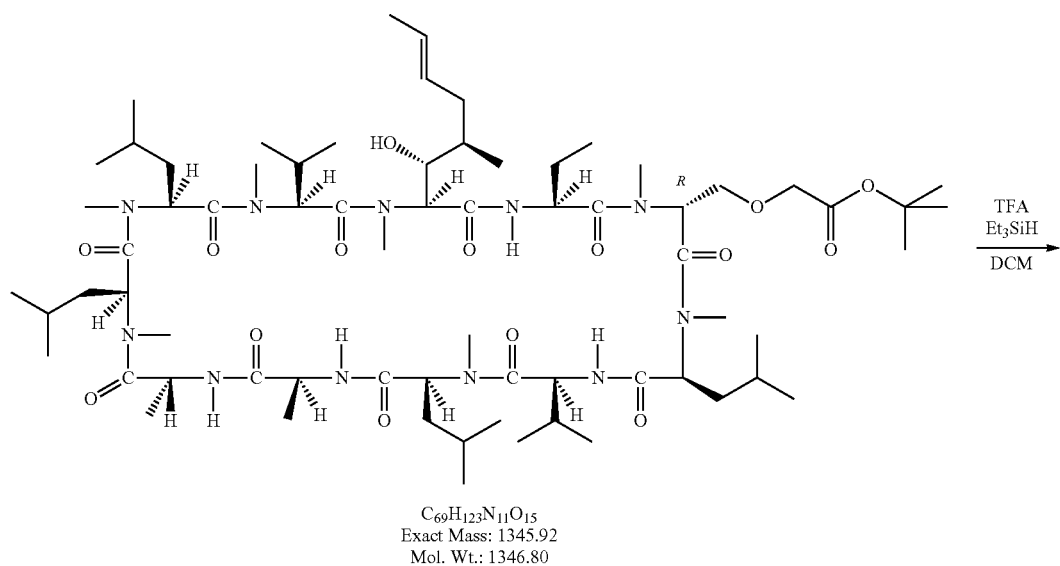

$C_{69}H_{123}N_{11}O_{15}$
Exact Mass: 1345.92
Mol. Wt.: 1346.80

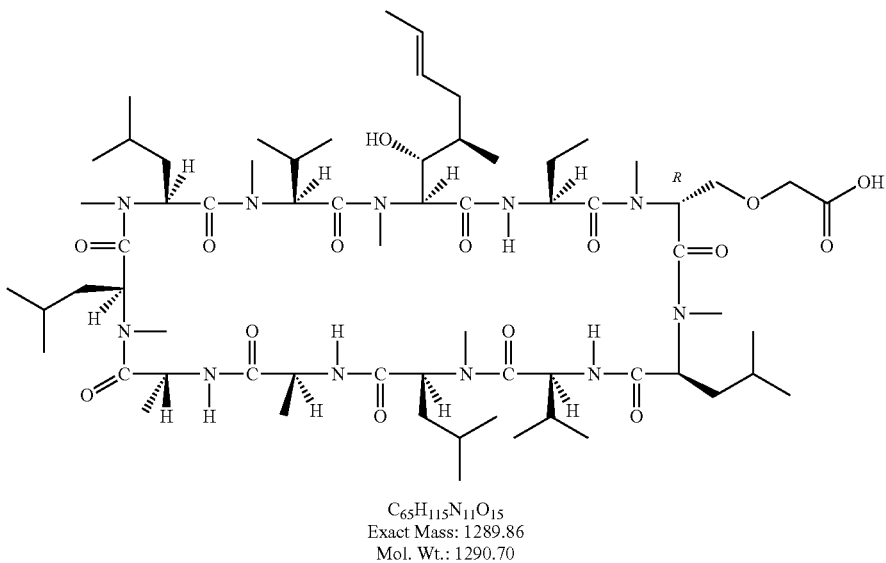

$C_{65}H_{115}N_{11}O_{15}$
Exact Mass: 1289.86
Mol. Wt.: 1290.70

To a solution of [(R)-((tert-butoxycarbonyl)methoxy)methyl-Sar]-3-cyclosporin (0.18 g, 0.13 mmol) in dichloromethane (5 ml) were added trifuloroacetic acid (1 ml) and triethylsilane (10 drops). The mixture was stirred at room temperature for 3 hours and concentrated under reduced pressure. Then dichloromethane (10 ml) and water (10 ml) were added and the mixture was separated. The dichloromethane layer was dried over magnesium sulfate and evaporated under reduced pressure. The residue was purified by C-18 chromatography (acetonitrile/water) to give 75 mg of product [Molecular Formula: $C_{65}H_{115}N_{11}O_{15}$; Exact Mass: 1289.86; MS (m/z): 1290.56 (M+1)$^+$; HPLC RT: 11.03 min (C8 reverse phase column: 250 mm; acetonitrile/water (0.05% trifluoroacetic acid); operation temperature: 64° C.; detector: 210 nm)].

Example 12

[(R)-(Carboxymethoxy)methyl-Sar]-3-cyclosporin-sodium salt

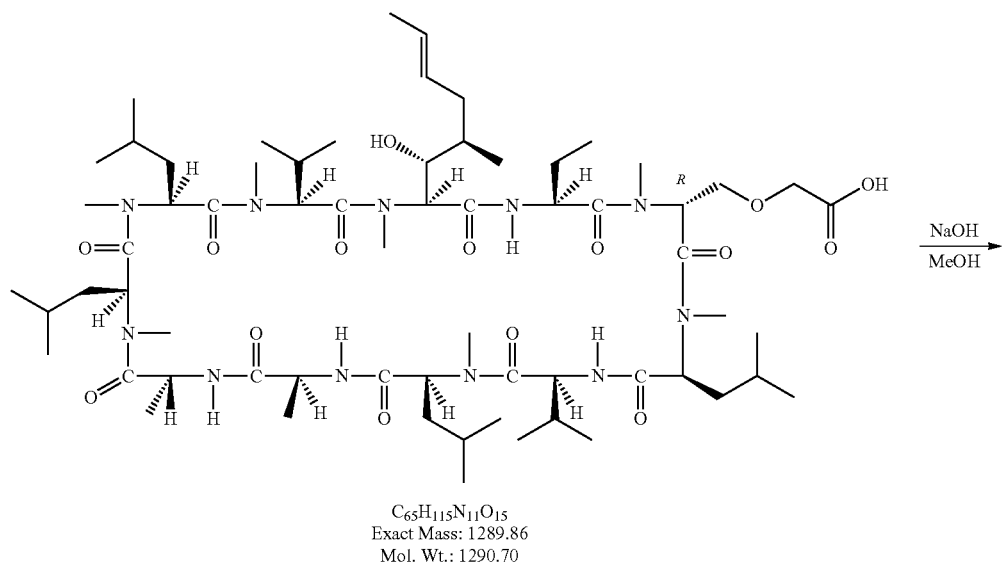

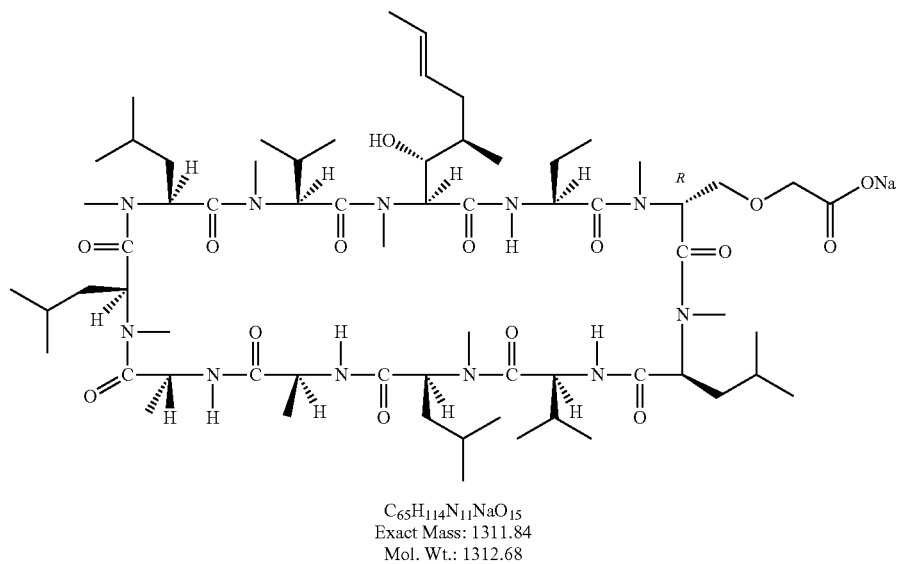

To a solution of [(R)-(carboxymethoxy)methyl-Sar]-3-cyclosporin (30 mg, 0.02 mmol) in methanol (1 ml) was added a solution of sodium hydroxide (1.00 mg, 0.02 mmol) in water (0.5 ml). The mixture was stirred at room temperature 1 hour and dried in high vacuum to give 28 mg of product [Molecular Formula: $C_{65}H_{114}N_{11}NaO_{15}$; Exact Mass: 1311.84; MS (m/z): 1290.56 (M+1-Na)$^+$; HPLC RT: 10.98 min (C8 reverse phase column: 250 mm; acetonitrile/water (0.05% trifluoroacetic acid); operation temperature: 64° C.; detector: 210 nm)].

Example 13

[(R)-(2-Hydroxyethoxy)methyl-Sar]-3-cyclosporin

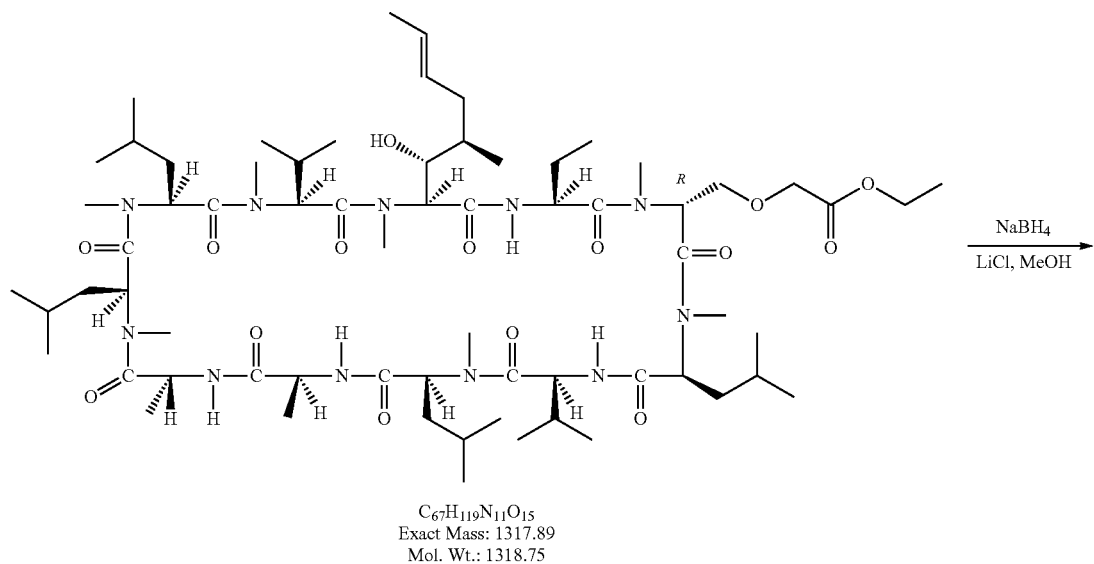

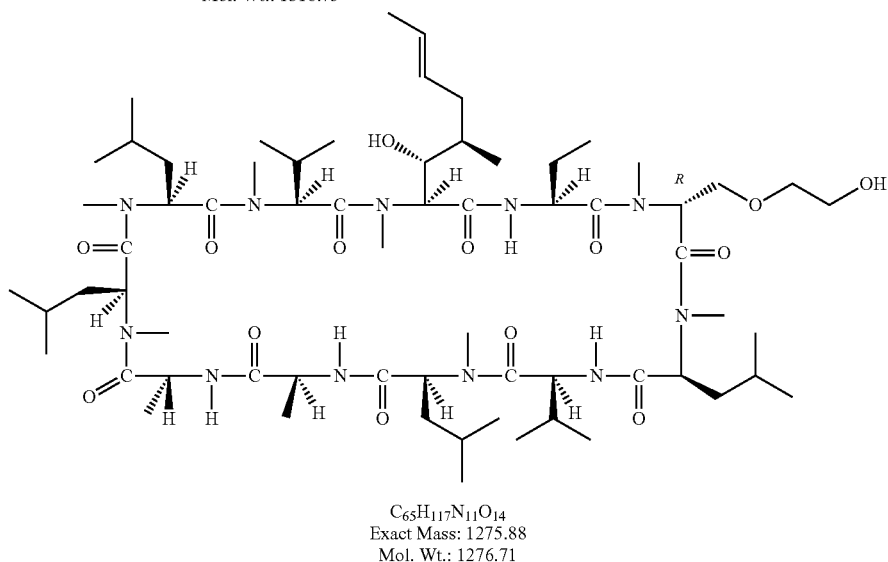

To a solution of [(R)-(ethoxycarbonylmethoxy)methyl-Sar]-3-cyclosporin (0.25 g, 0.19 mmol) in methanol (30 ml) were added lithium chloride (0.33 g, 7.85 mmol) and sodium borohydride (0.60 g, 15.89 mmol) in portions. After addition, the mixture was stirred at room temperature overnight. Most of solvent was then evaporated under reduced pressure. Ethyl acetate (50 ml) and water (50 ml) were added. The ethyl acetate layer was separated and washed with brine (30 ml), dried over magnesium sulfate and evaporated under reduced pressure. The residue was purified on silica gel column with (dichloromethane/methanol=95/5) to give the product [Molecular formula: $C_{65}H_{117}N_{11}O_{14}$; Exact Mass: 1275.88; MS (m/z): 1276.55 (M+1)$^+$; TLC Rf: 0.39 (dichloromethane/methanol=9/1); HPLC RT: 15.31 min (C8 reverse phase column: 250 mm; acetonitrile/water (0.05% trifuloroacetic acid); operation temp: 64° C.; Detector: 210 nm)].

Example 14

[(R)-(2-(N,N-Dimethylamino)ethoxy)methyl-Sar]-3-cyclosporin

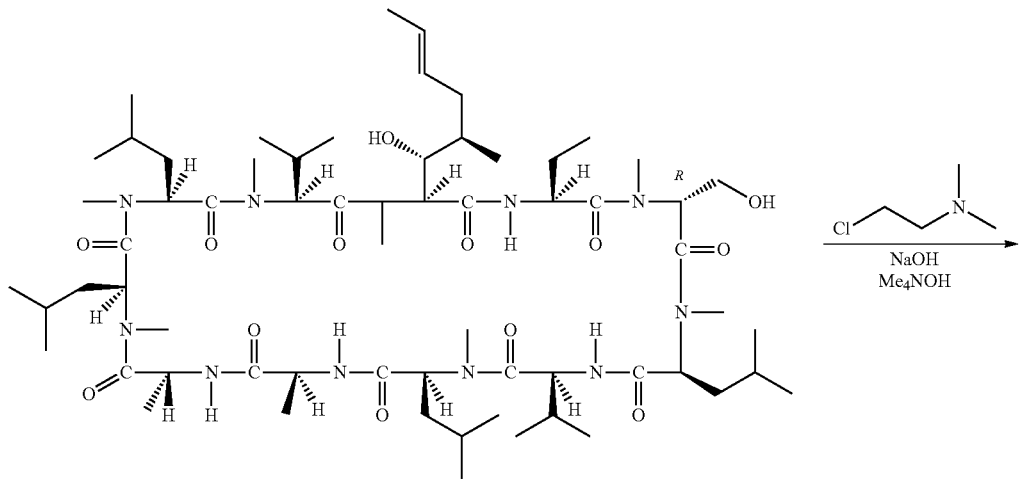

$C_{64}H_{114}N_{10}O_{13}$
Exact Mass: 1230.86
Mol. Wt.: 1231.67

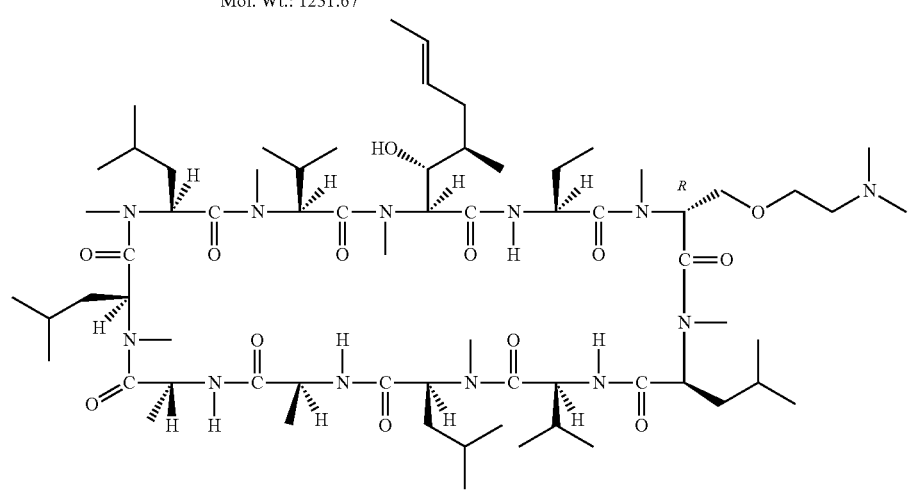

$C_{67}H_{122}N_{12}O_{13}$
Exact Mass: 1302.93
Mol. Wt.: 1303.78

To a solution of [(R)-α-hydroxymethyl-Sar]-3-cyclosporin (1.03 g, 0.84 mmol) in benzene (50 ml) were added a solution of sodium hydroxide (1.34 g, 33.47 mmol) in water (1.34 ml), tetramethylammonium hydroxide pentahydrate (3.04 g, 16.73 mmol) and 2-dimethylaminoethyl chloride hydrochloride (2.41 g, 16.73 mmol). The mixture was stirred at room temperature for 5 days. Sodium bicarbonate saturated solution (100 ml) was added and the mixture was separated. Then the aqueous layer was extracted with ethyl acetate (50 ml×2). The combined organic layers were dried over magnesium sulfate and evaporated under reduced pressure. After purified on silica gel, 303 mg of product was obtained [Molecular Formula: $C_{67}H_{122}N_{12}O_{13}$; Exact Mass: 1302.93; MS (m/z): 1303.70 $(M+1)^+$, 1325.85 $(M+Na)^+$; TLC $R_f$: 0.36 (dichloromethane/methanol=9/1); HPLC RT: 18.19 min (C8 reverse phase column: 250 mm; acetonitrile/0.077% ammonium acetate in water; operation temperature: 64° C.; detector: 210 nm)].

Example 15

[(R)-(2-(N-Morpholino)ethoxy)methyl-Sar]-3-cyclosporin

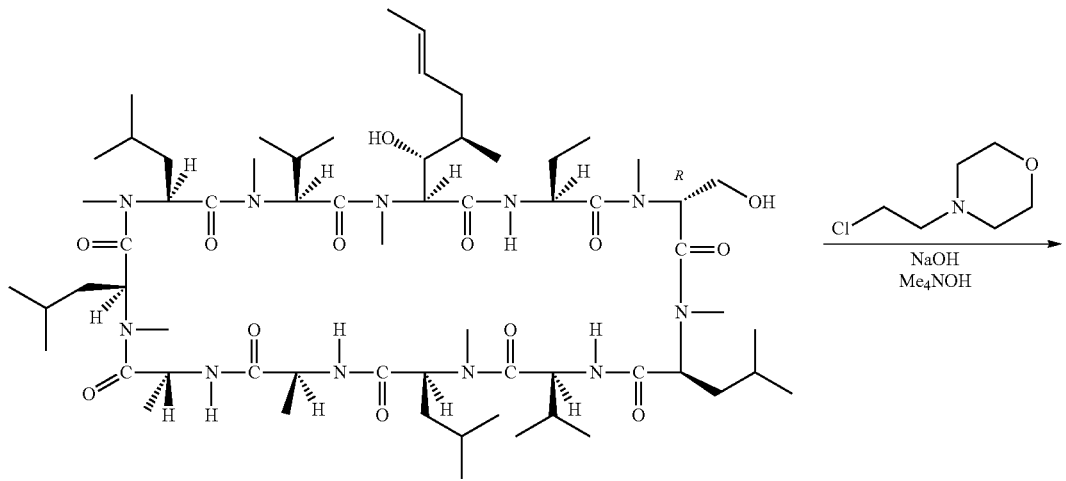

$C_{63}H_{113}N_{11}O_{13}$
Exact Mass: 1231.85
Mol. Wt.: 1232.66

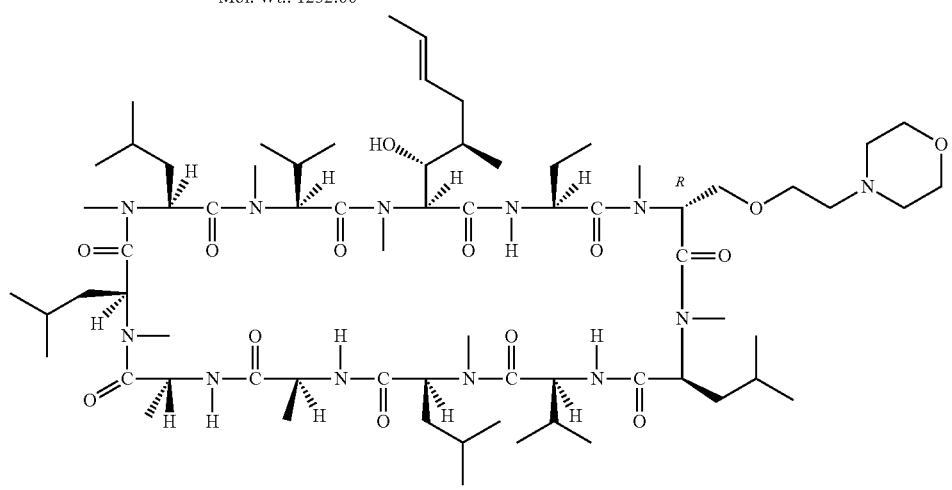

$C_{69}H_{124}N_{12}O_{14}$
Exact Mass: 1344.94
Mol. Wt.: 1345.82

To a solution of [(R)-α-hydroxymethyl-Sar]-3-cyclosporin (0.27 g, 0.22 mmol) in benzene (20 ml) were added a solution of sodium hydroxide (0.70 g, 17.55 mmol) in water (0.70 ml), tetramethylammonium hydroxide pentahydrate (0.80 g, 4.39 mmol) and 2-(4-morpholinyl)ethyl chloride hydrochloride (0.82 g, 4.39 mmol). The mixture was stirred at 30 to 40° C. for a week. Sodium bicarbonate saturated solution (30 ml) was added and then the mixture was separated. The aqueous layer was extracted with ethyl acetate (25 ml×2). The combined organic layers were dried over magnesium sulfate and evaporated under reduced pressure. After purified on silica gel, 56 mg of product was obtained [Molecular Formula: $C_{69}H_{124}N_{12}O_{14}$; Exact Mass: 1344.94; MS (m/z): LCMS: 1345.72 (M+1)$^+$, 1367.83 (M+Na)$^+$; TLC $R_f$: 0.50 (dichloromethane/methanol=9/1); HPLC RT: 16.64 min (C8 reverse phase column: 250 mm; acetonitrile/0.077% ammonium acetate in water; operation temperature: 64° C.; detector: 210 nm)].

Example 16

[(R)-(2-(N-Pyrrolidinyl)ethoxy)methyl-Sar]-3-cyclosporin $C_{62}H_{111}N_{11}O_{13}$
Exact Mass: 1217.84
Mol. Wt.: 1218.63

$C_{69}H_{124}N_{12}O_{13}$
Exact Mass: 1328.94
Mol. Wt.: 1329.82

To a solution of [(R)-α-hydroxymethyl-Sar]-3-cyclosporin (0.320 g, 0.26 mmol) in benzene (20 ml) were added a solution of sodium hydroxide (0.83 g, 20.80 mmol) in water (0.85 ml), tetramethylammonium hydroxide pentahydrate (0.95 g, 5.20 mmol) and 1-(2-chloroethyl)pyrrolidine hydrochloride (0.88 g, 5.20 mmol). The mixture was stirred at room temperature for a weekend. Sodium bicarbonate saturated solution (30 ml) was added and the mixture was separated. The aqueous layer was extracted with ethyl acetate (25 ml×2). The combined organic layers were dried over magnesium sulfate and evaporated under reduced pressure. After purified on silica gel, 103 mg of product was obtained [Molecular Formula: $C_{69}H_{124}N_{12}O_{13}$; Exact Mass: 1328.94; MS (m/z): 1329.75 (M+1)$^+$, 1351.82 (M+Na)$^-$; TLC R$_f$: 0.37 (dichloromethane/methanol=9/1); HPLC RT: 18.94 min (C8 reverse phase column: 250 mm; acetonitrile/ 0.077% ammonium acetate in water; operation temperature: 64° C.; detector: 210 nm)].

Example 17

[(R)-(2-(N-Piperidinyl)ethoxy)methyl-Sar]-3-cyclosporin

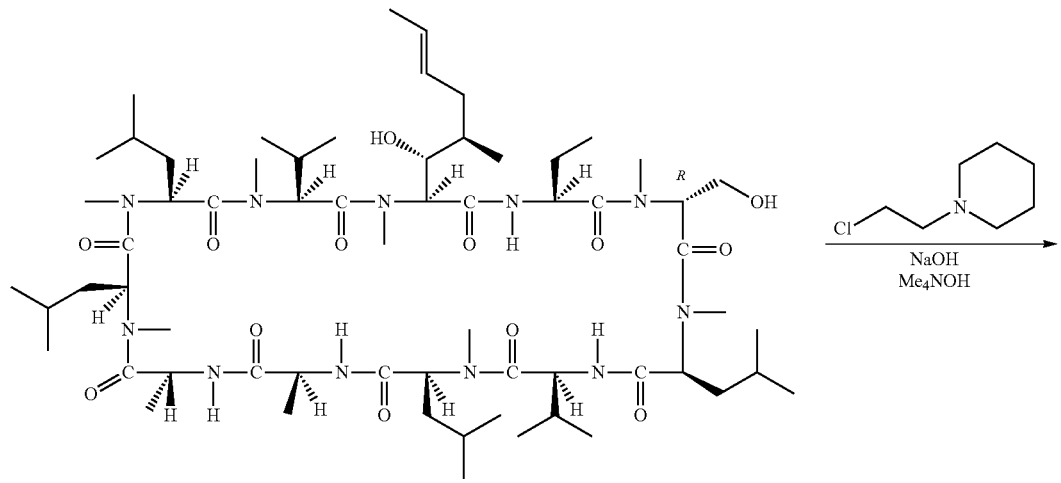

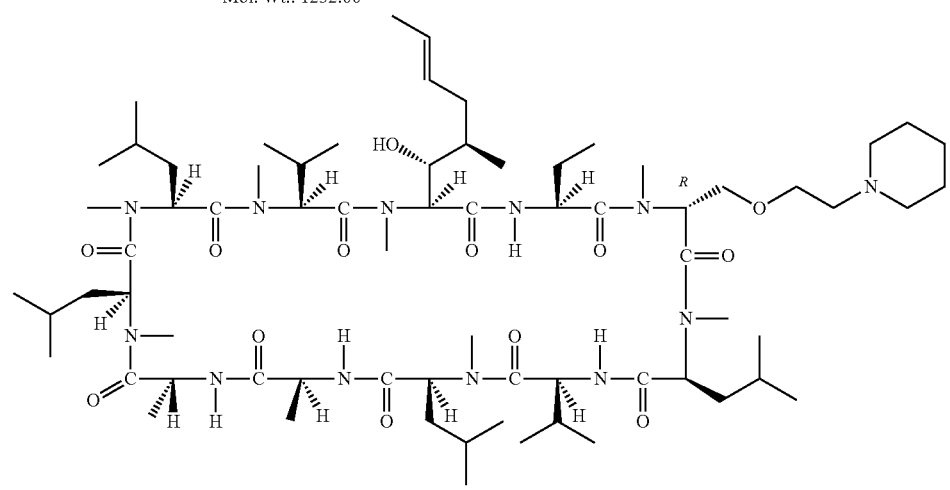

To a solution of [(R)-α-hydroxymethyl-Sar]-3-cyclosporin (0.28 g, 0.22 mmol) in benzene (20 ml) were added a solution of sodium hydroxide (0.36 g, 9.07 mmol) in water (0.36 ml), tetramethylammonium hydroxide pentahydrate (0.82 mg, 4.53 mmol) and 1-(2-chloroethyl)piperidine hydrochloride (0.83 g, 4.53 mmol). The mixture was stirred at 30 to 40° C. for 20 hours. Sodium bicarbonate saturated solution (30 ml) was added and the mixture was separated. Then the aqueous layer was extracted with ethyl acetate (25 ml×2). The combined organic layers were dried over magnesium sulfate and evaporated under reduced pressure. After purified on silica gel, 121 mg of product was obtained [Molecular Formula: $C_{70}H_{126}N_{12}O_{13}$; Exact Mass: 1342.96; MS (m/z): 1343.76 (M+1)$^+$, 1365.83 (M+Na)$^+$; TLC $R_f$: 0.44 (dichloromethane/methanol=9/1); HPLC RT: 19.26 min (C8 reverse phase column: 250 mm; acetonitrile/ 0.077% ammonium acetate in water; operation temperature: 64° C.; detector: 210 nm)].

Example 18

[(R)-(3,3-Dimethoxypropoxy)methyl-Sar]-3-cyclosporin

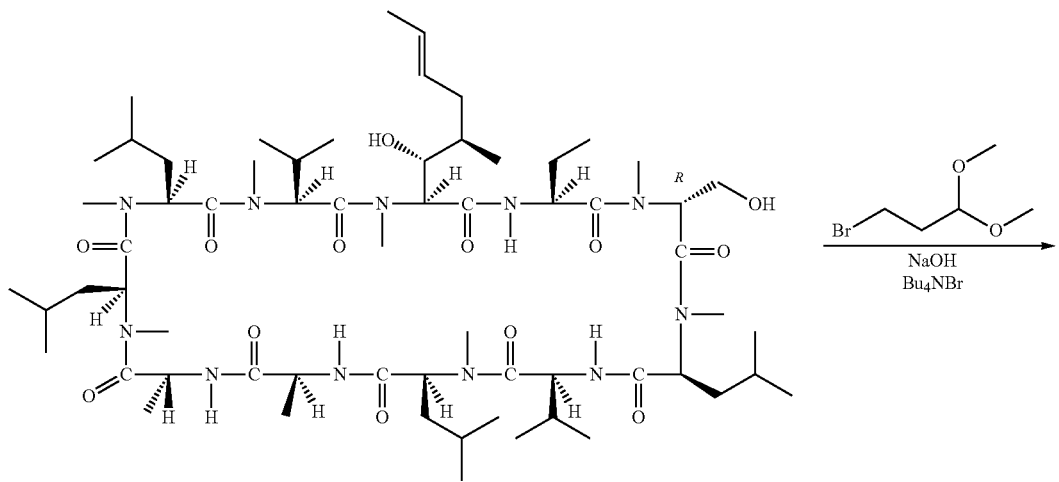

$C_{63}H_{113}N_{11}O_{13}$
Exact Mass: 1231.85
Mol. Wt.: 1232.66

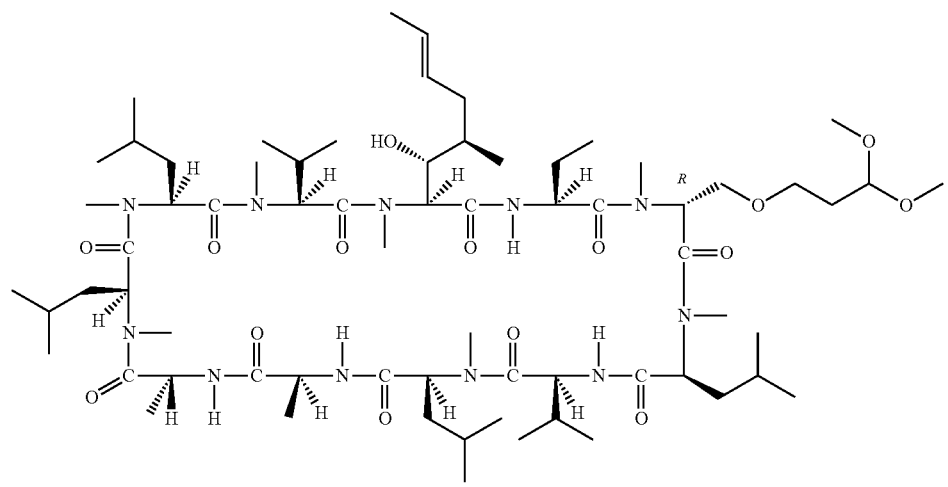

$C_{68}H_{123}N_{11}O_{15}$
Exact Mass: 1333.92
Mol. Wt.: 1334.79

To a solution of [(R)-hydroxymethyl-Sar]-3-cyclosporin (0.50 g, 0.41 mmol) in benzene (30 ml) were added a solution of sodium hydroxide (1.00 g, 25.00 mmol) in water (1 ml), 3-bromopropionaldehyde dimethyl acetal (1.80 g, 10.00 mmol) and tetra-n-butylammonium bromide (0.20 g, 0.62 mmol). After stirred at room temperature for 10 hours, the mixture was diluted with ice water and the mixture was separated. The aqueous layer was extracted with dichloromethane (20 ml). The combined organic layers were washed with brine, dried over magnesium sulfate and evaporated under reduced pressure to give 0.48 g of crude product, which was used for next step [Molecular Formula: $C_{68}H_{123}N_{11}O_{15}$; Exact Mass: 1333.92; MS (m/z): 1334.50 $(M+1)^+$].

Example 19

[(R)-(2-Formylethoxy)methyl-Sar]-3-cyclosporin

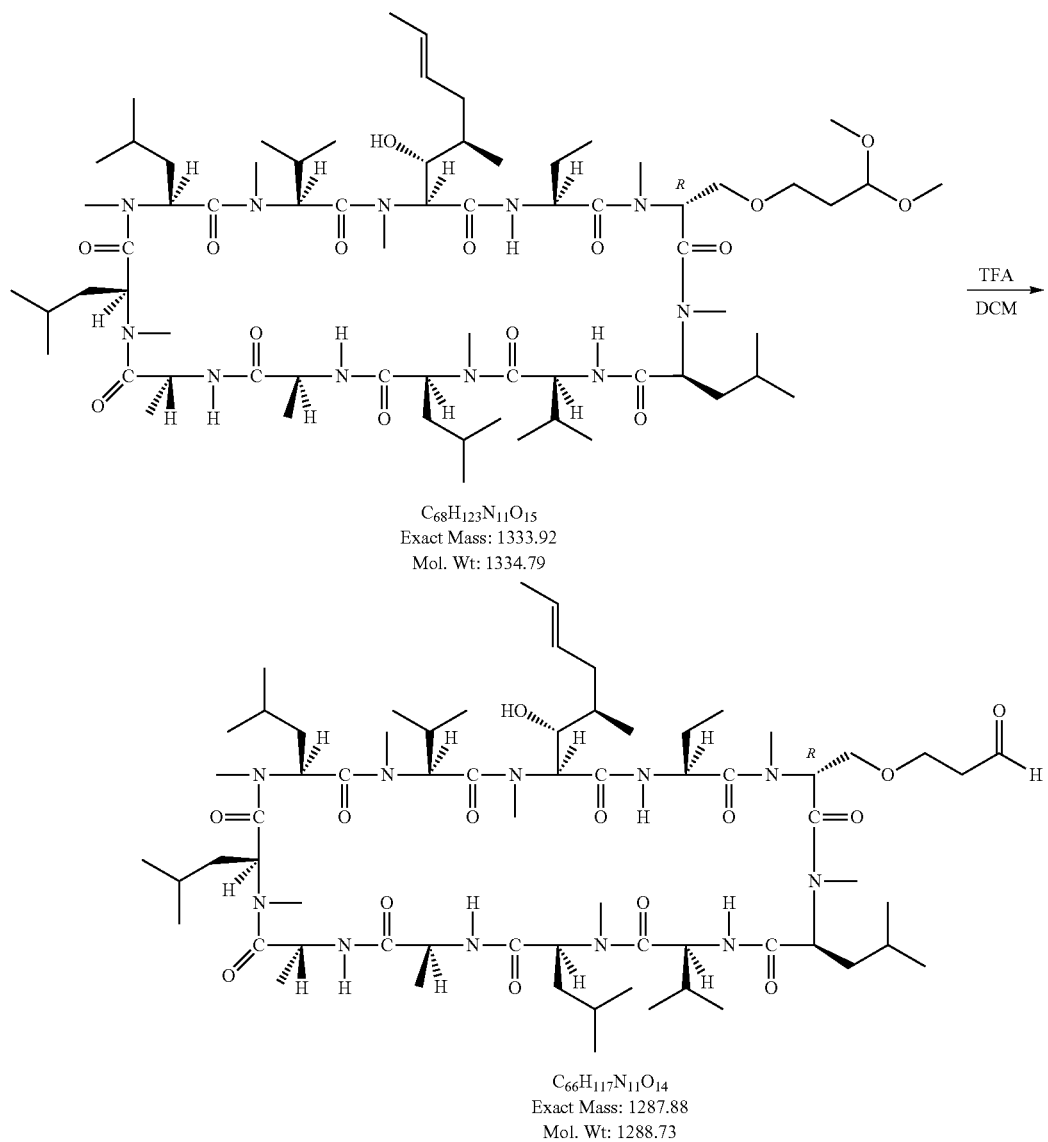

To a solution of crude [(R)-(3,3-dimethoxypropoxy)methyl-Sar]-3-cyclosporin (0.48 g, 0.36 mmol) in dichloromethane (30 ml) were added trifuloroacetic acid (5 ml) and water (4 ml) at 0° C. Then the mixture was allowed to warm to room temperature and stirred for 3 hours. After the mixture was separated, the dichloromethane layer was washed with saturated sodium bicarbonate solution (20 ml), dried over magnesium sulfate and evaporated under reduced pressure. The residue was purified by chromatography (hexane/acetone=2/1) to give 0.31 g of product [Molecular Formula: $C_{66}H_{117}N_{11}O_{14}$; Exact Mass: 1287.88; MS (m/z): 1288.63 $(M+1)^+$].

Example 20

[(R)-(3-(N,N-Dimethylamino)propoxy)methyl-Sar]-3-cyclosporin

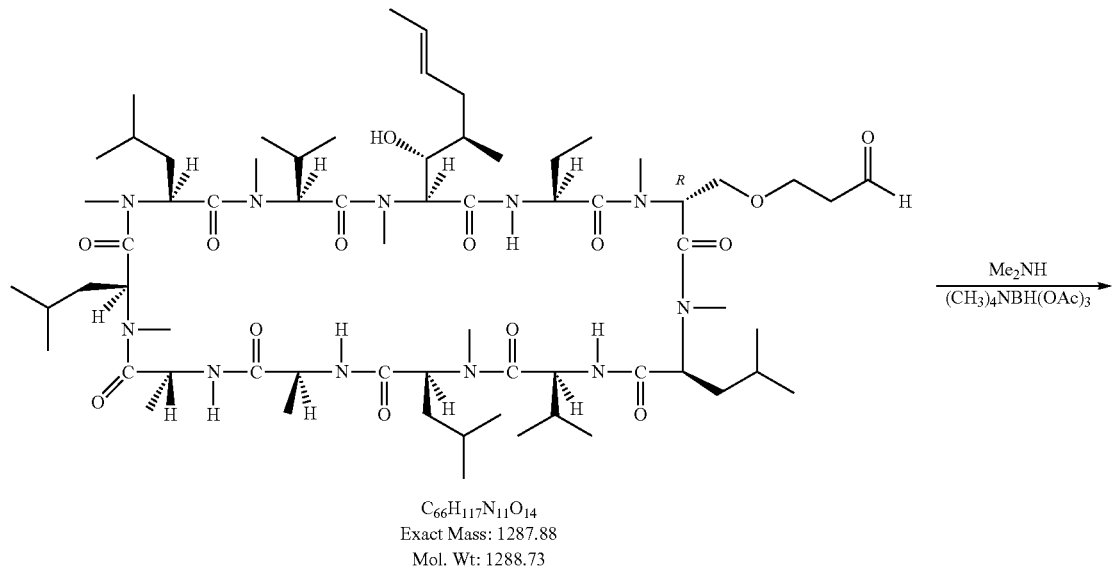

$C_{66}H_{117}N_{11}O_{14}$
Exact Mass: 1287.88
Mol. Wt: 1288.73

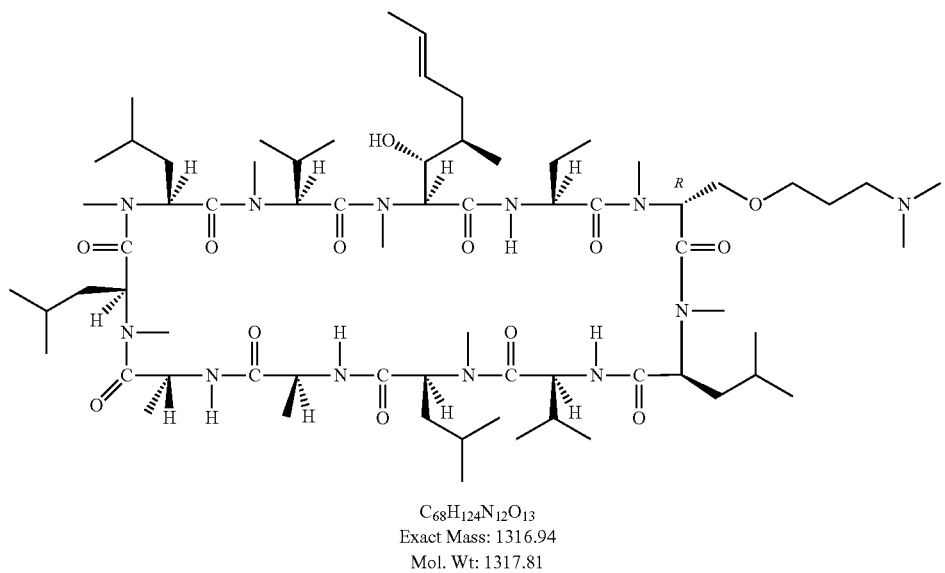

$C_{68}H_{124}N_{12}O_{13}$
Exact Mass: 1316.94
Mol. Wt: 1317.81

To a solution of [(R)-(2-formylethoxy)methyl-Sar]-3-cyclosporin (0.13 g, 0.10 mmol) in chloroform (5 ml) were added dimethylamine hydrochloride (0.10 g, 1.22 mmol) and acetic acid (5 drops). After the mixture was stirred at room temperature for 5 minutes, tetramethylammonium triacetoxyborohydride (65 mg, 0.25 mmol) was added in portions and stirring was continued for one hour. Then dichloromethane (10 ml) and saturated sodium bicarbonate solution (10 ml) were added and separated. The organic layer was washed with brine, dried over magnesium sulfate and evaporated under reduced pressure. The residue was purified by chromatography (dichloromethane/methanol=96/4) to give 89 mg of product [Molecular Formula: $C_{68}H_{124}N_{12}O_{13}$; Exact Mass: 1316.94; MS (m/z): 1317.64 (M+1)$^-$; TLC $R_f$: 0.39 (dichloromethane/methanol=95/5); HPLC RT: 13.92 min (C8 reverse phase column: 250 mm; acetonitrile/0.077% ammonium acetate in water; operation temperature: 64° C.; detector: 210 nm)].

Example 21

[(R)-(3-(N, N-Diethylamino)propoxy)methyl-Sar]-3-cyclosporin

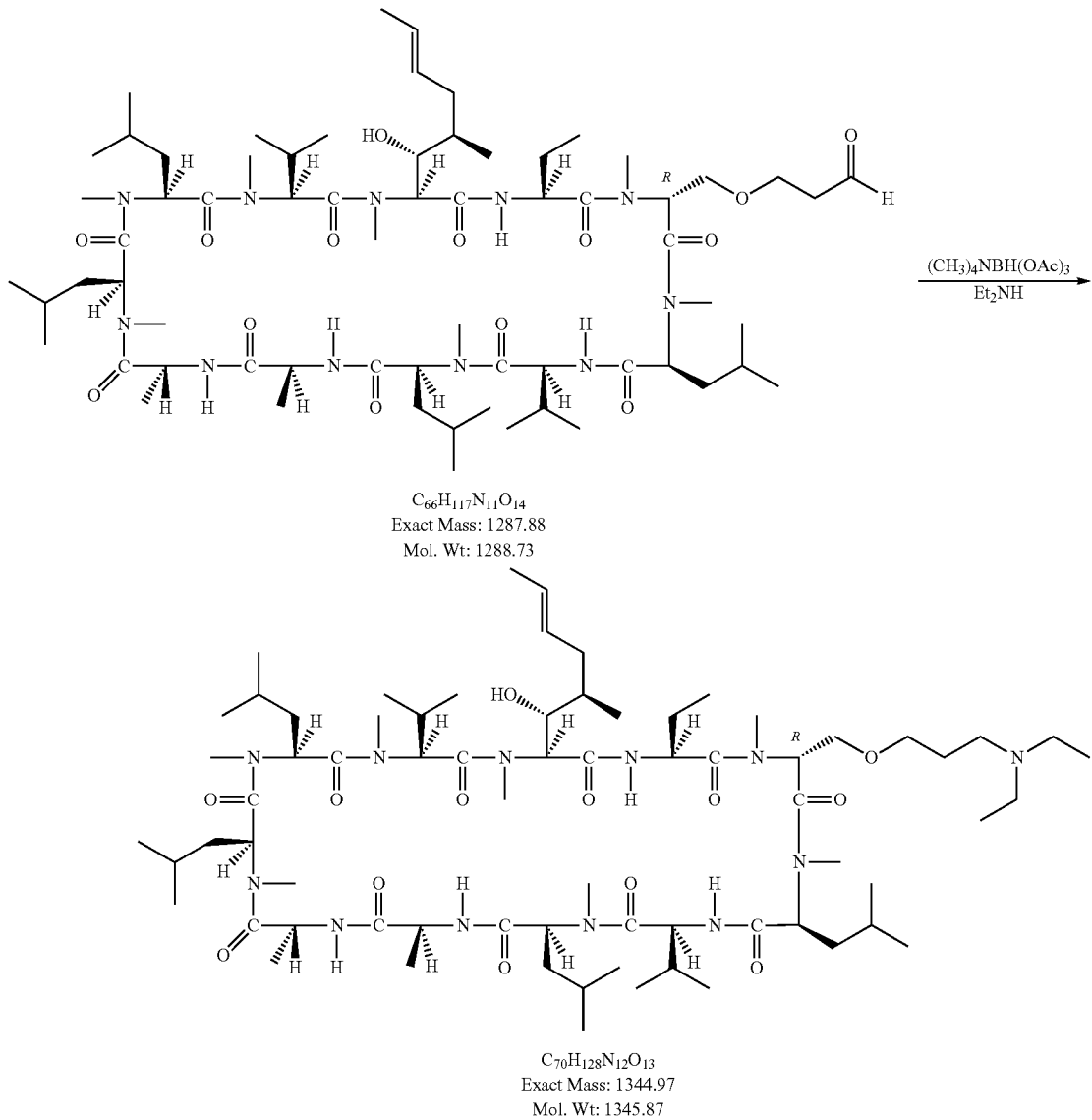

To a solution of [(R)-(2-formylethoxy)methyl-Sar]-3-cyclosporin (100 mg, 0.08 mmol) in chloroform (4 ml) were added diethylamine (100 mg, 1.37 mmol) and acetic acid (4 drops). After the mixture was stirred at room temperature for 5 minutes, tetramethylammonium triacetoxyborohydride (50 mg, 0.19 mmol) was added in portions and stirring was continued for 1 hour. Then dichloromethane (10 ml) and saturated sodium bicarbonate solution (10 ml) were added and the mixture was separated. The organic layer was washed with brine, dried over magnesium sulfate and evaporated under reduced pressure. The residue was purified by chromatography (dichloromethane/methanol=96/4) to give 56 mg of product [Molecular Formula: $C_{70}H_{128}N_{12}O_{13}$; Exact Mass: 1344.97; MS (m/z): 1345.71 (M+1)$^-$; TLC $R_f$: 0.40 (dichloromethane/methanol=95/5); HPLC RT: 14.59 min (C8 reverse phase column: 250 mm; acetonitrile/0.077% ammonium acetate in water; operation temperature: 64° C.; detector: 210 nm)].

Example 22

[(R)-(3-(N-Morpholino)propoxy)methyl-Sar]-3-cyclosporin

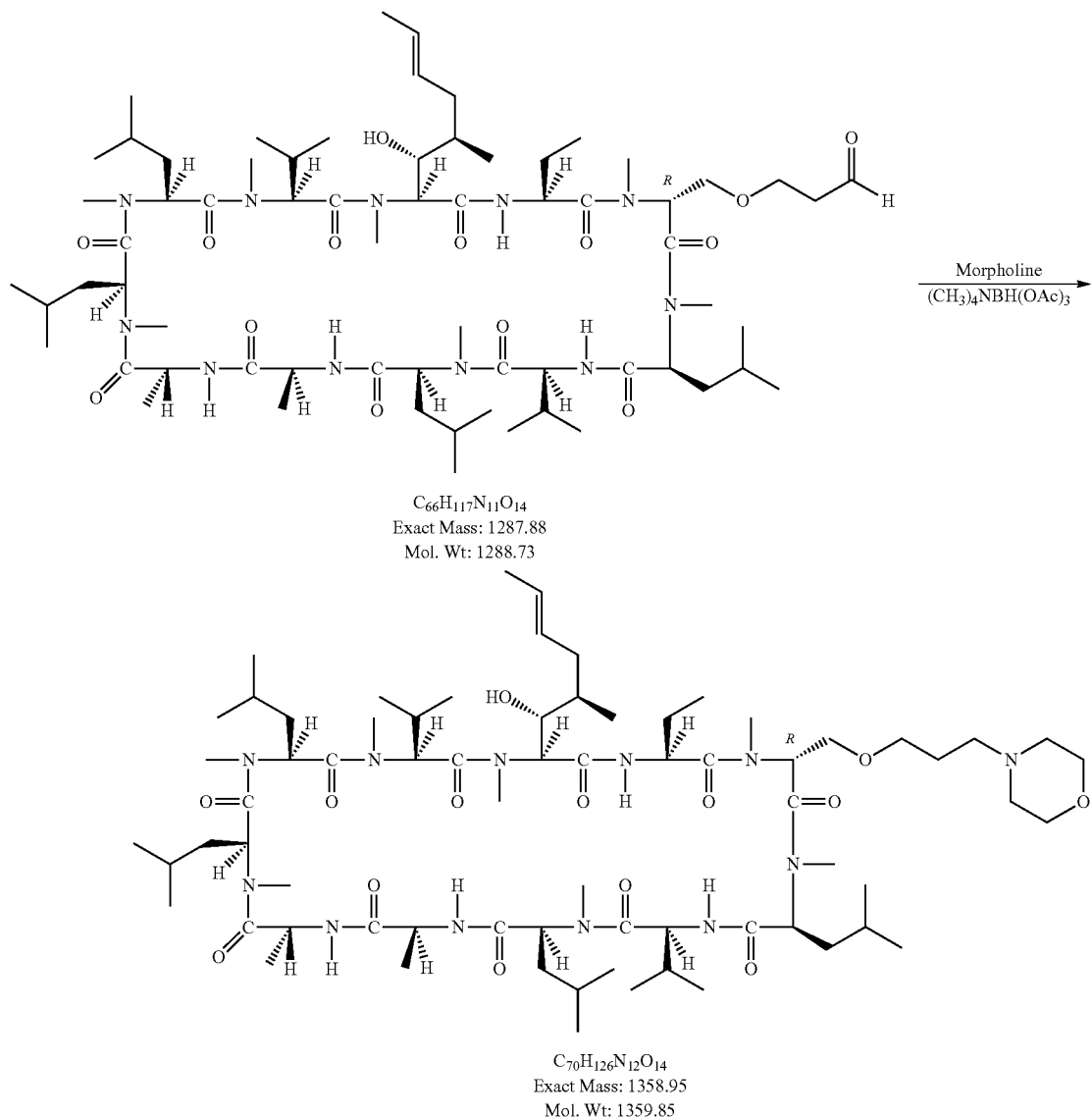

To a solution of [(R)-(2-formylethoxy)methyl-Sar]-3-cyclosporin (300 mg, 0.23 mmol) in dichloromethane (15 ml) were added morpholine (101 mg, 1.16 mmol) and tetramethylammonium triacetoxyborohydride (306 mg, 1.16 mmol). The reaction mixture was stirred at room temperature for two hours. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 124 mg of product was obtained [Molecular Formula: $C_{70}H_{126}N_{12}O_{14}$; Exact Mass: 1358.95; MS (m/z): 1359.71(M+1)$^+$, 1381.79 (M+Na)$^+$; TLC $R_f$: 0.40 (dichloromethane/methanol=9/1); HPLC RT: 14.2 min (C8 reverse phase column: 250 mm; acetonitrile/0.077% ammonium acetate in water; operation temperature: 64° C.; detector: 210 nm)].

Example 23

[(R)-(3-(N-Pyrrolidinyl)propoxy)methyl-Sar]-3-cyclosporin

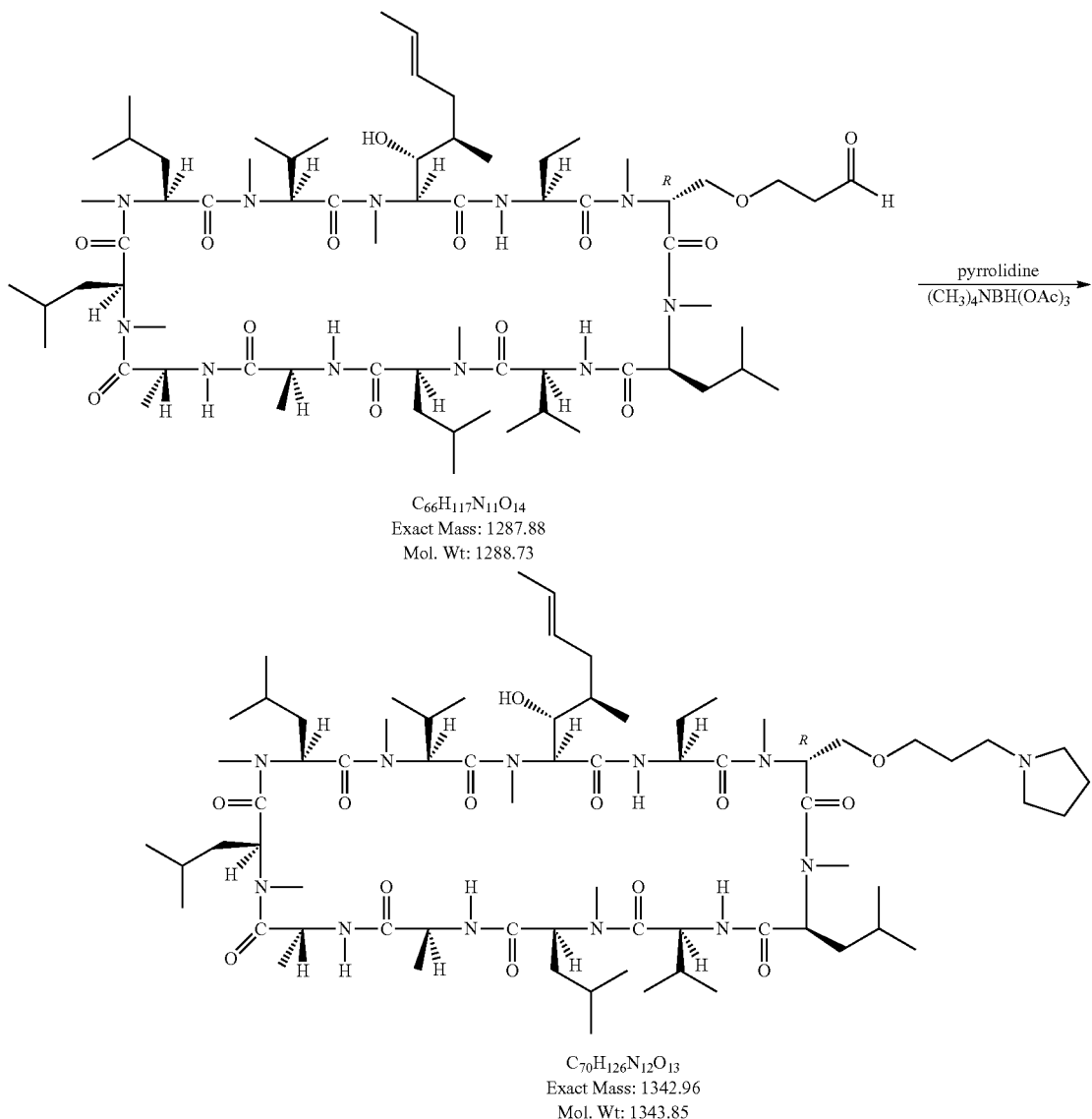

To a solution of [(R)-α-hydroxymethyl-Sar]-3-cyclosporin (315 mg, 0.24 mmol) in dichloromethane (15 ml) were added pyrrolidine (87 mg, 1.22 mmol) and tetramethylammonium triacetoxyborohydride (322 mg, 1.22 mmol). The reaction mixture was stirred at room temperature for two hours. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 22 mg of product was obtained [Molecular Formula: $C_{70}H_{126}N_{12}O_{13}$; Exact Mass: 1342.96; MS (m/z): 1343.75 $(M+1)^+$, 1365.82 $(M+Na)^+$; TLC $R_f$: 0.33 (dichloromethane/methanol=9/1); HPLC RT: 14.3 min (C8 reverse phase column: 250 mm; acetonitrile/ 0.077% ammonium acetate in water; operation temperature: 64° C.; detector: 210 nm)].

Example 24

[(R)-(3-(N-Piperidinyl)propoxy)methyl-Sar]-3-cyclosporin

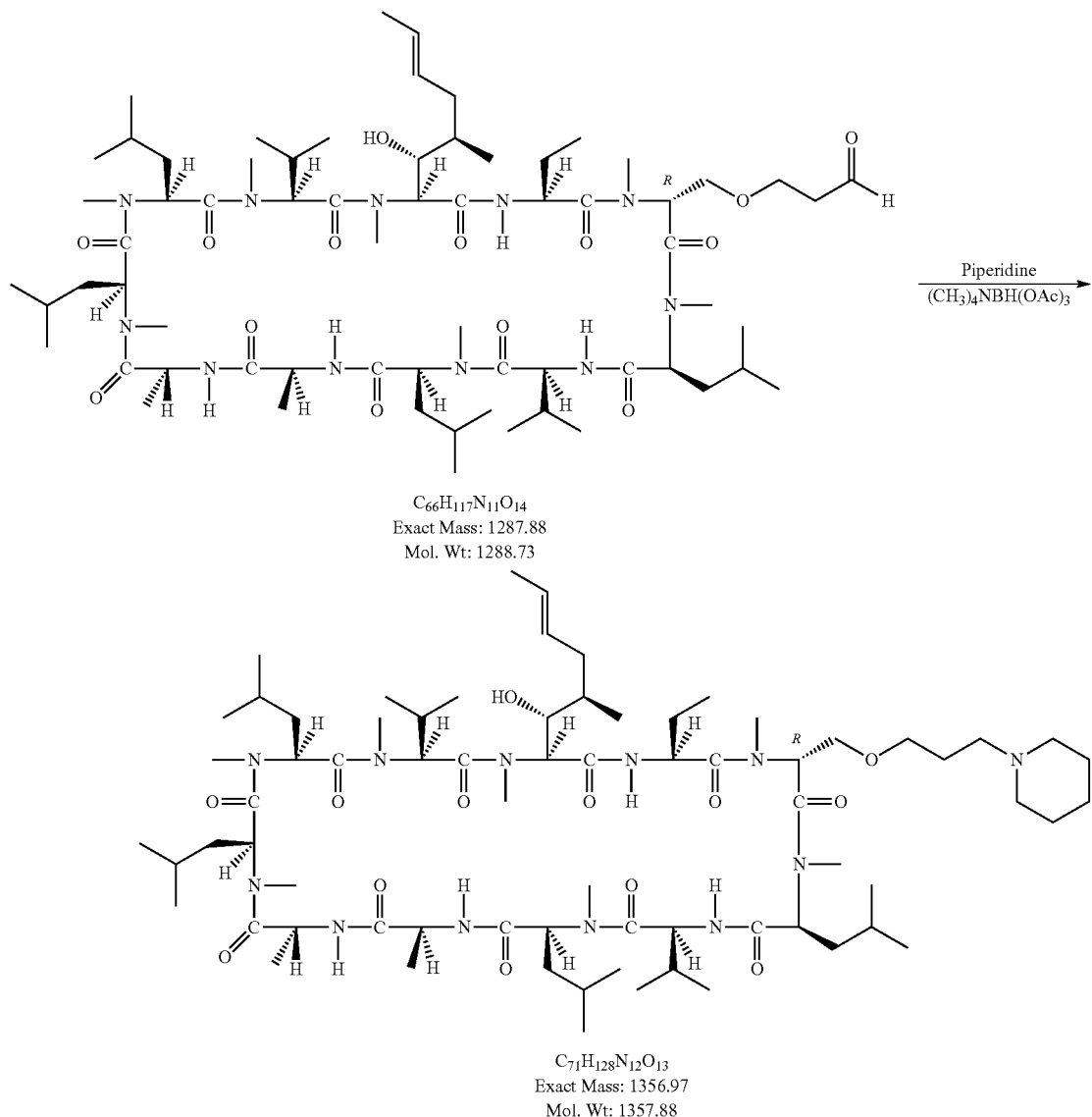

To a solution of [(R)-(2-formylethoxy)methyl-Sar]-3-cyclosporine (350 mg, 0.27 mmol) in dichloromethane (20 ml) were added piperidine (115 mg, 1.34 mmol) and tetramethylammonium triacetoxyborohydride (352 mg, 1.34 mmol). The reaction mixture was stirred overnight at room temperature. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 35 mg of product was obtained [Molecular Formula: $C_{71}H_{128}N_{12}O_{13}$; Exact Mass: 1356.97; MS (m/z): 1357.76 (M+1)$^+$, 1379.83 (M+Na)$^+$; TLC R$_f$: 0.36 (dichloromethane/methanol=9/1); HPLC RT: 14.4 min (C8 reverse phase column: 250 mm; acetonitrile/ 0.077% ammonium acetate in water; operation temperature: 64° C.; detector: 210 nm)].

Example 25

[α-Carboxy-Sar]-3-[(γ-hydroxy)-NMeLeu]-4-cyclosporin

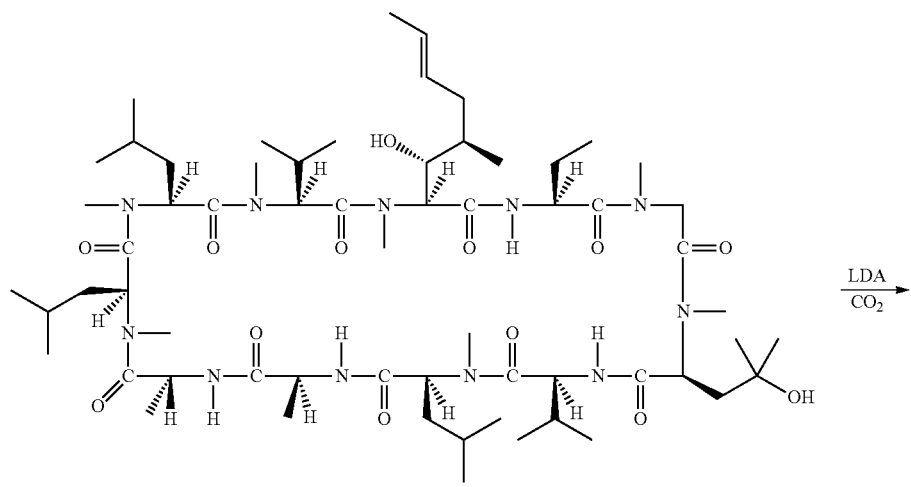

$C_{62}H_{111}N_{11}O_{13}$
Exact Mass: 1217.84
Mol. Wt: 1218.63

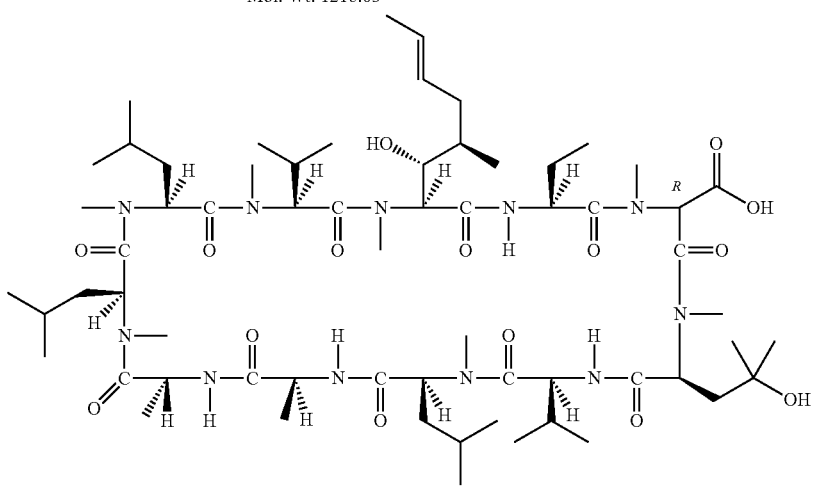

$C_{63}H_{111}N_{11}O_{15}$
Exact Mass: 1261.83
Mol. Wt: 1262.64

To a solution of LDA (2.0 M in tetrahydrofuran, 23 ml, 46 mmol) in tetrahydrofuran (80 ml) at −78° C. under nitrogen, [(γ-hydroxy)-N-MeLeu]-4-cyclosporin (4.40 g, 3.61 mmol) in tetrahydrofuran (15 ml) was added over 3 min. After the mixture was stirred at −78° C. for 3 hours, carbon dioxide gas was bubbled into the reaction mixture for 1 hour. Then the mixture was allowed to warm to room temperature slowly and kept stirring for 3 hours. Most of tetrahydrofuran was evaporated. Dichloromethane (100 ml) and water (50 ml) were added. The PH of the mixture was adjusted to around 5 by adding aqueous citric acid solution. The mixture was separated and the organic layer was washed with brine, dried over magnesium sulfate and evaporated under reduced pressure to give 3.20 g of crude product, which was used for next step without purification [Molecular Formula: $C_{63}H_{111}N_{11}O_{15}$; Exact Mass: 1261.83; MS (m/z): 1262.49 $(M+1)^+$].

[(γ-Hydroxy)-N-MeLeu]-4-cyclosporin was prepared by Sebekia benihana biotransformation according to a method described by Kuhnt M. et al., 1996, Microbial Biotransformation Products of Cyclosporin A, *J. Antibiotics,* 49 (8), 781.

Example 26

[α-Methoxycarbonyl-Sar]-3-[(γ-hydroxy)-NMeLeu]-4-cyclosporin

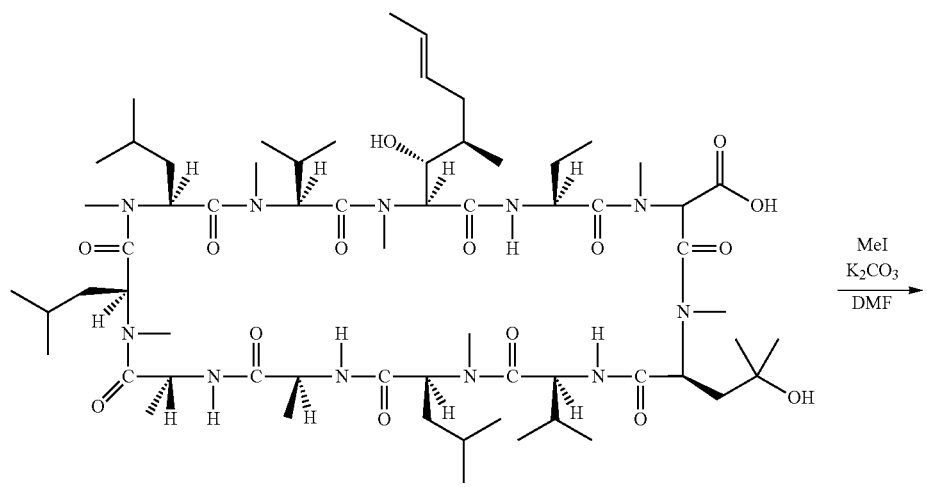

$C_{63}H_{111}N_{11}O_{15}$
Exact Mass: 1261.83
Mol. Wt: 1262.64

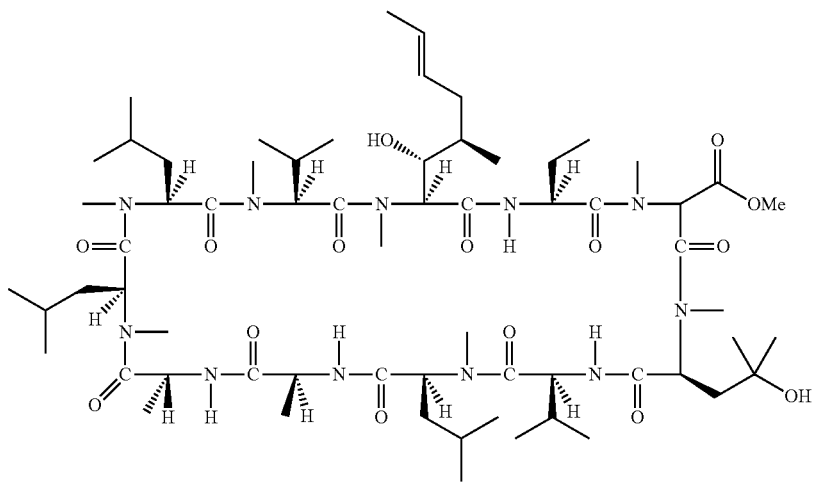

$C_{64}H_{113}N_{11}O_{15}$
Exact Mass: 1275.84
Mol. Wt: 1276.67

To a mixture of [α-carboxy-Sar]-3-[(γ-hydroxy)-N-Me-Leu]-4-cyclosporin (3.20 g 2.53 mmol) and potassium carbonate (1.30 g, 9.40 mmol) in N,N-dimethylformamide (20 ml) was added iodomethane (1.80 g, 12.70 mmol). The mixture was stirred overnight at room temperature. Dichloromethane (80 ml) and water (50 ml) were added and the mixture was separated. The dichloromethane layer was washed with water (25 ml) and brine (25 ml), dried over magnesium sulfate and evaporated under reduced pressure to give crude 3.00 g of product [Molecular Formula: $C_{64}H_{113}N_{11}O_{15}$; Exact Mass: 1275.84; MS (m/z): 1276.75 $(M+1)^{31}$].

Example 27

[(R)-α-Hydroxymethyl-Sar]-3-[(γ-hydroxy)-NMeLeu]-4-cyclosporin

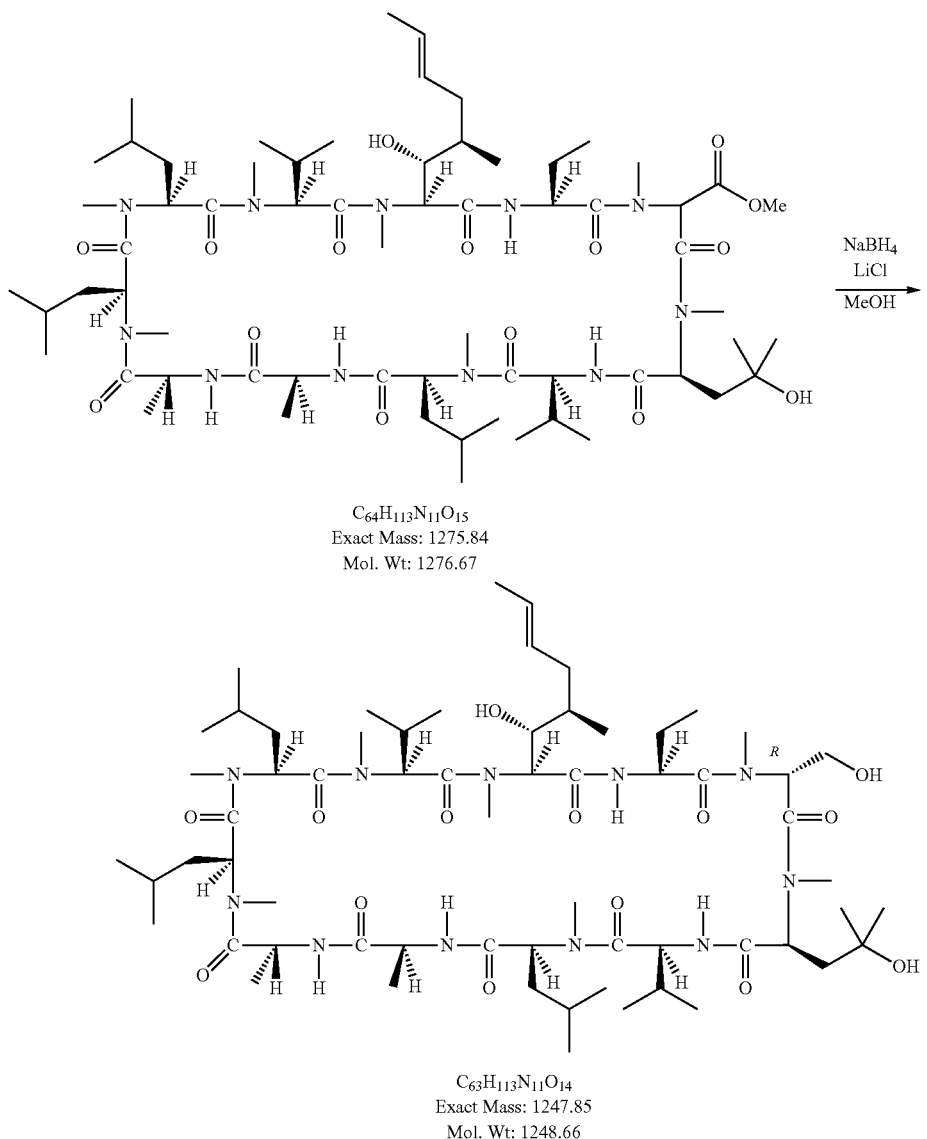

C$_{64}$H$_{113}$N$_{11}$O$_{15}$
Exact Mass: 1275.84
Mol. Wt: 1276.67

C$_{63}$H$_{113}$N$_{11}$O$_{14}$
Exact Mass: 1247.85
Mol. Wt: 1248.66

To a suspension of [α-methoxycarbonyl-Sar]-3-[(γ-hydroxy)-N-MeLeu]-4-cyclosporin (3.00 g, 2.35 mmol) and lithium chloride (1.50 g, 35.30 mmol) in methanol (100 ml) was added sodium borohydride (2.50 g, 66.10 mmol) in portions. The mixture was stirred overnight at room temperature. Most of solvent was evaporated under reduced pressure. Dichloromethane (80 ml) and water (50 ml) were added and the mixture was separated. The dichloromethane layer was washed with brine, dried over magnesium sulfate and evaporated under reduced pressure. The residue was purified by chromatography (dichloromethane/methanol=96/4) to give 1.30 g of product [Molecular Formula: C$_{63}$H$_{113}$N$_{11}$O$_{14}$; Exact Mass: 1247.85; MS (m/z): 1248.48 (M+1)$^+$; $^1$H NMR spectrum (600 MHz, CDCl$_3$, δ in ppm): 0.68 (d, J=5.4 Hz, 3H), 0.80-1.00 (m, 30H), 1.07 (d, J=6.0 Hz, 3H), 1.16-1.29 (m, 10H), 1.32 (d, J=7.2 Hz, 3H), 1.39-1.46 (m, 2H), 1.59-1.63 (m, 6H), 1.68-1.83 (m, 7H), 2.02-2.11 (m, 4H), 2.31-2.33 (m, 1H), 2.37-2.42 (m, 2H), 2.67 (s, 6H), 3.09 (s, 3H), 3.19 (s, 3H), 3.20 (s, 3H), 3.22 (s, 3H), 3.47 (s, 3H), 3.72-3.75 (m, 1H), 3.82 (br, 1H), 3.97-3.99 (m, 1H), 4.07-4.10 (m, 1H), 4.50-4.52 (m, 1H), 4.65-4.67 (t, J=8.4 Hz, 1H), 4.79-4.81 (m, 1H), 4.90-4.95 (m, 2H), 5.00-5.05 (m, 2H), 5.09 (d, J=10.8 Hz, 1H), 5.30-5.35 (m, 2H), 5.46 (d, J=6.0 Hz, 1H), 5.52-5.53 (m, 1H), 5.66-5.68 (m, 1H), 7.12 (d, J=7.8 Hz, 1H), 7.47 (d, J=8.4 Hz, 1H), 7.60 (d, J=7.2 Hz, 1H), 7.87-7.89 (d, J=9.6 Hz, 1H)].

Example 28

[α-Methylene-Sar]-3-[(γ-hydroxy)-NMeLeu]-4-cyclosporin

Method 1

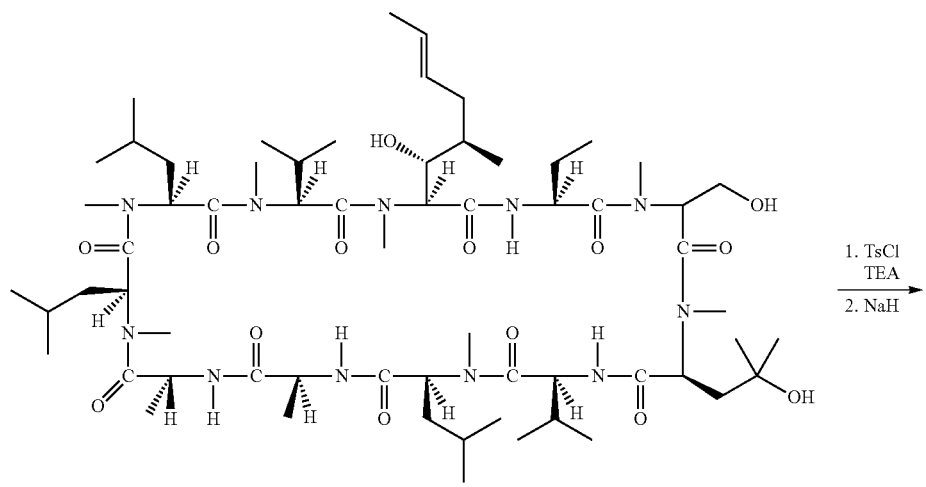

$C_{63}H_{113}N_{11}O_{14}$
Exact Mass: 1247.85
Mol. Wt: 1248.66

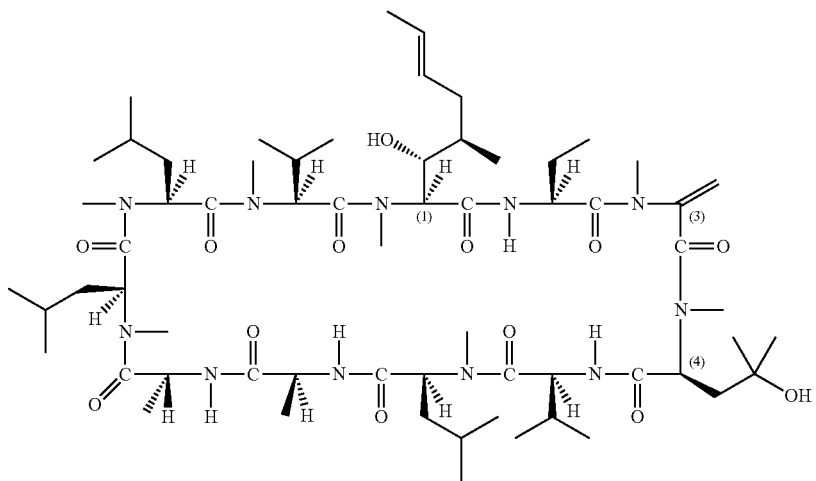

$C_{63}H_{111}N_{11}O_{13}$
Exact Mass: 1229.84
Mol. Wt: 1230.65

To a solution of [α-hydroxymethyl-Sar]-3-[(γ-hydroxy)-NMeLeu]-4-cyclosporin (250 mg, 0.20 mmol) in dichloromethane (10 mL) at room temperature were added triethylamine (0.33 mL, d 0.726, 2.40 mmol) and triethylamine hydrochloride (95.6 mg, 1.00 mmol), followed by adding p-toluenesulfonyl chloride (0.23 g, 1.20 mmol) under stirring. The mixture was stirred at room temperature overnight. Then the reaction mixture was washed with brine, dried over magnesium sulfate and the solvent was evaporated under reduced pressure. The reaction mixture of [α-chloromethyl-Sar]-3-[(γ-hydroxy)-NMeLeu]-4-cyclosporin [Molecular formula: $C_{63}H_{112}ClN_{11}O_{13}$; Exact Mass: 1265.81; MS (m/z): 1266.32 (M+1)$^+$, 1288.43 (M+Na)$^+$] and [α-p-toluenesulfonylmethyl-Sar]-3-[(γ-hydroxy)-NMeLeu]-4-cyclosporin [Molecular formula: $C_{70}H_{119}N_{11}O_{16}S$; Exact Mass: 1401.856; MS (m/z): 1402.34 (M+1)$^+$, 1424.62 (M+Na)$^+$] was directly used in next step reaction without further purification. To a solution of the above mixture in tetrahydrofuran (20 ml) was added sodium hydride (320 mg, 60% in oil, 8 mmol) at 0° C. The mixture was stirred at 0° C. for one hour and then warmed up to room temperature for 30 minutes. The reaction was quenched with a saturated ammonia chloride solution. After removing tetrahydrofuran, the crude product was extracted with ethyl acetate. The ethyl acetate layer was washed with brine, dried over magnesium sulfate and evaporated under reduced pressure. The residue was purified by chromatography on silica gel using ethyl acetate/methanol (20/1) to give 45 mg of product (yield:

18%) [Molecular formula: $C_{63}H_{111}N_{11}O_{13}$; Exact Mass: 1229.84; MS (m/z): 1230.6 $(M+1)^+$, 1252.82 $(M+Na)^+$; TLC $R_f$: 0.50 (ethyl acetate/methanol=10/1); HPLC RT: 15.38 min (C8 reverse phase column: 250 mm; acetonitrile/water (0.05% trifluoroacetic acid); operation temperature: 64° C.; detector: 210 nm); $^1$H NMR spectrum (600 MHz, CDCl$_3$, δ in ppm): 0.72 (d, J=5.4 Hz, 3H), 0.84-1.00 (m, 30H), 1.17-1.26 (m, 15H), 1.34 (d, J=6.0 Hz, 3H), 1.44-1.47 (m, 2H), 1.59-1.62 (m, 6H), 1.69-1.76 (m, 4H), 1.94-1.99 (m, 1H), 2.09-2.13 (m, 3H), 2.34-2.37 (m, 3H), 2.65(s, 3H), 2.67 (s, 3H), 3.09 (s, 3H)), 3.10 (s, 3H), 3.19 (s, 3H), 3.44 (s, 3H), 3.46 (s, 3H), 3.80 (m, 1H), 3.91 (m, 1H), 4.47-4.50 (m, 1H), 4.68-4.71(t, J=9.0 Hz, 1H), 4.78-4.81 (m, 1H), 4.98-5.02 (m, 2H), 5.06-5.11 (m, 3H), 5.24 (s, 1H), 5.32 (m, 2H), 5.41-5.43 (m, 2H), 5.64-5.66 (m, 1H), 7.11 (d, J=7.2 Hz, 1H), 7.49 (d, J=7.2 Hz, 1H), 7.74 (d, J=8.4 Hz, 1H), 7.84 (d, J=9.6 Hz, 1H)].

Method 2

[(R)-α-Hydroxymethyl-Sar]-3-[(γ-hydroxy)-NMeLeu]-4-cyclosporin (crude, 2.00 g), carbon tetrabromide (2.66 g, 8.02 mmol) and triphenylphosphine (2.11 g, 8.02 mmol) were dissolved in dichloromethane (30 ml). The mixture was stirred under nitrogen at room temperature for two hours. Then the mixture was added into a suspension of sodium hydride (60% dispersion in mineral oil) (0.77 g, 19.25 mmol) in tetrahydrofuran (30 ml) under nitrogen at 0° C. The mixture was stirred at 0° C. for one hour. Most of solvents then were evaporated under reduced pressure. The residue was treated with water (10 ml) slowly at 0° C. Ethyl acetate (30 ml) and water (30 ml) were added and the mixture was separated. The ethyl acetate layer was washed with brine, dried over magnesium sulfate and evaporated under reduced pressure. The residue was purified by chromatography (hexane/acetone from 90/10 to 70/30) to give 0.68 g product of [α-methylene-Sar]-3-[(γ-hydroxy)-

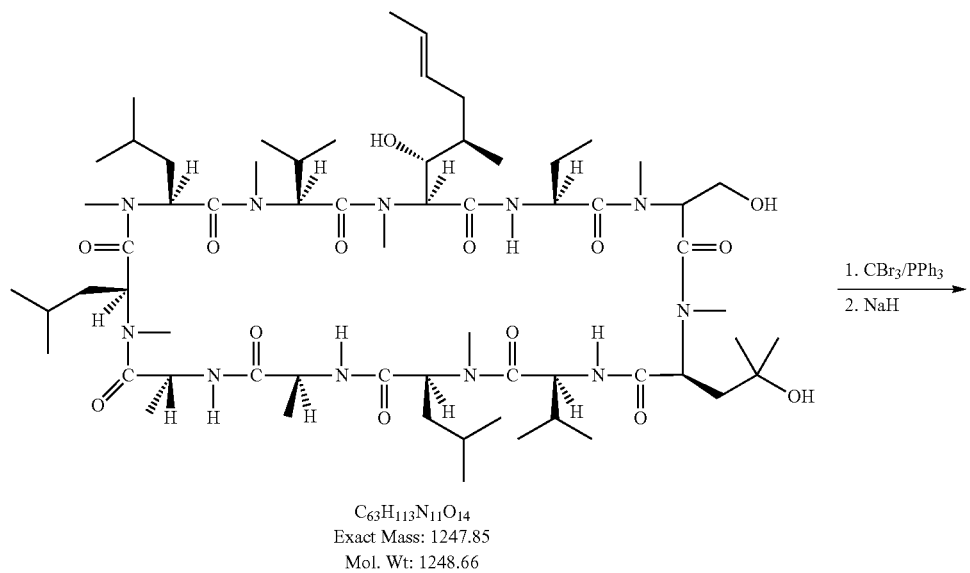

$C_{63}H_{113}N_{11}O_{14}$
Exact Mass: 1247.85
Mol. Wt: 1248.66

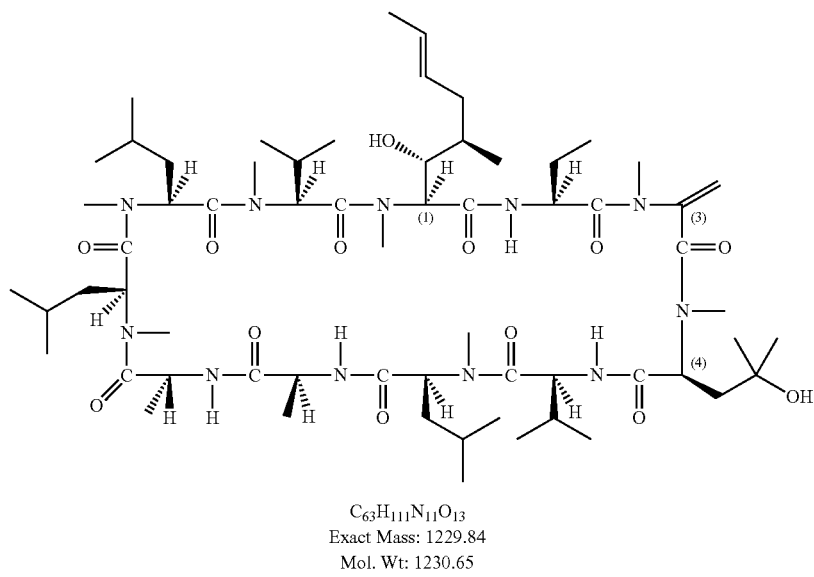

$C_{63}H_{111}N_{11}O_{13}$
Exact Mass: 1229.84
Mol. Wt: 1230.65

NMeLeu]-4-cyclosporin [Molecular Formula: $C_{63}H_{111}N_{11}O_{13}$; Exact Mass: 1229.84; MS (m/z): 1230.50 (M+1)$^+$, 1252.68 (M+Na)$^+$; TLC $R_f$: 0.50 (ethyl acetate/methanol=10/1); HPLC RT: 15.36 min (C8 reverse phase column: 250 mm; acetonitrile/water (0.05% trifluoroacetic acid); operation temperature: 64° C.; detector: 210 nm)].

Method 3 lecular formula: $C_{63}H_{112}ClN_{11}O_{13}$; Exact Mass: 1265.81; MS (m/z): 1266.32 (M+1)$^+$, 1288.43 (M+Na)$^+$] was used in next step reaction without further purification. To a solution of the above crude product in tetrahydrofuran (20 ml) was added sodium hydride (320 mg, 60% in oil, 8 mmol) at 0° C. under stirring. The mixture was stirred at 0° C. for one hour and then warmed up to room temperature for another 30 minutes. The reaction was then quenched with a saturated ammonia chloride solution. After removing tetrahydrofuran,

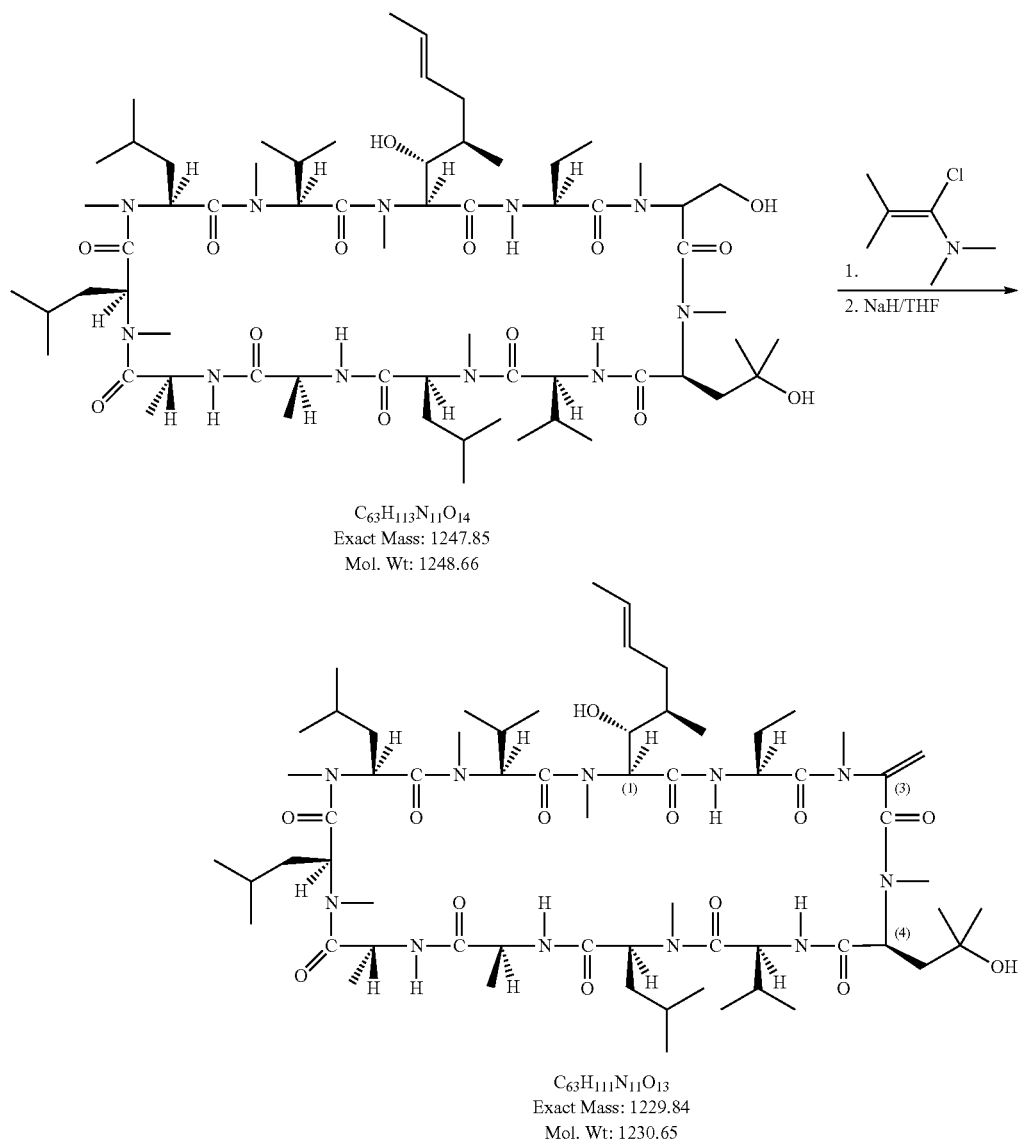

To a solution of [(R)-α-hydroxymethyl-Sar]-3-[(γ-hydroxy)-NMeLeu]-4-cyclosporin (250 mg, 0.20 mmol) in methylene chloride (10 mL) was added dropwise 1-chloro-N,N,2-trimethyl-1-propenylamine (131 μl, d 1.01, 1.0 mmol) at 0° C. under nitrogen atmosphere. After stirred for 30 minutes at 0° C., the mixture was allowed to warm to room temperature and stirred for another hour. The reaction mixture was washed with sodium bicarbonate solution, brine, dried over magnesium sulfate and evaporated under reduced pressure. The crude product containing [α-chloromethyl-Sar]-3-[(γ-hydroxy)-NMeLeu]-4-cyclosporin [Mothe residue was extracted with ethyl acetate. The ethyl acetate layer was washed with brine, dried over magnesium sulfate and evaporated under reduced pressure. The residue was purified by chromatography on silica gel using ethyl acetate/methanol (20/1) to give 33 mg of product (yield: 13%) [Molecular formula: $C_{63}H_{111}N_{11}O_{13}$; Exact Mass: 1229.84; MS (m/z): 1230.45(M+1)$^+$, 1252.65 (M+Na)$^+$; TLC $R_f$: 0.50 (ethyl acetate/methanol=10/1); HPLC RT: 15.36 min (C8 reverse phase column: 250 mm; acetonitrile/water (0.05% trifluoroacetic acid); operation temperature: 64° C.; detector: 210 nm)].

Method 4
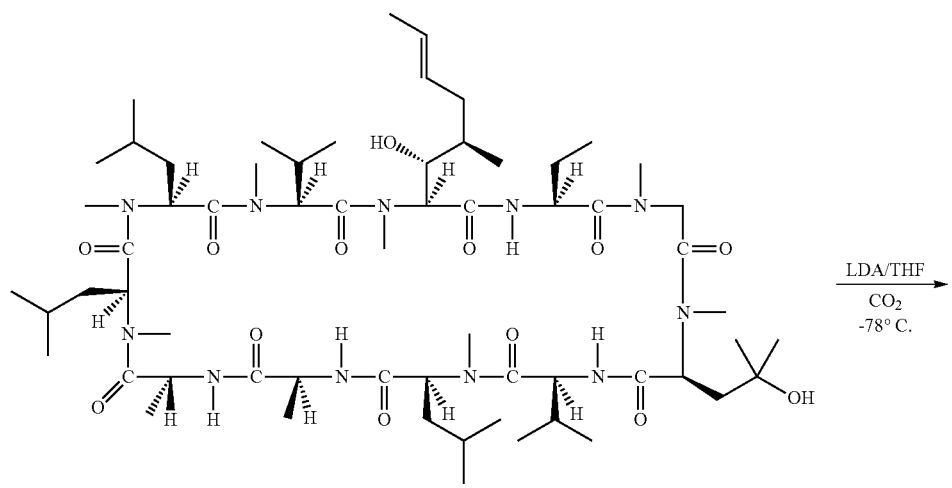
C$_{62}$H$_{111}$N$_{11}$O$_{13}$
Exact Mass: 1217.84
Mol. Wt: 1218.63
LDA/THF
CO$_2$
-78° C.
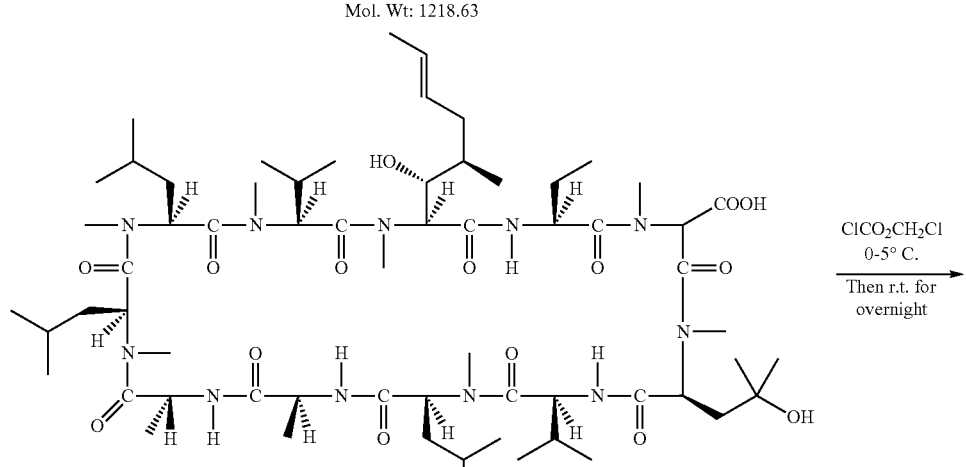
C$_{63}$H$_{111}$N$_{11}$O$_{15}$
Exact Mass: 1261.83
Mol. Wt: 1262.64
ClCO$_2$CH$_2$Cl
0-5° C.
Then r.t. for overnight
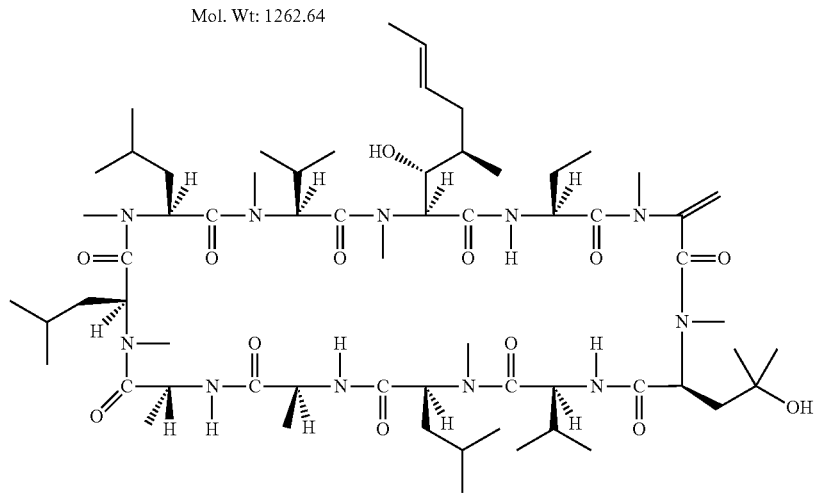
C$_{63}$H$_{111}$N$_{11}$O$_{13}$
Exact Mass: 1229.84
Mol. Wt: 1230.65 n-BuLi (2.2 M, 49.30 ml, 108.46 mmol) was added into a solution of diisopropylamine (15.39 ml, 108.46 mmol) in tetrahydrofuran (150 ml) at −78° C. under nitrogen. After the reaction mixture was stirred for an hour, a solution of [(γ-hydroxy)-NMeLeu]-4-cyclosporin (12.00 g, 9.86 mmol) in tetrahydrofuran (30 ml) was added over 10 min. The stirring was continued at −78° C. for two hours. Carbon dioxide gas was bubbled through the reaction mixture for two hour and the mixture was stirred at −78° C. for another hour. Then the cooling bath was removed and the reaction mixture was allowed to warm up to room temperature slowly with bubbling out of unreacted carbon dioxide. The mixture was cooled to about 0-5° C. by ice bath and chloromethyl chloroformate (13.98 g, 108.46 mmol) was added. The mixture was allowed to warm to room temperature and stirred for overnight. Water (30 ml) was added to quench the reaction. Most of solvent was then evaporated under reduced pressure. Ethyl acetate (100 ml) and water (80 ml) were added. The ethyl acetate layer was separated and washed with brine, dried over magnesium sulfate and evaporated under reduced pressure. The residue was purified by chromatography with hexane/acetone (from 90:10 to 70:30) as eluent to give 4.74 g of pure product of [α-Methylene-Sar]-3-[(γ-hydroxy)-NMeLeu]-4-cyclosporin* [Molecular Formula: $C_{63}H_{111}N_{11}O_{13}$; Exact Mass: 1229.84; MS (m/z): 1230.39 (M+1)$^+$, 152.59 (M+Na)$^+$; TLC $R_f$: 0.50 (ethyl acetate/methanol=10/1); HPLC RT: 15.38 min (C8 reverse phase column: 250 mm; acetonitrile/water (0.05% trifluoroacetic acid); operation temperature: 64° C.; detector: 210 nm)].

Synthesis of [α-Methylene-Sar]-3-cyclosporin can also be prepared using a method analogous to that described in WO2012/051194A1.

Example 29

[(S)-(Methoxycarbonylmethylthio)methyl-Sar]-3-[(γ-hydroxy)-NMeLeu]-4-cyclosporin

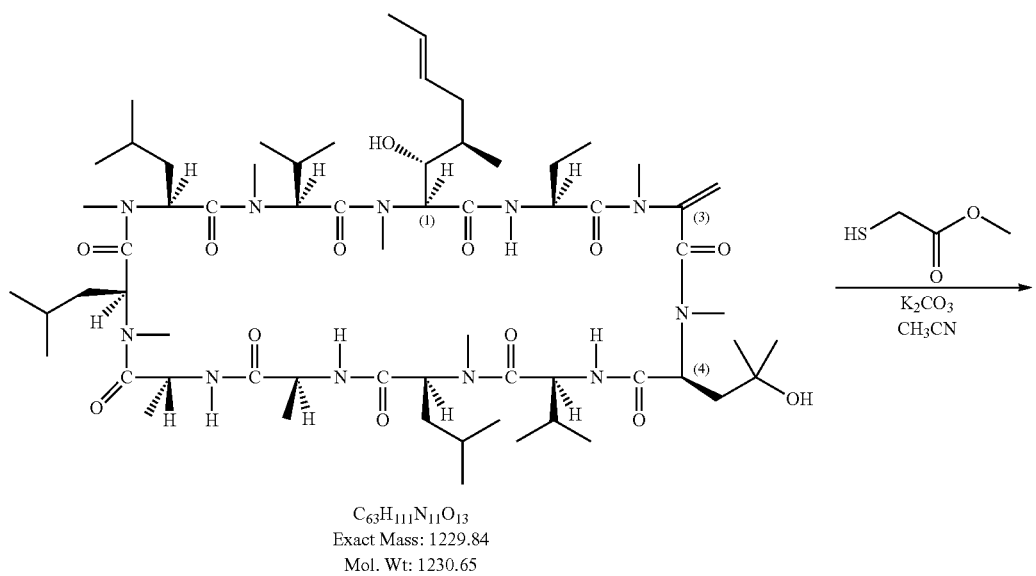

$C_{63}H_{111}N_{11}O_{13}$
Exact Mass: 1229.84
Mol. Wt: 1230.65

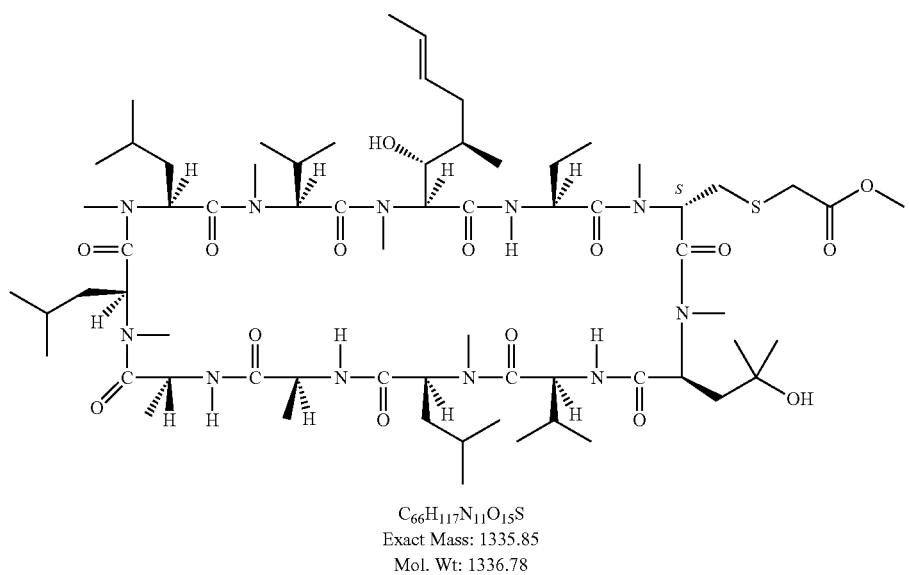

$C_{66}H_{117}N_{11}O_{15}S$
Exact Mass: 1335.85
Mol. Wt: 1336.78

[α-Methylene-Sar]-3-[(γ-hydroxy)-N-MeLeu]-4-cyclosporin (0.25 g, 0.20 mmol) and methylmercaptoacetate (0.24 g, 2.00 mmol) were dissolved in acetonitrile (15 ml), followed by adding 20 equivalents of potassium carbonate (0.55 g, 4.0 mmol). The mixture was stirred overnight at room temperature. After removal of solvents, the residue was dissolved in dichloromethane (20 ml). The dichloromethane solution was washed with brine, dried over magnesium sulfate and evaporated under reduced pressure. The residue was subject to the flash chromatography using ethyl acetate/methanol as eluent to give product. [Molecular formula: $C_{66}H_{117}N_{11}O_{15}S$; Exact Mass: 1335.84; MS (m/z): 1336.50 (M+1)$^+$, 1358.80 (M+Na)$^+$; TLC $R_f$: 0.30 (ethyl acetate/methanol=20/1); HPLC RT: 14.33 min (C8 reverse phase column: 250 mm; acetonitrile/water (0.05% trifluoroacetic acid); operation temp: 64° C.; Detector: 210 nm)].

Example 30

[(S)-(2-Aminoethylthio)methyl-Sar]-3-[(γ-hydroxy)-NMeLeu]-4-cyclosporin

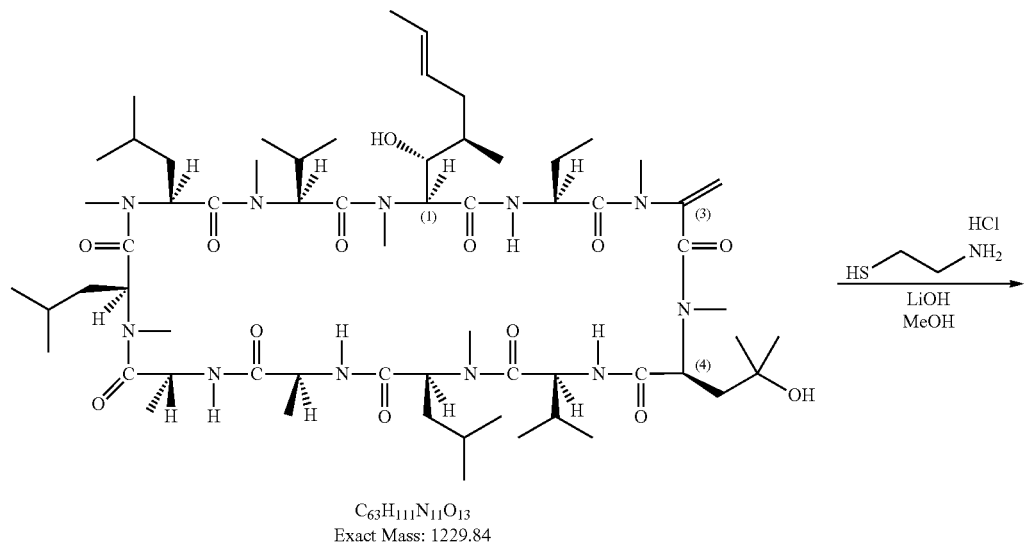

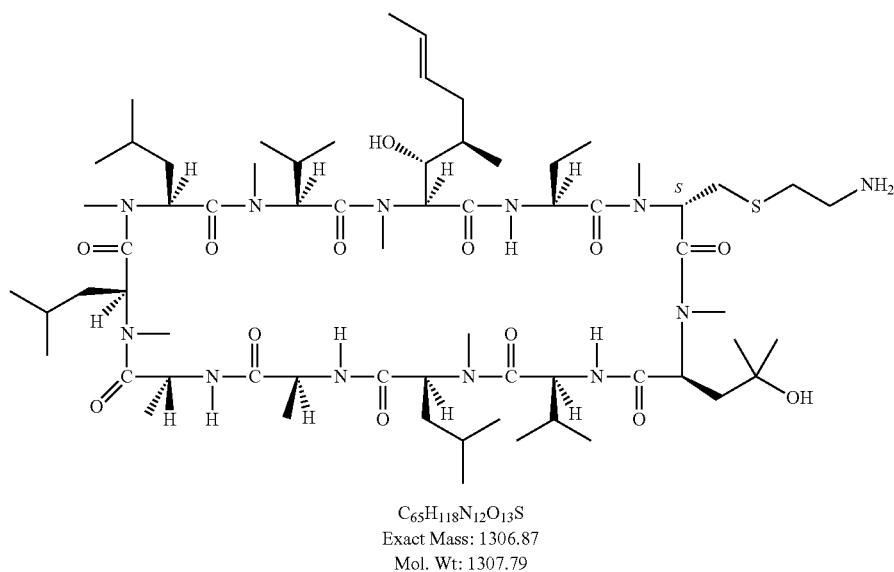

[α-Methylene-Sar]-3-[(γ-hydroxy)-N-MeLeu]-4-cyclosporin (0.86 g, 0.70 mmol) and 2-aminoethanethiol hydrochloride (0.80 g, 7.00 mmol) were dissolved in methanol (80 ml), followed by adding 20 equivalents of lithium hydroxide (0.17 g, 7.00 mmol). The mixture was stirred overnight at room temperature. After removal of solvent, the residue was subjected to the flash chromatography using dichloromethane/methanol as eluent to give 0.60 g of product [Molecular Formula: $C_{65}H_{118}N_{12}O_{13}S$; Exact Mass: 1306.87; MS (m/z): 1307.56(M+1)$^+$, 1329.73 (M+Na)$^-$, TLC $R_f$: 0.025 (dichloromethane/methanol=5/1); HPLC RT: 10.97 min (C8 reverse phase column: 250 mm; acetonitrile/water (0.05% trifluoroacetic acid); operation temperature: 64° C.; detector: 210 nm)].

Example 31

[(S)-(2-(N,N-Dimethylamino)ethylthio)methyl-Sar]-3-[(γ-hydroxy)-NMeLeu]-4-cyclosporin (Isomer B) and [(R)-(2-(N,N-Dimethylamino)ethylthio)methyl-Sar]-3-[(γ-hydroxy)-NMeLeu]-4-cyclosporin (Isomer A)

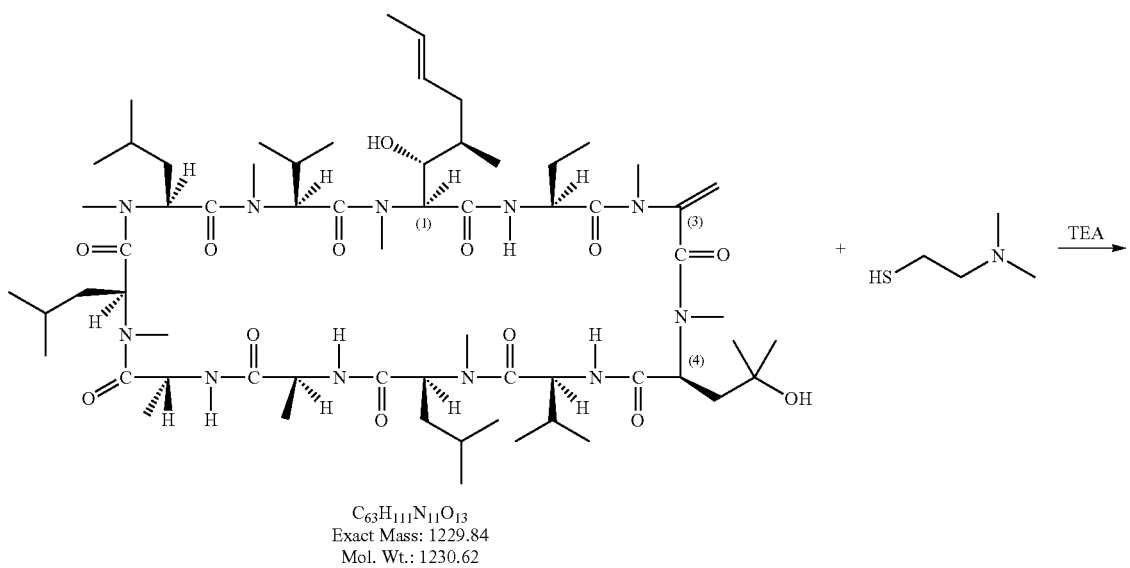

$C_{63}H_{111}N_{11}O_{13}$
Exact Mass: 1229.84
Mol. Wt.: 1230.62

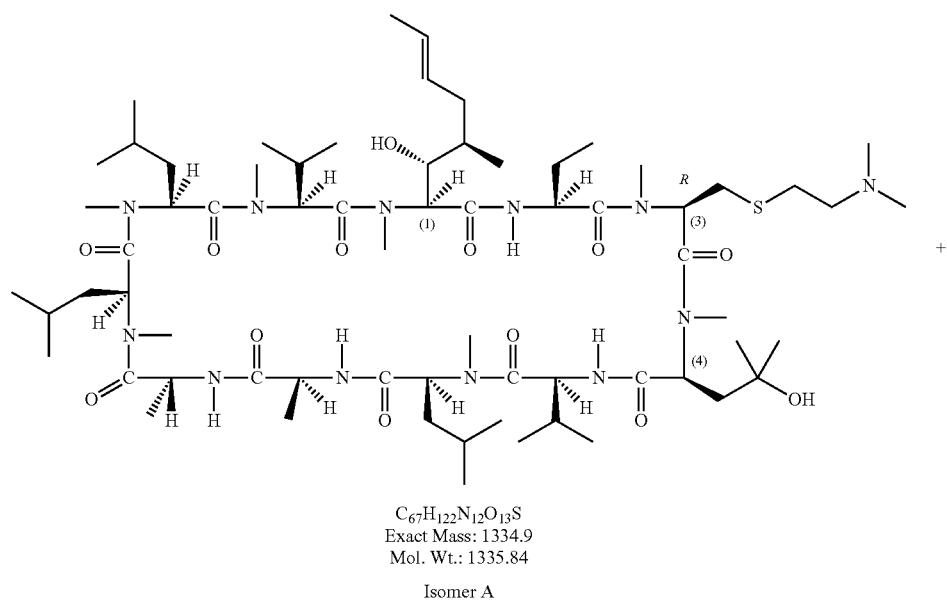

$C_{67}H_{122}N_{12}O_{13}S$
Exact Mass: 1334.9
Mol. Wt.: 1335.84

Isomer A

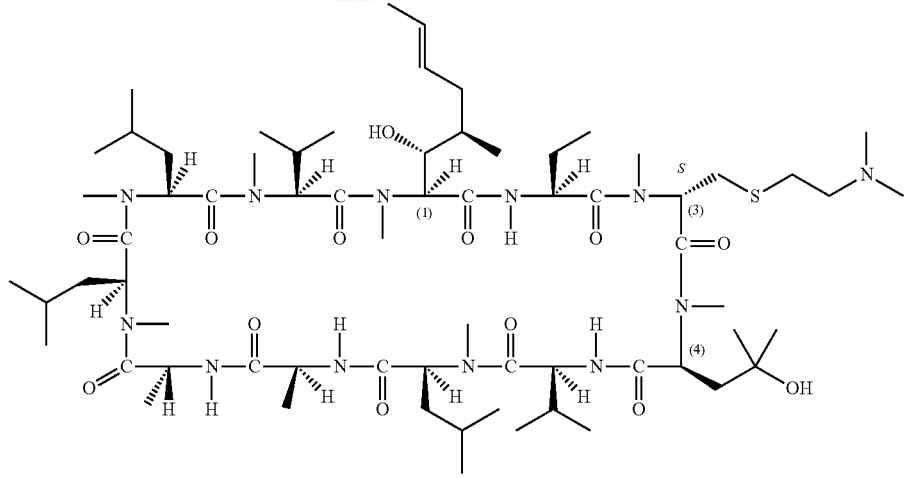

C₆₇H₁₂₂N₁₂O₁₃S
Exact Mass: 1334.9
Mol. Wt.: 1335.84

Isomer B

[α-Methylene-Sar]-3-[(γ-hydroxy)-N-MeLeu]-4-cyclosporin (0.62 g, 0.50 mmol) and 2-(dimethylamino)ethanethiol (0.49 g, 6.00 mmol) were dissolved in methanol (30 ml) followed by adding triethylamine (0.82 ml, 6.00 mmol). The mixture was stirred overnight at room temperature. After removal of solvent, the residue was subjected to chromatography using dichloromethane/methanol as eluent to yield 0.41 g of [(R)-(2-(N,N-dimethylamino)ethylthio)methyl-Sar]-3-[(γ-hydroxy)-N-MeLeu]-4-cyclosporin (isomer A) and 0.18 g of [(S)-(2-(N,N-dimethylamino)ethylthio) methyl-Sar]-3-[(γ-hydroxy)-N-MeLeu]-4-cyclosporin (isomer B) [Molecular Formula: C₆₇H₁₂₂N₁₂O₁₃S; Exact Mass: 1334.9; MS (m/z): 1335.7(M+1)⁺; TLC R$_f$: 0.05 (ethyl acetate/methanol=5/1); HPLC RT: 10.88 min (isomer A) and 11.30 min (isomer B) (C8 reverse phase column: 250 mm; acetonitrile/water (0.05% trifluoroacetic acid); operation temperature: 64° C.; detector: 210 nm)].

Example 32

[(S)-(2-(N,N-Diethylamino)ethylthio)methyl-Sar]-3-[(γ-hydroxy)-NMeLeu]-4-cyclosporin (Isomer B) and [(R)-(2-(N,N-Diethylamino)ethylthio)methyl-Sar]-3-[(γ-hydroxy)-NMeLeu]-4-cyclosporin (Isomer A)

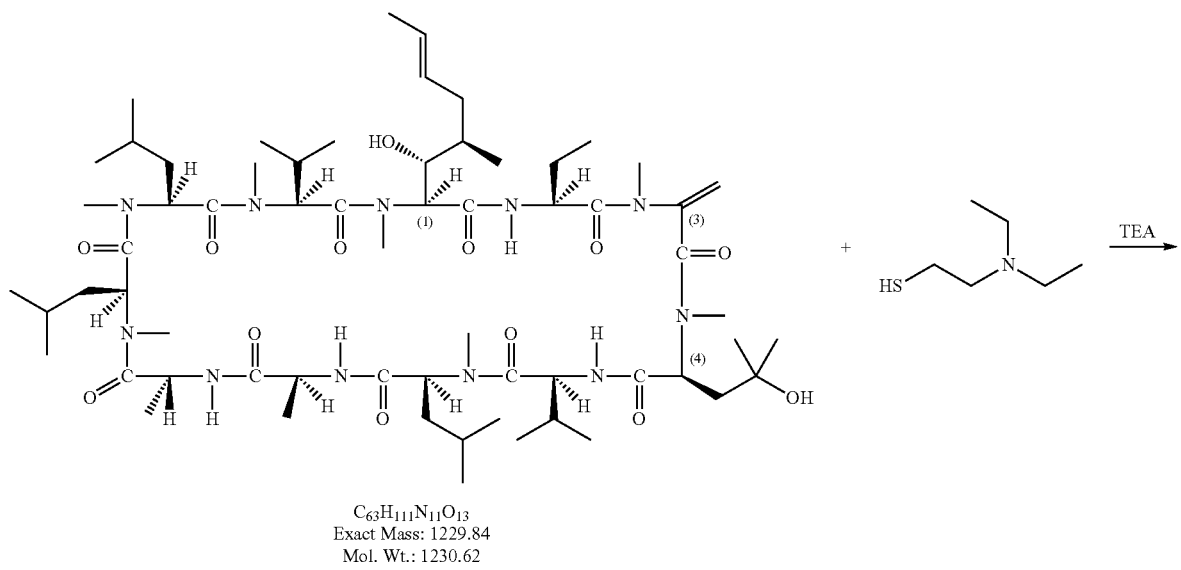

C₆₃H₁₁₁N₁₁O₁₃
Exact Mass: 1229.84
Mol. Wt.: 1230.62

-continued

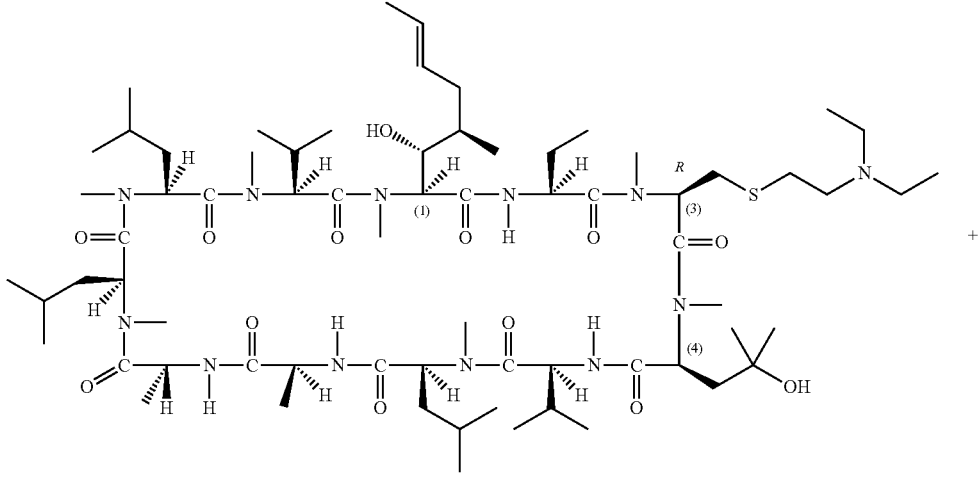

C₆₉H₁₂₆N₁₂O₁₃S
Exact Mass: 1362.93
Mol. Wt.: 1363.90

Isomer A

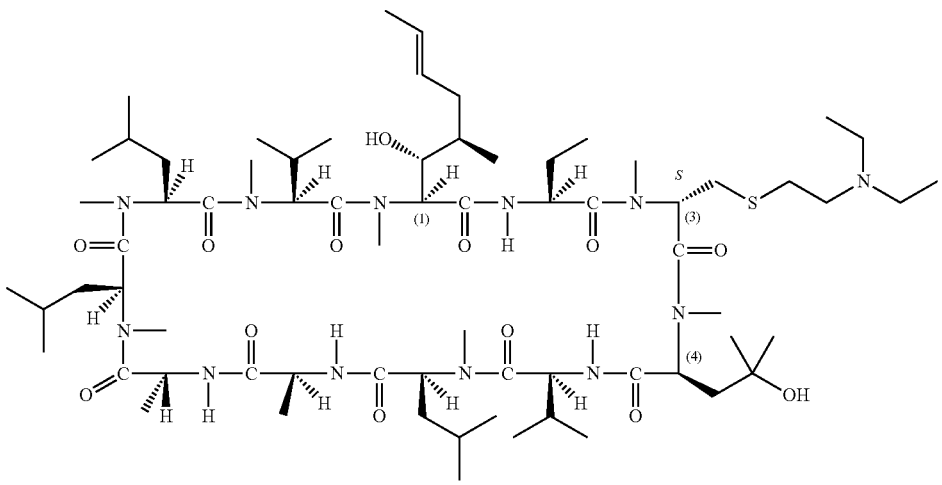

C₆₉H₁₂₆N₁₂O₁₃S
Exact Mass: 1362.93
Mol. Wt.: 1363.90

Isomer B

[α-Methylene-Sar]-3-[(γ-hydroxy)-N-MeLeu]-4-cyclosporin (0.31 g, 0.25 mmol) and 2-diethylaminoethanethiol (0.40 g, 3.00 mmol) were dissolved in methanol (30 ml), followed by adding triethylamine (0.41 ml, 3.00 mmol). The mixture was stirred overnight at room temperature. After removal of solvent, the residue was subjected to chromatography using dichloromethane/methanol as eluent to yield 0.15 g of [(R)-(2-(N,N-diethylamino)ethylthio)methyl-Sar]-3-[(γ-hydroxy-N-MeLeu]-4-cyclosporin (isomer A) and 0.10 g of [(S)-(2-(N,N-diethylamino)ethylthio)methyl-Sar]-3-[(γ-hydroxy-N-MeLeu]-4-cyclosporin (isomer B) [Molecular Formula: $C_{69}H_{126}N_{12}O_{13}S$; Exact Mass: 1362.93; MS (m/z): 1363.75 (M+1)⁻; TLC $R_f$: 0.1 (ethyl acetate/methanol=5/1); HPLC RT: 11.64 min (isomer A) and 11.85 min (isomer B) (C8 reverse phase column: 250 mm; acetonitrile/water (0.05% trifluoroacetic acid); operation temperature: 64° C.; detector: 210 nm)].

Example 33

[(S)-(2-(N-Isopropylamino)ethylthio)methyl-Sar]-3-[(γ-hydroxy)-NMeLeu]-4-cyclosporin

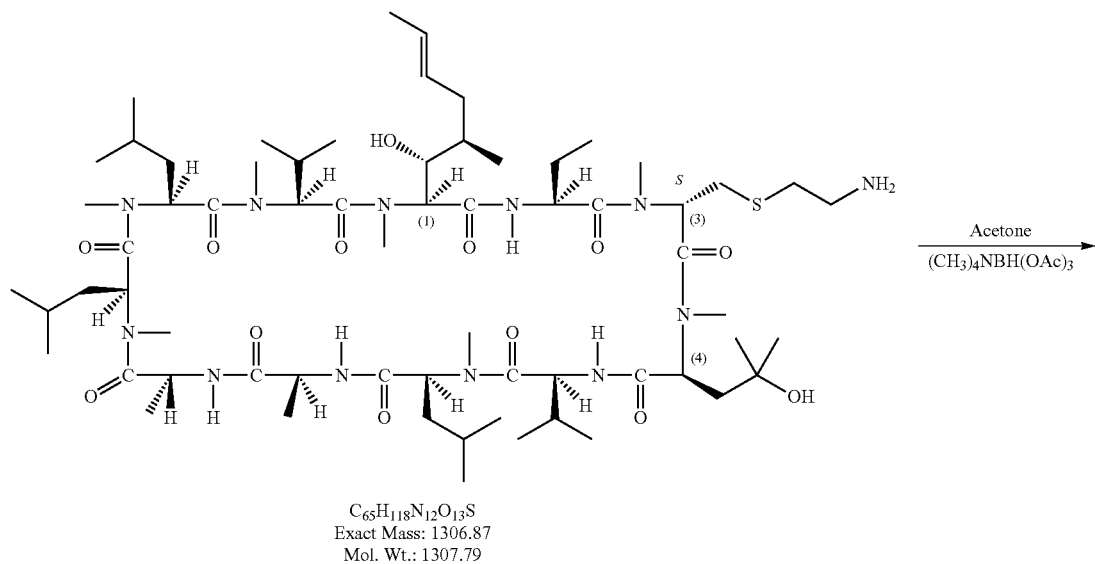

$C_{65}H_{118}N_{12}O_{13}S$
Exact Mass: 1306.87
Mol. Wt.: 1307.79

Acetone
$(CH_3)_4NBH(OAc)_3$

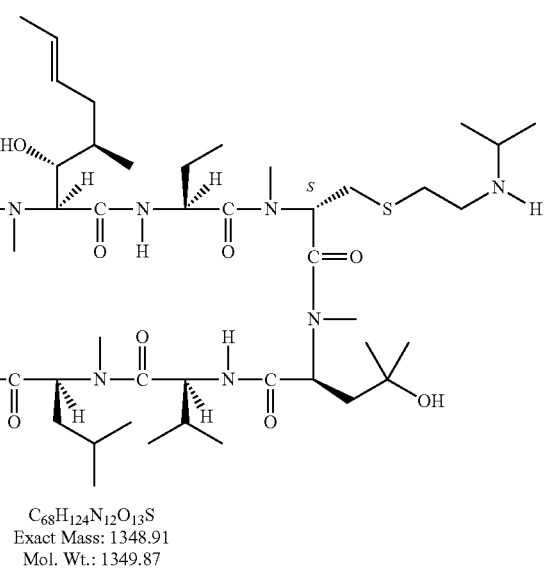

$C_{68}H_{124}N_{12}O_{13}S$
Exact Mass: 1348.91
Mol. Wt.: 1349.87

[(S)-(2-(Amino)ethylthio)methyl-Sar]-3-[(γ-hydroxy)-N-MeLeu]-4-cyclosporin (0.31 g, 0.25 mmol) and acetone (0.40 ml, 5.44 mmol) were dissolved in chloroform (30 ml), followed by adding 2.5 equivalents of tetramethylammonium triacetoxyborohydride (164 mg, 0.63 mmol) in portions and a few drops of acetic acid. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using methylene/methanol as eluent to give 0.25 g of pure product [Molecular Formula: $C_{68}H_{124}N_{12}O_{13}S$; Exact Mass: 1348.91; MS (m/z): 1349.59 (M+1)$^+$; TLC $R_f$: 0.1 (ethyl acetate/methanol=5/1); HPLC RT: 11.97 min (C8 reverse phase column: 250 mm; acetonitrile/water (0.05% trifluoroacetic acid); operation temperature: 64° C.; detector: 210 nm)].

Example 34

[(S)-(2-(N-Isopropyl-N-methylamino)ethylthio)methyl-Sar]-3-[(γ-hydroxy)-NMeLeu]-4-cyclosporin

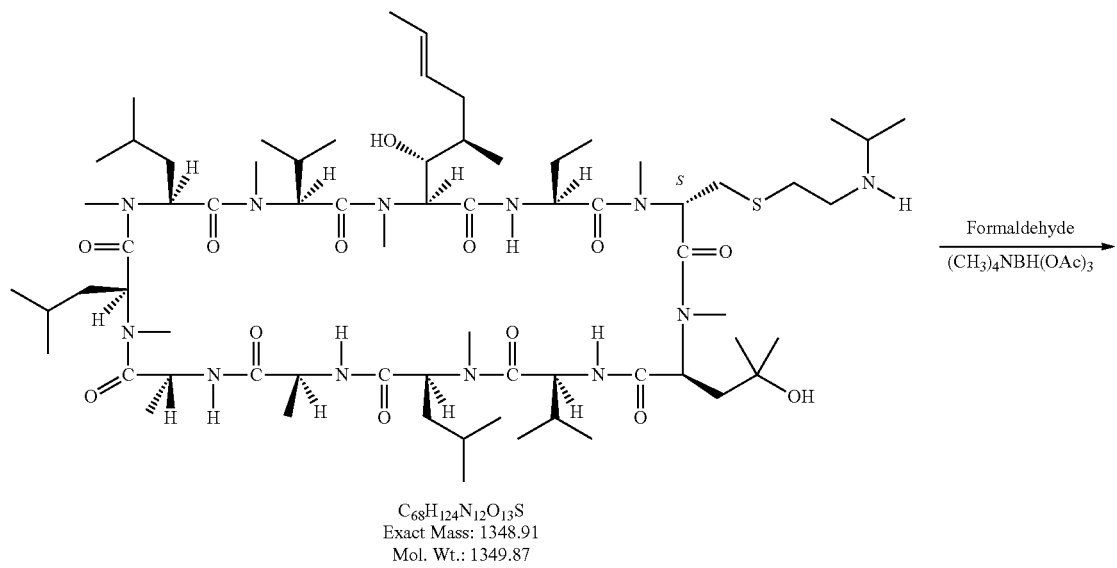

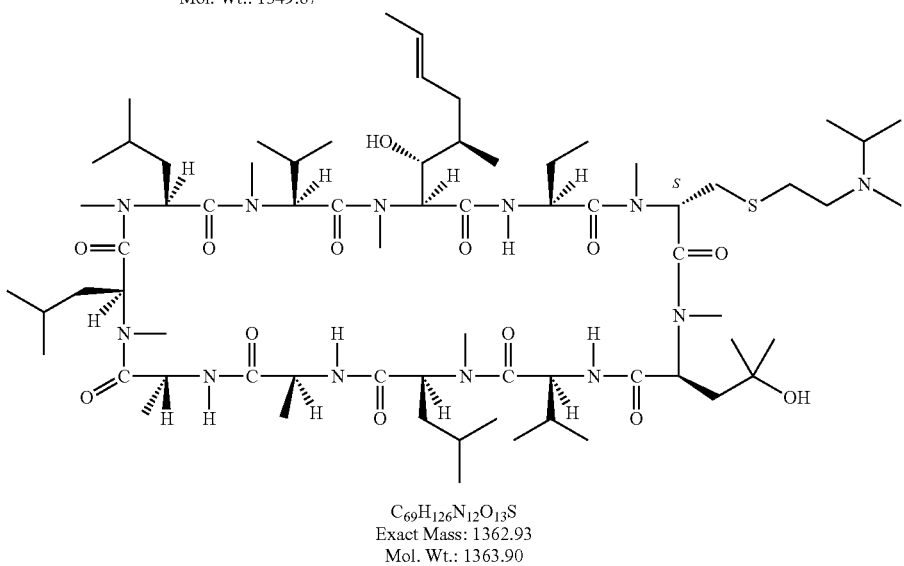

[(S)-(2-(N-Isopropylamino)ethylthio)methyl-Sar]-3-[(γ-hydroxy)-N-MeLeu]-4-cyclosporin (49 mg, 0.034 mmol) and formaldehyde (100 μl, 37% in water) were mixed with chloroform (10 ml), followed by adding 2.5 equivalents of tetramethylammonium triacetoxyborohydride (22 mg, 0.085 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 30 mg of pure product [Molecular Formula: $C_{69}H_{126}N_{12}O_{13}S$; Exact Mass: 1362.93; MS (m/z): 1363.72(M+1)$^+$, 1385.81(M+Na)$^+$; TLC $R_f$: 0.15 (ethyl acetate/methanol=5:1); HPLC RT: 12.26 min (C8 reverse phase column: 250 mm; acetonitrile/water (0.05% trifluoroacetic acid); operation temperature: 64° C.; detector: 210 nm)].

Example 35

[(S)-(2-(N-Ethyl-N-isopropylamino)ethylthio)methyl-Sar]-3-[(γ-hydroxy)-NMeLeu]-4-cyclosporin

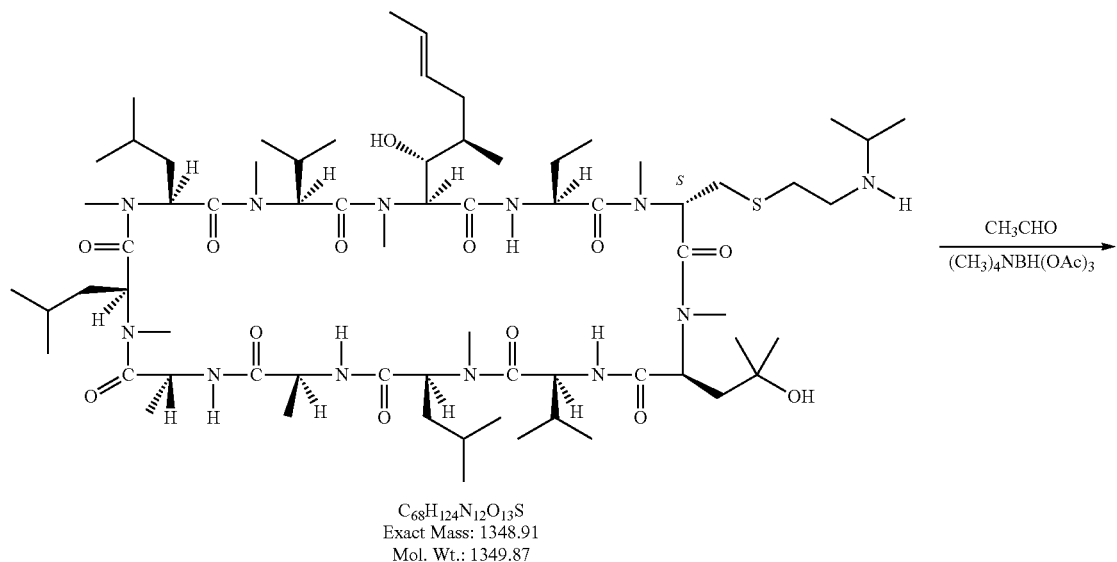

$C_{68}H_{124}N_{12}O_{13}S$
Exact Mass: 1348.91
Mol. Wt.: 1349.87

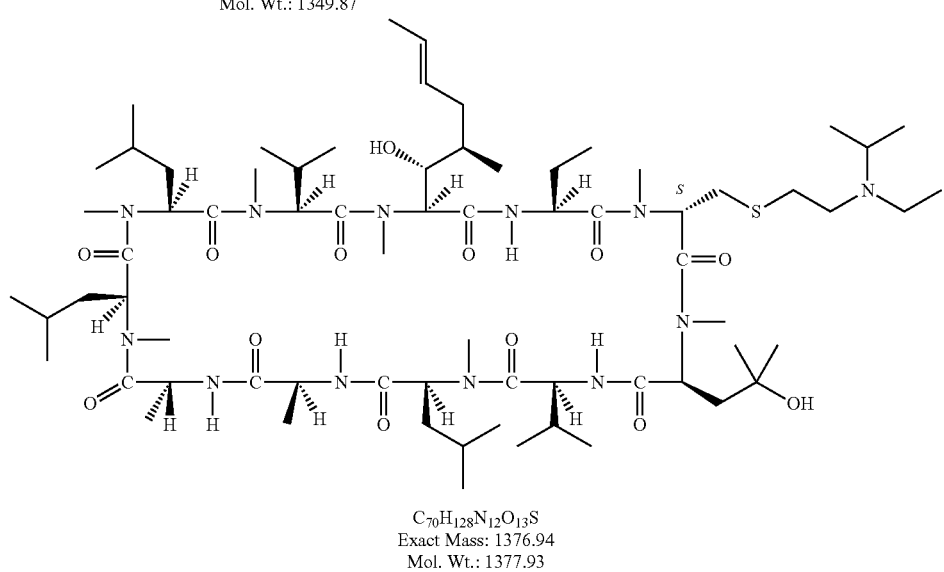

$C_{70}H_{128}N_{12}O_{13}S$
Exact Mass: 1376.94
Mol. Wt.: 1377.93

[(S)-(2-(N-Isopropylamino)ethylthio)methyl-Sar]-3-[(γ-hydroxy)-N-MeLeu]-4-cyclosporin (49 mg, 0.034 mmol) and acetaldehyde (100 μl, 37% in water) were mixed with chloroform (10 ml), followed by adding 2.5 equivalents of tetramethylammonium triacetoxyborohydride (22 mg, 0.085 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 37 mg of pure product [Molecular Formula: $C_{70}H_{128}N_{12}O_{13}S$; Exact Mass: 1376.94; MS (m/z): 1377.84 (M+1)$^+$; TLC $R_f$: 0.15 (ethyl acetate/methanol=5/1); HPLC RT: 12.36 min (C8 reverse phase column: 250 mm; acetonitrile/water (0.05% trifluoroacetic acid); operation temperature: 64° C.; detector: 210 nm)].

Example 36

[(S)-(2-(N-Isobutylamino-N-isopropyl)ethylthio)methyl-Sar]-3-[(γ-hydroxy)-NMeLeu]-4-cyclosporin

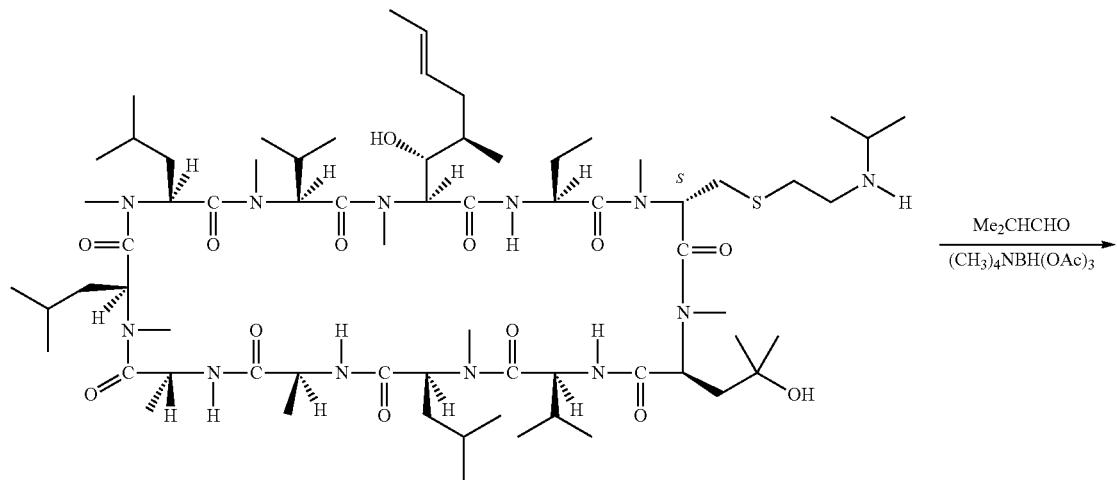

$C_{68}H_{124}N_{12}O_{13}S$
Exact Mass: 1348.91
Mol. Wt.: 1349.87

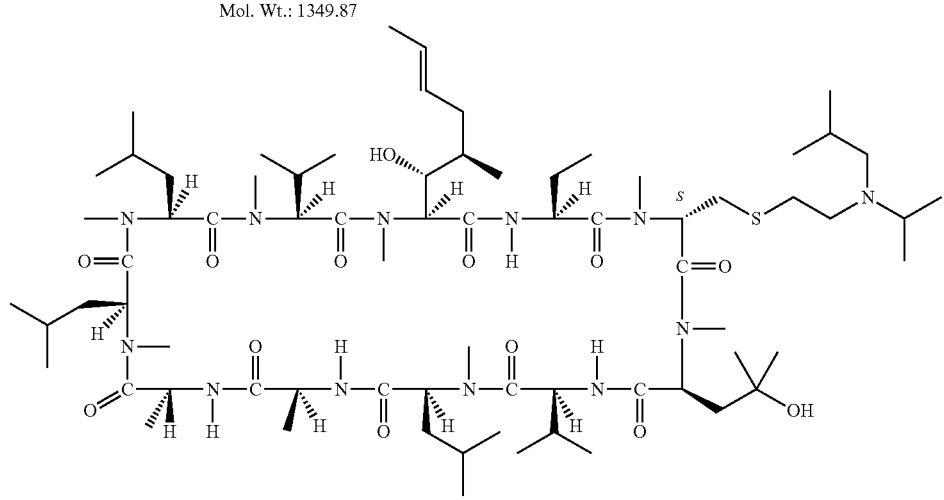

$C_{72}H_{132}N_{12}O_{13}S$
Exact Mass: 1404.98
Mol. Wt.: 1405.98

[(S)-(2-(N-isopropylamino)ethylthio)methyl-Sar]-3-[(γ-hydroxy)-N-MeLeu]-4-cyclosporin (0.25 g, 0.20 mmol) and isobutyraldehyde (91 μl, 10 mmol) were dissolved in chloroform (30 ml), followed by adding 2.5 equivalents of tetramethylammonium triacetoxyborohydride (0.13 g, 0.50 mmol) in portion. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 19 mg of pure product [Molecular Formula: $C_{72}H_{132}N_{12}O_{13}S$; Exact Mass: 1404.98; MS (m/z): 1405.89 (M+1)$^+$, 1427.94 (M+Na)$^+$; TLC $R_f$: 0.25 (ethyl acetate/methanol=5/1); HPLC RT: 14.46 min (C8 reverse phase column: 250 mm; acetonitrile/water (0.05% trifluoroacetic acid); operation temperature: 64° C.; detector: 210 nm)].

Example 37

[(S)-(2-(N,N-Diisobutylamino)ethylthio)methyl-Sar]-3-[(γ-hydroxy)-NMeLeu]-4-cyclosporin

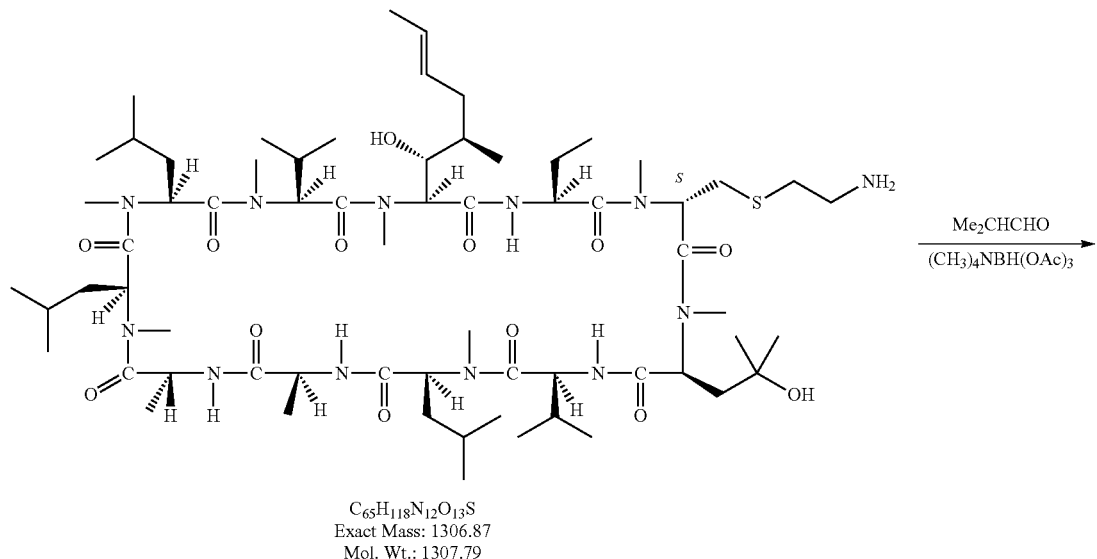

[(S)-(2-Aminoethylthio)methyl-Sar]-3-[(γ-hydroxy)-N-MeLeu]-4-cyclosporin (42 mg, 0.032 mmol) and isobutyraldehyde (15 0.165 mmol) were dissolved in chloroform (10 ml), followed by adding 2.5 equivalents of tetramethylammonium triacetoxyborohydride (21 mg, 0.080 mmol) in portions. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 23 mg of pure product [Molecular Formula: $C_{73}H_{134}N_{12}O_{13}S$; Exact Mass: 1418.99; MS (m/z): 1419.73(M+1)$^+$, 1441.87 (M+Na)$^+$; TLC $R_f$: 0.36 (ethyl acetate/methanol=5:1); HPLC RT: 14.46 min (C8 reverse phase column: 250 mm; acetonitrile/water (0.05% trifluoroacetic acid); operation temperature: 64° C.; detector: 210 nm)].

Example 38

[(S)-(2-(N-Neopentylamino)ethylthio)methyl-Sar]-3-[(γ-hydroxy)-NMeLeu]-4-cyclosporin

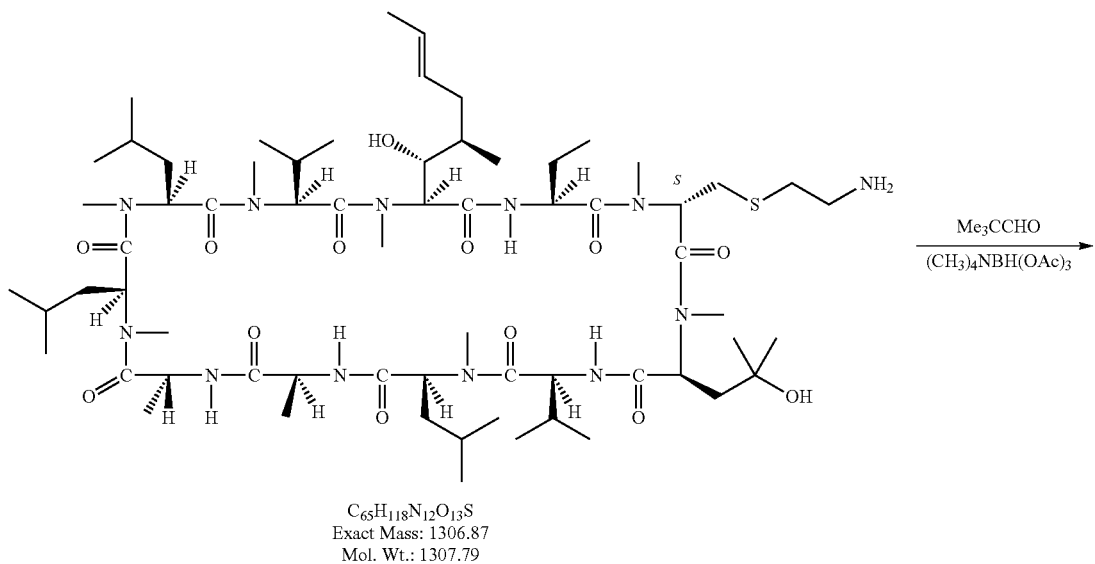

$C_{65}H_{118}N_{12}O_{13}S$
Exact Mass: 1306.87
Mol. Wt.: 1307.79

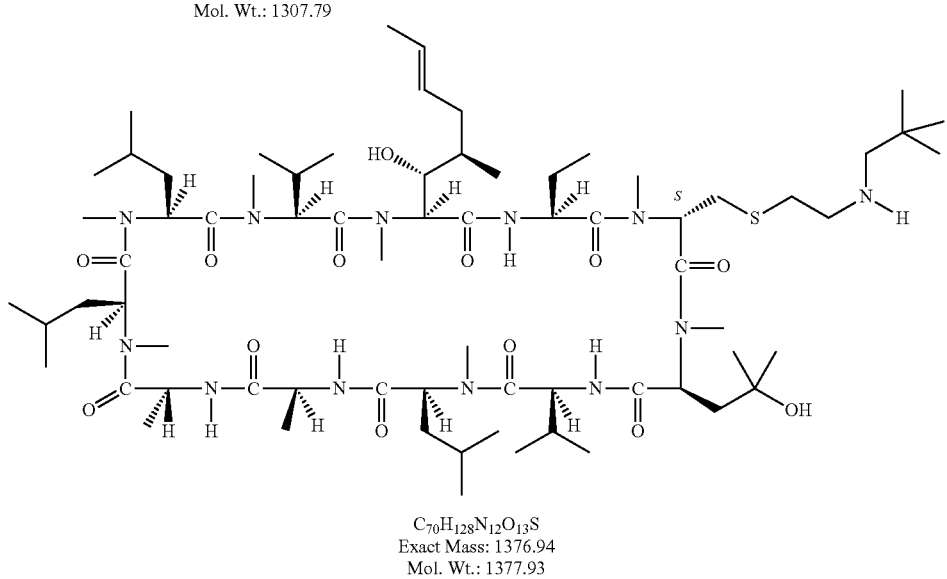

$C_{70}H_{128}N_{12}O_{13}S$
Exact Mass: 1376.94
Mol. Wt.: 1377.93

[(S)-(2-(Amino)ethylthio)methyl-Sar]-3-[(γ-hydroxy)-N-MeLeu]-4-cyclosporin (0.45 g, 0.34 mmol) and pivalaldehyde (100 μl, 37% in water) were mixed with chloroform (50 ml), followed by adding 2.5 equivalents of tetramethylammonium triacetoxyborohydride (0.22 g, 0.85 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 11 mg of pure product [Molecular Formula: $C_{70}H_{128}N_{12}O_{13}S$; Exact Mass: 1376.94; MS (m/z): 1377.72 (M+1)$^+$, 1399.82 (M+Na)$^+$; TLC $R_f$: 0.15 (ethyl acetate/methanol=5/1); HPLC RT: 12.36 min (C8 reverse phase column: 250 mm; acetonitrile/water (0.05% trifluoroacetic acid); operation temperature: 64° C.; detector: 210 nm)].

Example 39

[(S)-(2-(N-Methyl-N-neopentylamino)ethylthio)methyl-Sar]-3-[(γ-hydroxy)-NMeLeu]-4-cyclosporin

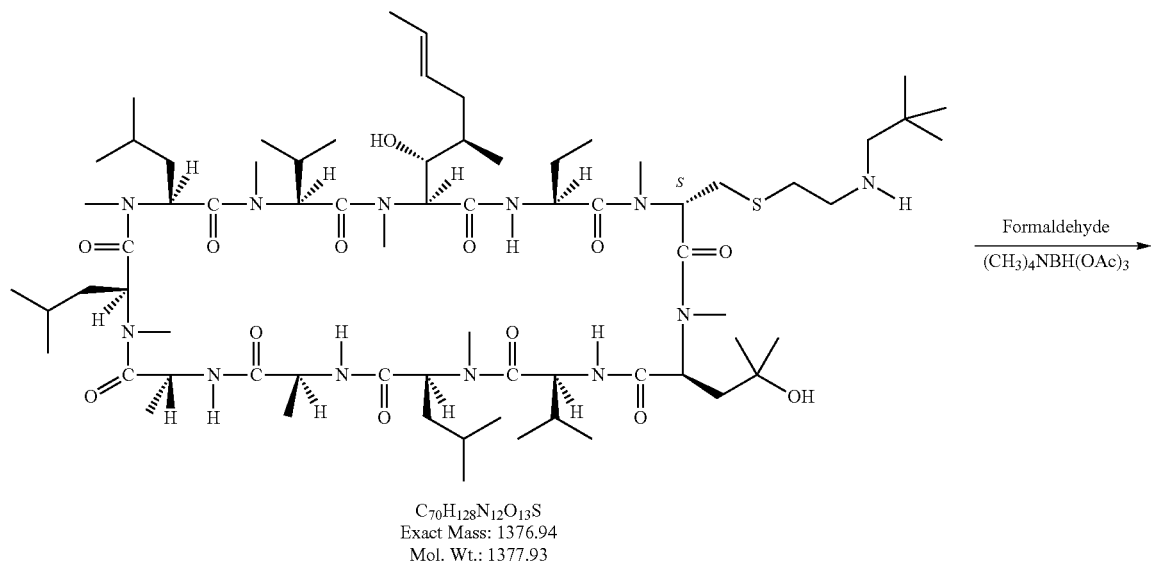

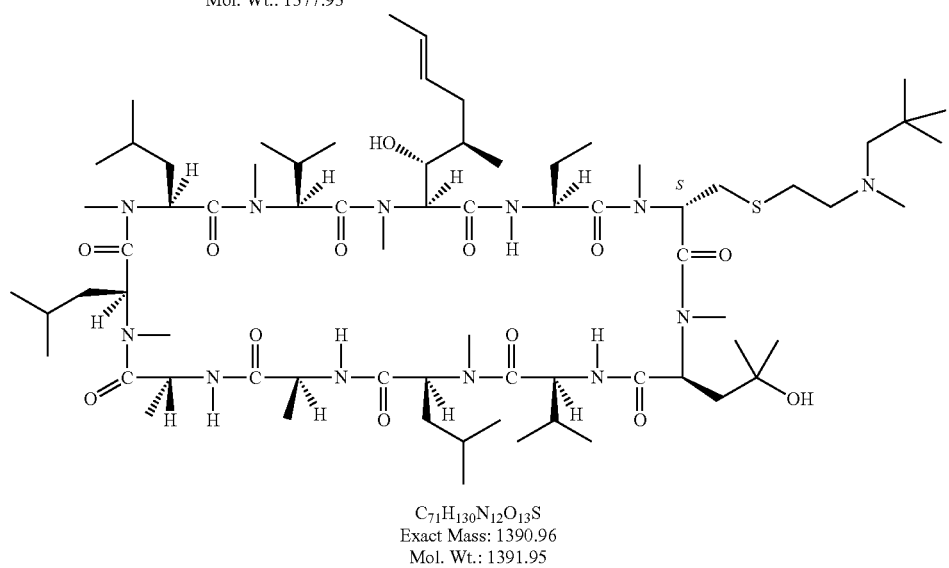

[(S)-(2-(N-Neopentylamino)ethylthio)methyl-Sar]-3-[(γ-hydroxy)-N-MeLeu]-4-cyclosporin (49 mg, 0.034 mmol) and formaldehyde (100 μl, 37% in water) were mixed with chloroform (10 ml), followed by adding 2.5 equivalents of tetramethylammonium triacetoxyborohydride (22 mg, 0.085 mmol. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 31 mg of pure product [Molecular Formula: $C_{71}H_{130}N_{12}O_{13}S$; Exact Mass: 1390.96; MS (m/z): 1391.71 $(M+1)^+$, 1413.86 $(M+Na)^+$; TLC $R_f$: 0.25 (ethyl acetate/methanol=5/1); HPLC RT: 13.28 min (C8 reverse phase column: 250 mm; acetonitrile/water (0.05% trifluoroacetic acid); operation temperature: 64° C.; detector: 210 nm)].

Example 40

[(S)-(2-(N-Ethyl-N-neopentylamino)ethylthio)methyl-Sar]-3-[(γ-hydroxy)-NMeLeu]-4-cyclosporin

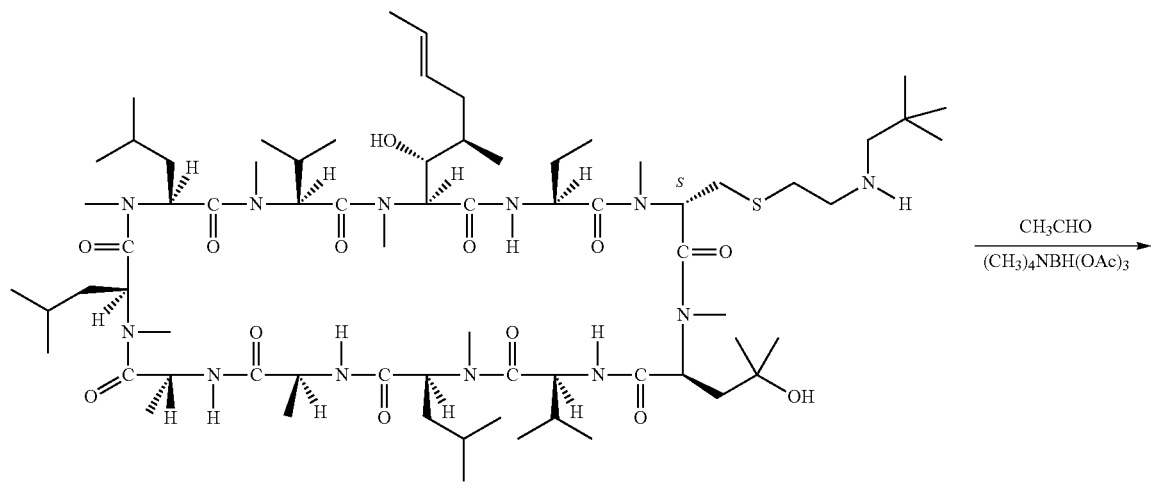

$C_{70}H_{128}N_{12}O_{13}S$
Exact Mass: 1376.94
Mol. Wt.: 1377.9

$\xrightarrow{\text{CH}_3\text{CHO}}{(\text{CH}_3)_4\text{NBH}(\text{OAc})_3}$

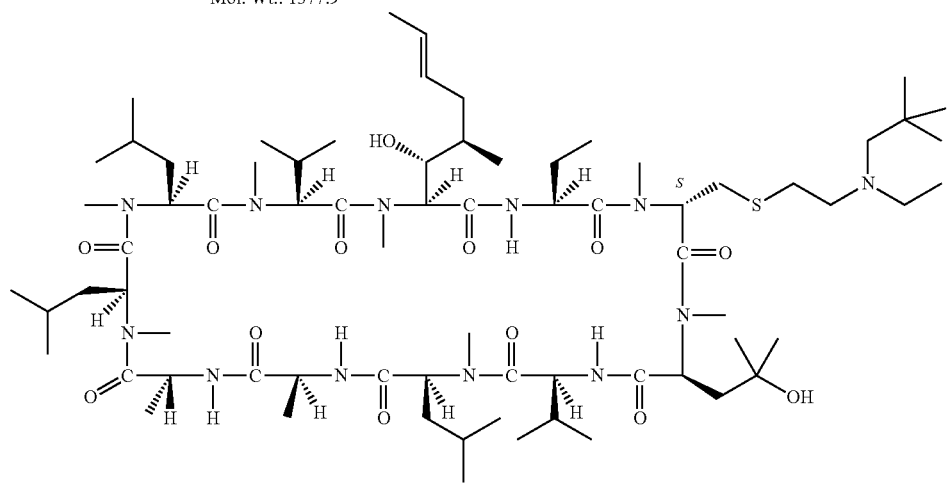

$C_{72}H_{132}N_{12}O_{13}S$
Exact Mass: 1404.98
Mol. Wt.: 1405.96

[(S)-(2-(N-Neopentylamino)ethylthio)methyl-Sar]-3-[(γ-hydroxy)-N-MeLeu]-4-cyclosporin (46 mg, 0.034 mmol) and acetaldehyde (10 μl, 0.17 mmol) were dissolved in chloroform/methanol, followed by adding 2.5 equivalents of tetramethylammonium triacetoxyborohydride (22 mg, 0.085 mmol) in portions. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 28 mg of product [Molecular Formula: $C_{72}H_{132}N_{12}O_{13}S$; Exact Mass: 1404.98; MS (m/z): 1405.75 (M+1)$^+$, 1427.95 (M+Na)$^+$; TLC $R_f$: 0.25 (ethyl acetate/methanol=5/1); HPLC RT: 13.65 min (C8 reverse phase column: 250 mm; acetonitrile/water (0.05% trifluoroacetic acid); operation temperature: 64° C.; detector: 210 nm)].

Example 41

[(S)-(2-(N-Morpholino)ethylthio)methyl-Sar]-3-[(γ-hydroxy)-NMeLeu]-4-cyclosporin

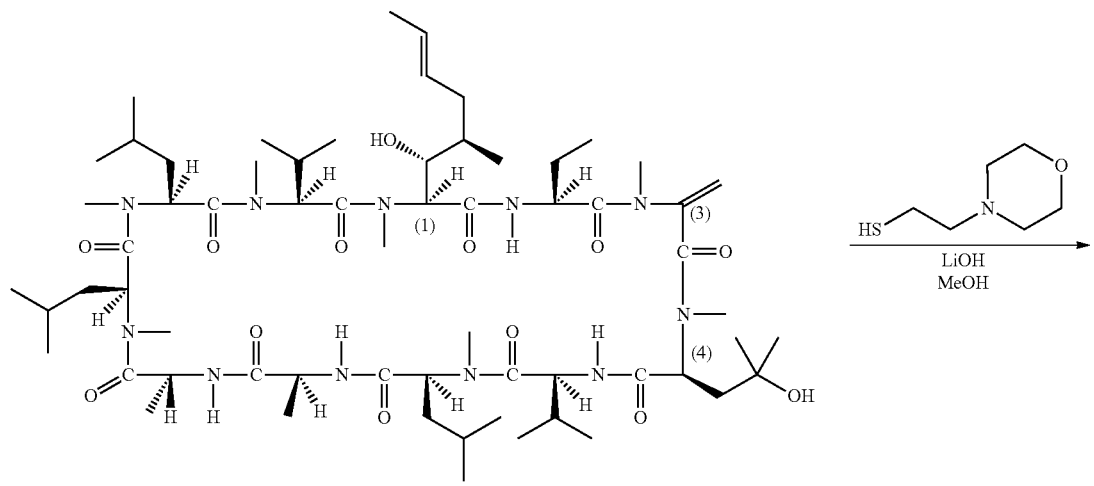

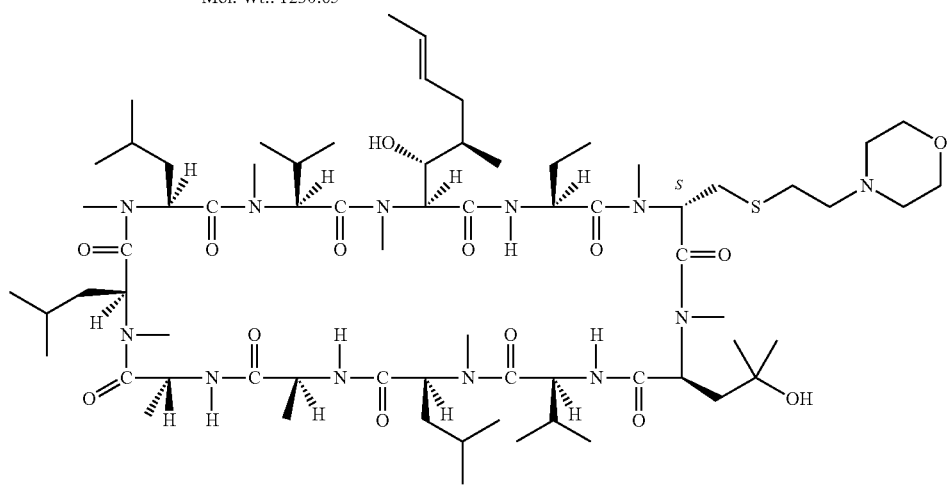

To a solution of [α-methylene-Sar]-3-[(γ-hydroxy)-N-MeLeu]-4-cyclosporin (260 mg, 0.21 mmol) and 2-morpholinoethanethiol (300 mg, 2.04 mmol) in methanol (30 ml) was added lithium hydroxide (140 mg, 5.83 mmol). The reaction mixture was stirred at room temperature overnight. Most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=97/3) to give 102 mg of product [Molecular Formula: $C_{69}H_{124}N_{12}O_{14}S$; Exact Mass: 1376.91; MS (m/z): 1399.85 (M+Na)⁻; TLC $R_f$: 0.30 (dichloromethane/methanol=9/1); HPLC RT: 11.03 min (C8 reverse phase column: 250 mm; acetonitrile/0.077% ammonium acetate in water; operation temperature: 64° C.; detector: 210 nm); ¹H NMR spectrum (600 MHz, CDCl₃, δ in ppm): 0.68 (d, J=6.6 Hz, 3H), 0.79 (d, J=6.6 Hz, 3H), 0.82 (m, 6H,), 0.85 (d, J=6.6 Hz, 3H), 0.88 (d, J=7.2 Hz, 3H), 0.90 (d, J=6.6 Hz, 3H), 0.93 (d, J=6.6 Hz, 3H), 0.97-1.00 (m, 9 H), 1.08 (d, J=6.6 Hz, 3H), 1.21-1.25 (m, 11H), 1.31 (d, J=7.2 Hz, 3H), 1.39-1.47 (m, 2 H), 1.54-1.61 (m, 8H), 1.66-1.70 (m, 2 H), 1.75 (m, 1H), 2.01-2.11 (m, 4 H), 2.36-2.43 (m, 7H), 2.55-2.59 (m, 2 H), 2.67 (m, 8 H), 2.93-3.04 (m, 2H), 3.10 (s, 3 H), 3.24 (s, 6H), 3.26 (s, 3H), 3.48 (s, 3H), 3.52 (br, 1H), 3.67 (m, 6H), 4.51 (m, 1H), 4.59 (t, J=8.4 Hz, 1H), 4.81 (m, 1 H), 4.94-5.00 (m, 2H), 5.04 (t, J=6.6 Hz, 1H), 5.08 (d, J=10.8 Hz,1H), 5.27-5.31 (m, 1H), 5.33-5.37 (m, 1H),5.48 (m, 2H), 5.67 (m,1H), 7.14 (d, J=7.8 Hz, 1H), 7.49 (d, J=7.8 Hz, 1H), 7.64 (d, J=8.4 Hz, 1H), 8.11 (d, J=9.6 Hz, 1H)].

Example 42

[(S)-(2-(N-Piperidinyl)ethylthio)methyl-Sar]-3-[(γ-hydroxy)-NMeLeu]-4-cyclosporin

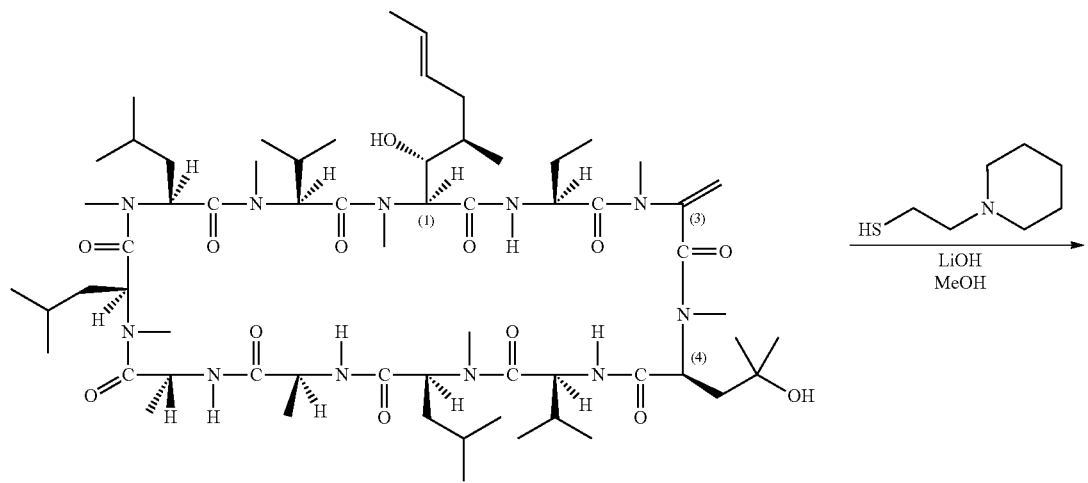

$C_{63}H_{111}N_{11}O_{13}$
Exact Mass: 1229.84
Mol. Wt.: 1230.65

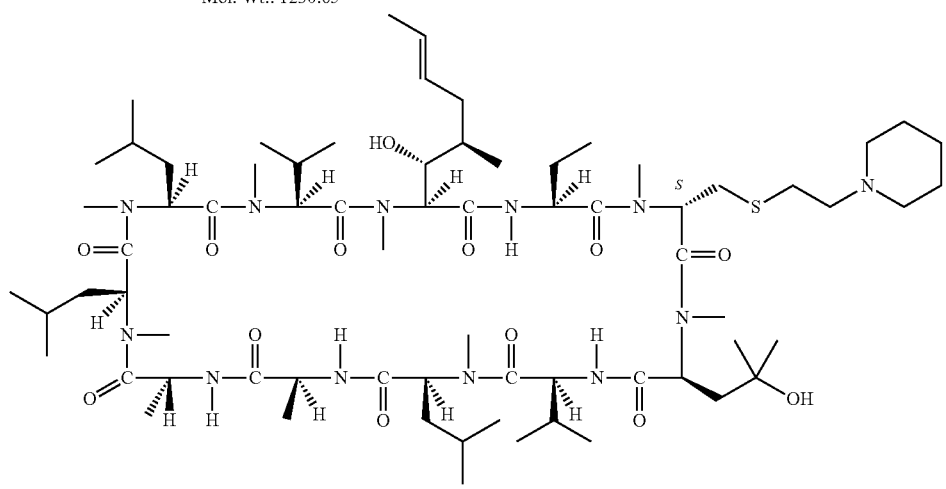

$C_{70}H_{126}N_{12}O_{13}S$
Exact Mass: 1374.93
Mol. Wt.: 1375.91

[α-Methylene-Sar]-3-[(γ-hydroxy)-N-MeLeu]-4-cyclosporin (0.37 g, 0.30 mmol) and 2-(N-piperidino)ethylthiol (0.44 g, 3.00 mmol) were dissolved in methanol (30 ml), followed by adding 10 equivalents of lithium hydroxide. The mixture was stirred overnight at room temperature. After removal of solvent, the residue was dissolved in dichloromethane (30 ml). The dichloromethane solution was washed with brine, dried over magnesium sulfate and evaporated under reduced pressure. The residue was purified by flash chromatography using dichloromethane/methanol as eluent to give 0.20 g of product [Molecular Formula: $C_{70}H_{126}N_{12}O_{13}S$; Exact Mass: 1374.93; MS (m/z): 1375.65 $(M+1)^+$, 1397.80 $(M+Na)^+$; TLC $R_f$: 0.18 (ethyl acetate/methanol=5/1); HPLC RT: 12.09 min (C8 reverse phase column: 250 mm; acetonitrile/water (0.05% trifluoroacetic acid); operation temperature: 64° C.; detector: 210 nm)].

Example 43

[(S)-2-(N-Piperazinylethylthio)methyl-Sar]-3-[(γ-hydroxy)-NMeLeu]-4-cyclosporin

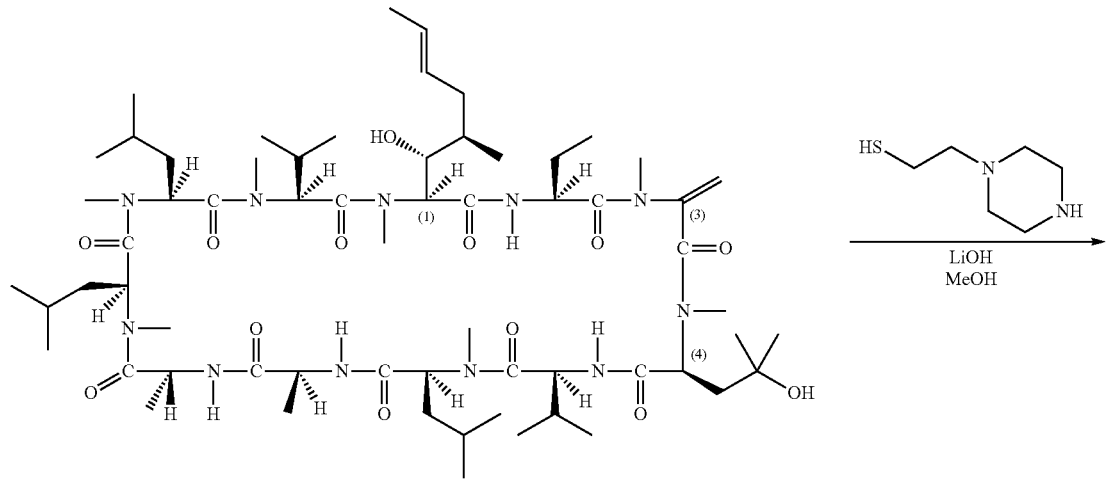

$C_{63}H_{111}N_{11}O_{13}$
Exact Mass: 1229.84
Mol. Wt.: 1230.65

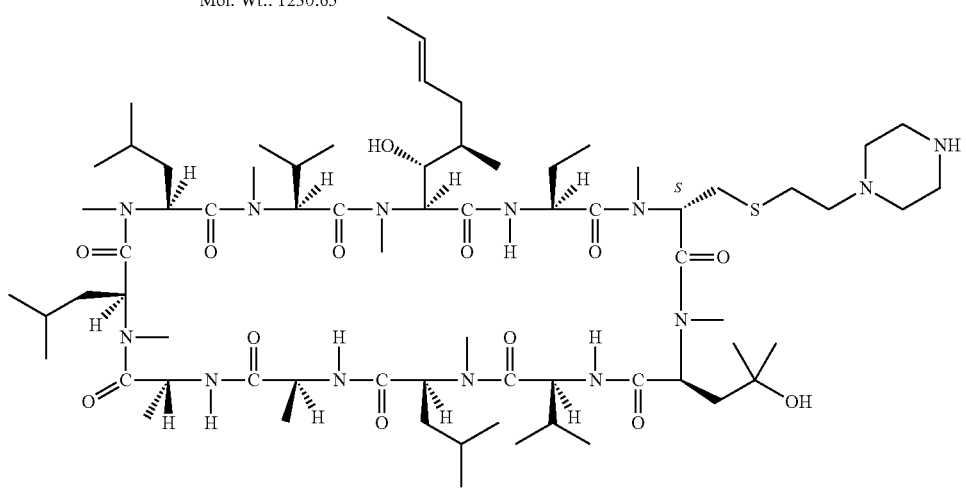

$C_{69}H_{125}N_{13}O_{13}S$
Exact Mass: 1375.92
Mol. Wt.: 1376.90

[α-Methylene-Sar]-3-[(γ-hydroxy)-N-MeLeu]-4-cyclosporin (1.37 g, 1.11 mmol) and 2-mercaptoethylpiperazine (0.49 g, 3.33 mmol) were dissolved in methanol (25 ml), followed by adding lithium hydroxide (0.26 g, 11.10 mmol). The mixture was stirred at room temperature overnight. Most of solvent was evaporated under reduced pressure. The residue was mixed with ethyl acetate (60 ml) and saturated sodium bicarbonate solution (60 ml) and separated. The ethyl acetate layer was washed with brine, dried over magnesium sulfate and evaporated under reduced pressure. The crude product was purified by chromatography on silica gel using dichloromethane/methanol as eluent to give product [Molecular Formula: $C_{69}H_{125}N_{13}O_{13}S$; Exact Mass: 1375.92; MS (m/z): 1376.55 (M+1)$^+$, 1398.69 (M+Na)$^+$; TLC $R_f$: 0.11 (dichloromethane/methanol=9:1); HPLC RT: 8.06 min (C8 reverse phase column: 250 mm; acetonitrile/water (0.05% trifluoroacetic acid); operation temperature: 64° C.; detector: 210 nm)].

Example 44

[(S)-(2-(4-Methyl-N-piperazinyl)ethylthio)methyl-Sar]-3-[(γ-hydroxy)-NMeLeu]-4-cyclosporin

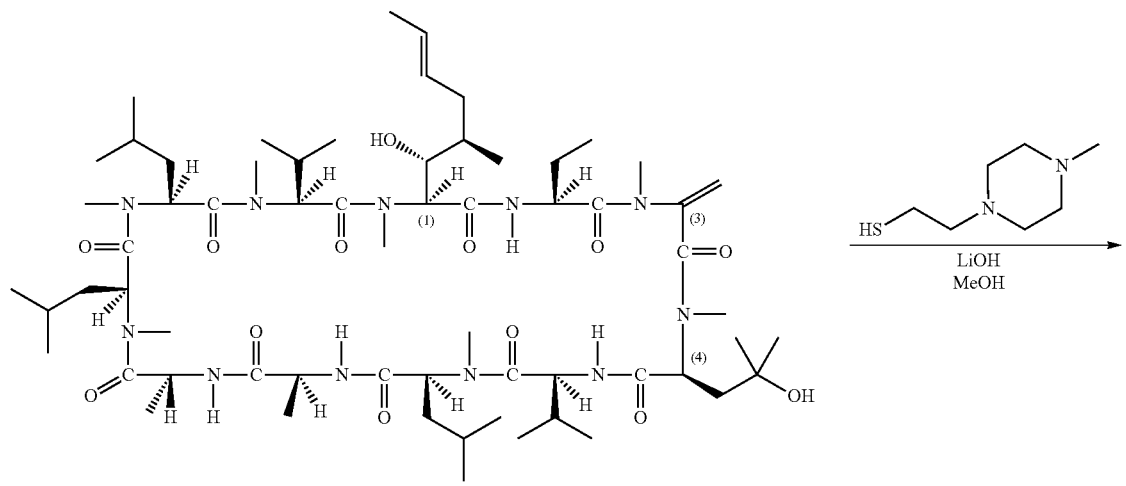

$C_{63}H_{111}N_{11}O_{13}$
Exact Mass: 1229.84
Mol. Wt.: 1230.65

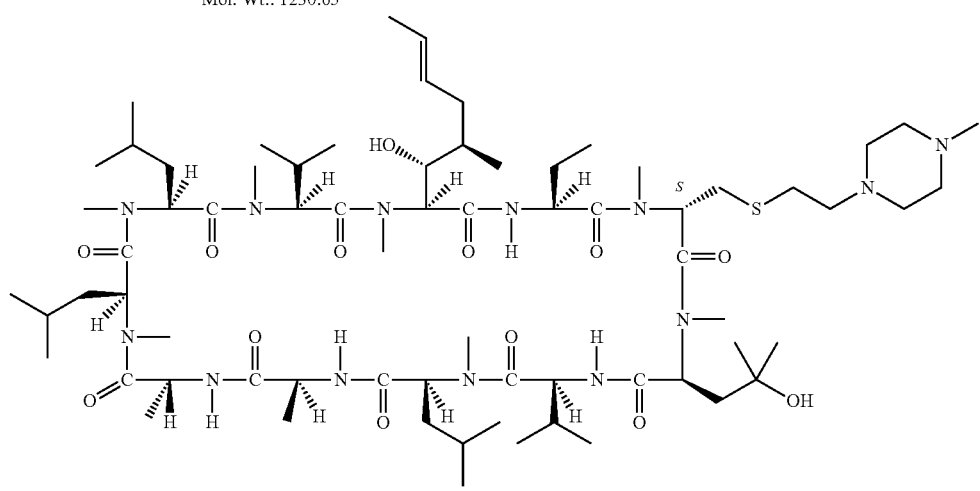

$C_{70}H_{127}N_{13}O_{13}S$
Exact Mass: 1389.94
Mol. Wt.: 1390.92

[α-Methylene-Sar]-3-[(γ-hydroxy)-N-MeLeu]-4-cyclosporin (0.30 g, 0.24 mmol) and 2-(4-methylpiperazino)ethylthiol (0.42 g, 2.62 mmol) were dissolved in methanol (30 ml), followed by adding 10 equivalents of lithium hydroxide. The mixture was stirred overnight at room temperature. After removal of solvent, the residue was dissolved in methylene chloride (30 ml). The dichloromethane solution was washed with brine, dried over magnesium sulfate and evaporated under reduced pressure. The residue was purified by flash chromatography using dichloromethane/methanol as eluent to give 0.22 g of product [Molecular Formula: $C_{70}H_{127}N_{13}O_{13}S$; Exact Mass: 1389.94; MS (m/z): 1390.9 (M+1)$^+$; TLC $R_f$: 0.08 (ethyl acetate/methanol=5/1); HPLC RT: 10.07 min (C8 reverse phase column: 250 mm; acetonitrile/water (0.05% trifluoroacetic acid); operation temperature: 64° C.; detector: 210 nm)].

Example 45

[(S)-(2-(4-Ethyl-N-piperazinyl)ethylthio)methyl-Sar]-3-[(γ-hydroxy)-NMeLeu]-4-cyclosporin

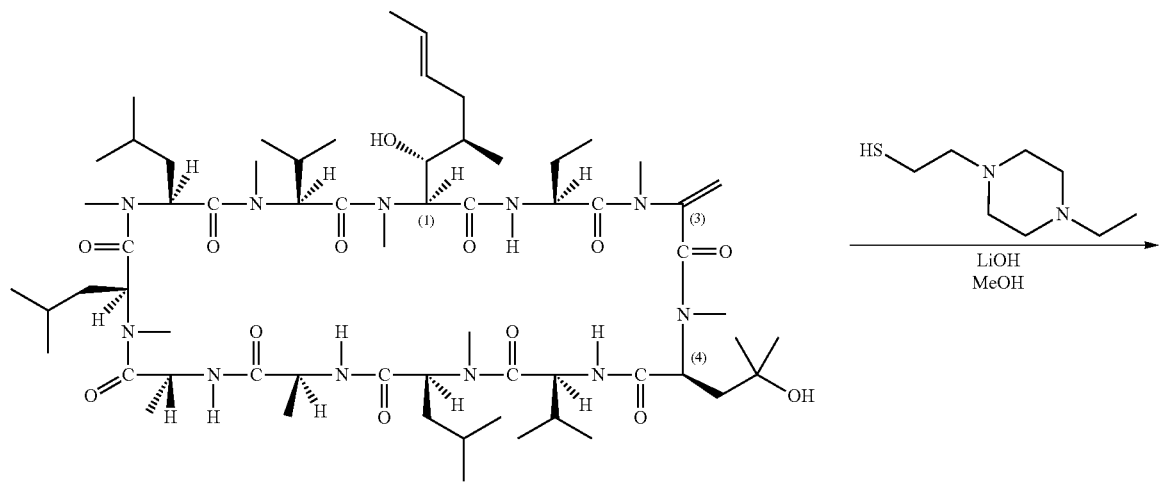

$C_{63}H_{111}N_{11}O_{13}$
Exact Mass: 1229.84
Mol. Wt.: 1230.65

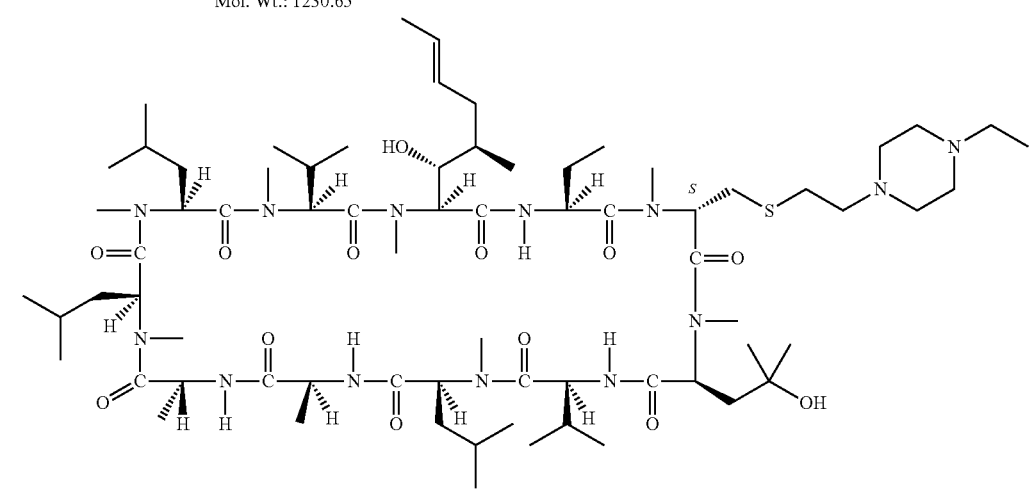

$C_{71}H_{129}N_{13}O_{13}S$
Exact Mass: 1403.96
Mol. Wt.: 1404.95

[α-Methylene-Sar]-3-[(γ-hydroxy)-N-MeLeu]-4-cyclosporin (0.30 g, 0.24 mmol) and 3-(1-ethyl-4-piperazino)ethylthiol (0.30 g, 1.72 mmol) were dissolved in methanol (15 ml), followed by adding lithium hydroxide (58 mg, 2.41 mmol). The mixture was stirred overnight at room temperature. Then most of the solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (dichloromethane/methanol=94/6) to give product [Molecular formula: $C_{71}H_{129}N_{13}O_{13}S$; Exact Mass: 1403.96; MS (m/z): 1404.55 (M+1)$^-$; TLC $R_f$: 0.30 (dichloromethane/methanol=85/15); HPLC RT: 8.83 min (C8 reverse phase column: 250 mm; acetonitrile/water (0.05% trifuloroacetic acid); operation temp: 64° C.; Detector: 210 nm)].

Example 46

[(S)-2-(4-Propyl-N-piperazinylethylthio)methyl-Sar]-3-[(γ-hydroxy)-NMeLeu]-4-cyclosporin

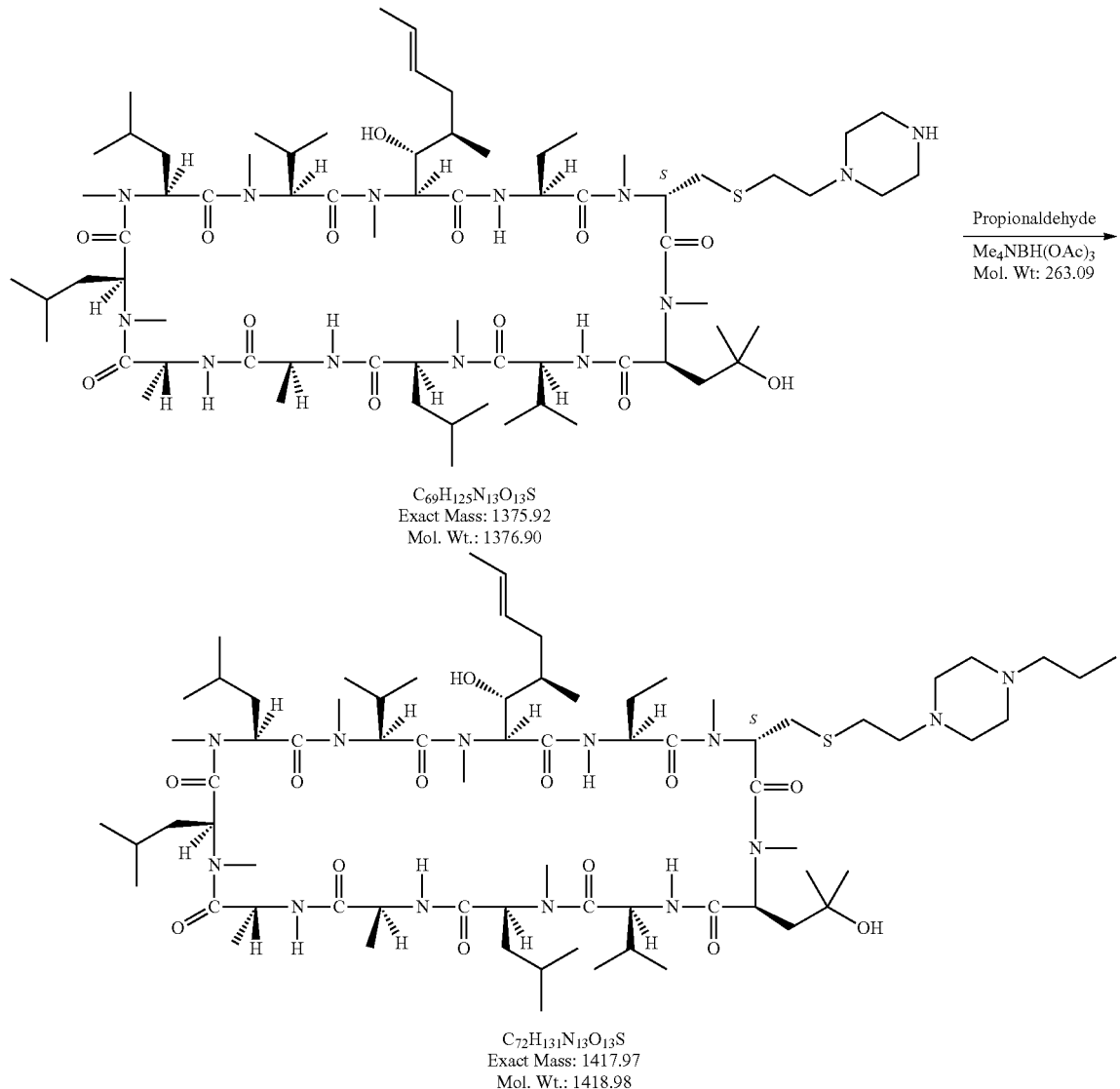

[(S)-(2-(N-Piperazinyl)ethylthio)methyl-Sar]-3-[(γ-hydroxy)-N-MeLeu]-4-cyclosporin (80 mg, 0.058 mmol) and propionaldehyde (MW 58.08, d 0.81, 42 μl, 0.580 mmol) were dissolved in dichloromethane (25 ml), followed by adding tetramethylammonium triacetoxyborohydride (153 mg, 0.580 mmol) in portions and acetic acid (3 drops). The mixture was stirred at room temperature overnight. Then the reaction mixture was washed with saturated sodium bicarbonate solution and brine, dried over magnesium sulfate and evaporated under reduced pressure. The residue was purified by chromatography on silica gel using dichloromethane and methanol as eluent to give product [Molecular Formula: $C_{72}H_{131}N_{13}O_{13}S$; Exact Mass: 1417.97; MS (m/z): 1418.60 $(M+1)^+$, 1440.79 $(M+Na)^+$; TLC $R_f$: 0.37 (dichloromethane/methanol=9:1); HPLC RT: 9.61 min (C8 reverse phase column: 250 mm; acetonitrile/water (0.05% trifluoroacetic acid); operation temperature: 64° C.; detector: 210 nm)].

Example 47

[(S)-(2-(4-Isobutyl-N-piperazinyl)ethylthio)methyl-Sar]-3-[(γ-hydroxy)-NMeLeu]-4-cyclosporin

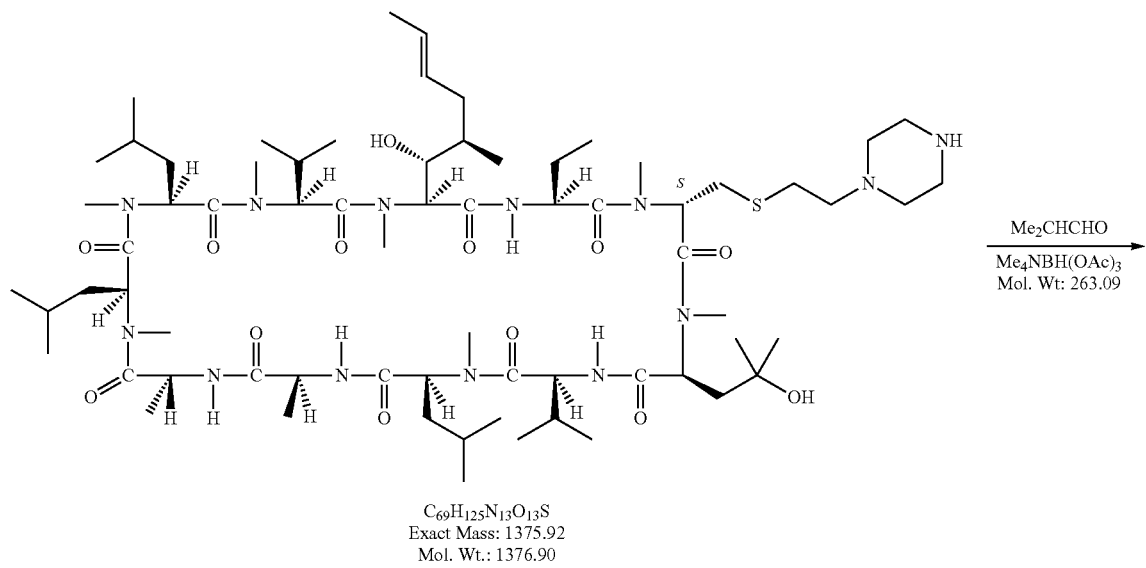

C$_{69}$H$_{125}$N$_{13}$O$_{13}$S
Exact Mass: 1375.92
Mol. Wt.: 1376.90

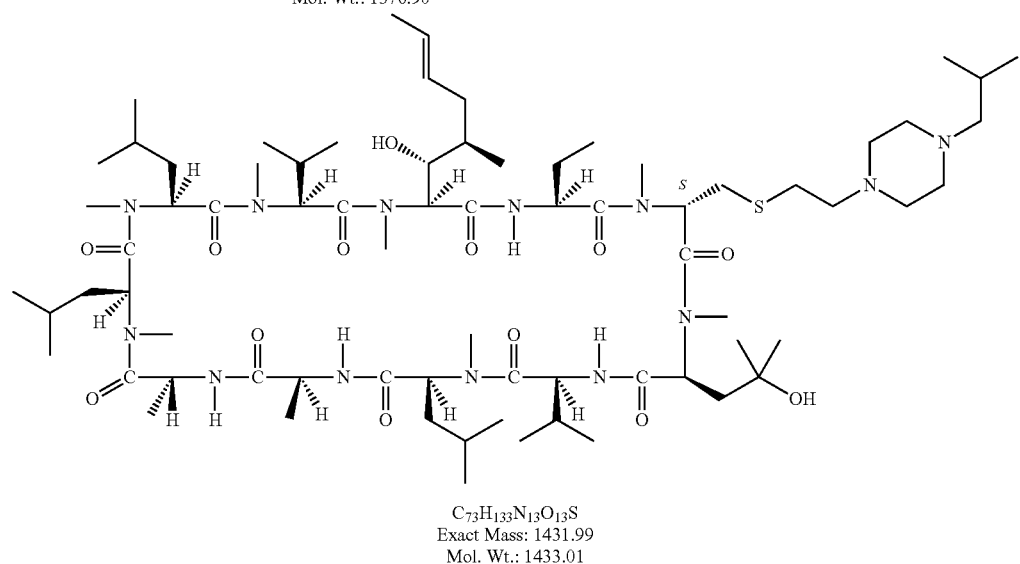

C$_{73}$H$_{133}$N$_{13}$O$_{13}$S
Exact Mass: 1431.99
Mol. Wt.: 1433.01

[(S)-(2-(N-piperazinyl)ethylthio)methyl-Sar]-3-[(γ-hydroxy)-N-MeLeu]-4-cyclosporin (80 mg, 0.058 mmol) and isobutyraldehyde (MW 72.11, d 0.794, 53 μl, 0.58 mmol) were dissolved in dichloromethane (25 ml), followed by adding tetramethylammonium triacetoxyborohydride (153 mg, 0.58 mmol) in portions and acetic acid (3 drops). The mixture was stirred at room temperature overnight. Then the reaction mixture was washed with saturated sodium bicarbonate solution and brine, dried over magnesium sulfate and evaporated under reduced pressure. The residue was purified by chromatography on silica gel using dichloromethane and methanol as eluent to give product [Molecular Formula: C$_{73}$H$_{133}$N$_{13}$O$_{13}$S; Exact Mass: 1431.99; MS (m/z): 1432.63 (M+1)$^+$, 1454.78 (M+Na)$^+$; TLC R$_f$: 0.44 (dichloromethane/methanol=9:1); HPLC RT: 10.08 min (C8 reverse phase column: 250 mm; acetonitrile/water (0.05% trifluoroacetic acid); operation temperature: 64° C.; detector: 210 nm)].

Example 48

[(S)-(2-(4-(2-Hydroxyethyl)-N-piperazinyl)ethyl-thio)methyl-Sar]-3-[(γ-hydroxy)-NMeLeu]-4-cyclosporin

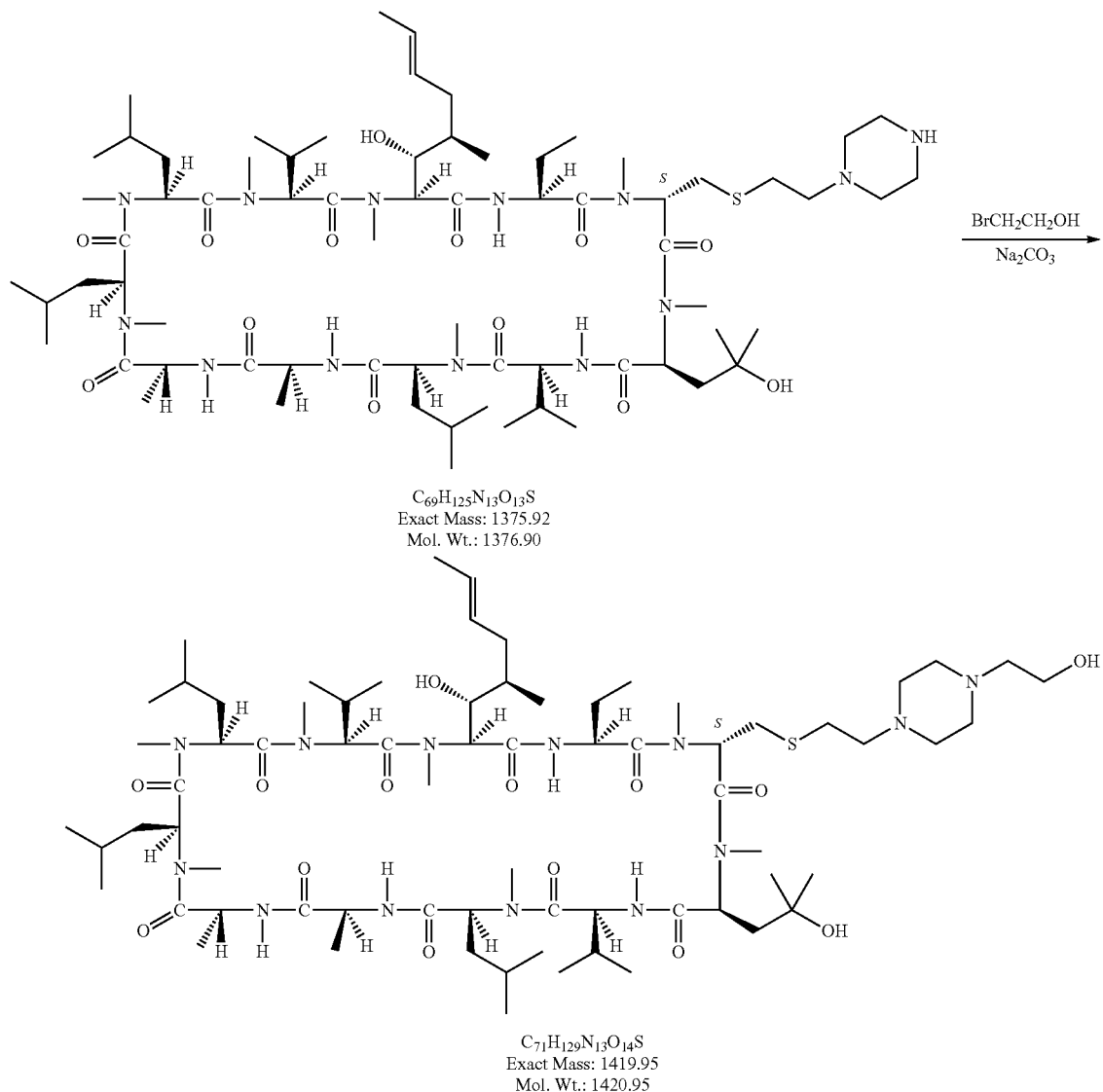

[(S)-(2-(N-Piperazinyl)ethylthio)methyl-Sar]-3-[(γ-hydroxy)-NMeLeu]-4-cyclosporin (80 mg, 0.058 mmol) and 2-bromoethanol (FW 124.97, d 1.762, 41 μl, 0.58 mmol) were dissolved in dichloromethane (15 ml), followed by adding sodium carbonate (15.4 mg, 0.15 mmol). The mixture was stirred at room temperature for a weekend. Then the reaction mixture was washed with brine, dried over magnesium sulfate and evaporated under reduced pressure. The residue was purified by chromatography on silica gel using dichloromethane and methanol as eluent to give 20.8 mg of product [Molecular Formula: $C_{71}H_{129}N_{13}O_{14}S$; Exact Mass: 1419.95; MS (m/z): 1420.52 $(M+1)^-$, 1442.72 $(M+Na)^+$; TLC $R_f$: 0.20 (dichloromethane/methanol=9:1); HPLC RT: 8.79 min (C8 reverse phase column: 250 mm; acetonitrile/water (0.05% trifluoroacetic acid); operation temperature: 64° C.; detector: 210 nm)].

Example 49

[(S)-(2-(N-Pyrrolidinyl)ethylthio)methyl-Sar]-3-[(γ-hydroxy)-NMeLeu]-4-cyclosporin

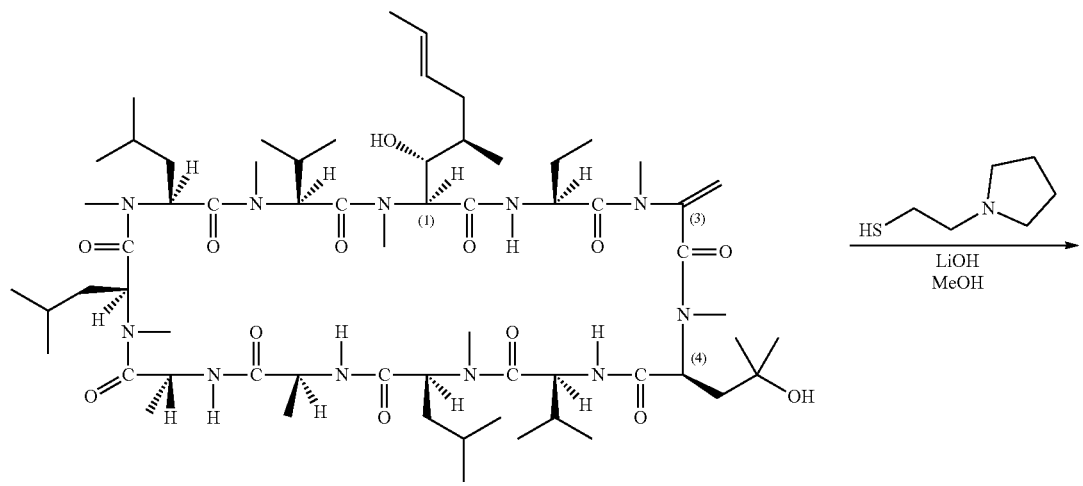

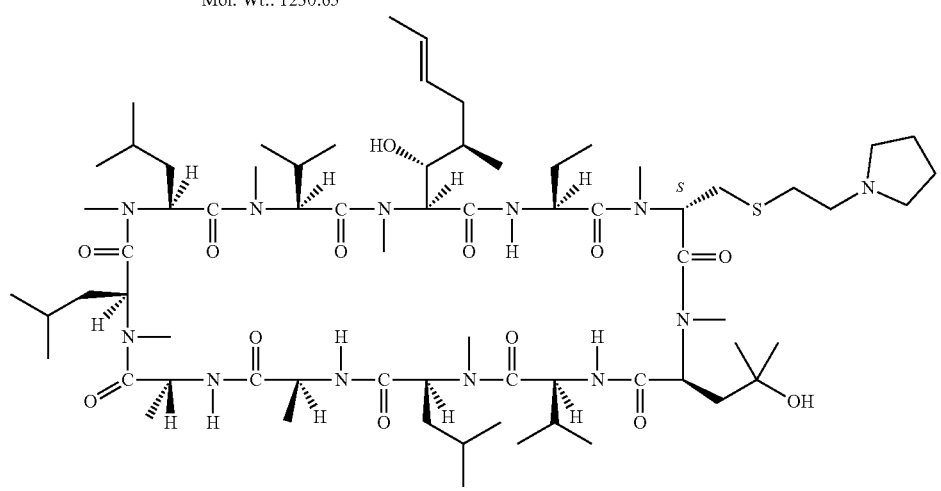

To a solution of [α-methylene-Sar]-3-[(γ-hydroxy)-N-MeLeu]-4-cyclosporin (280 mg, 0.23 mmol) and 2-(N-pyrrolidinyl)ethanethiol (280 mg, 2.14 mmol) in methanol (30 ml) was added lithium hydroxide (114 mg, 4.75 mmol). The reaction mixture was stirred overnight at room temperature. Most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=96/4) to give 126 mg of product [Molecular Formula: $C_{69}H_{124}N_{12}O_{13}S$; Exact Mass: 1360.91; MS (m/z): 1361.80 (M+1)$^+$; TLC $R_f$: 0.23 (dichloromethane/methanol=95/5); HPLC RT: 11.59 min (C8 reverse phase column: 250 mm; acetonitrile/0.077% ammonium acetate in water; operation temperature: 64° C.; detector: 210 nm)].

Example 50

[(S)-(2-Hydroxyethylthio)methyl-Sar]-3-[(γ-hydroxy)-NMeLeu]-4-cyclosporin

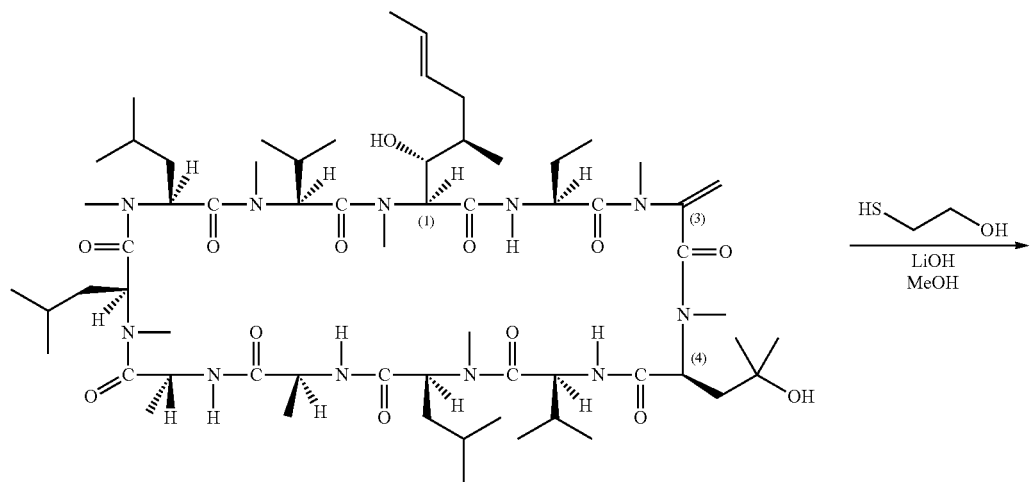

$C_{63}H_{111}N_{11}O_{13}$
Exact Mass: 1229.84
Mol. Wt.: 1230.65

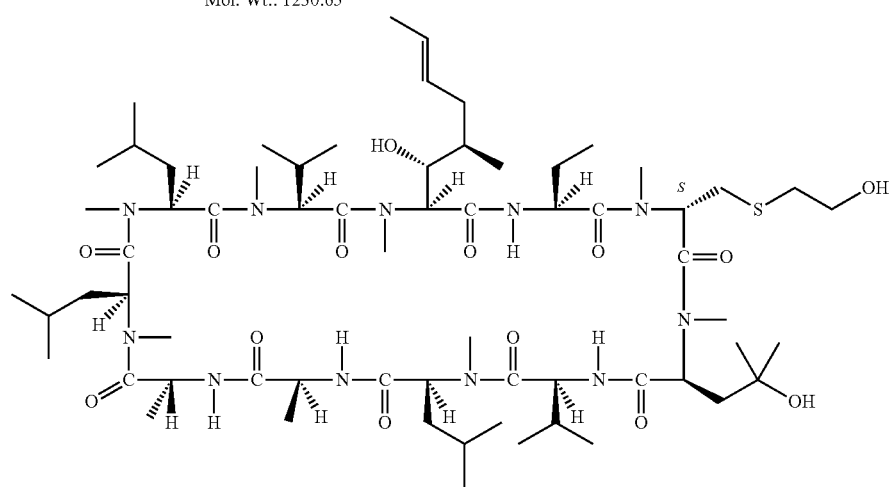

$C_{65}H_{117}N_{11}O_{14}S$
Exact Mass: 1307.85
Mol. Wt.: 1308.77

50

[α-Methylene-Sar]-3-[(γ-hydroxy)-N-MeLeu]-4-cyclosporin (200 mg, 0.16 mmol) and 2-mercaptoethanol (MW 78.13, d 1.114, 112 µl, 1.60 mmol) were dissolved in methanol (10 ml), followed by adding lithium hydroxide (23 mg, 0.96 mmol). The mixture was stirred at room temperature overnight. Most of solvent was evaporated under reduced pressure. The residue was mixed with ethyl acetate (20 ml) and saturated sodium bicarbonate solution (20 ml) and separated. The ethyl acetate layer was washed with brine, dried over magnesium sulfate and evaporated under reduced pressure. The residue was purified by chromatography on silica gel using dichloromethane/methanol as eluent to give product [Molecular Formula: $C_{65}H_{117}N_{11}O_{14}S$; Exact Mass: 1307.85; MS (m/z): 1308.44 (M+1)$^+$, 1330.68 (M+Na)$^+$; TLC $R_f$: 0.41 (dichloromethane/methanol=9:1); HPLC RT: 12.61 min (C8 reverse phase column: 250 mm; acetonitrile/water (0.05% trifluoroacetic acid); operation temperature: 64° C.; detector: 210 nm)].

Example 51

[(S)-2-Ethoxyethylthiomethyl-Sar]-3-[(γ-hydroxy)-N-MeLeu]-4-cyclosporin

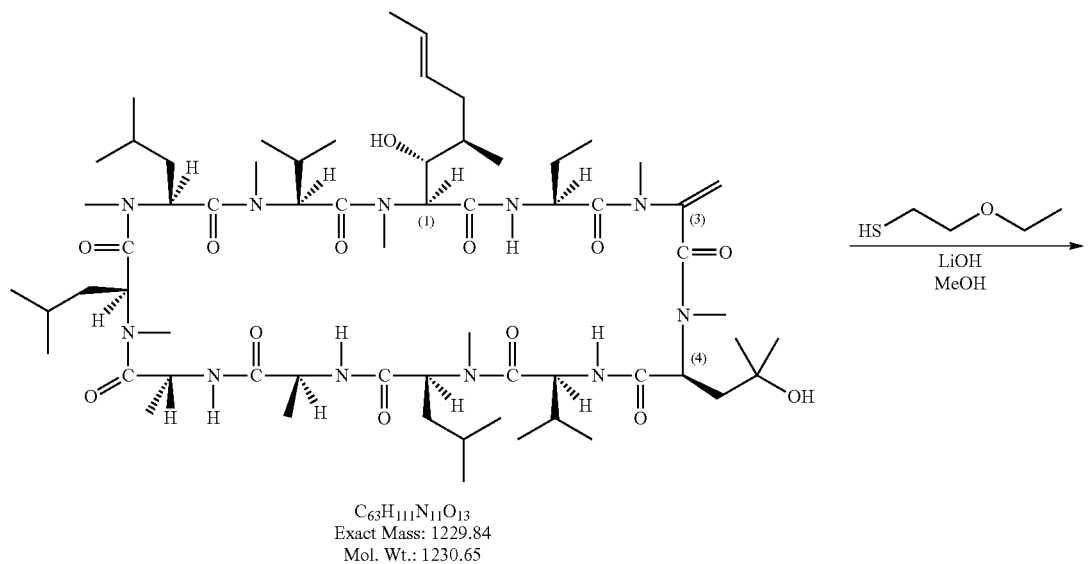

$C_{63}H_{111}N_{11}O_{13}$
Exact Mass: 1229.84
Mol. Wt.: 1230.65

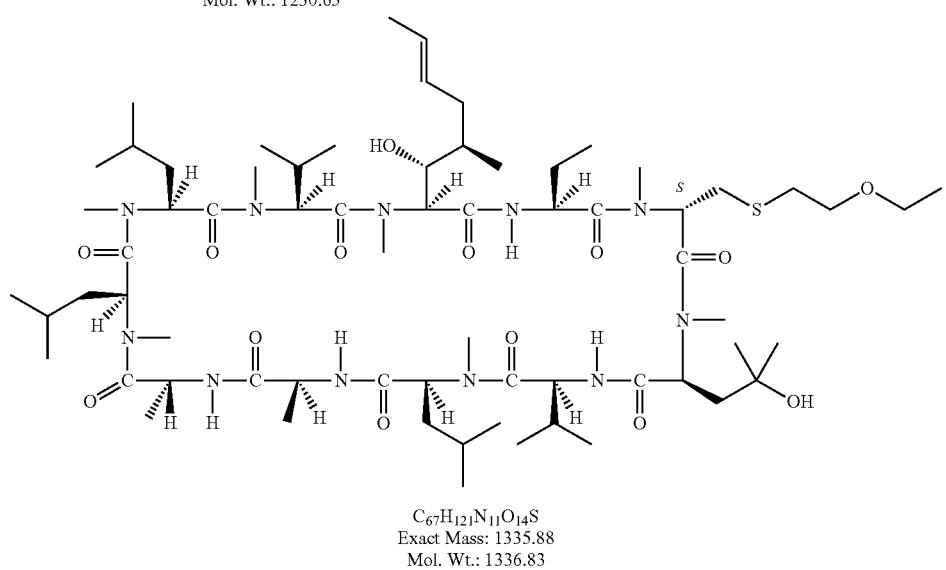

$C_{67}H_{121}N_{11}O_{14}S$
Exact Mass: 1335.88
Mol. Wt.: 1336.83

To a solution of [α-methylene-Sar]-3-[(γ-hydroxy)-N-MeLeu]-4-cyclosporin (150 mg, 0.12 mmol) and 2-ethoxyethanethiol (160 mg, 1.51 mmol) in methanol (10 ml) was added lithium hydroxide (50 mg, 2.08 mmol). The reaction mixture was stirred at room temperature overnight. Then most of solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (ethyl acetate/methanol=97/3) to give a pure product [Molecular formula: $C_{67}H_{121}N_{11}O_{14}S$; Exact Mass: 1335.88; MS (m/z): 1336.49 (M+1)$^+$; TLC Rf: 0.43 (dichloromethane/methanol=97/3); HPLC RT: 15.51 min (C8 reverse phase column: 250 mm; acetonitrile/water (0.05% trifuloroacetic acid); operation temp: 64° C.; Detector: 210 nm)].

Example 52

[(S)-(2-(Ethoxycarbonylmethoxy)ethylthio)methyl-Sar]-3-[(γ-hydroxy)-N-MeLeu]-4-cyclosporin

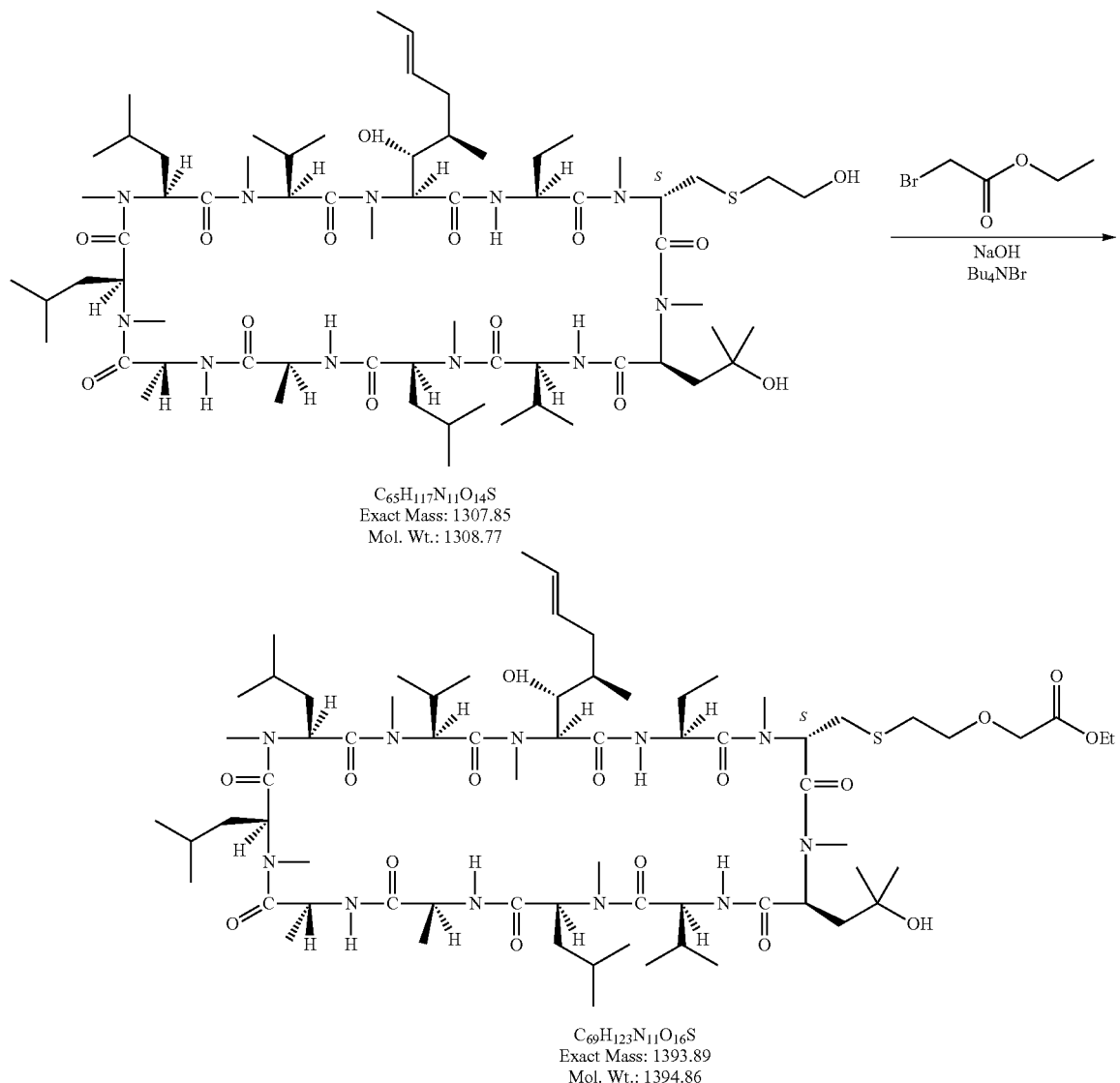

To a solution of [(S)-(2-hydroxyethylthio)methyl-Sar]-3-[(γ-hydroxy)-N-MeLeu]-4-cyclosporin (0.28 g, 0.21 mmol) in benzene (15 ml) were added a solution of sodium hydroxide (0.60 g, 15.00 mmol) in water (1 ml), ethyl bromoacetate (1.50 g, 8.98 mmol) and tetra-n-butylammonium bromide (0.20 g, 0.62 mmol). The mixture was stirred at room temperature for 10 hours. After diluted with ice water, the mixture was separated. The aqueous layer was extracted with dichloromethane (15 ml). The combined organic layers were washed with brine, dried over magnesium sulfate and evaporated under reduced pressure. The residue was purified by chromatography (ethyl acetate/methanol=97/3) to give a pure product [Molecular Formula: $C_{69}H_{123}N_{11}O_{16}S$; Exact Mass: 1393.89; MS (m/z): 1394.48 (M+1)$^+$; TLC $R_f$: 0.45 (dichloromethane/methanol=95/5); HPLC RT: 15.28 min (C8 reverse phase column: 250 mm; acetonitrile/water (0.05% trifuloroacetic acid); operation temp: 64° C.; Detector: 210 nm)].

Example 53

[(S)-(2-(2-Hydroxyethoxy)ethylthio)methyl-Sar]-3-[(γ-hydroxy)-N-MeLeu]-4-cyclosporin

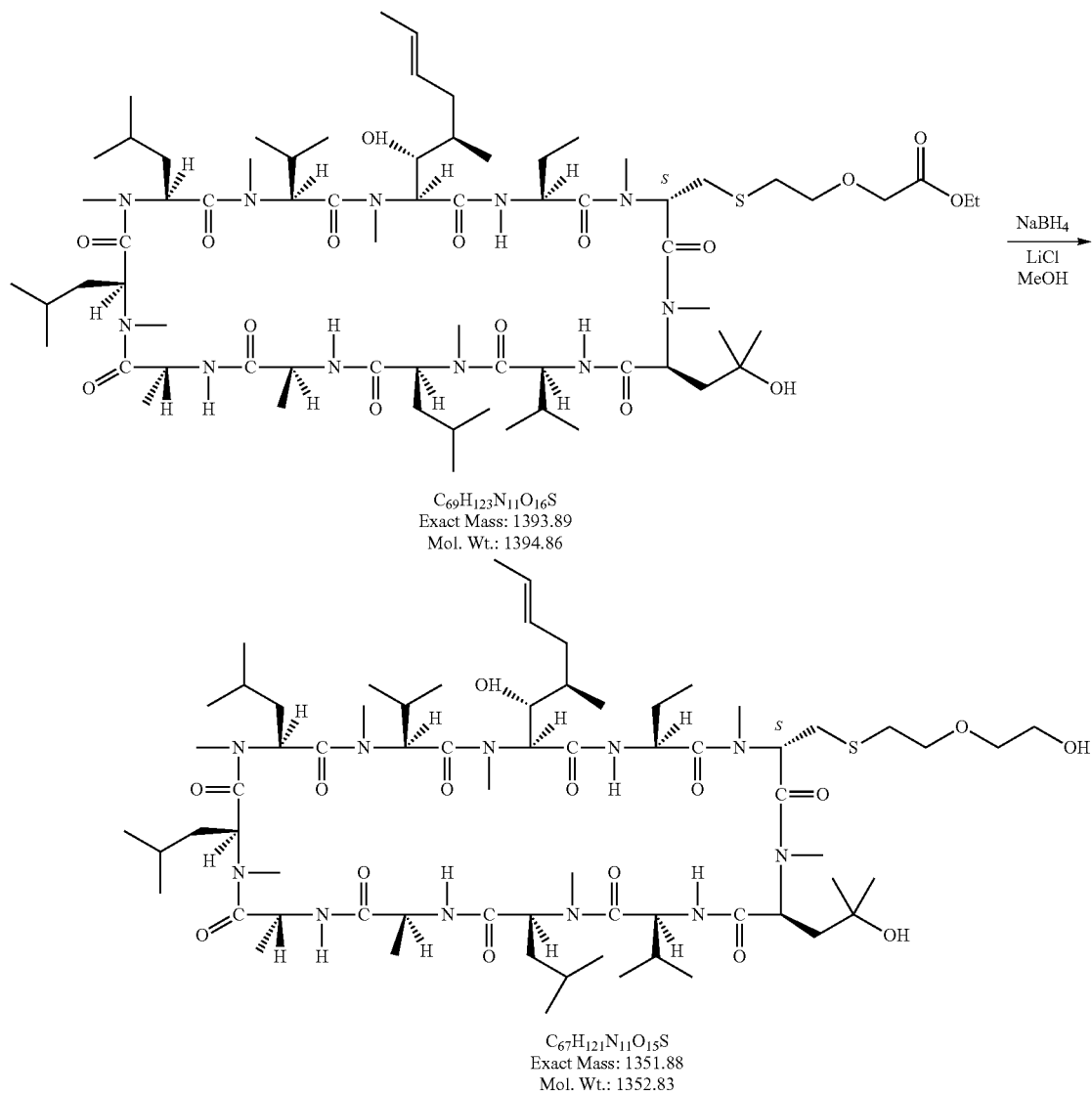

To a suspension of [(S)-((ethoxycarbonylmethoxy)ethylthio)methyl-Sar]-3-[(γ-hydroxy)-N-MeLeu]-4-cyclosporin (100 mg, 0.07 mmol) and lithium chloride (15 mg, 0.35 mmol) in methanol (10 ml) was added sodium borohydride (125 mg, 3.29 mmol) in portions. The mixture was stirred overnight at room temperature for 6 hours. Most of solvent was evaporated under reduced pressure. Dichloromethane (50 ml) and water (200 ml) were added and separated. The dichloromethane layer was washed with brine, dried over magnesium sulfate and evaporated under reduced pressure. The residue was purified by chromatography (dichloromethane/methanol=97/3) to give the product [Molecular formula: $C_{67}H_{121}N_{11}O_{15}S$; Exact Mass: 1351.88; MS (m/z): 1352.46 (M+1)$^-$; TLC $R_f$: 0.32 (dichloromethane/methanol=95/5); HPLC RT: 12.87 min (C8 reverse phase column: 250 mm; acetonitrile/water (0.05% trifuloroacetic acid); operation temp: 64° C.; Detector: 210 nm)].

Example 54

[(S)-(2-(2-Methoxyethoxy)ethylthio)methyl-Sar]-3-[(γ-hydroxy)-N-MeLeu]-4-cyclosporin

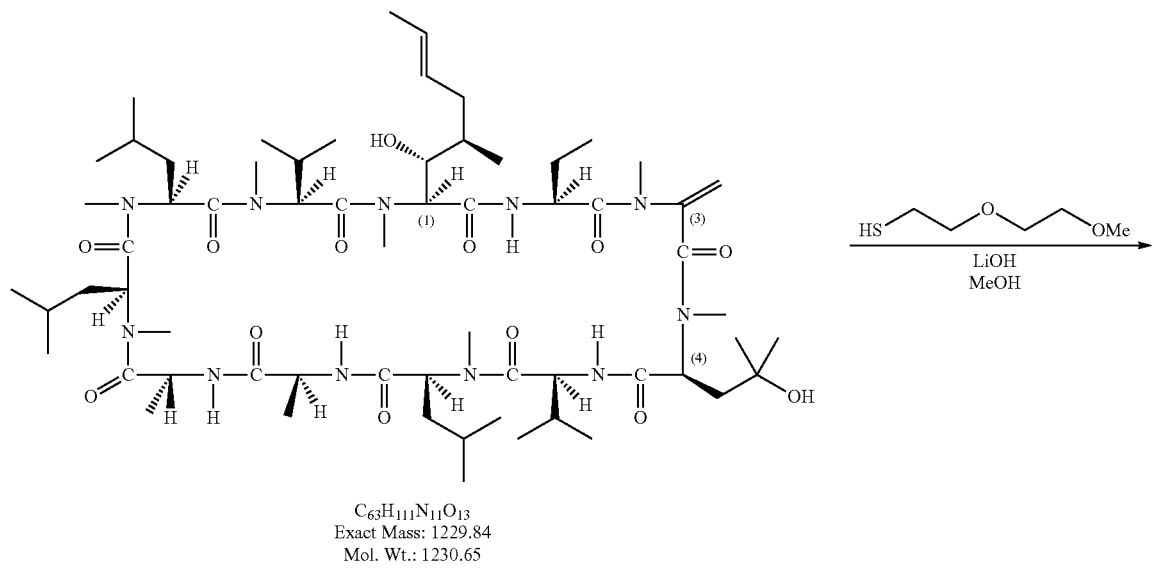

$C_{63}H_{111}N_{11}O_{13}$
Exact Mass: 1229.84
Mol. Wt.: 1230.65

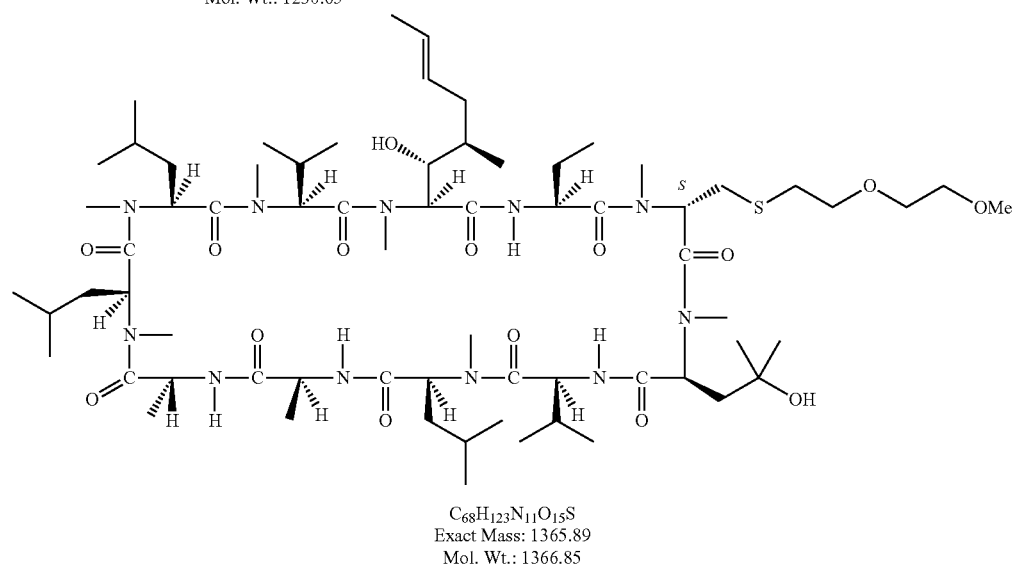

$C_{68}H_{123}N_{11}O_{15}S$
Exact Mass: 1365.89
Mol. Wt.: 1366.85

To a solution of [α-methylene-Sar]-3-[(γ-hydroxy)-N-MeLeu]-4-cyclosporin (300 mg, 0.24 mmol) and 2-(2-methoxyethoxy)ethanethiol (330 mg, 2.42 mmol) in methanol (20 ml) was added lithium hydroxide (60 mg, 2.50 mmol). The reaction mixture was stirred at room temperature overnight. Then most of solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (ethyl acetate/methanol=97/3) to give a pure product [Molecular formula: $C_{68}H_{123}N_{11}O_{15}S$; Exact Mass: 1365.89; MS (m/z): 1366.49 (M+1)[+]; TLC Rf: 0.37 (dichloromethane/methanol=97/3); HPLC RT: 14.72 min (C8 reverse phase column: 250 mm; acetonitrile/water (0.05% trifuloroacetic acid); operation temp: 64° C.; Detector: 210 nm)].

Example 55

[(S)-(3-Aminopropylthio)methyl-Sar]-3-[(γ-hydroxy)-NMeLeu]-4-cyclosporin

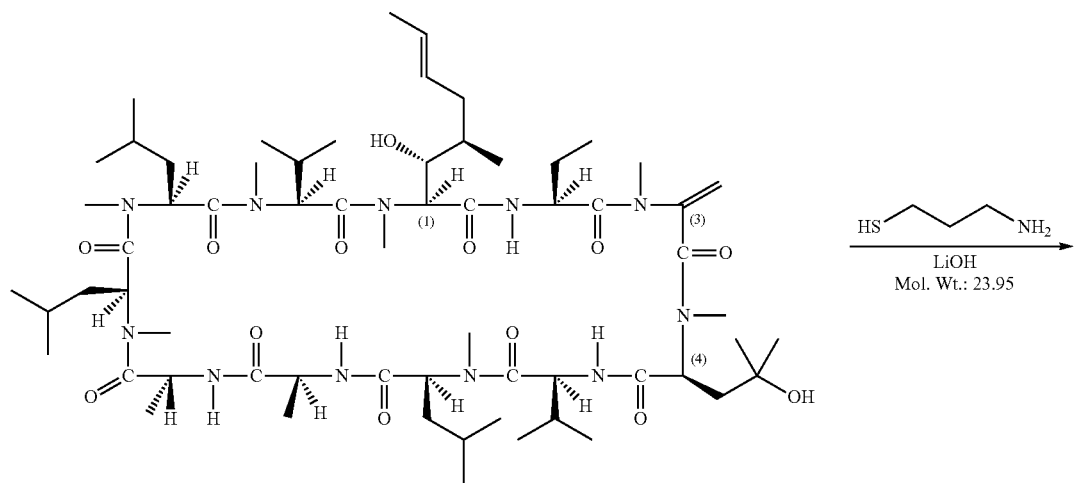

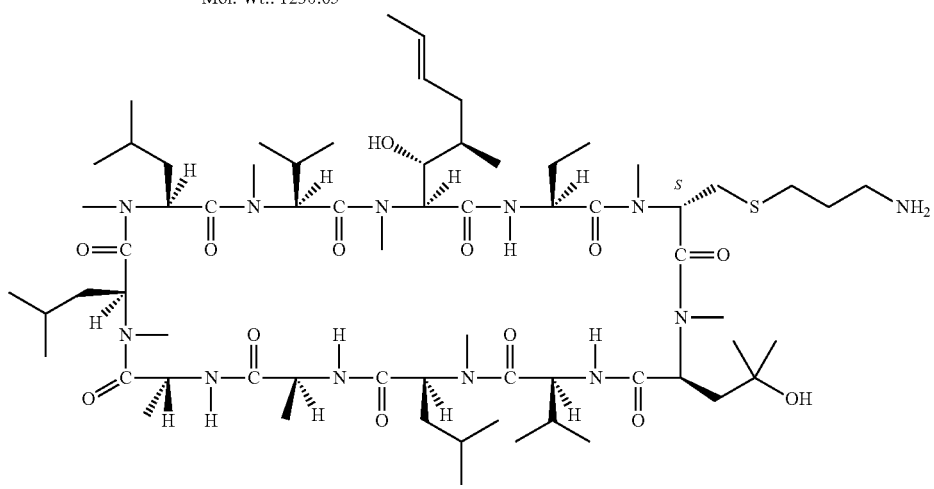

[α-Methylene-Sar]-3-[(γ-hydroxy)-N-MeLeu]-4-cyclosporin (3.00 g, 2.44 mmol) and 3-aminopropanethiol (1.33 g, 14.59 mmol) were dissolved in methanol (80 ml), followed by adding lithium hydroxide (0.35 g, 14.65 mmol). The mixture was stirred at room temperature for a weekend. After removal of solvent, the residue was purified by chromatography using dichloromethane/methanol as eluent to give product [Molecular Formula: $C_{66}H_{120}N_{12}O_{13}S$; Exact Mass: 1320.88; MS (m/z): 1321.52 (M+1)$^+$, 1343.67 (M+Na)$^+$, TLC R$_f$: 0.028 (dichloromethane/methanol=5/1); HPLC RT: 10.24 min (C8 reverse phase column: 250 mm; acetonitrile/water (0.05% trifluoroacetic acid); operation temperature: 64° C.; detector: 210 nm)].

Example 56

[(S)-(3-(N,N-Dimethylamino)propylthio)methyl-Sar]-3-[(γ-hydroxy)-NMeLeu]-4-cyclosporin

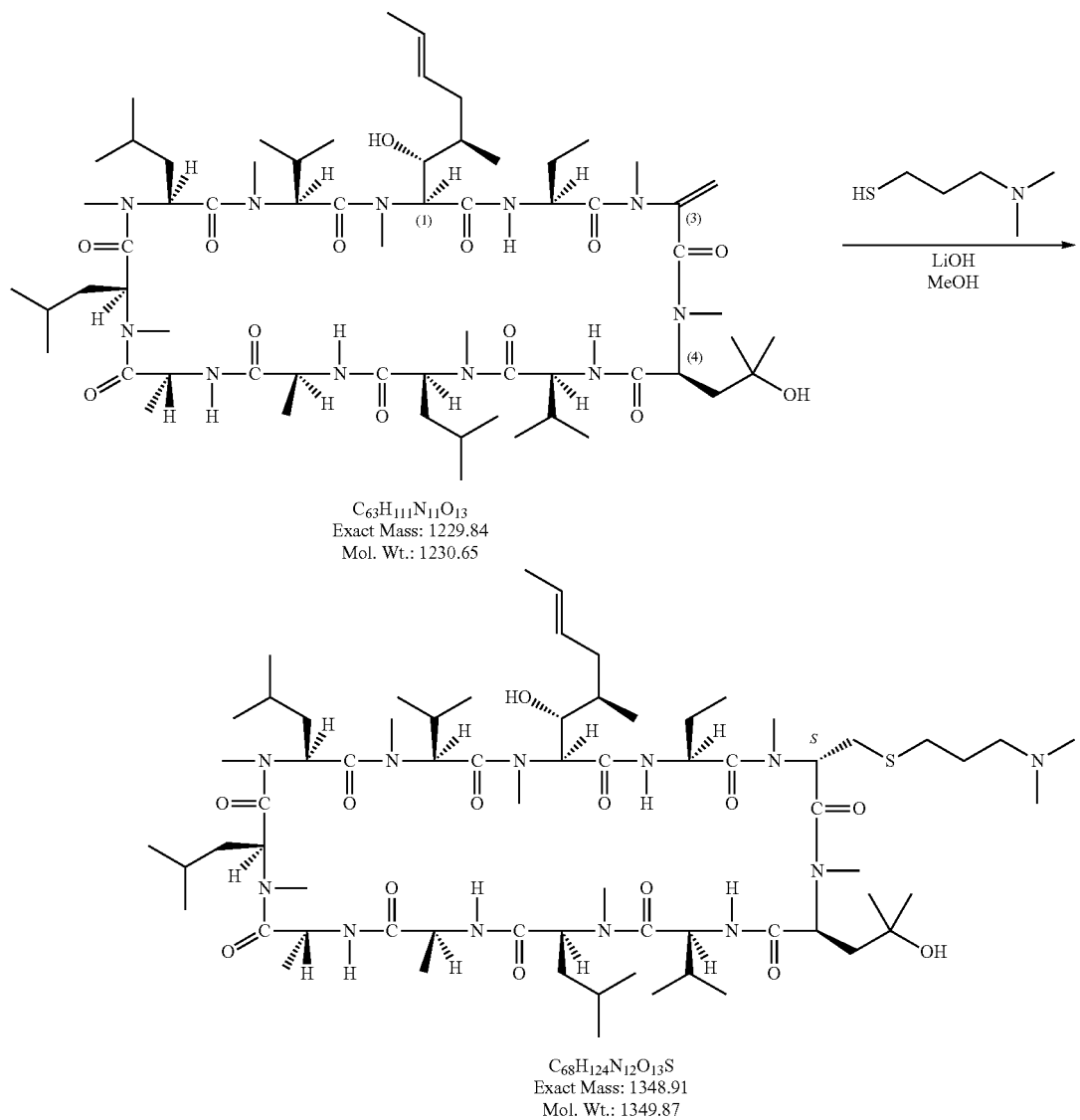

[α-Methylene-Sar]-3-[(γ-hydroxy)-N-MeLeu]-4-cyclosporin (0.30 g, 0.24 mmol) and 3-(N,N-dimethyl)propylthiol (0.36 g, 2.40 mmol) were dissolved in methanol (25 ml), followed by adding lithium hydroxide (59 mg, 2.44 mmol). The mixture was stirred at room temperature overnight. After removal of solvent, the residue was purified by flash chromatography using dichloromethane/methanol as eluent to give 0.18 g of pure product [Molecular Formula: $C_{68}H_{124}N_{12}O_{13}S$; Exact Mass: 1348.91; MS (m/z): 1349.70 $(M+1)^+$, 1371.83 (M+Na); TLC $R_f$: 0.15 (ethyl acetate/methanol=5/1); HPLC RT: 11.53 min (C8 reverse phase column: 250 mm; acetonitrile/water (0.05% trifluoroacetic acid); operation temperature: 64° C.; detector: 210 nm)].

Example 57

[(S)-(3-(N,N-Diethylamino)propylthio)methyl-Sar]-3-[(γ-hydroxy)-NMeLeu]-4-cyclosporin

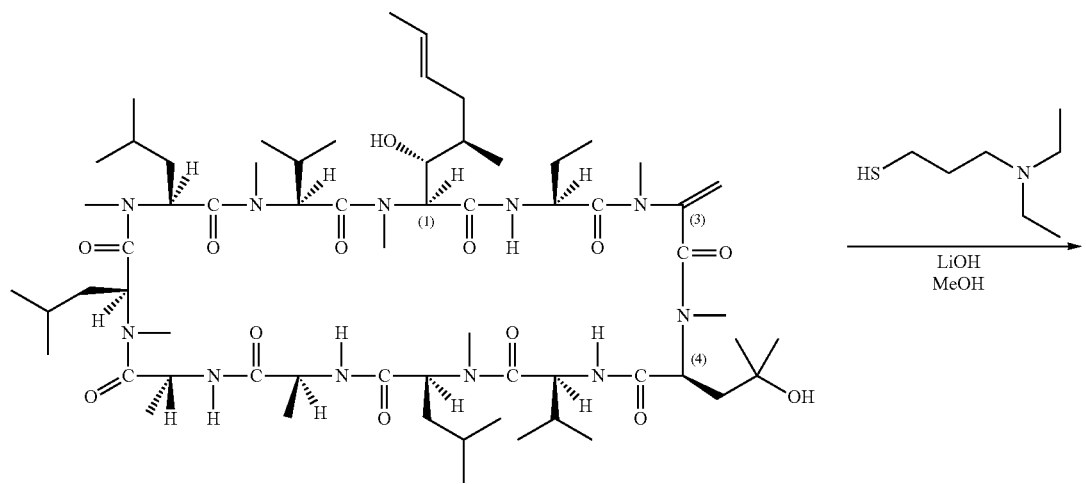

$C_{63}H_{111}N_{11}O_{13}$
Exact Mass: 1229.84
Mol. Wt.: 1230.65

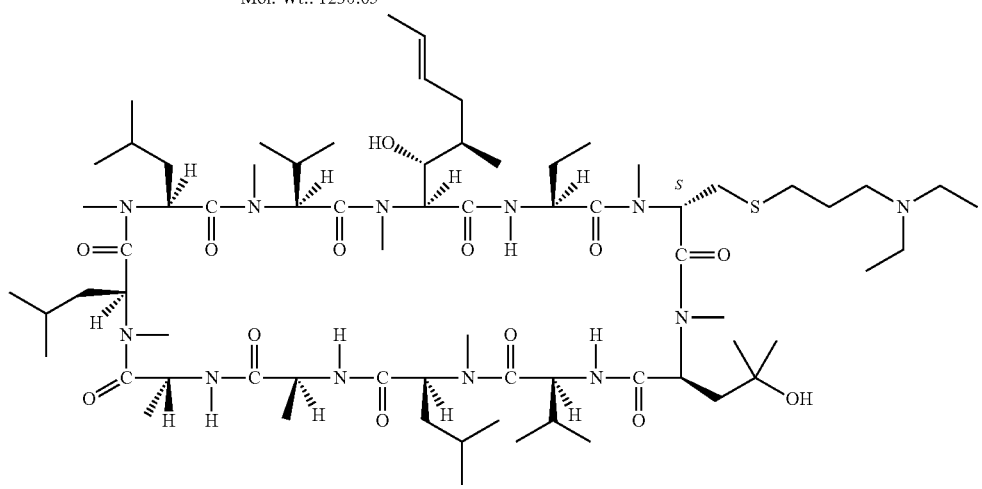

$C_{70}H_{128}N_{12}O_{13}S$
Exact Mass: 1376.94
Mol. Wt.: 1377.93

[α-Methylene-Sar]-3-[(γ-hydroxy)-N-MeLeu]-4-cyclosporin (0.30 g, 0.24 mmol) and 3-(N,N-dimethyl)propylthiol (0.36 g, 2.44 mmol) were dissolved in methanol (25 ml), followed by adding lithium chloride (59 mg, 2.4 mmol). The mixture was stirred at room temperature overnight. After removal of solvent, the residue was purified by flash chromatography using dichloromethane/methanol as eluent to give 0.30 g of product [Molecular Formula: $C_{70}H_{128}N_{12}O_{13}S$; Exact Mass: 1376.94; MS (m/z): 1377.90 (M+1)+, 1399.76 (M+Na)+; TLC $R_f$: 0.17 (ethyl acetate/methanol=5/1); HPLC RT: 12.06 min (C8 reverse phase column: 250 mm; acetonitrile/water (0.05% trifluoroacetic acid); operation temperature: 64° C.; detector: 210 nm)].

Example 58

[(S)-(3-(N-Isopropylamino)propylthio)methyl-Sar]-
3-[(γ-hydroxy)-NMeLeu]-4-cyclosporin

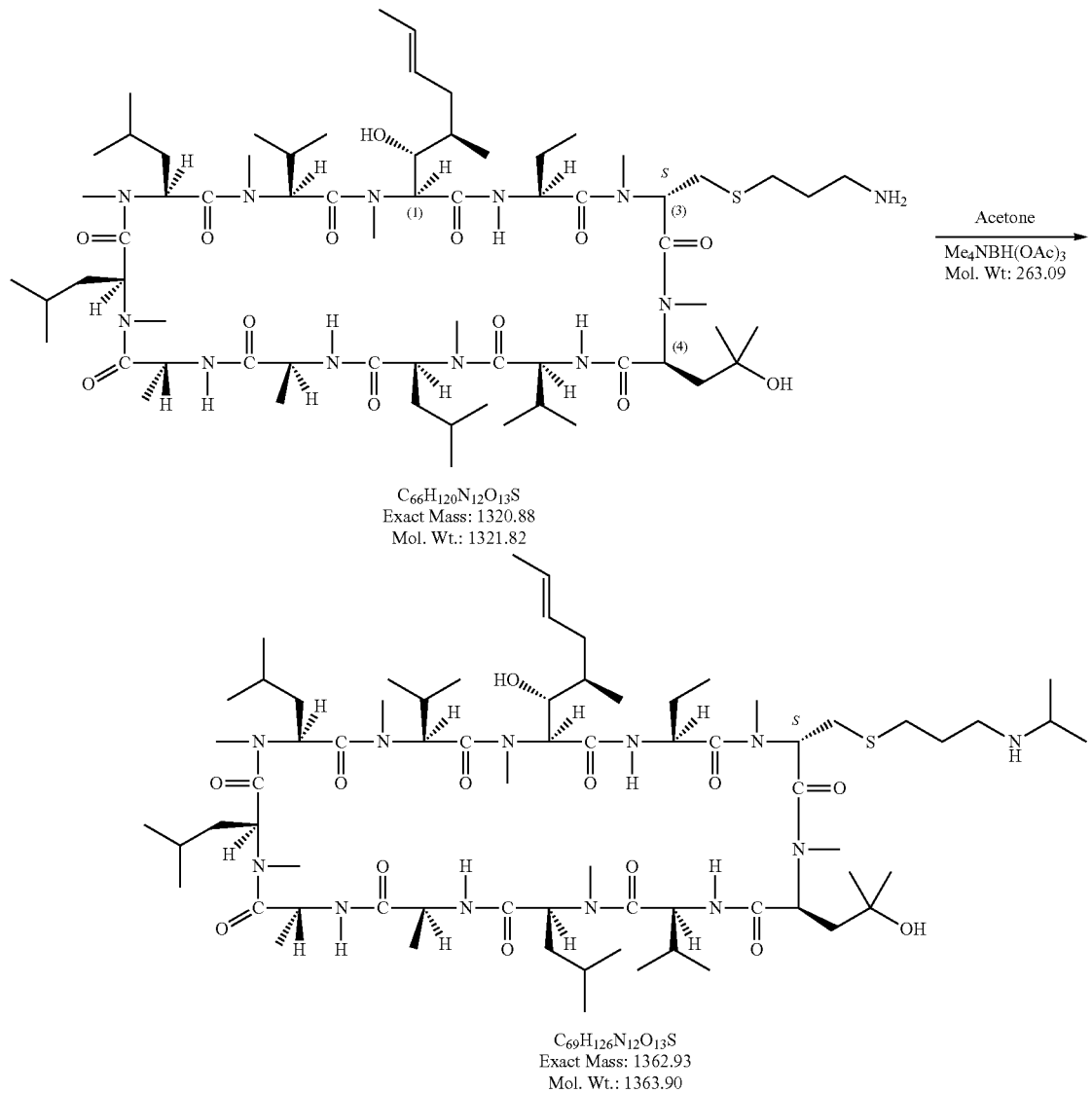

[(S)-(3-Aminopropylthio)methyl-Sar]-3-[(γ-hydroxy)-N-MeLeu]-4-cyclosporin (150 mg, 0.11 mmol) and acetone (MW 58.08, d 0.791, 42 µl, 0.57 mmol) were dissolved in 10 ml of dichloromethane, followed by adding tetramethylammonium triacetoxyborohydride (74.7 mg, 0.28 mmol) in portions and a few drops of acetic acid. The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give product [Molecular Formula: $C_{69}H_{126}N_{12}O_{13}S$; Exact Mass: 1362.93; MS (m/z): 1363.60 $(M+1)^+$; TLC $R_f$: 0.38 (dichloromethane/methanol=9/1); HPLC RT: 10.89 min (C8 reverse phase column: 250 mm; acetonitrile/water (0.05% trifluoroacetic acid); operation temperature: 64° C.; detector: 210 nm)].

Example 59

[(S)-(3-(N-Ethyl-N-isopropylamino)propylthio)methyl-Sar]-3-[(γ-hydroxy)-NMeLeu]-4-cyclosporin

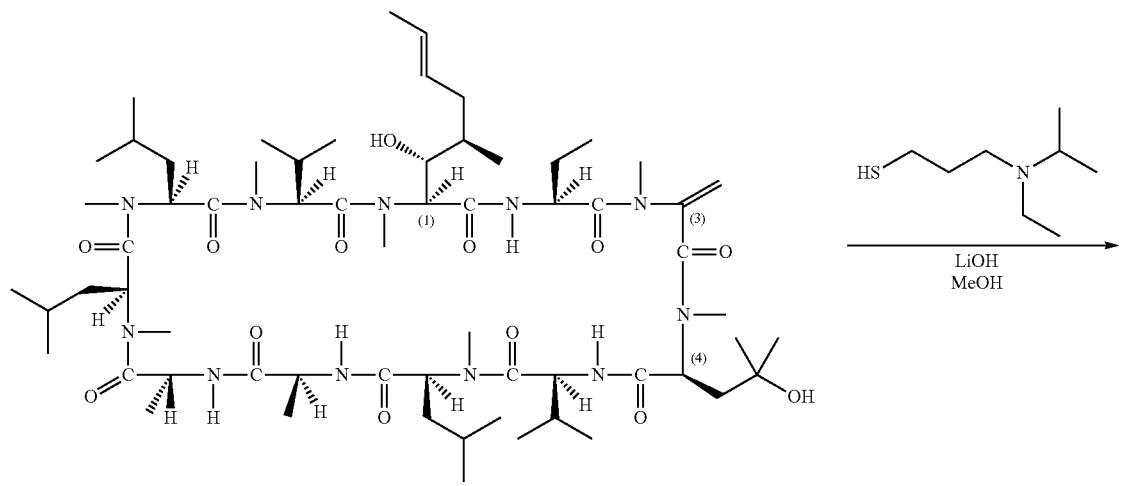

$C_{63}H_{111}N_{11}O_{13}$
Exact Mass: 1229.84
Mol. Wt.: 1230.65

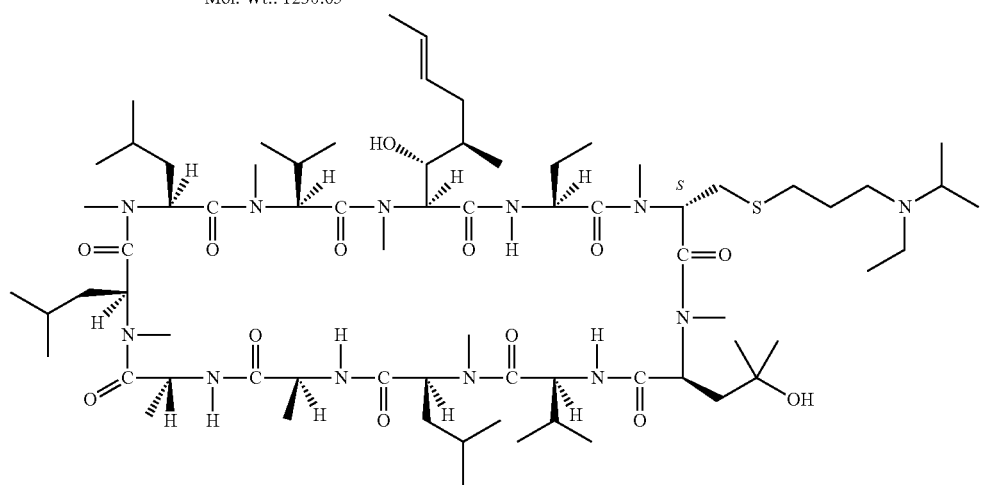

$C_{71}H_{130}N_{12}O_{13}S$
Exact Mass: 1390.96
Mol. Wt.: 1391.95

To a solution of [α-methylene-Sar]-3-[(γ-hydroxy)-N-MeLeu]-4-cyclosporin (200 mg, 0.16 mmol) and 3-(N-ethyl-N-isopropylamino)propylthiol (200 mg, 1.25 mmol) in methanol (25 ml) was added lithium hydroxide (89 mg, 3.71 mmol). The reaction mixture was stirred at room temperature overnight. Then most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=97/3) to give 88 mg of product [Molecular Formula: $C_{71}H_{130}N_{12}O_{13}S$; Exact Mass: 1390.96; MS (m/z): 1413.81 (M+Na)$^+$; TLC Rf: 0.40 (dichloromethane/methanol=9/1); HPLC RT: 12.49 min (C8 reverse phase column: 250 mm; acetonitrile/0.077% ammonium acetate in water; operation temperature: 64° C.; detector: 210 nm)].

Example 60

[(S)-(3-(N-Isobutylamino)propylthio)methyl-Sar]-3-[(γ-hydroxy)-NMeLeu]-4-cyclosporin

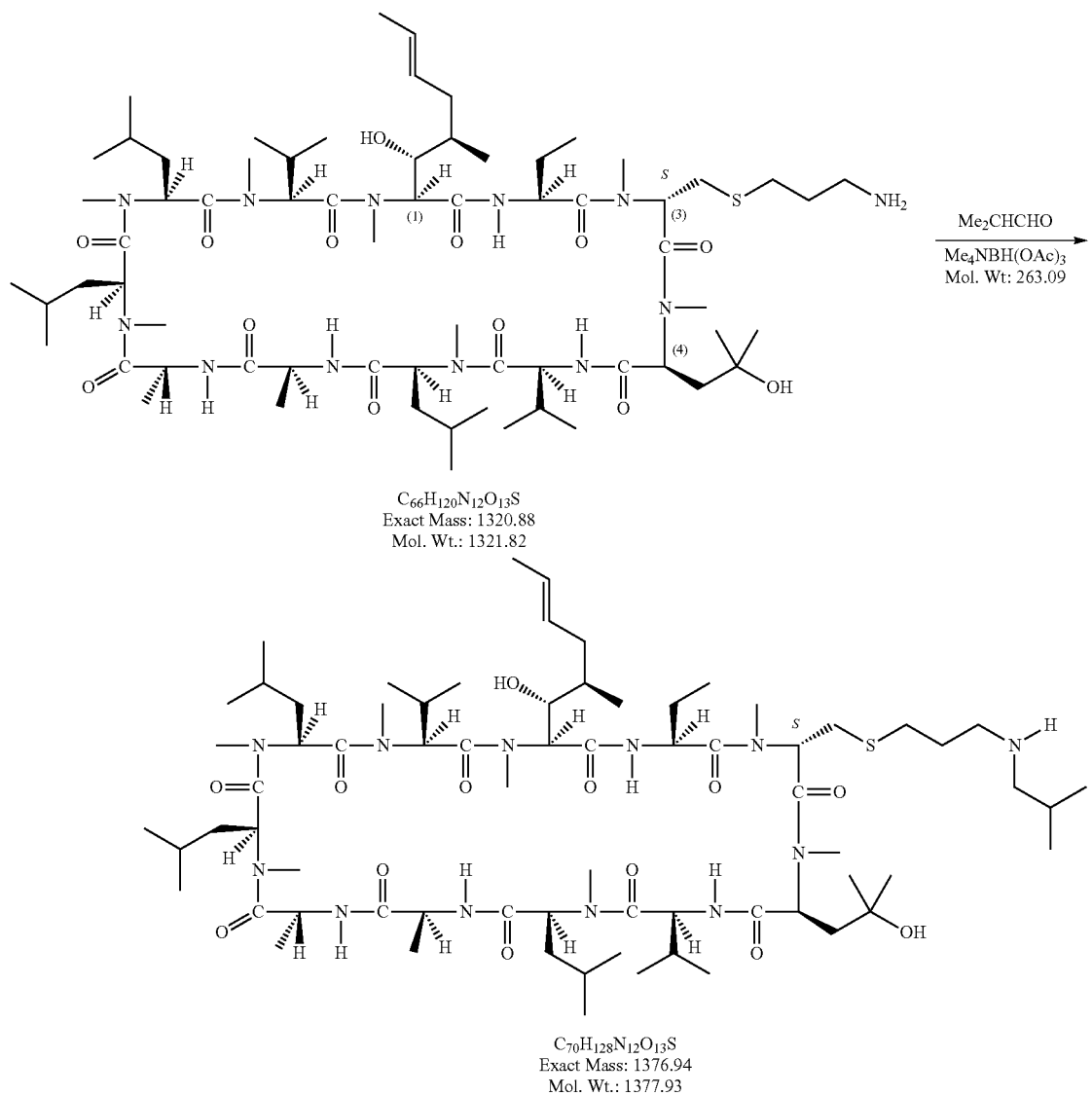

[(S)-(3-Aminopropylthio)methyl-Sar]-3-[(γ-hydroxy)-N-MeLeu]-4-cyclosporin (150 mg, 0.11 mmol) and isobutyraldehyde (MW 72.11, d 0.794, 15 μl, 0.17 mmol) were dissolved in dichloromethane (25 ml), followed by adding a few drops of acetic acid and tetramethylammonium triacetoxyborohydride (30 mg, 0.11 mmol) in portions. The mixture was stirred at room temperature overnight. Then the reaction mixture was washed with saturated sodium bicarbonate solution (25 ml) and brine (25 ml), dried over magnesium sulfate and evaporated under reduced pressure. The residue was purified by flash chromatography on silica gel using dichloromethane/methanol as eluent to give product [Molecular Formula: $C_{70}H_{128}N_{12}O_{13}S$; Exact Mass: 1376.94; MS (m/z): 1477.56 (M+1)$^+$, 1399.71 (M+Na)$^+$; TLC R$_f$: 0.18 (dichloromethane/methanol=9:1); HPLC RT: 11.70 min (C8 reverse phase column: 250 mm; acetonitrile/water (0.05% trifluoroacetic acid); operation temperature: 64° C.; detector: 210 nm)].

Example 61

[(S)-(3-(N,N-Diisobutylamino)propylthio)methyl-Sar]-3-[(γ-hydroxy)-NMeLeu]-4-cyclosporin

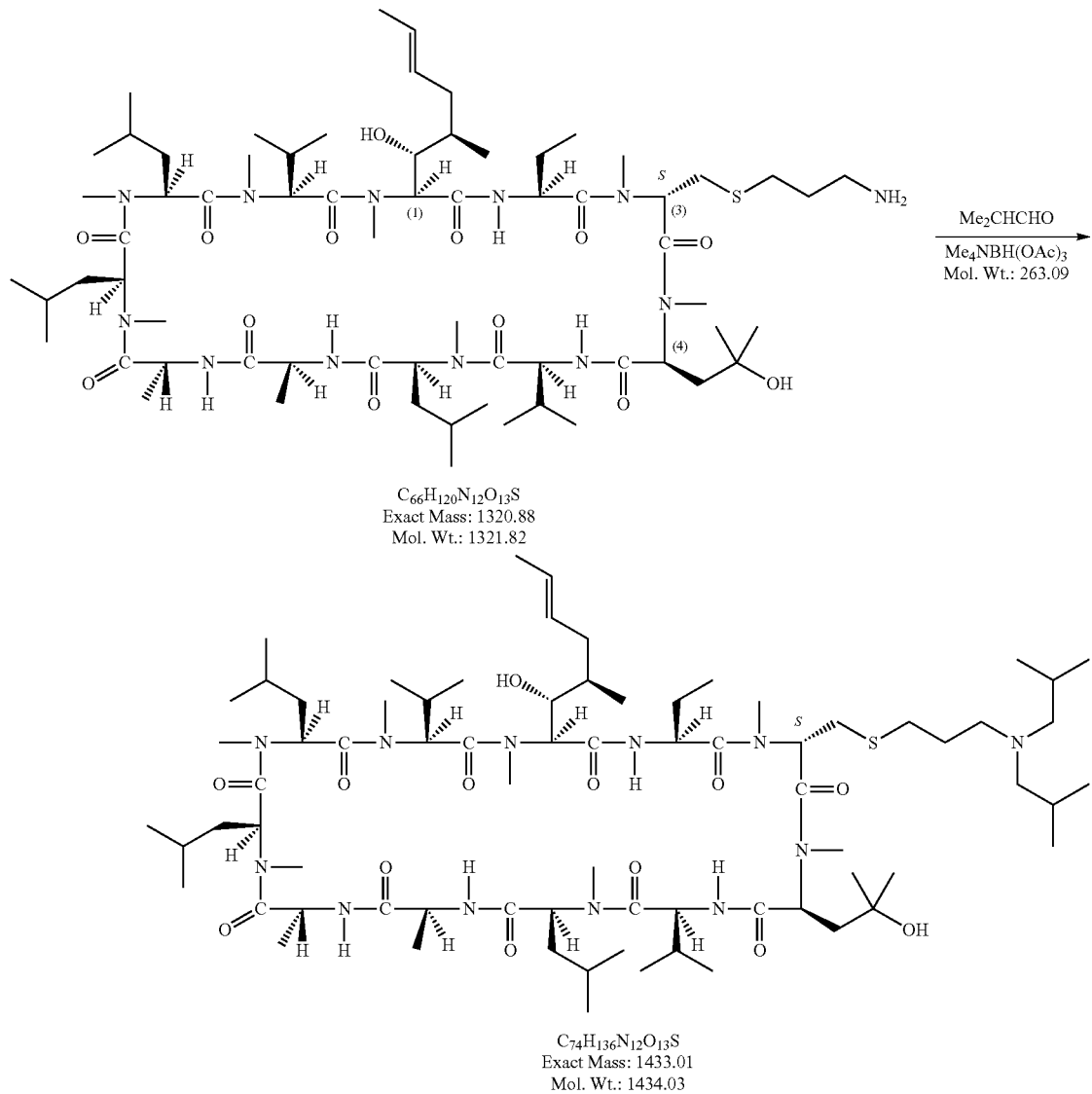

[(S)-(3-Aminopropylthio)methyl-Sar]-3-[(γ-hydroxy)-N-MeLeu]-4-cyclosporin (150 mg, 0.11 mmol) and isobutyraldehyde (MW 72.11, d 0.794, 15 μl, 0.17 mmol) were dissolved in dichloromethane (25 ml), followed by adding a few drops of acetic acid and tetramethylammonium triacetoxyborohydride (30 mg, 0.11 mmol in portions. The mixture was stirred at room temperature overnight. Then the reaction mixture was washed with saturated sodium bicarbonate solution (25 ml) and brine (25 ml), dried over magnesium sulfate and evaporated under reduced pressure. The residue was purified by flash chromatography on silica gel using dichloromethane/methanol as eluent to give product [Molecular Formula: $C_{73}H_{134}N_{12}O_{13}S$; Exact Mass: 1433.01; MS (m/z): 1433.64 $(M+1)^+$, 1455.78 $(M+Na)^+$; TLC $R_f$: 0.24 (dichloromethane/methanol=95:5); HPLC RT: 14.45 min (C8 reverse phase column: 250 mm; acetonitrile/water (0.05% trifluoroacetic acid); operation temperature: 64° C.; detector: 210 nm)].

Example 62

[(S)-(3-(N-Neopentylamino)propylthio)methyl-Sar]-3-[(γ-hydroxy)-NMeLeu]-4-cyclosporin

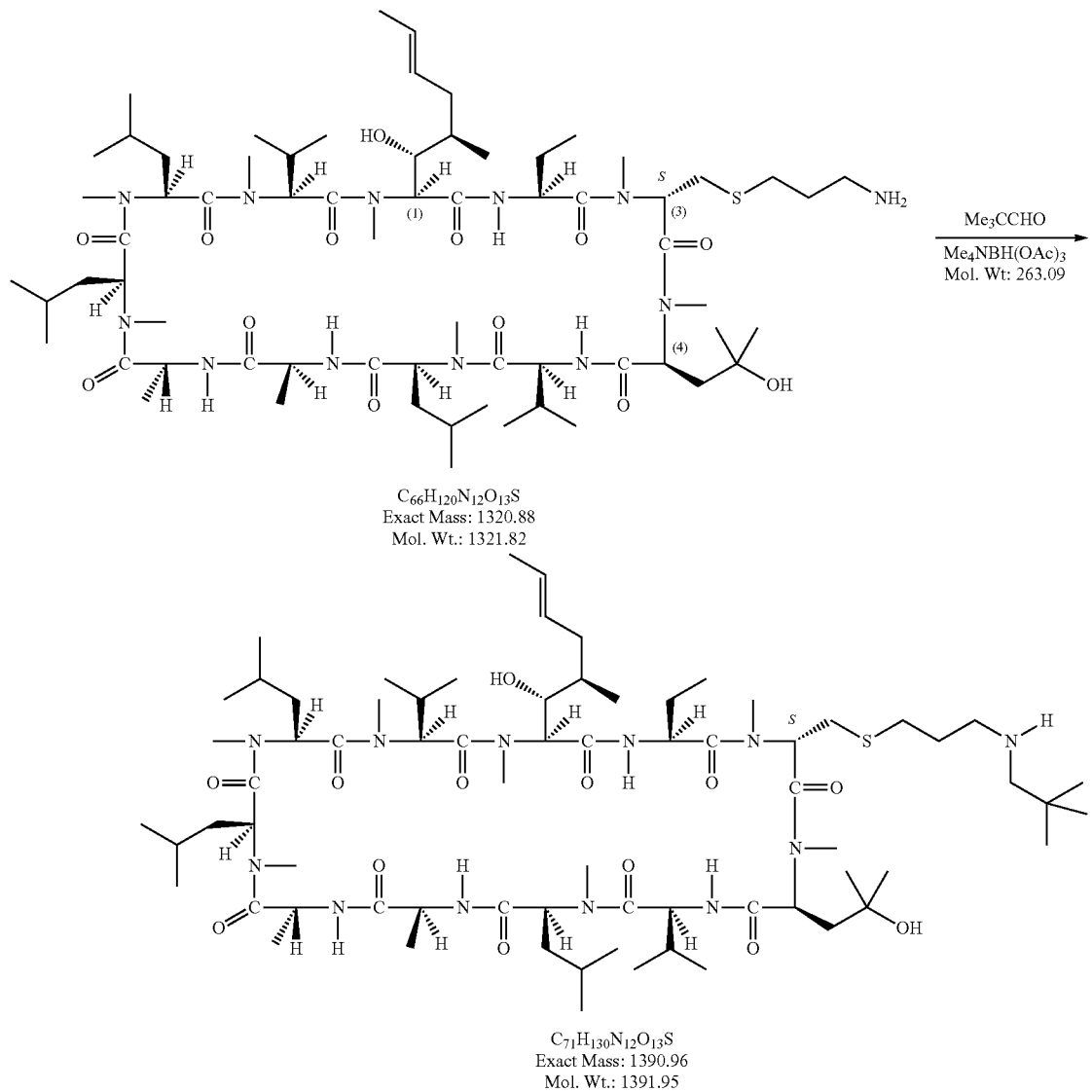

[(S)-(3-Aminopropylthio)methyl-Sar]-3-[(γ-hydroxy)-N-MeLeu]-4-cyclosporin (50 mg, 0.04 mmol) and pivalaldehyde (MW 86.13, d 0.793, 21 μl, 0.19 mmol) were mixed with 20 ml of dichloromethane, followed by adding tetramethylammonium triacetoxyborohydride (24.9 mg, 0.10 mmol) and a few drops of acetic acid. The mixture was stirred at room temperature for 6 hours. Then the reaction mixture was washed with saturated sodium bicarbonate solution (30 ml) and brine (30 ml), dried over magnesium sulfate and evaporated under reduced pressure. The residue was purified by flash chromatography on silica gel using dichloromethane/methanol as eluent to give product [Molecular Formula: $C_{71}H_{130}N_{12}O_{13}S$; Exact Mass: 1390.96; MS (m/z): 1391.54 $(M+1)^+$, 1413.69 $(M+Na)^+$; TLC $R_f$: 0.24 (dichloromethane/methanol=5/1); HPLC RT: 13.21 min (C8 reverse phase column: 250 mm; acetonitrile/water (0.05% trifluoroacetic acid); operation temperature: 64° C.; detector: 210 nm)].

Example 63

[(S)-(3-(N-Piperidinyl)propylthio)methyl-Sar]-3-[(γ-hydroxy)-NMeLeu]-4-cyclosporin

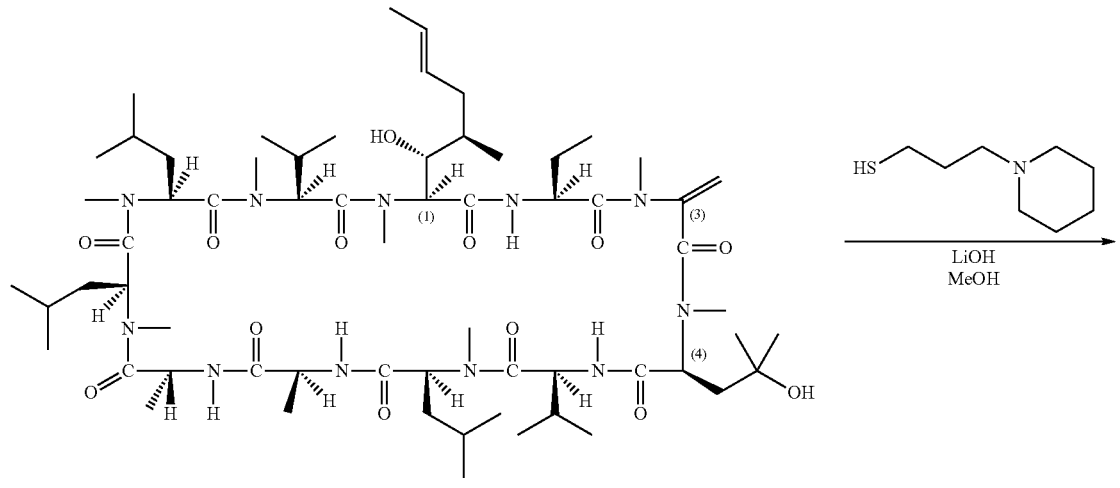

$C_{63}H_{111}N_{11}O_{13}$
Exact Mass: 1229.84
Mol. Wt.: 1230.62

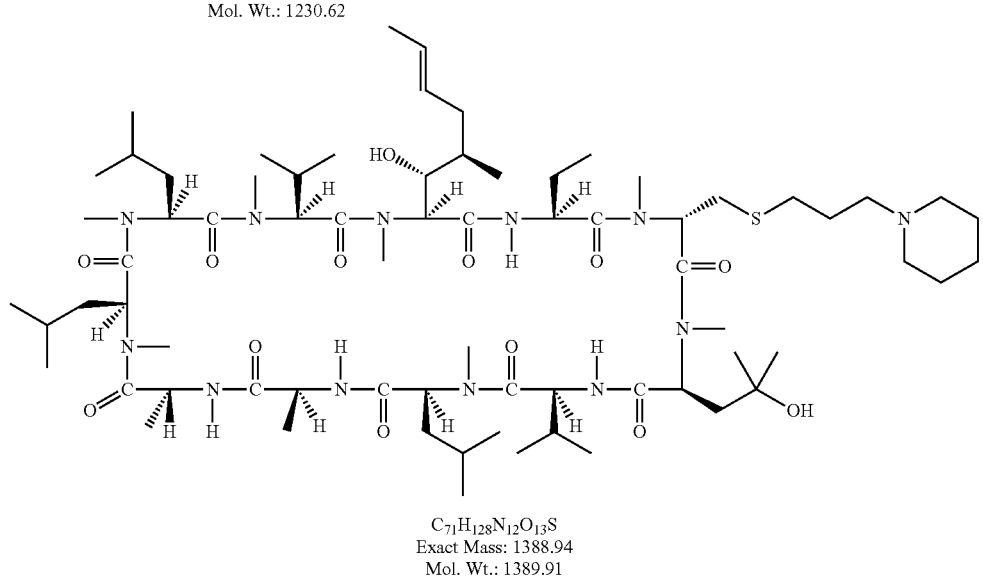

$C_{71}H_{128}N_{12}O_{13}S$
Exact Mass: 1388.94
Mol. Wt.: 1389.91

To a solution of [α-methylene-Sar]-3-[(γ-hydroxy)-N-MeLeu]-4-cyclosporin (250 mg, 0.20 mmol) and 3-(N-piperidinyl)propanethiol (318 mg, 2.00 mmol) in methanol (30 ml) was added lithium hydroxide (96 mg, 4.00 mmol). The reaction mixture was stirred at room temperature overnight. Then most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=96/4) to give 135 mg of product [Molecular Formula: $C_{71}H_{128}N_{12}O_{13}S$; Exact Mass: 1388.94; MS (m/z): 1389.84 $(M+1)^+$; TLC Rf: 0.30 (dichloromethane/methanol=95/5); HPLC RT: 12.19 min (C8 reverse phase column: 250 mm; acetonitrile/0.077% ammonium acetate in water; operation temperature: 64° C.; detector: 210 nm); $^1$H NMR spectrum (600 MHz, CDCl$_3$, δ in ppm): 0.68 (d, J=6.0 Hz, 3H), 0.79 (d, J=6.0 Hz, 3H), 0.82-0.86 (m, 9H), 0.88 (d, J=6.6 Hz, 3H), 0.91 (d, J=6.6 Hz, 3H), 0.93 (d, J=6.6 Hz, 3H), 0.97-1.00 (m, 9H), 1.09 (d, J=6.6 Hz, 3H), 1.21-1.24 (m, 11H), 1.31-1.46 (m, 8H), 1.53 (m, 5H), 1.61 (m, 11H), 1.67-1.70 (m, 2H), 1.74-1.76 (m, 2H), 1.99-2.11 (m, 4H), 2.31-2.35 (m, 4H), 2.37-2.41 (m, 2H), 2.53-2.60 (m, 2H), 2.67 (s, 6H), 2.91-2.98 (m. 2H), 3.09 (s, 3H), 3.24 (s, 6H), 3.26 (s, 3H), 3.48 (s, 3H), 3.56 (m, 1H), 3.65 (m, 1H), 4.51 (m, 1H), 4.58 (t, J=8.4 Hz, 1H), 4.81 (m, 1H), 4.94-5.02 (m, 2H), 5.04 (t, J=6.6 Hz, 1H), 5.08 (d, J=10.8 Hz, 1H), 5.28-5.32 (m, 1H), 5.33-5.37 (m, 1H), 5.49 (m, 2H), 5.67 (dd, J=10.8 Hz and 3.6 Hz, 1H), 7.14 (d, J=8.4 Hz, 1H), 7.49 (d, J=8.4 Hz, 1H), 7.64 (d, J=8.4 Hz, 1H), 8.09 (d, J=10.2 Hz, 1H)].

Example 64

[(S)-(3-(N-Pyrrolidinyl)propylthio)methyl-Sar]-3-[(γ-hydroxy)-NMeLeu]-4-cyclosporin

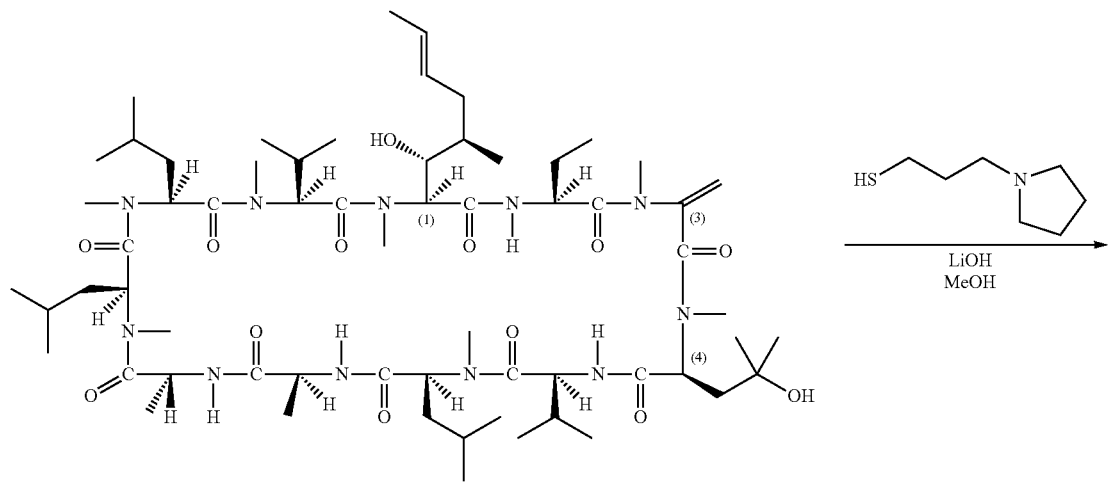

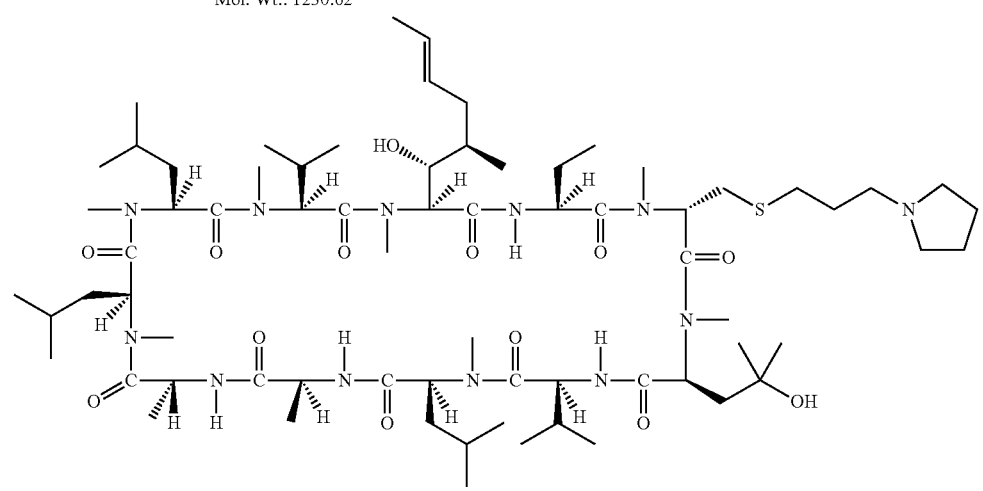

To a solution of [α-methylene-Sar]-3-[(γ-hydroxy)-N-MeLeu]-4-cyclosporin (213 mg, 0.17 mmol) and 3-(N-pyrrolidinyl)propanethiol (280 mg, 1.93 mmol) in methanol (25 ml) was added lithium hydroxide (94 mg, 3.92 mmol). The reaction mixture was stirred at room temperature overnight. Then most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=95/5) to give 57 mg of product [Molecular Formula: $C_{70}H_{126}N_{12}O_{13}S$; Exact Mass: 1374.93; MS (m/z): 1375.75 (M+1)$^+$; TLC Rf: 0.23 (dichloromethane/methanol=95/5); HPLC RT: 11.83 min (C8 reverse phase column: 250 mm; acetonitrile/0.077% ammonium acetate in water; operation temperature: 64° C.; detector: 210 nm)].

Example 65

[(S)-(3-(N-Morpholino)propylthio)methyl-Sar]-3-[(γ-hydroxy)-NMeLeu]-4-cyclosporin

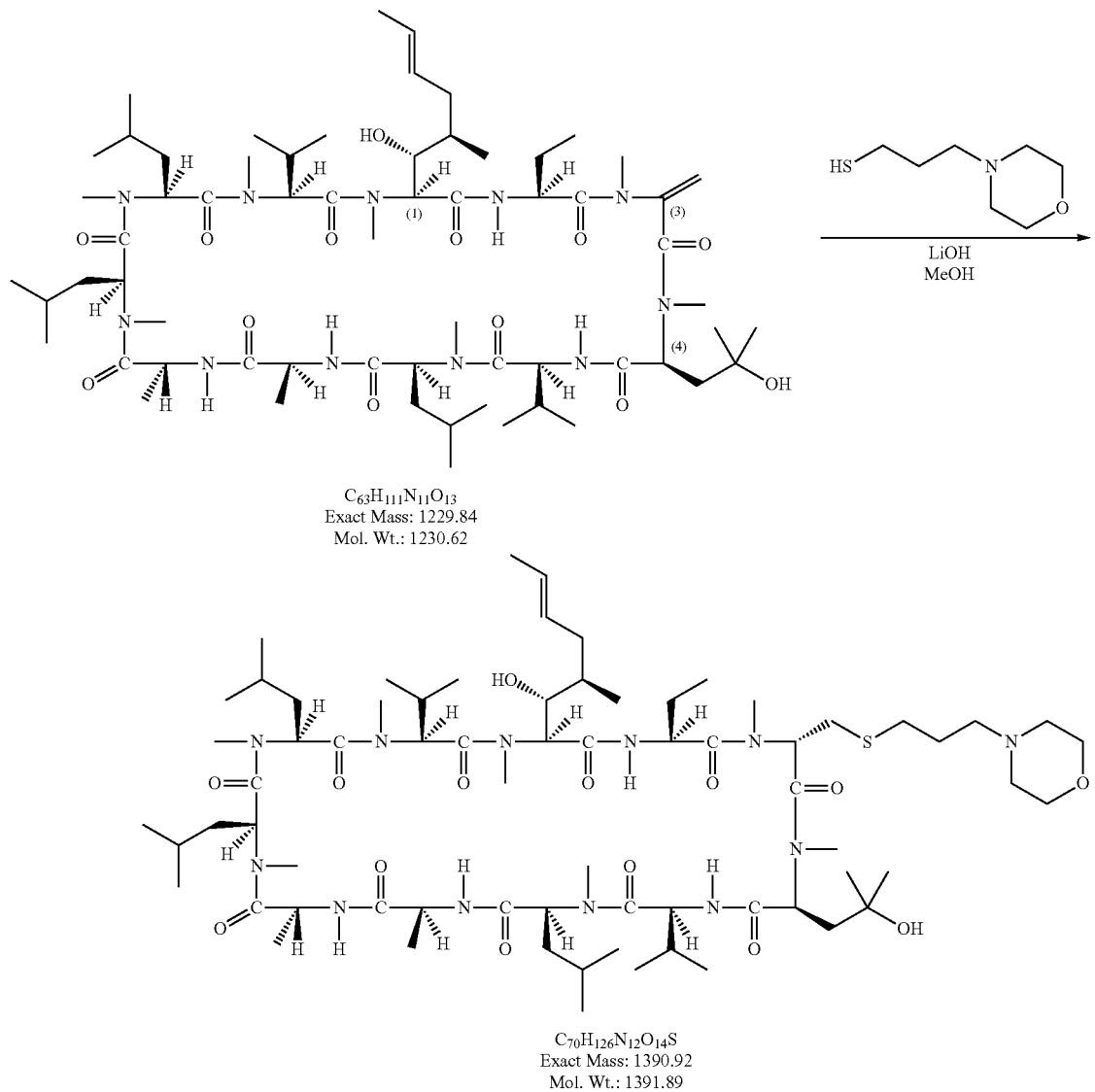

To a solution of [α-methylene-Sar]-3-[(γ-hydroxy)-N-MeLeu]-4-cyclosporin (210 mg, 0.17 mmol) and 3-morpholinopropanethiol (300 mg, 1.86 mmol) in methanol (25 ml) was added lithium hydroxide (140 mg, 5.83 mmol). The reaction mixture was stirred at room temperature overnight. Then most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=97/3) to give 78 mg of product [Molecular Formula: $C_{70}H_{126}N_{12}O_{14}S$; Exact Mass: 1390.92; MS (m/z): 1413.77 (M+Na)⁻; TLC Rf: 0.33 (dichloromethane/methanol=9/1); HPLC RT: 11.35 min (C8 reverse phase column: 250 mm; acetonitrile/0.077% ammonium acetate in water; operation temperature: 64° C.; detector: 210 nm); $^1$H NMR spectrum (600 MHz, CDCl$_3$, δ in ppm): 0.68 (d, J=6.0 Hz, 3H), 0.79 (d, J=5.4 Hz, 3H), 0.82-0.86 (m, 9H), 0.88 (d, J=6.6 Hz, 3H), 0.91 (d, J=6.6 Hz, 3H), 0.93 (d, J=6.6 Hz, 3H), 0.97-1.00 (m, 9H), 1.09 (d, J=6.6 Hz, 3H), 1.21-1.24 (m, 11H), 1.31 (d, J=7.2 Hz, 3H), 1.38-1.46 (m, 2H), 1.61 (m, 11H), 1.67-1.70 (m, 2H), 1.74-1.76 (m, 2H), 2.03-2.11 (m, 4H), 2.35-2.43 (m, 8H), 2.55-2.63 (m, 2H), 2.67 (s, 6H), 2.91-2.98 (m. 2H), 3.10 (s, 3H), 3.24 (3, 6H), 3.26 (s, 3H), 3.49 (s, 3H), 3.52 (m, 1H), 3.65-3.67 (m, 5H), 4.51 (m, 1H), 4.59 (t, J=8.4 Hz, 1H), 4.81 (m, 1H), 4.94-5.01 (m, 2H), 5.04 (t, J=6.6 Hz, 1H), 5.08 (d, J=12 Hz, 1H), 5.28-5.30 (m, 1H), 5.33-5.37 (m, 1H), 5.49 (m, 2H), 5.67 (m, 1H), 7.14 (d, J=7.8 Hz, 1H), 7.49 (d, J=8.4 Hz, 1H), 7.65 (d, J=7.2 Hz, 1H), 8.12 (d, J=9.6 Hz, 1H)].

Example 66

[(S)-(3-(N-Morpholino)propylsulfinyl)methyl-Sar]-
3-[(γ-hydroxy)-NMeLeu]-4-cyclosporin

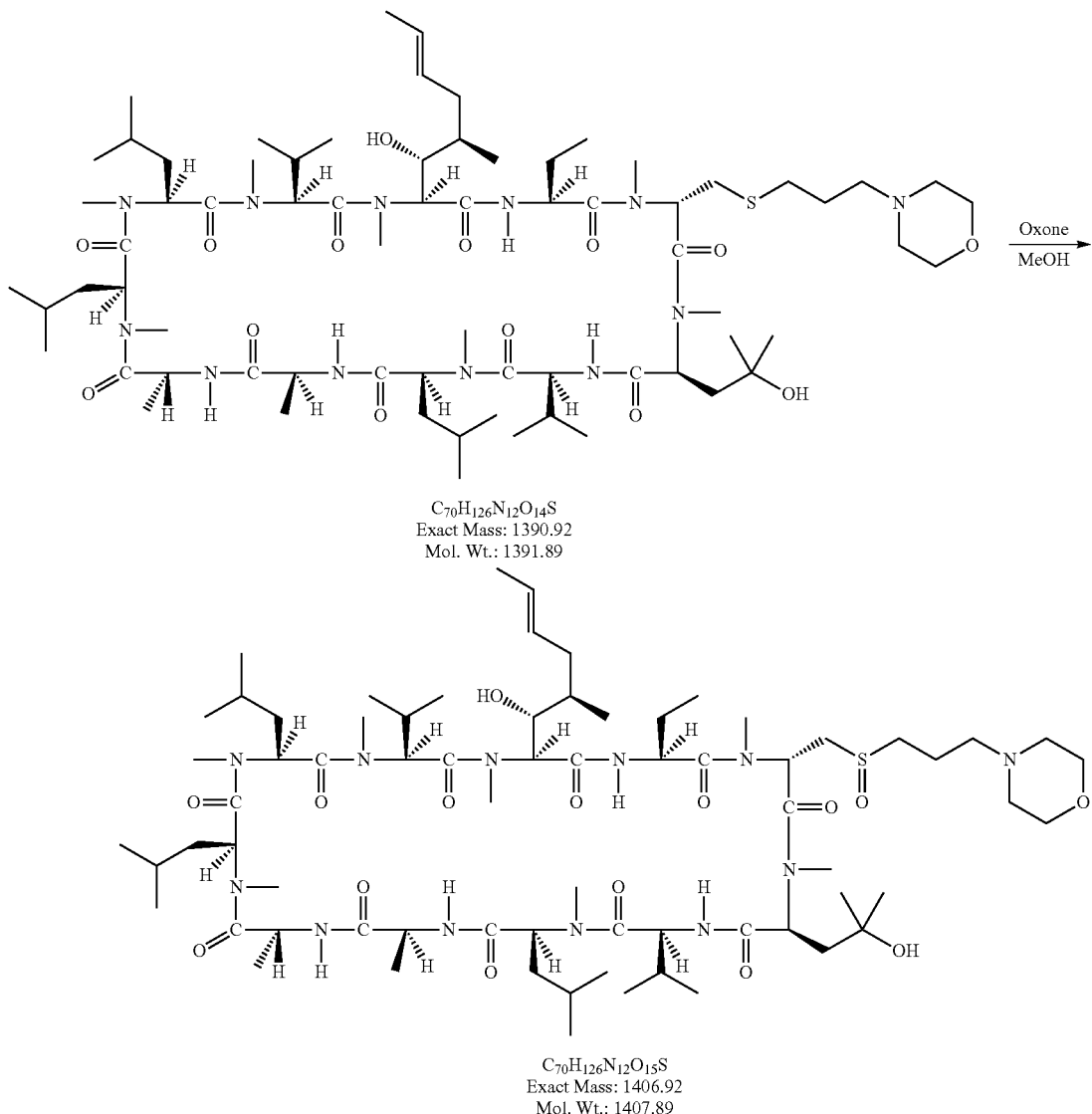

To a solution of [(S)-(3-(N-Morpholino)propylthio)methyl-Sar]-3-[(γ-hydroxyl)-N-MeLeu]-4-cyclosporin (27 mg, 0.02 mmol) in methanol (5 ml) was added oxone (25 mg, 0.04 mmol). The reaction mixture was stirred at room temperature for one hour. Then most of the solvent was evaporated under reduced pressure. Dichloromethane (20 ml) and saturated sodium bicarbonate solution (5 ml) were added and separated. The organic layer was washed with water and brine, dried over magnesium sulfate and evaporated under reduced pressure. The residue was purified by chromatography (dichloromethane/methanol=96/4) to give product [Molecular formula: $C_{70}H_{126}N_{12}O_{15}S$; Exact Mass: 1406.92; MS (m/z): 1407.47 (M+1)$^+$; TLC Rf 0.23 (dichloromethane/methanol=9/1); HPLC RT: 9.35 min (C8 reverse phase column: 250 mm; acetonitrile/water (0.05% trifuloroacetic acid); operation temp: 64° C.; Detector: 210 nm)].

Example 67

[(S)-(3-(N-Morpholino)propylsulfonyl)methyl-Sar]-
3-[(γ-hydroxy)-NMeLeu]-4-cyclosporin

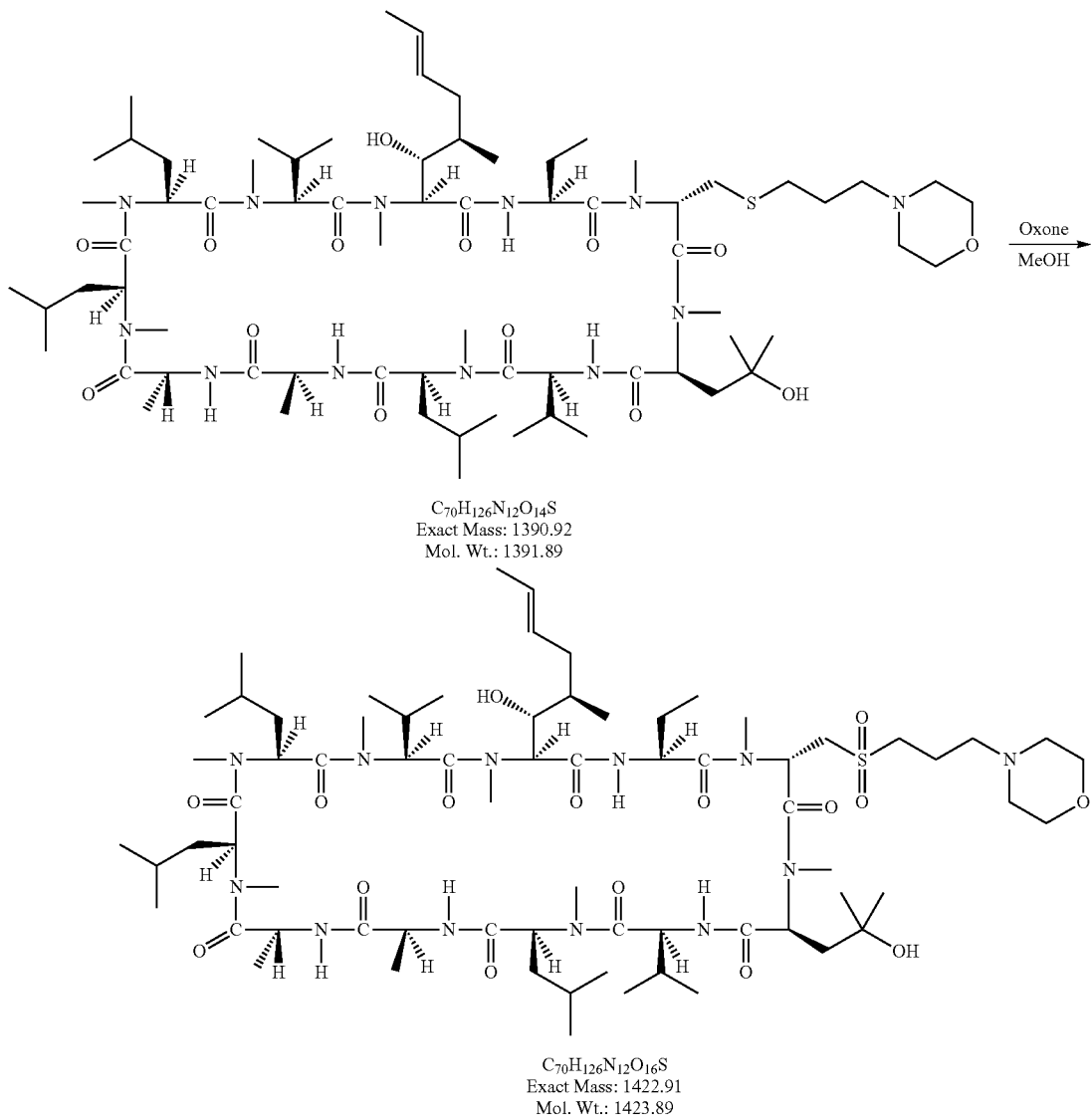

To a solution of [(S)-(3-(N-Morpholino)propylthio)methyl-Sar]-3-[(γ-hydroxyl)-N-MeLeu]-4-cyclosporin (30 mg, 0.02 mmol) in methanol (5 ml) were added oxone (40 mg, 0.07 mmol) and water (0.3 ml) at 0° C. The reaction mixture was stirred at room temperature 1 hour. Dichloromethane (30 ml) and cold saturated sodium bicarbonate solution (5 ml) were added and separated. The organic layer was washed with water and brine, dried over magnesium sulfate and evaporated under reduced pressure. The residue was purified by chromatography (dichloromethane/methanol=96/4) to give product [Molecular formula: $C_{70}H_{126}N_{12}O_{16}S$; Exact Mass: 1422.91; MS (m/z): 1423.54 $(M+1)^+$; TLC Rf: 0.28 (dichloromethane/methanol=9/1); HPLC RT: 9.38 min (C8 reverse phase column: 250 mm; acetonitrile/water (0.05% trifuloroacetic acid); operation temp: 64° C.; Detector: 210 nm)].

Example 68

[(S)-(3-(N-Thiomorpholino)propylthio)methyl-Sar]-
3-[(γ-hydroxy)-NMeLeu]-4-cyclosporin

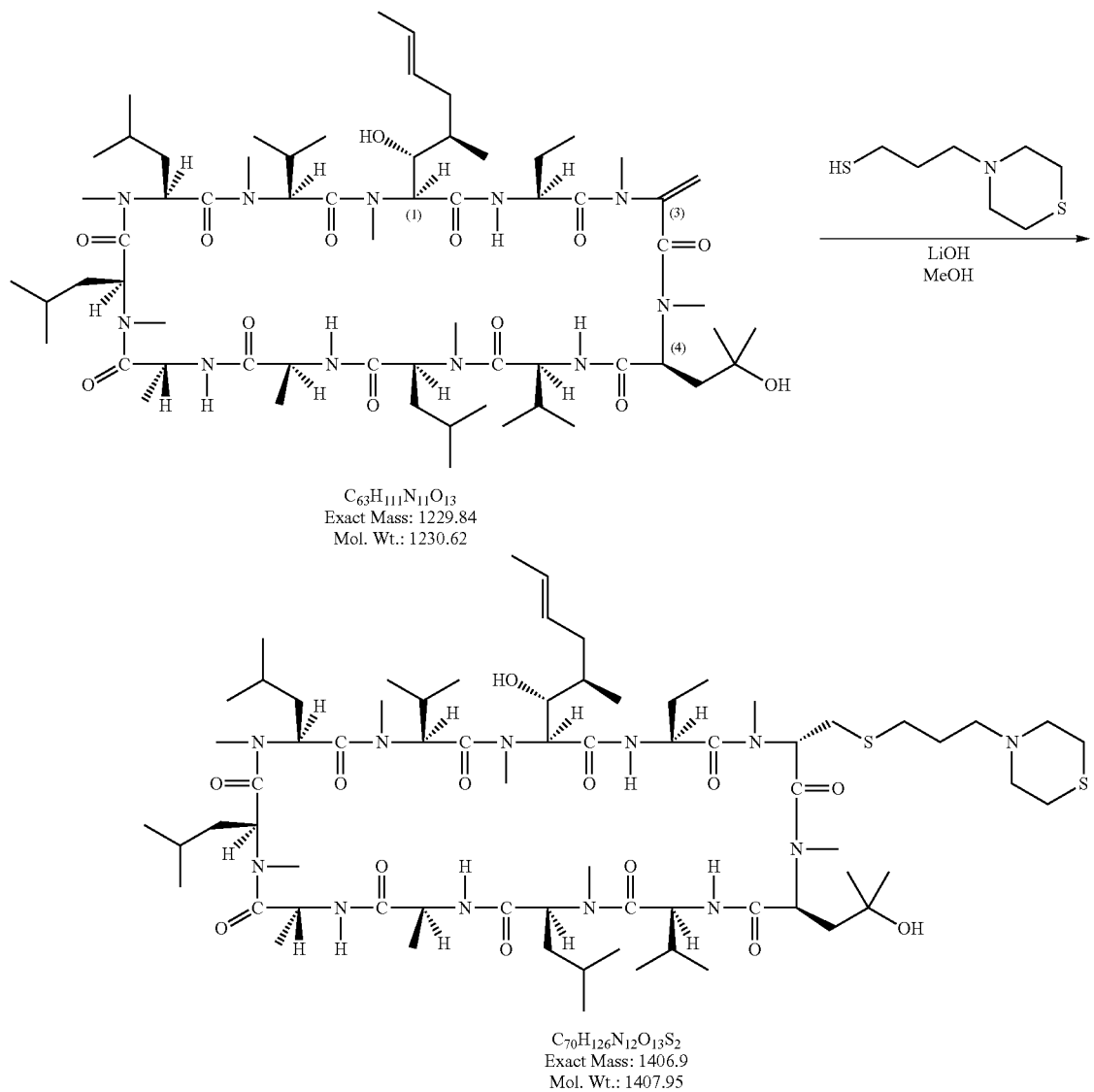

To a solution of [α-methylene-Sar]-3-[(γ-hydroxy)-N-MeLeu]-4-cyclosporin (280 mg, 0.23 mmol) and 4-(3-thiopropyl)thiomorpholine (280 mg, 1.58 mmol) in methanol (15 ml) was added lithium hydroxide (80 mg, 3.33 mmol). The reaction mixture was stirred at room temperature overnight. Then most of the solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (dichloromethane/methanol=97/3) to give product [Molecular formula: $C_{70}H_{126}N_{12}O_{13}S_2$; Exact Mass: 1406.90; MS (m/z): 1407.51 (M+1)$^-$; TLC Rf: 0.35 (dichloromethane/methanol=9/1); HPLC RT: 11.18 min (C8 reverse phase column: 250 mm; acetonitrile/water (0.05% trifuloroacetic acid); operation temp: 64° C.; Detector: 210 nm)].

Example 69

[(S)-(3-(4-N-Boc-N-piperazinyl)propylthio)methyl-Sar]-3-[(γ-hydroxy)-NMeLeu]-4-cyclosporin

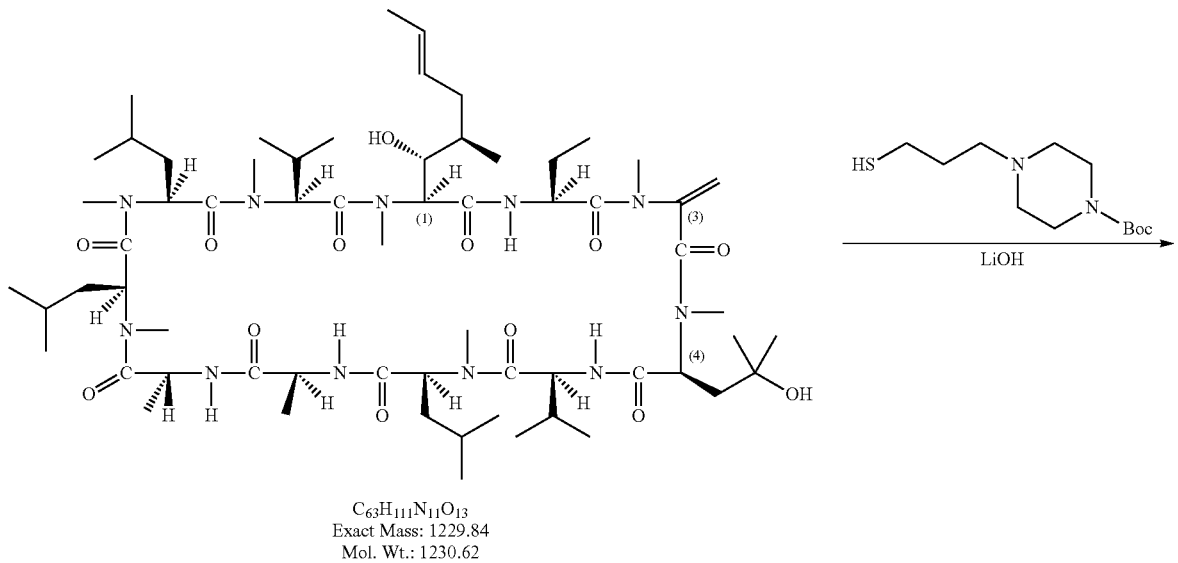

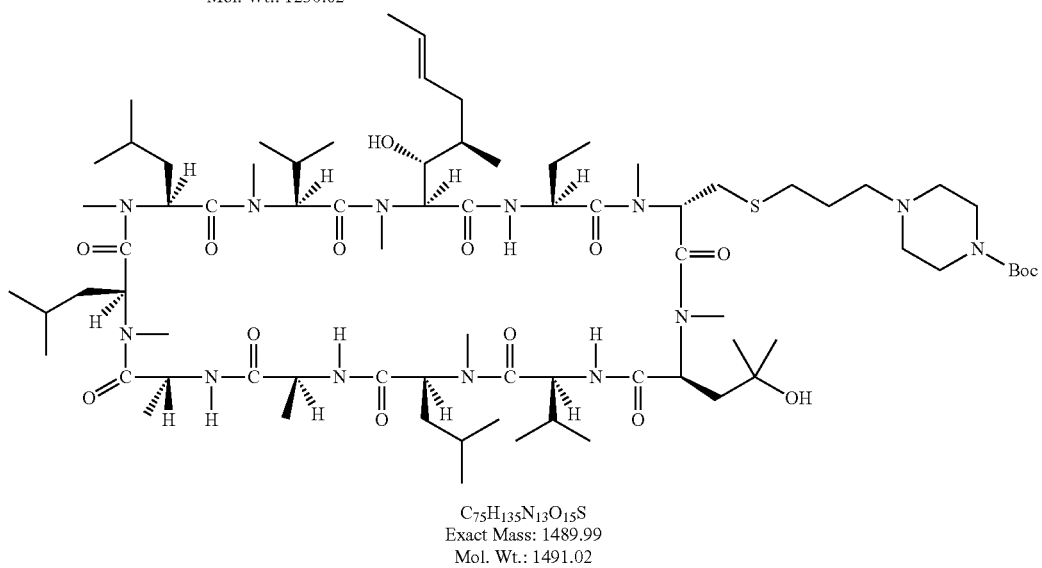

[α-Methylene-Sar]-3-[(γ-hydroxy)-N-MeLeu]-4-cyclosporin (2.95 g, 2.40 mmol) and 1-Boc-4-(3-mercaptopropanyl)piperazine (MW: 260.4, 3.18 g, 5.10 mmol) were dissolved in methanol (75 ml), followed by adding lithium hydroxide (MW: 23.95, 0.35 g, 14.4 mmol). The mixture was stirred at room temperature overnight. After removal of solvent, the residue was purified by chromatography on silica gel using dichloromethane/methanol as eluent to give product [Molecular Formula: $C_{75}H_{135}N_{13}O_{15}S$; Exact Mass: 1489.99; MS (m/z): 1490.54 $(M+1)^+$, 1512.63 $(M+Na)^+$; HPLC RT: 12.51 min (C8 reverse phase column: 250 mm; acetonitrile/water (0.05% trifluoroacetic acid); operation temperature: 64° C.; detector: 210 nm)].

Example 70

[(S)-(3-(N-Piperazinyl)propylthio)methyl-Sar]-3-[(γ-hydroxy)-NMeLeu]-4-cyclosporin

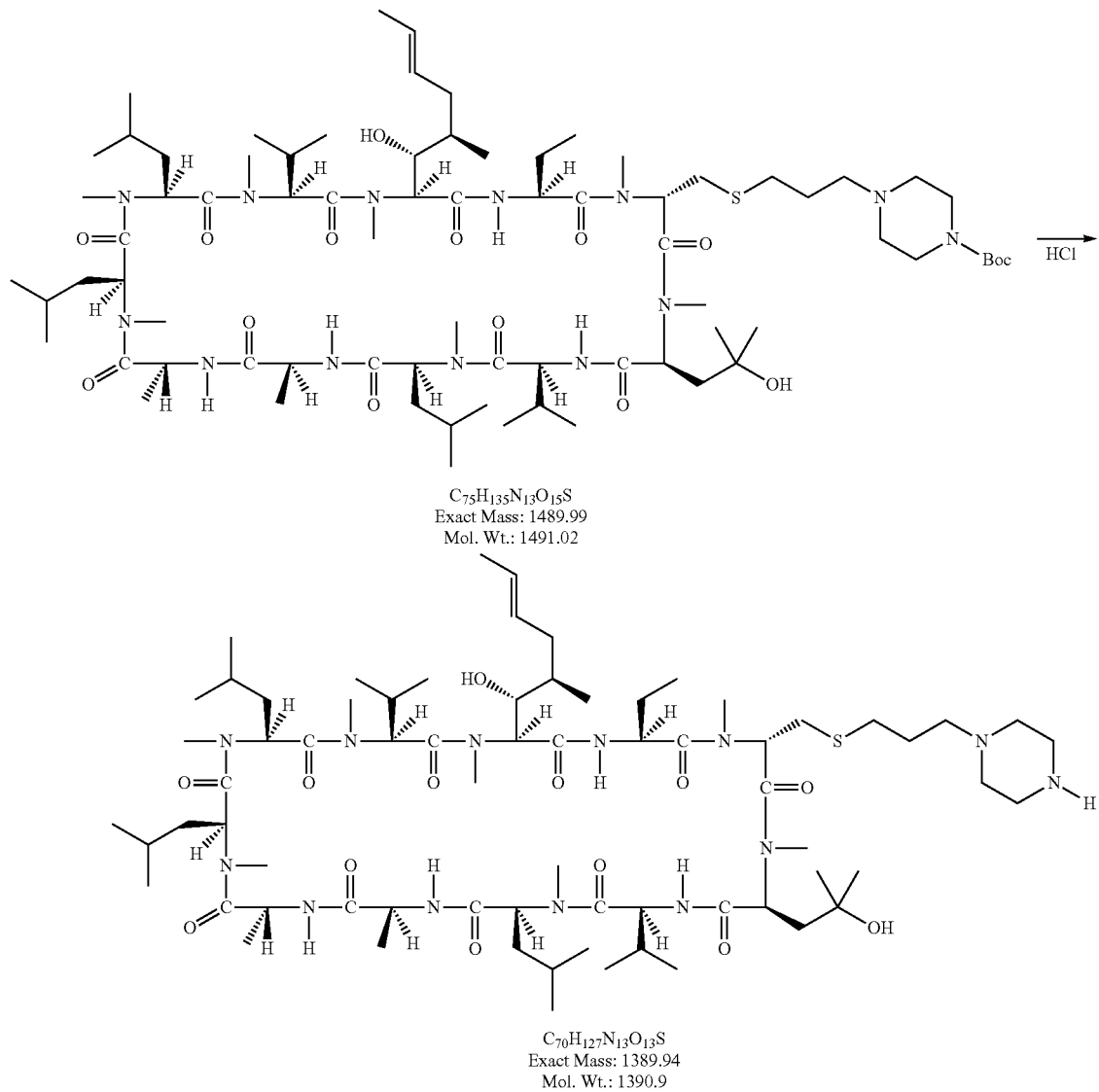

[(R)-(3-(4-N-Boc-N-piperazinyl)propylthio)methyl-Sar]-3-[(γ-hydroxy)-N-MeLeu]-4-cyclosporin (1.59 g, 1.07 mmol) was dissolved in methanol (20 ml). Then 4 M hydrochloric acid in dioxane (4 ml) was added. The mixture was stirred at room temperature for one hour. Most of solvent was evaporated under reduced pressure. The residue was mixed ethyl acetate (60 ml) and saturated sodium bicarbonate solution (60 ml) and separated. The ethyl acetate layer was washed with brine, dried over magnesium sulfate and evaporated under reduced pressure. The crude product was purified by chromatography on silica gel using dichloromethane/methanol as eluent to give product [Molecular Formula: $C_{70}H_{127}N_{13}O_{13}S$; Exact Mass: 1389.94; MS (m/z): 1390.56 $(M+1)^-$, 1412.70 $(M+Na)^+$; TLC $R_f$: 0.37 (dichloromethane/methanol=5:1); HPLC RT: 8.20 min (C8 reverse phase column: 250 mm; acetonitrile/water (0.05% trifluoroacetic acid); operation temperature: 64° C.; detector: 210 nm)].

Example 71

[(S)-(3-(4-Methyl-N-piperazinyl)propylthio)methyl-Sar]-3-[(γ-hydroxy)-NMeLeu]-4-cyclosporin

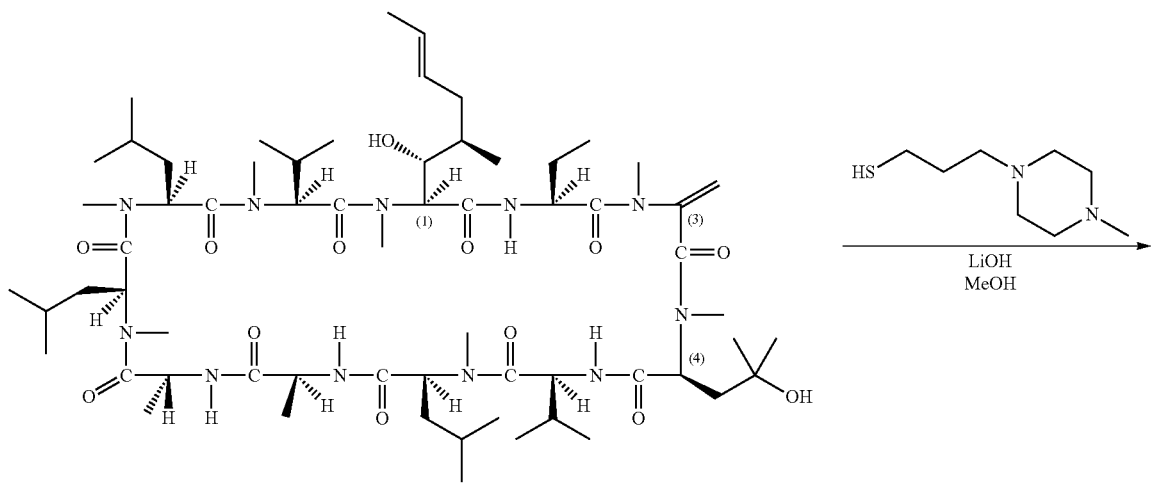
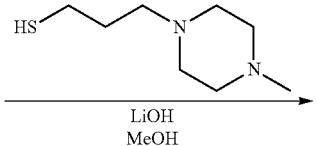
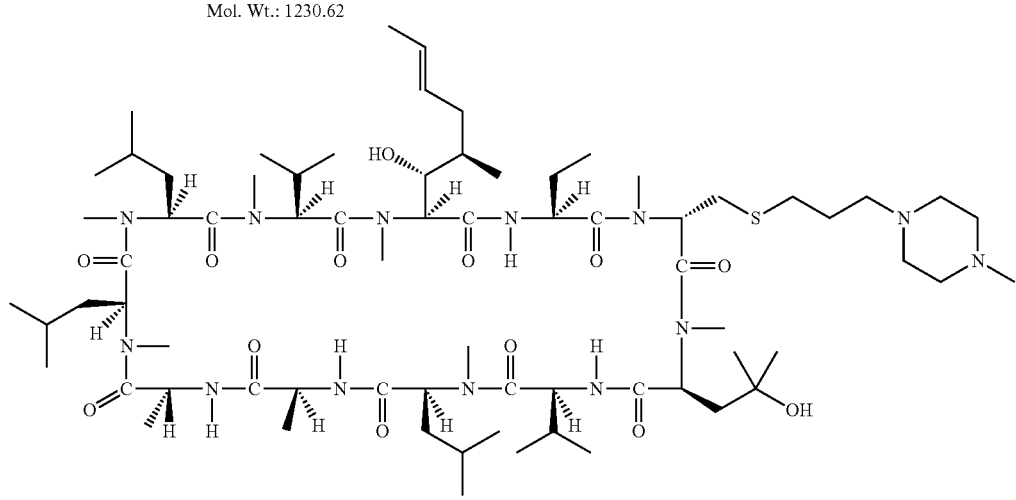

[α-Methylene-Sar]-3-[(γ-hydroxy)-N-MeLeu]-4-cyclosporin (0.30 g, 0.24 mmol) and 3-(4-methylpiperazino)propylthiol (MW: 174.31, 0.42 g, 2.44 mmol) were dissolved in methanol (25 ml), followed by adding 10 equivalents of lithium hydroxide (58 mg, 2.40 mmol). The mixture was stirred overnight at room temperature. After removal of solvent, the residue was purified by flash chromatography using dichloromethane/methanol as eluent to give 0.20 g of product [Molecular Formula: $C_{71}H_{129}N_{13}O_{13}S$; Exact Mass: 1403.96; MS (m/z): 1404.9 $(M+1)^+$, 1426.9 $(M+Na)^+$; TLC $R_f$: 0.10 (ethyl acetate/methanol=5/1); HPLC RT: 10.07 min (C8 reverse phase column: 250 mm; acetonitrile/water (0.05% trifluoroacetic acid); operation temperature: 64° C.; detector: 210 nm)].

Example 72

[(S)-(3-(4-Ethyl-N-piperazinyl)propylthio)methyl-Sar]-3-[(γ-hydroxy)-NMeLeu]-4-cyclosporin

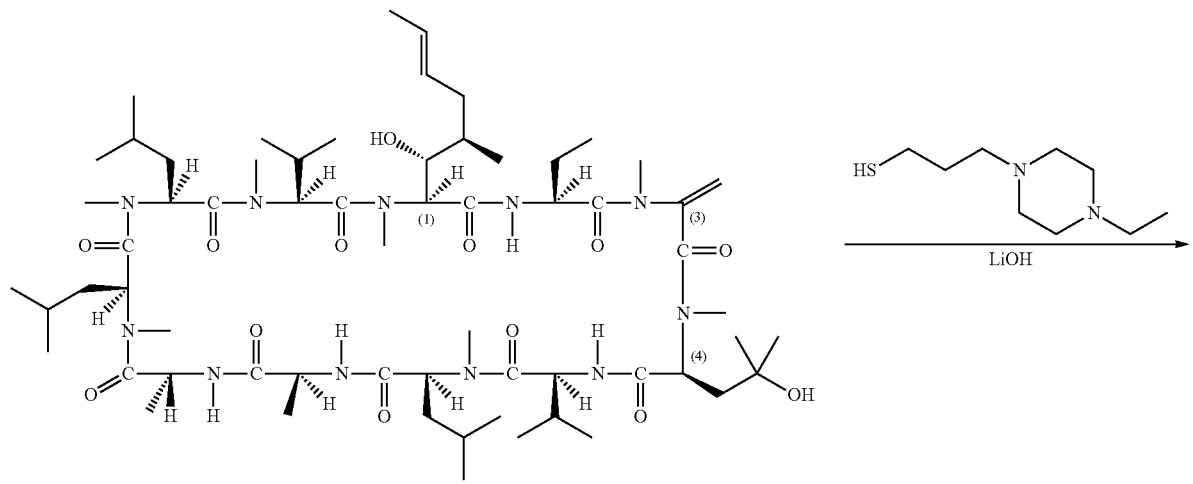

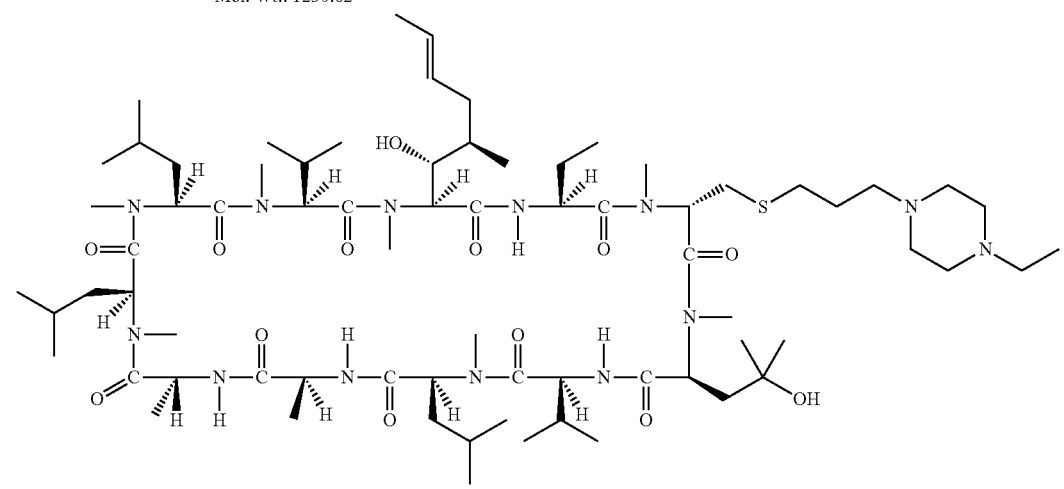

[α-Methylene-Sar]-3-[(γ-hydroxy)-N-MeLeu]-4-cyclosporin (0.25 g, 0.20 mmol) and 3-(1-ethyl-4-piperazino)propylthiol (MW: 188.33, 0.20 g, 1.06 mmol) were dissolved in methanol (15 ml), followed by adding lithium hydroxide (MW: 23.95, 48 mg, 20 mmol). The mixture was stirred overnight at room temperature. After removal of solvents, the residue was subject to chromatography using dichloromethane/methanol as eluent to give product [Molecular formula: $C_{72}H_{131}N_{13}O_{13}S$; Exact Mass: 1417.97; MS (m/z): 1418.58(M+1)$^+$; TLC $R_f$: 0.13 (ethyl acetate/methanol=5/1)]. HPLC RT: 8.70 min (C8 reverse phase column: 250 mm; acetonitrile/water (0.05% trifuloroacetic acid); operation temp: 64° C.; Detector: 210 nm)].

Example 73

[(S)-(3-(4-N-n-Propyl-N-piperazinyl)propylthio)methyl-Sar]-3-[(γ-hydroxy)-NMeLeu]-4-cyclosporin

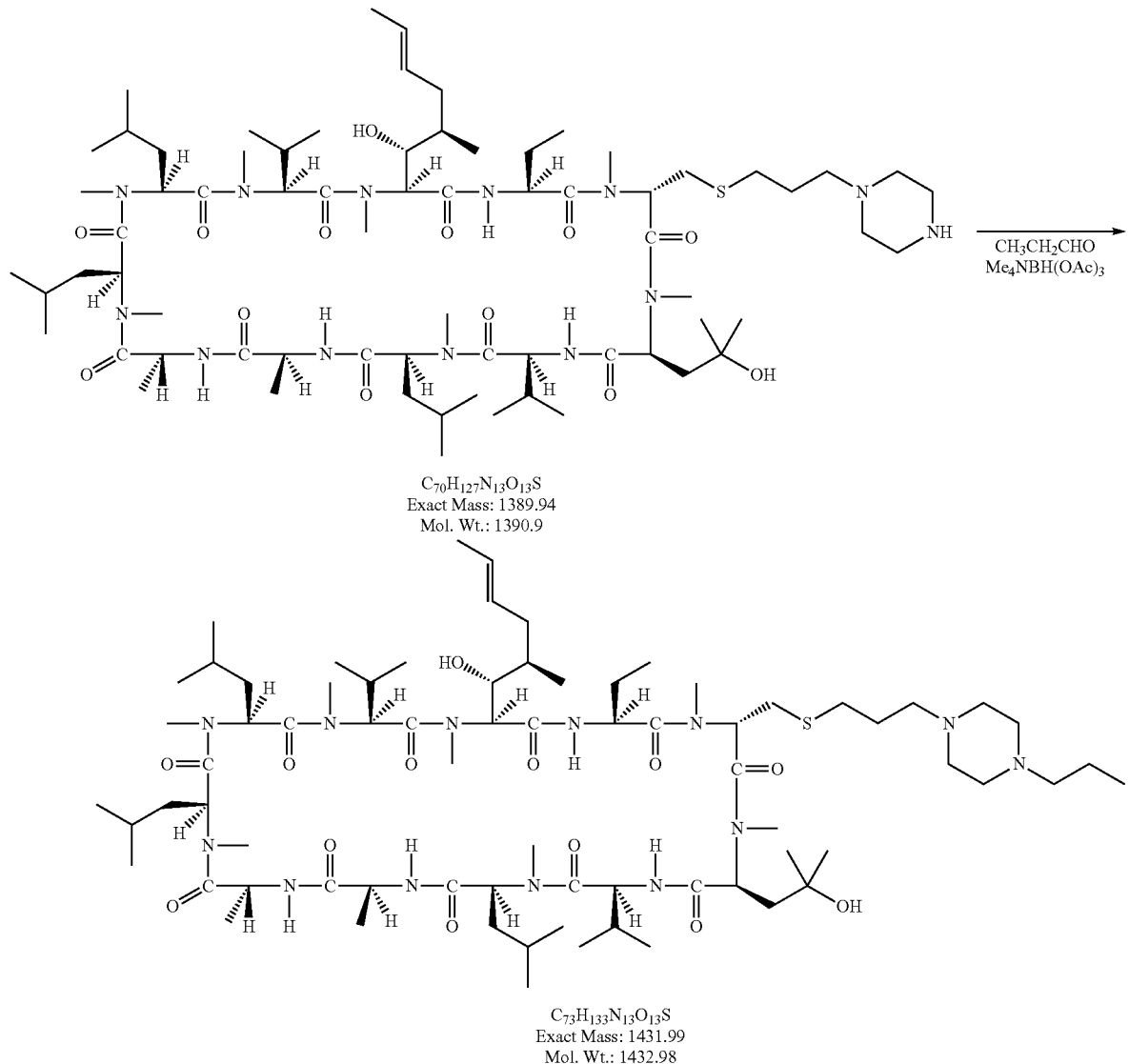

[(S)-(3-(N-Piperazinyl)propylthio)methyl-Sar]-3-[(γ-hydroxy)-N-MeLeu]-4-cyclosporin (150 mg, 0.11 mmol) and propionaldehyde (MW 58.08, d 0.81, 80 µl, 1.11 mmol) were dissolved in dichloromethane (20 ml), followed by adding acetic acid (5 drops) and tetramethylammonium triacetoxyborohydride (MW: 263.09, 72 mg, 0.28 mmol) in portions. The mixture was stirred at room temperature overnight. Then the reaction mixture was washed with saturated sodium bicarbonate solution and brine, dried over magnesium sulfate and evaporated under reduced pressure. The residue was purified by chromatography on silica gel using dichloromethane and methanol as eluent to give product [Molecular Formula: $C_{73}H_{133}N_{13}O_{13}S$; Exact Mass: 1431.99; MS (m/z): 1432.61 $(M+1)^+$, 1454.69 $(M+Na)^+$; TLC $R_f$: 0.24 (dichloromethane/methanol=9:1); HPLC RT: 9.07 min (C8 reverse phase column: 250 mm; acetonitrile/water (0.05% trifluoroacetic acid); operation temperature: 64° C.; detector: 210 nm)].

Example 74

[(S)-(3-(4-N-Isopropyl-N-piperazinyl)propylthio)methyl-Sar]-3-[(γ-hydroxy)-NMeLeu]-4-cyclosporin

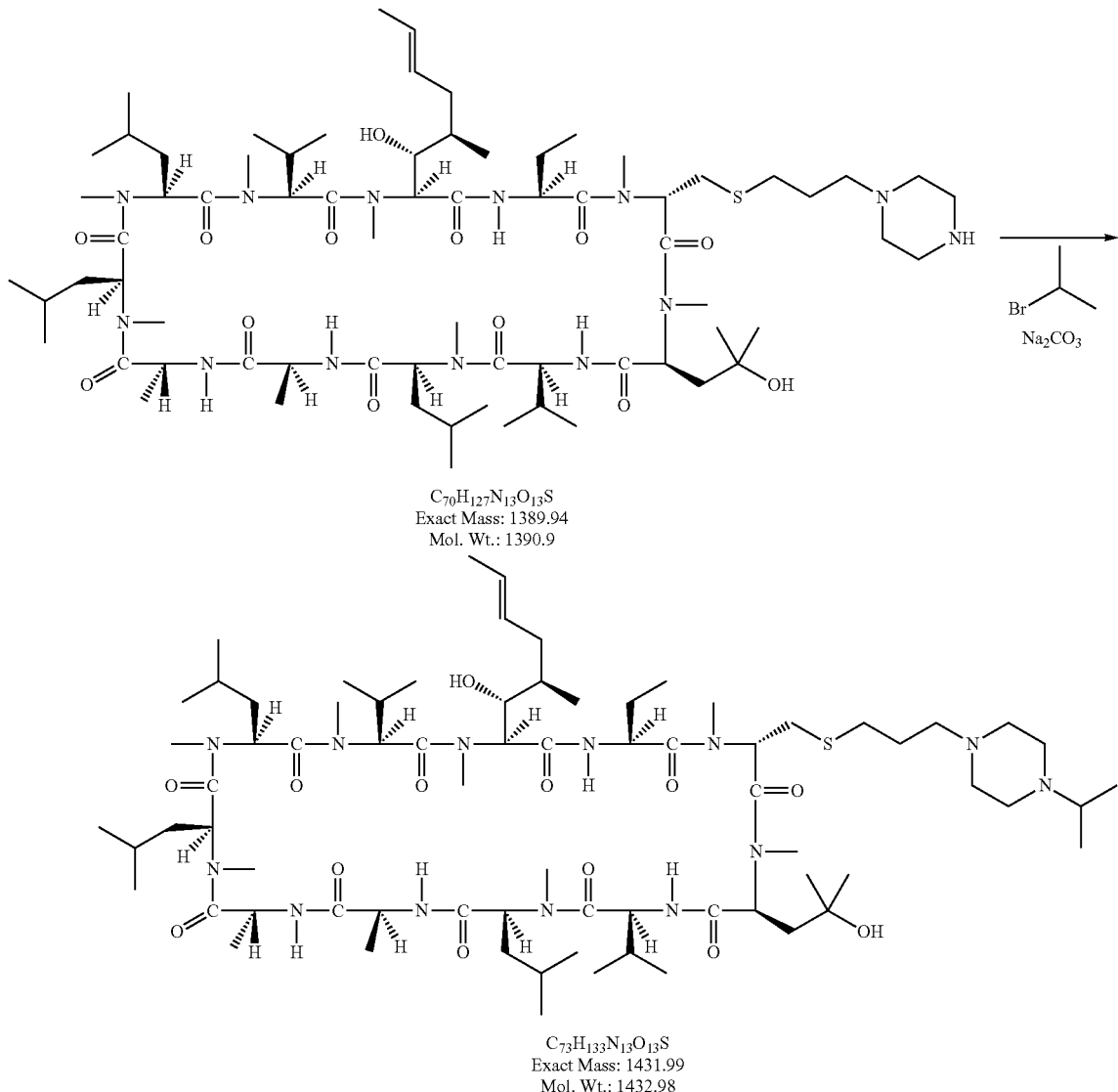

[(S)-3-(N-Piperazinylpropylthio)methyl-Sar]-3-[(γ-hydroxy)-N-MeLeu]-4-cyclosporin (150 mg, 0.11 mmol) and 2-bromopropane (MW 123.00, d 1.310, 102 μl, 1.08 mmol) were dissolved in dichloromethane (15 ml), followed by adding sodium carbonate (MW: 105.99, 28.6 mg, 0.27 mmol). The mixture was stirred at room temperature overnight. Then the reaction mixture was washed with brine, dried over magnesium sulfate and evaporated under reduced pressure. The residue was purified by chromatography on silica gel using dichloromethane and methanol as eluent to give product [Molecular Formula: $C_{73}H_{135}N_{13}O_{13}S$; Exact Mass: 1431.99; MS (m/z): 1432.58 (M+1)$^+$, 1454.72 (M+Na)$^+$; TLC R$_f$: 0.14 (dichloromethane/methanol=9:1); HPLC RT: 8.74 min (C8 reverse phase column: 250 mm; acetonitrile/water (0.05% trifluoroacetic acid); operation temperature: 64° C.; detector: 210 nm)].

Example 75

[(S)-(3-(4-N-Isobutyl-N-piperazinyl)propylthio)methyl-Sar]-3-[(γ-hydroxy)-NMeLeu]-4-cyclosporin

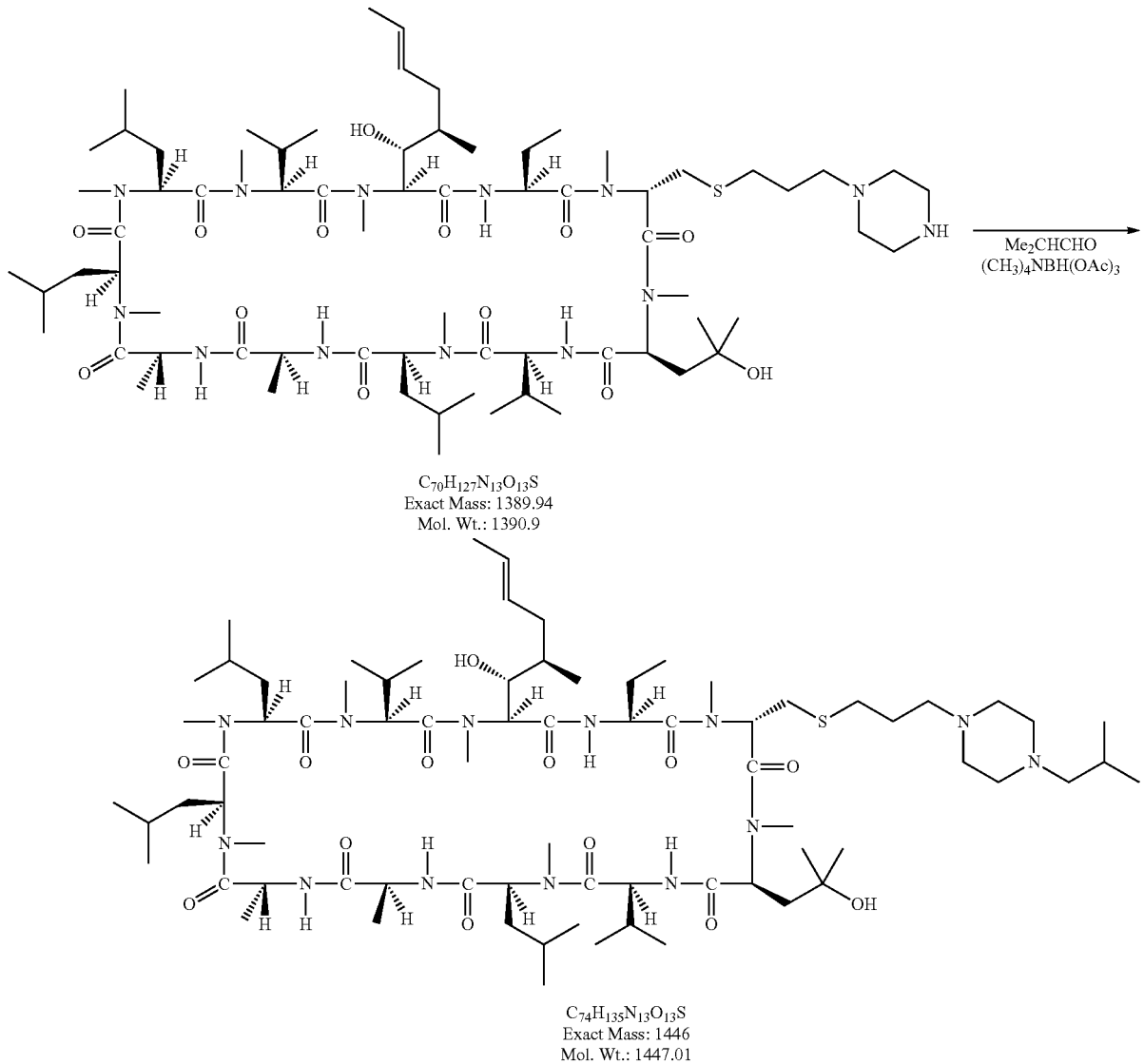

[(S)-3-(N-Piperazinylpropylthio)methyl-Sar]-3-[(γ-hydroxy)-N-MeLeu]-4-cyclosporin (168 mg, 0.12 mmol) and isobutyraldehyde (MW 72.11, d 0.794, 110 μl, 1.21 mmol) were dissolved in dichloromethane (25 ml), followed by adding acetic acid (5 drops) and tetramethylammonium triacetoxyborohydride (79.5 mg, 0.30 mmol) in portions. The mixture was stirred at room temperature overnight. Then the reaction mixture was washed with saturated sodium bicarbonate solution and brine, dried over magnesium sulfate and evaporated under reduced pressure. The residue was purified by chromatography on silica gel using dichloromethane and methanol as eluent to give product [Molecular Formula: $C_{74}H_{135}N_{13}O_{13}S$; Exact Mass: 1446.00; MS (m/z): 1446.58 $(M+1)^+$, 1468.69 $(M+Na)^+$; TLC $R_f$: 0.43 (dichloromethane/methanol=9:1); HPLC RT: 9.59 min (C8 reverse phase column: 250 mm; acetonitrile/water (0.05% trifluoroacetic acid); operation temperature: 64° C.; detector: 210 nm)].

Example 76

[(S)-(3-(4-N-Neopentyl-N-piperazinyl)propylthio)methyl-Sar]-3-[(γ-hydroxy)-NMeLeu]-4-cyclosporin

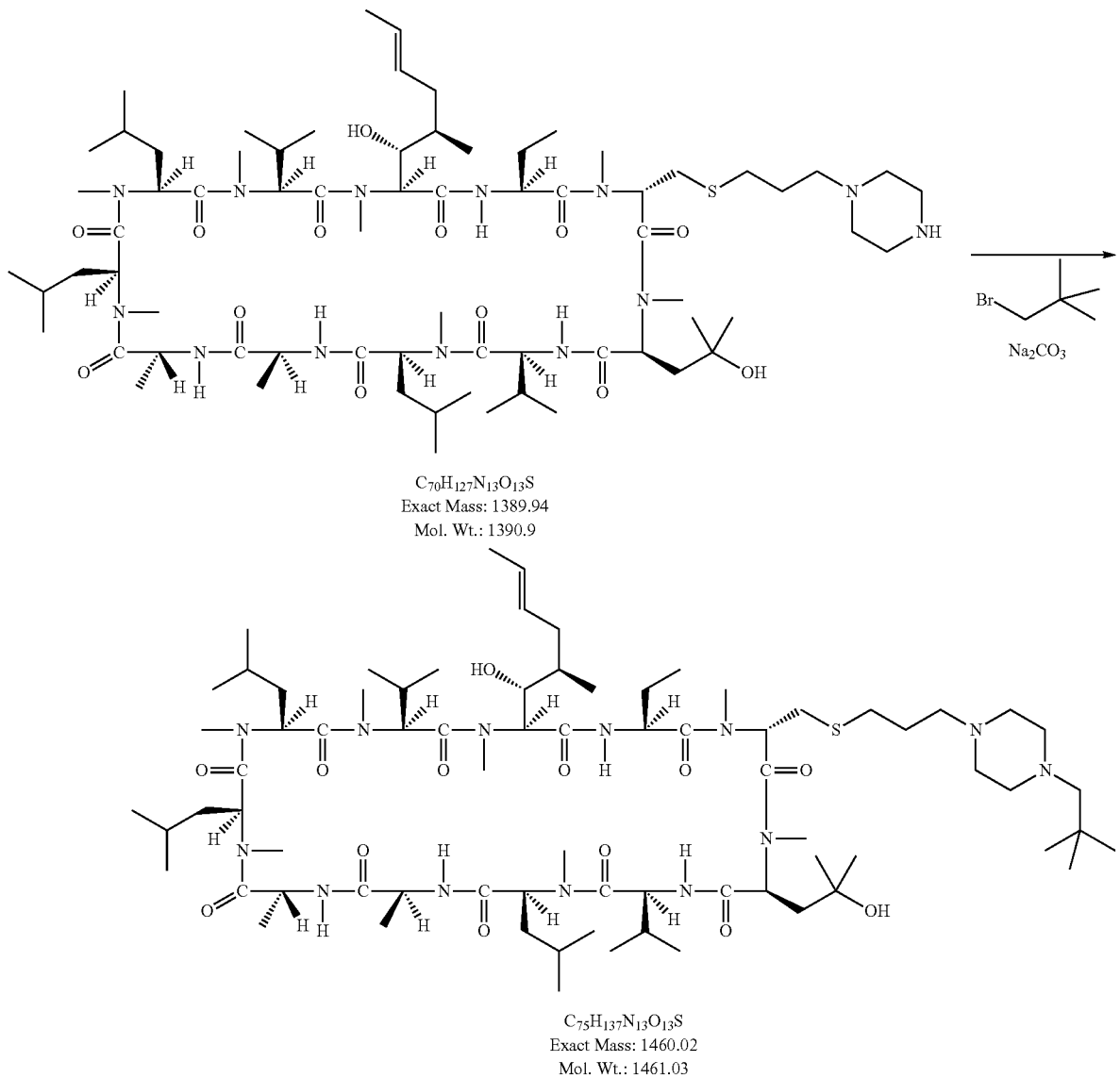

[(S)-3-(N-Piperazinylpropylthio)methyl-Sar]-3-[(γ-hydroxy)-N-MeLeu]-4-cyclosporin (150 mg, 0.11 mmol) and neopentyl bromide (MW 151.05, d 1.195, 136 µl, 1.08 mmol) were dissolved in dichloromethane (20 ml), followed by adding sodium carbonate (MW: 105.99, 28.6 mg, 0.27 mmol). The mixture was stirred at room temperature overnight. Then the reaction mixture was washed with brine, dried over magnesium sulfate and evaporated under reduced pressure. The residue was purified by chromatography on silica gel using dichloromethane and methanol as eluent to give product [Molecular Formula: $C_{75}H_{137}N_{13}O_{13}S$; Exact Mass: 1460.02; MS (m/z): 1460.64 $(M+1)^+$, 1482.72 $(M+Na)^+$; TLC $R_f$: 0.43 (dichloromethane/methanol=9:1); HPLC RT: 11.25 min (C8 reverse phase column: 250 mm; acetonitrile/water (0.05% trifluoroacetic acid); operation temperature: 64° C.; detector: 210 nm)].

Example 77
[(S)-(2-(Methoxycarbonyl)ethylthio)methyl-Sar]-3-[(γ-hydroxy)-NMeLeu]-4-cyclosporin and [(R)-(2-(Methoxycarbonyl)ethylthio)methyl-Sar]-3-[(γ-hydroxy)-NMeLeu]-4-cyclosporin
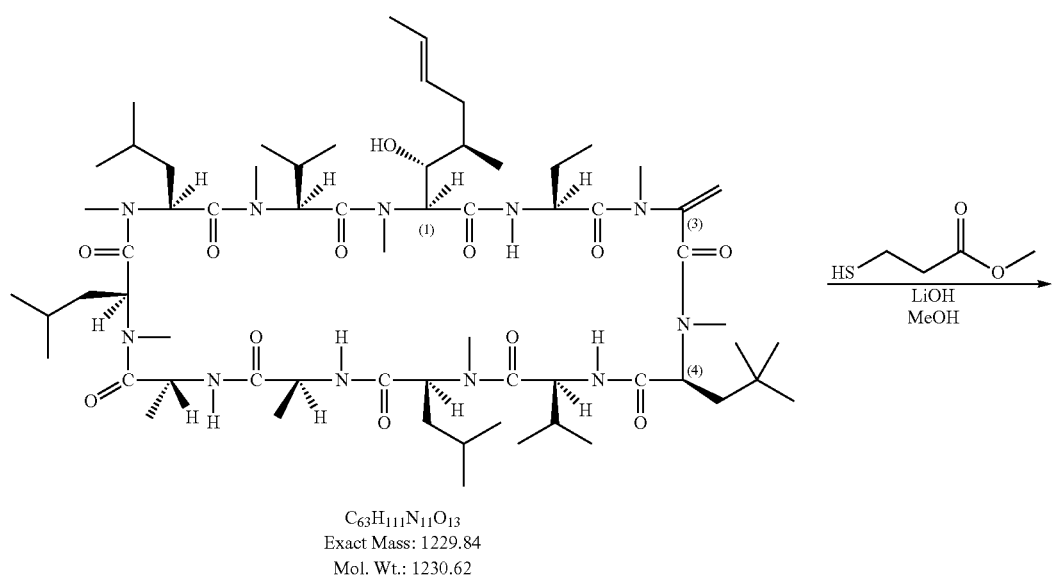
$C_{63}H_{111}N_{11}O_{13}$
Exact Mass: 1229.84
Mol. Wt.: 1230.62
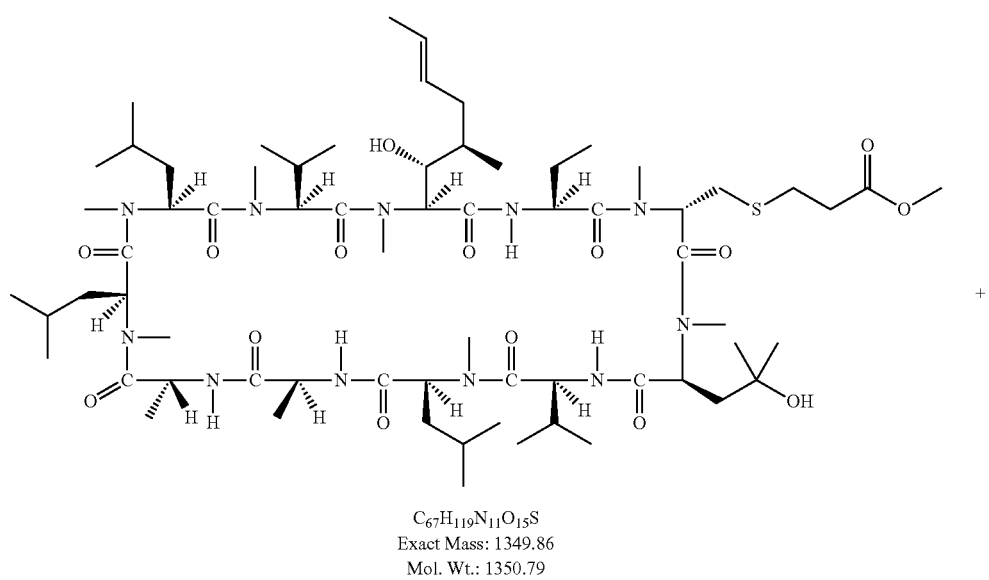
$C_{67}H_{119}N_{11}O_{15}S$
Exact Mass: 1349.86
Mol. Wt.: 1350.79

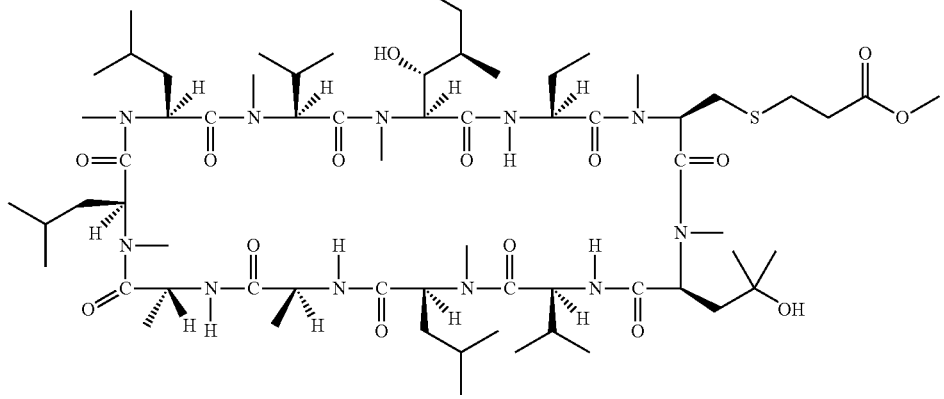

C$_{67}$H$_{119}$N$_{11}$O$_{15}$S
Exact Mass: 1349.86
Mol. Wt.: 1350.79

To a solution of [α-methylene-Sar]-3-[(γ-hydroxy)-NMeLeu]-4-cyclosporin (600 mg, 0.49 mmol) and methyl 3-mercaptopropionate (0.54 ml, d 1.085, 4.88 mmol) in methanol (15 ml) was added lithium hydroxide (94 mg, 3.90 mmol). The reaction mixture was stirred at room temperature for 4 hours. Most of solvent was evaporated under reduced pressure. Ethyl acetate (30 ml) and brine (30 ml) were added and the mixture was separated. The organic layer was dried over magnesium sulfate and evaporated under reduced pressure. The residue was purified by chromatography (hexane/acetone) to give 270 mg of [(S)-(2-(methoxycarbonyl)ethylthio)methyl-Sar]-3-[(γ-hydroxy)-NMeLeu]-4-cyclosporin [Molecular Formula: C$_{67}$H$_{119}$N$_{11}$O$_{15}$S; Exact Mass: 1349.86. MS (m/z): 1350.43(M+1)$^{+}$, 1372.62 (M+Na)$^{+}$] and 260 mg of [(R)-(2-(methoxycarbonyl)ethylthio)methyl-Sar]-3-[(γ-hydroxy)-NMeLeu]-4-cyclosporin [Molecular Formula: C$_{67}$H$_{119}$N$_{11}$O$_{15}$S; Exact Mass: 1349.86. MS (m/z): 1350.42(M+1)$^{+}$, 1372.63 (M+Na)$^{+}$].

Example 78

[(S)-(3-Hydroxylpropylthio)methyl-Sar]-3-[(γ-hydroxy)-NMeLeu]-4-cyclosporin and [(R)-(3-Hydroxylpropylthio)methyl-Sar]-3-[(γ-hydroxy)-NMeLeu]-4-cyclosporin

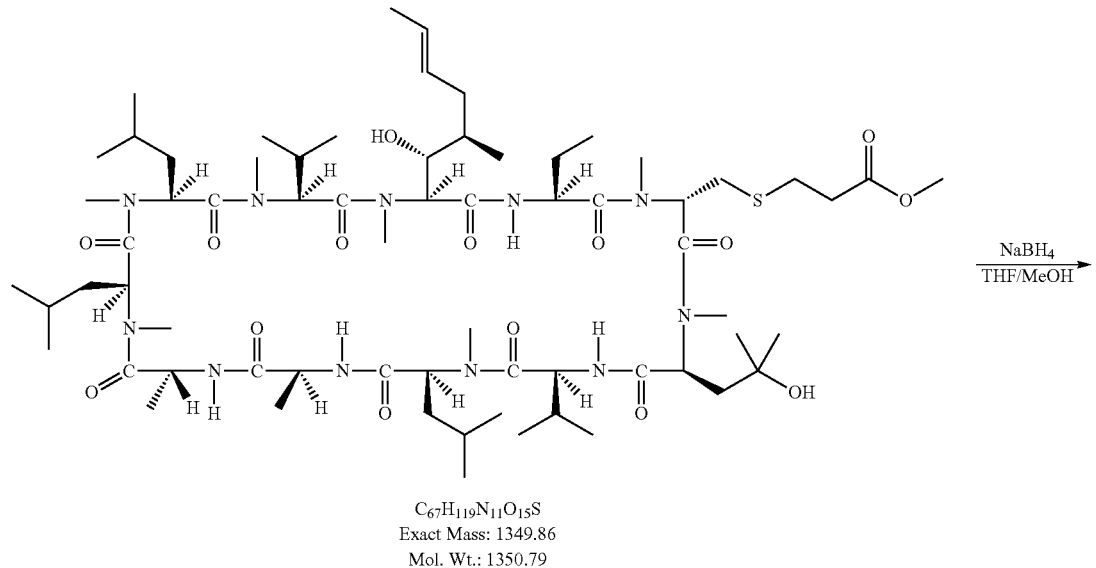

C$_{67}$H$_{119}$N$_{11}$O$_{15}$S
Exact Mass: 1349.86
Mol. Wt.: 1350.79

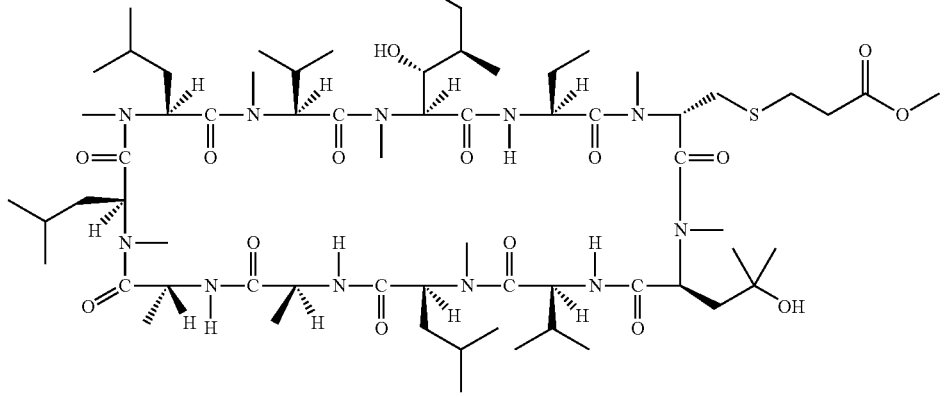

C<sub>66</sub>H<sub>119</sub>N<sub>11</sub>O<sub>14</sub>S
Exact Mass: 1321.87
Mol. Wt.: 1322.78

[(S)-(2-(Methoxycarbonyl)ethylthio)methyl-Sar]-3-[(γ-hydroxy)-NMeLeu]-4-cyclosporin (170 mg, 0.13 mmol) was dissolved in tetrahydrofuran (30 ml), followed by adding cesium chloride (1.00 g, 5.94 mmol) and sodium borohydride (1.00 g, 26.43 mmol). Then 30 ml of methanol was added dropwise to the mixture over 30 minutes. After addition, the mixture was stirred at room temperature one hour. Most solvent was then evaporated under reduced pressure. Ethyl acetate (30 ml) and water (30 ml) were added. The ethyl acetate layer was separated and washed with brine, dried over magnesium sulfate and evaporated under reduced pressure. The residue was purified by chromatography with dichloromethane/methanol (from 100:0 to 96:4) as eluent to give the 55 mg of pure product [Molecular Formula: $C_{66}H_{119}N_{11}O_{14}S$; Exact Mass: 1321.87; MS (m/z): 1322.45 (M+1)$^+$, 1344.67 (M+Na)$^+$; TLC $R_f$: 0.54 (dichloromethane/methanol=9:1); HPLC RT: 13.06 min (C8 reverse phase column: 250 mm; acetonitrile/water (0.05% trifluoroacetic acid); operation temperature: 64° C.; detector: 210 nm)].

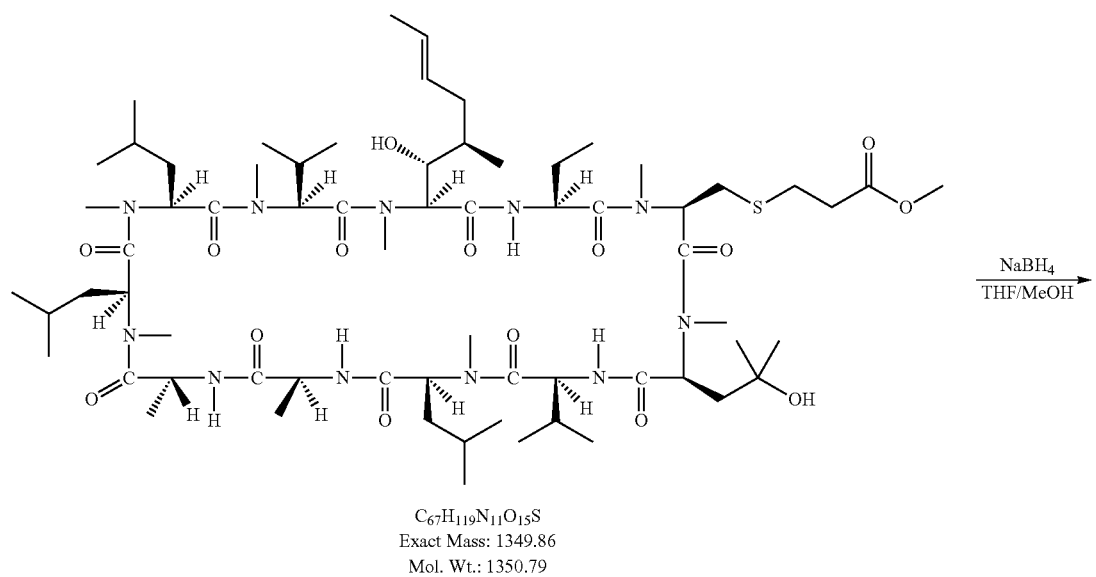

C<sub>67</sub>H<sub>119</sub>N<sub>11</sub>O<sub>15</sub>S
Exact Mass: 1349.86
Mol. Wt.: 1350.79

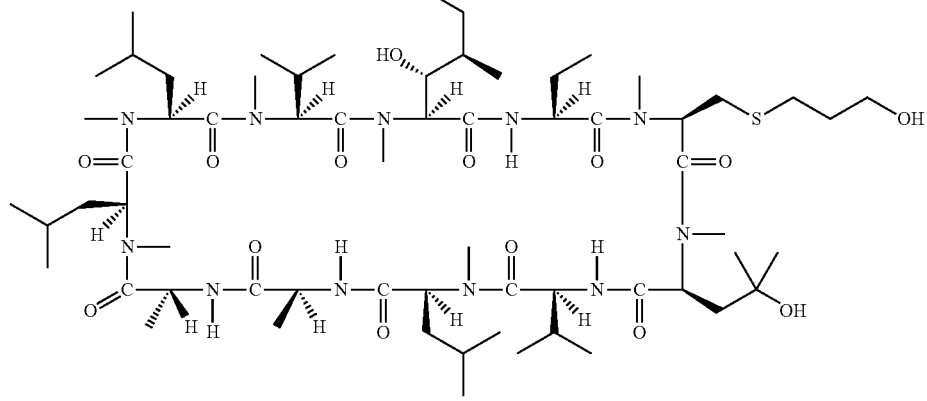

$C_{66}H_{119}N_{11}O_{14}S$
Exact Mass: 1321.87
Mol. Wt.: 1322.78

According this method, 28 mg of pure [(R)-(3-Hydroxypropylthio)methyl-Sar]-3-[(γ-hydroxy)-NMeLeu]-4-cyclosporin [Molecular Formula: $C_{66}H_{119}N_{11}O_{14}S$; Exact Mass: 1321.87; MS (m/z): 1322.44 (M+1)$^+$, 1344.69 (M+Na)$^+$; TLC R$_f$: 0.54 (dichloromethane/methanol=9:1); HPLC RT: 13.02 min (C8 reverse phase column: 250 mm; acetonitrile/water (0.05% trifluoroacetic acid); operation temperature: 64° C.; detector: 210 nm)] was obtained.

Example 79

[(S)-(3-Hydroxylpropylthio)methyl-Sar]-3-[(γ-hydroxy)-NMeLeu]-4-cyclosporin

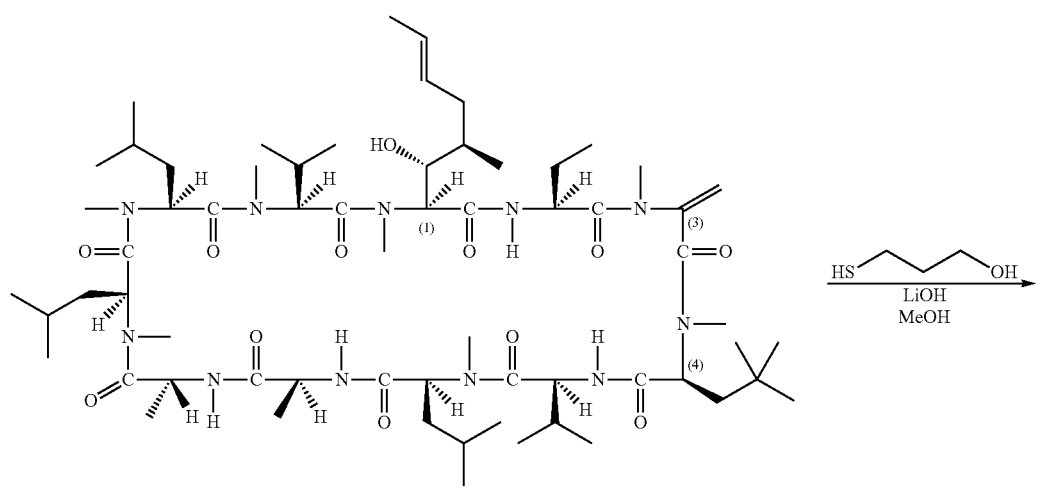

$C_{63}H_{111}N_{11}O_{13}$
Exact Mass: 1229.84
Mol. Wt.: 1230.62

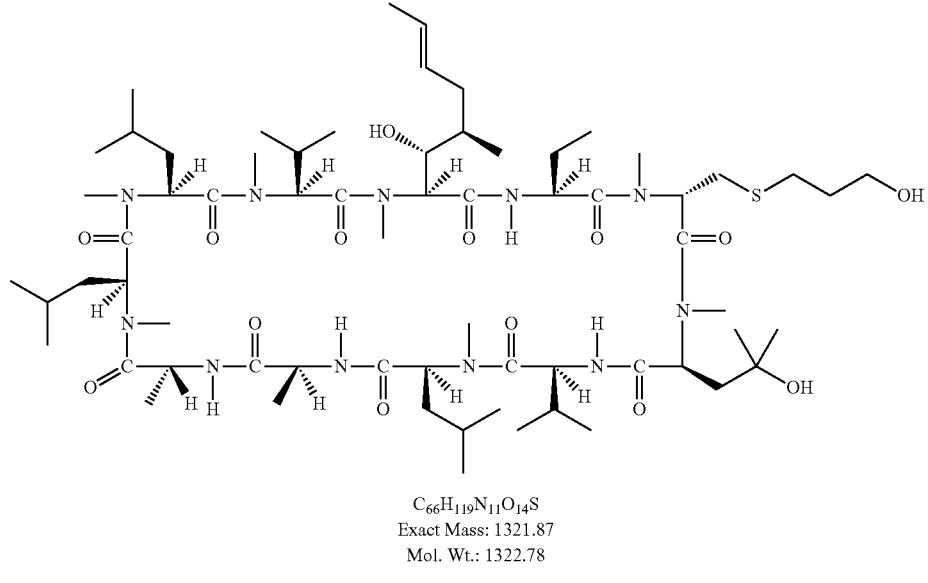

C₆₆H₁₁₉N₁₁O₁₄S
Exact Mass: 1321.87
Mol. Wt.: 1322.78

To a solution of [α-methylene-Sar]-3-[(γ-hydroxy)-N-MeLeu]-4-cyclosporin (200 mg, 0.16 mmol) and 3-mercapto-1-propanol (125 mg, 1.36 mmol) in methanol (15 ml) was added lithium hydroxide (80 mg, 3.33 mmol). The reaction mixture was stirred at room temperature overnight. Then most of the solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (dichloromethane/methanol=97/3) to give product of [(R)-(3-Hydroxypropylthio)methyl-Sar]-3-[(γ-hydroxy)-NMeLeu]-4-cyclosporin [Molecular formula: C₆₆H₁₁₉N₁₁O₁₄S; Exact Mass: 1321.87; MS (m/z): 1322.53 (M+1)⁺; TLC Rf: 0.54 (dichloromethane/methanol=9/1); HPLC RT: 13.02 min (C8 reverse phase column: 250 mm; acetonitrile/water (0.05% trifuloroacetic acid); operation temp: 64° C.; Detector: 210 nm)].

Example 80

[(S)-(3-Methoxypropylthio)methyl-Sar]-3-[(γ-hydroxy)-N-MeLeu]-4-cyclosporin

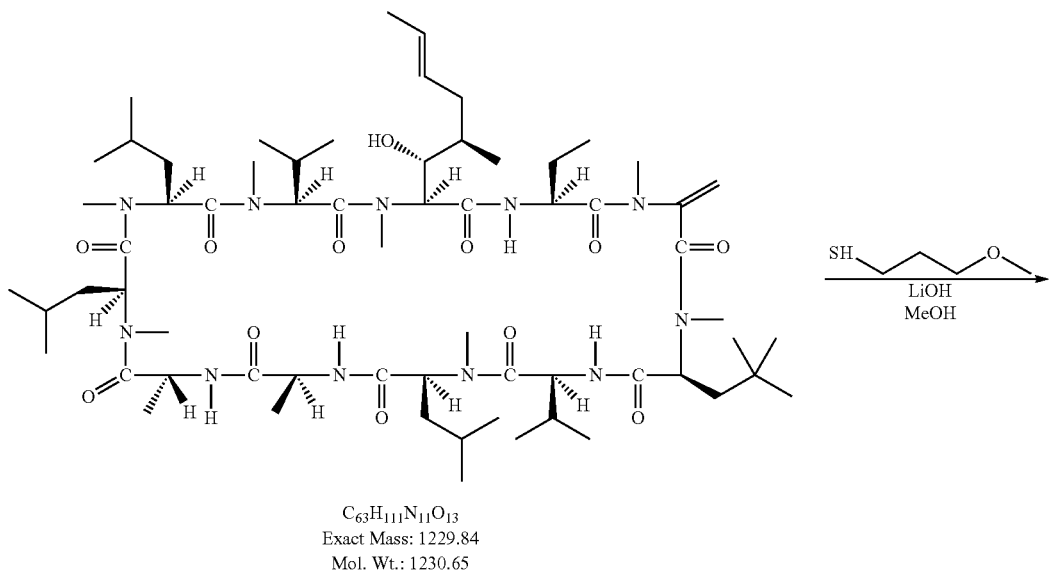

C₆₃H₁₁₁N₁₁O₁₃
Exact Mass: 1229.84
Mol. Wt.: 1230.65

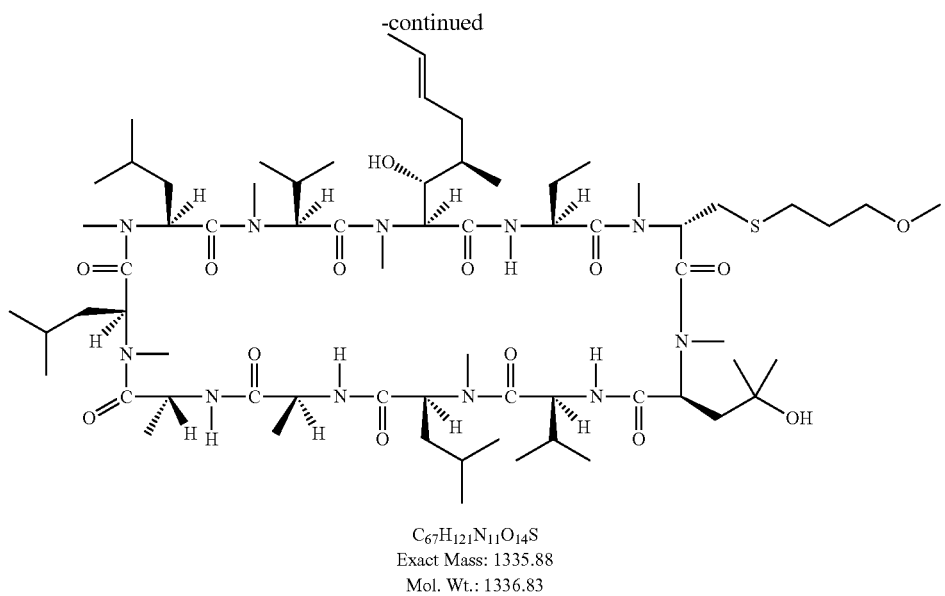

C₆₇H₁₂₁N₁₁O₁₄S
Exact Mass: 1335.88
Mol. Wt.: 1336.83

[α-Methylene-Sar]-3-[(γ-hydroxy)-N-MeLeu]-4-cyclosporin (0.31 g, 0.25 mmol) and 1-mercapto-3-methoxypropane (265 mg, 10 mmol) were dissolved in methanol (10 ml), followed by adding 10 equivalents of lithium hydroxide (60 mg). The mixture was stirred overnight at room temperature. After removal of solvents, the residue was dissolved in ethyl acetate (15 ml). The ethyl acetate solution was washed with brine, dried over magnesium sulfite and evaporated under reduced pressure. The residue was subject to a flash chromatography using ethyl acetate/methanol as eluent to give 35 mg of pure product [Molecular formula: $C_{67}H_{121}N_{11}O_{14}S$; Exact Mass: 1335.88; MS (m/z): 1336.43 $(M+1)^+$, 1358.74 $(M+Na)^+$; TLC $R_f$: 0.31 (ethyl acetate/methanol=20/1); HPLC RT: 15.21 min (C8 reverse phase column: 250 mm; acetonitrile/water (0.05% trifluoroacetic acid); operation temp: 64° C.; Detector: 210 nm)].

Example 81

[(S)-(3-Methoxy-3-methyl)butylthiomethyl-Sar]-3-[(γ-hydroxy)-N-MeLeu]-4-cyclosporin

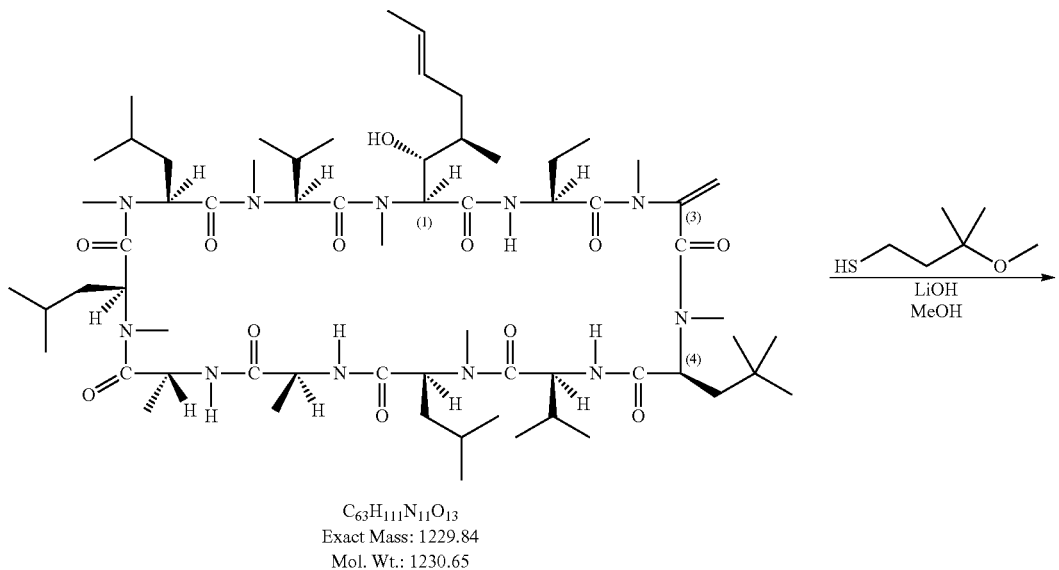

C₆₃H₁₁₁N₁₁O₁₃
Exact Mass: 1229.84
Mol. Wt.: 1230.65

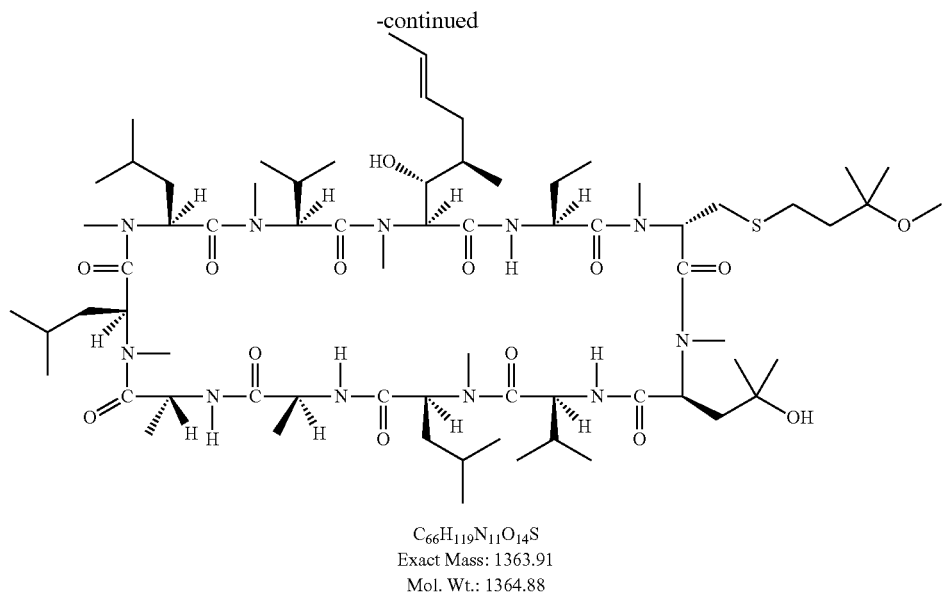

C₆₆H₁₁₉N₁₁O₁₄S
Exact Mass: 1363.91
Mol. Wt.: 1364.88

To a solution of [α-methylene-Sar]-3-[(γ-hydroxy)-N-MeLeu]-4-cyclosporin (150 mg, 0.12 mmol) and 3-methyl-3-methoxybutanethiol (165 mg, 1.23 mmol) in methanol (10 ml) was added lithium hydroxide (50 mg, 2.08 mmol). The reaction mixture was stirred at room temperature overnight. Then most of solvent was evaporated under reduced pressure. Dichloromethane (30 ml) and water (30 ml) were added and separated. The organic layer was washed with water and brine, dried over magnesium sulfate and evaporated under reduced pressure. The residue was purified by chromatography (ethyl acetate/methanol=98/2) to give a pure product [Molecular formula: $C_{69}H_{125}N_{11}O_{14}S$; Exact Mass: 1363.91; MS (m/z): 1364.53 (M+1)⁻; TLC Rf: 0.33 (ethyl acetate/methanol=98/2); HPLC RT: 16.10 min (C8 reverse phase column: 250 mm; acetonitrile/water (0.05% trifuloroacetic acid); operation temp: 64° C.; Detector: 210 nm)].

Example 82

[(S)-(4-Aminobutylthio)methyl-Sar]-3-[(γ-hydroxy)-NMeLeu]-4-cyclosporin

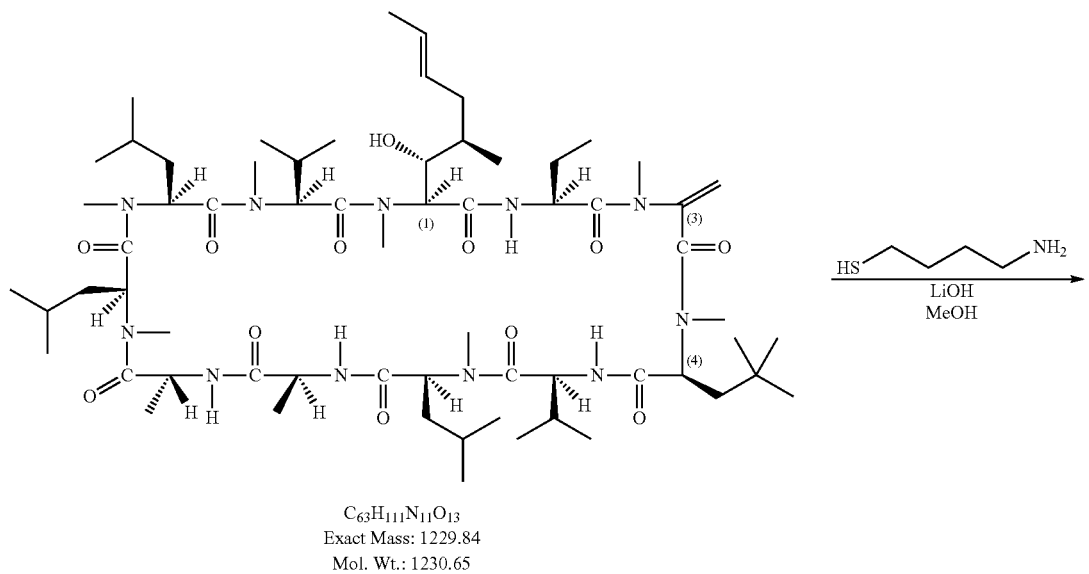

C₆₃H₁₁₁N₁₁O₁₃
Exact Mass: 1229.84
Mol. Wt.: 1230.65

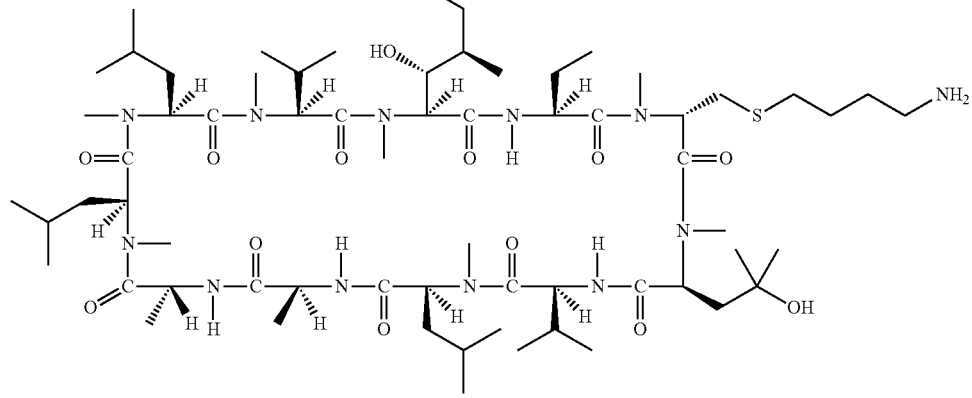

C₆₇H₁₂₂N₁₂O₁₃S
Exact Mass: 1334.9
Mol. Wt.: 1335.84

[α-Methylene-Sar]-3-[(γ-hydroxy)-N-MeLeu]-4-cyclosporin (1.23 g, 1.0 mmol) and 4-aminobutylthiol (1.06 g, 10.00 mmol) were dissolved in methanol (80 ml), followed by adding 10 equivalents of lithium hydroxide (0.24 g, 10.00 mmol). The mixture was stirred overnight at room temperature. After removal of solvents, the residue was subjected to the flash chromatography using dichloromethane/methanol as eluents to give 0.40 g of product [Molecular formula: C₆₇H₁₂₂N₁₂O₁₃S; Exact Mass: 1334.89; MS (m/z): 1335.55 (M+1)⁺, 1357.64 (M+Na)⁺, TLC R_f: 0.05 (dichloromethane/methanol=5/1); HPLC RT: 10.53 min (C8 reverse phase column: 250 mm; acetonitrile/water (0.05% trifluoroacetic acid); operation temp: 64° C.; Detector: 210 nm)].

Example 83

[(S)-(4-(N,N-Diethylamino)butylthio)methyl-Sar]-3-[(γ-hydroxy)-NMeLeu]-4-cyclosporin

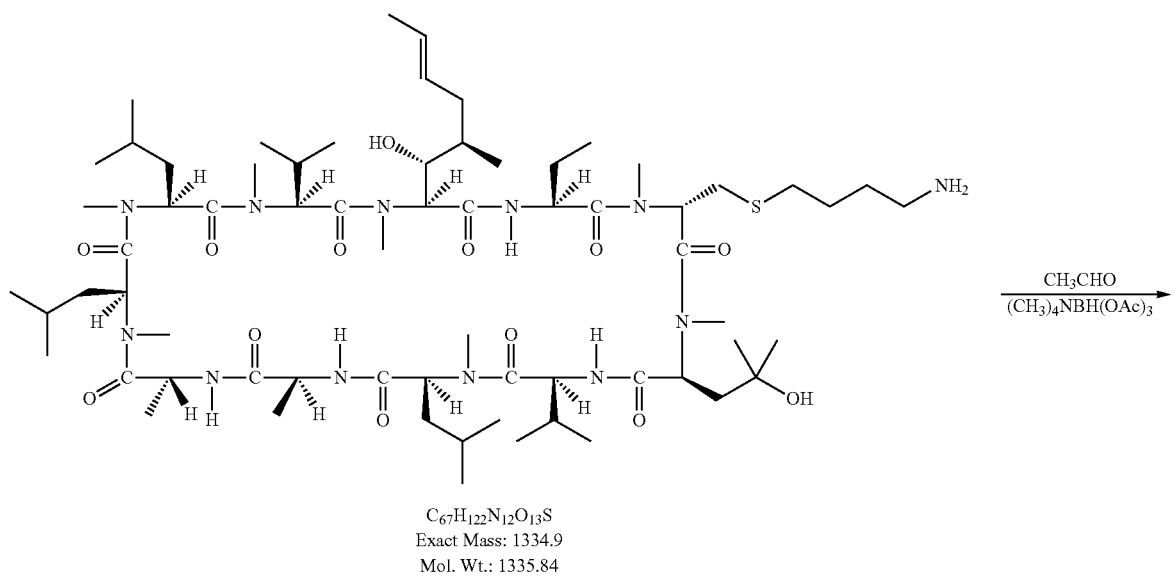

C₆₇H₁₂₂N₁₂O₁₃S
Exact Mass: 1334.9
Mol. Wt.: 1335.84

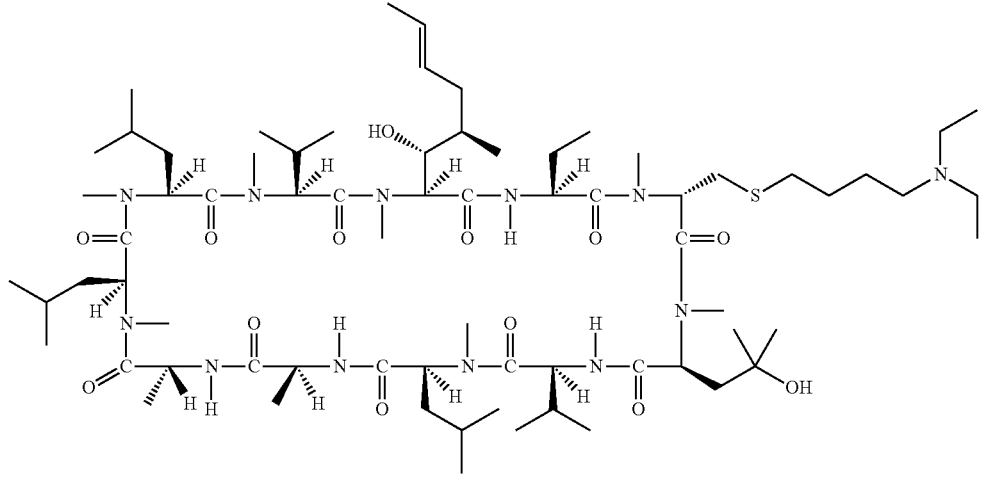

C₇₁H₁₃₀N₁₂O₁₃S
Exact Mass: 1390.96
Mol. Wt.: 1391.95

[(S)-(4-Aminobuylthio)methyl-Sar]-3-[(γ-hydroxy)-N-MeLeu]-4-cyclosporin (70 mg, 0.05 mmol) and acetaldehyde (MW 44.05, d 0.78, 100 μl, 0.18 mmol)) were dissolved in chloroform (5 ml), followed by adding 2.5 equivalents of tetramethylammonium triacetoxyborohydride (32.87 mg, 0.125 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give product [Molecular formula: C₇₁H₁₃₀N₁₂O₁₃S; Exact Mass: 1390.96; MS (m/z): 1391.63 (M+1)⁺, 1413.79 (M+Na)⁺; TLC R$_f$: 0.17 (ethyl acetate/methanol=5/1); HPLC RT: 12.55 min (C8 reverse phase column: 250 mm; acetonitrile/water (0.05% trifuloroacetic acid); operation temp: 64° C.; Detector: 210 nm)].

Example 84

[(S)-(4-(N-Isopropylamino)butylthio)methyl-Sar]-3-[(γ-hydroxy)-NMeLeu]-4-cyclosporin

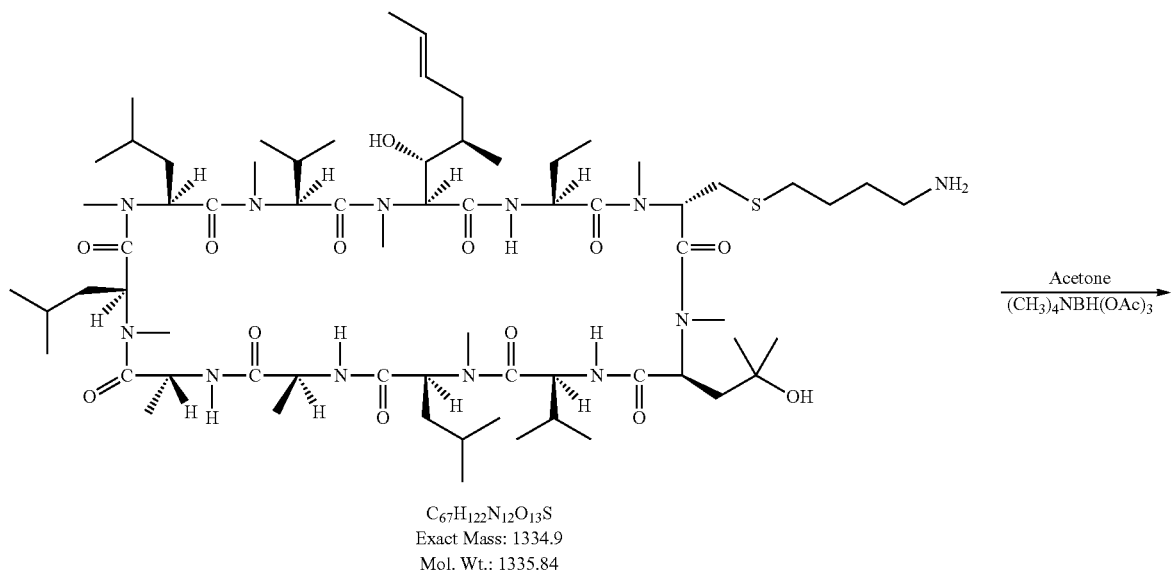

C₆₇H₁₂₂N₁₂O₁₃S
Exact Mass: 1334.9
Mol. Wt.: 1335.84

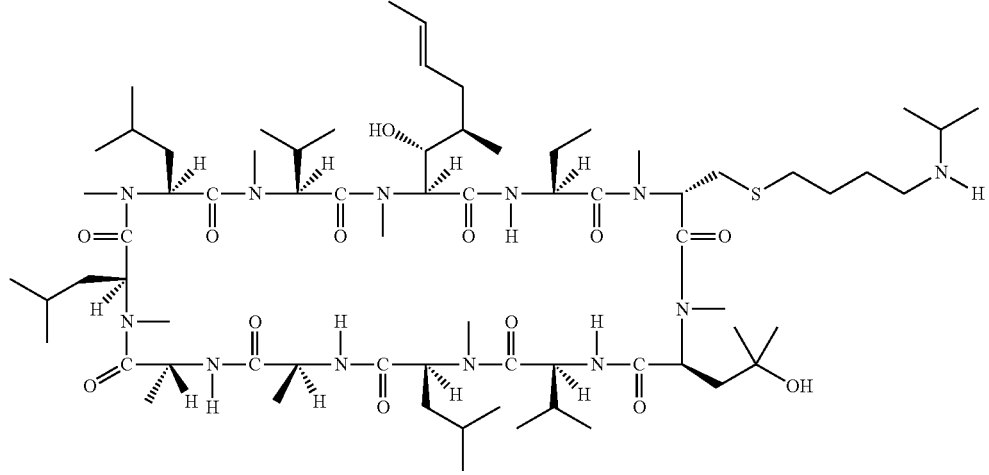

C₇₀H₁₂₈N₁₂O₁₃S
Exact Mass: 1376.94
Mol. Wt.: 1377.93

[(S)-(4-Aminobuylthio)methyl-Sar]-3-[(γ-hydroxy)-N-MeLeu]-4-cyclosporin (60 mg, 0.05 mmol) and acetone (100 μl) were dissolved in chloroform (5 ml), followed by adding tetramethylammonium triacetoxyborohydride (29.5 mg, 0.11 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give product. [Molecular formula: $C_{70}H_{128}N_{12}O_{13}S$; Exact Mass: 1376.94; MS (m/z): 1377.58 $(M+1)^+$, 1399.79 $(M+Na)^+$; TLC $R_f$: 0.15 (ethyl acetate/methanol=5/1); HPLC RT: 11.21 min (C8 reverse phase column: 250 mm; acetonitrile/water (0.05% trifluoroacetic acid); operation temp: 64° C.; Detector: 210 nm)].

Example 85

[(S)-(4-(N-Isobutylamino)butylthio)methyl-Sar]-3-[(γ-hydroxy)-NMeLeu]-4-cyclosporin

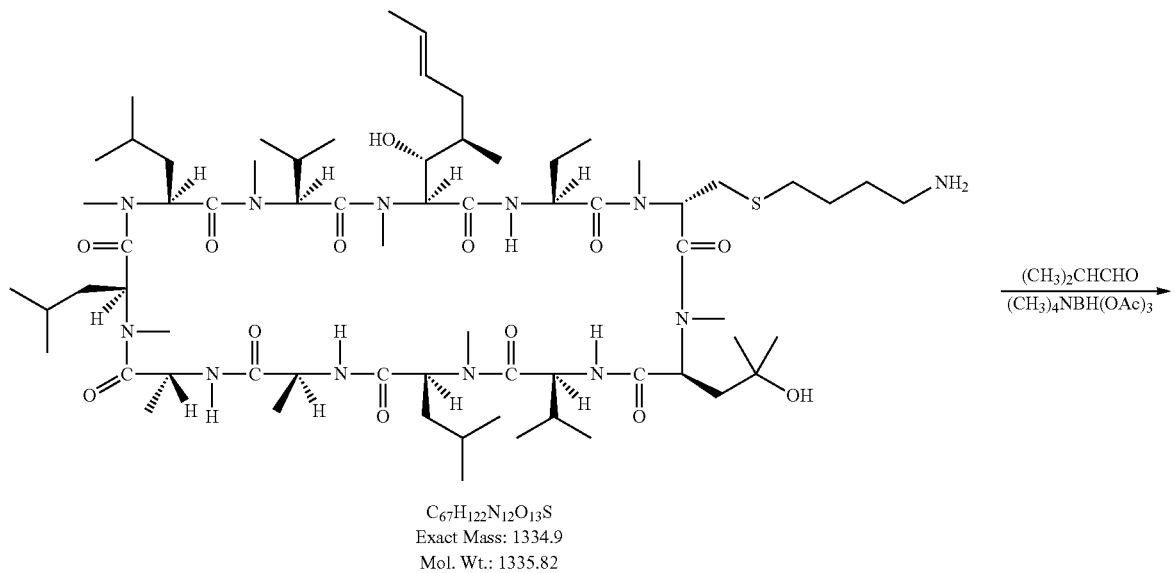

C₆₇H₁₂₂N₁₂O₁₃S
Exact Mass: 1334.9
Mol. Wt.: 1335.82

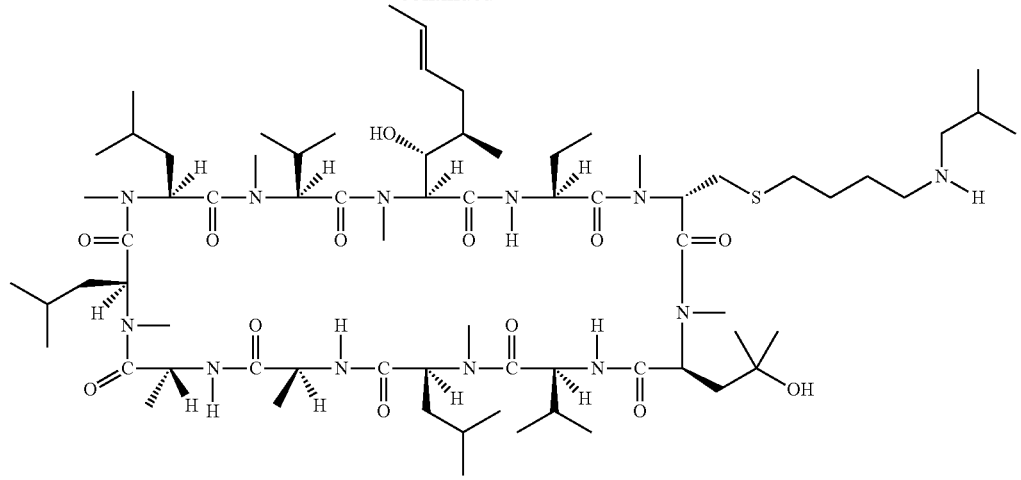

C₇₁H₁₃₀N₁₂O₁₃S
Exact Mass: 1390.96
Mol. Wt.: 1391.93

[(S)-(4-Aminobuylthio)methyl-Sar]-3-[(γ-hydroxy)-N-MeLeu]-4-cyclosporin (80 mg, 0.060 mmol) and isobutyraldehyde (MW 72.11, d 0.794, 27 μl, 0.3 mmol) were dissolved in chloroform (5.0 ml), followed by adding 2.5 equivalents of tetramethylammonium triacetoxyborohydride (39.4 mg, 0.15 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give product [Molecular formula: $C_{71}H_{130}N_{12}O_{13}S$; Exact Mass: 1390.96; MS (m/z): 1391.58 $(M+1)^+$, 1413.74 $(M+Na)^+$; TLC $R_f$: 0.20 (ethyl acetate/methanol=5/1); HPLC RT: 11.99 min (C8 reverse phase column: 250 mm; acetonitrile/water (0.05% trifuloroacetic acid); operation temp: 64° C.; Detector: 210 nm)].

Example 86

[(S)-(4-(N,N-Diisobutylamino)butylthio)methyl-Sar]-3-[(γ-hydroxy)-NMeLeu]-4-cyclosporin

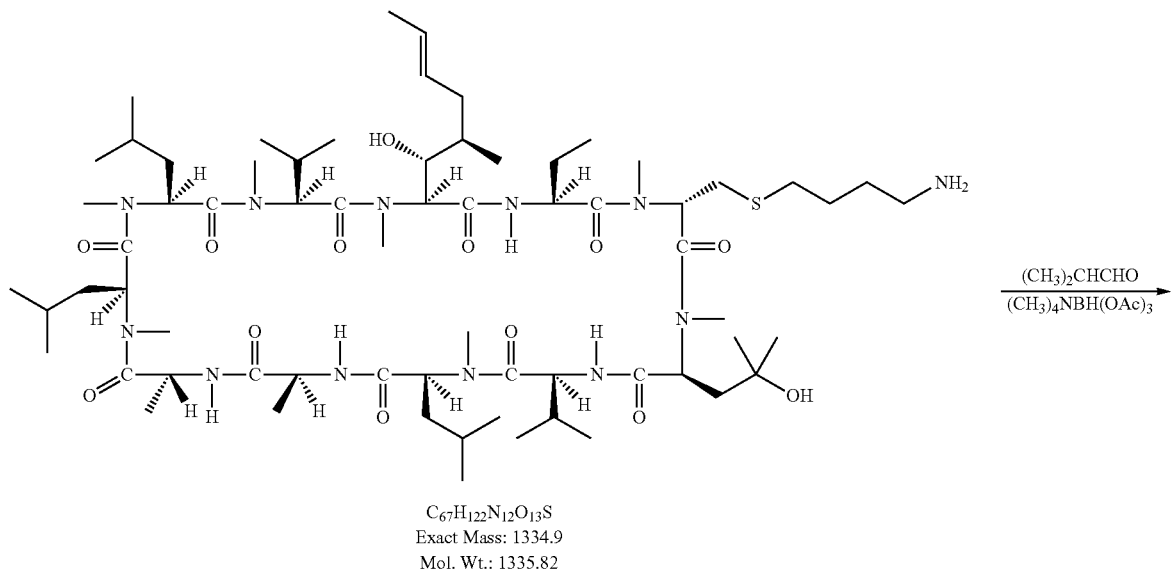

C₆₇H₁₂₂N₁₂O₁₃S
Exact Mass: 1334.9
Mol. Wt.: 1335.82

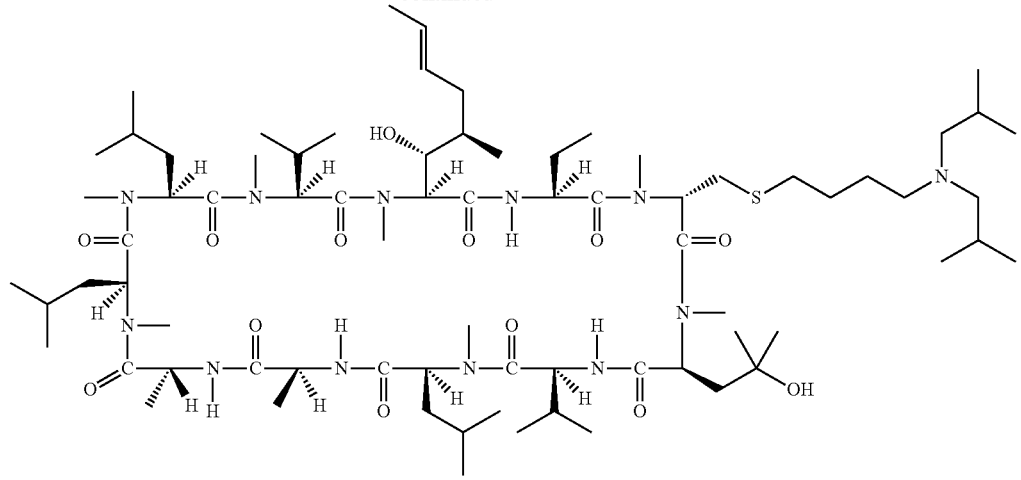

C₇₅H₁₃₈N₁₂O₁₃S
Exact Mass: 1447.02
Mol. Wt.: 1448.04

[(S)-(4-Aminobuylthio)methyl-Sar]-3-[(γ-hydroxy)-N-MeLeu]-4-cyclosporin (80 mg, 0.060 mmol) and isobutyraldehyde (MW 72.11, d 0.794, 27 μl, 0.3 mmol) were dissolved in chloroform (5.0 ml), followed by adding 2.5 equivalents of tetramethylammonium triacetoxyborohydride (39.4 mg, 0.15 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give product [Molecular formula: C₇₅H₁₃₈N₁₂O₁₃S; Exact Mass: 1447.023; MS (m/z): 1447.63 (M+1)⁺, 1470.84 (M+Na)⁺; TLC $R_f$: 0.25 (ethyl acetate/methanol=5/1); HPLC RT: 13.84 min (C8 reverse phase column: 250 mm; acetonitrile/water (0.05% trifuloroacetic acid); operation temp: 64° C.; Detector: 210 nm)].

Example 87

[(S)-(4-(N-Neopentylamino)butylthio)methyl-Sar]-3-[(γ-hydroxy)-NMeLeu]-4-cyclosporin

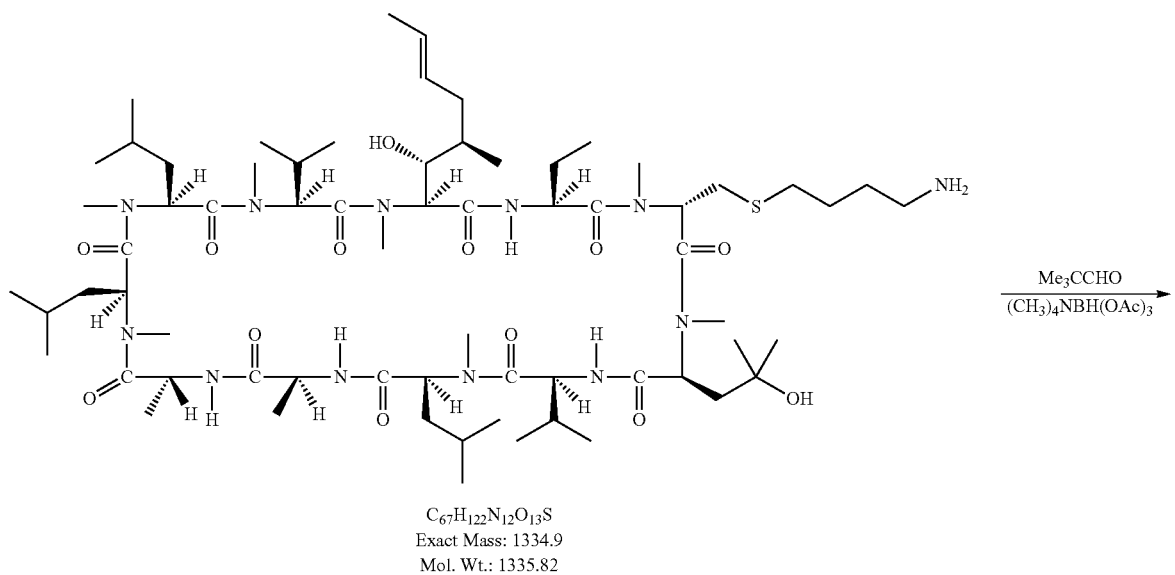

C₆₇H₁₂₂N₁₂O₁₃S
Exact Mass: 1334.9
Mol. Wt.: 1335.82

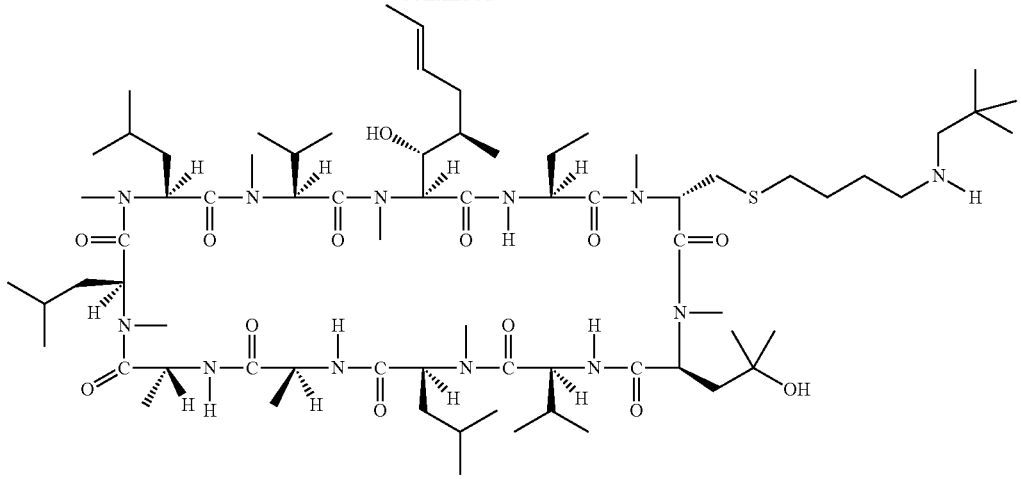

C₇₂H₁₃₂N₁₂O₁₃S
Exact Mass: 1404.98
Mol. Wt.: 1405.96

[(S)-(4-Aminobuylthio)methyl-Sar]-3-[(γ-hydroxy)-N-MeLeu]-4-cyclosporin (67 mg, 0.05 mmol) and trimethylacetaldehyde (MW 86.13, d 0.781, 27.6 μl, 0.25 mmol) were dissolved in chloroform (5 ml), followed by adding 2.5 equivalents of tetramethylammonium triacetoxyborohydride (32.87 mg, 0.125 mmol). The mixture was stirred at room temperature for two hours. Then the reaction mixture was washed with saturated sodium bicarbonate solution and brine, dried over magnesium sulfate and evaporated under reduced pressure. The residue was purified by flash chromatography on silica gel using dichloromethane/methanol as eluent to give 25 mg of pure product [Molecular formula: C₇₂H₁₃₂N₁₂O₁₃S; Exact Mass: 1404.98; MS (m/z): 1405.54 (M+1)⁺, 1427.72 (M+Na)⁺; TLC R$_f$: 0.17 (ethyl acetate/methanol=5/1); HPLC RT: 12.66 min (C8 reverse phase column: 250 mm; acetonitrile/water (0.05% trifluoroacetic acid); operation temp: 64° C.; Detector: 210 nm)].

Example 88

[(S)-(4-Hydroxylbutylthio)methyl-Sar]-3-[(γ-hydroxy)-N-MeLeu]-4-cyclosporin and [(R)-(4-hydroxylbutylthio)methyl-Sar]-3-[(γ-hydroxy)-N-MeLeu]-4-cyclosporin

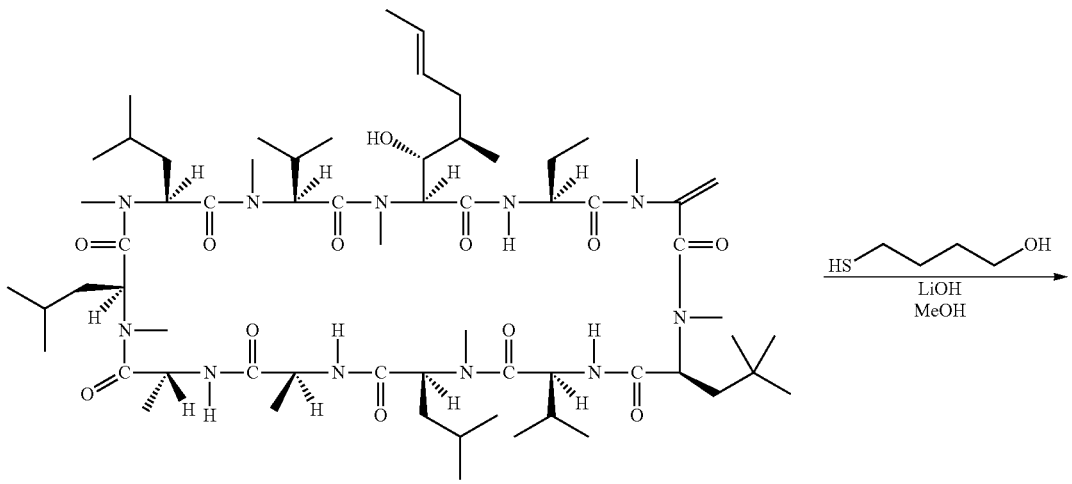

C₆₃H₁₁₁N₁₁O₁₃
Exact Mass: 1229.84
Mol. Wt.: 1230.62

-continued

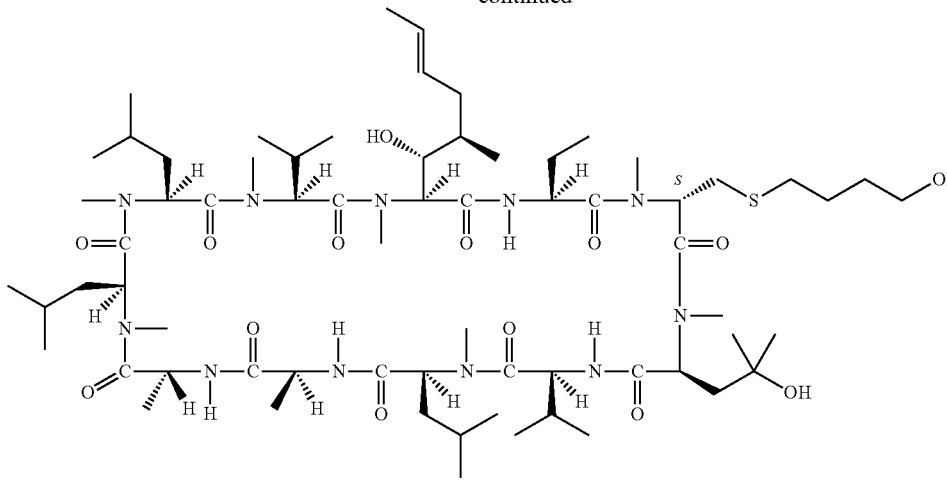

Isomer A

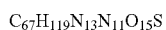

Exact Mass: 1349.86
Mol. Wt.: 1350.79

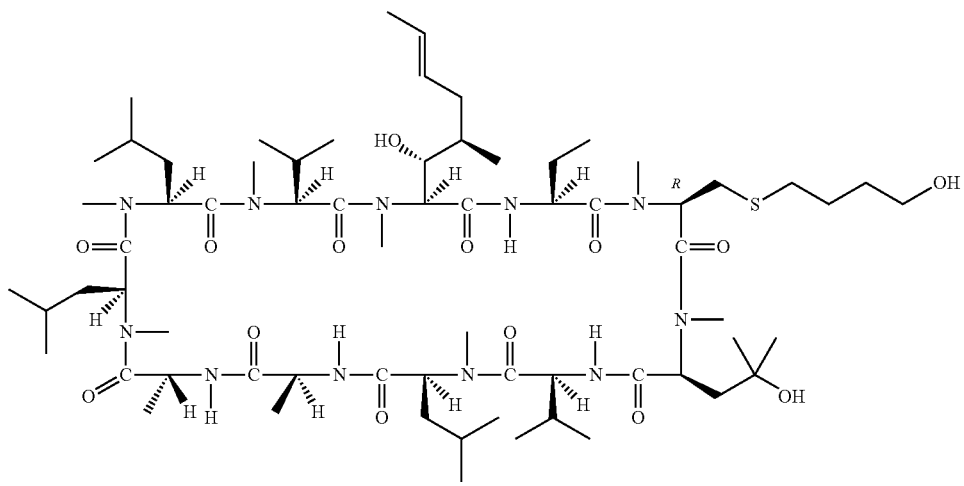

Isomer B

Exact Mass: 1335.88
Mol. Wt.: 1336.83

To a solution of [α-methylene-Sar]-3-[(γ-hydroxy)-N-MeLeu]-4-cyclosporin (213 mg, 0.17 mmol) and 4-mercapto-1-butanol (156 mg, 1.44 mmol) in methanol (25 ml) was added lithium hydroxide (94 mg, 3.92 mmol). The reaction mixture was stirred at room temperature overnight. Then most of the solvent was evaporated under reduced pressure. Dichloromethane (30 ml) and water (30 ml) were added and separated. The organic layer was washed with water and brine, dried over magnesium sulfate and evaporated under reduced pressure. The residue was subject to a flash chromatography using ethyl acetate/methanol as eluent to give product of isomer A as [(S)-(4-hydroxylbutylthio)methyl-Sar]-3-[(γ-hydroxy)-N-MeLeu]-4-cyclosporin and product of isomer B as [(R)-(4-hydroxylbutylthio)methyl-Sar]-3-[(γ-hydroxy)-N-MeLeu]-4-cyclosporin [Molecular formula: $C_{67}H_{121}N_{11}O_{14}S$; Exact Mass: 1335.88; MS (m/z): 1336.44 (M+1)$^-$, 1358.67 (M+Na)$^+$; TLC Rf: 0.38 (dichloromethane/methanol=9/1); TLC Rf (isomer A): 0.25 (ethyl acetate/methanol=20/1, twice development), and TLC Rf (isomer B): 0.20 (ethyl acetate/methanol=20/1, twice development); HPLC RT: 13.57 min (C8 reverse phase column: 250 mm; acetonitrile/water (0.05% trifluoroacetic acid); operation temp: 64° C.; Detector: 210 nm)].

Example 89
[(S)-(3-(Methoxycarbonyl)propylthio)methyl-Sar]-3-[(γ-hydroxy)-NMeLeu]-4-cyclosporin and [(R)-(3-(methoxycarbonyl)propylthio)methyl-Sar]-3-[(γ-hydroxy)-NMeLeu]-4-cyclosporin
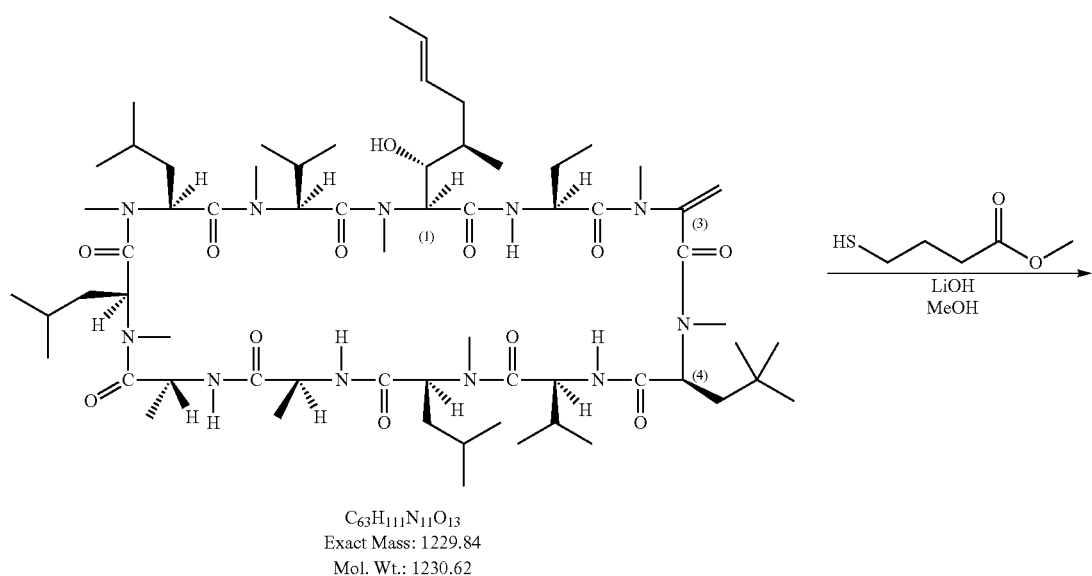
$C_{63}H_{111}N_{11}O_{13}$
Exact Mass: 1229.84
Mol. Wt.: 1230.62
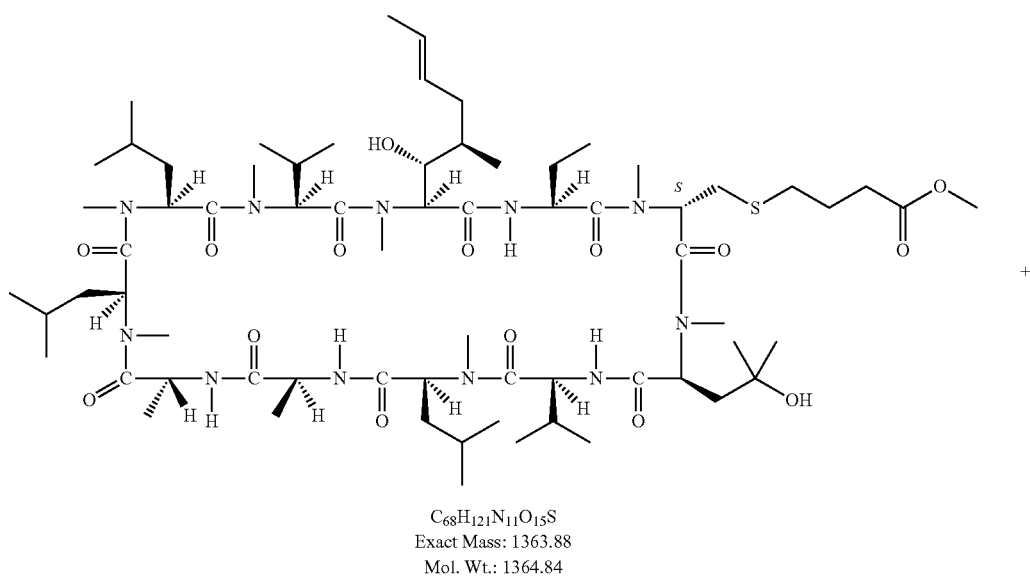
$C_{68}H_{121}N_{11}O_{15}S$
Exact Mass: 1363.88
Mol. Wt.: 1364.84
+

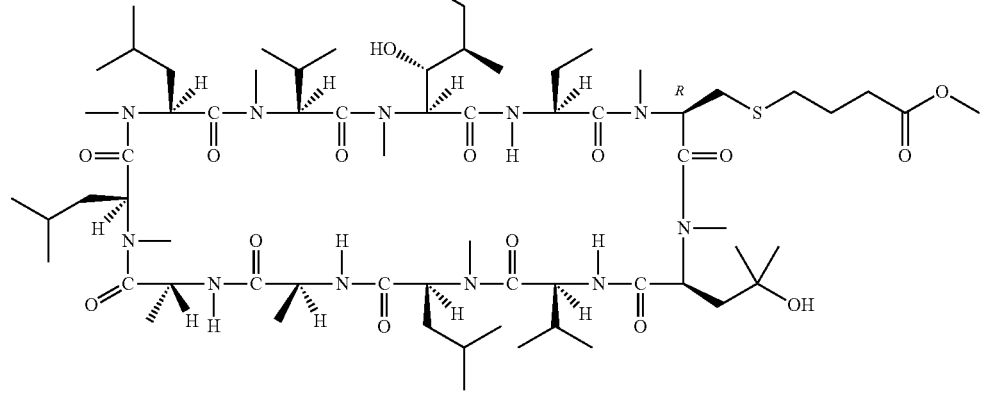

C₆₈H₁₂₁N₁₁O₁₅S
Exact Mass: 1363.88
Mol. Wt.: 1364.84

To a solution of [α-methylene-Sar]-3-[(γ-hydroxy)-NMeLeu]-4-cyclosporin (1.28 g, 1.04 mmol) and methyl 4-mercaptobutanoate (0.84 g, 6.24 mmol) in methanol (25 ml) was added lithium hydroxide (0.15 g, 6.24 mmol). The reaction mixture was stirred at room temperature overnight. Most of solvent was evaporated under reduced pressure. Ethyl acetate (30 ml) and brine (30 ml) were added and the mixture was separated. The organic layer was dried over magnesium sulfate and evaporated under reduced pressure. The residue was purified by chromatography (hexane/acetone) to give 300 mg of [(S)-(4-(methoxycarbonyl)propylthio)methyl-Sar]-3-[(γ-hydroxy)-NMeLeu]-4-cyclosporin [Molecular Formula: $C_{68}H_{128}N_{11}O_{15}S$; Exact Mass: 1363.88; MS (m/z): 1364.43 (M+1)⁻, 1386.64 (M+Na)⁺; HPLC RT: 15.26 min (C8 reverse phase column: 250 mm; acetonitrile/water (0.05% trifluoroacetic acid); operation temperature: 64° C.; detector: 210 nm)] and 220 mg of [(R)-(4-(methoxycarbonyl)propylthio)methyl-Sar]-3-[(γ-hydroxy)-NMeLeu]-4-cyclosporin [Molecular Formula: $C_{68}H_{128}N_{11}O_{15}S$; Exact Mass: 1363.88; MS (m/z): 1364.43 (M+1)⁻, 1386.64 (M+Na)⁺; HPLC RT: 15.13 min (C8 reverse phase column: 250 mm; acetonitrile/water (0.05% trifluoroacetic acid); operation temperature: 64° C.; detector: 210 nm)].

Example 90

[(S)-(4-Hydroxybutylthio)methyl-Sar]-3-[(γ-hydroxy)-NMeLeu]-4-cyclosporin and [(R)-(4-hydroxybutylthio)methyl-Sar]-3-[(γ-hydroxy)-NMeLeu]-4-cyclosporin

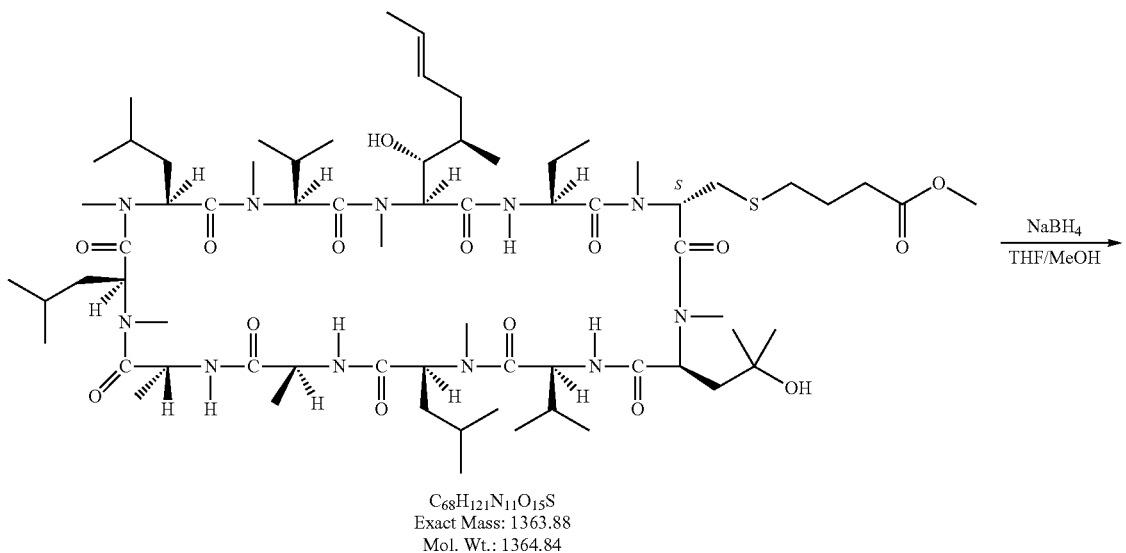

C₆₈H₁₂₁N₁₁O₁₅S
Exact Mass: 1363.88
Mol. Wt.: 1364.84

-continued

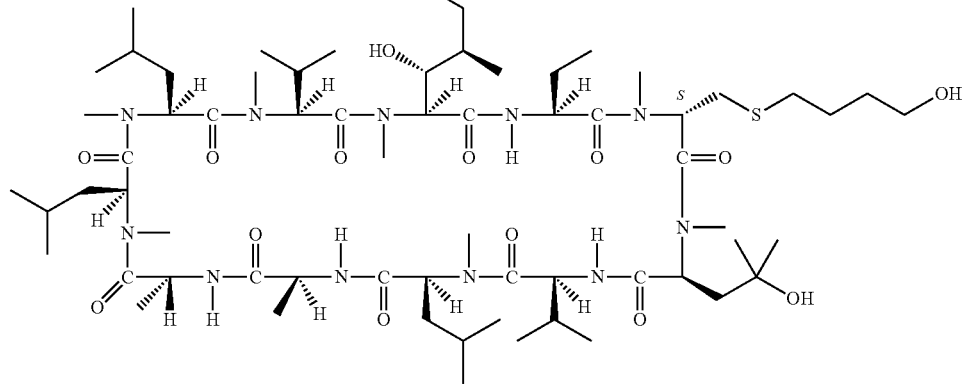

C₆₇H₁₂₁N₁₁O₁₄S
Exact Mass: 1335.88
Mol. Wt.: 1336.83

[(S)-(4-(Methoxycarbonyl)propylthio)methyl-Sar]-3-[(γ-hydroxy)-NMeLeu]-4-cyclosporin (200 mg, 0.15 mmol) was dissolved in tetrahydrofuran (15 ml), followed by adding cesium chloride (200 mg, 1.18 mmol) and sodium borohydride (300 mg, 7.93 mmol). Then 10 ml of methanol was added dropwise to the mixture over 30 minutes. After addition, the mixture was stirred at room temperature one hour. Most solvent was then evaporated under reduced pressure. Ethyl acetate (30 ml) and water (30 ml) were added. The ethyl acetate layer was separated and washed with brine, dried over magnesium sulfate and evaporated under reduced pressure. The residue was purified by chromatography with dichloromethane/methanol (from 100:0 to 96:4) as eluent to give 13 mg of pure product [Molecular Formula: $C_{67}H_{121}N_{11}O_{14}S$; Exact Mass: 1335.88; MS (m/z): 1336.50 (M+1)⁺, 1358.70 (M+Na)⁺; TLC $R_f$: 0.39 (dichloromethane/methanol=9:1); HPLC RT: 13.25 min (C8 reverse phase column: 250 mm; acetonitrile/water (0.05% trifluoroacetic acid); operation temperature: 64° C.; detector: 210 nm)].

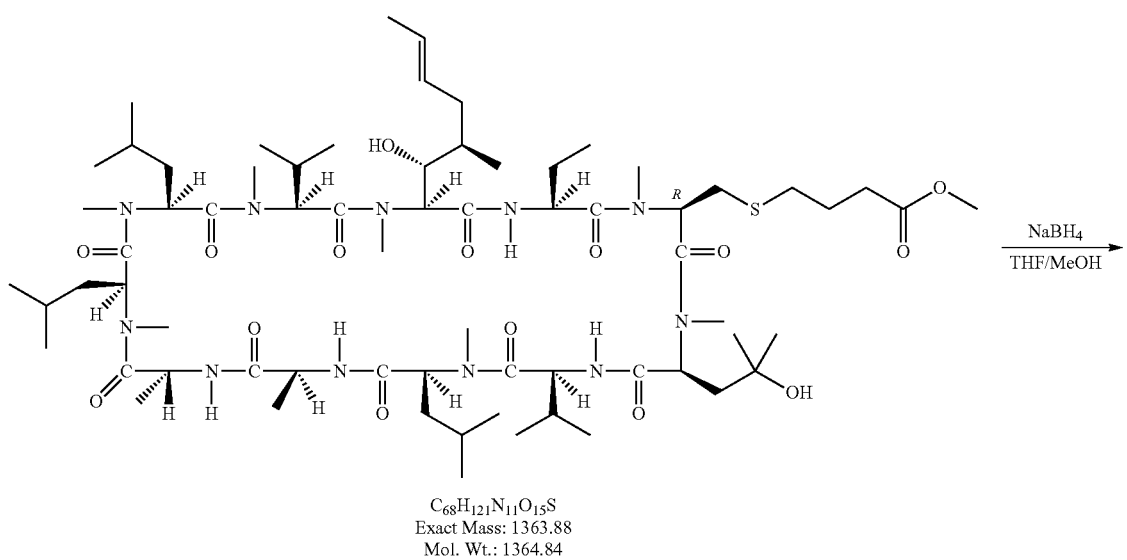

C₆₈H₁₂₁N₁₁O₁₅S
Exact Mass: 1363.88
Mol. Wt.: 1364.84

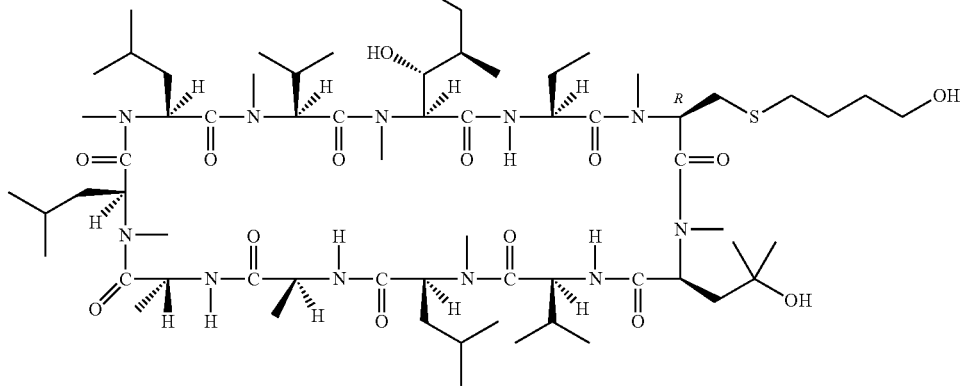

$C_{67}H_{121}N_{11}O_{14}S$
Exact Mass: 1335.88
Mol. Wt.: 1336.83

According to this method, 11 mg of pure [(R)-(4-hydroxy-butylthio)methyl-Sar]-3-[(γ-hydroxy)-NMeLeu]-4-cyclosporin was obtained [Molecular Formula: $C_{67}H_{121}N_{11}O_{14}S$; Exact Mass: 1335.88; MS (m/z): 1336.50 $(M+1)^+$, 1358.70 $(M+Na)^+$; TLC $R_f$: 0.39 (dichloromethane/methanol=9:1); HPLC RT: 13.28 min (C8 reverse phase column: 250 mm; acetonitrile/water (0.05% trifluoroacetic acid); operation temperature: 64° C.; detector: 210 nm)].

Example 91

[(S)-(4-Methoxybutylthio)methyl-Sar]-3-[(γ-hydroxy)-N-MeLeu]-4-cyclosporin

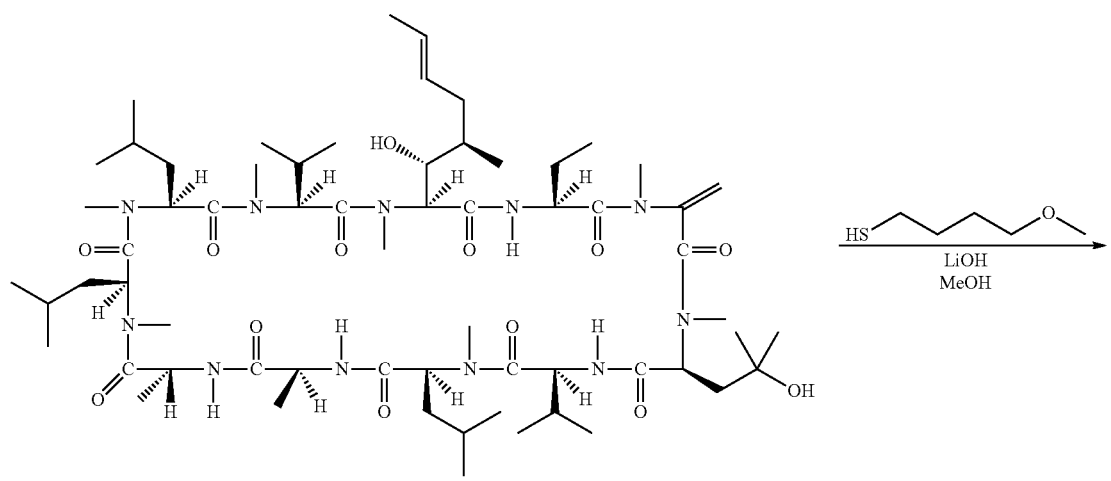

$C_{63}H_{111}N_{11}O_{13}$
Exact Mass: 1229.84
Mol. Wt.: 1230.65

-continued

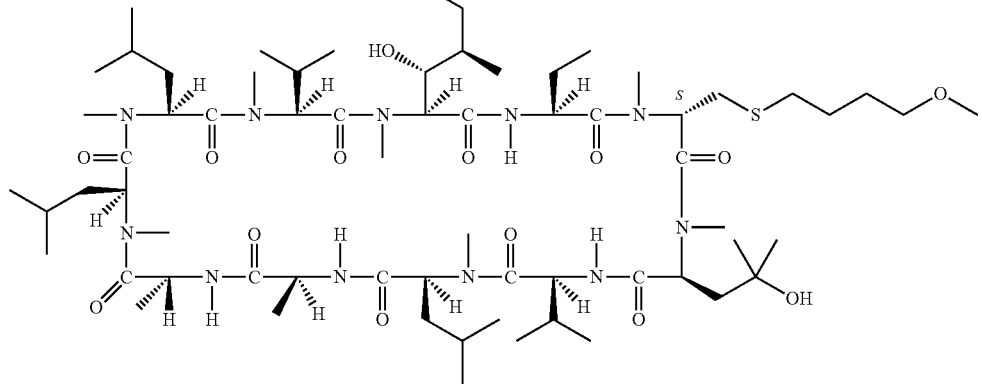

C$_{68}$H$_{123}$N$_{11}$O$_{14}$S
Exact Mass: 1349.90
Mol. Wt.: 1350.86

[α-Methylene-Sar]-3-[(γ-hydroxy)-N-MeLeu]-4-cyclosporin (300 mg, 0.244 mmol) and 1-mercapto-4-methoxybutane (MW: 120.21, 292 mg, 10 mmol) were dissolved in methanol (10 ml), followed by adding six equivalents of lithium hydroxide (35 mg). The mixture was stirred overnight at room temperature. After removal of solvents, the residue was dissolved in ethyl acetate (15 ml). The ethyl acetate solution was washed with brine, dried over magnesium sulfate and evaporated under reduced pressure. The residue was subject to the flash chromatography using methylene chloride/methanol as eluent to give 57 mg of pure product [Molecular formula: C$_{66}$H$_{123}$N$_{11}$O$_{14}$S; Exact Mass: 1349.90; MS (m/z): 1350.45 (M+1)$^+$, 1372.58 (M+Na)$^+$; TLC R$_f$: 0.30 (methylene chloride/methanol=20/1); HPLC RT: 15.54 min (C8 reverse phase column: 250 mm; acetonitrile/water (0.05% trifluoroacetic acid); operation temp: 64° C.; Detector: 210 nm)].

Example 92

[(S)-(4-(2-(N,N-Diethylamino)ethoxy)butylthio) methyl-Sar]-3-[(γ-hydroxy)-NMeLeu]-4-cyclosporin

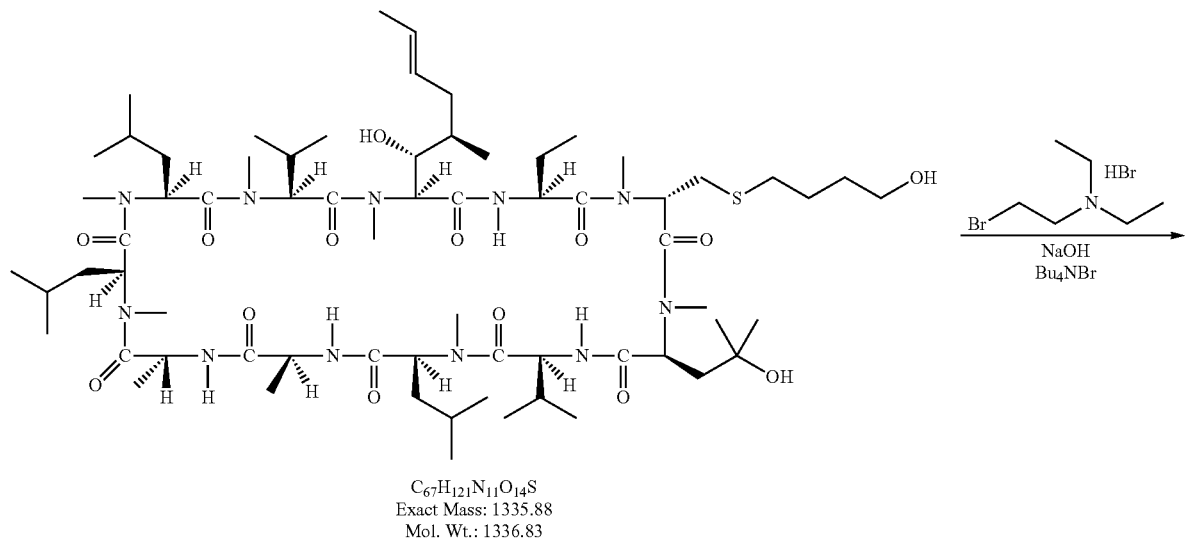

C$_{67}$H$_{121}$N$_{11}$O$_{14}$S
Exact Mass: 1335.88
Mol. Wt.: 1336.83

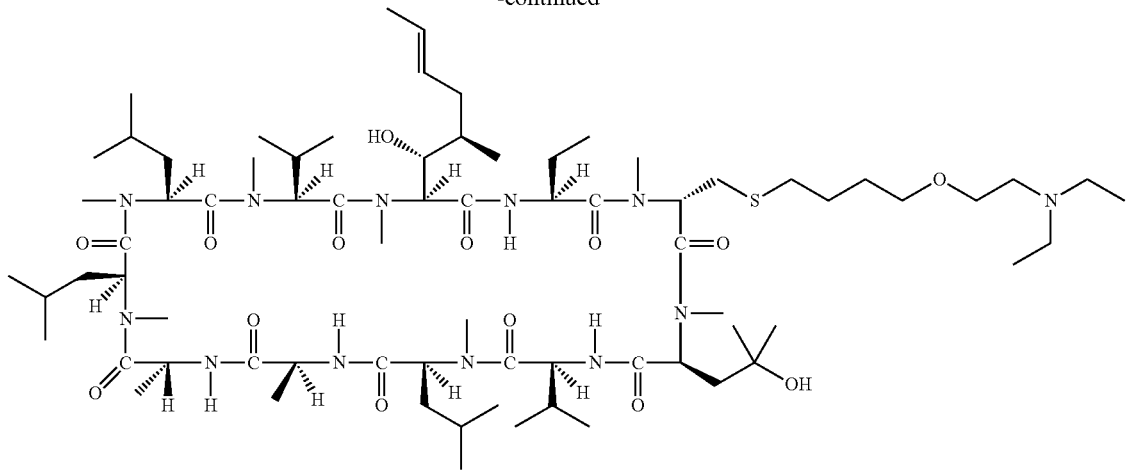

C$_{73}$H$_{134}$N$_{12}$O$_{14}$S
Exact Mass: 1434.99
Mol. Wt.: 1436.01

To a solution of [(S)-(4-hydroxylbutylthio)methyl-Sar]-3-[(γ-hydroxy)-N-MeLeu]-4-cyclosporin (0.32 g, 0.24 mmol) in benzene (30 ml) were added a solution of sodium hydroxide (1.20 g, 30 mmol) in water (2 ml), 2-bromo-N,N-diethylethylamine hydrobromide (MW: 261, 3.80 g, 14.56 mmol) and tetra-n-butylammonium bromide (0.20 g, 0.62 mmol). The reaction mixture was stirred at 30° C. for 48 hours. After diluted with ice water, the mixture was separated. The aqueous layer was extracted with dichloromethane (30 ml). The combined organic layers were washed with brine, dried over magnesium sulfate and evaporated under reduced pressure. The residue was purified by chromatography (dichloromethane/methanol=95/5) to give product [Molecular formula: C$_{73}$H$_{134}$N$_{12}$O$_{14}$S; Exact Mass: 1434.99; MS (m/z): 1435.64(M+1)$^+$; TLC R$_f$: 0.30 (dichloromethane/methanol=9/1); HPLC RT: 12.06 min (C8 reverse phase column: 250 mm; acetonitrile/water (0.05% trifuloroacetic acid); operation temp: 64° C.; Detector: 210 nm)].

Example 93

[(S)-(4-Oxopentylthio)methyl-Sar]-3-[(γ-hydroxy)-N-MeLeu]-4-cyclosporin

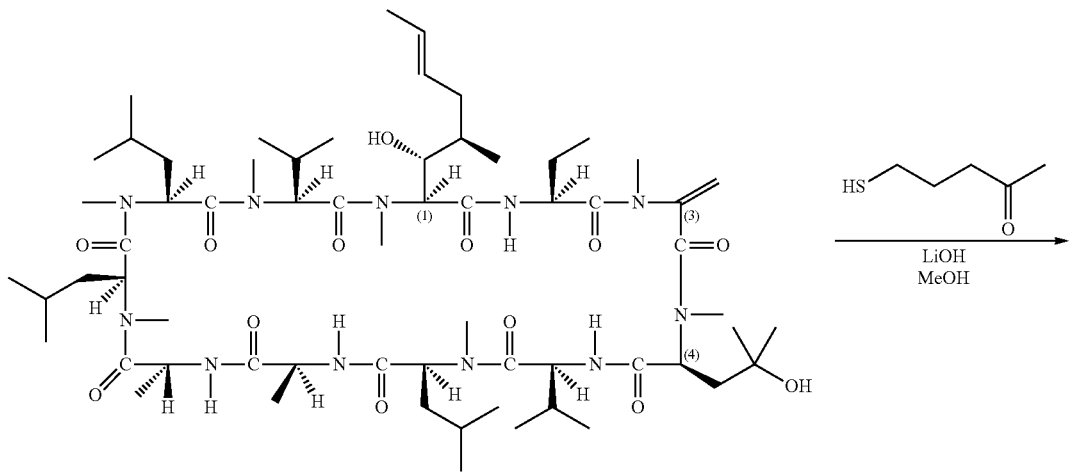

C$_{63}$H$_{111}$N$_{11}$O$_{13}$
Exact Mass: 1229.84
Mol. Wt.: 1230.65

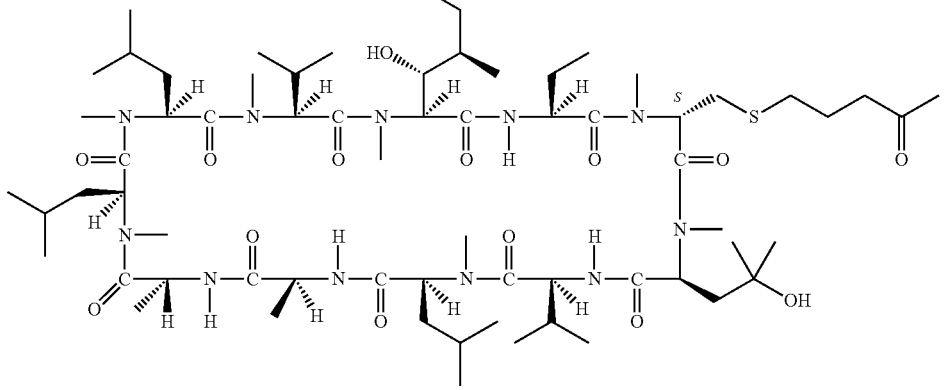

C₆₈H₁₂₁N₁₁O₁₄S
Exact Mass: 1347.88
Mol. Wt.: 1348.84

To a solution of [α-methylene-Sar]-3-[(γ-hydroxy)-N-MeLeu]-4-cyclosporin (480 mg, 0.39 mmol) and 5-mercapto-2-pentanone (MW: 118.19, 500 mg, 4.24 mmol) in methanol (30 ml) was added lithium hydroxide (120 mg, 5.00 mmol). The reaction mixture was stirred at room temperature overnight. Then most of solvent was evaporated under reduced pressure. Dichloromethane (80 ml) and water (30 ml) were added and separated. The organic layer was washed with water and brine, dried over magnesium sulfate and evaporated under reduced pressure. The residue was purified by chromatography (ethyl acetate) to give a pure product [Molecular formula: C₆₈H₁₂₁N₁₁O₁₄S; Exact Mass: 1347.88; MS (m/z): 1348.49 (M+1)⁺; TLC Rf: 0.46 (dichloromethane/methanol=97/3); HPLC RT: 14.86 min (C8 reverse phase column: 250 mm; acetonitrile/water (0.05% trifuloroacetic acid); operation temp: 64° C.; Detector: 210 nm)].

Example 94

[(S)-(4-Hydroxypentylthio)methyl-Sar]-3-[(γ-hydroxy)-N-MeLeu]-4-cyclosporin

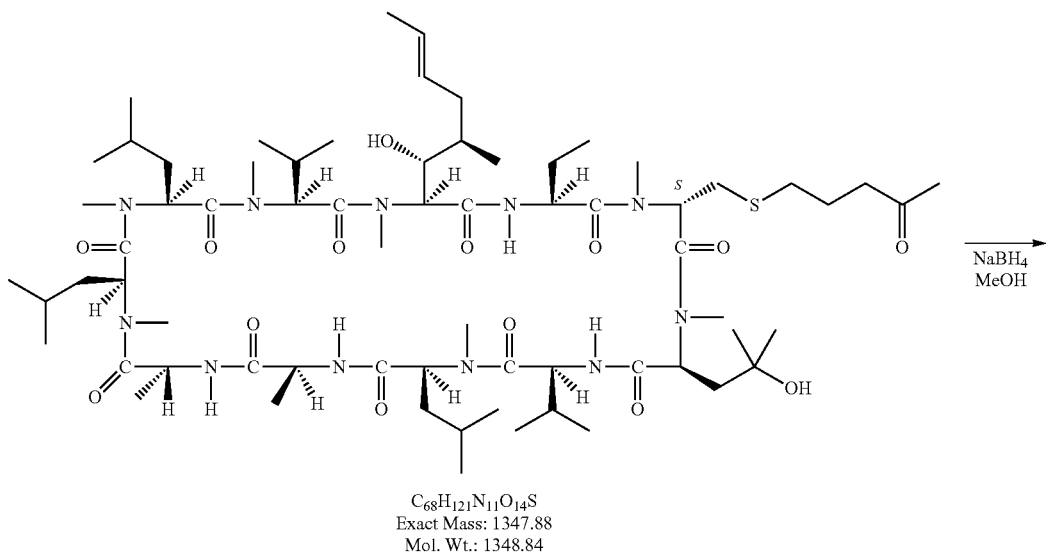

C₆₈H₁₂₁N₁₁O₁₄S
Exact Mass: 1347.88
Mol. Wt.: 1348.84

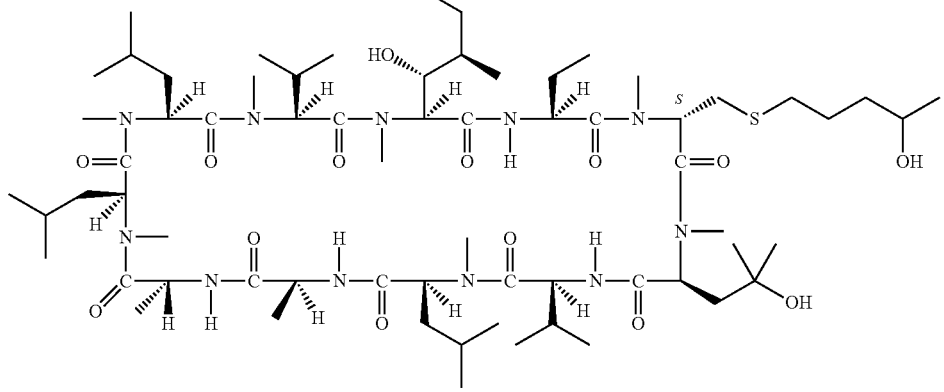

$C_{68}H_{123}N_{11}O_{14}S$
Exact Mass: 1349.90
Mol. Wt.: 1350.86

To a solution of [(S)-4-oxopentylthiomethyl-Sar]-3-[(γ-hydroxy)-N-MeLeu]-4-cyclosporin (80 mg, 0.06 mmol) in methanol (5 ml) was added sodium borohydride (36 mg, 0.95 mmol) in portions. After addition, the mixture was stirred at room temperature for one hour. Most of solvent was then evaporated under reduced pressure. Dichloromethane (30 ml) and water (30 ml) were added. The dichloromethane layer was separated and washed with brine (30 ml), dried over magnesium sulfate and evaporated under reduced pressure. The residue was purified on silica gel column with (ethyl acetate/methanol=99/1) to give a pure product [Molecular formula: $C_{68}H_{123}N_{11}O_{14}S$; Exact Mass: 1349.90; MS (m/z): 1350.49(M+1)$^+$; TLC Rf: 0.35 (dichloromethane/methanol=97/3); HPLC RT: 14.25 min (C8 reverse phase column: 250 mm; acetonitrile/water (0.05% trifuloroacetic acid); operation temp: 64° C.; Detector: 210 nm)].

Example 95

[(S)-(4-Hydroxy-4-methylpentylthio)methyl-Sar]-3-[(γ-hydroxy)-N-MeLeu]-4-cyclosporin

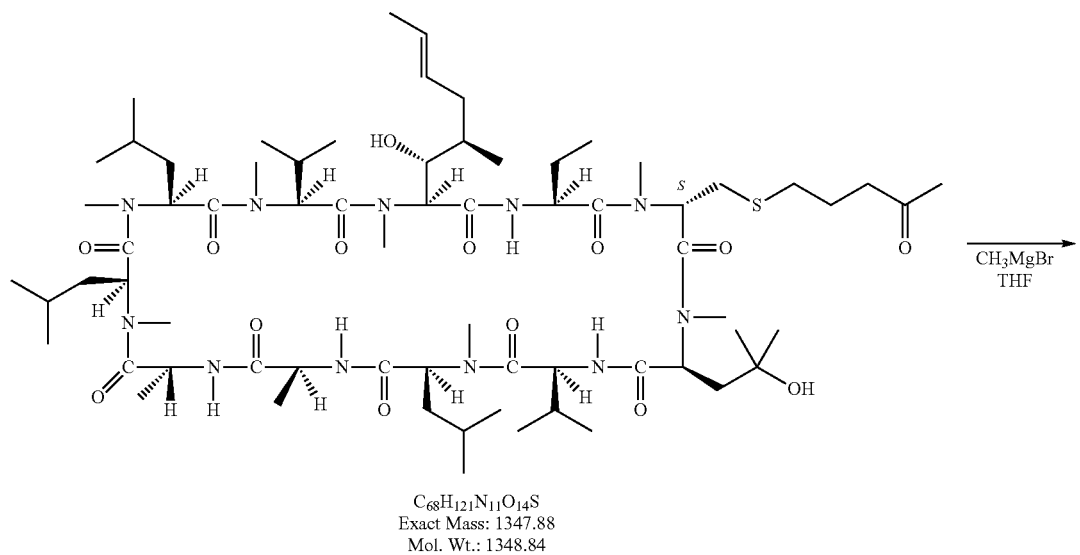

$C_{68}H_{121}N_{11}O_{14}S$
Exact Mass: 1347.88
Mol. Wt.: 1348.84

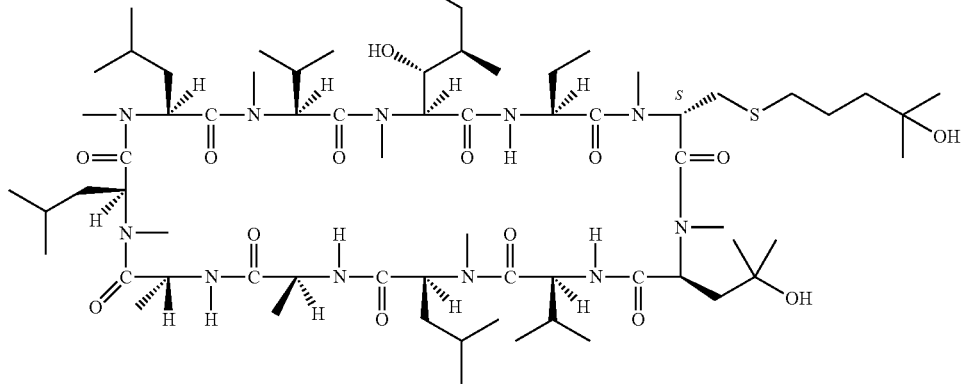

C₆₉H₁₂₅N₁₁O₁₄S
Exact Mass: 1363.91
Mol. Wt.: 1364.88

To a solution of [(S)-4-oxopentylthiomethyl-Sar]-3-[(γ-hydroxy)-N-MeLeu]-4-cyclosporin (100 mg, 0.07 mmol) in tetrahydrofuran (25 ml) at 0° C. was added a solution of methylmagnesium bromide in ether (1 ml, 3 M, 3.00 mmol). After addition, the mixture was slowly warmed to room temperature and stirred at room temperature for one and half hour. Then the reaction was quenched by adding aqueous ammonium chloride solution. Dichloromethane (30 ml) and water (30 ml) were added. The dichloromethane layer was separated and washed with brine (30 ml), dried over magnesium sulfate and evaporated under reduced pressure. The residue was purified on silica gel column with (ethyl acetate/methanol=99/1) to give a pure product [Molecular formula:

$C_{69}H_{125}N_{11}O_{14}S$; Exact Mass: 1363.91; MS (m/z): 1364.48 (M+1)⁺; TLC Rf: 0.42 (dichloromethane/methanol=97/3); HPLC RT: 14.74 min (C8 reverse phase column: 250 mm; acetonitrile/water (0.05% trifuloroacetic acid); operation temp: 64° C.; Detector: 210 nm)].

Example 96

[(S)-(4-(Methoxycarbonyl)butylthio)methyl-Sar]-3-[(γ-hydroxy)-NMeLeu]-4-cyclosporin and [(R)-(4-(methoxycarbonyl)butylthio)methyl-Sar]-3-[(γ-hydroxy)-NMeLeu]-4-cyclosporin

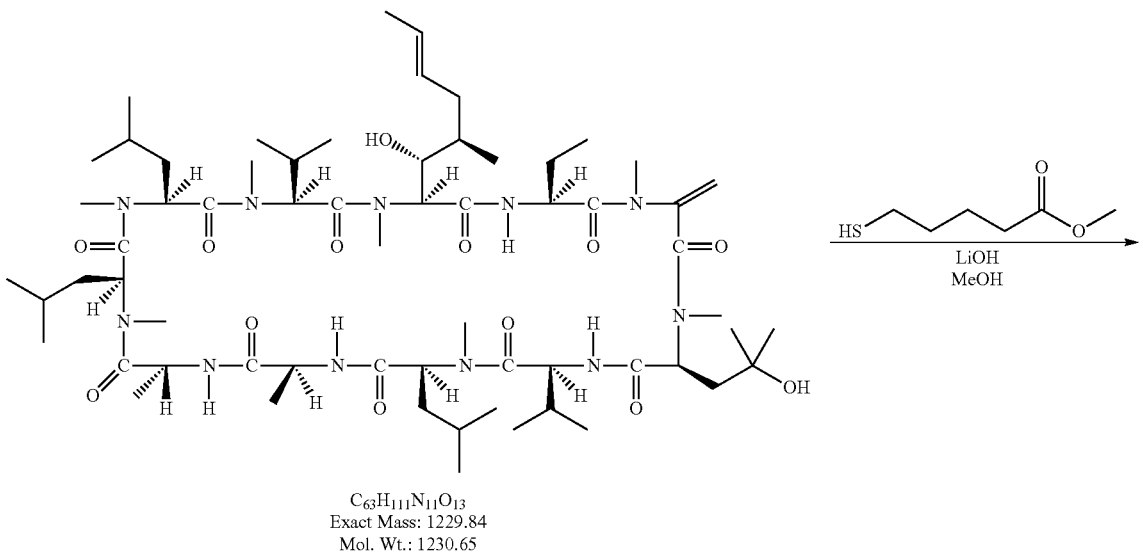

C₆₃H₁₁₁N₁₁O₁₃
Exact Mass: 1229.84
Mol. Wt.: 1230.65

-continued

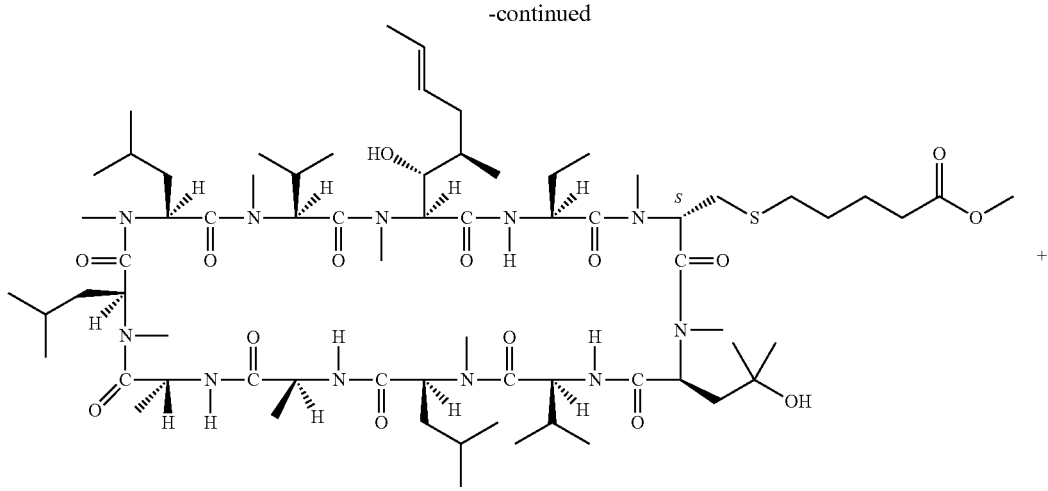

C<sub>69</sub>H<sub>123</sub>N<sub>11</sub>O<sub>15</sub>S
Exact Mass: 1377.89
Mol. Wt.: 1378.86

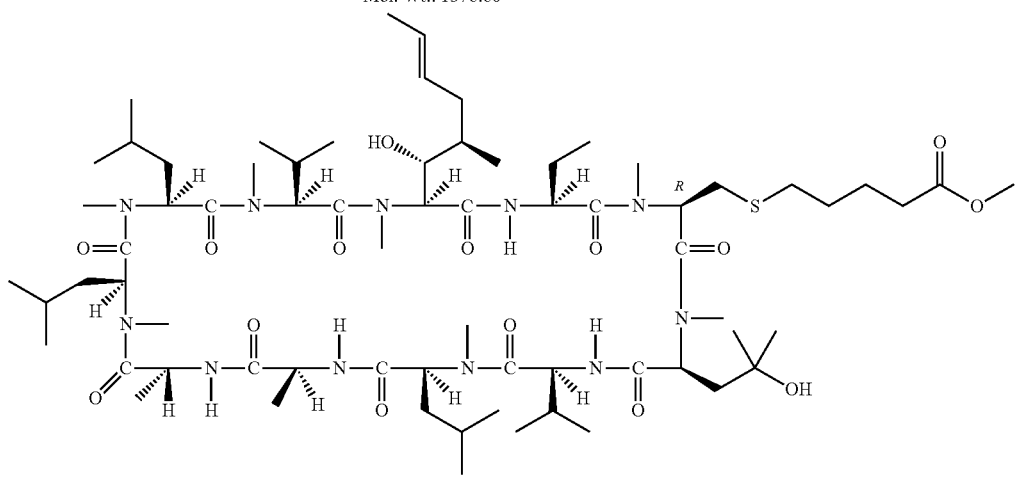

C<sub>69</sub>H<sub>123</sub>N<sub>11</sub>O<sub>15</sub>S
Exact Mass: 1377.89
Mol. Wt.: 1378.86

To a solution of [α-methylene-Sar]-3-[(γ-hydroxy)-NMeLeu]-4-cyclosporin (1.00 g, 0.81 mmol) and methyl 5-mercaptopentanoate (0.72 g, 4.88 mmol) in methanol (30 ml) was added lithium hydroxide (195 mg, 8.13 mmol). The reaction mixture was stirred at room temperature for 3 hours. Most of solvent was evaporated under reduced pressure. Ethyl acetate (30 ml) and brine (30 ml) were added and the mixture was separated. The organic layer was dried over magnesium sulfate and evaporated under reduced pressure. The residue was purified by chromatography (hexane/acetone) to give 210 mg of [(S)-(4-(methoxycarbonyl)butyl-thio)methyl-Sar]-3-[(γ-hydroxy)-NMeLeu]-4-cyclosporin [Molecular Formula: $C_{69}H_{123}N_{11}O_{15}S$; Exact Mass: 1377.89; MS (m/z): 1378.49 (M+1)$^+$, 1400.67 (M+Na)$^+$; HPLC RT: 15.72 min (C8 reverse phase column: 250 mm; acetonitrile/water (0.05% trifluoroacetic acid); operation temperature: 64° C.; detector: 210 nm)] and 270 mg of [(R)-(4-(methoxycarbonyl)butylthio)methyl-Sar]-3-[(γ-hydroxy)-NMeLeu]-4-cyclosporin [Molecular Formula: $C_{69}H_{123}N_{11}O_{15}S$; Exact Mass: 1377.89; MS (m/z): 1378.50 (M+1)$^+$, 1400.68 (M+Na)$^+$; HPLC RT: 15.53 min (C8 reverse phase column: 250 mm; acetonitrile/water (0.05% trifluoroacetic acid); operation temperature: 64° C.; detector: 210 nm)].

Example 97

[(S)-(5-Hydroxypentylthio)methyl-Sar]-3-[(γ-hydroxy)-NMeLeu]-4-cyclosporin and [(R)-(5-Hydroxypentylthio)methyl-Sar]-3-[(γ-hydroxy)-NMeLeu]-4-cyclosporin

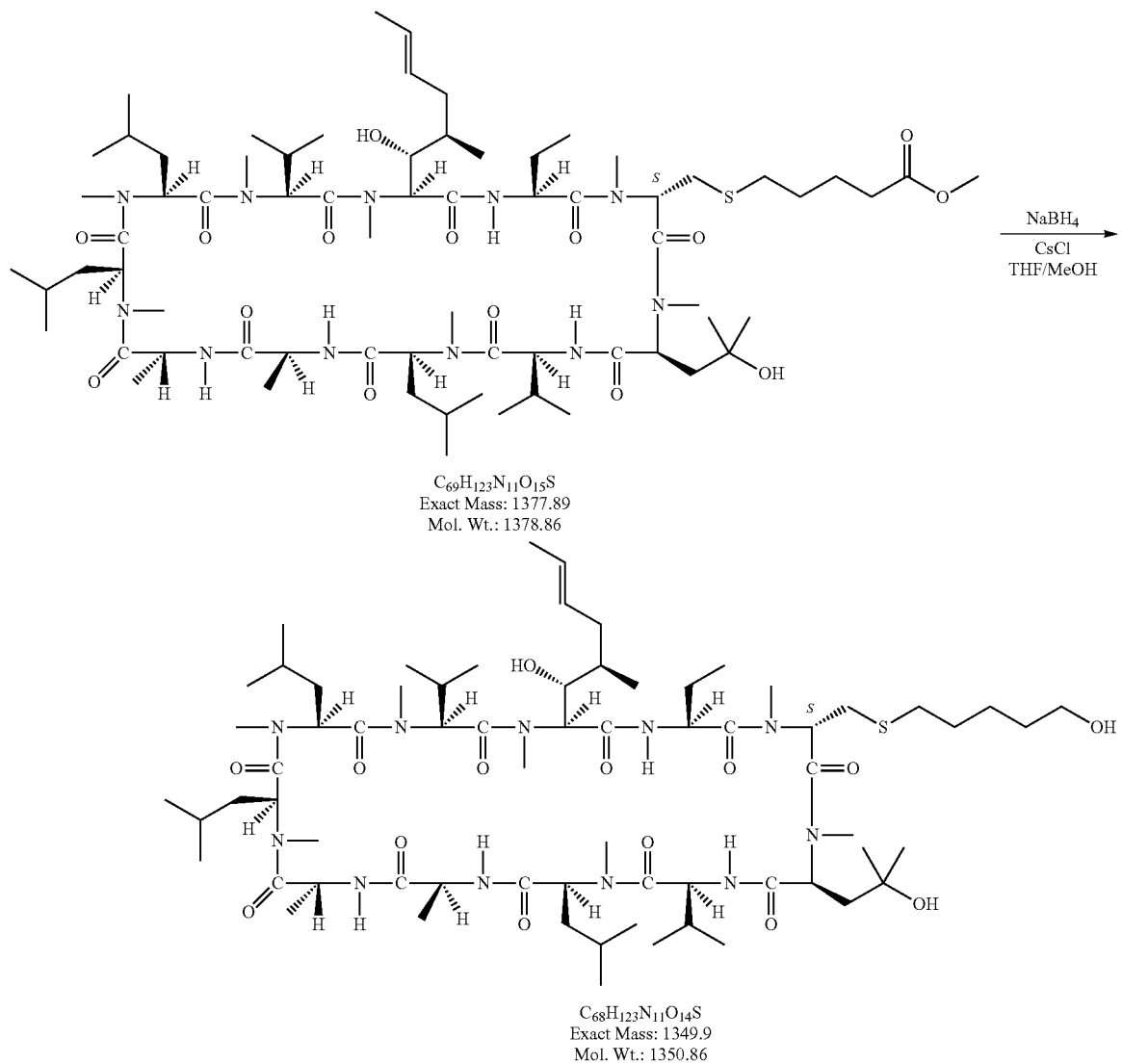

$C_{69}H_{123}N_{11}O_{15}S$
Exact Mass: 1377.89
Mol. Wt.: 1378.86

$C_{68}H_{123}N_{11}O_{14}S$
Exact Mass: 1349.9
Mol. Wt.: 1350.86

[(S)-(4-(Methoxycarbonyl)butylthio)methyl-Sar]-3-[(γ-hydroxy)-NMeLeu]-4-cyclosporin (170 mg, 0.13 mmol) was dissolved in tetrahydrofuran (30 ml), followed by adding cesium chloride (1.00 g, 5.94 mmol) and sodium borohydride (1.00 g, 26.43 mmol). Then 30 ml of methanol was added dropwise to the mixture over 30 minutes. After addition, the mixture was stirred at room temperature one hour. Most solvent was then evaporated under reduced pressure. Ethyl acetate (30 ml) and water (30 ml) were added. The ethyl acetate layer was separated and washed with brine, dried over magnesium sulfate and evaporated under reduced pressure. The residue was purified by chromatography with dichloromethane/methanol (from 100:0 to 96:4) as eluent to give 47 mg of pure product of [(S)-(5-hydroxypentylthio)methyl-Sar]-3-[(γ-hydroxy)-NMeLeu]-4-cyclosporin [Molecular Formula: $C_{68}H_{123}N_{11}O_{14}S$; Exact Mass: 1349.90; MS (m/z): 1350.52 $(M+1)^+$, 1372.72 $(M+Na)^+$; TLC $R_f$: 0.54 (dichloromethane/methanol=9:1); HPLC RT: 14.19 min (C8 reverse phase column: 250 mm; acetonitrile/water (0.05% trifluoroacetic acid); operation temperature: 64° C.; detector: 210 nm)].

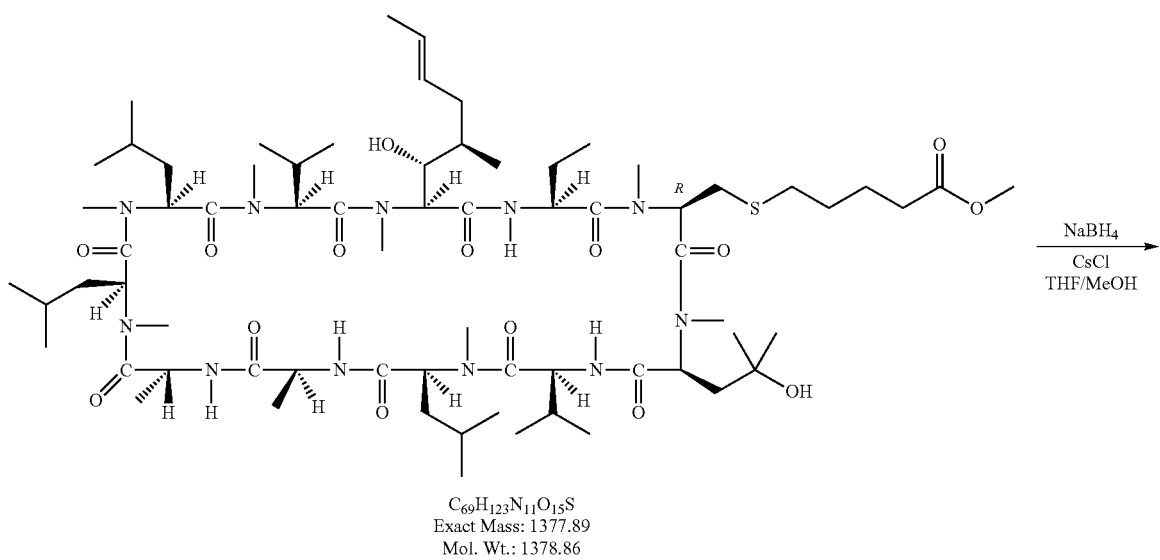
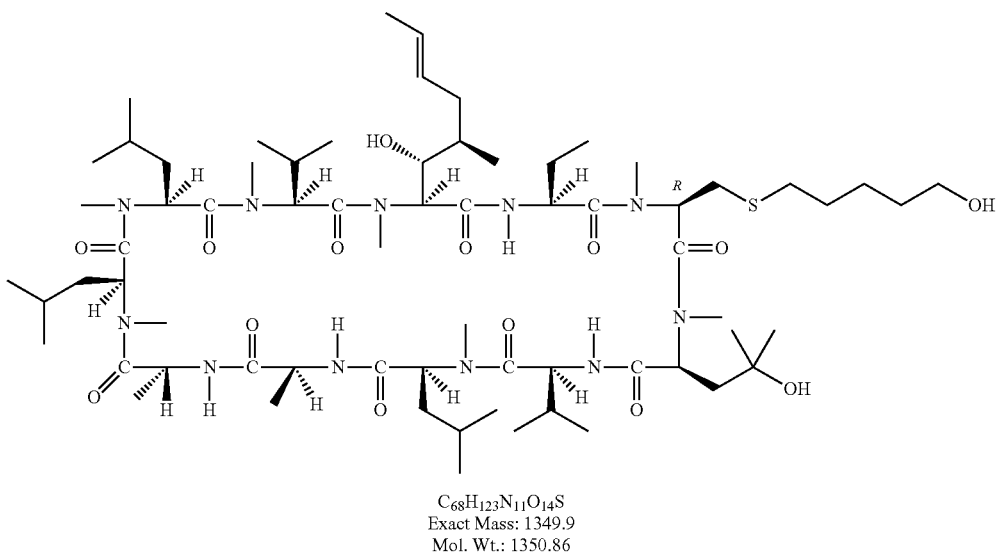
According this method, 48 mg of pure [(R)-(5-hydroxypentylthio)methyl-Sar]-3-[(γ-hydroxy)-NMeLeu]-4-cyclosporin was obtained [Molecular Formula: $C_{68}H_{123}N_{11}O_{14}S$; Exact Mass: 1349.90; MS (m/z): 1350.47 (M+1)$^+$, 1372.71 (M+Na)$^+$; TLC $R_f$: 0.54 (dichloromethane/methanol=9:1); HPLC RT: 14.14 min (C8 reverse phase column: 250 mm; acetonitrile/water (0.05% trifluoroacetic acid); operation temperature: 64° C.; detector: 210 nm)].

Example 98

[(S)-((5-Hydroxy-5-methyl)hexylthio)methyl-Sar]-3-[(γ-hydroxy)-NMeLeu]-4-cyclosporin and [(R)-((5-Hydroxy-5-methyl)hexylthiothio)methyl-Sar]-3-[(γ-hydroxy)-NMeLeu]-4-cyclosporin

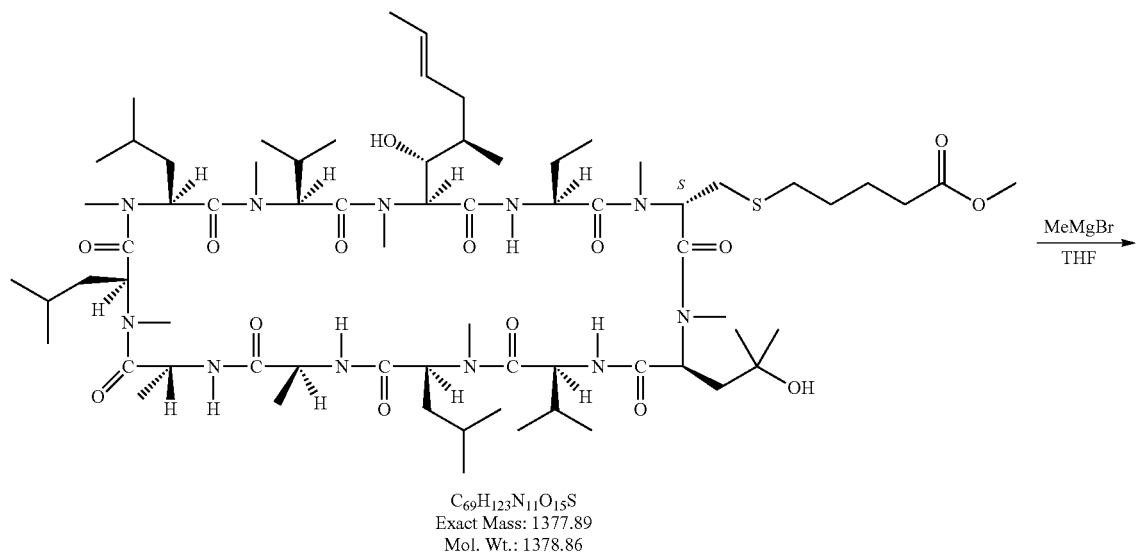

$C_{69}H_{123}N_{11}O_{15}S$
Exact Mass: 1377.89
Mol. Wt.: 1378.86

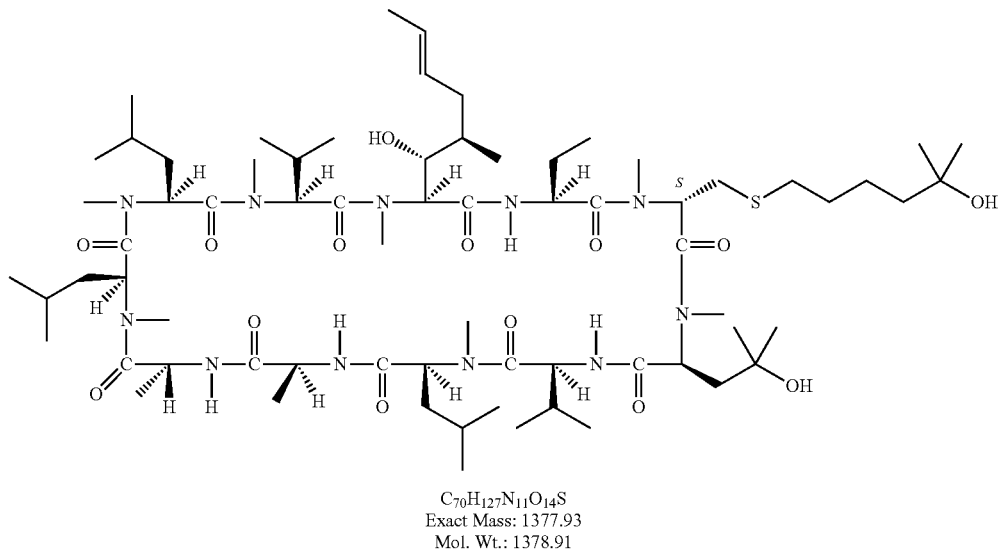

$C_{70}H_{127}N_{11}O_{14}S$
Exact Mass: 1377.93
Mol. Wt.: 1378.91

[(S)-(4-(Methoxycarbonyl)butylthio)methyl-Sar]-3-[(γ-hydroxy)-NMeLeu]-4-cyclosporin (340 mg, 0.25 mmol) was dissolved in tetrahydrofuran (10 ml) and put into an ice bath. Then 0.63 ml of 3 M methylmagnesium bromide in ether (1.89 mmol) was added dropwise to the mixture over one hour. After the mixture was stirred 0° C. for two hour, 3 ml of brine was added dropwise to quench the reaction. Most solvent was then evaporated under reduced pressure. Ethyl acetate (10 ml) and water (10 ml) were added. The ethyl acetate layer was separated and washed with brine, dried over magnesium sulfate and evaporated under reduced pressure. The residue was purified by chromatography with dichloromethane/methanol as eluent to give 17 mg of pure product [Molecular Formula: $C_{70}H_{127}N_{11}O_{14}S$; Exact Mass: 1377.93; MS (m/z): 1378.55 (M+1)$^-$, 1400.79 (M+Na)$^+$; TLC R$_f$: 0.48 (dichloromethane/methanol=9:1); HPLC RT: 15.22 min (C8 reverse phase column: 250 mm; acetonitrile/water (0.05% trifluoroacetic acid); operation temperature: 64° C.; detector: 210 nm)].

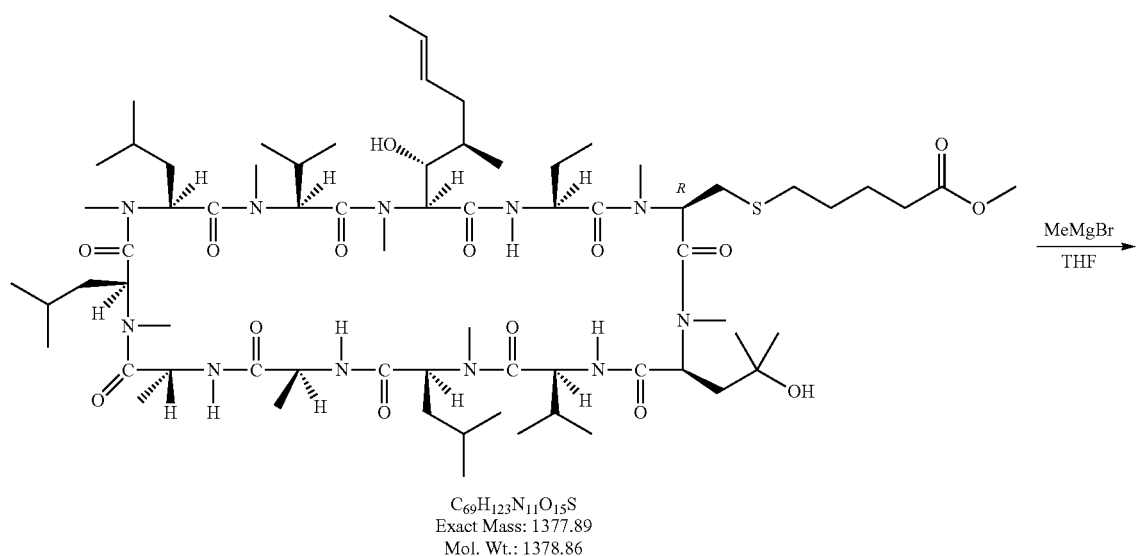
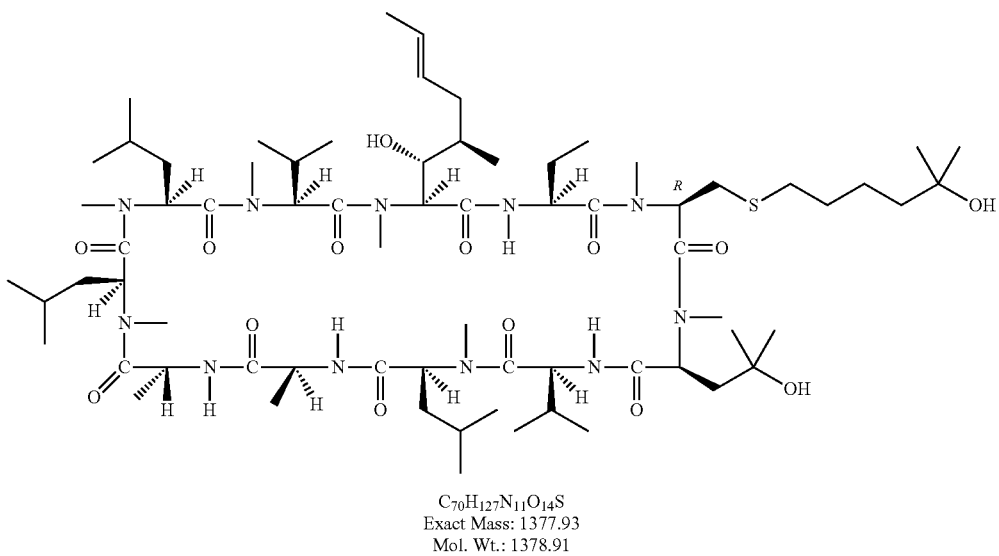
According to this method, 48 mg of pure [(R)-(5-hydroxy-5-methylhexylthio)methyl-Sar]-3-[(γ-hydroxy)-NMeLeu]-4-cyclosporin was obtained [Molecular Formula: $C_{70}H_{127}N_{11}O_{14}S$; Exact Mass: 1377.93; MS (m/z): 1378.45 $(M+1)^+$, 1400.70 $(M+Na)^+$; TLC $R_f$: 0.41 (dichloromethane/methanol=9:1); HPLC RT: 15.11 min (C8 reverse phase column: 250 mm; acetonitrile/water (0.05% trifluoroacetic acid); operation temperature: 64° C.; detector: 210 nm)].

Example 99

[(S)—((R)-5-hydroxyhexylthio)methyl-Sar]-3-[(γ-hydroxy)-N-MeLeu]-4-cyclosporin

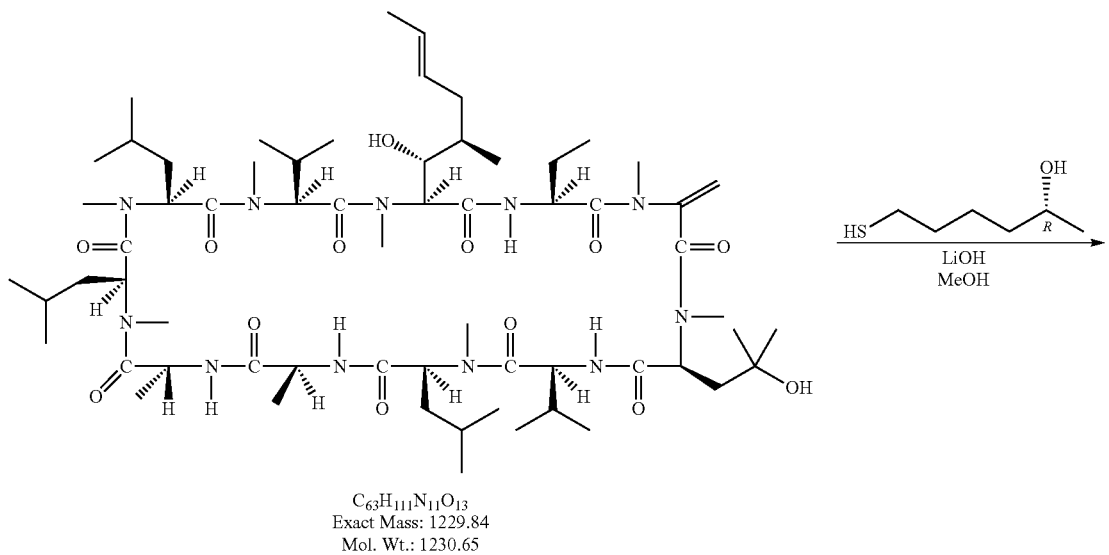

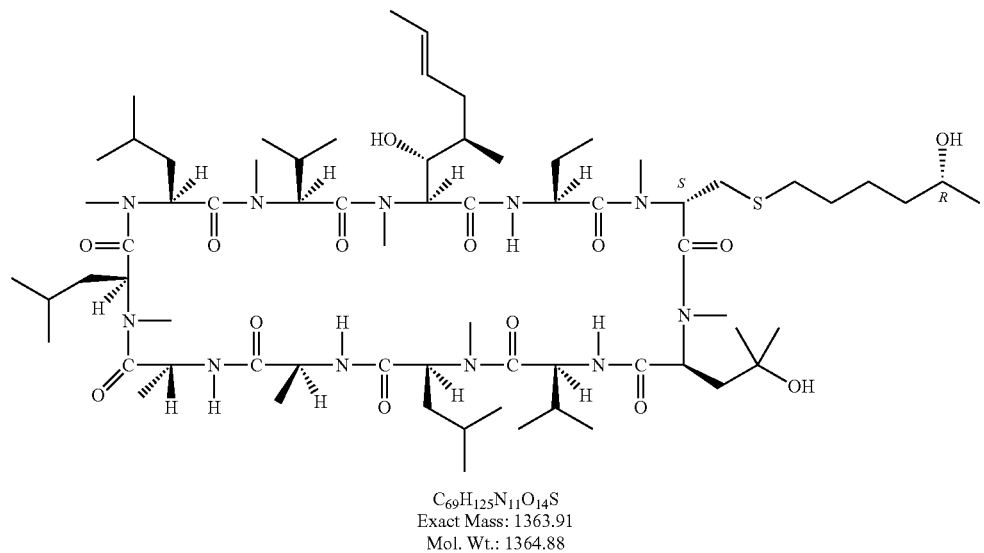

[α-Methylene-Sar]-3-[(γ-hydroxy)-N-MeLeu]-4-cyclosporin (123 mg, 0.1 mmol) and (R)-1-mercapto-5-hexanol (110 mg, 10 mmol) were dissolved in methanol (10 ml), followed by adding 10 equivalents of lithium hydroxide (14.4 mg). The mixture was stirred overnight at room temperature. After removal of solvents, the residue was dissolved in ethyl acetate (15 ml). The ethyl acetate solution was washed with brine, dried over magnesium sulfite and evaporated under reduced pressure. The residue was subject to a flash chromatography using ethyl acetate/methanol as eluent to give 25 mg of pure product [Molecular formula: $C_{69}H_{125}N_{11}O_{14}S$; Exact Mass: 1363.91; MS (m/z): 1364.68 $(M+1)^+$, 1386.87 $(M+Na)^+$; TLC $R_f$: 0.31 (methylene chloride/methanol=20/1); HPLC RT: 14.72 min (C8 reverse phase column: 250 mm; acetonitrile/water (0.05% trifluoroacetic acid); operation temp: 64° C.; Detector: 210 nm)].

Example 100

[(S)-(6-Hydroxylhexylthio)methyl-Sar]-3-[(γ-hydroxy)-NMeLeu]-4-cyclosporin

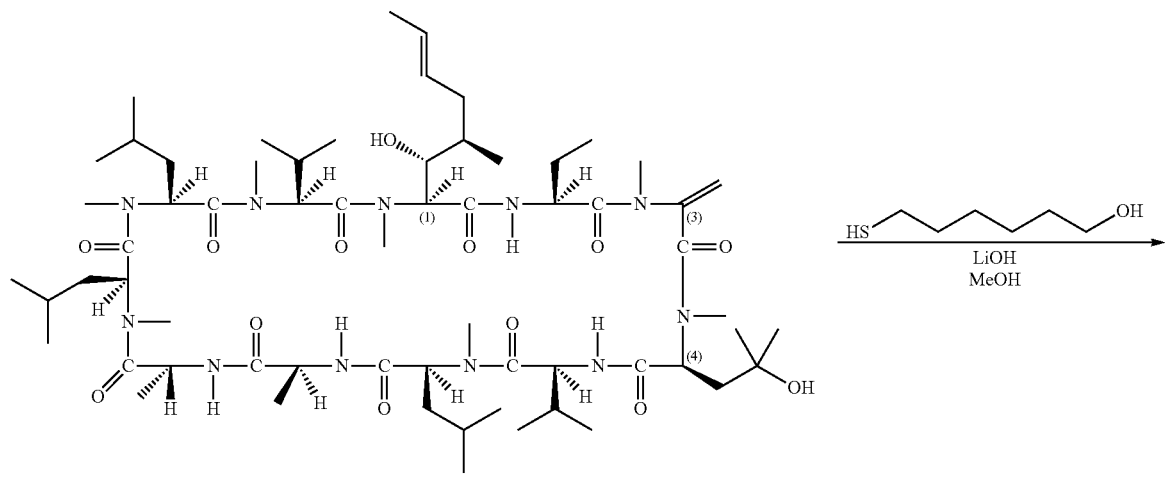

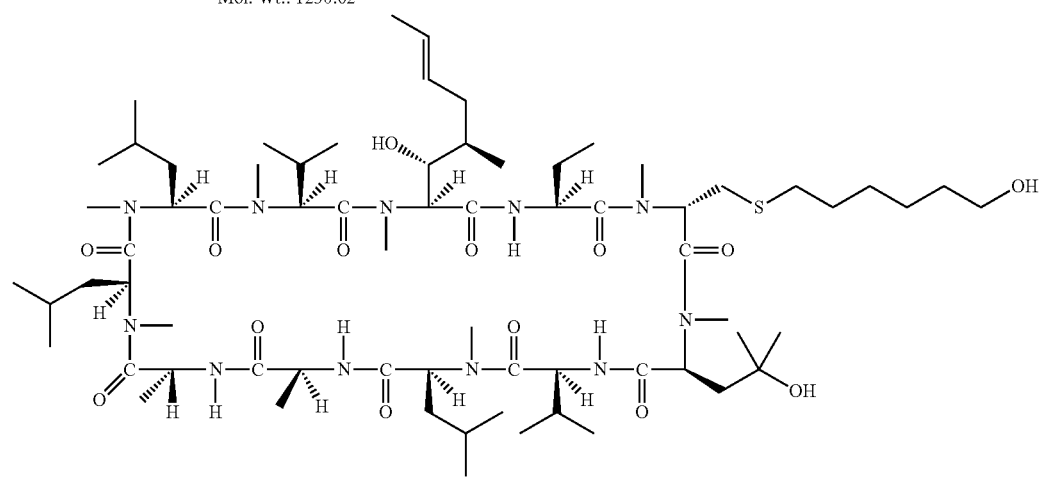

[α-Methylene-Sar]-3-[(γ-hydroxy)-N-MeLeu]-4-cyclosporin (0.25 g, 0.20 mmol) and 6-mercapto-1-hexanol (MW: 134.24, 0.27 g, 2.00 mmol) were dissolved in methanol (30 ml), followed by adding 10 equivalents of lithium hydroxide (48 mg, 2.00 mmol). The mixture was stirred overnight at room temperature. After removal of solvents, the residue was dissolved in dichloromethane (30 ml). The dichloromethane solution was washed with brine, dried over magnesium sulfate and evaporated under reduced pressure. The residue was subject to the flash chromatography using ethyl acetate/methanol as eluent to give 58 mg of product. [Molecular formula: $C_{69}H_{125}N_{11}O_{14}S$; Exact Mass: 1363.91; MS (m/z): 1364.59 $(M+1)^+$, 1386.76 $(M+Na)^+$; TLC $R_f$: 0.28 (ethyl acetate/methanol=20/1); HPLC RT: 14.84 min (C8 reverse phase column: 250 mm; acetonitrile/water (0.05% trifluoroacetic acid); operation temp: 64° C.; Detector: 210 nm)].

Example 101

[(S)-(6-Methoxy-(5-methoxycarbonyl)-6-oxohexyl-thio)methyl-Sar]-3-[(γ-hydroxy)-N-MeLeu]-4-cyclosporin

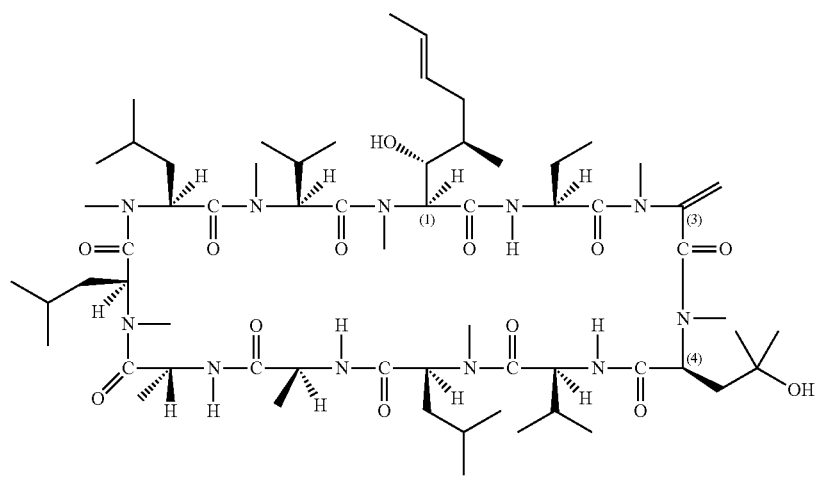

$C_{63}H_{111}N_{11}O_{13}$
Exact Mass: 1229.84
Mol. Wt.: 1230.65

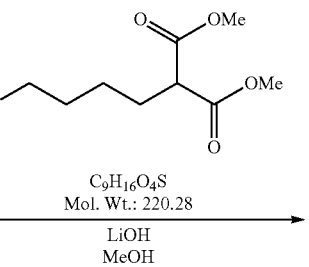

$C_9H_{16}O_4S$
Mol. Wt.: 220.28
LiOH
MeOH

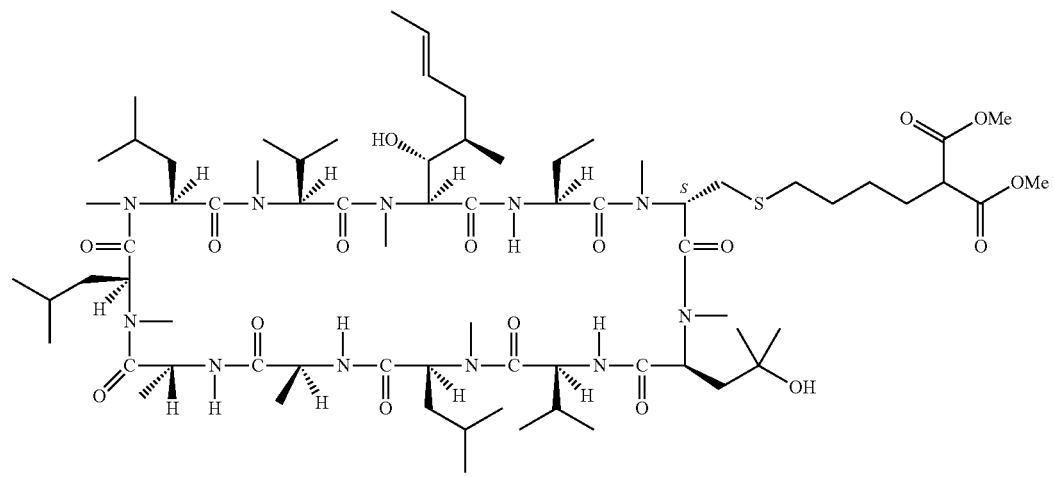

$C_{72}H_{127}N_{11}O_{17}S$
Exact Mass: 1449.91
Mol. Wt.: 1450.93

To a solution of [α-methylene-Sar]-3-[(γ-hydroxy)-N-MeLeu]-4-cyclosporin (500 mg, 0.41 mmol) and dimethyl 4-mercaptobutylmalonate (650 mg, 2.95 mmol) in methanol (80 ml) was added lithium hydroxide (110 mg, 4.58 mmol). The reaction mixture was stirred at room temperature overnight. Then most of solvent was evaporated under reduced pressure. Dichloromethane (100 ml) and water (30 ml) were added and separated. The organic layer was washed with water and brine, dried over magnesium sulfate and evaporated under reduced pressure. The residue was used for next step. [Molecular formula: $C_{72}H_{127}N_{11}O_{17}S$; Exact Mass: 1449.91; MS (m/z): 1450.37 (M+1)$^+$.

Example 102

[(S)-(6-Hydroxy-(5-hydroxymethyl)hexylthiomethyl-Sar]-3-[(γ-hydroxy)-N-MeLeu]-4-cyclosporin

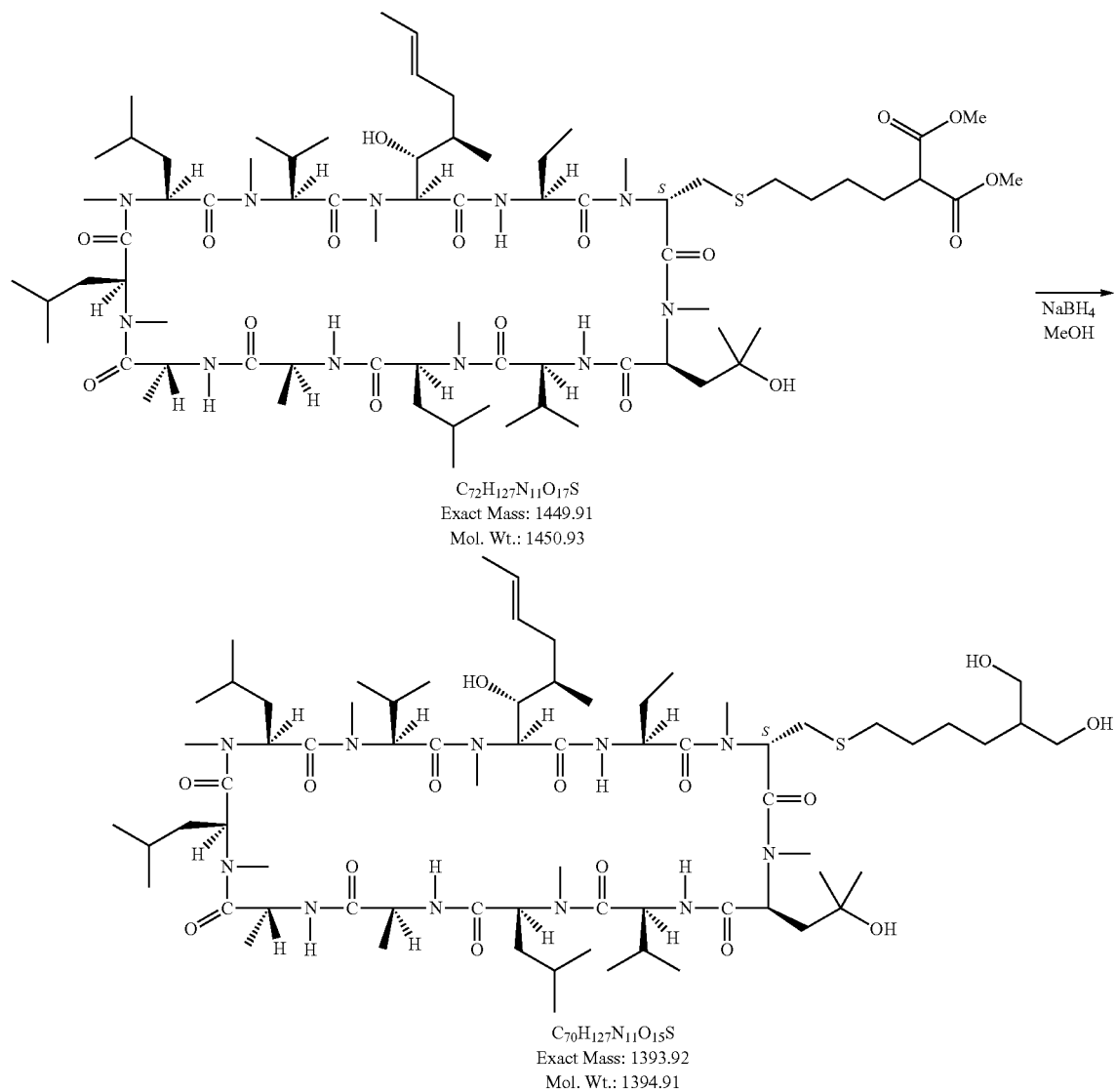

To a solution of [(S)-(6-methoxy-5-methoxycarbonyl)-6-oxohexylthiomethyl-Sar]-3-[(γ-hydroxy)-N-MeLeu]-4-cyclosporin (250 mg, 0.17 mmol) in methanol (40 ml) was added sodium borohydride (350 mg, 9.26 mmol) in portions. The reaction mixture was stirred at room temperature 3 hours. Then most of solvent was evaporated under reduced pressure. Dichloromethane (100 ml) and water (30 ml) were added and separated. The organic layer was washed with water and brine, dried over magnesium sulfate and evaporated under reduced pressure. The residue was purified by chromatography (dichloromethane/methanol=96/4) to give a pure product [Molecular formula: $C_{70}H_{127}N_{11}O_{15}S$; Exact Mass: 1393.92; MS (m/z): 1394.45 (M+1)⁻; TLC Rf: 0.25 (dichloromethane/methanol=95/5); HPLC RT: 12.62 min (C8 reverse phase column: 250 mm; acetonitrile/water (0.05% trifuloroacetic acid); operation temp: 64° C.; Detector: 210 nm)].

Example 103
[(S)-(2-Hydroxypropylthio)methyl-Sar]-3-[(γ-hydroxy)-N-MeLeu]-4-cyclosporin and [(R)-(2-Hydroxypropylthio)methyl-Sar]-3-[(γ-hydroxy)-N-MeLeu]-4-cyclosporin
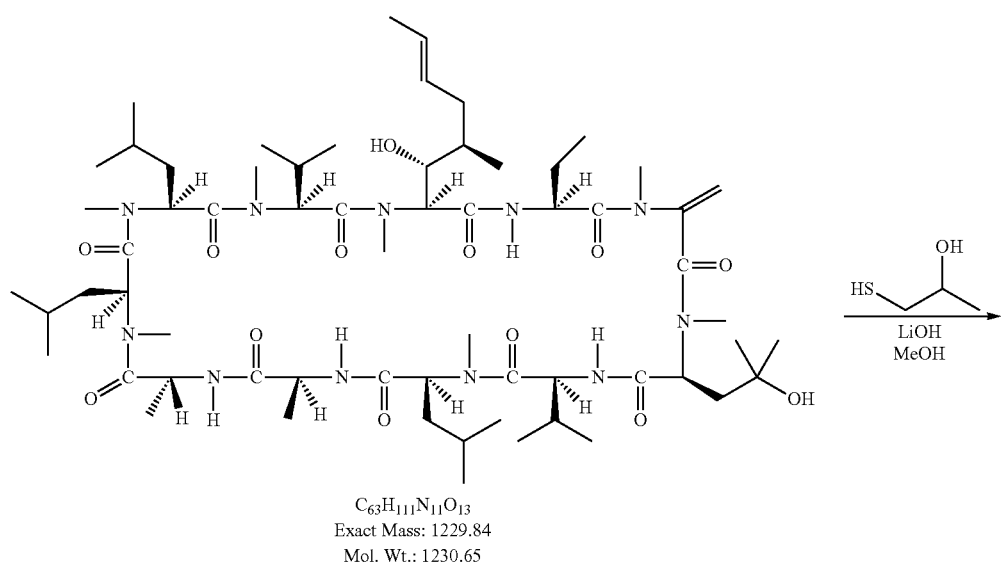
C₆₃H₁₁₁N₁₁O₁₃
Exact Mass: 1229.84
Mol. Wt.: 1230.65
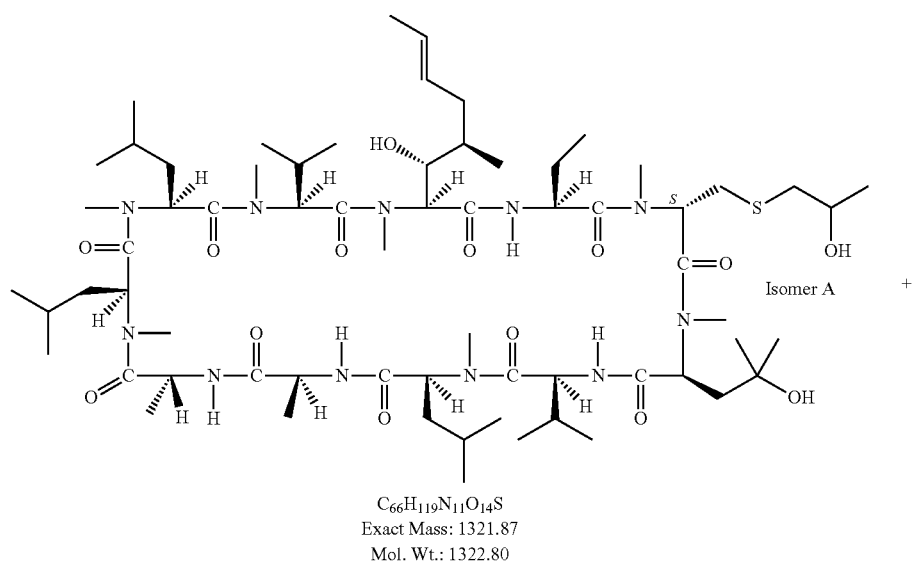
Isomer A +
C₆₆H₁₁₉N₁₁O₁₄S
Exact Mass: 1321.87
Mol. Wt.: 1322.80

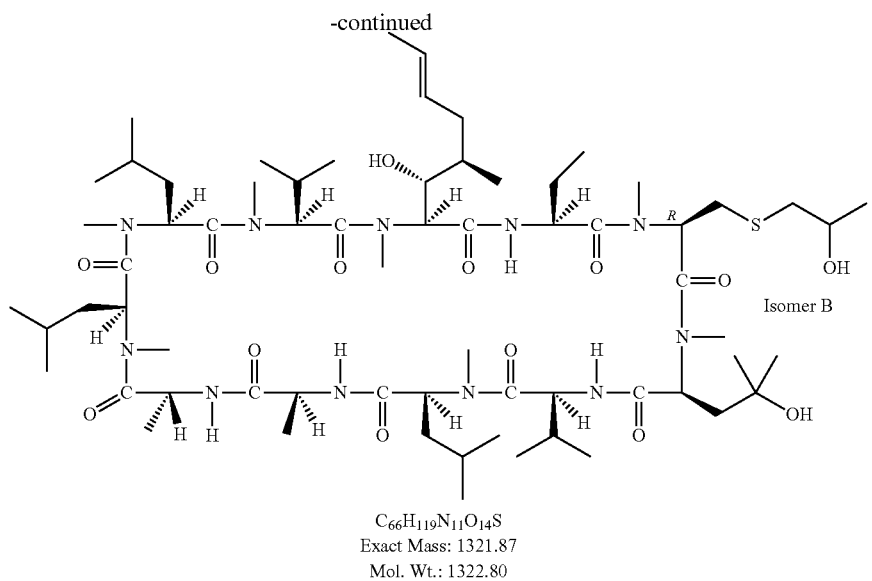

$C_{66}H_{119}N_{11}O_{14}S$
Exact Mass: 1321.87
Mol. Wt.: 1322.80

[α-Methylene-Sar]-3-[(γ-hydroxy)-N-MeLeu]-4-cyclosporin (0.246 g, 0.2 mmol) and 1-mercapto-2-propanol (0.184 g, 2 mmol) were dissolved in methanol (10 ml), followed by adding 10 equivalents of lithium hydroxide (48 mg). The mixture was stirred overnight at room temperature. After removal of solvent, the residue was dissolved in ethyl acetate (15 ml). The ethyl acetate solution was washed with brine, dried over magnesium sulfite and evaporated under reduced pressure. The residue was subject to a flash chromatography using ethyl acetate/methanol as eluent to give the product of isomer A as [(S)-(2-Hydroxypropylthio) methyl-Sar]-3-[(γ-hydroxy)-N-MeLeu]-4-cyclosporin and the product of isomer B as [(R)-(2-Hydroxypropylthio) methyl-Sar]-3-[(γ-hydroxy)-N-MeLeu]-4-cyclosporin [Molecular formula: $C_{66}H_{119}N_{11}O_{14}S$; Exact Mass: 1321.87; MS (m/z): 1322.50 (M+1)$^+$, 1344.76 (M+Na)$^+$; TLC $R_f$ (isomer A): 0.29 (methylene chloride/methanol=20/1, twice development); TLC $R_f$ (isomer B): 0.26 (methylene chloride/methanol=20/1, twice development); HPLC RT: 13.62 min (C8 reverse phase column: 250 mm; acetonitrile/water (0.05% trifluoroacetic acid); operation temp: 64° C.; Detector: 210 nm)].

Example 104

[(S)-(2-Methyl-4-oxypentan-2-ylthio)methyl-Sar]-3-[(γ-hydroxy)-NMeLeu]-4-cyclosporin

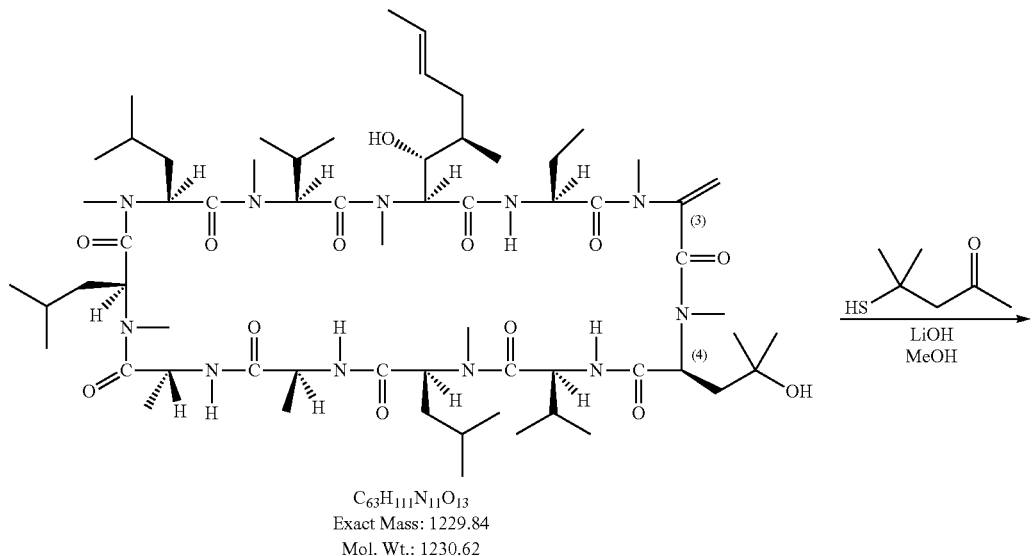

$C_{63}H_{111}N_{11}O_{13}$
Exact Mass: 1229.84
Mol. Wt.: 1230.62

-continued

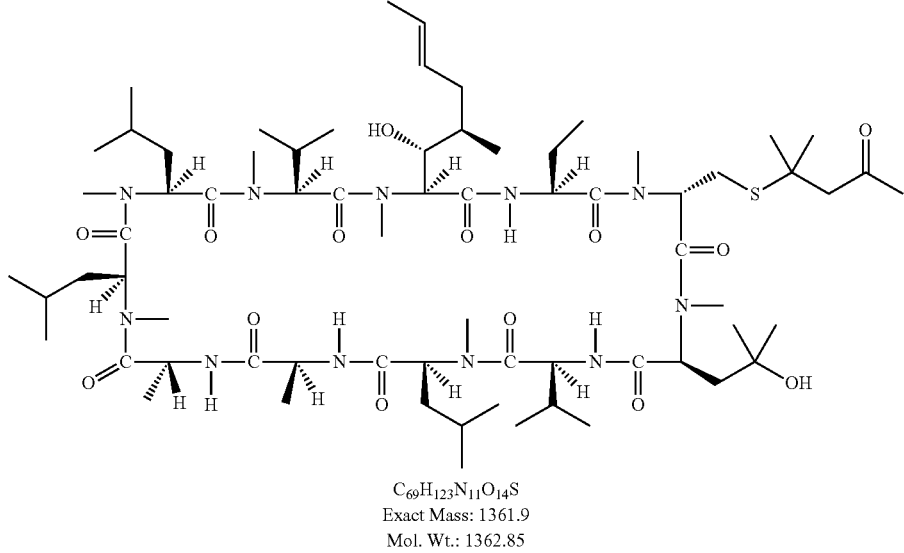

$C_{69}H_{123}N_{11}O_{14}S$
Exact Mass: 1361.9
Mol. Wt.: 1362.85

To a solution of [α-methylene-Sar]-3-[(γ-hydroxy)-NMeLeu]-4-cyclosporin (500 mg, 0.41 mmol) and 4-mercapto-4-methyl-2-pentanone (680 mg, 5.15 mmol) in methanol (25 ml) was added lithium hydroxide (160 mg, 6.66 mmol). The reaction mixture was stirred at room temperature for 3 days. Then most of the solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (ethyl acetate) to give the product [Molecular formula: $C_{69}H_{123}N_{11}O_{14}S$; Exact Mass: 1361.90; MS (m/z): 1362.50 (M+1)$^+$; TLC Rf: 0.47 (dichloromethane/methanol=97/3); HPLC RT: 15.51 min (C8 reverse phase column: 250 mm; acetonitrile/water (0.05% trifuloroacetic acid); operation temp: 64° C.; Detector: 210 nm)].

Example 105

[(S)-(2-Methyl-4-hydroxypentan-2-ylthio)methyl-Sar]-3-[(γ-hydroxy)-NMeLeu]-4-cyclosporin

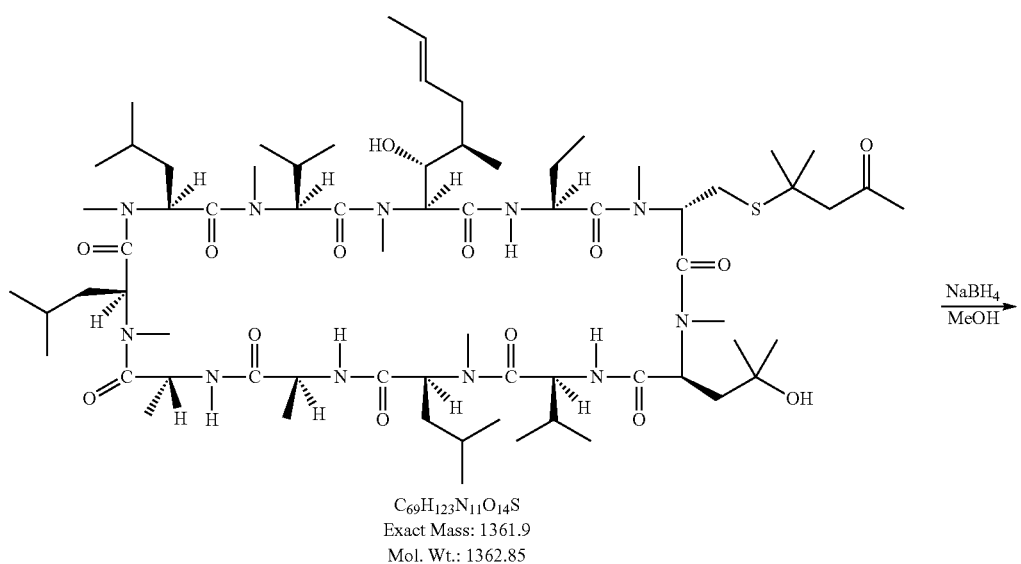

$C_{69}H_{123}N_{11}O_{14}S$
Exact Mass: 1361.9
Mol. Wt.: 1362.85

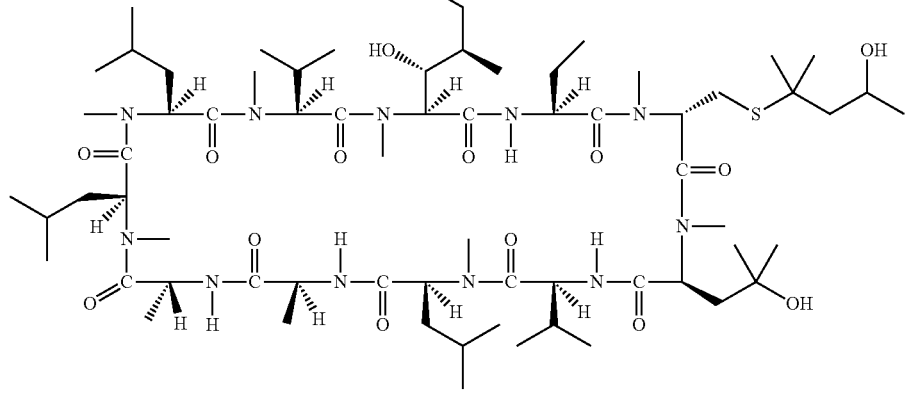

C$_{69}$H$_{125}$N$_{11}$O$_{14}$S
Exact Mass: 1363.91
Mol. Wt.: 1364.86

To a solution of [(S)-(2-methyl-4-oxypentan-2-ylthio)methyl-Sar]-3-[(γ-hydroxy)-N-MeLeu]-4-cyclosporin (68 mg, 0.03 mmol) in methanol (5 ml) were added sodium borohydride (36 mg, 0.95 mmol) in portions. After addition, the mixture was stirred at room temperature one hour. Most solvent was then evaporated under reduced pressure. Dichloromethane (30 ml) and water (30 ml) were added and the mixture was separated. The dichloromethane layer was washed with brine (30 ml), dried over magnesium sulfate and evaporated under reduced pressure. The residue was purified on silica gel column with dichloromethane/methanol (95/5) as eluent to give the product [Molecular formula: C$_{69}$H$_{125}$N$_{11}$O$_{14}$S; Exact Mass: 1363.91; MS (m/z): 1364.44 (M+1)$^+$; TLC Rf: 0.38 (dichloromethane/methanol=97/3); HPLC RT: 15.03 min (C8 reverse phase column: 250 mm; acetonitrile/water (0.05% trifuloroacetic acid); operation temp: 64° C.; Detector: 210 nm)].

Example 106

[(S)-((5-Methoxy-4-methoxycarbonyl)-5-oxopentyl-thio)methyl-Sar]-3-[(γ-hydroxy)-N-MeLeu]-4-cyclosporin

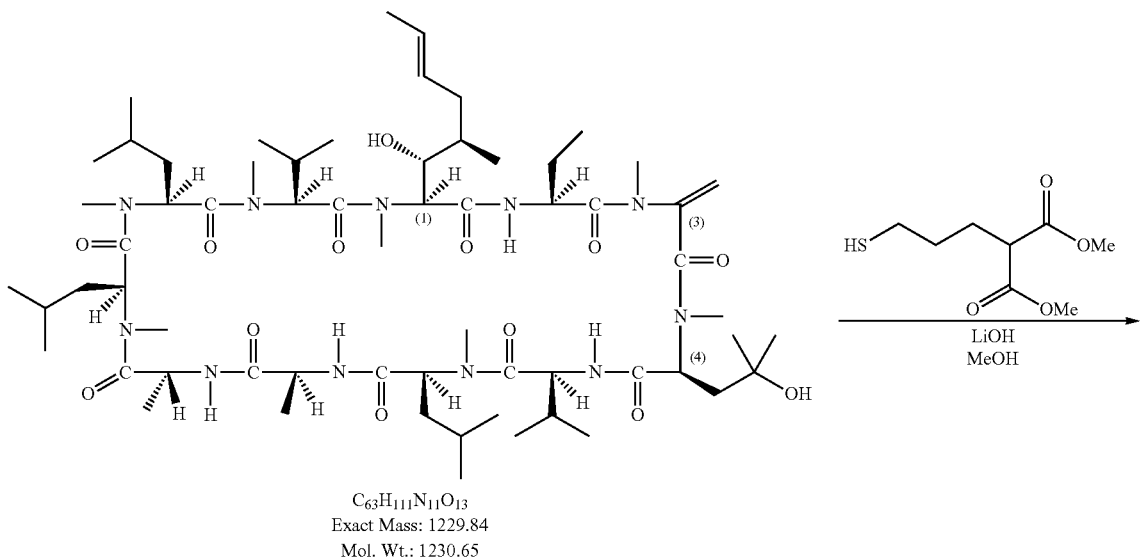

C$_{63}$H$_{111}$N$_{11}$O$_{13}$
Exact Mass: 1229.84
Mol. Wt.: 1230.65

-continued

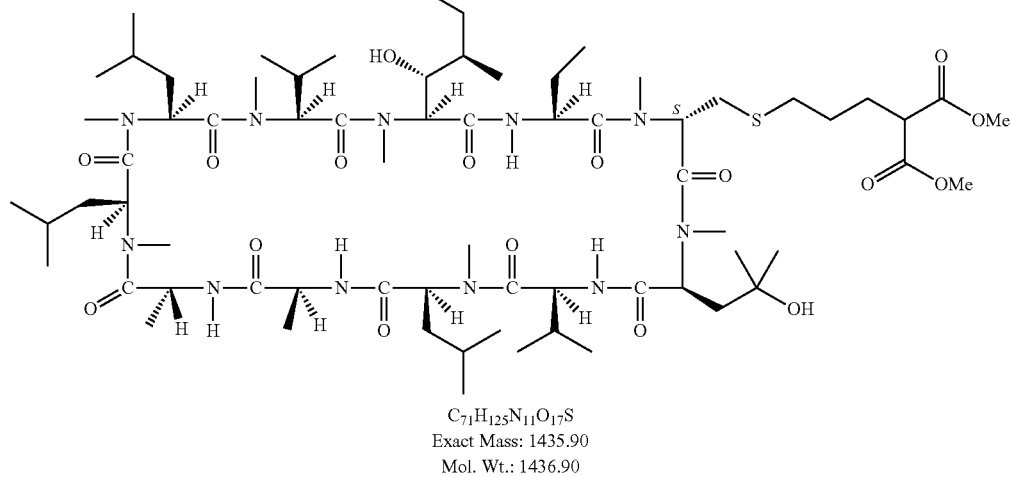

C₇₁H₁₂₅N₁₁O₁₇S
Exact Mass: 1435.90
Mol. Wt.: 1436.90

To a solution of [α-methylene-Sar]-3-[(γ-hydroxy)-N-MeLeu]-4-cyclosporin (580 mg, 0.47 mmol) and dimethyl 3-mercaptopropylmalonate (MW: 206.26, 600 mg, 2.91 mmol) in methanol (30 ml) was added lithium hydroxide (110 mg, 4.58 mmol). The reaction mixture was stirred at room temperature overnight. Then most of solvent was evaporated under reduced pressure. Dichloromethane (100 ml) and water (30 ml) were added and separated. The organic layer was washed with water and brine, dried over magnesium sulfate and evaporated under reduced pressure. The residue was used for next step. [Molecular formula: $C_{71}H_{125}N_{11}O_{17}S$; Exact Mass: 1435.90; MS (m/z): 1436.45 (M+1)⁺.

Example 107

[(S)-((5-Hydroxy-4-hydroxymethyl)pentylthio)methyl-Sar]-3-[(γ-hydroxy)-N-MeLeu]-4-cyclosporin

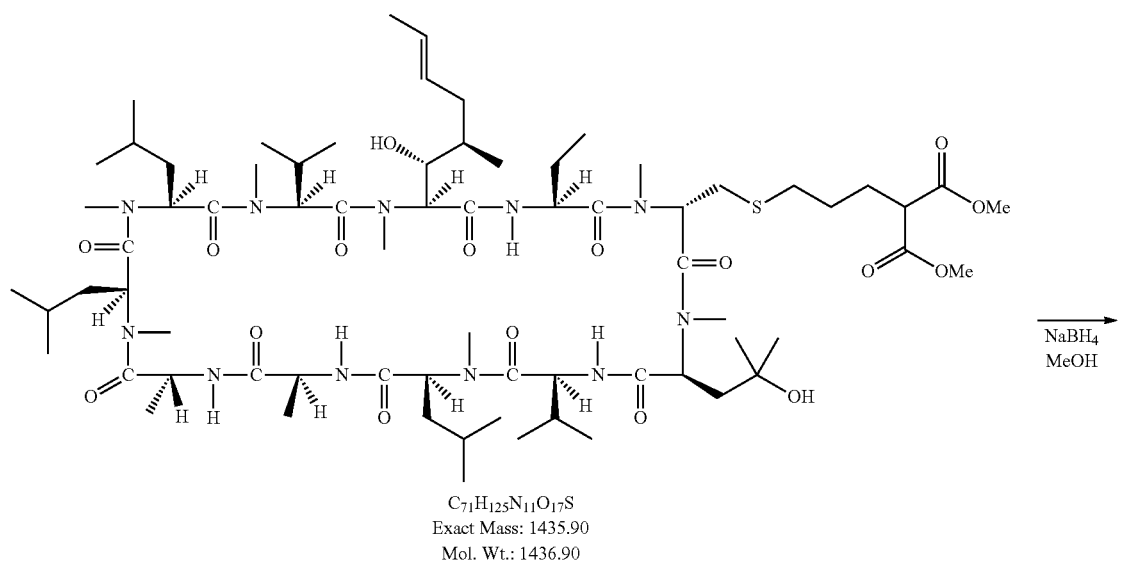

C₇₁H₁₂₅N₁₁O₁₇S
Exact Mass: 1435.90
Mol. Wt.: 1436.90

NaBH₄
MeOH

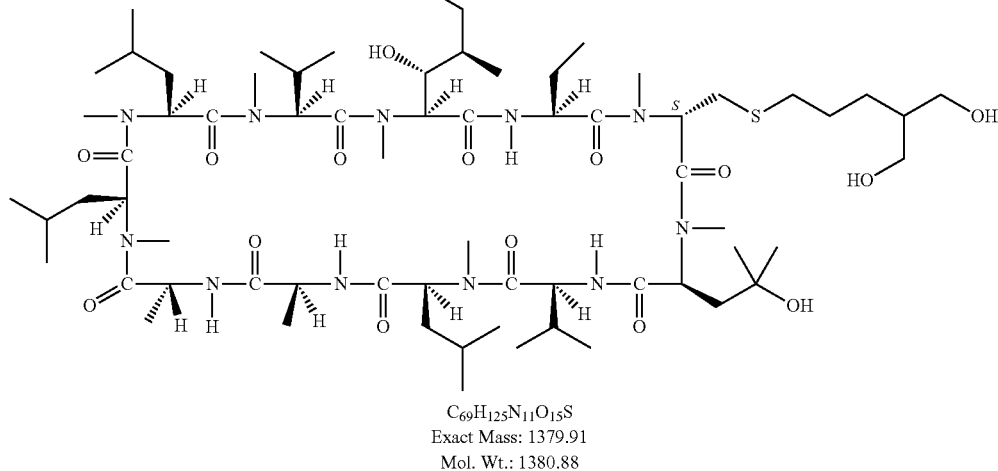

C₆₉H₁₂₅N₁₁O₁₅S
Exact Mass: 1379.91
Mol. Wt.: 1380.88

To a solution of [(S)-((5-methoxy-4-methoxycarbonyl)-5-oxopentylthio)methyl-Sar]-3-[(γ-hydroxy)-N-MeLeu]-4-cyclosporin (280 mg, 0.19 mmol) in methanol (30 ml) was added sodium borohydride (360 mg, 9.52 mmol) in portions. The reaction mixture was stirred at room temperature 3 hours. Then most of the solvent was evaporated under reduced pressure. Dichloromethane (100 ml) and water (30 ml) were added and separated. The organic layer was washed with water and brine, dried over magnesium sulfate and evaporated under reduced pressure. The residue was purified by chromatography (dichloromethane/methanol=96/4) to give a pure product [Molecular formula: $C_{69}H_{125}N_{11}O_{15}S$; Exact Mass: 1379.91; MS (m/z): 1380.49 (M+1)⁻; TLC Rf: 0.23 (dichloromethane/methanol=95/5); HPLC RT: 12.05 min (C8 reverse phase column: 250 mm; acetonitrile/water (0.05% trifuloroacetic acid); operation temp: 64° C.; Detector: 210 nm)].

Example 108

[(R)-(2-(N,N-Diethylamino)ethoxy)methyl-Sar]-3-[(γ-hydroxy)-NMeLeu]-4-cyclosporin

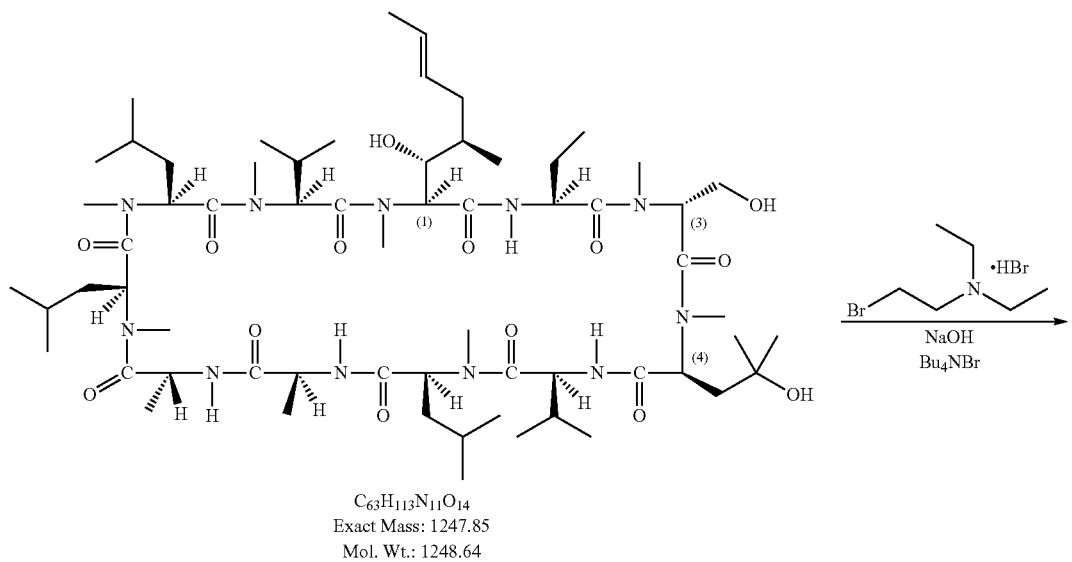

C₆₃H₁₁₃N₁₁O₁₄
Exact Mass: 1247.85
Mol. Wt.: 1248.64

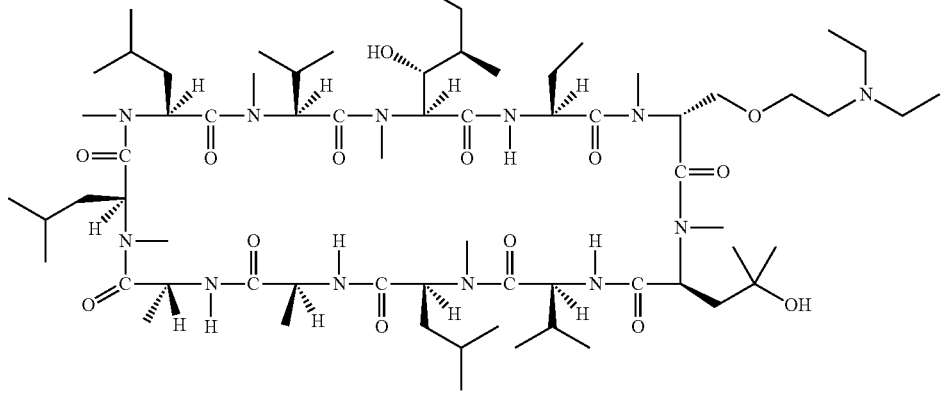

C₆₉H₁₂₆N₁₂O₁₄
Exact Mass: 1346.95
Mol. Wt.: 1347.81

To a solution of [(R)-α-hydroxymethyl-Sar]-3-[(γ-hydroxy)-N-MeLeu]-4-cyclosporin (0.25 g, 0.20 mmol) in benzene (30 ml) were added a solution of sodium hydroxide (1.00 g, 25 mmol) in water (2 ml), 2-bromo-N,N-diethylethylamine hydrobromide (MW: 261, 2.80 g, 10.72 mmol) and tetra-n-butylammonium bromide (0.2 g, 0.62 mmol). The mixture was stirred at 30° C. for 20 hours. Then ice water (30 ml) was added and the mixture was separated. The aqueous layer was extracted with dichloromethane (25 ml). The combined organic layers were washed with brine, dried over magnesium sulfate and concentrated under reduced pressure. The residue was purified by chromatography (dichloromethane/methanol=96/4) to give 240 mg of product [Molecular Formula: $C_{69}H_{126}N_{12}O_{14}$; Exact Mass: 1346.95; MS (m/z): 1347.59 (M+1)⁺; TLC Rf: 0.41 (dichloromethane/methanol=9/1); HPLC RT: 12.20 min (C8 reverse phase column: 250 mm; acetonitrile/0.077% ammonium acetate in water; operation temperature: 64° C.; detector: 210 nm)].

Example 109

[(R)-(2-(N-Piperidinyl)ethoxy)methyl-Sar]-3-[(γ-hydroxy)-NMeLeu]-4-cyclosporin

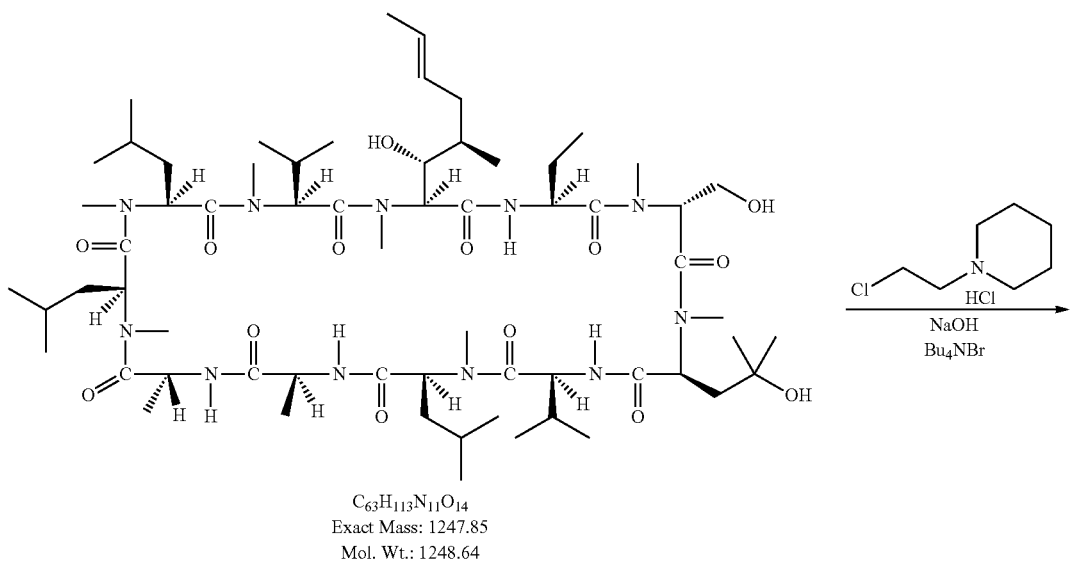

C₆₃H₁₁₃N₁₁O₁₄
Exact Mass: 1247.85
Mol. Wt.: 1248.64

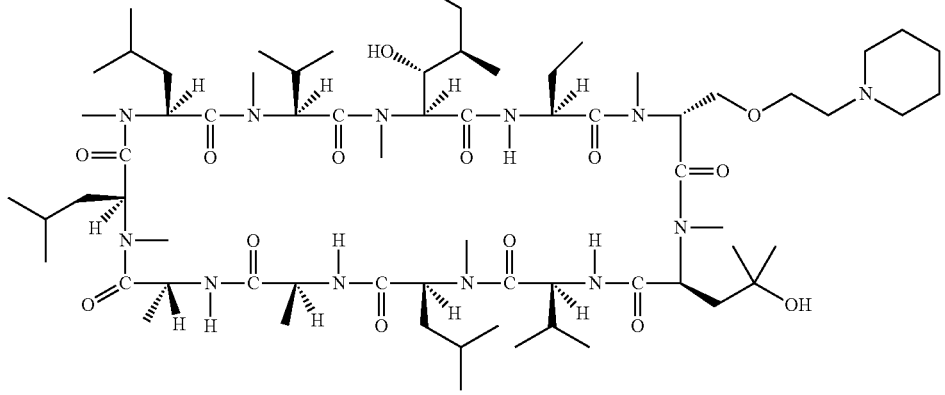

$C_{70}H_{126}N_{12}O_{14}$
Exact Mass: 1358.95
Mol. Wt.: 1359.82

To a solution of [(R)-α-hydroxymethyl-Sar]-3-[(γ-hydroxy)-N-MeLeu]-4-cyclosporin (300 mg, 0.24 mmol) in benzene (15 ml) were added sodium hydroxide (0.38 g. 9.60 mmol), tetramethylammonium hydroxide pentahydrate (0.44 g, 2.40 mmol) and 1-(2-chloroethyl)piperidine hydrochloride (MW: 184.10, 0.44 g, 2.40 mmol). The mixture was stirred at 30° C. for 36 hours. Then ice water (20 ml) was added and the mixture was separated. The aqueous layer was extracted with ethyl acetate (20 ml). The combined organic layers were washed with brine, dried over magnesium sulfate and evaporated under reduced pressure. The residue was purified by chromatography on silica gel with dichloromethane/methanol (95/5) as eluent to give 100 mg of pure product [Molecular Formula: $C_{70}H_{126}N_{12}O_{14}$; Exact Mass: 1358.95; MS (m/z): 1359.69 (M+1)$^+$, 1381.75 (M+Na)$^+$; TLC R$_f$: 0.05 (dichloromethane/methanol=20/1); HPLC RT: 12.43 min (C8 reverse phase column: 150 mm; acetonitrile/water (0.05% trifluoroacetic acid); operation temperature: 64° C.; detector: 210 nm)].

Example 110

[(R)-(2-(N-Morpholino)ethoxy)methyl-Sar]-3-[(γ-hydroxy)-NMeLeu]-4-cyclosporin

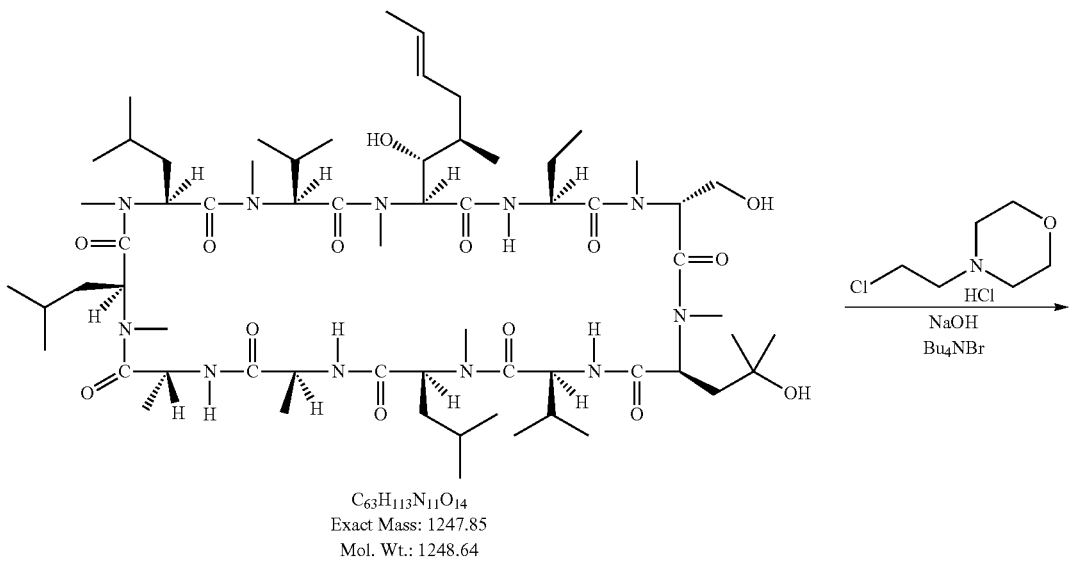

$C_{63}H_{113}N_{11}O_{14}$
Exact Mass: 1247.85
Mol. Wt.: 1248.64

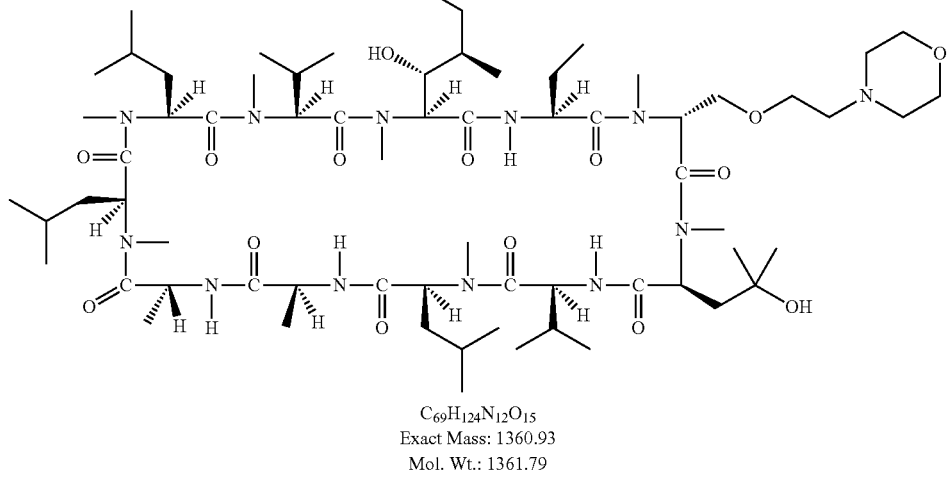

C$_{69}$H$_{124}$N$_{12}$O$_{15}$
Exact Mass: 1360.93
Mol. Wt.: 1361.79

To a solution of [(R)-α-hydroxymethyl-Sar]-3-[(γ-hydroxy)-N-MeLeu]-4-cyclosporin (0.50 g, 0.40 mmol) in benzene (20 ml) were added sodium hydroxide (0.64 g, 16.00 mmol), tetramethylammonium hydroxide pentahydrate (0.72 g, 4.00 mmol) and 4-(2-chloroethyl)morphorline hydrochloride (MW: 186.08, 0.74 g, 4.00 mmol). The mixture was stirred at 30° C. for a week. Then ice water (20 ml) was added and the mixture was separated. The aqueous layer was extracted with ethyl acetate (20 ml). The combined organic layers were washed with brine, dried over magnesium sulfate and evaporated under reduced pressure. The residue was purified by chromatography on silica gel with dichloromethane/methanol (95/5) as eluent to give 60 mg of product [Molecular Formula: C$_{69}$H$_{124}$N$_{12}$O$_{15}$; Exact Mass: 1360.93; MS (m/z): 1361.63 (M+1)$^-$, 1383.75 (M+Na)$^+$; TLC R$_f$: 0.10 (dichloromethane/methanol=5:1); HPLC RT: 11.49 min (C8 reverse phase column: 150 mm; acetonitrile/water (0.05% trifluoroacetic acid); operation temperature: 64° C.; detector: 210 nm)].

Example 111

[(R)-(2-(N,N-Dimethylamino)ethoxy)methyl-Sar]-3-[(γ-hydroxy)-NMeLeu]-4-cyclosporin

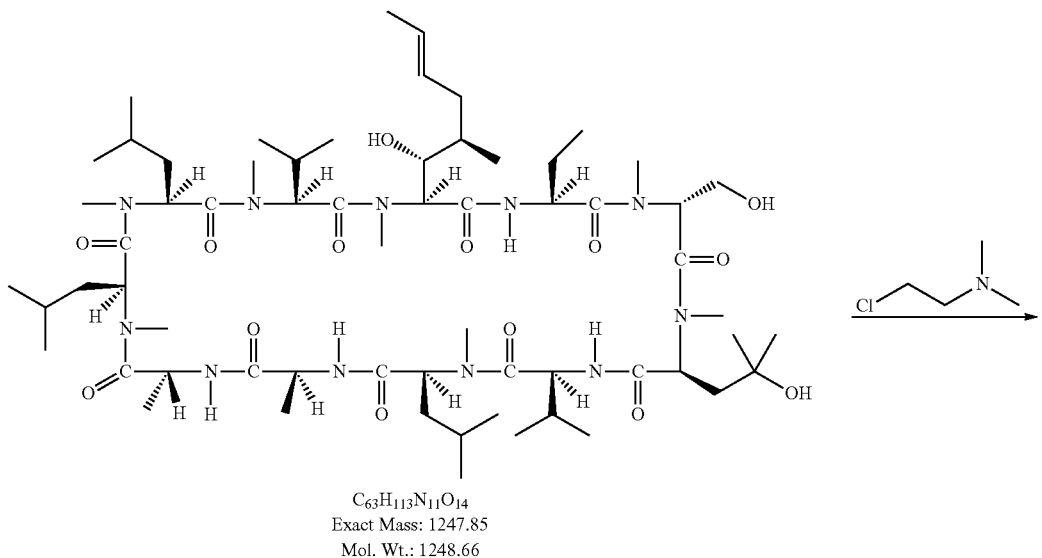

C$_{63}$H$_{113}$N$_{11}$O$_{14}$
Exact Mass: 1247.85
Mol. Wt.: 1248.66

-continued

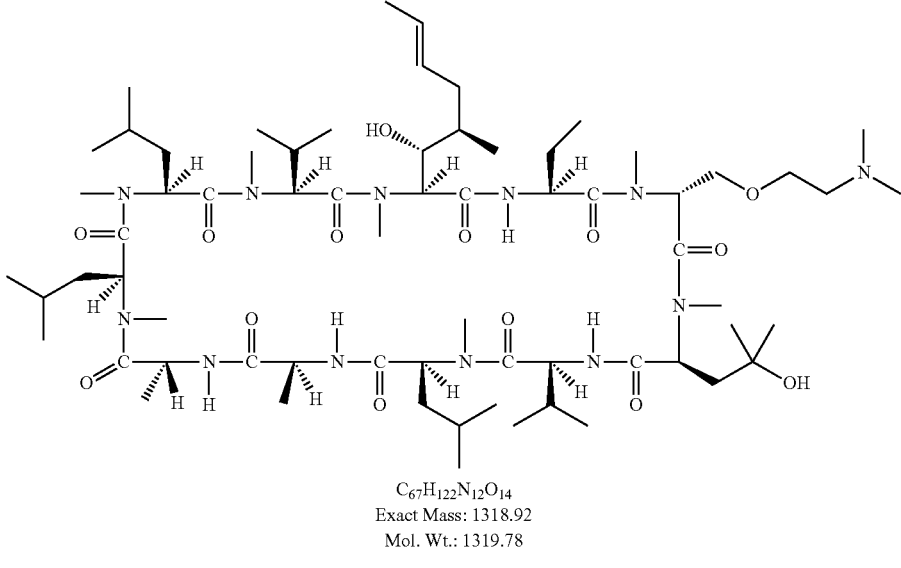

$C_{67}H_{122}N_{12}O_{14}$
Exact Mass: 1318.92
Mol. Wt.: 1319.78

To a solution of [(R)-α-hydroxymethyl-Sar]-3-[(γ-hydroxy)-N-MeLeu]-4-cyclosporin (0.37 g, 0.30 mmol) in benzene (15 ml) were added sodium hydroxide (0.48 g, 12.00 mmol), tetramethylammonium hydroxide pentahydrate (0.54 g, 3.00 mmol) and 3-dimethylaminoethyl chloride hydrochloride (0.43 g, 3.00 mmol). The mixture was stirred at 30° C. for 36 hours. Then ice water (20 ml) was added and the mixture was separated. The aqueous layer was extracted with ethyl acetate (20 ml). The combined organic layers were washed with brine, dried over magnesium sulfate and evaporated under reduced pressure. The residue was purified by chromatography on silica gel with dichloromethane/methanol (95/5) as eluent to give 90 mg of pure product [Molecular Formula: $C_{67}H_{122}N_{12}O_{14}$; Exact Mass: 1318.92; MS (m/z): 1319.70 (M+1)$^-$, 1341.80 (M+Na)$^+$); TLC $R_f$: 0.05 (dichloromethane/methanol=5:1); HPLC RT: 11.43 min (C8 reverse phase column: 150 mm; acetonitrile/water (0.05% trifluoroacetic acid); operation temperature: 64° C.; detector: 210 nm)].

Example 112

[(R)-(2-(N-Pyrrolidinyl)ethoxy)methyl-Sar]-3-[(γ-hydroxy)-NMeLeu]-4-cyclosporin

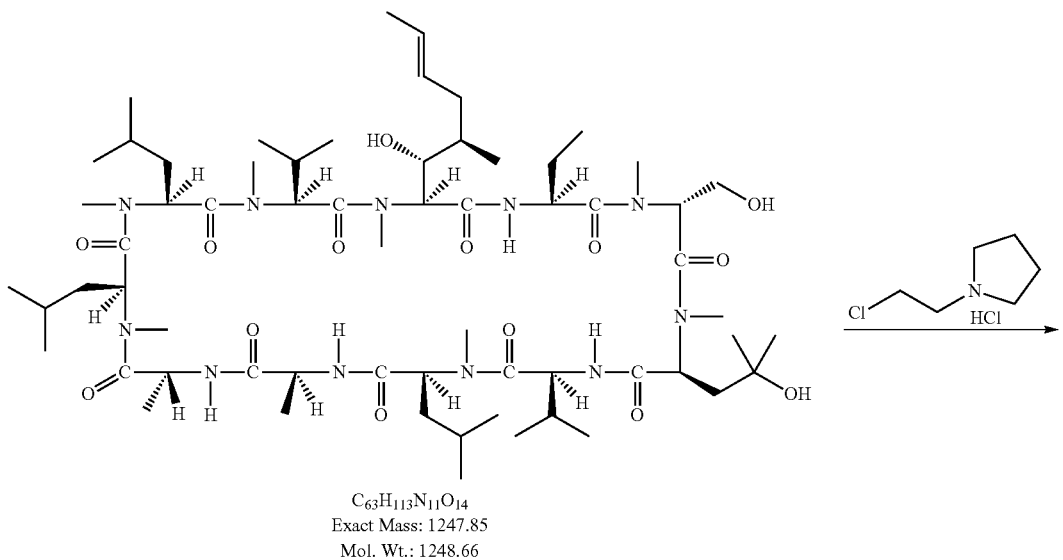

$C_{63}H_{113}N_{11}O_{14}$
Exact Mass: 1247.85
Mol. Wt.: 1248.66

-continued

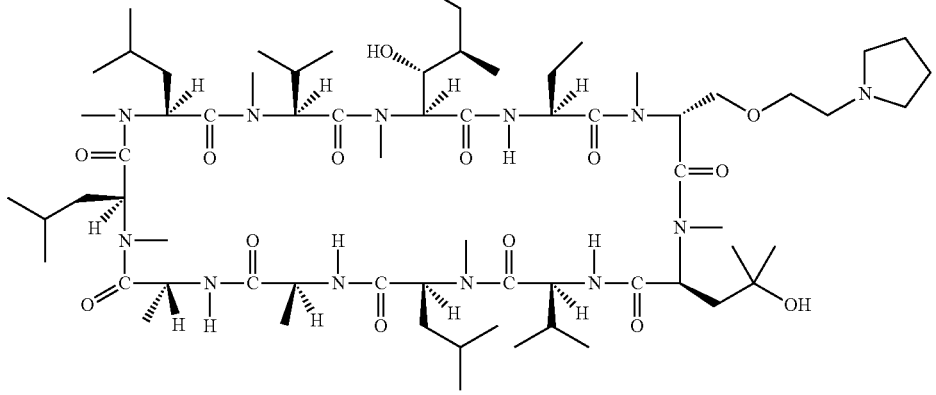

C₆₃H₁₂₄N₁₂O₁₄
Exact Mass: 1344.94
Mol. Wt.: 1345.82

To a solution of [(R)-α-hydroxymethyl-Sar]-3-[(γ-hydroxy)-N-MeLeu]-4-cyclosporin (0.38 g, 0.30 mmol) in benzene (15 ml) were added sodium hydroxide (0.48 g, 12.00 mmol), tetramethylammonium hydroxide pentahydrate (0.54 g, 3.00 mmol) and 1-(2-chloroethyl)pyrrolidine hydrochloride (0.44 g, 3.00 mmol). The mixture was stirred at 30° C. for 36 hours. Then ice water (20 ml) was added and the mixture was separated. The aqueous layer was extracted with ethyl acetate (20 ml). The combined organic layers were washed with brine, dried over magnesium sulfate and evaporated under reduced pressure. The residue was purified by chromatography on silica gel with dichloromethane/methanol (95/5) as eluent to give to give 120 mg of the expected isomer [Molecular Formula: $C_{69}H_{124}N_{12}O_{14}$; Exact Mass: 1344.94; MS (m/z): 1345.62 (M+1)⁺, 1367.76 (M+Na)⁺; TLC $R_f$: 0.05 (dichloromethane/methanol=10/1); HPLC RT: 12.09 min (C8 reverse phase column: 150 mm; acetonitrile/water (0.05% trifluoroacetic acid); operation temperature: 64° C.; detector: 210 nm)].

Example 113

[(R)-(Ethoxycarbonylmethoxy)methyl-Sar]-3-[(γ-hydroxy)-NMeLeu]-4-cyclosporin

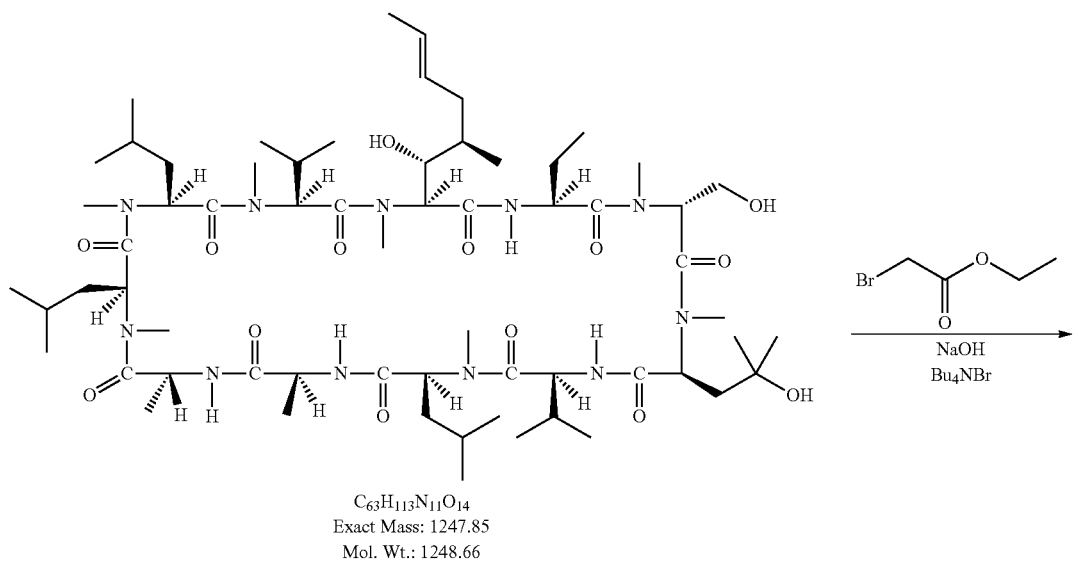

C₆₃H₁₁₃N₁₁O₁₄
Exact Mass: 1247.85
Mol. Wt.: 1248.66

-continued

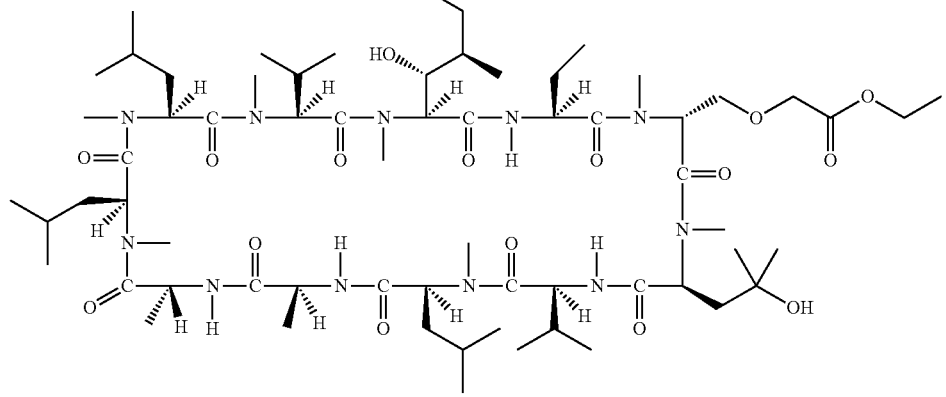

$C_{67}H_{119}N_{11}O_{16}$
Exact Mass: 1333.88
Mol. Wt.: 1334.75

To a solution of [(R)-α-hydroxymethyl-Sar]-3-[(γ-hydroxy)-N-MeLeu]-4-cyclosporin (0.36 g, 0.29 mmol) in benzene (20 ml) were added a solution of sodium hydroxide (0.60 g, 15.00 mmol) in water (1 ml), ethyl bromoacetate (1.60 g, 9.58 mmol) and tetra-n-butylammonium bromide (0.20 g, 0.62 mmol). The mixture was stirred at room temperature for 10 hours. After diluted with ice water, the mixture was separated. The aqueous layer was extracted with dichloromethane (15 ml). The combined organic layers were washed with brine, dried over magnesium sulfate and evaporated under reduced pressure. The residue was purified by chromatography (dichloromethane/methanol=97/3) to give the product [Molecular formula: $C_{67}H_{119}N_{11}O_{16}$; Exact Mass: 1333.88; MS (m/z): 1334.50 (M+1)$^+$; TLC $R_f$: 0.35 (dichloromethane/methanol=95/5); HPLC RT: 15.16 min (C8 reverse phase column: 250 mm; acetonitrile/0.077% NH$_4$OAc in water; operation temperature: 64° C.; Detector: 210 nm)].

Example 114

[(R)-(2-Hydroxyethoxy)methyl-Sar]-3-[(γ-hydroxy)-NMeLeu]-4-cyclosporin

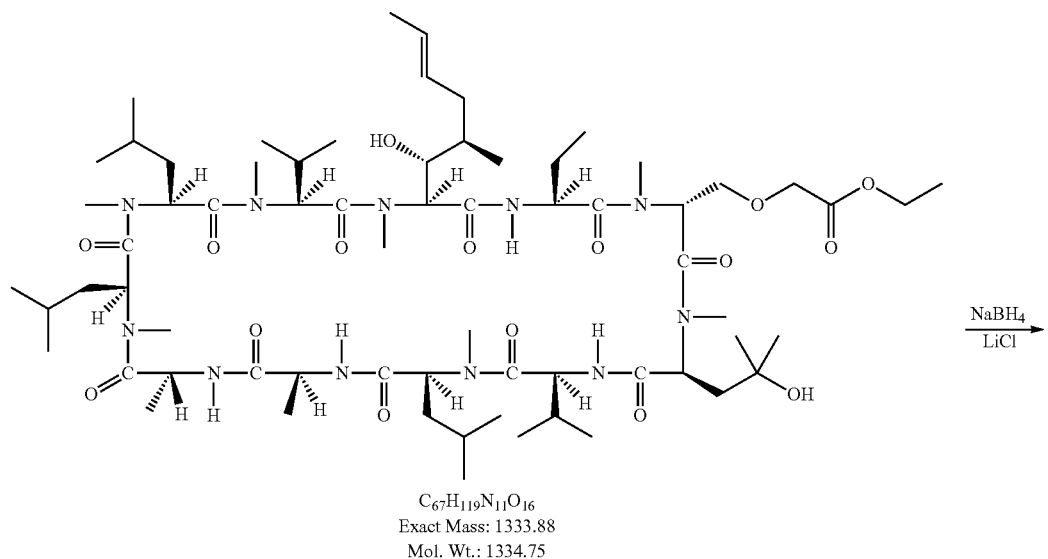

$C_{67}H_{119}N_{11}O_{16}$
Exact Mass: 1333.88
Mol. Wt.: 1334.75

-continued

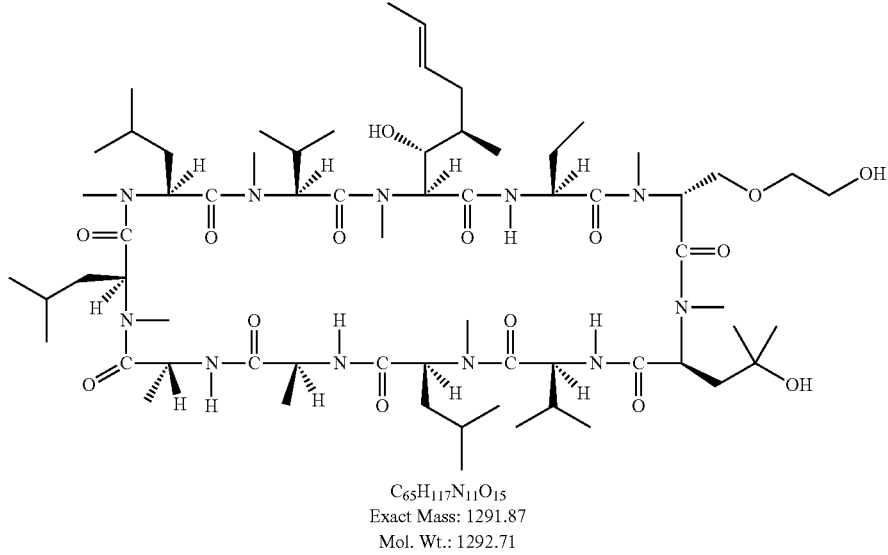

C$_{65}$H$_{117}$N$_{11}$O$_{15}$
Exact Mass: 1291.87
Mol. Wt.: 1292.71

To a solution of [(R)-(ethoxycarbonylmethoxy)methyl-Sar]-3-[(γ-hydroxy)-N-MeLeu]-4-cyclosporin (0.23 g, 0.17 mmol) in methanol (30 ml) were added lithium chloride (0.30 g, 7.14 mmol) and sodium borohydride (0.66 g, 17.46 mmol) in portions. After addition, the mixture was stirred at room temperature overnight. Most solvent was then evaporated under reduced pressure. Ethyl acetate (50 ml) and water (50 ml) were added. The ethyl acetate layer was separated and washed with brine (30 ml), dried over magnesium sulfate and evaporated under reduced pressure. The residue was purified on silica gel column with (dichloromethane/methanol=95/5) to give the product [Molecular formula: C$_{65}$H$_{117}$N$_{11}$O$_{15}$; Exact Mass: 1291.87; MS (m/z): 1292.51(M+1)$^+$; TLC Rf: 0.28 (dichloromethane/methanol=9/1); HPLC RT: 12.55 min (C8 reverse phase column: 250 mm; acetonitrile/water (0.05% trifuloroacetic acid); operation temp: 64° C.; Detector: 210 nm)].

Example 115

[(R)-(2-(1,3-Dioxan-2-yl)ethoxy)methyl-Sar]-3-[(γ-hydroxy)-NMeLeu]-4-cyclosporin

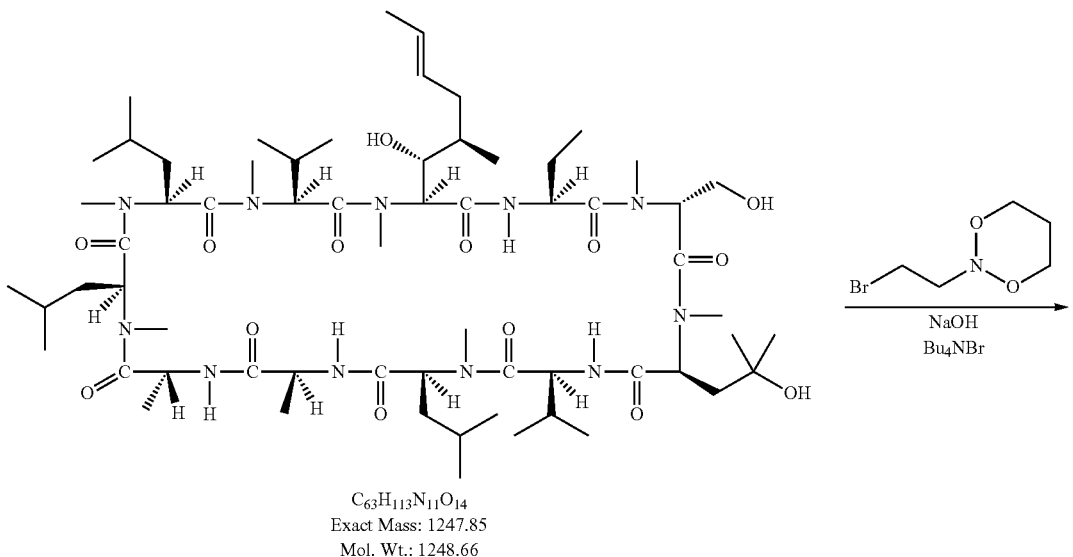

C$_{63}$H$_{113}$N$_{11}$O$_{14}$
Exact Mass: 1247.85
Mol. Wt.: 1248.66

-continued

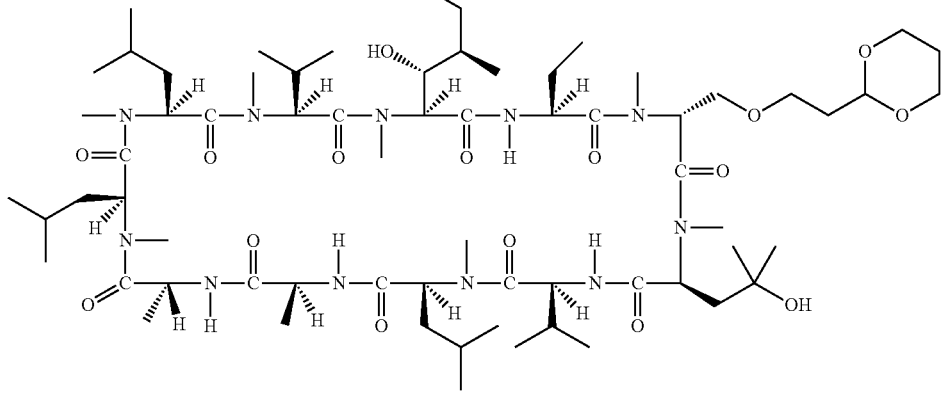

C₆₉H₁₂₃N₁₁O₁₆
Exact Mass: 1361.91
Mol. Wt.: 1362.80

[(R)-Hydroxymethyl-Sar]-3-[(γ-hydroxy)-N-MeLeu]-4-cyclosporin (5.00 g, 4.01 mmol) was dissolved in benzene (100 ml). 2-(2-Bromoethyl)-1,3-dioxane (7.82 g, 40.10 mmol), tetra-n-butylammonium bromide (0.99 g, 3.09 mmol), sodium hydroxide (3.21 g, 8.02 mmol) and water (3.3 ml) were added. The reaction mixture was stirred at 35° C. for nine hours. And the stirring was continued overnight at room temperature. Then 50 ml of brine was added and the mixture was separated. The aqueous layer was extracted with ethyl acetate (25 ml×2). The combined organic layers were dried over magnesium sulfate and evaporated under reduced pressure. After purified on silica gel with hexane/acetone as eluent, 1.50 g of product obtained [Molecular Formula: $C_{69}H_{123}N_{11}O_{16}$; Exact Mass: 1361.91; (m/z): 1362.64 (M+1)⁺, 1384.85 (M+Na)⁻].

Example 116

[(R)-(2-Formylethoxy)methyl-Sar]-3-[(γ-hydroxy)-NMeLeu]-4-cyclosporin

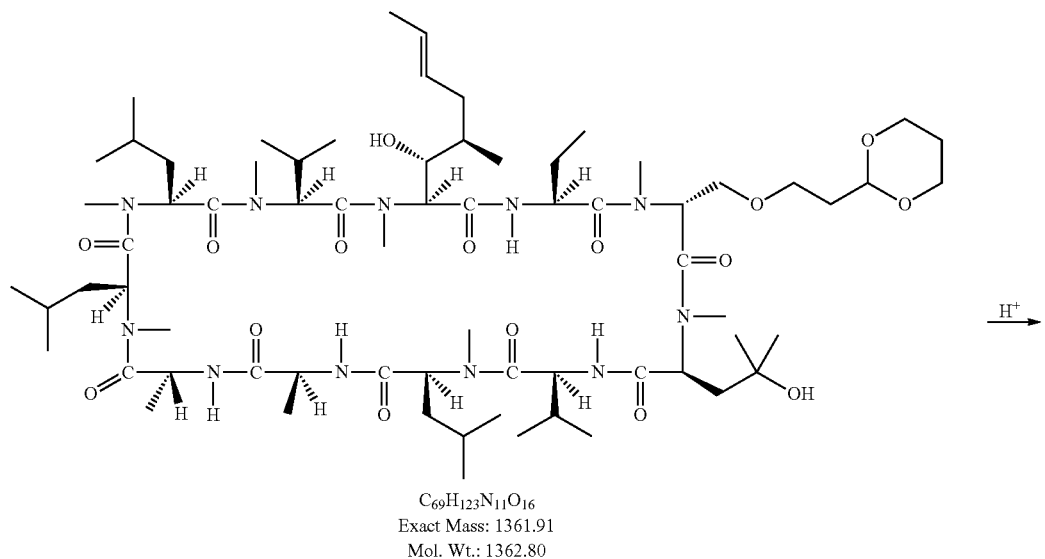

C₆₉H₁₂₃N₁₁O₁₆
Exact Mass: 1361.91
Mol. Wt.: 1362.80

H⁺→

-continued

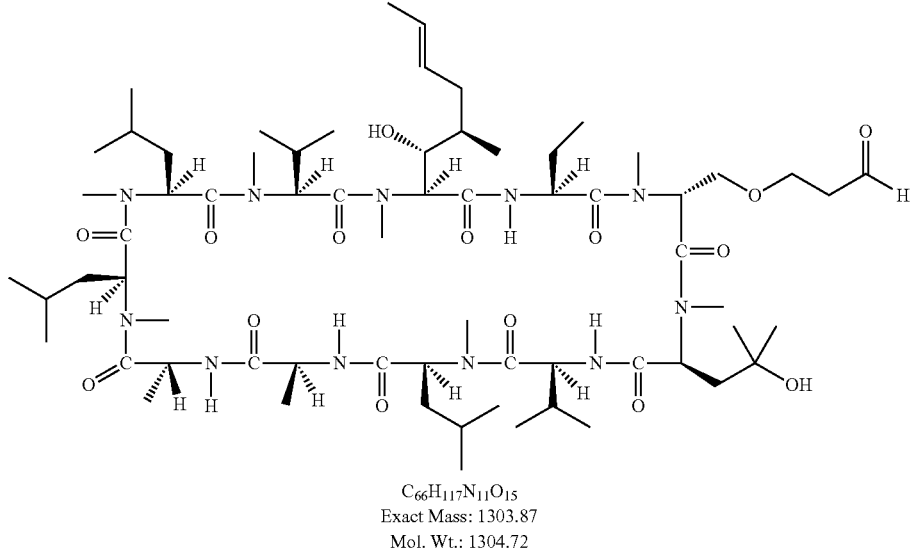

C<sub>66</sub>H<sub>117</sub>N<sub>11</sub>O<sub>15</sub>
Exact Mass: 1303.87
Mol. Wt.: 1304.72

[(R)-(2-(1,3-Dioxan-2-yl)ethoxy)methyl-Sar]-3-[(γ-hydroxy)-N-MeLeu]-4-cyclosporin (1.29 g, 0.95 mmol) was dissolved in dioxane (25 ml), followed by adding hydrochloric acid solution (1 N, 25 ml). The reaction mixture was stirred overnight at room temperature. Most of dioxane was evaporated under reduced pressure. Then the aqueous layer was extracted with ethyl acetate (25 ml×2). The combined ethyl acetate layers were dried over magnesium sulfate and evaporated under reduced pressure. The residue was purified on silica gel with hexane/acetone as eluent to give 600 mg of product [Molecular Formula: $C_{66}H_{117}N_{11}O_{15}$; Exact Mass: 1303.87; MS (m/z): 1304.59 $(M+1)^+$, 1326.78 $(M+Na)^+$; HPLC RT: 14.2 min (C8 reverse phase column: 250 mm; acetonitrile/water (0.05% trifluoroacetic acid); operation temperature: 64° C.; detector: 210 nm)].

Example 117

[(R)-(3-(N-Morpholino)propoxy)methyl-Sar]-3-[(γ-hydroxy)-NMeLeu]-4-cyclosporin

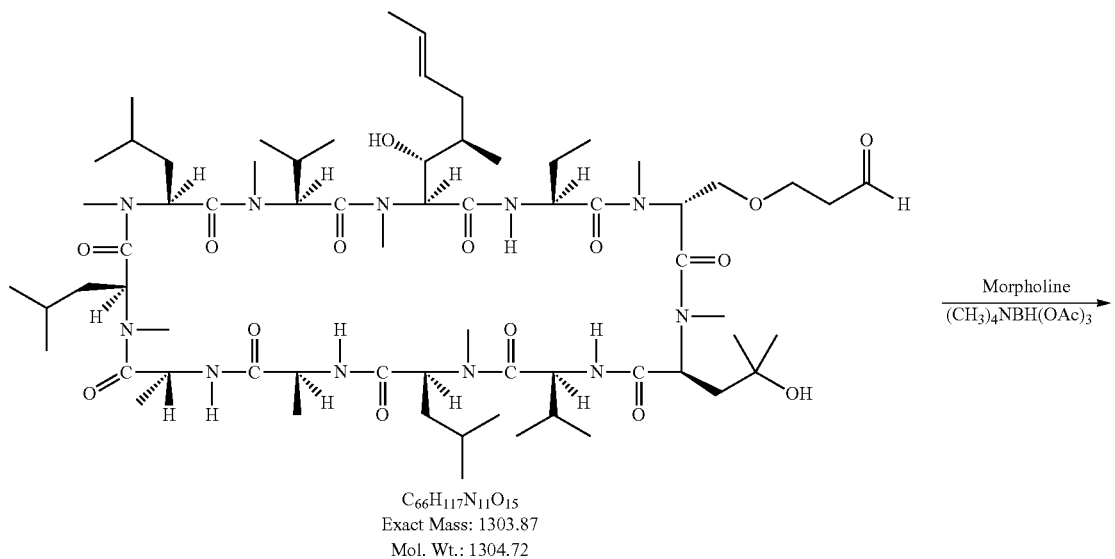

C<sub>66</sub>H<sub>117</sub>N<sub>11</sub>O<sub>15</sub>
Exact Mass: 1303.87
Mol. Wt.: 1304.72

Morpholine
(CH<sub>3</sub>)<sub>4</sub>NBH(OAc)<sub>3</sub>

-continued

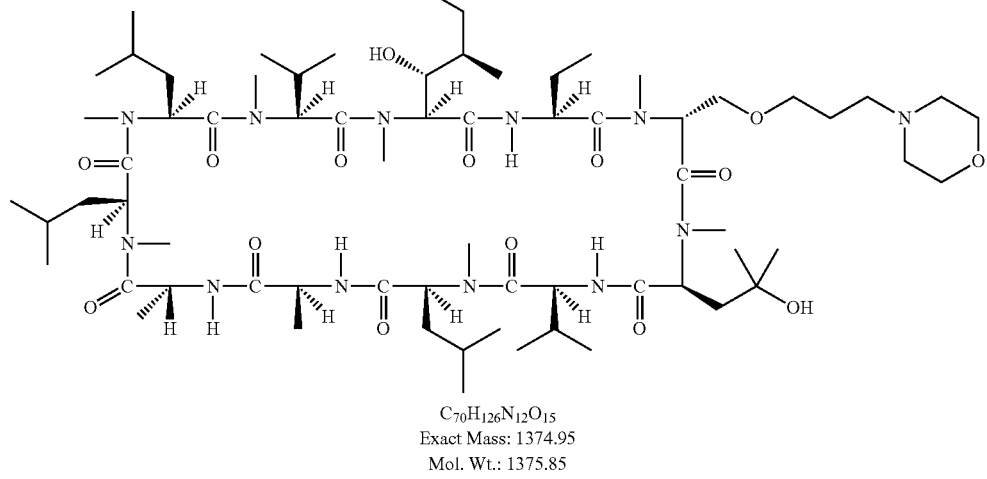

C₇₀H₁₂₆N₁₂O₁₅
Exact Mass: 1374.95
Mol. Wt.: 1375.85

[(R)-(2-Formylethoxy)methyl-Sar]-3-[(γ-hydroxy)-N-MeLeu]-4-cyclosporin (300 mg, 0.23 mmol) was dissolved in dichloromethane (15 ml). Morpholine (100 mg, 1.15 mmol) and tetramethylammonium triacetoxyborohydride (302 mg, 1.15 mmol) were added. The reaction mixture was stirred overnight at room temperature. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 105 mg of pure product was obtained [Molecular Formula: C₇₀H₁₂₆N₁₂O₁₅; Exact Mass: 1374.95; MS (m/z): 1375.70 (M+1)⁺, 1397.80 (M+Na)⁻; TLC R$_f$: 0.37 (dichloromethane/methanol=9/1); HPLC RT: 12.2 min (C8 reverse phase column: 250 mm; acetonitrile/0.077% ammonium acetate in water; operation temperature: 64° C.; detector: 210 nm)].

Example 118

[(R)-(3-(N-Pyrrolidinyl)propoxy)methyl-Sar]-3-[(γ-hydroxy)-NMeLeu]-4-cyclosporin

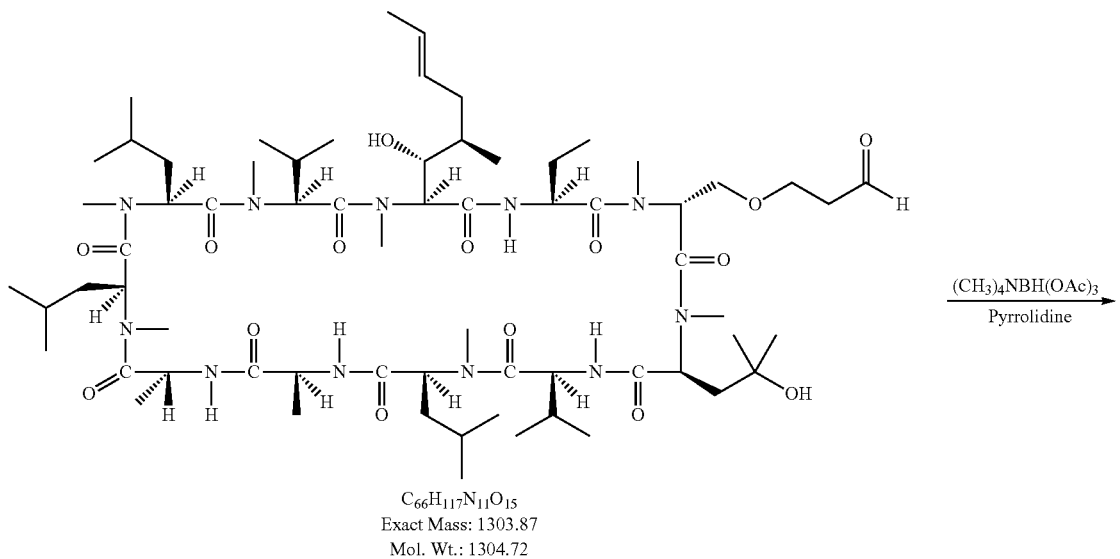

C₆₆H₁₁₇N₁₁O₁₅
Exact Mass: 1303.87
Mol. Wt.: 1304.72

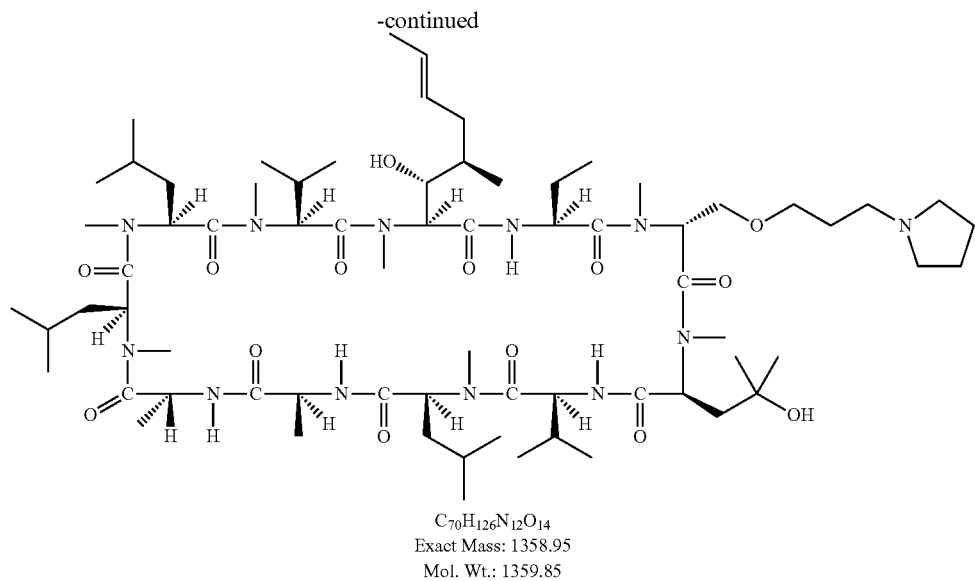

C<sub>70</sub>H<sub>126</sub>N<sub>12</sub>O<sub>14</sub>
Exact Mass: 1358.95
Mol. Wt.: 1359.85

[(R)-(2-Formylethoxy)methyl-Sar]-3-[(γ-hydroxy)-N-MeLeu]-4-cyclosporin (200 mg, 0.15 mmol) was dissolved in dichloromethane (15 ml). Pyrrolidine (95 mg, 1.34 mmol) and tetramethylammonium triacetoxyborohydride (353 mg, 1.34 mmol) were added. The reaction mixture was stirred overnight at room temperature. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 50 mg of pure product was obtained [Molecular Formula: $C_{70}H_{126}N_{12}O_{14}$; Exact Mass: 1358.95; MS (m/z): 1359.74 $(M+1)^+$, 1381.79 $(M+Na)^-$; TLC $R_f$: 0.40 (dichloromethane/methanol=9/1); HPLC RT: 12.7 min (C8 reverse phase column: 250 mm; acetonitrile/0.077% ammonium acetate in water; operation temperature: 64° C.; detector: 210 nm)].

Example 119

[(R)-(3-(N-Piperidinyl)propoxy)methyl-Sar]-3-[(γ-hydroxy)-NMeLeu]-4-cyclosporin

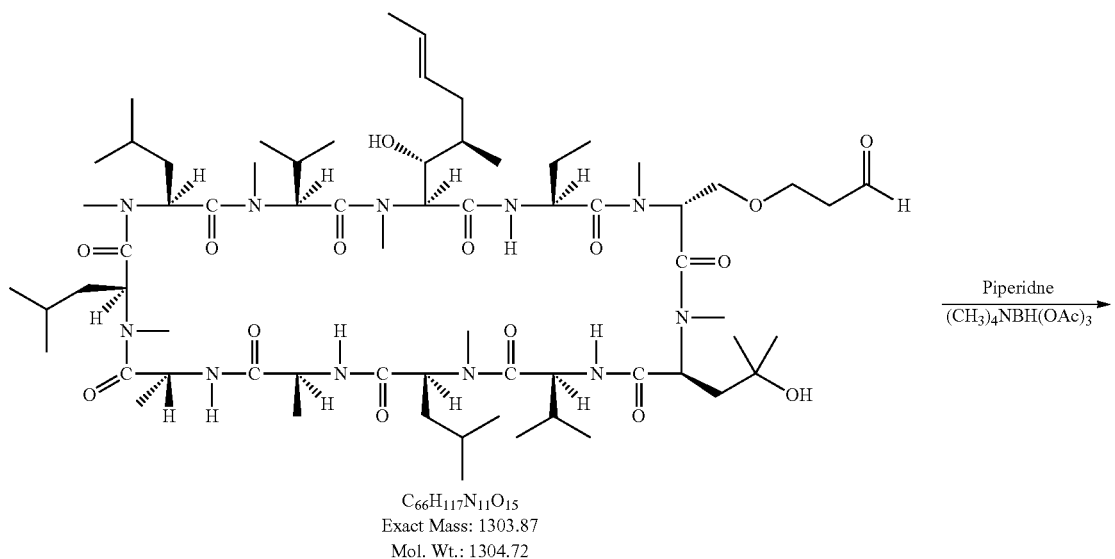

C<sub>66</sub>H<sub>117</sub>N<sub>11</sub>O<sub>15</sub>
Exact Mass: 1303.87
Mol. Wt.: 1304.72

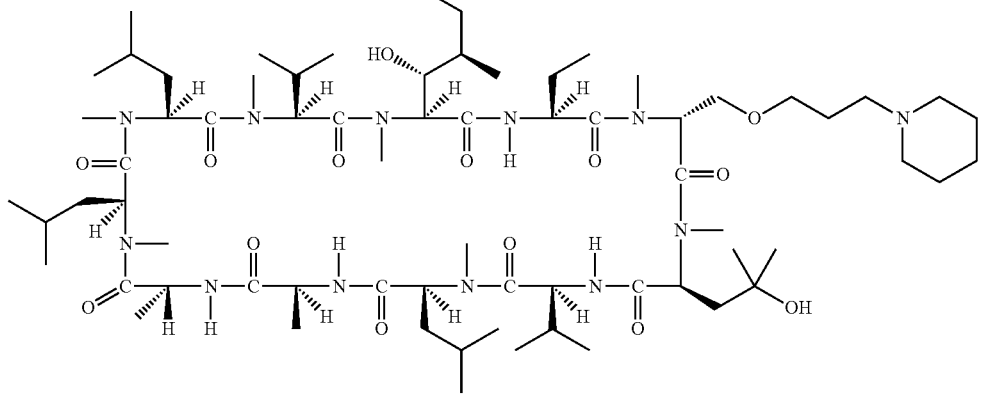

C₇₁H₁₂₈N₁₂O₁₄
Exact Mass: 1372.97
Mol. Wt.: 1373.88

[(R)-(2-Formylethoxy)methyl-Sar]-3-[(γ-hydroxy)-N-MeLeu]-4-cyclosporin (200 mg, 0.15 mmol) was dissolved in dichloromethane (15 ml). Piperidine (114 mg, 1.34 mmol) and tetramethylammonium triacetoxyborohydride (353 mg, 1.34 mmol) were added. The reaction mixture was stirred overnight at room temperature. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 43 mg of product was obtained [Molecular Formula: $C_{71}H_{128}N_{12}O_{14}$; Exact Mass: 1372.97; (m/z): MS (m/z): 1373.79 (M+1)⁺, 1395.86 (M+Na)⁺; TLC $R_f$: 0.27 (dichloromethane/methanol=9/1); HPLC RT: 17.8 min (C8 reverse phase column: 250 mm; acetonitrile/0.077% ammonium acetate in water; operation temperature: 64° C.; detector: 210 nm)].

Example 120

[(R)-(3-(3-Hydroxy-2,2-dimethylpropylamino)propoxy)methyl-Sar]-3-[(γ-hydroxy)-NMeLeu]-4-cyclosporin

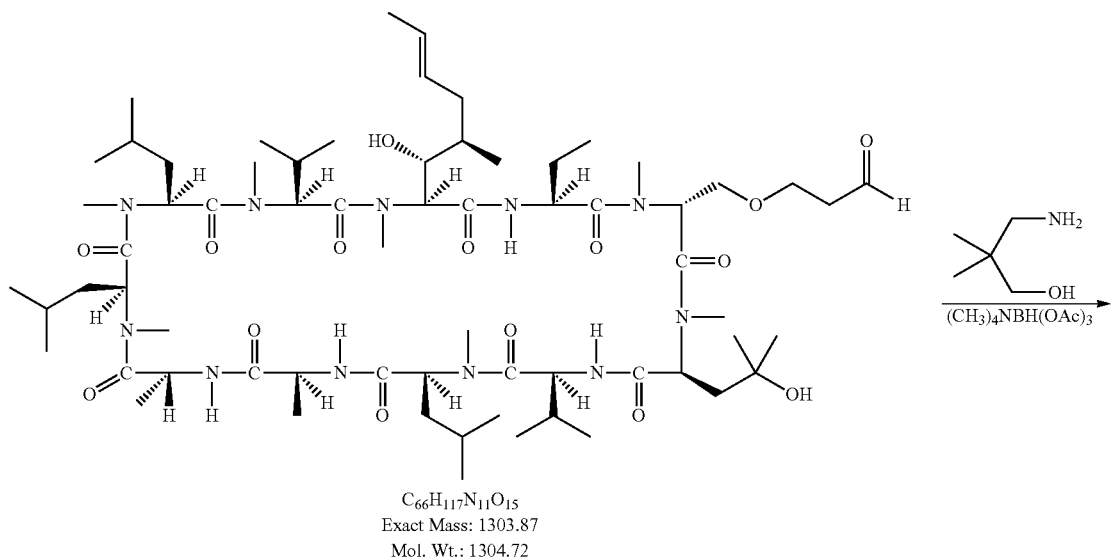

C₆₆H₁₁₇N₁₁O₁₅
Exact Mass: 1303.87
Mol. Wt.: 1304.72

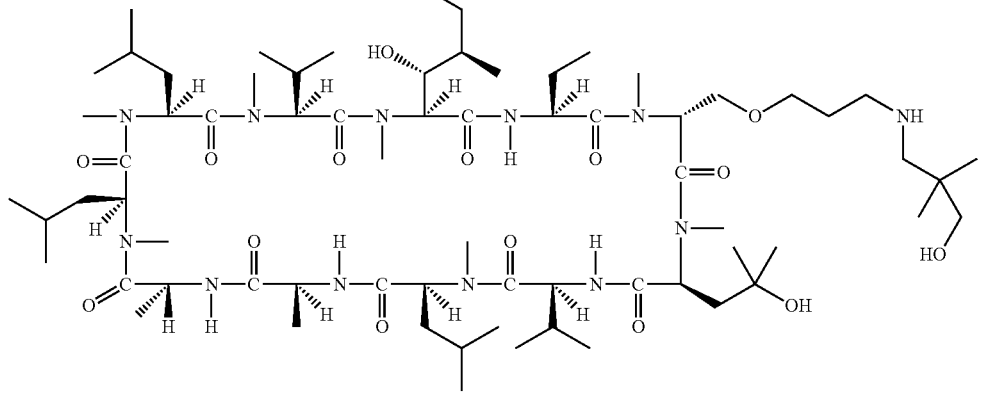

[(R)-(2-Formylethoxy)methyl-Sar]-3-[(γ-hydroxy)-NMeLeu]-4-cyclosporin (100 mg, 0.08 mmol) was dissolved in dichloromethane (15 ml). 3-Amino-2,2-dimethyl-1-propanol (40 mg, 0.39 mmol) and tetramethylammonium triacetoxyborohydride (100 mg, 0.39 mmol) were added. The reaction mixture was stirred at room temperature for 6 hours. Then sodium bicarbonate saturated solution (30 ml) and dichloromethane (15 ml) were added and the mixture was separated. The dichloromethane layer was dried over magnesium sulfate and evaporated under reduced pressure. After purified on silica gel, 10 mg of pure product was obtained [Molecular Formula: $C_{71}H_{130}N_{12}O_{15}$; Exact Mass: 1390.98; MS (m/z): 1391.64 $(M+1)^+$, 1413.77 $(M+Na)^-$; TLC $R_f$: 0.37 (dichloromethane/methanol=9/1); HPLC RT: 11.46 min (C8 reverse phase column: 250 mm; acetonitrile/0.077% ammonium acetate in water; operation temperature: 64° C.; detector: 210 nm)].

Example 121

[(R)-(3-(N,N-Dimethylamino)propoxy)methyl-Sar]-3-[(γ-hydroxy)-NMeLeu]-4-cyclosporin

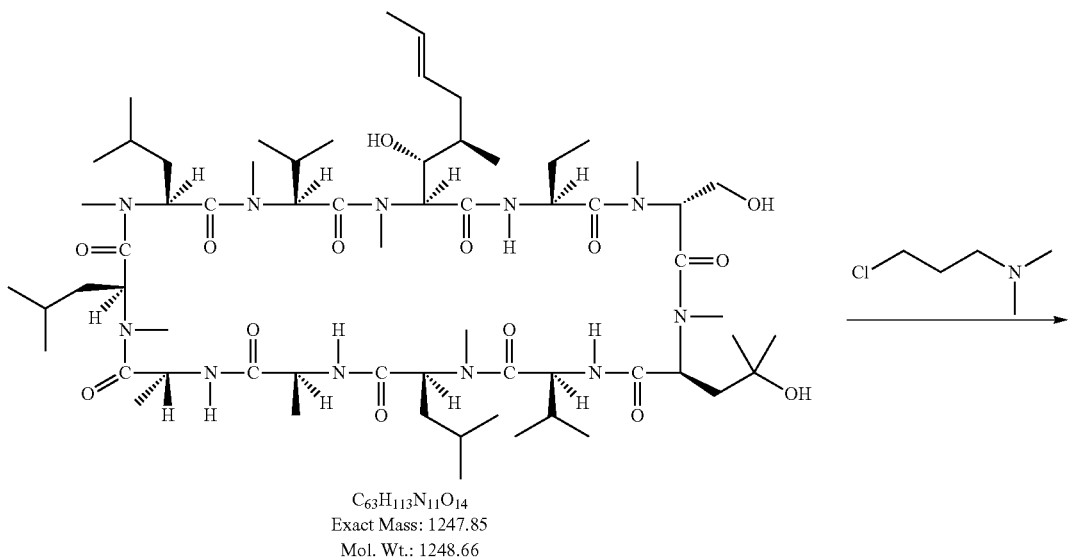

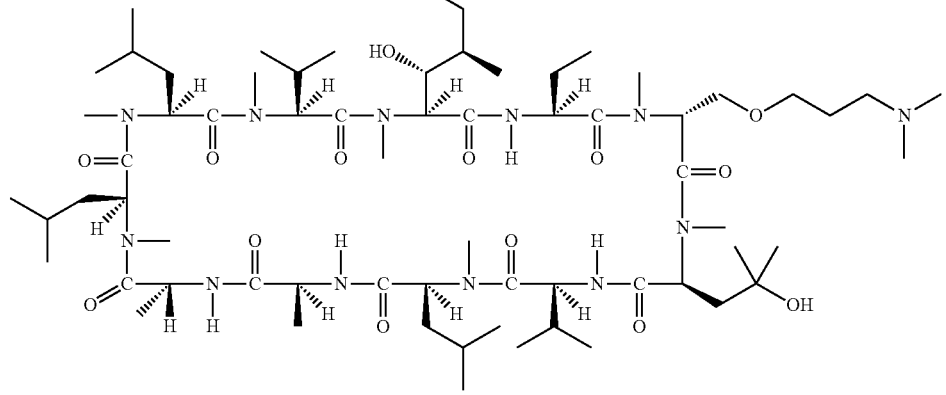

C₆₈H₁₂₄N₁₂O₁₄
Exact Mass: 1332.94
Mol. Wt.: 1333.81

To a solution of [(R)-α-hydroxymethyl-Sar]-3-[(γ-hydroxy)-N-MeLeu]-4-cyclosporin (0.38 g, 0.30 mmol) in benzene (15 ml) were added sodium hydroxide (0.48 g, 12.00 mmol), tetramethylammonia hydroxide (0.54 g, 3.0 mmol) and 3-dimethylaminoethyl chloride hydrochloride (0.43 g, 3.00 mmol). The mixture was stirred at 30° C. for 36 hours. Then ice water (20 ml) was added and the mixture was separated. The aqueous layer was extracted with ethyl acetate (20 ml). The combined organic layers were washed with brine, dried over magnesium sulfate and evaporated under reduced pressure. The residue was purified by chromatography on silica gel with dichloromethane/methanol (95/5) as eluent to give to give 70 mg of pure product [Molecular Formula: $C_{68}H_{124}N_{12}O_{14}$; Exact Mass: 1332.94. MS (m/z): 1333.64 (M+1)⁺, 1355.73 (M+Na)⁻; TLC $R_f$: 0.04 (dichloromethane/methanol=5/1); HPLC RT: 11.78 min (C8 reverse phase column: 150 mm; acetonitrile/water (0.05% trifluoroacetic acid); operation temperature: 64° C.; detector: 210 nm)].

Example 122

[(R)-(3-(N,N-Diethylamino)propoxy)methyl-Sar]-3-[(γ-hydroxy)-NMeLeu]-4-cyclosporin

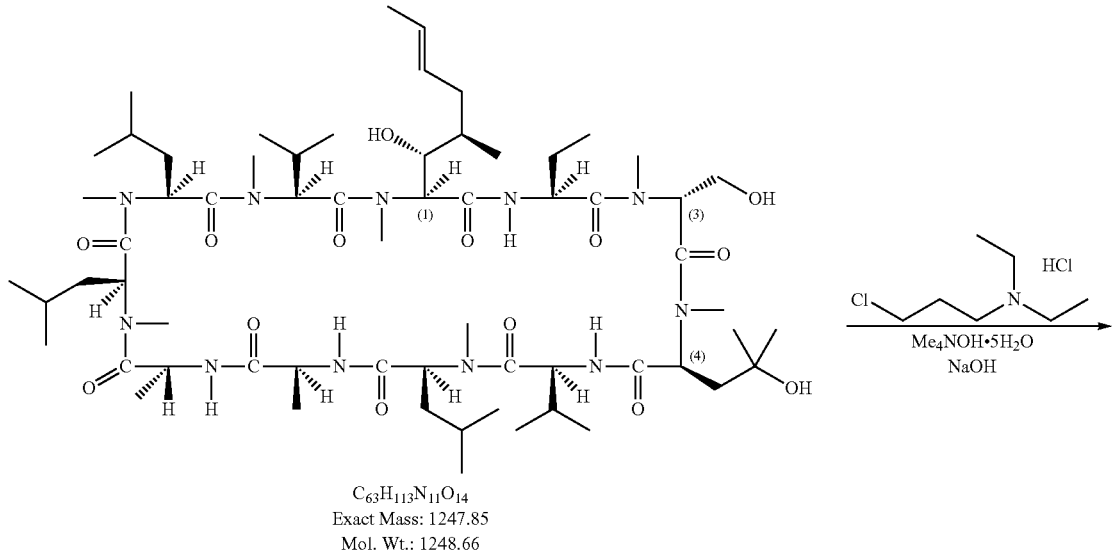

C₆₃H₁₁₃N₁₁O₁₄
Exact Mass: 1247.85
Mol. Wt.: 1248.66

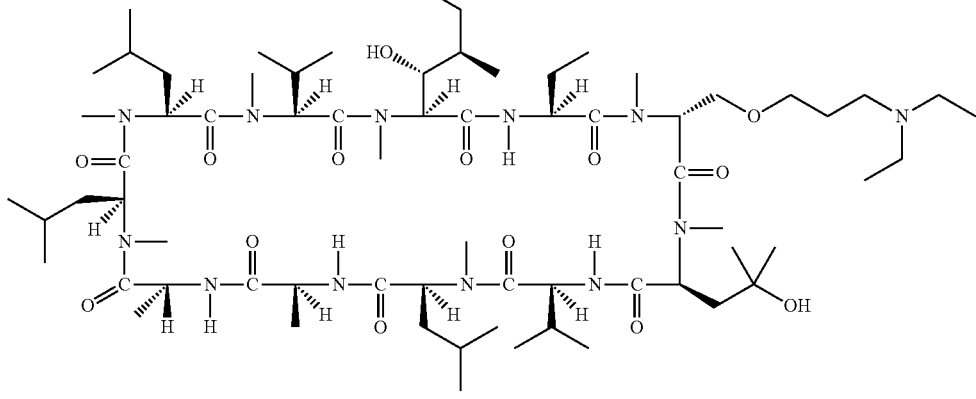

C₇₀H₁₂₈N₁₂O₁₄
Exact Mass: 1360.97
Mol. Wt.: 1361.86

To a solution of [(R)-α-hydroxymethyl-Sar]-3-[(γ-hydroxy)-N-MeLeu]-4-cyclosporin (250 mg, 0.20 mmol) in benzene (15 ml) were added a solution of sodium hydroxide (400 mg, 10.00 mmol) in water (0.5 ml), 3-diethylaminepropyl chloride hydrochloride (500 mg, 2.69 mmol) and tetramethylammonium hydroxide pentahydrate (430 mg, 2.41 mmol). The mixture was stirred at 32° C. for 4 days. Then ice water (30 ml) was added and the mixture was separated. The aqueous layer was extracted with dichloromethane (50 ml). The combined organic layers were washed with brine, dried over magnesium sulfate and concentrated under reduced pressure. The residue was purified by chromatography (dichloromethane/methanol=95/5) to give 120 mg of product [Molecular Formula: C₇₀H₁₂₈N₁₂O₁₄; Exact Mass: 1360.97; MS (m/z): 1361.72 (M+1)⁻; TLC Rf: 0.38 (dichloromethane/methanol=9/1); HPLC RT: 16.71 min (C8 reverse phase column: 250 mm; acetonitrile/0.077% ammonium acetate in water; operation temperature: 64° C.; detector: 210 nm)].

Example 123

[(R)-(3-Hydroxypropoxy)methyl-Sar]-3-[(γ-hydroxy)-NMeLeu]-4-cyclosporin

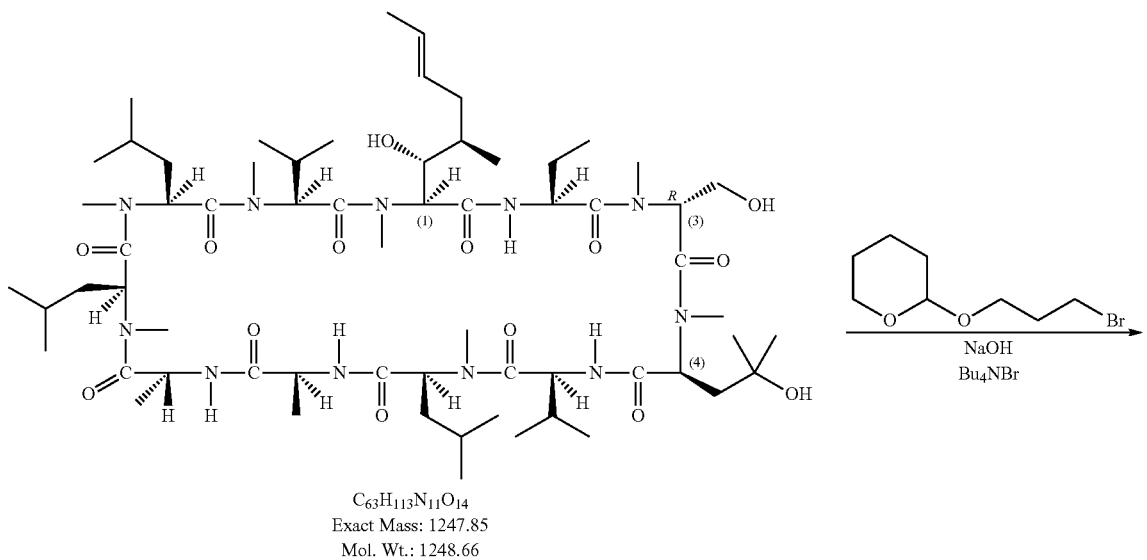

C₆₃H₁₁₃N₁₁O₁₄
Exact Mass: 1247.85
Mol. Wt.: 1248.66

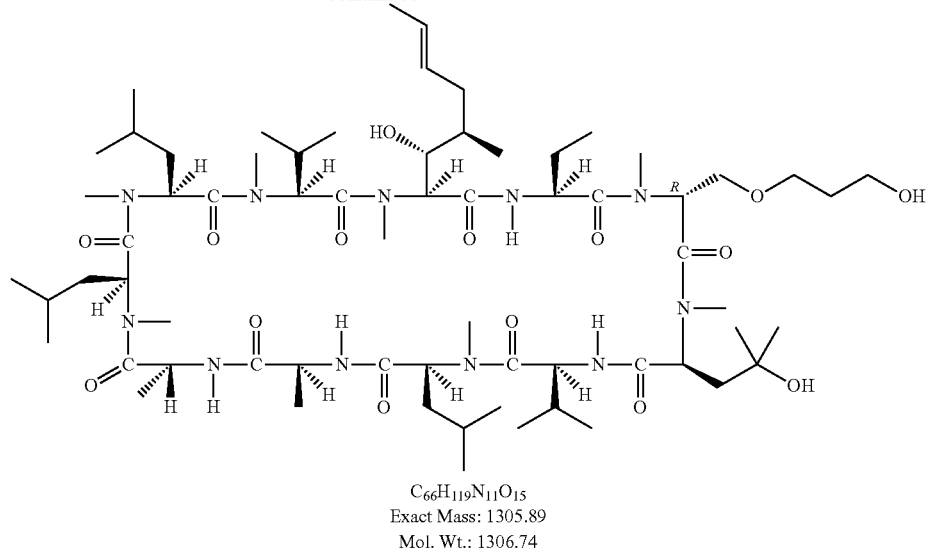

$C_{66}H_{119}N_{11}O_{15}$
Exact Mass: 1305.89
Mol. Wt.: 1306.74

To a solution of [(R)-α-hydroxymethyl-Sar]-3-[(γ-hydroxy)-NMeLeu]-4-cyclosporin (0.25 g, 0.20 mmol) in benzene (30 ml) were added a solution of sodium hydroxide (1.00 g, 25 mmol) in water (2 ml), 2-(3-bromopropoxy) tetrahydro-2H-pyran (2.50 g, 11.21 mmol) and tetra-n-butylammonium bromide (0.2 g, 0.62 mmol). The mixture was stirred at 30° C. for 4 hours. Then ice water (30 ml) was added and the mixture was separated. The aqueous layer was extracted with dichloromethane (25 ml). The combined organic layers were washed with brine, dried over magnesium sulfate and concentrated under reduced pressure. The residue was purified by chromatography (dichloromethane/methanol=97/3) to give the product [Molecular Formula: $C_{66}H_{119}N_{11}O_{15}$; Exact Mass: 1305.89; MS (m/z): 1306.46 (M+1)⁺; TLC Rf: 0.38 (dichloromethane/methanol=9/1); HPLC RT: 12.94 min (C8 reverse phase column: 250 mm; acetonitrile/water (0.05% trifuloroacetic acid); operation temp: 64° C.; Detector: 210 nm)].

Example 124

[(R)-(4-Acetoxybutyloxy)methyl-Sar]-3-[(γ-hydroxy)-NMeLeu]-4-cyclosporin

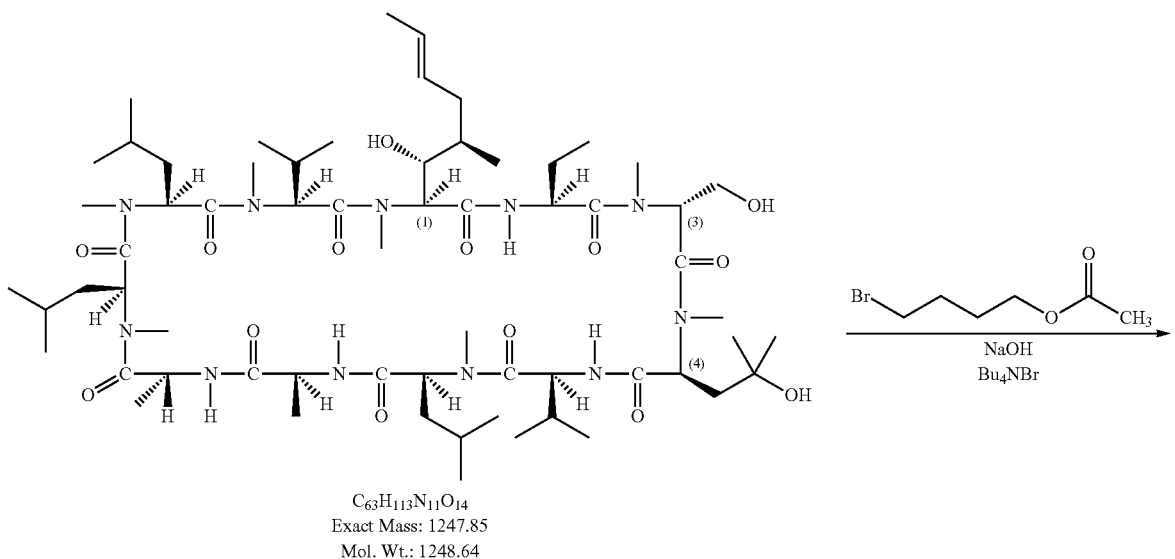

$C_{63}H_{113}N_{11}O_{14}$
Exact Mass: 1247.85
Mol. Wt.: 1248.64

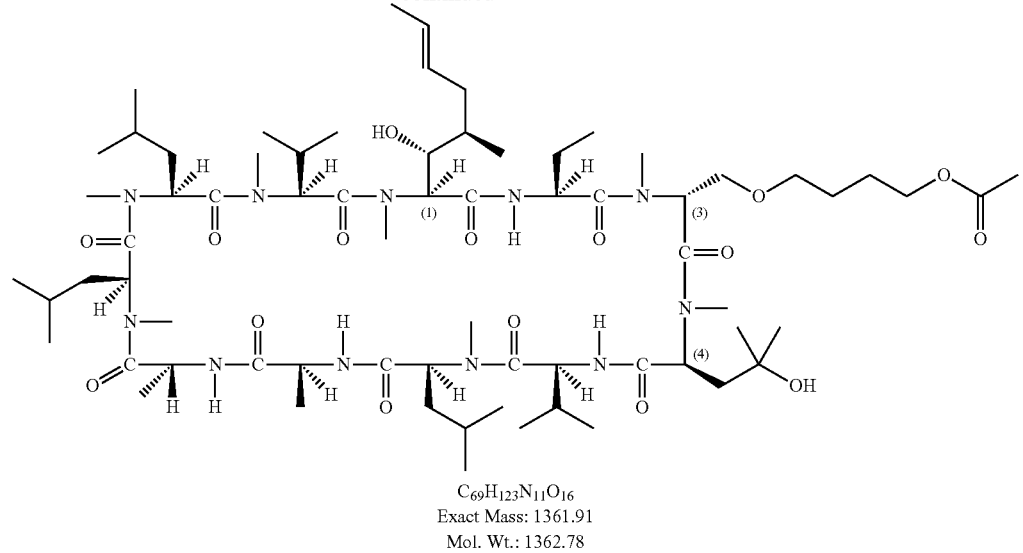

C₆₉H₁₂₃N₁₁O₁₆
Exact Mass: 1361.91
Mol. Wt.: 1362.78

To a solution of [(R)-α-hydroxymethyl-Sar]-3-[(γ-hydroxy)-NMeLeu]-4-cyclosporin (0.34 g, 0.27 mmol) in benzene (10.0 ml) were added 4-bromobutyl acetate (1.56 ml, d 1.348, 10.81 mmol), tetra-n-butylammonium bromide (0.30 g, 0.94 mmol) and sodium hydroxide (0.70 g, 17.6 mmol). The mixture was stirred at room temperature for two hours and then washed with brine, dried over magnesium sulfate. After removal of solvent under reduced pressure, the residue was purified by chromatography on silica gel to give pure product [Molecular formula: $C_{69}H_{123}N_{11}O_{16}$; Exact Mass: 1361.91; MS (m/z): 1362.51(M+1)⁺, 1385.77 (M+Na)⁺].

Example 125

[(R)-(4-Hydroxylbutoxy)methyl-Sar]-3-[(γ-hydroxy)-NMeLeu]-4-cyclosporin

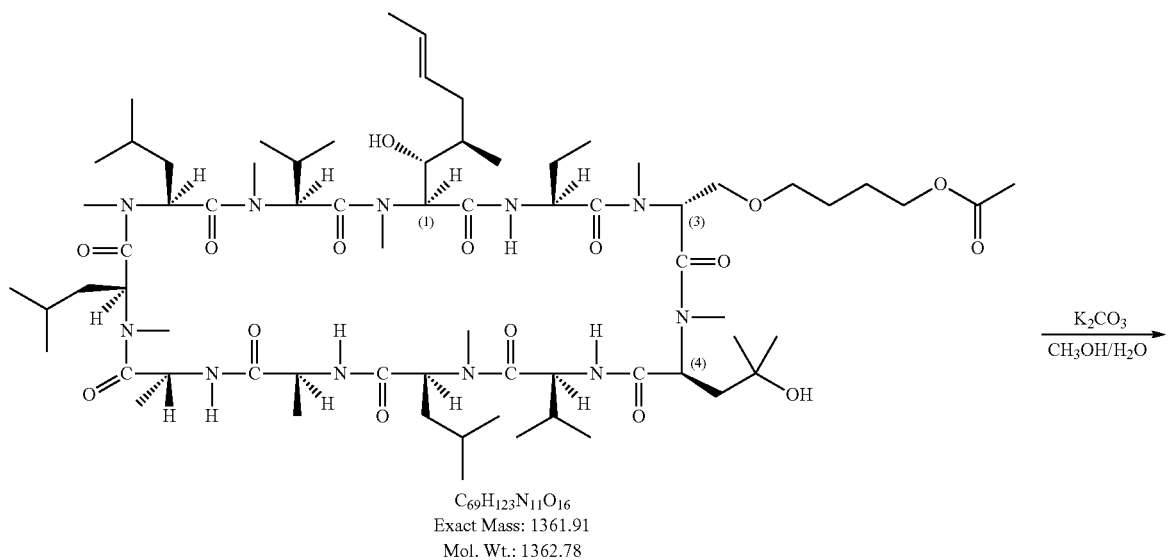

C₆₉H₁₂₃N₁₁O₁₆
Exact Mass: 1361.91
Mol. Wt.: 1362.78

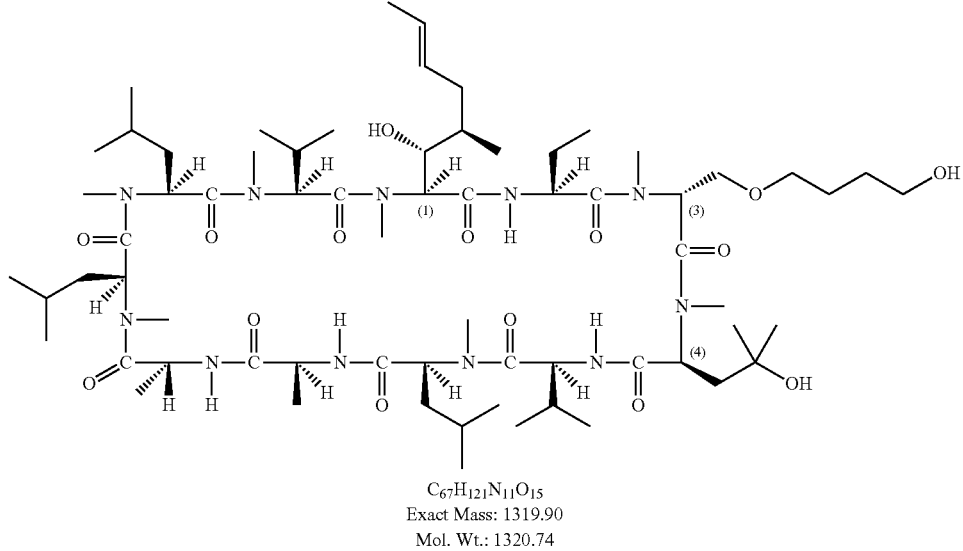

C₆₇H₁₂₁N₁₁O₁₅
Exact Mass: 1319.90
Mol. Wt.: 1320.74

[(R)-(4-Acetoxybutyloxy)methyl-Sar]-3-[(γ-hydroxy)-NMeLeu]-4-cyclosporin (49 mg, 0.036 mmol) was dissolved in methanol (5 ml). Water (3 ml) and potassium carbonate (99 mg, 0.72 mmol) were added and the mixture was stirred for two hours. After removal of methanol, the residue was dissolved in ethyl acetate (6 ml). The ethyl acetate layer was washed with brine, dried over magnesium sulfate and evaporated under reduced pressure. The residue was purified by flash chromatography on silica gel with ethyl acetate/methanol as eluent to give 22 mg of the pure product [Molecular formula: $C_{67}H_{121}N_{11}O_{15}$; Exact Mass: 1319.90; MS (m/z): 1320.58 (M+1)⁻, 1342.78 (M+Na)⁺; TLC R$_f$: 0.20 (methylene/methanol=25/1); HPLC RT: 13.62 min (C8 reverse phase column: 250 mm; acetonitrile/water (0.05% trifluoroacetic acid); operation temp: 64° C.; Detector: 210 nm)].

Example 126

[(R)-(4-Methoxylbutoxy)methyl-Sar]-3-[(γ-hydroxy)-NMeLeu]-4-cyclosporin

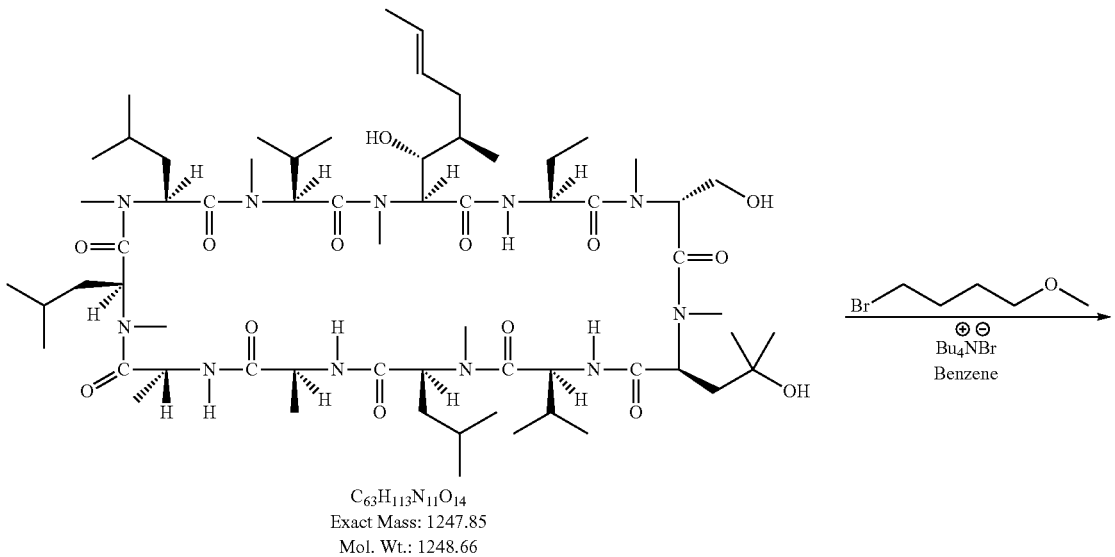

C₆₃H₁₁₃N₁₁O₁₄
Exact Mass: 1247.85
Mol. Wt.: 1248.66

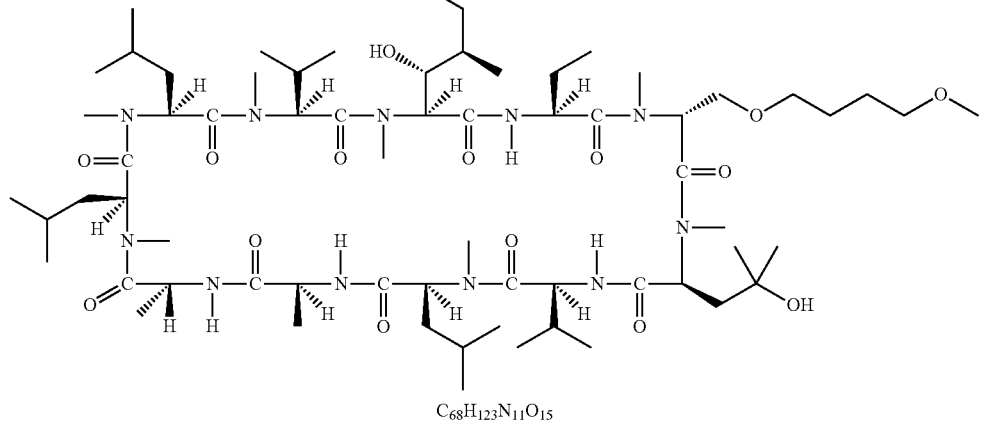

C₆₈H₁₂₃N₁₁O₁₅
Exact Mass: 1333.92
Mol. Wt.: 1334.79

To a solution of [(S)-α-hydroxymethyl-Sar]-3-[(γ-hydroxy)-N-MeLeu]-4-cyclosporin (0.624 g, 0.50 mmol) in benzene (20 ml) were added a solution of sodium hydroxide (1.40 g, 35 mmol) in water (2 ml), 1-bromo-4-methoxybutane (0.84 g, 5.0 mmol) and tetra-n-butylammonium bromide (0.563 g, 1.75 mmol). The mixture was stirred at room temperature overnight and then at 30° C. for 4 hours. Then ice water (30 ml) was added and separated. The aqueous layer was extracted with dichloromethane (25 ml). The combined organic layers were washed with brine, dried over magnesium sulfate and concentrated under reduced pressure. The residue was purified by chromatography (dichloromethane/methanol=20:1) to give 50 mg of product [Molecular formula: $C_{68}H_{123}N_{11}O_{15}$; Exact Mass: 1333.92; MS (m/z): 1334.44 (M+1)⁺, 1356.67 (M+Na); TLC Rf: 0.33 (dichloromethane/methanol=20/1); HPLC RT: 15.52 min (C8 reverse phase column: 250 mm; acetonitrile/0.077% NH₄OAc in water; operation temperature: 64° C.; Detector: 210 nm)].

Example 127

[(R)-(5-Hydroxypentyloxy)methyl-Sar]-3-[(γ-hydroxy)-NMeLeu]-4-cyclosporin

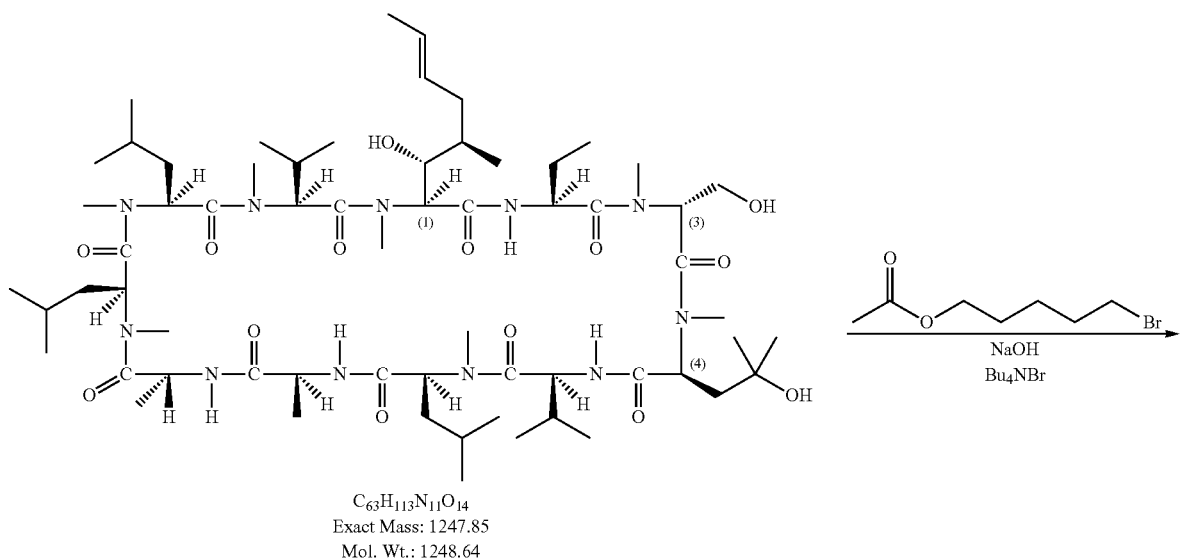

C₆₃H₁₁₃N₁₁O₁₄
Exact Mass: 1247.85
Mol. Wt.: 1248.64

-continued

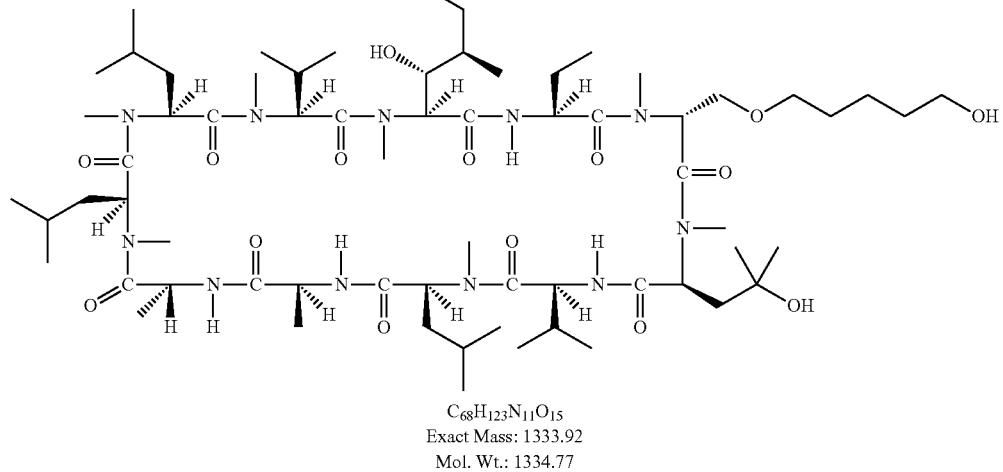

C₆₈H₁₂₃N₁₁O₁₅
Exact Mass: 1333.92
Mol. Wt.: 1334.77

To a solution of [(R)-α-hydroxymethyl-Sar]-3-[(γ-hydroxy)-NMeLeu]-4-cyclosporin (0.25 g, 0.20 mmol) in benzene (30 ml) were added a solution of sodium hydroxide (1.00 g, 25 mmol) in water (2 ml), 5-bromopentyl acetate (2.20 g, 10.53 mmol) and tetra-n-butylammonium bromide (0.2 g, 0.62 mmol). The mixture was stirred at 30° C. for 10 hours. Then ice water (30 ml) was added and the mixture was separated. The aqueous layer was extracted with dichloromethane (25 ml). The combined organic layers were washed with brine, dried over magnesium sulfate and concentrated under reduced pressure. The residue was purified by chromatography (dichloromethane/methanol=97/3) to give the product [Molecular Formula: $C_{68}H_{123}N_{11}O_{15}$; Exact Mass: 1333.92; MS (m/z): 1334.46 (M+1)⁺; TLC Rf: 0.30 (dichloromethane/methanol=95/5); HPLC RT: 14.22 min (C8 reverse phase column: 250 mm; acetonitrile/water (0.05% trifuloroacetic acid); operation temp: 64° C.; Detector: 210 nm)].

Example 128

[(γ-(Methylthio)methoxy)-NMeLeu]-4-cyclosporin

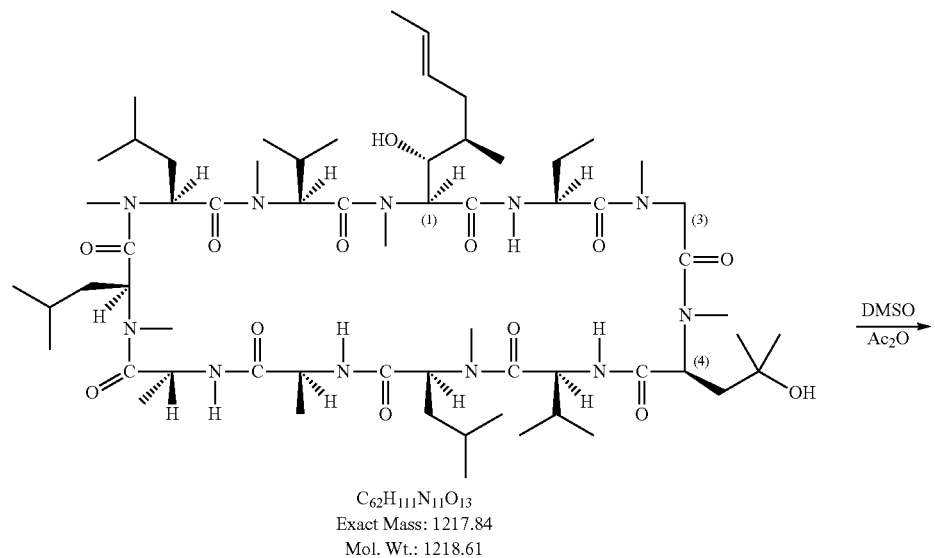

C₆₂H₁₁₁N₁₁O₁₃
Exact Mass: 1217.84
Mol. Wt.: 1218.61

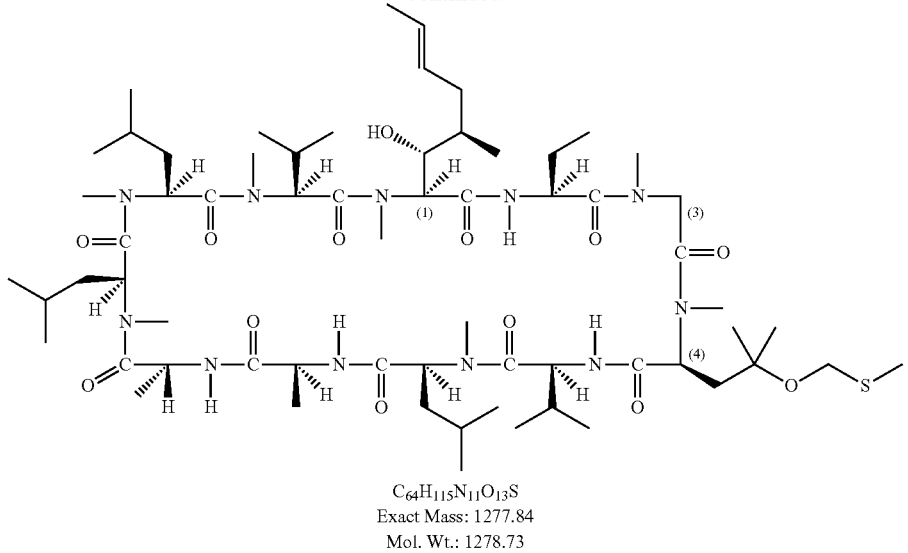

C$_{64}$H$_{115}$N$_{11}$O$_{13}$S
Exact Mass: 1277.84
Mol. Wt.: 1278.73

To a solution of [(γ-hydroxy)-N-MeLeu]-4-cyclosporin (4.50 g, 3.70 mmol) in anhydrous dimethyl sulfoxide (25 ml) was added acetic anhydride (15 ml). The reaction mixture was stirred at room temperature for 17 hours. After diluted with ethyl acetate (75 ml), the mixture was washed with saturated sodium bicarbonate water solution and brine, dried over magnesium sulfate and evaporated under reduced pressure. The residue was purified on silica gel chromatography with dichloromethane/methanol (98/2) as eluant to give 2.35 g of [(γ-methylthio)methoxy-N-MeLeu]-4-cyclosporin [Molecular Formula: C$_{64}$H$_{115}$N$_{11}$O$_{13}$S; Exact Mass: 1277.84; MS (m/z): 1300.70 (M+Na)$^+$; TLC R$_f$: 0.30 (dichloromethane/methanol=95/5); HPLC RT: 19.57 min (C8 reverse phase column: 250 mm; acetonitrile/0.077% ammonium acetate in water; operation temperature: 64° C.; detector: 210 nm)].

Example 129

[γ-(Methoxy)-NMeLeu]-4-cyclosporin

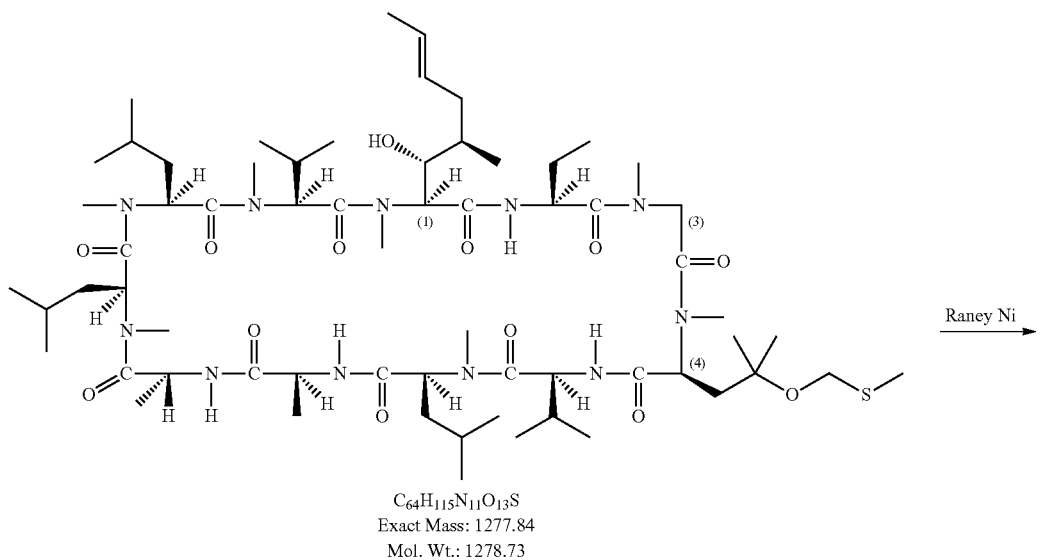

C$_{64}$H$_{115}$N$_{11}$O$_{13}$S
Exact Mass: 1277.84
Mol. Wt.: 1278.73

-continued

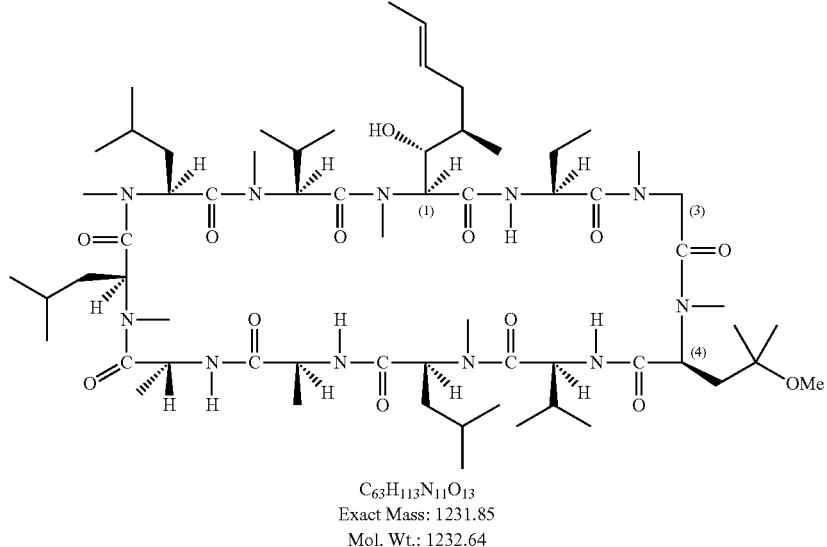

C₆₃H₁₁₃N₁₁O₁₃
Exact Mass: 1231.85
Mol. Wt.: 1232.64

To a solution of [γ-(Methylthio)methoxy-N-MeLeu]-4-cyclosporin (1.20 g, 0.94 mmol) in anhydrous tetrahydrofuran (40 ml) was added Raney Ni (~2 g). The resulting suspension was stirred and heated to 60° C. for 30 minutes and the reaction was monitored by LC-MS. The reaction mixture was filtered and the filter cake was washed with tetrahydrofuran. The filtrate was collected and evaporated under reduced pressure. The residue was purified by chromatography using eluant of ethyl acetate/methanol (97.5/2.5) to give 0.60 g of product [Molecular Formula: $C_{63}H_{113}N_{11}O_{13}$; Exact Mass: 1231.85; MS (m/z): 1232.70 (M+1)⁺; TLC R$_f$: 0.46 (dichloromethane/methanol=95/5); HPLC RT: 20.63 min (C8 reverse phase column: 250 mm; acetonitrile/0.077% ammonium acetate in water; operation temperature: 64° C.; detector: 210 nm)].

Example 130

[α-Carboxy-Sar]-3-[(γ-methoxy)-NMeLeu]-4-cyclosporin

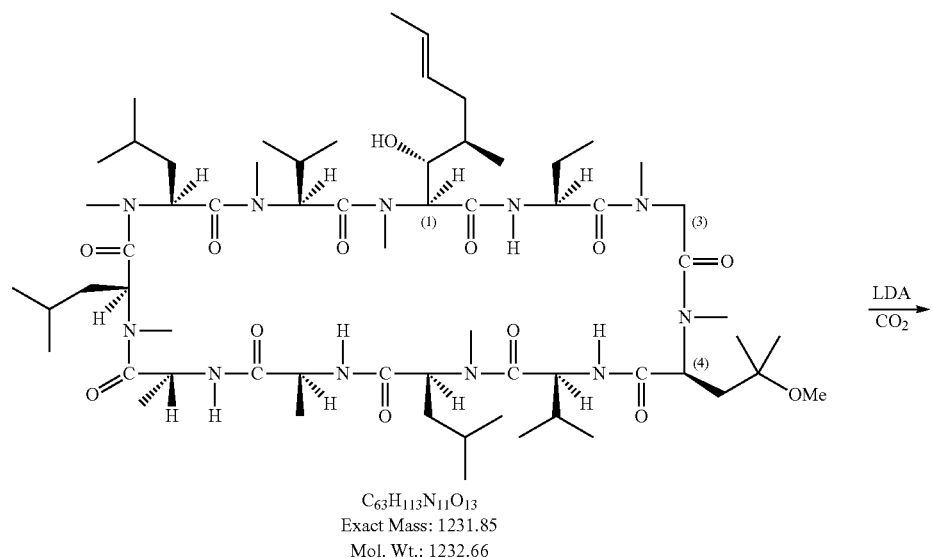

C₆₃H₁₁₃N₁₁O₁₃
Exact Mass: 1231.85
Mol. Wt.: 1232.66

$\xrightarrow{\text{LDA}}{\text{CO}_2}$

-continued

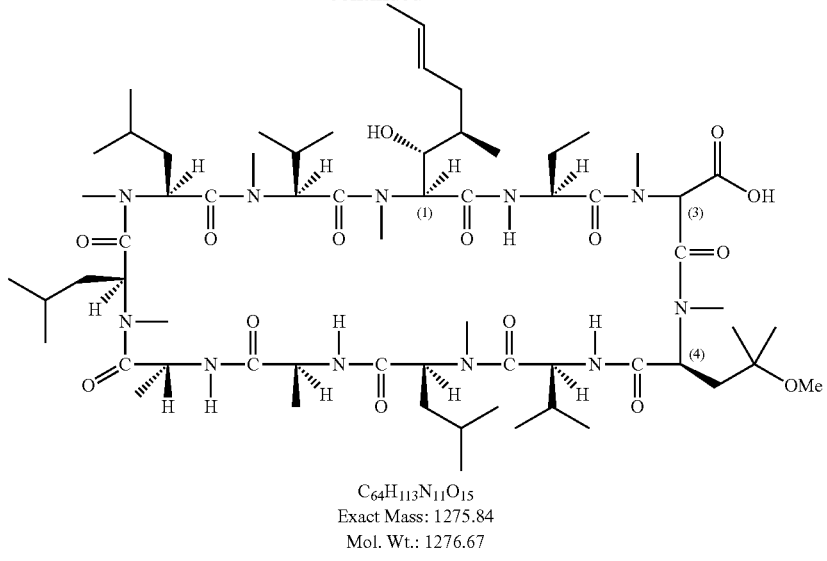

C₆₄H₁₁₃N₁₁O₁₅
Exact Mass: 1275.84
Mol. Wt.: 1276.67 n-Butyllithium (2.8 M in tetrahydrofuran/hexane, 5.00 ml, 14.00 mmol) was added to a solution of diisopropylamine (1.44 g, 14.30 mmol) in tetrahydrofuran (30 ml) at −78° C. under nitrogen atmosphere. After the mixture was stirred for one and half hour, a solution of [γ-(methoxy)-N-MeLeu]-4-cyclosporin (1.20 g, 0.97 mmol) in tetrahydrofuran (6 ml) was added slowly. The stirring was continued at −78° C. for 2 hours. Then carbon dioxide gas was bubbled into the reaction mixture for one hour. The mixture was allowed to warm to room temperature slowly and stirred for another 3 hours. After most of solvent was evaporated under reduced pressure, dichloromethane (30 ml) and water (30 ml) were added. The PH of the mixture was adjusted to around 5 by adding aqueous citric acid. The mixture was separated, and the dichloromethane layer was washed with brine, dried over magnesium sulfate and concentrated under reduced pressure to give 1.20 g of crude product used for next step [Molecular Formula: $C_{64}H_{113}N_{11}O_{15}$; Exact Mass: 1275.84; MS (m/z): 1298.53(M+Na)⁺].

Example 131

[α-Methoxycarbonyl-Sar]-3-[(γ-methoxy)-NMeLeu]-4-cyclosporin

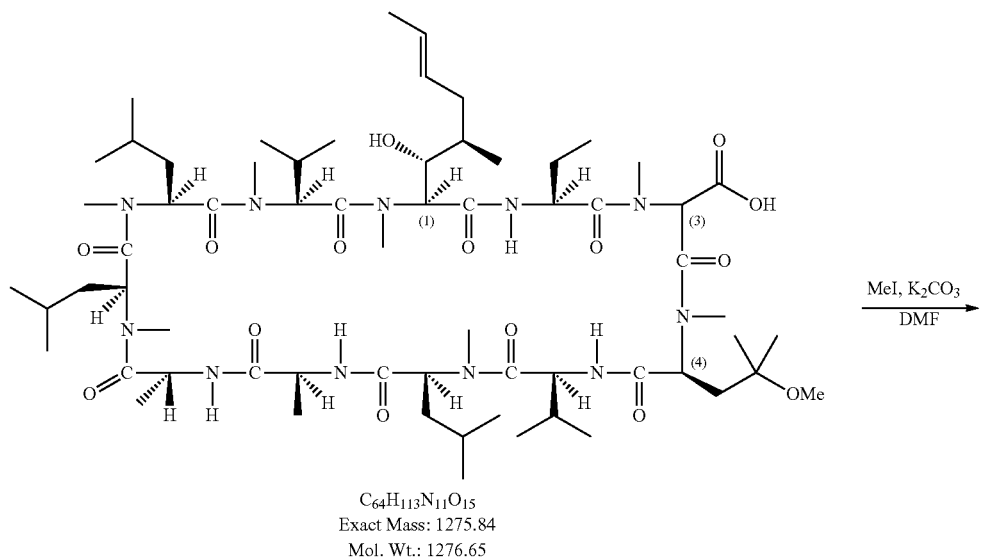

C₆₄H₁₁₃N₁₁O₁₅
Exact Mass: 1275.84
Mol. Wt.: 1276.65

-continued

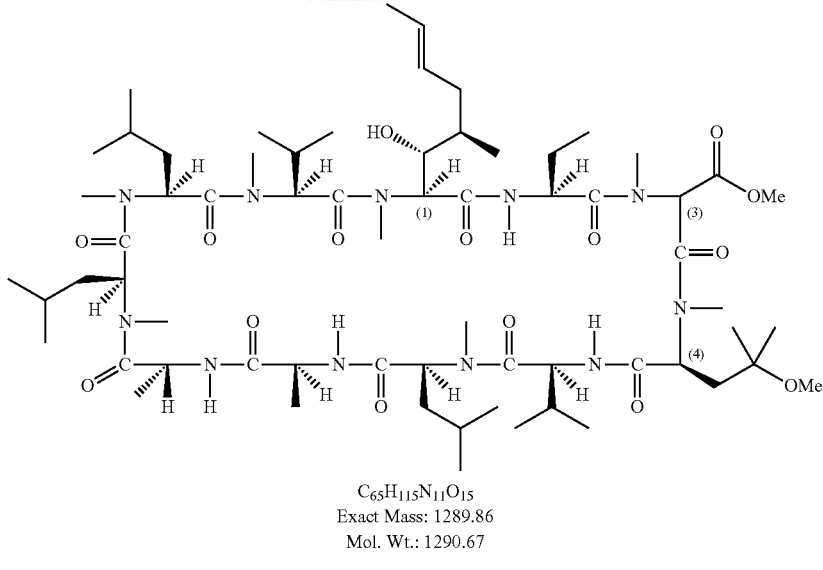

C$_{65}$H$_{115}$N$_{11}$O$_{15}$
Exact Mass: 1289.86
Mol. Wt.: 1290.67

To a mixture of [α-carboxy]-3-[(γ-methoxy)-N-MeLeu]-4-cyclosporin (1.20 g. 0.94 mmol) and potassium carbonate (0.80 g, 5.79 mmol) in N,N-dimethylformamide (25 ml) was added iodomethane (0.80 g, 5.63 mmol). The mixture was stirred at room temperature overnight. Dichloromethane (75 ml) and water (30 ml) were added and the mixture was separated. The dichloromethane layer was washed with water (25 ml) and brine (25 ml), dried magnesium sulfate and concentrated under reduced pressure to give 1.10 g of crude product [Molecular Formula: C$_{65}$H$_{115}$N$_{11}$O$_{15}$; Exact Mass: 1289.86; MS (m/z): 1312.72(M+Na)$^+$].

Example 132

[(R)-α-Hydroxymethyl-Sar]-3-[(γ-methoxy)-NMeLeu]-4-cyclosporin

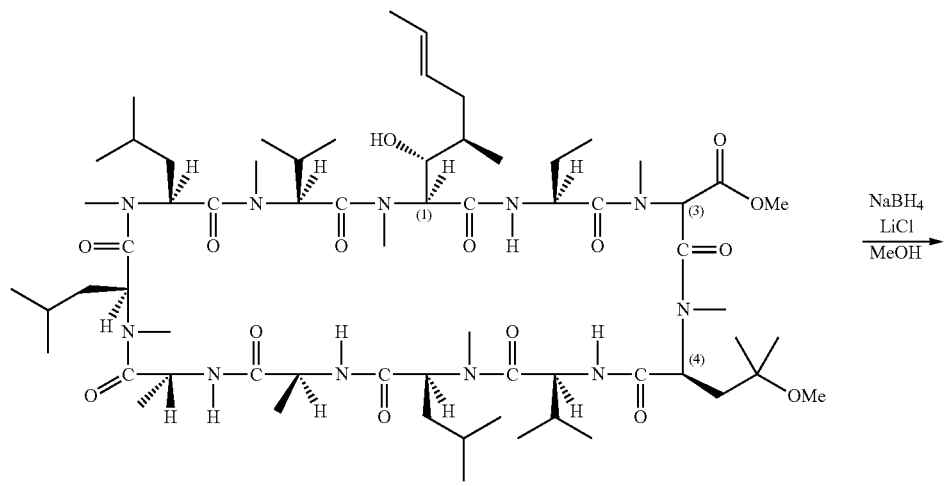

C$_{65}$H$_{115}$N$_{11}$O$_{15}$
Exact Mass: 1289.86
Mol. Wt.: 1290.67

-continued

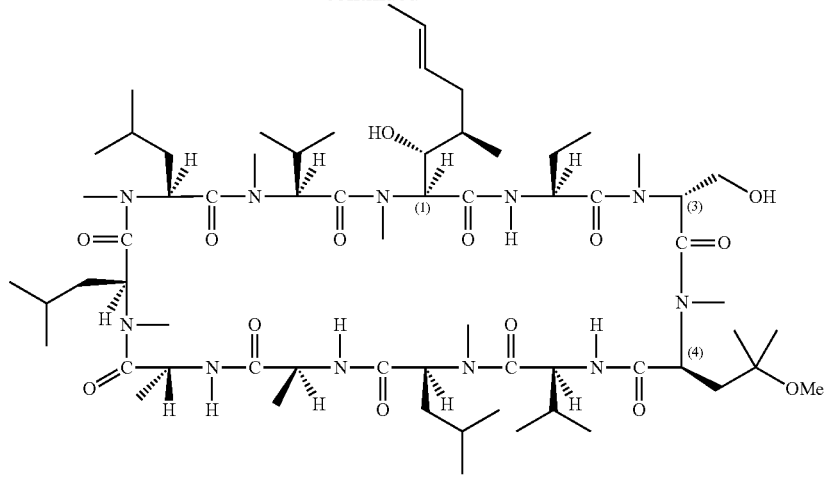

C$_{64}$H$_{115}$N$_{11}$O$_{14}$
Exact Mass: 1261.86
Mol. Wt.: 1262.66

To a suspension of [α-methoxycarbonyl-Sar]-3-[(γ-methoxy)-N-MeLeu]-4-cyclosporin (1.10 g, 0.85 mmol) and lithium chloride (1.00 g, 23.53 mmol) in methanol (80 ml) was added sodium borohydride (2.00 g, 52.91 mmol) in portions. The mixture was stirred at room temperature overnight and concentrated under reduced pressure. Dichloromethane (50 ml) and water (30 ml) were added and the mixture was separated. The dichloromethane layer was washed with brine, dried over magnesium sulfate and evaporated under reduced pressure. The residue was purified by chromatography (dichloromethane/methanol=97/3) to give 310 mg of product [Molecular Formula: C$_{64}$H$_{115}$N$_{11}$O$_{14}$; Exact Mass: 1261.86; MS (m/z): 1262.68 (M+1)$^+$].

Example 133

[α-Methylene-Sar]-3-[(γ-methoxy)-NMeLeu]-4-cyclosporin

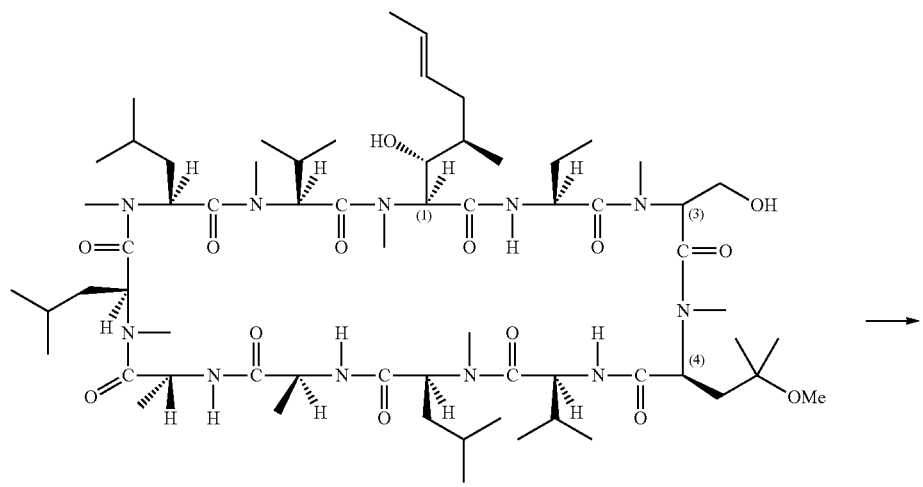

C$_{64}$H$_{115}$N$_{11}$O$_{14}$
Exact Mass: 1261.86
Mol. Wt.: 1262.66

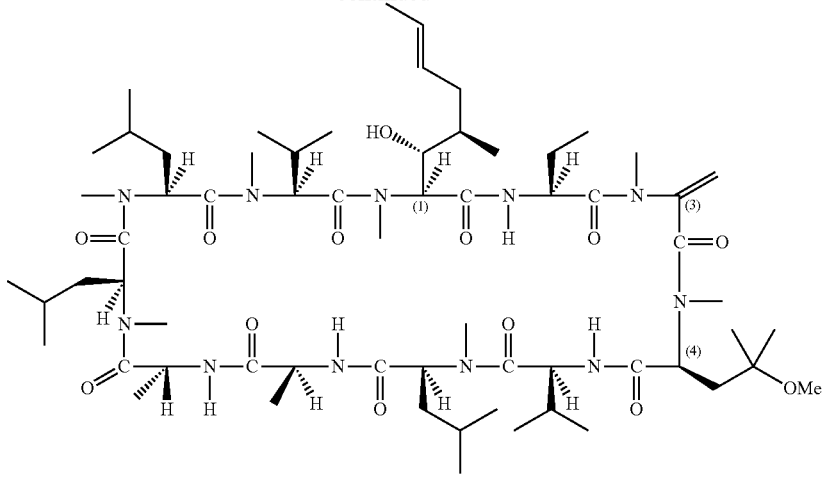

$C_{64}H_{113}N_{11}O_{13}$
Exact Mass: 1243.85
Mol. Wt.: 1244.65

[α-Methylene-Sar]-3-[(γ-methoxy)-N-MeLeu]-4-cyclosporin was prepared according to the method described in Example 28 [Molecular Formula: $C_{64}H_{113}N_{11}O_{13}$; Exact Mass: 1243.85; MS (m/z): 1244.57 (M+1)$^+$; TLC $R_f$: 0.34 (hexane/acetone=6/1); HPLC RT: 17.10 min (C8 reverse phase column: 250 mm; acetonitrile/water (0.05% trifuloroacetic acid), operation temperature: 64° C.; detector: 210 nm].

Example 134

[(S)-(2-(N,N-Dimethylamino)ethylthio)methyl-Sar]-3-[(γ-methoxy)-NMeLeu]-4-cyclosporin

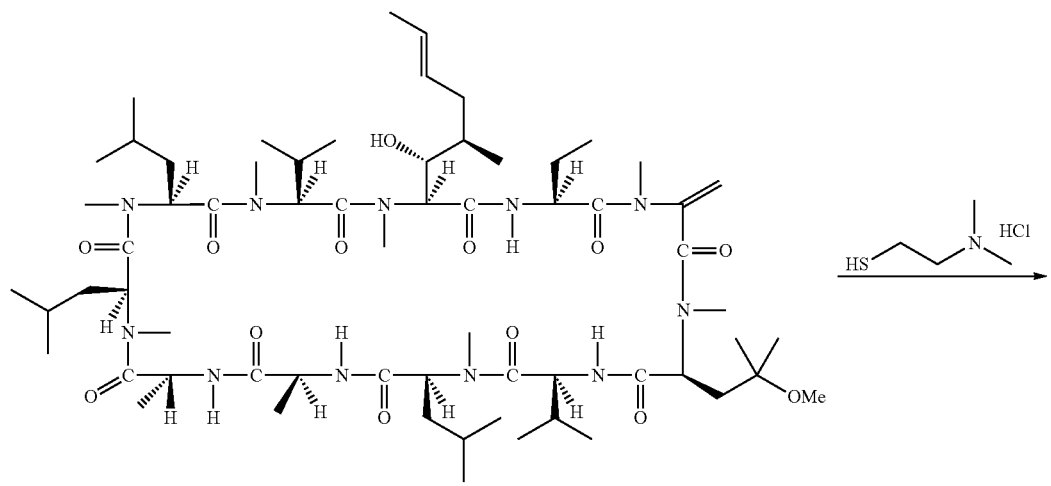

$C_{64}H_{113}N_{11}O_{13}$
Exact Mass: 1243.85
Mol. Wt.: 1244.67

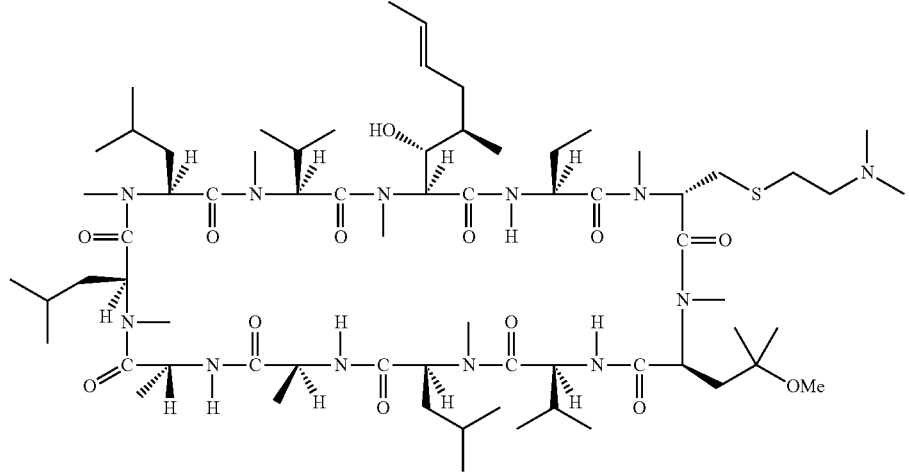

$C_{68}H_{124}N_{12}O_{13}S$
Exact Mass: 1348.91
Mol. Wt.: 1349.87

[α-Methylene-Sar]-3-[(γ-methoxy)-N-MeLeu]-4-cyclosporin (0.24 g, 0.19 mmol) and 2-(N,N-dimethylamino)ethylthiol hydrochloride (0.27 g, 1.91 mmol) was dissolved in methanol (30 ml), followed by adding 20 equivalents of lithium hydroxide (46 mg, 1.90 mmol). The mixture was stirred overnight at room temperature. After removal of solvent, the residue was purified by flash chromatography using methylene chloride/methanol (96/4) as eluent to give 0.11 g of pure product [Molecular Formula: $C_{68}H_{124}N_{12}O_{13}S$; Exact Mass: 1348.93; MS (m/e): 1349.85 $(M+1)^-$, 1371.81 $(M+Na)^+$; TLC $R_f$: 0.20 (ethyl acetate/methanol (5:1); HPLC RT: 12.42 min (C8 reverse phase column: 250 mm; acetonitrile/water (0.05% trifluoroacetic acid); operation temperature: 64° C.; detector: 210 nm)].

Example 135

[(S)-(2-(N,N-Diethylamino)ethylthio)methyl-Sar]-3-[(γ-methoxy)-NMeLeu]-4-cyclosporin

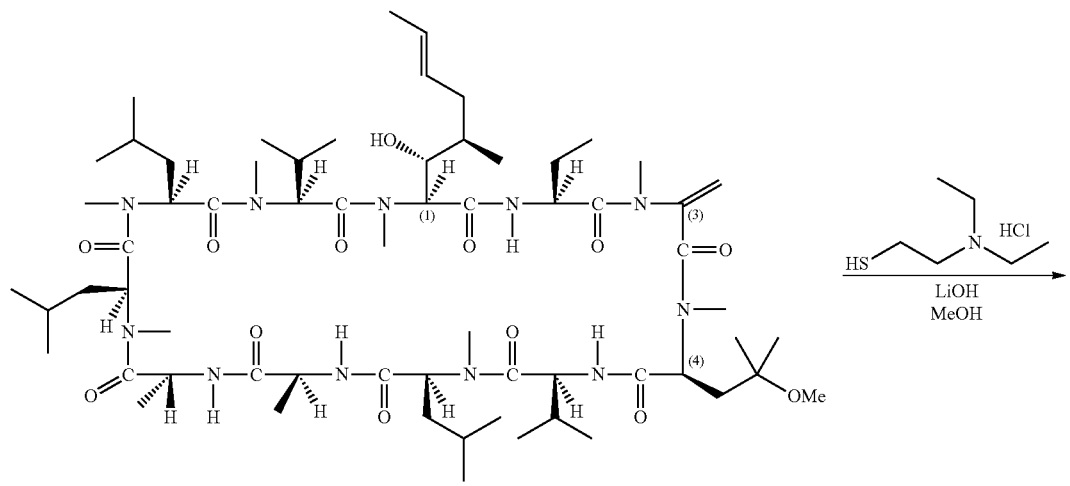

$C_{64}H_{113}N_{11}O_{13}$
Exact Mass: 1243.85
Mol. Wt.: 1244.67

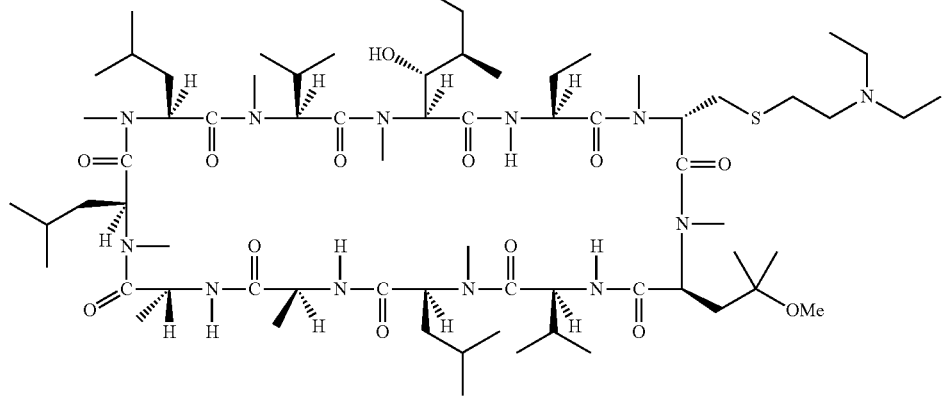

C₇₀H₁₂₈N₁₂O₁₃S
Exact Mass: 1376.94
Mol. Wt.: 1377.93

To a solution of [α-methylene-Sar]-3-[(γ-methoxy)-N-MeLeu]-4-cyclosporin (280 mg, 0.23 mmol) and 2-diethylaminoethanethiol hydrochloride (570 mg, 3.37 mmol) in methanol (15 ml) was added lithium hydroxide (142 mg, 5.92 mmol). The reaction mixture was stirred overnight at room temperature. Most of solvent was evaporated under reduced pressure. Dichloromethane (80 ml) and water (30 ml) were added and the mixture was separated. The organic layer was washed with water and brine, dried over magnesium sulfate and evaporated under reduced pressure. The residue was purified by chromatography (dichloromethane/methanol=97/3) to give 110 mg of product [Molecular Formula: $C_{70}H_{128}N_{12}O_{13}S$; Exact Mass: 1376.94; MS (m/z): 1377.67 (M+1)⁺; TLC $R_f$: 0.35 (dichloromethane/methanol=95/5); HPLC RT: 13.17 min (C8 reverse phase column: 250 mm; acetonitrile/water (0.05% trifluoroacetic acid); operation temperature: 64° C.; detector: 210 nm)].

Example 136

[(S)-(2-(N-Pyrrolidinyl)ethylthio)methyl-Sar]-3-[(γ-methoxy)-NMeLeu]-4-cycloporin

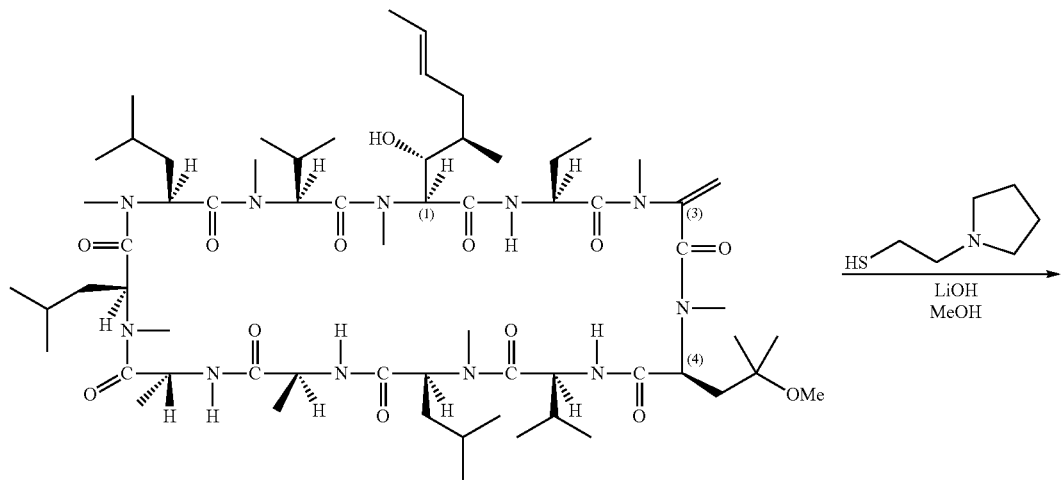

C₆₄H₁₁₃N₁₁O₁₃
Exact Mass: 1243.85
Mol. Wt.: 1244.65

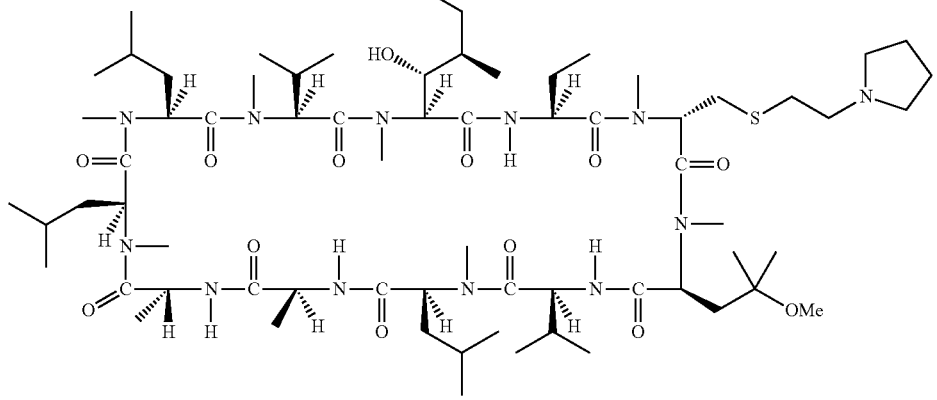

C₇₀H₁₂₆N₁₂O₁₃S
Exact Mass: 1374.93
Mol. Wt.: 1375.89

To a solution of [α-methylene-Sar]-3-[(γ-methoxy)-N-MeLeu]-4-cyclosporin (230 mg, 0.18 mmol) and 2-(N-pyrrolidinyl)ethanethiol (340 mg, 2.59 mmol) in methanol (15 ml) was added lithium hydroxide (120 mg, 5.00 mmol). The reaction mixture was stirred overnight at room temperature. Most of solvent was evaporated under reduced pressure. Dichloromethane (30 ml) and water (30 ml) were added and the mixture was separated. The organic layer was washed with water and brine, dried over magnesium sulfate and evaporated under reduced pressure. The residue was purified by chromatography (dichloromethane/methanol=96/4) to give 55 mg of product [Molecular Formula: C₇₀H₁₂₆N₁₂O₁₃S; Exact Mass: 1374.93; MS (m/z): 1375.57 (M+1)⁺; TLC R_f: 0.29 (dichloromethane/methanol=95/5); HPLC RT: 12.90 min (C8 reverse phase column: 250 mm; acetonitrile/water (0.05% trifluoroacetic acid); operation temperature: 64° C.; detector: 210 nm)].

Example 137

[(S)-(2-(N-Morpholino)ethylthio)methyl-Sar]-3-[(γ-methoxy)-NMeLeu]-4-cyclosporin

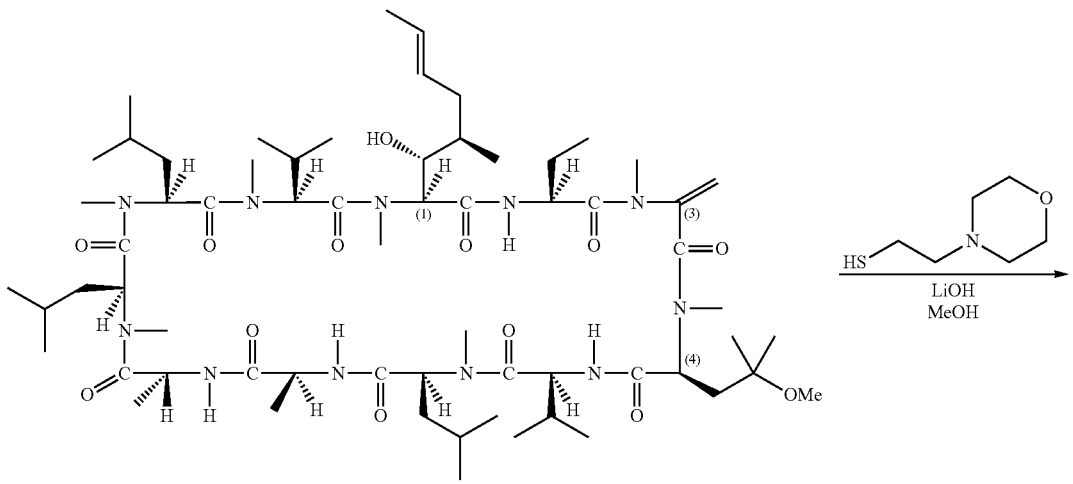

C₆₄H₁₁₃N₁₁O₁₃
Exact Mass: 1243.85
Mol. Wt.: 1244.65

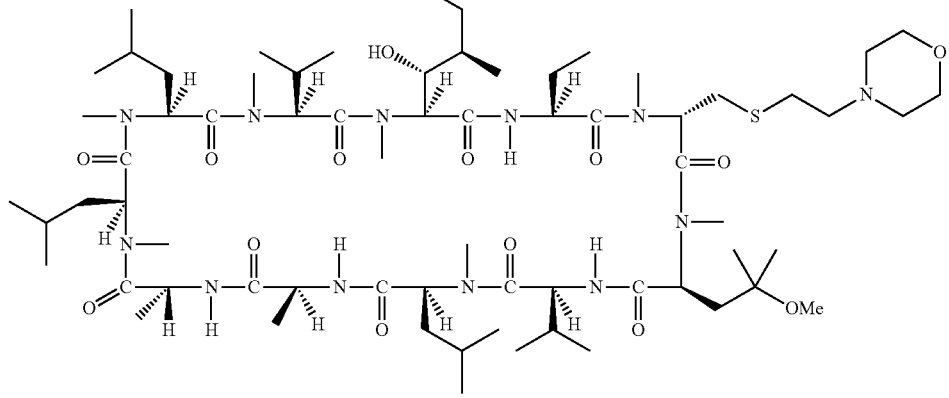

C₇₀H₁₂₆N₁₂O₁₄S
Exact Mass: 1390.92
Mol. Wt.: 1391.89

To a solution of [α-methylene-Sar]-3-[(γ-methoxy)-N-MeLeu]-4-cyclosporin (250 mg, 0.20 mmol) and 2-morpholinoethanethiol (260 mg, 1.76 mmol) in methanol (15 ml) was added lithium hydroxide (120 mg, 5.00 mmol). The reaction mixture was stirred at room temperature overnight. Most of solvent was evaporated under reduced pressure. Dichloromethane (60 ml) and water (30 ml) were added and the mixture was separated. The organic layer was washed with water and brine, dried over magnesium sulfate and evaporated under reduced pressure. The residue was purified by chromatography (dichloromethane/methanol=97/3) to give 70 mg of product [Molecular Formula: C₇₀H₁₂₆N₁₂O₁₄S; Exact Mass: 1390.92; MS (m/z): 1391.58 (M+1)⁺; TLC Rf: 0.38 (dichloromethane/methanol=9/1); HPLC RT: 12.48 min (C8 reverse phase column: 250 mm; acetonitrile/water (0.05% trifluoroacetic acid); operation temperature: 64° C.; detector: 210 nm)].

Example 138

[(S)-(3-(N,N-Dimethylamino)propylthio)methyl-Sar]-3-[(γ-methoxy)-NMeLeu]-4-cyclosporin

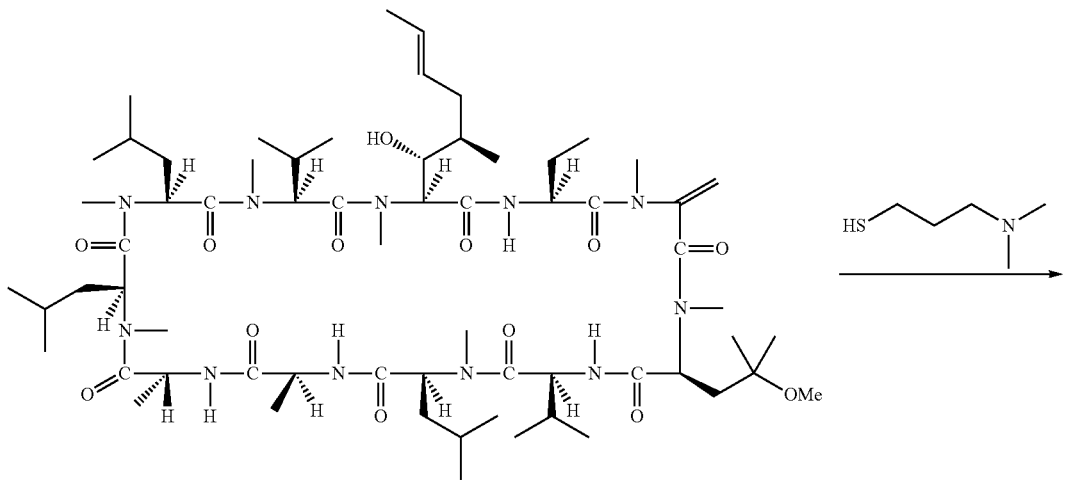

C₆₄H₁₁₃N₁₁O₁₃
Exact Mass: 1243.85
Mol. Wt.: 1244.65

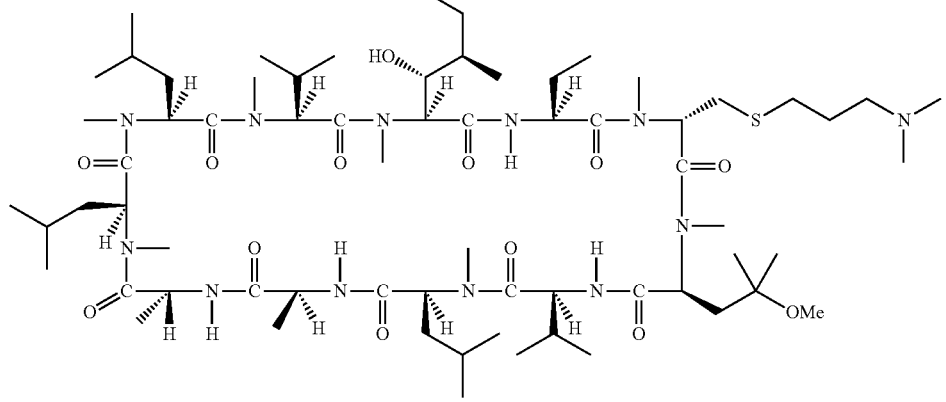

$C_{69}H_{126}N_{12}O_{13}S$
Exact Mass: 1362.93
Mol. Wt.: 1363.88

[α-Methylene-Sar]-3-[(γ-methoxy)-N-MeLeu]-4-cyclosporin (0.25 g, 0.20 mmol) and 3-(N,N-dimethylamino)propylthiol (0.24 g, 2.00 mmol) were dissolved in methanol (20 ml), followed by adding 10 equivalents of lithium hydroxide (48 mg, 2.00 mmol). The mixture was stirred overnight at room temperature. After removal of solvent, the residue was purified by flash chromatography using methylene chloride/methanol as eluent to give 80 mg of pure product [Molecular Formula: $C_{69}H_{126}N_{12}O_{13}S$; Exact Mass: 1362.93; MS (m/e): 1363.70 (M+1)$^+$. TLC $R_f$: 0.20 (ethyl acetate/methanol=10/1); HPLC RT: 12.82 min (C8 reverse phase column: 250 mm; acetonitrile/water (0.05% trifluoroacetic acid); operation temperature: 64° C.; detector: 210 nm)].

Example 139

[(S)-(3-(N,N-Diethylamino)propylthio)methyl-Sar]-3-[(γ-methoxy)-NMeLeu]-4-cyclosporin

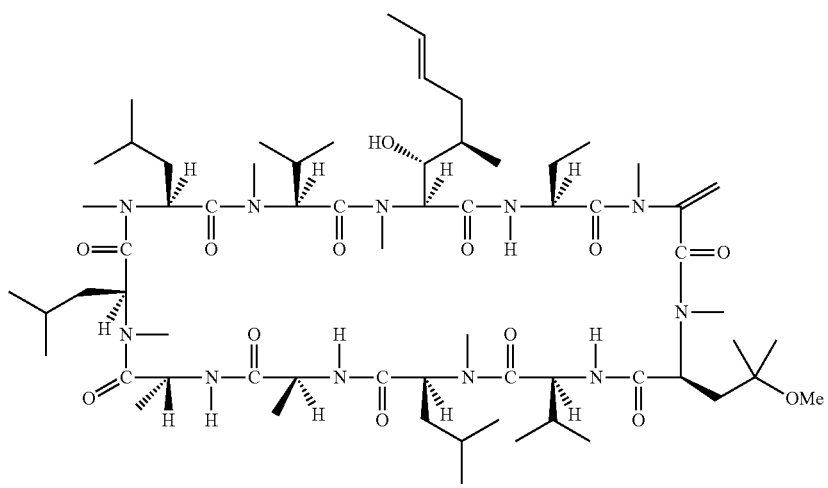 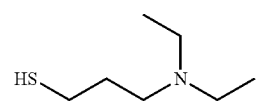

$C_{64}H_{113}N_{11}O_{13}$
Exact Mass: 1243.85
Mol. Wt.: 1244.65

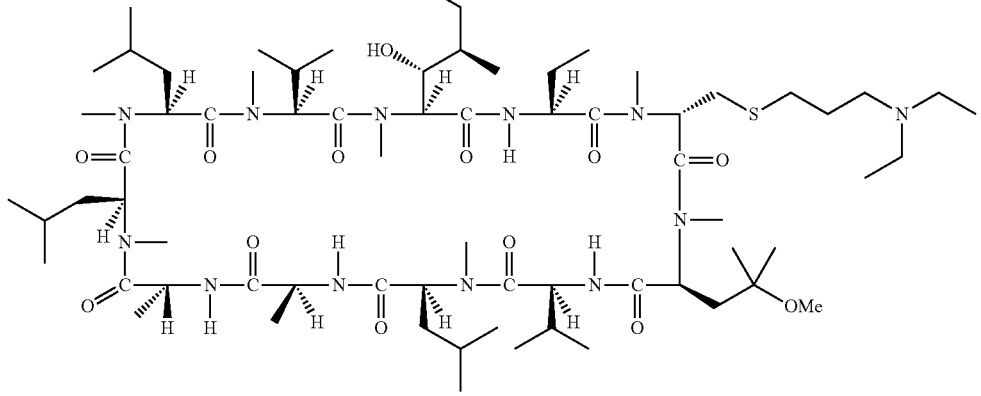

C₇₁H₁₃₀N₁₂O₁₃S
Exact Mass: 1390.96
Mol. Wt.: 1391.93

[α-Methylene-Sar]-3-[(γ-methoxy)-N-MeLeu]-4-cyclosporin (0.25 g, 0.20 mmol) and 3-(N,N-diethylamino)propylthiol (0.30 g, 2.00 mmol) were dissolved in methanol (20 ml), followed by adding 10 equivalents of lithium hydroxide (48 mg, 2.00 mmol). The mixture was stirred overnight at room temperature. After removal of solvent, the residue was purified by flash chromatography using methylene chloride/methanol as eluent to give 120 mg of pure product [Molecular Formula: $C_{71}H_{130}N_{12}S$; Exact Mass: 1390.96; MS (m/e): 1391.64 (M+1)⁺, 1413.79 (M+Na)⁻; TLC R_f: 0.25 (ethyl acetate/methanol=10/1); HPLC RT: 13.57 min (C8 reverse phase column: 250 mm; acetonitrile/water (0.05% trifluoroacetic acid); operation temperature: 64° C.; detector: 210 nm)].

Example 140

[(S)-(3-(N-Piperidinyl)propylthio)methyl-Sar]-3-[(γ-methoxy)-NMeLeu]-4-cyclosporin

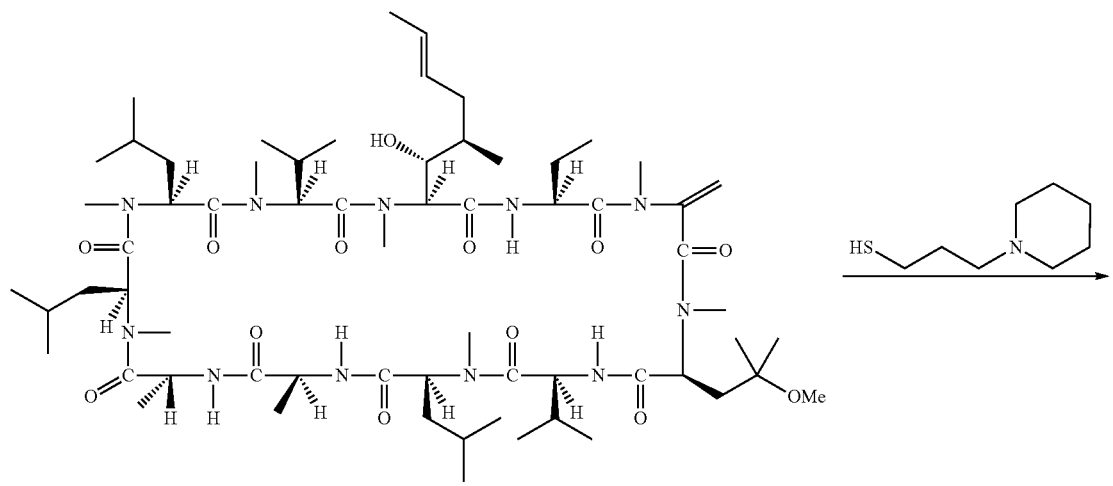

C₆₄H₁₁₃N₁₁O₁₃
Exact Mass: 1243.85
Mol. Wt.: 1244.65

-continued

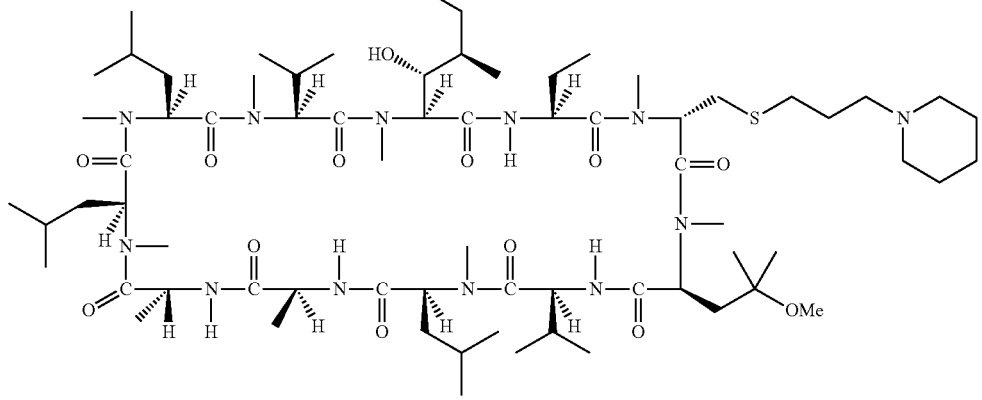

C₇₂H₁₃₀N₁₂O₁₃S
Exact Mass: 1402.96
Mol. Wt.: 1403.94

[α-Methylene-Sar]-3-[(γ-methoxy)-N-MeLeu]-4-cyclosporin (0.37 g, 0.30 mmol) and 3-(N-piperidino)propylthiol (0.48 g, 3.00 mmol) were dissolved in methanol (30 ml), followed by adding 10 equivalents of lithium hydroxide (72 mg, 3.00 mmol). The mixture was stirred overnight at room temperature. After removal of solvent, the residue was purified by flash chromatography using methylene chloride/methanol as eluent to give 60 mg of pure product [Molecular Formula: $C_{72}H_{130}N_{12}O_{13}S$; Exact Mass: 1402.96; MS (m/e): 1403.69 $(M+1)^+$, 1425 $(M+Na)^-$; TLC: $R_f$: 0.3 (ethyl acetate/methanol=10/1); HPLC RT: 13.59 min (C8 reverse phase column: 250 mm; acetonitrile/water (0.05% trifluoroacetic acid); operation temperature: 64° C.; detector: 210 nm)].

Example 141

[(S)-(3-(N-Pyrrolidinyl)propylthio)methyl-Sar]-3-[(γ-methoxy)-NMeLeu]-4-cyclosporin

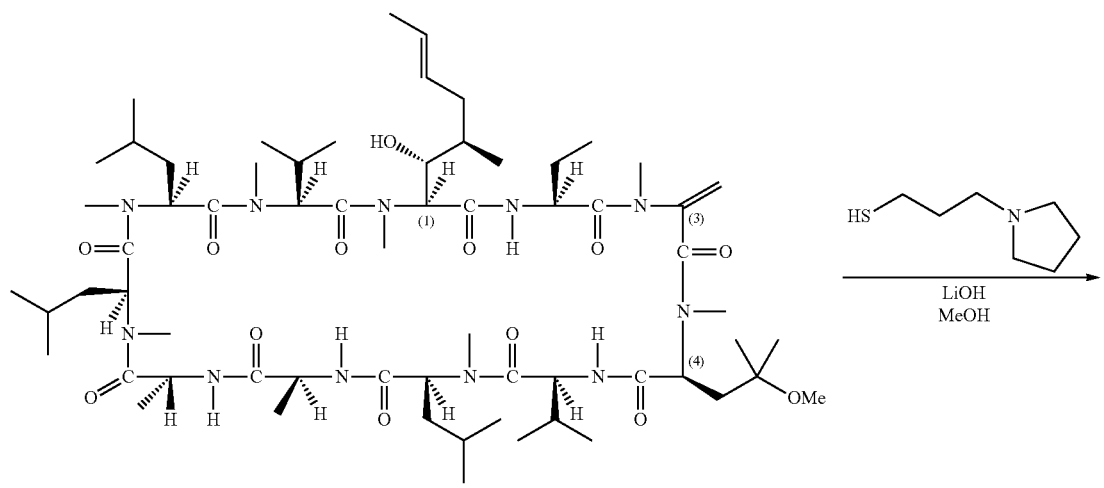

C₆₄H₁₁₃N₁₁O₁₃
Exact Mass: 1243.85
Mol. Wt.: 1244.65

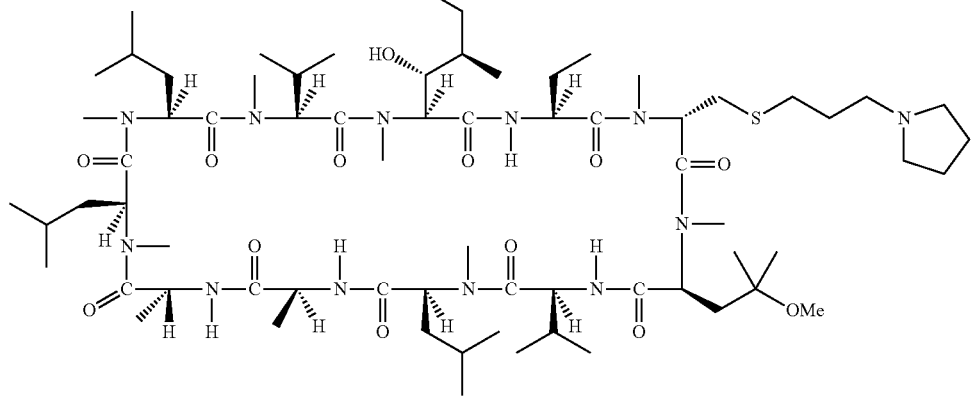

$C_{71}H_{128}N_{12}O_{13}S$
Exact Mass: 1388.94
Mol. Wt.: 1389.91

To a solution of [α-methylene-Sar]-3-[(γ-methoxy)-N-MeLeu]-4-cyclosporin (280 mg, 0.23 mmol) and 3-(N-pyrrolidinyl)propanethiol (350 mg, 2.41 mmol) in methanol (15 ml) was added lithium hydroxide (120 mg, 5.00 mmol). The reaction mixture was stirred at room temperature overnight. Then most of solvent was evaporated under reduced pressure. Dichloromethane (80 ml) and water (25 ml) were added and the mixture was separated. The organic layer was washed with water and brine, dried over magnesium sulfate and evaporated under reduced pressure. The residue was purified by chromatography (dichloromethane/methanol=94/6) to give 47 mg of product [Molecular Formula: $C_{71}H_{128}N_{12}O_{13}S$; Exact Mass: 1388.94; MS (m/z): 1389.68 $(M+1)^+$; TLC Rf: 0.30 (dichloromethane/methanol=95/5); HPLC RT: 13.25 min (C8 reverse phase column: 250 mm; acetonitrile/water (0.05% trifluoroacetic acid); operation temperature: 64° C.; detector: 210 nm)].

Example 142

[(S)-(3-(N-Morpholino)propylthio)methyl-Sar]-3-[(γ-methoxy)-NMeLeu]-4-cyclosporin

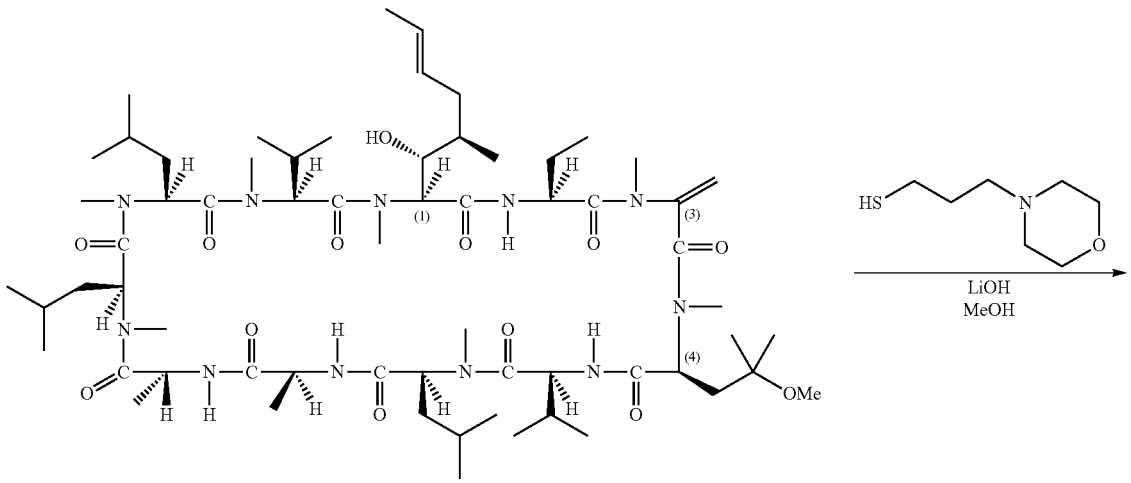

$C_{64}H_{113}N_{11}O_{13}$
Exact Mass: 1243.85
Mol. Wt.: 1244.65

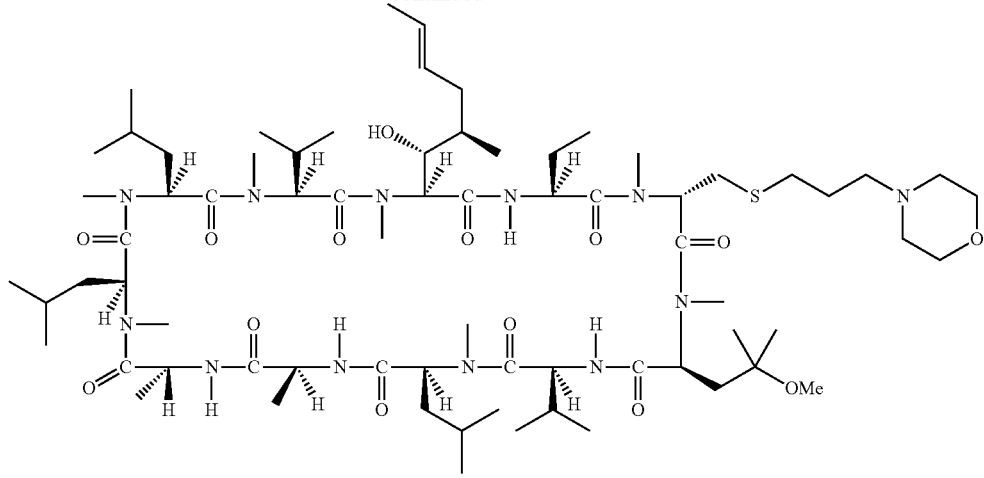

C₇₁H₁₂₈N₁₂O₁₄S
Exact Mass: 1404.94
Mol. Wt.: 1405.91

To a solution of [α-Methylene-Sar]-3-[(γ-methoxy)-N-MeLeu]-4-cyclosporin (320 mg, 0.26 mmol) and 3-morpholinopropanethiol (600 mg, 3.73 mmol) in methanol (25 ml) was added lithium hydroxide (140 mg, 5.83 mmol). The reaction mixture was stirred at room temperature overnight. Then most of solvent was evaporated under reduced pressure. Dichloromethane (60 ml) and water (25 ml) were added and the mixture was separated. The organic layer was washed with water and brine, dried over magnesium sulfate and evaporated under reduced pressure. The residue was purified by chromatography (dichloromethane/methanol=97/3) to give 58 mg of product [Molecular Formula: C₇₁H₁₂₈N₁₂O₁₄S; Exact Mass: 1404.94; MS (m/z): 1405.52 (M+1)⁺; TLC Rf: 0.39 (dichloromethane/methanol=9/1); HPLC RT: 15.96 min (C8 reverse phase column: 250 mm; acetonitrile/0.077% ammonium acetate in water; operation temperature: 64° C.; detector: 210 nm)].

Example 143

[(S)-(4-Methoxybutylthio)methyl-Sar]-3-[(γ-methoxy)-N-MeLeu]-4-cyclosporin

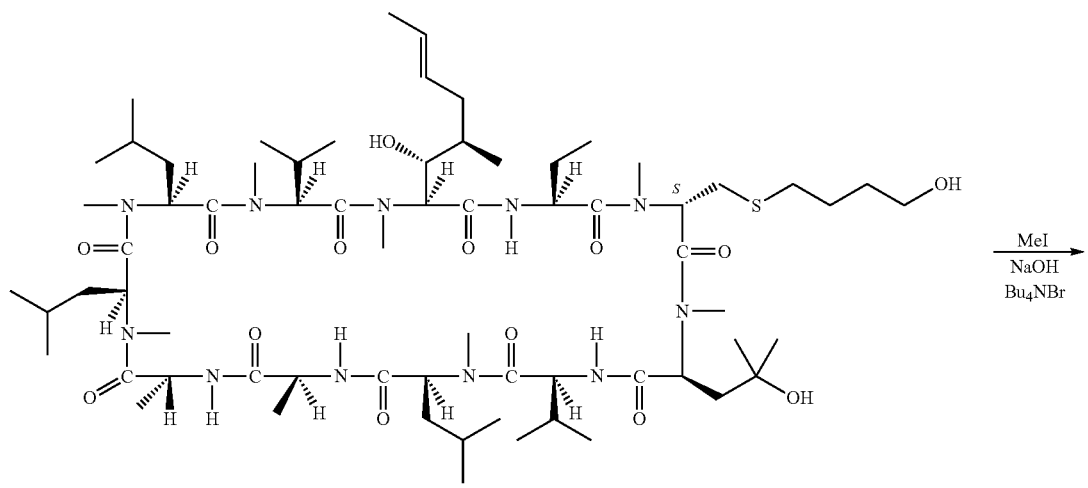

C₆₇H₁₂₁N₁₁O₁₄S
Exact Mass: 1335.88
Mol. Wt.: 1336.83

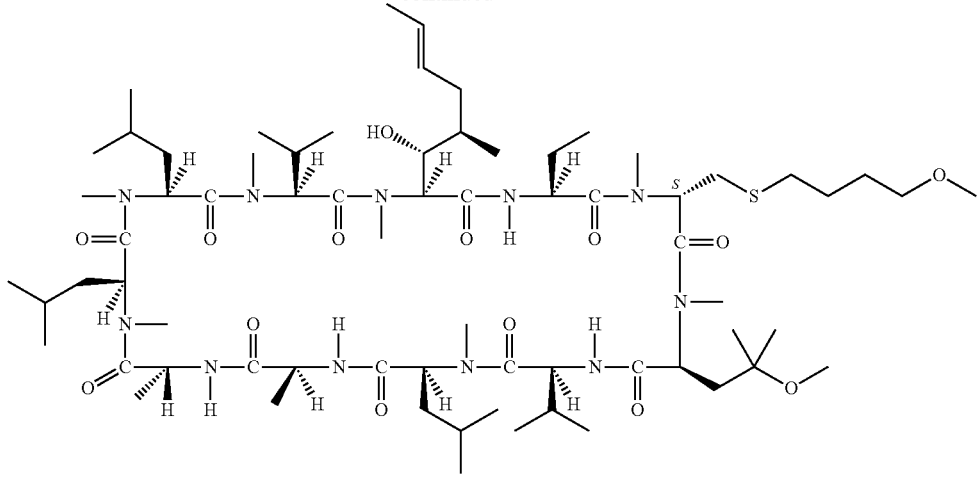

C<sub>69</sub>H<sub>125</sub>N<sub>11</sub>O<sub>14</sub>S
Exact Mass: 1363.91
Mol. Wt.: 1364.88

[(S)-(4-Hydroxylbutylthio)methyl-Sar]-3-[(γ-hydroxy)-N-MeLeu]-4-cyclosporin (100 mg, 0.075 mmol) was dissolved in of benzene (3 ml), followed by adding 3.5 equivalents of tetrabutylammonium bromide, 75 equivalents of 50% of sodium hydroxide and iodomethene (0.425 g, 3.00 mol). The mixture was stirred overnight at room temperature and diluted with benzene (10 ml). The organic mixture was washed with brine, dried over magnesium sulfite and evaporated under reduced pressure. The residue was subject to a flash chromatography using ethyl acetate/methanol as eluent to give 25 mg of product [Molecular formula: $C_{69}H_{125}N_{11}O_{14}S$; Exact Mass: 1363.91; MS (m/z): 1364.35 (M+1)$^+$, 1386.70 (M+Na)$^+$; TLC R$_f$: 0.38 (ethyl acetate/methanol=20/1); HPLC RT: 16.72 min (C8 reverse phase column: 250 mm; acetonitrile/water (0.05% trifluoroacetic acid); operation temp: 64° C.; Detector: 210 nm)].

Example 144

[(R)-(2-(N,N-Diethylamino)ethoxy)methyl-Sar]-3-[(γ-methoxy)-NMeLeu]-4-cyclsporin

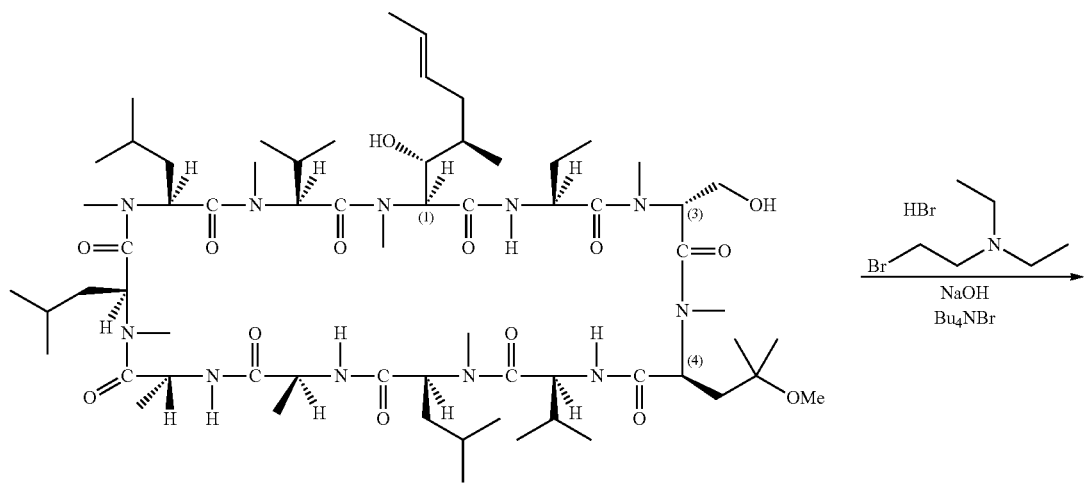

C<sub>64</sub>H<sub>115</sub>N<sub>11</sub>O<sub>14</sub>
Exact Mass: 1261.86
Mol. Wt.: 1262.69

-continued

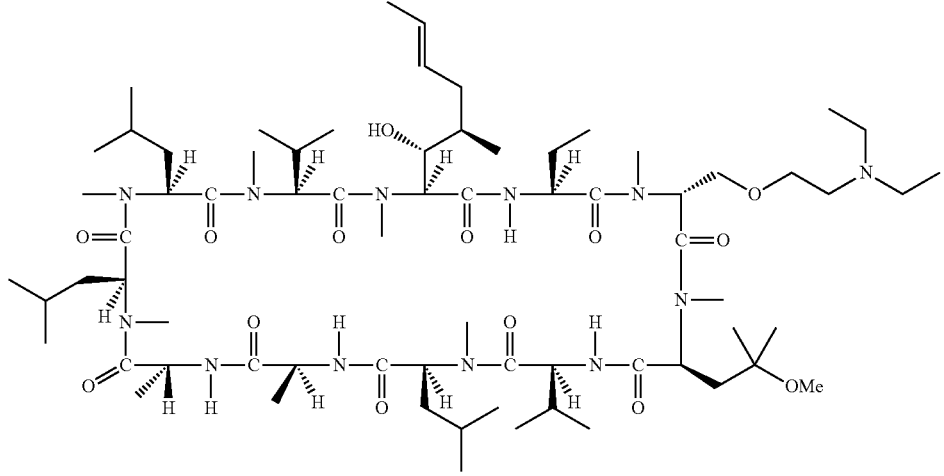

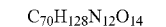
Exact Mass: 1360.97
Mol. Wt.: 1361.86

To a solution of [(R)-α-hydroxymethyl-Sar]-3-[(γ-methoxy)-N-MeLeu]-4-cyclosporin (0.20 g, 0.16 mmol) in benzene (10 ml) were added a solution of sodium hydroxide (0.48 g, 12.00 mmol) in water (1 ml), 2-bromo-N,N-diethylethylamine hydrobromide (1.10 g, 4.21 mmol) and tetra-n-butylammonium bromide (0.10 g, 0.31 mmol). The mixture was stirred at 35° C. for 40 hours. Ice water (10 ml) was added and the mixture was separated. The aqueous layer was extracted with dichloromethane (20 ml). The combined organic layers was washed with brine, dried over magnesium sulfate and concentrated under reduced pressure. The residue was purified by chromatography (dichloromethane/methanol=96/4) to give 36 mg of product [Molecular Formula: $C_{70}H_{128}N_{12}O_{14}$; Exact Mass: 1360.97; MS (m/z): 1383.74 (M+Na)$^+$; TLC $R_f$: 0.32 (dichloromethane/methanol=95/5); HPLC RT: 13.66 min (C8 reverse phase column: 250 mm; acetonitrile/0.077% ammonium acetate in water; operation temperature: 64° C.; detector: 210 nm); $^1$H NMR spectrum (600 MHz, CDCl$_3$, δ in ppm): 0.65(d, J=4.8 Hz, 3H), 0.82 (m, 9H), 0.87 (m, 6H), 0.91 (d, J=6. Hz, 3H), 0.93 (d, J=6.0 Hz, 3H), 0.98-1.01 (m, 15 H), 1.07 (d, J=6.6 Hz, 3H), 1.11(s, 6H), 1.23 (m, 6 H), 1.33 (d, J=7.2 Hz, 3H), 1.39-1.47 (m, 2H), 1.53-1.58 (m, 4H), 1.6 (m, 3H), 1.67-1.75 (m, 3H), 1.98-2.12 (m, 4H), 2.43-2.48 (m, 3H), 2.50-2.54 (m, 4H), 2.60 (t, J=6.0 Hz, 2H), 2.67 (s, 3H), 2.68 (s, 3H), 3.07 (s, 3H), 3.10 (s, 3H), 3.12 (s, 3H), 3.24 (s, 3H), 3.26 (s, 3H), 3.48 (m, 4H), 3.52-3.56 (m, 1H), 3.60-3.62 (m, 1H), 3.67-3.70 (m, 1H), 3.80 (m, 1H), 4.06 (t, J=9.6 Hz, 1H), 4.52 (m, 1H), 4.57 (m, 1H), 4.80 (m, 1H), 4.91 (t, J=7.8 Hz, 1H), 5.04 (m, 3H), 5.11 (d, J=11.4 Hz, 1H), 5.28-5.34 (m, 2 H), 5.50 (d, J=7.2 Hz, 1 H), 5.67 (m, 1H), 7.10 (d, J=7.8 Hz 1H), 7.48 (d, J=7.80 Hz,1H), 7.58 (d, J=7.2 Hz,1H), 7.91 (d, J=10.2 Hz,1H)].

Example 145

[(R)-(2-(N,N-Dimethylamino)ethoxy)methyl-Sar]-3-[(γ-methoxy)-NMeLeu]-4-cyclosporin

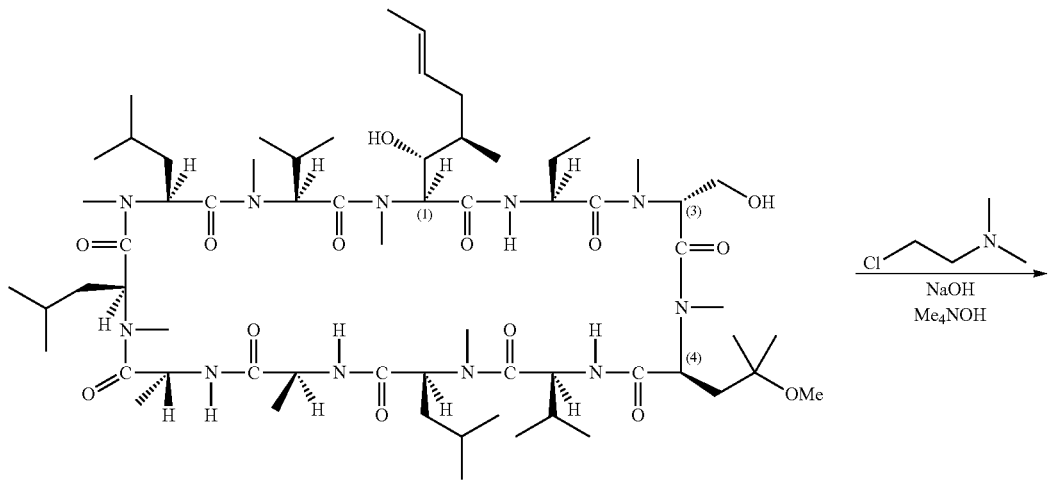

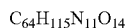
Exact Mass: 1261.86
Mol. Wt.: 1262.66

-continued

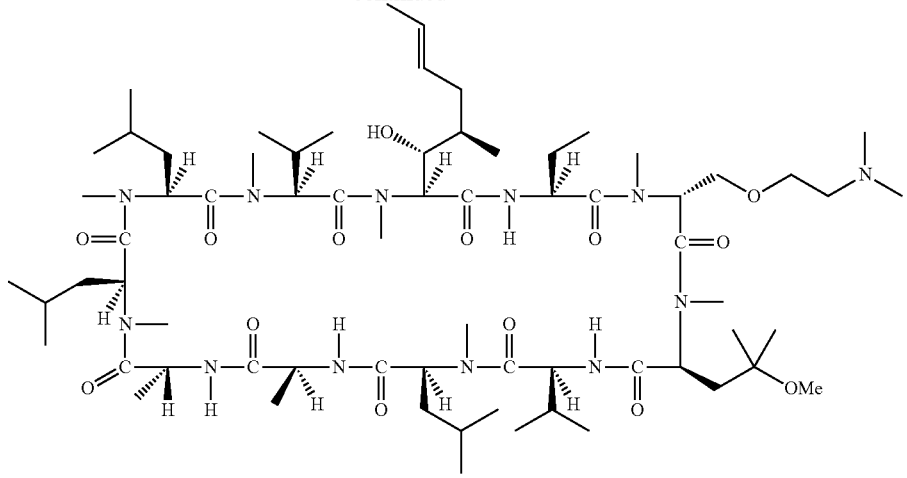

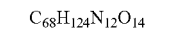

Exact Mass: 1332.94
Mol. Wt.: 1333.78

To a solution of [(R)-α-hydroxymethyl-Sar]-3-[(γ-methoxy)-N-MeLeu]-4-cyclosporin (250 mg, 0.20 mmol) in benzene (20 ml) were added a solution of sodium hydroxide (633 mg, 15.85 mmol) in water (0.70 ml), tetramethylammonium hydroxide pentahydrate (720 mg, 3.96 mmol) and 2-dimethylaminoethyl chloride hydrochloride (570 mg, 3.96 mmol). The mixture was stirred at 40 to 50° C. for two days. Sodium hydroxide (633 mg, 15.85 mmol) in water (0.70 ml), tetramethylammonium hydroxide pentahydrate (720 mg, 3.96 mmol) and 2-dimethylaminoethyl chloride hydrochloride (570 mg, 3.96 mmol) were added and the mixture was kept stirring at 40 to 50° C. for another two days. Another portion of 2-dimethylaminoethyl chloride hydrochloride (1.14 g, 7.91 mmol) was added and the stirring was continued at 40 to 50° C. for one more day. Sodium bicarbonate saturated solution (30 ml) was added and the mixture was separated. Then the aqueous layer was extracted with ethyl acetate (25 ml×2). The combined organic layers were dried over magnesium sulfate and evaporated under reduced pressure. The residue was dissolved in ethyl acetate (25 ml). The resulting ethyl acetate phase was washed with acetic acid solution (5 ml in 10 ml water) and sodium bicarbonate saturated solution (30 ml), dried over magnesium sulfate and evaporated under reduced pressure. After purified on silica gel, 21 mg product was obtained [Molecular Formula: $C_{68}H_{124}N_{12}O_{14}$; Exact Mass: 1332.94; MS (m/z): 1333.75 $(M+1)^+$, 1355.87 $(M+Na)^+$; TLC $R_f$: 0.22 (dichloromethane/methanol=9/1); HPLC RT: 17.3 min (C8 reverse phase column: 250 mm; acetonitrile/0.077% ammonium acetate in water; operation temperature: 64° C.; detector: 210 nm)]

Example 146

[(R)-(2-(N-Morpholino)ethoxy)methyl-Sar]-3-[(γ-methoxy)-NMeLeu]-4-cyclosporin

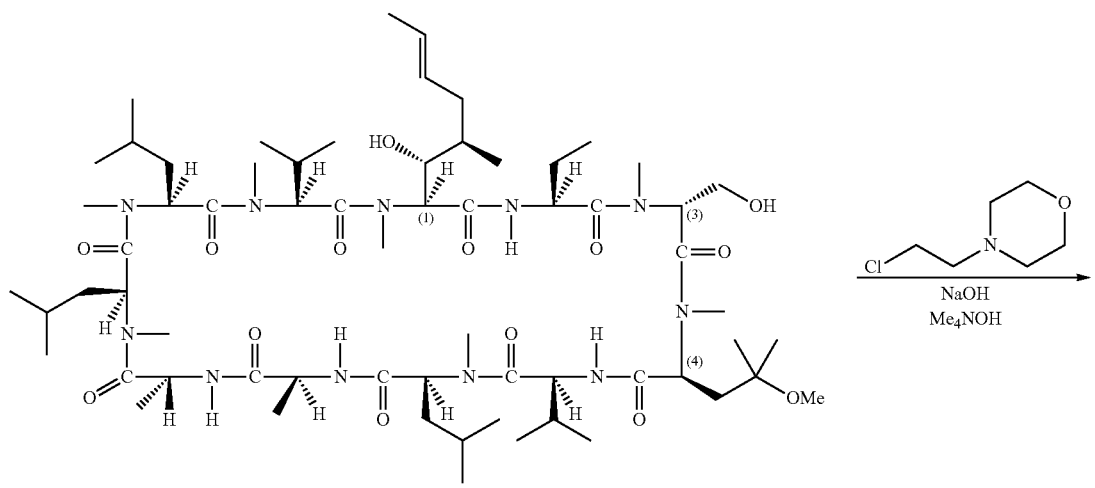

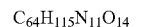

Exact Mass: 1261.86
Mol. Wt.: 1262.66

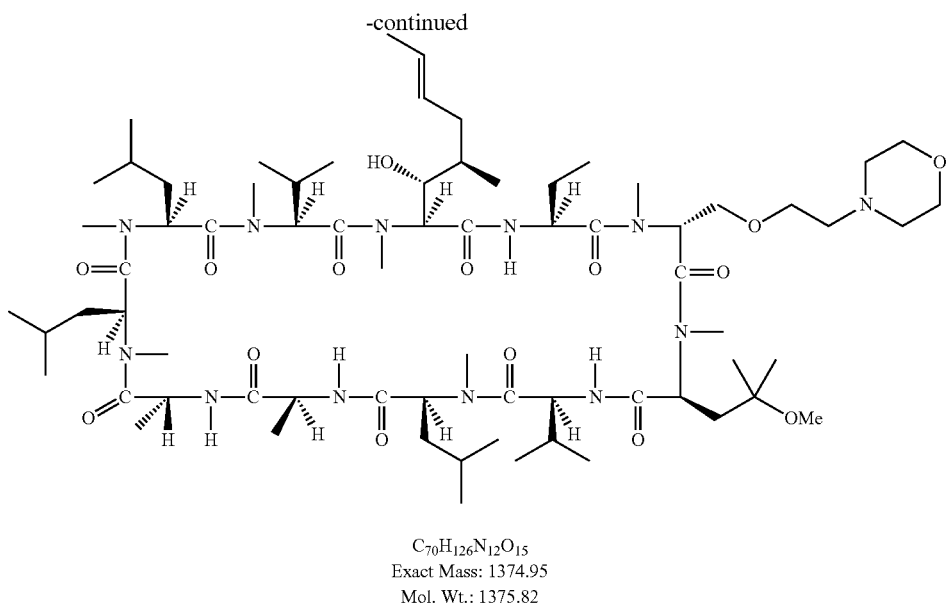

$C_{70}H_{126}N_{12}O_{15}$
Exact Mass: 1374.95
Mol. Wt.: 1375.82

To a solution of [(R)-α-hydroxymethyl-Sar]-3-[(γ-methoxy)-N-MeLeu]-4-cyclosporin (250 mg, 0.20 mmol) in benzene (20 ml) was added a solution of sodium hydroxide (633 mg, 15.85 mmol) in water (0.70 ml), followed by tetramethylammonium hydroxide pentahydrate (720 mg, 3.96 mmol) and 2-(4-morpholinyl)ethyl chloride hydrochloride (737 mg, 3.96 mmol). The mixture was stirred at 40 to 50° C. for two days. Sodium hydroxide (633 mg, 15.85 mmol) in water (0.70 ml), tetramethylammonium hydroxide pentahydrate (720 mg, 3.96 mmol) and 2-(4-morpholinyl) ethyl chloride hydrochloride (737 mg, 3.96 mmol) were added and the mixture was kept stirring at 40 to 50° C. for another two days. Another portion of 2-(4-morpholinyl)ethyl chloride hydrochloride (1.47 g, 7.91 mmol) was added and the stirring was continued at 40 to 50° C. for two more days. Sodium bicarbonate saturated solution (30 ml) was added and the mixture was separated. Then the aqueous layer was extracted with ethyl acetate (25 ml×2). The combined organic layers were dried over magnesium sulfate and evaporated under reduced pressure. The residue was dissolved in ethyl acetate (25 ml). And the resulting ethyl acetate phase was washed with acetic acid solution (5 ml in 10 ml water) and sodium bicarbonate saturated solution (30 ml), dried over magnesium sulfate and evaporated under reduced pressure. After purified on silica gel, 45 mg product was obtained [Molecular Formula: $C_{70}H_{126}N_{12}O_{15}$; Exact Mass: 1374.95; MS (m/z): 1375.63 (M+1)$^+$, 1397.79 (M+Na)$^+$; TLC $R_f$: 0.42 (dichloromethane/methanol=9/1); HPLC RT: 12.9 min (C8 reverse phase column: 250 mm; acetonitrile/0.077% ammonium acetate in water; operation temperature: 64° C.; detector: 210 nm)]

Example 147

[(R)-(3-(N,N-Dimethylamino)propoxy)methyl-Sar]-3-[(γ-methoxy)-NMeLeu]-4-cyclosporine

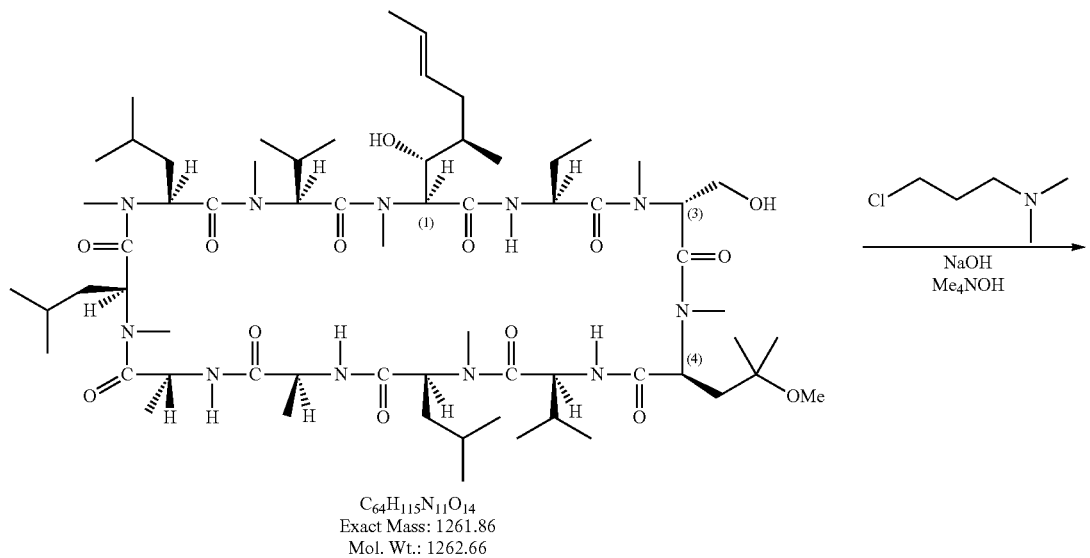

$C_{64}H_{115}N_{11}O_{14}$
Exact Mass: 1261.86
Mol. Wt.: 1262.66

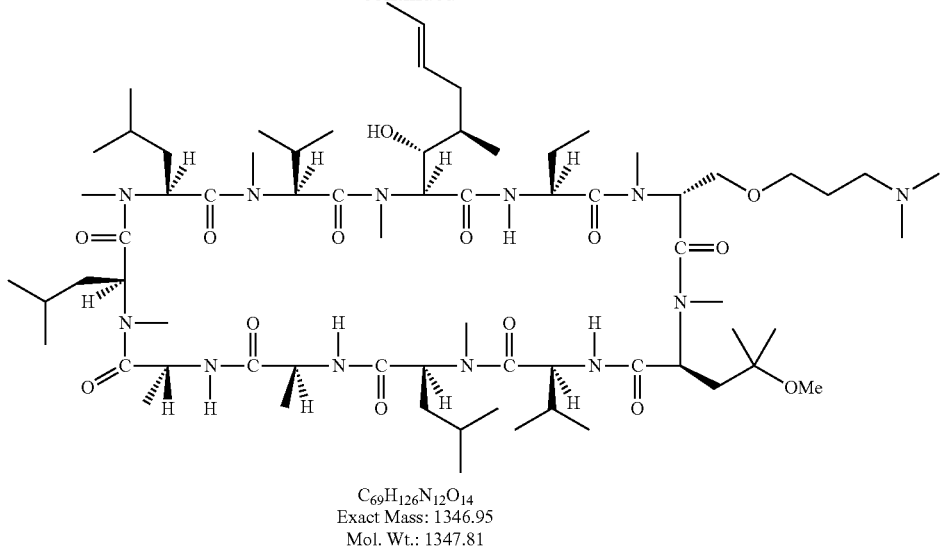

C<sub>69</sub>H<sub>126</sub>N<sub>12</sub>O<sub>14</sub>
Exact Mass: 1346.95
Mol. Wt.: 1347.81

To a solution of [(R)-α-hydroxymethyl-Sar]-3-[(γ-methoxy)-N-MeLeu]-4-cyclosporin (250 mg, 0.20 mmol) in benzene (20 ml) were added a solution of sodium hydroxide (633 mg, 15.85 mmol) in water (0.70 ml), tetramethylammonium hydroxide pentahydrate (720 mg, 3.96 mmol) and 3-dimethylaminopropyl chloride hydrochloride (626 mg, 3.96 mmol). The mixture was stirred at 40 to 50° C. for two days. Sodium hydroxide (633 mg, 15.85 mmol) in water (0.70 ml), tetramethylammonium hydroxide pentahydrate (720 mg, 3.96 mmol) and 3-dimethylaminopropyl chloride hydrochloride (626 mg, 3.96 mmol) were added and the mixture was kept stirring at 40 to 50° C. for another two days. Another portion of 3-dimethylaminopropyl chloride hydrochloride (1.25 g, 7.91 mmol) was added and the stirring was continued at 40 to 50° C. for one more day. Sodium bicarbonate saturated solution (30 ml) was added and the mixture was separated. Then the aqueous layer was extracted with ethyl acetate (25 ml×2). The combined organic layers were dried over magnesium sulfate and evaporated under reduced pressure. The residue was dissolved in ethyl acetate (25 ml). And the resulting ethyl acetate phase was washed with acetic acid solution (5 ml in 10 ml water) and sodium bicarbonate saturated solution (30 ml), dried over magnesium sulfate and evaporated under reduced pressure. After purified on silica gel, 36 mg product was obtained [Molecular Formula: $C_{69}H_{126}N_{12}O_{14}$; Exact Mass: 1346.95; MS (m/z): 1347.65 (M+1)$^+$, 1369.74 (M+Na)$^+$; TLC R$_f$: 0.21 (dichloromethane/methanol=9/1). HPLC RT: 18.8 min (C8 reverse phase column: 250 mm; acetonitrile/0.077% ammonium acetate in water; operation temperature: 64° C.; detector: 210 nm)].

Example 148

[(R)-(3-(N,N-Diethylamino)propoxy)methyl-Sar]-3-[(γ-methoxy)-NMeLeu]-4-cyclosporine

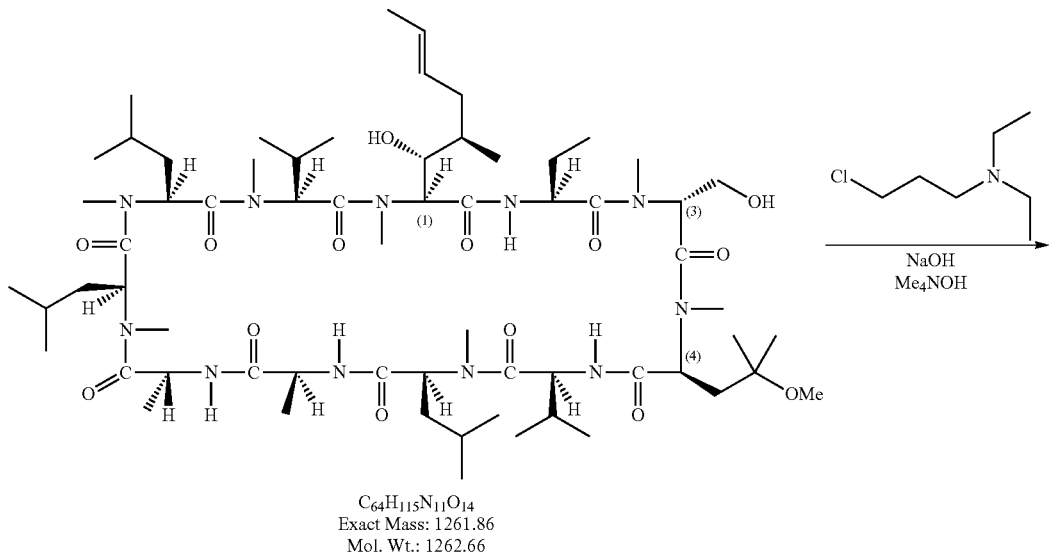

C<sub>64</sub>H<sub>115</sub>N<sub>11</sub>O<sub>14</sub>
Exact Mass: 1261.86
Mol. Wt.: 1262.66

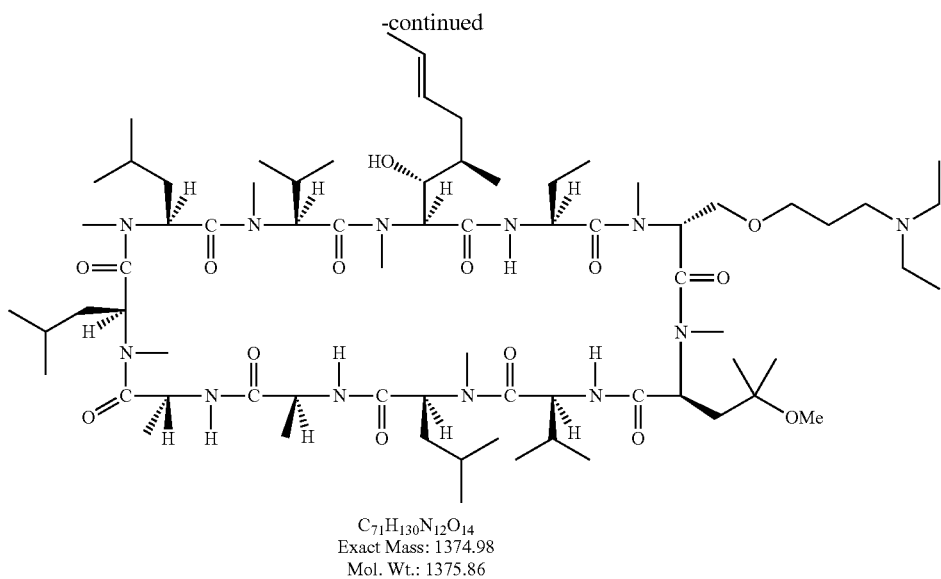

$C_{71}H_{130}N_{12}O_{14}$
Exact Mass: 1374.98
Mol. Wt.: 1375.86

To a solution of [(R)-α-hydroxymethyl-Sar]-3-[(γ-methoxy)-N-MeLeu]-4-cyclosporin (250 mg, 0.20 mmol) in benzene (20 ml) was added a solution of sodium hydroxide (633 mg, 15.85 mmol) in water (0.70 ml), followed by adding tetramethylammonium hydroxide pentahydrate (720 mg, 3.96 mmol) and 3-diethylaminopropyl chloride hydrochloride (737 mg, 3.96 mmol). The mixture was stirred at 40 to 50° C. for two days. Sodium hydroxide (633 mg, 15.85 mmol) in water (0.70 ml), tetramethylammonium hydroxide pentahydrate (720 mg, 3.96 mmol) and 3-diethylaminopropyl chloride hydrochloride (737 mg, 3.96 mmol) were added and the mixture was kept stirring at 40 to 50° C. for another two days. Another portion of 3-diethylaminopropyl chloride hydrochloride (1.47 g, 7.91 mmol) was added and the stirring was continued at 40 to 50° C. for two more days. Sodium bicarbonate saturated solution (30 ml) was added and the mixture was separated. The aqueous layer was extracted with ethyl acetate (25 ml×2). Then the combined organic layers were dried over magnesium sulfate and evaporated under reduced pressure. The residue was dissolved in ethyl acetate (25 ml). And the resulting ethyl acetate phase was washed with acetic acid solution (5 ml in 10 ml water) and sodium bicarbonate saturated solution (30 ml), dried over magnesium sulfate and evaporated under reduced pressure. After purified on silica gel, 38 mg product was obtained [Molecular Formula: $C_{71}H_{130}N_{12}O_{14}$; Exact Mass: 1374.98; MS (m/z): 1375.70 $(M+1)^+$, 1397.80 $(M+Na)^+$; TLC $R_f$: 0.24 (dichloromethane/methanol=9/1); HPLC RT: 19.6 min (C8 reverse phase column: 250 mm; acetonitrile/0.077% ammonium acetate in water; operation temperature: 64° C.; detector: 210 nm)]

Example 149

[α-Methylene-Sar]-3-[(γ-methylthiomethoxy)-NMeLeu]-4-cyclosporin

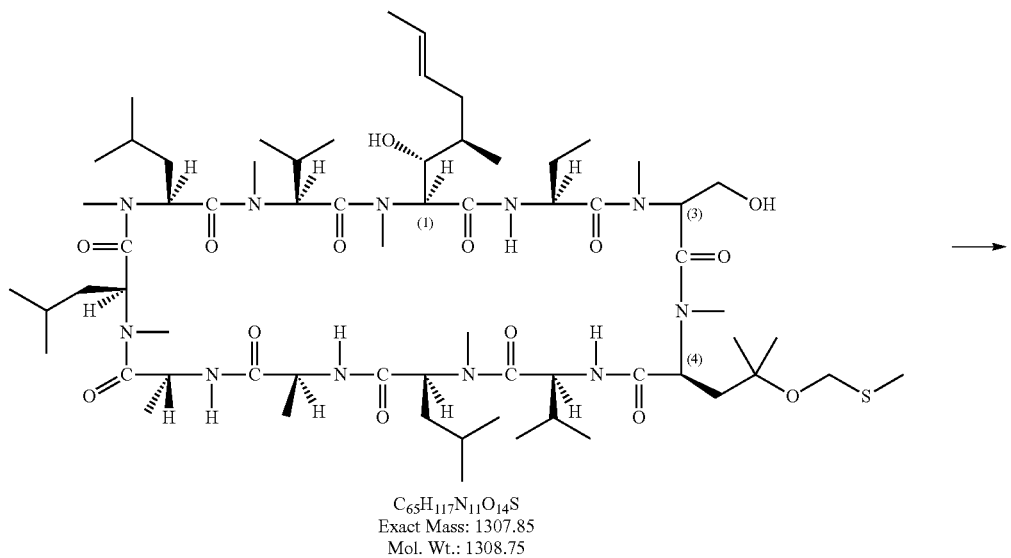

$C_{65}H_{117}N_{11}O_{14}S$
Exact Mass: 1307.85
Mol. Wt.: 1308.75

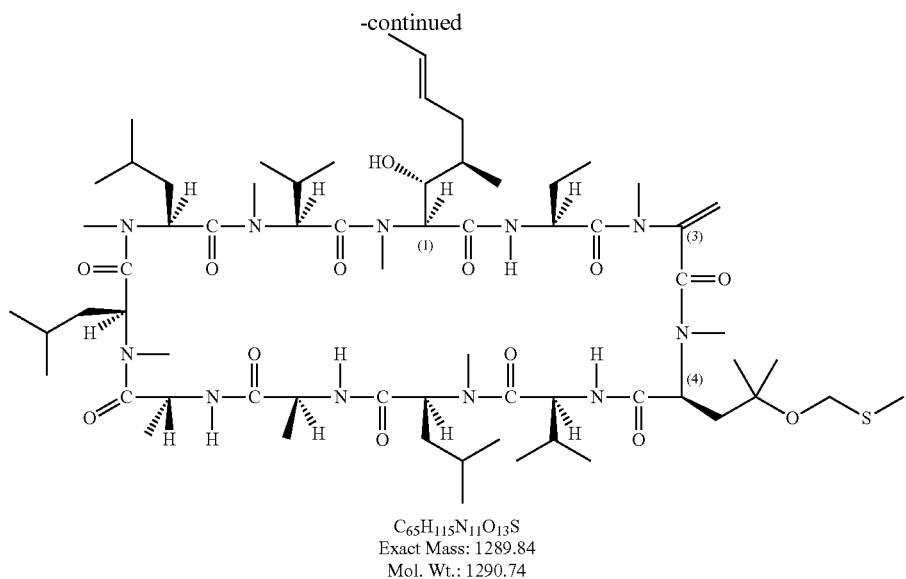

$C_{65}H_{115}N_{11}O_{13}S$
Exact Mass: 1289.84
Mol. Wt.: 1290.74

[α-Methylene-Sar]-3-[(γ-methylthiomethoxy)-N-Me-Leu]-4-cyclosporin was prepared according to the method described in Example 28. The product was purified by chromatography on silica gel (ethyl acetate/methanol) [Molecular Formula: $C_{65}H_{115}N_{11}O_{13}S$; Exact Mass: 1289.84; MS (m/z): 1290.70 (M+1)$^+$, 1312.67 (M+Na)$^+$].

Example 150

[(S)-(2-(N,N-Dimethylamino)ethylthio)methyl-Sar]-3-[(γ-methylthio)methoxy-NMeLeu]-4-cyclosporin

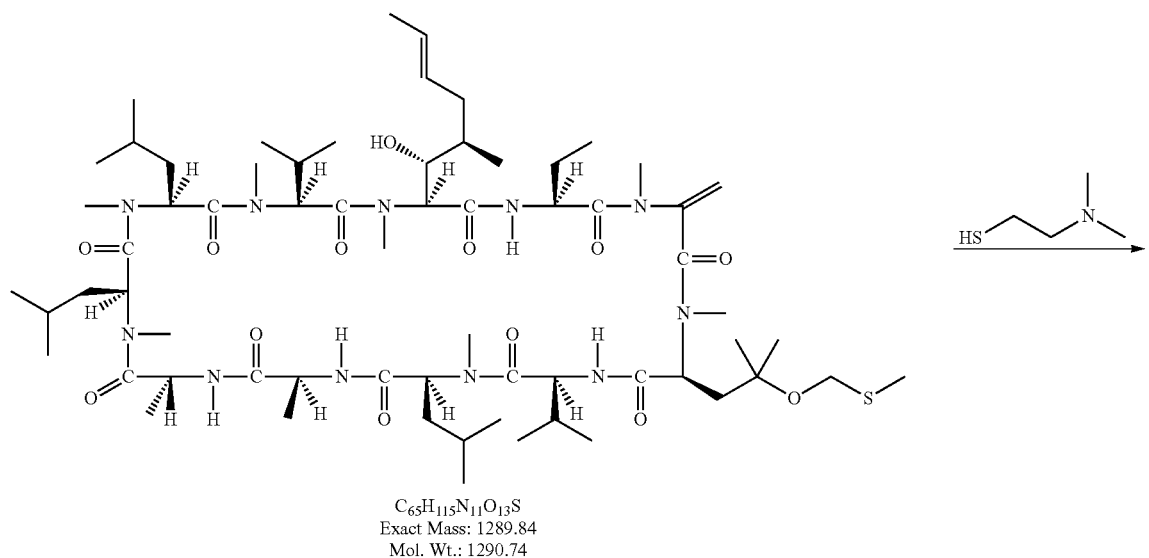

$C_{65}H_{115}N_{11}O_{13}S$
Exact Mass: 1289.84
Mol. Wt.: 1290.74

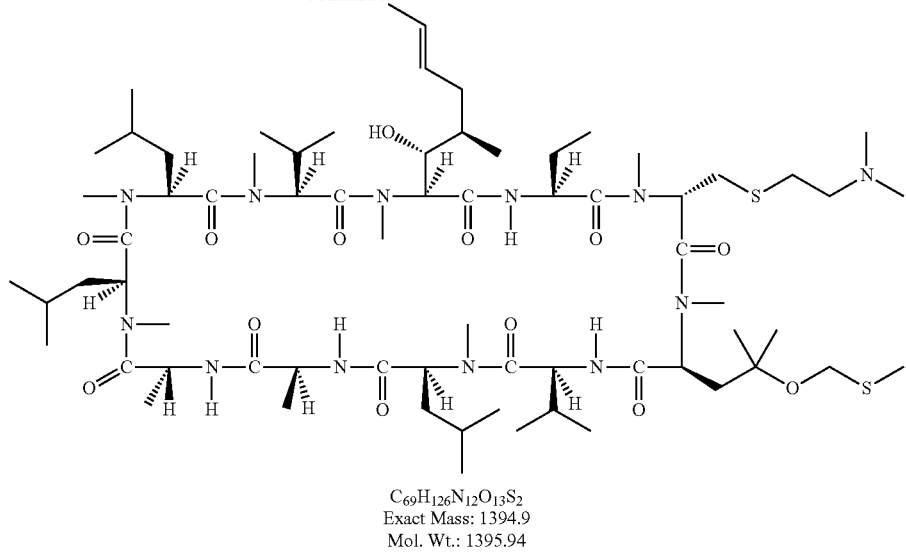

C₆₉H₁₂₆N₁₂O₁₃S₂
Exact Mass: 1394.9
Mol. Wt.: 1395.94

[α-Methylene-Sar]-3-[(γ-methylthiomethoxy)-N-Me-Leu]-4-cyclosporin (0.32 g, 0.25 mmol) and 2-(N,N-dimethyl)ethanethiol (0.26 g, 2.50 mmol) were dissolved in methanol (20 ml), followed by adding 24 equivalents of triethylamine. The mixture was stirred overnight. After removal of solvent, the residue was subject to chromatography using dichloromethane/methanol as eluent to give 0.14 g of pure product [Molecular Formula, C₆₉H₁₂₆N₁₂O₁₃S₂; Exact Mass: 1394.90; MS (m/z): 1395.70 (M+1)⁺, 1417.68 (M+Na)⁺; TLC R$_f$: 0.10 (ethyl acetate/methanol=10:1); HPLC RT: 13.30 min (C8 reverse phase column: 250 mm; acetonitrile/water (0.05% trifluoroacetic acid); operation temperature: 64° C.; detector: 210 nm)].

Example 151

[(S)-(2-(N,N-Diethylamino)ethylthio)methyl-Sar]-3-[(γ-methylthio)methoxy-NMeLeu]-4-cyclosporin

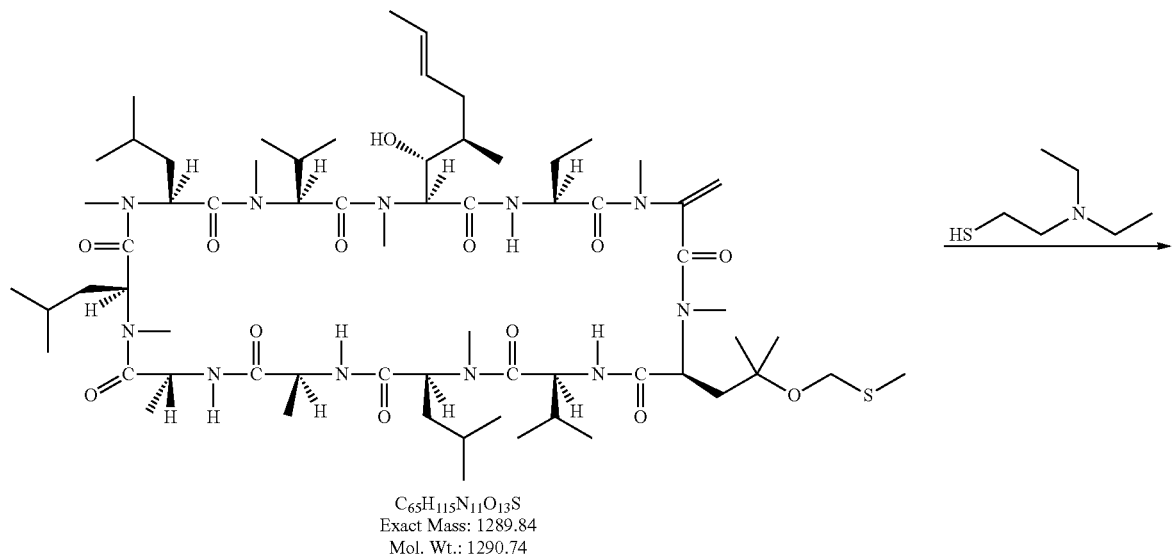

C₆₅H₁₁₅N₁₁O₁₃S
Exact Mass: 1289.84
Mol. Wt.: 1290.74

-continued

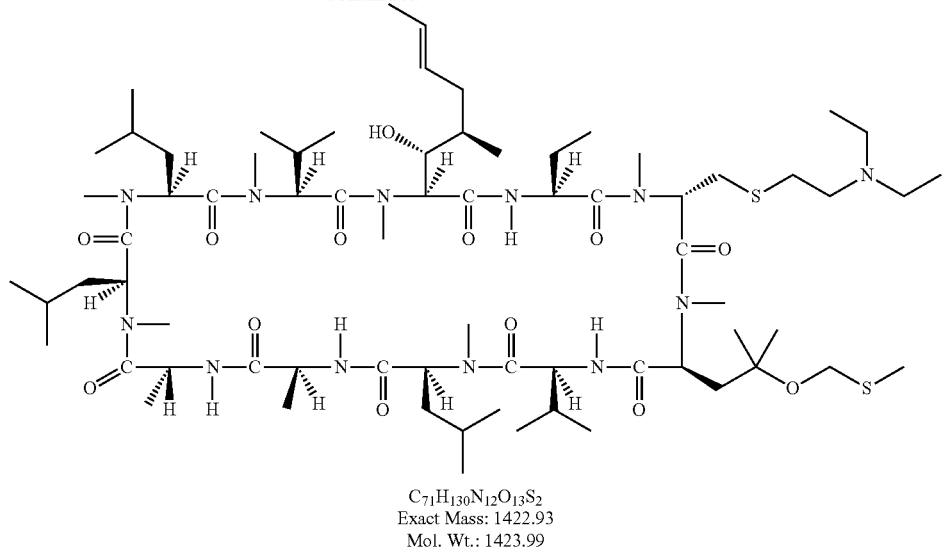

C₇₁H₁₃₀N₁₂O₁₃S₂
Exact Mass: 1422.93
Mol. Wt.: 1423.99

[α-Methylene-Sar]-3-[(γ-methylthiomethoxy)-N-Me-Leu]-4-cyclosporin (0.27 g, 0.21 mmol) and 2-(N,N-diethyl) ethanethiol (0.28 g, 2.10 mmol) were dissolved in methanol (20 ml), followed by adding 24 equivalents of triethylamine. The mixture was stirred overnight at room temperature. After removal of solvent, the residue was purified by chromatography on silica gel using dichloromethane/methanol as eluent to give 0.17 g of pure product [Molecular Formula, C₇₁H₁₃₀N₁₂O₁₃S₂; Exact Mass: 1422.93; MS (m/z): 1423.70 (M+1)⁺, 1445.67 (M+Na)⁺; TLC R$_f$: 0.35 (ethyl acetate/methanol=10:1); HPLC RT: 13.95 min (C8 reverse phase column: 250 mm; acetonitrile/water (0.05% trifluoroacetic acid); operation temperature: 64° C.; detector: 210 nm)].

Example 152

[γ-Ethoxymethoxy-NMeLeu]-4-cyclosporin

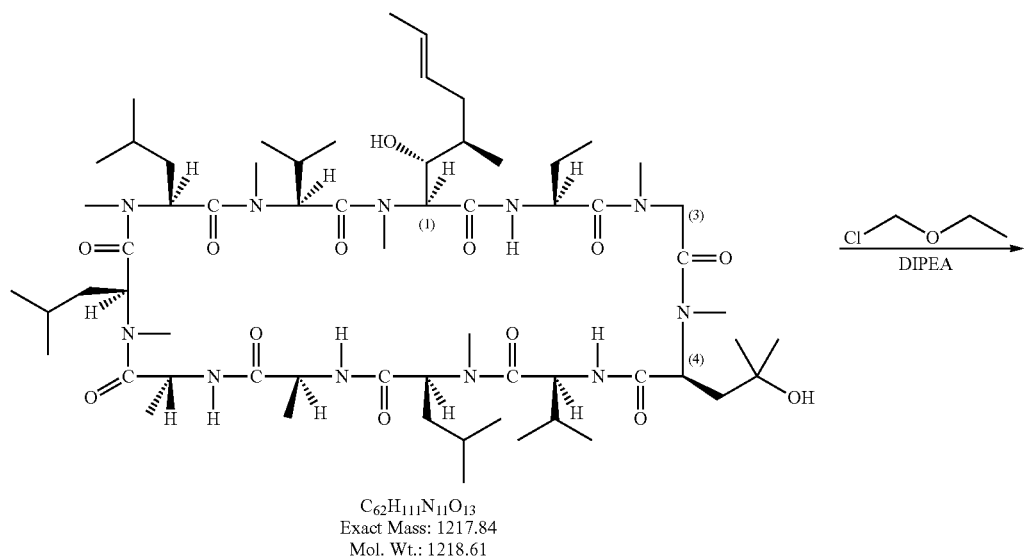

C₆₂H₁₁₁N₁₁O₁₃
Exact Mass: 1217.84
Mol. Wt.: 1218.61

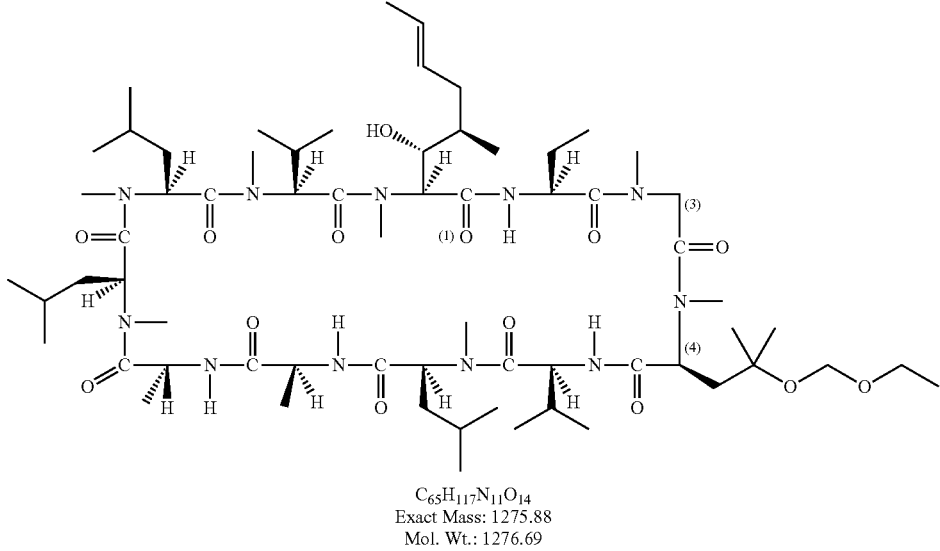

C_{65}H_{117}N_{11}O_{14}
Exact Mass: 1275.88
Mol. Wt.: 1276.69

To a solution of [(γ-hydroxy)-N-MeLeu]-4-cyclosporin (1.20 g, 0.99 mmol) in dichloromethane (80 ml) was added diisopropylethylamine (FW 129.25, d 0.742, 1.32 ml, 0.98 g, 7.60 mmol), followed by adding chloromethyl ethyl ether (FW 94.54, d 1.02, 2.22 ml, 2.27 g, 24 mmol) dropwise. The mixture was stirred overnight at room temperature and TLC was used to monitor the completion of the reaction. The reaction mixture was washed with 1 N hydrochloric acid, saturated sodium bicarbonate water solution and brine. After dried over magnesium sulfate, the mixture was evaporated under reduced pressure to give a yellowish oil, which was further purified by flash chromatography using dichloromethane/methanol as eluent to give 0.95 g of the product [Molecular Formula: $C_{65}H_{117}N_{11}O_{14}$; Exact Mass: 1275.88; MS (m/z): 1276.70 (M+H)$^+$, 1298.70 (M+Na)$^+$; TLC R$_f$: 0.37 (ethyl acetate)].

Example 153

[α-Methylene-Sar]-3-[(γ-ethoxymethoxy)-NMeLeu]-4-cyclosporin

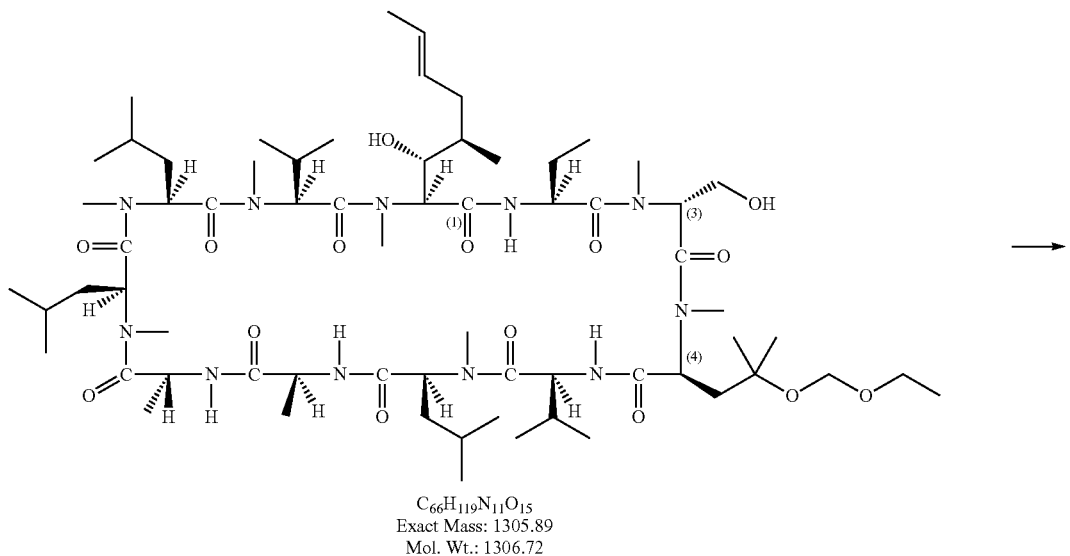

C_{66}H_{119}N_{11}O_{15}
Exact Mass: 1305.89
Mol. Wt.: 1306.72

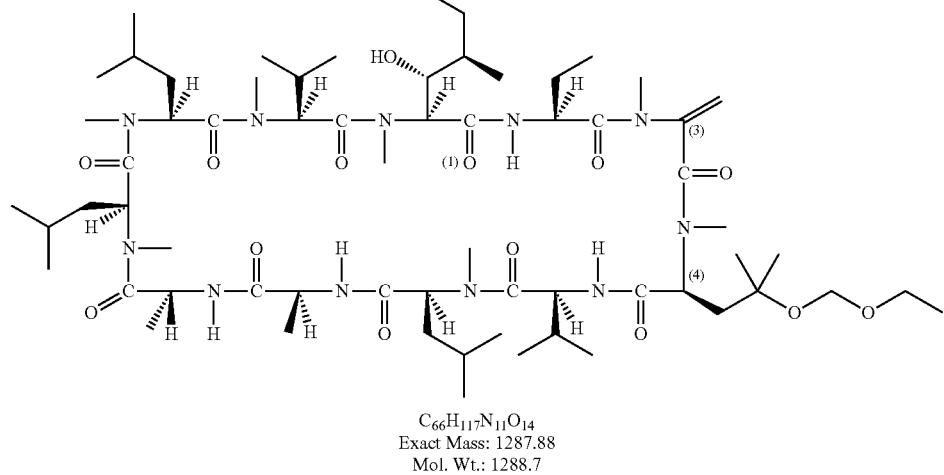

$C_{66}H_{117}N_{11}O_{14}$
Exact Mass: 1287.88
Mol. Wt.: 1288.7

[α-Methylen-Sar]-3-[(γ-ethoxymethoxy)-N-MeLeu]-4-cyclosporin was prepared according to the method described in Example 28. The product was purified by chromatography on silica gel with ethyl acetate/methanol as eluent [Molecular Formula: $C_{66}H_{117}N_{11}O_{14}$; Exact Mass: 1287.68; MS (m/z): 1288.72 $(M+1)^+$, 1310.70 $(M+Na)^+$].

Example 154

[(S)-(2-(N,N-Diethylamino)ethylthio)methyl-Sar]-3-[(γ-ethoxy)methoxy-NMeLeu]-4-cyclosporin

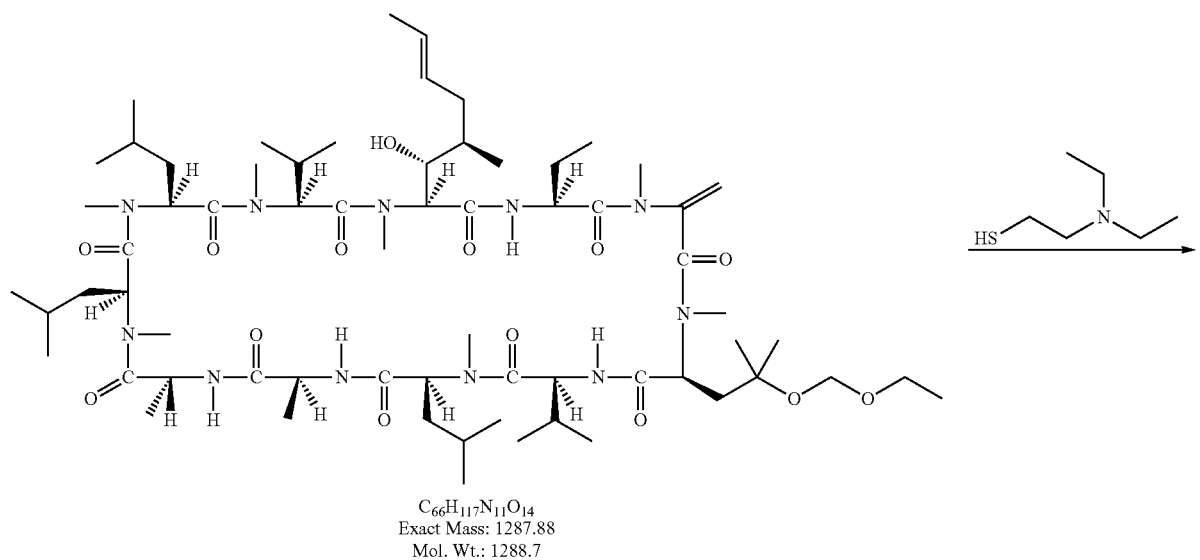

$C_{66}H_{117}N_{11}O_{14}$
Exact Mass: 1287.88
Mol. Wt.: 1288.7

-continued

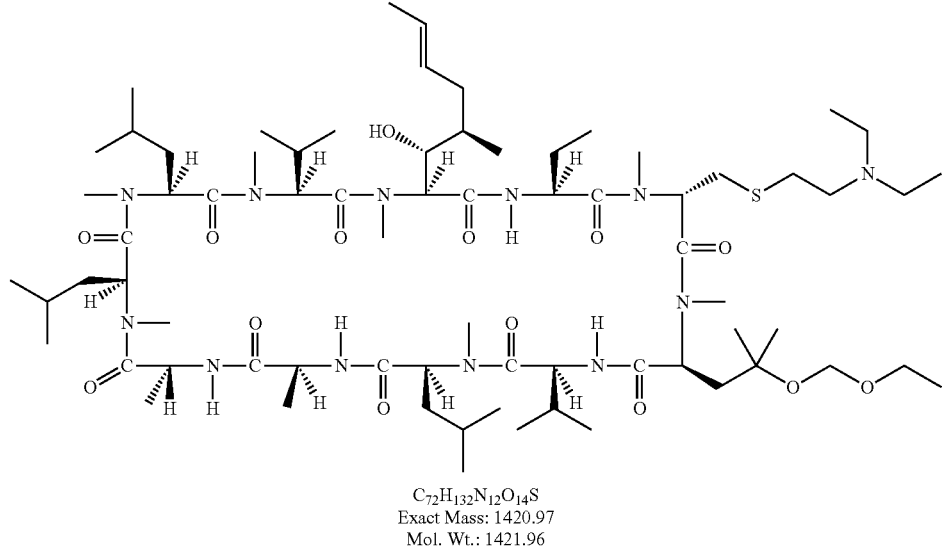

C$_{72}$H$_{132}$N$_{12}$O$_{14}$S
Exact Mass: 1420.97
Mol. Wt.: 1421.96

[α-Methylene-Sar]-3-[(γ-ethoxymethoxy)-N-MeLeu]-4-cyclosporin (0.27 g, 0.21 mmol) and 2-(N,N-diethyl)ethanethiol (0.28 g, 2.1 mmol) were dissolved in methanol (20 ml), followed by adding 12 equivalents of triethylamine. The mixture was stirred overnight at room temperature. After removal of solvent, the residue was purified by chromatography on silica gel using dichloromethane/methanol as eluent to give 90 mg of pure product [Molecular Formula: C$_{72}$H$_{132}$N$_{12}$O$_{14}$S; Exact Mass: 1420.97; MS (m/z): 1421.75 (M+1)$^+$, 1443.72 (M+Na)$^+$; TLC: R$_f$: 0.40 (ethyl acetate/methanol=10/1); HPLC RT: 13.58 min (C8 reverse phase column: 250 mm; acetonitrile/water (0.05% trifluoroacetic acid); operation temperature: 64° C.; detector: 210 nm)].

Example 155

[α-Carboxy-Sar]-3-[NMeIle]-4-cyclosporin

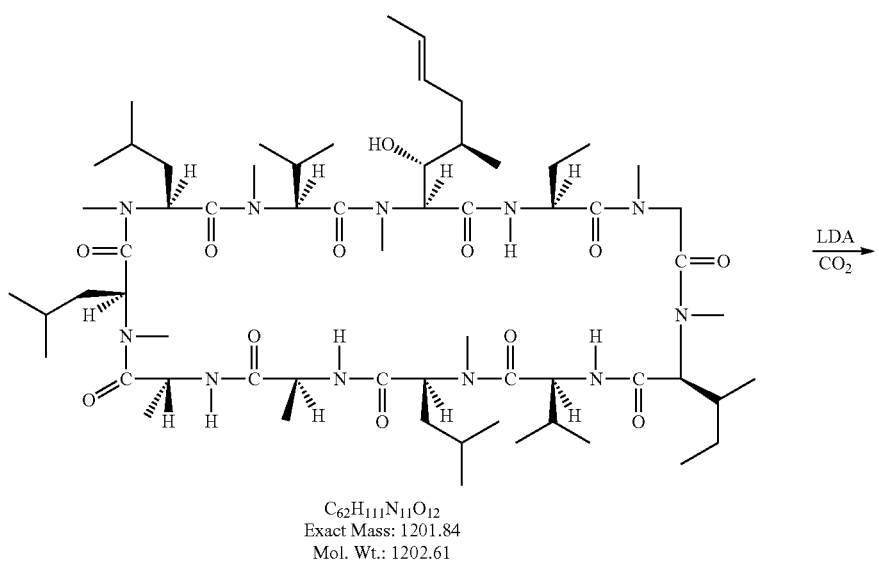

C$_{62}$H$_{111}$N$_{11}$O$_{12}$
Exact Mass: 1201.84
Mol. Wt.: 1202.61

-continued

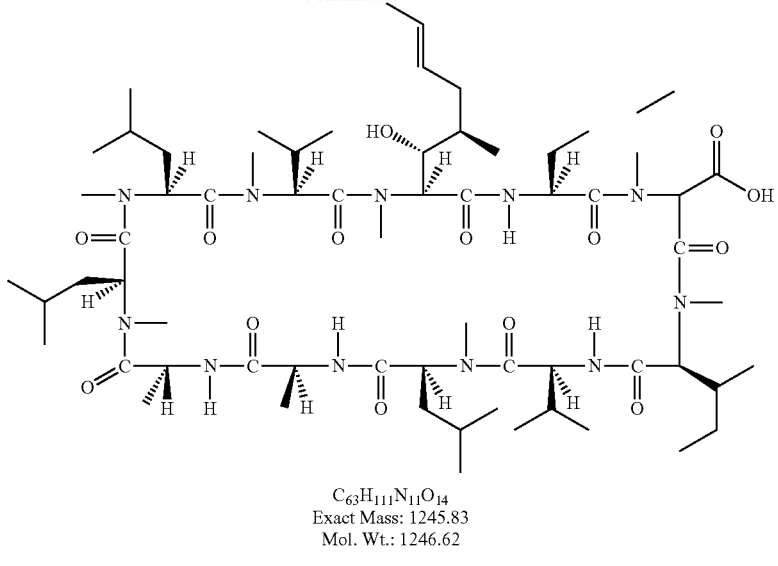

$C_{63}H_{111}N_{11}O_{14}$
Exact Mass: 1245.83
Mol. Wt.: 1246.62

To a solution of LDA (2.0 M in tetrahydrofuran, 5 ml, 10 mmol) in tetrahydrofuran (15 ml) at −78° C. under nitrogen atmosphere was added [N-MeIle]-4-cyclosporin (1.20 g, 1.00 mmol) in tetrahydrofuran (15 ml) over 3 min After the mixture was stirred at −78° C. for 3 hours, carbon dioxide gas was bubbled into the reaction mixture for 1 hour. Then the mixture was allowed to warm to room temperature slowly and kept stirring for another 3 hours. Most of tetrahydrofuran was evaporated under reduced pressure. Dichloromethane (100 ml) and water (50 ml) were added. The PH of the mixture was adjusted to around 5 by adding aqueous citric acid solution. The mixture was then separated and the organic layer was washed with brine, dried over magnesium sulfate and evaporated under reduced pressure to give 1.10 g of crude product, which was used for next step without purification [Molecular Formula: $C_{63}H_{111}N_{11}O_{14}$; Exact Mass: 1245.83; MS (m/z): 1246.68 (M+1)$^+$].

Example 156

[α-Methoxycarbonyl-Sar]-3-[NMeIle]-4-cyclosporin

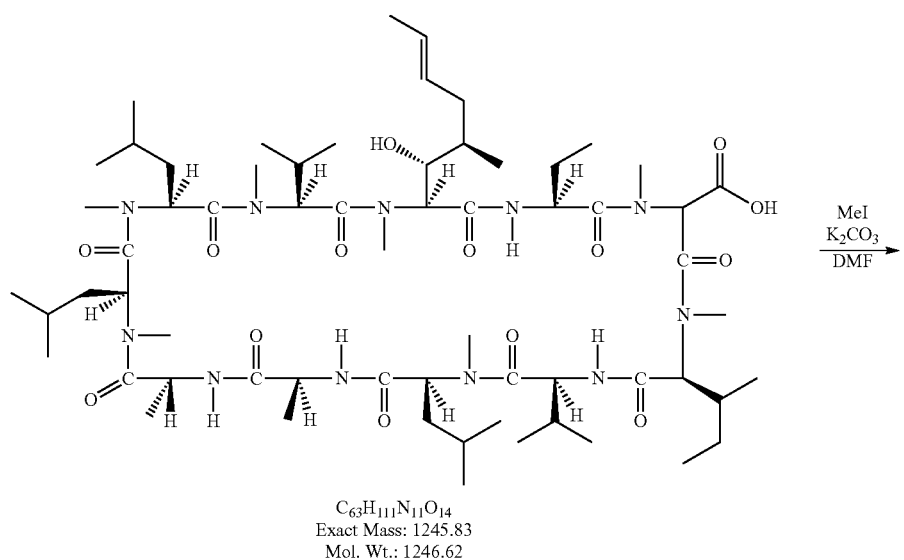

$C_{63}H_{111}N_{11}O_{14}$
Exact Mass: 1245.83
Mol. Wt.: 1246.62

-continued

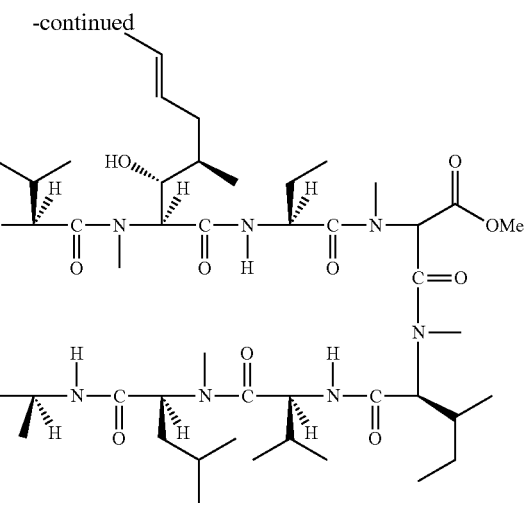

C$_{64}$H$_{113}$N$_{11}$O$_{14}$
Exact Mass: 1259.85
Mol. Wt.: 1260.65

To a mixture of [α-carboxy-Sar]-3-[N-MeIle]-4-cyclosporin (1.00 g, 0.80 mmol) and potassium carbonate (0.70 g, 5.07 mmol) in N,N-dimethylformamide (10 ml) was added iodomethane (1.50 g, 10.56 mmol). The mixture was stirred overnight at room temperature. Dichloromethane (80 ml) and water (50 ml) were added and the mixture was separated. The dichloromethane layer was washed with water (25 ml) and brine (25 ml), dried over magnesium sulfate and evaporated under reduced pressure to give crude 1.00 g of product [Molecular Formula: C$_{64}$H$_{113}$N$_{11}$O$_{14}$; Exact Mass: 1259.85; MS (m/z): 1260.51(M+1)$^+$].

Example 157

[(R)-α-Hydroxymethyl-Sar]-3-[N-MeIle]-4-cyclosporin

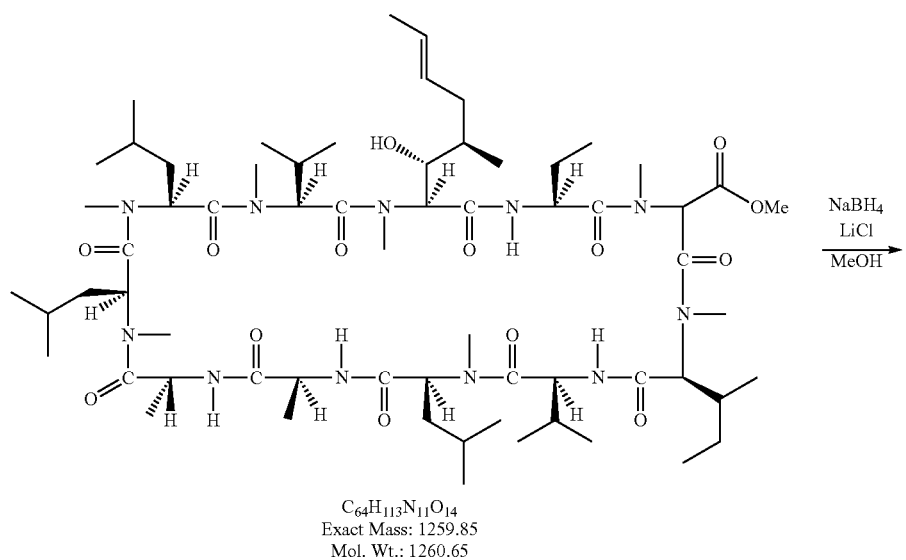

C$_{64}$H$_{113}$N$_{11}$O$_{14}$
Exact Mass: 1259.85
Mol. Wt.: 1260.65

-continued

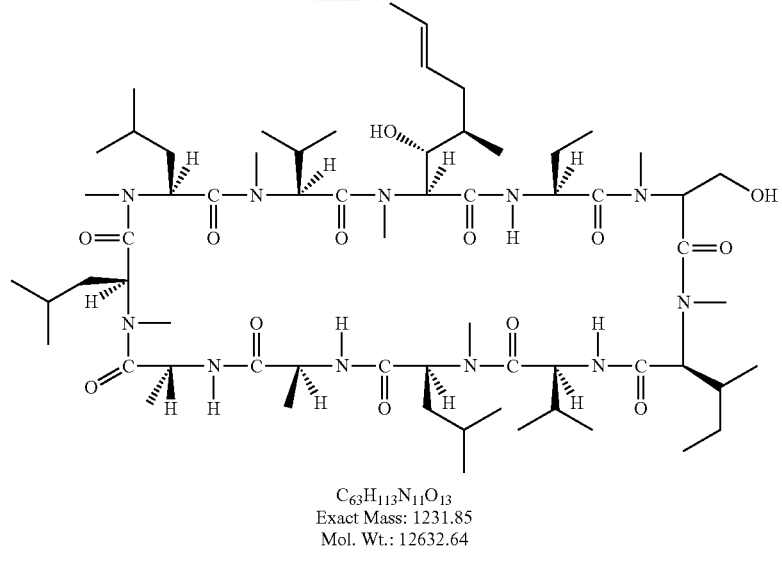

$C_{63}H_{113}N_{11}O_{13}$
Exact Mass: 1231.85
Mol. Wt.: 12632.64

To a suspension of [α-methoxycarbonyl-Sar]-3-[N-MeIle]-4-cyclosporin (1.00 g, 0.79 mmol) and lithium chloride (0.60 g, 14.11 mmol) in methanol (80 ml) was added sodium borohydride (3.00 g, 79.26 mmol) in portions. The mixture was stirred overnight at room temperature. Most of solvent was evaporated under reduced pressure. Dichloromethane (100 ml) and water (50 ml) were added and the mixture was separated. The dichloromethane layer was washed with brine, dried over magnesium sulfate and evaporated under reduced pressure. The residue was purified by chromatography (dichloromethane/methanol=97/3) to give 420 mg of product [Molecular Formula: $C_{63}H_{113}N_{11}O_{13}$; Exact Mass: 1231.85; MS (m/z): 1232.59 (M+1)$^+$; TLC Rf: 0.32 (dichloromethane/methanol=95/5); HPLC RT: 14.32 min (C8 reverse phase column: 250 mm; acetonitrile/water (0.05% trifluoroacetic acid); operation temperature: 64° C.; detector: 210 nm)].

Example 158

[α-Methylene-Sar]-3-[NMeIle]-4-cyclosporin

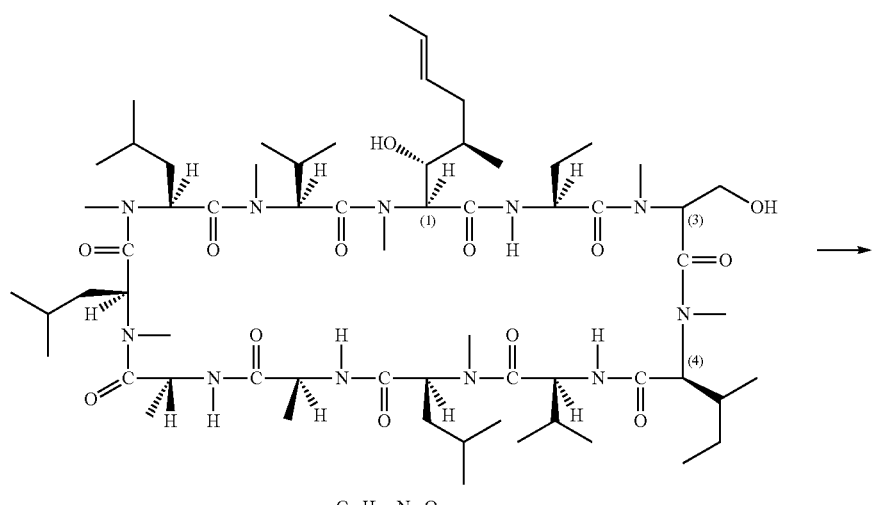

$C_{63}H_{113}N_{11}O_{13}$
Exact Mass: 1231.85
Mol. Wt.: 1232.64

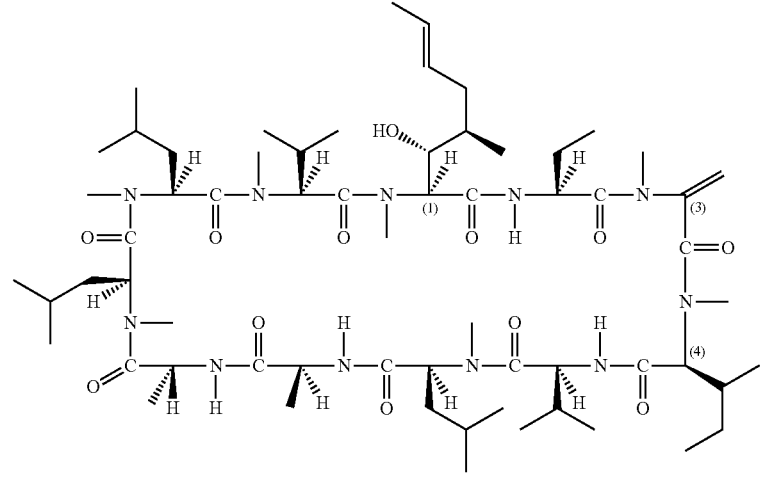

C$_{63}$H$_{113}$N$_{11}$O$_{12}$
Exact Mass: 1213.84
Mol. Wt.: 1214.62

[α-Methylene-Sar]-3-[N-MeIle]-4-cyclosporin was prepared according to the method described in Example 28 [Molecular Formula: C$_{63}$H$_{111}$N$_{11}$O$_{12}$; Exact Mass: 1213.84; MS (m/z): 1214.59 (M+1)$^+$; TLC R$_f$: 0.34 (hexane/acetone=6/1); HPLC RT: 17.47 min (C8 reverse phase column: 250 mm; acetonitrile/water (0.05% trifuloroacetic acid), operation temperature: 64° C.; detector: 210 nm].

Example 159

[(S)-(2-(N,N-Diethylamino)ethylthio)methyl-Sar]-3-[NMeIle]-4-cyclosporin

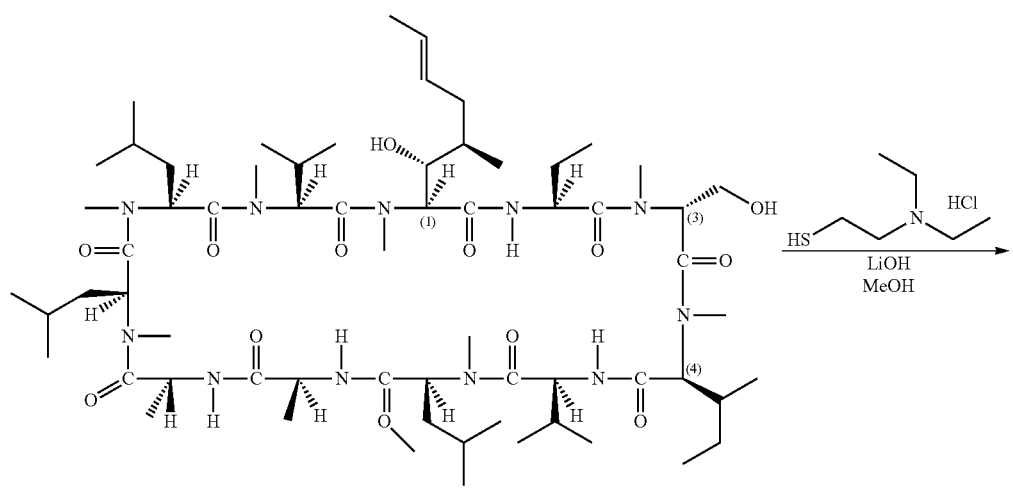

C$_{63}$H$_{111}$N$_{11}$O$_{12}$
Exact Mass: 1213.84
Mol. Wt.: 1214.62

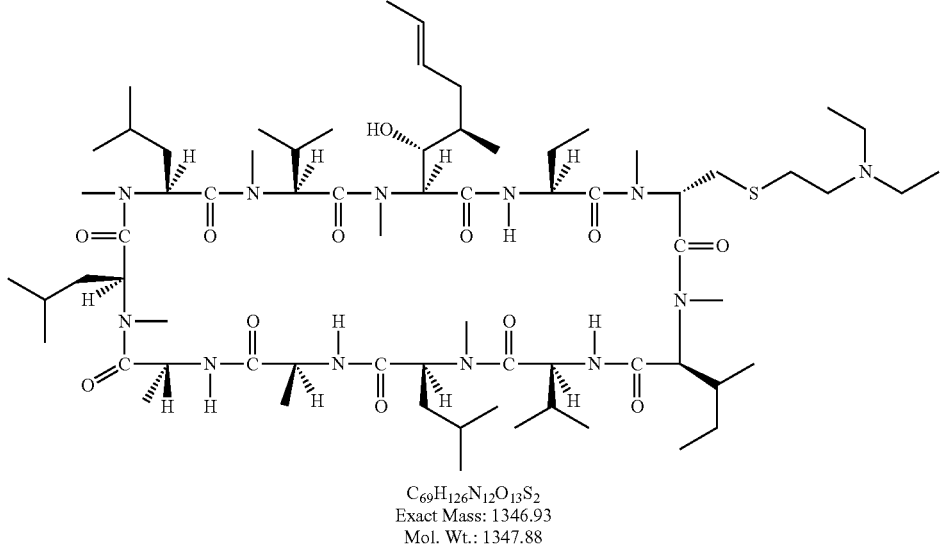

$C_{69}H_{126}N_{12}O_{13}S_2$
Exact Mass: 1346.93
Mol. Wt.: 1347.88

To a solution of [α-Methylene-Sar]-3-[N-MeIle]-4-cyclosporin (300 mg, 0.25 mmol) and 2-diethylaminoethanethiol hydrochloride (408 mg, 2.41 mmol) in methanol (20 ml) was added lithium hydroxide (116 mg, 4.83 mmol). The reaction mixture was stirred overnight at room temperature. Most of solvent was evaporated under reduced pressure. Dichloromethane (80 ml) and water (30 ml) were added and the mixture was separated. The organic layer was washed with water and brine, dried over magnesium sulfate and evaporated under reduced pressure. The residue was purified by chromatography (dichloromethane/methanol=96/4) to give 170 mg of product [Molecular Formula: $C_{69}H_{126}N_{12}O_{12}S$; Exact Mass: 1346.93; MS (m/z): 1347.68 $(M+1)^+$; TLC $R_f$: 0.32 (dichloromethane/methanol=95/5); HPLC RT: 13.54 min (C8 reverse phase column: 250 mm; acetonitrile/water (0.05% trifluoroacetic acid); operation temperature: 64° C.; detector: 210 nm)].

Example 160

[(R)-(2-(N,N-Diethylamino)ethoxy)methyl-Sar]-3-[NMeIle]-4-cyclosporin

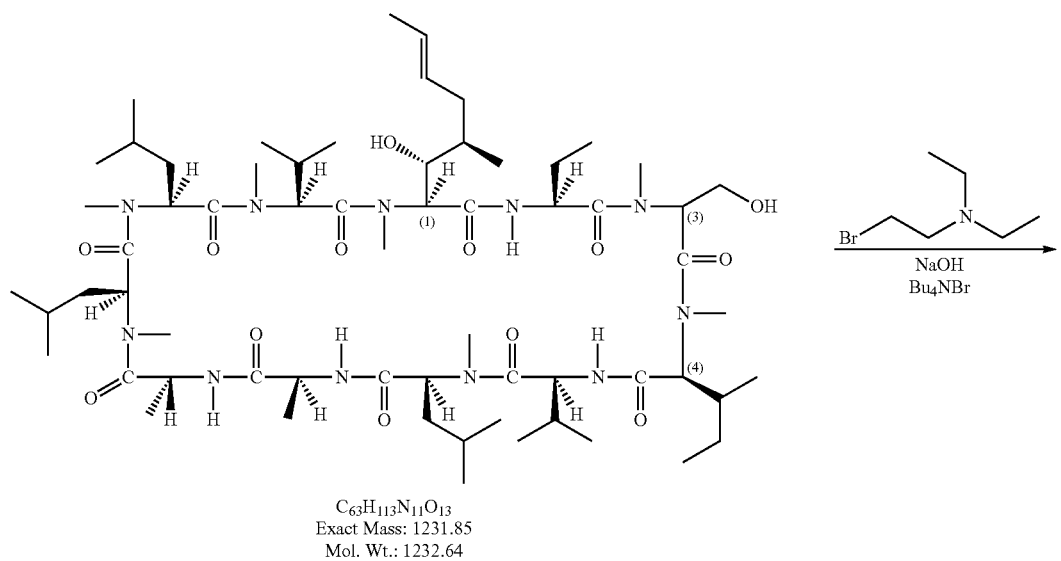

$C_{63}H_{113}N_{11}O_{13}$
Exact Mass: 1231.85
Mol. Wt.: 1232.64

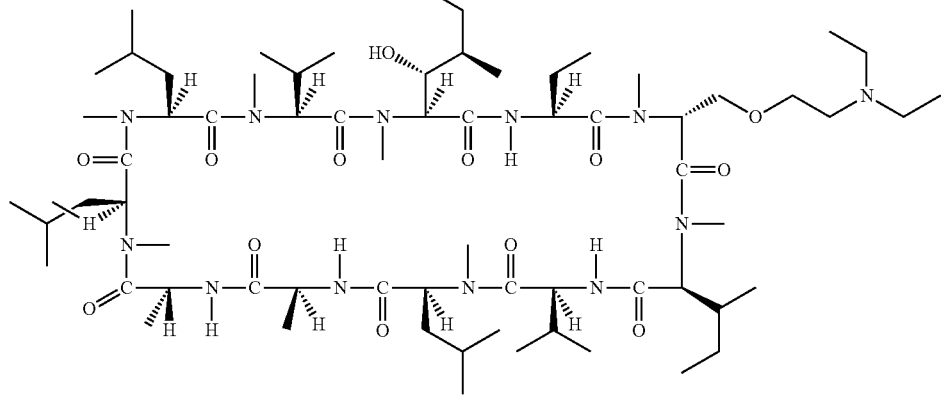

C₆₉H₁₂₆N₁₂O₁₃
Exact Mass: 1330.96
Mol. Wt.: 1331.81

To a solution of [(R)-α-hydroxymethyl-Sar]-3-[N-MeIle]-4-cyclosporin (0.39 g, 0.32 mmol) in benzene (20 ml) were added a solution of sodium hydroxide (0.80 g, 20 mmol) in water (1 ml), 2-bromo-N,N-diethylethylamine hydrobromide (2.40 g, 9.20 mmol) and tetra-n-butylammonium bromide (0.10 g, 3.10 mmol). The mixture was stirred at 30° C. for 40 hours. Ice water (10 ml) was added and the mixture was separated. The aqueous layer was extracted with dichloromethane (50 ml). The combined organic layers was washed with brine, dried over magnesium sulfate and concentrated under reduced pressure. The residue was purified by chromatography (dichloromethane/methanol=96/4) to give 270 mg of product [Molecular Formula: $C_{69}H_{126}N_{12}O_{13}$; Exact Mass: 1330.96; MS (m/z): 1331.73 (M+1)$^+$; TLC R$_f$: 0.34 (dichloromethane/methanol=95/5); HPLC RT: 13.42 min (C8 reverse phase column: 250 mm; acetonitrile/water (0.05% trifluoroacetic acid); operation temperature: 64° C.; detector: 210 nm)].

Example 161

[α-Methylene-Sar]-3-[NMeVal]-4-cyclosporin

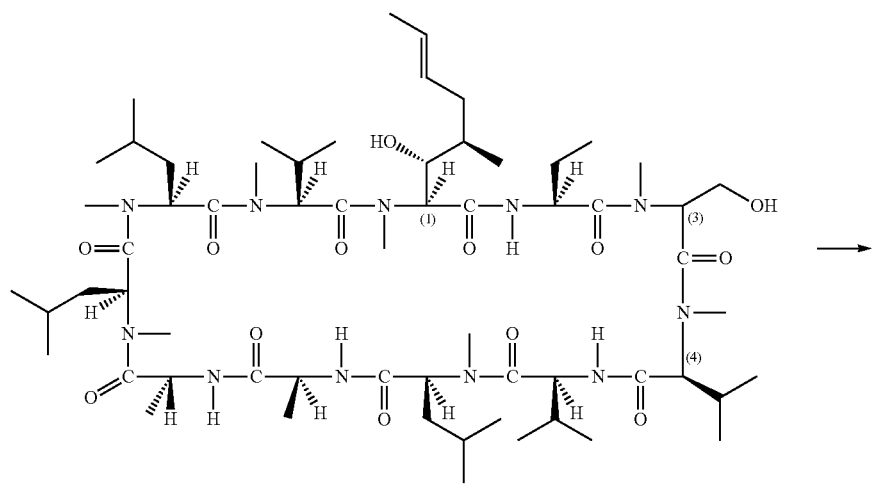

C₆₂H₁₁₁N₁₁O₁₃
Exact Mass: 1217.84
Mol. Wt.: 1218.61

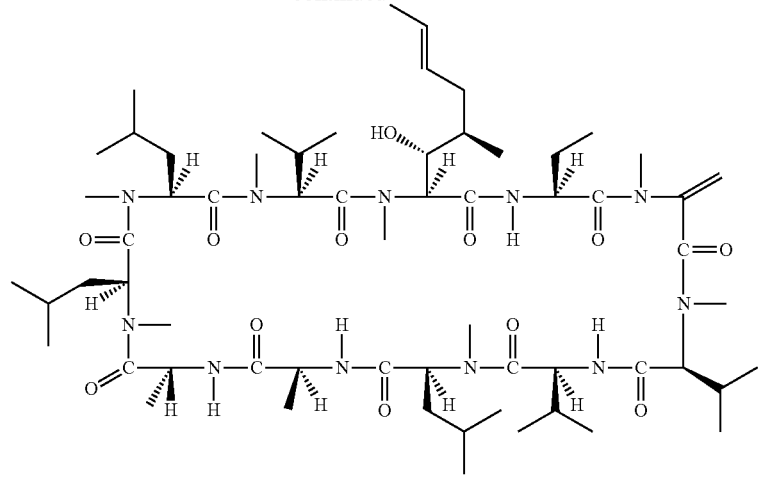
$C_{62}H_{109}N_{11}O_{12}$
Exact Mass: 1199.83
Mol. Wt.: 1200.6
[α-Methylene]-3-[N-MeVal]-4-cyclosporin was prepared according to the method described in Example 28. The product was purified by chromatography on silica gel (ethyl acetate/methanol). [Molecular Formula: $C_{62}H_{109}N_{11}O_{12}$; Exact Mass: 1199.83; MS (m/z): 1200.56 $(M+1)^+$, 1222.72 $(M+Na)^+$].
Example 162
[(S)-(2-(N,N-dimethylamino)ethylthio)methyl-Sar]-3-[NMeVal]-4-cyclosporin
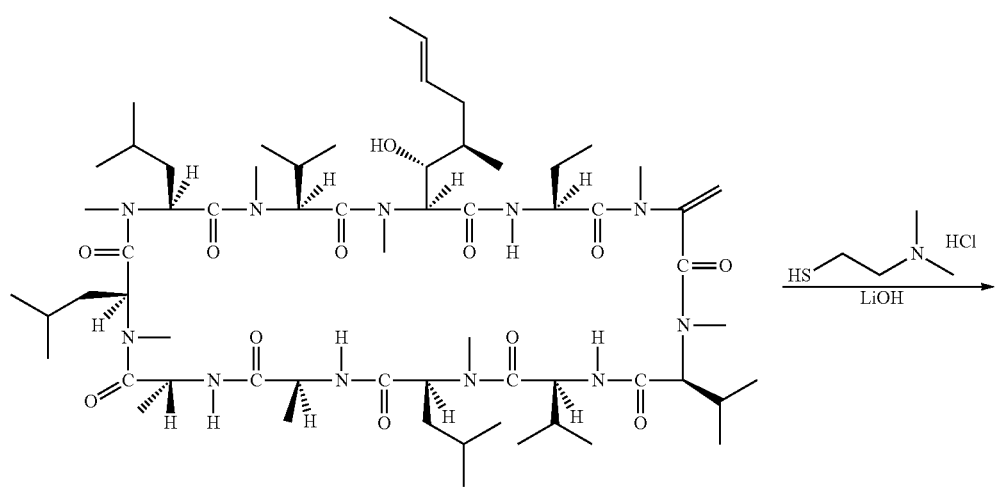
$C_{62}H_{109}N_{11}O_{12}$
Exact Mass: 1199.83
Mol. Wt.: 1200.6

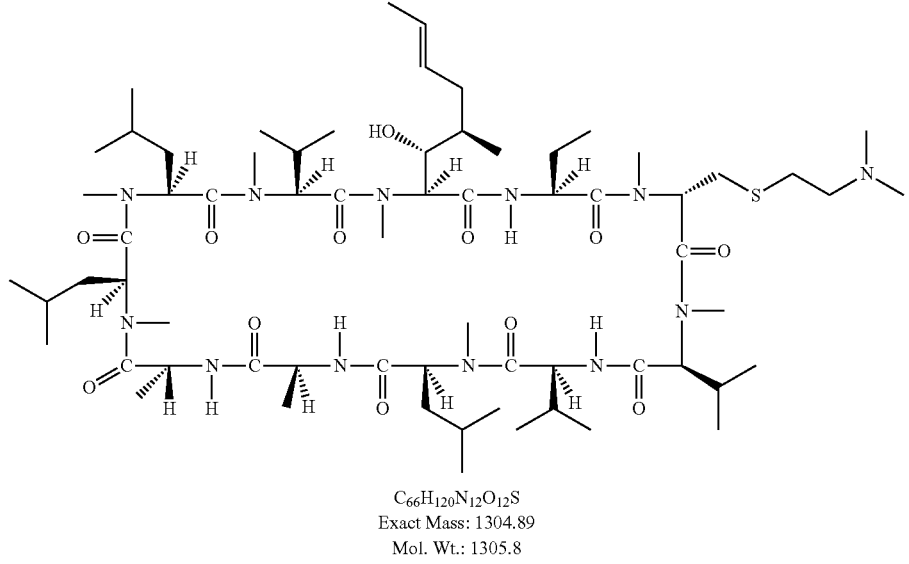

$C_{66}H_{120}N_{12}O_{12}S$
Exact Mass: 1304.89
Mol. Wt.: 1305.8

[α-Methylene-Sar]-3-[N-MeVal]-4-cyclosporin (88 mg, 0.07 mmol) and 2-(N,N-dimethyl)ethanethiol hydrochloride (0.10 g, 7.30 mmol) were dissolved in methanol (20 ml), followed by adding 20 equivalents of lithium hydroxide. The mixture was stirred overnight at room temperature. After removal of solvent, the residue was purified by flash chromatography using dichloromethane/methanol as eluent to give 30 mg of pure product [Molecular Formula: $C_{66}H_{120}N_{12}O_{12}S$; Exact Mass: 1304.89; MS (m/z): 1305.68 $(M+1)^+$, 1327.83 $(M+Na)^+$; TLC $R_f$: 0.05 (ethyl acetate/methanol=5/1); HPLC RT: 12.23 min (C8 reverse phase column: 250 mm; acetonitrile/water (0.05% trifluoroacetic acid); operation temperature: 64° C.; detector: 210 nm)].

Example 163

[(S)-(2-(N,N-Diethylamino)ethylthio)methyl-Sar]-3-[NMeVal]-4-cyclosporin

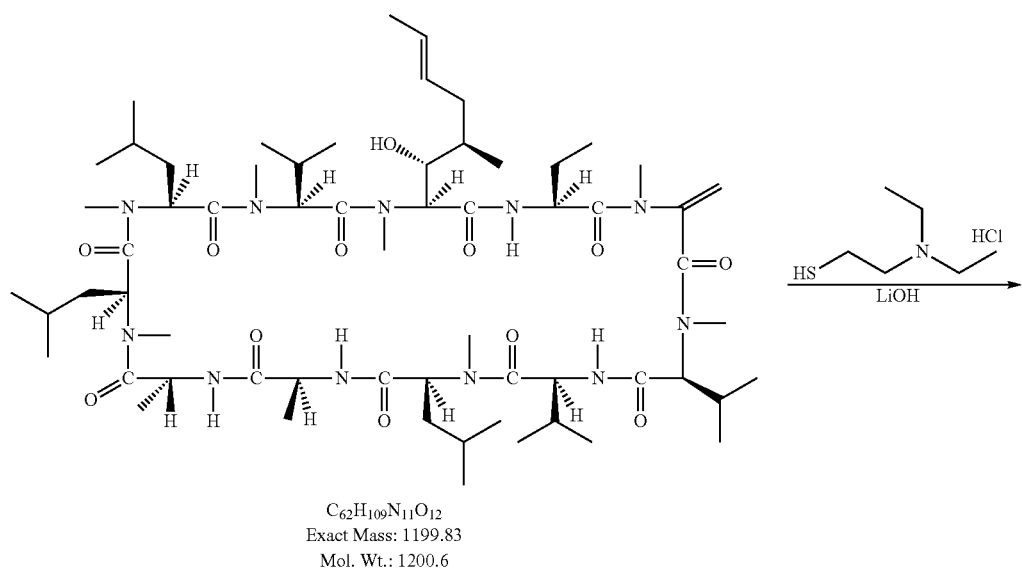

$C_{62}H_{109}N_{11}O_{12}$
Exact Mass: 1199.83
Mol. Wt.: 1200.6

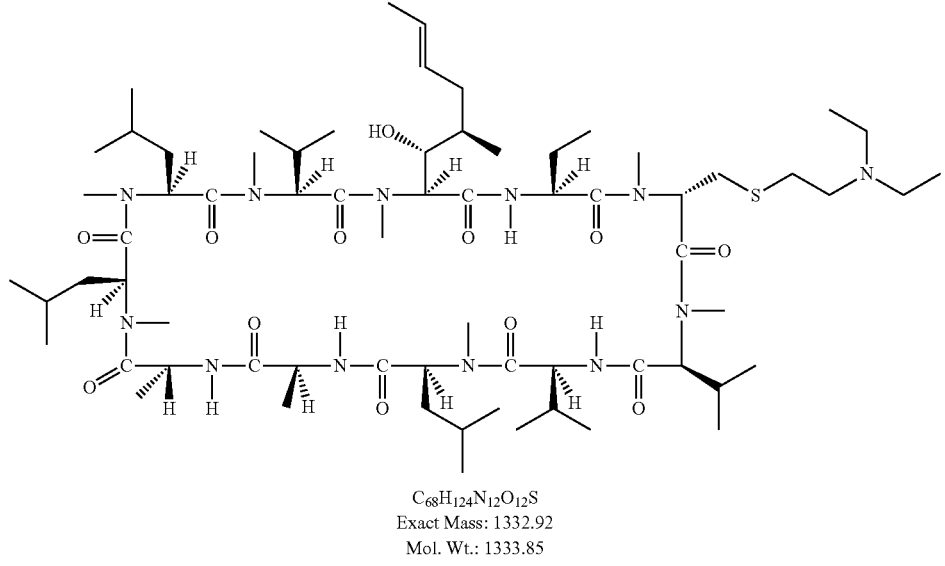

$C_{68}H_{124}N_{12}O_{12}S$
Exact Mass: 1332.92
Mol. Wt.: 1333.85

[α-Methylene-Sar]-3-[N-MeVal]-4-cyclosporin (0.20 g, 0.16 mmol) and 2-(N,N-9diethyl)ethanethiol hydrochloride (0.28 g, 1.70 mmol) were dissolved in methanol (20 ml), followed by adding 20 equivalents of lithium hydroxide (77 mg, 3.20 mmol). The mixture was stirred overnight. After removal of solvent, the residue was purified by chromatography on silica gel using dichloromethane/methanol as eluent to give 100 mg of pure product [Molecular Formula: $C_{68}H_{124}N_{12}O_{12}S$; Exact Mass: 1332.92; MS (m/e): 1333.58 (M+1)$^+$, 1355.79 (M+Na)$^+$; TLC R$_f$: 0.08 (ethyl acetate/methanol=5/1); HPLC RT: 12.77 min (C8 reverse phase column: 250 mm; acetonitrile/water (0.05% trifluoroacetic acid); operation temperature: 64° C.; detector: 210 nm)].

Example 164

[(R)-α-Hydroxymethyl-Sar]-3-[NMeVal]-4-cyclosporin

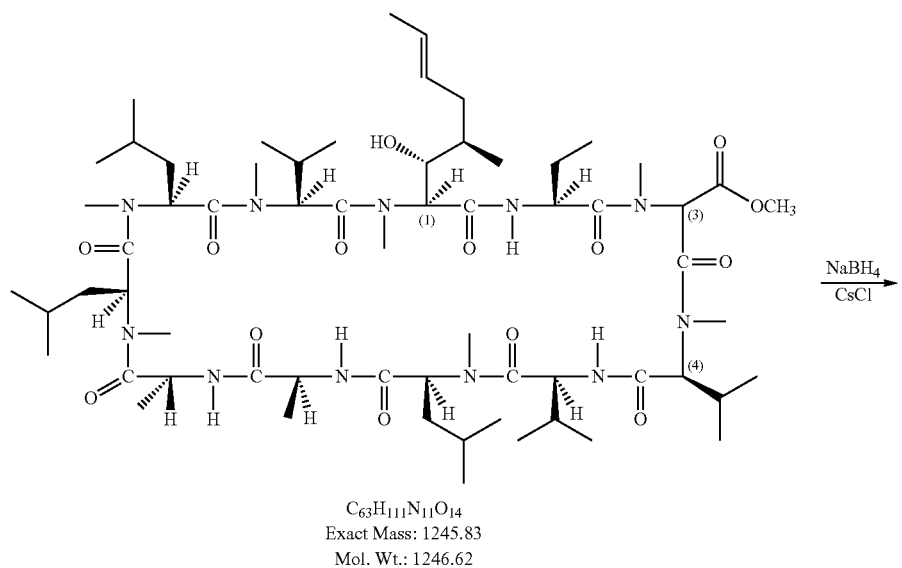

$C_{63}H_{111}N_{11}O_{14}$
Exact Mass: 1245.83
Mol. Wt.: 1246.62

-continued

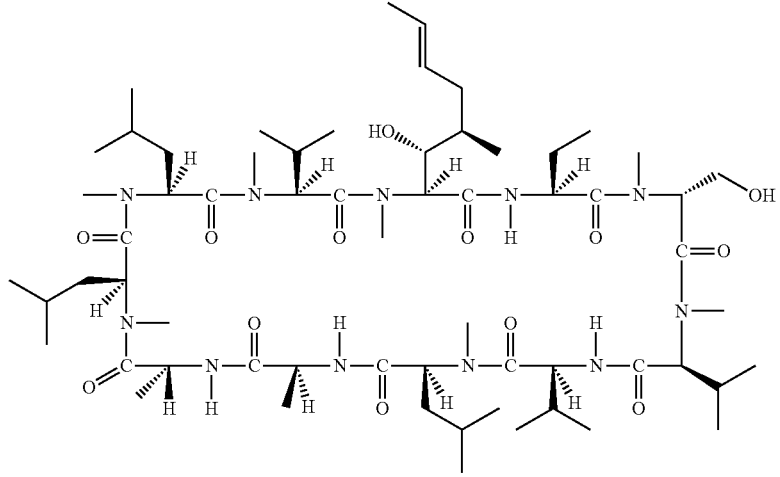

C$_{62}$H$_{111}$N$_{11}$O$_{13}$
Exact Mass: 1217.84
Mol. Wt.: 1218.61

[(R)-α-Hydroxymethyl-Sar]-3-[N-MeVal]-4-cyclosporin was prepared according to the method described in Example 2. The product was purified by chromatography on silica gel (ethyl acetate/methanol) [Molecular Formula: C$_{62}$H$_{111}$N$_{11}$O$_{13}$; Exact Mass: 1217.84; MS (m/z): 1218.56 (M+1)$^+$, 1240.75 (M+Na)$^+$].

Example 165

[(R)-(2-(N,N-dimethylamino)ethoxy)methyl-Sar]-3-[NMeVal]-4-cyclosporin

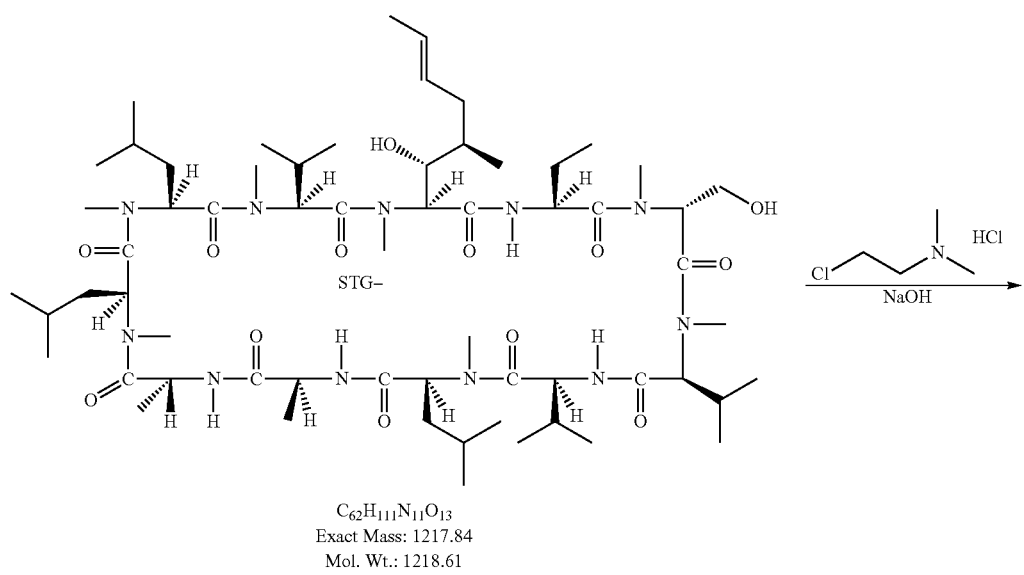

C$_{62}$H$_{111}$N$_{11}$O$_{13}$
Exact Mass: 1217.84
Mol. Wt.: 1218.61

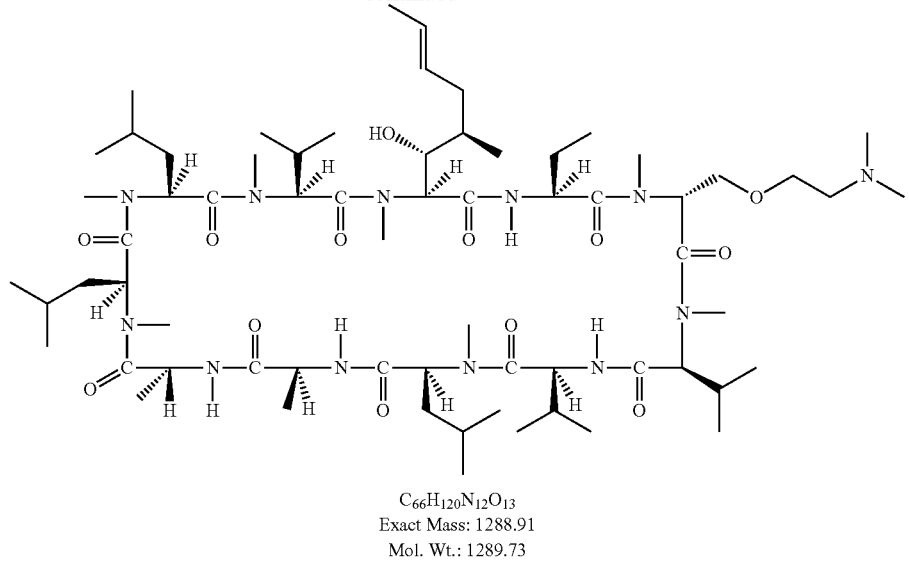

C$_{66}$H$_{120}$N$_{12}$O$_{13}$
Exact Mass: 1288.91
Mol. Wt.: 1289.73

To a solution of [(R)-α-hydroxymethyl-Sar]-3-[N-Me-Val]-4-cyclosporin (0.12 g, 0.10 mmol) in benzene (15 ml) were added sodium hydroxide (0.20 g, 5.00 mmol), tetramethylammonium hydroxide pentahydrate (0.18 g, 1.00 mmol) and 3-dimethylaminoethyl chloride hydrochloride (0.14 g, 1.00 mmol). The mixture was stirred at 30° C. overnight. Ice water (20 ml) was added and the mixture was separated. The aqueous layer was extracted with ethyl acetate (20 ml). The combined organic layers were washed with brine, dried over magnesium sulfate and evaporated under reduced pressure. The residue was subjected to chromatography on silica gel (dichloromethane/methanol=95/5) to give the 30 mg of pure product [Molecular Formula: C$_{66}$H$_{120}$N$_{12}$O$_{13}$; Exact Mass: 1288.91; MS (m/z): 1289.73 (M+1)$^+$, 1311.71 (M+Na)$^+$; TLC R$_f$: 0.14 (dichloromethane/methanol=10/1); HPLC RT: 12.00 min (C8 reverse phase column: 250 mm; acetonitrile/water (0.05% trifluoroacetic acid); operation temperature: 64° C.; detector: 210 nm)].

Example 166

[(R)—(N-Piperidinyl)methyl-Sar]-3-[(γ-hydroxy)-NMeLeu]-4-cyclosporin

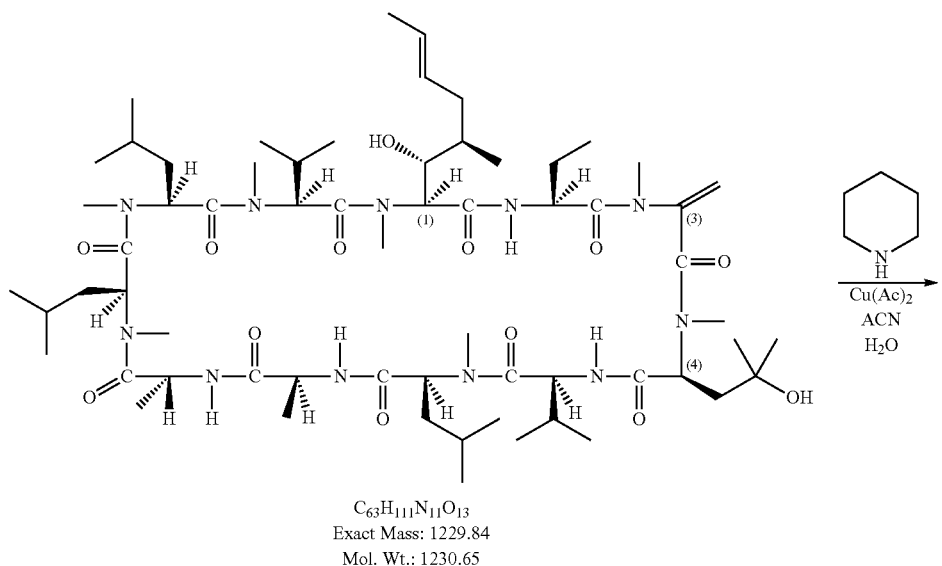

C$_{63}$H$_{111}$N$_{11}$O$_{13}$
Exact Mass: 1229.84
Mol. Wt.: 1230.65

-continued

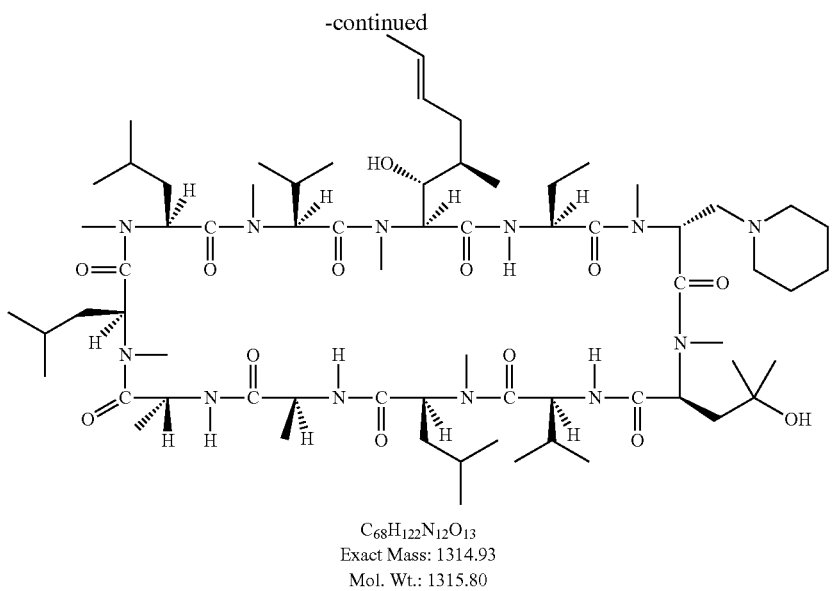

C₆₈H₁₂₂N₁₂O₁₃
Exact Mass: 1314.93
Mol. Wt.: 1315.80

[α-Methylene-Sar]-3-[(γ-hydroxy)-NMeLeu]-4-cyclosporin (0.37 g, 0.30 mmol) and piperidine (0.26 g, 3.00 mmol) were dissolved in acetonitrile/water (20 ml) in the presence of the catalytic amount of copper (II) acetate. The mixture was stirred overnight at room temperature. After removal of solvent, the residue was dissolved in dichloromethane (30 ml). The dichloromethane phase was washed with brine, dried over magnesium sulfate and evaporated under reduced pressure. The residue was further purified by chromatography on silica gel (dichloromethane/methanol, 96/4) to give 0.17 g of product [Molecular Formula: $C_{68}H_{122}N_{12}O_{13}$; Exact Mass: 1314.93; MS (m/z): 1315.74 (M+1)⁺, 1337.86 (M+Na)⁺; TLC R$_f$: 0.10 (ethyl acetate/methanol=5/1); HPLC RT: 11.70 min (C8 reverse phase column: 150 mm; acetonitrile/water (0.05% TFA); operation temperature: 64° C.; detector: 210 nm)].

Example 167

[(γ-Allyloxy)-NMeLeu]-4-cyclosporin

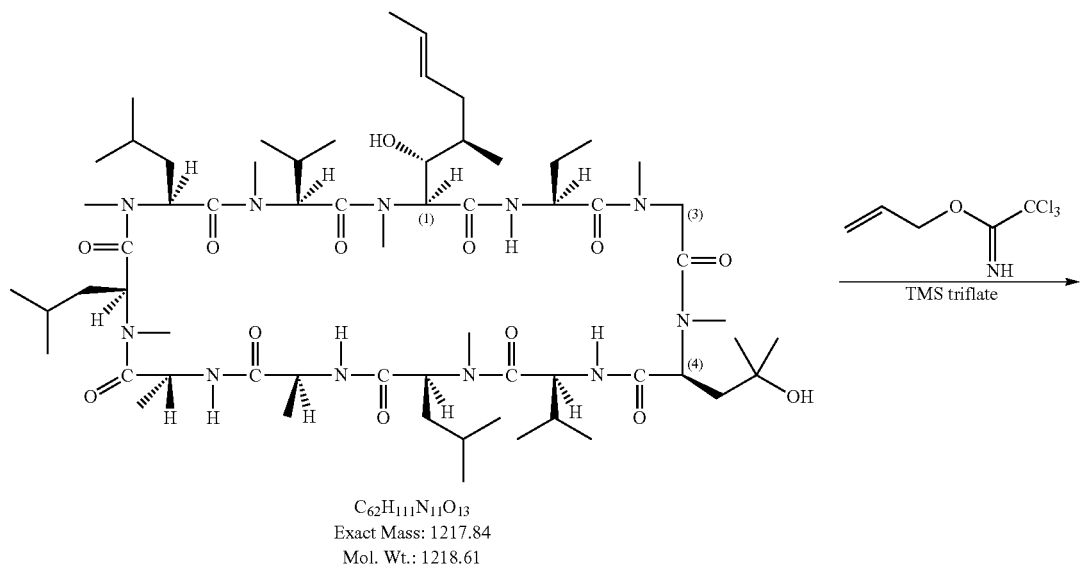

C₆₂H₁₁₁N₁₁O₁₃
Exact Mass: 1217.84
Mol. Wt.: 1218.61

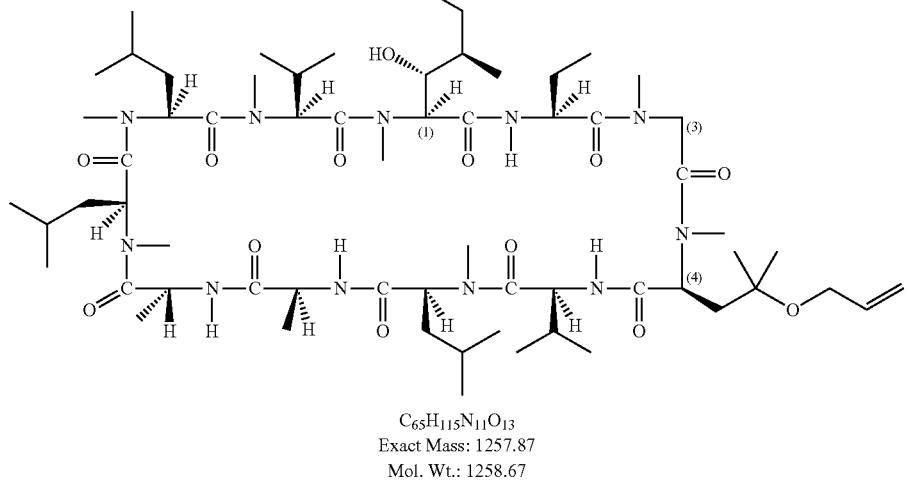

$C_{65}H_{115}N_{11}O_{13}$
Exact Mass: 1257.87
Mol. Wt.: 1258.67

Under nitrogen atmosphere, to a mixture of [(γ-Hydroxy)-NMeLeu]-4-cyclosporin (FW 1218.61, 800 mg, 0.66 mmol) and ally 2,2,2-trichloroacetimidate (FW 202.47, 930 mg, 4.6 mmol) in 150 ml of DCM was added trimethylsily trifluoromethanesulfonate (FW 222.26, d 1.228, 250 mg, 1.12 mmol) at 0° C. The resulting mixture was allowed to warm to room temperature and stirred for overnight. Then the mixture was washed with saturated NaHCO$_3$ water solution and brine. The organic layer was separated, dried over MgSO$_4$ and evaporated under vacuum. The residue was purified by column chromatography using DCM/MeOH (98/2) to give product [Molecular formula: $C_{65}H_{115}N_{11}O_{13}$; Exact Mass: 1257.87; MS (m/z): 1280.7 (M+Na)$^-$; TLC R$_f$: 0.46 (DCM/MeOH=95/5); HPLC RT: 16.45 minutes (C8 reverse phase column, 250 mm, acetonitrile/0.05% TFA in water, operation temperature: 64° C.; Detector: 210 nm)].

Example 168

[(R)-2-Nitroethyl-Sar]-3-cyclosporin

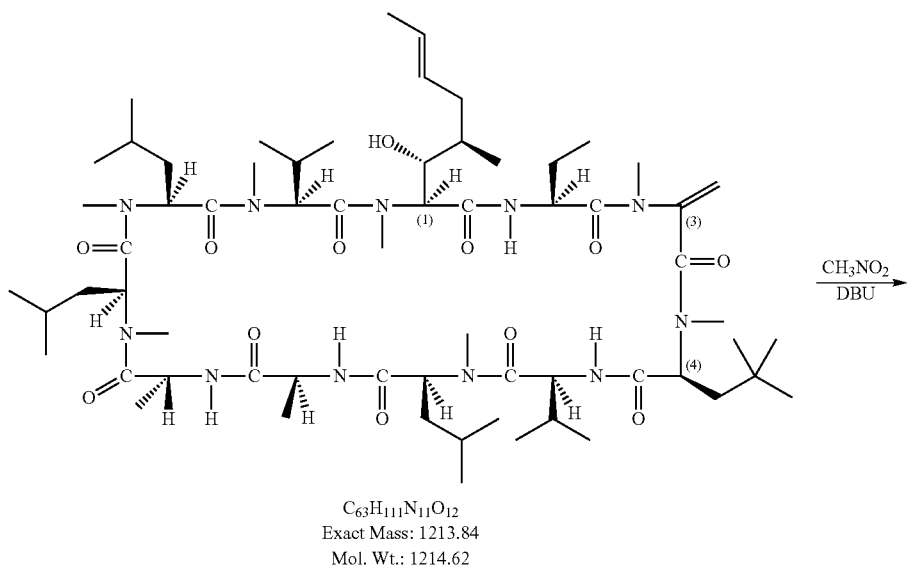

$C_{63}H_{111}N_{11}O_{12}$
Exact Mass: 1213.84
Mol. Wt.: 1214.62

-continued

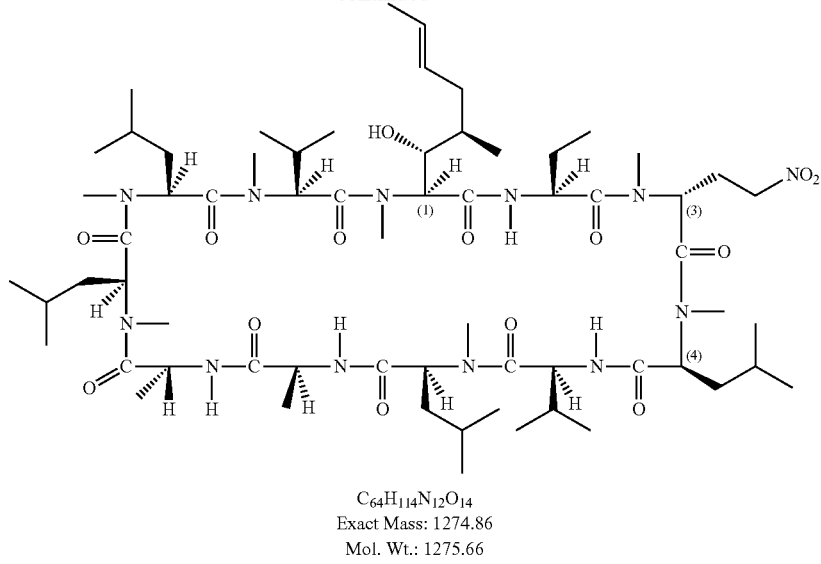

C$_{64}$H$_{114}$N$_{12}$O$_{14}$
Exact Mass: 1274.86
Mol. Wt.: 1275.66

To a solution of [α-methylene-Sar]-3-cyclosporin (FW 1214.62, 1.0 g, 0.82 mmol) in nitromethane (15 ml) was added 1,8-diazbicyclo[5,4,0]undec-7-ene (FW 152.24, 1.0 g, 6.6 mmol). After stirred at room temperature for 2 days, the reaction mixture was concentrated under reduced pressure. The residue was mixed with water dichloromethane. The dichloromethane layer was washed with aqueous citric acid solution and brine, dried over magnesium sulfate, filtered and concentrated under reduced pressure. The residue was purified by chromatography (hexane/acetone=3/1) to give the product [Molecular formula: C$_{64}$H$_{114}$N$_{12}$O$_{14}$; Exact Mass: 1274.86; MS (m/z): 1275.54 (M+1)$^{+}$].

Example 169

[(R)-2-Aminoethyl-Sar]-3-cyclosporin

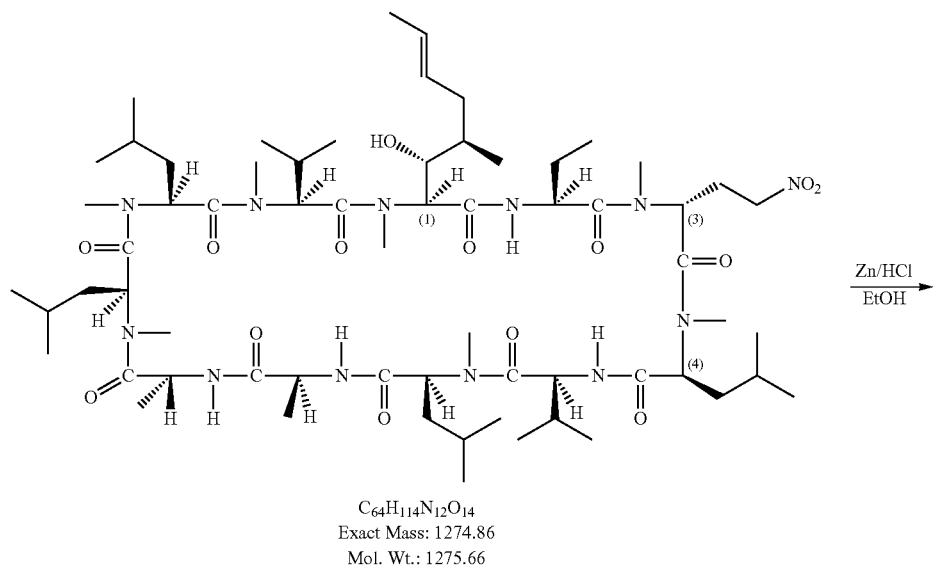

C$_{64}$H$_{114}$N$_{12}$O$_{14}$
Exact Mass: 1274.86
Mol. Wt.: 1275.66

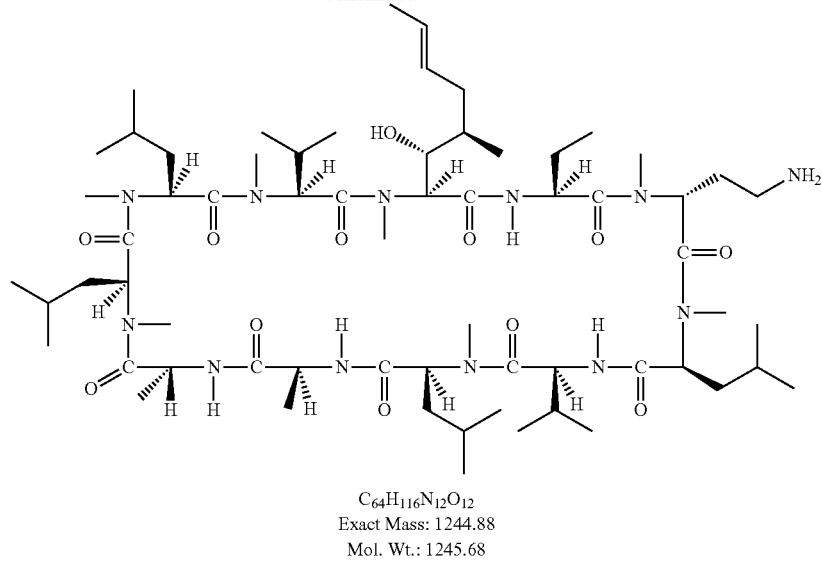

C₆₄H₁₁₆N₁₂O₁₂
Exact Mass: 1244.88
Mol. Wt.: 1245.68

To a mixture of [(R)-2-nitroethyl-Sar]-3-cyclosporin (FW 1275.66, 210 mg, 0.16 mmol) and zinc (FW 65.38, 1 g, 15.3 mmol) in ethanol (20 ml) was added 10% aqueous hydrochloric acid (10 ml). The reaction mixture was stirred at room temperature overnight (monitored by LC-MS) and filtered. The filter cake was washed with ethanol. The filtrate was concentrated and diluted with dichloromethane. The dichloromethan layer was washed with aqueous saturated sodium bicarbonate and brine, dried over magnesium sulfate, filtered and concentrated under reduced pressure. The residue was purified by chromatography (dichloromethane/methanol=95/5) to give the product [Molecular formula: $C_{64}H_{116}N_{12}O_{12}$; Exact Mass: 1244.88; MS (m/z): 1245.54 $(M+1)^+$].

Example 170

[(R)-2-(N, N-Dimethylamino)ethyl-Sar]-3-Cyclosporin

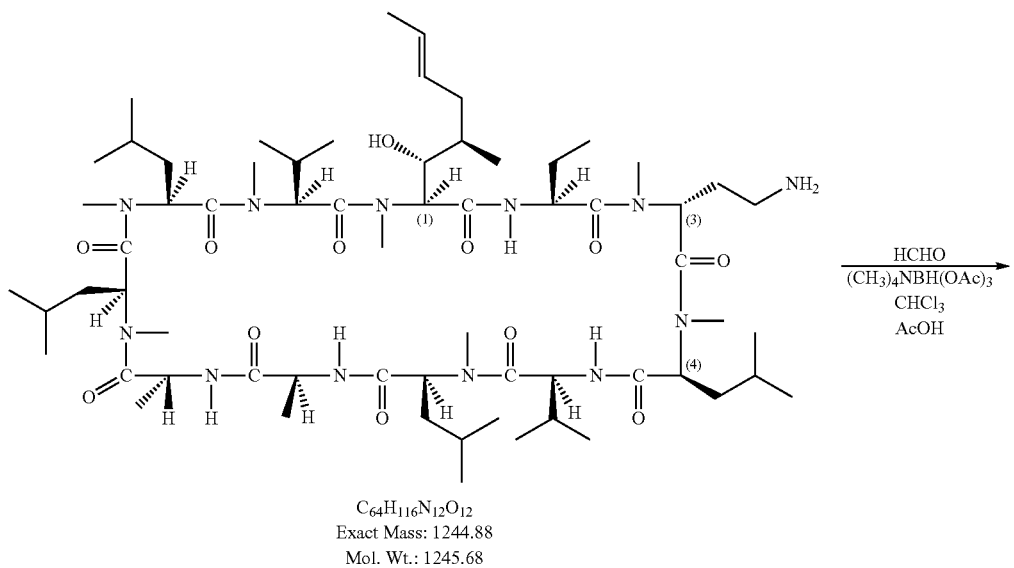

C₆₄H₁₁₆N₁₂O₁₂
Exact Mass: 1244.88
Mol. Wt.: 1245.68

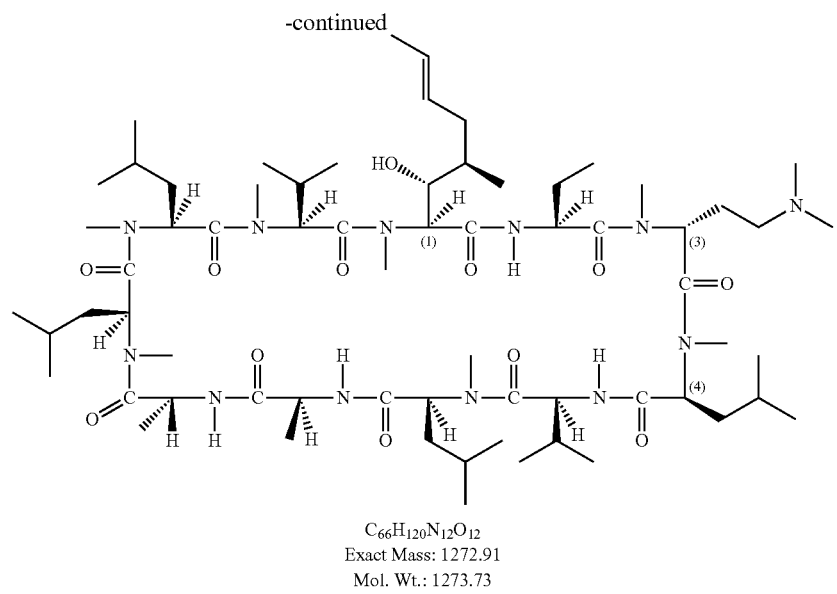

$C_{66}H_{120}N_{12}O_{12}$
Exact Mass: 1272.91
Mol. Wt.: 1273.73

To a solution of [(R)-2-aminoethyl-Sar]-3-Cyclosporin (FW 1245.68, 122 mg, 0.1 mmol) in chloroform (6 ml) were added formaldehyde aqueous 37% solution (0.6 ml) and acetic acid (6 drops). The reaction mixture was stirred at room temperature for 5 min. Then tetramethylammonium triacetoxyborohydride (FW 263.10, 131 mg, 0.5 mmol) was added and the reaction mixture was continued to stir for one hour. The mixture was diluted with dichloromethane. The organic layer was washed with aqueous saturated sodium bicarbonate and brine, dried over magnesium sulfate, filtered and concentrated under reduced pressure. The residue was purified by chromatography (dichloromethane/methanol=96/4) to give the product [Molecular formula: $C_{66}H_{120}N_{12}O_{12}$; Exact Mass: 1272.91; MS (m/z): 1273.70 $(M+1)^+$; TLC $R_f$: 0.27 (dichloromethane/methanol); HPLC RT: 12.42 minutes].

Example 171

[(R)-2-(N,N-Diethylamino)ethyl-Sar]-3-Cyclosporin

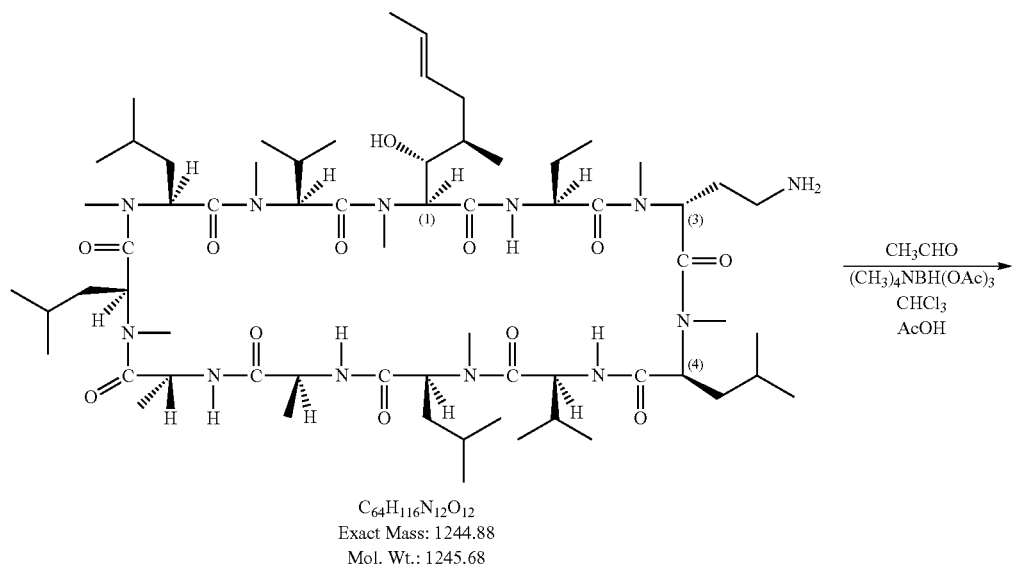

$C_{64}H_{116}N_{12}O_{12}$
Exact Mass: 1244.88
Mol. Wt.: 1245.68

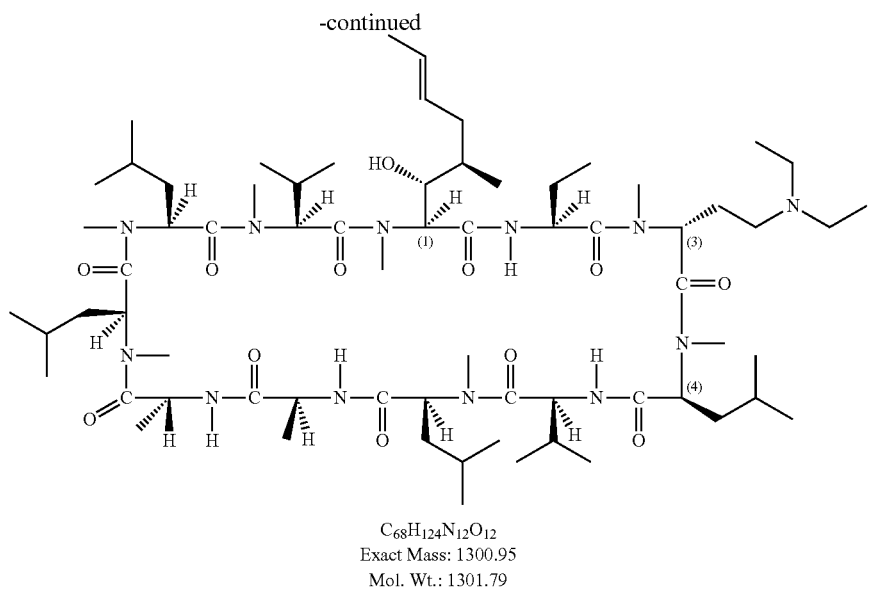

$C_{68}H_{124}N_{12}O_{12}$
Exact Mass: 1300.95
Mol. Wt.: 1301.79

To a solution of 3-amino cyclosporine (FW 1245.68, 124 mg, 0.1 mmol) in chloroform (6 ml) were added acetaldehyde (FW 44.06, 78 mg, 1.77 mmol) and acetic acid (drops). The reaction mixture was stirred at room temperature for 5 min. Then tetramethylammonium triacetoxyborohydride (FW 263.10, 126 mg, 0.48 mmol) was added and the reaction mixture was continued to stir for 1 hour. The mixture was diluted with dichloromethane. The organic layer was washed with aqueous saturated sodium bicarbonate solution and brine, dried over magnesium sulfate, filtered and concentrated under reduced pressure. The residue was purified by chromatography (dichloromethane/methanol=97/3) to give product [Molecular formula: $C_{68}H_{124}N_{12}O_{12}$; Exact Mass: 1300.95; MS (m/z): 1301.72 $(M+1)^+$; TLC $R_f$: 0.33 (dichloromethane/methanol=95/5); HPLC RT: 13.28 minutes (C8 reverse phase column, 250 mm, acetonitril-water/(0.05% trifluoroacetic acid); operation temperature: 64° C.; detector: 210 nm)].

Example 172

[(2-Methoxy-2-oxoethyl)-Sar]-3-cyclosporin

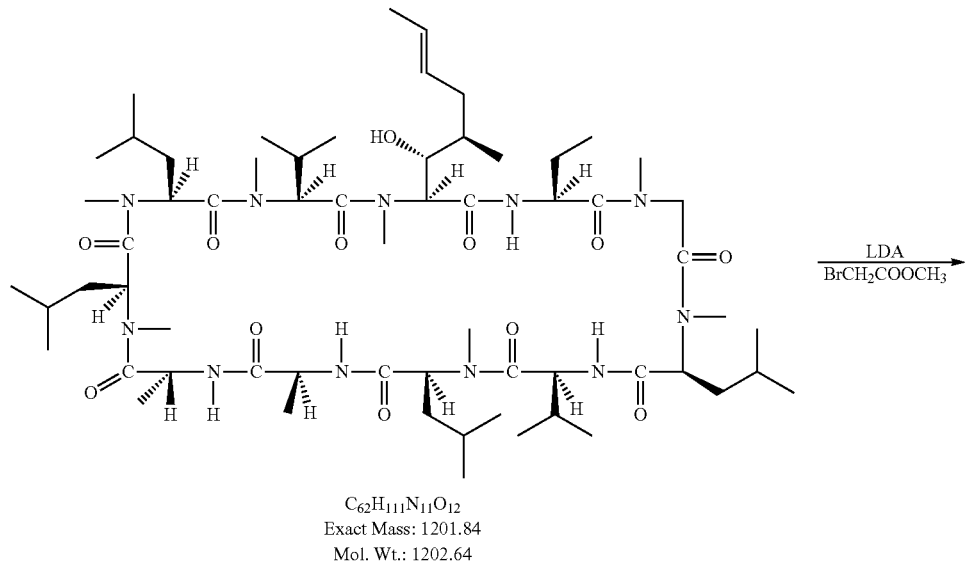

$C_{62}H_{111}N_{11}O_{12}$
Exact Mass: 1201.84
Mol. Wt.: 1202.64

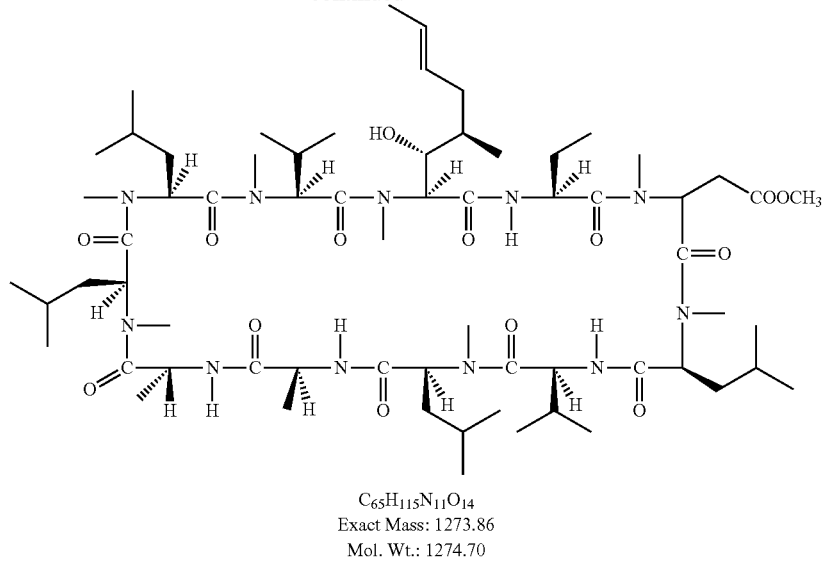

C₆₅H₁₁₅N₁₁O₁₄
Exact Mass: 1273.86
Mol. Wt.: 1274.70 n-Butyllithium (15.84 ml, 2.89 M, 45.79 mmol) was added to a solution of diisopropylamine (6.50 ml, 45.79 mmol) in tetrahydrofuran (80 ml) at −78° C. under nitrogen and the reaction mixture was stirred for an hour. A solution of cyclosporine A (5.00 g, 4.16 mmol) in tetrahydrofuran (20 ml) was added over 10 minutes and the mixture was stirred at −78° C. for another two hours. Then methyl bromoacetate (7.00 g, 45.79 mmol) and the reaction mixture was stirred at −78° C. for one hour. The reaction mixture was allowed to warm up to room temperature slowly and stirred overnight. Most of tetrahydrofuran was removed under vacuum at room temperature. Ethyl acetate (50 ml) and 50 ml brine were added and separated. The aqueous layer was extracted with ethyl acetate (20 ml×3). The combined ethyl acetate layers were dried over magnesium sulfate and evaporated under reduced pressure. The residue was purified by column to give to give 2.11 g of [(2-methoxy-2-oxoethyl)-Sar]-3-cyclosporin [Molecular Formula: $C_{65}H_{115}N_{11}O_{14}$; Exact Mass: 1273.86; MS (m/z): 1274.44 (M+1)⁺, 1296.63 (M+Na)⁻].

[(2-(t-Butoxy)-2-oxoethyl)-Sar]-3-cyclosporin was synthesized using a method analogous to a procedure described by Seebach D, et al., 1993, *Helv Chim Acta*, 76, 1564-1590.

Example 173

[(R)-(2-Hydroxyethyl)-Sar]-3-cyclosporin and [(S)-(2-hydroxyethyl)-Sar]-3-cyclosporin

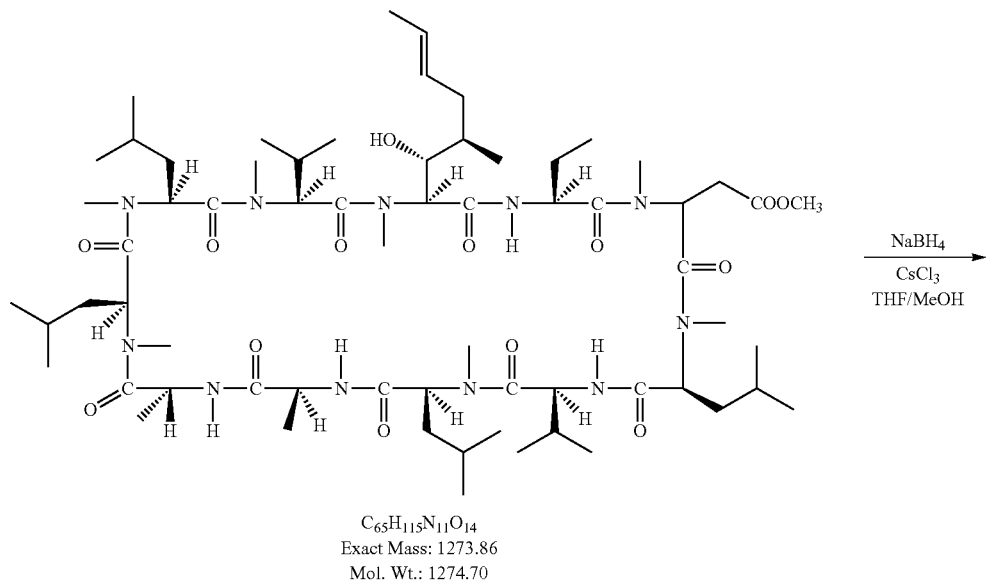

C₆₅H₁₁₅N₁₁O₁₄
Exact Mass: 1273.86
Mol. Wt.: 1274.70

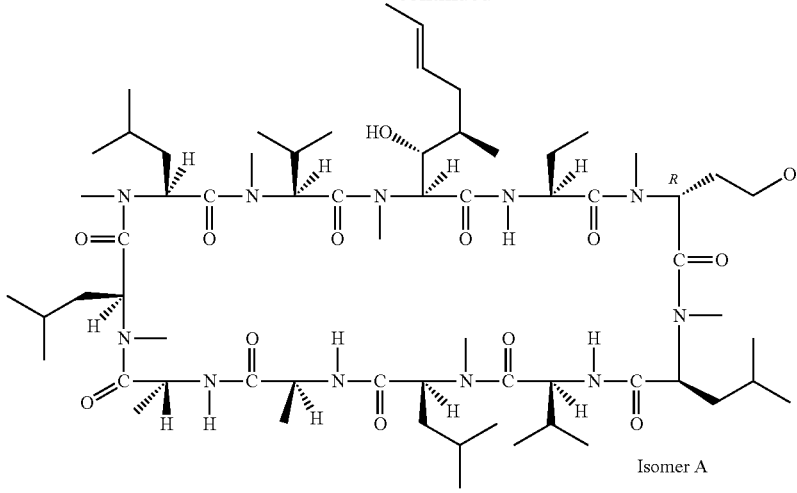

C₆₄H₁₁₅N₁₁O₁₃
Exact Mass: 1245.87
Mol. Wt.: 1246.69

Isomer A

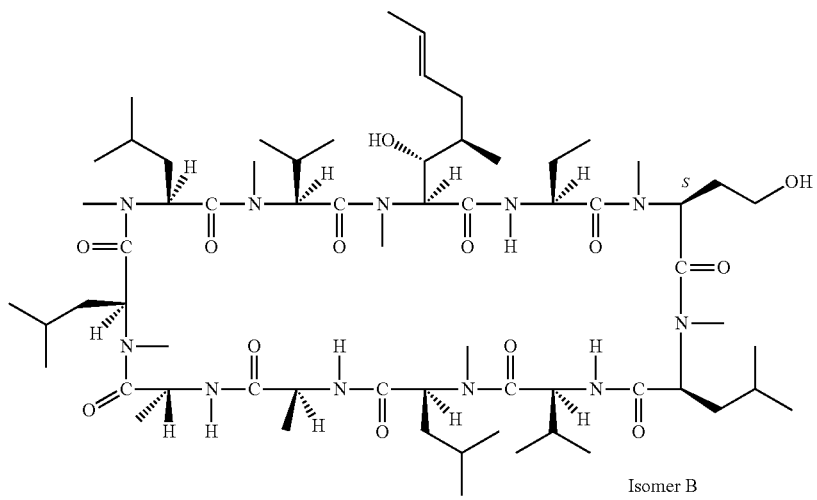

C₆₄H₁₁₅N₁₁O₁₃
Exact Mass: 1245.87
Mol. Wt.: 1246.69

Isomer B

[(2-Methoxy-2-oxoethyl)-Sar]-3-cyclosporin (1.00 g, 0.79 mmol) was dissolved in tetrahydrofuran (30 ml), followed by adding cesium chloride (1.00 g, 5.94 mmol) and sodium borohydride (1.00 g, 26.43 mmol). Then 30 ml of methanol was added dropwise to the mixture over one hour. After addition, the mixture was stirred at room temperature for another hour. Most solvent was then evaporated under reduced pressure. Ethyl acetate (30 ml) and water (30 ml) were added. The ethyl acetate layer was separated and washed with brine, dried over magnesium sulfate and evaporated under reduced pressure. The residue was purified by chromatography to give the product of isomer A as [(R)-(2-hydroxyethyl)-Sar]-3-cyclosporin [Molecular Formula: $C_{64}H_{115}N_{11}O_{13}$; Exact Mass: 1245.87; MS (m/z): 1246.49.52 $(M+1)^+$, 1268.72 $(M+Na)^+$; TLC $R_f$: 0.46 (dichloromethane/methanol=9:1); HPLC RT: 16.06 min (C8 reverse phase column: 250 mm; acetonitrile/water (0.05% trifluoroacetic acid); operation temperature: 64° C.; detector: 210 nm)] and the product of isomer B as [(S)-(2-hydroxyethyl)-Sar]-3-cyclosporin [Molecular Formula: $C_{64}H_{115}N_{11}O_{13}$; Exact Mass: 1245.87; MS (m/z): 1246.49 $(M+1)^+$, 1268.68 $(M+Na)^+$; TLC $R_f$: 0.46 (dichloromethane/methanol=9:1); HPLC RT: 15.15 min (C8 reverse phase column: 250 mm; acetonitrile/water (0.05% trifluoroacetic acid); operation temperature: 64° C.; detector: 210 nm)].

Example 174

[(R)-2-Nitroethyl-Sar]-3-[(γ-hydroxy)-NMeLeu]-4-Cyclosporin

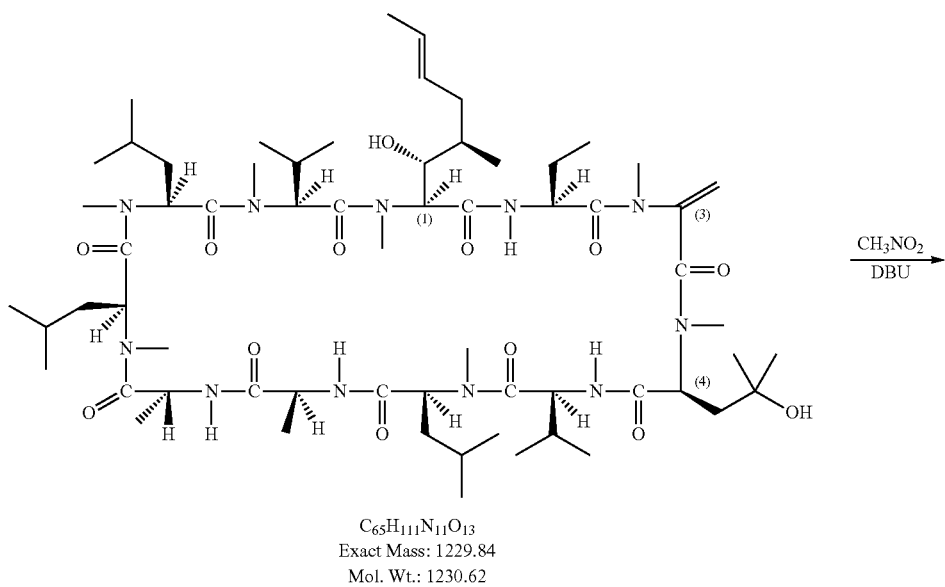

$C_{65}H_{111}N_{11}O_{13}$
Exact Mass: 1229.84
Mol. Wt.: 1230.62

$\xrightarrow{\text{CH}_3\text{NO}_2}{\text{DBU}}$

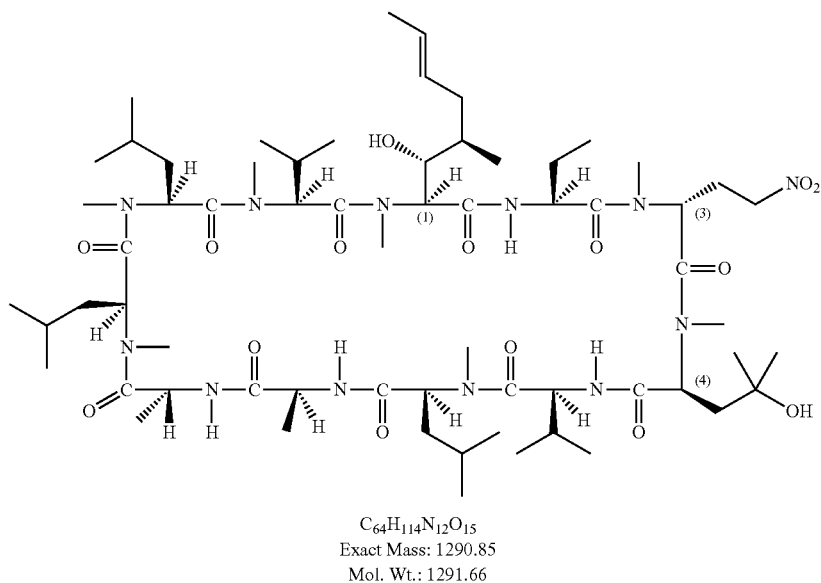

$C_{64}H_{114}N_{12}O_{15}$
Exact Mass: 1290.85
Mol. Wt.: 1291.66

To a solution of [α-Methylene-Sar]-3-[(γ-hydroxy)-N-MeLeu]-4-cyclosporin (FW 1230.62, 1.6 g, 1.3 mmol) in 20 ml of nitromethane was added 1,8-diazbicyclo[5,4,0]undec-7-ene (4 ml). The reaction mixture was stirred at room temperature overnight and concentrated under reduced pressure. The residue was mixed with water and dichloromethane and separated. The organic layer was washed with aqueous citric acid solution and brine, dried over magnesium sulfate, filtered and concentrated under reduced pressure. The residue was purified by chromatography (dichloromethane/methanol=97/3) to give the product (R-isomer) 600 mg [Molecular formula: $C_{64}H_{114}N_{12}O_{15}$; Exact Mass: 1290.85; MS (m/z): 1291.72(M+1)$^+$. HPLC RT: 14.95 minutes]. (S-isomer) 360 mg [Molecular formula: $C_{64}H_{114}N_{12}O_{15}$; Exact Mass: 1290.85; MS (m/z): 1291.72 (M+1)$^+$; HPLC RT: 14.43 minutes].

Example 175

[(R)-2-Aminoethyl-Sar]-3-[(γ-hydroxy)-NMeLeu]-4-Cyclosporin

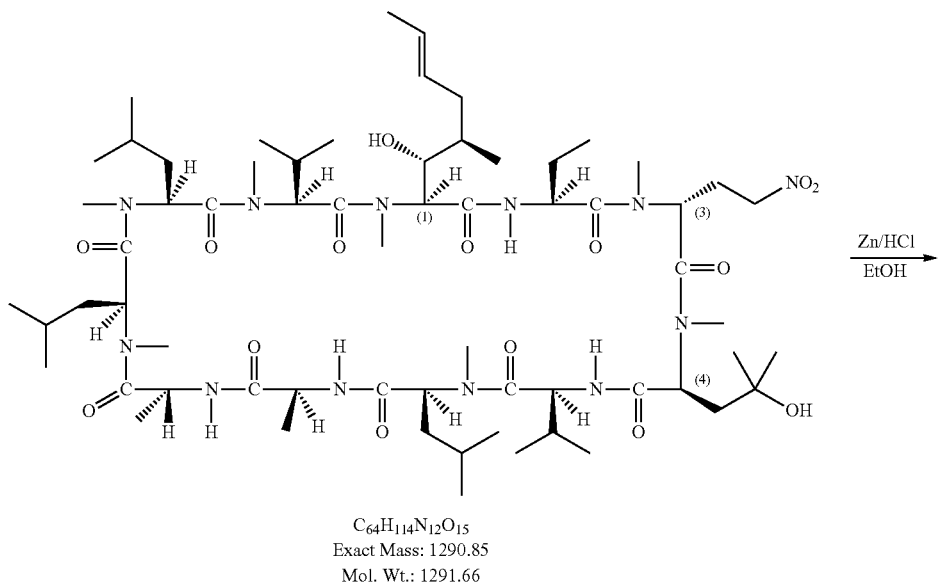

$C_{64}H_{114}N_{12}O_{15}$
Exact Mass: 1290.85
Mol. Wt.: 1291.66

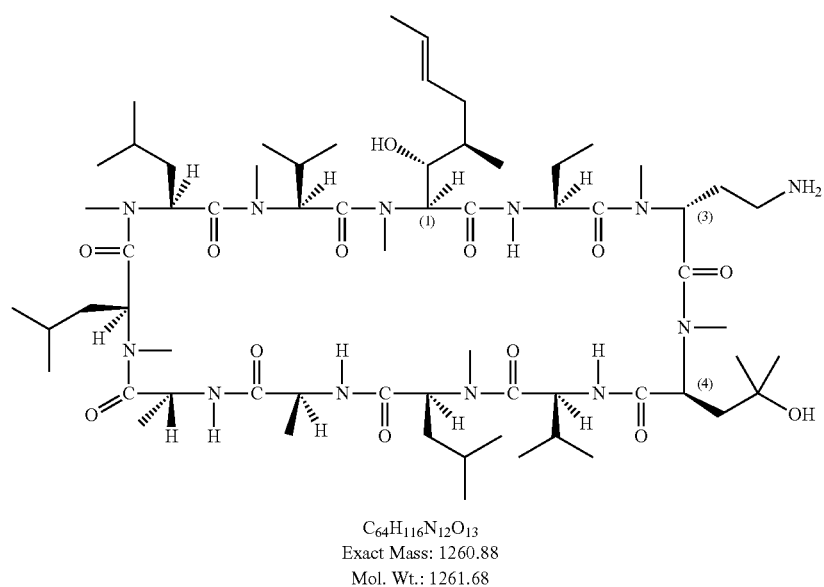

$C_{64}H_{116}N_{12}O_{13}$
Exact Mass: 1260.88
Mol. Wt.: 1261.68

To a mixture of [(R)-2-nitroethyl-Sar]-3-[(γ-hydroxy)-NMeLeu]-4-cyclosporin (FW 1291.66, 400 mg, 0.31 mmol) and zinc (1.5 g) in ethanol (30 ml) was added 10% aqueous hydrochloric acid (30 ml). The reaction mixture was stirred at room temperature overnight (monitored by LC-MS) and filtered. The filter cake was washed with ethanol. The combined filtrate was concentrated and diluted with dichloromethane. The organic layer was washed with aqueous saturated sodium bicarbonate solution and brine, dried over magnesium sulfate, filtered and concentrated under reduced pressure. The residue was purified by chromatography (dichloromethane/methanol=95/5) to give the product [Molecular formula: $C_{64}H_{116}N_{12}O_{13}$; Exact Mass: 1260.88; MS (m/z): 1261.70 (M+1)$^+$].

Example 176

[(R)-2-(N,N-Dimethylamino)ethyl-Sar]-3-[(γ-hydroxy)-NMeLeu]-4-cyclosporin

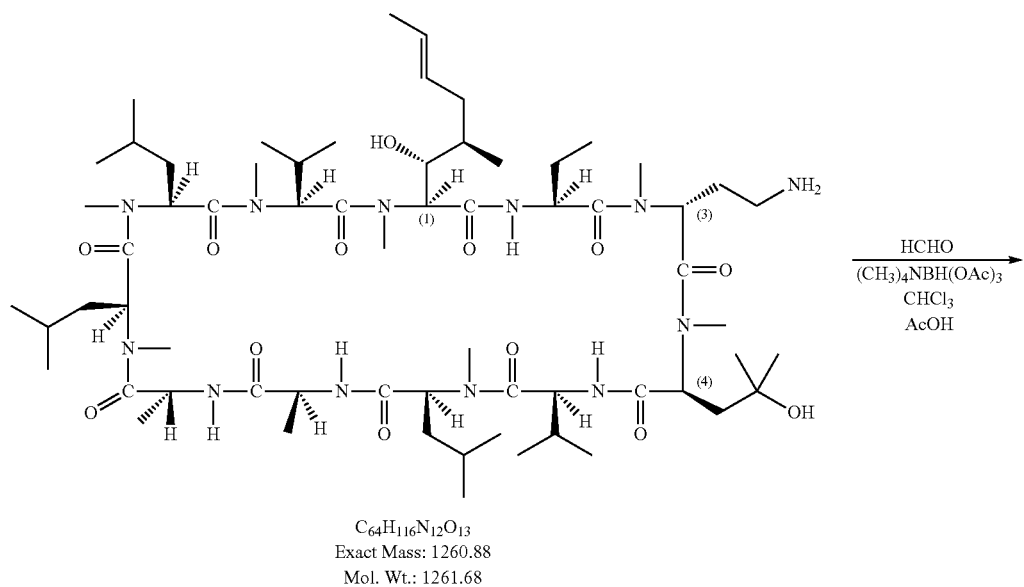

$C_{64}H_{116}N_{12}O_{13}$
Exact Mass: 1260.88
Mol. Wt.: 1261.68

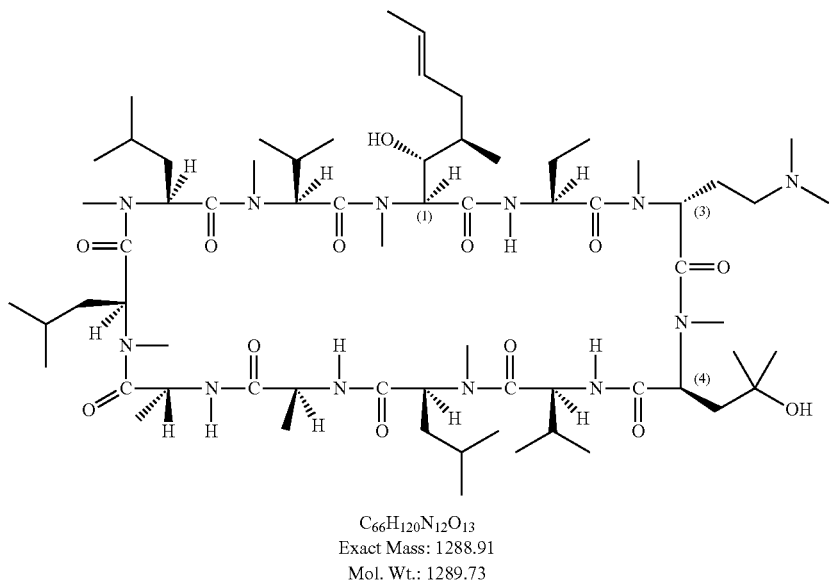

$C_{66}H_{120}N_{12}O_{13}$
Exact Mass: 1288.91
Mol. Wt.: 1289.73

To a solution of [(R)-2-aminoethyl-Sar]-3-[(γ-hydroxy)-NMeLeu]-4-cyclosporin (FW 1261.68, 180 mg, 0.14 mmol) in chloroform (6 ml) were added formaldehyde aqueous 37% solution (0.8 ml) and acetic acid (8 drops). The reaction mixture was stirred at room temperature for 5 min. Then tetramethylammonium triacetoxyborohydride (263.10, 200 mg, 0.76 mmol) was added and the reaction mixture was continued to stir for one hour. The mixture was diluted with dichloromethane. The organic layer was washed with aqueous saturated sodium bicarbonate solution and brine, dried over magnesium sulfate, filtered and concentrated under reduced pressure. The residue was purified by chromatography (dichloromethane/methanol=95/5) to give the product [Molecular formula: $C_{66}H_{120}N_{12}O_{13}$; Exact Mass: 1288.91; MS (m/z): 1289.76 (M+1)⁻; TLC $R_f$: 0.32 (dichloromethane/methanol=9/1); HPLC RT: 11.14 minutes].

Example 177

[(R)-2-(N,N-Diethylamino)ethyl-Sar]-3-[(γ-hydroxy)-NMeLeu]-4-Cyclosporin

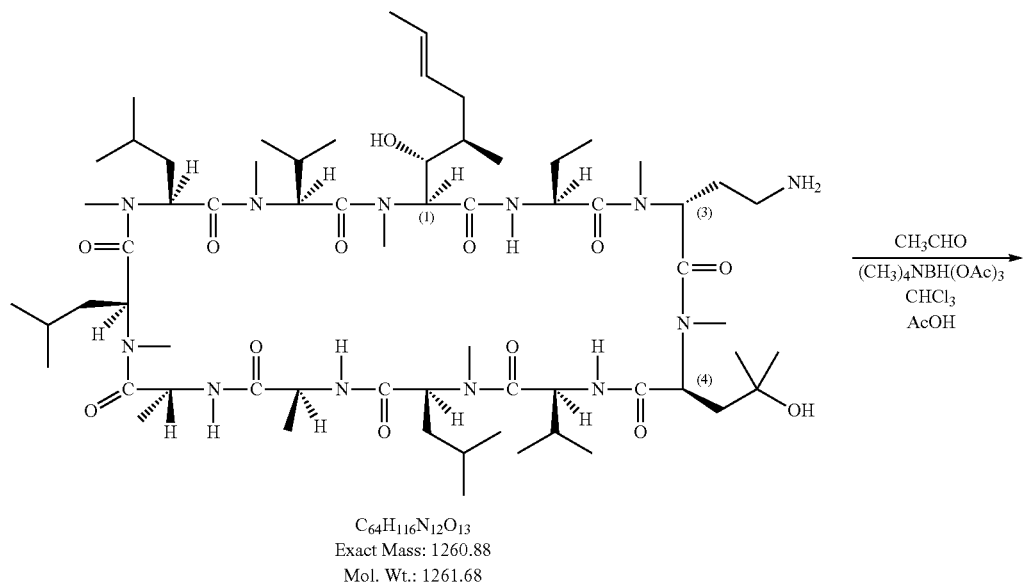

$C_{64}H_{116}N_{12}O_{13}$
Exact Mass: 1260.88
Mol. Wt.: 1261.68

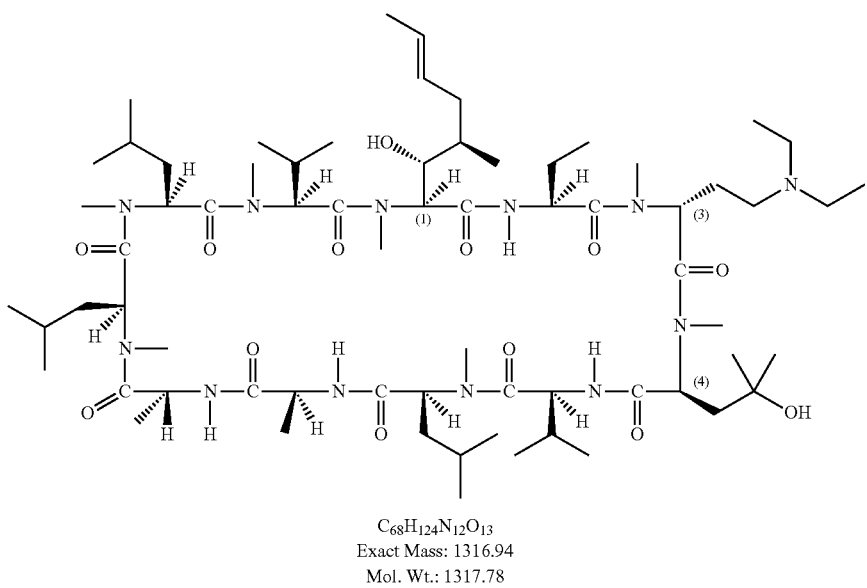

$C_{68}H_{124}N_{12}O_{13}$
Exact Mass: 1316.94
Mol. Wt.: 1317.78

To a solution of [(R)-2-aminoethyl-Sar]-3-[(γ-hydroxy)-NMeLeu]-4-cyclosporin (FW 1261.68, 129 mg, 0.10 mmol) in chloroform (10 ml) were added acetaldehyde (FW 44.06, 80 mg, 1.8 mmol) and acetic acid (7 drops). The reaction mixture was stirred at room temperature for 5 min. Then tetramethylammonium triacetoxyborohydride (FW 263.10, 200 mg, 0.76 mmol) was added and the reaction mixture was continued to stir for one hour. The mixture was diluted with dichloromethane. The organic layer was washed with aqueous saturated sodium bicarbonate solution and brine, dried over magnesium sulfate, filtered and concentrated under reduced pressure. The residue was purified by chromatography (dichloromethane/methanol=95/5) to give the product [Molecular formula: $C_{68}H_{124}N_{12}O_{13}$; Exact Mass: 1316.94; MS (m/z): 1317.70 (M+1)⁻; TLC $R_f$: 0.39 (Dichloromethane/methanol=9/1); HPLC RT: 12.06 minutes].

Example 178

[(S)-2-Aminoethyl-Sar]-3-[(γ-hydroxy)-NMeLeu]-4-cyclosporin

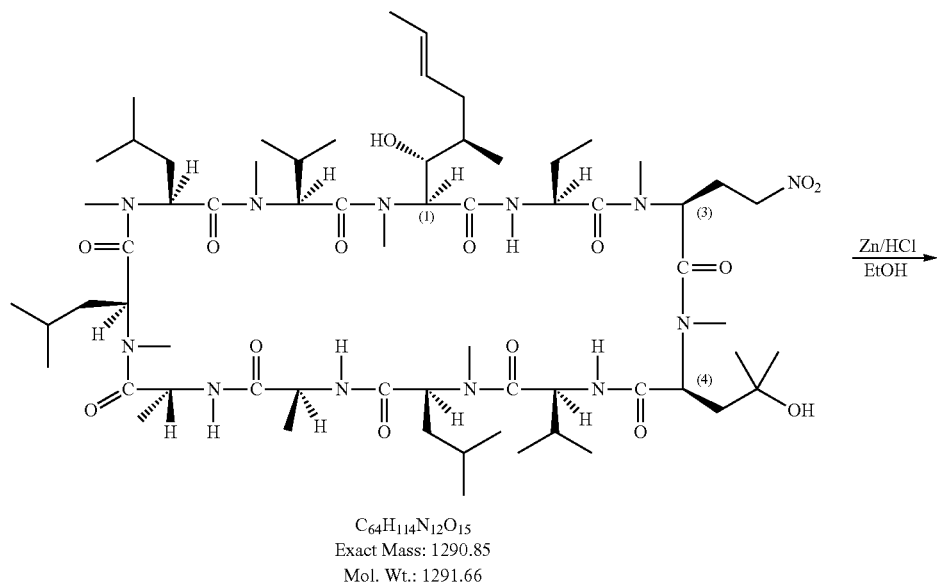

$C_{64}H_{114}N_{12}O_{15}$
Exact Mass: 1290.85
Mol. Wt.: 1291.66

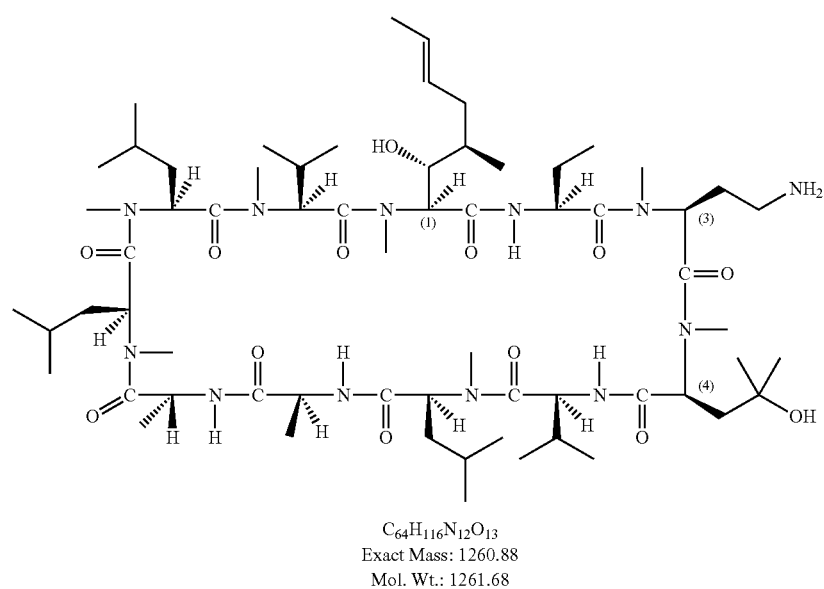

$C_{64}H_{116}N_{12}O_{13}$
Exact Mass: 1260.88
Mol. Wt.: 1261.68

To a mixture of [(S)-2-nitroethyl-Sar]-3-[(γ-hydroxy)-NMeLeu]-4-cyclosporin (FW 1291.66, 350 mg, 0.27 mmol) and zinc (1.5 g) in ethanol (25 ml) was added 10% aqueous hydrochloric acid (15 ml). The reaction mixture was stirred at room temperature overnight (monitored by LC-MS) and filtered. The filter cake was washed with ethanol. The combined filtrate was concentrated and diluted with dichloromethane. The organic solution was washed with aqueous saturated sodium bicarbonate solution and brine, dried over magnesium sulfate, filtered and concentrated under reduced pressure. The residue was purified by chromatography (dichloromethane/methanol=96/4) to give the product [Molecular formula: $C_{64}H_{116}N_{12}O_{13}$; Exact Mass: 1260.88; MS (m/z): 1261.64 (M+1)$^+$].

Example 179

[(S)-2-(N,N-Dimethylamino)ethyl-Sar]-3-[(γ-hydroxy)-NMeLeu]-4-Cyclosporin

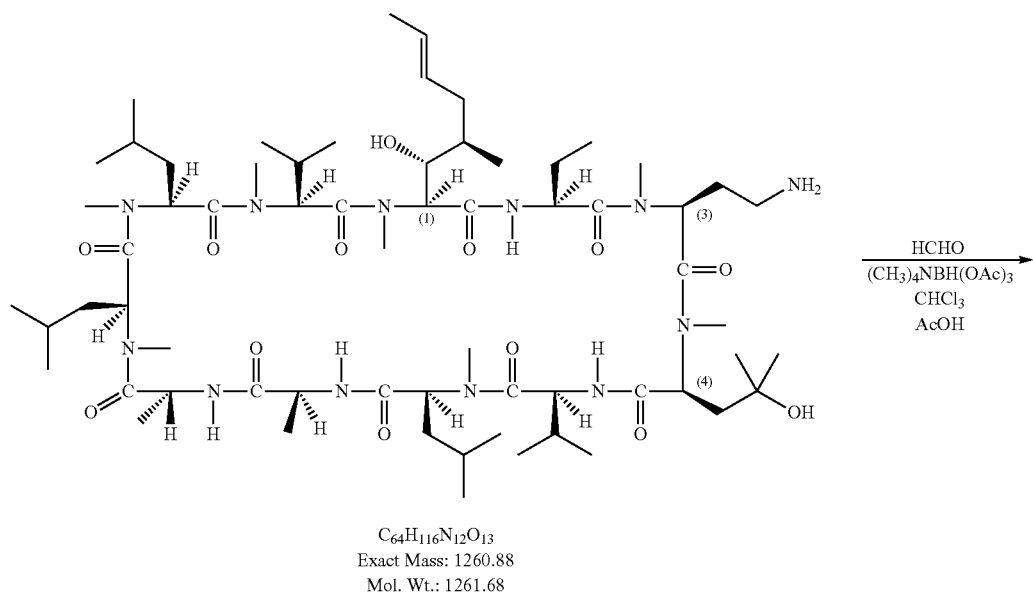

C₆₄H₁₁₆N₁₂O₁₃
Exact Mass: 1260.88
Mol. Wt.: 1261.68

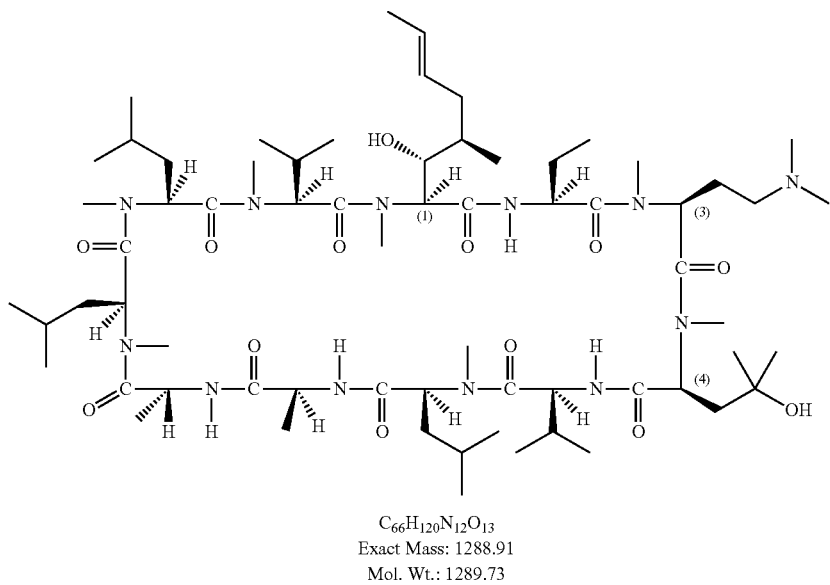

C₆₆H₁₂₀N₁₂O₁₃
Exact Mass: 1288.91
Mol. Wt.: 1289.73

To a solution of [(S)-2-aminoethyl-Sar]-3-[(γ-hydroxy)-NMeLeu]-4-cyclosporin (FW 1261.68, 130 mg, 0.10 mmol) in chloroform (10 ml) were added formaldehyde aqueous 37% solution (0.7 ml) and acetic acid (7 drops). The reaction mixture was stirred at room temperature for 5 min. Then tetramethylammonium triacetoxyborohydride (263.10, 200 mg, 0.76 mmol) was added and the reaction mixture was continued to stir for one hour. The mixture was diluted with dichloromethane. The organic layer was washed with aqueous saturated sodium bicarbonate solution and brine, dried over Magnesium sulfate, filtered and concentrated under reduced pressure. The residue was purified by chromatography (dichloromethane/methanol=95/5) to give the product [Molecular formula: $C_{66}H_{120}N_{12}O_{13}$; Exact Mass: 1288.91; MS (m/z): 1289.70 (M+1)⁻; TLC $R_f$: 0.35 (Dichloromethane/methanol=9/1); HPLC RT: 11.02 minutes].

Example 180

[(S)-2-(N,N-Diethylamino)ethyl-Sar]-3-[(γ-hydroxy)-NMeLeu]-4-Cyclosporin

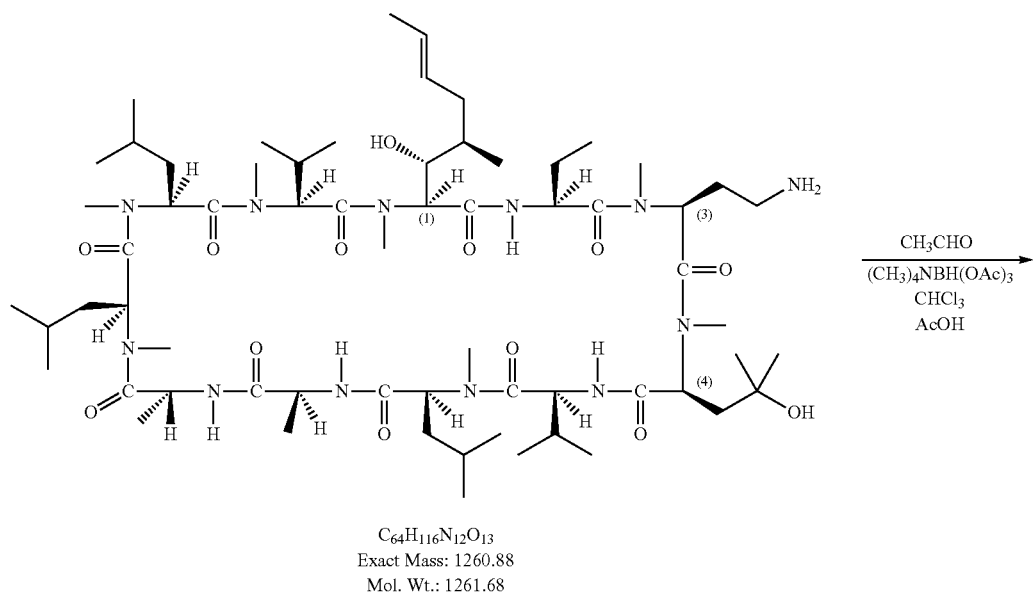

$C_{64}H_{116}N_{12}O_{13}$
Exact Mass: 1260.88
Mol. Wt.: 1261.68

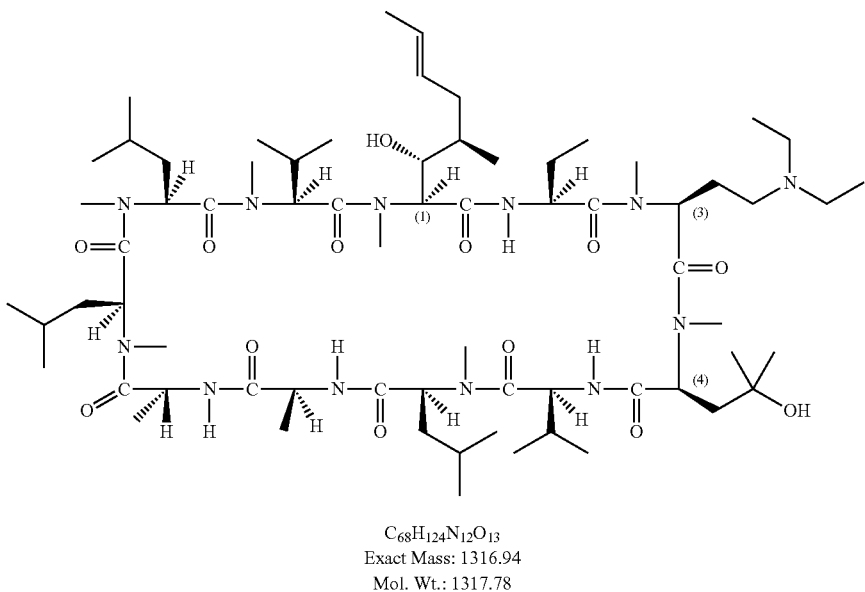

$C_{68}H_{124}N_{12}O_{13}$
Exact Mass: 1316.94
Mol. Wt.: 1317.78

To a solution of [(S)-2-aminoethyl-Sar]-3-[(γ-hydroxy)-NMeLeu]-4-cyclosporin (FW 1261.68, 129 mg, 0.10 mmol) in chloroform (10 ml) were added acetaldehyde (FW 44.06, 80 mg, 1.8 mmol) and acetic acid (7 drops). The reaction mixture was stirred at room temperature for 5 minutes. Then tetramethylammonium triacetoxyborohydride (FW 263.10, 200 mg, 0.76 mmol) was added and the reaction mixture was continued to stir for one hour. The mixture was diluted with dichloromethane. The organic layer was washed with aqueous saturated sodium bicarbonate solution and brine, dried over magnesium sulfate, filtered and concentrated under reduced pressure. The residue was purified by chromatography (dichloromethane/methanol=95/5) to give the product [Molecular formula: $C_{68}H_{124}N_{12}O_{13}$; Exact Mass: 1316.94; MS (m/z): 1317.70 (M+1)⁻; TLC $R_f$: 0.41 (Dichloromethane/methanol=9/1); HPLC RT: 11.96 minutes].

Example 181

[(R)-2-Nitro-3-(N,N-Dimethylamino)propyl-Sar]-3-Cyclosporin

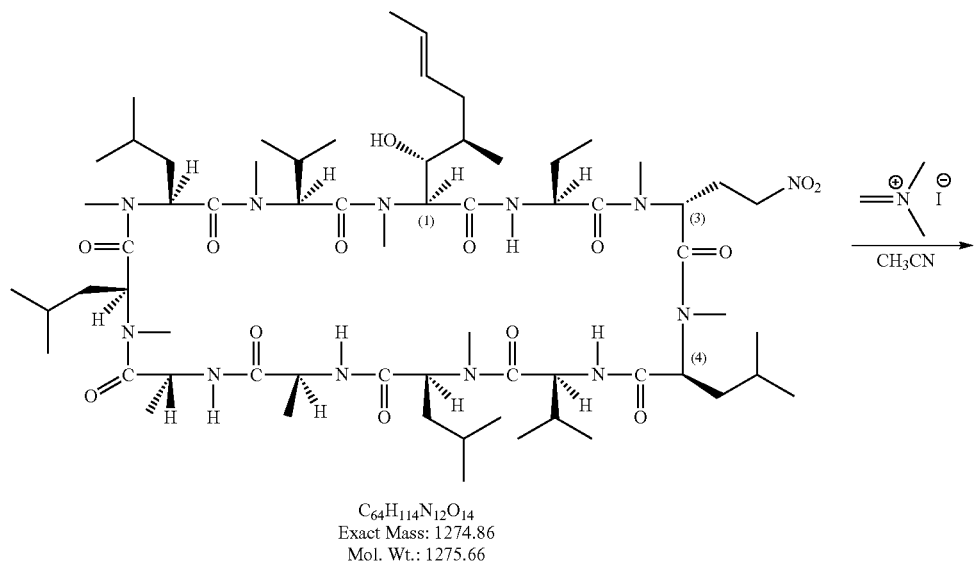

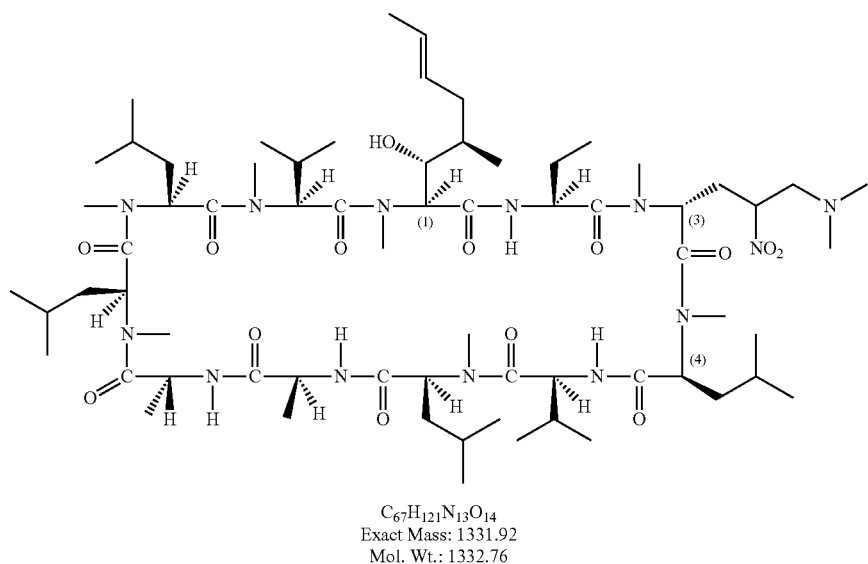

To a mixture of [(R)-2-nitroethyl-Sar]-3-cyclosporin (FW 1275.66, 360 mg, 0.28 mmol) and dimethymethyleneammonium iodide (FW 185.01, 550 mg, 15.4 mmol) acetonitrile (in 25 ml) was added triethylamine (10 drops). The reaction mixture was stirred at room temperature overnight (monitored by LC-MS). The mixture was concentrated and diluted with dichloromethane. The organic layer was washed with aqueous water and brine, dried over magnesium sulfate, filtered and concentrated under reduced pressure. The crude product was used for next step.

Example 182

[(R)-3-(N,N-Dimethylamino)propyl-Sar]-3-Cyclosporin

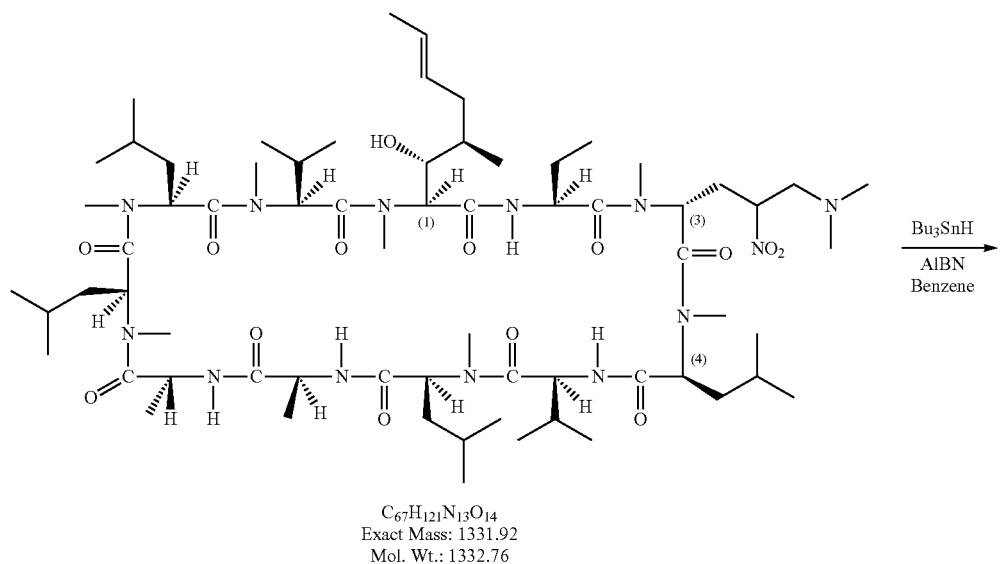

C₆₇H₁₂₁N₁₃O₁₄
Exact Mass: 1331.92
Mol. Wt.: 1332.76

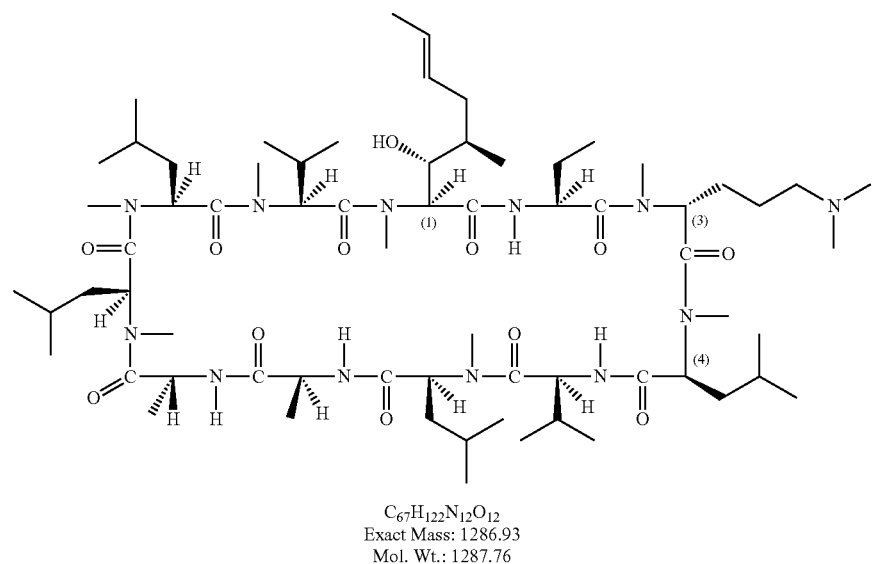

C₆₇H₁₂₂N₁₂O₁₂
Exact Mass: 1286.93
Mol. Wt.: 1287.76

To a mixture of cylcosporine (crude form previous step FW 1332.76, 0.28 mmol) and tri-n-butyltin hydride (FW 291.07, 0.41 g, 1.4 mmol) in benzene (25 ml) was added AIBN (FW 164.21, 46 mg, 0.28 mmol) under nitrogen atmosphere. The mixture was heated to reflux with stirring for 8 hours. After the reaction was completed (monitored by LC-MS), the reaction mixture was washed with aqueous saturated sodium bicarbonate solution and brine followed by evaporated under vacuum. The residue was purified by chromatography (Dichloromethane/methanol=95/5) to give the product [Molecular formula: $C_{67}H_{122}N_{12}O_{12}$; Exact Mass: 1286.93; MS (m/z): 1287.71 (M+1)⁺; TLC R$_f$: 0.36 (dichloromethane/methanol=95/5); HPLC RT: 12.57 minutes].

Example 183

[(R)-3-ethoxy-2-(ethoxycarbonyl)-3-oxopropyl)-Sar]-3-[(γ-hydroxy)-N-MeLeu]-4-cyclosporin

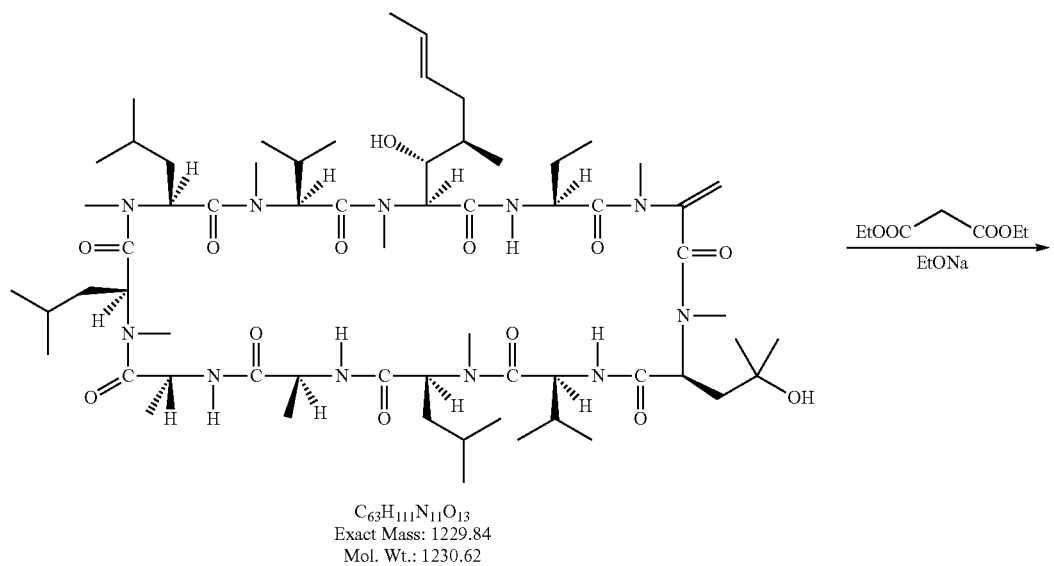

$C_{63}H_{111}N_{11}O_{13}$
Exact Mass: 1229.84
Mol. Wt.: 1230.62

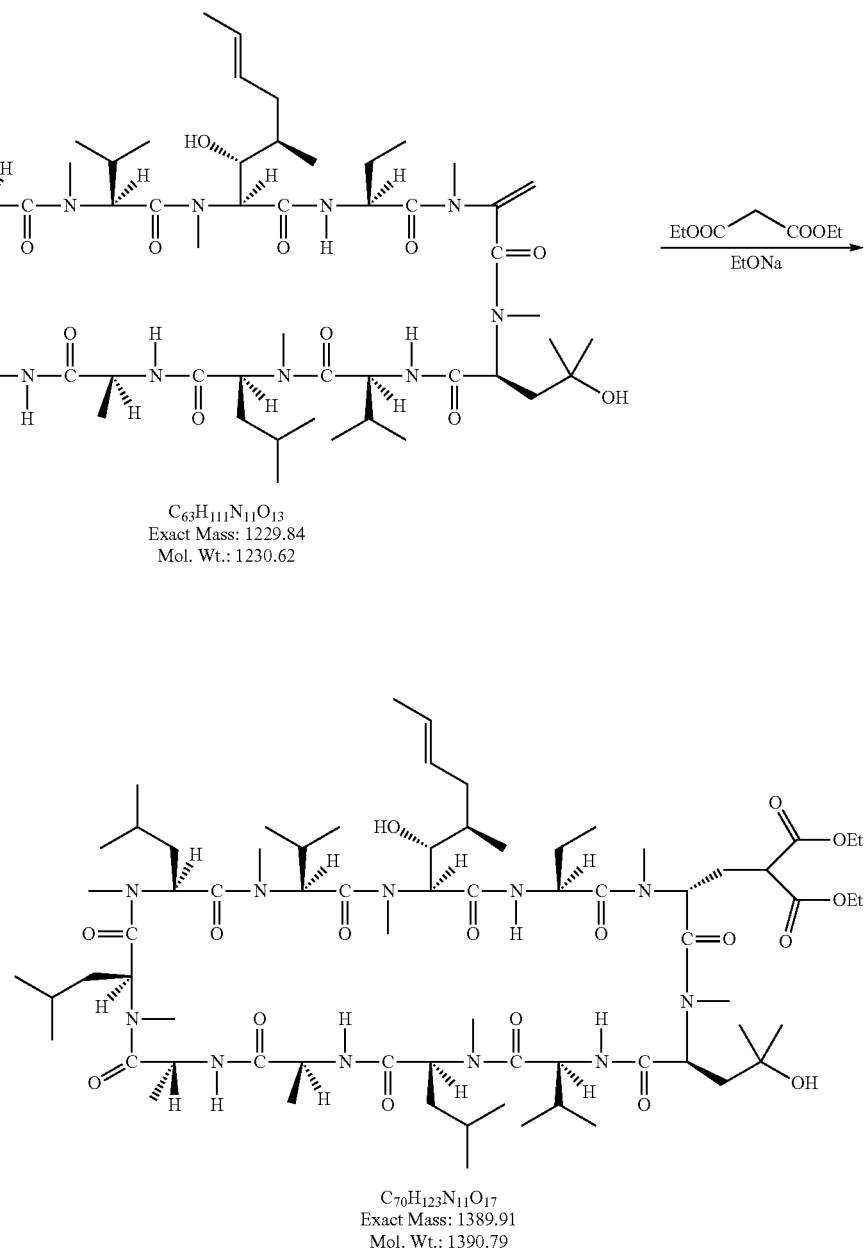

$C_{70}H_{123}N_{11}O_{17}$
Exact Mass: 1389.91
Mol. Wt.: 1390.79

To a solution of [α-methylene-Sar]-3-[(γ-hydroxy)-N-MeLeu]-4-cyclosporin (0.61 g, 0.50 mmol) and diethyl malonate (1.00 g, 6.25 mmol) in ethanol anhydrous (30 ml) was added sodium ethoxide (0.82 g, 12.05 mmol). The reaction mixture was stirred at room temperature overnight and concentrated under reduced pressure. The residue was mixed with water (30 ml) and dichloromethane (80 ml) and separated. The organic layer was washed with aqueous citric acid and brine, dried over magnesium sulfate, filtered and concentrated under reduced pressure. The residue was purified by chromatography (hexane/acetone=2/1) to give the product. [Molecular formula: $C_{70}H_{123}N_{11}O_{17}$; Exact Mass: 1389.91; MS (m/z): 1390.56(M+1)$^+$; TLC Rf: 0.30 (dichloromethane/methanol=95/5); HPLC RT: 15.32 min (C8 reverse phase column: 250 mm; acetonitrile/water(0.05% TFA); operation temperature: 64° C.; Detector: 210 nm)].

Example 184

[(R)-3-Hydroxy-2-(hydroxylmethyl)propyl)-Sar]-3-[(γ-hydroxy)-N-MeLeu]-4-cyclosporin

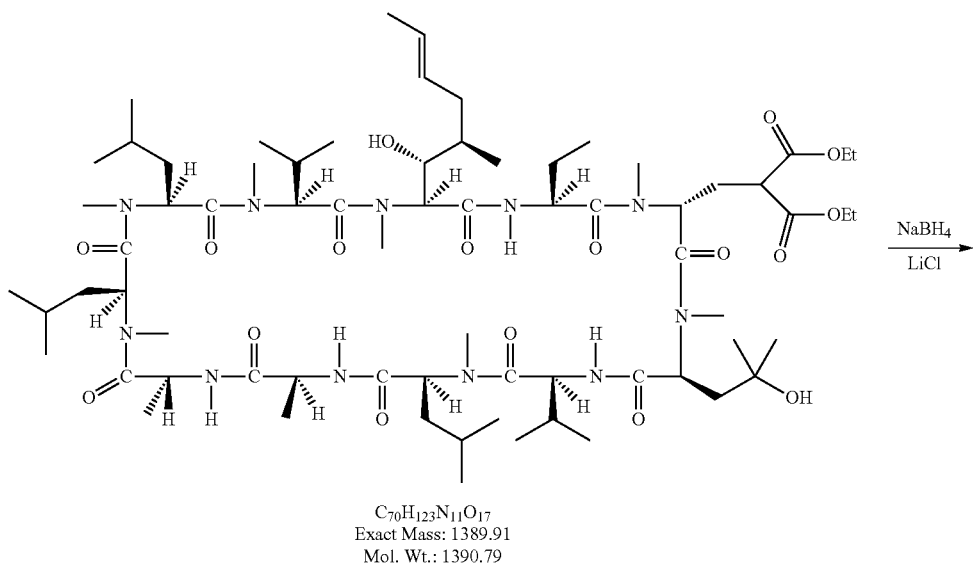

$C_{70}H_{123}N_{11}O_{17}$
Exact Mass: 1389.91
Mol. Wt.: 1390.79

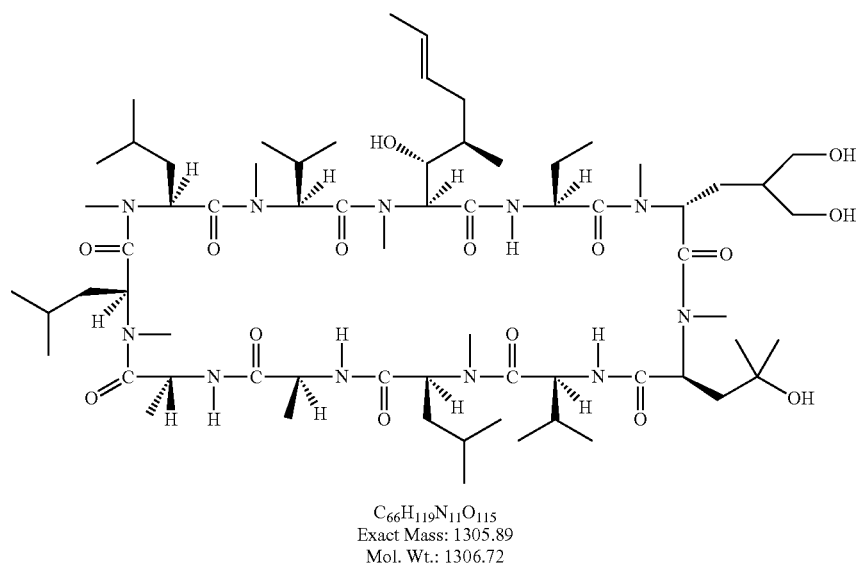

$C_{66}H_{119}N_{11}O_{115}$
Exact Mass: 1305.89
Mol. Wt.: 1306.72

To a suspension [(R)-3-ethoxy-2-(ethoxycarbonyl)-3-oxopropyl)-Sar]-3-[(γ-hydroxy)-N-MeLeu]-4-cyclosporin (150 mg, 0.11 mmol) and lithium chloride (580 mg, 13.81 mmol) in methanol (50 ml) was added sodium borohydride (1.20 g, 31.75 mmol) in portions. The mixture was stirred overnight at room temperature. Most of solvent was evaporated under reduced pressure. Dichloromethane (100 ml) and water (50 ml) were added and separated. The dichloromethane layer was washed with brine, dried over Magnesium sulfate and evaporated under reduced pressure. The residue was purified by chromatography (dichloromethane/methanol=97/3) to give product. [Molecular formula: $C_{66}H_{119}N_{11}O_{15}$; Exact Mass: 1305.89; MS (m/z): 1306.48 (M+1)$^+$; TLC Rf: 0.22 (dichloromethane/methanol=9/1); HPLC RT: 10.65 min (C8 reverse phase column: 250 mm; acetonitrile/water (0.05% TFA); operation temperature: 64° C.; Detector: 210 nm)].

Reference Example 1

[α-Carboxy-Sar]-3-cyclosporin

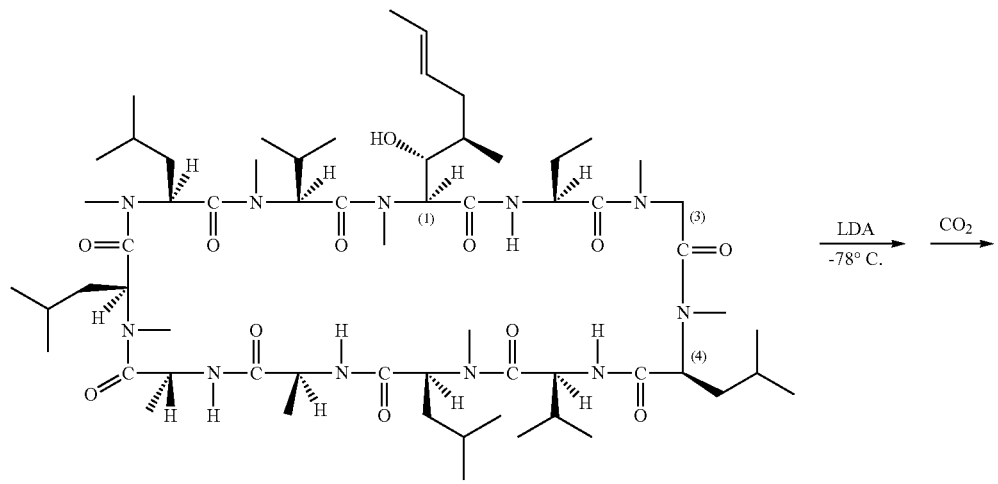

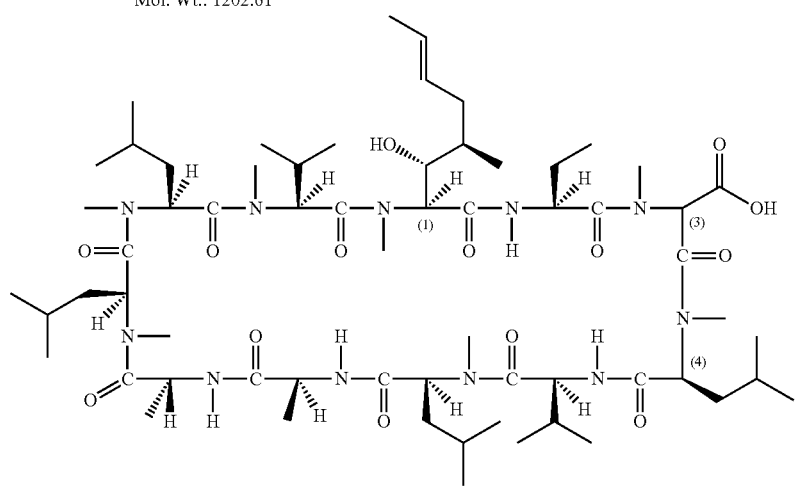

n-Butyllithium (2.87 M, 27 mmol, 9.4 ml, 10 eq) was added to a solution of diisopropylamine (3.8 ml, 27 mmol, 10 eq) in tetrahydrofuran (80 ml) at −78° C. under nitrogen. After the reaction mixture was stirred for an hour, a solution of cyclosporine A (3.2 g, 2.66 mmol) in tetrahydrofuran (15 ml) was added over 10 min. The stirring was continued at −78° C. for 2 hours. Carbon dioxide gas was bubbled through the reaction mixture for 20-25 minutes and stirred at −78° C. for another hour. Then the cooling bath was removed and the reaction mixture was allowed to warm up to 0° C. slowly. Most of tetrahydrofuran was removed under vacuum at room temperature. The residue was quenched by the addition of saturated citric acid solution and the pH of the mixture was adjusted to around 7-8. The unreacted cyclosporin was extracted with ether (40 ml×2). The PH of the aqueous layer was adjusted to 3~4 with 1 N hydrochloric acid and the precipitated oil was extracted with ethyl acetate (100 ml). The aqueous layer was extracted with ethyl acetate (100 ml×3). The combined ethyl acetate layers were washed with brine, dried over magnesium sulfate and evaporated under reduced pressure to give semi-solid product (2.61 g, yield: 78%) [Molecular Formula: $C_{63}H_{111}N_{11}O_{14}$; Exact Mass: 1245.83; MS (m/z): 1246.7 (M+1)⁻, 1268.7 (M+Na)⁺].

[α-Carboxy-Sar]-3-cyclosporin was synthesized according to a procedure described by Seebach D, et al., 1993, *Helv Chim Acta*, 76, 1564-1590.

Reference Example 2

[α-Methylene-Sar]-3-cyclosporin

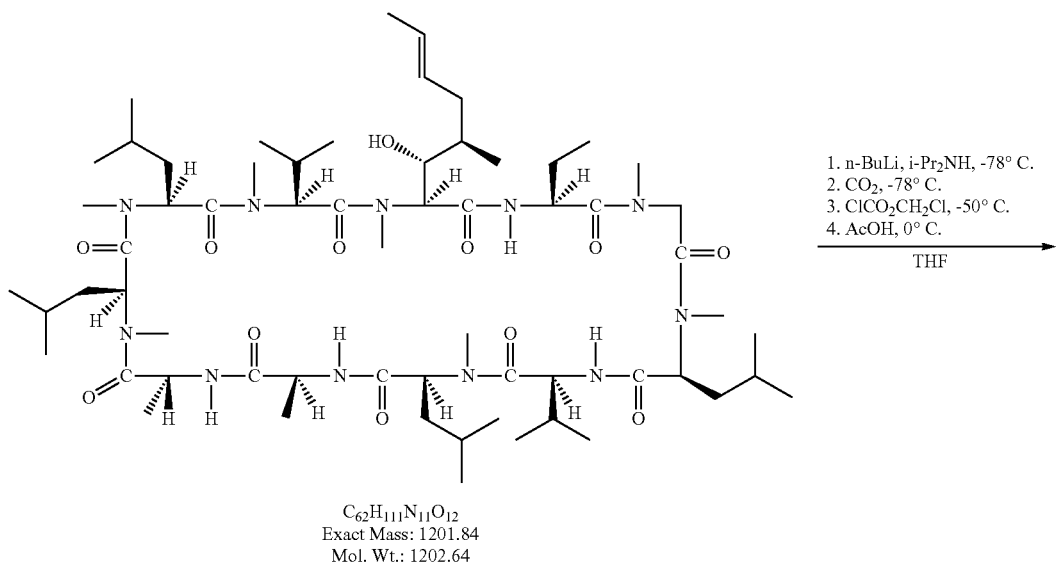

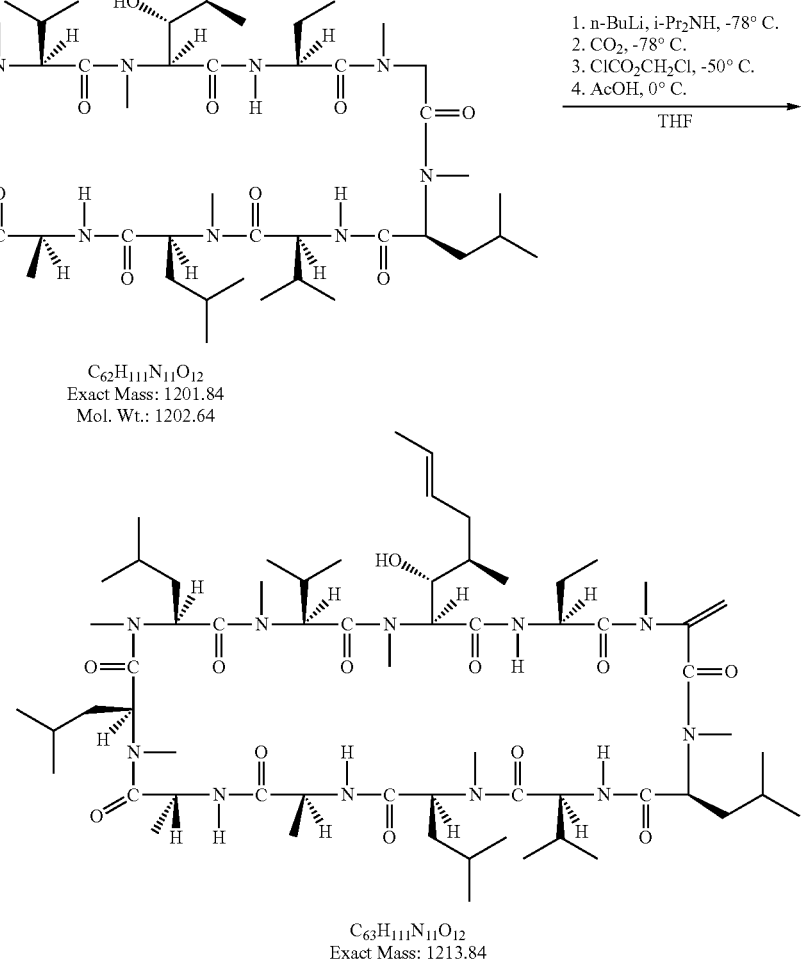

[α-Methylene-Sar]-3-cyclosporin can also be prepared using a method analogous to the procedure described in WO2012/051194A1.

Reference Example 3

Synthesis of [N-MeVal]-4-cyclosporin (SDZ-220-384)

[N-MeVal]-4-Cyclosporin (SDZ 220-384) was prepared according to procedures described by Papageorgiou C, et al., 1994, *Bioorg & Med Chem Lett*, 4, 267-272 and its key cylosporine ring-opening between position 3 and 4 cited as reference 14: Su Z and Wenger R, Unpublished results; Papageorgiou C, et al., 1994, *J. Med. Chem.*, 37, 3674-3676 and its key cylosporine ring-opening between position 3 and 4 cited as reference 11: Su Z and Wenger R, Unpublished results.

Cyclosporin A-acetate

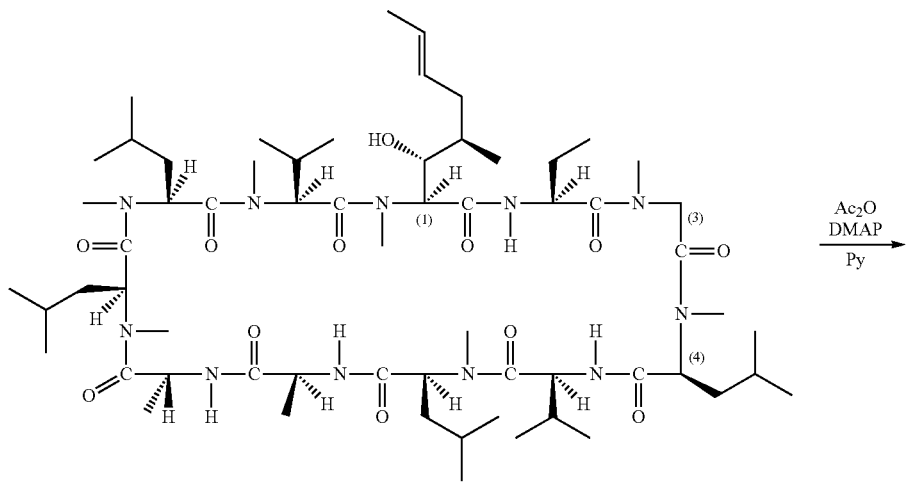

$C_{62}H_{111}N_{11}O_{12}$
Exact Mass: 1201.84
Mol. Wt.: 1202.61

Cyclosporin A/CsA 1

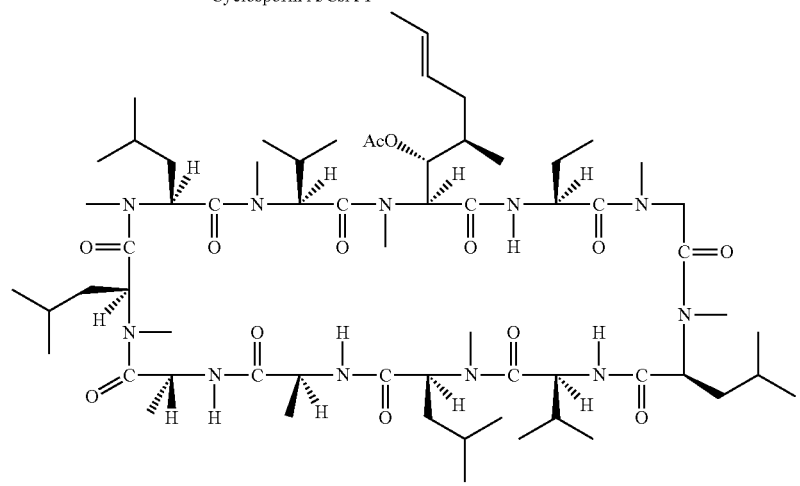

$C_{64}H_{113}N_{11}O_{13}$
Exact Mass: 1243.85
Mol. Wt.: 1244.65

2

To a solution of cyclosporin A (1) (12.00 g, 19.98 mmol) in acetic anhydride (MW: 102.09, d 1.082, 40 ml) were added pyridine (MW: 79.01, d 0.978, 40 ml) and 4-N,N-dimethylaminopyridine (MW: 122.17, 0.40 g). This mixture was stirred for overnight at room temperature, and then the mixture was diluted with 600 ml of ethyl acetate. The mixture was washed with brine, saturated ammonium chloride solution and 15% of sodium bicarbonate solution. The organic phase was dried over sodium sulphate, filtered and evaporated under the reduced pressure. Then all of pyridine was azeotropically evaporated out under the reduced pressure by adding toluene to the mixture to give a pale yellow solid residue, which was purified by flash chromatography on a silica gel column (100-200 mesh) with eluent of ethyl acetate/hexane (1/3) to give the 11.80 g (9.48 mmol, 95%) of cyclosporin A-acetate (2).

MeLeuValMeLeuAlaDAlaMeLeuMeLeuMe-
ValMeBmt(OAc)AbuSar-Ome

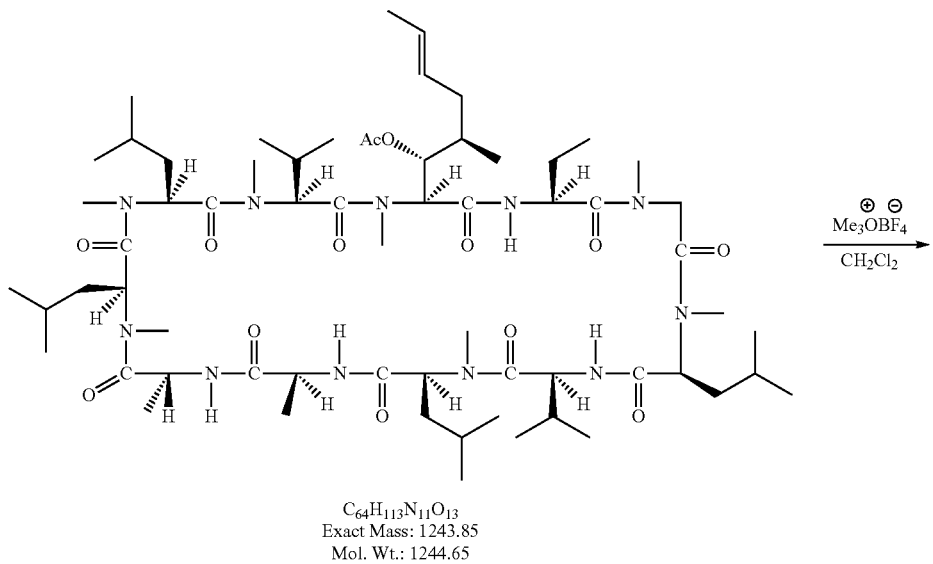

$C_{64}H_{113}N_{11}O_{13}$
Exact Mass: 1243.85
Mol. Wt.: 1244.65

2

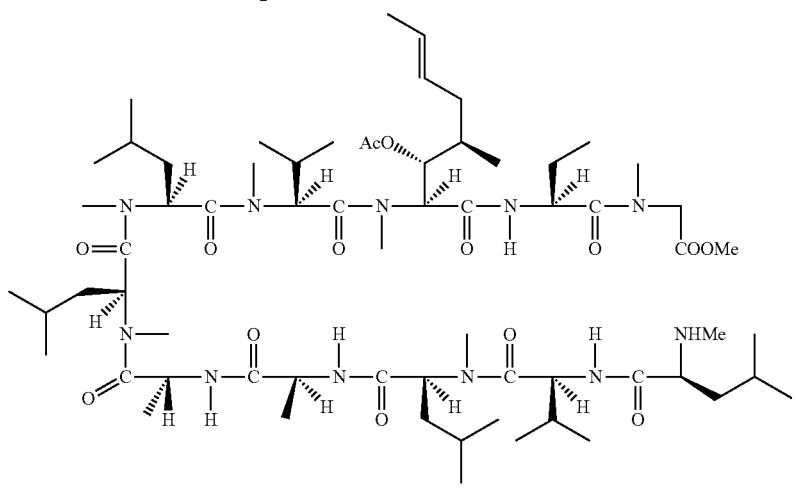

$C_{65}H_{117}N_{11}O_{14}$
Exact Mass: 1275.88
Mol. Wt.: 1276.69

3

To a suspension of trimethyloxonium-fluoroborate (MW: 147.91, 2.96 g, 20 mmol, 2.50 equiv.) in dichloromethane (80 ml) was added cyclosporine A-acetate (2) (10.00 g, 8.00 mmol). The suspension was stirred for 18 hours at room temperature, and then a solution of sodium methoxide (9.90 mmol) in methanol (40 ml) was added. After the mixture was stirred for another half hour, 2 N solution of sulfuric acid in methanol (40 ml) was added. The mixture was stirred for 15-30 minutes at room temperature and neutralized with 15% potassium bicarbonate solution. Then the mixture was extracted twice with 700 ml of ethyl acetate. The combined organic layers were washed with brine, dried over sodium sulphate and evaporated under reduced pressure. The residue was purified by flash chromatography on a silica column (100-200 mesh) with eluent of methanol/methyl t-butyl ether to give the 7.15 g (5.60 mmol, 70%) of linear undecapeptide peptide (3).

Phenylthiourea-MeLeuValMeLeuAlaDAlaMeLeu-
MeLeuMeValMeBmt(OAc)AbuSar-Ome

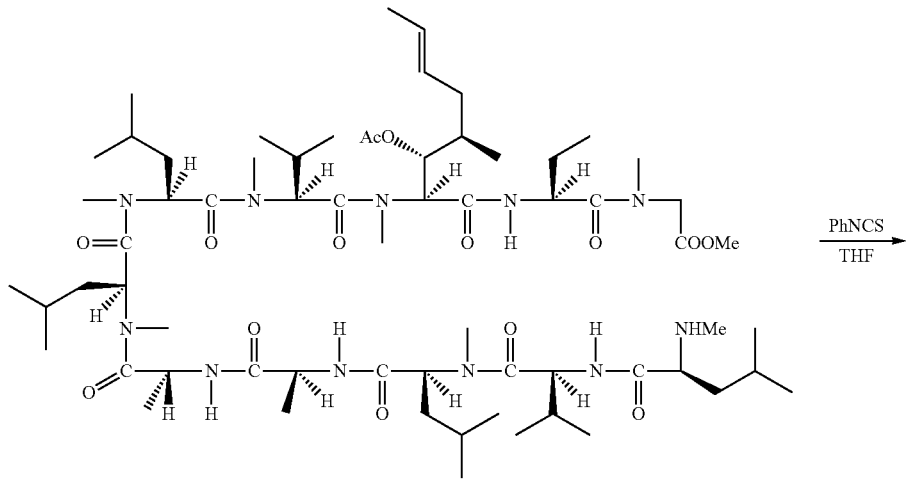

C₆₅H₁₁₇N₁₁O₁₄
Exact Mass: 1275.88
Mol. Wt.: 1276.69

3

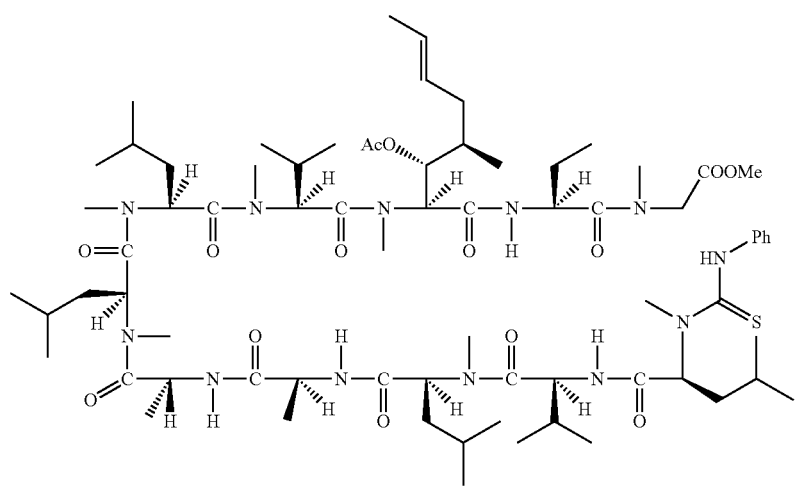

C₇₂H₁₂₂N₁₂O₁₄S
Exact Mass: 1410.89
Mol. Wt.: 1411.88

4

To a solution of linear undecapeptide peptide (3) (7.00 g, 5.50 mmol) in tetrahydrofuran (80 ml) was added phenyl isothiocyanate (MW: 135.19, d 1.130, 0.86 ml, 7.15 mmol, 1.30 equiv.). The mixture was stirred for 3 hours at room temperature and evaporated under reduced pressure. The residue was purified by flash chromatography on a silica gel column (100-200 mesh) with eluent of acetone in hexane (1/5) to give the 6.99 g (4.95 mmol, 90%) of linear phenyl-thiourea undecapeptide (4) [Exact Mass: 1410.89; MS m/z: 1433.88 (M+Na)⁺].

ValMeLeuAlaDAlaMeLeuMeLeuMe-
ValMeBmt(OAc)AbuSar-Ome

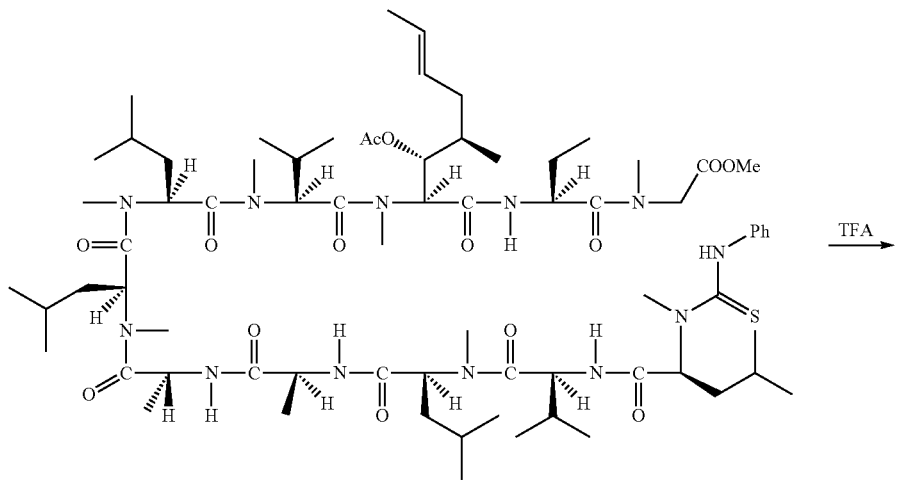

C₇₂H₁₂₂N₁₂O₁₄S
Exact Mass: 1410.89
Mol. Wt.: 1411.88

4

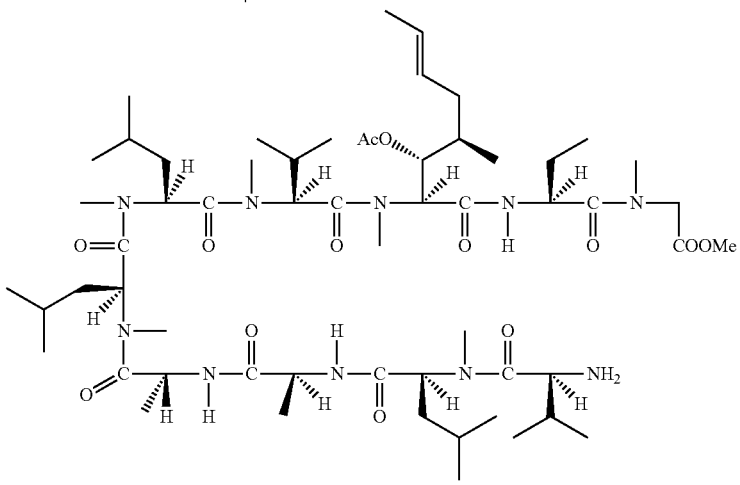

C₅₈H₁₀₄N₁₀O₁₃
Exact Mass: 1148.78
Mol. Wt.: 1149.51

5

To a solution of linear phenylthiourea undecapeptide (4) (6.80 g, 4.82 mmol) in toluene (300 ml) was added trifluoroacetic acid (MW: 114.02, d 1.480, 8.00 ml) at room temperature. The mixture was stirred for 1.5 to 2 hours and quenched by a slurry of sodium bicarbonate in water. Then the mixture was separated and the water phase was extracted with toluene (100 ml) and ethyl acetate (100 ml) subsequently. The combined organic layers were dried over sodium sulphate and evaporated under reduced pressure. The residue was purified by flash chromatography on a silica column (100-200 mesh) with eluent of acetone/hexane (3/1) to give the 3.88 g (3.37 mmol, 70%) of linear decapeptide peptide (5) [Exact Mass: 1148.78; MS m/z: 1149.78 $(M+1)^+$].

This Edman degradation was carried according to the similar method described by Edman P, et al, 1967, *Eur. J. Biochem.*, 1, 80.

BocMeValValMeLeuAlaDAlaMeLeuMeLeuMe-
ValMeBmt(OAc)AbuSar-Ome

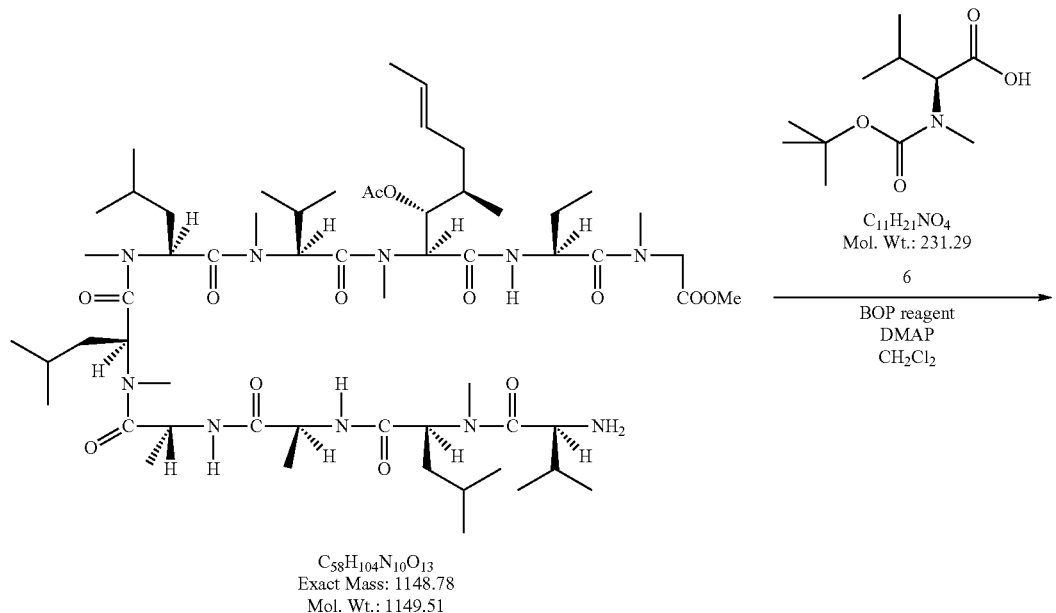

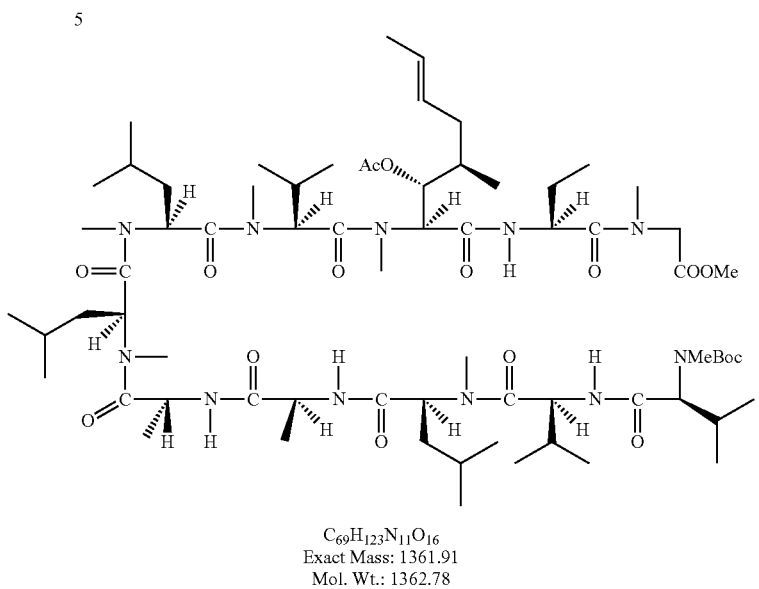

To a solution of linear decapeptide peptide (5) (3.80 g, 3.30 mmol) in dichloromethane (150 ml) were added Boc-MeVal (6) (MW: 231.29, 0.92 g, 3.96 mmol, 1.2 equiv.), 1-propanephosphonic acid cyclic anhydride (MW: 318.18, 2.10 ml, 50 wt. % solution in ethyl acetate) and triethylamine (MW: 101.19, d 0.726, 0.46 ml, 3.30 mmol) at 0° C. The resulting mixture was stirred at room temperature for 5 hours. Then the mixture was washed with brine. The aqueous layer was extracted with ethyl acetate (100 ml). The combined organic layers were dried over sodium sulphate. Removal of the solvent under reduced pressure gave the residue, which was purified by flash chromatography on a silica column (100-200 mesh) with eluent of acetone/hexane (1/2.5) to give the 4.05 g (2.97 mmol, 90%) of linear Boc-N-MeVal-decapeptide peptide (7) [Exact Mass: 1361.91; MS m/z: 1384.91 (M+Na)$^+$].

BocMeValValMeLeuAlaDAlaMeLeuMeLeuMe-
ValMeBmt(OAc)AbuSar-OH

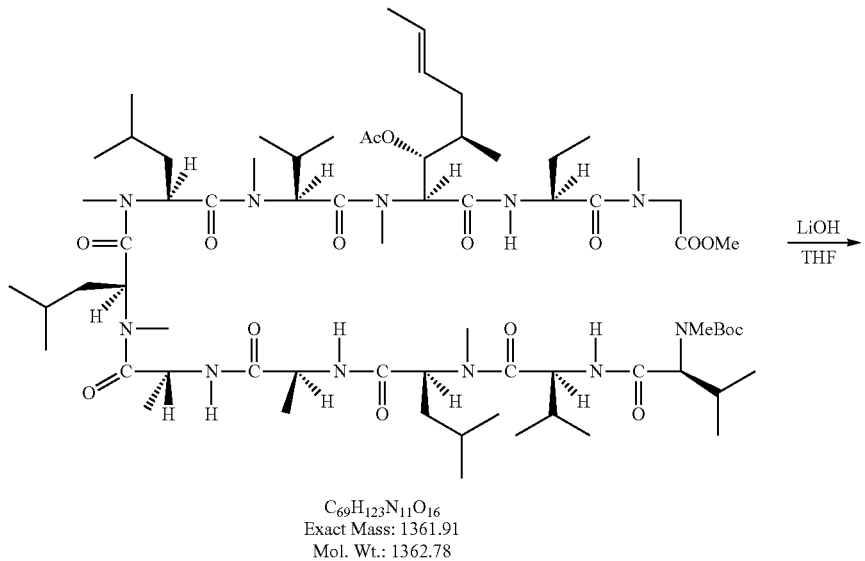

C₆₉H₁₂₃N₁₁O₁₆
Exact Mass: 1361.91
Mol. Wt.: 1362.78

7

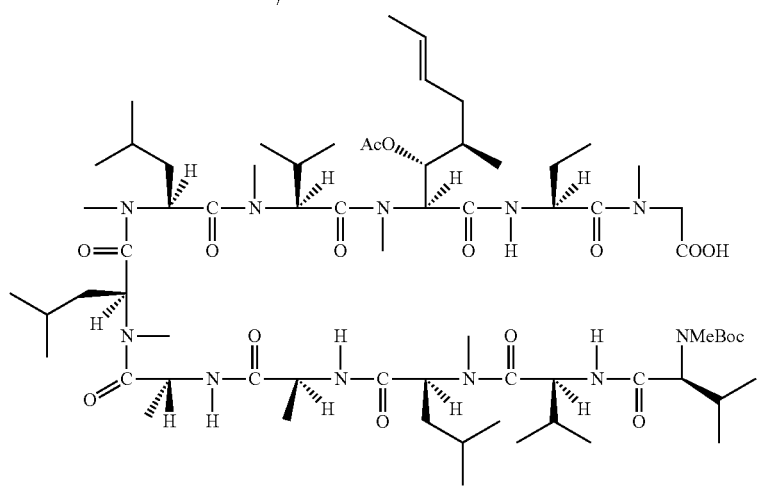

C₆₈H₁₂₁N₁₁O₁₆
Exact Mass: 1347.9
Mol. Wt.: 1348.75

8

To a solution of linear [Boc-N-MeVal]-4-decapeptide peptide (7) (4.00 g, 2.94 mmol) in ethyl alcohol (150 ml) at 0° C. was added 0.5 N sodium hydroxide solution (7.1 ml, 1.20 equiv.). The mixture was stirred and kept at 0° C. for 16 hours. Then the PH of the mixture was adjusted to around 3 by adding 0.5 N hydrochloric acid. Most of solvent was evaporated under the reduced pressure and the residue was dissolved in 200 ml of ethyl acetate. The mixture was washed with a pH 3 buffer, dried over sodium sulphate, filtered and evaporated under the reduced pressure. The residue was purified by flash chromatography on a silica column (100-200 mesh) with eluent of methanol/ethyl acetate (1/8) to yield 2.55 g (1.89 mmol, 64.3%) of the free acid (8).

MeValValMeLeuAlaDAlaMeLeuMeLeuMe-
ValMeBmt(OAc)AbuSar-OH

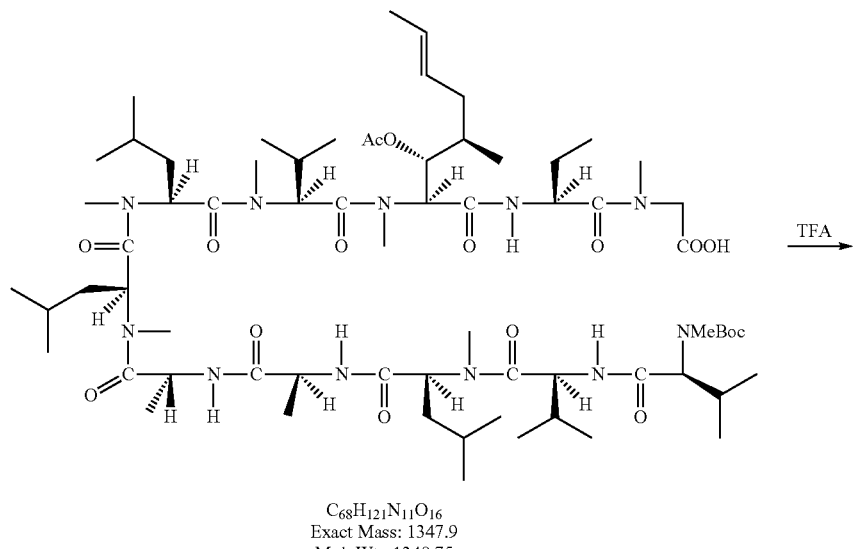

$C_{68}H_{121}N_{11}O_{16}$
Exact Mass: 1347.9
Mol. Wt.: 1348.75

8

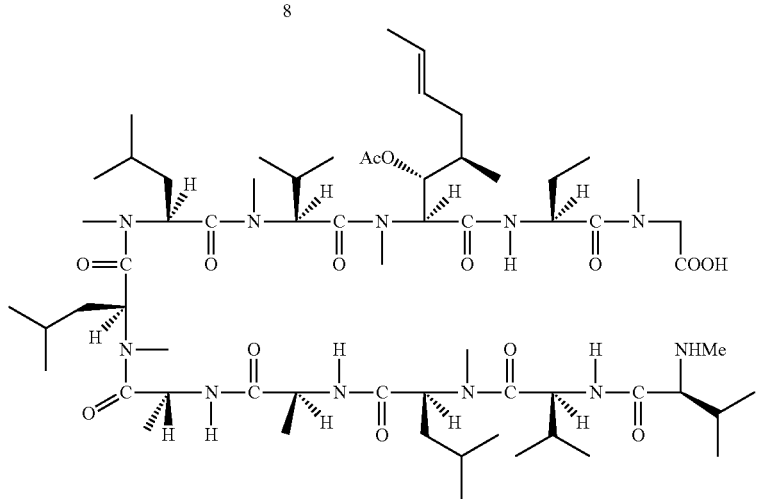

$C_{63}H_{113}N_{11}O_{14}$
Exact Mass: 1247.85
Mol. Wt.: 1248.64

9

To a solution of free acid (8) (2.55 g, 1.89 mmol) in dichloromethane (25 ml) was slowly added 5 ml of trifluoroacetic acid (MW: 114.02, d 1.480) at 0° C. The solution was stirred at room for 2 hours. Then ethyl acetate (300 ml) was added and the solvent was removed under reduced pressure. Another ethyl acetate (300 ml) was added and the solvent was removed under reduced pressure again. The residue was purified by flash chromatography on a silica gel column (100-200 mesh) with eluent of methanol/acetone (1/3) to give the 2.01 g (1.61 mmol, 85%) of linear [N-Me-Val]-4-decapeptide peptide free acid (9) [Exact Mass: 1247.85; MS m/z: 1248.85 (M+1)⁻].

[N-MeVal]-4-Cyclosporin acetate

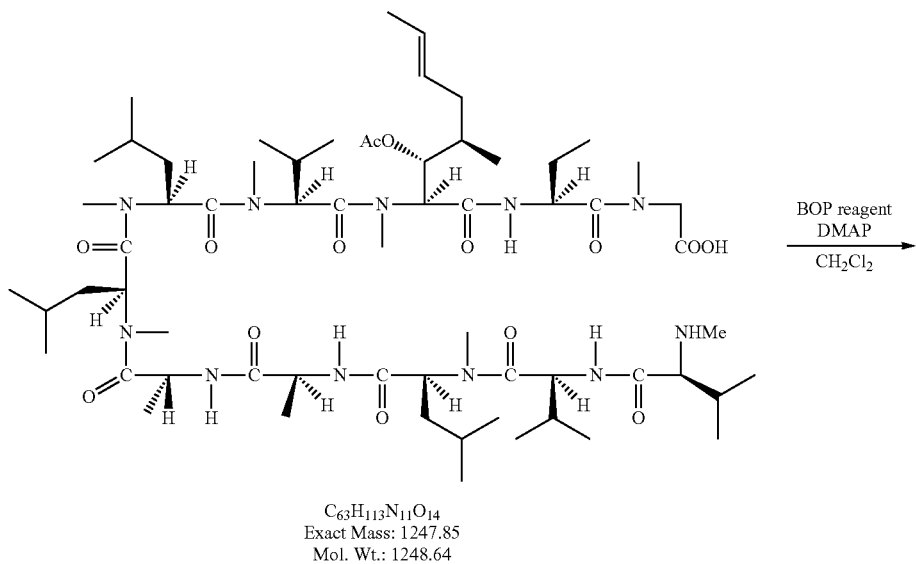

$C_{63}H_{113}N_{11}O_{14}$
Exact Mass: 1247.85
Mol. Wt.: 1248.64

9

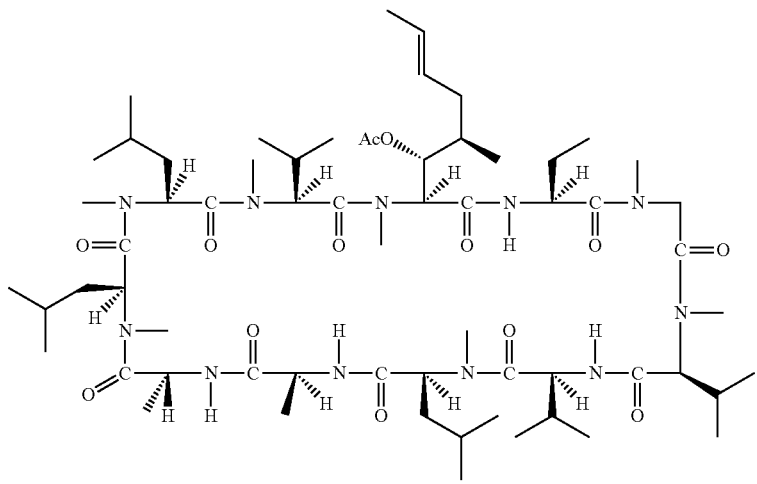

$C_{63}H_{111}N_{11}O_{13}$
Exact Mass: 1229.84
Mol. Wt.: 1230.62

10

To a solution of linear [N-MeVal]-4-decapeptide peptide free acid (9) (1.03 g, 0.83 mmol) in dichloromethane (250 ml) were added 1-propanephosphonic acid cyclic anhydride (MW: 318.18, 0.53 ml, 50 wt. % solution in ethyl acetate), 2,4,6-collidine (MW: 121.18, d 0.917, 0.11 ml, 0.83 mmol)) at 0° C. The mixture was stirred at room temperature for 24 hours. Then the mixture was passed through a thin layer of silica gel and washed twice by 40 ml of ethyl acetate. The collected organic solution was evaporated under the reduced pressure. The residue was purified by flash chromatography on a silica gel column (230-400 mesh) with eluent of methanol/acetone (1/6) to give the 611 mg (0.50 mmol, 60%) of (N-Methyl-Val)-4-Cyclosporin acetate (10) [Exact Mass: 1229.84; MS m/z: 1252.82 (M+Na)$^+$].

[N-MeVal]-4-Cyclosporin

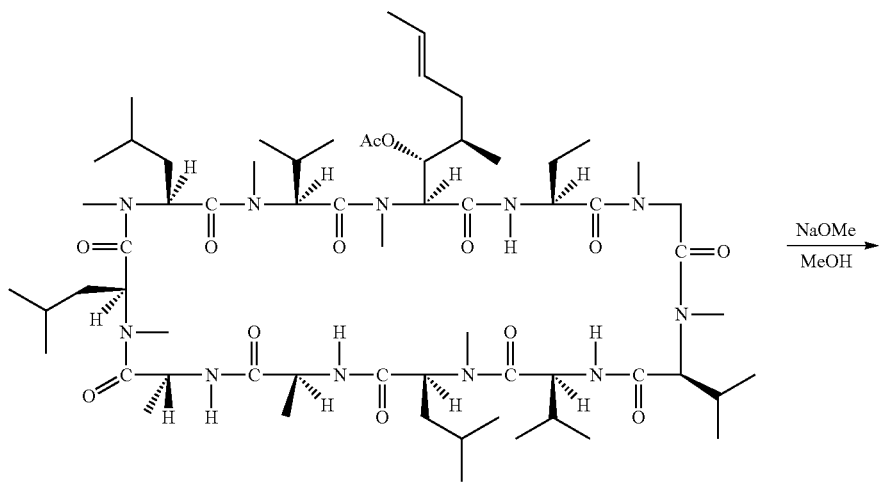

$C_{63}H_{111}N_{11}O_{13}$
Exact Mass: 1229.84
Mol. Wt.: 1230.62

10

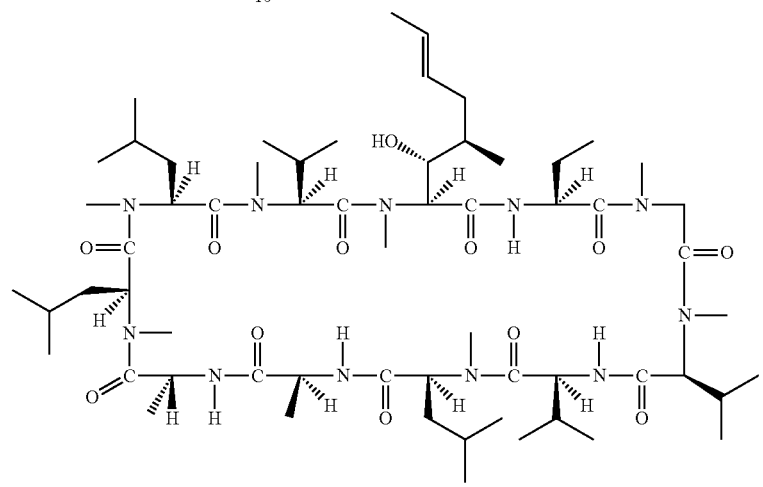

$C_{61}H_{109}N_{11}O_{12}$
Exact Mass: 1187.83
Mol. Wt.: 1188.58

N-MeVal-4-cyclosporin
SDZ 220-384

11

To a solution of [N-MeVal]-4-Cyclosporin acetate (10) (0.60 g, 0.49 mmol) in methanol (40 ml) was added a solution of sodium methoxide in methanol (0.5 M, 1.9 ml, 2.0 equiv.). The mixture was stirred for 0.5 hour at 0° C. and 24 hours at room temperature. The PH of the mixture was adjusted to around 6 by adding 0.5 N hydrochloric acid. After the solvent was evaporated under reduced pressure, the residue was dissolved in 200 ml of ethyl acetate. The organic solution was washed by aqueous sodium bicarbonate and brine, dried over sodium sulphate and filtered. After removal of solvent, the residue was purified by flash chromatography on a silica gel column (230-400 mesh) with eluent of acetone/hexane (1/2) to give the 406 mg (0.34 mmol, 70%) of [N-MeVal]-4-Cyclosporin (11) [Exact Mass: 1187.83;84; MS m/z: 1210.81 (M+Na].

Reference Example 4

[N-MeIle]-4-Cyclosporin (NIM-811) was prepared according to the procedure used for the synthesis of (N-Me-Val)-4-cyclosporin (SDZ 220-384).

Reference Example 5

[N-MeThr]-4-Cyclosporin can be prepared according to the procedure used for the synthesis of (N-MeVal)-4-cyclosporin (SDZ 220-384).

Reference Example 6

The side chain intermediates were synthesized according to procedures described by Urquhart G G, 1994, *Org Synth*, Coll. Vol III, 363

2-Morpholinoethanethiol

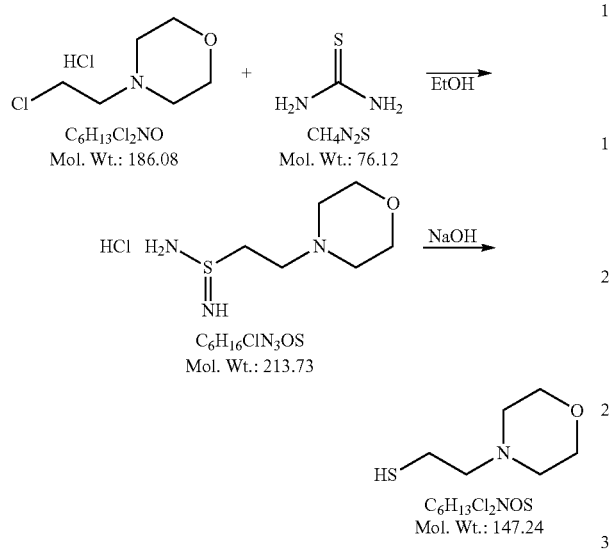

A mixture of 4-(2-chloroethyl)morpholine (7.00 g, 37 mmol) and thiourea (2.90 g, 38 mmol) in 95% ethanol (55 ml) was heated to reflux for 24 hours. A solution of sodium hydroxide (3.40 g, 85 mmol) in water (20 ml) was added, and the mixture was continued to reflux for another 3 hours. After cooled to room temperature, the mixture was evaporated under reduced pressure. The residue was mixed with benzene. The benzene layer was washed with brine, dried over magnesium sulfate and evaporated to provide 3.80 g of crude product, which was used for the addition reaction.

2-(N-Piperidinyl)ethanethiol

The mixture of 1-(2-chloroethyl)piperidine hydrochloride (7.00 g, 38 mmol) and thiourea (4.60 g, 61 mmol) in 95% ethanol (30 ml) was heated to reflux for 24 hours. A solution of sodium hydroxide (2.40 g) in water (20 ml) was added. The mixture was continued to reflux for another 3 hours. After cooled to room temperature, the mixture was evaporated under reduced pressure. The residue was mixed with ether. The organic layer was washed with brine, dried over magnesium sulfate and evaporated under reduced pressure to give 3.20 g of crude product, which was used for the addition reaction without purification.

2-(N-Pyrrolidinyl)ethanethiol

The mixture of 1-(2-chloroethyl)piperidine hydrochloride (7.0 g, 41 mmol) and thiourea (3.20 g, 40 mmol) in 95% ethanol (30 ml) was heated to reflux for 24 hours. A solution of sodium hydroxide (3.40 g, 85 mmol) in water (20 ml) was added. The mixture was continued to reflux for another 3 hours. After cooled to room temperature, the mixture was evaporated under reduced pressure. The residue was mixed with benzene. The organic layer was washed with brine, dried over magnesium sulfate and evaporated under reduced pressure to give 3.80 g of crude product, which was used for the addition reaction without purification.

3-(N-Pyrrolidinyl)propanethiol

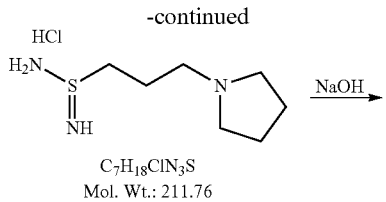

To a suspension of 1-bromoro-3-chloropropane (30.00 g, 191 mmol) and potassium carbonate (17.00 g, 123 mmol) in dichloromethane (160 ml) was added pyrrolidine (3.50 g, 49 mmol) portions. The mixture was stirred at room temperature overnight. Then the mixture was filtered and evaporated under reduced pressure. The residue was purified by chromatography (ethyl acetate/methanol=95/5) to give 6.00 g of product.

A mixture of 1-(3-chloropropyl)pyrrolidine (3.4 g, 23 mmol) and thiourea (1.8 g, 23 mmol) in 95% ethanol (55 ml) was heated to reflux for 24 hours. A solution of sodium hydroxide (1.20 g, 30 mmol) in water (10 ml) was added, and the mixture was continued to reflux for another 3 hours. After cooled to room temperature, the mixture was evaporated under reduced pressure. The residue was mixed with benzene. The organic layer was washed with brine, dried over magnesium sulfate and evaporated under reduced pressure to give 1.80 g of crude product, which was used for the addition reaction.

3-(N-Piperidinyl)propanethiol

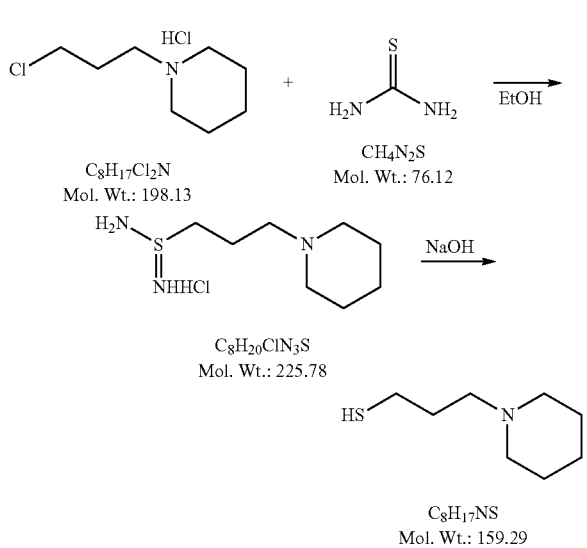

The mixture of 1-(3-chloropropyl)piperidine hydrochloride (7.50 g, 38 mmol) and thiourea (4.60 g, 61 mmol) in 95% ethanol (30 ml) was heated to reflux for 24 hours. A solution of sodium hydroxide (2.40 g) in water (20 ml) was added. The mixture was continued to reflux for another 3 hours. After cooled to room temperature, the mixture was evaporated under reduced pressure. The residue was mixed with ether. The organic layer was washed with brine, dried over magnesium sulfate and evaporated under reduced pressure to give 3.50 g of crude product, which was used for the addition reaction without purification.

3-Morpholinopropanethiol

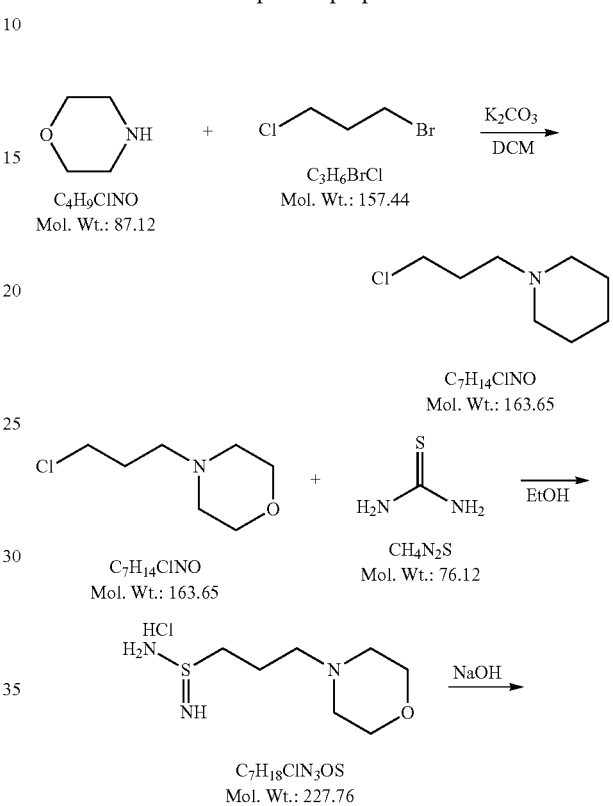

To a suspension of 1-bromoro-3-chloropropane (30.00 g, 191 mmol) and potassium carbonate (14.00 g, 101 mmol) in dichloromethane (160 ml) was added morpholine (4.00 g, 46 mmol) in portions. Then the mixture was stirred at room temperature overnight. The mixture was filtered and evaporated under reduced pressure. The residue was purified by chromatography (ethyl acetate) to give 5.60 g of product.

A mixture of 1-(3-chloropropyl)morpholine (4.20 g, 25.76 mmol) and thiourea (2.00 g, 26.27 mmol) in 95% ethanol (55 ml) was heated to reflux for 24 hours. A solution of sodium hydroxide (1.3 g, 32.50 mmol) in water (10 ml) was added, and the mixture was continued to reflux for another 3 hours. After cooled to room temperature, the mixture was evaporated under reduced pressure. The residue was mixed with benzene. The benzene layer was washed with brine, dried over magnesium sulfate and evaporated under reduced pressure to give 2.20 g of crude product, which was used for the addition reaction.

2-(4-Methyl-N-piperazinyl)ethanethiol

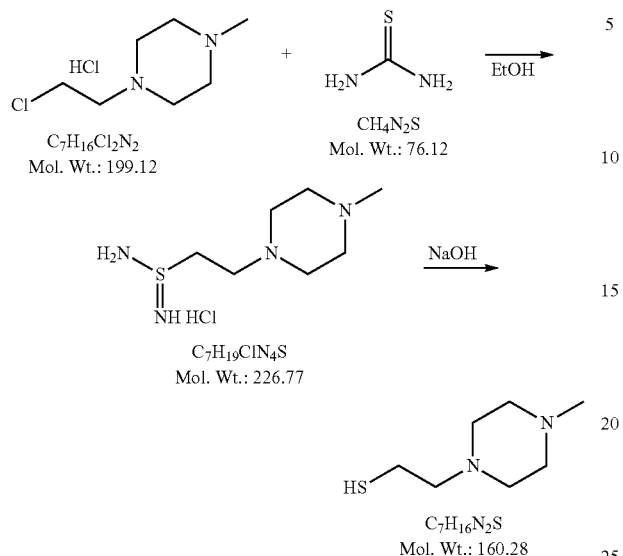

A mixture of 2-(4-methylpiperazino)ethyl chloride (8.00 g, 40 mmol) and thiourea (4.87 g, 64 mmol) in 95% ethanol (55 ml) was heated to reflux for 24 hours. A solution of sodium hydroxide (2.60 g) in water (20 ml) was added, and the mixture was continued to reflux for another 3 hours. After cooled to room temperature, the mixture was evaporated under reduced pressure. The residue was mixed with benzene. The benzene layer was washed with brine, dried magnesium sulfate and evaporated to provide 3.0 g of crude product, which was used for the addition reaction.

3-(4-Methyl-N-piperazinyl)propanethiol

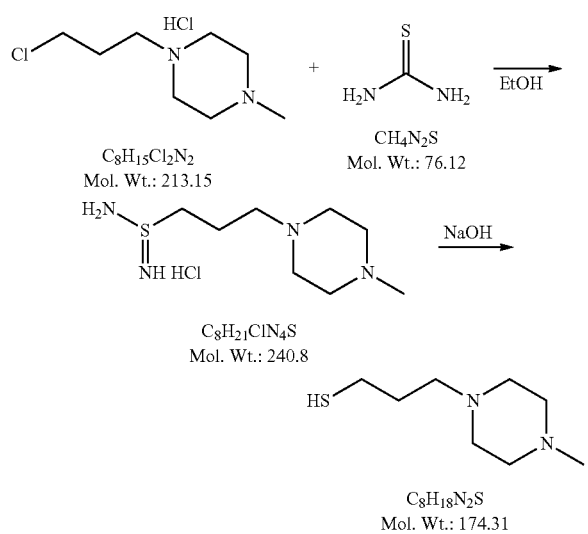

A mixture of 3-(4-methylpiperazino)propyl chloride (8.5 g, 40 mmol) and thiourea (4.87 g, 64 mmol) in 95% ethanol (70 ml) was heated to reflux for 24 hours. A solution of sodium hydroxide (2.6 g) in water (20 ml) was added, and the mixture was continued to reflux for another 3 hours. After cooled to room temperature, the mixture was evaporated under reduced pressure. The residue was mixed with ether. The organic layer was washed with brine, dried over magnesium sulfate and evaporated to provide 2.5 g of crude product, which was used for the addition reaction.

3-(N-Ethyl-N-isopropylamino)propanethiol

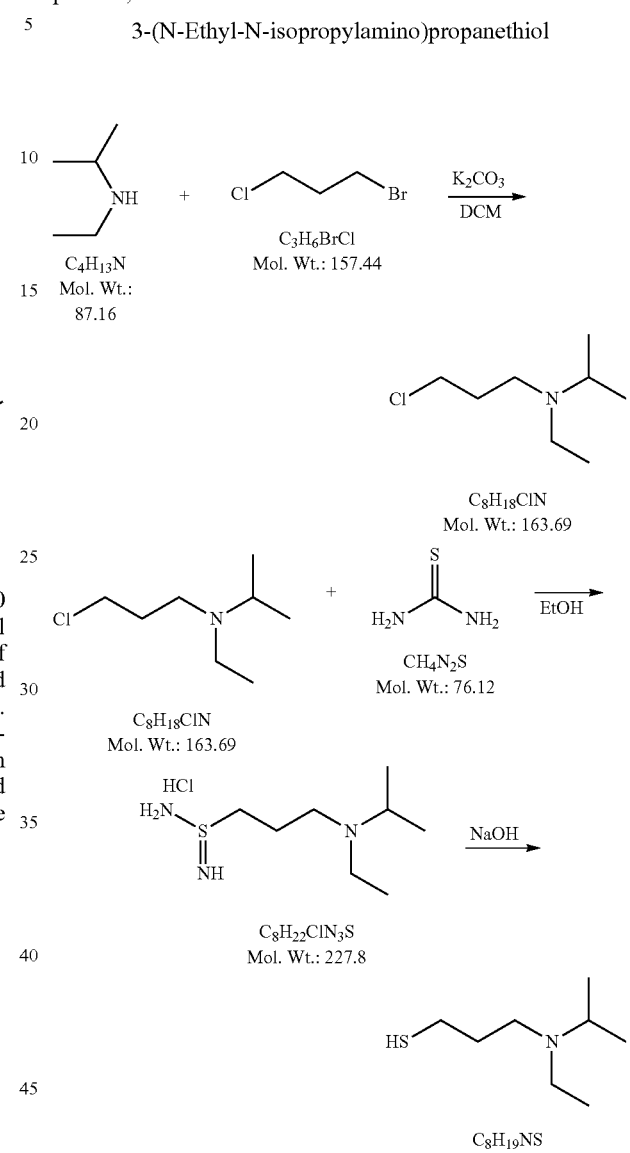

To a suspension of 1-bromoro-3-chloropropane (11.00 g, 70 mmol) and potassium carbonate (13.00 g, 94 mmol) in dichloromethane (100 ml) was added ethylisopropylamine (4.10 g, 47 mmol) in portions. The mixture was stirred at room temperature overnight. The mixture was filtered and concentrated under reduced pressure. The residue was purified by chromatography (ethyl acetate/methanol=95/5) to give 6.10 g of product.

A mixture of 3-chloropropylethylisopropylamiune (4.20 g, 25.66 mmol) and thiourea (2.00 g, 26.32 mmol) in 95% ethanol (55 ml) was heated to reflux for 24 hours. A solution of sodium hydroxide (1.30 g, 32.50 mmol) in water (10 ml) was added, and the mixture was continued to reflux for another 3 hours. After cooled to room temperature, the mixture was evaporated under reduced pressure. The residue was mixed with benzene. The benzene layer was washed with brine, dried over magnesium sulfate and evaporated under reduced pressure to give 1.20 g of crude product, which was used for the addition reaction.

3-Aminopropanethiol

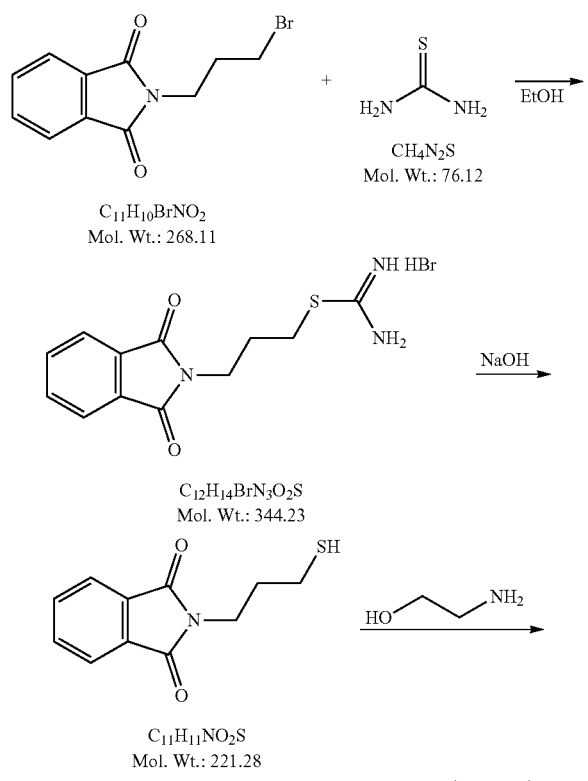

A mixture of N-(3-bromopropyl)phthalimide (20.00 g, 74.63 mmol) and thiourea (9.98 g, 131.34 mmol) in 95% ethanol (80 ml) was heated to reflux for 3 hours. A solution of sodium hydroxide (4.48 g, 111.94 mmol) in water (30 ml) was added, and the mixture was continued to reflux for another 3 hours. After cooled to room temperature, the mixture was evaporated under reduced pressure. The residue was mixed with ethyl acetate (50 ml) and brine (50 ml). The organic layer was separated and washed with brine, dried over magnesium sulfate and evaporated under reduced pressure. The residue was mixed with toluene (100 ml) and heated to reflux with removal of water azeotropically for two hours. After removal of toluene, the residue was purified by chromatography on silica gel with hexane and ethyl acetate as solvent to give 9.10 g of N-(3-mercaptopropyl)phthalimide. To a solution of N-(3-mercaptopropyl)phthalimide in methanol (50 ml) was added ethanolamine. The mixture was stirred and heated to reflux for two hours. After cooled to room temperature, the mixture was used for the addition reaction without further purification.

2-Mercaptoethylpiperazine

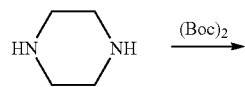

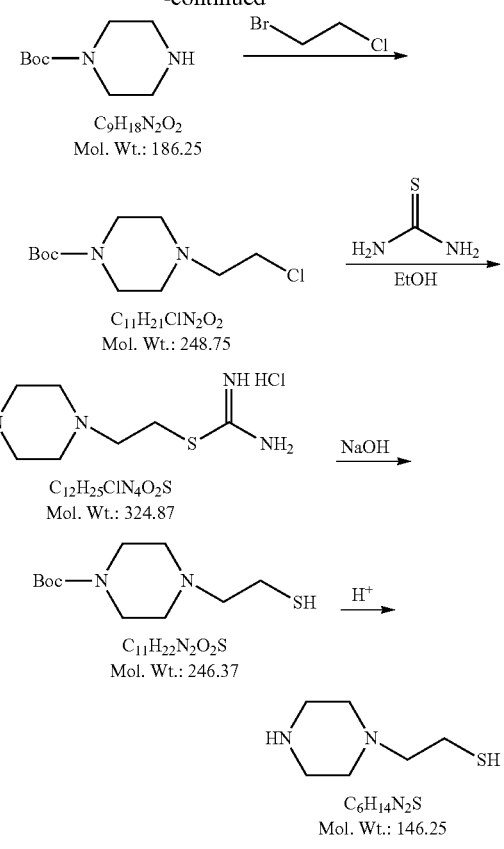

To a suspension of piperizaine (30.00 g, 348.27 mmol) and sodium carbonate (106 g, 348.27 mmol) in dichloromethane (200 ml) was added dropwise a solution of Di-tert-butyl dicarbonate (18.98 g, 87.07 mmol) in dichloromethane (30 ml) at room temperature for one hour. Then the mixture was stirred at room temperature overnight. The mixture was mixed with water (100 ml) and separated. The dichloromethane layer was dried over magnesium sulfate and evaporated under reduced pressure. The residue was dissolved in dichloromethane (150 ml). Sodium carbonate (15.55 g, 146.77 mmol) and 1-bromo-2-chloroethane (21.05 g, 146.77 mmol) were added. The mixture was stirred at room temperature for a weekend. The mixture was mixed with water (100 ml) and separated. The dichloromethane layer was dried over magnesium sulfate and evaporated under reduced pressure. The residue was purified by chromatography on silica gel using hexane and ethyl acetate as eluent to give 6.85 g of 1-Boc-4-(2-chloroethyl)piperazine.

To a solution of 1-Boc-4-(2-chloroethyl)piperazine (6.85 g, 27.62 mmol) in methanol (50 ml) was added thiourea (4.12 g, 55.24 mmol). The mixture was heated to reflux for 2 hours. A solution of sodium hydroxide (1.66 g, 41.43 mmol) in water (10 ml) was added, and the mixture was continued to reflux for another hour. Then most solvent was evaporated under reduced pressure. The residue was mixed with ethyl acetate (50 ml) and brine (30 ml) and separated. The ethyl acetate was dried over magnesium sulfate and evaporated under reduced pressure. The residue was dissolved in methanol (20 ml). 4 M hydrochloric acid in dioxane (10 ml) was added. The mixture was stirred at room temperature overnight and most of solvent was evaporated under reduced pressure. The residue was used for the addition reaction without further purification.

1-Boc-4-(3-mercaptopropanyl)piperazine

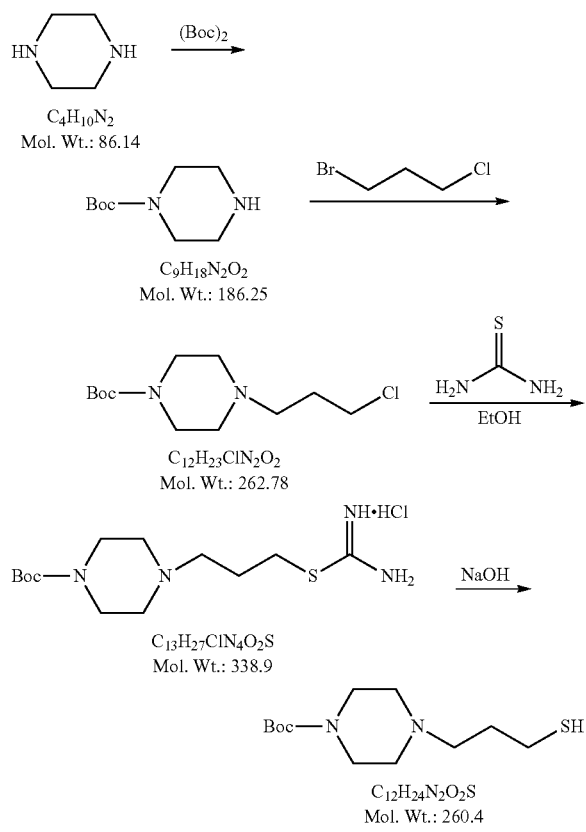

To a suspension of piperizaine (30.00 g, 348.27 mmol) and sodium carbonate (106 g, 348.27 mmol) in dichloromethane (200 ml) was added dropwise a solution of Di-tert-butyl dicarbonate (18.98 g, 87.07 mmol) in dichloromethane (30 ml) at room temperature for one hour. Then the mixture was stirred at room temperature overnight. The mixture was mixed with water (100 ml) and separated. The dichloromethane layer was dried over magnesium sulfate and evaporated under reduced pressure. The residue was dissolved in dichloromethane (100 ml). Sodium carbonate (15.44 g, 145.70 mmol) and 1-bromo-3-chloropropane (15.29 g, 97.13 mmol) were added. The mixture was stirred at room temperature overnight. The mixture was mixed with water (80 ml) and separated. The dichloromethane layer was dried over magnesium sulfate and evaporated under reduced pressure. The residue was purified by chromatography on silica gel using hexane and ethyl acetate as eluent to give 11.77 g of 1-Boc-4-(3-chloropropanyl)piperazine.

To a solution of 1-Boc-4-(3-chloropropanyl)piperazine (11.77 g, 44.90 mmol) in ethanol (100 ml) was added thiourea (6.82 g, 89.80 mmol). The mixture was heated to reflux for 4 hours. A solution of sodium hydroxide (2.69 g, 67.35 mmol) in water (40 ml) was added, and the mixture was continued to reflux for another 2 hours. Then most solvent was evaporated under reduced pressure. The residue was mixed with ethyl acetate (100 ml) and brine (50 ml) and separated. The ethyl acetate was dried over magnesium sulfate and evaporated under reduced pressure. The residue was purified by chromatography on silica gel using hexane and acetone as eluent to give 7.5 g of tert-butyl 4-N-Boc-1-(3-mercaptopropanyl)piperazine.

Examples 185-1836

Cyclosporin Derivatives

The following compounds can be prepared according to a method analogous to those described herein.

TABLE 1

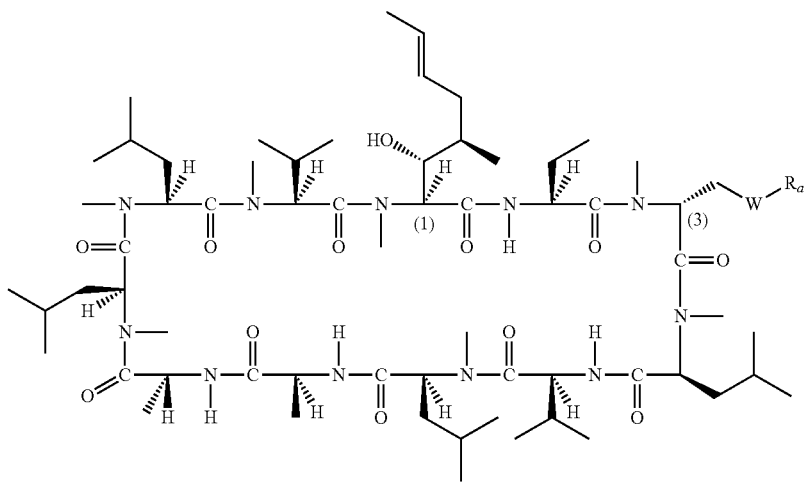

| Ex. No. | W | $R_a$ | Name |
|---|---|---|---|
| 185 | S | ⟩⟩⟩—CH₂—COOH | [(S)-(Carboxymethylthio)methyl-Sar]-3-cyclosporin |

TABLE 1-continued

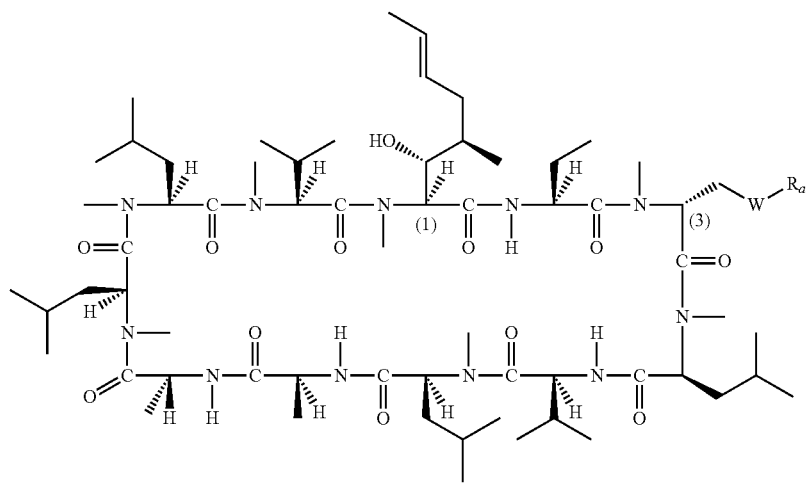

| Ex. No. | W | $R_a$ | Name |
|---|---|---|---|
| 186 | S | (CH₂C(O)OK) | [(S)-(Carboxymethylthio)methyl-Sar]-3-cyclosporin-potassium salt |
| 187 | S | (CH₂C(O)ONa) | [(S)-(Carboxymethylthio)methyl-Sar]-3-cyclosporin-sodium salt |
| 188 | S | (CH₂C(O)OEt) | [(S)-(Ethoxycarbonylmethylthio)methyl-Sar]-3-cyclosporin |
| 189 | S | (CH₂CH₂OH) | [(S)-(2-Hydroxyethylthio)methyl-Sar]-3-cyclosporin |
| 190 | S | (CH₂C(CH₃)₂OH) | [(S)-(2-Hydroxy-2-methylpropylthio)methyl-Sar]-3-cyclosporin |
| 191 | S | (CH₂CH₂NH-iPr) | [(S)-(2-(N-Isopropylamino)ethylthio)methyl-Sar]-3-cyclosporin |
| 192 | S | (CH₂CH₂N(CH₃)-iPr) | [(S)-(2-(N-Methyl-N-isopropylamino)ethylthio)methyl-Sar]-3-cyclosporin |
| 193 | S | (CH₂CH₂N(Et)-iPr) | [(S)-(2-(N-Ethyl-N-isopropylamino)ethylthio)methyl-Sar]-3-cyclosporin |
| 194 | S | (CH₂CH₂NH-iBu) | [(S)-(2-(N-Isobutylamino)ethylthio)methyl-Sar]-3-cyclosporin |

TABLE 1-continued

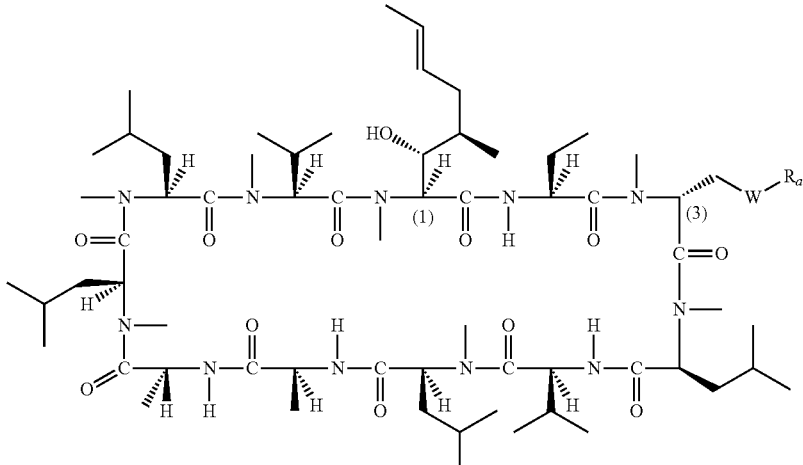

| Ex. No. | W | $R_a$ | Name |
|---|---|---|---|
| 195 | S | 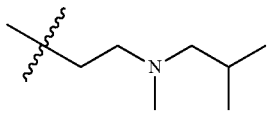 [SMILES: *CCN(C)CC(C)C] | [(S)-(2-(N-Methyl-N-isobutylamino)ethylthio)methyl-Sar]-3-cyclosporin |
| 196 | S | 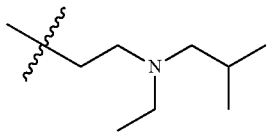 [SMILES: *CCN(CC)CC(C)C] | [(S)-(2-(N-Ethyl-N-isobutylamino)ethylthio)methyl-Sar]-3-cyclosporin |
| 197 | S | 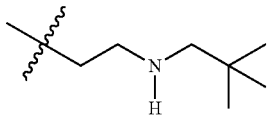 [SMILES: *CCNCC(C)(C)C] | [(S)-(2-(N-Neopentylamino)ethylthio)methyl-Sar]-3-cyclosporin |
| 198 | S | 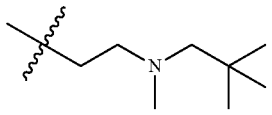 [SMILES: *CCN(C)CC(C)(C)C] | [(S)-(2-(N-Methyl-N-Neopentylamino)ethylthio)methyl-Sal]-3-cyclosporin |
| 199 | S | 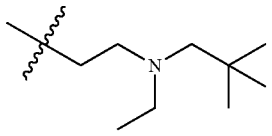 [SMILES: *CCN(CC)CC(C)(C)C] | [(S)-(2-(N-Ethyl-N-Neopentylamino)ethylthio)methyl-Sar]-3-cyclosporin |
| 200 | S | 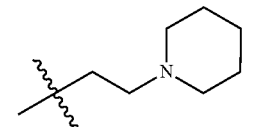 [SMILES: *CCN1CCCCC1] | [(S)-(2-(N-Piperidinyl)ethylthio)methyl-Sar]-3-cyclosporin |
| 201 | S | 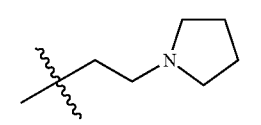 [SMILES: *CCN1CCCC1] | [(S)-(2-(N-Pyrrolidinyl)ethylthio)methyl-Sar]-3-cyclosporin |
| 202 | S | 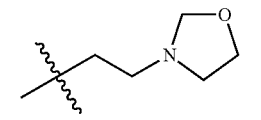 [SMILES: *CCN1CCOC1] | [(S)-(2-(N-Oxazolidinyl)ethylthio)methyl-Sar]-3-cyclosporin |

TABLE 1-continued

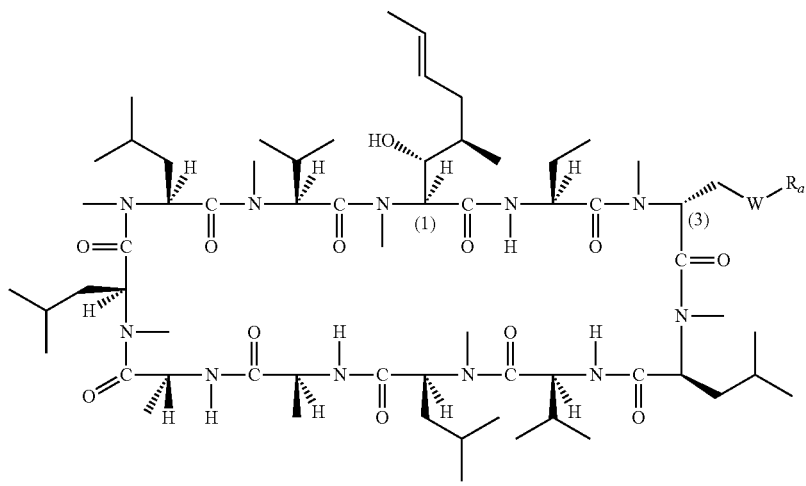

| Ex. No. | W | $R_a$ | Name |
|---|---|---|---|
| 203 | S | (propyl-morpholino) | [(S)-(2-(N-morpholino)ethylthio)methyl-Sar]-3-cyclosporin |
| 204 | S | (propyl-thiazolidinyl) | [(S)-(2-(N-Thiazolidinyl)ethylthio)methyl-Sar]-3-cyclosporin |
| 205 | S | (propyl-thiomorpholino) | [(S)-(2-(N-Thiomorpholino)ethylthio)methyl-Sar]-3-cyclosporin |
| 206 | S | (propyl-piperazinyl-H) | [(S)-(2-(N-Piperazinyl)ethylthio)methyl-Sar]-3-cyclosporin |
| 207 | S | (propyl-4-methylpiperazinyl) | [(S)-(2-(4-Methyl-N-piperazinyl)ethylthio)methyl-Sar]-3-cyclosporin |
| 208 | S | (propyl-4-ethylpiperazinyl) | [(S)-(2-(4-Ethyl-N-piperazinyl)ethylthio)methyl-Sar]-3-cyclosporin |
| 209 | S | (propyl-4-isopropylpiperazinyl) | [(S)-(2-(4-Isopropyl-N-piperazinyl)ethylthio)methyl-Sar]-3-cyclosporin |

TABLE 1-continued

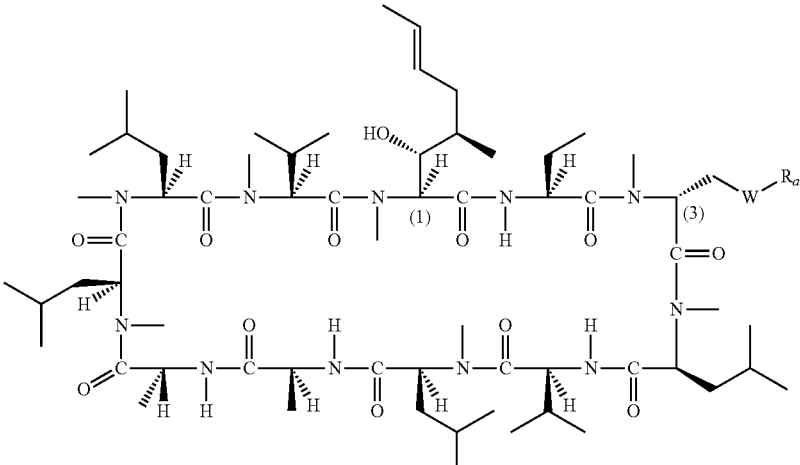

| Ex. No. | W | $R_a$ | Name |
|---|---|---|---|
| 210 | S |  | [(S)-(2-(4-Isobutyl-N-piperazinyl)ethylthio)methyl-Sar]-3-cyclosporin |
| 211 | S | 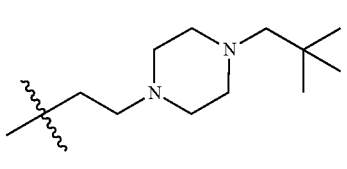 [SMILES: *CCN1CCN(CC(C)(C)C)CC1] | [(S)-(2-(4-Neopentyl-N-piperazinyl)ethylthio)methyl-Sar]-3-cyclosporin |
| 212 | S | 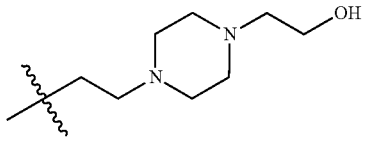 [SMILES: *CCN1CCN(CCO)CC1] | [(S)-(2-(4-(2-Hydroxyethyl)-N-piperazinyl)ethylthio)methyl-Sar]-3-cyclosporin |
| 213 | S |  | [(S)-(2-(4-(2-Hydroxy-2-methylpropyl)-N-piperazinyl)ethylthio)methyl-Sar]-3-cyclosporin |
| 214 | S |  | [(S)-(2-(4-(3-Hydroxy-3-methylbutyl)-N-piperazinyl)ethylthio)methyl-Sar]-3-cyclosporin |
| 215 | S |  | [(S)-(2-(4-(4-Hydroxy-4-methylpentyl)-N-piperazinyl)ethylthio)methyl-Sar]-3-cyclosporin |
| 216 | S | 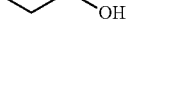 | [(S)-(2-Carboxyethylthio)methyl-Sar]-3-cyclosporin |

TABLE 1-continued

| Ex. No. | W | $R_a$ | Name |
|---|---|---|---|
| 217 | S | (CH2)2-C(=O)-ONa | [(S)-(2-Carboxyethylthio)methyl-Sar]-3-cyclosporin-sodium salt |
| 218 | S | (CH2)2-C(=O)-O-Et | [(S)-(2-(Ethoxycarbonyl)ethylthio)methyl-Sar]-3-cyclosporin |
| 219 | S | (CH2)3-OH | [(S)-(3-Hydroxypropylthio)methyl-Sar]-3-cyclosporin |
| 220 | S | CH2CH2C(CH3)2OH | [(S)-(3-Hydroxy-3-methylbutylthio)methyl-Sar]-3-cyclosporin |
| 221 | S | (CH2)3-N(CH3)2 | [(S)-(3-(N,N-Dimethylamino)propylthio)methyl-Sar]-3-cyclosporin |
| 222 | S | (CH2)3-N(Et)2 | [(S)-(3-(N,N-Diethylamino)propylthio)methyl-Sar]-3-cyclosporin |
| 223 | S | (CH2)3-NH-iPr | [(S)-(3-(N-Isopropylamino)propylthio)methyl-Sar]-3-cyclosporin |
| 224 | S | (CH2)3-N(CH3)(iPr) | [(S)-(3-(N-Isopropyl-N-methylamino)propylthio)methyl-Sar]-3-cyclosporin |
| 225 | S | (CH2)3-N(Et)(iPr) | [(S)-(3-(N-Ethyl-N-isopropylamino)propylthio)methyl-Sar]-3-cyclosporin |

TABLE 1-continued

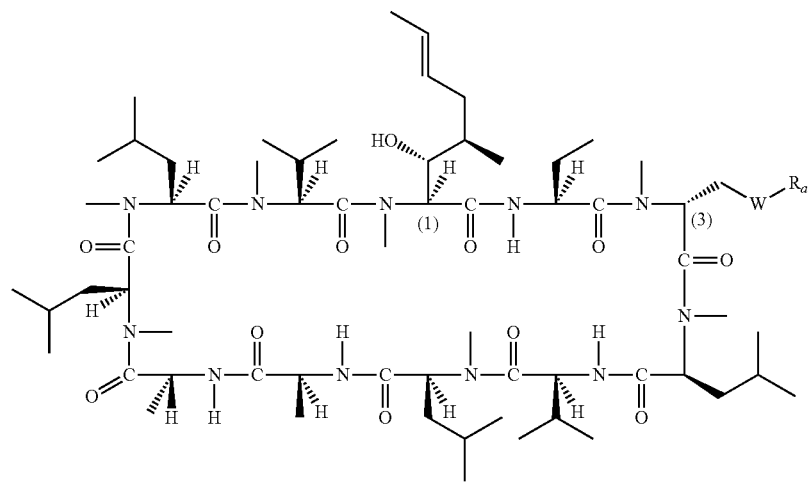

| Ex. No. | W | $R_a$ | Name |
|---|---|---|---|
| 226 | S | ~~~CH2CH2CH2-NH-CH2CH(CH3)2 | [(S)-(3-(N-Isobutylamino)propylthio)methyl-Sar]-3-cyclosporin |
| 227 | S | ~~~CH2CH2CH2-N(CH3)-CH2CH(CH3)2 | [(S)-(3-(N-Isobutyl-N-methylamino)propylthio)methyl-Sar]-3-cyclosporin |
| 228 | S | ~~~CH2CH2CH2-N(Et)-CH2CH(CH3)2 | [(S)-(3-(N-Ethyl-N-isobutylamino)propylthio)methyl-Sar]-3-cyclosporin |
| 229 | S | ~~~CH2CH2CH2-N(CH2CH(CH3)2)2 | [(S)-(3-(N,N-Diisobutylamino)propylthio)methyl-Sar]-3-cyclosporin |
| 230 | S | ~~~CH2CH2CH2-NH-CH2C(CH3)3 | [(S)-(3-(N-Neopentylamino)propylthio)methyl-Sar]-3-cyclosporin |
| 231 | S | ~~~CH2CH2CH2-N(CH3)-CH2C(CH3)3 | [(S)-(3-(N-Methyl-N-neopentylamino)propylthio)methyl-Sar]-3-cyclosporin |
| 232 | S | ~~~CH2CH2CH2-N(Et)-CH2C(CH3)3 | [(S)-(3-(N-Ethyl-N-neopentylamino)propylthio)methyl-Sar]-3-cyclosporin |
| 233 | S | ~~~CH2CH2CH2-pyrrolidinyl | [(S)-(3-(N-Pyrrolidinyl)propylthio)methyl-Sar]-3-cyclosporin |
| 234 | S | ~~~CH2CH2CH2-thiazolidinyl | [(S)-(3-(N-Thiazolidinyl)propylthio)methyl-Sar]-3-cyclosporin |

TABLE 1-continued

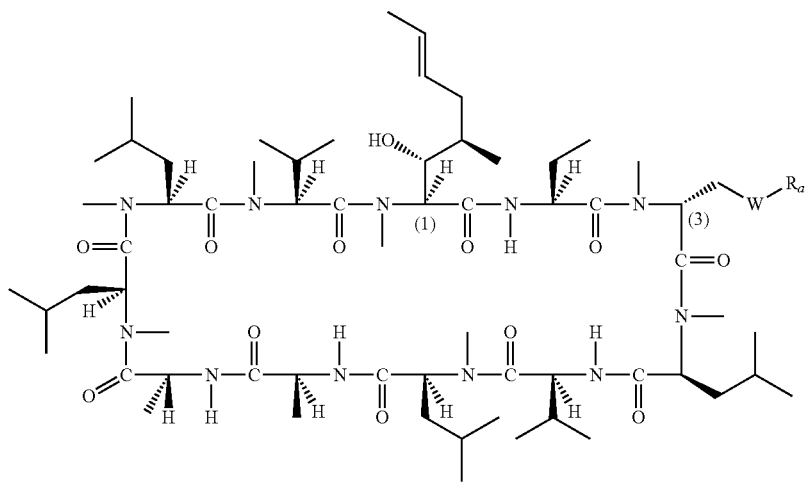

| Ex. No. | W | $R_a$ | Name |
|---|---|---|---|
| 235 | S | 4-(thiomorpholin-4-yl)butyl | [(S)-(3-(N-Thiomorpholino)propylthio)methyl-Sar]-3-cyclosporin |
| 236 | S | 4-(oxazolidin-3-yl)butyl | [(S)-(3-(N-Oxazolidinyl)propylthio)methyl-Sar]-3-cyclosporin |
| 237 | S | 4-(morpholin-4-yl)butyl | [(S)-(3-(N-Morpholino)propylthio)methyl-Sar]-3-cyclosporin |
| 238 | S | 4-(piperidin-1-yl)butyl | [(S)-(3-(N-Piperidinyl)propylthio)methyl-Sar]-3-cyclosporin |
| 239 | S | 4-(piperazin-1-yl)butyl | [(S)-(3-(N-Piperazinyl)propylthio)methyl-Sar]-3-cyclosporin |
| 240 | S | 4-(4-methylpiperazin-1-yl)butyl | [(S)-(3-(4-Methyl-N-piperazinyl)propylthio)methyl-Sar]-3-cyclosporin |
| 241 | S | 4-(4-ethylpiperazin-1-yl)butyl | [(S)-(3-(4-Ethyl-N-piperazinyl)propylthio)methyl-Sar]-3-cyclosporin |
| 242 | S | 4-(4-propylpiperazin-1-yl)butyl | [(S)-(3-(4-n-Propyl-N-piperazinyl)propylthio)methyl-Sar]-3-cyclosporin |

TABLE 1-continued

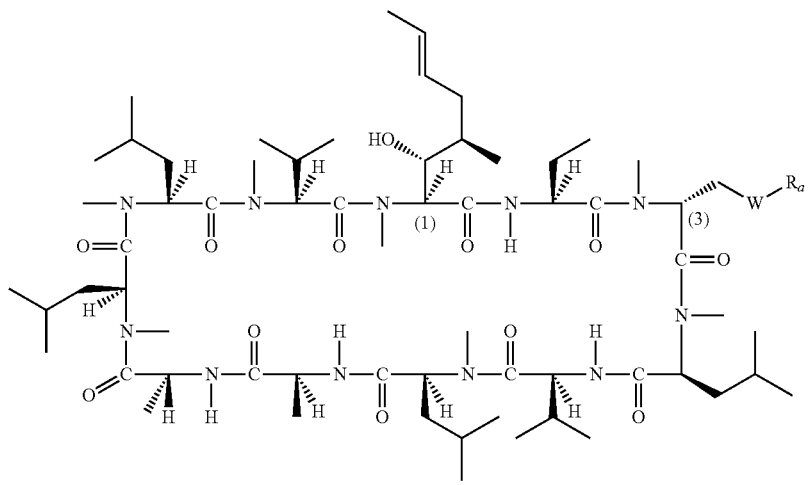

| Ex. No. | W | $R_a$ | Name |
|---|---|---|---|
| 243 | S | 3-(4-Isopropyl-N-piperazinyl)propyl | [(S)-(3-(4-Isopropyl-N-piperazinyl)propylthio)methyl-Sar]-3-cyclosporin |
| 244 | S | 3-(4-Isobutyl-N-piperazinyl)propyl | [(S)-(3-(4-Isobutyl-N-piperazinyl)propylthio)methyl-Sar]-3-cyclosporin |
| 245 | S | 3-(4-Neopentyl-N-piperazinyl)propyl | [(S)-(3-(4-Neopentyl-N-piperazinyl)propylthio)methyl-Sar]-3-cyclosporin |
| 246 | S | 3-(4-(2-Hydroxyethyl)-N-piperazinyl)propyl | [(S)-(3-(4-(2-Hydroxyethyl)-N-piperazinyl)propylthio)methyl-Sar]-3-cyclosporin |
| 247 | S | 3-(4-(2-Hydroxy-2-methylpropyl)-N-piperazinyl)propyl | [(S)-(3-(4-(2-Hydroxy-2-methylpropyl)-N-piperazinyl)propylthio)methyl-Sar]-3-cyclosporin |
| 248 | S | 3-(4-(3-Hydroxy-3-methylbutyl)-N-piperazinyl)propyl | [(S)-(3-(4-(3-Hydroxy-3-methylbutyl)-N-piperazinyl)propylthio)methyl-Sar]-3-cyclosporin |
| 249 | S | 3-(4-(4-Hydroxy-4-methylpentyl)-N-piperazinyl)propyl | [(S)-(3-(4-(4-Hydroxy-4-methylpentyl)-N-piperazinyl)propylthio)methyl-Sar]-3-cyclosporin |
| 250 | S | 3-Carboxypropyl | [(S)-(3-Carboxypropylthio)methyl-Sar]-3-cyclosporin |

TABLE 1-continued

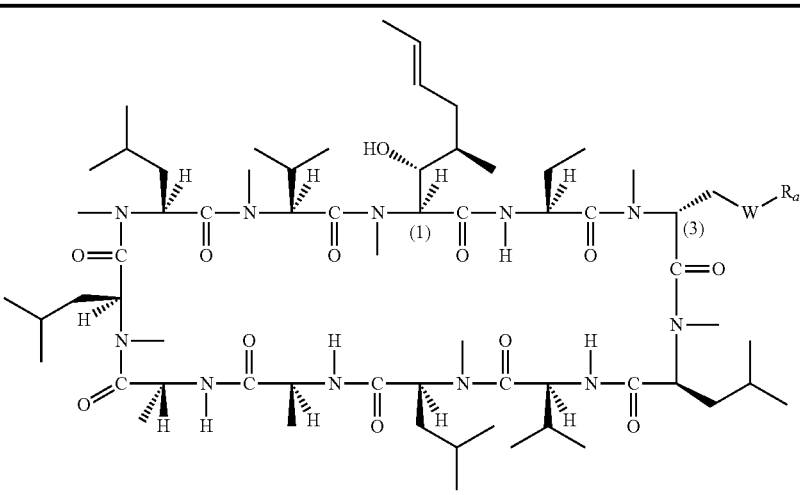

| Ex. No. | W | R$_a$ | Name |
|---|---|---|---|
| 251 | S | 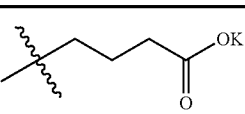 | [(S)-(3-Carboxypropylthio)methyl-Sar]-3-cyclosporin-potassium salt |
| 252 | S | 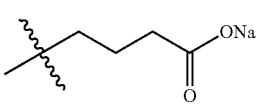 | [(S)-(3-Carboxypropylthio)methyl-Sar]-3-cyclosporin-sodium salt |
| 253 | S | 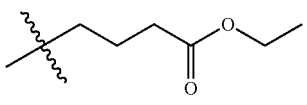 [SMILES: *CCCC(=O)OCC] | [(S)-(3-(Ethoxycarbonyl)propylthio)methyl-Sar]-3-cyclosporin |
| 254 | S | 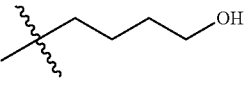 [SMILES: *CCCCO] | [(S)-(4-Hydroxybutylthio)methyl-Sar]-3-cyclosporin |
| 255 | S | 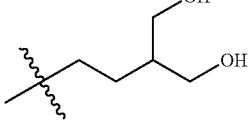 | [(S)-(4-Hydroxy-(3-hydroxymethyl)butylthio)methyl-Sar]-3-cyclosporin |
| 256 | S | 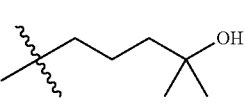 [SMILES: *CCCC(C)(C)O] | [S)-(4-Hydroxy-4-methylpentylthio)methyl-Sar]-3-cyclosporin |
| 257 | S | 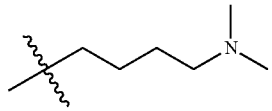 [SMILES: *CCCCN(C)C] | [(S)-(4-(N,N-Dimethylamino)butylthio)methyl-Sar]-3-cyclosporin |
| 258 | S | 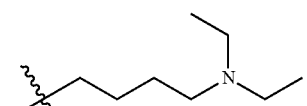 | [(S)-(4-(N,N-Diethylamino)butylthio)methyl-Sar]-3-cyclosporin |
| 259 | S | 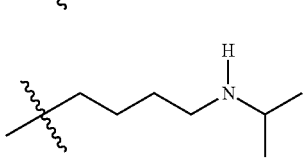 | [(S)-(4-(N-Isopropylamino)butylthio)methyl-Sar]-3-cyclosporin |

TABLE 1-continued

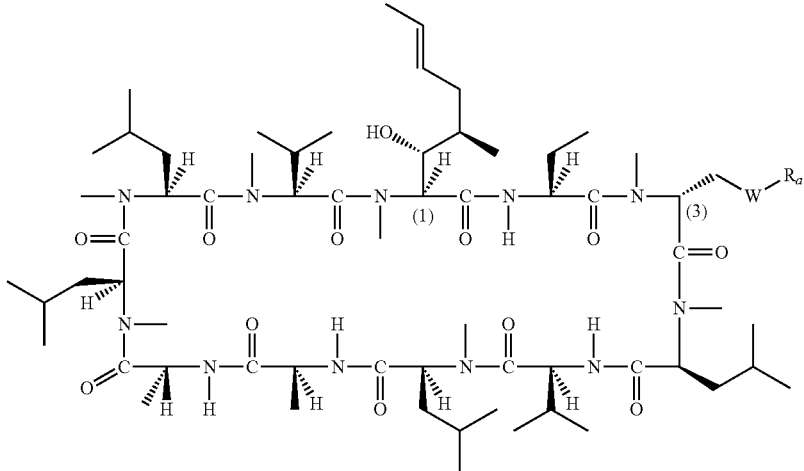

| Ex. No. | W | $R_a$ | Name |
|---|---|---|---|
| 260 | S | | [(S)-(4-(N-Isopropyl-N-methylamino)butylthio)methyl-Sar]-3-cyclosporin |
| 261 | S | | [(S)-(4-(N-Ethyl-N-isopropylamino)butylthio)methyl-Sar]-3-cyclosporin |
| 262 | S | | [(S)-(4-(N-Isobutylamino)butylthio)methyl-Sar]-3-cyclosporin |
| 263 | S | | [(S)-(4-(N-Isobutyl-N-methylamino)butylthio)methyl-Sar]-3-cyclosporin |
| 264 | S | | [(S)-(4-(N-Isobutyl-N-ethylamino)butylthio)methyl-Sar]-3-cyclosporin |
| 265 | S | | [(S)-(4-(N,N-Diisobutylamino)butylthio)methyl-Sar]-3-cyclosporin |
| 266 | S | | [(S)-(4-(N-Neopentylamino)butylthio)methyl-Sar]-3-cyclosporin |
| 267 | S | | [(S)-(4-(N-Methyl-N-Neopentylamino)butylthio)methyl-Sar]-3-cyclosporin |

TABLE 1-continued

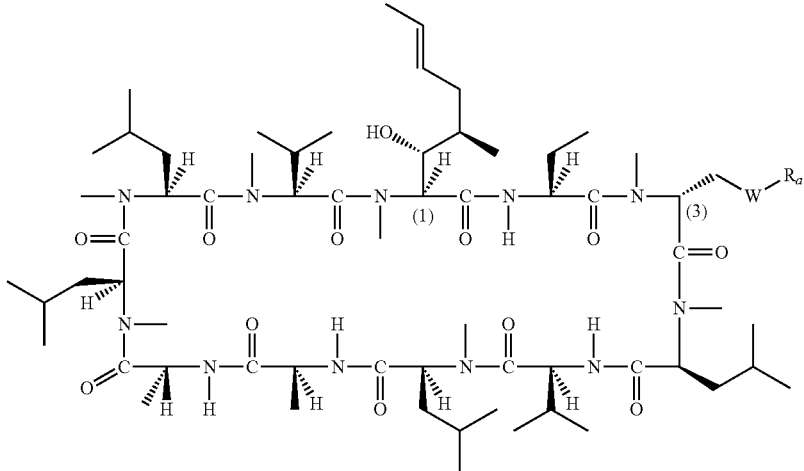

| Ex. No. | W | $R_a$ | Name |
|---|---|---|---|
| 268 | S | 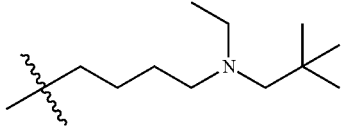 [SMILES: *CCCCN(CC)CC(C)(C)C] | [(S)-(4-(N-Ethyl-N-Neopentylamino)butylthio)methyl-Sar]-3-cyclosporin |
| 269 | S | 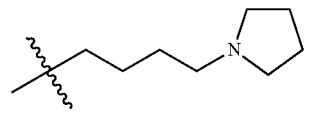 [SMILES: *CCCCN1CCCC1] | [(S)-(4-(N-Pyrrolidinyl)butylthio)methyl-Sar]-3-cyclosporin |
| 270 | S | 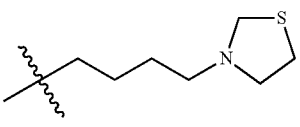 | [(S)-(4-(N-Thiazolidinyl)butylthio)methyl-Sar]-3-cyclosporin |
| 271 | S | 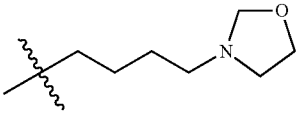 | [(S)-(4-(N-Oxazolidinyl)butylthio)methyl-Sar]-3-cyclosporin |
| 272 | S | 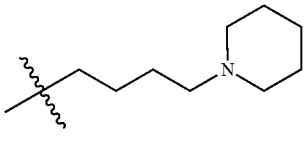 [SMILES: *CCCCN1CCCCC1] | [(S)-(4-(N-Piperidinyl)butylthio)methyl-Sar]-3-[(γ-hydroxy)-NMeLeu]-4-cyclosporin |
| 273 | S | 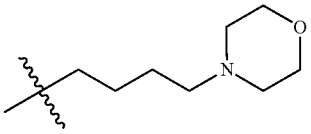 [SMILES: *CCCCN1CCOCC1] | [(S)-(4-(N-Morpholino)butylthio)methyl-Sar]-3-cyclosporin |
| 274 | S | 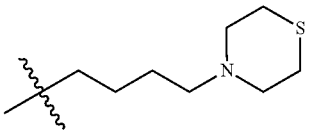 [SMILES: *CCCCN1CCSCC1] | [(S)-(4-(N-Thiomorpholino)butylthio)methyl-Sar]-3-cyclosporin |
| 275 | S | 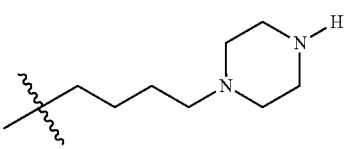 [SMILES: *CCCCN1CCNCC1] | [S)-(4-(N-Piperazinyl)butylthio)methyl-Sar]-3-cyclosporin |

TABLE 1-continued

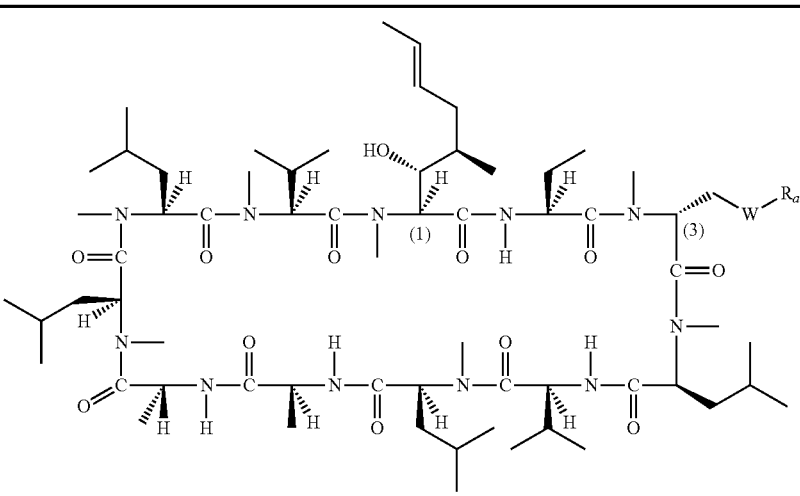

| Ex. No. | W | R$_a$ | Name |
|---|---|---|---|
| 276 | S |  | [(S)-(4-(4-Methyl-N-piperazinyl)butylthio)methyl-Sar]-3-cyclosporin |
| 277 | S |  | [(S)-(4-(4-Ethyl-N-piperazinyl)butylthio)methyl-Sar]-3-cyclosporin |
| 278 | S |  | [(S)-(4-(4-n-Propyl-N-piperazinyl)butylthio)methyl-Sar]-3-cyclosporin |
| 279 | S |  | [(S)-(4-(4-Isopropyl-N-piperazinyl)butylthio)methyl-Sar]-3-cyclosporin |
| 280 | S |  | [(S)-(4-(4-Isobutyl-N-piperazinyl)butylthio)methyl-Sar]-3-cyclosporin |
| 281 | S |  | [(S)-(4-(4-Neopentyl-N-piperazinyl)butylthio)methyl-Sar]-3-cyclosporin |
| 282 | S | 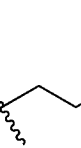 | [(S)-(4-(4-(2-Hydroxyethyl)-N-piperazinyl)butylthio)methyl-Sar]-3-cyclosporin |

TABLE 1-continued

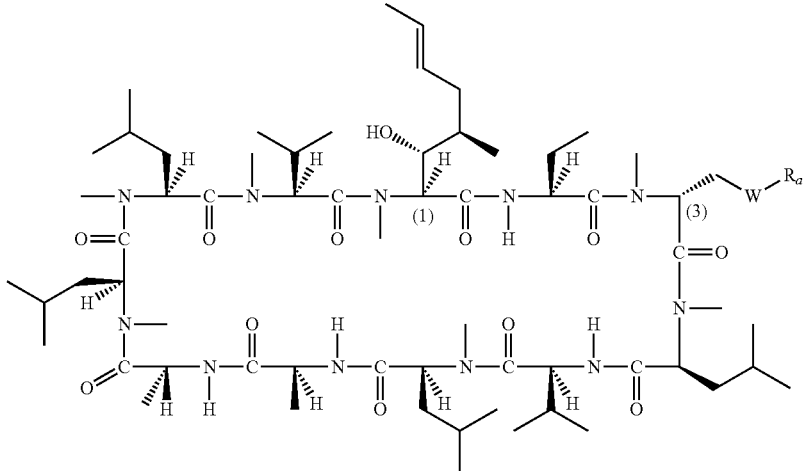

| Ex. No. | W | $R_a$ | Name |
|---|---|---|---|
| 283 | S | 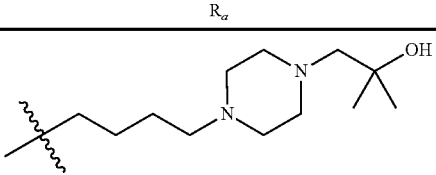 | [(S)-(4-(4-(2-Hydroxy-2-methylpropyl)-N-piperazinyl)butylthio)methyl-Sar]-3-cyclosporin |
| 284 | S | 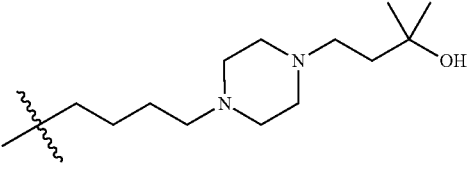 [SMILES: *CCCCN1CCN(CCC(C)(C)O)CC1] | [(S)-(4-(4-(3-Hydroxy-3-methylbutyl)-N-piperazinyl)butylthio)methyl-Sar]-3-cyclosporin |
| 285 | S | 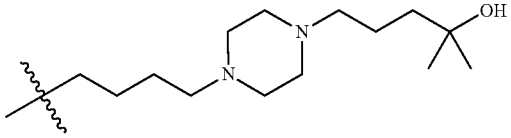 [SMILES: *CCCCN1CCN(CCCC(C)(C)O)CC1] | [(S)-(4-(4-(4-Hydroxy-4-methylpentyl)-N-piperazinyl)butylthio)methyl-Sar]-3-cyclosporin |
| 286 | S | 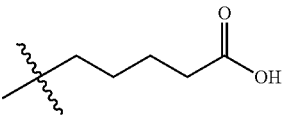 | [(S)-(4-Carboxybutylthio)methyl-Sar]-3-cyclosporin |
| 287 | S | 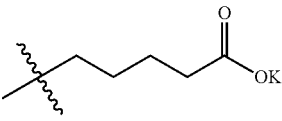 | [(S)-(4-Carboxybutylthio)methyl-Sar]-3-cyclosporin-potassium salt |
| 288 | S | 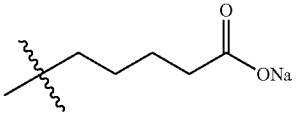 | [(S)-(4-Carboxybutylthio)methyl-Sar]-3-cyclosporin-sodium salt |
| 289 | S | 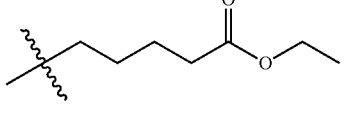 | [(S)-(4-(Ethoxycarbonyl)butylthio)methyl-Sar]-3-cyclosporin |
| 290 | S | 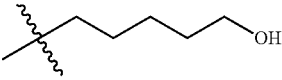 [SMILES: *CCCCCO] | [(S)-(5-Hydroxypentylthio)methyl-Sar]-3-cyclosporin |

TABLE 1-continued

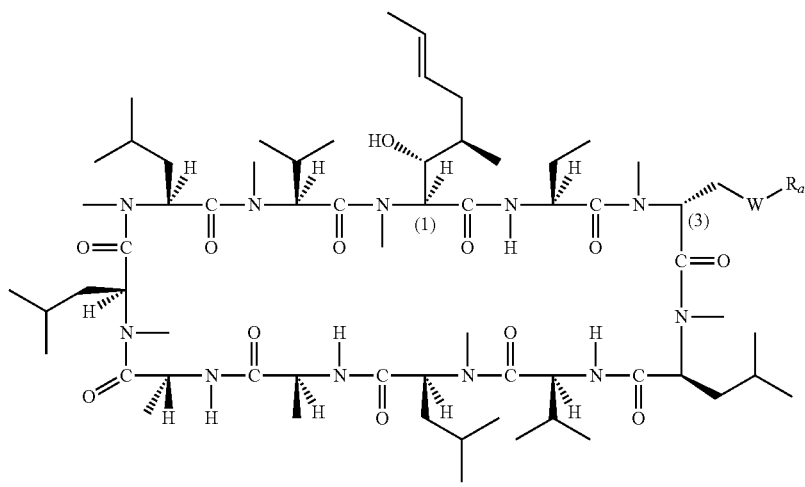

| Ex. No. | W | $R_a$ | Name |
|---|---|---|---|
| 291 | S | pentyl-COOH | [(S)-(5-Carboxypentylthio)methyl-Sar]-3-cyclosporin |
| 292 | S | pentyl-COOK | [(S)-(5-Carboxypentylthio)methyl-Sar]-3-cyclosporin-potassium salt |
| 293 | S | pentyl-COONa | [(S)-(5-Carboxypentylthio)methyl-Sar]-3-cyclosporin-sodium salt |
| 294 | S | pentyl-COOEt | [(S)-(5-(Ethoxycarbonyl)pentylthio)methyl-Sar]-3-cyclosporin |
| 295 | S | hexyl-COOH | [(S)-(4-Carboxyhexylthio)methyl-Sar]-3-cyclosporin |
| 296 | S | hexyl-COOK | [(S)-(4-Carboxyhexylthio)methyl-Sar]-3-cyclosporin-potassium salt |
| 297 | S | hexyl-COONa | [(S)-(4-Carboxyhexylthio)methyl-Sar]-3-cyclosporin-sodium salt |
| 298 | S | hexyl-COOEt | [(S)-(4-(Ethoxycarbonyl)hexylthio)methyl-Sar]-3-cyclosporin |
| 299 | S | heptyl-COOH | [(S)-(5-Carboxyheptylthio)methyl-Sar]-3-cyclosporin |

TABLE 1-continued

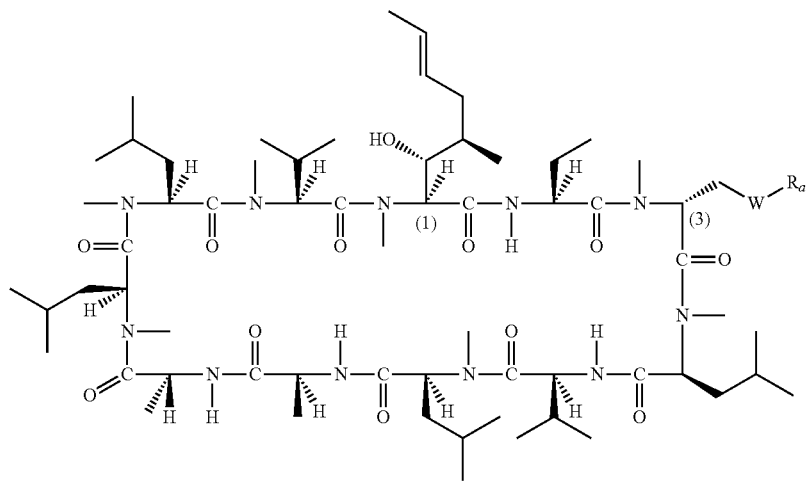

| Ex. No. | W | $R_a$ | Name |
|---|---|---|---|
| 300 | S | ~~~(CH2)7COOK | [(S)-(5-Carboxyheptylthio)methyl-Sar]-3-cyclosporin-potassium salt |
| 301 | S | ~~~(CH2)7COONa | [(S)-(5-Carboxyheptylthio)methyl-Sar]-3-cyclosporin-sodium salt |
| 302 | S | ~~~(CH2)7COOEt | [(S)-(5-(Ethoxycarbonyl)heptylthio)methyl-Sar]-3-cyclosporin |
| 303 | S | ~~~(CH2)8COOH | [(S)-(5-Carboxyoctylthio)methyl-Sar]-3-cyclosporin |
| 304 | S | ~~~(CH2)8COOK | [(S)-(5-Carboxyoctylthio)methyl-Sar]-3-cyclosporin-potassium salt |
| 305 | S | ~~~(CH2)8COONa | [(S)-(5-Carboxyoctylthio)methyl-Sar]-3-cyclosporin-potassium salt |
| 306 | S | ~~~(CH2)8COOEt | [(S)-(4-(Ethoxycarbonyl)octylthio)methyl-Sar]-3-cyclosporin |
| 307 | S | ~~~(CH2)9COOH | [(S)-(5-Carboxynonylthio)methyl-Sar]-3-cyclosporin |
| 308 | S | ~~~(CH2)9COOK | [(S)-(5-Carboxynonylthio)methyl-Sar]-3-cyclosporin-potassium salt |

TABLE 1-continued

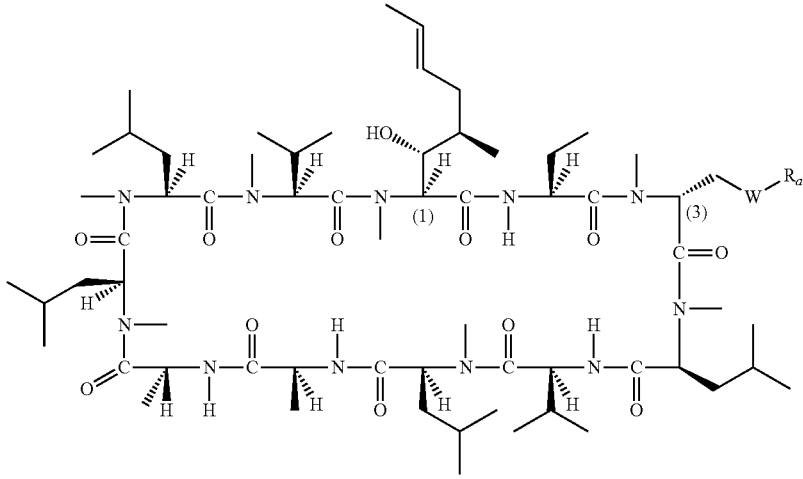

| Ex. No. | W | $R_a$ | Name |
|---|---|---|---|
| 309 | S |  | [(S)-(5-Carboxynonylthio)methyl-Sar]-3-cyclosporin-potassium salt |
| 310 | S |  | [(S)-(4-(Ethoxycarbonyl)nonylthio)methyl-Sar]-3-cyclosporin |
| 311 | S | 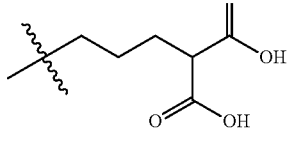 | [(S)-((4,4'-Dicarboxy)butylthio)methyl-Sar]-3-cyclosporin |
| 312 | S | 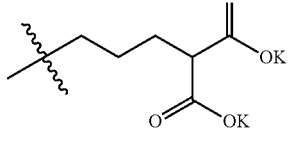 | [(S)-((4,4'-Dicarboxy)butylthio)methyl-Sar]-3-cyclosporin-dipotassium salt |
| 313 | S | 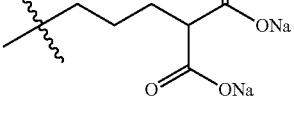 | [(S)-((4,4'-Dicarboxy)butylthio)methyl-Sar]-3-cyclosporin-disodium salt |
| 314 | S | 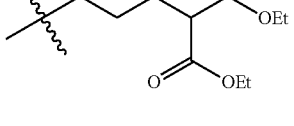 | [(S)-(4,4'-Diethoxycarbonyl)butylthio)methyl-Sar]-3-cyclosporin |
| 315 | S | 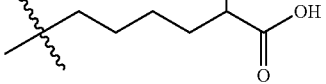 | [(S)-((5,5'-Dicarboxy)pentylthio)methyl-Sar]-3-cyclosporin |

TABLE 1-continued

| Ex. No. | W | $R_a$ | Name |
|---|---|---|---|
| 316 | S | (pentyl chain with CH(C(O)OK)(C(O)OK)) | [(S)-((5,5'-Dicarboxy)pentylthio)methyl-Sar]-3-cyclosporin-dipotassium salt |
| 317 | S | (pentyl chain with CH(C(O)ONa)(C(O)ONa)) | [(S)-((5,5'-Dicarboxy)pentylthio)methyl-Sar]-3-cyclosporin-disodium salt |
| 318 | S | (pentyl chain with CH(C(O)OEt)(C(O)OEt)) | [(S)-(4,4'-Diethoxycarbonyl)pentylthio)methyl-Sar]-3-cyclosporin |
| 319 | S | (hexyl chain with OH) | [(S)-(6-Hydroxyhexylthio)methyl-Sar]-3-cyclosporin |
| 320 | S | (hexyl chain with CH(C(O)OH)(C(O)OH)) | [(S)-((6,6'-Dicarboxy)hexylthio)methyl-Sar]-3-cyclosporin |
| 321 | S | (hexyl chain with CH(C(O)OK)(C(O)OK)) | [(S)-((6,6'-Dicarboxy)hexylthio)methyl-Sar]-3-cyclosporin-dipotassium salt |
| 322 | S | (hexyl chain with CH(C(O)ONa)(C(O)ONa)) | [(S)-((6,6'-Dicarboxy)hexylthio)methyl-Sar]-3-cyclosporin-disodium salt |

TABLE 1-continued

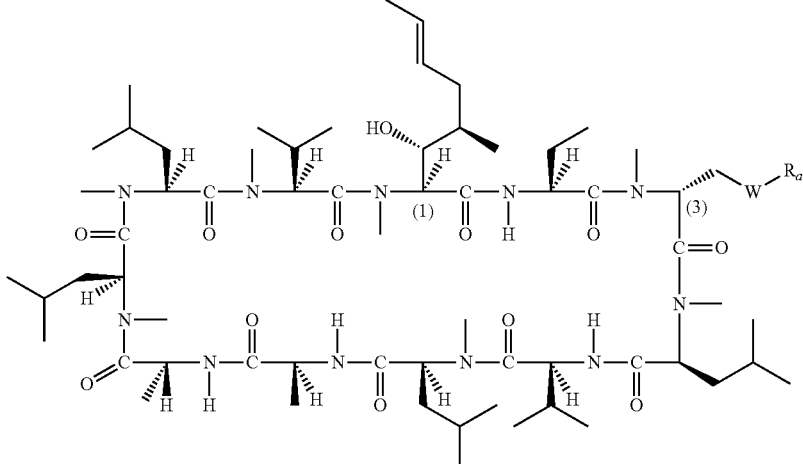

| Ex. No. | W | $R_a$ | Name |
|---|---|---|---|
| 323 | S | 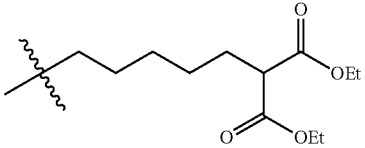 [SMILES: *CCCCCC(C(=O)OCC)C(=O)OCC] | [(S)-(6,6'-Diethoxycarbonyl)hexylthio)methyl-Sar]-3-cyclosporin |
| 324 | S | 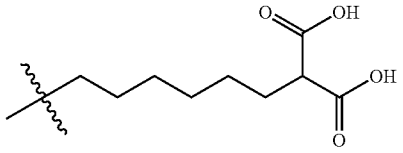 | [(S)-((7,7'-Dicarboxy)heptylthio)methyl-Sar]-3-cyclosporin |
| 325 | S | 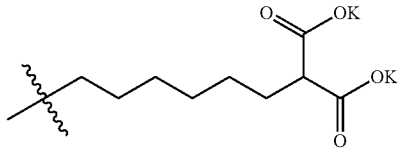 | [(S)-((7,7'-Dicarboxy)heptylthio)methyl-Sar]-3-cyclosporin-dipotassium salt |
| 326 | S | 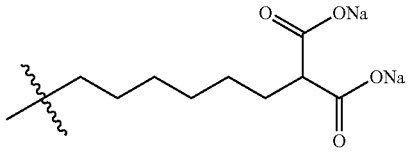 | [(S)-((7,7'-Dicarboxy)heptylthio)methyl-Sar]-3-cyclosporin-disodium salt |
| 327 | S | 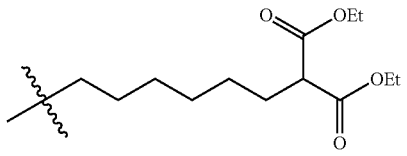 [SMILES: *CCCCCCC(C(=O)OCC)C(=O)OCC] | [(S)-(7,7'-Diethoxycarbonyl)heptylthio)methyl-Sar]-3-cyclosporin |
| 328 | S | 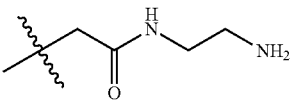 [SMILES: *CC(=O)NCCN] | [(S)-[(N-(2-Aminoethyl)carbamoyl)methylthio]methyl-Sar]-3-cyclosporin |
| 329 | S | 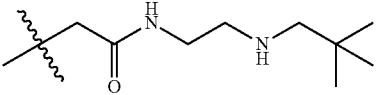 [SMILES: *CC(=O)NCCNCC(C)(C)C] | [(S)-[(N-(2-(Neopentylamino)ethyl)carbamoyl)methylthio]methyl-Sar]-3-cyclosporin |

TABLE 1-continued

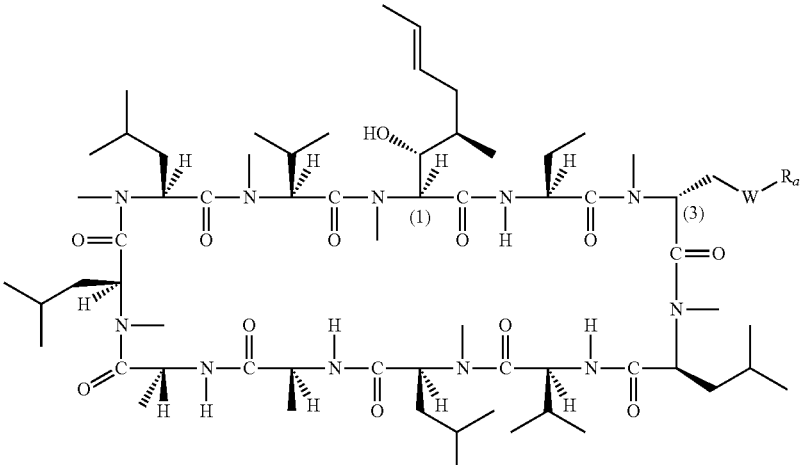

| Ex. No. | W | R$_a$ | Name |
|---|---|---|---|
| 330 | S | 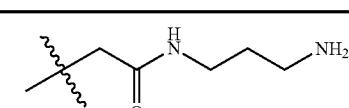 | [(S)-[(N-(3-Aminopropyl)carbamoyl)methylthio]methyl-Sar]-3-cyclosporin |
| 331 | S | 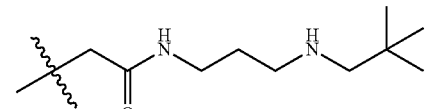 | [(S)-[(N-(3-(Neopentylamino)propyl)carbamoyl)methylthio]methyl-Sar]-3-cyclosporin |
| 332 | S | 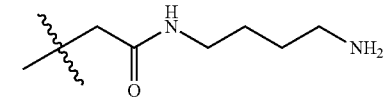 [SMILES: *CC(=O)NCCCCN] | [(S)-[(N-(4-Aminobutyl)carbamoyl)methylthio]methyl-Sar]-3-cyclosporin |
| 333 | S | 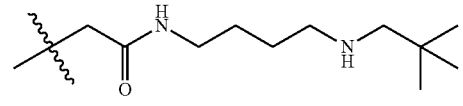 [SMILES: *CC(=O)NCCCCNCC(C)(C)C] | [(S)-[(N-(4-(Neopentylamino)butyl)carbamoyl)methylthio]methyl-Sar]-3-cyclosporin |
| 334 | S | 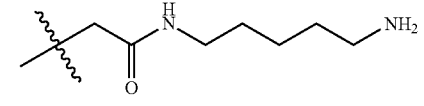 [SMILES: *CC(=O)NCCCCCN] | [(S)-[(N-(5-Aminopentyl)carbamoyl)methylthio]methyl-Sar]-3-cyclosporin |
| 335 | S | 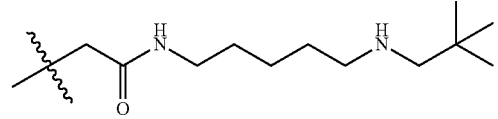 [SMILES: *CC(=O)NCCCCCNCC(C)(C)C] | [(S)-[(N-(5-(Neopentylamino)pentyl)carbamoyl)methylthio]methyl-Sar]-3-cyclosporin |
| 336 | S | 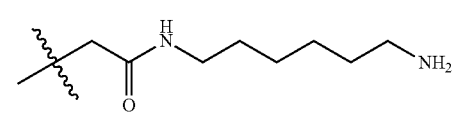 [SMILES: *CC(=O)NCCCCCCN] | [(S)-[(N-(6-Aminohexyl)carbamoyl)methylthio]methyl-Sar]-3-cyclosporin |
| 337 | S | 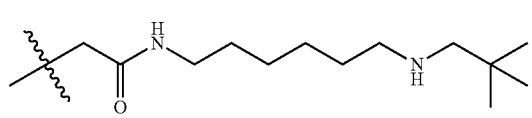 [SMILES: *CC(=O)NCCCCCCNCC(C)(C)C] | [(S)-[(N-(6-Neopentylamino)hexyl)carbamoyl)methylthio]methyl-Sar]-3-cyclosporin |
| 338 | S | 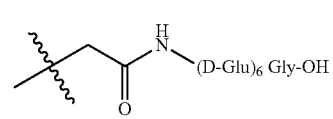 | [(S)-[([HO-Gly-(D-Glu)$_6$]carbamoyl)methylthio]methyl-Sar]-3-cyclosporin |

TABLE 1-continued

| Ex. No. | W | R$_a$ | Name |
|---|---|---|---|
| 339 | S | (structure: -CH(CH₃)-CH₂-C(=O)-NH-(D-Glu)₆Gly-OH) | [(S)-[([HO-Gly-(D-Glu)₆]carbamoyl)ethylthio]methyl-Sar]-3-cyclosporin |
| 340 | S | (structure: -CH(CH₃)-(CH₂)₃-C(=O)-NH-(D-Glu)₆Gly-OH) | [(S)-[([HO-Gly-(D-Glu)₆]carbamoyl)propylthio]methyl-Sar]-3-cyclosporin |
| 341 | S | (structure: -CH(CH₃)-CH₂-O-CH₂-C(=O)-NH-(D-Glu)₆Gly-OH) | [(S)-((2-[([HO-Gly-(D-Glu)₆]carbamoyl)methoxy]ethyl)sulfanyl)methyl-Sar]-3-cyclosporin |
| 342 | S | (structure: -CH(CH₃)-(CH₂)₃-O-CH₂-C(=O)-NH-(D-Glu)₆Gly-OH) | [(S)-((3-[([HO-Gly-(D-Glu)₆]carbamoyl)methoxy]propyl)sulfanyl)methyl-Sar]-3-cyclosporin |
| 343 | S | (structure: -CH(CH₃)-(CH₂)₄-O-CH₂-C(=O)-NH-(D-Glu)₆Gly-OH) | [(S)-((4-[([HO-Gly-(D-Glu)₆]carbamoyl)methoxy]butyl)sulfanyl)methyl-Sar]-3-cyclosporin |
| 344 | S | (structure: -CH(CH₃)-(CH₂)₅-O-CH₂-C(=O)-NH-(D-Glu)₆Gly-OH) | [(S)-((5-[([HO-Gly-(D-Glu)₆]carbamoyl)methoxy]pentyl)sulfanyl)methyl-Sar]-3-cyclosporin |
| 345 | S | (structure: -CH(CH₃)-(CH₂)₆-O-CH₂-C(=O)-NH-(D-Glu)₆Gly-OH) | [(S)-((6-[([HO-Gly-(D-Glu)₆]carbamoyl)methoxy]hexyl)sulfanyl)methyl-Sar]-3-cyclosporin |
| 346 | S | (structure: branched chain with CH₂OH and imidazol-1-yl hexyl group) | [(S)-(((R)-3-Hydroxymethyl-6-(imidazol-1-yl)hexyl)thio)methyl-Sar]-3-cyclosporin |

TABLE 1-continued

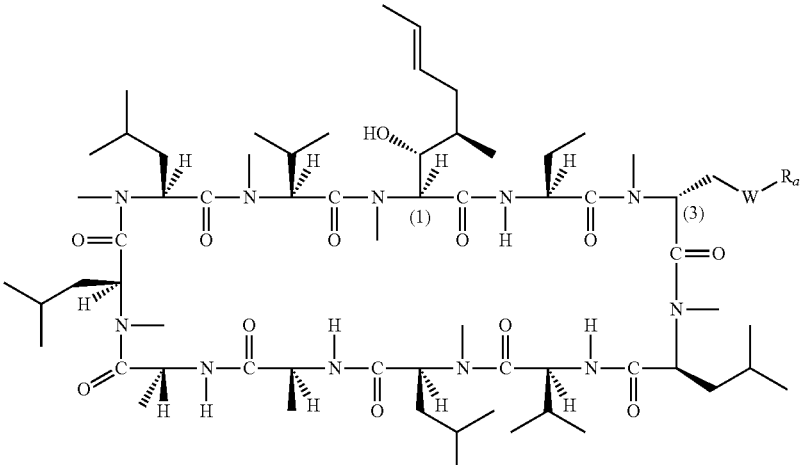

| Ex. No. | W | $R_a$ | Name |
|---|---|---|---|
| 347 | S | 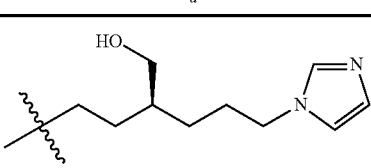 | [(S)-(((S)-3-Hydroxymethyl-6-(imidazo-1-yl)hexyl)thio)methyl-Sar]-3-cyclosporin |
| 348 | S | 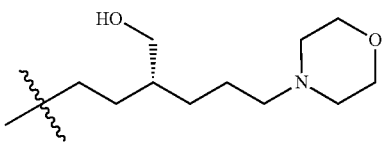 [SMILES: *CC[C@H](CO)CCCN1CCOCC1] | [(S)-(((R)-3-Hydroxymethyl-6-morpholinohexyl)thio)methyl-Sar]-3-cyclosporin |
| 349 | S | 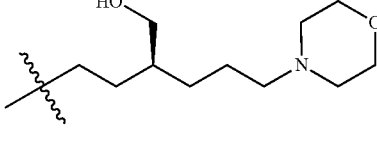 | [(S)-(((S)-3-Hydroxymethyl-6-morpholinohexyl)thio)methyl-Sar]-3-cyclosporin |
| 350 | S | 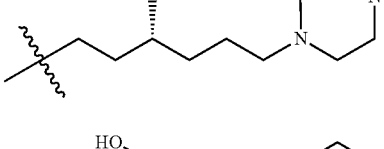 | [(S)-(((R)-3-Hydroxymethyl-6-(4-methylpiperazin-1-yl)hexyl)thio)methyl-Sar]-3-cyclosporin |
| 351 | S | 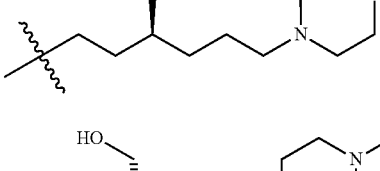 | [(S)-(((S)-3-Hydroxymethyl-6-(4-methylpiperazin-1-yl)hexyl)thio)methyl-Sar]-3-cyclosporin |
| 352 | S | 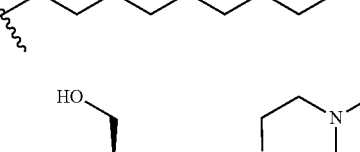 | [(S)-(((R)-3-Hydroxymethyl-6-(4-ethylpiperazin-1-yl)hexyl)thio)methyl-Sar]-3-cyclosporin |
| 353 | S |  | [(S)-(((S)-3-Hydroxymethyl-6-(4-isopropylpiperazin-1-yl)hexyl)thio)methyl-Sar]-3-cyclosporin |

TABLE 1-continued

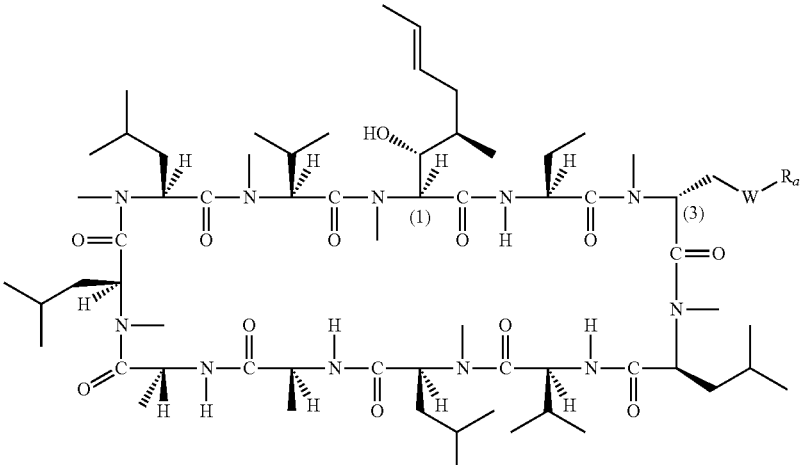

| Ex. No. | W | R_a | Name |
|---|---|---|---|
| 354 | S | 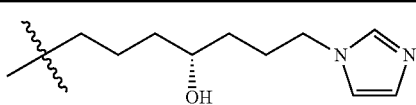 | [(S)-(((S)-4-Hydroxy-7-(imidazol-1-yl)heptyl)thio)methyl-Sar]-3-cyclosporin |
| 355 | S | 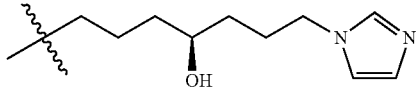 | [(S)-(((R)-4-Hydroxy-7-(imidazo-1-yl)heptyl)thio)methyl-Sar]-3-cyclosporin |
| 356 | S | 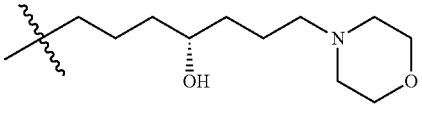 [SMILES: *CCC[C@@H](O)CCCN1CCOCC1] | [(S)-(((S)-4-Hydroxy-7-morpholinoheptyl)thio)methyl-Sar]-3-cyclosporin |
| 357 | S | 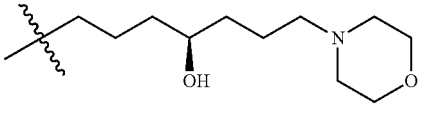 [SMILES: *CCC[C@H](O)CCCN1CCOCC1] | [(S)-(((R)-4-Hydroxy-7-morpholinoheptyl)thio)methyl-Sar]-3-cyclosporin |
| 358 | S | 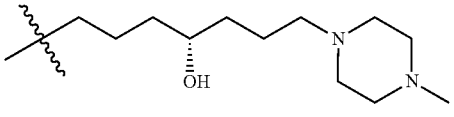 [SMILES: *CCC[C@@H](O)CCCN1CCN(C)CC1] | [(S)-(((S)-4-Hydroxy-7-(4-methylpiperazin-1-yl)heptyl)thio)methyl-Sar]-3-cyclosporin |
| 359 | S | 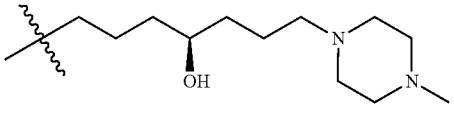 [SMILES: *CCC[C@H](O)CCCN1CCN(C)CC1] | [(S)-(((R)-4-Hydroxy-7-(4-methylpiperazin-1-yl)heptyl)thio)methyl-Sar]-3-cyclosporin |
| 360 | S | 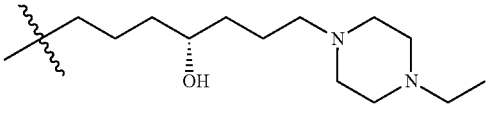 [SMILES: *CCC[C@@H](O)CCCN1CCN(CC)CC1] | [(S)-(((S)-4-Hydroxy-7-(4-ethylpiperazin-1-yl)heptyl)thio)methyl-Sar]-3-cyclosporin |
| 361 | S | 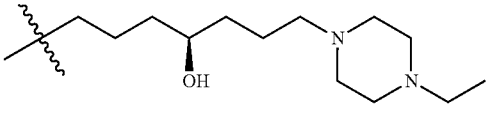 [SMILES: *CCC[C@H](O)CCCN1CCN(CC)CC1] | [(S)-(((R)-4-Hydroxy-7-(4-ethylpiperazin-1-yl)heptyl)thio)methyl-Sar]-3-cyclosporin |
| 362 | O | 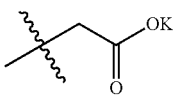 | [(R)-(Carboxymethyloxy)methyl-Sar]-3-cyclosporin-potassium salt |

TABLE 1-continued

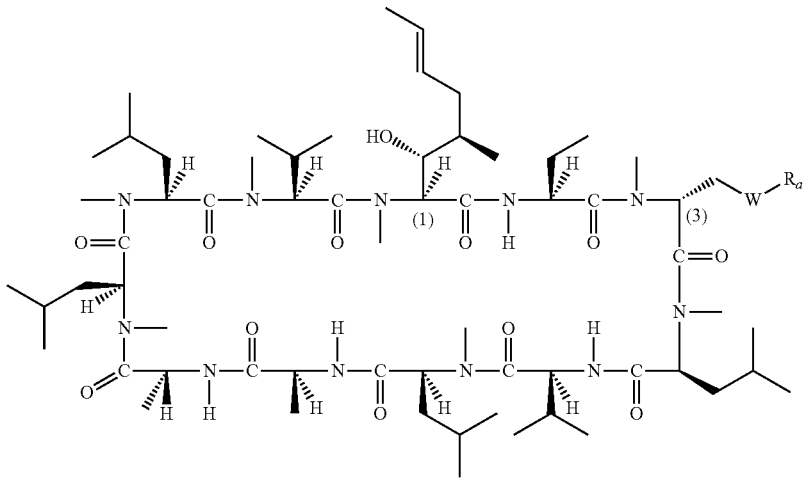

| Ex. No. | W | R_a | Name |
|---|---|---|---|
| 363 | O | 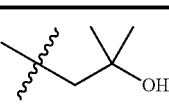 | [(R)-(2-Hydroxy-2,2-dimethylethoxy)methyl-Sar]-3-cyclosporin |
| 364 | O | 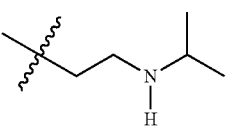 [SMILES: *CCNC(C)C] | [(R)-(2-(N-Isopropylamino)ethoxy)methyl-Sar]-3-cyclosporin |
| 365 | O | 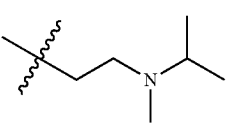 [SMILES: *CCN(C)C(C)C] | [(R)-(2-(N-Isopropyl-N-methylamino)ethoxy)methyl-Sar]-3-cyclosporin |
| 366 | O | 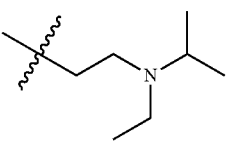 [SMILES: *CCN(CC)C(C)C] | [(R)-(2-(N-Ethyl-N-isopropylamino)ethoxy)methyl-Sar]-3-cyclosporin |
| 367 | O | 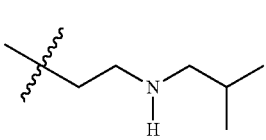 [SMILES: *CCNCC(C)C] | [(R)-(2-(N-Isobutylamino)ethoxy)methyl-Sar]-3-cyclosporin |
| 368 | O | 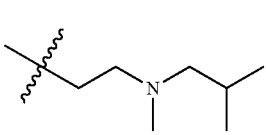 [SMILES: *CCN(C)CC(C)C] | [(R)-(2-(N-Isobutyl-N-methylamino)ethoxy)methyl-Sar]-3-cyclosporin |
| 369 | O | 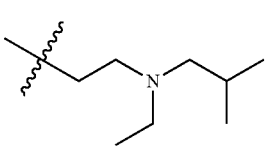 [SMILES: *CCN(CC)CC(C)C] | [(R)-(2-(N-Ethyl-N-isobutylamino)ethoxy)methyl-Sar]-3-cyclosporin |
| 370 | O | 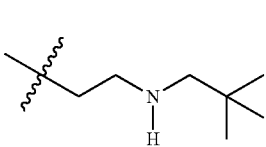 [SMILES: *CCNCC(C)(C)C] | [(R)-(2-(N-Neopentylamino)ethoxy)methyl-Sar]-3-cyclosporin |

TABLE 1-continued

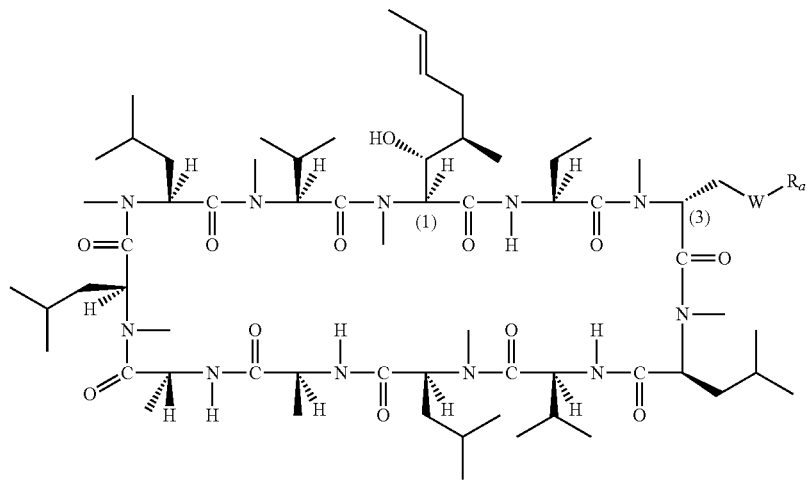

| Ex. No. | W | $R_a$ | Name |
|---|---|---|---|
| 371 | O | (CH2)-N(CH3)-CH2-C(CH3)3 | [(R)-(2-(N-Methyl-N-Neopentylamino)ethoxy)methyl-Sar]-3-cyclosporin |
| 372 | O | (CH2)-N(C2H5)-CH2-C(CH3)3 | [(R)-(2-(N-Ethyl-N-Neopentylamino)ethoxy)methyl-Sar]-3-cyclosporin |
| 373 | O | (CH2)-oxazolidinyl | [(R)-(2-(N-Oxazolidinyl)ethoxy)methyl-Sar]-3-cyclosporin |
| 374 | O | (CH2)-thiazolidinyl | [(R)-(2-(N-Thiazolidinyl)ethoxy)methyl-Sar]-3-cyclosporin |
| 375 | O | (CH2)-thiomorpholino | [(R)-(2-(N-Thiomorpholino)ethoxy)methyl-Sar]-3-cyclosporin |
| 376 | O | (CH2)-piperazinyl-NH | [(R)-(2-(N-Piperazinyl)ethoxy)methyl-Sar]-3-cyclosporin |
| 377 | O | (CH2)-piperazinyl-N-CH3 | [(R)-(2-(4-Methyl-N-piperazinyl)ethoxy)methyl-Sar]-3-cyclosporin |
| 378 | O | (CH2)-piperazinyl-N-C2H5 | [(R)-(2-(4-Ethyl-N-piperazinyl)ethoxy)methyl-Sar]-3-cyclosporin |

TABLE 1-continued

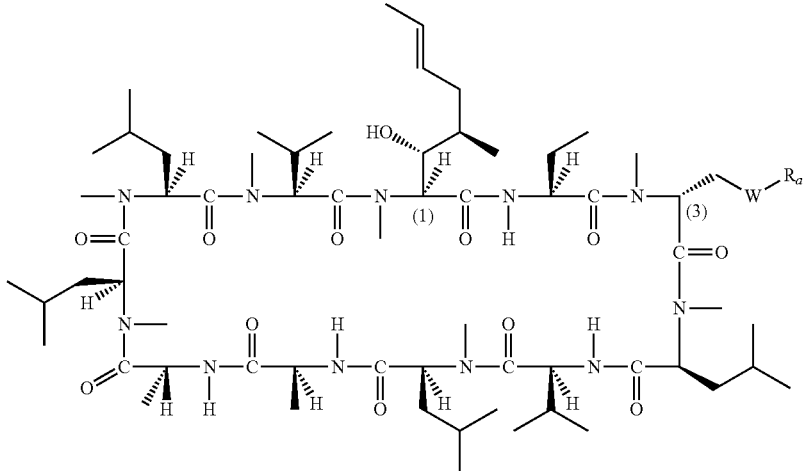

| Ex. No. | W | $R_a$ | Name |
|---|---|---|---|
| 379 | O | 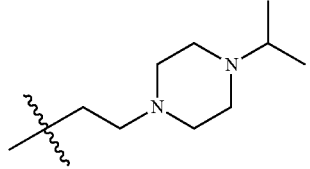 [SMILES: *CCN1CCN(C(C)C)CC1] | [(R)-(2-(4-Isopropyl-N-piperazinyl)ethoxy)methyl-Sar]-3-cyclosporin |
| 380 | O | 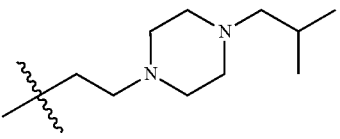 [SMILES: *CCN1CCN(CC(C)C)CC1] | [(R)-(2-(4-Isobutyl-N-piperazinyl)ethoxy)methyl-Sar]-3-cyclosporin |
| 381 | O | 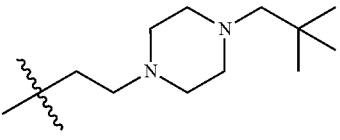 [SMILES: *CCN1CCN(CC(C)(C)C)CC1] | [(R)-(2-(4-Neopentyl-N-piperazinyl)ethoxy)methyl-Sar]-3-cyclosporin |
| 382 | O | 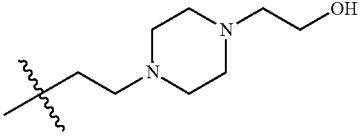 [SMILES: *CCN1CCN(CCO)CC1] | [(R)-(2-(4-(2-Hydroxyethyl)-N-piperazinyl)ethoxy)methyl-Sar]-3-cyclosporin |
| 383 | O | 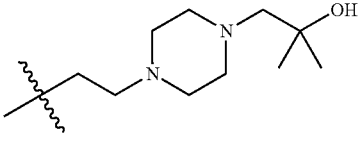 [SMILES: *CCN1CCN(CC(C)(C)O)CC1] | [(R)-(2-(4-(2-Hydroxy-2-methylpropyl)-N-piperazinyl)ethoxy)methyl-Sar]-3-cyclosporin |
| 384 | O | 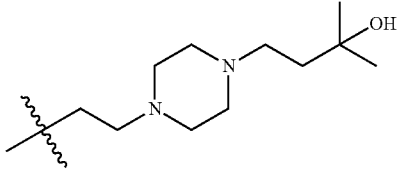 [SMILES: *CCN1CCN(CCC(C)(C)O)CC1] | [(R)-(2-(4-(3-Hydroxy-3-methylbutyl)-N-piperazinyl)ethoxy)methyl-Sar]-3-cyclosporin |
| 385 | O | 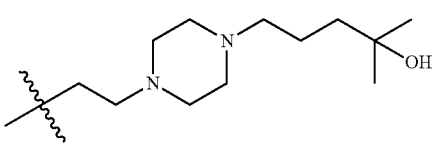 [SMILES: *CCN1CCN(CCCC(C)(C)O)CC1] | [(R)-(2-(4-(4-Hydroxy-4-methylpentyl)-N-piperazinyl)ethoxy)methyl-Sar]-3-cyclosporin |

TABLE 1-continued

| Ex. No. | W | R$_a$ | Name |
|---|---|---|---|
| 386 | O | (CH$_2$CH$_2$COOH branch) | [(R)-(2-Carboxyethoxy)methyl-Sar]-3-cyclosporin |
| 387 | O | (CH$_2$CH$_2$COONa branch) | [(R)-(2-Carboxyethoxy)methyl-Sar]-3-cyclosporin-sodium salt |
| 388 | O | (CH$_2$CH$_2$COOEt branch) | [(R)-(2-(Ethoxycarbonyl)ethoxy)methyl-Sar]-3-cyclosporin |
| 389 | O | (CH$_2$CH$_2$CH$_2$OH branch) | [(R)-(3-Hydroxypropoxy)methyl-Sar]-3-cyclosporin |
| 390 | O | (CH$_2$CH$_2$C(CH$_3$)$_2$OH branch) | [(R)-(3-Hydroxy-3-methylbutoxy)methyl-Sar]-3-cyclosporin |
| 391 | O | (CH$_2$CH$_2$CH$_2$NH-iPr branch) | [(R)-(3-(N-Isopropylamino)propoxy)methyl-Sar]-3-cyclosporin |
| 392 | O | (CH$_2$CH$_2$CH$_2$N(Me)(iPr) branch) | [(R)-(3-(N-Isopropyl-N-methylamino)propoxy)methyl-Sar]-3-cyclosporin |
| 393 | O | (CH$_2$CH$_2$CH$_2$N(Et)(iPr) branch) | [(R)-(3-(N-Ethyl-N-isopropylamino)propoxy)methyl-Sar]-3-cyclosporin |

TABLE 1-continued

| Ex. No. | W | $R_a$ | Name |
|---|---|---|---|
| 394 | O | -CH₂CH₂CH₂-NH-CH₂C(CH₃)₃ | [(R)-(3-(N-Neopentylamino)propoxy)methyl-Sar]-3-cyclosporin |
| 395 | O | -CH₂CH₂CH₂-N(CH₃)-CH₂C(CH₃)₃ | [(R)-(3-(N-Methyl-N-Neopentylamino)propoxy)methyl-Sar]-3-cyclosporin |
| 396 | O | -CH₂CH₂CH₂-N(Et)-CH₂C(CH₃)₃ | [(R)-(3-(N-Ethyl-N-Neopentylamino)propoxy)methyl-Sar]-3-cyclosporin |
| 397 | O | -CH₂CH₂CH₂-N(thiazolidinyl) | [(R)-(3-(N-Thiazolidinyl)propoxymethyl-Sar]-3-cyclosporin |
| 398 | O | -CH₂CH₂CH₂-N(thiomorpholino) | [(R)-(3-(N-Thiomorpholino)propoxy)methyl-Sar]-3-cyclosporin |
| 399 | O | -CH₂CH₂CH₂-N(piperazinyl)H | [(R)-(3-(N-Piperazinyl)propoxy)methyl-Sar]-3-cyclosporin |
| 400 | O | -CH₂CH₂CH₂-N(4-Me-piperazinyl) | [(R)-(3-(4-Methyl-N-piperazinyl)propoxy)methyl-Sar]-3-cyclosporin |
| 401 | O | -CH₂CH₂CH₂-N(4-Et-piperazinyl) | [(R)-(3-(4-Ethyl-N-piperazinyl)propoxy)methyl-Sar]-3-cyclosporin |
| 402 | O | -CH₂CH₂CH₂-N(4-iPr-piperazinyl) | [(R)-(3-(4-Isopropyl-N-piperazinyl)propoxy)methyl-Sar]-3-cyclosporin |

TABLE 1-continued

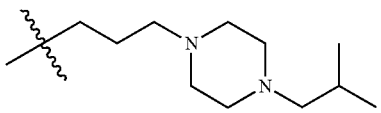 [SMILES: *CCCN1CCN(CC(C)C)CC1]

| Ex. No. | W | R_a | Name |
|---|---|---|---|
| 403 | O | 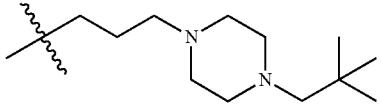 [SMILES: *CCCN1CCN(CC(C)(C)C)CC1] | [(R)-(3-(4-Isobutyl-N-piperazinyl)propoxy)methyl-Sar]-3-cyclosporin |
| 404 | O | | [(R)-(3-(4-Neopentyl-N-piperazinyl)propoxy)methyl-Sar]-3-cyclosporin |
| 405 | O | 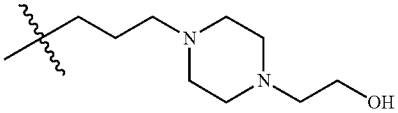 [SMILES: *CCCN1CCN(CCO)CC1] | [(R)-(3-(4-(2-Hydroxyethyl)-N-piperazinyl)propoxy)methyl-Sar]-3-cyclosporin |
| 406 | O | | [(R)-(3-(4-(2-Hydroxy-2-methylpropyl)-N-piperazinyl)propoxy)methyl-Sar]-3-cyclosporin |
| 407 | O | 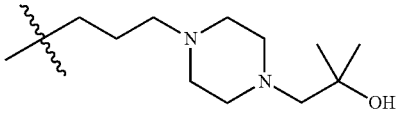 [SMILES: *CCCN1CCN(CC(C)(C)O)CC1] | [(R)-(3-(4-(3-Hydroxy-3-methylbutyl)-N-piperazinyl)propoxy)methyl-Sar]-3-cyclosporin |
| 408 | O | | [(R)-(3-(4-(4-Hydroxy-4-methylpentyl)-N-piperazinyl)propoxy)methyl-Sar]-3-cyclosporin |
| 409 | O | 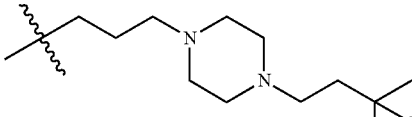 | [(R)-(3-Carboxypropoxy)methyl-Sar]-3-cyclosporin |
| 410 | O | 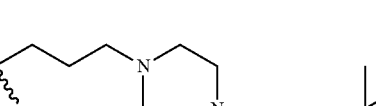 | [(R)-(3-Carboxypropoxy)methyl-Sar]-3-cyclosporin-potassium salt |

TABLE 1-continued

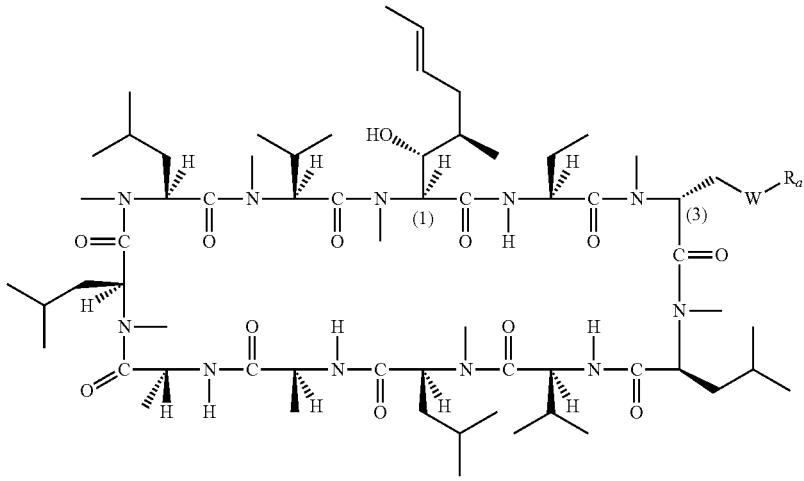

| Ex. No. | W | R$_a$ | Name |
|---|---|---|---|
| 411 | O | 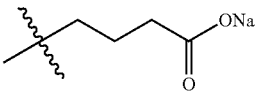 | [(R)-(3-Carboxypropoxy)methyl-Sar]-3-cyclosporin-sodium salt |
| 412 | O | 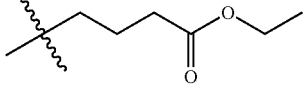 [SMILES: *CCCC(=O)OCC] | [(R)-(3-(Ethoxycarbonyl)propoxy)methyl-Sar]-3-cyclosporin |
| 413 | O | 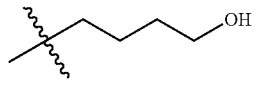 [SMILES: *CCCCO] | [(R)-(4-Hydroxybutoxy)methyl-Sar]-3-cyclosporin |
| 414 | O | 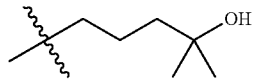 [SMILES: *CCCC(C)(C)O] | [(R)-(4-Hydroxy-4-methylpentyloxy)methyl-Sar]-3-cyclosporin |
| 415 | O | 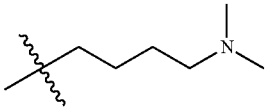 [SMILES: *CCCCN(C)C] | [(R)-(4-(N,N-Dimethylamino)butoxy)methyl-Sar]-3-cyclosporin |
| 416 | O | 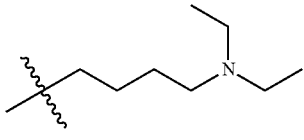 [SMILES: *CCCCN(CC)CC] | [(R)-(4-(N,N-Diethylamino)butoxy)methyl-Sar]-3-cyclosporin |
| 417 | O | 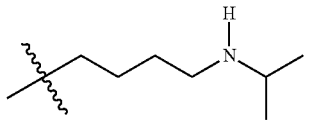 [SMILES: *CCCCNC(C)C] | [(R)-(4-(N-Isopropylamino)butoxy)methyl-Sar]-3-cyclosporin |
| 418 | O | 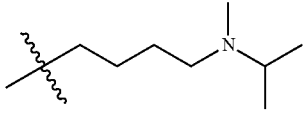 [SMILES: *CCCCN(C)C(C)C] | [(R)-(4-(N-Isopropyl-N-methylamino)butoxy)methyl-Sar]-3-cyclosporin |
| 419 | O | 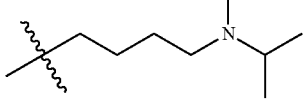 | [(R)-(4-(N-Ethyl-N-isopropylamino)butoxy)methyl-Sar]-3-cyclosporin |

TABLE 1-continued

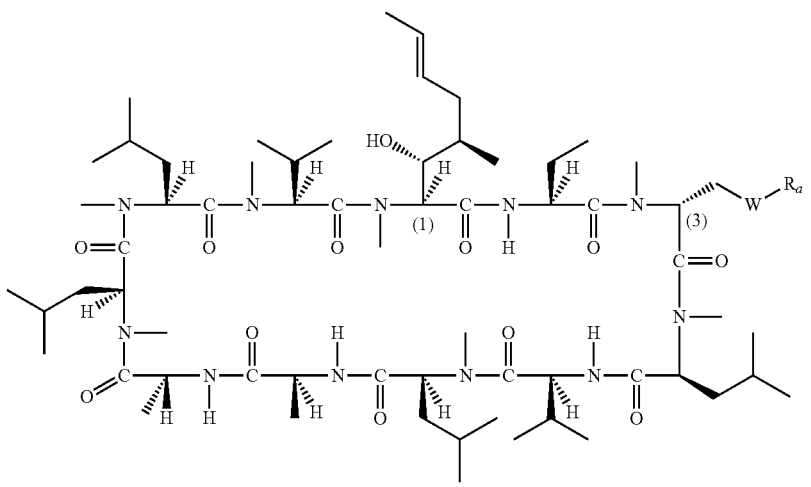

| Ex. No. | W | $R_a$ | Name |
|---|---|---|---|
| 420 | O | 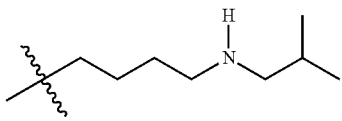 [SMILES: *CCCCNCC(C)C] | [(R)-(4-(N-Isobutylamino)butoxy)methyl-Sar]-3-cyclosporin |
| 421 | O | 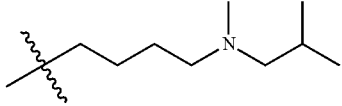 [SMILES: *CCCCN(C)CC(C)C] | [(R)-(4-(N-Isobutyl-N-methylamino)butoxy)methyl-Sar]-3-cyclosporin |
| 422 | O | 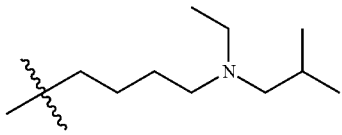 [SMILES: *CCCCN(CC)CC(C)C] | [(R)-(4-(N-Ethyl-N-isobutylamino)butoxy)methyl-Sar]-3-cyclosporin |
| 423 | O | 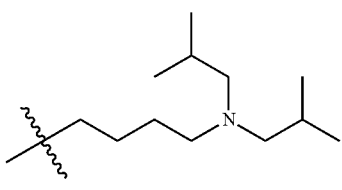 [SMILES: *CCCCN(CC(C)C)CC(C)C] | [(R)-(4-(N,N-Diisobutylamino)butoxy)methyl-Sar]-3-cyclosporin |
| 424 | O | 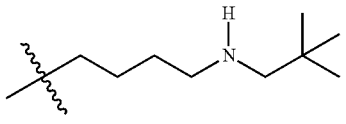 [SMILES: *CCCCNCC(C)(C)C] | [(R)-(4-(N-Neopentylamino)butoxy)methyl-Sar]-3-cyclosporin |
| 425 | O | 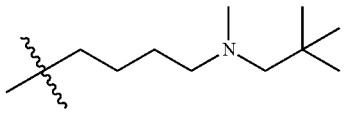 [SMILES: *CCCCN(C)CC(C)(C)C] | [(R)-(4-(N-Methyl-N-neopentylamino)butoxy)methyl-Sar]-3-cyclosporin |
| 426 | O | 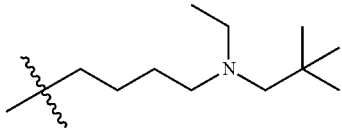 [SMILES: *CCCCN(CC)CC(C)(C)C] | [(R)-(4-(N-Ethyl-N-neopentylamino)butoxy)methyl-Sar]-3-cyclosporin |
| 427 | O | 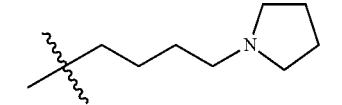 | [(R)-(4-(N-Pyrrolidinyl)butoxy)methyl-Sar]-3-cyclosporin |

TABLE 1-continued

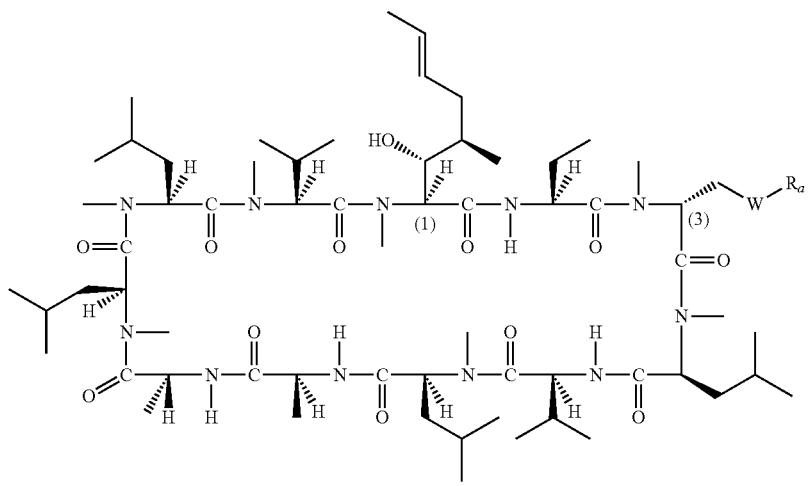

| Ex. No. | W | $R_a$ | Name |
|---|---|---|---|
| 428 | O | (CH2)4-N-thiazolidinyl | [(R)-(4-(N-Thiazolidinyl)butoxy)methyl-Sar]-3-cyclosporin |
| 429 | O | (CH2)4-N-oxazolidinyl | [(R)-(4-(N-Oxazolidinyl)butoxy)methyl-Sar]-3-cyclosporin |
| 430 | O | (CH2)4-N-piperidinyl | [(R)-(4-(N-Piperidinyl)butoxy)methyl-Sar]-3-cyclosporin |
| 431 | O | (CH2)4-N-morpholino | [(R)-(4-(N-Morpholino)butoxy)methyl-Sar]-3-cyclosporin |
| 432 | O | (CH2)4-N-thiomorpholino | [(R)-(4-(N-Thiomorpholino)butoxy)methyl-Sar]-3-cyclosporin |
| 433 | O | (CH2)4-N-piperazinyl | [(R)-(4-(N-Piperazinyl)butoxy)methyl-Sar]-3-cyclosporin |
| 434 | O | (CH2)4-N-(4-methylpiperazinyl) | [(R)-(4-(4-Methyl-N-piperazinyl)butoxy)methyl-Sar]-3-cyclosporin |

TABLE 1-continued

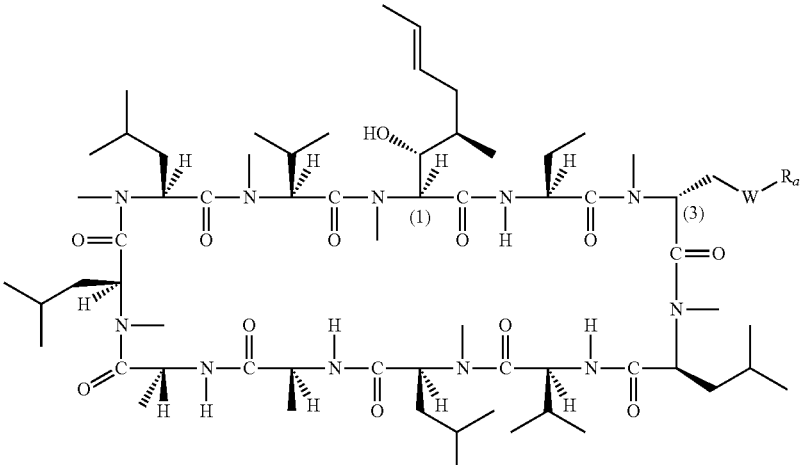

| Ex. No. | W | $R_a$ | Name |
|---|---|---|---|
| 435 | O | 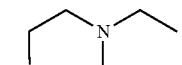 | [(R)-(4-(4-Ethyl-N-piperazinyl)butoxy)methyl-Sar]-3-cyclosporin |
| 436 | O | 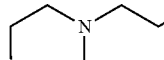 | [(R)-(4-(4-n-Propyl-N-piperazinyl)butoxy)methyl-Sar]-3-cyclosporin |
| 437 | O | 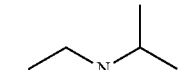 | [(R)-(4-(4-Isopropyl-N-piperazinyl)butoxy)methyl-Sar]-3-cyclosporin |
| 438 | O | 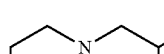 | [(R)-(4-(4-Isobutyl-N-piperazinyl)butoxy)methyl-Sar]-3-cyclosporin |
| 439 | O | 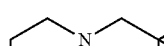 | [(R)-(4-(4-Neopentyl-N-piperazinyl)butoxy)methyl-Sar]-3-cyclosporin |
| 440 | O | 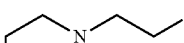 | [(R)-(4-(4-(2-Hydroxyethyl)-N-piperazinyl)butoxy)methyl-Sar]-3-cyclosporin |
| 441 | O | 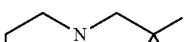 | [(R)-(4-(4-(2-Hydroxy-2-methylpropyl)-N-piperazinyl)butoxy)methyl-Sar]-3-cyclosporin |

TABLE 1-continued

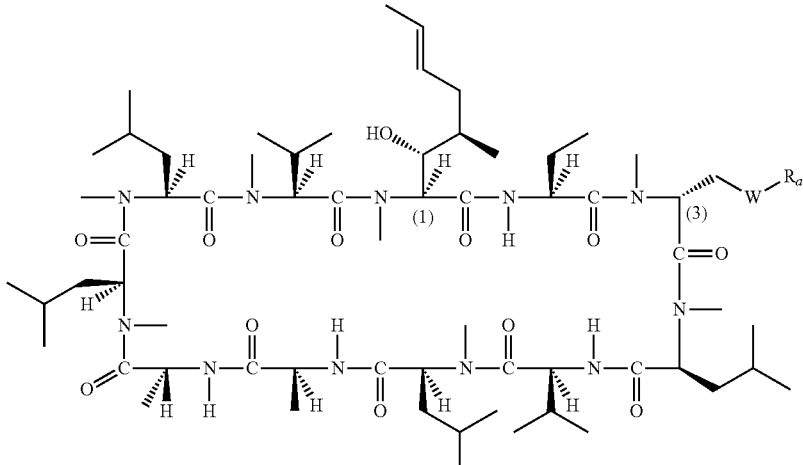

| Ex. No. | W | $R_a$ | Name |
|---|---|---|---|
| 442 | O | 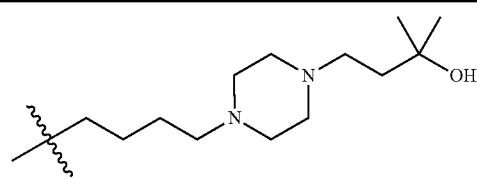 | [(R)-(4-(4-(3-Hydroxy-3-methylbutyl)-N-piperazinyl)butoxy)methyl-Sar]-3-cyclosporin |
| 443 | O | 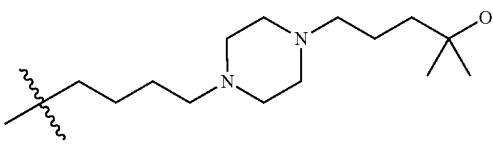 | [(R)-(4-(4-(4-Hydroxy-4-methylpentyl)-N-piperazinyl)butoxy)methyl-Sar]-3-cyclosporin |
| 444 | O | 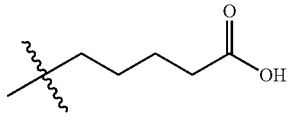 [SMILES: *CCCCC(=O)O] | [(R)-(4-Carboxybutoxy)methyl-Sar]-3-cyclosporin |
| 445 | O | 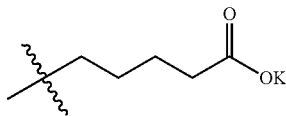 | [(R)-(4-Carboxybutoxy)methyl-Sar]-3-cyclosporin-potassium salt |
| 446 | O | 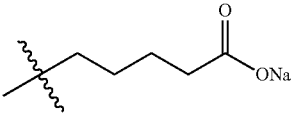 | [(R)-(4-Carboxybutoxy)methyl-Sar]-3-cyclosporin-sodium salt |
| 447 | O | 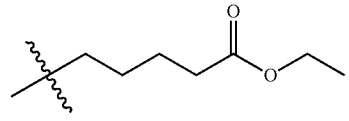 [SMILES: *CCCCC(=O)OCC] | [(R)-(4-(Ethoxycarbonyl)butoxy)methyl-Sar]-3-cyclosporin |
| 448 | O | 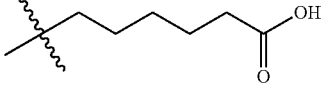 | [(R)-(5-(Carboxypentyl)oxy)methyl-Sar]-3-cyclosporin |
| 449 | O | 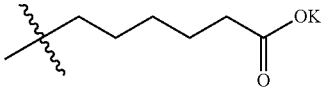 | [(R)-(5-(Carboxypentyl)oxy)methyl-Sar]-3-cyclosporin-potassium salt |

TABLE 1-continued

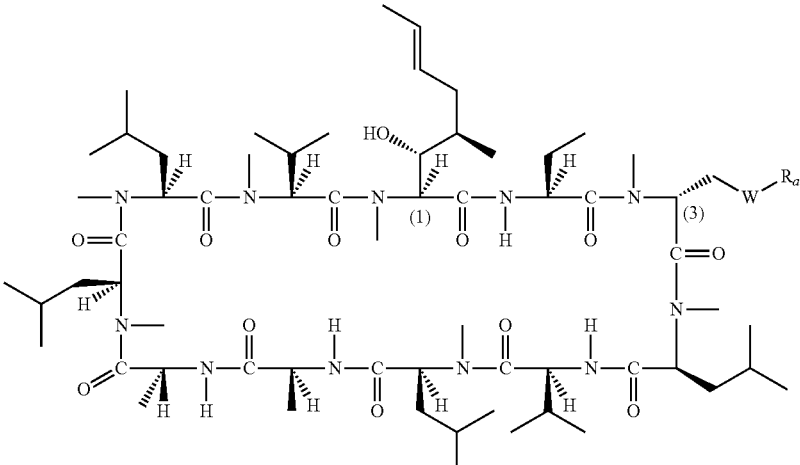

| Ex. No. | W | $R_a$ | Name |
|---|---|---|---|
| 450 | O |  | [(R)-(5-(Carboxypentyl)oxy)methyl-Sar]-3-cyclosporin-sodium salt |
| 451 | O | 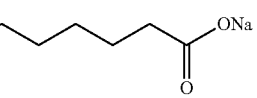 | [(R)-(((5-(Ethoxycarbonyl)pentyl)oxy)methyl-Sar]-3-cyclosporin |
| 452 | O |  | [(R)-(5-Carboxyheptyloxy)methyl-Sar]-3-cyclosporin |
| 453 | O | 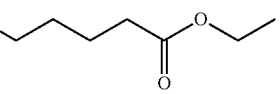 | [(R)-(5-Carboxyheptyloxy)methyl-Sar]-3-cyclosporin-potassium salt |
| 454 | O |  | [(R)-(5-Carboxyheptyloxy)methyl-Sar]-3-cyclosporin-sodium salt |
| 455 | O | 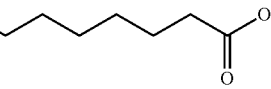 | [(R)-(5-(Ethoxycarbonyl)heptyloxy)methyl-Sar]-3-cyclosporin |
| 456 | O |  | [(R)-(5-Carboxyoctyloxy)methyl-Sar]-3-cyclosporin |
| 457 | O | 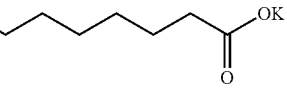 | [(R)-(5-Carboxyoctyloxy)methyl-Sar]-3-cyclosporin-potassium salt |
| 458 | O |  | [(R)-(5-Carboxyoctyloxy)methyl-Sar]-3-cyclosporin-potassium salt |

TABLE 1-continued

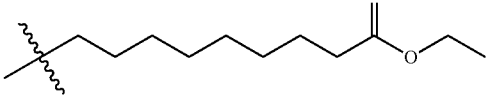

| Ex. No. | W | R_a | Name |
|---|---|---|---|
| 459 | O |  | [(R)-(4-(Ethoxycarbonyl)octyloxy)methyl-Sar]-3-cyclosporin |
| 460 | O |  | [(R)-(5-Carboxynonyloxy)methyl-Sar]-3-cyclosporin |
| 461 | O |  | [(R)-(5-Carboxynonyloxy)methyl-Sar]-3-cyclosporin-potassium salt |
| 462 | O | 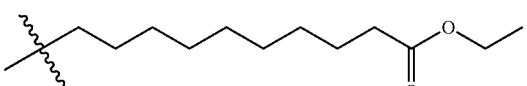 | [(R)-(5-Carboxynonyloxy)methyl-Sar]-3-cyclosporin-potassium salt |
| 463 | O |  | [(R)-(4-(Ethoxycarbonyl)nonyloxy)methyl-Sar]-3-cyclosporin |
| 464 | O |  | [(R)-((4,4'-Dicarboxy)butoxy)methyl-Sar]-3-cyclosporin |
| 465 | O | 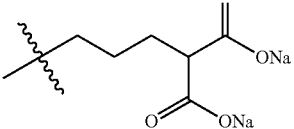 | [(R)-((4,4'-Dicarboxy)butoxy)methyl-Sar]-3-cyclosporin-dipotassium salt |
| 466 | O |  | [(R)-((4,4'-Dicarboxy)butoxy)methyl-Sar]-3-cyclosporin-disodium salt |

TABLE 1-continued

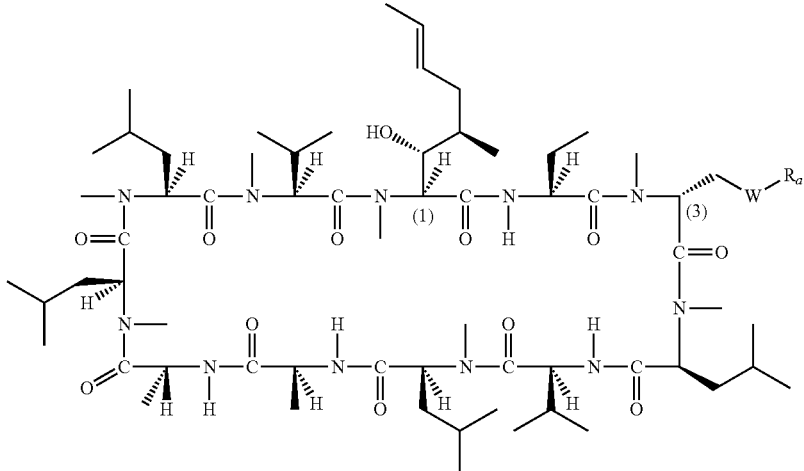

| Ex. No. | W | $R_a$ | Name |
|---|---|---|---|
| 467 | O | 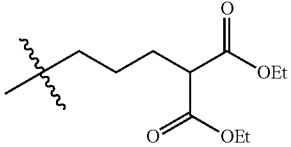 [SMILES: *CCCC(C(=O)OCC)C(=O)OCC] | [(R)-(4,4'-Di(ethoxycarbonyl)butoxy)methyl-Sar]-3-cyclosporin |
| 468 | O | 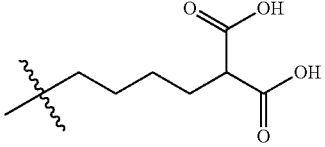 [SMILES: *CCCCC(C(=O)O)C(=O)O] | [(R)-((5,5'-Dicarboxy)pentyloxy)methyl-Sar]-3-cyclosporin |
| 469 | O | 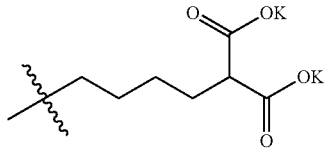 | [(R)-((5,5'-Dicarboxy)pentyloxymethyl-Sar]-3-cyclosporin-dipotassium salt |
| 470 | O | 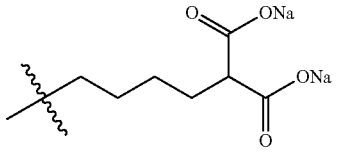 | [(R)-((5,5'-Dicarboxy)pentyloxy)methyl-Sar]-3-cyclosporin-disodium salt |
| 471 | O | 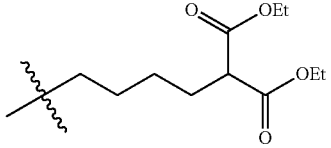 [SMILES: *CCCCC(C(=O)OCC)C(=O)OCC] | [(R)-(4,4'-Diethoxycarbonyl)pentyloxy)methyl-Sar]-3-cyclosporin |
| 472 | O |  | [(R)-((6,6'-Dicarboxy)hexyloxy)methyl-Sar]-3-cyclosporin |
| 473 | O |  | [(R)-((6,6'-Dicarboxy)hexyloxy)methyl-Sar]-3-cyclosporin-dipotassium salt |

TABLE 1-continued

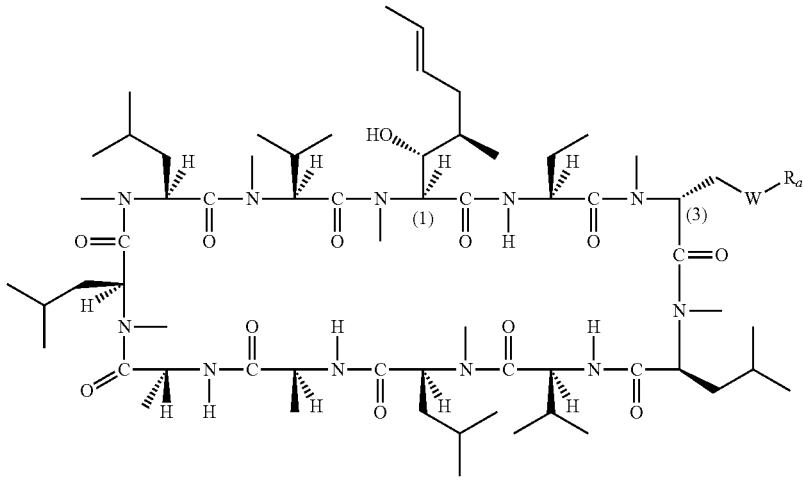

| Ex. No. | W | $R_a$ | Name |
|---|---|---|---|
| 474 | O | 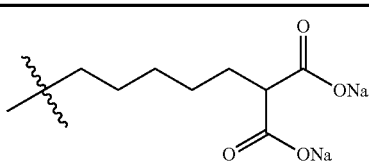 | [(R)-((6,6'-Dicarboxy)hexyloxy)methyl-Sar]-3-cyclosporin-disodium salt |
| 475 | O | 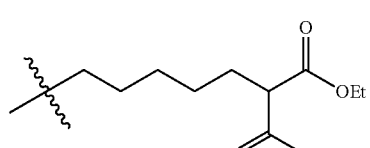 | [(R)-(6,6'-Diethoxycarbonyl)hexyloxy)methyl-Sar]-3-cyclosporin |
| 476 | O | 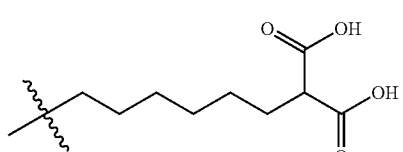 | [(R)-((7,7'-Dicarboxy)heptyloxy)methyl-Sar]-3-cyclosporin |
| 477 | O | 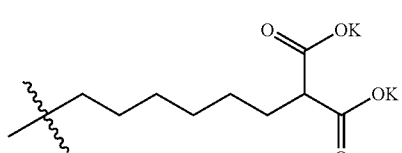 | [(R)-((7,7'-Dicarboxy)heptyloxy)methyl-Sar]-3-cyclosporin-dipotassium salt |
| 478 | O | 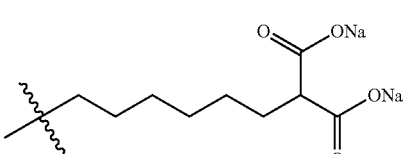 | [(R)-((7,7'-Dicarboxy)heptyloxy)methyl-Sar]-3-cyclosporin-disodium salt |
| 479 | O | 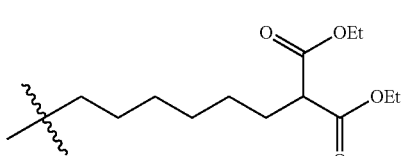 | [(R)-(7,7'-Diethoxycarbonyl)heptyloxy)methyl-Sar]-3-cyclosporin |
| 480 | O | 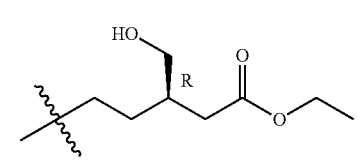 | [(R)-((R)-3-Hydroxymethyl-4-ethoxycarbonybutoxy)methyl-Sar]-3-cyclosporin |

TABLE 1-continued

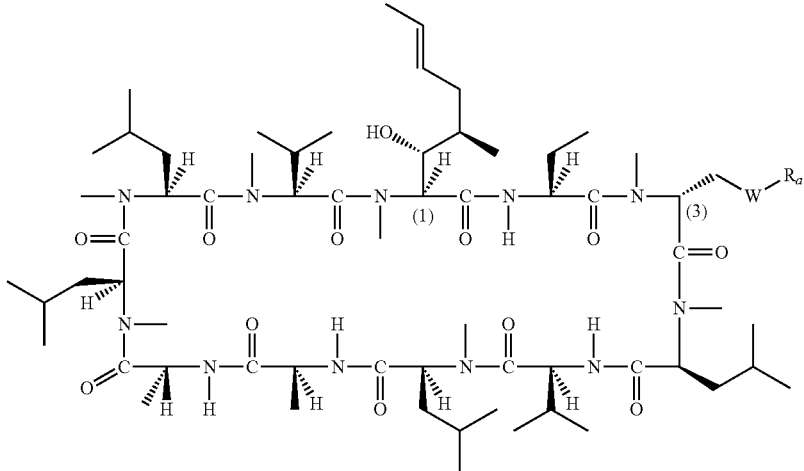

| Ex. No. | W | $R_a$ | Name |
|---|---|---|---|
| 481 | O | 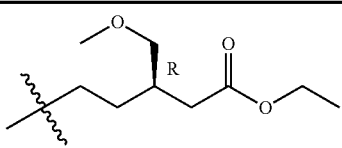 | [(R)-((R)-3-Methoxymethyl-4-ethoxycarbonybutoxy)methyl-Sar]-3-cyclosporin |
| 482 | O | 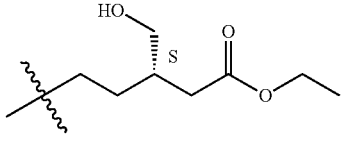 | [(R)-((S)-3-Hydroxymethyl-4-ethoxycarbonybutoxy)methyl-Sar]-3-cyclosporin |
| 483 | O | 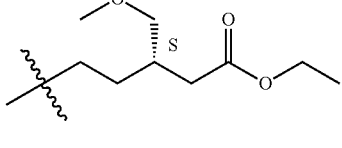 | [(R)-((S)-3-Methoxymethyl-4-ethoxycarbonybutoxy)methyl-Sar]-3-cyclosporin |
| 484 | O | 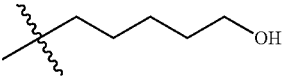 [SMILES: *CCCCCO] | [(R)-(5-Hydroxypentyloxy)methyl-Sar]-3-cyclosporin |
| 485 | O | 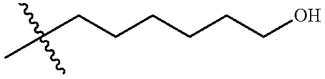 [SMILES: *CCCCCCO] | [(R)-(6-Hydroxyhexyloxy)methyl-Sar]-3-cyclosporin |
| 486 | O | 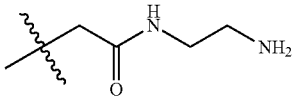 [SMILES: *CC(=O)NCCN] | [(R)-[(N-(2-Aminoethyl)carbamoyl)methoxy]methyl-Sar]-3-cyclosporin |
| 487 | O | 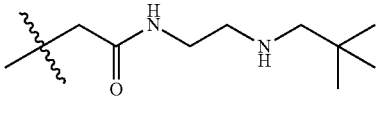 [SMILES: *CC(=O)NCCNCC(C)(C)C] | [(R)-[(N-(2-(Neopentylamino)ethyl)carbamoyl)methoxy]methyl-Sar]-3-cyclosporin |
| 488 | O | 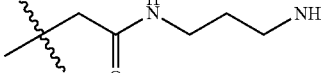 | [(R)-[(N-(3-Aminopropyl)carbamoyl)methoxy]methyl-Sar]-3-cyclosporin |
| 489 | O | 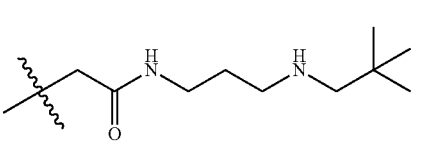 [SMILES: *CC(=O)NCCCNCC(C)(C)C] | [(R)-[(N-(3-(Neopentylamino)propyl)carbamoyl)methoxy]methyl-Sar]-3-cyclosporin |

TABLE 1-continued

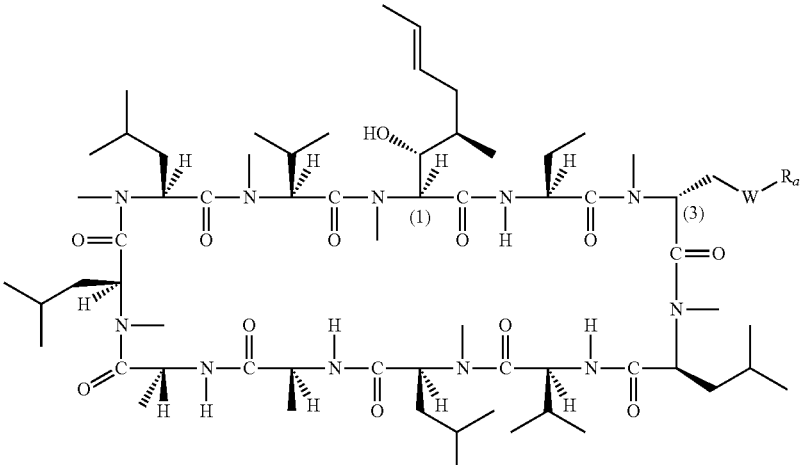

| Ex. No. | W | R_a | Name |
|---|---|---|---|
| 490 | O | 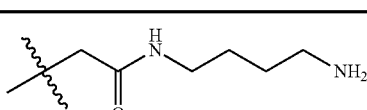 | [(R)-[(N-(4-Aminobutyl)carbamoyl)methoxy]methyl-Sar]-3-cyclosporin |
| 491 | O | 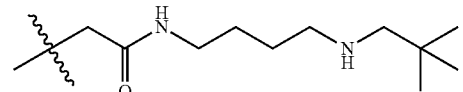 | [(R)-[(N-(4-(Neopentylamino)butyl)carbamoyl)methoxy]methyl-Sar]-3-cyclosporin |
| 492 | O | 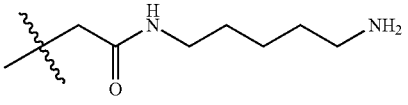 [SMILES: *CC(=O)NCCCCCN] | [(R)-[(N-(5-Aminopentyl)carbamoyl)methoxy]methyl-Sar]-3-cyclosporin |
| 493 | O | 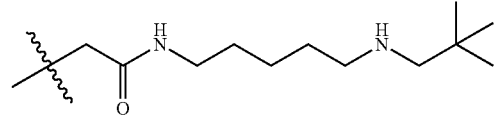 [SMILES: *CC(=O)NCCCCCNCC(C)(C)C] | [(R)-[(N-(5-(Neopentylamino)pentyl)carbamoyl)methoxy]methyl-Sar]-3-cyclosporin |
| 494 | O | 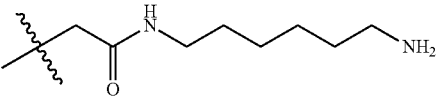 [SMILES: *CC(=O)NCCCCCCN] | [(R)-[(N-(6-Aminohexyl)carbamoyl)methoxy]methyl-Sar]-3-cyclosporin |
| 495 | O | 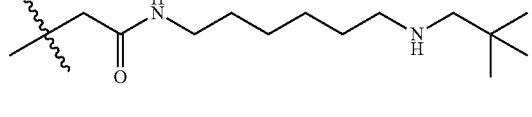 | [(R)-[(N-(6-(Neopentylamino)hexyl)carbamoyl)methoxy]methyl-Sar]-3-cyclosporin |
| 496 | O | 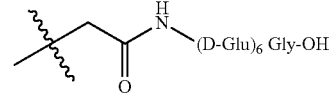 | [(R)-[([HO-Gly-(D-Glu)$_6$]carbamoyl)methoxy]methyl-Sar]-3-cyclosporin |
| 497 | O | 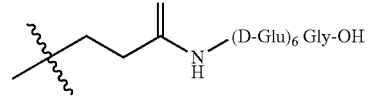 | [(R)-[([HO-Gly-(D-Glu)$_6$]carbamoyl)ethoxy]methyl-Sar]-3-cyclosporin |
| 498 | O | 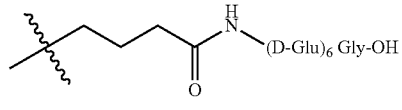 | [(R)-[([HO-Gly-(D-Glu)$_6$]carbamoyl)propoxy]methyl-Sar]-3-cyclosporin |

TABLE 1-continued

| Ex. No. | W | R$_a$ | Name |
|---|---|---|---|
| 499 | O | ~~~CH$_2$CH$_2$-O-CH$_2$-C(=O)-NH-(D-Glu)$_6$ Gly-OH | [(R)-((2-[([HO-Gly-(D-Glu)$_6$]carbamoyl)methoxy]ethoxy)methyl-Sar]-3-cyclosporin |
| 500 | O | ~~~(CH$_2$)$_3$-O-CH$_2$-C(=O)-NH-(D-Glu)$_6$ Gly-OH | [(R)-((3-[([HO-Gly-(D-Glu)$_6$]carbamoyl)methoxy]propoxy)methyl-Sar]-3-cyclosporin |
| 501 | O | ~~~(CH$_2$)$_4$-O-CH$_2$-C(=O)-NH-(D-Glu)$_6$ Gly-OH | [(R)-((4-[([HO-Gly-(D-Glu)$_6$]carbamoyl)methoxy]butoxy)methyl-Sar]-3-cyclosporin |
| 502 | O | ~~~(CH$_2$)$_5$-O-CH$_2$-C(=O)-NH-(D-Glu)$_6$ Gly-OH | [(R)-((5-[([HO-Gly-(D-Glu)$_6$]carbamoyl)methoxy]pentyloxy)methyl-Sar]-3-cyclosporin |
| 503 | O | ~~~(CH$_2$)$_6$-O-CH$_2$-C(=O)-NH-(D-Glu)$_6$ Gly-OH | [(R)-((6-[([HO-Gly-(D-Glu)$_6$]carbamoyl)methoxy]hexyloxy)methyl-Sar]-3-cyclosporin |
| 504 | O | (R)-CH(CH$_2$OH)-(CH$_2$)$_3$-imidazol-1-yl with tether | [(R)-(((R)-3-Hydroxymethyl-6-(imidazol-1-yl)hexyl)oxy)methyl-Sar]-3-cyclosporin |
| 505 | O | (S)-CH(CH$_2$OH)-(CH$_2$)$_3$-imidazol-1-yl with tether | [(R)-(((S)-3-Hydroxymethyl-6-(imidazo-1-yl)hexyl)oxy)methyl-Sar]-3-cyclosporin |
| 506 | O | (R)-CH(CH$_2$OH)-(CH$_2$)$_3$-morpholino with tether | [(R)-(((R)-3-Hydroxymethyl-6-morpholinohexyl)oxy)methyl-Sar]-3-cyclosporin |

TABLE 1-continued

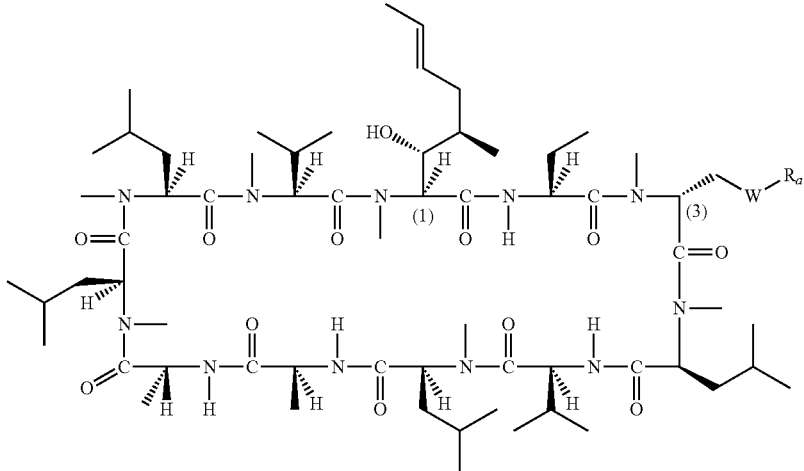

| Ex. No. | W | $R_a$ | Name |
|---|---|---|---|
| 507 | O | 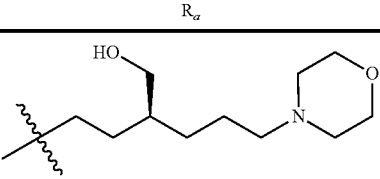 | [(R)-(((S)-3-Hydroxymethyl-6-morpholinohexyl)oxy)methyl-Sar]-3-cyclosporin |
| 508 | O | 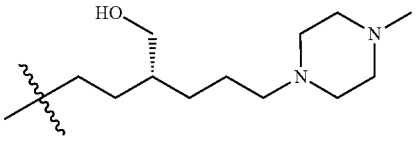 [SMILES: *CC[C@H](CO)CCCN1CCN(C)CC1] | [(R)-(((R)-3-Hydroxymethyl-6-(4-methylpiperazin-1-yl)hexyl)oxy)methyl-Sar]-3-cyclosporin |
| 509 | O | 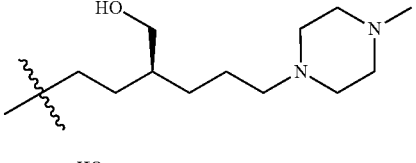 | [(R)-(((S)-3-Hydroxymethyl-6-(4-methylpiperazin-1-yl)hexyl)oxy)methyl-Sar]-3-cyclosporin |
| 510 | O | 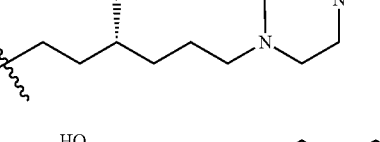 | [(R)-(((R)-3-Hydroxymethyl-6-(4-ethylpiperazin-1-yl)hexyl)oxy)methyl-Sar]-3-cyclosporin |
| 511 | O | 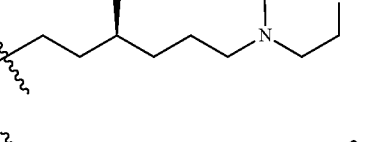 | [(R)-(((S)-3-Hydroxymethyl-6-(4-isopropylpiperazin-1-yl)hexyl)oxy)methyl-Sar]-3-cyclosporin |
| 512 | O | 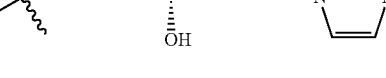 | [(R)-(((S)-4-Hydroxy-7-(imidazol-1-yl)heptyl)oxy)methyl-Sar]-3-cyclosporin |
| 513 | O | 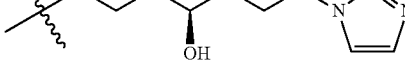 | [(R)-(((R)-4-Hydroxy-7-(imidazo-1-yl)heptyl)oxy)methyl-Sar]-3-cyclosporin |
| 514 | O | 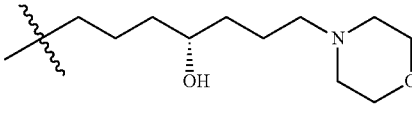 | [(R)-(((S)-4-Hydroxy-7-morpholinoheptyl)oxy)methyl-Sar]-3-cyclosporin |

TABLE 1-continued

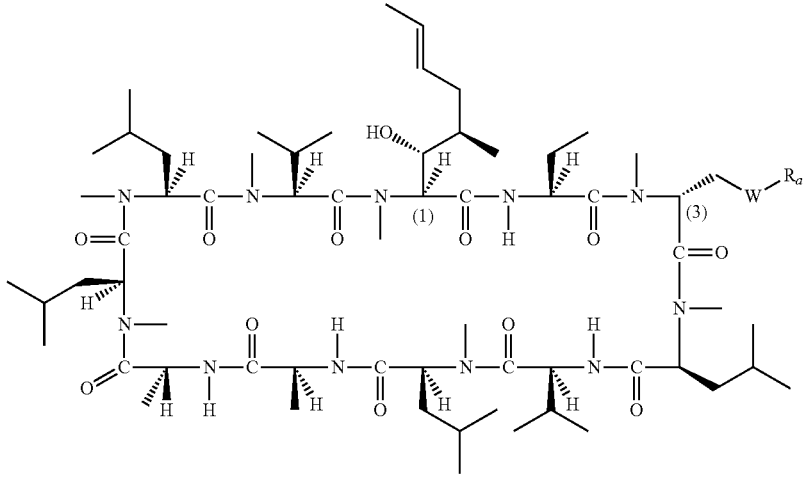

| Ex. No. | W | R$_a$ | Name |
|---|---|---|---|
| 515 | O | 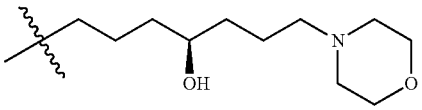 [SMILES: *CCC[C@H](O)CCCN1CCOCC1] | [(R)-(((R)-4-Hydroxy-7-morpholinoheptyl)oxy)methyl-Sar]-3-cyclosporin |
| 516 | O | 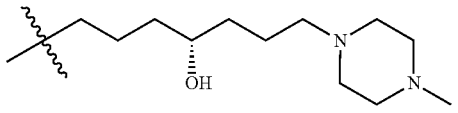 [SMILES: *CCC[C@@H](O)CCCN1CCN(C)CC1] | [(R)-(((S)-4-Hydroxy-7-(4-methylpiperazin-1-yl)heptyl)oxy)methyl-Sar]-3-cyclosporin |
| 517 | O | 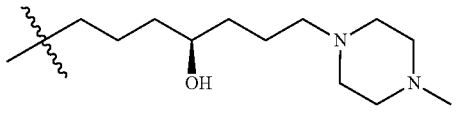 [SMILES: *CCC[C@H](O)CCCN1CCN(C)CC1] | [(R)-(((R)-4-Hydroxy-7-(4-methylpiperazin-1-yl)heptyl)oxy)methyl-Sar]-3-cyclosporin |
| 518 | O | 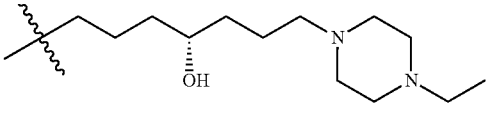 [SMILES: *CCC[C@@H](O)CCCN1CCN(CC)CC1] | [(R)-(((S)-4-Hydroxy-7-(4-ethylpiperazin-1-yl)heptylcyclos)oxy)methyl-Sar]-3-cyclosporin |
| 519 | O | 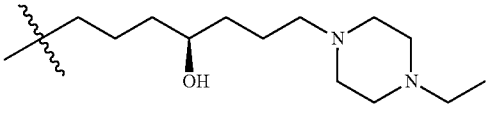 [SMILES: *CCC[C@H](O)CCCN1CCN(CC)CC1] | [(R)-(((R)-4-Hydroxy-7-(4-ethylpiperazin-1-yl)heptyl)oxy)methyl-Sar]-3-cyclosporin |
| 520 | CH$_2$ | —(COOEt)$_2$ | [(R)-2,2-Di(ethoxycarbonyl)ethyl)-Sar]-3-cyclosporin |
| 521 | CH$_2$ | —(COOH)$_2$ | [(R)-2,2-Di(carboxy)ethyl)-Sar]-3-cyclosporin |
| 522 | CH$_2$ | —(CH$_2$OH)$_2$ | [(R)-2,2-Di(hydroxylmethyl)ethyl)-Sar]-3-cyclosporin |

TABLE 2

| Ex. No. | W | $R_a$ | Name |
|---|---|---|---|
| 523 | S | (CH(CH3))-CH2-C(=O)-OH | [(S)-(Carboxymethylthio)methyl-Sar]-3-[(γ-hydroxy)-N-MeLeu]-4-cyclosporin |
| 524 | S | (CH(CH3))-CH2-C(=O)-OK | [(S)-(Carboxymethylthio)methyl-Sar]-3-[(γ-hydroxy)-N-MeLeu]-4-cyclosporin-potassium salt |
| 525 | S | (CH(CH3))-CH2-C(=O)-ONa | [(S)-(Carboxymethylthio)methyl-Sar]-3-[(γ-hydroxy)-N-MeLeu]-4-cyclosporin-sodium salt |
| 526 | S | (CH(CH3))-CH2-C(=O)-O-ethyl | [(S)-(Ethoxycarbonylmethylthio)methyl-Sar]-3-[(γ-hydroxy)-N-MeLeu]-4-cyclosporin |
| 527 | S | -C(CH3)2-OH | [(S)-(2-Hydroxy-2-methylpropylthio)methyl-Sar]-3-[(γ-hydroxy)-N-MeLeu]-4-cyclosporin |
| 528 | S | -CH2-CH2-O-CH3 | [(S)-(2-Methoxyethylthio)methyl-Sar]-3-[(γ-hydroxy)-N-MeLeu]-4-cyclosporin |
| 529 | S | -CH2-CH2-NH-isobutyl | [(S)-(2-(N-Isobutylamino)ethylthio)methyl-Sar]-3-[(γ-hydroxy)-N-MeLeu]-4-cyclosporin |
| 530 | S | -CH2-CH2-N(CH3)-isobutyl | [(S)-(2-(N-Isobutyl-N-methylamino)ethylthio)methyl-Sar]-3-[(γ-hydroxy)-N-MeLeu]-4-cyclosporin |
| 531 | S | -CH2-CH2-N(ethyl)-isobutyl | [(S)-(2-(N-Ethyl-N-isobutylamino)ethylthio)methyl-Sar]-3-[(γ-hydroxy)-N-MeLeu]-4-cyclosporin |

TABLE 2-continued

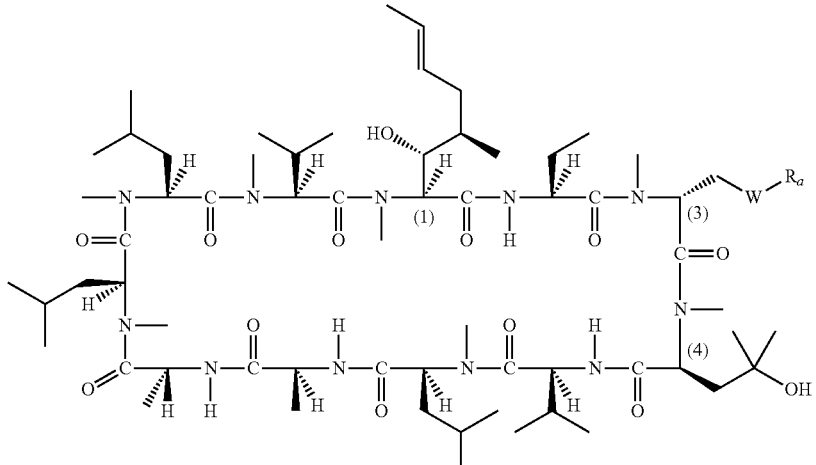

| Ex. No. | W | R$_a$ | Name |
|---|---|---|---|
| 532 | S | 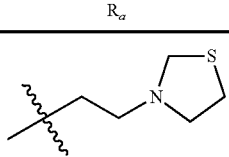 | [(S)-(2-(N-Thiazolidinyl)ethylthio)methyl-Sar]-3-[(γ-hydroxy)-N-MeLeu]-4-cyclosporin |
| 533 | S | 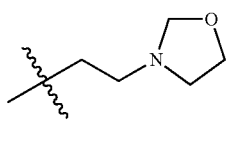 [SMILES: *CCN1CCOC1] | [(S)-(2-(N-Oxazolidinyl)ethylthio)methyl-Sar]-3-[(γ-hydroxy)-N-MeLeu]-4-cyclosporin |
| 534 | S | 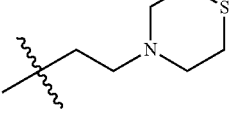 | [(S)-(2-(N-Thiomorpholino)ethylthio)methyl-Sar]-3-[(γ-hydroxy)-N-MeLeu]-4-cyclosporin |
| 535 | S | 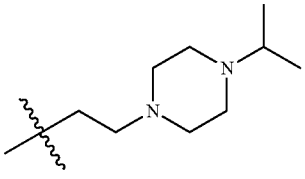 [SMILES: *CCN1CCN(C(C)C)CC1] | [(S)-(2-(4-Isopropyl-N-piperazinyl)ethylthio)methyl-Sar-3-[(γ-hydroxy)-N-MeLeu]-4-cyclosporin |
| 536 | S | 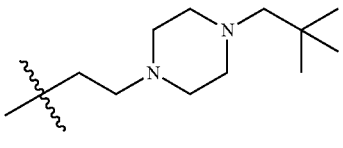 [SMILES: *CCN1CCN(CC(C)(C)C)CC1] | [(S)-(2-(4-Neopentyl-N-piperazinyl)ethylthio)methyl-Sar-3-[(γ-hydroxy)-N-MeLeu]-4-cyclosporin |
| 537 | S | 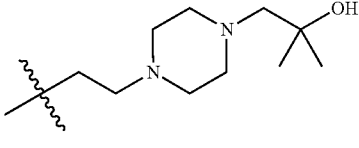 [SMILES: *CCN1CCN(CC(C)(C)O)CC1] | [(S)-(2-(4-(2-Hydroxy-2-methylethyl)-N-piperazinyl)propylthio)methyl-Sar]-3-[(γ-hydroxy)-N-MeLeu]-4-cyclosporin |
| 538 | S | 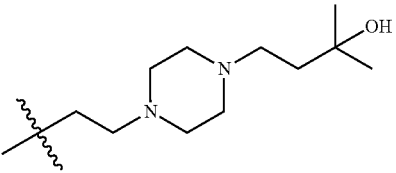 [SMILES: *CCN1CCN(CCC(C)(C)O)CC1] | [(S)-(2-(4-(3-Hydroxy-3-methylbutyl)-N-piperazinyl)ethylthio)methyl-Sar]-3-[(γ-hydroxy)-N-MeLeu]-4-cyclosporin |

TABLE 2-continued

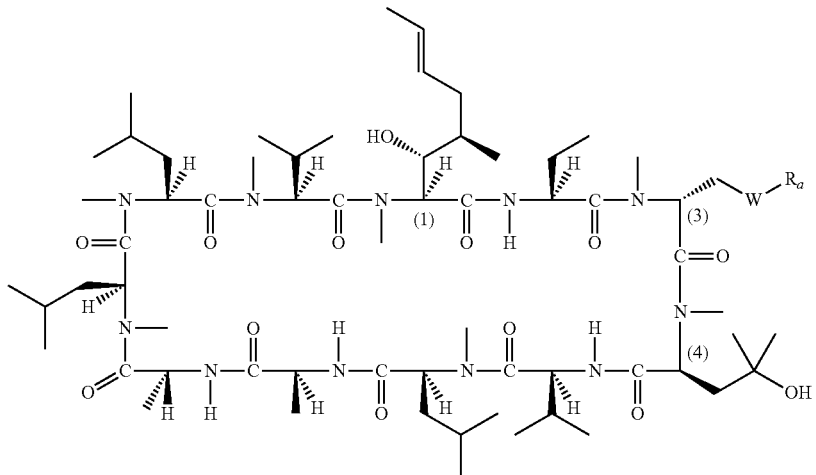

| Ex. No. | W | $R_a$ | Name |
|---|---|---|---|
| 539 | S | 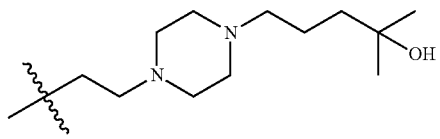 [SMILES: *CCN1CCN(CCCC(C)(C)O)CC1] | [(S)-(2-(4-(4-Hydroxy-4-methylpentyl)-N-piperazinyl)ethylthio)methyl-Sar]-3-[(γ-hydroxy)-N-MeLeu]-4-cyclosporin |
| 540 | S | 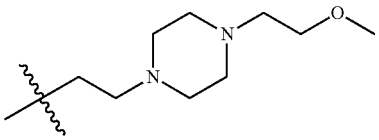 [SMILES: *CCN1CCN(CCOC)CC1] | [(S)-(2-(4-(2-Methoxyethyl)-N-piperazinyl)ethylthio)methyl-Sar]-3-[(γ-hydroxy)-N-MeLeu]-4-cyclosporin |
| 541 | S | 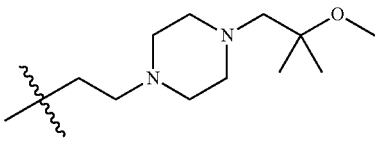 [SMILES: *CCN1CCN(CC(C)(C)OC)CC1] | [(S)-(2-(4-(2-Methoxy-2-methylpropyl)-N-piperazinyl)ethylthio)methyl-Sar]-3-[(γ-hydroxy)-N-MeLeu]-4-cyclosporin |
| 542 | S | 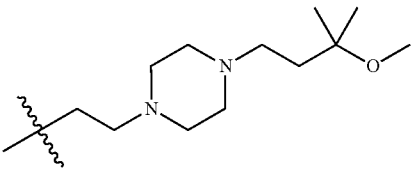 [SMILES: *CCN1CCN(CCC(C)(C)OC)CC1] | [(S)-(2-(4-(3-Methoxy-3-methylbutyl)-N-piperazinyl)ethylthio)methyl-Sar]-3-[(γ-hydroxy)-N-MeLeu]-4-cyclosporin |
| 543 | S | 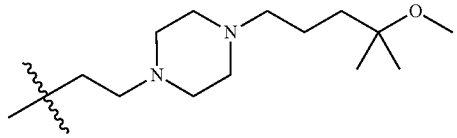 [SMILES: *CCN1CCN(CCCC(C)(C)OC)CC1] | [(S)-(2-(4-(4-Methoxy-4-methylpentyl)-N-piperazinyl)ethylthio)methyl-Sar]-3-[(γ-hydroxy)-N-MeLeu]-4-cyclosporin |
| 544 | S | 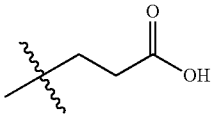 [SMILES: *CCC(=O)O] | [(S)-(2-Carboxyethylthio)methyl-Sar]-3-[(γ-hydroxy)-N-MeLeu]-4-cyclospori |
| 545 | S | 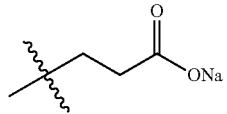 | [(S)-(2-Carboxyethylthio)methyl-Sar]-3-[(γ-hydroxy)-N-MeLeu]-4-cyclospori-sodium salt |

TABLE 2-continued

| Ex. No. | W | R$_a$ | Name |
|---|---|---|---|
| 546 | S | (ethyl ester of propanoate) | [(S)-((2-Ethoxycarbonyl)ethylthio)methyl-Sar]-3-[(γ-hydroxy)-N-MeLeu]-4-cyclospori |
| 547 | S | propyl-N(Me)(iPr) | [(S)-(3-(N-Isopropyl-N-methylamino)propylthio)methyl-Sar]-3-[(γ-hydroxy)-N-MeLeu]-4-cyclosporin |
| 548 | S | propyl-N(Me)(iBu) | [(S)-(3-(N-Isobutyl-N-methylamino)propylthio)methyl-Sar]-3-[(γ-hydroxy)-N-MeLeu]-4-cyclosporin |
| 549 | S | propyl-N(Et)(iBu) | [(S)-(3-(N-Isobutyl-N-ethylamino)propylthio)methyl-Sar]-3-[(γ-hydroxy)-N-MeLeu]-4-cyclosporin |
| 550 | S | propyl-N(Me)(neopentyl) | [(S)-(3-(N-Methyl-N-Neopentylamino)propylthio)methyl-Sar]-3-[(γ-hydroxy)-N-MeLeu]-4-cyclosporin |
| 551 | S | propyl-N(Et)(neopentyl) | [(S)-(3-(N-Ethyl-N-Neopentylamino)propylthio)methyl-Sar]-3-[(γ-hydroxy)-N-MeLeu]-4-cyclosporin |
| 552 | S | propyl-thiazolidinyl | [(S)-(3-(N-Thiazolidinyl)propylthio)methyl-Sar]-3-[(γ-hydroxy)-N-MeLeu]-4-cyclosporin |
| 553 | S | propyl-oxazolidinyl | [(S)-(3-(N-Oxazolidinyl)propylthio)methyl-Sar]-3-[(γ-hydroxy)-N-MeLeu]-4-cyclosporin |
| 554 | S | propyl-piperazinyl-N-ethyl-OH | [(S)-(3-(4-(2-Hydroxyethyl)-N-piperazinyl)propylthio)methyl-Sar]-3-[(γ-hydroxy)-N-MeLeu]-4-cyclosporin |

TABLE 2-continued

| Ex. No. | W | R$_a$ | Name |
|---|---|---|---|
| 555 | S | (3-piperazinyl-propyl with 2-hydroxy-2-methylpropyl on N) | [(S)-(3-(4-(2-Hydroxy-2-methylpropyl)-N-piperazinyl)propylthio)methyl-Sar]-3-[(γ-hydroxy)-N-MeLeu]-4-cyclosporin |
| 556 | S | (3-piperazinyl-propyl with 3-hydroxy-3-methylbutyl on N) | [(S)-(3-(4-(3-Hydroxy-3-methylbutyl)-N-piperazinyl)propylthio)methyl-Sar]-3-[(γ-hydroxy)-N-MeLeu]-4-cyclosporin |
| 557 | S | (3-piperazinyl-propyl with 4-hydroxy-4-methylpentyl on N) | [(S)-(3-(4-(4-Hydroxy-4-methylpentyl)-N-piperazinyl)propylthio)methyl-Sar]-3-[(γ-hydroxy)-N-MeLeu]-4-cyclosporin |
| 558 | S | (3-piperazinyl-propyl with 2-methoxyethyl on N) | [(S)-(3-(4-(2-Methoxyethyl)-N-piperazinyl)propylthio)methyl-Sar]-3-[(γ-hydroxy)-N-MeLeu]-4-cyclosporin |
| 559 | S | (3-piperazinyl-propyl with 2-methoxy-2-methylpropyl on N) | [(S)-(3-(4-(2-Methoxy-2-methylpropyl)-N-piperazinyl)propylthio)methyl-Sar]-3-[(γ-hydroxy)-N-MeLeu]-4-cyclosporin |
| 560 | S | (3-piperazinyl-propyl with 3-methoxy-3-methylbutyl on N) | [(S)-(3-(4-(3-Methoxy-3-methylbutyl)-N-piperazinyl)propylthio)methyl-Sar]-3-[(γ-hydroxy)-N-MeLeu]-4-cyclosporin |
| 561 | S | (3-piperazinyl-propyl with 4-methoxy-4-methylpentyl on N) | [(S)-(3-(4-(4-Methoxy-4-methylpentyl)-N-piperazinyl)propylthio)methyl-Sar]-3-[(γ-hydroxy)-N-MeLeu]-4-cyclosporin |
| 562 | S | (carboxypropyl) | [(S)-(3-Carboxypropylthio)methyl-Sar]-3-[(γ-hydroxy)-N-MeLeu]-4-cyclosporin |

TABLE 2-continued

| Ex. No. | W | $R_a$ | Name |
|---|---|---|---|
| 563 | S | (3-carboxypropylthio, K salt) | [(S)-(3-Carboxypropylthio)methyl-Sar]-3-[(γ-hydroxy)-N-MeLeu]-4-cyclosporin-potassium salt |
| 564 | S | (3-carboxypropylthio, Na salt) | [(S)-(3-Carboxypropylthio)methyl-Sar]-3-[(γ-hydroxy)-N-MeLeu]-4-cyclosporin-sodium salt |
| 565 | S | (3-ethoxycarbonylpropylthio) | [(S)-(3-Ethoxycarbonylpropylthio)methyl-Sar]-3-[(γ-hydroxy)-N-MeLeu]-4-cyclosporin |
| 566 | S | (3-isobutoxycarbonylpropylthio) | [(S)-(3-Isobutoxycarbonylpropylthio)methyl-Sar]-3-[(γ-hydroxy)-N-MeLeu]-4-cyclosporin |
| 567 | S | (5-hydroxy-2-methylpentan-2-yl)thio | [(S)-((5-Hydroxy-2-methylpentan-2-yl)thio)methyl-Sar]-3-[(γ-hydroxy)-N-MeLeu]-4-cyclosporin |
| 568 | S | (4-hydroxy-2,2-dimethylbutyl)thio | [(S)-((4-Hydroxy-2,2-dimethylbutyl)thio)methyl-Sar]-3-[(γ-hydroxy)-N-MeLeu]-4-cyclosporin |
| 569 | S | (4-hydroxy-3,3-dimethylbutyl)thio | [(S)-((4-Hydroxy-3,3-dimethylbutyl)thio)methyl-Sar]-3-[(γ-hydroxy)-N-MeLeu]-4-cyclosporin |
| 570 | S | (4-methoxy-4-methylpentyl)thio | [(S)-(4-Methoxy-4-methylpentylthio)methyl-Sar]-3-[(γ-hydroxy)-N-MeLeu]-4-cyclosporin |
| 571 | S | 3-(1-hydroxycyclopropyl)propylthio | [(S)-(3-(1-Hydroxycyclopropyl)propylthio)methyl-Sar]-3-[(γ-hydroxy)-N-MeLeu]-4-cyclosporin |
| 572 | S | (2-(1-(hydroxymethyl)cyclopropyl)ethyl)thio | [(S)-(((2-(1-(Hydroxymethyl)cyclopropyl)ethyl)thio)methyl-Sar]-3-[(γ-hydroxy)-N-MeLeu]-4-cyclosporin |

TABLE 2-continued

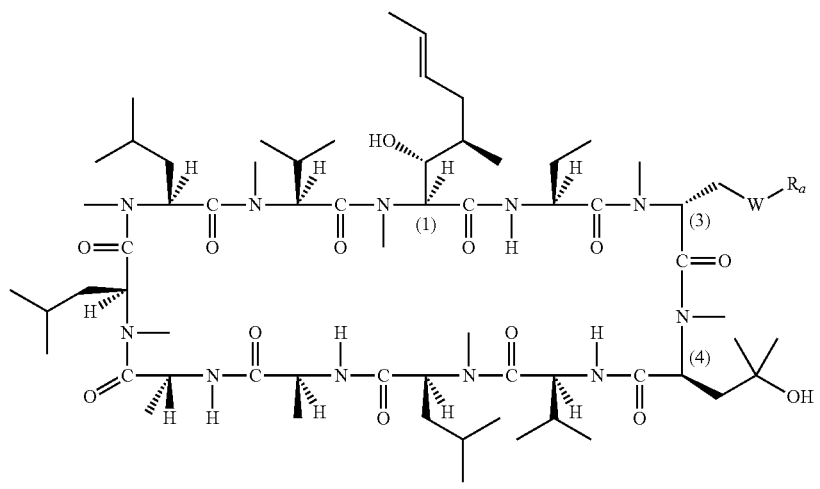

| Ex. No. | W | $R_a$ | Name |
|---|---|---|---|
| 573 | S | (1-(2-hydroxyethyl)cyclopropyl)methyl | [(S)-(((1-(2-Hydroxyethyl)cyclopropyl)methyl)thio)methyl-Sar]-3-[(γ-hydroxy)-N-MeLeu]-4-cyclosporin |
| 574 | S | (1-(3-hydroxypropyl)cyclopropyl) | [(S)-((1-(3-Hydroxypropyl)cyclopropyl)thio)methyl-Sar]-3-[(γ-hydroxy)-N-MeLeu]-4-cyclosporin |
| 575 | S | (S)-4-hydroxyhexyl | [(S)-((S)-4-Hydroxyhexylthio)methyl-Sar]-3-[(γ-hydroxy)-N-MeLeu]-4-cyclosporin |
| 576 | S | (R)-4-hydroxyhexyl | [(S)-((R)-4-Hydroxyhexylthio)methyl-Sar]-3-[(γ-hydroxy)-N-MeLeu]-4-cyclosporin |
| 577 | S | (S)-3-(hydroxymethyl)pentyl | [(S)-(((S)-3-(Hydroxymethyl)pentyl)thio)methyl-Sar]-3-[(γ-hydroxy)-N-MeLeu]-4-cyclosporin |
| 578 | S | (R)-3-(hydroxymethyl)pentyl | [(S)-(((R)-3-(Hydroxymethyl)pentyl)thio)methyl-Sar]-3-[(γ-hydroxy)-N-MeLeu]-4-cyclosporin |
| 579 | S | (S)-2-ethyl-4-hydroxybutyl | [(S)-(((S)-2-Ethyl-4-hydroxybutyl)thio)methyl-Sar]-3-[(γ-hydroxy)-N-MeLeu]-4-cyclosporin |
| 580 | S | (R)-2-ethyl-4-hydroxybutyl | [(S)-(((R)-2-Ethyl-4-hydroxybutyl)thio)methyl-Sar]-3-[(γ-hydroxy)-N-MeLeu]-4-cyclosporin |
| 581 | S | (S)-4,5-dihydroxypentyl | [(S)-(((S)-4,5-Dihydroxy-pentyl)thio)methyl-Sar]-3-[(γ-hydroxy)-N-MeLeu]-4-cyclosporin |

TABLE 2-continued

| Ex. No. | W | R$_a$ | Name |
|---|---|---|---|
| 582 | S | (pentyl with (R)-OH at 4, CH$_2$OH at 5) | [(S)-(((R)-4,5-Dihydroxy-pentyl)thio)methyl-Sar]-3-[(γ-hydroxy)-N-MeLeu]-4-cyclosporin |
| 583 | S | (4-methylpentyl with (S)-OH at 4, CH$_2$OH) | [(S)-(((S)-4,5-Dihydroxy-4-methylpentyl)thio)methyl-Sar]-3-[(γ-hydroxy)-N-MeLeu]-4-cyclosporin |
| 584 | S | (4-methylpentyl with (R)-OH at 4, CH$_2$OH) | [(S)-(((R)-4,5-Dihydroxy-4-methylpentyl)thio)methyl-Sar]-3-[(γ-hydroxy)-N-MeLeu]-4-cyclosporin |
| 585 | S | (hexyl with (R)-OH at 4, OH at 6) | [(S)-(((R)-4,6-Dihydroxyhexyl)thio)methyl-Sar]-3-[(γ-hydroxy)-N-MeLeu]-4-cyclosporin |
| 586 | S | (hexyl with (S)-OH at 4, OH at 6) | [(S)-(((S)-4,6-Dihydroxyhexyl)thio)methyl-Sar]-3-[(γ-hydroxy)-N-MeLeu]-4-cyclosporin |
| 587 | S | (pentyl with (R)-CH$_2$OH at 3, OH at 5) | [(S)-(((R)-5-Hydroxy-3-(hydroxymethyl)pentyl)thio)methyl-Sar]-3-[(γ-hydroxy)-N-MeLeu]-4-cyclosporin |
| 588 | S | (pentyl with (S)-CH$_2$OH at 3, OH at 5) | [(S)-(((S)-5-Hydroxy-3-(hydroxymethyl)pentyl)thio)methyl-Sar]-3-[(γ-hydroxy)-N-MeLeu]-4-cyclosporin |
| 589 | S | (butyl with 2-(2-hydroxyethyl), 4-OH) | [(S)-((4-Hydroxy-2-(2-hydroxyethyl)butyl)thio)methyl-Sar]-3-[(γ-hydroxy)-N-MeLeu]-4-cyclosporin |

TABLE 2-continued

| Ex. No. | W | $R_a$ | Name |
|---|---|---|---|
| 590 | S | (4-hydroxymethyl-pent-4-en-1-yl) | [(S)-((4-(Hydroxymethyl)pent-4-en-1-yl)thio)methyl)-Sar]-3-[(γ-hydroxy)-N-MeLeu]-4-cyclosporin |
| 591 | S | (5-hydroxy-3-methylenepentyl) | [(S)-((5-Hydroxy-3-methylenepentyl)thio)methyl)-Sar]-3-[(γ-hydroxy)-N-MeLeu]-4-cyclosporin |
| 592 | S | (5-hydroxy-2-methylenepentyl) | [(S)-((5-Hydroxy-2-methylenepentyl)thio)methyl)-Sar]-3-[(γ-hydroxy)-N-MeLeu]-4-cyclosporin |
| 593 | S | (2-(2-(hydroxymethyl)oxiran-2-yl)ethyl) | [(S)-((2-(2-(Hydroxymethyl)oxiran-2-yl)ethyl)thio)methyl-Sar]-3-[(γ-hydroxy)-N-MeLeu]-4-cyclosporin |
| 594 | S | ((2-(2-hydroxyethyl)oxiran-2-yl)methyl) | [(S)-(((2-(2-Hydroxyethyl)oxiran-2-yl)methyl)thio)methyl-Sar]-3-[(γ-hydroxy)-N-MeLeu]-4-cyclosporin |
| 595 | S | (3-(3-hydroxyoxetan-3-yl)propyl) | [(S)-((3-(3-Hydroxyoxetan-3-yl)propyl)thio)methyl)-Sar]-3-[(γ-hydroxy)-N-MeLeu]-4-cyclosporin |
| 596 | S | (4,5-dihydroxy-4-(hydroxymethyl)pentyl) | [(S)-((4,5-Dihydroxy-4-(hydroxymethyl)pentyl)thio)methyl-Sar]-3-[(γ-hydroxy)-N-MeLeu]-4-cyclosporin |
| 597 | S | (3-(2-(hydroxymethyl)oxiran-2-yl)propyl) | [(S)-((3-(2-(Hydroxymethyl)oxiran-2-yl)propyl)thio)methyl-Sar]-3-[(γ-hydroxy)-N-MeLeu]-4-cyclosporin |
| 598 | S | (2-(2-(2-hydroxyethyl)oxiran-2-yl)ethyl) | [(S)-((2-(2-(2-Hydroxyethyl)oxiran-2-yl)ethyl)thio)methyl-Sar]-3-[(γ-hydroxy)-N-MeLeu]-4-cyclosporin |

TABLE 2-continued

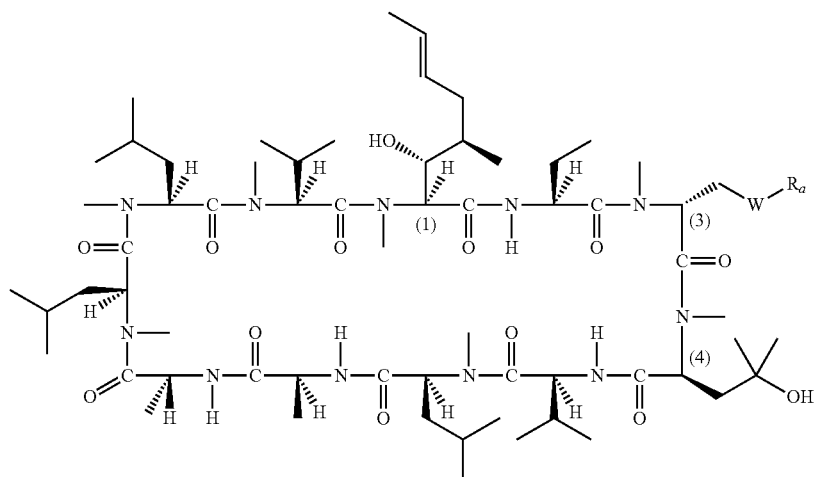

| Ex. No. | W | R_a | Name |
|---|---|---|---|
| 599 | S | (2-(3-hydroxypropyl)oxiran-2-yl)methyl group | [(S)-(((2-(3-Hydroxypropyl)oxiran-2-yl)methyl)thio)methyl-Sar]-3-[(γ-hydroxy)-N-MeLeu]-4-cyclosporin |
| 600 | S | 5-hydroxy-4-oxopentyl-like group | [(S)-((5-Hydroxy-4-oxohexyl)thio)methyl-Sar]-3-[(γ-hydroxy)-N-MeLeu]-4-cyclosporin |
| 601 | S | 6-hydroxy-5-oxohexyl group | [(S)-((6-Hydroxy-5-oxohexyl)thio)methyl-Sar]-3-[(γ-hydroxy)-N-MeLeu]-4-cyclosporin |
| 602 | S | alternative 6-hydroxy-5-oxohexyl group | [(S)-((6-Hydroxy-5-oxohexyl)thio)methyl-Sar]-3-[(γ-hydroxy)-N-MeLeu]-4-cyclosporin |
| 603 | S | (R)-4-hydroxy-5-(pyrrolidin-1-yl)pentyl | [(S)-(((R)-4-Hydroxy-5-(pyrrolidin-1-yl)pentyl)thio)methyl-Sar]-3-[(γ-hydroxy)-N-MeLeu]-4-cyclosporin |
| 604 | S | (S)-4-hydroxy-5-(pyrrolidin-1-yl)pentyl | [(S)-(((S)-4-Hydroxy-5-(pyrrolidin-1-yl)pentyl)thio)methyl-Sar]-3-[(γ-hydroxy)-N-MeLeu]-4-cyclosporin |
| 605 | S | (R)-4-hydroxy-6-(pyrrolidin-1-yl)hexyl | [(S)-(((R)-4-Hydroxy-6-(pyrrolidin-1-yl)hexyl)thio)methyl-Sar]-3-[(γ-hydroxy)-N-MeLeu]-4-cyclosporin |
| 606 | S | (S)-4-hydroxy-6-(piperidin-1-yl)hexyl | [(S)-(((S)-4-Hydroxy-6-(piperidin-1-yl)hexyl)thio)methyl-Sar]-3-[(γ-hydroxy)-N-MeLeu]-4-cyclosporin |
| 607 | S | (R)-4-hydroxy-5-(imidazol-1-yl)pentyl | [(S)-(((R)-4-Hydroxy-5-(imidazol-1-yl)pentyl)thio)methyl-Sar]-3-[(γ-hydroxy)-N-MeLeu]-4-cyclosporin |

TABLE 2-continued

| Ex. No. | W | $R_a$ | Name |
|---|---|---|---|
| 608 | S | (S)-5-hydroxy branched chain with imidazole | [(S)-(((S)-4-Hydroxy-5-(imidazo-1-yl)pentyl)thio)methyl-Sar]-3-[(γ-hydroxy)-N-MeLeu]-4-cyclosporin |
| 609 | S | (R)-4-hydroxy branched chain with imidazole | [(S)-(((R)-4-Hydroxy-6-(imidazo-1-yl)hexyl)thio)methyl-Sar]-3-[(γ-hydroxy)-N-MeLeu]-4-cyclosporin |
| 610 | S | (S)-4-hydroxy branched chain with imidazole | [(S)-(((S)-4-Hydroxy-6-(imidazo-1-yl)hexyl)thio)methyl-Sar]-3-[(γ-hydroxy)-N-MeLeu]-4-cyclosporin |
| 611 | S | (R)-3-hydroxymethyl branched chain with imidazole | [(S)-(((R)-3-Hydroxymethyl-4-(imidazol-1-yl)butyl)thio)methyl-Sar]-3-[(γ-hydroxy)-N-MeLeu]-4-cyclosporin |
| 612 | S | (S)-3-hydroxymethyl branched chain with imidazole | [(S)-(((S)-3-Hydroxymethyl-4-(imidazo-1-yl)butyl)thio)methyl-Sar]-3-[(γ-hydroxy)-N-MeLeu]-4-cyclosporin |
| 613 | S | (R)-3-hydroxymethyl pentyl chain with imidazole | [(S)-(((R)-3-Hydroxymethyl-5-(imidazo-1-yl)pentyl)thio)methyl-Sar]-3-[(γ-hydroxy)-N-MeLeu]-4-cyclosporin |
| 614 | S | (S)-3-hydroxymethyl pentyl chain with imidazole | [(S)-(((S)-3-Hydroxymethyl-5-(imidazo-1-yl)pentyl)thio)methyl-Sar]-3-[(γ-hydroxy)-N-MeLeu]-4-cyclosporin |

TABLE 2-continued

| Ex. No. | W | $R_a$ | Name |
|---|---|---|---|
| 615 | S | (R)-5-(piperidin-1-yl)-4-hydroxypentyl | [(S)-(((R)-4-Hydroxy-5-(piperidin-1-yl)pentyl)thio)methy-Sar]-3-[(γ-hydroxy)-N-MeLeu]-4-cyclosporin |
| 616 | S | (S)-5-(piperidin-1-yl)-4-hydroxypentyl | [(S)-(((S)-4-Hydroxy-5-(piperidin-1-yl)pentyl)thio)methy-Sar]-3-[(γ-hydroxy)-N-MeLeu]-4-cyclosporin |
| 617 | S | (R)-6-(piperidin-1-yl)-4-hydroxyhexyl | [(S)-(((R)-4-Hydroxy-5-(piperidin-1-yl)hexyl)thio)methyl-Sar]-3-[(γ-hydroxy)-N-MeLeu]-4-cyclosporin |
| 618 | S | (S)-6-(piperidin-1-yl)-4-hydroxyhexyl | [(S)-(((S)-4-Hydroxy-5-(piperidin-1-yl)hexyl)thio)methyl-Sar]-3-[(γ-hydroxy)-N-MeLeu]-4-cyclosporin |
| 619 | S | (R)-6-morpholino-4-hydroxyhexyl | [(S)-(((R)-4-Hydroxy-6-morpholinohexyl)thio)methyl-Sar]-3-[(γ-hydroxy)-N-MeLeu]-4-cyclosporin |
| 620 | S | (S)-6-morpholino-4-hydroxyhexyl | [(S)-(((S)-4-Hydroxy-6-morpholinohexyl)thio)methyl-Sar]-3-[(γ-hydroxy)-N-MeLeu]-4-cyclosporin |
| 621 | S | (R)-2-(hydroxymethyl)-4-morpholinobutyl | [(S)-(((R)-2-(Hydroxymethyl)-4-morpholinobutyl)thio)methyl-Sar]-3-[(γ-hydroxy)-N-MeLeu]-4-cyclosporin |

TABLE 2-continued

| Ex. No. | W | R_a | Name |
|---|---|---|---|
| 622 | S | (structure: branched chain with CH₂OH and morpholinoethyl group) | [(S)-(((S)-2-(Hydroxymethyl)-4-morpholinobutyl)thio)methyl-Sar]-3-[(γ-hydroxy)-N-MeLeu]-4-cyclosporin |
| 623 | S | (structure: branched chain with morpholinoethyl and hydroxyethyl groups, S config) | [(S)-(((S)-4-Hydroxy-2-(2-morpholinoethyl)butyl)thio)methyl-Sar]-3-[(γ-hydroxy)-N-MeLeu]-4-cyclosporin |
| 624 | S | (structure: branched chain with morpholinoethyl and hydroxyethyl groups, R config) | [(S)-(((R)-4-Hydroxy-2-(2-morpholinoethyl)butyl)thio)methyl-Sar]-3-[(γ-hydroxy)-N-MeLeu]-4-cyclosporin |
| 625 | S | (structure: hexyl chain with OH and 4-methylpiperazinyl group, S config) | [(S)-(((S)-4-Hydroxy-6-(4-methylpiperazin-1-yl)hexyl)thio)methyl-Sar]-3-[(γ-hydroxy)-N-MeLeu]-4-cyclosporin |
| 626 | S | (structure: hexyl chain with OH and 4-methylpiperazinyl group, R config) | [(S)-(((R)-4-Hydroxy-6-(4-methylpiperazin-1-yl)hexyl)thio)methyl-Sar]-3-[(γ-hydroxy)-N-MeLeu]-4-cyclosporin |
| 627 | S | (structure: hexyl chain with OH and 4-ethylpiperazinyl group, S config) | [(S)-(((S)-4-Hydroxy-6-(4-ethylpiperazin-1-yl)hexyl)thio)methyl-Sar]-3-[(γ-hydroxy)-N-MeLeu]-4-cyclosporin |

TABLE 2-continued

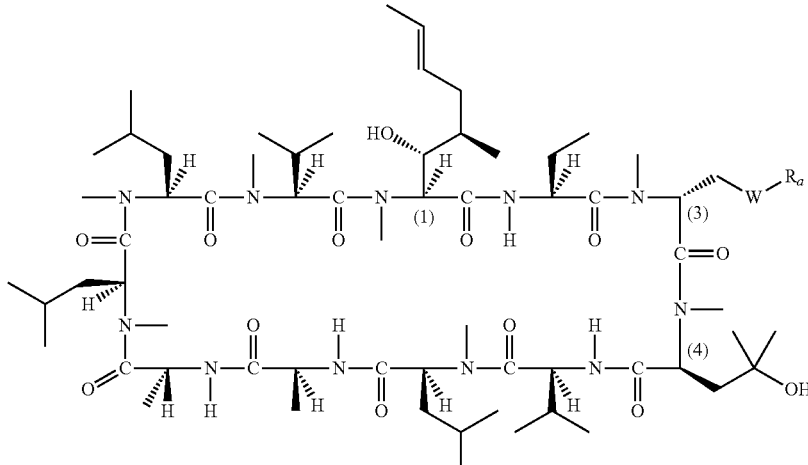

| Ex. No. | W | R$_a$ | Name |
|---|---|---|---|
| 628 | S | 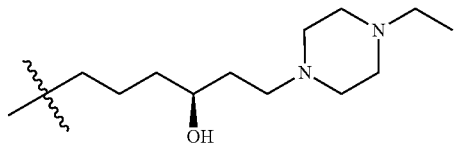 [SMILES: *CCC[C@H](O)CCN1CCN(CC)CC1] | [(S)-(((R)-4-Hydroxy-6-(4-ethylpiperazin-1-yl)hexyl)thio)methyl-Sar]-3-[(γ-hydroxy)-N-MeLeu]-4-cyclosporin |
| 629 | S | 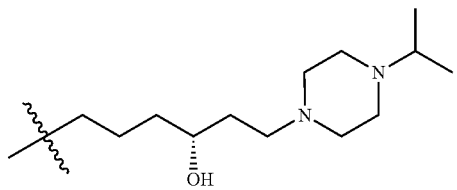 [SMILES: *CCC[C@@H](O)CCN1CCN(C(C)C)CC1] | [(S)-(((R)-4-Hydroxy-6-(4-isopropylpiperazin-1-yl)hexyl)thio)methyl-Sar]-3-[(γ-hydroxy)-N-MeLeu]-4-cyclosporin |
| 630 | S | 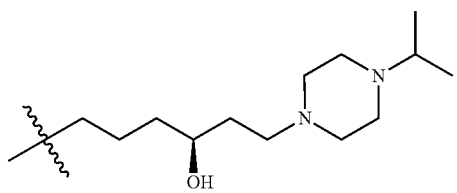 [SMILES: *CCC[C@H](O)CCN1CCN(C(C)C)CC1] | [(S)-(((S)-4-Hydroxy-6-(4-isopropylpiperazin-1-yl)hexyl)thio)methyl-Sar]-3-[(γ-hydroxy)-N-MeLeu]-4-cyclosporin |
| 631 | S | 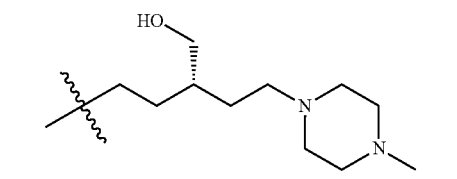 [SMILES: *CC[C@H](CO)CCN1CCN(C)CC1] | [(S)-(((S)-3-Hydroxymethyl-5-(4-methylpiperazin-1-yl)pentyl)thio)methyl-Sar]-3-[(γ-hydroxy)-N-MeLeu]-4-cyclosporin |
| 632 | S | 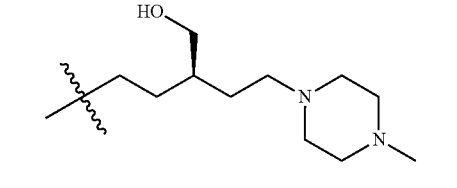 [SMILES: *CC[C@@H](CO)CCN1CCN(C)CC1] | [(S)-(((R)-3-Hydroxymethyl-5-(4-methylpiperazin-1-yl)pentyl)thio)methyl-Sar]-3-[(γ-hydroxy)-N-MeLeu]-4-cyclosporin |
| 633 | S | 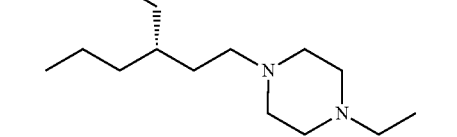 | [(S)-(((S)-3-Hydroxymethyl-5-(4-ethylpiperazin-1-yl)pentyl)thio)methyl-Sar]-3-[(γ-hydroxy)-N-MeLeu]-4-cyclosporin |

TABLE 2-continued

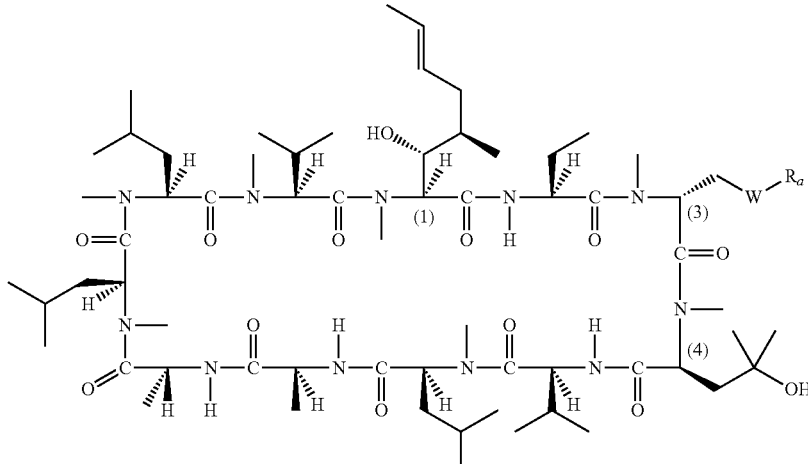

| Ex. No. | W | $R_a$ | Name |
|---|---|---|---|
| 634 | S | 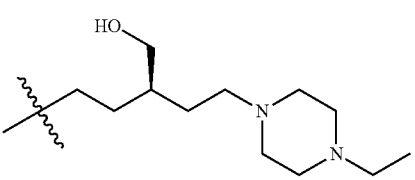 [SMILES: *CC[C@@H](CO)CCN1CCN(CC)CC1] | [(S)-(((R)-3-Hydroxymethyl-5-(4-ethylpiperazin-1-yl)pentyl)thio)methyl-Sar]-3-[(γ-hydroxy)-N-MeLeu]-4-cyclosporin |
| 635 | S | 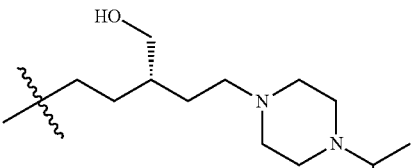 | [(S)-(((R)-3-Hydroxymethyl-5-(4-isopropylpiperazin-1-yl)pentyl)thio)methyl-Sar]-3-[(γ-hydroxy)-N-MeLeu]-4-cyclosporin |
| 636 | S | 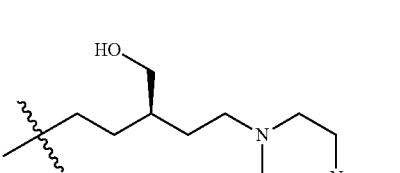 | [(S)-(((S)-3-Hydroxymethyl-5-(4-isopropylpiperazin-1-yl)pentyl)thio)methyl-Sar]-3-[(γ-hydroxy)-N-MeLeu]-4-cyclosporin |
| 637 | S | 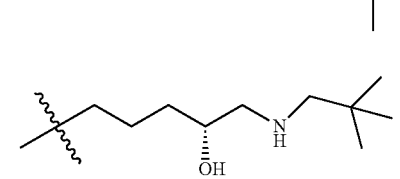 | [(S)-(((R)-4-Hydroxy-5-(neopentylamino)pentyl)thio)methyl-Sar]-3-[(γ-hydroxy)-N-MeLeu]-4-cyclosporin |
| 638 | S | 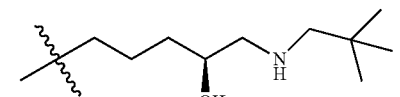 | [(S)-(((S)-4-Hydroxy-5-(neopentylamino)pentyl)thio)methyl-Sar]-3-[(γ-hydroxy)-N-MeLeu]-4-cyclosporin |
| 639 | S | 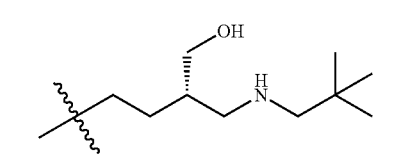 [SMILES: *CC[C@H](CO)CNCC(C)(C)C] | [(S)-(((S)-4-Hydroxy-3-((neopentylamino)methyl)butyl)thio)methyl-Sar]-3-[(γ-hydroxy)-N-MeLeu]-4-cyclosporin |

TABLE 2-continued

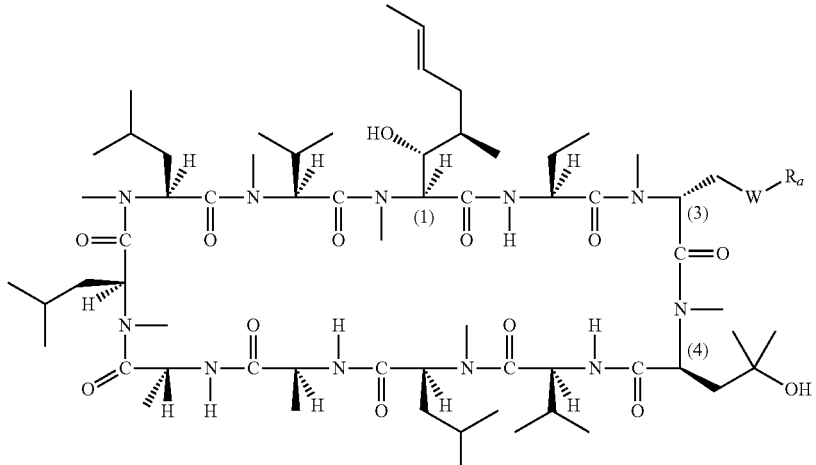

| Ex. No. | W | R_a | Name |
|---|---|---|---|
| 640 | S | 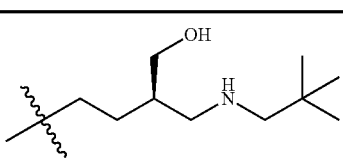 | [(S)-(((R)-4-Hydroxy-3-((neopentylamino)methyl)butyl)thio)methyl-Sar]-3-[(γ-hydroxy)-N-MeLeu]-4-cyclosporin |
| 641 | S | 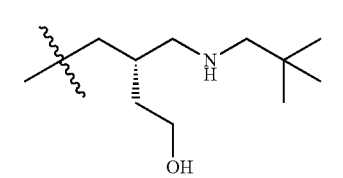 [SMILES: *C[C@@H](CCO)CNCC(C)(C)C] | [(S)-(((S)-4-Hydroxy-2-((neopentylamino)methyl)butyl)thio)methyl-Sar]-3-[(γ-hydroxy)-N-MeLeu]-4-cyclosporin |
| 642 | S | 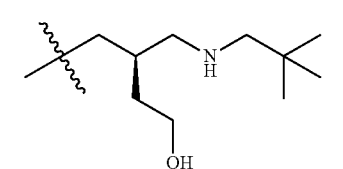 [SMILES: *C[C@H](CCO)CNCC(C)(C)C] | [(S)-(((R)-4-Hydroxy-2-((neopentylamino)methyl)butyl)thio)methyl-Sar]-3-[(γ-hydroxy)-N-MeLeu]-4-cyclosporin |
| 643 | S | 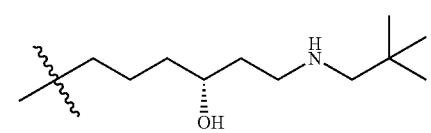 [SMILES: *CCC[C@@H](O)CCNCC(C)(C)C] | [(S)-(((R)-4-Hydroxy-6-(neopentylamino)hexyl)thio)methyl-Sar]-3-[(γ-hydroxy)-N-MeLeu]-4-cyclosporin |
| 644 | S | 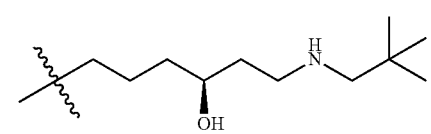 [SMILES: *CCC[C@H](O)CCNCC(C)(C)C] | [(S)-(((S)-4-Hydroxy-6-(neopentylamino)hexyl)thio)methyl-Sar]-3-[(γ-hydroxy)-N-MeLeu]-4-cyclosporin |
| 645 | S | 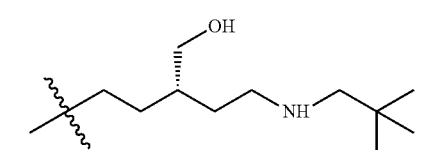 | [(S)-(((R)-3-(Hydroxymethyl)-5-(neopentylamino)pentyl)thio)methyl-Sar]-3-[(γ-hydroxy)-N-MeLeu]-4-cyclosporin |
| 646 | S | 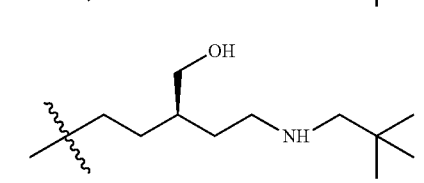 | [(S)-(((S)-3-(Hydroxymethyl)-5-(neopentylamino)pentyl)thio)methyl-Sar]-3-[(γ-hydroxy)-N-MeLeu]-4-cyclosporin |

TABLE 2-continued

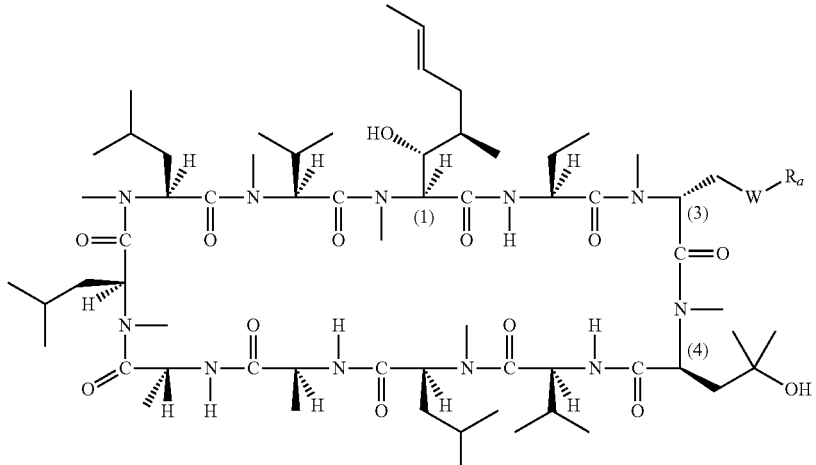

| Ex. No. | W | Ra | Name |
|---|---|---|---|
| 647 | S | 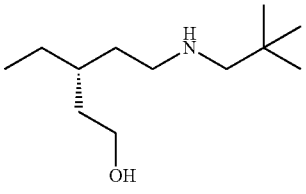 | [(S)-(((R)-4-Hydroxy-2-(2-(neopentylamino)ethyl)butyl)thio)methyl-Sar]-3-[(γ-hydroxy)-N-MeLeu]-4-cyclosporin |
| 648 | S | 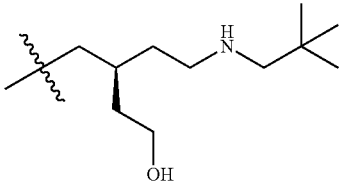 [SMILES: *C[C@H](CCO)CCNCC(C)(C)C] | [(S)-(((S)-4-Hydroxy-2-(2-(neopentylamino)ethyl)butyl)thio)methyl-Sar]-3-[(γ-hydroxy)-N-MeLeu]-4-cyclosporin |
| 649 | S | 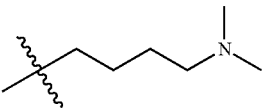 [SMILES: *CCCCN(C)C] | [(S)-(4-(N,N-Dimethylamino)butylthio)methyl-Sar]-3-[(γ-hydroxy)-N-MeLeu]-4-cyclosporin |
| 650 | S | 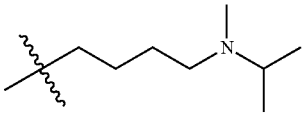 [SMILES: *CCCCN(C)C(C)C] | [(S)-(4-(N-Isopropyl-N-methylamino)butylthio)methyl-Sar]-3-[(γ-hydroxy)-N-MeLeu]-4-cyclosporin |
| 651 | S | 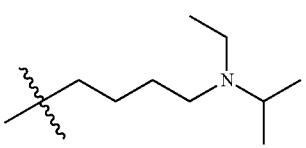 [SMILES: *CCCCN(CC)C(C)C] | [(S)-(4-(N-Ethyl-N-isopropylamino)butylthio)methyl-Sar]-3-[(γ-hydroxy)-N-MeLeu]-4-cyclosporin |
| 652 | S | 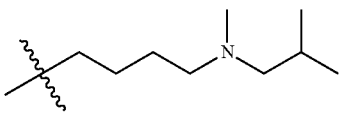 [SMILES: *CCCCN(C)CC(C)C] | [(S)-(4-(N-Isobutyl-N-methylamino)butylthio)methyl-Sar]-3-[(γ-hydroxy)-N-MeLeu]-4-cyclosporin |
| 653 | S | 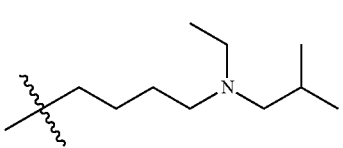 [SMILES: *CCCCN(CC)CC(C)C] | [(S)-(4-(N-Isobutyl-N-ethylamino)butylthio)methyl-Sar]-3-[(γ-hydroxy)-N-MeLeu]-4-cyclosporin |

TABLE 2-continued

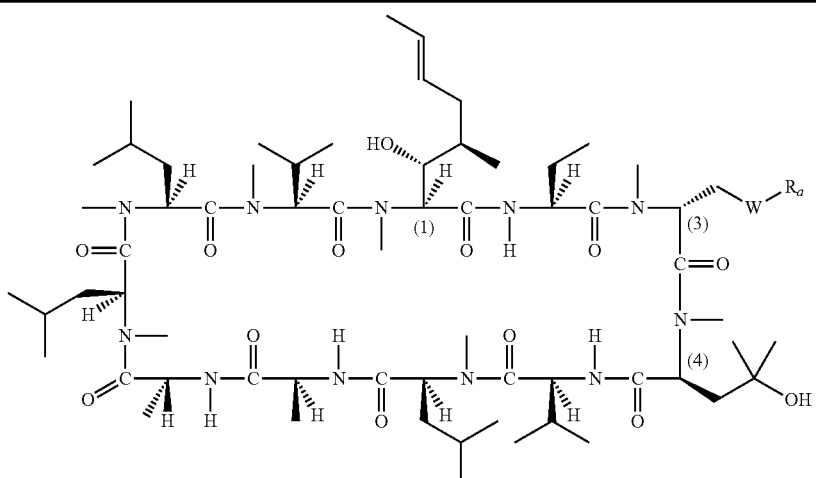

| Ex. No. | W | $R_a$ | Name |
|---|---|---|---|
| 654 | S | 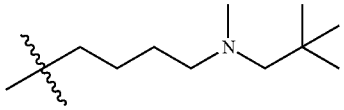 [SMILES: *CCCCN(C)CC(C)(C)C] | [(S)-(4-(N-Methyl-N-Neopentylamino)butylthio)methyl-Sar]-3-[(γ-hydroxy)-N-MeLeu]-4-cyclosporin |
| 655 | S | 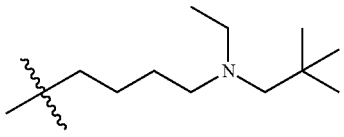 [SMILES: *CCCCN(CC)CC(C)(C)C] | [(S)-(4-(N-Ethyl-N-Neopentylamino)butylthio)methyl-Sar]-3-[(γ-hydroxy)-N-MeLeu]-4-cyclosporin |
| 656 | S | 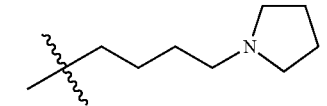 [SMILES: *CCCCN1CCCC1] | [(S)-(4-(N-Pyrrolidinyl)butylthio)methyl-Sar]-3-[(γ-hydroxy)-N-MeLeu]-4-cyclosporin |
| 657 | S | 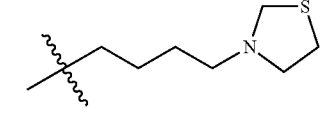 [SMILES: *CCCCN1CCSC1] | [(S)-(4-(N-Thiazolidinyl)butylthio)methyl-Sar]-3-[(γ-hydroxy)-N-MeLeu]-4-cyclosporin |
| 658 | S | 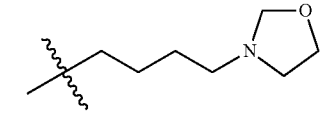 | [(S)-(4-(N-Oxazolidinyl)butylthio)methyl-Sar]-3-[(γ-hydroxy)-N-MeLeu]-4-cyclosporin |
| 659 | S | 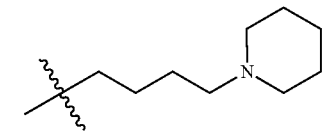 [SMILES: *CCCCN1CCCCC1] | [(S)-(4-(N-Piperidinyl)butylthio)methyl-Sar]-3-[(γ-hydroxy)-N-MeLeu]-4-cyclosporin |
| 660 | S | 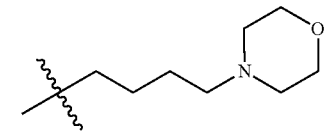 [SMILES: *CCCCN1CCOCC1] | [(S)-(4-(N-Morpholino)butylthio)methyl-Sar]-3-[(γ-hydroxy)-N-MeLeu]-4-cyclosporin |
| 661 | S | 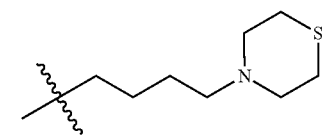 [SMILES: *CCCCN1CCSCC1] | [(S)-(4-(N-Thiomorpholino)butylthio)methyl-Sar]-3-[(γ-hydroxy)-N-MeLeu]-4-cyclosporin |

TABLE 2-continued

| Ex. No. | W | R$_a$ | Name |
|---|---|---|---|
| 662 | S | piperazine-NH with butyl linker | [(S)-(4-(N-Piperazinyl)butylthio)methyl-Sar]-3-[(γ-hydroxy)-N-MeLeu]-4-cyclosporin |
| 663 | S | 4-methylpiperazine with butyl linker | [(S)-(4-(4-Methyl-N-piperazinyl)butylthio)methyl-Sar]-3-[(γ-hydroxy)-N-MeLeu]-4-cyclosporin |
| 664 | S | 4-ethylpiperazine with butyl linker | [(S)-(4-(4-Ethyl-N-piperazinyl)butylthio)methyl-Sar]-3-[(γ-hydroxy)-N-MeLeu]-4-cyclosporin |
| 665 | S | 4-n-propylpiperazine with butyl linker | [(S)-(4-(4-n-Propyl-N-piperazinyl)butylthio)methyl-Sar]-3-[(γ-hydroxy)-N-MeLeu]-4-cyclosporin |
| 666 | S | 4-isopropylpiperazine with butyl linker | [(S)-(4-(4-Isopropyl-N-piperazinyl)butylthio)methyl-Sar]-3-[(γ-hydroxy)-N-MeLeu]-4-cyclosporin |
| 667 | S | 4-isobutylpiperazine with butyl linker | [(S)-(4-(4-Isobutyl-N-piperazinyl)butylthio)methyl-Sar]-3-[(γ-hydroxy)-N-MeLeu]-4-cyclosporin |
| 668 | S | 4-neopentylpiperazine with butyl linker | [(S)-(4-(4-Neopentyl-N-piperazinyl)butylthio)methyl-Sar]-3-[(γ-hydroxy)-N-MeLeu]-4-cyclosporin |

TABLE 2-continued

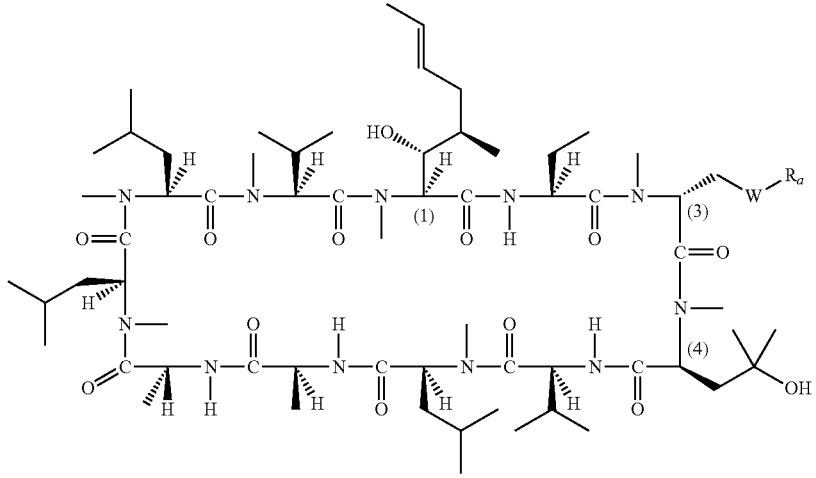

| Ex. No. | W | R_a | Name |
|---|---|---|---|
| 669 | S | 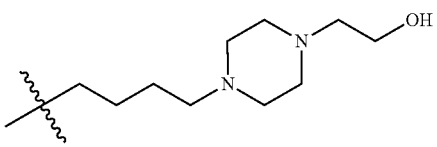 [SMILES: *CCCCN1CCN(CCO)CC1] | [(S)-(4-(4-(2-Hydroxyethyl)-N-piperazinyl)butylthio)methyl-Sar]-3-[(γ-hydroxy)-N-MeLeu]-4-cyclosporin |
| 670 | S | 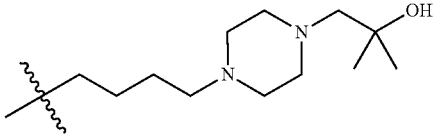 [SMILES: *CCCCN1CCN(CC(C)(C)O)CC1] | [(S)-(4-(4-(2-Hydroxy-2-methylpropyl)-N-piperazinyl)butylthio)methyl-Sar]-3-[(γ-hydroxy)-N-MeLeu]-4-cyclosporin |
| 671 | S | 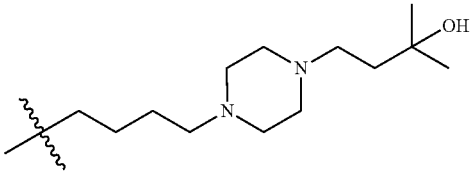 [SMILES: *CCCCN1CCN(CCC(C)(C)O)CC1] | [(S)-(4-(4-(3-Hydroxy-3-dimethylbutyl)-N-piperazinyl)butylthio)methyl-Sar]-3-[(γ-hydroxy)-N-MeLeu]-4-cyclosporin |
| 672 | S | 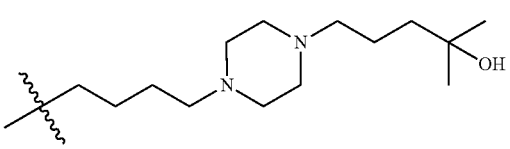 [SMILES: *CCCCN1CCN(CCCC(C)(C)O)CC1] | [(S)-(4-(4-(4-Hydroxy-4-methylpentyl)-N-piperazinyl)butylthio)methyl-Sar]-3-[(γ-hydroxy)-N-MeLeu]-4-cyclosporin |
| 673 | S | 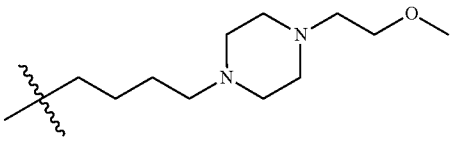 [SMILES: *CCCCN1CCN(CCOC)CC1] | [(S)-(4-(4-(2-Methoxyethyl)-N-piperazinyl)butylthio)methyl-Sar]-3-[(γ-hydroxy)-N-MeLeu]-4-cyclosporin |
| 674 | S | 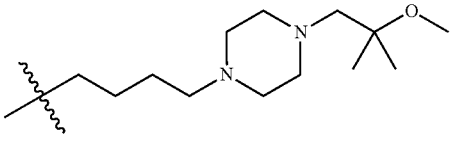 [SMILES: *CCCCN1CCN(CC(C)(C)OC)CC1] | [(S)-(4-(4-(2-Methoxy-2-methylproyl)-N-piperazinyl)butylthio)methyl-Sar]-3-[(γ-hydroxy)-N-MeLeu]-4-cyclosporin |
| 675 | S | 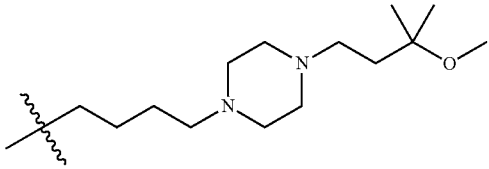 [SMILES: *CCCCN1CCN(CCC(C)(C)OC)CC1] | [(S)-(4-(4-(3-Methoxy-3-methylbutyl)-N-piperazinyl)butylthio)methyl-Sar]-3-[(γ-hydroxy)-N-MeLeu]-4-cyclosporin |

TABLE 2-continued

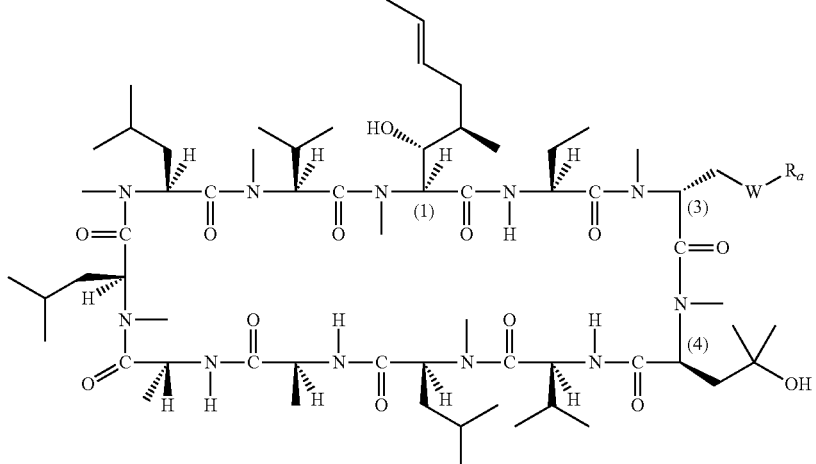

| Ex. No. | W | $R_a$ | Name |
|---|---|---|---|
| 676 | S | 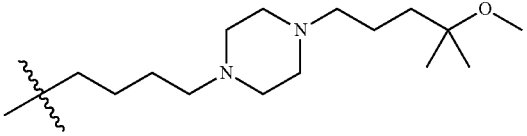 [SMILES: *CCCCN1CCN(CCCC(C)(C)OC)CC1] | [(S)-(4-(4-(4-Methoxy-4-methylpentyl)-N-piperazinyl)butylthio)methyl-Sar]-3-[(γ-hydroxy)-N-MeLeu]-4-cyclosporin |
| 677 | S | 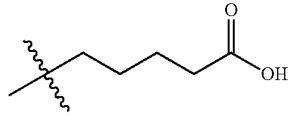 | [(S)-(4-Carboxybutylthio)methyl-Sar]-3-[(γ-hydroxy)-N-MeLeu]-4-cyclosporin |
| 678 | S | 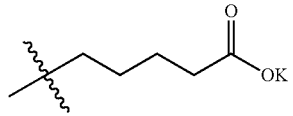 | [(S)-(4-Carboxybutylthio)methyl-Sar]-3-[(γ-hydroxy)-N-MeLeu]-4-cyclosporin-potassium salt |
| 679 | S | 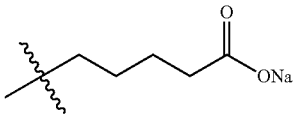 | [(S)-(4-Carboxybutylthio)methyl-Sar]-3-[(γ-hydroxy)-N-MeLeu]-4-cyclosporin-sodium salt |
| 680 | S | 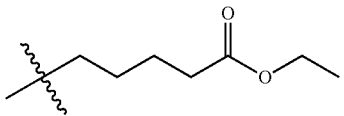 [SMILES: *CCCCC(=O)OCC] | [(S)-(4-Ethoxycarbonylbutylthio)methyl-Sar]-3-[(γ-hydroxy)-N-MeLeu]-4-cyclosporin |
| 681 | S | 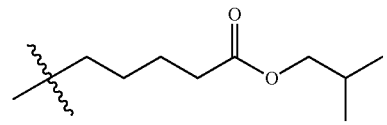 [SMILES: *CCCCC(=O)OCC(C)C] | [(S)-(4-isoButoxycarbonylbutylthio)methyl-Sar]-3-[(γ-hydroxy)-N-MeLeu]-4-cyclosporin |
| 682 | S | 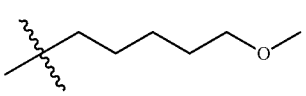 [SMILES: *CCCCCOC] | [(S)-(5-Methoxypentylthio)methyl-Sar]-3-[(γ-hydroxy)-N-MeLeu]-4-cyclosporin |
| 683 | S | 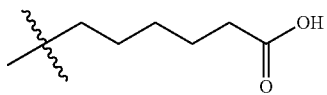 [SMILES: *CCCCCC(=O)O] | [(S)-(4-Carboxypentylthio)methyl-Sar]-3-[(γ-methoxy)-N-MeLeu]-4-cyclosporin |

TABLE 2-continued

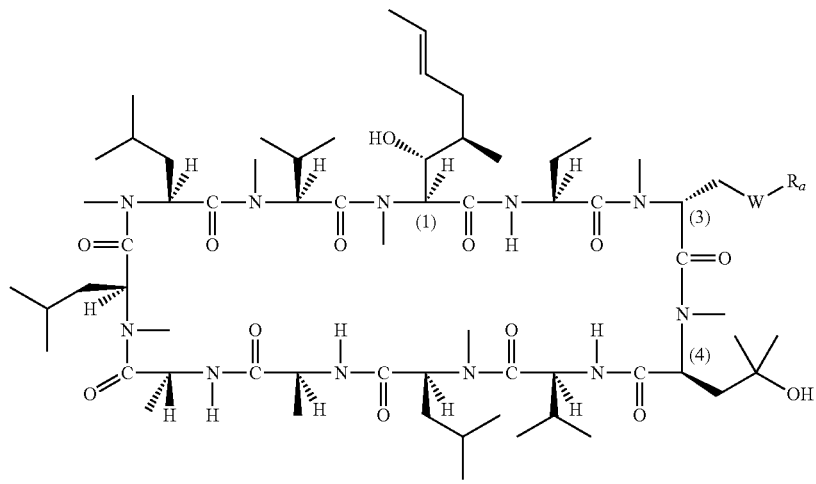

| Ex. No. | W | $R_a$ | Name |
|---|---|---|---|
| 684 | S | (pentyl chain with -C(=O)OK) | [(S)-(4-Carboxypentylthio)methyl-Sar]-3-[(γ-hydroxy)-N-MeLeu]-4-cyclosporin-potassium salt |
| 685 | S | (pentyl chain with -C(=O)ONa) | [(S)-(4-Carboxypentylthio)methyl-Sar]-3-[(γ-hydroxy)-N-MeLeu]-4-cyclosporin-sodium salt |
| 686 | S | (pentyl chain with -C(=O)OEt) | [(S)-(4-Ethoxycarbonylpentylthio)methyl-Sar]-3-[(γ-hydroxy)-N-MeLeu]-4-cyclosporin |
| 687 | S | (butyl chain with -CH(COOH)$_2$) | [(S)-(4,4'-Di(carboxy)butylthio)methyl-Sar]-3-[(γ-hydroxy)-N-MeLeu]-4-cyclosporin |
| 688 | S | (butyl chain with -CH(COOK)$_2$) | [(S)-(4,4'-Di(carboxy)butylthio)methyl-Sar]-3-[(γ-hydroxy)-N-MeLeu]-4-cyclosporin-dipotassium salt |
| 689 | S | (butyl chain with -CH(COONa)$_2$) | [(S)-(4,4'-Di(carboxy)butylthio)methyl-Sar]-3-[(γ-hydroxy)-N-MeLeu]-4-cyclosporin-disodium salt |
| 690 | S | (butyl chain with -CH(COOEt)$_2$) | [(S)-(4,4'-Di(ethoxycarbonyl)butylthio)methyl-Sar]-3-[(γ-hydroxy)-N-MeLeu]-4-cyclosporin |

TABLE 2-continued

| Ex. No. | W | $R_a$ | Name |
|---|---|---|---|
| 691 | S | (branched chain with dicarboxylic acid: -CH2-(CH2)4-CH(COOH)2) | [(S)-(6,6'-Di(carboxy)hexylthio)methyl-Sar]-3-[(γ-hydroxy)-N-MeLeu]-4-cyclosporin |
| 692 | S | (branched chain with dipotassium dicarboxylate: -CH2-(CH2)4-CH(COOK)2) | [(S)-(6,6'-Di(carboxy)hexylthio)methyl-Sar]-3-[(γ-hydroxy)-N-MeLeu]-4-cyclosporin-dipotassium salt |
| 693 | S | (branched chain with disodium dicarboxylate: -CH2-(CH2)4-CH(COONa)2) | [(S)-(6,6'-Di(carboxy)hexylthio)methyl-Sar]-3-[(γ-hydroxy)-N-MeLeu]-4-cyclosporin-disodium salt |
| 694 | S | (branched chain with diethyl diester: -CH2-(CH2)4-CH(COOEt)2) | [(S)-(6,6'-Di(ethoxycarbonyl)hexylthio)methyl-Sar]-3-[(γ-hydroxy)-N-MeLeu]-4-cyclosporin |
| 695 | S | (branched chain with dicarboxylic acid: -CH2-(CH2)5-CH(COOH)2) | [(S)-(7,7'-Di(carboxy)heptylthio)methyl-Sar]-3-[(γ-hydroxy)-N-MeLeu]-4-cyclosporin |
| 696 | S | (branched chain with dipotassium dicarboxylate: -CH2-(CH2)5-CH(COOK)2) | [(S)-(7,7'-Di(carboxy)heptylthio)methyl-Sar]-3-[(γ-hydroxy)-N-MeLeu]-4-cyclosporin-dipotassium salt |

TABLE 2-continued

| Ex. No. | W | $R_a$ | Name |
|---|---|---|---|
| 697 | S | (heptyl with CH(CO-ONa)$_2$) | [(S)-((7,7'-Dicarboxy)heptylthio)methyl-Sar]-3-[(γ-hydroxy)-N-MeLeu]-4-cyclosporin-disodium salt |
| 698 | S | (heptyl with CH(CO-OEt)$_2$) | [(S)-(7,7'-Di(ethoxycarbonyl)heptylthio)methyl-Sar]-3-[(γ-hydroxy)-N-MeLeu]-4-cyclosporin |
| 699 | S | ((R)-3-hydroxymethyl-6-methoxy-6-oxohexyl) | [(S)-(((R)-3-Hydroxymethyl-6-methoxy-6-oxohexyl)thio)methyl-Sar]-3-[(γ-hydroxy)-N-MeLeu]-4-cyclosporin |
| 700 | S | ((S)-3-hydroxymethyl-6-methoxy-6-oxohexyl) | [(S)-(((S)-3-Hydroxy-6-methoxy-6-oxohexyl)thio)methyl-Sar]-3-[(γ-hydroxy)-N-MeLeu]-4-cyclosporin |
| 701 | S | ((R)-3-hydroxymethyl-6-ethoxy-6-oxohexyl) | [(S)-(((R)-3-Hydroxy-6-methoxy-6-oxohexyl)thio)methyl-Sar]-3-[(γ-hydroxy)-N-MeLeu]-4-cyclosporin |
| 702 | S | ((S)-3-hydroxymethyl-6-ethoxy-6-oxohexyl) | [(S)-(((S)-3-Hydroxy-6-ethoxy-6-oxohexyl)thio)methyl-Sar]-3-[(γ-hydroxy)-N-MeLeu]-4-cyclosporin |
| 703 | S | ((R)-3-hydroxymethyl-6-(neopentylamino)hexyl) | [(S)-(((R)-3-Hydroxy-6-(neopentylamino)hexyl)thio)methyl-Sar]-3-[(γ-hydroxy)-N-MeLeu]-4-cyclosporin |

TABLE 2-continued

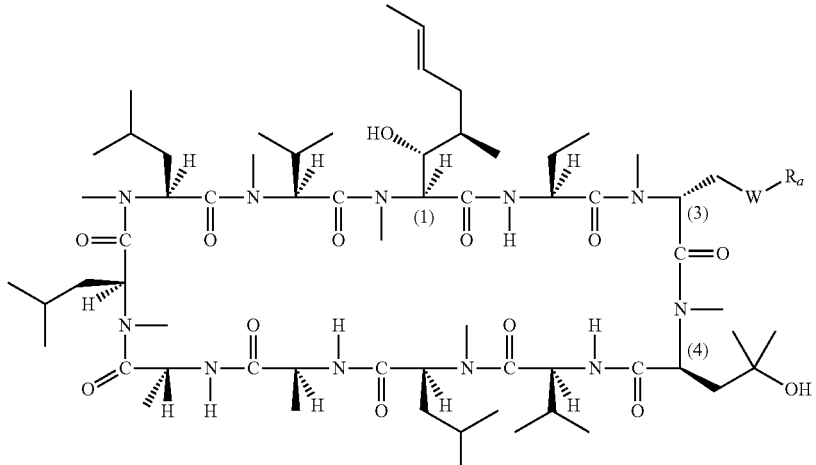

| Ex. No. | W | Rₐ | Name |
|---|---|---|---|
| 704 | S | 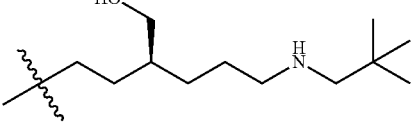 | [(S)-(((S)-3-Hydroxy-6-(neopentylamino)hexyl)thio)methyl-Sar]-3-[(γ-hydroxy)-N-MeLeu]-4-cyclosporin |
| 705 | S | 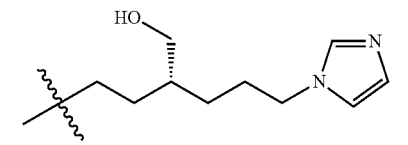 [SMILES: *CC[C@H](CO)CCCn1ccnc1] | [(S)-(((R)-3-Hydroxymethyl-6-(imidazol-1-yl)hexyl)thio)methyl-Sar]-3-[(γ-hydroxy)-N-MeLeu]-4-cyclosporin |
| 706 | S | 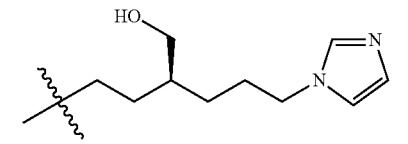 [SMILES: *CC[C@@H](CO)CCCn1ccnc1] | [(S)-(((S)-3-Hydroxymethyl-6-(imidazo-1-yl)hexyl)thio)methyl-Sar]-3-[(γ-hydroxy)-N-MeLeu]-4-cyclosporin |
| 707 | S | 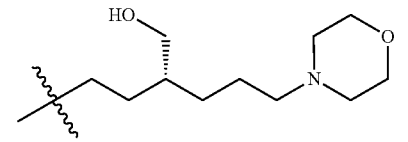 [SMILES: *CC[C@H](CO)CCCN1CCOCC1] | [(S)-(((R)-3-Hydroxymethyl-6-morpholinohexyl)thio)methyl-Sar]-3-[(γ-hydroxy)-N-MeLeu]-4-cyclosporin |
| 708 | S | 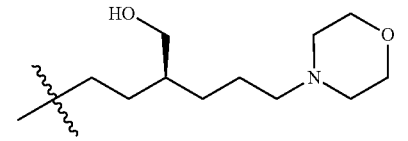 [SMILES: *CC[C@@H](CO)CCCN1CCOCC1] | [(S)-(((S)-3-Hydroxymethyl-6-morpholinohexyl)thio)methyl-Sar]-3-[(γ-hydroxy)-N-MeLeu]-4-cyclosporin |
| 709 | S | 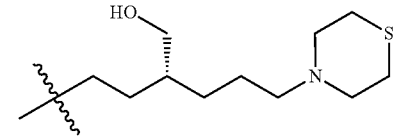 [SMILES: *CC[C@H](CO)CCCN1CCSCC1] | [(S)-(((R)-3-Hydroxymethyl-6-thiomorpholinohexyl)thio)methyl-Sar]-3-[(γ-hydroxy)-N-MeLeu]-4-cyclosporin |
| 710 | S | 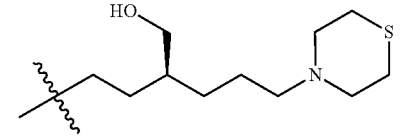 [SMILES: *CC[C@@H](CO)CCCN1CCSCC1] | [(S)-(((S)-3-Hydroxymethyl-6-thiomorpholinohexyl)thio)methyl-Sar]-3-[(γ-hydroxy)-N-MeLeu]-4-cyclosporin |

TABLE 2-continued

| Ex. No. | W | R<sub>a</sub> | Name |
|---|---|---|---|
| 711 | S | (structure) | [(S)-(((R)-3-Hydroxymethyl-6-piperazin-1-ylhexyl)thio)methyl-Sar]-3-[(γ-hydroxy)-N-MeLeu]-4-cyclosporin |
| 712 | S | (structure) | [(S)-(((S)-3-Hydroxymethyl-6-piperazin-1-ylhexyl)thio)methyl-Sar]-3-[(γ-hydroxy)-N-MeLeu]-4-cyclosporin |
| 713 | S | (structure) | [(S)-(((R)-3-Hydroxymethyl-6-(4-methylpiperazin-1-yl)hexyl)thio)methyl-Sar]-3-[(γ-hydroxy)-N-MeLeu]-4-cyclosporin |
| 714 | S | (structure) | [(S)-(((S)-3-Hydroxymethyl-6-(4-methylpiperazin-1-yl)hexyl)thio)methyl-Sar]-3-[(γ-hydroxy)-N-MeLeu]-4-cyclosporin |
| 715 | S | (structure) | [(S)-(((R)-3-Hydroxymethyl-6-(4-ethylpiperazin-1-yl)hexyl)thio)methyl-Sar]-3-[(γ-hydroxy)-N-MeLeu]-4-cyclosporin |
| 716 | S | (structure) | [(S)-(((S)-3-Hydroxymethyl-6-(4-isopropylpiperazin-1-yl)hexyl)thio)methyl-Sar]-3-[(γ-hydroxy)-N-MeLeu]-4-cyclosporin |
| 717 | S | (structure) | [(S)-(((R)-3-Hydroxymethyl-6-(4-isopropylpiperazin-1-yl)hexyl)thio)methyl-Sar]-3-[(γ-hydroxy)-N-MeLeu]-4-cyclosporin |

TABLE 2-continued

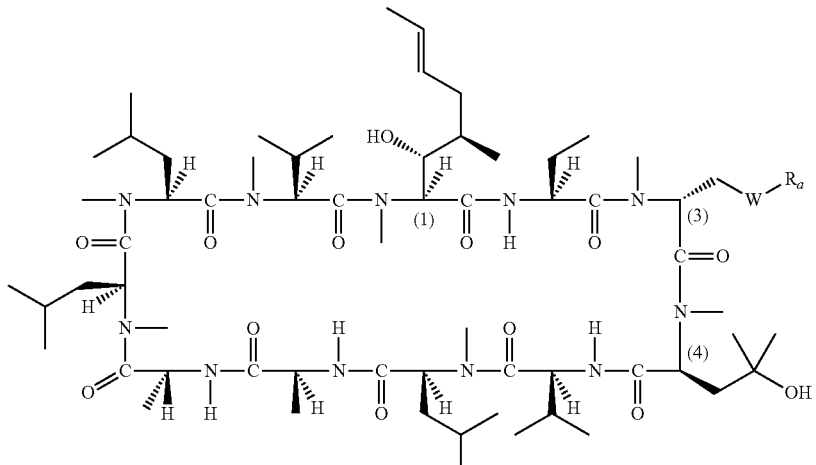

| Ex. No. | W | $R_a$ | Name |
|---|---|---|---|
| 718 | S | 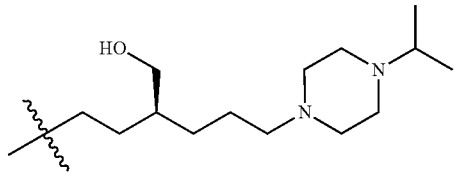 [SMILES: *CC[C@@H](CO)CCCN1CCN(C(C)C)CC1] | [(S)-(((S)-3-Hydroxymethyl-6-(4-ethylpiperazin-1-yl)hexyl)thio)methyl-Sar]-3-[(γ-hydroxy)-N-MeLeu]-4-cyclosporin |
| 719 | S | 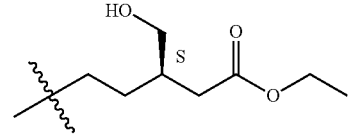 | [(S)-((S)-3-Hydroxymethyl-4-ethoxycarbonylbutylthio)methyl-Sar]-3-cyclosporin |
| 720 | S | 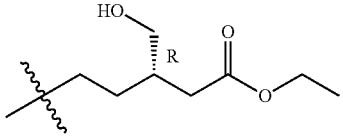 | [(S)-((R)-3-Hydroxymethyl-4-ethoxycarbonylbutylthio)methyl-Sar]-3-cyclosporin |
| 721 | S | 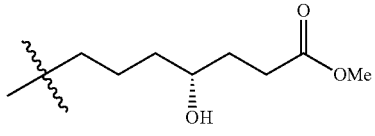 [SMILES: *CCC[C@@H](O)CCC(=O)OC] | [(S)-(((S)-4-Hydroxy-7-methoxy-7-oxoheptyl)thio)methyl-Sar]-3-[(γ-hydroxy)-N-MeLeu]-4-cyclosporin |
| 722 | S | 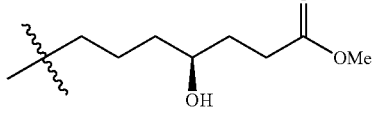 | [(S)-(((R)-4-Hydroxy-7-methoxy-7-oxoheptyl)thio)methyl-Sar]-3-[(γ-hydroxy)-N-MeLeu]-4-cyclosporin |
| 723 | S | 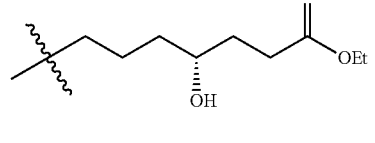 | [(S)-(((S)-4-Hydroxy-7-ethoxy-7-oxoheptyl)thio)methyl-Sar]-3-[(γ-hydroxy)-N-MeLeu]-4-cyclosporin |
| 724 | S | 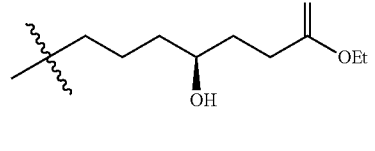 | [(S)-(((R)-4-Hydroxy-7-ethoxy-7-oxoheptyl)thio)methyl-Sar]-3-[(γ-hydroxy)-N-MeLeu]-4-cyclosporin |

TABLE 2-continued

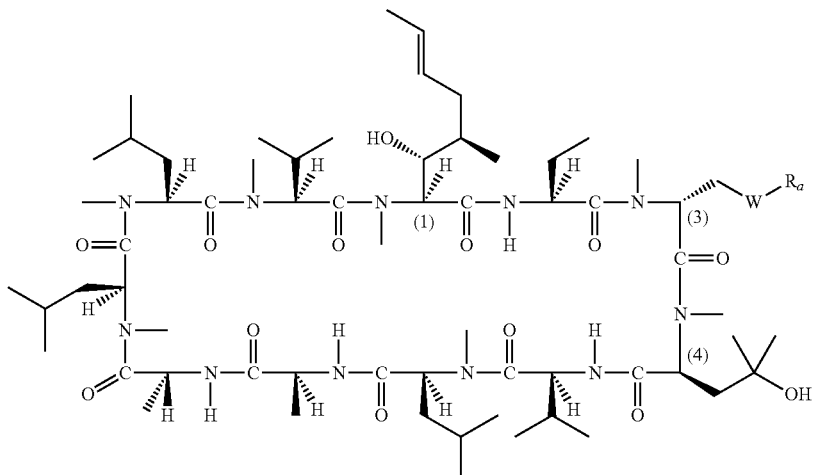

| Ex. No. | W | $R_a$ | Name |
|---|---|---|---|
| 725 | S | 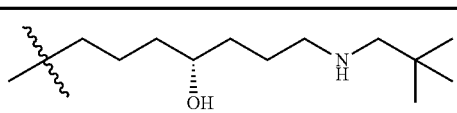 | [(S)-(((S)-4-Hydroxy-7-(neopentylamino)heptyl)thio)methyl-Sar]-3-[(γ-hydroxy)-N-MeLeu]-4-cyclosporin |
| 726 | S | 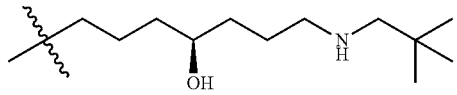 [SMILES: *CCC[C@H](O)CCCNCC(C)(C)C] | [(S)-(((R)-4-Hydroxy-7-(neopentylamino)heptyl)thio)methyl-Sar]-3-[(γ-hydroxy)-N-MeLeu]-4-cyclosporin |
| 727 | S | 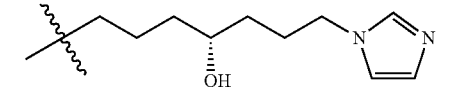 [SMILES: *CCC[C@@H](O)CCCn1ccnc1] | [(S)-(((S)-4-Hydroxy-7-(imidazol-1-yl)heptyl)thio)methyl-Sar]-3-[(γ-hydroxy)-N-MeLeu]-4-cyclosporin |
| 728 | S | 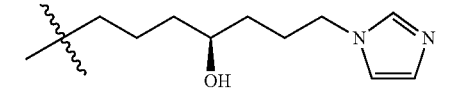 [SMILES: *CCC[C@H](O)CCCn1ccnc1] | [(S)-(((R)-4-Hydroxy-7-(imidazo-1-yl)heptyl)thio)methyl-Sar]-3-[(γ-hydroxy)-N-MeLeu]-4-cyclosporin |
| 729 | S | 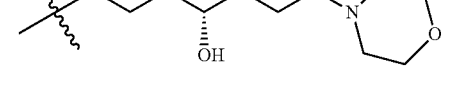 | [(S)-(((S)-4-Hydroxy-7-morpholinoheptyl)thio)methyl-Sar]-3-[(γ-hydroxy)-N-MeLeu]-4-cyclosporin |
| 730 | S | 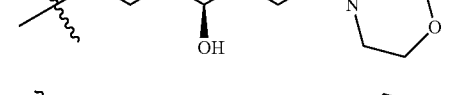 | [(S)-(((R)-4-Hydroxy-7-morpholinoheptyl)thio)methyl-Sar]-3-[(γ-hydroxy)-N-MeLeu]-4-cyclosporin |
| 731 | S | 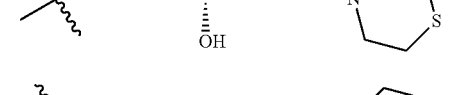 | [(S)-(((S)-4-Hydroxy-7-thiomorpholinoheptyl)thio)methyl-Sar]-3-[(γ-hydroxy)-N-MeLeu]-4-cyclosporin |
| 732 | S | 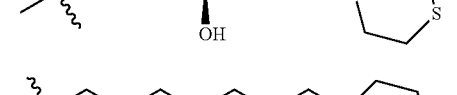 | [(S)-(((R)-4-Hydroxy-7-thiomorpholinoheptyl)thio)methyl-Sar]-3-[(γ-hydroxy)-N-MeLeu]-4-cyclosporin |
| 733 | S | 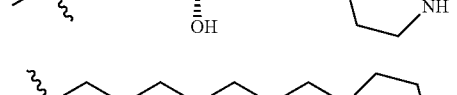 | [(S)-(((S)-4-Hydroxy-7-piperazin-1-ylheptyl)thio)methyl-Sar]-3-[(γ-hydroxy)-N-MeLeu]-4-cyclosporin |
| 734 | S |  | [(S)-(((R)-4-Hydroxy-7-piperazin-1-ylheptyl)thio)methyl-Sar]-3-[(γ-hydroxy)-N-MeLeu]-4-cyclosporin |

TABLE 2-continued

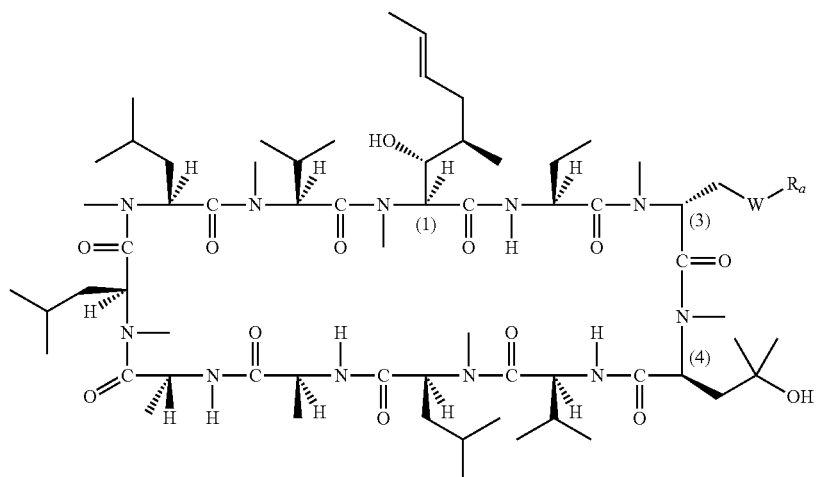

| Ex. No. | W | $R_a$ | Name |
|---|---|---|---|
| 735 | S | (heptyl chain with (S)-OH, 4-methylpiperazine) | [(S)-(((S)-4-Hydroxy-7-(4-ethylpiperazin-1-yl)heptyl)thio)methyl-Sar]-3-[(γ-hydroxy)-N-MeLeu]-4-cyclosporin |
| 736 | S | (heptyl chain with (R)-OH, 4-methylpiperazine) | [(S)-(((R)-4-Hydroxy-7-(4-ethylpiperazin-1-yl)heptyl)thio)methyl-Sar]-3-[(γ-hydroxy)-N-MeLeu]-4-cyclosporin |
| 737 | S | (heptyl chain with (S)-OH, 4-ethylpiperazine) | [(S)-(((S)-4-Hydroxy-7-(4-ethylpiperazin-1-yl)heptyl)thio)methyl-Sar]-3-[(γ-hydroxy)-N-MeLeu]-4-cyclosporin |
| 738 | S | (heptyl chain with (R)-OH, 4-ethylpiperazine) | [(S)-(((R)-4-Hydroxy-7-(4-ethylpiperazin-1-yl)heptyl)thio)methyl-Sar]-3-[(γ-hydroxy)-N-MeLeu]-4-cyclosporin |
| 739 | S | (heptyl chain with (S)-OH, 4-isopropylpiperazine) | [(S)-(((S)-4-Hydroxy-7-(4-isopropylpiperazin-1-yl)heptyl)thio)methyl-Sar]-3-[(γ-hydroxy)-N-MeLeu]-4-cyclosporin |
| 740 | S | (heptyl chain with (R)-OH, 4-isopropylpiperazine) | [(S)-(((R)-4-Hydroxy-7-(4-isopropylpiperazin-1-yl)heptyl)thio)methyl-Sar]-3-[(γ-hydroxy)-N-MeLeu]-4-cyclosporin |
| 741 | S | (6-methoxyhexyl) | [(S)-(6-Methoxyhexylthio)methyl-Sar]-3-[(γ-hydroxy)-N-MeLeu]-4-cyclosporin |
| 742 | S | (CH2-C(=O)-NH-CH2CH2-NH2) | [(S)-[(N-(2-Aminoethyl)carbamoyl)methylthio]methyl-Sar]-3-[(γ-hydroxy)-N-MeLeu]-4-cyclosporin |
| 743 | S | (CH2-C(=O)-NH-CH2CH2-NH-neopentyl) | [(S)-[(N-(2-(Neopentylamino)ethyl)carbamoyl)methylthio]methyl-Sar]-3-[(γ-hydroxy)-N-MeLeu]-4-cyclosporin |

TABLE 2-continued

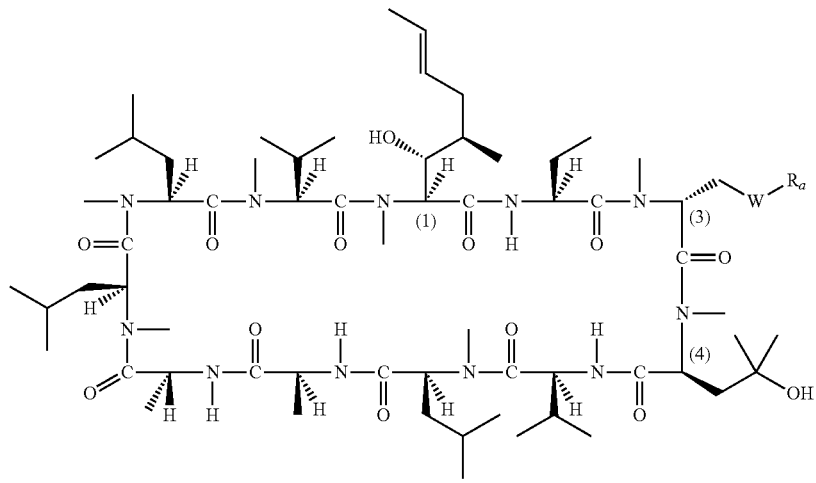

| Ex. No. | W | $R_a$ | Name |
|---|---|---|---|
| 744 | S | ~CH2C(O)NH(CH2)3NH2 | [(S)-[(N-(3-Aminopropyl)carbamoyl)methylthio]methyl-Sar]-3-cyclosporin |
| 745 | S | ~CH2C(O)NH(CH2)3NHCH2C(CH3)3 | [(S)-[(N-(3-(Neopentylamino)propyl)carbamoyl)methylthio]methyl-Sar]-3-[(γ-hydroxy)-N-MeLeu]-4-cyclosporin |
| 746 | S | ~CH2C(O)NH(CH2)4NH2 | [(S)-[(N-(4-Aminobutyl)carbamoyl)methylthio]methyl-Sar]-3-[(γ-hydroxy)-N-MeLeu]-4-cyclosporin |
| 747 | S | ~CH2C(O)NH(CH2)4NHCH2C(CH3)3 | [(S)-[(N-(4-(Neopentylamino)butyl)carbamoyl)methylthio]methyl-Sar]-3-[(γ-hydroxy)-N-MeLeu]-4-cyclosporin |
| 748 | S | ~CH2C(O)NH(CH2)5NH2 | [(S)-[(N-(5-Aminopentyl)carbamoyl)methylthio]methyl-Sar]-3-[(γ-hydroxy)-N-MeLeu]-4-cyclosporin |
| 749 | S | ~CH2C(O)NH(CH2)5NHCH2C(CH3)3 | [(S)-[(N-(5-(Neopentylamino)pentyl)carbamoyl)methylthio]methyl-Sar]-3-[(γ-hydroxy)-N-MeLeu]-4-cyclosporin |
| 750 | S | ~CH2C(O)NH(CH2)6NH2 | [(S)-[(N-(6-Aminohexyl)carbamoyl)methylthio]methyl-Sar]-3-[(γ-hydroxy)-N-MeLeu]-4-cyclosporin |
| 751 | S | ~CH2C(O)NH(CH2)6NHCH2C(CH3)3 | [(S)-[(N-(6-Neopentylamino)hexyl)carbamoyl)methylthio]methyl-Sar]-3-[(γ-hydroxy)-N-MeLeu]-4-cyclosporin |
| 752 | S | ~CH2C(O)NH-(D-Glu)6Gly-OH | [(S)-[([HO-Gly-(D-Glu)6]carbamoyl)methylthio]methyl-Sar]-3-[(γ-hydroxy)-N-MeLeu]-4-cyclosporin |

TABLE 2-continued

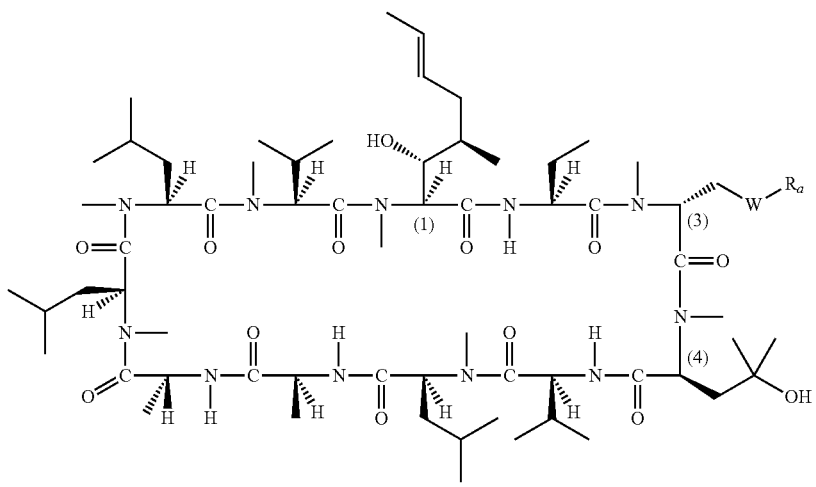

| Ex. No. | W | $R_a$ | Name |
|---|---|---|---|
| 753 | S | 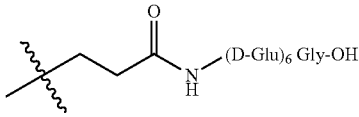 | [(S)-[([HO-Gly-(D-Glu)$_6$]carbamoyl)ethylthio]methyl-Sar]-3-[(γ-hydroxy)-N-MeLeu]-4-cyclosporin |
| 754 | S | 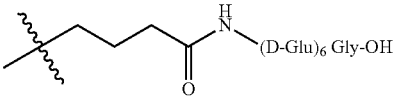 | [(S)-[([HO-Gly-(D-Glu)$_6$]carbamoyl)propylthio]methyl-Sar]-3-[(γ-hydroxy)-N-MeLeu]-4-cyclosporin |
| 755 | S | 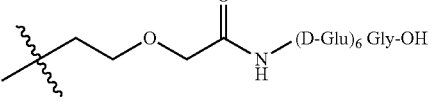 | [(S)-((2-[([HO-Gly-(D-Glu)$_6$]carbamoyl)methoxy]ethyl)sulfanyl)methyl-Sar]-3-[(γ-hydroxy)-N-MeLeu]-4-cyclosporin |
| 756 | S | 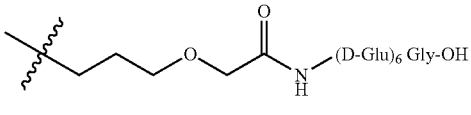 | [(S)-((3-[([HO-Gly-(D-Glu)$_6$]carbamoyl)methoxy]propyl)sulfanyl)methyl-Sar]-3-[(γ-hydroxy)-N-MeLeu]-4-cyclosporin |
| 757 | S | 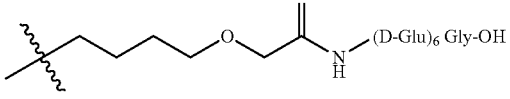 | [(S)-((4-[([HO-Gly-(D-Glu)$_6$]carbamoyl)methoxy]butyl)sulfanyl)methyl-Sar]-3-[(γ-hydroxy)-N-MeLeu]-4-cyclosporin |
| 758 | S | 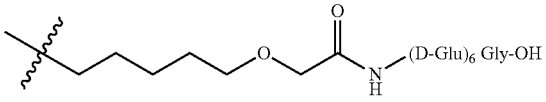 | [(S)-((5-[([HO-Gly-(D-Glu)$_6$]carbamoyl)methoxy]pentyl)sulfanyl)methyl-Sar]-3-[(γ-hydroxy)-N-MeLeu]-4-cyclosporin |
| 759 | S | 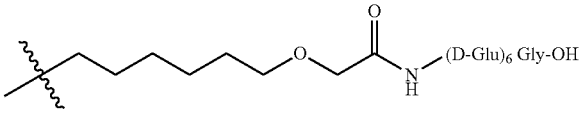 | [(S)-((6-[([HO-Gly-(D-Glu)$_6$]carbamoyl)methoxy]hexyl)sulfanyl)methyl-Sar]-3-[(γ-hydroxy)-N-MeLeu]-4-cyclosporin |
| 760 | S | 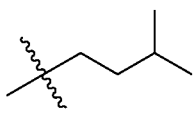 [SMILES: *CCC(C)C] | [(S)-(Isopentylthio)methyl-Sar]-3-[(γ-hydroxy)-N-MeLeu]-4-cyclosporin |
| 761 | S | 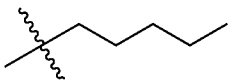 [SMILES: *CCCCC] | [(S)-(5-n-Pentylthio)methyl-Sar]-3-[(γ-hydroxy)-N-MeLeu]-4-cyclosporin |

TABLE 2-continued

| Ex. No. | W | $R_a$ | Name |
|---|---|---|---|
| 762 | S | (hexyl chain) | [(S)-(6-n-Hexylthio)methyl-Sar]-3-[(γ-hydroxy)-N-MeLeu]-4-cyclosporin |
| 763 | S | (heptyl chain) | [(S)-(7-n-Heptylthio)methyl-Sar]-3-[(γ-hydroxy)-N-MeLeu]-4-cyclosporin |
| 764 | O | –CH$_2$C(O)OH | [(R)-(Carboxymethoxy)methyl-Sar]-3-[(γ-hydroxy)-N-MeLeu]-4-cyclosporin |
| 765 | O | –CH$_2$C(O)OK | [(R)-(Carboxymethoxy)methyl-Sar]-3-[(γ-hydroxy)-N-MeLeu]-4-cyclosporin-potassium salt |
| 766 | O | –CH$_2$C(O)ONa | [(R)-(Carboxymethoxy)methyl-Sar]-3-[(γ-hydroxy)-N-MeLeu]-4-cyclosporin-sodium salt |
| 767 | O | –C(CH$_3$)$_2$OH | [(R)-(2-Hydroxy-2,2-dimethylethoxy)methyl-Sar]-3-[(γ-hydroxy)-N-MeLeu]-4-cyclosporin |
| 768 | O | –CH$_2$CH$_2$OCH$_3$ | [(R)-(2-Methoxyethoxy)methyl-Sar]-3-[(γ-hydroxy)-N-MeLeu]-4-cyclosporin |
| 769 | O | –C(CH$_3$)$_2$OCH$_3$ | [(R)-(2-Methoxy-2-methylpropoxy)methyl-Sar]-3-[(γ-hydroxy)-N-MeLeu]-4-cyclosporin |
| 770 | O | –CH$_2$CH$_2$NHCH(CH$_3$)$_2$ | [(R)-(2-(N-Isopropylamino)ethoxy)methyl-Sar]-3-[(γ-hydroxy)-N-MeLeu]-4-cyclosporin |
| 771 | O | –CH$_2$CH$_2$N(CH$_3$)CH(CH$_3$)$_2$ | [(R)-(2-(N-Isopropyl-N-methylamino)ethoxy)methyl-Sar]-3-[(γ-hydroxy)-N-MeLeu]-4-cyclosporin |

TABLE 2-continued

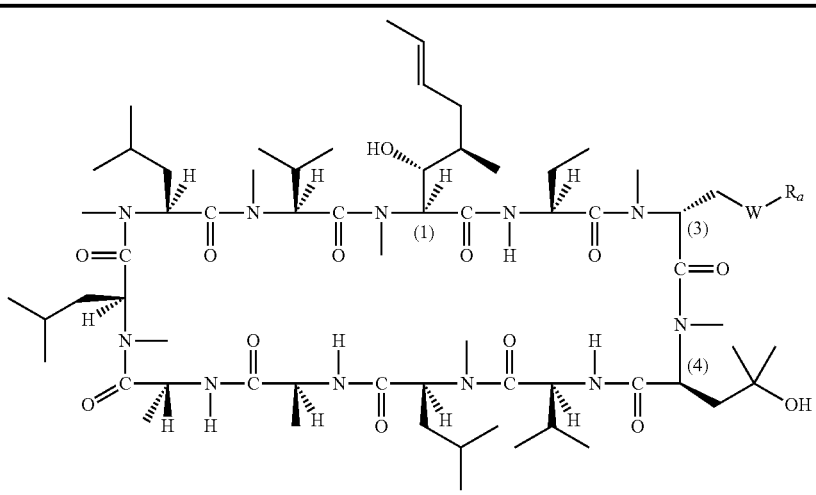

| Ex. No. | W | $R_a$ | Name |
|---|---|---|---|
| 772 | O | 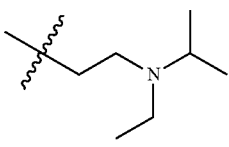 [SMILES: *CCN(CC)C(C)C] | [(R)-(2-(N-Ethyl-N-isopropylamino)ethoxy)methyl-Sar]-3-[(γ-hydroxy)-N-MeLeu]-4-cyclosporin |
| 773 | O | 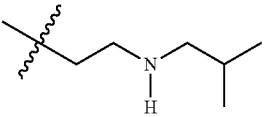 [SMILES: *CCNCC(C)C] | [(R)-(2-(N-Isobutylamino)ethoxy)methyl-Sar]-3-[(γ-hydroxy)-N-MeLeu]-4-cyclosporin |
| 774 | O | 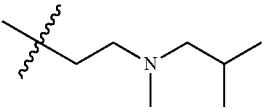 [SMILES: *CCN(C)CC(C)C] | [(R)-(2-(N-Isobutyl-N-methylamino)ethoxy)methyl-Sar]-3-[(γ-hydroxy)-N-MeLeu]-4-cyclosporin |
| 775 | O | 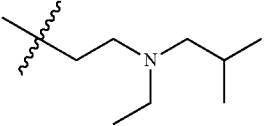 [SMILES: *CCN(CC)CC(C)C] | [(R)-(2-(N-Isobutyl-N-ethylamino)ethoxy)methyl-Sar]-3-[(γ-hydroxy)-N-MeLeu]-4-cyclosporin |
| 776 | O | 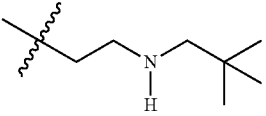 [SMILES: *CCNCC(C)(C)C] | [(R)-(2-(N-Neopentylamino)ethoxy)methyl-Sar]-3-[(γ-hydroxy)-N-MeLeu]-4-cyclosporin |
| 777 | O | 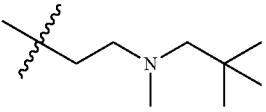 [SMILES: *CCN(C)CC(C)(C)C] | [(R)-(2-(N-Methyl-N-neopentylamino)ethoxy)methyl-Sar]-3-[(γ-hydroxy)-N-MeLeu]-4-cyclosporin |
| 778 | O | 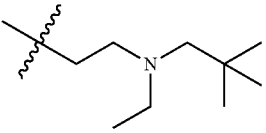 [SMILES: *CCN(CC)CC(C)(C)C] | [(R)-(2-(N-Ethyl-N-neopentylamino)ethoxy)methyl-Sar]-3-[(γ-hydroxy)-N-MeLeu]-4-cyclosporin |
| 779 | O | 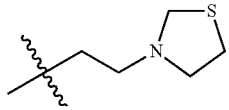 [SMILES: *CCN1CCSC1] | [(R)-(2-(N-Thiazolidinyl)ethoxy)methyl-Sar]-3-[(γ-hydroxy)-N-MeLeu]-4-cyclosporin |

TABLE 2-continued

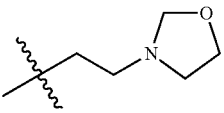 [SMILES: *CCN1CCOC1]

| Ex. No. | W | R$_a$ | Name |
|---|---|---|---|
| 780 | O | 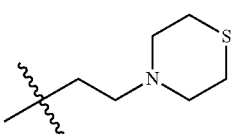 [SMILES: *CCN1CCSCC1] | [(R)-(2-(N-Oxazolidinyl)ethoxy)methyl-Sar]-3-[(γ-hydroxy)-N-MeLeu]-4-cyclosporin |
| 781 | O | 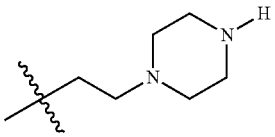 [SMILES: *CCN1CCNCC1] | [(R)-(2-(N-Thiomorpholino)ethoxy)methyl-Sar]-3-[(γ-hydroxy)-N-MeLeu]-4-cyclosporin |
| 782 | O | 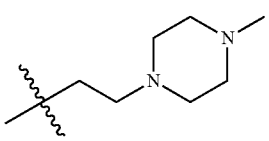 [SMILES: *CCN1CCN(C)CC1] | [(R)-(2-(N-Piperazinyl)ethoxy)methyl-Sar]-3-[(γ-hydroxy)-N-MeLeu]-4-cyclosporin |
| 783 | O | 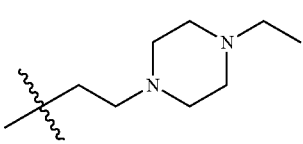 [SMILES: *CCN1CCN(CC)CC1] | [(R)-(2-(4-Methyl-N-piperazinyl)ethoxy)methyl-Sar]-3-[(γ-hydroxy)-N-MeLeu]-4-cyclosporin |
| 784 | O | 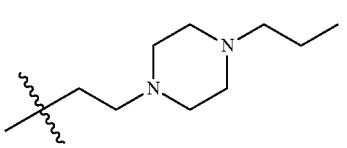 [SMILES: *CCN1CCN(CCC)CC1] | [(R)-(2-(4-Ethyl-N-piperazinyl)ethoxy)methyl-Sar]-3-[(γ-hydroxy)-N-MeLeu]-4-cyclosporin |
| 785 | O | 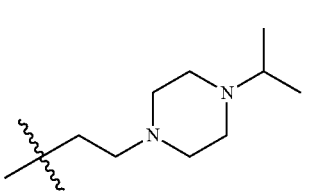 [SMILES: *CCN1CCN(C(C)C)CC1] | [(R)-(2-(4-n-Propyl-N-piperazinyl)ethoxy)methyl-Sar]-3-[(γ-hydroxy)-N-MeLeu]-4-cyclosporin |
| 786 | O |  | [(R)-(2-(4-Isopropyl-N-piperazinyl)ethoxy)methyl-Sar]-3-[(γ-hydroxy)-N-MeLeu]-4-cyclosporin |

TABLE 2-continued

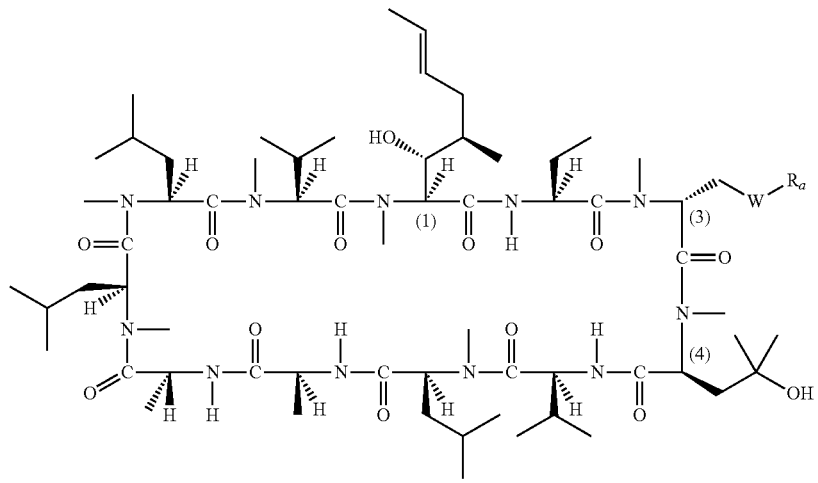

| Ex. No. | W | R$_a$ | Name |
|---|---|---|---|
| 787 | O | | [(R)-(2-(4-Isobutyl-N-piperazinyl)ethoxy)methyl-Sar]-3-[(γ-hydroxy)-N-MeLeu]-4-cyclosporin |
| 788 | O | | [(R)-(2-(4-Neopentyl-N-piperazinyl)ethoxy)methyl-Sar]-3-[(γ-hydroxy)-N-MeLeu]-4-cyclosporin |
| 789 | O | | [(R)-(2-(4-(2-Hydroxyethyl)-N-piperazinyl)ethoxy)methyl-Sar]-3-[(γ-hydroxy)-N-MeLeu]-4-cyclosporin |
| 790 | O | | [(R)-(2-(4-(2-Hydroxy-2-methylbutyl)-N-piperazinyl)ethoxy)methyl-Sar]-3-[(γ-hydroxy)-N-MeLeu]-4-cyclosporin |
| 791 | O | | [(R)-(2-(4-(3-Hydroxy-3-methylbutyl)-N-piperazinyl)ethoxy)methyl-Sar]-3-[(γ-hydroxy)-N-MeLeu]-4-cyclosporin |
| 792 | O | | [(R)-(2-(4-(4-Hydroxy-4-methylpentyl)-N-piperazinyl)ethoxy)methyl-Sar]-3-[(γ-hydroxy)-N-MeLeu]-4-cyclosporin |
| 793 | O | | [(R)-(2-(4-(2-Methoxyethyl)-N-piperazinyl)ethoxy)methyl-Sar]-3-[(γ-hydroxy)-N-MeLeu]-4-cyclosporin |

TABLE 2-continued

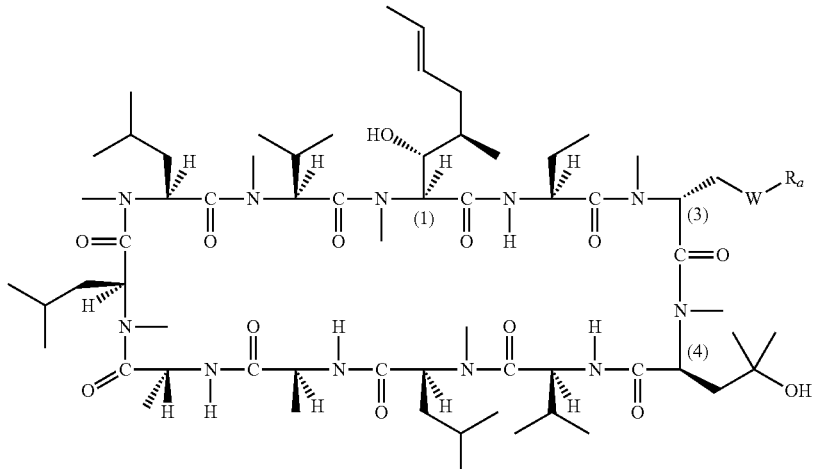

| Ex. No. | W | $R_a$ | Name |
|---|---|---|---|
| 794 | O | 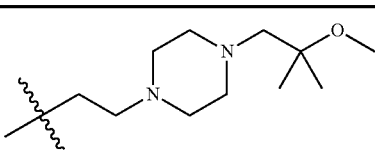 | [(R)-(2-(4-(2-Methoxy-2-methylpropyl)-N-piperazinyl)ethoxy)methyl-Sar]-3-[(γ-hydroxy)-N-MeLeu]-4-cyclosporin |
| 795 | O | 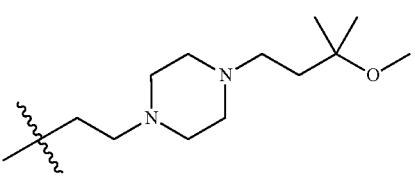 [SMILES: *CCN1CCN(CCC(C)(C)OC)CC1] | [(R)-(2-(4-(3-Methoxy-3-methylbutyl)-N-piperazinyl)ethoxy)methyl-Sar]-3-[(γ-hydroxy)-N-MeLeu]-4-cyclosporin |
| 796 | O | 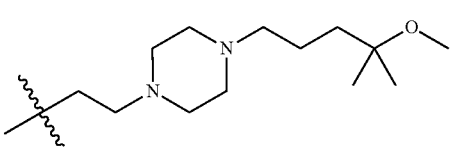 [SMILES: *CCN1CCN(CCCC(C)(C)OC)CC1] | [(R)-(2-(4-(4-Methoxy-4-methylpentyl)-N-piperazinyl)ethoxy)methyl-Sar]-3-[(γ-hydroxy)-N-MeLeu]-4-cyclosporin |
| 797 | O | 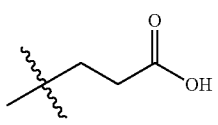 [SMILES: *CCC(=O)O] | [(R)-(2-Carboxyethoxy)methyl-Sar]-3-[(γ-hydroxy)-N-MeLeu]-4-cyclosporin |
| 798 | O | 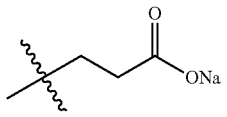 | [(R)-(2-Carboxyethoxy)methyl-Sar]-3-[(γ-hydroxy)-N-MeLeu]-4-cyclosporin-sodium salt |
| 799 | O | 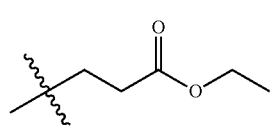 [SMILES: *CCC(=O)OCC] | [(R)-(2-(Ethoxycarbonyl)ethoxy)methyl-Sar]-3-[(γ-hydroxy)-N-MeLeu]-4-cyclosporin |
| 800 | O | 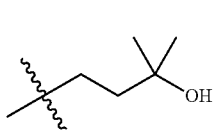 [SMILES: *CCC(C)(C)O] | [(R)-(3-Hydroxy-3-methylbutoxy)methyl-Sar]-3-[(γ-hydroxy)-N-MeLeu]-4-cyclosporin |
| 801 | O | 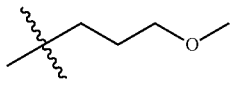 [SMILES: *CCCOC] | [(R)-(3-Methoxypropoxy)methyl-Sar]-3-[(γ-hydroxy)-N-MeLeu]-4-cyclosporin |

TABLE 2-continued

| Ex. No. | W | R$_a$ | Name |
|---|---|---|---|
| 802 | O | (3-methoxy-3-methylbutoxy) group | [(R)-(3-Methoxy-3-methylbutoxy)methyl-Sar]-3-[(γ-hydroxy)-N-MeLeu]-4-cyclosporin |
| 803 | O | 3-(N-isopropylamino)propoxy group | [(R)-(3-(N-Isopropylamino)propoxy)methyl-Sar]-3-[(γ-hydroxy)-N-MeLeu]-4-cyclosporin |
| 804 | O | 3-(N-isopropyl-N-methylamino)propoxy group | [(R)-(3-(N-Isopropyl-N-methylamino)propoxy)methyl-Sar]-3-[(γ-hydroxy)-N-MeLeu]-4-cyclosporin |
| 805 | O | 3-(N-ethyl-N-isopropylamino)propoxy group | [(R)-(3-(N-Ethyl-N-isopropylamino)propoxy)methyl-Sar]-3-[(γ-hydroxy)-N-MeLeu]-4-cyclosporin |
| 806 | O | 3-(N-isobutylamino)propoxy group | [(R)-(3-(N-Isobutylamino)propoxy)methyl-Sar]-3-[(γ-hydroxy)-N-MeLeu]-4-cyclosporin |
| 807 | O | 3-(N-isobutyl-N-methylamino)propoxy group | [(R)-(3-(N-Isobutyl-N-methylamino)propoxy)methyl-Sar]-3-[(γ-hydroxy)-N-MeLeu]-4-cyclosporin |
| 808 | O | 3-(N-isobutyl-N-ethylamino)propoxy group | [(R)-(3-(N-Isobutyl-N-ethylamino)propoxy)methyl-Sar]-3-[(γ-hydroxy)-N-MeLeu]-4-cyclosporin |
| 809 | O | 3-(N,N-diisobutylamino)propoxy group | [(R)-(3-(N,N-Diisobutylamino)propoxy)methyl-Sar]-3-[(γ-hydroxy)-N-MeLeu]-4-cyclosporin |

TABLE 2-continued

| Ex. No. | W | R$_a$ | Name |
|---|---|---|---|
| 810 | O | (butyl-NH-neopentyl) | [(R)-(3-(N-Neopentylamino) propoxy)methyl-Sar]-3-[(γ-hydroxy)-N-MeLeu]-4-cyclosporin |
| 811 | O | (butyl-N(Me)-neopentyl) | [(R)-(3-(N-Methyl-N-Neopentylamino) propoxy)methyl-Sar]-3-[(γ-hydroxy)-N-MeLeu]-4-cyclosporin |
| 812 | O | (butyl-N(Et)-neopentyl) | [(R)-(3-(N-Ethyl-N-Neopentylamino) propoxy)methyl-Sar]-3-[(γ-hydroxy)-N-MeLeu]-4-cyclosporin |
| 813 | O | (propyl-thiazolidinyl) | [(R)-(3-(N-Thiazolidinyl) propoxymethyl-Sar]-3-[(γ-hydroxy)-N-MeLeu]-4-cyclosporin |
| 814 | O | (propyl-oxazolidinyl) | [(R)-(3-(N-Oxazolidinyl) propoxymethyl-Sar]-3-[(γ-hydroxy)-N-MeLeu]-4-cyclosporin |
| 815 | O | (propyl-thiomorpholino) | [(R)-(3-(N-Thiomorpholino) propoxy)methyl-Sar]-3-[(γ-hydroxy)-N-MeLeu]-4-cyclosporin |
| 816 | O | (propyl-piperazinyl) | [(R)-(3-(N-Piperazinyl) propoxy)methyl-Sar]-3-[(γ-hydroxy)-N-MeLeu]-4-cyclosporin |
| 817 | O | (propyl-4-methylpiperazinyl) | [(R)-(3-(4-Methyl-N-piperazinyl) propoxy)methyl-Sar]-3-[(γ-hydroxy)-N-MeLeu]-4-cyclosporin |
| 818 | O | (propyl-4-ethylpiperazinyl) | [(R)-(3-(4-Ethyl-N-piperazinyl) propoxy)methyl-Sar]-3-[(γ-hydroxy)-N-MeLeu]-4-cyclosporin |

TABLE 2-continued

| Ex. No. | W | $R_a$ | Name |
|---|---|---|---|
| 819 | O | 4-(4-propyl-piperazin-1-yl)butyl | [(R)-(3-(4-Propyl-N-piperazinyl)propoxy)methyl-Sar]-3-[(γ-hydroxy)-N-MeLeu]-4-cyclosporin |
| 820 | O | 4-(4-isopropyl-piperazin-1-yl)butyl | [(R)-(3-(4-Isopropyl-N-piperazinyl)propoxy)methyl-Sar]-3-[(γ-hydroxy)-N-MeLeu]-4-cyclosporin |
| 821 | O | 4-(4-isobutyl-piperazin-1-yl)butyl | [(R)-(3-(4-Isobutyl-N-piperazinyl)propoxy)methyl-Sar]-3-[(γ-hydroxy)-N-MeLeu]-4-cyclosporin |
| 822 | O | 4-(4-neopentyl-piperazin-1-yl)butyl | [(R)-(3-(4-Neopentyl-N-piperazinyl)propoxy)methyl-Sar]-3-[(γ-hydroxy)-N-MeLeu]-4-cyclosporin |
| 823 | O | 4-(4-(2-hydroxyethyl)-piperazin-1-yl)butyl | [(R)-(3-(4-(2-Hydroxyethyl)-N-piperazinyl)propoxy)methyl-Sar]-3-[(γ-hydroxy)-N-MeLeu]-4-cyclosporin |
| 824 | O | 4-(4-(2-hydroxy-2,2-dimethylethyl)-piperazin-1-yl)butyl | [(R)-(3-(4-(2-Hydroxy-2,2-dimethylethyl)-N-piperazinyl)propoxy)methyl-Sar]-3-[(γ-hydroxy)-N-MeLeu]-4-cyclosporin |
| 825 | O | 4-(4-(3-hydroxy-3,3-dimethylpropyl)-piperazin-1-yl)butyl | [(R)-(3-(4-(3-Hydroxy-3,3-dimethylpropyl)-N-piperazinyl)propoxy)methyl-Sar]-3-[(γ-hydroxy)-N-MeLeu]-4-cyclosporin |
| 826 | O | 4-(4-(4-hydroxy-4,4-dimethylbutyl)-piperazin-1-yl)butyl | [(R)-(3-(4-(4-Hydroxy-4,4-dimethylbutyl)-N-piperazinyl)propoxy)methyl-Sar]-3-[(γ-hydroxy)-N-MeLeu]-4-cyclosporin |

TABLE 2-continued

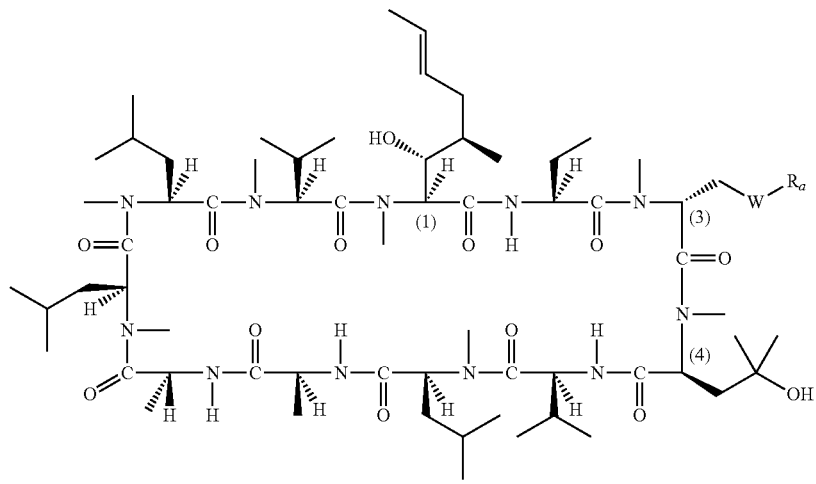

| Ex. No. | W | R_a | Name |
|---|---|---|---|
| 827 | O | (4-(2-methoxyethyl)piperazinyl)propoxy | [(R)-(3-(4-(2-Methoxyethyl)-N-piperazinyl)propoxy)methyl-Sar]-3-[(γ-hydroxy)-N-MeLeu]-4-cyclosporin |
| 828 | O | (4-(2-methoxy-2-methylpropyl)piperazinyl)propoxy | [(R)-(3-(4-(2-Methoxy-2-methylpropyl)-N-piperazinyl)propoxy)methyl-Sar]-3-[(γ-hydroxy)-N-MeLeu]-4-cyclosporin |
| 829 | O | (4-(3-methoxy-3-methylbutyl)piperazinyl)propoxy | [(R)-(3-(4-(3-Methoxy-3-methylbutyl)-N-piperazinyl)propoxy)methyl-Sar]-3-[(γ-hydroxy)-N-MeLeu]-4-cyclosporin |
| 830 | O | (4-(4-methoxy-4-methylpentyl)piperazinyl)propoxy | [(R)-(3-(4-(4-Methoxy-4-methylpentyl)-N-piperazinyl)propoxy)methyl-Sar]-3-[(γ-hydroxy)-N-MeLeu]-4-cyclosporin |
| 831 | O | carboxypropoxy | [(R)-(3-Carboxypropoxy)methyl-Sar]-3-[(γ-hydroxy)-N-MeLeu]-4-cyclosporin |
| 832 | O | carboxypropoxy potassium salt | [(R)-(3-Carboxypropoxy)methyl-Sar]-3-[(γ-hydroxy)-N-MeLeu]-4-cyclosporin-potassium salt |
| 833 | O | carboxypropoxy sodium salt | [(R)-(3-Carboxypropoxy)methyl-Sar]-3-[(γ-hydroxy)-N-MeLeu]-4-cyclosporin-sodium salt |
| 834 | O | ethoxycarbonylpropoxy | [(R)-(3-(Ethoxycarbonyl)propoxy)methyl-Sar]-3-[(γ-hydroxy)-N-MeLeu]-4-cyclosporin |
| 835 | O | 4-hydroxy-4,4-dimethylbutoxy | [(R)-(4-Hydroxy-4,4-dimethylbutoxy)methyl-Sar]-3-[(γ-hydroxy)-N-MeLeu]-4-cyclosporin |

TABLE 2-continued

| Ex. No. | W | $R_a$ | Name |
|---|---|---|---|
| 836 | O | (CH₃)₂C-CH₂CH₂-OH (5-hydroxy-2-methylpentan-2-yl, attached via gem-dimethyl C) | [(R)-((5-Hydroxy-2-methylpentan-2-yl)oxy)methyl-Sar]-3-[(γ-hydroxy)-N-MeLeu]-4-cyclosporin |
| 837 | O | -C(CH₃)₂CH₂OH extended (4-Hydroxy-2,2-dimethylbutoxy) | [(R)-(4-Hydroxy-2,2-dimethylbutoxy)methyl-Sar]-3-[(γ-hydroxy)-N-MeLeu]-4-cyclosporin |
| 838 | O | -CH₂C(CH₃)₂CH₂OH (4-Hydroxy-3,3-dimethylbutoxy) | [(R)-(4-Hydroxy-3,3-dimethylbutoxy)methyl-Sar]-3-[(γ-hydroxy)-N-MeLeu]-4-cyclosporin |
| 839 | O | (4-Methoxy-4-methylpentyloxy) | [(R)-(4-Methoxy-4-methylpentyloxy)methyl-Sar]-3-[(γ-hydroxy)-N-MeLeu]-4-cyclosporin |
| 840 | O | 3-(1-Hydroxycyclopropyl)propoxy | [(R)-(3-(1-Hydroxycyclopropyl)propoxy)methyl-Sar]-3-[(γ-hydroxy)-N-MeLeu]-4-cyclosporin |
| 841 | O | 2-(1-(Hydroxymethyl)cyclopropyl)ethoxy | [(R)-((2-(1-(Hydroxymethyl)cyclopropyl)ethoxy)methyl-Sar]-3-[(γ-hydroxy)-N-MeLeu]-4-cyclosporin |
| 842 | O | ((1-(2-Hydroxyethyl)cyclopropyl)methyl)oxy | [(R)-(((1-(2-Hydroxyethyl)cyclopropyl)methyl)oxy)methyl-Sar]-3-[(γ-hydroxy)-N-MeLeu]-4-cyclosporin |
| 843 | O | (1-(3-Hydroxypropyl)cyclopropyl)oxy | [(R)-((1-(3-Hydroxypropyl)cyclopropyl)oxy)methyl-Sar]-3-[(γ-hydroxy)-N-MeLeu]-4-cyclosporin |
| 844 | O | (S)-4-Hydroxyhexyloxy | [(R)-((S)-4-Hydroxyhexyloxy)methyl-Sar]-3-[(γ-hydroxy)-N-MeLeu]-4-cyclosporin |
| 845 | O | (R)-4-Hydroxyhexyloxy | [(R)-((R)-4-Hydroxyhexyloxy)methyl-Sar]-3-[(γ-hydroxy)-N-MeLeu]-4-cyclosporin |

TABLE 2-continued

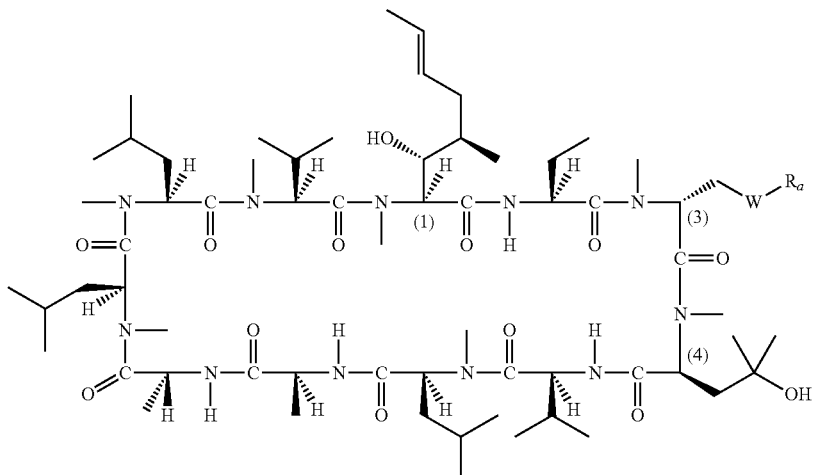

| Ex. No. | W | $R_a$ | Name |
|---|---|---|---|
| 846 | O | 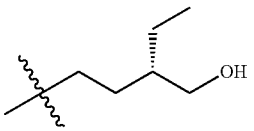 [SMILES: *CC[C@H](CC)CO] | [(R)-(((S)-3-(Hydroxymethyl)pentyl)oxy)methyl-Sar]-3-[(γ-hydroxy)-N-MeLeu]-4-cyclosporin |
| 847 | O | 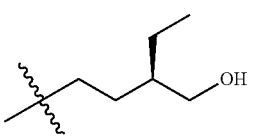 [SMILES: *CC[C@@H](CC)CO] | [(R)-(((R)-3-(Hydroxymethyl)pentyl)oxy)methyl-Sar]-3-[(γ-hydroxy)-N-MeLeu]-4-cyclosporin |
| 848 | O | 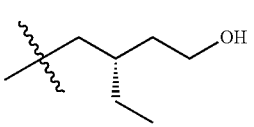 [SMILES: *C[C@@H](CC)CCO] | [(R)-((S)-2-Ethyl-4-hydroxybutoxy)methyl-Sar]-3-[(γ-hydroxy)-N-MeLeu]-4-cyclosporin |
| 849 | O | 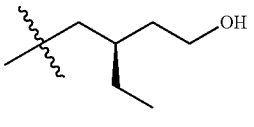 [SMILES: *C[C@H](CC)CCO] | [(R)-(((R)-2-Ethyl-4-hydroxybutoxy)methyl-Sar]-3-[(γ-hydroxy)-N-MeLeu]-4-cyclosporin |
| 850 | O | 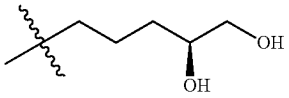 [SMILES: *CCC[C@H](O)CO] | [(R)-(((S)-4,5-Dihydroxy-pentyl)oxy)methyl-Sar]-3-[(γ-hydroxy)-N-MeLeu]-4-cyclosporin |
| 851 | O | 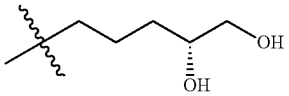 [SMILES: *CCC[C@@H](O)CO] | [(R)-(((R)-4,5-Dihydroxy-pentyl)oxy)methyl-Sar]-3-[(γ-hydroxy)-N-MeLeu]-4-cyclosporin |
| 852 | O | 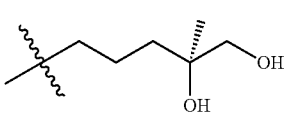 [SMILES: *CCC[C@](C)(O)CO] | [(R)-(((S)-4,5-Dihydroxy-4-methylpentyl)oxy)methyl-Sar]-3-[(γ-hydroxy)-N-MeLeu]-4-cyclosporin |
| 853 | O | 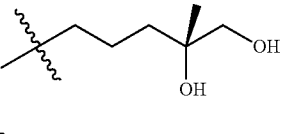 | [(R)-(((R)-4,5-Dihydroxy-4-methylpentyl)oxy)methyl-Sar]-3-[(γ-hydroxy)-N-MeLeu]-4-cyclosporin |
| 854 | O | 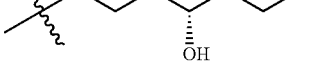 | [(R)-(((R)-4,6-Dihydroxyhexyl)oxy)methyl-Sar]-3-[(γ-hydroxy)-N-MeLeu]-4-cyclosporin |

TABLE 2-continued

| Ex. No. | W | $R_a$ | Name |
|---|---|---|---|
| 855 | O | (S)-4,6-dihydroxyhexyl chain | [(R)-(((S)-4,6-Dihydroxyhexyl)oxy)methyl-Sar]-3-[(γ-hydroxy)-N-MeLeu]-4-cyclosporin |
| 856 | O | (R)-5-hydroxy-3-(hydroxymethyl)pentyl chain | [(R)-(((R)-5-Hydroxy-3-(hydroxymethyl)pentyl)oxy)methyl-Sar]-3-[(γ-hydroxy)-N-MeLeu]-4-cyclosporin |
| 857 | O | (S)-5-hydroxy-3-(hydroxymethyl)pentyl chain | [(R)-(((S)-5-Hydroxy-3-(hydroxymethyl)pentyl)oxy)methyl-Sar]-3-[(γ-hydroxy)-N-MeLeu]-4-cyclosporin |
| 858 | O | 4-hydroxy-2-(2-hydroxyethyl)butyl chain | [(R)-(4-Hydroxy-2-(2-hydroxyethyl)butoxy)methyl-Sar]-3-[(γ-hydroxy)-N-MeLeu]-4-cyclosporin |
| 859 | O | 4-(hydroxymethyl)pent-4-en-1-yl chain | [(R)-((4-(Hydroxymethyl)pent-4-en-1-yl)oxy)methyl-Sar]-3-[(γ-hydroxy)-N-MeLeu]-4-cyclosporin |
| 860 | O | 5-hydroxy-3-methylenepentyl chain | [(R)-((5-Hydroxy-3-methylenepentyl)oxy)methyl-Sar]-3-[(γ-hydroxy)-N-MeLeu]-4-cyclosporin |
| 861 | O | 5-hydroxy-2-methylenepentyl chain | [(R)-((5-Hydroxy-2-methylenepentyl)oxy)methyl-Sar]-3-[(γ-hydroxy)-N-MeLeu]-4-cyclosporin |
| 862 | O | 2-(2-(hydroxymethyl)oxiran-2-yl)ethyl chain | [(R)-(2-(2-(Hydroxymethyl)oxiran-2-yl)ethoxy)methyl-Sar]-3-[(γ-hydroxy)-N-MeLeu]-4-cyclosporin |

TABLE 2-continued

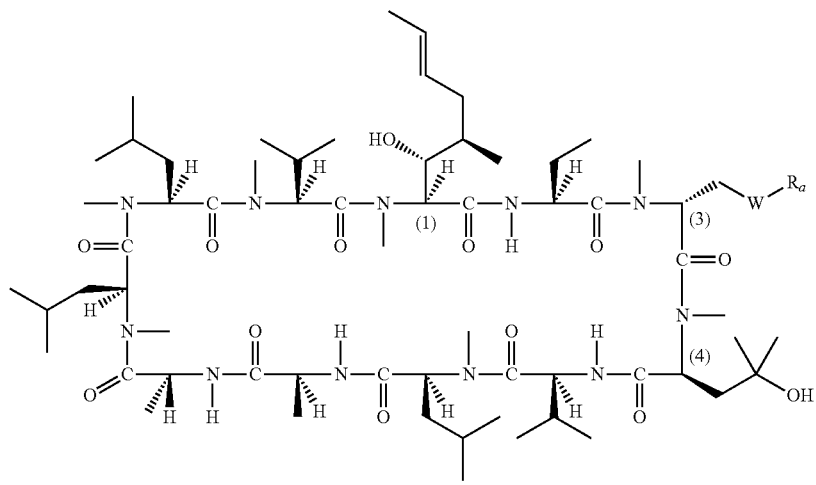

| Ex. No. | W | $R_a$ | Name |
|---|---|---|---|
| 863 | O | (2-(2-hydroxyethyl)oxiran-2-yl)methoxy group | [(R)-((2-(2-Hydroxyethyl)oxiran-2-yl)methoxy)methyl-Sar]-3-[(γ-hydroxy)-N-MeLeu]-4-cyclosporin |
| 864 | O | 3-(3-hydroxyoxetan-3-yl)propoxy group | [(R)-(3-(3-Hydroxyoxetan-3-yl)propoxy)methyl-Sar]-3-[(γ-hydroxy)-N-MeLeu]-4-cyclosporin |
| 865 | O | (4,5-dihydroxy-4-(hydroxymethyl)pentyl)oxy group | [(R)-((4,5-Dihydroxy-4-(hydroxymethyl)pentyl)oxy)methyl-Sar]-3-[(γ-hydroxy)-N-MeLeu]-4-cyclosporin |
| 866 | O | 3-(2-(hydroxymethyl)oxiran-2-yl)propoxy group | [(R)-(3-(2-(Hydroxymethyl)oxiran-2-yl)propoxy)methyl-Sar]-3-[(γ-hydroxy)-N-MeLeu]-4-cyclosporin |
| 867 | O | 2-(2-(2-hydroxyethyl)oxiran-2-yl)ethoxy group | [(R)-(2-(2-(2-Hydroxyethyl)oxiran-2-yl)ethoxy)methyl-Sar]-3-[(γ-hydroxy)-N-MeLeu]-4-cyclosporin |
| 868 | O | (2-(3-hydroxypropyl)oxiran-2-yl)methoxy group | [(R)-((2-(3-Hydroxypropyl)oxiran-2-yl)methoxy)methyl-Sar]-3-[(γ-hydroxy)-N-MeLeu]-4-cyclosporin |
| 869 | O | (5-hydroxy-4-oxohexyl)oxy group | [(R)-((5-Hydroxy-4-oxohexyl)oxy)methyl-Sar]-3-[(γ-hydroxy)-N-MeLeu]-4-cyclosporin |
| 870 | O | (6-hydroxy-5-oxohexyl)oxy group | [(R)-((6-Hydroxy-5-oxohexyl)oxy)methyl-Sar]-3-[(γ-hydroxy)-N-MeLeu]-4-cyclosporin |
| 871 | O | (6-hydroxy-5-oxohexyl)oxy group | [(R)-((6-Hydroxy-5-oxohexyl)oxy)methyl-Sar]-3-[(γ-hydroxy)-N-MeLeu]-4-cyclosporin |

TABLE 2-continued

| Ex. No. | W | R$_a$ | Name |
|---|---|---|---|
| 872 | O | 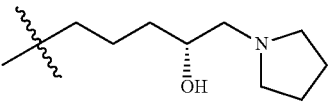 [SMILES: *CCC[C@@H](O)CN1CCCC1] | [(R)-(((R)-4-Hydroxy-5-(pyrrolidin-1-yl)pentyl)oxy)methyl-Sar]-3-[(γ-hydroxy)-N-MeLeu]-4-cyclosporin |
| 873 | O |  | [(R)-(((S)-4-Hydroxy-5-(pyrrolidin-1-yl)pentyl)oxy)methyl-Sar]-3-[(γ-hydroxy)-N-MeLeu]-4-cyclosporin |
| 874 | O | 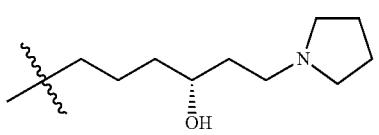 [SMILES: *CCC[C@@H](O)CCN1CCCC1] | [(R)-(((R)-4-Hydroxy-6-(pyrrolidin-1-yl)hexyl)oxy)methyl-Sar]-3-[(γ-hydroxy)-N-MeLeu]-4-cyclosporin |
| 875 | O |  | [(R)-(((S)-4-Hydroxy-6-(piperidin-1-yl)hexyl)oxy)methyl-Sar]-3-[(γ-hydroxy)-N-MeLeu]-4-cyclosporin |
| 876 | O |  | [(R)-(((R)-4-Hydroxy-5-(imidazol-1-yl)pentyl)oxy)methyl-Sar]-3-[(γ-hydroxy)-N-MeLeu]-4-cyclosporin |
| 877 | O |  | [(R)-(((S)-4-Hydroxy-5-(imidazo-1-yl)pentyl)oxy)methyl-Sar]-3-[(γ-hydroxy)-N-MeLeu]-4-cyclosporin |
| 878 | O |  | [(R)-(((R)-4-Hydroxy-6-(imidazo-1-yl)hexyl)oxy)methyl-Sar]-3-[(γ-hydroxy)-N-MeLeu]-4-cyclosporin |
| 879 | O |  | [(R)-(((S)-4-Hydroxy-6-(imidazo-1-yl)hexyl)oxy)methyl-Sar]-3-[(γ-hydroxy)-N-MeLeu]-4-cyclosporin |

TABLE 2-continued

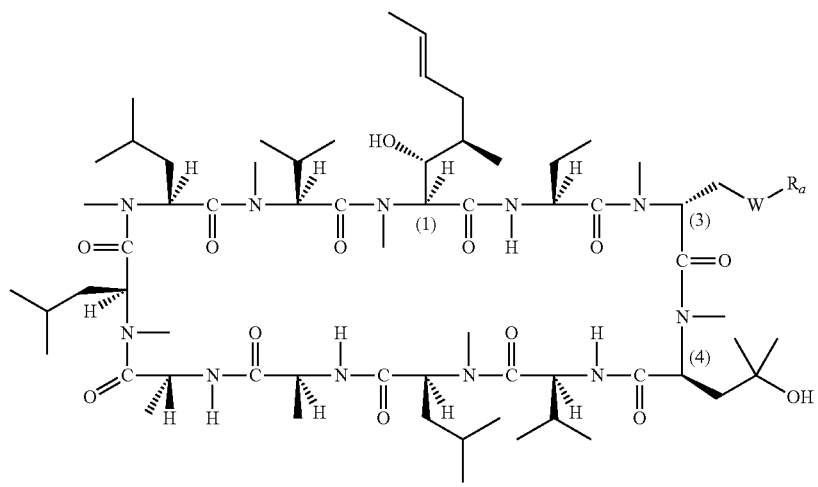

| Ex. No. | W | R_a | Name |
|---|---|---|---|
| 880 | O | (HO-CH2, imidazol-1-yl on butyl chain, R) | [(R)-((R)-3-Hydroxymethyl-4-(imidazol-1-yl)butoxy)methyl-Sar]-3-[(γ-hydroxy)-N-MeLeu]-4-cyclosporin |
| 881 | O | (HO-CH2, imidazol-1-yl on butyl chain, S) | [(R)-((S)-3-Hydroxymethyl-4-(imidazol-1-yl)butoxy)methyl-Sar]-3-[(γ-hydroxy)-N-MeLeu]-4-cyclosporin |
| 882 | O | (HO-CH2, imidazol-1-yl on pentyl chain, R) | [(R)-(((R)-3-Hydroxymethyl-5-(imidazo-1-yl)pentyl)oxy)methyl-Sar]-3-[(γ-hydroxy)-N-MeLeu]-4-cyclosporin |
| 883 | O | (HO-CH2, imidazol-1-yl on pentyl chain, S) | [(R)-(((S)-3-Hydroxymethyl-5-(imidazo-1-yl)pentyl)oxy)methyl-Sar]-3-[(γ-hydroxy)-N-MeLeu]-4-cyclosporin |
| 884 | O | (piperidin-1-yl pentyl, OH, R) | [(R)-(((R)-4-Hydroxy-5-(piperidin-1-yl)pentyl)oxy)methyl-Sar]-3-[(γ-hydroxy)-N-MeLeu]-4-cyclosporin |
| 885 | O | (piperidin-1-yl pentyl, OH, S) | [(R)-(((S)-4-Hydroxy-5-(piperidin-1-yl)pentyl)oxy)methyl-Sar]-3-[(γ-hydroxy)-N-MeLeu]-4-cyclosporin |
| 886 | O | (piperidin-1-yl hexyl, OH, R) | [(R)-(((R)-4-Hydroxy-5-(piperidin-1-yl)hexyl)oxy)methyl-Sar]-3-[(γ-hydroxy)-N-MeLeu]-4-cyclosporin |

TABLE 2-continued

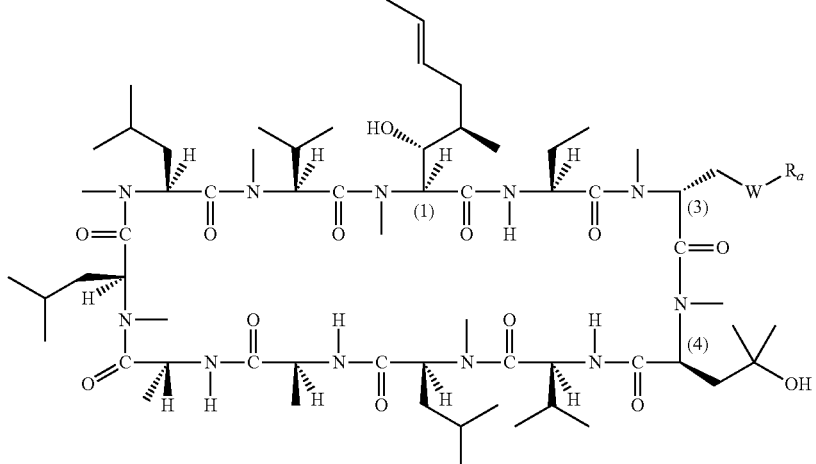

| Ex. No. | W | $R_a$ | Name |
|---|---|---|---|
| 887 | O | 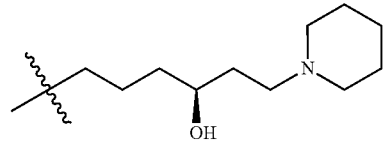 [SMILES: *CCC[C@H](O)CCN1CCCCC1] | [(R)-(((S)-4-Hydroxy-5-(piperidin-1-yl)hexyl)oxy)methyl-Sar]-3-[(γ-hydroxy)-N-MeLeu]-4-cyclosporin |
| 888 | O | 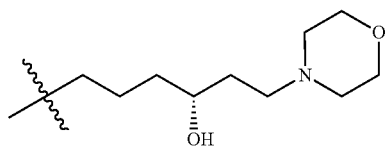 [SMILES: *CCC[C@@H](O)CCN1CCOCC1] | [(R)-(((R)-4-Hydroxy-6-morpholinohexyl)oxy)methyl-Sar]-3-[(γ-hydroxy)-N-MeLeu]-4-cyclosporin |
| 889 | O | 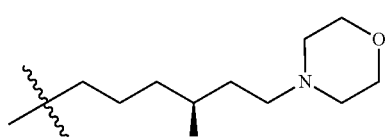 | [(R)-(((S)-4-Hydroxy-6-morpholinohexyl)oxy)methyl-Sar]-3-[(γ-hydroxy)-N-MeLeu]-4-cyclosporin |
| 890 | O | 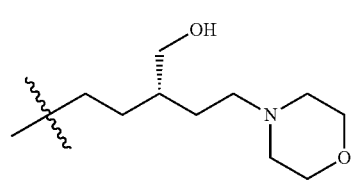 [SMILES: *CC[C@H](CO)CCN1CCOCC1] | [(R)-((R)-2-(Hydroxymethyl)-4-morpholinobutoxy)methyl-Sar]-3-[(γ-hydroxy)-N-MeLeu]-4-cyclosporin |
| 891 | O | 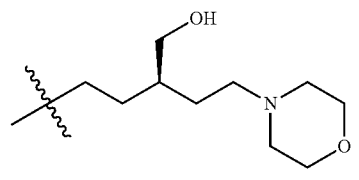 [SMILES: *CC[C@@H](CO)CCN1CCOCC1] | [(R)-((S)-2-(Hydroxymethyl)-4-morpholinobutoxy)methyl-Sar]-3-[(γ-hydroxy)-N-MeLeu]-4-cyclosporin |
| 892 | O | 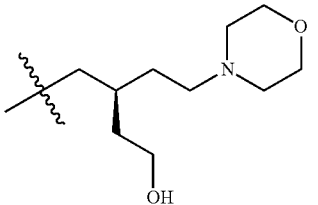 [SMILES: *C[C@H](CCO)CCN1CCOCC1] | [(R)-((S)-4-Hydroxy-2-(2-morpholinoethyl)butoxy)methyl-Sar]-3-[(γ-hydroxy)-N-MeLeu]-4-cyclosporin |

TABLE 2-continued

| Ex. No. | W | $R_a$ | Name |
|---|---|---|---|
| 893 | O | | [(R)-((R)-4-Hydroxy-2-(2-morpholinoethyl)butoxy)methyl-Sar]-3-[(γ-hydroxy)-N-MeLeu]-4-cyclosporin |
| 894 | O | | [(R)-(((S)-4-Hydroxy-6-(4-methylpiperazin-1-yl)hexyl)oxy)methyl-Sar]-3-[(γ-hydroxy)-N-MeLeu]-4-cyclosporin |
| 895 | O | | [(R)-(((R)-4-Hydroxy-6-(4-methylpiperazin-1-yl)hexyl)oxy)methyl-Sar]-3-[(γ-hydroxy)-N-MeLeu]-4-cyclosporin |
| 896 | O | | [(R)-(((S)-4-Hydroxy-6-(4-ethylpiperazin-1-yl)hexyl)oxy)methyl-Sar]-3-[(γ-hydroxy)-N-MeLeu]-4-cyclosporin |
| 897 | O | | [(R)-(((R)-4-Hydroxy-6-(4-ethylpiperazin-1-yl)hexyl)oxy)methyl-Sar]-3-[(γ-hydroxy)-N-MeLeu]-4-cyclosporin |
| 898 | O | | [(R)-(((R)-4-Hydroxy-6-(4-isopropylpiperazin-1-yl)hexyl)oxy)methyl-Sar]-3-[(γ-hydroxy)-N-MeLeu]-4-cyclosporin |

TABLE 2-continued

| Ex. No. | W | $R_a$ | Name |
|---|---|---|---|
| 899 | O | (piperazine-containing hexyl with OH, isopropyl on piperazine) | [(R)-(((S)-4-Hydroxy-6-(4-isopropylpiperazin-1-yl)hexyl)oxy)methyl-Sar]-3-[(γ-hydroxy)-N-MeLeu]-4-cyclosporin |
| 900 | O | (pentyl with hydroxymethyl branch, 4-methylpiperazine) | [(R)-(((S)-3-Hydroxymethyl-5-(4-methylpiperazin-1-yl)pentyl)oxy)methyl-Sar]-3-[(γ-hydroxy)-N-MeLeu]-4-cyclosporin |
| 901 | O | (pentyl with hydroxymethyl branch, 4-methylpiperazine) | [(R)-(((R)-3-Hydroxymethyl-5-(4-methylpiperazin-1-yl)pentyl)oxy)methyl-Sar]-3-[(γ-hydroxy)-N-MeLeu]-4-cyclosporin |
| 902 | O | (pentyl with hydroxymethyl branch, 4-ethylpiperazine) | [(R)-(((S)-3-Hydroxymethyl-5-(4-ethylpiperazin-1-yl)pentyl)oxy)methyl-Sar]-3-[(γ-hydroxy)-N-MeLeu]-4-cyclosporin |
| 903 | O | (pentyl with hydroxymethyl branch, 4-ethylpiperazine) | [(R)-(((R)-3-Hydroxymethyl-5-(4-ethylpiperazin-1-yl)pentyl)oxy)methyl-Sar]-3-[(γ-hydroxy)-N-MeLeu]-4-cyclosporin |
| 904 | O | (pentyl with hydroxymethyl branch, 4-isopropylpiperazine) | [(R)-(((R)-3-Hydroxymethyl-5-(4-isopropylpiperazin-1-yl)pentyl)oxy)methyl-Sar]-3-[(γ-hydroxy)-N-MeLeu]-4-cyclosporin |

TABLE 2-continued

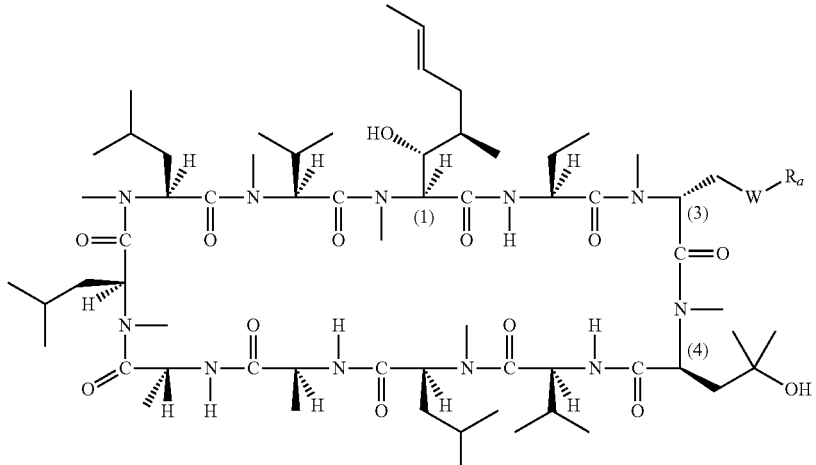

| Ex. No. | W | R$_a$ | Name |
|---|---|---|---|
| 905 | O | 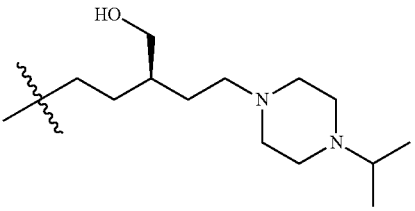 [SMILES: *CC[C@@H](CO)CCN1CCN(C(C)C)CC1] | [(R)-(((S)-3-Hydroxymethyl-5-(4-isopropylpiperazin-1-yl)pentyl)oxy)methyl-Sar]-3-[(γ-hydroxy)-N-MeLeu]-4-cyclosporin |
| 906 | O | 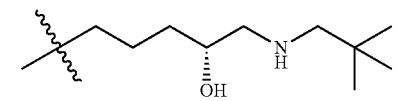 [SMILES: *CCC[C@@H](O)CNCC(C)(C)C] | [(R)-(((R)-4-Hydroxy-5-(neopentylamino)pentyl)oxy)methyl-Sar]-3-[(γ-hydroxy)-N-MeLeu]-4-cyclosporin |
| 907 | O | 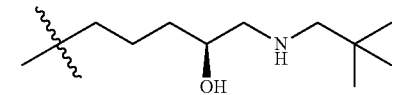 [SMILES: *CCC[C@H](O)CNCC(C)(C)C] | [(R)-(((S)-4-Hydroxy-5-(neopentylamino)pentyl)oxy)methyl-Sar]-3-[(γ-hydroxy)-N-MeLeu]-4-cyclosporin |
| 908 | O | 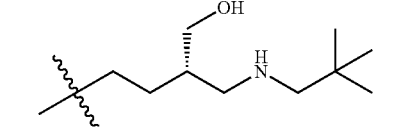 [SMILES: *CC[C@H](CO)CNCC(C)(C)C] | [(R)-(((S)-4-Hydroxy-3-((neopentylamino)methyl)butyl)oxy)methyl-Sar]-3-[(γ-hydroxy)-N-MeLeu]-4-cyclosporin |
| 909 | O | 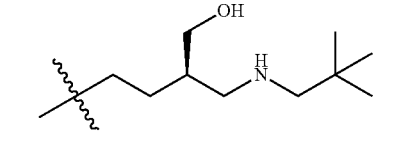 [SMILES: *CC[C@@H](CO)CNCC(C)(C)C] | [(R)-((R)-4-Hydroxy-3-((neopentylamino)methyl)butoxy)methyl-Sar]-3-[(γ-hydroxy)-N-MeLeu]-4-cyclosporin |
| 910 | O | 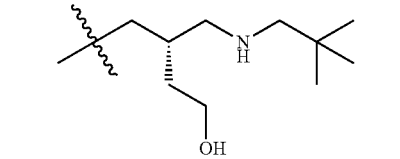 [SMILES: *C[C@@H](CCO)CNCC(C)(C)C] | [(R)-((S)-4-Hydroxy-2-((neopentylamino)methyl)butoxy)methyl-Sar]-3-[(γ-hydroxy)-N-MeLeu]-4-cyclosporin |
| 911 | O | 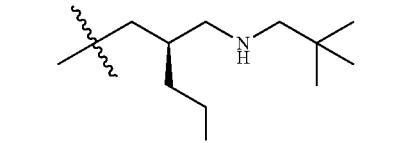 | [(R)-((R)-4-Hydroxy-2-((neopentylamino)methyl)butoxy)methyl-Sar]-3-[(γ-hydroxy)-N-MeLeu]-4-cyclosporin |

TABLE 2-continued

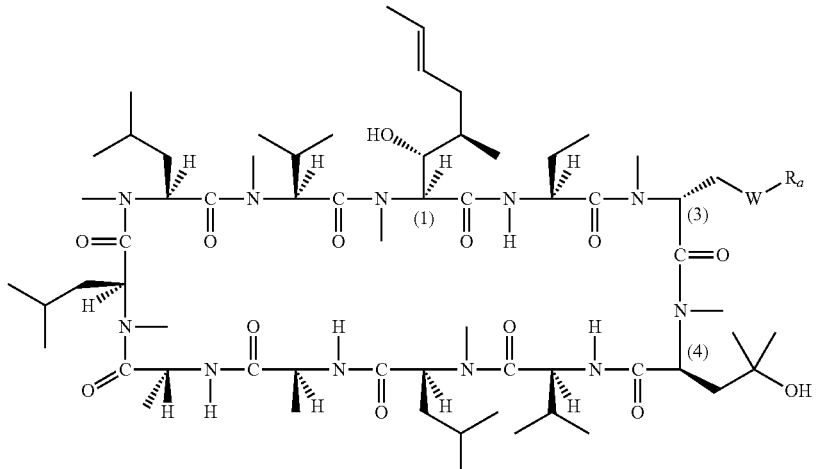

| Ex. No. | W | $R_a$ | Name |
|---|---|---|---|
| 912 | O | 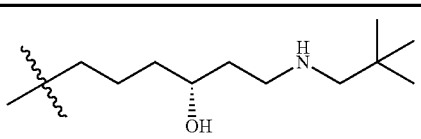 | [(R)-(((R)-4-Hydroxy-6-(neopentylamino)hexyl)oxy)methyl-Sar]-3-[(γ-hydroxy)-N-MeLeu]-4-cyclosporin |
| 913 | O | 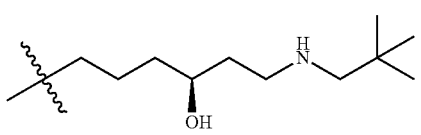 [SMILES: *CCC[C@H](O)CCNCC(C)(C)C] | [(R)-(((S)-4-Hydroxy-6-(neopentylamino)hexyl)oxy)methyl-Sar]-3-[(γ-hydroxy)-N-MeLeu]-4-cyclosporin |
| 914 | O | 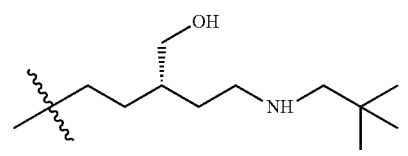 [SMILES: *CC[C@H](CO)CCNCC(C)(C)C] | [(R)-(((R)-3-(Hydroxymethyl)-5-(neopentylamino)pentyl)oxy)methyl-Sar]-3-[(γ-hydroxy)-N-MeLeu]-4-cyclosporin |
| 915 | O |  | [(R)-(((S)-3-(Hydroxymethyl)-5-(neopentylamino)pentyl)oxy)methyl-Sar]-3-[(γ-hydroxy)-N-MeLeu]-4-cyclosporin |
| 916 | O | 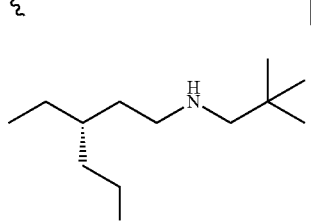 | [(R)-((R)-4-Hydroxy-2-(2-(neopentylamino)ethyl)butoxy)methyl-Sar]-3-[(γ-hydroxy)-N-MeLeu]-4-cyclosporin |
| 917 | O | 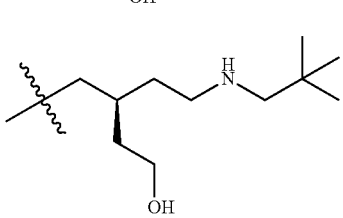 | [(R)-((S)-4-Hydroxy-2-(2-(neopentylamino)ethyl)butoxy)methyl-Sar]-3-[(γ-hydroxy)-N-MeLeu]-4-cyclosporin |
| 918 | O | 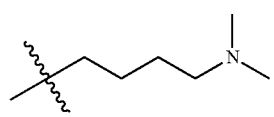 [SMILES: *CCCCN(C)C] | [(R)-(4-(N,N-Dimethylamino)butoxy)methyl-Sar]-3-[(γ-hydroxy)-N-MeLeu]-4-cyclosporin |

TABLE 2-continued

| Ex. No. | W | R$_a$ | Name |
|---|---|---|---|
| 919 | O | (CH$_2$)$_4$N(Et)$_2$ | [(R)-(4-(N,N-Diethylamino)butoxy)methyl-Sar]-3-[(γ-hydroxy)-N-MeLeu]-4-cyclosporin |
| 920 | O | (CH$_2$)$_4$NH-iPr | [(R)-(4-(N-Isopropylamino)butoxy)methyl-Sar]-3-[(γ-hydroxy)-N-MeLeu]-4-cyclosporin |
| 921 | O | (CH$_2$)$_4$N(Me)(iPr) | [(R)-(4-(N-Isopropyl-N-methylamino)butoxy)methyl-Sar]-3-[(γ-hydroxy)-N-MeLeu]-4-cyclosporin |
| 922 | O | (CH$_2$)$_4$N(Et)(iPr) | [(R)-(4-(N-Ethyl-N-isopropylamino)butoxy)methyl-Sar]-3-[(γ-hydroxy)-N-MeLeu]-4-cyclosporin |
| 923 | O | (CH$_2$)$_4$NH-iBu | [(R)-(4-(N-Isobutylamino)butoxy)methyl-Sar]-3-[(γ-hydroxy)-N-MeLeu]-4-cyclosporin |
| 924 | O | (CH$_2$)$_4$N(Me)(iBu) | [(R)-(4-(N-Isobutyl-N-methylamino)butoxy)methyl-Sar]-3-[(γ-hydroxy)-N-MeLeu]-4-cyclosporin |
| 925 | O | (CH$_2$)$_4$N(Et)(iBu) | [(R)-(4-(N-Isobutyl-N-ethylamino)butoxy)methyl-Sar]-3-[(γ-hydroxy)-N-MeLeu]-4-cyclosporin |

TABLE 2-continued

| Ex. No. | W | R<sub>a</sub> | Name |
| --- | --- | --- | --- |
| 926 | O | (isobutyl)₂N-CH₂CH₂CH₂CH₂- branched | [(R)-(4-(N,N-Diisobutylamino)butoxy)methyl-Sar]-3-[(γ-hydroxy)-N-MeLeu]-4-cyclosporin |
| 927 | O | (neopentyl)NH-CH₂CH₂CH₂CH₂- branched | [(R)-(4-(N-Neopentylamino)butoxy)methyl-Sar]-3-[(γ-hydroxy)-N-MeLeu]-4-cyclosporin |
| 928 | O | (neopentyl)(Me)N-CH₂CH₂CH₂CH₂- branched | [(R)-(4-(N-Methyl-N-neopentylamino)butoxy)methyl-Sar]-3-[(γ-hydroxy)-N-MeLeu]-4-cyclosporin |
| 929 | O | (neopentyl)(Et)N-CH₂CH₂CH₂CH₂- branched | [(R)-(4-(N-Ethyl-N-neopentylamino)butoxy)methyl-Sar]-3-[(γ-hydroxy)-N-MeLeu]-4-cyclosporin |
| 930 | O | pyrrolidinyl-CH₂CH₂CH₂CH₂- branched | [(R)-(4-(N-Pyrrolidinyl)butoxy)methyl-Sar]-3-[(γ-hydroxy)-N-MeLeu]-4-cyclosporin |
| 931 | O | thiazolidinyl-CH₂CH₂CH₂CH₂- branched | [(R)-(4-(N-Thiazolidinyl)butoxy)methyl-Sar]-3-[(γ-hydroxy)-N-MeLeu]-4-cyclosporin |
| 932 | O | oxazolidinyl-CH₂CH₂CH₂CH₂- branched | [(R)-(4-(N-Oxazolidinyl)butoxy)methyl-Sar]-3-[(γ-hydroxy)-N-MeLeu]-4-cyclosporin |
| 933 | O | piperidinyl-CH₂CH₂CH₂CH₂- branched | [(R)-(4-(N-Piperidinyl)butoxy)methyl-Sar]-3-[(γ-hydroxy)-N-MeLeu]-4-cyclosporin |

TABLE 2-continued

| Ex. No. | W | $R_a$ | Name |
| --- | --- | --- | --- |
| 934 | O | (morpholinobutyl) | [(R)-(4-(N-Morpholino)butoxy)methyl-Sar]-3-[(γ-hydroxy)-N-MeLeu]-4-cyclosporin |
| 935 | O | (thiomorpholinobutyl) | [(R)-(4-(N-Thiomorpholino)butoxy)methyl-Sar]-3-[(γ-hydroxy)-N-MeLeu]-4-cyclosporin |
| 936 | O | (piperazinylbutyl) | [(R)-(4-(N-Piperazinyl)butoxy)methyl-Sar]-3-[(γ-hydroxy)-N-MeLeu]-4-cyclosporin |
| 937 | O | (4-methylpiperazinylbutyl) | [(R)-(4-(4-Methyl-N-piperazinyl)butoxy)methyl-Sar]-3-[(γ-hydroxy)-N-MeLeu]-4-cyclosporin |
| 938 | O | (4-ethylpiperazinylbutyl) | [(R)-(4-(4-Ethyl-N-piperazinyl)butoxy)methyl-Sar]-3-[(γ-hydroxy)-N-MeLeu]-4-cyclosporin |
| 939 | O | (4-n-propylpiperazinylbutyl) | [(R)-(4-(4-n-Propyl-N-piperazinyl)butoxy)methyl-Sar]-3-[(γ-hydroxy)-N-MeLeu]-4-cyclosporin |
| 940 | O | (4-isopropylpiperazinylbutyl) | [(R)-(4-(4-Isopropyl-N-piperazinyl)butoxy)methyl-Sar]-3-([γ-hydroxy)-N-MeLeu]-4-cyclosporin |

TABLE 2-continued

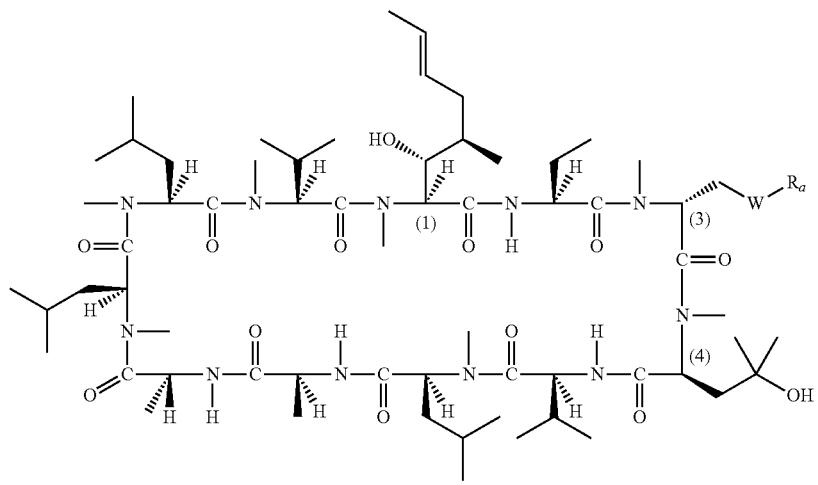

| Ex. No. | W | R_a | Name |
|---|---|---|---|
| 941 | O | (piperazine with isobutyl) | [(R)-(4-(4-Isobutyl-N-piperazinyl)butoxy)methyl-Sar]-3-[(γ-hydroxy)-N-MeLeu]-4-cyclosporin |
| 942 | O | (piperazine with neopentyl) | [(R)-(4-(4-Neopentyl-N-piperazinyl)butoxy)methyl-Sar]-3-[(γ-hydroxy)-N-MeLeu]-4-cyclosporin |
| 943 | O | (piperazine with 2-hydroxyethyl) | [(R)-(4-(4-(2-Hydroxyethyl)-N-piperazinyl)butoxy)methyl-Sar]-3-[(γ-hydroxy)-N-MeLeu]-4-cyclosporin |
| 944 | O | (piperazine with 2-hydroxy-2-methylpropyl) | [(R)-(4-(4-(2-Hydroxy-2-methylpropyl)-N-piperazinyl)butoxy)methyl-Sar]-3-[(γ-hydroxy)-N-MeLeu]-4-cyclosporin |
| 945 | O | (piperazine with 3-hydroxy-3-methylbutyl) | [(R)-(4-(4-(3-Hydroxy-3-methylbutyl)-N-piperazinyl)butoxy)methyl-Sar]-3-[(γ-hydroxy)-N-MeLeu]-4-cyclosporin |
| 946 | O | (piperazine with 4-hydroxy-4,4-dimethylbutyl) | [(R)-(4-(4-(4-Hydroxy-4,4-dimethylbutyl)-N-piperazinyl)butoxy)methyl-Sar]-3-[(γ-hydroxy)-N-MeLeu]-4-cyclosporin |
| 947 | O | (piperazine with 2-methoxyethyl) | [(R)-(4-(4-(2-Methoxyethyl)-N-piperazinyl)butoxy)methyl-Sar]-3-[(γ-hydroxy)-N-MeLeu]-4-cyclosporin |

TABLE 2-continued

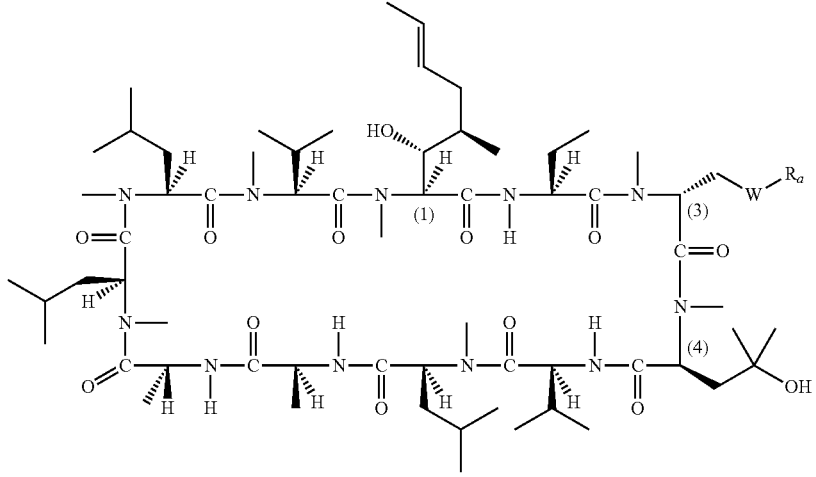

| Ex. No. | W | $R_a$ | Name |
|---|---|---|---|
| 948 | O | 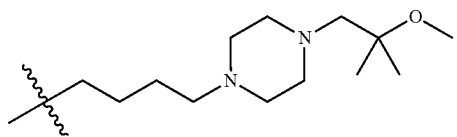 [SMILES: *CCCCN1CCN(CC(C)(C)OC)CC1] | [(R)-(4-(4-(2-Methoxy-2-methylpropyl)-N-piperazinyl)butoxy)methyl-Sar]-3-[(γ-hydroxy)-N-MeLeu]-4-cyclosporin |
| 949 | O | 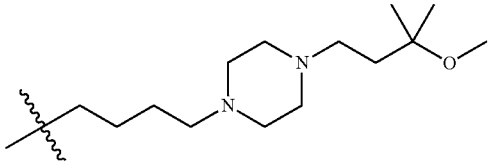 [SMILES: *CCCCN1CCN(CCC(C)(C)OC)CC1] | [(R)-(4-(4-(3-Methoxy-3-methylbutyl)-N-piperazinyl)butoxy)methyl-Sar]-3-[(γ-hydroxy)-N-MeLeu]-4-cyclosporin |
| 950 | O | 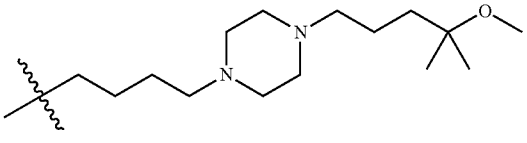 [SMILES: *CCCCN1CCN(CCCC(C)(C)OC)CC1] | [(R)-(4-(4-(4-methoxy-4-methylpentyl)-N-piperazinyl)butoxy)methyl-Sar]-3-[(γ-hydroxy)-N-MeLeu]-4-cyclosporin |
| 951 | O | 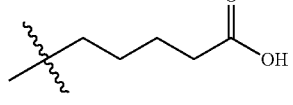 | [(R)-(4-Carboxybutoxy)methyl-Sar]-3-[(γ-hydroxy)-N-MeLeu]-4-cyclosporin |
| 952 | O | 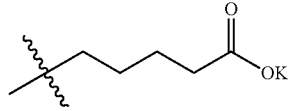 | [(R)-(4-Carboxybutoxy)methyl-Sar]-3-[(γ-hydroxy)-N-MeLeu]-4-cyclosporin-potassium salt |
| 953 | O | 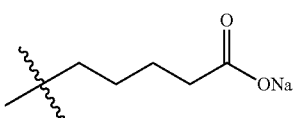 | [(R)-(4-Carboxybutoxy)methyl-Sar]-3-[(γ-hydroxy)-N-MeLeu]-4-cyclosporin-sodium salt |
| 954 | O | 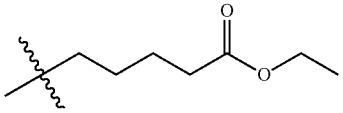 [SMILES: *CCCCC(=O)OCC] | [(R)-(4-(Ethoxycarbonyl)butoxy)methyl-Sar]-3-[(γ-hydroxy)-N-MeLeu]-4-cyclosporin |
| 955 | O | 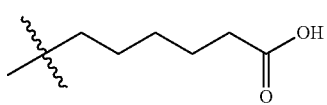 | [(R)-(5-Carboxypentyloxy)methyl-Sar]-3-[(γ-hydroxy)-N-MeLeu]-4-cyclosporin |

TABLE 2-continued

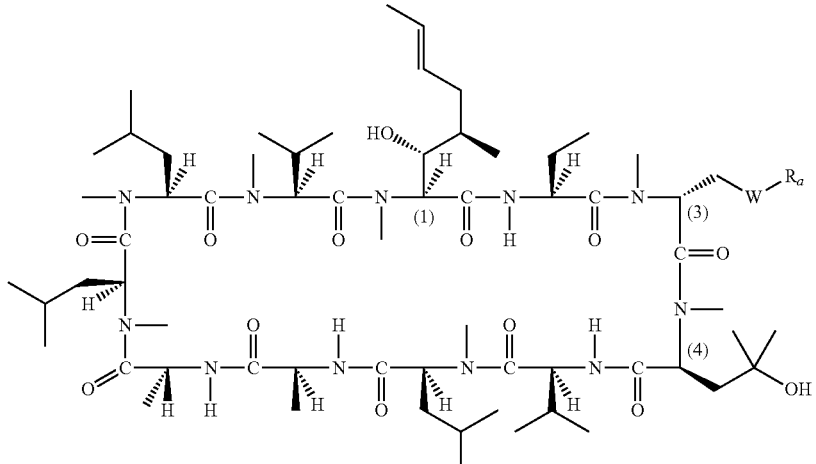

| Ex. No. | W | $R_a$ | Name |
|---|---|---|---|
| 956 | O | (5-carboxypentyloxy, K salt) | [(R)-(5-Carboxypentyloxy)methyl-Sar]-3-[(γ-hydroxy)-N-MeLeu]-4-cyclosporin-potassium salt |
| 957 | O | (5-carboxypentyloxy, Na salt) | [(R)-(5-Carboxypentyloxy)methyl-Sar]-3-[(γ-hydroxy)-N-MeLeu]-4-cyclosporin-sodium salt |
| 958 | O | (5-ethoxycarbonylpentyloxy) | [(R)-(5-(Ethoxycarbonyl)pentyloxy)methyl-Sar]-3-[(γ-hydroxy)-N-MeLeu]-4-cyclosporin |
| 959 | O | (4,4'-dicarboxybutoxy) | [(R)-((4,4'-Dicarboxy)butoxy)methyl-Sar]-3-[(γ-hydroxy)-N-MeLeu]-4-cyclosporin |
| 960 | O | (4,4'-dicarboxybutoxy, K salt) | [(R)-((4,4'-Dicarboxy)butoxy)methyl-Sar]-3-[(γ-hydroxy)-N-MeLeu]-4-cyclosporin-dipotassium salt |
| 961 | O | (6,6'-dicarboxyhexyloxy) | [(R)-(6,6'-Di(carboxy)hexyloxy)methyl-Sar]-3-[(γ-hydroxy)-N-MeLeu]-4-cyclosporin |
| 962 | O | (6,6'-dicarboxyhexyloxy, K salt) | [(R)-(6,6'-Di(carboxy)hexyloxy)methyl-Sar]-3-[(γ-hydroxy)-N-MeLeu]-4-cyclosporin-dipotassium salt |

TABLE 2-continued

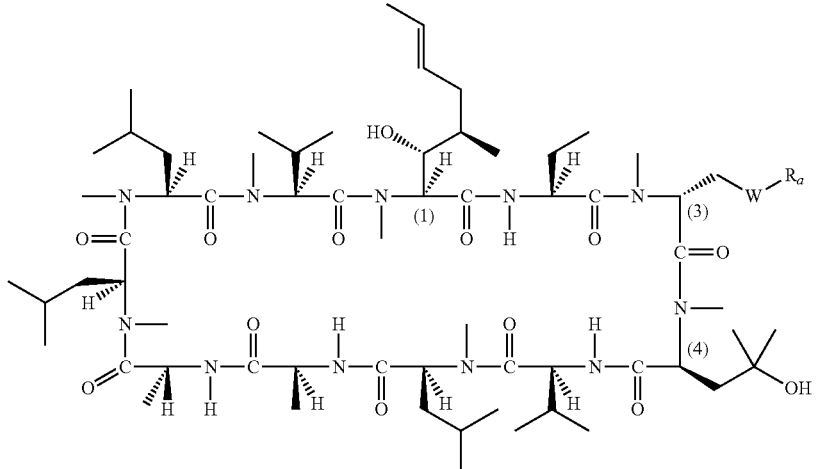

| Ex. No. | W | R$_a$ | Name |
|---|---|---|---|
| 963 | O | 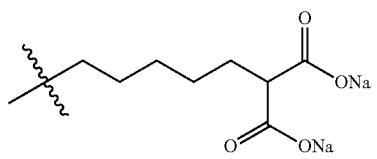 | [(R)-(6,6'-Di(carboxy)hexyloxy)methyl-Sar]-3-[(γ-hydroxy)-N-MeLeu]-4-cyclosporin-disodium salt |
| 964 | O | 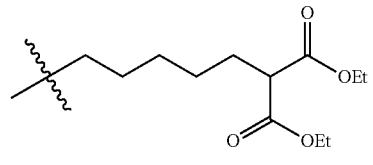 [SMILES: *CCCCCC(C(=O)OCC)C(=O)OCC] | [(R)-(6,6'-Di(ethoxycarbonyl)hexyloxy)methyl-Sar]-3-[(γ-hydroxy)-N-MeLeu]-4-cyclosporin |
| 965 | O | 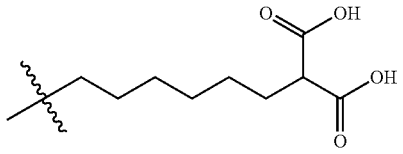 [SMILES: *CCCCCCC(C(=O)O)C(=O)O] | [(R)-(7,7'-Di(carboxy)heptyloxy)methyl-Sar]-3-[(γ-hydroxy)-N-MeLeu]-4-cyclosporin |
| 966 | O | 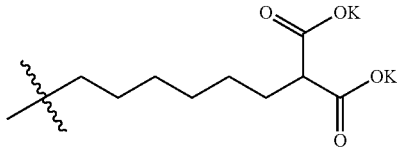 | [(R)-(7,7'-Di(carboxy)heptyloxy)methyl-Sar]-3-[(γ-hydroxy)-N-MeLeu]-4-cyclosporin-dipotassium salt |
| 967 | O | 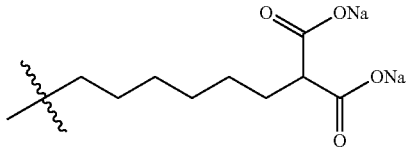 | [(R)-(7,7'-Di(carboxy)heptyloxy)methyl-Sar]-3-[(γ-hydroxy)-N-MeLeu]-4-cyclosporin-disodium salt |
| 968 | O | 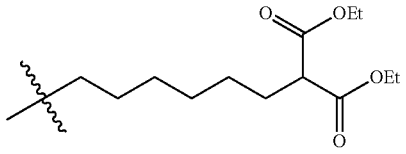 [SMILES: *CCCCCCC(C(=O)OCC)C(=O)OCC] | [(R)-(7,7'-Di(ethoxycarbonyl)heptyloxy)methyl-Sar]-3-[(γ-hydroxy)-N-MeLeu]-4-cyclosporin |
| 969 | O | 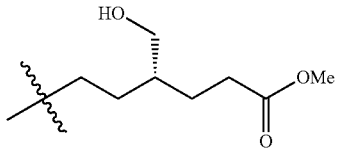 [SMILES: *CC[C@H](CO)CCC(=O)OC] | [(R)-(((R)-3-Hydroxymethyl-6-methoxy-6-oxohexyl)thio)methyl-Sar]-3-[(γ-hydroxy)-N-MeLeu]-4-cyclosporin |

TABLE 2-continued

| Ex. No. | W | $R_a$ | Name |
|---|---|---|---|
| 970 | O | (4-(hydroxymethyl)-6-methoxy-6-oxohexyl, OMe ester) | [(R)-(((S)-3-Hydroxy-6-methoxy-6-oxohexyl)thio)methyl-Sar]-3-[(γ-hydroxy)-N-MeLeu]-4-cyclosporin |
| 971 | O | (4-(hydroxymethyl)-6-ethoxy-6-oxohexyl, OEt ester, R) | [(R)-(((R)-3-Hydroxy-6-ethoxy-6-oxohexyl)thio)methyl-Sar]-3-[(γ-hydroxy)-N-MeLeu]-4-cyclosporin |
| 972 | O | (4-(hydroxymethyl)-6-ethoxy-6-oxohexyl, OEt ester, S) | [(R)-(((S)-3-Hydroxy-6-ethoxy-6-oxohexyl)thio)methyl-Sar]-3-[(γ-hydroxy)-N-MeLeu]-4-cyclosporin |
| 973 | O | (4-(hydroxymethyl)-6-(neopentylamino)hexyl, R) | [(R)-(((R)-3-Hydroxy-6-(neopentylamino)hexyl)thio)methyl-Sar]-3-[(γ-hydroxy)-N-MeLeu]-4-cyclosporin |
| 974 | O | (4-(hydroxymethyl)-6-(neopentylamino)hexyl, S) | [(R)-(((S)-3-Hydroxy-6-(neopentylamino)hexyl)thio)methyl-Sar]-3-[(γ-hydroxy)-N-MeLeu]-4-cyclosporin |
| 975 | O | (4-(hydroxymethyl)-6-(imidazol-1-yl)hexyl, R) | [(R)-(((R)-3-Hydroxymethyl-6-(imidazo-1-yl)hexyl)thio)methyl-Sar]-3-[(γ-hydroxy)-N-MeLeu]-4-cyclosporin |
| 976 | O | (4-(hydroxymethyl)-6-(imidazol-1-yl)hexyl, S) | [(R)-(((S)-3-Hydroxymethyl-6-(imidazo-1-yl)hexyl)thio)methyl-Sar]-3-[(γ-hydroxy)-N-MeLeu]-4-cyclosporin |

TABLE 2-continued

| Ex. No. | W | $R_a$ | Name |
|---|---|---|---|
| 977 | O | HO with morpholine | [(R)-(((R)-3-Hydroxymethyl-6-morpholinohexyl)thio)methyl-Sar]-3-[(γ-hydroxy)-N-MeLeu]-4-cyclosporin |
| 978 | O | HO with morpholine | [(R)-(((S)-3-Hydroxymethyl-6-morpholinohexyl)thio)methyl-Sar]-3-[(γ-hydroxy)-N-MeLeu]-4-cyclosporin |
| 979 | O | HO with thiomorpholine | [(R)-(((R)-3-Hydroxymethyl-6-thiomorpholinohexyl)thio)methyl-Sar]-3-[(γ-hydroxy)-N-MeLeu]-4-cyclosporin |
| 980 | O | HO with thiomorpholine | [(R)-(((S)-3-Hydroxymethyl-6-thiomorpholinohexyl)thio)methyl-Sar]-3-[(γ-hydroxy)-N-MeLeu]-4-cyclosporin |
| 981 | O | HO with piperazine | [(R)-(((R)-3-Hydroxymethyl-6-piperazin-1-ylhexyl)thio)methyl-Sar]-3-[(γ-hydroxy)-N-MeLeu]-4-cyclosporin |
| 982 | O | HO with piperazine | [(R)-(((S)-3-Hydroxymethyl-6-piperazin-1-ylhexyl)thio)methyl-Sar]-3-[(γ-hydroxy)-N-MeLeu]-4-cyclosporin |
| 983 | O | HO with N-methylpiperazine | [(R)-(((R)-3-Hydroxymethyl-6-(4-methylpiperazin-1-yl)hexyl)thio)methyl-Sar]-3-[(γ-hydroxy)-N-MeLeu]-4-cyclosporin |

TABLE 2-continued

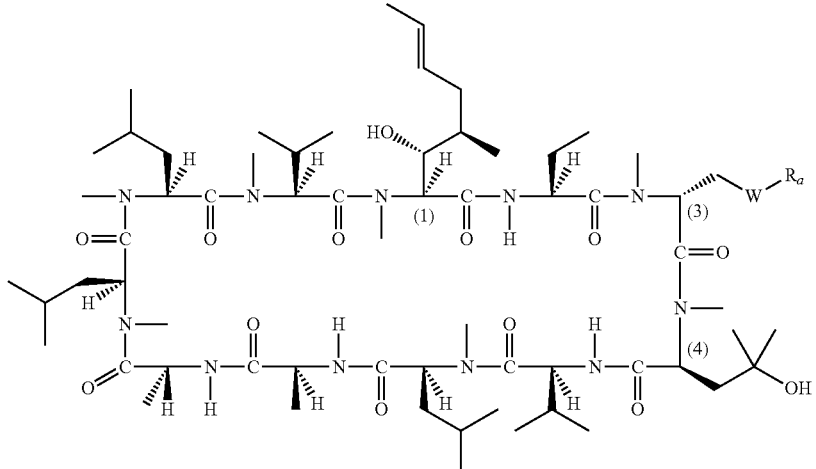

| Ex. No. | W | R$_a$ | Name |
|---|---|---|---|
| 984 | O | 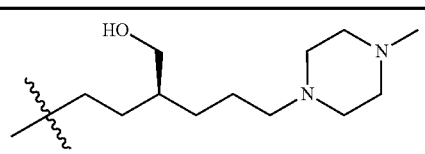 | [(R)-(((S)-3-Hydroxymethyl-6-(4-methylpiperazin-1-yl)hexyl)thio)methyl-Sar]-3-[(γ-hydroxy)-N-MeLeu]-4-cyclosporin |
| 985 | O | 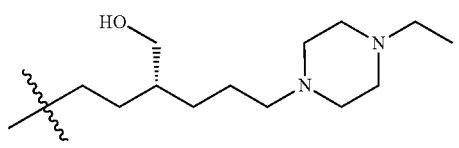 [SMILES: *CC[C@H](CO)CCCN1CCN(CC)CC1] | [(R)-(((R)-3-Hydroxymethyl-6-(4-ethylpiperazin-1-yl)hexyl)thio)methyl-Sar]-3-[(γ-hydroxy)-N-MeLeu]-4-cyclosporin |
| 986 | O | 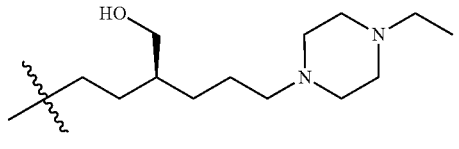 [SMILES: *CC[C@@H](CO)CCCN1CCN(CC)CC1] | [(R)-(((S)-3-Hydroxymethyl-6-(4-isopropylpiperazin-1-yl)hexyl)thio)methyl-Sar]-3-[(γ-hydroxy)-N-MeLeu]-4-cyclosporin |
| 987 | O | 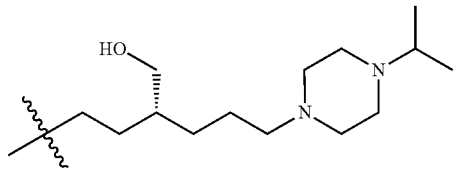 [SMILES: *CC[C@H](CO)CCCN1CCN(C(C)C)CC1] | [(R)-(((R)-3-Hydroxymethyl-6-(4-isopropylpiperazin-1-yl)hexyl)thio)methyl-Sar]-3-[(γ-hydroxy)-N-MeLeu]-4-cyclosporin |
| 988 | O | 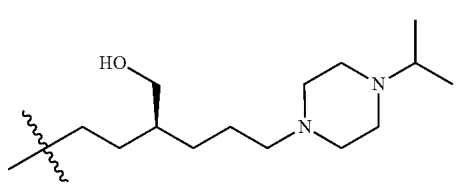 [SMILES: *CC[C@@H](CO)CCCN1CCN(C(C)C)CC1] | [(R)-(((S)-3-Hydroxymethyl-6-(4-ethylpiperazin-1-yl)hexyl)thio)methyl-Sar]-3-[(γ-hydroxy)-N-MeLeu]-4-cyclosporin |
| 989 | O | 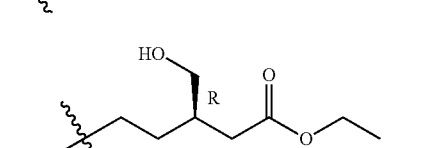 | [(R)-((R)-3-Hydroxymethyl-4-ethoxycarbonybutoxy)methyl-Sar]-3-[(γ-hydroxy)-N-MeLeu]-4-cyclosporin |
| 990 | O | 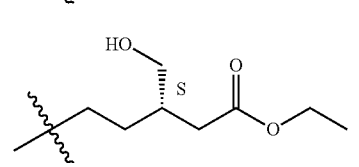 | [(R)-((S)-3-Hydroxymethyl-4-ethoxycarbonybutoxy)methyl-Sar]-3-[(γ-hydroxy)-N-MeLeu]-4-cyclosporin |

TABLE 2-continued

| Ex. No. | W | $R_a$ | Name |
|---|---|---|---|
| 991 | O | (R)-4-hydroxy-7-methoxy-7-oxoheptyl, OMe with OH | [(R)-(((R)-4-Hydroxy-7-methoxy-7-oxoheptyl)thio)methyl-Sar]-3-[(γ-hydroxy)-N-MeLeu]-4-cyclosporin |
| 992 | O | (S)-4-hydroxy-7-methoxy-7-oxoheptyl, OMe with OH | [(R)-(((S)-4-Hydroxy-7-methoxy-7-oxoheptyl)thio)methyl-Sar]-3-[(γ-hydroxy)-N-MeLeu]-4-cyclosporin |
| 993 | O | (R)-4-hydroxy-7-ethoxy-7-oxoheptyl, OEt with OH | [(R)-(((R)-4-Hydroxy-7-ethoxy-7-oxoheptyl)thio)methyl-Sar]-3-[(γ-hydroxy)-N-MeLeu]-4-cyclosporin |
| 994 | O | (S)-4-hydroxy-7-ethoxy-7-oxoheptyl, OEt with OH | [(R)-(((S)-4-Hydroxy-7-ethoxy-7-oxoheptyl)thio)methyl-Sar]-3-[(γ-hydroxy)-N-MeLeu]-4-cyclosporin |
| 995 | O | (S)-4-hydroxy-7-neopentylaminoheptyl | [(R)-(((S)-4-Hydroxy-7-(neopentylamino)heptyl)thio)methyl-Sar]-3-[(γ-hydroxy)-N-MeLeu]-4-cyclosporin |
| 996 | O | (R)-4-hydroxy-7-neopentylaminoheptyl | [(R)-(((R)-4-Hydroxy-7-(neopentylamino)heptyl)thio)methyl-Sar]-3-[(γ-hydroxy)-N-MeLeu]-4-cyclosporin |
| 997 | O | (S)-4-hydroxy-7-(imidazol-1-yl)heptyl | [(R)-(((S)-4-Hydroxy-7-(imidazol-1-yl)heptyl)thio)methyl-Sar]-3-[(γ-hydroxy)-N-MeLeu]-4-cyclosporin |
| 998 | O | (R)-4-hydroxy-7-(imidazol-1-yl)heptyl | [(R)-(((R)-4-Hydroxy-7-(imidazo-1-yl)heptyl)thio)methyl-Sar]-3-[(γ-hydroxy)-N-MeLeu]-4-cyclosporin |
| 999 | O | (S)-4-hydroxy-7-morpholinoheptyl | [(R)-(((S)-4-Hydroxy-7-morpholinoheptyl)thio)methyl-Sar]-3-[(γ-hydroxy)-N-MeLeu]-4-cyclosporin |

TABLE 2-continued

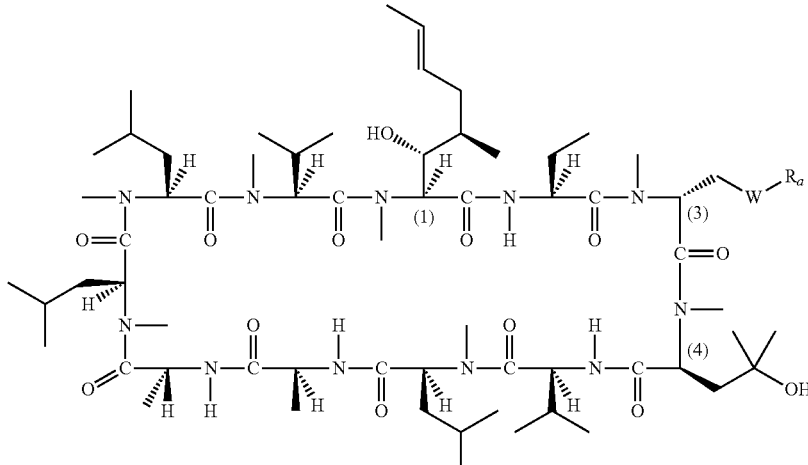

| Ex. No. | W | $R_a$ | Name |
|---|---|---|---|
| 1000 | O | 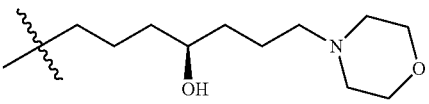 | [(R)-(((R)-4-Hydroxy-7-morpholinoheptyl)thio)methyl-Sar]-3-[(γ-hydroxy)-N-MeLeu]-4-cyclosporin |
| 1001 | O | 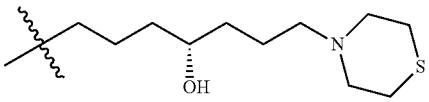 [SMILES: *CCC[C@@H](O)CCCN1CCSCC1] | [(R)-(((S)-4-Hydroxy-7-thiomorpholinoheptyl)thio)methyl-Sar]-3-[(γ-hydroxy)-N-MeLeu]-4-cyclosporin |
| 1002 | O | 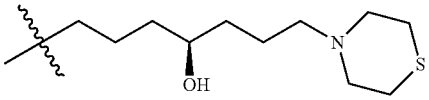 [SMILES: *CCC[C@H](O)CCCN1CCSCC1] | [(R)-(((R)-4-Hydroxy-7-thiomorpholinoheptyl)thio)methyl-Sar]-3-[(γ-hydroxy)-N-MeLeu]-4-cyclosporin |
| 1003 | O | 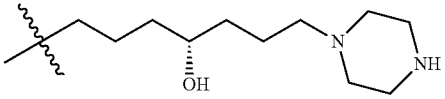 [SMILES: *CCC[C@@H](O)CCCN1CCNCC1] | [(R)-(((S)-4-Hydroxy-7-piperazin-1-ylheptyl)thio)methyl-Sar]-3-[(γ-hydroxy)-N-MeLeu]-4-cyclosporin |
| 1004 | O | 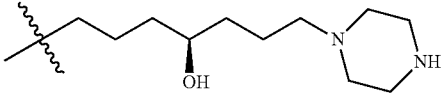 [SMILES: *CCC[C@H](O)CCCN1CCNCC1] | [(R)-(((R)-4-Hydroxy-7-piperazin-1-ylheptyl)thio)methyl-Sar]-3-[(γ-hydroxy)-N-MeLeu]-4-cyclosporin |
| 1005 | O | 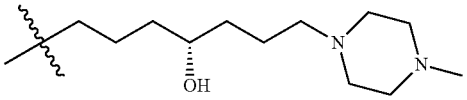 [SMILES: *CCC[C@@H](O)CCCN1CCN(C)CC1] | [(R)-(((S)-4-Hydroxy-7-(4-ethylpiperazin-1-yl)heptyl)thio)methyl-Sar]-3-[(γ-hydroxy)-N-MeLeu]-4-cyclosporin |
| 1006 | O | 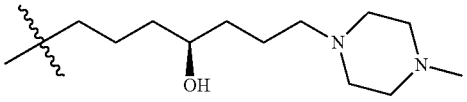 [SMILES: *CCC[C@H](O)CCCN1CCN(C)CC1] | [(R)-(((R)-4-Hydroxy-7-(4-ethylpiperazin-1-yl)heptyl)thio)methyl-Sar]-3-[(γ-hydroxy)-N-MeLeu]-4-cyclosporin |
| 1007 | O | 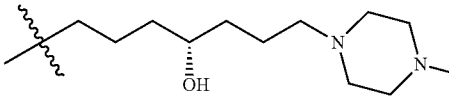 | [(R)-(((S)-4-Hydroxy-7-(4-ethylpiperazin-1-yl)heptyl)thio)methyl-Sar]-3-[(γ-hydroxy)-N-MeLeu]-4-cyclosporin |
| 1008 | O | 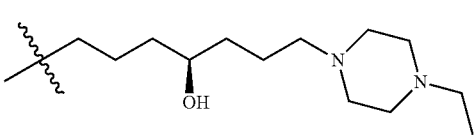 [SMILES: *CCC[C@H](O)CCCN1CCN(CC)CC1] | [(R)-(((R)-4-Hydroxy-7-(4-ethylpiperazin-1-yl)heptyl)thio)methyl-Sar]-3-[(γ-hydroxy)-N-MeLeu]-4-cyclosporin |

TABLE 2-continued

| Ex. No. | W | R$_a$ | Name |
|---|---|---|---|
| 1009 | O | (S)-hydroxy heptyl-piperazinyl-isopropyl chain | [(R)-(((S)-4-Hydroxy-7-(4-isopropylpiperazin-1-yl)heptyl)thio)methyl-Sar]-3-[(γ-hydroxy)-N-MeLeu]-4-cyclosporin |
| 1010 | O | (R)-hydroxy heptyl-piperazinyl-isopropyl chain | [(R)-(((R)-4-Hydroxy-7-(4-isopropylpiperazin-1-yl)heptyl)thio)methyl-Sar]-3-[(γ-hydroxy)-N-MeLeu]-4-cyclosporin |
| 1011 | O | pentyloxy-methyl chain | [(R)-(5-Methoxypentyloxy)methyl-Sar]-3-[(γ-hydroxy)-N-MeLeu]-4-cyclosporin |
| 1012 | O | hexyloxy-hydroxy chain | [(R)-(6-Hydroxyhexyloxy)methyl-Sar]-3-[(γ-hydroxy)-N-MeLeu]-4-cyclosporin |
| 1013 | O | hexyloxy-methoxy chain | [(R)-(6-Methoxyhexyloxy)methyl-Sar]-3-[(γ-hydroxy)-N-MeLeu]-4-cyclosporin |
| 1014 | O | acetamido-ethylamine chain | [(R)-[(N-(2-Aminoethyl)carbamoyl)methoxy]methyl-Sar]-3-[(γ-hydroxy)-N-MeLeu]-4-cyclosporin |
| 1015 | O | acetamido-ethyl-neopentylamine chain | [(R)-[(N-(2-(Neopentylamino)ethyl)carbamoyl)methoxy]methyl-Sar]-3-[(γ-hydroxy)-N-MeLeu]-4-cyclosporin |
| 1016 | O | acetamido-propylamine chain | [(R)-[(N-(3-Aminopropyl)carbamoyl)methoxy]methyl-Sar]-3-[(γ-hydroxy)-N-MeLeu]-4-cyclosporin |
| 1017 | O | acetamido-propyl-neopentylamine chain | [(R)-[(N-(3-(Neopentylamino)propyl)carbamoyl)methoxy]methyl-Sar]-3-[(γ-hydroxy)-N-MeLeu]-4-cyclosporin |

TABLE 2-continued

| Ex. No. | W | Rₐ | Name |
|---|---|---|---|
| 1018 | O | -CH₂-C(=O)-NH-(CH₂)₄-NH₂ | [(R)-[(N-(4-Aminobutyl)carbamoyl)methoxy]methyl-Sar]-3-[(γ-hydroxy)-N-MeLeu]-4-cyclosporin |
| 1019 | O | -CH₂-C(=O)-NH-(CH₂)₃-NH-CH₂C(CH₃)₃ | [(R)-[(N-(4-(Neopentylamino)butyl)carbamoyl)methoxy]methyl-Sar]-3-[(γ-hydroxy)-N-MeLeu]-4-cyclosporin |
| 1020 | O | -CH₂-C(=O)-NH-(CH₂)₅-NH₂ | [(R)-[(N-(5-Aminopentyl)carbamoyl)methoxy]methyl-Sar]-3-[(γ-hydroxy)-N-MeLeu]-4-cyclosporin |
| 1021 | O | -CH₂-C(=O)-NH-(CH₂)₄-NH-CH₂C(CH₃)₃ | [(R)-[(N-(5-(Neopentylamino)pentyl)carbamoyl)methoxy]methyl-Sar]-3-cyclosporin |
| 1022 | O | -CH₂-C(=O)-NH-(CH₂)₆-NH₂ | [(R)-[(N-(6-Aminohexyl)carbamoyl)methoxy]methyl-Sar]-3-[(γ-hydroxy)-N-MeLeu]-4-cyclosporin |
| 1023 | O | -CH₂-C(=O)-NH-(CH₂)₆-NH-CH₂C(CH₃)₃ | [(R)-[(N-(6-(Neopentylamino)hexyl)carbamoyl)methoxy]methyl-Sar]-3-cyclosporin |
| 1024 | O | -CH₂-C(=O)-NH-(D-Glu)₆-Gly-OH | [(R)-[([HO-Gly-(D-Glu)₆]carbamoyl)methoxy]methyl-Sar]-3-[(γ-hydroxy)-N-MeLeu]-4-cyclosporin |
| 1025 | O | -(CH₂)₂-C(=O)-NH-(D-Glu)₆-Gly-OH | [(R)-[([HO-Gly-(D-Glu)₆]carbamoyl)ethoxy]methyl-Sar]-3-[(γ-hydroxy)-N-MeLeu]-4-cyclosporin |
| 1026 | O | -(CH₂)₃-C(=O)-NH-(D-Glu)₆-Gly-OH | [(R)-[([HO-Gly-(D-Glu)₆]carbamoyl)propoxy]methyl-Sar]-3-[(γ-hydroxy)-N-MeLeu]-4-cyclosporin |

TABLE 2-continued

| Ex. No. | W | $R_a$ | Name |
|---|---|---|---|
| 1027 | O | ⟨structure: -CH2CH2-O-CH2-C(=O)-NH-(D-Glu)6 Gly-OH⟩ | [(R)-((2-[([HO-Gly-(D-Glu)6]carbamoyl)methoxy]ethoxy)methyl-Sar]-3-[(γ-hydroxy)-N-MeLeu]-4-cyclosporin |
| 1028 | O | ⟨structure: -(CH2)3-O-CH2-C(=O)-NH-(D-Glu)6 Gly-OH⟩ | [(R)-((3-[([HO-Gly-(D-Glu)6]carbamoyl)methoxy]propoxy)methyl-Sar]-3-[(γ-hydroxy)-N-MeLeu]-4-cyclosporin |
| 1029 | O | ⟨structure: -(CH2)4-O-CH2-C(=O)-NH-(D-Glu)6 Gly-OH⟩ | [(R)-((4-[([HO-Gly-(D-Glu)6]carbamoyl)methoxy]butoxy)methyl-Sar]-3-[(γ-hydroxy)-N-MeLeu]-4-cyclosporin |
| 1030 | O | ⟨structure: -(CH2)5-O-CH2-C(=O)-NH-(D-Glu)6 Gly-OH⟩ | [(R)-((5-[([HO-Gly-(D-Glu)6]carbamoyl)methoxy]pentyloxy)methyl-Sar]-3-[(γ-hydroxy)-N-MeLeu]-4-cyclosporin |
| 1031 | O | ⟨structure: -(CH2)6-O-CH2-C(=O)-NH-(D-Glu)6 Gly-OH⟩ | [(R)-((6-[([HO-Gly-(D-Glu)6]carbamoyl)methoxy]hexyloxy)methyl-Sar]-3-[(γ-hydroxy)-N-MeLeu]-4-cyclosporin |
| 1032 | O | ⟨structure: butyl⟩ | [(R)-(4-Butoxy)methyl-Sar]-3-[(γ-hydroxy)-N-MeLeu]-4-cyclosporin |
| 1033 | O | ⟨structure: pentyl⟩ | [(R)-(5-Pentyloxy)methyl-Sar]-3-[(γ-hydroxy)-N-MeLeu]-4-cyclosporin |
| 1034 | O | ⟨structure: hexyl⟩ | [(R)-(6-Hexyloxy)methyl-Sar]-3-[(γ-hydroxy)-N-MeLeu]-4-cyclosporin |
| 1035 | O | ⟨structure: heptyl⟩ | [(R)-(7-Heptyloxy)methyl-Sar]-3-[(γ-hydroxy)-N-MeLeu]-4-cyclosporin |
| 1036 | $CH_2$ | —$CH_2N(CH_3)_2$ | [(R)-2-(N,N-Dimethylamino)propyl-Sar]-3-[(γ-hydroxy)-N-MeLeu]-4-cyclosporin |

TABLE 3

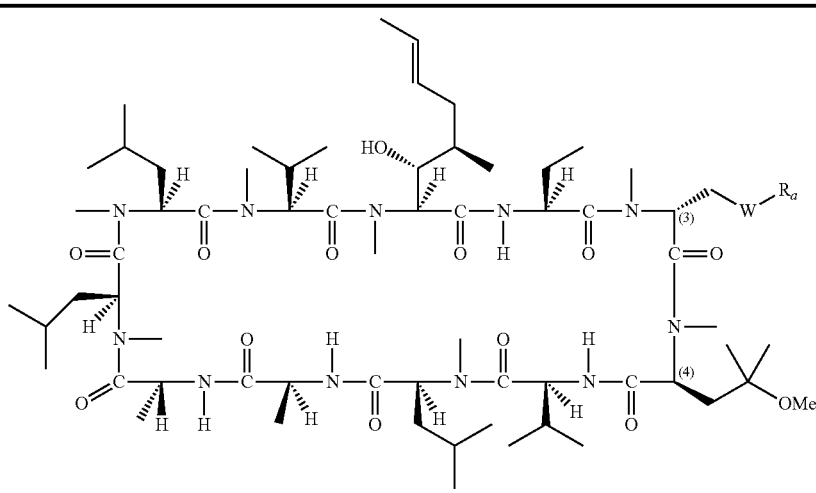

| Ex. No. | W | R_a | Name |
|---|---|---|---|
| 1037 | S | —CH₂C(O)OH | [(S)-(Carboxymethylthio)methyl-Sar]-3-[(γ-methoxy)-N-MeLeu]-4-cyclosporin |
| 1038 | S | —CH₂C(O)OK | [(S)-(Carboxymethylthio)methyl-Sar]-3-[(γ-methoxy)-N-MeLeu]-4-cyclosporin-potassium salt |
| 1039 | S | —CH₂C(O)ONa | [(S)-(Carboxymethylthio)methyl-Sar]-3-[(γ-methoxy)-N-MeLeu]-4-cyclosporin-sodium salt |
| 1040 | S | —CH₂C(O)OEt | [(S)-(Ethoxycarbonylmethylthio)methyl-Sar]-3-[(γ-methoxy)-N-MeLeu]-4-cyclosporin |
| 1041 | S | —CH₂C(O)OtBu | [(S)-(tert-butoxycarbonylmethylthio)methyl-Sar]-3-[(γ-methoxy)-N-MeLeu]-4-cyclosporin |
| 1042 | S | —CH₂CH₂OH | [(S)-(2-Hydroxyethylthio)methyl-Sar]-3-[(γ-methoxy)-N-MeLeu]-4-cyclosporin |
| 1043 | S | —CH₂C(CH₃)₂OH | [(S)-(2-Hydroxy-2-methylpropylthio)methyl-Sar]-3-[(γ-methoxy)-N-MeLeu]-4-cyclosporin |
| 1044 | S | —CH₂CH₂OMe | [(S)-(2-Methoxyethylthio)methyl-Sar]-3-[(γ-methoxy)-N-MeLeu]-4-cyclosporin |
| 1045 | S | —CH₂C(CH₃)₂OMe | [(S)-(2-Methoxy-2-methylpropylthio)methyl-Sar]-3-[(γ-methoxy)-N-MeLeu]-4-cyclosporin |
| 1046 | S | —CH₂CH₂NHiPr | [(S)-(2-(N-Isopropylamino)ethylthio)methyl-Sar]-3-[(γ-methoxy)-N-MeLeu]-4-cyclosporin |

TABLE 3-continued

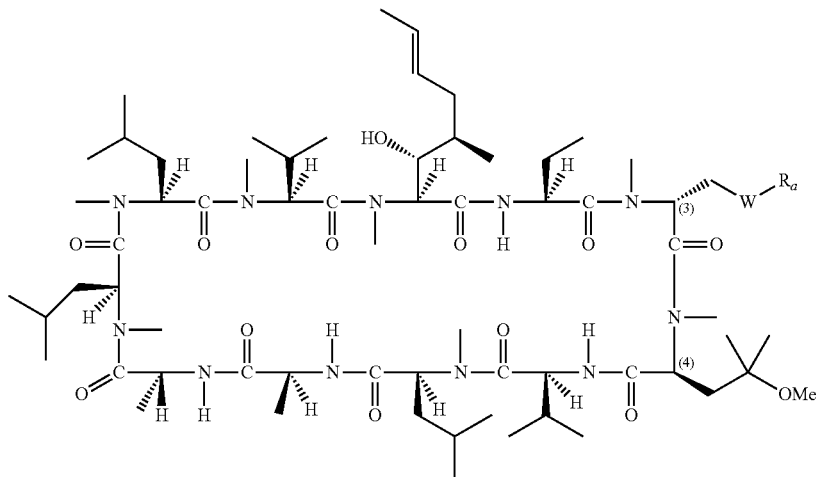

| Ex. No. | W | $R_a$ | Name |
|---|---|---|---|
| 1047 | S | (CH₂CH₂N(Me)iPr) | [(S)-(2-(N-Isopropyl-N-methylamino)ethylthio)methyl-Sar]-3-[(γ-methoxy)-N-MeLeu]-4-cyclosporin |
| 1048 | S | (CH₂CH₂N(Et)iPr) | [(S)-(2-(N-Isopropyl-N-ethylamino)ethylthio)methyl-Sar]-3-[(γ-methoxy)-N-MeLeu]-4-cyclosporin |
| 1049 | S | (CH₂CH₂NH-iBu) | [(S)-(2-(N-Isobutylamino)ethylthio)methyl-Sar]-3-[(γ-methoxy)-N-MeLeu]-4-cyclosporin |
| 1050 | S | (CH₂CH₂N(Me)iBu) | [(S)-(2-(N-Isobutyl-N-methylamino)ethylthio)methyl-Sar]-3-[(γ-methoxy)-N-MeLeu]-4-cyclosporin |
| 1051 | S | (CH₂CH₂N(Et)iBu) | [(S)-(2-(N-Isobutyl-N-ethylamino)ethylthio)methyl-Sar]-3-[(γ-methoxy)-N-MeLeu]-4-cyclosporin |
| 1052 | S | (CH₂CH₂NH-neopentyl) | [(S)-(2-(N-Neopentylamino)ethylthio)methyl-Sar]-3-[(γ-methoxy)-N-MeLeu]-4-cyclosporin |
| 1053 | S | (CH₂CH₂N(Me)neopentyl) | [(S)-(2-(N-Methyl-N-neopentylamino)ethylthio)methyl-Sar]-3-[(γ-methoxy)-N-MeLeu]-4-cyclosporin |
| 1054 | S | (CH₂CH₂N(Et)neopentyl) | [(S)-(2-(N-Ethyl-N-neopentylamino)ethylthio)methyl-Sar]-3-[(γ-methoxy)-N-MeLeu]-4-cyclosporin |

TABLE 3-continued

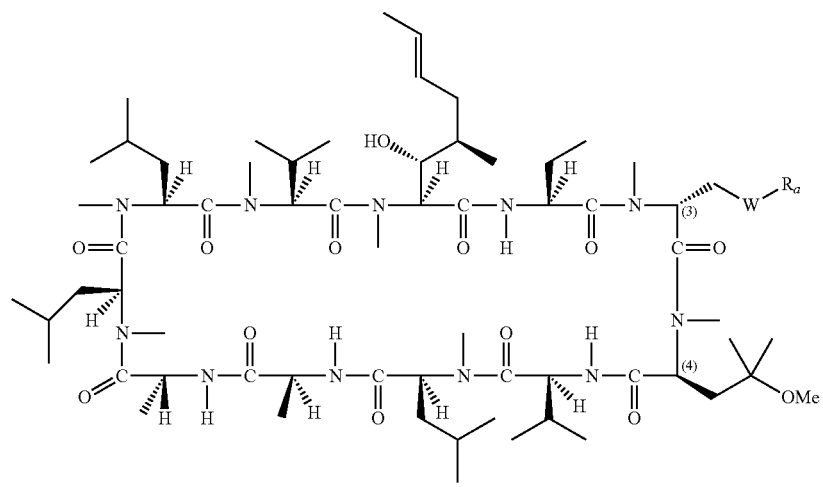

| Ex. No. | W | $R_a$ | Name |
|---|---|---|---|
| 1055 | S | (thiazolidine-ethyl) | [(S)-(2-(N-Thiazolidinyl)ethylthio)methyl-Sar]-3-[(γ-methoxy)-N-MeLeu]-4-cyclosporin |
| 1056 | S | (oxazolidine-ethyl) | [(S)-(2-(N-Oxazolidinyl)ethylthio)methyl-Sar]-3-[(γ-methoxy)-N-MeLeu]-4-cyclosporin |
| 1057 | S | (piperidine-ethyl) | [(S)-(2-(N-Piperidinyl)ethylthio)methyl-Sar]-3-[(γ-methoxy)-N-MeLeu]-4-cyclosporin |
| 1058 | S | (thiomorpholine-ethyl) | [(S)-(2-(N-Thiomorpholino)ethylthio)methyl-Sar]-3-[(γ-methoxy)-N-MeLeu]-4-cyclosporin |
| 1059 | S | (piperazine-ethyl) | [(S)-(2-(N-Piperazinyl)ethylthio)methyl-Sar]-3-[(γ-methoxy)-N-MeLeu]-4-cyclosporin |
| 1060 | S | (4-methyl-piperazine-ethyl) | [(S)-(2-(4-Methyl-N-piperazinyl)ethylthio)methyl-Sar]-3-[(γ-methoxy)-N-MeLeu]-4-cyclosporin |
| 1061 | S | (4-ethyl-piperazine-ethyl) | [(S)-(2-(4-Ethyl-N-piperazinyl)ethylthio)methyl-Sar]-3-[(γ-methoxy)-N-MeLeu]-4-cyclosporin |

TABLE 3-continued

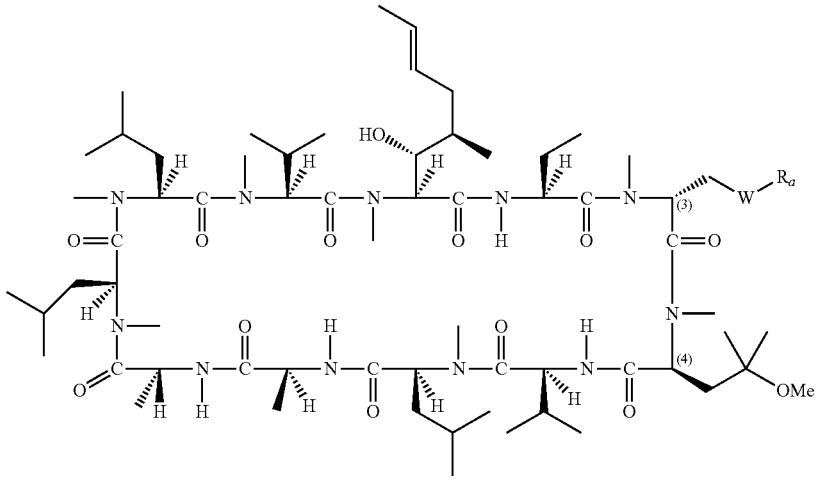

| Ex. No. | W | $R_a$ | Name |
|---|---|---|---|
| 1062 | S | 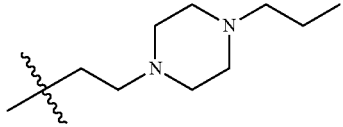 [SMILES: *CCN1CCN(CCC)CC1] | [(S)-(2-(4-Propyl-N-piperazinyl)ethylthio)methyl-Sar]-3-[(γ-methoxy)-N-MeLeu]-4-cyclosporin |
| 1063 | S | 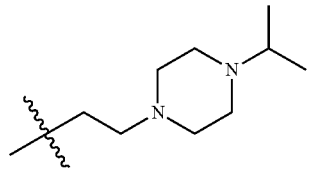 [SMILES: *CCN1CCN(C(C)C)CC1] | [(S)-(2-(4-Isopropyl-N-piperazinyl)ethylthio)methyl-Sar-3-[(γ-methoxy)-N-MeLeu]-4-cyclosporin |
| 1064 | S | 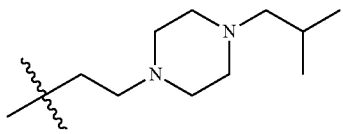 [SMILES: *CCN1CCN(CC(C)C)CC1] | [(S)-(2-(4-Isobutyl-N-piperazinyl)ethylthio)methyl-Sar-3-[(γ-methoxy)-N-MeLeu]-4-cyclosporin |
| 1065 | S | 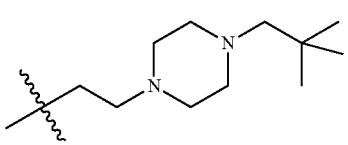 [SMILES: *CCN1CCN(CC(C)(C)C)CC1] | [(S)-(2-(4-Neopentyl-N-piperazinyl)ethylthio)methyl-Sar-3-[(γ-methoxy)-N-MeLeu]-4-cyclosporin |
| 1066 | S | 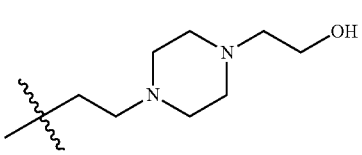 [SMILES: *CCN1CCN(CCO)CC1] | [(S)-(2-(4-(2-Hydroxyethyl)-N-piperazinyl)ethylthio)methyl-Sar-3-[(γ-methoxy)-N-MeLeu]-4-cyclosporin |
| 1067 | S | 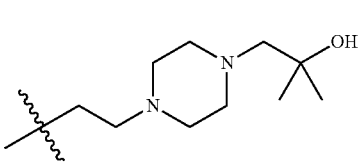 [SMILES: *CCN1CCN(CC(C)(C)O)CC1] | [(S)-(2-(4-(2-Hydroxy-2-methylpropyl)-N-piperazinyl)ethylthio)methyl-Sar]-3-[(γ-methoxy)-N-MeLeu]-4-cyclosporin |

TABLE 3-continued

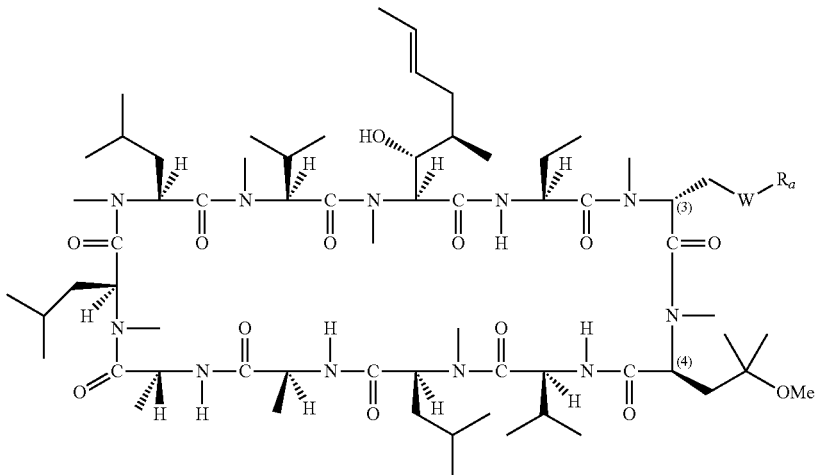

| Ex. No. | W | $R_a$ | Name |
|---|---|---|---|
| 1068 | S | 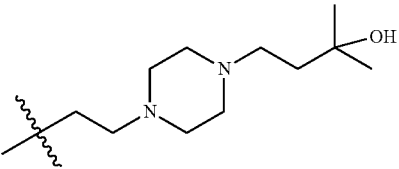 [SMILES: *CCN1CCN(CCC(C)(C)O)CC1] | [(S)-(2-(4-(3-Hydroxy-3-methylbutyl)-N-piperazinyl)ethylthio)methyl-Sar]-3-[(γ-methoxy)-N-MeLeu]-4-cyclosporin |
| 1069 | S | 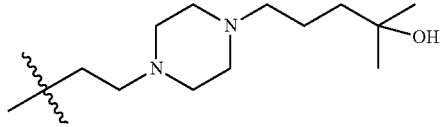 [SMILES: *CCN1CCN(CCCC(C)(C)O)CC1] | [(S)-(2-(4-(4-Hydroxy-4-methylpentyl)-N-piperazinyl)ethylthio)methyl-Sar]-3-[(γ-methoxy)-N-MeLeu]-4-cyclosporin |
| 1070 | S | 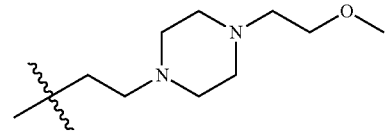 [SMILES: *CCN1CCN(CCOC)CC1] | [(S)-(2-(4-(2-Methoxyethyl)-N-piperazinyl)ethylthio)methyl-Sar--3[(γ-methoxy)-N-MeLeu]-4-cyclosporin |
| 1071 | S | 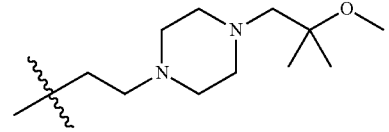 [SMILES: *CCN1CCN(CC(C)(C)OC)CC1] | [(S)-(2-(4-(2-Methoxy-2-methylproyl)-N-piperazinyl)ethylthio)methyl-Sar]-3-[(γ-methoxy)-N-MeLeu]-4-cyclosporin |
| 1072 | S | 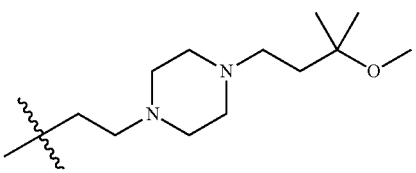 [SMILES: *CCN1CCN(CCC(C)(C)OC)CC1] | [(S)-(2-(4-(3-Methoxy-3-methylbutyl)-N-piperazinyl)ethylthio)methyl-Sar]-3-[(γ-methoxy)-N-MeLeu]-4-cyclosporin |
| 1073 | S | 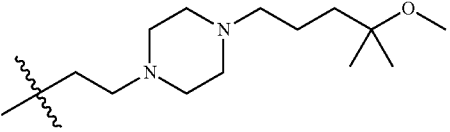 [SMILES: *CCN1CCN(CCCC(C)(C)OC)CC1] | [(S)-(2-(4-(4-methoxy-4-methylpentyl)-N-piperazinyl)ethylthio)methyl-Sar]-3-[(γ-methoxy)-N-MeLeu]-4-cyclosporin |
| 1074 | S | 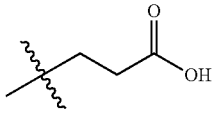 [SMILES: *CCC(=O)O] | [(S)-(2-Carboxyethylthio)methyl-Sar]-3-[(γ-methoxy)-N-MeLeu]-4-cyclosporin |

TABLE 3-continued

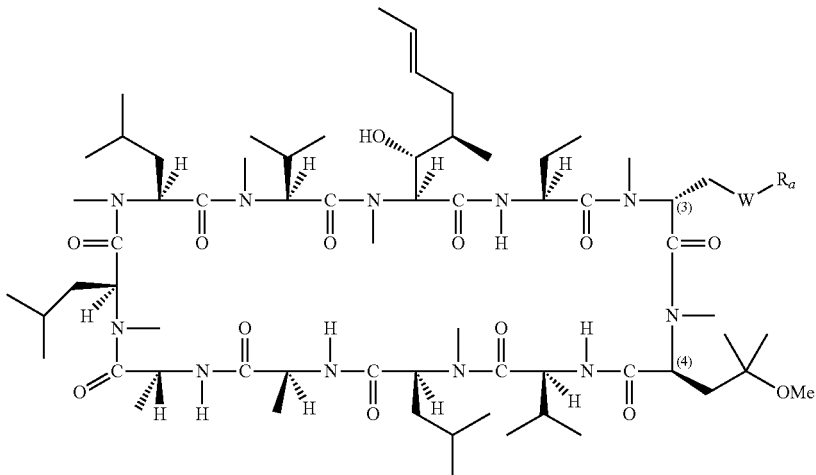

| Ex. No. | W | $R_a$ | Name |
|---|---|---|---|
| 1075 | S | 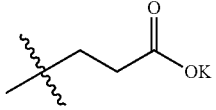 | [(S)-(2-Carboxyethylthio)methyl-Sar]-3-[(γ-methoxy)-N-MeLeu]-4-cyclosporin |
| 1076 | S | 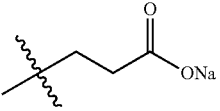 | [(S)-(2-Carboxyethylthio)methyl-Sar]-3-[(γ-methoxy)-N-MeLeu]-4-cyclosporin-sodium salt |
| 1077 | S | 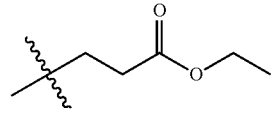 [SMILES: *CCC(=O)OCC] | [(S)-(2-(Ethoxycarbonyl)ethylthio)methyl-Sar]-3-[(γ-methoxy)-N-MeLeu]-4-cyclosporin |
| 1078 | S | 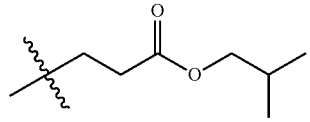 [SMILES: *CCC(=O)OCC(C)C] | [(S)-(2-(isoButoxycarbonyl)ethylthio)methyl-Sar]-3-[(γ-methoxy)-N-MeLeu]-4-cyclosporin |
| 1079 | S | 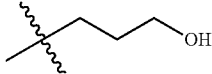 [SMILES: *CCCO] | [(S)-(3-Hydroxypropylthio)methyl-Sar]-3-[(γ-methoxy)-N-MeLeu]-4-[(γ-methoxy)-N-MeLeu]-4-cyclosporin |
| 1080 | S | 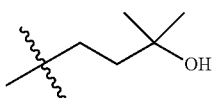 [SMILES: *CCC(C)(C)O] | [(S)-(3-Hydroxy-3-methylbutylthio)methyl-Sar]-3-[(γ-methoxy)-N-MeLeu]-4-cyclosporin |
| 1081 | S | 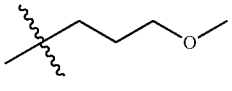 [SMILES: *CCCOC] | [(S)-(3-Methoxypropylthio)methyl-Sar]-3-[(γ-methoxy)-N-MeLeu]-4-[(γ-methoxy)-N-MeLeu]-4-cyclosporin |
| 1082 | S | 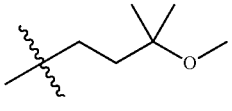 [SMILES: *CCC(C)(C)OC] | [(S)-(3-Methoxy-3-methylbutylthio)methyl-Sar]-3-[(γ-methoxy)-N-MeLeu]-4-cyclosporin |
| 1083 | S | 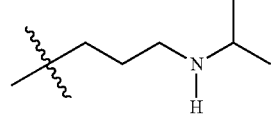 [SMILES: *CCCNC(C)C] | [(S)-(3-(N-Isopropylamino)propylthio)methyl-Sar]-3-[(γ-methoxy)-N-MeLeu]-4-cyclosporin |

TABLE 3-continued

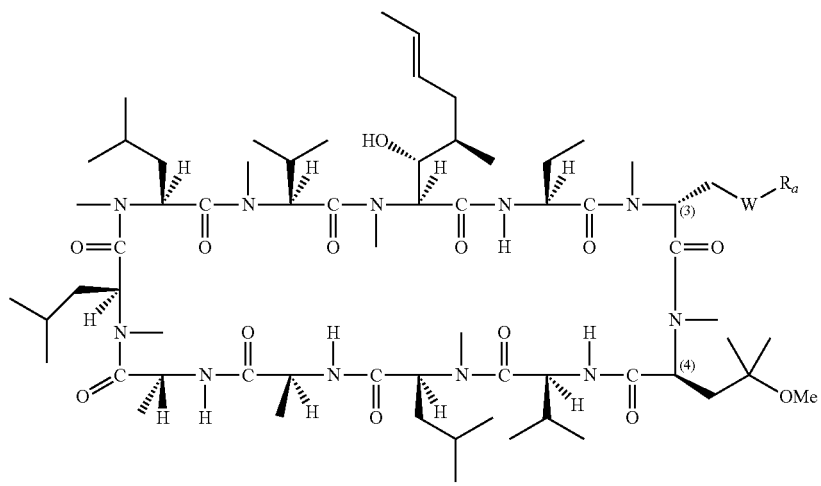

| Ex. No. | W | $R_a$ | Name |
|---|---|---|---|
| 1084 | S | (3-(N-Isopropyl-N-methylamino)propyl) | [(S)-(3-(N-Isopropyl-N-methylamino)propylthio)methyl-Sar]-3-[(γ-methoxy)-N-MeLeu]-4-cyclosporin |
| 1085 | S | (3-(N-Ethyl-N-isopropylamino)propyl) | [(S)-(3-(N-Ethyl-N-isopropylamino)propylthio)methyl-Sar]-3-[(γ-methoxy)-N-MeLeu]-4-cyclosporin |
| 1086 | S | (3-(N-Isobutylamino)propyl) | [(S)-3-(N-Isobutylamino)propylthio)methyl-Sar]-3-[(γ-methoxy)-N-MeLeu]-4-cyclosporin |
| 1087 | S | (3-(N-Isobutyl-N-methylamino)propyl) | [(S)-(3-(N-Isobutyl-N-methylamino)propylthio)methyl-Sar]-3-[(γ-methoxy)-N-MeLeu]-4-cyclosporin |
| 1088 | S | (3-(N-Isobutyl-N-ethylamino)propyl) | [(S)-(3-(N-Isobutyl-N-ethylamino)propylthio)methyl-Sar]-3-[(γ-methoxy)-N-MeLeu]-4-cyclosporin |
| 1089 | S | (3-(N,N-Diisobutylamino)propyl) | [(S)-(3-(N,N-Diisobutylamino)propylthio)methyl-Sar]-3-[(γ-methoxy)-N-MeLeu]-4-cyclosporin |
| 1090 | S | (3-(N-Neopentylamino)propyl) | [(S)-3-(N-Neopentylamino)propylthio)methyl-Sar]-3-[(γ-methoxy)-N-MeLeu]-4-cyclosporin |
| 1091 | S | (3-(N-Methyl-N-neopentylamino)propyl) | [(S)-(3-(N-Methyl-N-neopentylamino)propylthio)methyl-Sar]-3-[(γ-methoxy)-N-MeLeu]-4-cyclosporin |

TABLE 3-continued

| Ex. No. | W | R$_a$ | Name |
|---|---|---|---|
| 1092 | S | (4-(N-ethyl-N-neopentylamino)butyl) | [(S)-(3-(N-Ethyl-N-neopentylamino)propylthio)methyl-Sar]-3-[(γ-methoxy)-N-MeLeu]-4-cyclosporin |
| 1093 | S | (4-(N-thiazolidinyl)butyl) | [(S)-(3-(N-Thiazolidinyl)propylthio)methyl-Sar]-3-[(γ-methoxy)-NMeLeu]-4-cyclosporin |
| 1094 | S | (4-(N-oxazolidinyl)butyl) | [(S)-(3-(N-Oxazolidinyl)propylthio)methyl-Sar]-3-[(γ-methoxy)-NMeLeu]-4-cyclosporin |
| 1095 | S | (4-(N-thiomorpholino)butyl) | [(S)-(3-(N-Thiomorpholino)propylthio)methyl-Sar]-3-[(γ-methoxy)-N-MeLeu]-4-cyclosporin |
| 1096 | S | (4-(N-piperazinyl)butyl) | [(S)-(3-(N-Piperazinyl)propylthio)methyl-Sar]-3-[(γ-methoxy)-N-MeLeu]-4-cyclosporin |
| 1097 | S | (4-(4-methyl-N-piperazinyl)butyl) | [(S)-(3-(4-Methyl-N-piperazinyl)propylthio)methyl-Sar]-3-[(γ-methoxy)-N-MeLeu]-4-cyclosporin |
| 1098 | S | (4-(4-ethyl-N-piperazinyl)butyl) | [(S)-(3-(4-Ethyl-N-piperazinyl)propylthio)methyl-Sar]-3-[(γ-methoxy)-N-MeLeu]-4-cyclosporin |
| 1099 | S | (4-(4-n-propyl-N-piperazinyl)butyl) | [(S)-(3-(4-n-Propyl-N-piperazinyl)propylthio)methyl-Sar]-3-[(γ-methoxy)-N-MeLeu]-4-cyclosporin |

TABLE 3-continued

| Ex. No. | W | $R_a$ | Name |
|---|---|---|---|
| 1100 | S | (butyl-piperazinyl-isopropyl) | [(S)-(3-(4-Isopropyl-N-piperazinyl)propylthio)methyl-Sar]-3-[(γ-methoxy)-N-MeLeu]-4-cyclosporin |
| 1101 | S | (butyl-piperazinyl-isobutyl) | [(S)-(3-(4-Isobutyl-N-piperazinyl)propylthio)methyl-Sar]-3-[(γ-methoxy)-N-MeLeu]-4-cyclosporin |
| 1102 | S | (butyl-piperazinyl-neopentyl) | [(S)-(3-(4-Neopentyl-N-piperazinyl)propylthio)methyl-Sar]-3-[(γ-methoxy)-N-MeLeu]-4-cyclosporin |
| 1103 | S | (butyl-piperazinyl-ethyl-OH) | [(S)-(3-(4-(2-Hydroxyethyl)-N-piperazinyl)propylthio)methyl-Sar]-3-[(γ-methoxy)-N-MeLeu]-4-cyclosporin |
| 1104 | S | (butyl-piperazinyl-2-hydroxy-2,2-dimethylethyl) | [(S)-(3-(4-(2-Hydroxy-2-dimethylpropyl)-N-piperazinyl)propylthio)methyl-Sar]-3-[(γ-methoxy)-N-MeLeu]-4-cyclosporin |
| 1105 | S | (butyl-piperazinyl-3-hydroxy-3-methylbutyl) | [(S)-(3-(4-(3-Hydroxy-3-methylbutyl)-N-piperazinyl)propylthio)methyl-Sar]-3-[(γ-methoxy)-N-MeLeu]-4-cyclosporin |
| 1106 | S | (butyl-piperazinyl-4-hydroxy-4-methylpentyl) | [(S)-(3-(4-(4-Hydroxy-4-methylpentyl)-N-piperazinyl)propylthio)methyl-Sar]-3-[(γ-methoxy)-N-MeLeu]-4-cyclosporin |
| 1107 | S | (butyl-piperazinyl-2-methoxyethyl) | [(S)-(3-(4-(2-Methoxyethyl)-N-piperazinyl)propylthio)methyl-Sar]-3-[(γ-methoxy)-N-MeLeu]-4-cyclosporin |

TABLE 3-continued

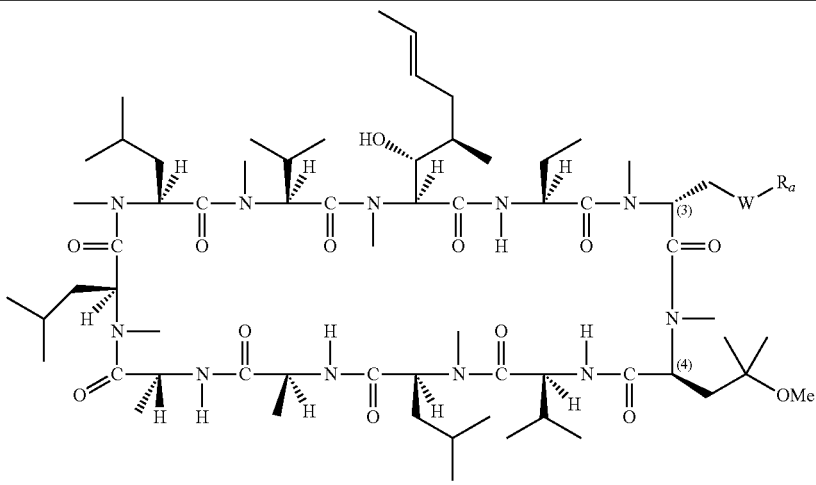

| Ex. No. | W | $R_a$ | Name |
|---|---|---|---|
| 1108 | S | 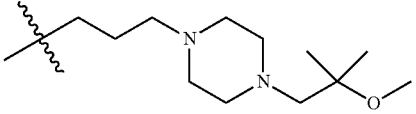 [SMILES: *CCCN1CCN(CC(C)(C)OC)CC1] | [(S)-(3-(4-(2-Methoxy-2-methylpropyl)-N-piperazinyl)propylthio)methyl-Sar]-3-[(γ-methoxy)-N-MeLeu]-4-cyclosporin |
| 1109 | S | 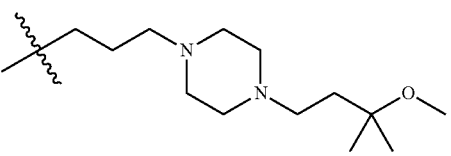 [SMILES: *CCCN1CCN(CCC(C)(C)OC)CC1] | [(S)-(3-(4-(3-Methoxy-3-methylbutyl)-N-piperazinyl)propylthio)methyl-Sar]-3-[(γ-methoxy)-N-MeLeu]-4-cyclosporin |
| 1110 | S | 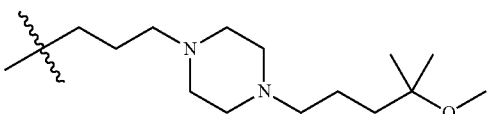 | [(S)-(3-(4-(4-Methoxy-4-methylpentyl)-N-piperazinyl)propylthio)methyl-Sar-3-[(γ-methoxy)-N-MeLeu]-4-cyclosporin |
| 1111 | S | 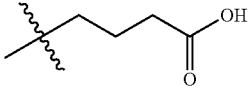 [SMILES: *CCCC(=O)O] | [(S)-(3-Carboxypropylthio)methyl-Sar]-3-[(γ-methoxy)-N-MeLeu]-4-cyclosporin |
| 1112 | S | 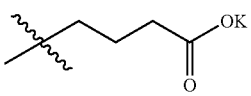 | [(S)-(3-Carboxypropylthio)methyl-Sar]-3-[(γ-methoxy)-N-MeLeu]-4-cyclosporin-potassium salt |
| 1113 | S | 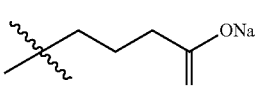 | [(S)-(3-Carboxypropylthio)methyl-Sar]-3-[(γ-methoxy)-N-MeLeu]-4-cyclosporin-sodium salt |
| 1114 | S | 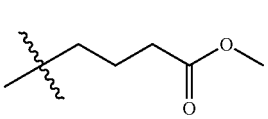 [SMILES: *CCCC(=O)OC] | [(S)-(3-Methoxycarbonylpropylthio)methyl-Sar]-3-[(γ-methoxy)-N-MeLeu]-4-cyclosporin |
| 1115 | S | 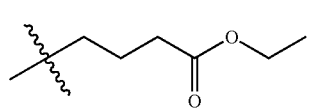 [SMILES: *CCCC(=O)OCC] | [(S)-(3-Ethoxycarbonylpropylthio)methyl-Sar]-3-[(γ-methoxy)-N-MeLeu]-4-cyclosporin |
| 1116 | S | 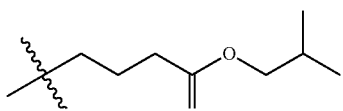 | [(S)-(3-Isobutoxycarbonylpropylthio)methyl-Sar]-3-[(γ-methoxy)-N-MeLeu]-4-cyclosporin |

TABLE 3-continued

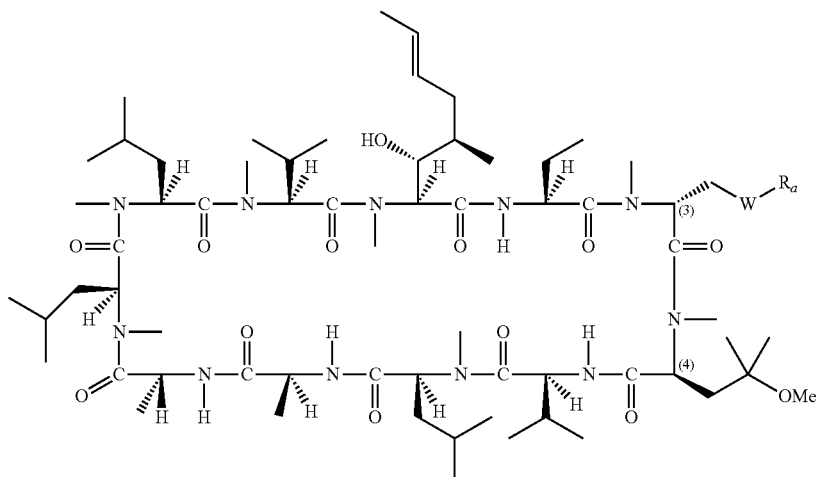

| Ex. No. | W | $R_a$ | Name |
|---|---|---|---|
| 1117 | S | ~~~~~OH | [(S)-(4-Hydroxybutylthio)methyl-Sar]-3-[(γ-methoxy)-N-MeLeu]-4-cyclosporin |
| 1118 | S | ~~~~~OH (gem-dimethyl) | [(S)-(4-Hydroxy-4-methylpentylthio)methyl-Sar]-3-[(γ-methoxy)-N-MeLeu]-4-cyclosporin |
| 1119 | S | ~~~~~OH | [(S)-((5-Hydroxy-2-methylpentan-2-yl)thio)methyl-Sar]-3-[(γ-methoxy)-N-MeLeu]-4-cyclosporin |
| 1120 | S | ~~~~~OH | [(S)-((4-Hydroxy-2,2-dimethylbutyl)thio)methyl-Sar]-3-[(γ-methoxy)-N-MeLeu]-4-cyclosporin |
| 1121 | S | ~~~~~OH | [(S)-((4-Hydroxy-3,3-dimethylbutyl)thio)methyl-Sar]-3-[(γ-methoxy)-N-MeLeu]-4-cyclosporin |
| 1122 | S | ~~~~~cyclopropyl-OH | [(S)-(3-(1-Hydroxycyclopropyl)propylthio)methyl-Sar]-3-[(γ-methoxy)-N-MeLeu]-4-cyclosporin |
| 1123 | S | ~~~~~cyclopropyl-OH | [(S)-(((2-(1-(Hydroxymethyl)cyclopropyl)ethyl)thio)methyl-Sar]-3-[(γ-methoxy)-N-MeLeu]-4-cyclosporin |
| 1124 | S | ~~~~~cyclopropyl-OH | [(S)-(((1-(2-Hydroxyethyl)cyclopropyl)methyl)thio)methyl-Sar]-3-[(γ-methoxy)-N-MeLeu]-4-cyclosporin |
| 1125 | S | ~~~~~cyclopropyl-OH | [(S)-((1-(3-Hydroxypropyl)cyclopropyl)thio)methyl-Sar]-3-[(γ-methoxy)-N-MeLeu]-4-cyclosporin |
| 1126 | S | ~~~~~OH | [(S)-((S)-4-Hydroxyhexylthio)methyl-Sar]-3-[(γ-methoxy)-N-MeLeu]-4-cyclosporin |

TABLE 3-continued

| Ex. No. | W | $R_a$ | Name |
|---|---|---|---|
| 1127 | S | (R)-hexyl chain with OH | [(S)-((R)-4-Hydroxyhexylthio)methyl-Sar]-3-[(γ-methoxy)-N-MeLeu]-4-cyclosporin |
| 1128 | S | (S)-3-(hydroxymethyl)pentyl | [(S)-(((S)-3-(Hydroxymethyl)pentyl)thio)methyl-Sar]- -[(γ-methoxy)-N-MeLeu]-4-cyclosporin |
| 1129 | S | (R)-3-(hydroxymethyl)pentyl | [(S)-(((R)-3-(Hydroxymethyl)pentyl)thio)methyl-Sar]-3-[(γ-methoxy)-N-MeLeu]-4-cyclosporin |
| 1130 | S | (S)-2-ethyl-4-hydroxybutyl | [(S)-(((S)-2-Ethyl-4-hydroxybutyl)thio)methyl-Sar]-3-[(γ-methoxy)-N-MeLeu]-4-cyclosporin |
| 1131 | S | (R)-2-ethyl-4-hydroxybutyl | [(S)-(((R)-2-Ethyl-4-hydroxybutyl)thio)methyl-Sar]-3-[(γ-methoxy)-N-MeLeu]-4-cyclosporin |
| 1132 | S | (S)-4,5-dihydroxypentyl | [(S)-(((S)-4,5-Dihydroxy-4-pentyl)thio)methyl-Sar]-3-[(γ-methoxy)-N-MeLeu]-4-cyclosporin |
| 1133 | S | (R)-4,5-dihydroxypentyl | [(S)-(((R)-4,5-Dihydroxy-4-pentyl)thio)methyl-Sar]-3-[(γ-methoxy)-N-MeLeu]-4-cyclosporin |
| 1134 | S | (S)-4,5-dihydroxy-4-methylpentyl | [(S)-(((S)-4,5-Dihydroxy-4-methylpentyl)thio)methyl-Sar]-3-[(γ-methoxy)-N-MeLeu]-4-cyclosporin |
| 1135 | S | (R)-4,5-dihydroxy-4-methylpentyl | [(S)-(((R)-4,5-Dihydroxy-4-methylpentyl)thio)methyl-Sar]-3-[(γ-methoxy)-N-MeLeu]-4-cyclosporin |

TABLE 3-continued

| Ex. No. | W | $R_a$ | Name |
|---|---|---|---|
| 1136 | S | (structure: 4,6-dihydroxyhexyl with (R)-OH) | [(S)-(((R)-4,6-Dihydroxyhexyl)thio)methyl-Sar]-3-[(γ-methoxy)-N-MeLeu]-4-cyclosporin |
| 1137 | S | (structure: 4,6-dihydroxyhexyl with (S)-OH) | [(S)-(((S)-4,6-Dihydroxyhexyl)thio)methyl-Sar]-3-[(γ-methoxy)-N-MeLeu]-4-cyclosporin |
| 1138 | S | (structure: 5-hydroxy-3-(hydroxymethyl)pentyl, R) | [(S)-(((R)-5-Hydroxy-3-(hydroxymethyl)pentyl)thio)methyl-Sar]-3-[(γ-methoxy)-N-MeLeu]-4-cyclosporin |
| 1139 | S | (structure: 5-hydroxy-3-(hydroxymethyl)pentyl, S) | [(S)-(((S)-5-Hydroxy-3-(hydroxymethyl)pentyl)thio)methyl-Sar]-3-[(γ-hydroxy)-N-MeLeu]-4-cyclosporin |
| 1140 | S | (structure: 4-hydroxy-2-(2-hydroxyethyl)butyl) | [(S)-((4-Hydroxy-2-(2-hydroxyethyl)butyl)thio)methyl-Sar]-3-[(γ-methoxy)-N-MeLeu]-4-cyclosporin |
| 1141 | S | (structure: 4-(hydroxymethyl)pent-4-en-1-yl) | [(S)-((4-(Hydroxymethyl)pent-4-en-1-yl)thio)methyl)-Sar]-3-[(γ-methoxy)-N-MeLeu]-4-cyclosporin |
| 1142 | S | (structure: 5-hydroxy-3-methylenepentyl) | [(S)-((5-Hydroxy-3-methylenepentyl)thio)methyl)-Sar]-3-[(γ-methoxy)-N-MeLeu]-4-cyclosporin |
| 1143 | S | (structure: 5-hydroxy-2-methylenepentyl) | [(S)-((5-Hydroxy-2-methylenepentyl)thio)methyl)-Sar]-3-[(γ-methoxy)-N-MeLeu]-4-cyclosporin |
| 1144 | S | (structure: 2-(2-(hydroxymethyl)oxiran-2-yl)ethyl) | [(S)-((2-(2-(Hydroxymethyl)oxiran-2-yl)ethyl)thio)methyl-Sar]-3-[(γ-methoxy)-N-MeLeu]-4-cyclosporin |

TABLE 3-continued

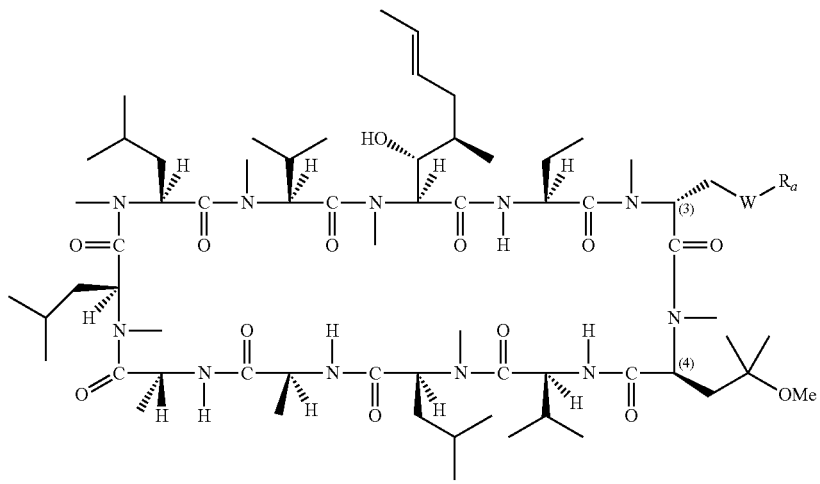

| Ex. No. | W | $R_a$ | Name |
|---|---|---|---|
| 1145 | S | (2-(2-hydroxyethyl)oxiran-2-yl)methyl, with CH2CH2OH on oxirane | [(S)-(((2-(2-Hydroxyethyl)oxiran-2-yl)methyl)thio)methyl-Sar]-3-[(γ-methoxy)-N-MeLeu]-4-cyclosporin |
| 1146 | S | 3-(3-hydroxyoxetan-3-yl)propyl | [(S)-((3-(3-Hydroxyoxetan-3-yl)propyl)thio)methyl-Sar]-3-[(γ-methoxy)-N-MeLeu]-4-cyclosporin |
| 1147 | S | 4,5-dihydroxy-4-(hydroxymethyl)pentyl | [(S)-((4,5-Dihydroxy-4-(hydroxymethyl)pentyl)thio)methyl-Sar]-3-[(γ-methoxy)-N-MeLeu]-4-cyclosporin |
| 1148 | S | 3-(2-(hydroxymethyl)oxiran-2-yl)propyl | [(S)-((3-(2-(Hydroxymethyl)oxiran-2-yl)propyl)thio)methyl-Sar]-3-[(γ-methoxy)-N-MeLeu]-4-cyclosporin |
| 1149 | S | 2-(2-(2-hydroxyethyl)oxiran-2-yl)ethyl | [(S)-((2-(2-(2-Hydroxyethyl)oxiran-2-yl)ethyl)thio)methyl-Sar]-3-[(γ-methoxy)-N-MeLeu]-4-cyclosporin |
| 1150 | S | (2-(3-hydroxypropyl)oxiran-2-yl)methyl | [(S)-(((2-(3-Hydroxypropyl)oxiran-2-yl)methyl)thio)methyl-Sar]-3-[(γ-methoxy)-N-MeLeu]-4-cyclosporin |
| 1151 | S | 5-hydroxy-4-oxopentyl | [(S)-((5-Hydroxy-4-oxohexyl)thio)methyl-Sar]-3-[(γ-methoxy)-N-MeLeu]-4-cyclosporin |
| 1152 | S | 6-hydroxy-5-oxohexyl | [(S)-((6-Hydroxy-5-oxohexyl)thio)methyl-Sar]-3-[(γ-methoxy)-N-MeLeu]-4-cyclosporin |
| 1153 | S | 6-hydroxy-5-oxohexyl | [(S)-((6-Hydroxy-5-oxohexyl)thio)methyl-Sar]-3-[(γ-methoxy)-N-MeLeu]-4-cyclosporin |

TABLE 3-continued

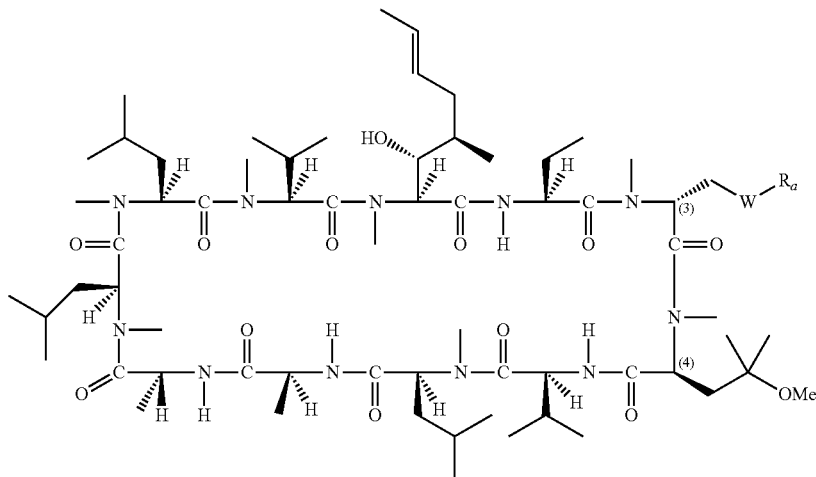

| Ex. No. | W | $R_a$ | Name |
|---|---|---|---|
| 1154 | S | (R)-OH, pyrrolidine | [(S)-(((R)-4-Hydroxy-5-(pyrrolidin-1-yl)pentyl)thio)methyl-Sar]-3-[(γ-methoxy)-N-MeLeu]-4-cyclosporin |
| 1155 | S | (S)-OH, pyrrolidine | [(S)-(((S)-4-Hydroxy-5-(pyrrolidin-1-yl)pentyl)thio)methyl-Sar]-3-[(γ-methoxy)-N-MeLeu]-4-cyclosporin |
| 1156 | S | (R)-OH, pyrrolidine hexyl | [(S)-(((R)-4-Hydroxy-6-(pyrrolidin-1-yl)hexyl)thio)methyl-Sar]-3-[(γ-methoxy)-N-MeLeu]-4-cyclosporin |
| 1157 | S | (S)-OH, pyrrolidine hexyl | [(S)-(((S)-4-Hydroxy-6-(piperidin-1-yl)hexyl)thio)methyl-Sar]-3-[(γ-methoxy)-N-MeLeu]-4-cyclosporin |
| 1158 | S | (R)-OH, imidazole pentyl | [(S)-(((R)-4-Hydroxy-5-(imidazol-1-yl)pentyl)thio)methyl-Sar]-3-[(γ-methoxy)-N-MeLeu]-4-cyclosporin |
| 1159 | S | (S)-OH, imidazole pentyl | [(S)-(((S)-4-Hydroxy-5-(imidazo-1-yl)pentyl)thio)methyl-Sar]-3-[(γ-methoxy)-N-MeLeu]-4-cyclosporin |
| 1160 | S | (R)-OH, imidazole hexyl | [(S)-(((R)-4-Hydroxy-6-(imidazo-1-yl)hexyl)thio)methyl-Sar]-3-[(γ-methoxy)-N-MeLeu]-4-cyclosporin |
| 1161 | S | (S)-OH, imidazole hexyl | [(S)-(((S)-4-Hydroxy-6-(imidazo-1-yl)hexyl)thio)methyl-Sar]-3-[(γ-methoxy)-N-MeLeu]-4-cyclosporin |

TABLE 3-continued

| Ex. No. | W | $R_a$ | Name |
|---|---|---|---|
| 1162 | S | | [(S)-(((R)-3-Hydroxymethyl-4-(imidazol-1-yl)butyl)thio)methyl-Sar]-3-[(γ-methoxy)-N-MeLeu]-4-cyclosporin |
| 1163 | S | | [(S)-(((S)-3-Hydroxymethyl-4-(imidazo-1-yl)butyl)thio)methyl-Sar]-3-[(γ-methoxy)-N-MeLeu]-4-cyclosporin |
| 1164 | S | | [(S)-(((R)-3-Hydroxymethyl-5-(imidazo-1-yl)pentyl)thio)methyl-Sar]-3-[(γ-methoxy)-N-MeLeu]-4-cyclosporin |
| 1165 | S | | [(S)-(((S)-3-Hydroxymethyl-5-(imidazo-1-yl)pentyl)thio)methyl-Sar]-3-[(γ-methoxy)-N-MeLeu]-4-cyclosporin |
| 1166 | S | | [(S)-(((R)-4-Hydroxy-5-(piperidin-1-yl)pentyl)thio)methyl-Sar]-3-[(γ-methoxy)-N-MeLeu]-4-cyclosporin |
| 1167 | S | | [(S)-(((S)-4-Hydroxy-5-(piperidin-1-yl)pentyl)thio)methy-Sar]-3-[(γ-methoxy)-N-MeLeu]-4-cyclosporin |
| 1168 | S | | [(S)-(((R)-4-Hydroxy-5-(piperidin-1-yl)hexyl)thio)methyl-Sar]-3-[(γ-methoxy)-N-MeLeu]-4-cyclosporin |

TABLE 3-continued

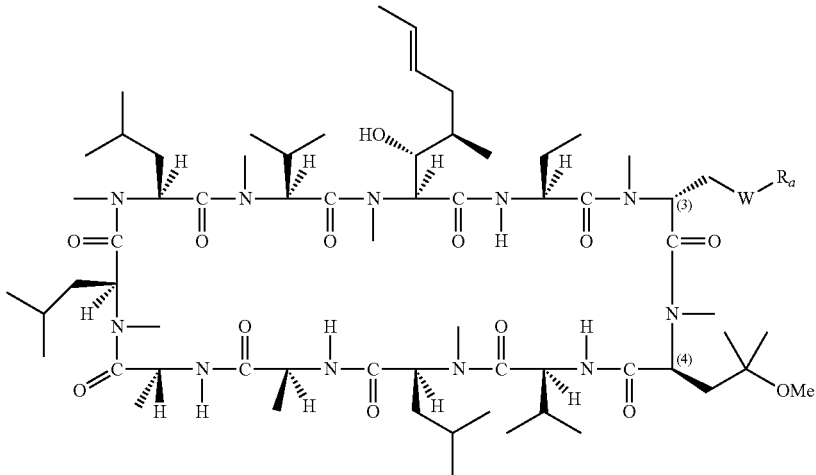

| Ex. No. | W | Ra | Name |
|---|---|---|---|
| 1169 | S | 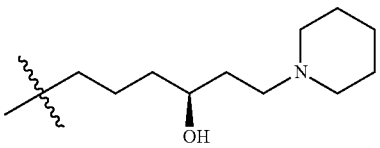 [SMILES: *CCC[C@H](O)CCN1CCCCC1] | [(S)-(((S)-4-Hydroxy-5-(piperidin-1-yl)hexyl)thio)methyl-Sar]-3-[(γ-methoxy)-N-MeLeu]-4-cyclosporin |
| 1170 | S | 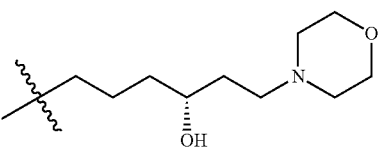 [SMILES: *CCC[C@@H](O)CCN1CCOCC1] | [(S)-(((R)-4-Hydroxy-6-morpholinohexyl)thio)methyl-Sar]-3-[(γ-methoxy)-N-MeLeu]-4-cyclosporin |
| 1171 | S | 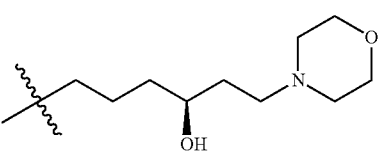 [SMILES: *CCC[C@H](O)CCN1CCOCC1] | [(S)-(((S)-4-Hydroxy-6-morpholinohexyl)thio)methyl-Sar]-3-[(γ-methoxy)-N-MeLeu]-4-cyclosporin |
| 1172 | S | 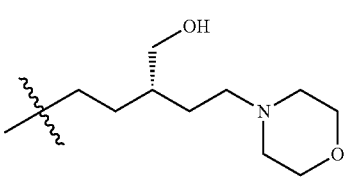 [SMILES: *CC[C@H](CO)CCN1CCOCC1] | [(S)-(((R)-2-(Hydroxymethyl)-4-morpholinobutyl)thio)methyl-Sar]-3-[(γ-methoxy)-N-MeLeu]-4-cyclosporin |
| 1173 | S | 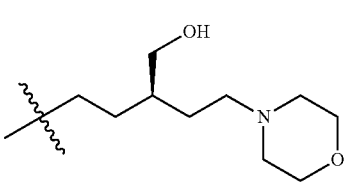 [SMILES: *CC[C@@H](CO)CCN1CCOCC1] | [(S)-(((S)-2-(Hydroxymethyl)-4-morpholinobutyl)thio)methyl-Sar]-3-[(γ-methoxy)-N-MeLeu]-4-cyclosporin |
| 1174 | S | 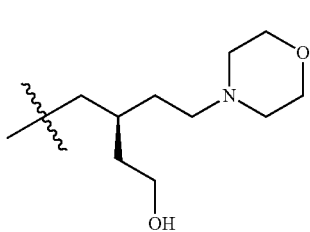 [SMILES: *C[C@H](CCO)CCN1CCOCC1] | [(S)-(((S)-4-Hydroxy-2-(2-morpholinoethyl)butyl)thio)methyl-Sar]-3-[(γ-methoxy)-N-MeLeu]-4-cyclosporin |

TABLE 3-continued

| Ex. No. | W | R_a | Name |
|---|---|---|---|
| 1175 | S | (3-hydroxypropyl, 2-morpholinoethyl substituted methyl branch) | [(S)-(((R)-4-Hydroxy-2-(2-morpholinoethyl)butyl)thio)methyl-Sar]-3-[(γ-methoxy)-N-MeLeu]-4-cyclosporin |
| 1176 | S | (S)-4-hydroxy-6-(4-methylpiperazin-1-yl)hexyl | [(S)-(((S)-4-Hydroxy-6-(4-methylpiperazin-1-yl)hexyl)thio)methyl-Sar]-3-[(γ-methoxy)-N-MeLeu]-4-cyclosporin |
| 1177 | S | (R)-4-hydroxy-6-(4-methylpiperazin-1-yl)hexyl | [(S)-(((R)-4-Hydroxy-6-(4-methylpiperazin-1-yl)hexyl)thio)methyl-Sar]-3-[(γ-methoxy)-N-MeLeu]-4-cyclosporin |
| 1178 | S | (S)-4-hydroxy-6-(4-ethylpiperazin-1-yl)hexyl | [(S)-(((S)-4-Hydroxy-6-(4-ethylpiperazin-1-yl)hexyl)thio)methyl-Sar]-3-[(γ-methoxy)-N-MeLeu]-4-cyclosporin |
| 1179 | S | (R)-4-hydroxy-6-(4-ethylpiperazin-1-yl)hexyl | [(S)-(((R)-4-Hydroxy-6-(4-ethylpiperazin-1-yl)hexyl)thio)methyl-Sar]-3-[(γ-methoxy)-N-MeLeu]-4-cyclosporin |
| 1180 | S | (R)-4-hydroxy-6-(4-isopropylpiperazin-1-yl)hexyl | [(S)-(((R)-4-Hydroxy-6-(4-isopropylpiperazin-1-yl)hexyl)thio)methyl-Sar]-3-[(γ-methoxy)-N-MeLeu]-4-cyclosporin |

TABLE 3-continued

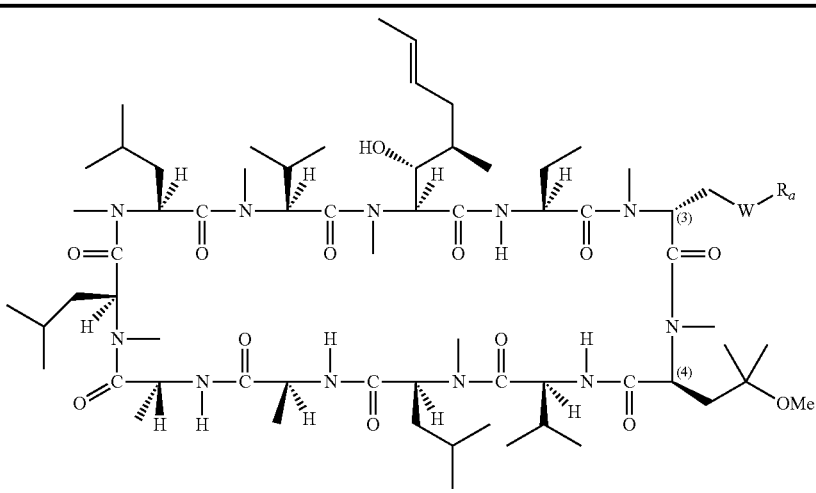

| Ex. No. | W | $R_a$ | Name |
|---|---|---|---|
| 1181 | S | 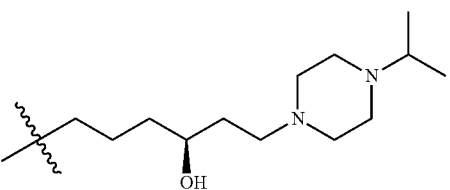 [SMILES: *CCC[C@H](O)CCN1CCN(C(C)C)CC1] | [(S)-(((S)-4-Hydroxy-6-(4-isopropylpiperazin-1-yl)hexyl)thio)methyl-Sar]-3-[(γ-methoxy)-N-MeLeu]-4-cyclosporin |
| 1182 | S | 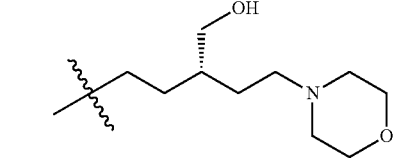 [SMILES: *CC[C@H](CO)CCN1CCOCC1] | [(S)-(((R)-2-(Hydroxymethyl)-4-morpholinobutyl)thio)methyl-Sar]-3-[(γ-methoxy)-N-MeLeu]-4-cyclosporin |
| 1183 | S | 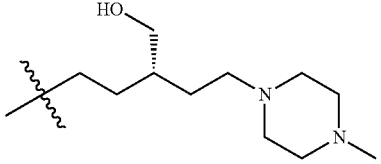 [SMILES: *CC[C@H](CO)CCN1CCN(C)CC1] | [(S)-(((S)-3-Hydroxymethyl-5-(4-methylpiperazin-1-yl)pentyl)thio)methyl-Sar]-3-[(γ-methoxy)-N-MeLeu]-4-cyclosporin |
| 1184 | S | 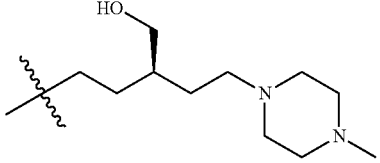 [SMILES: *CC[C@@H](CO)CCN1CCN(C)CC1] | [(S)-(((R)-3-Hydroxymethyl-5-(4-methylpiperazin-1-yl)pentyl)thio)methyl-Sar]-3-[(γ-methoxy)-N-MeLeu]-4-cyclosporin |
| 1185 | S | 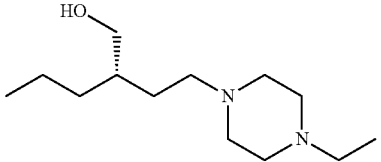 | [(S)-(((S)-3-Hydroxymethyl-5-(4-ethylpiperazin-1-yl)pentyl)thio)methyl-Sar]-3-[(γ-methoxy)-N-MeLeu]-4-cyclosporin |
| 1186 | S | 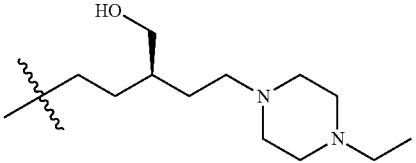 [SMILES: *CC[C@@H](CO)CCN1CCN(CC)CC1] | [(S)-(((R)-3-Hydroxymethyl-5-(4-ethylpiperazin-1-yl)pentyl)thio)methyl-Sar]-3-[(γ-methoxy)-N-MeLeu]-4-cyclosporin |

TABLE 3-continued

| Ex. No. | W | $R_a$ | Name |
|---|---|---|---|
| 1187 | S | (structure with hydroxymethyl, pentyl chain, 4-isopropylpiperazine; (R)-configuration) | [(S)-(((R)-3-Hydroxymethyl-5-(4-isopropylpiperazin-1-yl)pentyl)thio)methyl-Sar]-3-[(γ-methoxy)-N-MeLeu]-4-cyclosporin |
| 1188 | S | (structure with hydroxymethyl, pentyl chain, 4-isopropylpiperazine; (S)-configuration) | [(S)-(((S)-3-Hydroxymethyl-5-(4-isopropylpiperazin-1-yl)pentyl)thio)methyl-Sar]-3-[(γ-methoxy)-N-MeLeu]-4-cyclosporin |
| 1189 | S | (structure with hydroxymethyl, butyl chain, morpholine; (R)-configuration) | [(S)-(((R)-2-(Hydroxymethyl)-4-morpholinobutyl)thio)methyl-Sar]-3-[(γ-methoxy)-N-MeLeu]-4-cyclosporin |
| 1190 | S | (structure with hydroxymethyl, butyl chain, morpholine; (S)-configuration) | [(S)-(((S)-2-(Hydroxymethyl)-4-morpholinobutyl)thio)methyl-Sar]-3-[(γ-methoxy)-N-MeLeu]-4-cyclosporin |
| 1191 | S | (structure with 4-hydroxy, 2-(2-morpholinoethyl)butyl; (S)-configuration) | [(S)-(((S)-4-Hydroxy-2-(2-morpholinoethyl)butyl)thio)methyl-Sar]-3-[(γ-methoxy)-N-MeLeu]-4-cyclosporin |

TABLE 3-continued

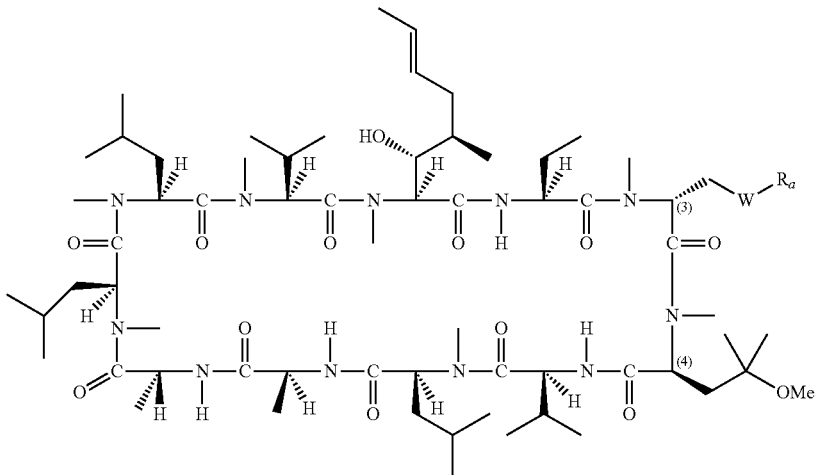

| Ex. No. | W | $R_a$ | Name |
|---|---|---|---|
| 1192 | S | 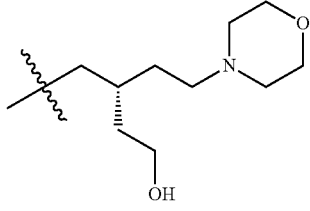 [SMILES: *C[C@@H](CCO)CCN1CCOCC1] | [(S)-(((R)-4-Hydroxy-2-(2-morpholinoethyl)butyl)thio)methyl-Sar]-3-[(γ-methoxy)-N-MeLeu]-4-cyclosporin |
| 1193 | S | 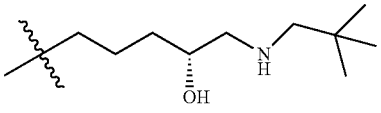 [SMILES: *CCC[C@@H](O)CNCC(C)(C)C] | [(S)-(((R)-4-Hydroxy-5-(neopentylamino)pentyl)thio)methyl-Sar]-3-[(γ-methoxy)-N-MeLeu]-4-cyclosporin |
| 1194 | S | 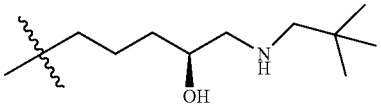 [SMILES: *CCC[C@H](O)CNCC(C)(C)C] | [(S)-(((S)-4-Hydroxy-5-(neopentylamino)pentyl)thio)methyl-Sar]-3-[(γ-methoxy)-N-MeLeu]-4-cyclosporin |
| 1195 | S | 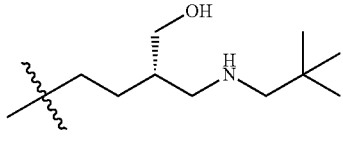 [SMILES: *CC[C@H](CO)CNCC(C)(C)C] | [(S)-(((S)-4-Hydroxy-3-((neopentylamino)methyl)butyl)thio)methyl-Sar]-3-[(γ-methoxy)-N-MeLeu]-4-cyclosporin |
| 1196 | S | 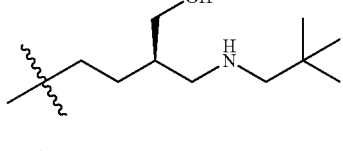 | [(S)-(((R)-4-Hydroxy-3-((neopentylamino)methyl)butyl)thio)methyl-Sar]-3-[(γ-methoxy)-N-MeLeu]-4-cyclosporin |
| 1197 | S | 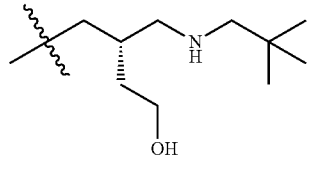 [SMILES: *C[C@@H](CCO)CNCC(C)(C)C] | [(S)-(((S)-4-Hydroxy-2-((neopentylamino)methyl)butyl)thio)methyl-Sar]-3-[(γ-methoxy)-N-MeLeu]-4-cyclosporin |
| 1198 | S | 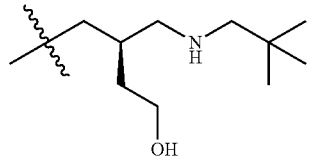 [SMILES: *C[C@H](CCO)CNCC(C)(C)C] | [(S)-(((R)-4-Hydroxy-2-((neopentylamino)methyl)butyl)thio)methyl-Sar]-3-[(γ-methoxy)-N-MeLeu]-4-cyclosporin |

TABLE 3-continued

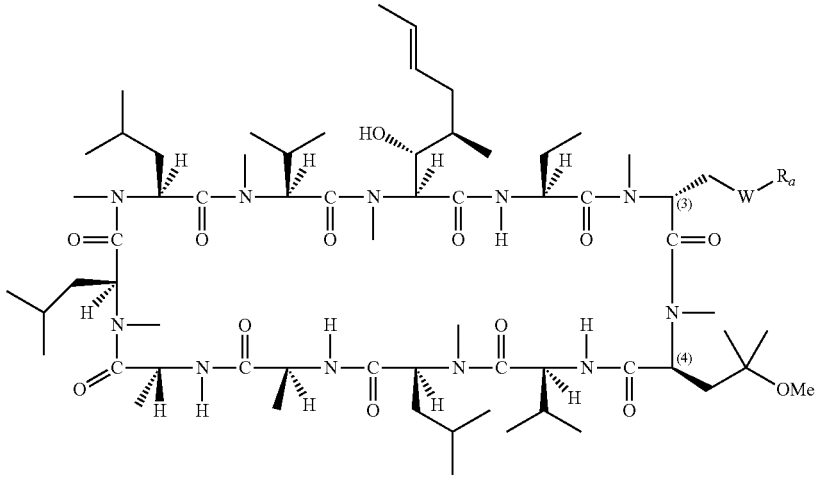

| Ex. No. | W | R$_a$ | Name |
|---|---|---|---|
| 1199 | S | 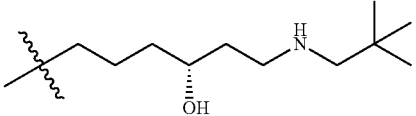 [SMILES: *CCC[C@@H](O)CCNCC(C)(C)C] | [(S)-(((R)-4-Hydroxy-6-(neopentylamino)hexyl)thio)methyl-Sar]-3-[(γ-methoxy)-N-MeLeu]-4-cyclosporin |
| 1200 | S | 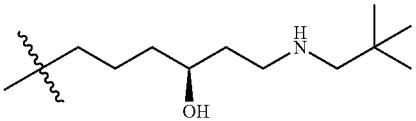 [SMILES: *CCC[C@H](O)CCNCC(C)(C)C] | [(S)-(((S)-4-Hydroxy-6-(neopentylamino)hexyl)thio)methyl-Sar]-3-[(γ-methoxy)-N-MeLeu]-4-cyclosporin |
| 1201 | S | 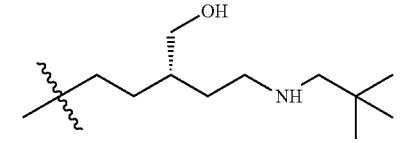 [SMILES: *CC[C@H](CO)CCNCC(C)(C)C] | [(S)-(((R)-3-(Hydroxymethyl)-5-(neopentylamino)pentyl)thio)methyl-Sar]-3-[(γ-methoxy)-N-MeLeu]-4-cyclosporin |
| 1202 | S | 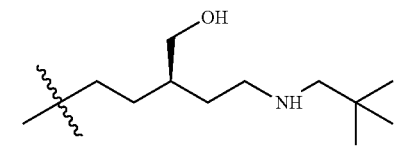 [SMILES: *CC[C@@H](CO)CCNCC(C)(C)C] | [(S)-(((S)-3-(Hydroxymethyl)-5-(neopentylamino)pentyl)thio)methyl-Sar]-3-[(γ-methoxy)-N-MeLeu]-4-cyclosporin |
| 1203 | S | 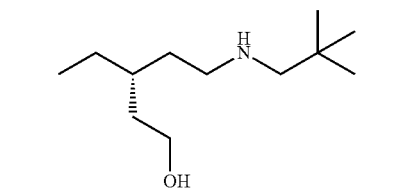 | [(S)-(((R)-4-Hydroxy-2-(2-(neopentylamino)ethyl)butyl)thio)methyl-Sar]-3-[(γ-methoxy)-N-MeLeu]-4-cyclosporin |
| 1204 | S | 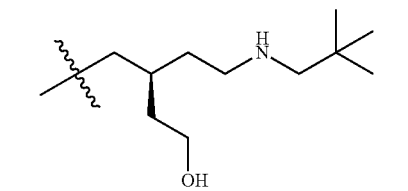 [SMILES: *C[C@H](CCO)CCNCC(C)(C)C] | [(S)-(((S)-4-Hydroxy-2-(2-(neopentylamino)ethyl)butyl)thio)methyl-Sar[-3-[(γ-methoxy)-N-MeLeu]-4-cyclosporin |
| 1205 | S | 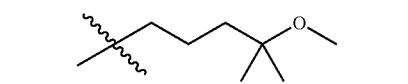 [SMILES: *CCCC(C)(C)OC] | [(S)-(4-Methoxy-4-methylpentylthio)methyl-Sar]-3-[(γ-methoxy)-N-MeLeu]-4-cyclosporin |

TABLE 3-continued

| Ex. No. | W | R_a | Name |
|---|---|---|---|
| 1206 | S | ~~~CH₂CH₂CH₂CH₂N(CH₃)₂ | [(S)-(4-(N,N-Dimethylamino)butylthio)methyl-Sar]-3-[(γ-methoxy)-N-MeLeu]-4-cyclosporin |
| 1207 | S | ~~~CH₂CH₂CH₂CH₂N(Et)₂ | [(S)-(4-(N,N-Diethylamino)butylthio)methyl-Sar]-3-[(γ-methoxy)-N-MeLeu]-4-cyclosporin |
| 1208 | S | ~~~CH₂CH₂CH₂CH₂NH-iPr | [(S)-(4-(N-Isopropylamino)butylthio)methyl-Sar]-3-[(γ-methoxy)-N-MeLeu]-4-cyclosporin |
| 1209 | S | ~~~CH₂CH₂CH₂CH₂N(CH₃)(iPr) | [(S)-(4-(N-Isopropyl-N-methylamino)butylthio)methyl-Sar]-3-[(γ-methoxy)-N-MeLeu]-4-cyclosporin |
| 1210 | S | ~~~CH₂CH₂CH₂CH₂N(Et)(iPr) | [(R)-(4-(N-Ethyl-N-isopropylamino)butylthio)methyl-Sar]-3-[(γ-methoxy)-N-MeLeu]-4-cyclosporin |
| 1211 | S | ~~~CH₂CH₂CH₂CH₂NH-iBu | [(S)-(4-(N-Isobutylamino)butylthio)methyl-Sar]-3-[(γ-methoxy)-N-MeLeu]-4-cyclosporin |
| 1212 | S | ~~~CH₂CH₂CH₂CH₂N(CH₃)(iBu) | [(S)-(4-(N-Isobutyl-N-methylamino)butylthio)methyl-Sar]-3-[(γ-methoxy)-N-MeLeu]-4-cyclosporin |
| 1213 | S | ~~~CH₂CH₂CH₂CH₂N(Et)(iBu) | [(S)-(4-(N-Isobutyl-N-ethylamino)butylthio)methyl-Sar]-3-[(γ-methoxy)-N-MeLeu]-4-cyclosporin |

TABLE 3-continued

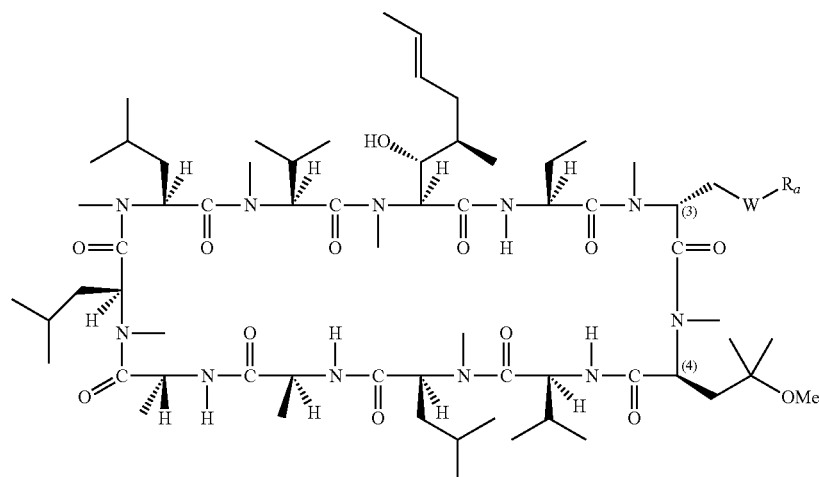

| Ex. No. | W | $R_a$ | Name |
|---|---|---|---|
| 1214 | S | (CH2)4-N(iBu)2 | [(S)-(4-(N,N-Diisobutylamino)butylthio)methyl-Sar]-3-[(γ-methoxy)-N-MeLeu]-4-cyclosporin |
| 1215 | S | (CH2)4-NH-CH2C(CH3)3 | [(S)-(4-(N-Neopentylamino)butylthio)methyl-Sar]-3-[(γ-methoxy)-N-MeLeu]-4-cyclosporin |
| 1216 | S | (CH2)4-N(Me)-CH2C(CH3)3 | [(S)-(4-(N-Methyl-N-neopentylamino)butylthio)methyl-Sar]-3-[(γ-methoxy)-N-MeLeu]-4-cyclosporin |
| 1217 | S | (CH2)4-N(Et)-CH2C(CH3)3 | [(S)-(4-(N-Ethyl-N-neopentylamino)butylthio)methyl-Sar]-3-[(γ-methoxy)-N-MeLeu]-4-cyclosporin |
| 1218 | S | (CH2)4-pyrrolidinyl | [(S)-(4-(N-Pyrrolidinyl)butylthio)methyl-Sar]-3-[(γ-methoxy)-N-MeLeu]-4-cyclosporin |
| 1219 | S | (CH2)4-thiazolidinyl | [(S)-(4-(N-Thiazolidinyl)butylthio)methyl-Sar]-3-[(γ-methoxy)-N-MeLeu]-4-cyclosporin |
| 1220 | S | (CH2)4-oxazolidinyl | [(S)-(4-(N-Oxazolidinyl)butylthio)methyl-Sar]-3-[(γ-methoxy)-N-MeLeu]-4-cyclosporin |

TABLE 3-continued

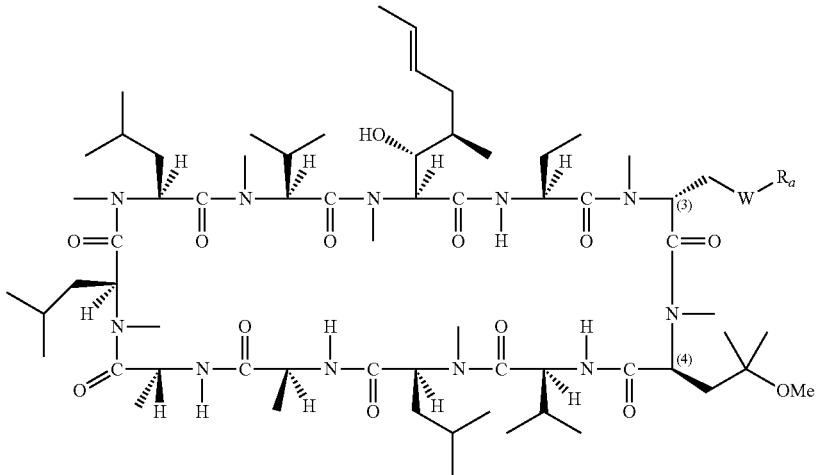

| Ex. No. | W | $R_a$ | Name |
|---|---|---|---|
| 1221 | S | 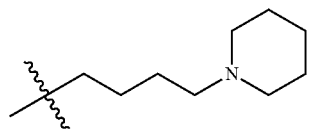 [SMILES: *CCCCN1CCCCC1] | [(S)-(4-(N-Piperidinyl)butylthio)methyl-Sar]-3-[(γ-methoxy)-NMeLeu]-4-cyclosporin |
| 1222 | S | 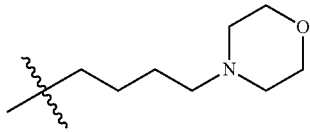 [SMILES: *CCCCN1CCOCC1] | [(S)-(4-(N-Morpholino)butylthio)methyl-Sar]-3-[(γ-methoxy)-N-MeLeu]-4-cyclosporin |
| 1223 | S | 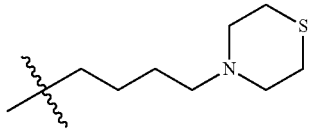 [SMILES: *CCCCN1CCSCC1] | [(S)-(4-(N-Thiomorpholino)butylthio)methyl-Sar]-3-[(γ-methoxy)-N-MeLeu]-4-cyclosporin |
| 1224 | S | 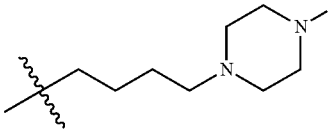 | [(S)-(4-(N-Piperazinyl)butylthio)methyl-Sar]-3-[(γ-methoxy)-N-MeLeu]-4-cyclosporin |
| 1225 | S | 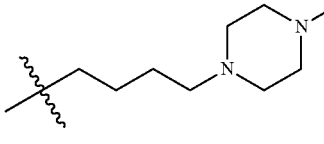 | [(S)-(4-(4-Methyl-N-piperazinyl)butylthio)methyl-Sar]-3-[(γ-methoxy)-N-MeLeu]-4-cyclosporin |
| 1226 | S | 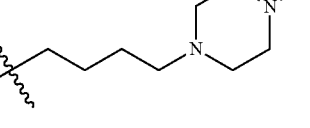 | [(S)-(4-(4-Ethyl-N-piperazinyl)butylthio)methyl-Sar]-3-[(γ-methoxy)-N-MeLeu]-4-cyclosporin |
| 1227 | S | 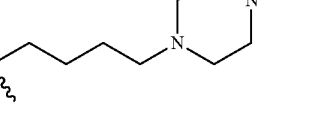 | [(S)-(4-(4-n-Propyl-N-piperazinyl)butylthio)methyl-Sar]-3-[(γ-methoxy)-N-MeLeu]-4-cyclosporin |

TABLE 3-continued

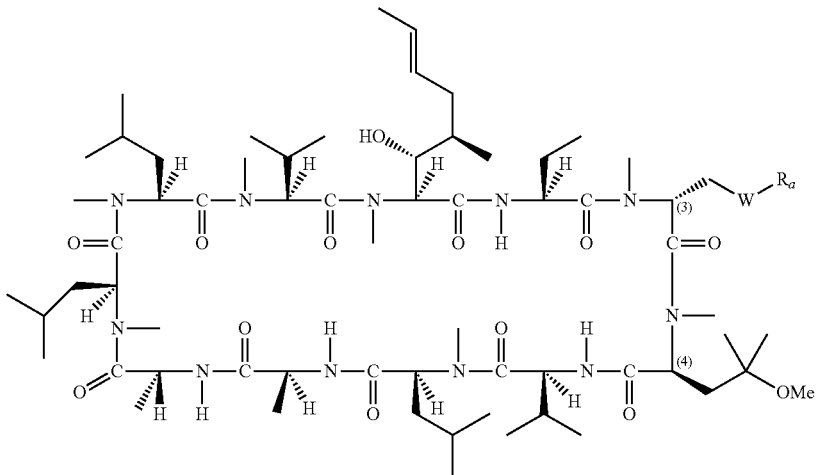

| Ex. No. | W | $R_a$ | Name |
|---|---|---|---|
| 1228 | S | 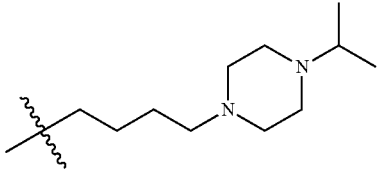 [SMILES: *CCCCN1CCN(C(C)C)CC1] | [(S)-(4-(4-Isopropyl-N-piperazinyl)butylthio)methyl-Sar]-3-[(γ-methoxy)-N-MeLeu]-4-cyclosporin |
| 1229 | S | 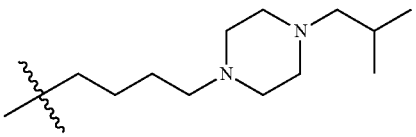 [SMILES: *CCCCN1CCN(CC(C)C)CC1] | [(S)-(4-(4-Isobutyl-N-piperazinyl)butylthio)methyl-Sar]-3-[(γ-methoxy)-N-MeLeu]-4-cyclosporin |
| 1230 | S | 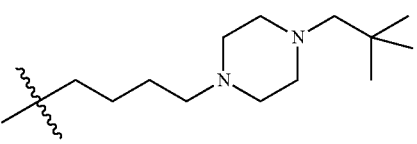 [SMILES: *CCCCN1CCN(CC(C)(C)C)CC1] | [(S)-(4-(4-Neopentyl-N-piperazinyl)butylthio)methyl-Sar]-3-[(γ-methoxy)-N-MeLeu]-4-cyclosporin |
| 1231 | S | 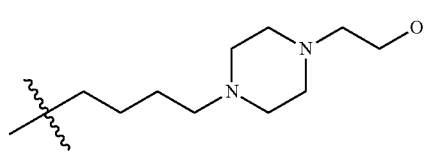 | [(S)-(4-(4-(2-Hydroxyethyl)-N-piperazinyl)butylthio)methyl-Sar]-3-[(γ-methoxy)-N-MeLeu]-4-cyclosporin |
| 1232 | S | 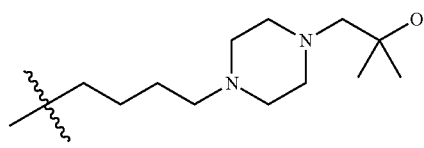 | [(S)-(4-(4-(2-Hydroxy-2-methylpropyl)-N-piperazinyl)butylthio)methyl-Sar]-3-[(γ-methoxy)-N-MeLeu]-4-cyclosporin |
| 1233 | S | 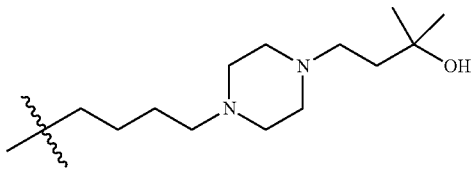 [SMILES: *CCCCN1CCN(CCC(C)(C)O)CC1] | [(S)-(4-(4-(3-Hydroxy-3-methylbutyl)-N-piperazinyl)butylthio)methyl-Sar]-3-[(γ-methoxy)-N-MeLeu]-4-cyclosporin |
| 1234 | S | 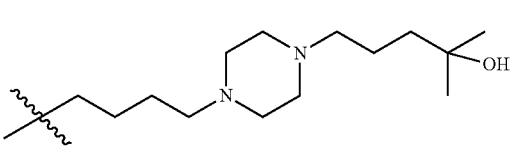 [SMILES: *CCCCN1CCN(CCCC(C)(C)O)CC1] | [(S)-(4-(4-(4-Hydroxy-4-methylpentyl)-N-piperazinyl)butylthio)methyl-Sar]-3-[(γ-methoxy)-N-MeLeu]-4-cyclosporin |

TABLE 3-continued

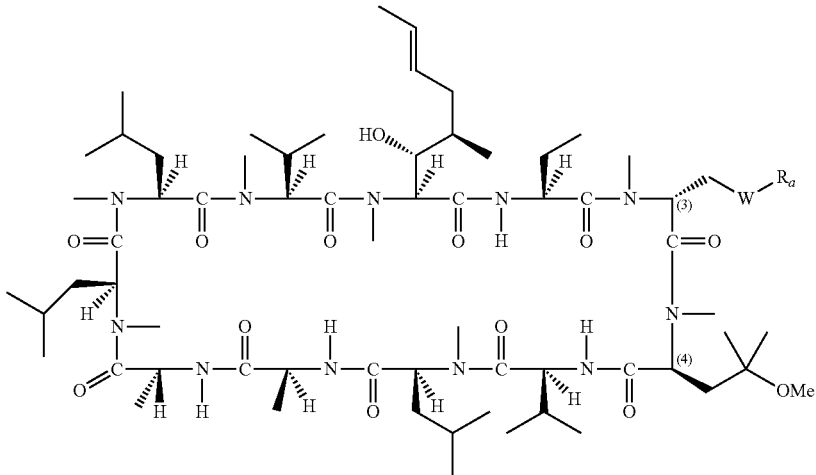

| Ex. No. | W | $R_a$ | Name |
|---|---|---|---|
| 1235 | S | 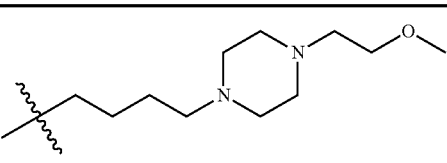 | [(S)-(4-(4-(2-Methoxyethyl)-N-piperazinyl)butylthio)methyl-Sar]-3-[(γ-methoxy)-N-MeLeu]-4-cyclosporin |
| 1236 | S | 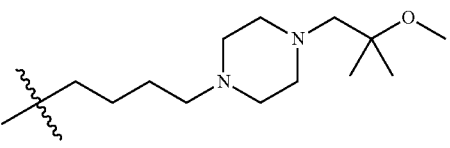 [SMILES: *CCCCN1CCN(CC(C)(C)OC)CC1] | [(S)-(4-(4-(2-Methoxy-2-methylpropyl)-N-piperazinyl)butylthio)methyl-Sar]-3-[(γ-methoxy)-N-MeLeu]-4-cyclosporin |
| 1237 | S | 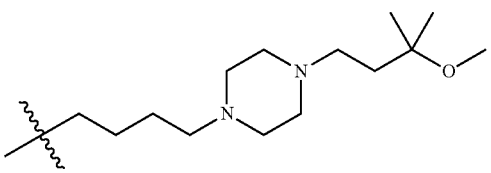 [SMILES: *CCCCN1CCN(CCC(C)(C)OC)CC1] | [(S)-(4-(4-(3-Methoxy-3-methylbutyl)-N-piperazinyl)butylthio)methyl-Sar]-3-[(γ-methoxy)-N-MeLeu]-4-cyclosporin |
| 1238 | S | 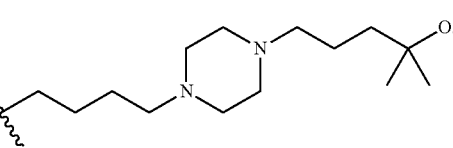 | [(S)-(4-(4-(4-Methoxy-4-methylpentyl)-N-piperazinyl)butylthio)methyl-Sar]-3-[(γ-methoxy)-N-MeLeu]-4-cyclosporin |
| 1239 | S | 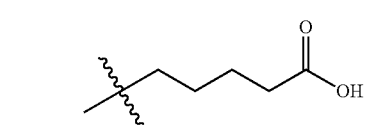 | [(S)-(4-Carboxybutylthio)methyl-Sar]-3-[(γ-methoxy)-N-MeLeu]-4-cyclosporin |
| 1240 | S | 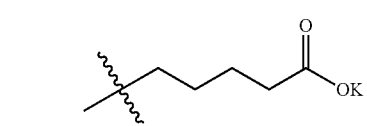 | [(S)-(4-Carboxybutylthio)methyl-Sar]-3-[(γ-methoxy)-N-MeLeu]-4-cyclosporin-potassium salt |
| 1241 | S | 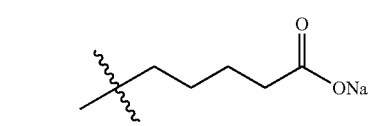 | [(S)-(4-Carboxybutylthio)methyl-Sar]-3-[(γ-methoxy)-N-MeLeu]-4-cyclosporin-sodium salt |

TABLE 3-continued

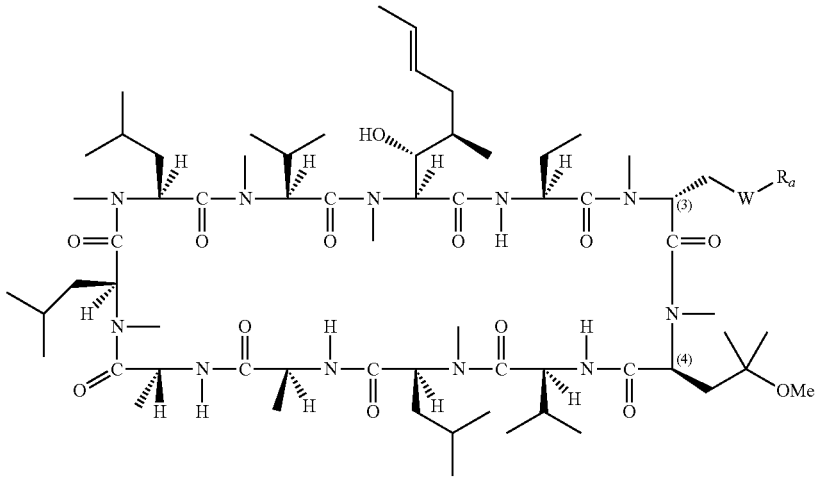

| Ex. No. | W | $R_a$ | Name |
|---|---|---|---|
| 1242 | S | 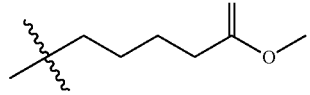 | [(S)-(4-Methoxycarbonylbutylthio)methyl-Sar]-3-[(γ-methoxy)-N-MeLeu]-4-cyclosporin |
| 1243 | S | 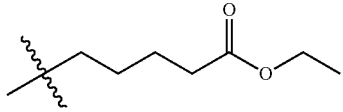 [SMILES: *CCCCC(=O)OCC] | [(S)-(4-Ethoxycarbonylbutylthio)methyl-Sar]-3-[(γ-methoxy)-N-MeLeu]-4-cyclosporin |
| 1244 | S | 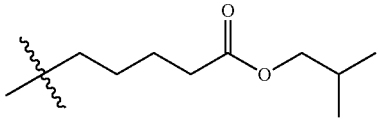 [SMILES: *CCCCC(=O)OCC(C)C] | [(S)-(4-isoButoxycarbonylbutylthio)methyl-Sar]-3-[(γ-methoxy)-N-MeLeu]-4-cyclosporin |
| 1245 | S | 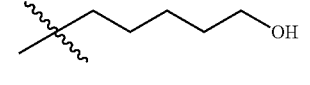 [SMILES: *CCCCCO] | [(S)-(5-Hydroxypentylthio)methyl-Sar]-3-[(γ-methoxy)-N-MeLeu]-4-cyclosporin |
| 1246 | S | 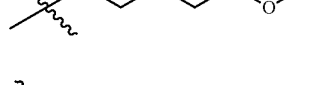 | [(S)-(5-Methoxypentylthio)methyl-Sar]-3-[(γ-methoxy)-N-MeLeu]-4-cyclosporin |
| 1247 | S |  | [(S)-(4-Carboxypentylthio)methyl-Sar]-3-[(γ-methoxy)-N-MeLeu]-4-cyclosporin |
| 1248 | S |  | [(S)-(4-Carboxypentylthio)methyl-Sar]-3-[(γ-methoxy)-N-MeLeu]-4-cyclosporin-potassium salt |
| 1249 | S |  | [(S)-(4-Carboxypentylthio)methyl-Sar]-3-[(γ-methoxy)-N-MeLeu]-4-cyclosporin-sodium salt |
| 1250 | S |  | [(S)-(4-Ethoxycarbonylpentylthio)methyl-Sar]-3-[(γ-methoxy)-N-MeLeu]-4-cyclosporin |

TABLE 3-continued

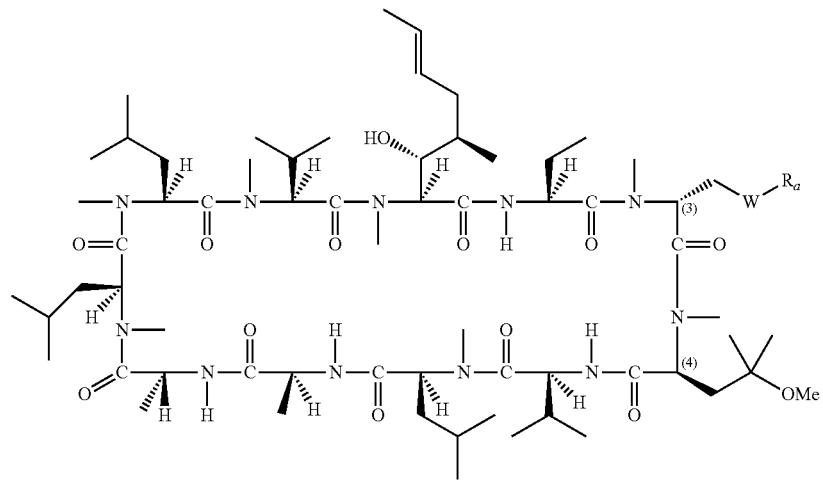

| Ex. No. | W | $R_a$ | Name |
|---|---|---|---|
| 1251 | S | (4,4'-dicarboxybutyl group, –CH(COOH)₂ terminated chain) | [(S)-((4,4'-Dicarboxy)butylthio)methyl-Sar]-3-[(γ-methoxy)-N-MeLeu]-4-cyclosporin |
| 1252 | S | (4,4'-dipotassium dicarboxylate butyl chain, –CH(COOK)₂) | [(S)-((4,4'-Dicarboxy)butylthio)methyl-Sar]-3-[(γ-methoxy)-N-MeLeu]-4-cyclosporin-dipotassium salt |
| 1253 | S | (S)-3-Hydroxymethyl-4-ethoxycarbonylbutyl chain | [(S)-((S)-3-Hydroxymethyl-4-ethoxycarbonybutylthio)methyl-Sar]-3-[(γ-methoxy)-N-MeLeu]-4-cyclosporin |
| 1254 | S | (R)-3-Hydroxymethyl-4-ethoxycarbonylbutyl chain | [(S)-((R)-3-Hydroxymethyl-4-ethoxycarbonybutylthio)methyl-Sar]-3-[(γ-methoxy)-N-MeLeu]-4-cyclosporin |
| 1255 | S | 6-Hydroxyhexyl | [(S)-(6-Hydroxyhexylthio)methyl-Sar]-3-[(γ-methoxy)-N-MeLeu]-4-cyclosporin |
| 1256 | S | 6-Methoxyhexyl | [(S)-(6-Methoxyhexylthio)methyl-Sar]-3-[(γ-methoxy)-N-MeLeu]-4-cyclosporin |
| 1257 | S | –CH₂C(O)NHCH₂CH₂NH₂ | [(S)-[(N-(2-Aminoethyl)carbamoyl)methylthio)methyl-Sar]-3-[(γ-methoxy)-N-MeLeu]-4-cyclosporin |
| 1258 | S | –CH₂C(O)NHCH₂CH₂NH-neopentyl | [(S)-[(N-(2-(Neopentylamino)ethyl)carbamoyl)methylthio]methyl-Sar]-3-[(γ-methoxy)-N-MeLeu]-4-cyclosporin |

TABLE 3-continued

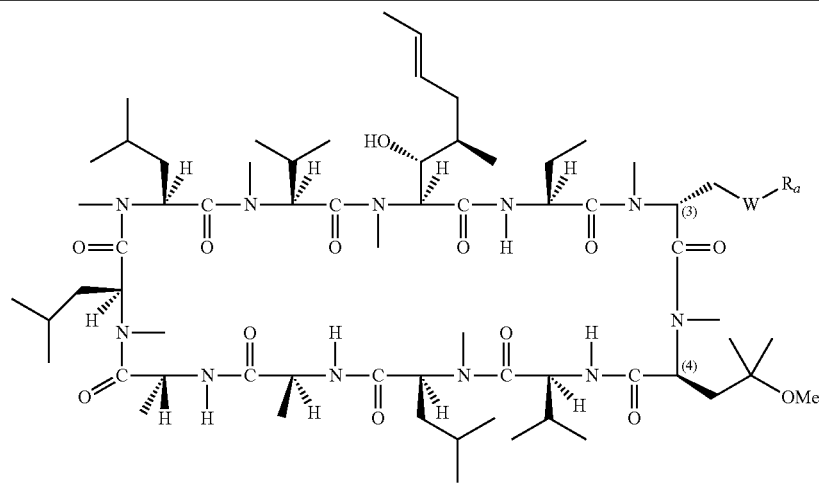

| Ex. No. | W | $R_a$ | Name |
|---|---|---|---|
| 1259 | S | -CH2-C(O)-NH-(CH2)3-NH2 | [(S)-[(N-(3-Aminopropyl)carbamoyl)methylthio]methyl-Sar]-3-[(γ-methoxy)-N-MeLeu]-4-cyclosporin |
| 1260 | S | -CH2-C(O)-NH-(CH2)3-NH-CH2-C(CH3)3 | [(S)-[(N-(3-(Neopentylamino)propyl)carbamoyl)methylthio]methyl-Sar]-3-cyclosporin |
| 1261 | S | -CH2-C(O)-NH-(CH2)4-NH2 | [(S)-[(N-(4-Aminobutyl)carbamoyl)methylthio]methyl-Sar]-3-[(γ-methoxy)-N-MeLeu]-4-cyclosporin |
| 1262 | S | -CH2-C(O)-NH-(CH2)4-NH-CH2-C(CH3)3 | [(S)-[(N-(4-(Neopentylamino)butyl)carbamoyl)methylthio]methyl-Sar]-3-[(γ-methoxy)-N-MeLeu]-4-cyclosporin |
| 1263 | S | -CH2-C(O)-NH-(CH2)5-NH2 | [(S)-[(N-(5-Aminopentyl)carbamoyl)methylthio]methyl-Sar]-3-[(γ-methoxy)-N-MeLeu]-4-cyclosporin |
| 1264 | S | -CH2-C(O)-NH-(CH2)5-NH-CH2-C(CH3)3 | [(S)-[(N-(5-(Neopentylamino)pentyl)carbamoyl)methylthio]methyl-Sar]-3-[(γ-methoxy)-N-MeLeu]-4-cyclosporin |
| 1265 | S | -CH2-C(O)-NH-(CH2)6-NH2 | [(S)-[(N-(6-Aminohexyl)carbamoyl)methylthio]methyl-Sar]-3-[(γ-methoxy)-N-MeLeu]-4-cyclosporin |
| 1266 | S | -CH2-C(O)-NH-(CH2)6-NH-CH2-C(CH3)3 | [(S)-[(N-(6-Neopentylamino)hexyl)carbamoyl)methylthio]methyl-Sar]-3-[(γ-methoxy)-N-MeLeu]-4-cyclosporin |
| 1267 | S | -CH2-C(O)-NH-(D-Glu)6Gly-OH | [(S)-[([HO-Gly-(D-Glu)6]carbamoyl)methylthio]methyl-Sar]-3-[(γ-methoxy)-N-MeLeu]-4-cyclosporin |

TABLE 3-continued

| Ex. No. | W | $R_a$ | Name |
|---|---|---|---|
| 1268 | S | ~~~CH2CH2C(O)NH-(D-Glu)6Gly-OH | [(S)-[([HO-Gly-(D-Glu)6]carbamoyl)ethylthio]methyl-Sar]-3-[(γ-methoxy)-N-MeLeu]-4-cyclosporin |
| 1269 | S | ~~~(CH2)3C(O)NH-(D-Glu)6Gly-OH | [(S)-[([HO-Gly-(D-Glu)6]carbamoyl)propylthio]methyl-Sar]-3-[(γ-methoxy)-N-MeLeu]-4-cyclosporin |
| 1270 | S | ~~~CH2CH2OCH2C(O)NH-(D-Glu)6Gly-OH | [(S)-((2-[([HO-Gly-(D-Glu)6]carbamoyl)methoxy]ethyl)sulfanyl)methyl-Sar]-3-[(γ-methoxy)-N-MeLeu]-4-cyclosporin |
| 1271 | S | ~~~(CH2)3OCH2C(O)NH-(D-Glu)6Gly-OH | [(S)-((3-[([HO-Gly-(D-Glu)6]carbamoyl)methoxy]propyl)sulfanyl)methyl-Sar]-3-[(γ-methoxy)-N-MeLeu]-4-cyclosporin |
| 1272 | S | ~~~(CH2)4OCH2C(O)NH-(D-Glu)6Gly-OH | [(S)-((4-[([HO-Gly-(D-Glu)6]carbamoyl)methoxy]butyl)sulfanyl)methyl-Sar]-3-[(γ-methoxy)-N-MeLeu]-4-cyclosporin |
| 1273 | S | ~~~(CH2)5OCH2C(O)NH-(D-Glu)6Gly-OH | [(S)-((5-[([HO-Gly-(D-Glu)6]carbamoyl)methoxy]pentyl)sulfanyl)methyl-Sar]-3-[(γ-methoxy)-N-MeLeu]-4-cyclosporin |
| 1274 | S | ~~~(CH2)6OCH2C(O)NH-(D-Glu)6Gly-OH | [(S)-((6-[([HO-Gly-(D-Glu)6]carbamoyl)methoxy]hexyl)sulfanyl)methyl-Sar]-3-[(γ-methoxy)-N-MeLeu]-4-cyclosporin |
| 1275 | S | ~~~CH2CH2CH(CH3)2 | [(S)-(Isopentylthio)methyl-Sar]-3-[(γ-methoxy)-N-MeLeu]-4-cyclosporin |
| 1276 | S | ~~~(CH2)4CH3 | [(S)-(5-n-Pentylthio)methyl-Sar]-3-[(γ-methoxy)-N-MeLeu]-4-cyclosporin |

TABLE 3-continued

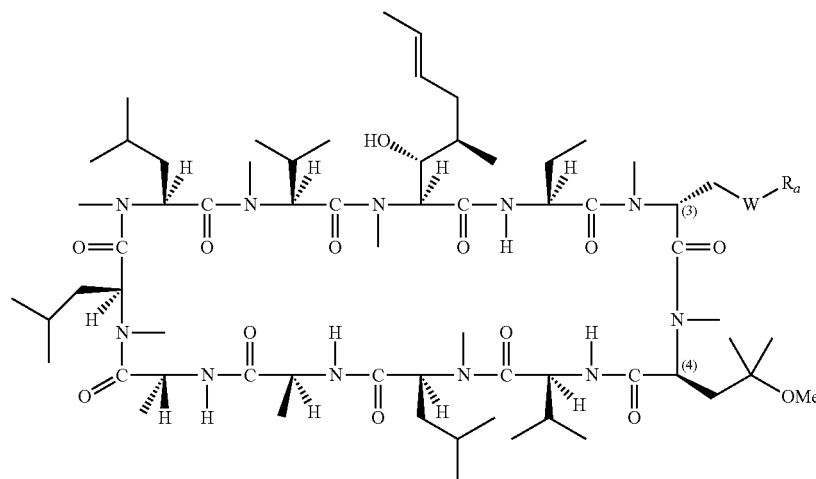

| Ex. No. | W | $R_a$ | Name |
|---|---|---|---|
| 1277 | S | (hexyl chain) | [(S)-(6-n-Hexylthio)methyl-Sar]-3-[(γ-methoxy)-N-MeLeu]-4-cyclosporin |
| 1278 | S | (heptyl chain) | [(S)-(7-n-Heptylthio)methyl-Sar]-3-[(γ-methoxy)-N-MeLeu]-4-cyclosporin |
| 1279 | O | CH₂COOH | [(R)-(Carboxymethoxy)methyl-Sar]-3-[(γ-methoxy)-N-MeLeu]-4-cyclosporin |
| 1280 | O | CH₂COOK | [(R)-(Carboxymethoxy)methyl-Sar]-3-[(γ-methoxy)-N-MeLeu]-4-cyclosporin-potassium salt |
| 1281 | O | CH₂COONa | [(R)-(Carboxymethoxy)methyl-Sar]-3-[(γ-methoxy)-N-MeLeu]-4-cyclosporin-sodium salt |
| 1282 | O | CH₂COOEt | [(R)-((Ethoxycarbonyl)methoxy)methyl-Sar]-3-[(γ-methoxy)-N-MeLeu]-4-cyclosporin |
| 1283 | O | CH₂CH₂OH | [(R)-(2-Hydroxyethoxy)methyl-Sar]-3-[(γ-methoxy)-N-MeLeu]-4-cyclosporin |
| 1284 | O | C(CH₃)₂CH₂OH | [(R)-(2-Hydroxy-2,2-dimethylethoxy)methyl-Sar]-3-[(γ-methoxy)-N-MeLeu]-4-cyclosporin |
| 1285 | O | CH₂CH₂OCH₃ | [(R)-(2-Methoxyethoxy)methyl-Sar]-3-[(γ-methoxy)-N-MeLeu]-4-cyclosporin |
| 1286 | O | C(CH₃)₂OCH₃ | [(R)-(2-Methoxy-2-methylpropoxy)methyl-Sar]-3-[(γ-methoxy)-N-MeLeu]-4-cyclosporin |

TABLE 3-continued

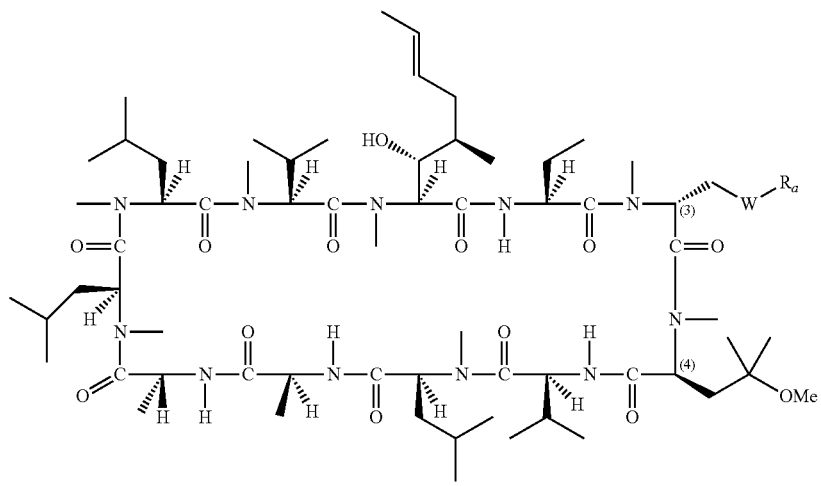

| Ex. No. | W | $R_a$ | Name |
|---|---|---|---|
| 1287 | O | (CH2CH2NH-iPr) | [(R)-(2-(N-Isopropylamino)ethoxy)methyl-Sar]-3-[(γ-methoxy)-N-MeLeu]-4-cyclosporin |
| 1288 | O | (CH2CH2N(Me)iPr) | [(R)-(2-(N-Isopropyl-N-methylamino)ethoxy)methyl-Sar]-3-[(cyclosporinmethoxy)-N-MeLeu]-4-cyclosporin |
| 1289 | O | (CH2CH2N(Et)iPr) | [(R)-(2-(N-Ethyl-N-isopropylamino)ethoxy)methyl-Sar]-3-[(γ-methoxy)-N-MeLeu]-4-cyclosporin |
| 1290 | O | (CH2CH2NH-iBu) | [(R)-(2-(N-Isobutylamino)ethoxy)methyl-Sar]-3-[(γ-methoxy)-N-MeLeu]-4-cyclosporin |
| 1291 | O | (CH2CH2N(Me)iBu) | [(R)-(2-(N-Isobutyl-N-methylamino)ethoxy)methyl-Sar]-3-[(γ-methoxy)-N-MeLeu]-4-cyclosporin |
| 1292 | O | (CH2CH2N(Et)iBu) | [(R)-(2-(N-Isobutyl-N-ethylamino)ethoxy)methyl-Sar]-3-[(γ-methoxy)-N-MeLeu]-4-cyclosporin |
| 1293 | O | (CH2CH2NH-neopentyl) | [(R)-(2-(N-Neopentylamino)ethoxy)methyl-Sar]-3-[(γ-methoxy)-N-MeLeu]-4-cyclosporin |
| 1294 | O | (CH2CH2N(Me)neopentyl) | [(R)-(2-(N-Methyl-N-neopentylamino)ethoxy)methyl-Sar]-3-[(γ-methoxy)-N-MeLeu]-4-cyclosporin |

TABLE 3-continued

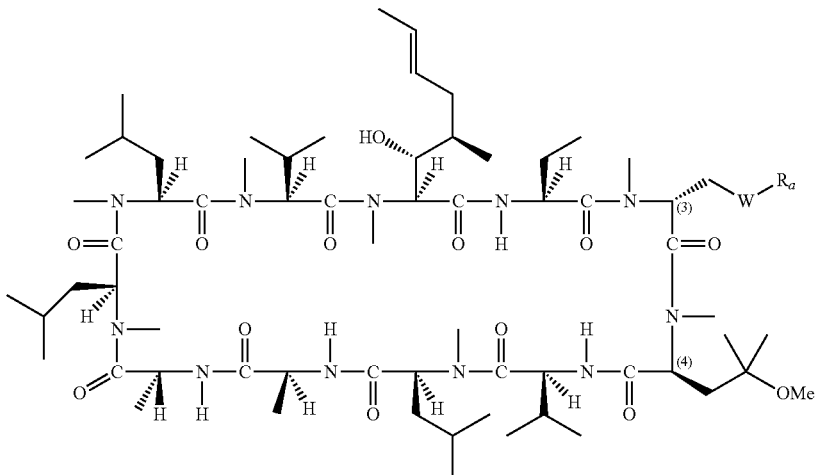

| Ex. No. | W | $R_a$ | Name |
|---|---|---|---|
| 1295 | O | 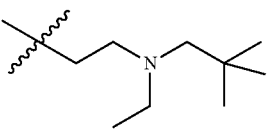 [SMILES: *CCN(CC)CC(C)(C)C] | [(R)-(2-(N-Ethyl-N-neopentylamino)ethoxy)methyl-Sar]-3-[(γ-methoxy)-N-MeLeu]-4-cyclosporin |
| 1296 | O | 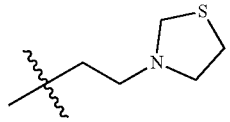 [SMILES: *CCN1CCSC1] | [(R)-(2-(N-Thiazolidinyl)ethoxy)methyl-Sar]-3-[(γ-methoxy)-N-MeLeu]-4-cyclosporin |
| 1297 | O | 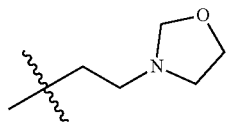 [SMILES: *CCN1CCOC1] | [(R)-(2-(N-Oxazolidinyl)ethoxy)methyl-Sar]-3-[(γ-methoxy)-N-MeLeu]-4-cyclosporin |
| 1298 | O | 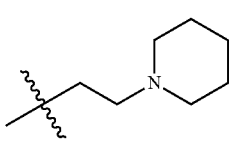 [SMILES: *CCN1CCCCC1] | [(R)-(2-(N-Piperidinyl)ethoxy)methyl-Sar]-3-[(γ-methoxy)-N-MeLeu]-4-cyclosporin |
| 1299 | O | 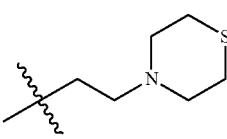 | [(R)-(2-(N-Thiomorpholino)ethoxy)methyl-Sar]-3-[(γ-methoxy)-N-MeLeu]-4-cyclosporin |
| 1300 | O | 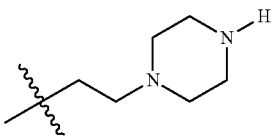 [SMILES: *CCN1CCNCC1] | [(R)-(2-(N-Piperazinyl)ethoxy)methyl-Sar]-3-[(γ-methoxy)-N-MeLeu]-4-cyclosporin |
| 1301 | O | 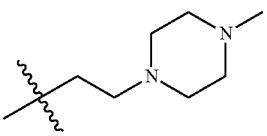 [SMILES: *CCN1CCN(C)CC1] | [(R)-(2-(4-Methyl-N-piperazinyl)ethoxy)methyl-Sar]-3-[(γ-methoxy)-N-MeLeu]-4-cyclosporin |

TABLE 3-continued

| Ex. No. | W | R$_a$ | Name |
|---|---|---|---|
| 1302 | O | (4-ethyl-piperazinyl-propyl) | [(R)-(2-(4-Ethyl-N-piperazinyl)ethoxy)methyl-Sar]-3-[(γ-methoxy)-N-MeLeu]-4-cyclosporin |
| 1303 | O | (4-propyl-piperazinyl-propyl) | [(R)-(2-(4-Propyl-N-piperazinyl)ethoxy)methyl-Sar]-3-[(γ-methoxy)-N-MeLeu]-4-cyclosporin |
| 1304 | O | (4-isopropyl-piperazinyl-propyl) | [(R)-(2-(4-Isopropyl-N-piperazinyl)ethoxy)methyl-Sar]-3-[(γ-methoxy-N-MeLeu]-4-cyclosporin |
| 1305 | O | (4-isobutyl-piperazinyl-propyl) | [(R)-(2-(4-Isobutyl-N-piperazinyl)ethoxy)methyl-Sar]-3-[(γ-methoxy)-N-MeLeu]-4-cyclosporin |
| 1306 | O | (4-neopentyl-piperazinyl-propyl) | [(R)-(2-(4-Neopentyl-N-piperazinyl)ethoxy)methyl-Sar]-3-[(γ-methoxy)-N-MeLeu]-4-cyclosporin |
| 1307 | O | (4-(2-hydroxyethyl)-piperazinyl-propyl) | [(R)-(2-(4-(2-Hydroxyethyl)-N-piperazinyl)ethoxy)methyl-Sar]-3-[(γ-methoxy)-N-MeLeu]-4-cyclosporin |
| 1308 | O | (4-(2-hydroxy-2-methylpropyl)-piperazinyl-propyl) | [(R)-(2-(4-(2-Hydroxy-2-methylpropyl)-N-piperazinyl)ethoxy)methyl-Sar]-3-[(γ-methoxy)-N-MeLeu]-4-cyclosporin |

TABLE 3-continued

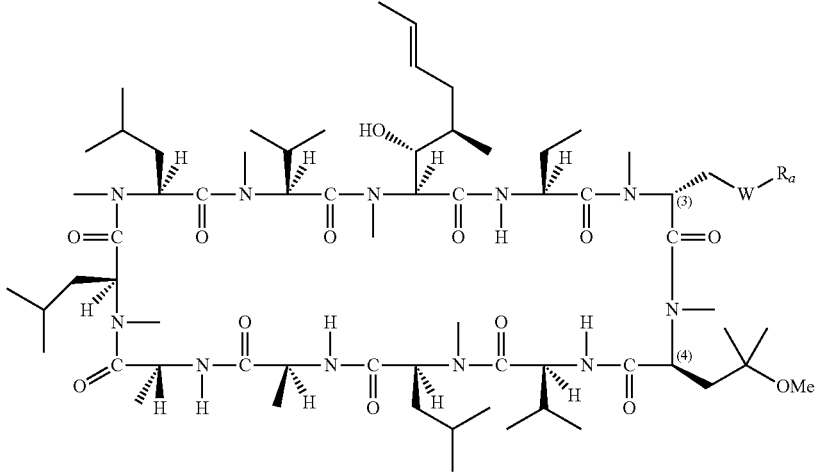

| Ex. No. | W | $R_a$ | Name |
|---|---|---|---|
| 1309 | O | 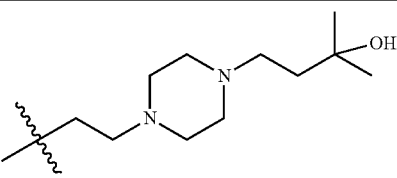 | [(R)-(2-(4-(3-Hydroxy-3-methylbutyl)-N-piperazinyl)ethoxy)methyl-Sar]-3-[(γ-methoxy)-N-MeLeu]-4-cyclosporin |
| 1310 | O | 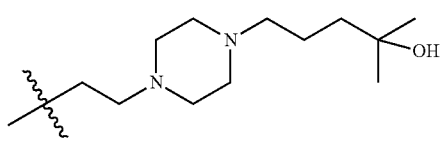 [SMILES: *CCN1CCN(CCCC(C)(C)O)CC1] | [(R)-(2-(4-(4-Hydroxy-4-methylpentyl)-N-piperazinyl)ethoxy)methyl-Sar]-3-[(γ-methoxy)-N-MeLeu]-4-cyclosporin |
| 1311 | O | 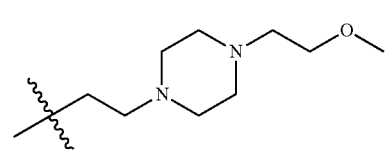 [SMILES: *CCN1CCN(CCOC)CC1] | [(R)-(2-(4-(2-Methoxyethyl)-N-piperazinyl)ethoxy)methyl-Sar]-3-[(γ-methoxy)-N-MeLeu]-4-cyclosporin |
| 1312 | O | 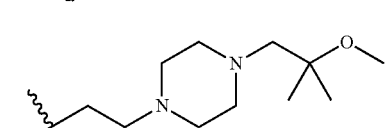 | [(R)-(2-(4-(2-Methoxy-2-methylpropyl)-N-piperazinyl)ethoxy)methyl-Sar]-3-[(γ-methoxy)-N-MeLeu]-4-cyclosporin |
| 1313 | O | 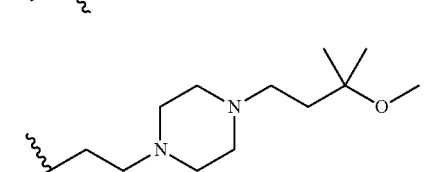 | [(R)-(2-(4-(3-Methoxy-3-methylbutyl)-N-piperazinyl)ethoxy)methyl-Sar]-3-[(γ-methoxy)-N-MeLeu]-4-cyclosporin |
| 1314 | O | 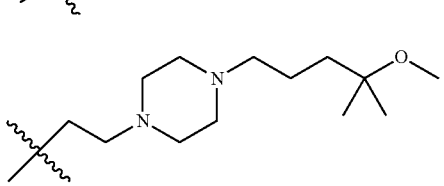 | [(R)-(2-(4-(4-Methoxy-4-methylpentyl)-N-piperazinyl)ethoxy)methyl-Sar]-3-[(γ-methoxy)-N-MeLeu]-4-cyclosporin |
| 1315 | O | 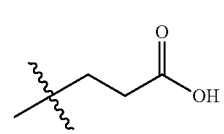 | [(R)-(2-Carboxyethoxy)methyl-Sar]-3-[(γ-methoxy)-N-MeLeu]-4-cyclosporin |

TABLE 3-continued

| Ex. No. | W | $R_a$ | Name |
|---|---|---|---|
| 1316 | O | —CH₂C(CH₃)₂CH₂C(O)OK | [(R)-(2-Carboxyethoxy)methyl-Sar]-3-[(γ-methoxy)-N-MeLeu]-4-cyclosporin-potassium salt |
| 1317 | O | —CH₂C(CH₃)₂CH₂C(O)ONa | [(R)-(2-Carboxyethoxy)methyl-Sar]-3-[(γ-methoxy)-N-MeLeu]-4-cyclosporin-sodium salt |
| 1318 | O | —CH₂C(CH₃)₂CH₂C(O)OEt | [(R)-(2-(Ethoxycarbonyl)ethoxy)methyl-Sar]-3-[(γ-methoxy)-N-MeLeu]-4-cyclosporin |
| 1319 | O | —CH₂CH₂CH₂OH | [(R)-(3-Hydroxypropoxy)methyl-Sar]-3-[(γ-methoxy)-N-MeLeu]-4-cyclosporin |
| 1320 | O | —CH₂CH₂C(CH₃)₂OH | [(R)-(3-Hydroxy-3-methylbutoxy)methyl-Sar]-3-[(γ-methoxy)-N-MeLeu]-4-cyclosporin |
| 1321 | O | —CH₂CH₂CH₂OMe | [(R)-(3-Methoxypropoxy)methyl-Sar]-3-[(γ-methoxy)-N-MeLeu]-4-cyclosporin |
| 1322 | O | —CH₂CH₂C(CH₃)₂OMe | [(R)-(3-Methoxy-3-methylbutoxy)methyl-Sar]-3-[(γ-methoxy)-N-MeLeu]-4-cyclosporin |
| 1323 | O | —CH₂CH₂CH₂NH-iPr | [(R)-(3-(N-Isopropylamino)propoxy)methyl-Sar]-3-[(γ-methoxy)-N-MeLeu]-4-cyclosporin |
| 1324 | O | —CH₂CH₂CH₂N(Me)(iPr) | [(R)-(3-(N-Isopropyl-N-methylamino)propoxy)methyl-Sar]-3-[(γ-methoxy)-N-MeLeu]-4-cyclosporin |

TABLE 3-continued

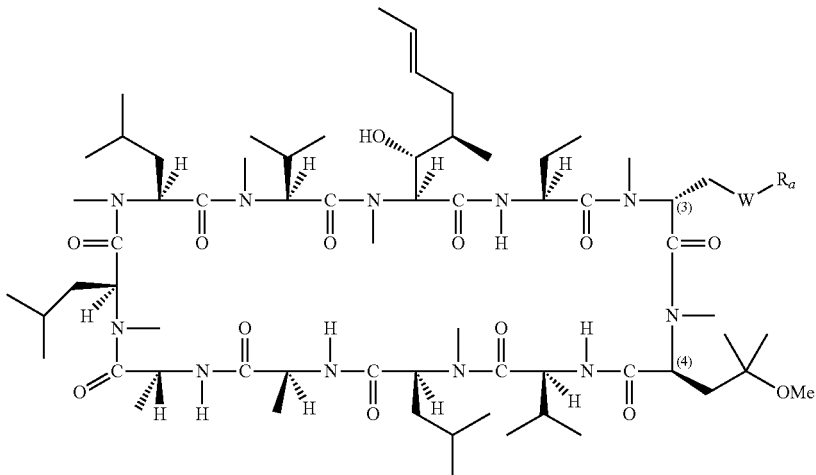

| Ex. No. | W | R_a | Name |
|---|---|---|---|
| 1325 | O | 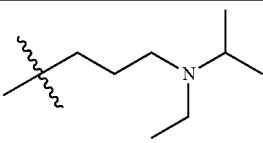 | [(R)-(3-(N-Ethyl-N-isopropylamino)propoxy)methyl-Sar]-3-[(γ-methoxy)-N-MeLeu]-4-cyclosporin |
| 1326 | O | 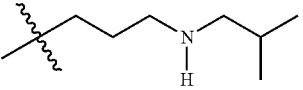 [SMILES: *CCCNCC(C)C] | [(R)-(3-(N-Isobutylamino)propoxy)methyl-Sar]-3-[(γ-methoxy)-N-MeLeu]-4-cyclosporin |
| 1327 | O | 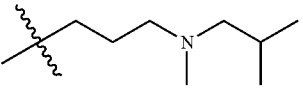 [SMILES: *CCCN(C)CC(C)C] | [(R)-(3-(N-Isobutyl-N-methylamino)propoxy)methyl-Sar]-3-[(γ-methoxy)-N-MeLeu]-4-cyclosporin |
| 1328 | O | 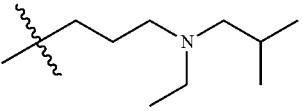 [SMILES: *CCCN(CC)CC(C)C] | [(R)-(3-(N-Ethyl-N-isobutylamino)propoxy)methyl-Sar]-3-[(γ-methoxy)-N-MeLeu]-4-cyclosporin |
| 1329 | O | 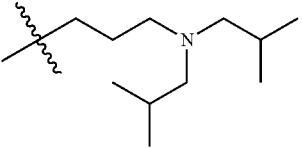 [SMILES: *CCCN(CC(C)C)CC(C)C] | [(R)-(3-(N,N-Diisobutylamino)propoxy)methyl-Sar]-3-[(γ-methoxy)-N-MeLeu]-4-cyclosporin |
| 1330 | O | 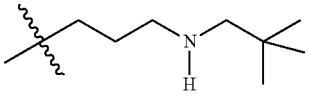 [SMILES: *CCCNCC(C)(C)C] | [(R)-(3-(N-Neopentylamino)propoxy)methyl-Sar]-3-[(γ-methoxy)-N-MeLeu]-4-cyclosporin |
| 1331 | O | 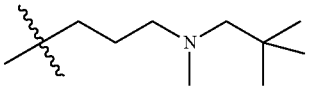 [SMILES: *CCCN(C)CC(C)(C)C] | [(R)-(3-(N-Methyl-N-neopentylamino)propoxy)methyl-Sar]-3-[(γ-methoxy)-N-MeLeu]-4-cyclosporin |
| 1332 | O | 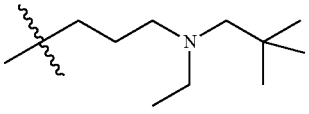 [SMILES: *CCCN(CC)CC(C)(C)C] | [(R)-(3-(N-Ethyl-N-neopentylamino)propoxy)methyl-Sar]-3-[(γ-methoxy)-N-MeLeu]-4-cyclosporin |
| 1333 | O | 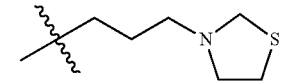 | [(R)-(3-(N-Thiazolidinyl)propoxymethyl-Sar]-3-[(γ-methoxy)-NMeLeu]-4-cyclosporin |

TABLE 3-continued

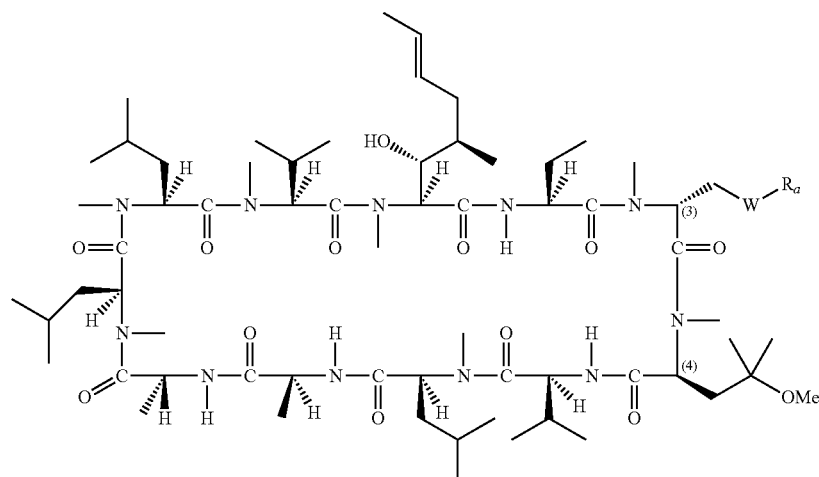

| Ex. No. | W | $R_a$ | Name |
|---|---|---|---|
| 1334 | O | (CH₂)₃-N-oxazolidinyl | [(R)-(3-(N-Oxazolidinyl)propoxymethyl-Sar]-3-[(γ-methoxy)-NMeLeu]-4-cyclosporin |
| 1335 | O | (CH₂)₃-N-piperidinyl | [(R)-(3-(N-Piperidinyl)propoxy)methyl-Sar]-3-[(γ-methoxy)-N-MeLeu]-4-cyclosporin |
| 1336 | O | (CH₂)₃-N-morpholino | [(R)-(3-(N-Morpholino)propoxy)methyl-Sar]-3-[(γ-methoxy)-N-MeLeu]-4-cyclosporin |
| 1337 | O | (CH₂)₃-N-thiomorpholino | [(R)-(3-(N-Thiomorpholino)propooxy)methyl-Sar]-3-[(γ-methoxy)-N-MeLeu]-4-cyclosporin |
| 1338 | O | (CH₂)₃-N-piperazinyl | [(R)-(3-(N-Piperazinyl)propoxy)methyl-Sar]-3-[(γ-methoxy)-N-MeLeu]-4-cyclosporin |
| 1339 | O | (CH₂)₃-N-(4-methylpiperazinyl) | [(R)-(3-(4-Methyl-N-Piperazinyl)propoxy)methyl-Sar]-3-[(γ-methoxy)-N-MeLeu]-4-cyclosporin |
| 1340 | O | (CH₂)₃-N-(4-ethylpiperazinyl) | [(R)-(3-(4-Ethyl-N-piperazinyl)propoxy)methyl-Sar]-3-[(γ-methoxy)-N-MeLeu]-4-cyclosporin |
| 1341 | O | (CH₂)₃-N-(4-propylpiperazinyl) | [(R)-(3-(4-Propyl-N-piperazinyl)propoxy)methyl-Sar]-3-[(γ-methoxy)-N-MeLeu]-4-cyclosporin |

TABLE 3-continued

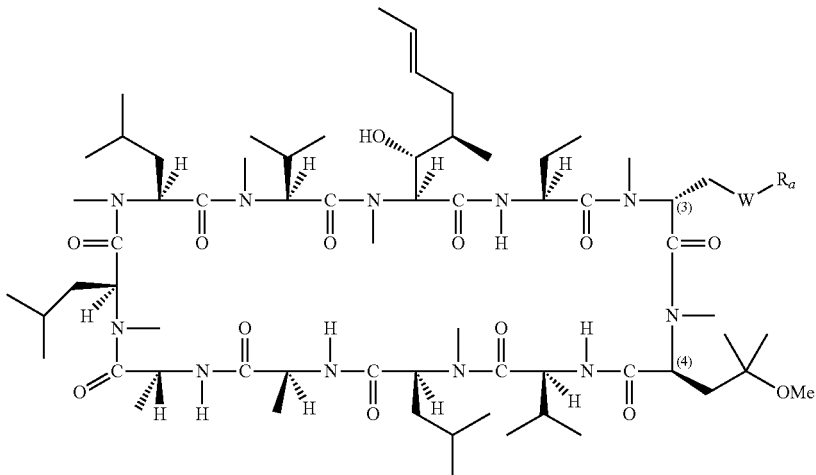

| Ex. No. | W | $R_a$ | Name |
|---|---|---|---|
| 1342 | O | 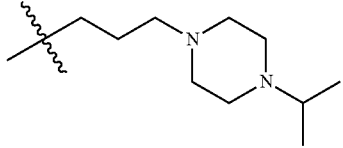 [SMILES: *CCCN1CCN(C(C)C)CC1] | [(R)-(3-(4-Isopropyl-N-piperazinyl)propoxy)methyl-Sar]-3-[(γ-methoxy)-N-MeLeu]-4-cyclosporin |
| 1343 | O | 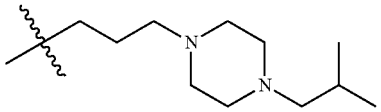 [SMILES: *CCCN1CCN(CC(C)C)CC1] | [(R)-(3-(4-Isobutyl-N-piperazinyl)propoxy)methyl-Sar]-3-[(γ-methoxy)-N-MeLeu]-4-cyclosporin |
| 1344 | O | 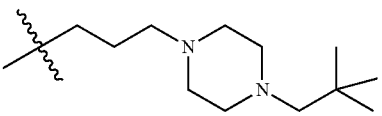 [SMILES: *CCCN1CCN(CC(C)(C)C)CC1] | [(R)-(3-(4-Neopentyl-N-piperazinyl)propoxy)methyl-Sar]-3-[(γ-methoxy)-N-MeLeu]-4-cyclosporin |
| 1345 | O | 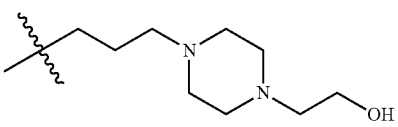 [SMILES: *CCCN1CCN(CCO)CC1] | [(R)-(3-(4-(2-Hydroxyethyl)-N-piperazinyl)propoxy)methyl-Sar]-3-[(γ-methoxy)-N-MeLeu]-4-cyclosporin |
| 1346 | O | 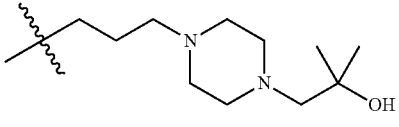 [SMILES: *CCCN1CCN(CC(C)(C)O)CC1] | [(R)-(3-(4-(2-Hydroxy-2,2-dimethylethyl)-N-piperazinyl)propoxy)methyl-Sar]-3-[(γ-methoxy)-N-MeLeu]-4-cyclosporin |
| 1347 | O | 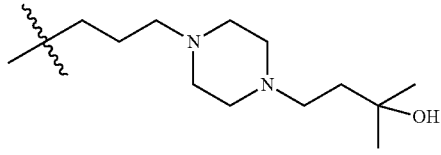 [SMILES: *CCCN1CCN(CCC(C)(C)O)CC1] | [(R)-(3-(4-(3-Hydroxy-3,3-dimethylpropyl)-N-piperazinyl)propoxy)methyl-Sar]-3-[(γ-methoxy)-N-MeLeu]-4-cyclosporin |
| 1348 | O | 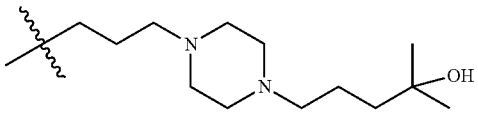 [SMILES: *CCCN1CCN(CCCC(C)(C)O)CC1] | [(R)-(3-(4-(4-Hydroxy-4,4-dimethylbutyl)-N-piperazinyl)propoxy)methyl-Sar]-3-[(γ-methoxy)-N-MeLeu]-4-cyclosporin |
| 1349 | O | 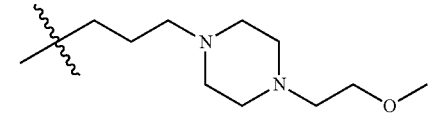 [SMILES: *CCCN1CCN(CCOC)CC1] | [(R)-(3-(4-(2-Methoxyethyl)-N-piperazinyl)propoxy)methyl-Sar]-3-[(γ-methoxy)-N-MeLeu]-4-cyclosporin |

TABLE 3-continued

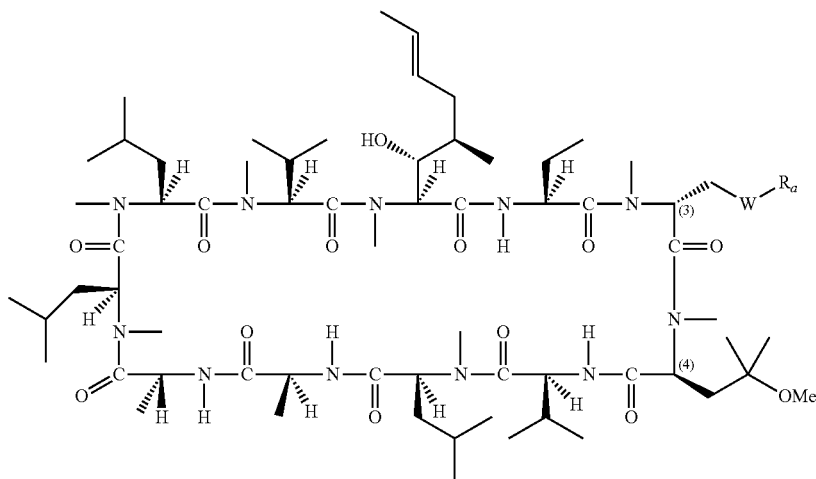

| Ex. No. | W | $R_a$ | Name |
|---|---|---|---|
| 1350 | O | (piperazinyl-CH₂C(CH₃)₂OMe chain) | [(R)-(3-(4-(2-Methoxy-2-methylpropyl)-N-piperazinyl)propoxy)methyl-Sar]-3-[(γ-methoxy)-N-MeLeu]-4-cyclosporin |
| 1351 | O | (piperazinyl-CH₂CH₂C(CH₃)₂OMe chain) | [(R)-(3-(4-(3-Methoxy-3-methylbutyl)-N-piperazinyl)propoxy)methyl-Sar]-3-[(γ-methoxy)-N-MeLeu]-4-cyclosporin |
| 1352 | O | (piperazinyl-(CH₂)₃C(CH₃)₂OMe chain) | [(R)-(3-(4-(4-Methoxy-4-methylpentyl)-N-piperazinyl)propoxy)methyl-Sar]-3-[(γ-methoxy)-N-MeLeu]-4-cyclosporin |
| 1353 | O | -CH₂CH₂CH₂C(O)OH | [(R)-3-(Carboxypropoxy)methyl-Sar]-3-[(γ-methoxy)-N-MeLeu]-4-cyclosporin |
| 1354 | O | -CH₂CH₂CH₂C(O)OK | [(R)-3-(Carboxypropoxy)methyl-Sar]-3-[(γ-methoxy)-N-MeLeu]-4-cyclosporin-potassium salt |
| 1355 | O | -CH₂CH₂CH₂C(O)ONa | [(R)-3-(Carboxypropoxy)methyl-Sar]-3-[(γ-methoxy)-N-MeLeu]-4-cyclosporin-sodium salt |
| 1356 | O | -CH₂CH₂CH₂C(O)OEt | [(R)-3-(Ethoxycarbonyl)propoxy)methyl-Sar]-3-[(γ-methoxy)-N-MeLeu]-4-cyclosporin |
| 1357 | O | -(CH₂)₄OH | [(R)-(4-Hydroxybutoxy)methyl-Sar]-3-[(γ-methoxy)-N-MeLeu]-4-cyclosporin |
| 1358 | O | -C(CH₃)₂CH₂CH₂CH₂OH | [(R)-((5-Hydroxy-2-methylpentan-2-yl)oxy)methyl-Sar]-3-[(γ-methoxy)-N-MeLeu]-4-cyclosporin |

TABLE 3-continued

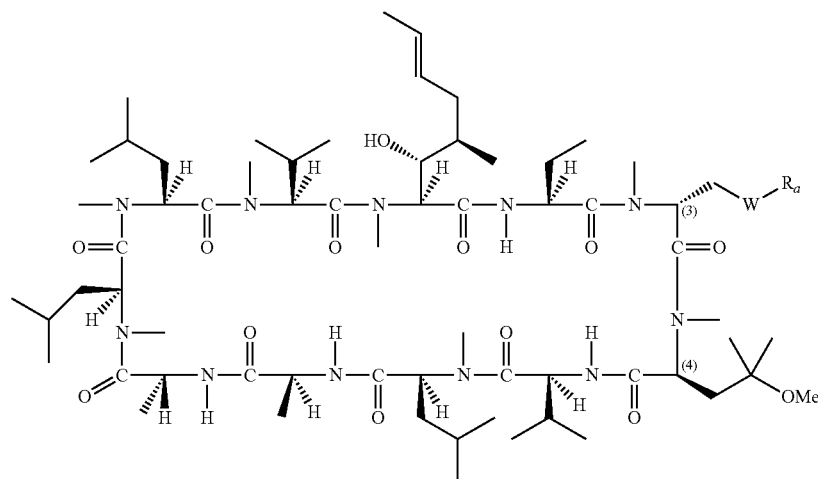

| Ex. No. | W | $R_a$ | Name |
|---|---|---|---|
| 1359 | O | (4-hydroxy-2,2-dimethylbutoxy) | [(R)-(4-Hydroxy-2,2-dimethylbutoxy)methyl-Sar]-3-[(γ-methoxy)-N-MeLeu]-4-cyclosporin |
| 1360 | O | (4-hydroxy-3,3-dimethylbutoxy) | [(R)-(4-Hydroxy-3,3-dimethylbutoxy)methyl-Sar]-3-[(γ-methoxy)-N-MeLeu]-4-cyclosporin |
| 1361 | O | (4-hydroxy-4-methylpentyloxy) | [(R)-(4-Hydroxy-4-methylpentyloxy)methyl-Sar]-3-[(γ-methoxy)-N-MeLeu]-4-cyclosporin |
| 1362 | O | (4-methoxybutoxy) | [(R)-(4-Methoxybutoxy)methyl-Sar]-3-[(γ-methoxy)-N-MeLeu]-4-cyclosporin |
| 1363 | O | (4-methoxy-4-methylpentyloxy) | [(R)-(4-Methoxy-4-methylpentyloxy)methyl-Sar]-3-[(γ-methoxy)-N-MeLeu]-4-cyclosporin |
| 1364 | O | (3-(1-hydroxycyclopropyl)propoxy) | [(R)-(3-(1-Hydroxycyclopropyl)propoxy)methyl-Sar]-3-[(γ-methoxy)-N-MeLeu]-4-cyclosporin |
| 1365 | O | (2-(1-(hydroxymethyl)cyclopropyl)ethoxy) | [(R)-((2-(1-(Hydroxymethyl)cyclopropyl)ethoxy)methyl-Sar]-3-[(γ-methoxy)-N-MeLeu]-4-cyclosporin |
| 1366 | O | ((1-(2-hydroxyethyl)cyclopropyl)methyl)oxy | [(R)-(((1-(2-Hydroxyethyl)cyclopropyl)methyl)oxy)methyl-Sar]-3-[(γ-methoxy)-N-MeLeu]-4-cyclosporin |
| 1367 | O | ((1-(3-hydroxypropyl)cyclopropyl)oxy) | [(R)-((1-(3-Hydroxypropyl)cyclopropyl)oxy)methyl-Sar]-3-[(γ-methoxy)-N-MeLeu]-4-cyclosporin |
| 1368 | O | (S)-4-hydroxyhexyloxy | [(R)-((S)-4-Hydroxyhexyloxy)methyl-Sar]-3-[(γ-methoxy)-N-MeLeu]-4-cyclosporin |

TABLE 3-continued

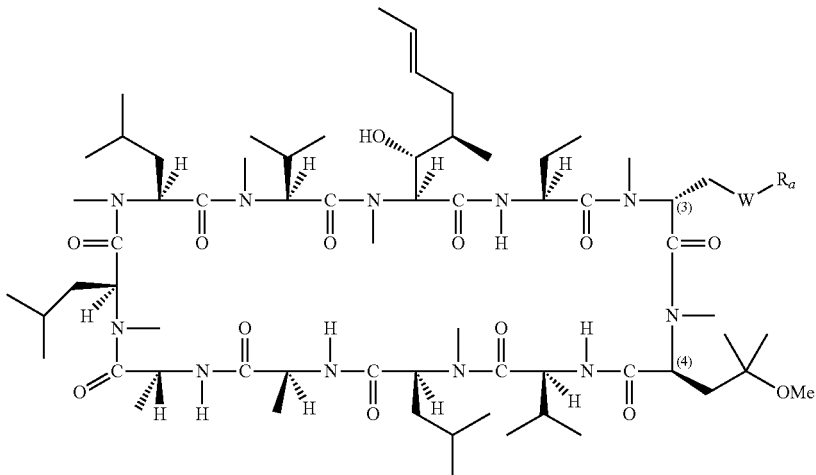

| Ex. No. | W | $R_a$ | Name |
|---|---|---|---|
| 1369 | O | 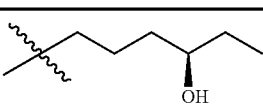 | [(R)-((R)-4-Hydroxyhexyloxy)methyl-Sar]-3-[(γ-methoxy)-N-MeLeu]-4-cyclosporin |
| 1370 | O | 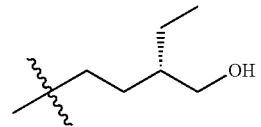 [SMILES: *CC[C@H](CC)CO] | [(R)-(((S)-3-(Hydroxymethyl)pentyl)oxy)methyl-Sar]-3-[(γ-methoxy)-N-MeLeu]-4-cyclosporin |
| 1371 | O | 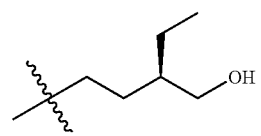 [SMILES: *CC[C@@H](CC)CO] | [(R)-(((R)-3-(Hydroxymethyl)pentyl)oxy)methyl-Sar]-3-[(γ-methoxy)-N-MeLeu]-4-cyclosporin |
| 1372 | O | 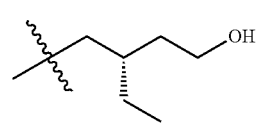 [SMILES: *C[C@@H](CC)CCO] | [(R)-((S)-2-Ethyl-4-hydroxybutoxy)methyl-Sar]-3-[(γ-methoxy)-N-MeLeu]-4-cyclosporin |
| 1373 | O | 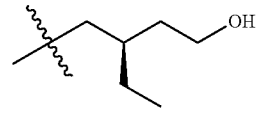 [SMILES: *C[C@H](CC)CCO] | [(R)-(((R)-2-Ethyl-4-hydroxybutoxy)methyl-Sar]-3-[(γ-methoxy)-N-MeLeu]-4-cyclosporin |
| 1374 | O | 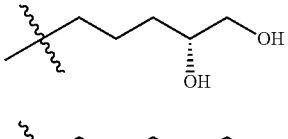 | [(R)-(((S)-4,5-Dihydroxy-4-pentyl)oxy)methyl-Sar]-3-[(γ-methoxy)-N-MeLeu]-4-cyclosporin |
| 1375 | O | 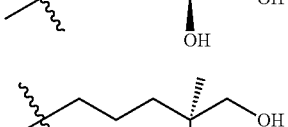 | [(R)-(((R)-4,5-Dihydroxy-4-pentyl)oxy)methyl-Sar]-3-[(γ-methoxy)-N-MeLeu]-4-cyclosporin |
| 1376 | O | 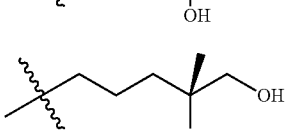 | [(R)-(((S)-4,5-Dihydroxy-4-methylpentyl)oxy)methyl-Sar]-3-[(γ-methoxy)-N-MeLeu]-4-cyclosporin |
| 1377 | O |  | [(R)-(((R)-4,5-Dihydroxy-4-methylpentyl)oxy)methyl-Sar]-3-[(γ-methoxy)-N-MeLeu]-4-cyclosporin |

TABLE 3-continued

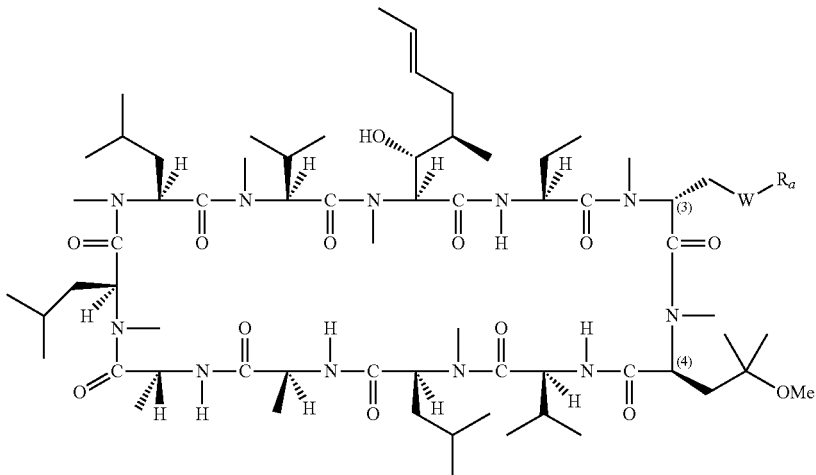

| Ex. No. | W | $R_a$ | Name |
|---|---|---|---|
| 1378 | O | (R)-4,5-dihydroxyhexyl chain | [(R)-(((R)-4,5-Dihydroxyhexyl)oxy)methyl-Sar]-3-[(γ-methoxy)-N-MeLeu]-4-cyclosporin |
| 1379 | O | (S)-4,6-dihydroxyhexyl chain | [(R)-(((S)-4,6-Dihydroxyhexyl)oxy)methyl-Sar]-3-[(γ-methoxy)-N-MeLeu]-4-cyclosporin |
| 1380 | O | (R)-5-hydroxy-3-(hydroxymethyl)pentyl | [(R)-(((R)-5-Hydroxy-3-(hydroxymethyl)pentyl)oxy)methyl-Sar]-3-[(γ-methoxy)-N-MeLeu]-4-cyclosporin |
| 1381 | O | (S)-5-hydroxy-3-(hydroxymethyl)pentyl | [(R)-(((S)-5-Hydroxy-3-(hydroxymethyl)pentyl)oxy)methyl-Sar]-3-[(γ-methoxy)-N-MeLeu]-4-cyclosporin |
| 1382 | O | 4-hydroxy-2-(2-hydroxyethyl)butoxy | [(R)-(4-Hydroxy-2-(2-hydroxyethyl)butoxy)methyl-Sar]-3-[(γ-methoxy)-N-MeLeu]-4-cyclosporin |
| 1383 | O | 4-(hydroxymethyl)pent-4-en-1-yl | [(R)-((4-(Hydroxymethyl)pent-4-en-1-yl)oxy)methyl-Sar]-3-[(γ-methoxy)-N-MeLeu]-4-cyclosporin |
| 1384 | O | 5-hydroxy-3-methylenepentyl | [(R)-((5-Hydroxy-3-methylenepentyl)oxy)methyl-Sar]-3-[(γ-methoxy)-N-MeLeu]-4-cyclosporin |
| 1385 | O | 5-hydroxy-2-methylenepentyl | [(R)-((5-Hydroxy-2-methylenepentyl)oxy)methyl-Sar]-3-[(γ-methoxy)-N-MeLeu]-4-cyclosporin |
| 1386 | O | 2-(2-(hydroxymethyl)oxiran-2-yl)ethoxy | [(R)-(2-(2-(Hydroxymethyl)oxiran-2-yl)ethoxy)methyl-Sar]-3-[(γ-methoxy)-N-MeLeu]-4-cyclosporin |

TABLE 3-continued

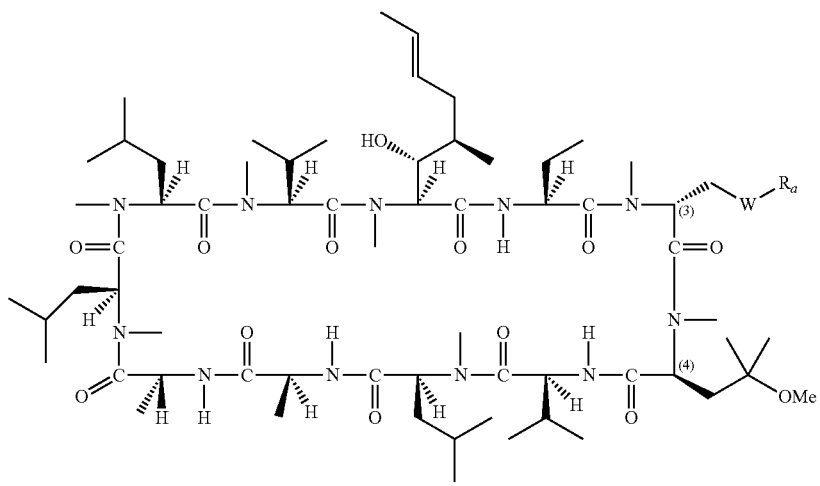

| Ex. No. | W | $R_a$ | Name |
|---|---|---|---|
| 1387 | O | (2-(2-hydroxyethyl)oxiran-2-yl)methoxy group | [(R)-((2-(2-Hydroxyethyl)oxiran-2-yl)methoxy)methyl-Sar]-3-[(γ-methoxy)-N-MeLeu]-4-cyclosporin |
| 1388 | O | (3-(3-hydroxyoxetan-3-yl)propoxy group | [(R)-(3-(3-Hydroxyoxetan-3-yl)propoxy)methyl-Sar]-3-[(γ-methoxy)-N-MeLeu]-4-cyclosporin |
| 1389 | O | (4,5-dihydroxy-4-(hydroxymethyl)pentyl)oxy group | [(R)-((4,5-Dihydroxy-4-(hydroxymethyl)pentyl)oxy)methyl-Sar]-3-[(γ-methoxy)-N-MeLeu]-4-cyclosporin |
| 1390 | O | (3-(2-(hydroxymethyl)oxiran-2-yl)propoxy group | [(R)-(3-(2-(Hydroxymethyl)oxiran-2-yl)propoxy)methyl-Sar]-3-[(γ-methoxy)-N-MeLeu]-4-cyclosporin |
| 1391 | O | (2-(2-(2-hydroxyethyl)oxiran-2-yl)ethoxy group | [(R)-(2-(2-(2-Hydroxyethyl)oxiran-2-yl)ethoxy)methyl-Sar]-3-[(γ-methoxy)-N-MeLeu]-4-cyclosporin |
| 1392 | O | (2-(3-hydroxypropyl)oxiran-2-yl)methoxy group | [(R)-((2-(3-Hydroxypropyl)oxiran-2-yl)methoxy)methyl-Sar]-3-[(γ-methoxy)-N-MeLeu]-4-cyclosporin |
| 1393 | O | (5-hydroxy-4-oxohexyl)oxy group | [(R)-((5-Hydroxy-4-oxohexyl)oxy)methyl-Sar]-3-[(γ-methoxy)-N-MeLeu]-4-cyclosporin |
| 1394 | O | (6-hydroxy-5-oxohexyl)oxy group | [(R)-((6-Hydroxy-5-oxohexyl)oxy)methyl-Sar]-3-[(γ-methoxy)-N-MeLeu]-4-cyclosporin |
| 1395 | O | (6-hydroxy-5-oxohexyl)oxy group | [(R)-((6-Hydroxy-5-oxohexyl)oxy)methyl-Sar]-3-[(γ-methoxy)-N-MeLeu]-4-cyclosporin |

TABLE 3-continued

| Ex. No. | W | $R_a$ | Name |
|---|---|---|---|
| 1396 | O | (pentyl chain with (R)-OH and CH₂-pyrrolidin-1-yl) | [(R)-(((R)-4-Hydroxy-5-(pyrrolidin-1-yl)pentyl)oxy)methyl-Sar]-3-[(γ-methoxy)-N-MeLeu]-4-cyclosporin |
| 1397 | O | (pentyl chain with (S)-OH and CH₂-pyrrolidin-1-yl) | [(R)-(((S)-4-Hydroxy-5-(pyrrolidin-1-yl)pentyl)oxy)methyl-Sar]-3-[(γ-methoxy)-N-MeLeu]-4-cyclosporin |
| 1398 | O | (hexyl chain with (R)-OH and CH₂CH₂-pyrrolidin-1-yl) | [(R)-(((R)-4-Hydroxy-6-(pyrrolidin-1-yl)hexyl)oxy)methyl-Sar]-3-[(γ-methoxy)-N-MeLeu]-4-cyclosporin |
| 1399 | O | (hexyl chain with (S)-OH and CH₂CH₂-pyrrolidin-1-yl) | [(R)-(((S)-4-Hydroxy-6-(piperidin-1-yl)hexyl)oxy)methyl-Sar]-3-[(γ-methoxy)-N-MeLeu]-4-cyclosporin |
| 1400 | O | (pentyl chain with (R)-OH and CH₂-imidazol-1-yl) | [(R)-(((R)-4-Hydroxy-5-(imidazol-1-yl)pentyl)oxy)methyl-Sar]-3-[(γ-methoxy)-N-MeLeu]-4-cyclosporin |
| 1401 | O | (pentyl chain with (S)-OH and CH₂-imidazol-1-yl) | [(R)-(((S)-4-Hydroxy-5-(imidazo-1-yl)pentyl)oxy)methyl-Sar]-3-[(γ-methoxy)-N-MeLeu]-4-cyclosporin |
| 1402 | O | (hexyl chain with (R)-OH and CH₂CH₂-imidazol-1-yl) | [(R)-(((R)-4-Hydroxy-6-(imidazo-1-yl)hexyl)oxy)methyl-Sar]-3-[(γ-methoxy)-N-MeLeu]-4-cyclosporin |
| 1403 | O | (hexyl chain with (S)-OH and CH₂CH₂-imidazol-1-yl) | [(R)-(((S)-4-Hydroxy-6-(imidazo-1-yl)hexyl)oxy)methyl-Sar]-3-[(γ-methoxy)-N-MeLeu]-4-cyclosporin |

TABLE 3-continued

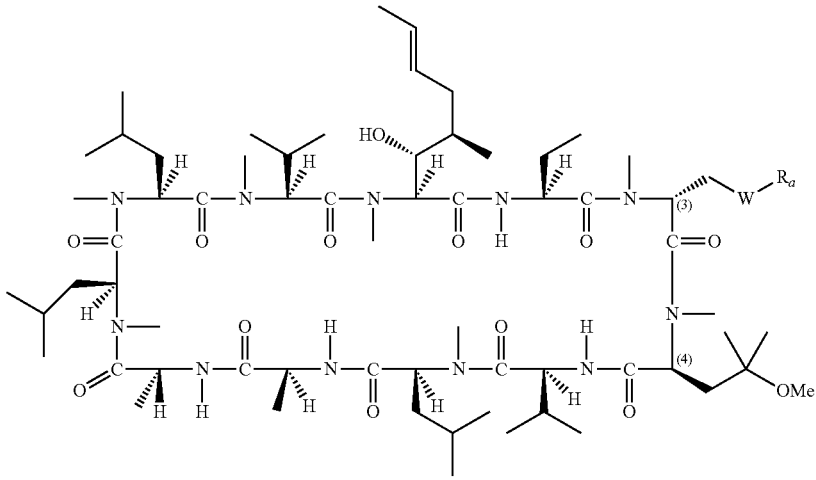

| Ex. No. | W | R_a | Name |
|---|---|---|---|
| 1404 | O | 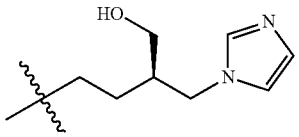 [SMILES: *CC[C@@H](CO)Cn1ccnc1] | [(R)-((R)-3-Hydroxymethyl-4-(imidazol-1-yl)butoxy)methyl-Sar]-3-[(γ-methoxy)-N-MeLeu]-4-cyclosporin |
| 1405 | O | 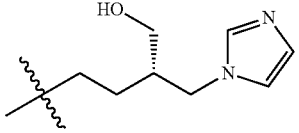 [SMILES: *CC[C@H](CO)Cn1ccnc1] | [(R)-((S)-3-Hydroxymethyl-4-(imidazo-1-yl)butoxy)methyl-Sar]-3-[(γ-methoxy)-N-MeLeu]-4-cyclosporin |
| 1406 | O | 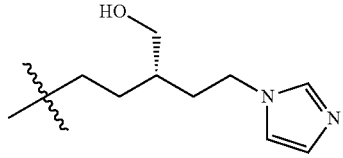 [SMILES: *CC[C@H](CO)CCn1ccnc1] | [(R)-(((R)-3-Hydroxymethyl-5-(imidazo-1-yl)pentyl)oxy)methyl-Sar]-3-[(γ-methoxy)-N-MeLeu]-4-cyclosporin |
| 1407 | O | 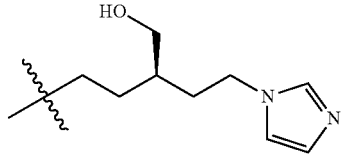 [SMILES: *CC[C@@H](CO)CCn1ccnc1] | [(R)-(((S)-3-Hydroxymethyl-5-(imidazo-1-yl)pentyl)oxy)methyl-Sar]-3-[(γ-methoxy)-N-MeLeu]-4-cyclosporin |
| 1408 | O | 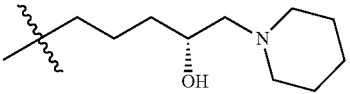 [SMILES: *CCC[C@@H](O)CN1CCCCC1] | [(R)-(((R)-4-Hydroxy-5-(piperidin-1-yl)pentyl)oxy)methyl-Sar]-3-[(γ-methoxy)-N-MeLeu]-4-cyclosporin |
| 1409 | O | 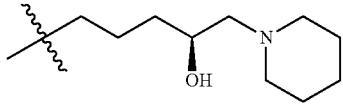 [SMILES: *CCC[C@H](O)CN1CCCCC1] | [(R)-(((S)-4-Hydroxy-5-(piperidin-1-yl)pentyl)oxy)methyl-Sar]-3-[(γ-methoxy)-N-MeLeu]-4-cyclosporin |
| 1410 | O | 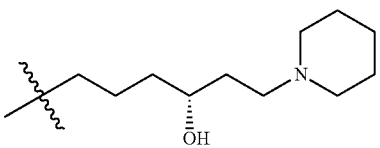 [SMILES: *CCC[C@@H](O)CCN1CCCCC1] | [(R)-(((R)-4-Hydroxy-5-(piperidin-1-yl)hexyl)oxy)methyl-Sar]-3-[(γ-methoxy)-N-MeLeu]-4-cyclosporin |

TABLE 3-continued

| Ex. No. | W | $R_a$ | Name |
|---|---|---|---|
| 1411 | O | (branched chain with OH and piperidine) | [(R)-(((S)-4-Hydroxy-5-(piperidin-1-yl)hexyl)oxy)methyl-Sar]-3-[(γ-methoxy)-N-MeLeu]-4-cyclosporin |
| 1412 | O | (branched chain with OH and morpholine, R) | [(R)-(((R)-4-Hydroxy-6-morpholinohexyl)oxy)methyl-Sar]-3-[(γ-methoxy)-N-MeLeu]-4-cyclosporin |
| 1413 | O | (branched chain with OH and morpholine, S) | [(R)-(((S)-4-Hydroxy-6-morpholinohexyl)oxy)methyl-Sar]-3-[(γ-methoxy)-N-MeLeu]-4-cyclosporin |
| 1414 | O | (branched chain with hydroxymethyl and morpholine, R) | [(R)-((R)-2-(Hydroxymethyl)-4-morpholinobutoxy)methyl-Sar]-3-[(γ-methoxy)-N-MeLeu]-4-cyclosporin |
| 1415 | O | (branched chain with hydroxymethyl and morpholine, S) | [(R)-((S)-2-(Hydroxymethyl)-4-morpholinobutoxy)methyl-Sar]-3-[(γ-methoxy)-N-MeLeu]-4-cyclosporin |
| 1416 | O | (branched chain with OH and morpholinoethyl) | [(R)-((S)-4-Hydroxy-2-(2-morpholinoethyl)butoxy)methyl-Sar]-3-[(γ-methoxy)-N-MeLeu]-4-cyclosporin |

TABLE 3-continued

| Ex. No. | W | R$_a$ | Name |
|---|---|---|---|
| 1417 | O | (3-(2-morpholinoethyl), CH2CH2OH branch) | [(R)-((R)-4-Hydroxy-2-(2-morpholinoethyl)butoxy)methyl-Sar]-3-[(γ-methoxy)-N-MeLeu]-4-cyclosporin |
| 1418 | O | (S)-4-OH-6-(4-methylpiperazin-1-yl)hexyl | [(R)-(((S)-4-Hydroxy-6-(4-methylpiperazin-1-yl)hexyl)oxy)methyl-Sar]-3-[(γ-methoxy)-N-MeLeu]-4-cyclosporin |
| 1419 | O | (R)-4-OH-6-(4-methylpiperazin-1-yl)hexyl | [(R)-(((R)-4-Hydroxy-6-(4-methylpiperazin-1-yl)hexyl)oxy)methyl-Sar]-3-[(γ-methoxy)-N-MeLeu]-4-cyclosporin |
| 1420 | O | (S)-4-OH-6-(4-ethylpiperazin-1-yl)hexyl | [(R)-(((S)-4-Hydroxy-6-(4-ethylpiperazin-1-yl)hexyl)oxy)methyl-Sar]-3-[(γ-methoxy)-N-MeLeu]-4-cyclosporin |
| 1421 | O | (R)-4-OH-6-(4-ethylpiperazin-1-yl)hexyl | [(R)-(((R)-4-Hydroxy-6-(4-ethylpiperazin-1-yl)hexyl)oxy)methyl-Sar]-3-[(γ-methoxy)-N-MeLeu]-4-cyclosporin |
| 1422 | O | (R)-4-OH-6-(4-isopropylpiperazin-1-yl)hexyl | [(R)-(((R)-4-Hydroxy-6-(4-isopropylpiperazin-1-yl)hexyl)oxy)methyl-Sar]-3-[(γ-methoxy)-N-MeLeu]-4-cyclosporin |

TABLE 3-continued

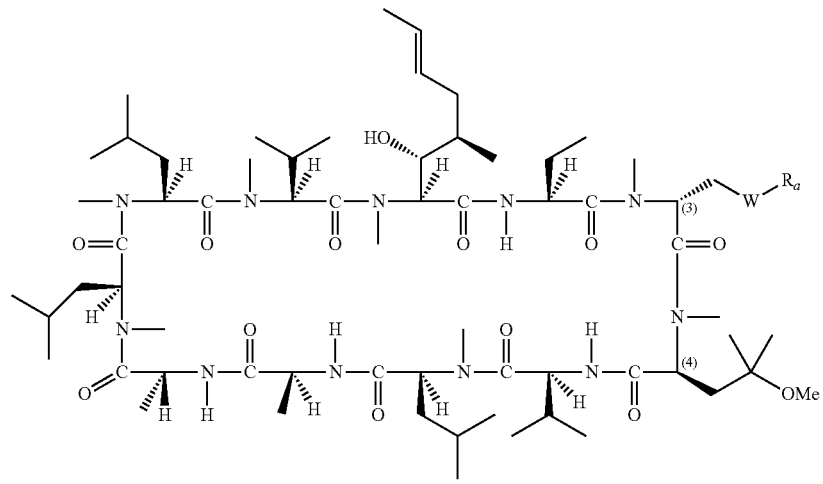

| Ex. No. | W | $R_a$ | Name |
|---|---|---|---|
| 1423 | O | | [(R)-(((S)-4-Hydroxy-6-(4-isopropylpiperazin-1-yl)hexyl)oxy)methyl-Sar]-3-[(γ-methoxy)-N-MeLeu]-4-cyclosporin |
| 1424 | O | | [(R)-(((S)-3-Hydroxymethyl-5-(4-methylpiperazin-1-yl)pentyl)oxy)methyl-Sar]-3-[(γ-methoxy)-N-MeLeu]-4-cyclosporin |
| 1425 | O | | [(R)-(((R)-3-Hydroxymethyl-5-(4-methylpiperazin-1-yl)pentyl)oxy)methyl-Sar]-3-[(γ-methoxy)-N-MeLeu]-4-cyclosporin |
| 1426 | O | | [(R)-(((S)-3-Hydroxymethyl-5-(4-ethylpiperazin-1-yl)pentyl)oxy)methyl-Sar]-3-[(γ-methoxy)-N-MeLeu]-4-cyclosporin |
| 1427 | O | | [(R)-(((R)-3-Hydroxymethyl-5-(4-ethylpiperazin-1-yl)pentyl)oxy)methyl-Sar]-3-[(γ-methoxy)-N-MeLeu]-4-cyclosporin |

TABLE 3-continued

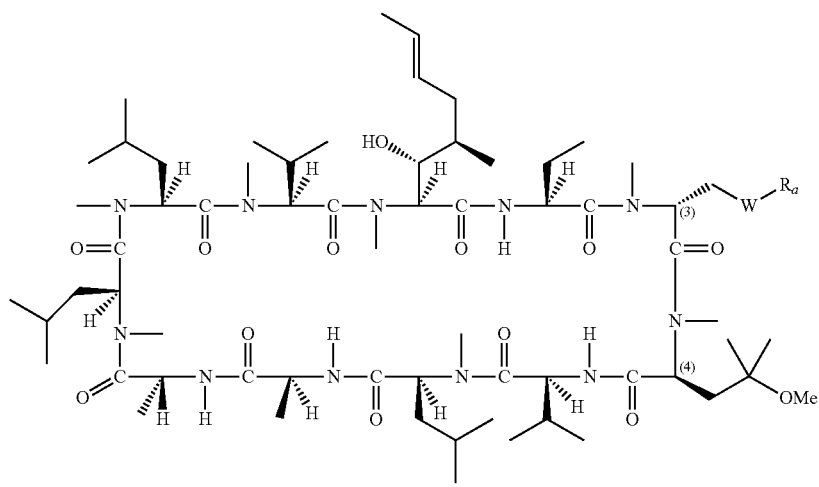

| Ex. No. | W | $R_a$ | Name |
|---|---|---|---|
| 1428 | O | | [(R)-(((R)-3-Hydroxymethyl-5-(4-isopropylpiperazin-1-yl)pentyl)oxy)methyl-Sar]-3-[(γ-methoxy)-N-MeLeu]-4-cyclosporin |
| 1429 | O | | [(R)-(((S)-3-Hydroxymethyl-5-(4-isopropylpiperazin-1-yl)pentyl)oxy)methyl-Sar]-3-[(γ-methoxy)-N-MeLeu]-4-cyclosporin |
| 1430 | O | | [(R)-(((R)-2-(Hydroxymethyl)-4-morpholinobutyl)oxy)methyl-Sar]-3-[(γ-methoxy)-N-MeLeu]-4-cyclosporin |
| 1431 | O | | [(R)-((S)-2-(Hydroxymethyl)-4-morpholinobutoxy)methyl-Sar]-3-[(γ-methoxy)-N-MeLeu]-4-cyclosporin |
| 1432 | O | | [(R)-((S)-4-Hydroxy-2-(2-morpholinoethyl)butoxy)methyl-Sar]-3-[(γ-methoxy)-N-MeLeu]-4-cyclosporin |

TABLE 3-continued

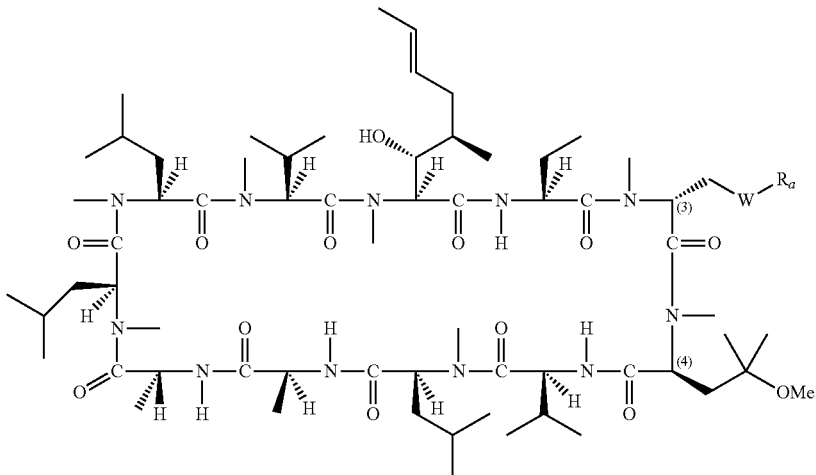

| Ex. No. | W | R$_a$ | Name |
|---|---|---|---|
| 1433 | O | 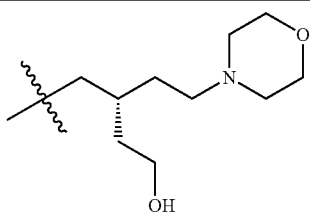 | [(R)-((R)-4-Hydroxy-2-(2-morpholinoethyl)butoxy)methyl-Sar]-3-[(γ-methoxy)-N-MeLeu]-4-cyclosporin |
| 1434 | O | 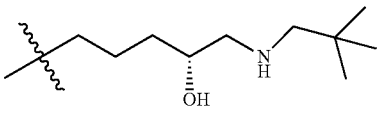 [SMILES: *CCC[C@@H](O)CNCC(C)(C)C] | [(R)-(((R)-4-Hydroxy-5-(neopentylamino)pentyl)oxy)methyl-Sar]-3-[(γ-methoxy)-N-MeLeu]-4-cyclosporin |
| 1435 | O | 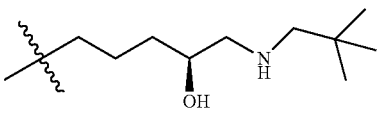 [SMILES: *CCC[C@H](O)CNCC(C)(C)C] | [(R)-(((S)-4-Hydroxy-5-(neopentylamino)pentyl)oxy)methyl-Sar]-3-[(γ-methoxy)-N-MeLeu]-4-cyclosporin |
| 1436 | O | 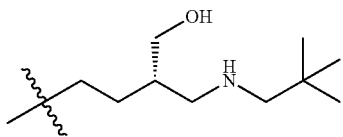 [SMILES: *CC[C@H](CO)CNCC(C)(C)C] | [(R)-(((S)-4-Hydroxy-3-((neopentylamino)methyl)butyl)oxy)methyl-Sar]-3-[(γ-methoxy)-N-MeLeu]-4-cyclosporin |
| 1437 | O | 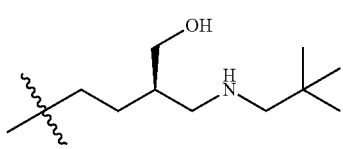 [SMILES: *CC[C@@H](CO)CNCC(C)(C)C] | [(R)-((R)-4-Hydroxy-3-((neopentylamino)methyl)butoxy)methyl-Sar]-3-[(γ-methoxy)-N-MeLeu]-4-cyclosporin |
| 1438 | O | 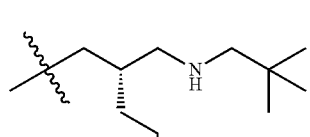 | [(R)-((S)-4-Hydroxy-2-((neopentylamino)methyl)butoxy)methyl-Sar]-3-[(γ-methoxy)-N-MeLeu]-4-cyclosporin |
| 1439 | O | 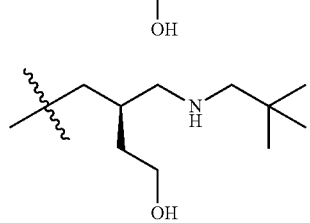 | [(R)-((R)-4-Hydroxy-2-((neopentylamino)methyl)butoxy)methyl-Sar]-3-[(γ-methoxy)-N-MeLeu]-4-cyclosporin |

TABLE 3-continued

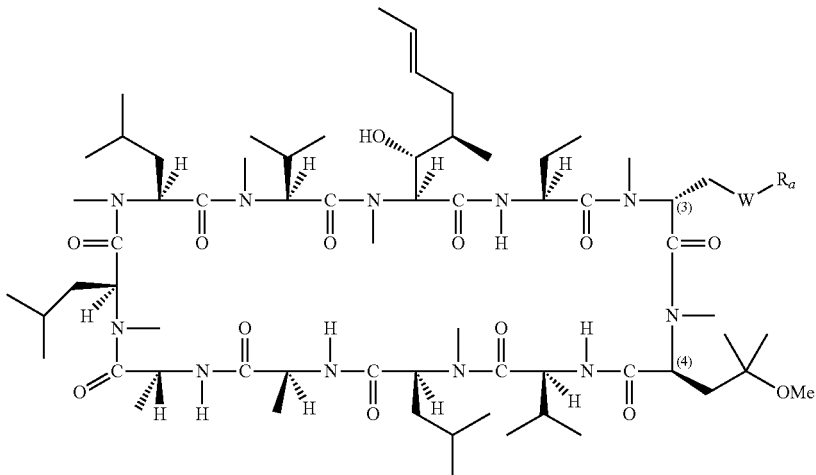

| Ex. No. | W | $R_a$ | Name |
|---|---|---|---|
| 1440 | O | 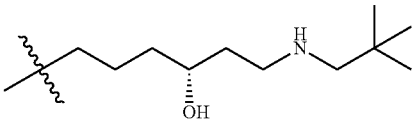 [SMILES: *CCC[C@@H](O)CCNCC(C)(C)C] | [(R)-(((R)-4-Hydroxy-6-(neopentylamino)hexyl)oxy)methyl-Sar]-3-[(γ-methoxy)-N-MeLeu]-4-cyclosporin |
| 1441 | O | 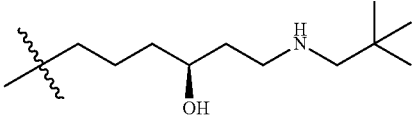 [SMILES: *CCC[C@H](O)CCNCC(C)(C)C] | [(R)-(((S)-4-Hydroxy-6-(neopentylamino)hexyl)oxy)methyl-Sar]-3-[(γ-methoxy)-N-MeLeu]-4-cyclosporin |
| 1442 | O | 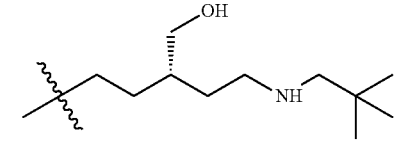 [SMILES: *CC[C@H](CO)CCNCC(C)(C)C] | [(R)-(((R)-3-(Hydroxymethyl)-5-(neopentylamino)pentyl)oxy)methyl-Sar]-3-[(γ-methoxy)-N-MeLeu]-4-cyclosporin |
| 1443 | O | 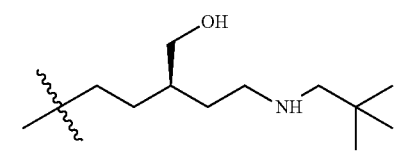 [SMILES: *CC[C@@H](CO)CCNCC(C)(C)C] | [(R)-(((S)-3-(Hydroxymethyl)-5-(neopentylamino)pentyl)oxy)methyl-Sar]-3-[(γ-methoxy)-N-MeLeu]-4-cyclosporin |
| 1444 | O | 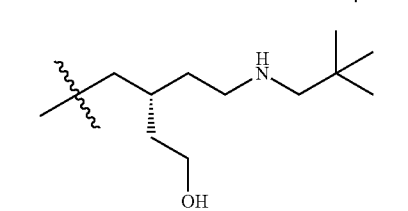 | [(R)-((R)-4-Hydroxy-2-(2-(neopentylamino)ethyl)butoxy)methyl-Sar]-3-[(γ-methoxy)-N-MeLeu]-4-cyclosporin |
| 1445 | O | 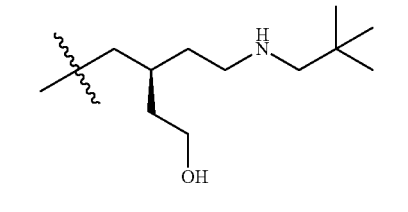 [SMILES: *C[C@H](CCO)CCNCC(C)(C)C] | [(R)-((S)-4-Hydroxy-2-(2-(neopentylamino)ethyl)butoxy)methyl-Sar]-3-[(γ-methoxy)-N-MeLeu]-4-cyclosporin |
| 1446 | O | 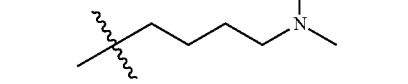 | [(R)-(4-(N,N-Dimethylamino)butoxy)methyl-Sar]-3-[(γ-methoxy)-N-MeLeu]-4-cyclosporin |

TABLE 3-continued

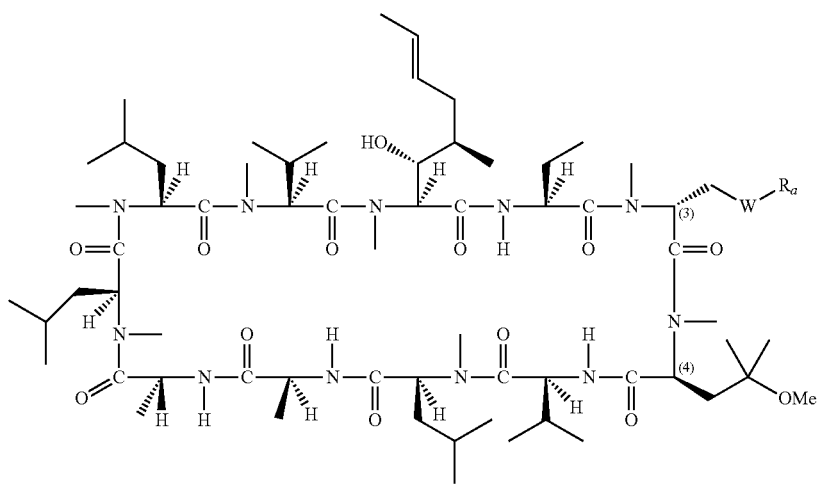

| Ex. No. | W | $R_a$ | Name |
|---|---|---|---|
| 1447 | O | (CH2)4-N(Et)2 | [(R)-(4-(N,N-Diethylamino)butoxy)methyl-Sar]-3-[(γ-methoxy)-N-MeLeu]-4-cyclosporin |
| 1448 | O | (CH2)4-NH-iPr | [(R)-(4-(N-Isopropylamino)butoxy)methyl-Sar]-3-[(γ-methoxy)-N-MeLeu]-4-cyclosporin |
| 1449 | O | (CH2)4-N(Me)(iPr) | [(R)-(4-(N-Isopropyl-N-methylamino)butoxy)methyl-Sar]-3-[(γ-methoxy)-N-MeLeu]-4-cyclosporin |
| 1450 | O | (CH2)4-N(Et)(iPr) | [(R)-(4-(N-Ethyl-N-isopropylamino)butoxy)methyl-Sar]-3-[(γ-methoxy)-N-MeLeu]-4-cyclosporin |
| 1451 | O | (CH2)4-NH-iBu | [(R)-(4-(N-Isobutylamino)butoxy)methyl-Sar]-3-[(γ-methoxy)-N-MeLeu]-4-cyclosporin |
| 1452 | O | (CH2)4-N(Me)(iBu) | [(R)-(4-(N-Isobutyl-N-methylamino)butoxy)methyl-Sar]-3-[(γ-methoxy)-N-MeLeu]-4-cyclosporin |
| 1453 | O | (CH2)4-N(Et)(iBu) | [(R)-(4-(N-ethyl-N-isobutylamino)butoxy)methyl-Sar]-3-[(γ-methoxy)-N-MeLeu]-4-cyclosporin |

TABLE 3-continued

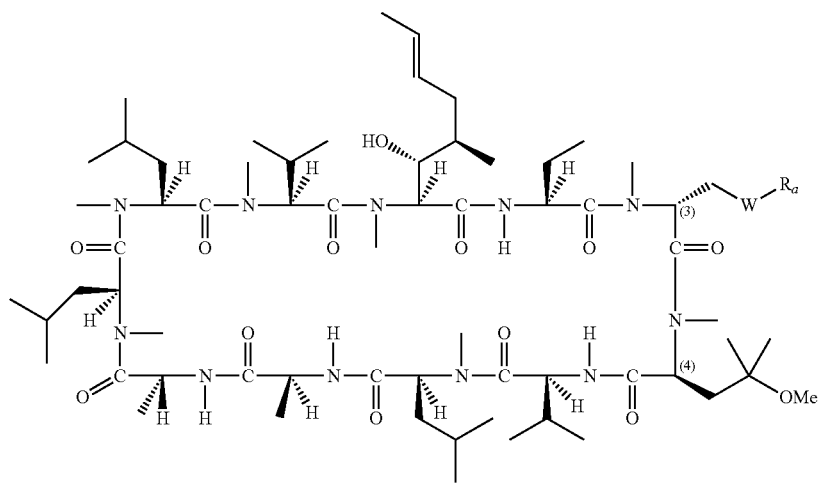

| Ex. No. | W | $R_a$ | Name |
|---|---|---|---|
| 1454 | O | (isobutyl-N-isobutyl chain) | [(R)-(4-(N,N-Diisobutylamino)butoxy)methyl-Sar]-3-[(γ-methoxy)-N-MeLeu]-4-cyclosporin |
| 1455 | O | (neopentylamino chain) | [(R)-(4-(N-Neopentylamino)butoxy)methyl-Sar]-3-[(γ-methoxy)-N-MeLeu]-4-cyclosporin |
| 1456 | O | (N-methyl-N-neopentylamino chain) | [(R)-(4-(N-Methyl-N-neopentylamino)butoxy)methyl-Sar]-3-[(γ-methoxy)-N-MeLeu]-4-cyclosporin |
| 1457 | O | (N-ethyl-N-neopentylamino chain) | [(R)-(4-(N-Ethyl-N-neopentylamino)butoxy)methyl-Sar]-3-[(γ-methoxy)-N-MeLeu]-4-cyclosporin |
| 1458 | O | (pyrrolidinyl chain) | [(R)-(4-(N-Pyrrolidinyl)butoxy)methyl-Sar]-3-[(γ-methoxy)-N-MeLeu]-4-cyclosporin |
| 1459 | O | (thiazolidinyl chain) | [(R)-(4-(N-Thiazolidinyl)butoxy)methyl-Sar]-3-[(γ-methoxy)-N-MeLeu]-4-cyclosporin |
| 1460 | O | (oxazolidinyl chain) | [(R)-(4-(N-Oxazolidinyl)butoxy)methyl-Sar]-3-[(γ-methoxy)-N-MeLeu]-4-cyclosporin |

TABLE 3-continued

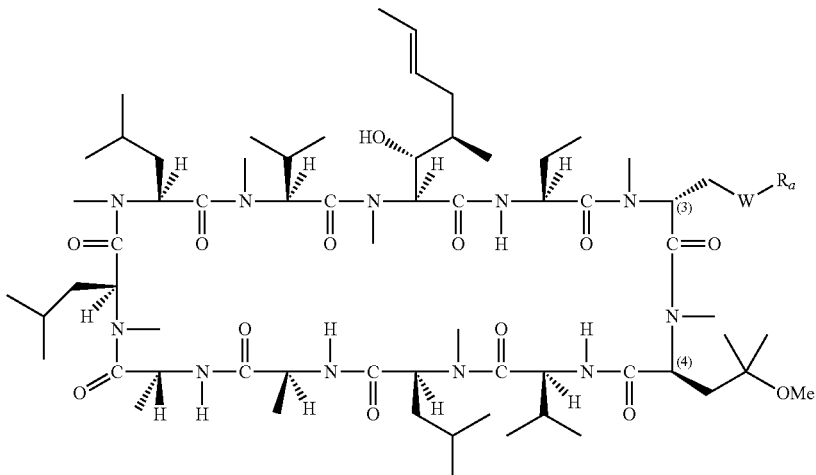

| Ex. No. | W | R_a | Name |
|---|---|---|---|
| 1461 | O | 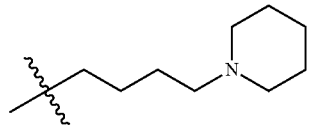 | [(R)-(4-(N-Piperidinyl)butoxy)methyl-Sar]-3-[(γ-methoxy)-N-MeLeu]-4-cyclosporin |
| 1462 | O | 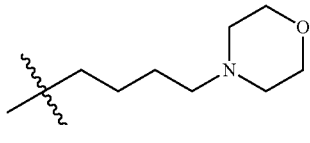 [SMILES: *CCCCN1CCOCC1] | [(R)-(4-(N-Morpholino)butoxy)methyl-Sar]-3-[(γ-methoxy)-N-MeLeu]-4-cyclosporin |
| 1463 | O | 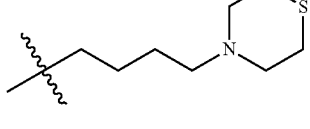 | [(R)-(4-(N-Thiomorpholino)butoxy)methyl-Sar]-3-[(γ-methoxy)-N-MeLeu]-4-cyclosporin |
| 1464 | O | 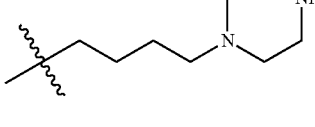 | [(R)-(4-(N-Piperazinyl)butoxy)methyl-Sar]-3-[(γ-methoxy)-N-MeLeu]-4-cyclosporin |
| 1465 | O | 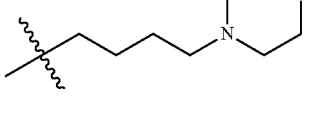 | [(R)-(4-(4-Methyl-N-piperazinyl)butoxy)methyl-Sar]-3-[(γ-methoxy)-N-MeLeu]-4-cyclosporin |
| 1466 | O | 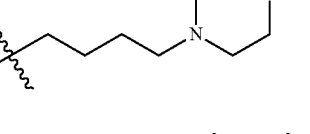 | [(R)-(4-(4-Ethyl-N-piperazinyl)butoxy)methyl-Sar]-3-[(γ-methoxy)-N-MeLeu]-4-cyclosporin |
| 1467 | O | 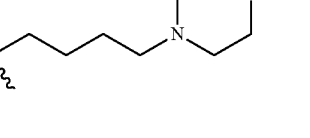 | [(R)-(4-(4-Propyl-N-piperazinyl)butoxy)methyl-Sar]-3-[(γ-methoxy)-N-MeLeu]-4-cyclosporin |

TABLE 3-continued

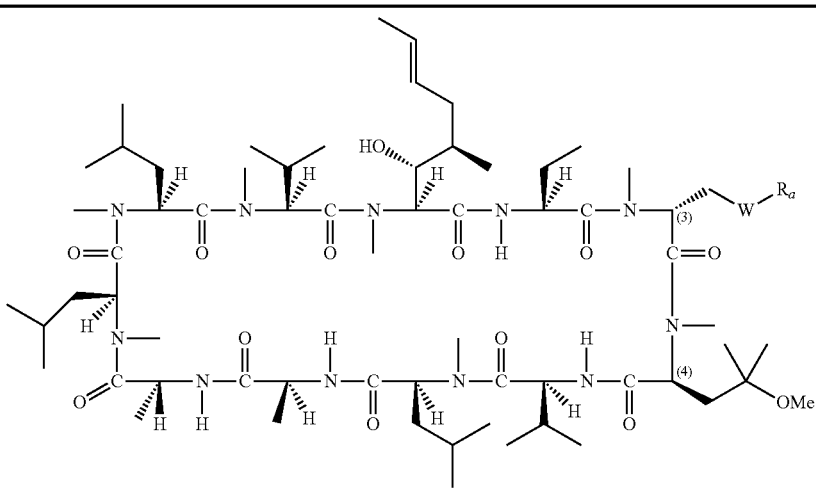

| Ex. No. | W | $R_a$ | Name |
|---|---|---|---|
| 1468 | O | 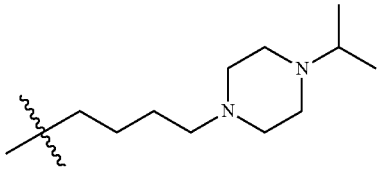 [SMILES: *CCCCN1CCN(C(C)C)CC1] | [(R)-(4-(4-Isopropyl-N-piperazinyl)butoxy)methyl-Sar]-3-[(γ-methoxy)-N-MeLeu]-4-cyclosporin |
| 1469 | O | 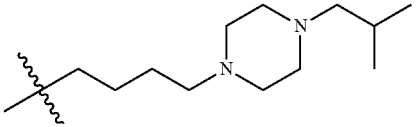 [SMILES: *CCCCN1CCN(CC(C)C)CC1] | [(R)-(4-(4-Isobutyl-N-piperazinyl)butoxy)methyl-Sar]-3-[(γ-methoxy)-N-MeLeu]-4-cyclosporin |
| 1470 | O | 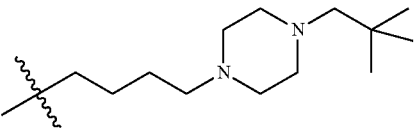 [SMILES: *CCCCN1CCN(CC(C)(C)C)CC1] | [(R)-(4-(4-Neopentyl-N-piperazinyl)butoxy)methyl-Sar]-3-[(γ-methoxy)-N-MeLeu]-4-cyclosporin |
| 1471 | O | 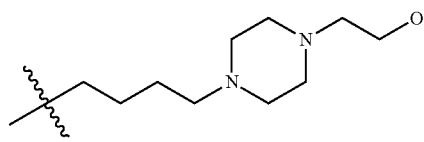 | [(R)-(4-(4-(2-Hydroxyethyl)-N-piperazinyl)butoxy)methyl-Sar]-3-[(γ-methoxy)-N-MeLeu]-4-cyclosporin |
| 1472 | O | 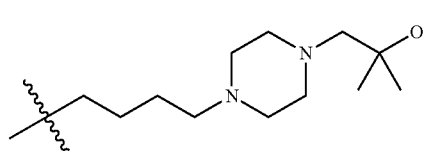 | [(R)-(4-(4-(2-Hydroxy-2-methylpropyl)-N-piperazinyl)butoxy)methyl-Sar]-3-[(γ-methoxy)-N-MeLeu]-4-cyclosporin |
| 1473 | O | 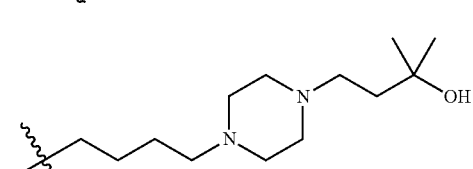 | [(R)-(4-(4-(3-Hyroxy-3-methylbutyl)-N-piperazinyl)butoxy)methyl-Sar]-3-[(γ-methoxy)-N-MeLeu]-4-cyclosporin |
| 1474 | O | 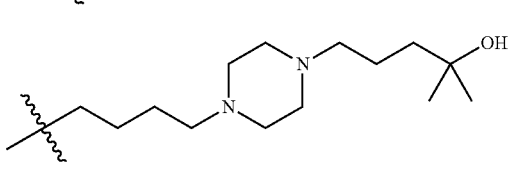 | [(R)-(4-(4-(4-Hydroxy-4-methylpentyl)-N-piperazinyl)butoxy)methyl-Sar]-3-[(γ-methoxy)-N-MeLeu]-4-cyclosporin |

TABLE 3-continued

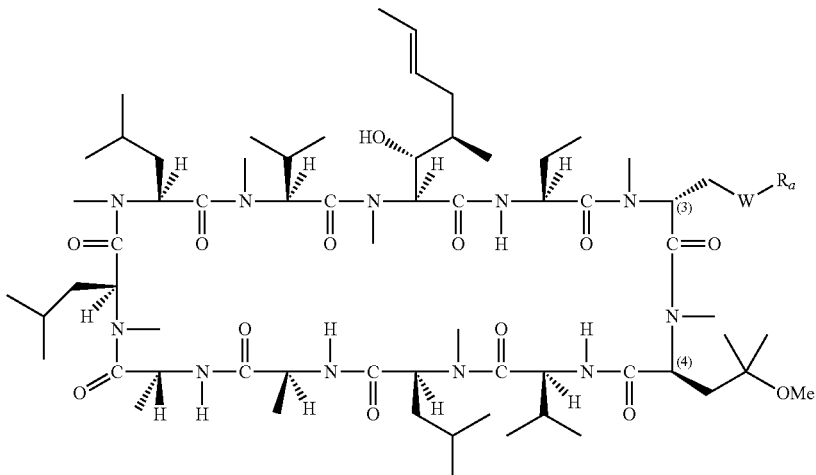

| Ex. No. | W | R$_a$ | Name |
|---|---|---|---|
| 1475 | O | 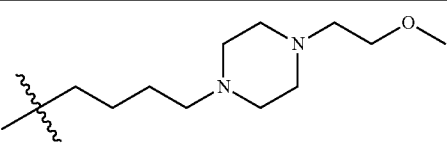 | [(R)-(4-(4-(2-Methoxyethyl)-N-piperazinyl)butoxy)methyl-Sar]-3-[(γ-methoxy)-N-MeLeu]-4-cyclosporin |
| 1476 | O | 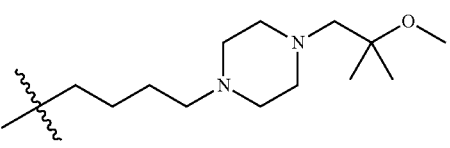 [SMILES: *CCCCN1CCN(CC(C)(C)OC)CC1] | [(R)-(4-(4-(2-Methoxy-2-methylpropyl)-N-piperazinyl)butoxy)methyl-Sar]-3-[(γ-methoxy)-N-MeLeu]-4-cyclosporin |
| 1477 | O | 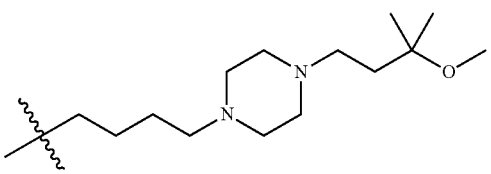 [SMILES: *CCCCN1CCN(CCC(C)(C)OC)CC1] | [(R)-(4-(4-(3-Methoxy-3-methylbutyl)-N-piperazinyl)butoxy)methyl-Sar]-3-[(γ-methoxy)-N-MeLeu]-4-cyclosporin |
| 1478 | O | 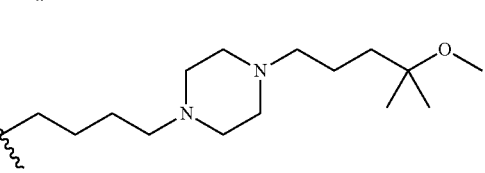 | [(R)-(4-(4-(4-Methoxy-4-methylpentyl)-N-piperazinyl)butoxy)methyl-Sar]-3-[(γ-methoxy)-N-MeLeu]-4-cyclosporin |
| 1479 | O | 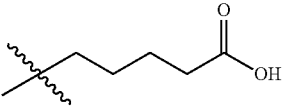 [SMILES: *CCCCC(=O)O] | [(R)-(4-Carboxybutoxy)methyl-Sar]-3-[(γ-methoxy)-N-MeLeu]-4-cyclosporin |
| 1480 | O | 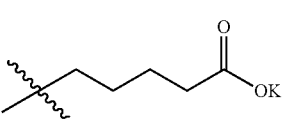 | [(R)-(4-Carboxybutoxy)methyl-Sar]-3-[(γ-methoxy)-N-MeLeu]-4-cyclosporin-potassium salt |
| 1481 | O | 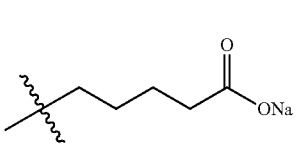 | [(R)-(4-Carboxybutoxy)methyl-Sar]-3-[(γ-methoxy)-N-MeLeu]-4-cyclosporin-sodium salt |

TABLE 3-continued

| Ex. No. | W | $R_a$ | Name |
|---|---|---|---|
| 1482 | O | (ethyl ester, 5-carbon chain with C(=O)OEt) | [(R)-(4-(Ethoxycarbonyl)butoxy)methyl-Sar]-3-[(γ-methoxy)-N-MeLeu]-4-cyclosporin |
| 1483 | O | (5-carbon chain with COOH) | [(R)-(5-Carboxypentyloxy)methyl-Sar]-3-[(γ-methoxy)-N-MeLeu]-4-cyclosporin |
| 1484 | O | (5-carbon chain with COONa) | [(R)-(5-Carboxypentyloxy)methyl-Sar]-3-[(γ-methoxy)-N-MeLeu]-4-cyclosporin-sodium salt |
| 1485 | O | (longer chain with ethyl ester) | [(R)-5-((Ethoxycarbonyl)pentyloxy)methyl-Sar]-3-[(γ-methoxy)-N-MeLeu]-4-cyclosporin |
| 1486 | O | (pentyloxy with OH) | [(R)-(5-Hydroxypentyloxy)methyl-Sar]-3-[(γ-methoxy)-N-MeLeu]-4-cyclosporin |
| 1487 | O | (pentyloxy with OMe) | [(R)-(5-Methoxypentyloxy)methyl-Sar]-3-[(γ-methoxy)-N-MeLeu]-4-cyclosporin |
| 1488 | O | (branched chain with COOH) | [(R)-(4-Carboxypentyloxy)methyl-Sar]-3-[(γ-methoxy)-N-MeLeu]-4-cyclosporin |
| 1489 | O | (branched chain with COOK) | [(R)-(4-Carboxypentyloxy)methyl-Sar]-3-[(γ-methoxy)-N-MeLeu]-4-cyclosporin-potassium salt |
| 1490 | O | (branched chain with COONa) | [(R)-(4-Carboxypentyloxy)methyl-Sar]-3-[(γ-methoxy)-N-MeLeu]-4-cyclosporin-sodium salt |
| 1491 | O | (branched chain with ethyl ester) | [(R)-(4-Ethoxycarbonylpentyloxy)methyl-Sar]-3-[(γ-methoxy)-N-MeLeu]-4-cyclosporin |

TABLE 3-continued

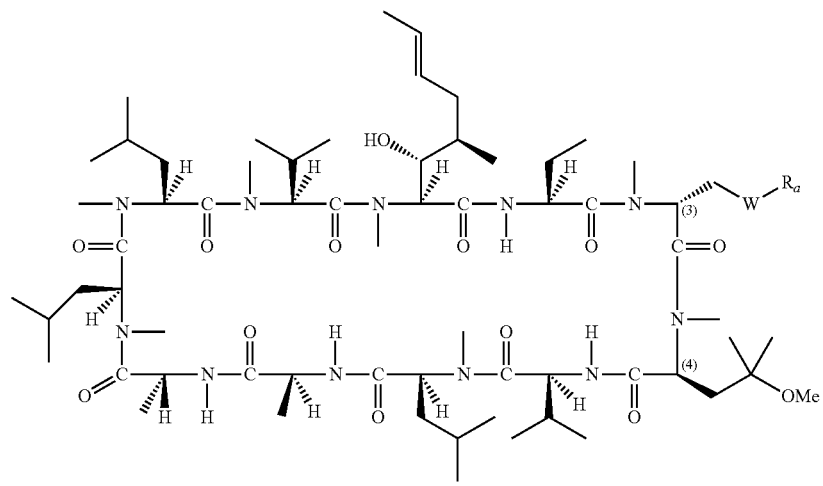

| Ex. No. | W | $R_a$ | Name |
|---|---|---|---|
| 1492 | O | | [(R)-((4,4'-Dicarboxy)butoxy)methyl-Sar]-3-[(γ-methoxy)-N-MeLeu]-4-cyclosporin |
| 1493 | O | | [(R)-((4,4'-Dicarboxy)butoxy)methyl-Sar]-3-[(γ-methoxy)-N-MeLeu]-4-cyclosporin-dipotassium salt |
| 1494 | O | | [(R)-((R)-3-Hydroxymethyl-4-ethoxycarbonybutoxy)methyl-Sar]-3-[(γ-methoxy)-N-MeLeu]-4-cyclosporin |
| 1495 | O | | [(R)-((S)-3-Hydroxymethyl-4-ethoxycarbonybutoxy)methyl-Sar]-3-[(γ-methoxy)-N-MeLeu]-4-cyclosporin |
| 1496 | O | | [(R)-(6-Hydroxyhexyloxy)methyl-Sar]-3-[(γ-methoxy)-N-MeLeu]-4-cyclosporin |
| 1497 | O | | [(R)-(6-Methoxyhexyloxy)methyl-Sar]-3-[(γ-methoxy)-N-MeLeu]-4-cyclosporin |
| 1498 | O | | [(R)-[(N-(2-Aminoethyl)carbamoyl)methoxy]methyl-Sar]-3-[(γ-methoxy)-N-MeLeu]-4-cyclosporin |
| 1499 | O | | [(R)-[(N-(2-(Neopentylamino)ethyl)carbamoyl)methoxy]methyl-Sar]-3-[(γ-methoxy)-N-MeLeu]-4-cyclosporin |

TABLE 3-continued

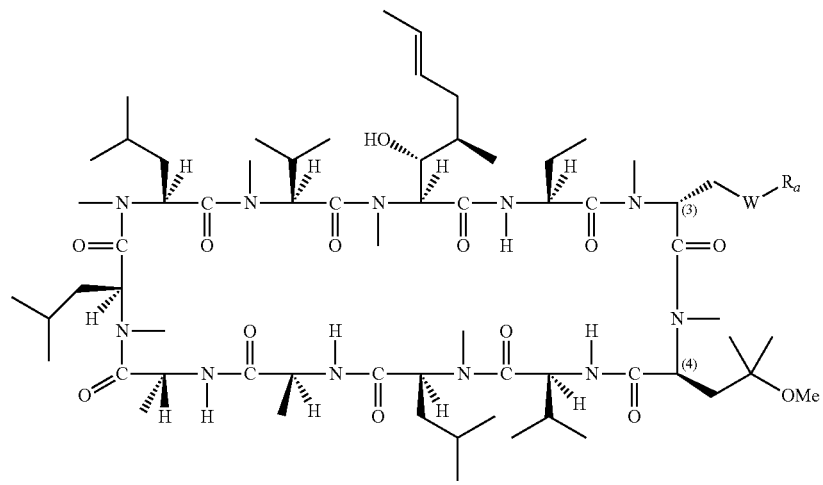

| Ex. No. | W | $R_a$ | Name |
|---|---|---|---|
| 1500 | O | ~~~C(CH3)2-CH2-C(=O)-NH-(CH2)3-NH2 | [(R)-[(N-(3-Aminopropyl)carbamoyl)methoxy]methyl-Sar]-3-[(γ-methoxy)-N-MeLeu]-4-cyclosporin |
| 1501 | O | ~~~C(CH3)2-CH2-C(=O)-NH-(CH2)3-NH-CH2-C(CH3)3 | [(R)-[(N-(3-(Neopentylamino)propyl)carbamoyl)methoxy]methyl-Sar]-3-[(γ-methoxy)-N-MeLeu]-4-cyclosporin |
| 1502 | O | ~~~C(CH3)2-CH2-C(=O)-NH-(CH2)4-NH2 | [(R)-[(N-(4-Aminobutyl)carbamoyl)methoxy]methyl-Sar]-3-[(γ-methoxy)-N-MeLeu]-4-cyclosporin |
| 1503 | O | ~~~C(CH3)2-CH2-C(=O)-NH-(CH2)4-NH-CH2-C(CH3)3 | [(R)-[(N-(4-(Neopentylamino)butyl)carbamoyl)methoxy]methyl-Sar]-3-[(γ-methoxy)-N-MeLeu]-4-cyclosporin |
| 1504 | O | ~~~C(CH3)2-CH2-C(=O)-NH-(CH2)5-NH2 | [(R)-[(N-(5-Aminopentyl)carbamoyl)methoxy]methyl-Sar]-3-[(γ-methoxy)-N-MeLeu]-4-cyclosporin |
| 1505 | O | ~~~C(CH3)2-CH2-C(=O)-NH-(CH2)5-NH-CH2-C(CH3)3 | [(R)-[(N-(5-(Neopentylamino)pentyl)carbamoyl)methoxy]methyl-Sar]-3-[(γ-methoxy)-N-MeLeu]-4-cyclosporin |
| 1506 | O | ~~~C(CH3)2-CH2-C(=O)-NH-(CH2)6-NH2 | [(R)-[(N-(6-Aminohexyl)carbamoyl)methoxy]methyl-Sar]-3-[(γ-methoxy)-N-MeLeu]-4-cyclosporin |
| 1507 | O | ~~~C(CH3)2-CH2-C(=O)-NH-(CH2)6-NH-CH2-C(CH3)3 | [(R)-[(N-(6-(Neopentylamino)hexyl)carbamoyl)methoxy]methyl-Sar]-3-[(γ-methoxy)-N-MeLeu]-4-cyclosporin |
| 1508 | O | ~~~C(CH3)2-CH2-C(=O)-NH-(D-Glu)6Gly-OH | [(R)-[([HO-Gly-(D-Glu)6]carbamoyl)methoxy]methyl-Sar]-3-[(γ-methoxy)-N-MeLeu]-4-cyclosporin |

TABLE 3-continued

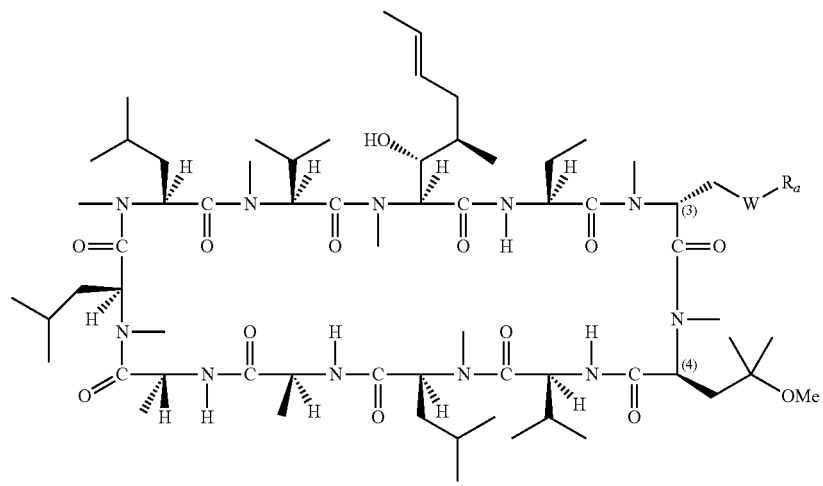

| Ex. No. | W | $R_a$ | Name |
|---|---|---|---|
| 1509 | O | ![structure] -C(=O)-NH-(D-Glu)₆Gly-OH (propyl chain) | [(R)-[([HO-Gly-(D-Glu)6]carbamoyl)ethoxy]methyl-Sar]-3-[(γ-methoxy)-N-MeLeu]-4-cyclosporin |
| 1510 | O | butyl-C(=O)-NH-(D-Glu)₆Gly-OH | [(R)-[([HO-Gly-(D-Glu)6]carbamoyl)propoxy]methyl-Sar]-3-[(γ-methoxy)-N-MeLeu]-4-cyclosporin |
| 1511 | O | -CH₂CH₂-O-CH₂-C(=O)-NH-(D-Glu)₆Gly-OH | [(R)-((2-[([HO-Gly-(D-Glu)6]carbamoyl)methoxy]ethoxy)methyl-Sar]-3-[(γ-methoxy)-N-MeLeu]-4-cyclosporin |
| 1512 | O | -(CH₂)₃-O-CH₂-C(=O)-NH-(D-Glu)₆Gly-OH | [(R)-((3-[([HO-Gly-(D-Glu)6]carbamoyl)methoxy]propoxy)methyl-Sar]-3-[(γ-methoxy)-N-MeLeu]-4-cyclosporin |
| 1513 | O | -(CH₂)₄-O-CH₂-C(=O)-NH-(D-Glu)₆Gly-OH | [(R)-((4-[([HO-Gly-(D-Glu)6]carbamoyl)methoxy]butoxy)methyl-Sar]-3-[(γ-methoxy)-N-MeLeu]-4-cyclosporin |
| 1514 | O | -(CH₂)₅-O-CH₂-C(=O)-NH-(D-Glu)₆Gly-OH | [(R)-((5-[([HO-Gly-(D-Glu)6]carbamoyl)methoxy]pentyloxy)methyl-Sar]-3-[(γ-methoxy)-N-MeLeu]-4-cyclosporin |
| 1515 | O | -(CH₂)₆-O-CH₂-C(=O)-NH-(D-Glu)₆Gly-OH | [(R)-((6-[([HO-Gly-(D-Glu)6]carbamoyl)methoxy]hexyloxy)methyl-Sar]-3-[(γ-methoxy)-N-MeLeu]-4-cyclosporin |
| 1516 | O | butyl chain | [(R)-(4-Butoxy)methyl-Sar]-3-[(γ-methoxy)-N-MeLeu]-4-cyclosporin |
| 1517 | O | pentyl chain | [(R)-(5-Pentyloxy)methyl-Sar]-3-[(γ-methoxy)-N-MeLeu]-4-cyclosporin |

TABLE 3-continued

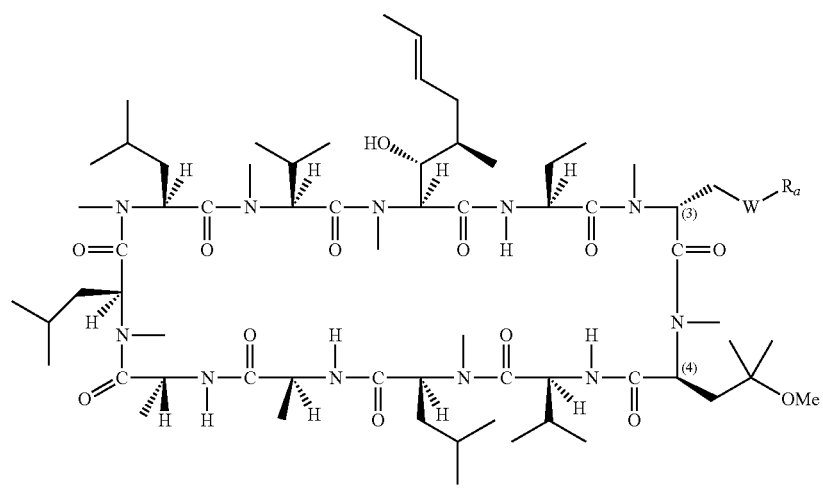

| Ex. No. | W | $R_a$ | Name |
|---|---|---|---|
| 1518 | O | hexyl chain | [(R)-(6-Hexyloxy)methyl-Sar]-3-[(γ-methoxy)-N-MeLeu]-4-cyclosporin |
| 1519 | O | heptyl chain | [(R)-(7-Heptyloxy)methyl-Sar]-3-[(γ-methoxy)-N-MeLeu]-4-cyclosporin |
| 1520 | $CH_2$ | —$NO_2$ | [(R)-2-Nitroethyl-Sar]-3-[(γ-methoxy)-N-MeLeu]-4-cyclosporin |
| 1521 | $CH_2$ | —$NH_2$ | [(R)-2-Aminoethyl-Sar]-3-[(γ-methoxy)-N-MeLeu]-4-cyclosporin |
| 1522 | $CH_2$ | —$N(CH_3)_2$ | [(R)-2-(N,N-Dimethylamino)ethyl-Sar]-3-[(γ-methoxy)-N-MeLeu]-4-cyclosporin |
| 1523 | $CH_2$ | —$N(CH_2CH_3)_2$ | [(R)-2-(N,N-Diethylamino)ethyl-Sar]-3-[(γ-methoxy)-N-MeLeu]-4-cyclosporin |
| 1524 | $CH_2$ | —$CH_2N(CH_3)_2$ | [(R)-2-(N,N-Dimethylamino)propyl-Sar]-3-[(γ-methoxy)-N-MeLeu]-4-cyclosporin |
| 1525 | $CH_2$ | —$(COOEt)_2$ | [(R)-2,2-Di(ethoxycarbonyl)ethyl)-Sar]-3-[(γ-methoxy)-N-MeLeu]-4-cyclosporin |
| 1526 | $CH_2$ | —$(CH_2OH)_2$ | [(R)-2,2-Di(hydroxylmethyl)ethyl)-Sar]-3-[(γ-methoxy)-N-MeLeu]-4-cyclosporin |

TABLE 4

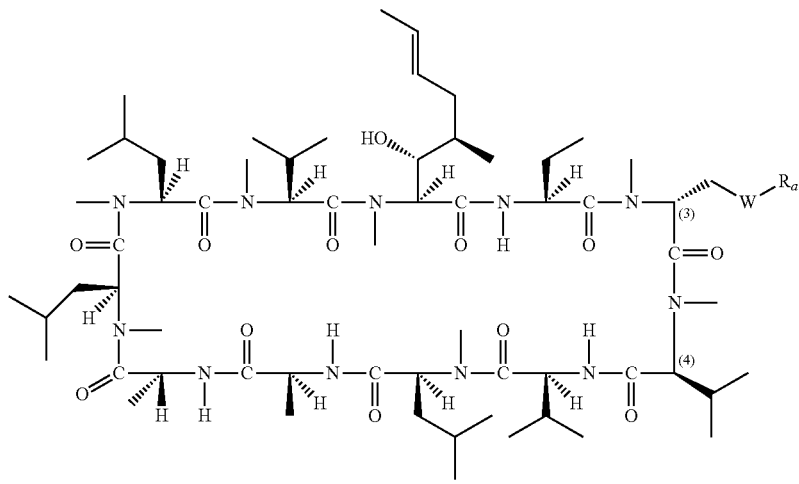

| Ex. No. | W | $R_a$ | Name |
|---|---|---|---|
| 1527 | S | 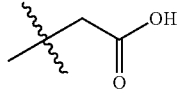 | [(S)-(Carboxymethylthio)methyl-Sar]-3-[N-MeVal]-4-cyclosporin |
| 1528 | S | 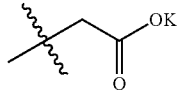 | [(S)-(Carboxymethylthio)methyl-Sar]-3-[N-MeVal]-4-cyclosporin-potassium salt |
| 1529 | S | 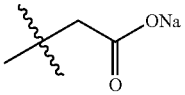 | [(S)-(Carboxymethylthio)methyl-Sar]-3-[N-MeVal]-4-cyclosporin-sodium salt |
| 1530 | S | 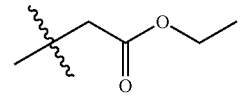 [SMILES: *CC(=O)OCC] | [(S)-(Ethoxycarbonylmethylthio)methyl-Sar]-3-[N-MeVal]-4-cyclosporin |
| 1531 | S | 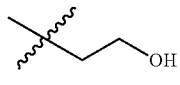 [SMILES: *CCO] | [(S)-(2-Hydroxyethylthio)methyl-Sar]-3-[N-MeVal]-4-cyclosporin |
| 1532 | S |  | [(S)-(2-Hydroxy-2,2-dimethylethylthio)methyl-Sar]-3-[N-MeVal]-4-cyclosporin |
| 1533 | S | 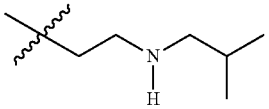 [SMILES: *CCNCC(C)C] | [(S)-(2-(N-Isobutylamino)ethylthio)methyl-Sar]-3-[N-MeVal]-4-cyclosporin |
| 1534 | S | 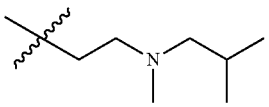 [SMILES: *CCN(C)CC(C)C] | [(S)-(2-(N-Isobutyl-N-methylamino)ethylthio)methyl-Sar]-3-[N-MeVal]-4-cyclosporin |
| 1535 | S | 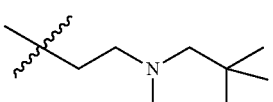 | [(S)-(2-(N-Neopentylamino)ethylthio)methyl-Sar]-3-[N-MeVal]-4-cyclosporin |
| 1536 | S | 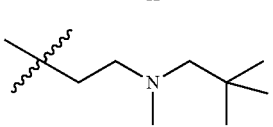 [SMILES: *CCN(C)CC(C)(C)C] | [(S)-(2-(N-Methyl-N-neopentylamino)ethylthio)methyl-Sar]-3-[N-MeVal]-4-cyclosporin |

TABLE 4-continued

| Ex. No. | W | $R_a$ | Name |
|---|---|---|---|
| 1537 | S | (CH2)2-N-pyrrolidinyl | [(S)-(2-(N-Pyrrolidinyl)ethylthio)methyl-Sar]-3-[N-MeVal]-4-cyclosporin |
| 1538 | S | (CH2)2-N-piperidinyl | [(S)-(2-(N-Piperidinyl)ethylthio)methyl-Sar]-3-[N-MeVal]-4-cyclosporin |
| 1539 | S | (CH2)2-N-morpholino | [(S)-(2-(N-Morpholino)ethylthio)methyl-Sar]-3-[N-MeVal]-4-cyclosporin |
| 1540 | S | (CH2)2-N-thiomorpholino | [(S)-(2-(N-Thiomorpholino)ethylthio)methyl-Sar]-3-[N-MeVal]-4-cyclosporin |
| 1541 | S | (CH2)3-OH | [(S)-(3-Hydroxypropylthio)methyl-Sar]-3-[N-MeVal]-4-cyclosporin |
| 1542 | S | CH2C(CH3)2OH | [(S)-(3-Hydroxy-3-methylbutylthio)methyl-Sar]-3-[N-MeVal]-4-cyclosporin |
| 1543 | S | (CH2)3-N(CH3)2 | [(S)-(3-(N,N-Dimethylamino)propylthio)methyl-Sar]-3-[N-MeVal]-4-cyclosporin |
| 1544 | S | (CH2)3-N(CH2CH3)2 | [(S)-(3-(N,N-Diethylamino)propylthio)methyl-Sar]-3-[N-MeVal]-4-cyclosporin |

TABLE 4-continued

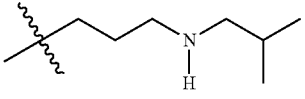 [SMILES: *CCCNCC(C)C]

| Ex. No. | W | $R_a$ | Name |
|---|---|---|---|
| 1545 | S |  | [(S)-(3-(N-Isobutylamino)propylthio)methyl-Sar]-3-[N-MeVal]-4-cyclosporin |
| 1546 | S | 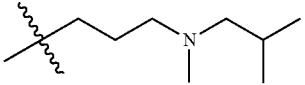 [SMILES: *CCCN(C)CC(C)C] | [(S)-(3-(N-Isobutyl-N-methylamino)propylthio)methyl-Sar]-3-[N-MeVal]-4-cyclosporin |
| 1547 | S |  | [(S)-(3-(N,N-Diisobutylamino)propylthio)methyl-Sar]-3-[N-MeVal]-4-cyclosporin |
| 1548 | S | 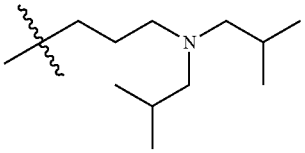 [SMILES: *CCCN(CC(C)C)CC(C)C] | [(S)-(3-(N-Neopentylamino)propylthio)methyl-Sar]-3-[N-MeVal]-4-cyclosporin |
| 1549 | S |  | [(S)-(3-(N-Methyl-N-neopentylamino)propylthio)methyl-Sar]-3-[N-MeVal]-4-cyclosporin |
| 1550 | S | 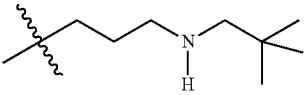 [SMILES: *CCCNCC(C)(C)C] | [(S)-(3-(N-Pyrrolidinyl)propylthio)methyl-Sar]-3-[N-MeVal]-4-cyclosporin |
| 1551 | S |  | [(S)-(3-(N-Piperidinyl)propylthio)methyl-Sar]-3-[N-MeVal]-4-cyclosporin |
| 1552 | S | 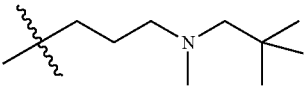 [SMILES: *CCCN(C)CC(C)(C)C] | [(S)-(3-(N-Morpholino)propylthio)methyl-Sar]-3-[N-MeVal]-4-cyclosporin |
| 1553 | S |  | [(S)-(3-(N-Thiomorpholino)propylthio)methyl-Sar]-3-[N-MeVal]-4-cyclosporin |

TABLE 4-continued

| Ex. No. | W | $R_a$ | Name |
|---|---|---|---|
| 1554 | S | (4-hydroxybutyl) | [(S)-(4-Hydroxybutylthio)methyl-Sar]-3-[N-MeVal]-4-cyclosporin |
| 1555 | S | (4-hydroxy-4-methylpentyl) | [(S)-(4-Hydroxy-4-methylpentylthio)methyl-Sar]-3-[N-MeVal]-4-cyclosporin |
| 1556 | S | (4-(N,N-dimethylamino)butyl) | [(S)-(4-(N,N-Dimethylamino)butylthio)methyl-Sar]-3-[N-MeVal]-4-cyclosporin |
| 1557 | S | (4-(N,N-diethylamino)butyl) | [(S)-(4-(N,N-Diethylamino)butylthio)methyl-Sar]-3-[N-MeVal]-4-cyclosporin |
| 1558 | S | (4-(N-isobutylamino)butyl) | [(S)-(4-(N-Isobutylamino)butylthio)methyl-Sar]-3-[N-MeVal]-4-cyclosporin |
| 1559 | S | (4-(N-isobutyl-N-methylamino)butyl) | [(S)-(4-(N-Isobutyl-N-methylamino)butylthio)methyl-Sar]-3-[N-MeVal]-4-cyclosporin |
| 1560 | S | (4-(N,N-diisobutylamino)butyl) | [(S)-(4-(N,N-Diisobutylamino)butylthio)methyl-Sar]-3-[N-MeVal]-4-cyclosporin |
| 1561 | S | (4-(N-neopentylamino)butyl) | [(S)-(4-(N-Neopentylamino)butylthio)methyl-Sar]-3-[N-MeVal]-4-cyclosporin |

TABLE 4-continued

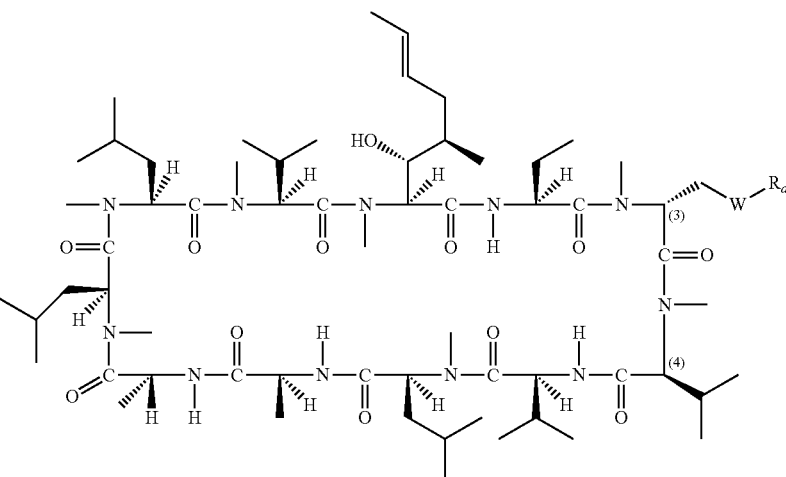

| Ex. No. | W | $R_a$ | Name |
|---|---|---|---|
| 1562 | S | (CH₂)₄-N(Me)-neopentyl | [(S)-(4-(N-Methyl-N-Neopentylamino)butylthio)methyl-Sar]-3-[N-MeVal]-4-cyclosporin |
| 1563 | S | (CH₂)₄-pyrrolidinyl | [(S)-(4-(N-Pyrrolidinyl)butylthio)methyl-Sar]-3-[N-MeVal]-4-cyclosporin |
| 1564 | S | (CH₂)₄-piperidinyl | [(S)-(4-(N-Piperidinyl)butylthio)methyl-Sar]-3-[N-MeVal]-4-cyclosporin |
| 1565 | S | (CH₂)₄-morpholino | [(S)-(4-(N-Morpholino)butylthio)methyl-Sar]-3-[N-MeVal]-4-cyclosporin |
| 1566 | S | (CH₂)₄-thiomorpholino | [(S)-(4-(N-Thiomorpholino)butylthio)methyl-Sar]-3-[N-MeVal]-4-cyclosporin |
| 1567 | S | (CH₂)₃-COOH | [(S)-(3-Carboxypropylthio)methyl-Sar]-3-[N-MeVal]-4-cyclosporin |
| 1568 | S | (CH₂)₃-COOK | [(S)-(3-Carboxypropylthio)methyl-Sar]-3-[N-MeVal]-4-cyclosporin-potassium salt |
| 1569 | S | (CH₂)₃-COONa | [(S)-(3-Carboxypropylthio)methyl-Sar]-3-[N-MeVal]-4-cyclosporin-sodium salt |

TABLE 4-continued

| Ex. No. | W | $R_a$ | Name |
|---|---|---|---|
| 1570 | S | (ethyl ester, 3-carbon chain) | [(S)-(3-Ethoxycarbonylpropylthio)methyl-Sar]-3-[N-MeVal]-4-cyclosporin |
| 1571 | O | CH₂COOH | [(R)-(Carboxymethoxy)methyl-Sar]-3-[N-MeVal]-4-cyclosporin |
| 1572 | O | CH₂COOK | [(R)-(Carboxymethoxy)methyl-Sar]-3-[N-MeVal]-4-cyclosporin-potassium salt |
| 1573 | O | CH₂COONa | [(R)-(Carboxymethoxy)methyl-Sar]-3-[N-MeVal]-4-cyclosporin-sodium salt |
| 1574 | O | CH₂COOEt | [(R)-((Ethoxycarbonyl)methoxy)methyl-Sar]-3-[N-MeVal]-4-cyclosporin |
| 1575 | O | CH₂CH₂OH | [(R)-(2-Hydroxyethoxy)methyl-Sar]-3-[N-MeVal]-4-cyclosporin |
| 1576 | O | C(CH₃)₂CH₂OH | [(R)-(2-Hydroxy-2-methylprpoxy)methyl-Sar]-3-[N-MeVal]-4-cyclosporin |
| 1577 | O | CH₂CH₂NHiBu | [(R)-(2-(N-Isobutylamino)ethoxy)methyl-Sar]-3-[N-MeVal]-4-cyclosporin |
| 1578 | O | CH₂CH₂N(Me)iBu | [(R)-(2-(N-Isobutyl-N-methylamino)ethoxy)methyl-Sar]-3-[N-MeVal]-4-cyclosporin |
| 1579 | O | CH₂CH₂NHCH₂C(CH₃)₃ | [(R)-(2-(N-Neopentylamino)ethoxy)methyl-Sar]-3-[N-MeVal]-4-cyclosporin |

TABLE 4-continued

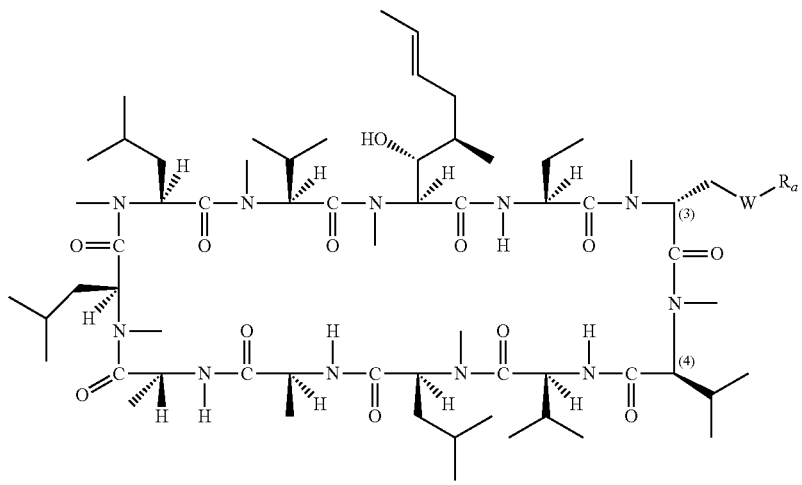

| Ex. No. | W | R$_a$ | Name |
|---|---|---|---|
| 1580 | O | 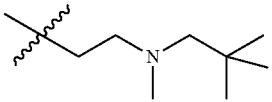 | [(R)-(2-(N-Methyl-N-neopentylamino)ethoxy)methyl-Sar]-3-[N-MeVal]-4-cyclosporin |
| 1581 | O | 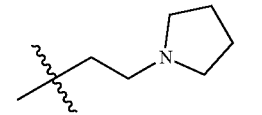 | [(R)-(2-(N-Pyrrolidinyl)ethoxy)methyl-Sar]-3-[N-MeVal]-4-cyclosporin |
| 1582 | O | 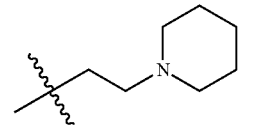 [SMILES: *CCN1CCCCC1] | [(R)-(2-(N-Piperidinyl)ethoxy)methyl-Sar]-3-[N-MeVal]-4-cyclosporin |
| 1583 | O | 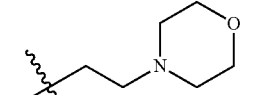 | [(R)-(2-(N-Morpholino)ethoxy)methyl-Sar]-3-[N-MeVal]-4-cyclosporin |
| 1584 | O | 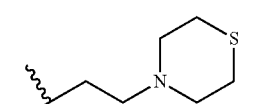 | [(R)-(2-(N-Thiomorpholino)ethoxy)methyl-Sar]-3-[N-MeVal]-4-cyclosporin |
| 1585 | O | 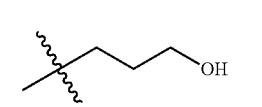 [SMILES: *CCCO] | [(R)-(3-Hydroxypropoxy)methyl-Sar]-3-[N-MeVal]-4-cyclosporin |
| 1586 | O | 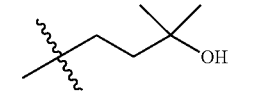 [SMILES: *CCC(C)(C)O] | [(R)-(3-Hydroxy-3-methylbutoxy)methyl-Sar]-3-[N-MeVal]-4-cyclosporin |
| 1587 | O | 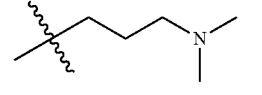 [SMILES: *CCCN(C)C] | [(R)-(3-(N,N-Dimethylamino)propoxy)methyl-Sar]-3-[N-MeVal]-4-cyclosporin |

TABLE 4-continued

| Ex. No. | W | R$_a$ | Name |
|---|---|---|---|
| 1588 | O | (propyl)-N(Et)$_2$ | [(R)-(3-(N,N-Diethylamino)propoxy)methyl-Sar]-3-[N-MeVal]-4-cyclosporin |
| 1589 | O | (propyl)-NH-iBu | [(R)-(3-(N-Isobutylamino)propoxy)methyl-Sar]-3-[N-MeVal]-4-cyclosporin |
| 1590 | O | (propyl)-N(Me)(iBu) | [(R)-(3-(N-Isobutyl-N-methylamino)propoxy)methyl-Sar]-3-[N-MeVal]-4-cyclosporin |
| 1591 | O | (propyl)-N(iBu)$_2$ | [(R)-(3-(N,N-Diisobutylamino)propoxy)methyl-Sar]-3-[N-MeVal]-4-cyclosporin |
| 1592 | O | (propyl)-NH-neopentyl | [(R)-(3-(N-Neopentylamino)propoxy)methyl-Sar]-3-[N-MeVal]-4-cyclosporin |
| 1593 | O | (propyl)-N(Me)(neopentyl) | [(R)-(3-(N-Methyl-N-neopentylamino)propoxy)methyl-Sar]-3-[N-MeVal]-4-cyclosporin |
| 1594 | O | (propyl)-pyrrolidinyl | [(R)-(3-(N-Pyrrolidinyl)propoxy)methyl-Sar]-3-[N-MeVal]-4-cyclosporin |
| 1595 | O | (propyl)-piperidinyl | [(R)-(3-(N-Piperidinyl)propoxy)methyl-Sar]-3-[N-MeVal]-4-cyclosporin |
| 1596 | O | (propyl)-morpholino | [(R)-(3-(N-Morpholino)propoxy)methyl-Sar]-3-[N-MeVal]-4-cyclosporin |

TABLE 4-continued

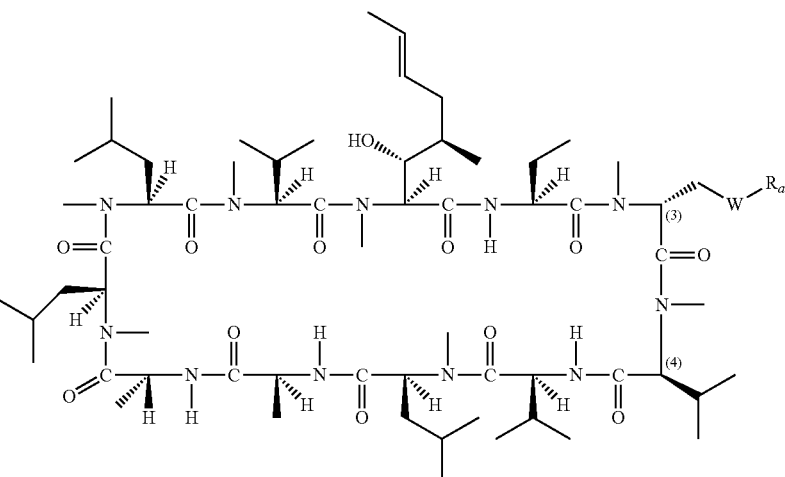

| Ex. No. | W | $R_a$ | Name |
|---|---|---|---|
| 1597 | O | (4-(N-thiomorpholino)butyl) | [(R)-(3-(N-Thiomorpholino)propoxy)methyl-Sar]-3-[N-MeVal]-4-cyclosporin |
| 1598 | O | (3-carboxypropyl) | [(R)-(3-Carboxypropoxy)methyl-Sar]-3-[N-MeVal]-4-cyclosporin |
| 1599 | O | (3-carboxypropyl potassium salt) | [(R)-(3-Carboxypropoxy)methyl-Sar]-3-[N-MeVal]-4-cyclosporin-potassium salt |
| 1600 | O | (3-carboxypropyl sodium salt) | [(R)-(3-Carboxypropoxy)methyl-Sar]-3-[N-MeVal]-4-cyclosporin-sodium salt |
| 1601 | O | (3-ethoxycarbonylpropyl) | [(R)-(3-(Ethoxycarbonyl)propoxy)methyl-Sar]-3-[N-MeVal]-4-cyclosporin |
| 1602 | O | (4-hydroxybutyl) | [(R)-(4-Hydroxybutoxy)methyl-Sar]-3-[N-MeVal]-4-cyclosporin |
| 1603 | O | (4-hydroxy-4-methylpentyl) | [(R)-(4-Hydroxy-4-methylpentyloxy)methyl-Sar]-3-[N-MeVal]-4-cyclosporin |
| 1604 | O | (4-(N,N-dimethylamino)butyl) | [(R)-(4-(N,N-Dimethylamino)butoxy)methyl-Sar]-3-[N-MeVal]-4-cyclosporin |
| 1605 | O | (4-(N,N-diethylamino)butyl) | [(R)-(4-(N,N-Diethylamino)butoxy)methyl-Sar]-3-[N-MeVal]-4-cyclosporin |

TABLE 4-continued

| Ex. No. | W | $R_a$ | Name |
|---|---|---|---|
| 1606 | O | (CH2)4-NH-CH2CH(CH3)2 | [(R)-(4-(N-Isobutylamino)butoxy)methyl-Sar]-3-[N-MeVal]-4-cyclosporin |
| 1607 | O | (CH2)4-N(CH3)-CH2CH(CH3)2 | [(R)-(4-(N-Isobutyl-N-methylamino)butoxy)methyl-Sar]-3-[N-MeVal]-4-cyclosporin |
| 1608 | O | (CH2)4-N(CH2CH(CH3)2)2 | [(R)-(4-(N,N-Diisobutylamino)butoxy)methyl-Sar]-3-[N-MeVal]-4-cyclosporin |
| 1609 | O | (CH2)4-NH-CH2C(CH3)3 | [(R)-(4-(N-Neopentylamino)butoxy)methyl-Sar]-3-[N-MeVal]-4-cyclosporin |
| 1610 | O | (CH2)4-N(CH3)-CH2C(CH3)3 | [(R)-(4-(N-Methyl-N-neopentylamino)butoxy)methyl-Sar]-3-[N-MeVal]-4-cyclosporin |
| 1611 | O | (CH2)4-pyrrolidinyl | [(R)-(4-(N-Pyrrolidinyl)butoxy)methyl-Sar]-3-[N-MeVal]-4-cyclosporin |
| 1612 | O | (CH2)4-piperidinyl | [(R)-(4-(N-Piperidinyl)butoxy)methyl-Sar]-3-[N-MeVal]-4-cyclosporin |
| 1613 | O | (CH2)4-morpholino | [(R)-(4-(N-Morpholino)butoxy)methyl-Sar]-3-[N-MeVal]-4-cyclosporin |

TABLE 4-continued
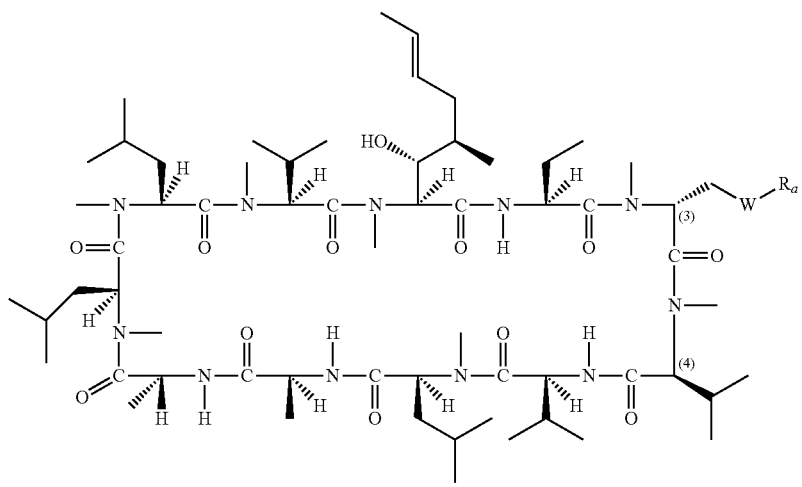
| Ex. No. | W | $R_a$ | Name |
|---|---|---|---|
| 1614 | O | 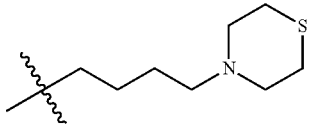 | [(R)-(4-(N-Thiomorpholino)butoxy)methyl-Sar]-3-[N-MeVal]-4-cyclosporin |
TABLE 5
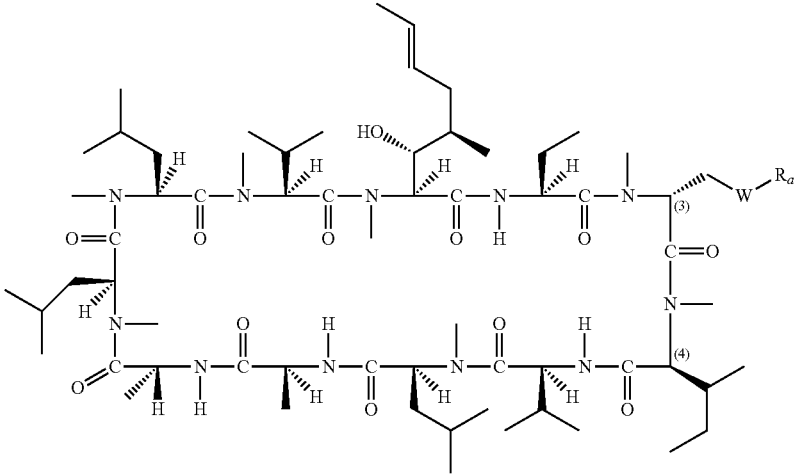
| Ex. No. | W | $R_a$ | Name |
|---|---|---|---|
| 1615 | S | 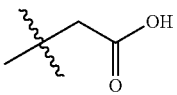 | [(S)-(Carboxymethylthio)methyl-Sar]-3-[N-MeIle]-4-cyclosporin |
| 1616 | S | 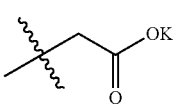 | [(S)-(Carboxymethylthio)methyl-Sar]-3-[N-MeIle]-4-cyclosporin-potassium salt |
| 1617 | S | 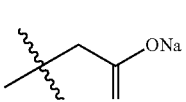 | [(S)-(Carboxymethylthio)methyl-Sar]-3-[N-MeIle]-4-cyclosporin-sodium salt |

TABLE 5-continued

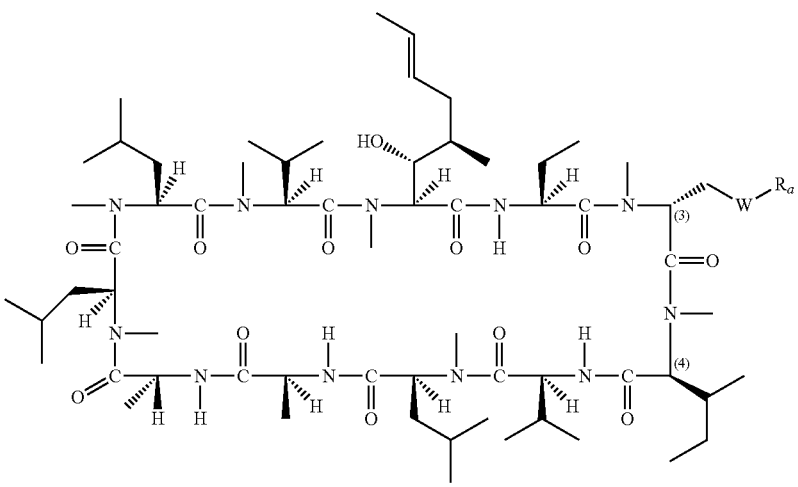

| Ex. No. | W | $R_a$ | Name |
|---|---|---|---|
| 1618 | S | (ethyl ester -CH2-C(=O)-O-CH2CH3) | [(S)-(Ethoxycarbonylmethylthio)methyl-Sar]-3-[N-MeIle]-4-cyclosporin |
| 1619 | S | -CH2CH2-OH | [(S)-(2-Hydroxyethylthio)methyl-Sar]-3-[N-MeIle]-4-cyclosporin |
| 1620 | S | -CH2-C(CH3)2-OH | [(S)-(2-Hydroxy-2-methylpropylthio)methyl-Sar]-3-[N-MeIle]-4-cyclosporin |
| 1621 | S | -CH2CH2-NH-iBu | [(S)-(2-(N-Isobutylamino)ethylthio)methyl-Sar]-3-[N-MeIle]-4-cyclosporin |
| 1622 | S | -CH2CH2-N(CH3)-iBu | [(S)-(2-(N-Isobutyl-N-methylamino)ethylthio)methyl-Sar]-3-[N-MeIle]-4-cyclosporin |
| 1623 | S | -CH2CH2-NH-CH2C(CH3)3 | [(S)-(2-(N-Neopentylamino)ethylthio)methyl-Sar]-3-[N-MeIle]-4-cyclosporin |
| 1624 | S | -CH2CH2-N(CH3)-CH2C(CH3)3 | [(S)-(2-(N-Methyl-N-neopentylamino)ethylthio)methyl-Sar]-3-[N-MeIle]-4-cyclosporin |
| 1625 | S | -CH2CH2-N(pyrrolidinyl) | [(S)-(2-(N-Pyrrolidinyl)ethylthio)methyl-Sar]-3-[N-MeIle]-4-cyclosporin |
| 1626 | S | -CH2CH2-N(piperidinyl) | [(S)-(2-(N-Piperidinyl)ethylthio)methyl-Sar]-3-[N-MeIle]-4-cyclosporin |

TABLE 5-continued

| Ex. No. | W | R$_a$ | Name |
|---|---|---|---|
| 1627 | S | (morpholinoethyl) | [(S)-(2-(N-Morpholino)ethylthio)methyl-Sar]-3-[N-MeIle]-4-cyclosporin |
| 1628 | S | (thiomorpholinoethyl) | [(S)-(2-(N-Thiomorpholino)ethylthio)methyl-Sar]-3-[N-MeIle]-4-cyclosporin |
| 1629 | S | (3-hydroxypropyl) | [(S)-(3-Hydroxypropylthio)methyl-Sar]-3-[N-MeIle]-4-cyclosporin |
| 1630 | S | (3-hydroxy-3-methylbutyl) | [(S)-(3-Hydroxy-3-methylbutylthio)methyl-Sar]-3-[N-MeIle]-4-cyclosporin |
| 1631 | S | (3-(N,N-dimethylamino)propyl) | [(S)-(3-(N,N-Dimethylamino)propylthio)methyl-Sar]-3-[N-MeIle]-4-cyclosporin |
| 1632 | S | (3-(N,N-diethylamino)propyl) | [(S)-(3-(N,N-Diethylamino)propylthio)methyl-Sar]-3-[N-MeIle]-4-cyclosporin |
| 1633 | S | (3-(N-isobutylamino)propyl) | [(S)-(3-(N-Isobutylamino)propylthio)methyl-Sar]-3-[N-MeIle]-4-cyclosporin |
| 1634 | S | (3-(N-isobutyl-N-methylamino)propyl) | [(S)-(3-(N-Isobutyl-N-methylamino)propylthio)methyl-Sar]-3-[N-MeIle]-4-cyclosporin |
| 1635 | S | (3-(N,N-diisobutylamino)propyl) | [(S)-(3-(N,N-Diisobutylamino)propylthio)methyl-Sar]-3-[N-MeIle]-4-cyclosporin |

TABLE 5-continued

| Ex. No. | W | R_a | Name |
|---|---|---|---|
| 1636 | S | (CH2)3-NH-CH2C(CH3)3 | [(S)-(3-(N-Neopentylamino)propylthio)methyl-Sar]-3-[N-MeIle]-4-cyclosporin |
| 1637 | S | (CH2)3-N(CH3)-CH2C(CH3)3 | [(S)-(3-(N-Methyl-N-neopentylamino)propylthio)methyl-Sar]-3-[N-MeIle]-4-cyclosporin |
| 1638 | S | (CH2)3-pyrrolidinyl | [(S)-(3-(N-Pyrrolidinyl)propylthio)methyl-Sar]-3-[N-MeIle]-4-cyclosporin |
| 1639 | S | (CH2)3-piperidinyl | [(S)-(3-(N-Piperidinyl)propylthio)methyl-Sar]-3-[N-MeIle]-4-cyclosporin |
| 1640 | S | (CH2)3-morpholino | [(S)-(3-(N-Morpholino)propylthio)methyl-Sar]-3-[N-MeIle]-4-cyclosporin |
| 1641 | S | (CH2)3-thiomorpholino | [(S)-(3-(N-Thiomorpholino)propylthio)methyl-Sar]-3-[N-MeIle]-4-cyclosporin |
| 1642 | S | (CH2)3-COOH | [(S)-(3-Carboxypropylthio)methyl-Sar]-3-[N-MeIle]-4-cyclosporin |
| 1643 | S | (CH2)3-COOK | [(S)-(3-Carboxypropylthio)methyl-Sar]-3-[N-MeIle]-4-cyclosporin-potassium salt |
| 1644 | S | (CH2)3-COONa | [(S)-(3-Carboxypropylthio)methyl-Sar]-3-[N-MeIle]-4-cyclosporin-sodium salt |

TABLE 5-continued

| Ex. No. | W | R_a | Name |
|---|---|---|---|
| 1645 | S | (ethyl ester chain) | [(S)-(3-Ethoxycarbonylpropylthio)methyl-Sar]-3-[N-MeIle]-4-cyclosporin |
| 1646 | S | (butyl-OH chain) | [(S)-(4-Hydroxybutylthio)methyl-Sar]-3-[N-MeIle]-4-cyclosporin |
| 1647 | S | (4-hydroxy-4-methylpentyl chain) | [(S)-(4-Hydroxy-4-methylpentylthio)methyl-Sar]-3-[N-MeIle]-4-cyclosporin |
| 1648 | S | (4-N,N-dimethylaminobutyl chain) | [(S)-(4-(N,N-Dimethylamino)butylthio)methyl-Sar]-3-[N-MeIle]-4-cyclosporin |
| 1649 | S | (4-N,N-diethylaminobutyl chain) | [(S)-(4-(N,N-Diethylamino)butylthio)methyl-Sar]-3-[N-MeIle]-4-cyclosporin |
| 1650 | S | (4-N-isobutylaminobutyl chain) | [(S)-(4-(N-Isobutylamino)butylthio)methyl-Sar]-3-[N-MeIle]-4-cyclosporin |
| 1651 | S | (4-N-isobutyl-N-methylaminobutyl chain) | [(S)-(4-(N-Isobutyl-N-methylamino)butylthio)methyl-Sar]-3-[N-MeIle]-4-cyclosporin |
| 1652 | S | (4-N,N-diisobutyl-N-methylaminobutyl chain) | [(S)-(4-(N,N-Diisobutyl-N-methylamino)butylthio)methyl-Sar]-3-[N-MeIle]-4-cyclosporin |

TABLE 5-continued

| Ex. No. | W | $R_a$ | Name |
|---|---|---|---|
| 1653 | S | 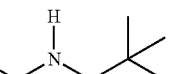 | [(S)-(4-(N-Neopentylamino)butylthio)methyl-Sar]-3-[N-MeIle]-4-cyclosporin |
| 1654 | S |  | [(S)-(4-(N-Methyl-N-Neopentylamino)butylthio)methyl-Sar]-3-[N-MeIle]-4-cyclosporin |
| 1655 | S | 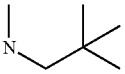 | [(S)-(4-(N-Pyrrolidinyl)butylthio)methyl-Sar]-3-[N-MeIle]-4-cyclosporin |
| 1656 | S |  | [(S)-(4-(N-Piperidinyl)butylthio)methyl-Sar]-3-[N-MeIle]-4-cyclosporin |
| 1657 | S |  | [(S)-(4-(N-Morpholino)butylthio)methyl-Sar]-3-[N-MeIle]-4-cyclosporin |
| 1658 | S |  | [(S)-(4-(N-Thiomorpholino)butylthio)methyl-Sar]-3-[N-MeIle]-4-cyclosporin |
| 1659 | S |  | [(S)-(4-Carboxypentylthio)methyl-Sar]-3-[N-MeIle]-4-cyclosporin |
| 1660 | S |  | [(S)-(4-Carboxypentylthio)methyl-Sar]-3-[N-MeIle]-4-cyclosporin-potassium salt |

TABLE 5-continued

| Ex. No. | W | $R_a$ | Name |
|---|---|---|---|
| 1661 | S | (4-carboxypentylthio, ONa salt) | [(S)-(4-Carboxypentylthio)methyl-Sar]-3-[N-MeIle]-4-cyclosporin-sodium salt |
| 1662 | S | (4-ethoxycarbonylpentylthio) | [(S)-4-Ethoxycarbonylpentylpentylthio)methyl-Sar]-3-[N-MeIle]-4-cyclosporin |
| 1663 | S | (4,4'-dicarboxybutylthio) | [(S)-((4,4'-Dicarboxy)butylthio)methyl-Sar]-3-[N-MeIle]-4-cyclosporin |
| 1664 | S | (4,4'-dicarboxybutylthio, dipotassium) | [(S)-((4,4'-Dicarboxy)butylthio)methyl-Sar]-3-[N-MeIle]-4-cyclosporin-dipotassium salt |
| 1665 | S | (S)-3-hydroxymethyl-4-ethoxycarbonylbutylthio | [(S)-((S)-3-Hydroxymethyl-4-ethoxycarbonylbutylthio)methyl-Sar]-3-[N-MeIle]-4-cyclosporin |
| 1666 | S | (R)-3-hydroxymethyl-4-ethoxycarbonylbutylthio | [(S)-((R)-3-Hydroxymethyl-4-ethoxycarbonylbutylthio)methyl-Sar]-3-[N-MeIle]-4-cyclosporin |
| 1667 | O | carboxymethoxy, OH | [(R)-(Carboxymethoxy)methyl-Sar]-3-[N-MeIle]-4-cyclosporin |
| 1668 | O | carboxymethoxy, OK | [(R)-(Carboxymethoxy)methyl-Sar]-3-[N-MeIle]-4-cyclosporin-potassium salt |

TABLE 5-continued

| Ex. No. | W | $R_a$ | Name |
|---|---|---|---|
| 1669 | O | -CH2-C(=O)-ONa | [(R)-(Carboxymethoxy)methyl-Sar]-3-[N-MeIle]-4-cyclosporin-sodium salt |
| 1670 | O | -CH2-C(=O)-OEt | [(R)-((Ethoxycarbonyl)methoxy)methyl-Sar]-3-[N-MeIle]-4-cyclosporin |
| 1671 | O | -CH2CH2-OH | [(R)-(2-Hydroxyethoxy)methyl-Sar]-3-[N-MeIle]-4-cyclosporin |
| 1672 | O | -CH2-C(CH3)2-OH | [(R)-(2-Hydroxy-2-methylpropoxy)methyl-Sar]-3-[N-MeIle]-4-cyclosporin |
| 1673 | O | -CH2CH2-NH-iBu | [(R)-(2-(N-Isobutylamino)ethoxy)methyl-Sar]-3-[N-MeIle]-4-cyclosporin |
| 1674 | O | -CH2CH2-N(Me)(iBu) | [(R)-(2-(N-Isobutyl-N-methylamino)ethoxy)methyl-Sar]-3-[N-MeIle]-4-cyclosporin |
| 1675 | O | -CH2CH2-NH-neopentyl | [(R)-(2-(N-Neopentylamino)ethoxy)methyl-Sar]-3-[N-MeIle]-4-cyclosporin |
| 1676 | O | -CH2CH2-N(Me)(neopentyl) | [(R)-(2-(N-Methyl-N-neopentylamino)ethoxy)methyl-Sar]-3-[N-MeIle]-4-cyclosporin |
| 1677 | O | -CH2CH2-N(pyrrolidinyl) | [(R)-(2-(N-Pyrrolidinyl)ethoxy)methyl-Sar]-3-[N-MeIle]-4-cyclosporin |

TABLE 5-continued

| Ex. No. | W | $R_a$ | Name |
|---|---|---|---|
| 1678 | O | (3-(N-piperidinyl)propyl) | [(R)-(2-(N-Piperidinyl)ethoxy)methyl-Sar]-3-[N-MeIle]-4-cyclosporin |
| 1679 | O | (3-(N-morpholino)propyl) | [(R)-(2-(N-Morpholino)ethoxy)methyl-Sar]-3-[N-MeIle]-4-cyclosporin |
| 1680 | O | (3-(N-thiomorpholino)propyl) | [(R)-(2-(N-Thiomorpholino)ethoxy)methyl-Sar]-3-[N-MeIle]-4-cyclosporin |
| 1681 | O | 3-hydroxypropyl | [(R)-(3-Hydroxypropoxy)methyl-Sar]-3-[N-MeIle]-4-cyclosporin |
| 1682 | O | 3-hydroxy-3-methylbutyl | [(R)-(3-Hydroxy-3-methylbutoxy)methyl-Sar]-3-[N-MeIle]-4-cyclosporin |
| 1683 | O | 3-(N,N-dimethylamino)propyl | [(R)-(3-(N,N-Dimethylamino)propoxy)methyl-Sar]-3-[N-MeIle]-4-cyclosporin |
| 1684 | O | 3-(N,N-diethylamino)propyl | [(R)-(3-(N,N-Diethylamino)propoxy)methyl-Sar]-3-[N-MeIle]-4-cyclosporin |
| 1685 | O | 3-(N-isobutylamino)propyl | [(R)-(3-(N-Isobutylamino)propoxy)methyl-Sar]-3-[N-MeIle]-4-cyclosporin |
| 1686 | O | 3-(N-isobutyl-N-methylamino)propyl | [(R)-(3-(N-Isobutyl-N-methylamino)propoxy)methyl-Sar]-3-[N-MeIle]-4-cyclosporin |

TABLE 5-continued

| Ex. No. | W | $R_a$ | Name |
|---|---|---|---|
| 1687 | O | (CH₂)₃N(iBu)₂ | [(R)-(3-(N,N-Diisobutylamino)propoxy)methyl-Sar]-3-[N-MeIle]-4-cyclosporin |
| 1688 | O | (CH₂)₃NH(neopentyl) | [(R)-(3-(N-Neopentylamino)propoxy)methyl-Sar]-3-[N-MeIle]-4-cyclosporin |
| 1689 | O | (CH₂)₃N(Me)(neopentyl) | [(R)-(3-(N-Methyl-N-neopentylamino)propoxy)methyl-Sar]-3-[N-MeIle]-4-cyclosporin |
| 1690 | O | (CH₂)₃-pyrrolidinyl | [(R)-(3-(N-Pyrrolidinyl)propoxy)methyl-Sar]-3-[N-MeIle]-4-cyclosporin |
| 1691 | O | (CH₂)₃-piperidinyl | [(R)-(3-(N-Piperidinyl)propoxy)methyl-Sar]-3-[N-MeIle]-4-cyclosporin |
| 1692 | O | (CH₂)₃-morpholino | [(R)-(3-(N-Morpholino)propoxy)methyl-Sar]-3-[N-MeIle]-4-cyclosporin |
| 1693 | O | (CH₂)₃-thiomorpholino | [(R)-(3-(N-Thiomorpholino)propoxy)methyl-Sar]-3-[N-MeIle]-4-cyclosporin |
| 1694 | O | (CH₂)₃COOH | [(R)-(3-Carboxypropoxy)methyl-Sar]-3-[N-MeIle]-4-cyclosporin |
| 1695 | O | (CH₂)₃COOK | [(R)-(3-Carboxypropoxy)methyl-Sar]-3-[N-MeIle]-4-cyclosporin-potassium salt |

TABLE 5-continued

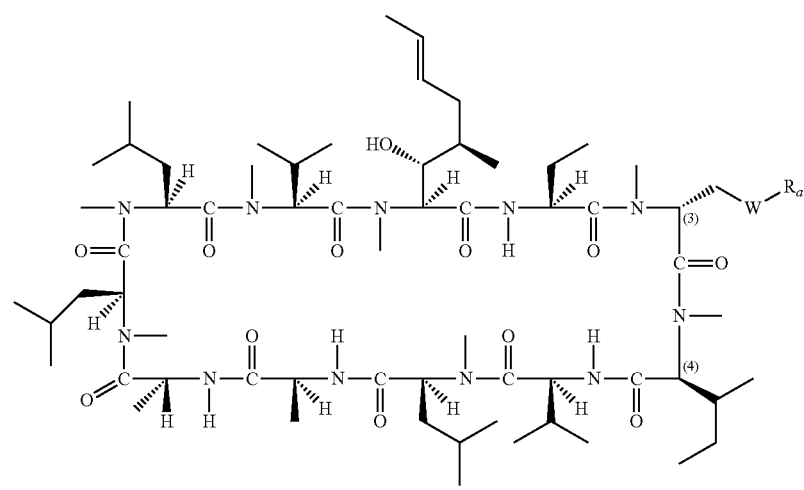

| Ex. No. | W | $R_a$ | Name |
|---|---|---|---|
| 1696 | O | (3-carboxypropoxy, ONa salt) | [(R)-(3-Carboxypropoxy)methyl-Sar]-3-[N-MeIle]-4-cyclosporin-sodium salt |
| 1697 | O | (3-ethoxycarbonylpropoxy) | [(R)-(3-(Ethoxycarbonyl)propoxy)methyl-Sar]-3-[N-MeIle]-4-cyclosporin |
| 1698 | O | (4-hydroxybutoxy) | [(R)-(4-Hydroxybutoxy)methyl-Sar]-3-[N-MeIle]-4-cyclosporin |
| 1699 | O | (4-hydroxy-4-methylpentyloxy) | [(R)-(4-Hydroxy-4-methylpentyloxy)methyl-Sar]-3-[N-MeIle]-4-cycloporin |
| 1700 | O | (4-N,N-dimethylaminobutoxy) | [(R)-(4-(N,N-Dimethylamino)butoxy)methyl-Sar]-3-[N-MeIle]-4-cyclosporin |
| 1701 | O | (4-N,N-diethylaminobutoxy) | [(R)-(4-(N,N-Diethylamino)butoxy)methyl-Sar]-3-[N-MeIle]-4-cyclosporin |
| 1702 | O | (4-N-isobutylaminobutoxy) | [(R)-(4-(N-Isobutylamino)butoxy)methyl-Sar]-3-[N-MeIle]-4-cyclosporin |
| 1703 | O | (4-N-isobutyl-N-methylaminobutoxy) | [(R)-(4-(N-Isobutyl-N-methylamino)butoxy)methyl-Sar]-3-[N-MeIle]-4-cyclosporin |

TABLE 5-continued

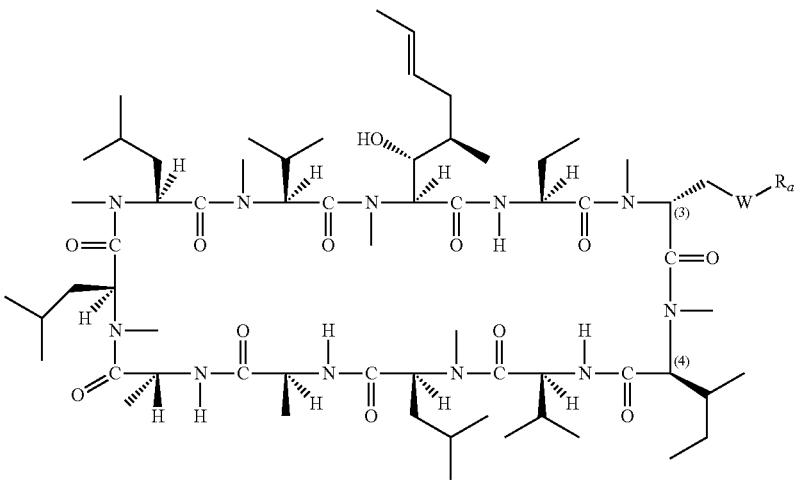

| Ex. No. | W | $R_a$ | Name |
|---|---|---|---|
| 1704 | O | 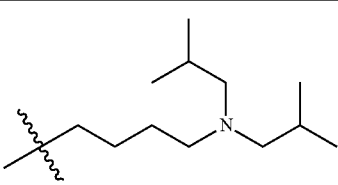 | [(R)-(4-(N,N-Diisobutylamino)butoxy)methyl-Sar]-3-[N-MeIle]-4-cyclosporin |
| 1705 | O | 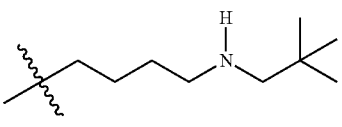 [SMILES: *CCCCNCC(C)(C)C] | [(R)-(4-(N-Neopentylamino)butoxy)methyl-Sar]-3-[N-MeIle]-4-cyclosporin |
| 1706 | O | 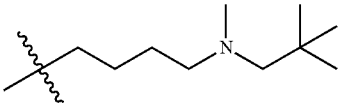 [SMILES: *CCCCN(C)CC(C)(C)C] | [(R)-(4-(N-Methyl-N-neopentylamino)butoxy)methyl-Sar]-3-[N-MeIle]-4-cyclosporin |
| 1707 | O | 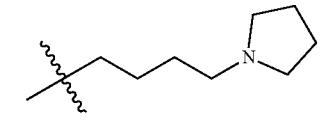 [SMILES: *CCCCN1CCCC1] | [(R)-(4-(N-Pyrrolidinyl)butoxy)methyl-Sar]-3-[N-MeIle]-4-cyclosporin |
| 1708 | O | 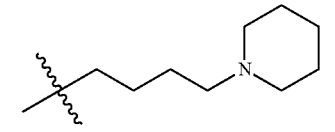 [SMILES: *CCCCN1CCCCC1] | [(R)-(4-(N-Piperidinyl)butoxy)methyl-Sar]-3-[N-MeIle]-4-cyclosporin |
| 1709 | O | 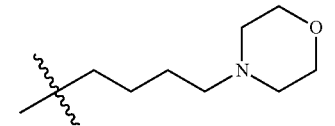 [SMILES: *CCCCN1CCOCC1] | [(R)-(4-(N-Morpholino)butoxy)methyl-Sar]-3-[N-MeIle]-4-cyclosporin |
| 1710 | O | 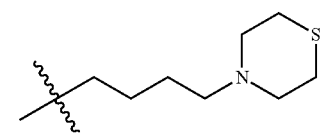 [SMILES: *CCCCN1CCSCC1] | [(R)-(4-(N-Thiomorpholino)butoxy)methyl-Sar]-3-[N-MeIle]-4-cyclosporin |

TABLE 5-continued

| Ex. No. | W | $R_a$ | Name |
|---|---|---|---|
| 1711 | O | (4-carboxypentyl chain, -OH) | [(R)-(4-Carboxypentyloxy)methyl-Sar]-3-[N-MeIle]-4-cyclosporin |
| 1712 | O | (4-carboxypentyl chain, -OK) | [(R)-(4-Carboxypentyloxy)methyl-Sar]-3-[N-MeIle]-4-cyclosporin-potassium salt |
| 1713 | O | (4-carboxypentyl chain, -ONa) | [(R)-(4-Carboxypentyloxy)methyl-Sar]-3-[N-MeIle]-4-cyclosporin-sodium salt |
| 1714 | O | (4-ethoxycarbonylpentyl chain) | [(R)-(4-Ethoxycarbonylpentyloxy)methyl-Sar]-3-[N-MeIle]-4-cyclosporin |
| 1715 | O | (4,4'-dicarboxybutyl chain) | [(R)-((4,4'-Dicarboxy)butoxy)methyl-Sar]-3-[N-MeIle]-4-cyclosporin |
| 1716 | O | (4,4'-dicarboxybutyl chain, di-OK) | [(R)-((4,4'-Dicarboxy)butoxy)methyl-Sar]-3-[N-MeIle]-4-cyclosporin-dipotassium salt |
| 1717 | O | ((R)-3-hydroxymethyl-4-ethoxycarbonylbutyl) | [(R)-((R)-3-Hydroxymethyl-4-ethoxycarbonybutoxy)methyl-Sar]-3-[N-MeIle]-4-cyclosporin |
| 1718 | O | ((S)-3-hydroxymethyl-4-ethoxycarbonylbutyl) | [(R)-((S)-3-Hydroxymethyl-4-ethoxycarbonybutoxy)methyl-Sar]-3-[N-MeIle]-4-cyclosporin |
| 1719 | $CH_2$ | —$NO_2$ | [(R)-2-Nitroethyl-Sar]-3-[N-MeIle]-4-cyclosporin |

TABLE 5-continued

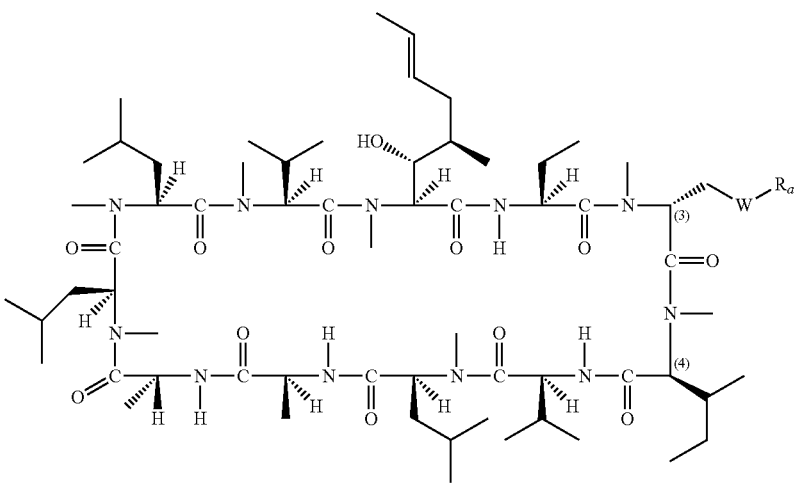

| Ex. No. | W | $R_a$ | Name |
|---|---|---|---|
| 1720 | $CH_2$ | —$NH_2$ | [(R)-2-Aminoethyl-Sar]-3-[N-MeIle]-4-cyclosporin |
| 1721 | $CH_2$ | —$N(CH_3)_2$ | [(R)-2-(N,N-Dimethylamino)ethyl-Sar]-3-[N-MeIle]-4-cyclosporin |
| 1722 | $CH_2$ | —$N(CH2CH_3)_2$ | [(R)-2-(N,N-Diethylamino)ethyl-Sar]-3-[N-MeIle]-4-cyclosporin |
| 1723 | $CH_2$ | —$CH_2N(CH_3)_2$ | [(R)-2-(N,N-Dimethylamino)propyl-Sar]-3-[N-MeIle]-4-cyclosporin |
| 1724 | $CH_2$ | —$(COOEt)_2$ | [(R)-2,2-Di(ethoxycarbonyl)ethyl)-Sar]-3-[N-MeIle]-4-cyclosporin |
| 1725 | $CH_2$ | —$(CH_2OH)_2$ | [(R)-2,2-Di(hydroxylmethyl)ethyl)-Sar]-3-[N-MeIle]-4-cyclosporin |

TABLE 6

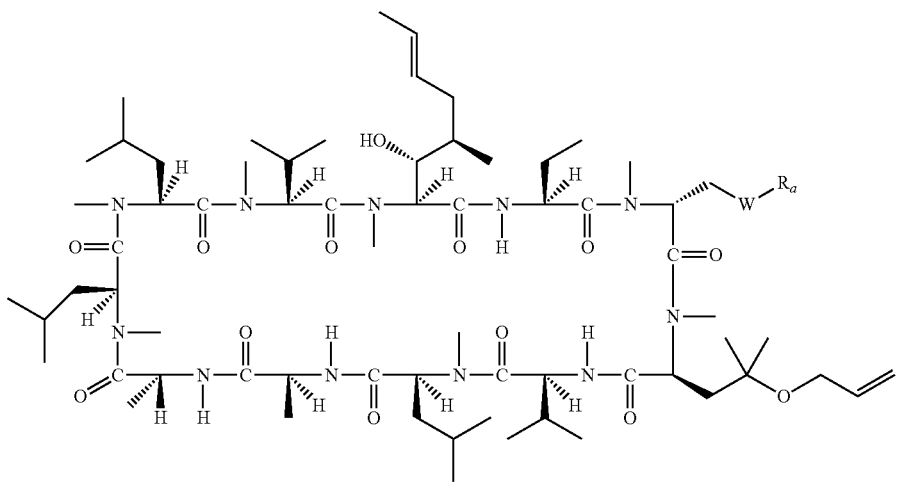

| Ex. No. | W | $R_a$ | Name |
|---|---|---|---|
| 1726 | S | ![](OH, O) | [(S)-(Carboxymethylthio)methyl-Sar]-3-[(γ-allyloxy)-NMeLeu]-4-cyclosporin |
| 1727 | S | ![](OK, O) | [(S)-(Carboxymethylthio)methyl-Sar]-3-[(γ-allyloxy)-NMeLeu]-4-cyclosporin-potassium salt |

TABLE 6-continued

| Ex. No. | W | $R_a$ | Name |
|---|---|---|---|
| 1728 | S | —CH₂—C(O)—ONa | [(S)-(Carboxymethylthio)methyl-Sar]-3-[(γ-allyloxy)-NMeLeu]-4-cyclosporin-sodium salt |
| 1729 | S | —CH₂—C(O)—OEt | [(S)-(Ethoxycarbonylmethylthio)methyl-Sar]-3-[(γ-allyloxy)-NMeLeu]-4-cyclosporin |
| 1730 | S | —CH₂CH₂OH | [(S)-(2-Hydroxyethylthio)methyl-Sar]-3-[(γ-allyloxy)-NMeLeu]-4-cyclosporin |
| 1731 | S | —CH₂—C(CH₃)₂—OH | [(S)-(2-Hydroxy-2-methylpropylthio)methyl-Sar]-3-[(γ-allyloxy)-NMeLeu]-4-cyclosporin |
| 1732 | S | —CH₂CH₂—NH—CH₂CH(CH₃)₂ | [(S)-(2-(N-Isobutylamino)ethylthio)methyl-Sar]-3-[(γ-allyloxy)-NMeLeu]-4-cyclosporin |
| 1733 | S | —CH₂CH₂—N(CH₃)—CH₂CH(CH₃)₂ | [(S)-(2-(N-Isobutyl-N-methylamino)ethylthio)methyl-Sar]-3-[(γ-allyloxy)-NMeLeu]-4-cyclosporin |
| 1734 | S | —CH₂CH₂—NH—CH₂C(CH₃)₃ | [(S)-(2-(N-Neopentylamino)ethylthio)methyl-Sar]-3-[(γ-allyloxy)-NMeLeu]-4-cyclosporin |
| 1735 | S | —CH₂CH₂—N(CH₃)—CH₂C(CH₃)₃ | [(S)-(2-(N-Methyl-N-neopentylamino)ethylthio)methyl-Sar]-3-[(γ-allyloxy)-NMeLeu]-4-cyclosporin |
| 1736 | S | —CH₂CH₂—(N-pyrrolidinyl) | [(S)-(2-(N-Pyrrolidinyl)ethylthio)methyl-Sar]-3-[(γ-allyloxy)-NMeLeu]-4-cyclosporin |

TABLE 6-continued

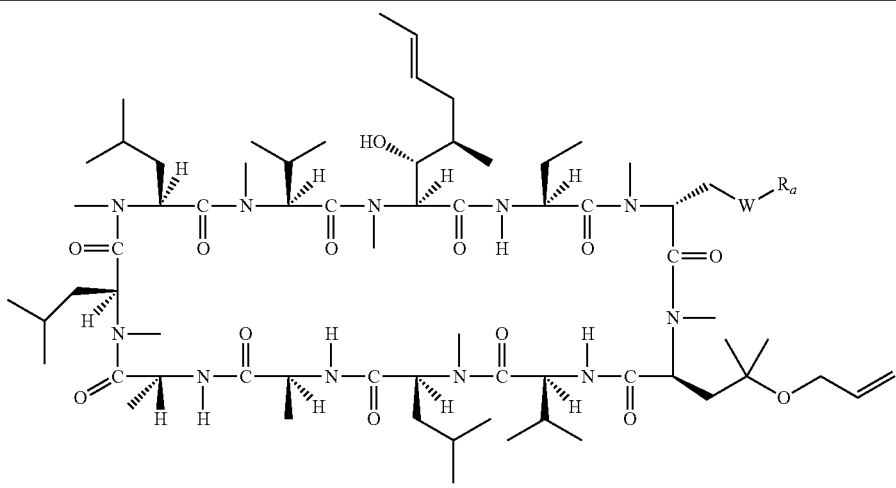

| Ex. No. | W | R$_a$ | Name |
|---|---|---|---|
| 1737 | S | (piperidinylpropyl) | [(S)-(2-(N-Piperidinyl)ethylthio)methyl-Sar]-3-[(γ-allyloxy)-NMeLeu]-4-cyclosporin |
| 1738 | S | (morpholinopropyl) | [(S)-(2-(N-Morpholino)ethylthio)methyl-Sar]-3-[(γ-allyloxy)-NMeLeu]-4-cyclosporin |
| 1739 | S | (thiomorpholinopropyl) | [(S)-(2-(N-Thiomorpholino)ethylthio)methyl-Sar]-3-[(γ-allyloxy)-NMeLeu]-4-cyclosporin |
| 1740 | S | (3-hydroxypropyl) | [(S)-(3-Hydroxypropylthio)methyl-Sar]-3-[(γ-allyloxy)-NMeLeu]-4-cyclosporin |
| 1741 | S | (3-hydroxy-3-methylbutyl) | [(S)-(3-Hydroxy-3-methylbutylthio)methyl-Sar]-3-[(γ-allyloxy)-NMeLeu]-4-cyclosporin |
| 1742 | S | (3-(N,N-dimethylamino)propyl) | [(S)-(3-(N,N-Dimethylamino)propylthio)methyl-Sar]-3-[(γ-allyloxy)-NMeLeu]-4-cyclosporin |
| 1743 | S | (3-(N,N-diethylamino)propyl) | [(S)-(3-(N,N-Diethylamino)propylthio)methyl-Sar]-3-[(γ-allyloxy)-NMeLeu]-4-cyclosporin |
| 1744 | S | (3-(N-isobutylamino)propyl) | [(S)-(3-(N-Isobutylamino)propylthio)methyl-Sar]-3-[(γ-allyloxy)-NMeLeu]-4-cyclosporin |
| 1745 | S | (3-(N-isobutyl-N-methylamino)propyl) | [(S)-(3-(N-Isobutyl-N-methylamino)propylthio)methyl-Sar]-3-[(γ-allyloxy)-NMeLeu]-4-cyclosporin |

TABLE 6-continued

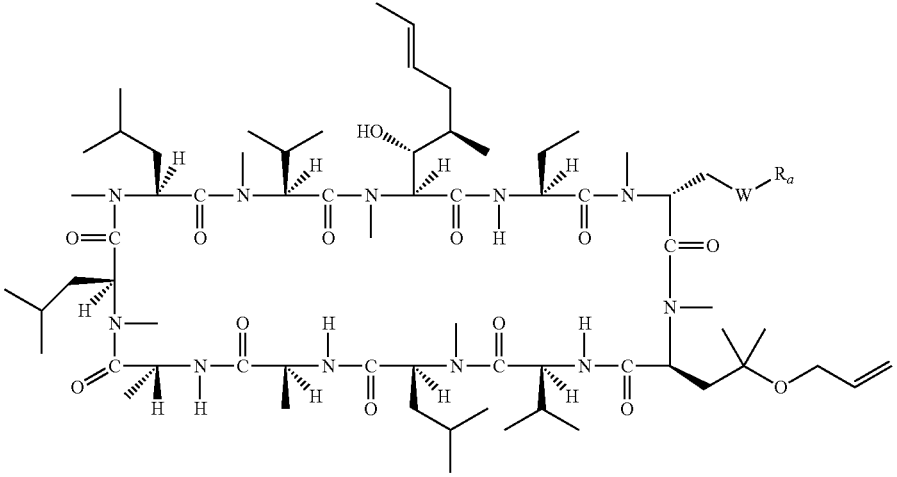

| Ex. No. | W | $R_a$ | Name |
|---|---|---|---|
| 1746 | S | 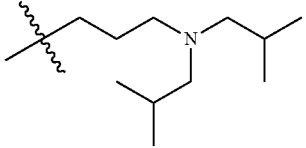 [SMILES: *CCCN(CC(C)C)CC(C)C] | [(S)-(3-(N,N-Diisobutylamino)propylthio)methyl-Sar]-3-[(γ-allyloxy)-NMeLeu]-4-cyclosporin |
| 1747 | S | 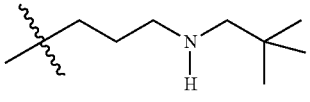 [SMILES: *CCCNCC(C)(C)C] | [(S)-(3-(N-Neopentylamino)propylthio)methyl-Sar]-3-[(γ-allyloxy)-NMeLeu]-4-cyclosporin |
| 1748 | S | 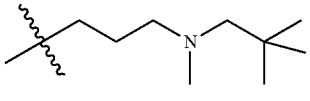 [SMILES: *CCCN(C)CC(C)(C)C] | [(S)-(3-(N-Methyl-N-neopentylamino)propylthio)methyl-Sar]-3-[(γ-allyloxy)-NMeLeu]-4-cyclosporin |
| 1749 | S | 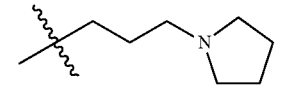 [SMILES: *CCCN1CCCC1] | [(S)-(3-(N-Pyrrolidinyl)propylthio)methyl-Sar]-3-[(γ-allyloxy)-NMeLeu]-4-cyclosporin |
| 1750 | S | 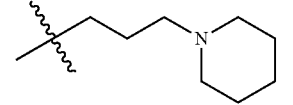 [SMILES: *CCCN1CCCCC1] | [(S)-(3-(N-Piperidinyl)propylthio)methyl-Sar]-3-[(γ-allyloxy)-NMeLeu]-4-cyclosporin |
| 1751 | S | 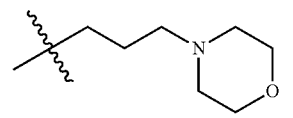 | [(S)-(3-(N-Morpholino)propylthio)methyl-Sar]-3-[(γ-allyloxy)-NMeLeu]-4-cyclosporin |
| 1752 | S | 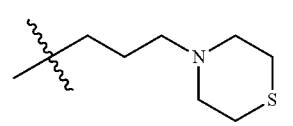 [SMILES: *CCCN1CCSCC1] | [(S)-(3-(N-Thiomorpholino)propylthio)methyl-Sar]-3-[(γ-allyloxy)-NMeLeu]-4-cyclosporin |
| 1753 | S | 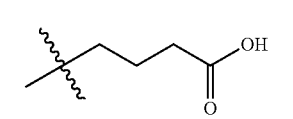 [SMILES: *CCCC(=O)O] | [(S)-(3-Carboxypropylthio)methyl-Sar]-3-[(γ-allyloxy)-NMeLeu]-4-cyclosporin |
| 1754 | S | 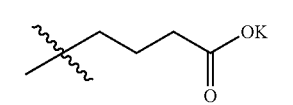 | [(S)-(3-Carboxypropylthio)methyl-Sar]-3-[(γ-allyloxy)-NMeLeu]-4-cyclosporin-potassium salt |

TABLE 6-continued

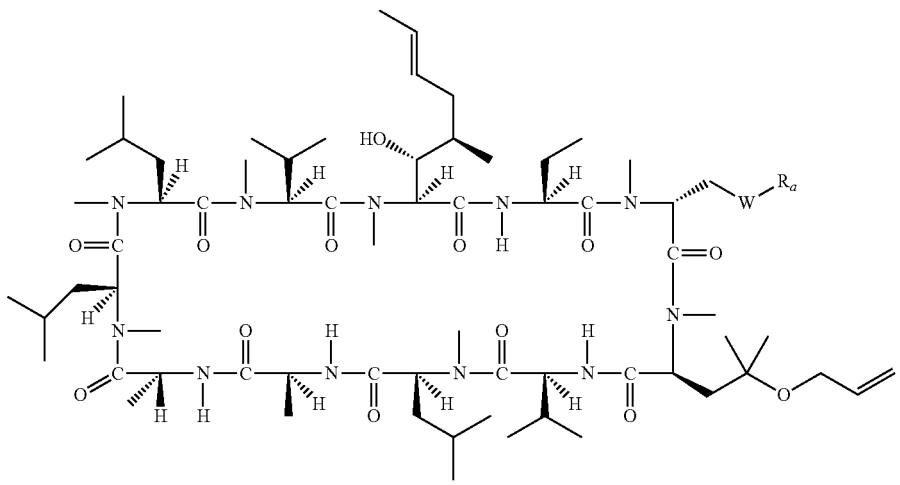

| Ex. No. | W | $R_a$ | Name |
|---|---|---|---|
| 1755 | S | (CH2)3COONa | [(S)-(3-Carboxypropylthio)methyl-Sar]-3-[(γ-allyloxy)-NMeLeu]-4-cyclosporin-sodium salt |
| 1756 | S | (CH2)3COOEt | [(S)-(3-Ethoxycarbonylpropylthio)methyl-Sar]-3-[(γ-allyloxy)-NMeLeu]-4-cyclosporin |
| 1757 | S | (CH2)4OH | [(S)-(4-Hydroxybutylthio)methyl-Sar]-3-[(γ-allyloxy)-NMeLeu]-4-cyclosporin |
| 1758 | S | (CH2)3C(CH3)2OH | [(S)-(4-Hydroxy-4-methylpentylthio)methyl-Sar]-3-[(γ-allyloxy)-NMeLeu]-4-cyclosporin |
| 1759 | S | (CH2)4N(CH3)2 | [(S)-(4-(N,N-Dimethylamino)butylthio)methyl-Sar]-3-[(γ-allyloxy)-NMeLeu]-4-cycloporin |
| 1760 | S | (CH2)4N(Et)2 | [(S)-(4-(N,N-Diethylamino)butylthio)methyl-Sar]-3-[(γ-allyloxy)-NMeLeu]-4-cyclosporin |
| 1761 | S | (CH2)4NHiBu | [(S)-(4-(N-Isobutylamino)butylthio)methyl-Sar]-3-[(γ-allyloxy)-NMeLeu]-4-cyclosporin |
| 1762 | S | (CH2)4N(Me)iBu | [(S)-(4-(N-Isobutyl-N-methylamino)butylthio)methyl-Sar]-3-[(γ-allyloxy)-NMeLeu]-4-cyclosporin |

TABLE 6-continued

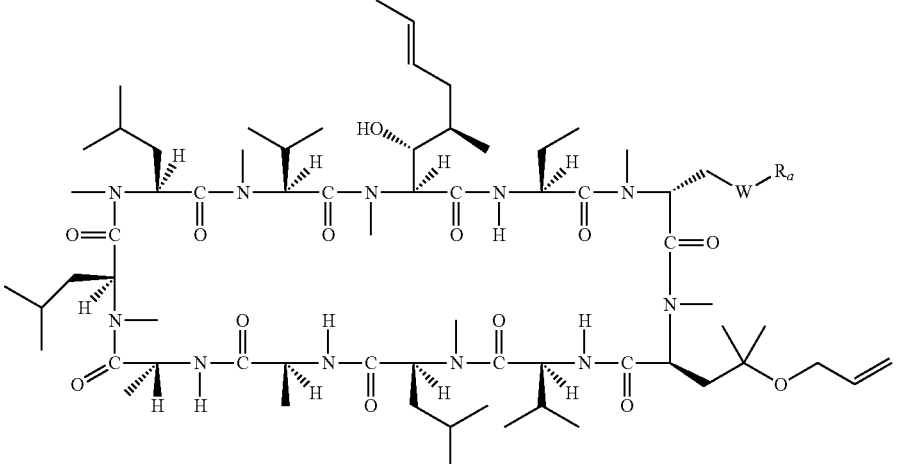

| Ex. No. | W | Rₐ | Name |
|---|---|---|---|
| 1763 | S | 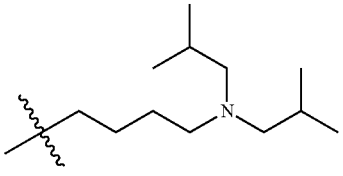 [SMILES: *CCCCN(CC(C)C)CC(C)C] | [(S)-(4-(N,N-Diisobutylamino)butylthio)methyl-Sar]-3-[(γ-allyloxy)-NMeLeu]-4-cyclosporin |
| 1764 | S | 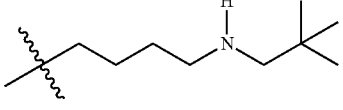 | [(S)-(4-(N-Neopentylamino)butylthio)methyl-Sar]-3-[(γ-allyloxy)-NMeLeu]-4-cyclosporin |
| 1765 | S | 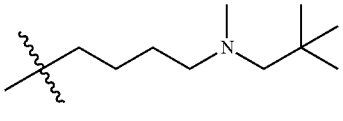 [SMILES: *CCCCN(C)CC(C)(C)C] | [(S)-(4-(N-Methyl-N-Neopentylamino)butylthio)methyl-Sar]-3-[(γ-allyloxy)-NMeLeu]-4-cyclosporin |
| 1766 | S | 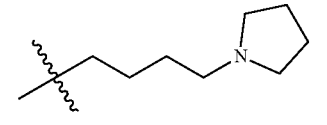 [SMILES: *CCCCN1CCCC1] | [(S)-(4-(N-Pyrrolidinyl)butylthio)methyl-Sar]-3-[(γ-allyloxy)-NMeLeu]-4-cyclosporin |
| 1767 | S | 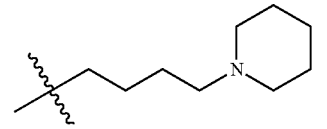 [SMILES: *CCCCN1CCCCC1] | [(S)-(4-(N-Piperidinyl)butylthio)methyl-Sar]-3-[(γ-allyloxy)-NMeLeu]-4-cyclosporin |
| 1768 | S | 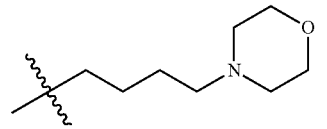 [SMILES: *CCCCN1CCOCC1] | [(S)-(4-(N-Morpholino)butylthio)methyl-Sar]-3-[(γ-allyloxy)-NMeLeu]-4-cyclosporin |
| 1769 | S | 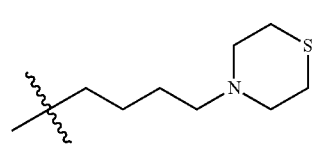 [SMILES: *CCCCN1CCSCC1] | [(S)-(4-(N-Thiomorpholino)butylthio)methyl-Sar]-3-[(γ-allyloxy)-NMeLeu]-4-cyclosporin |

TABLE 6-continued

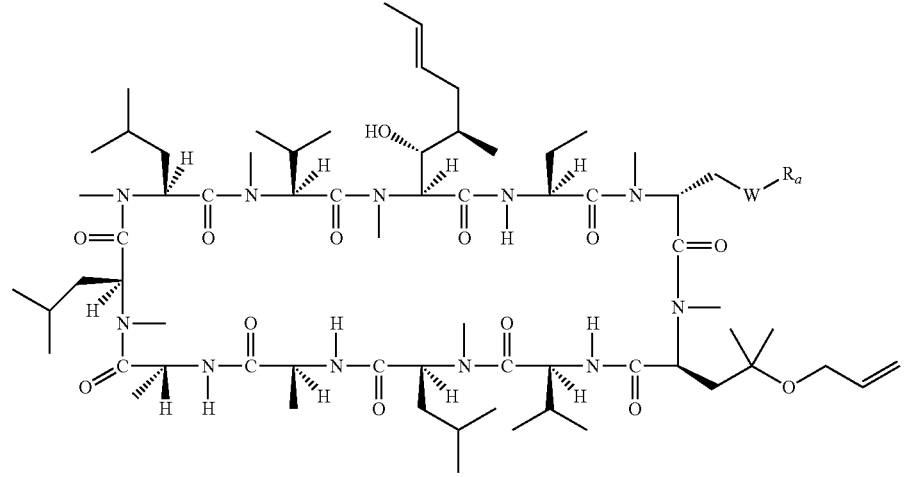

| Ex. No. | W | R<sub>a</sub> | Name |
|---|---|---|---|
| 1770 | S |  | [(S)-(4-Carboxypentylthio)methyl-Sar]-3-[(γ-allyloxy)-NMeLeu]-4-cyclosporin |
| 1771 | S |  | [(S)-(4-Carboxypentylthio)methyl-Sar]-3-[(γ-allyloxy)-NMeLeu]-4-cyclosporin-potassium salt |
| 1772 | S |  | [(S)-(4-Carboxypentylthio)methyl-Sar]-3-[(γ-allyloxy)-NMeLeu]-4-cyclosporin-sodium salt |
| 1773 | S |  | [(S)-(4-Ethoxycarbonylpentylthio)methyl-Sar]-3-[(γ-allyloxy)-NMeLeu]-4-cyclosporin |
| 1774 | S |  | [(S)-((4,4'-Dicarboxy)butylthio)methyl-Sar]-3-[(γ-allyloxy)-NMeLeu]-4-cyclosporin |
| 1775 | S |  | [(S)-((4,4'-Dicarboxy)butylthio)methyl-Sar]-3-[(γ-allyloxy)-NMeLeu]-4-cyclosporin-dipotassium salt |
| 1776 | S |  | [(S)-((S)-3-Hydroxymethyl-4-ethoxycarbonybutylthio)methyl-Sar]-3-[(γ-allyloxy)-NMeLeu]-4-cyclosporin |
| 1777 | S |  | [(S)-((R)-3-Hydroxymethyl-4-ethoxycarbonybutylthio)methyl-Sar]-3-[(γ-allyloxy)-NMeLeu]-4-cyclosporin |

TABLE 6-continued

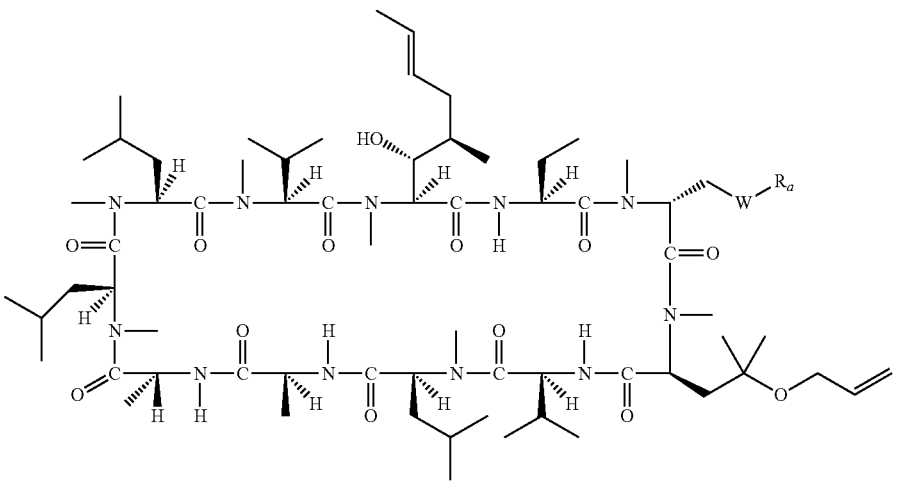

| Ex. No. | W | $R_a$ | Name |
|---|---|---|---|
| 1778 | O | 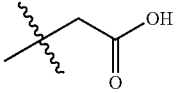 | [(R)-(Carboxymethoxy)methyl-Sar]-3-[(γ-allyloxy)-NMeLeu]-4-cyclosporin |
| 1779 | O | 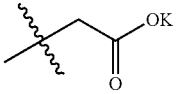 | [(R)-(Carboxymethoxy)methyl-Sar]-3-[(γ-allyloxy)-NMeLeu]-4-cyclosporin-potassium salt |
| 1780 | O | 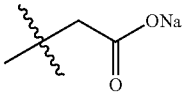 | [(R)-(Carboxymethoxy)methyl-Sar]-3-[(γ-allyloxy)-NMeLeu]-4-cyclosporin-sodium salt |
| 1781 | O | 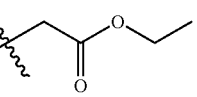 | [(R)-((Ethoxycarbonyl)methoxy)methyl-Sar]-3-[(γ-allyloxy)-NMeLeu]-4-cyclosporin |
| 1782 | O | 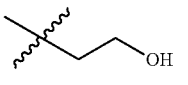 | [(R)-(2-Hydroxyethoxy)methyl-Sar]-3-[(γ-allyloxy)-NMeLeu]-4-cyclosporin |
| 1783 | O | 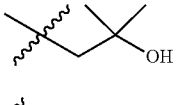 | [(R)-(2-Hydroxy-2-methylpropoxy)methyl-Sar]-3-[(γ-allyloxy)-NMeLeu]-4-cyclosporin |
| 1784 | O | 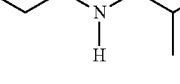 | [(R)-(2-(N-Isobutylamino)ethoxy)methyl-Sar]-3-[(γ-allyloxy)-NMeLeu]-4-cyclosporin |
| 1785 | O | 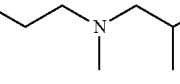 | [(R)-(2-(N-Isobutyl-N-methylamino)ethoxy)methyl-Sar]-3-[(γ-allyloxy)-NMeLeu]-4-cyclosporin |
| 1786 | O | 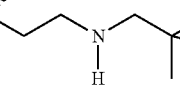 | [(R)-(2-(N-Neopentylamino)ethoxy)methyl-Sar]-3-[(γ-allyloxy)-NMeLeu]-4-cyclosporin |
| 1787 | O | 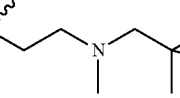 | [(R)-(2-(N-Methyl-N-neopentylamino)ethoxy)methyl-Sar]-3-[(γ-allyloxy)-NMeLeu]-4-cyclosporin |

TABLE 6-continued

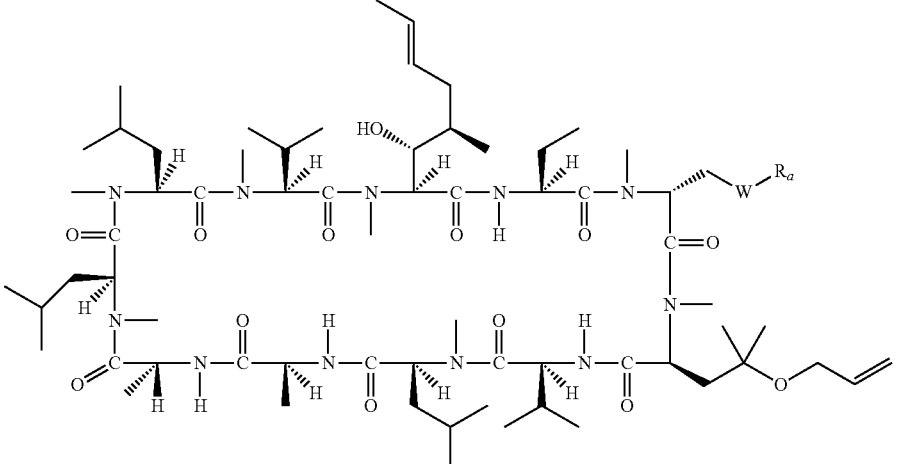

| Ex. No. | W | $R_a$ | Name |
|---|---|---|---|
| 1788 | O | 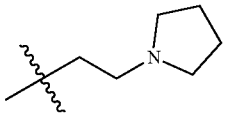 [SMILES: *CCN1CCCC1] | [(R)-(2-(N-Pyrrolidinyl)ethoxy)methyl-Sar]-3-[(γ-allyloxy)-NMeLeu]-4-cyclosporin |
| 1789 | O | 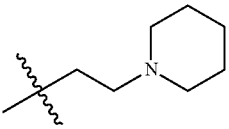 [SMILES: *CCN1CCCCC1] | [(R)-(2-(N-Piperidinyl)ethoxy)methyl-Sar]-3-[(γ-allyloxy)-NMeLeu]-4-cyclosporin |
| 1790 | O | 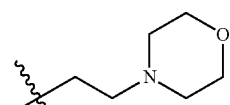 | [(R)-(2-(N-Morpholino)ethoxy)methyl-Sar]-3-[(γ-allyloxy)-NMeLeu]-4-cyclosporin |
| 1791 | O | 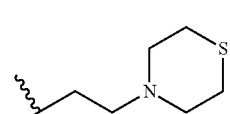 | [(R)-(2-(N-Thiomorpholino)ethoxy)methyl-Sar]-3-[(γ-allyloxy)-NMeLeu]-4-cyclosporin |
| 1792 | O | 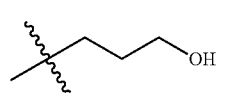 [SMILES: *CCCO] | [(R)-(3-Hydroxypropoxy)methyl-Sar]-3-[(γ-allyloxy)-NMeLeu]-4-cyclosporin |
| 1793 | O | 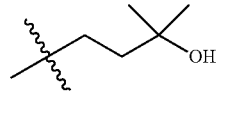 [SMILES: *CCC(C)(C)O] | [(R)-(3-Hydroxy-3-methylbutoxy)methyl-Sar]-3-[(γ-allyloxy)-NMeLeu]-4-cyclosporin |
| 1794 | O | 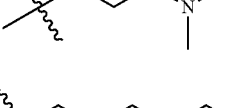 | [(R)-(3-(N,N-Dimethylamino)propoxy)methyl-Sar]-3-[(γ-allyloxy)-NMeLeu]-4-cyclosporin |
| 1795 | O | 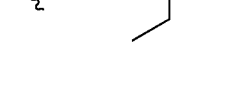 | [(R)-(3-(N,N-Diethylamino)propoxy)methyl-Sar]-3-[(γ-allyloxy)-NMeLeu]-4-cyclosporin |

TABLE 6-continued

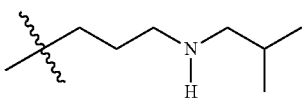 [SMILES: *CCCNCC(C)C]

| Ex. No. | W | $R_a$ | Name |
|---|---|---|---|
| 1796 | O | 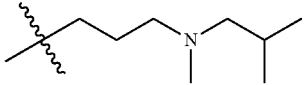 [SMILES: *CCCN(C)CC(C)C] | [(R)-(3-(N-Isobutylamino)propoxy)methyl-Sar]-3-[(γ-allyloxy)-NMeLeu]-4-cyclosporin |
| 1797 | O | 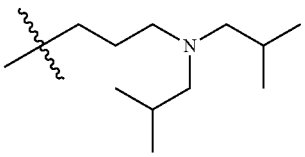 [SMILES: *CCCN(CC(C)C)CC(C)C] | [(R)-(3-(N-Isobutyl-N-methylamino)propoxy)methyl-Sar]-3-[(γ-allyloxy)-NMeLeu]-4-cyclosporin |
| 1798 | O | 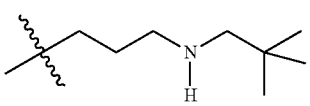 | [(R)-(3-(N,N-Diisobutylamino)propoxy)methyl-Sar]-3-[(γ-allyloxy)-NMeLeu]-4-cyclosporin |
| 1799 | O | 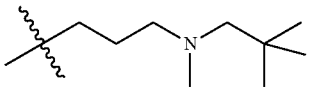 [SMILES: *CCCN(C)CC(C)(C)C] | [(R)-(3-(N-Neopentylamino)propoxy)methyl-Sar]-3-[(γ-allyloxy)-NMeLeu]-4-cyclosporin |
| 1800 | O | 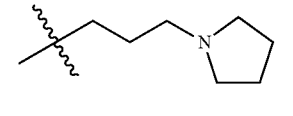 [SMILES: *CCCN1CCCC1] | [(R)-(3-(N-Methyl-N-neopentylamino)propoxy)methyl-Sar]-3-[(γ-allyloxy)-NMeLeu]-4-cyclosporin |
| 1801 | O | 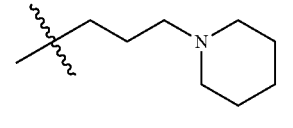 [SMILES: *CCCN1CCCCC1] | [(R)-(3-(N-Pyrrolidinyl)propoxy)methyl-Sar]-3-[(γ-allyloxy)-NMeLeu]-4-cyclosporin |
| 1802 | O | 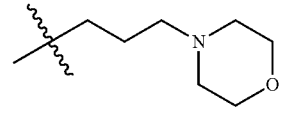 [SMILES: *CCCN1CCOCC1] | [(R)-(3-(N-Piperidinyl)propoxy)methyl-Sar]-3-[(γ-allyloxy)-NMeLeu]-4-cyclosporin |
| 1803 | O | 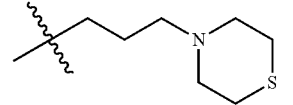 [SMILES: *CCCN1CCSCC1] | [(R)-(3-(N-Morpholino)propoxy)methyl-Sar]-3-[(γ-allyloxy)-NMeLeu]-4-cyclosporin |
| 1804 | O | | [(R)-(3-(N-Thiomorpholino)propoxy)methyl-Sar]-3-[(γ-allyloxy)-NMeLeu]-4-cyclosporin |

TABLE 6-continued

| Ex. No. | W | $R_a$ | Name |
|---|---|---|---|
| 1805 | O | (CH2)3-COOH | [(R)-(3-Carboxypropoxy)methyl-Sar]-3-[(γ-allyloxy)-NMeLeu]-4-cyclosporin |
| 1806 | O | (CH2)3-COOK | [(R)-(3-Carboxypropoxy)methyl-Sar]-3-[(γ-allyloxy)-NMeLeu]-4-cyclosporin-potassium salt |
| 1807 | O | (CH2)3-COONa | [(R)-(3-Carboxypropoxy)methyl-Sar]-3-[(γ-allyloxy)-NMeLeu]-4-cyclosporin-sodium salt |
| 1808 | O | (CH2)3-COOEt | [(R)-(3-(Ethoxycarbonyl)propoxy)methyl-Sar]-3-[(γ-allyloxy)-NMeLeu]-4-cyclosporin |
| 1809 | O | (CH2)4-OH | [(R)-(4-Hydroxybutoxy)methyl-Sar]-3-[(γ-allyloxy)-NMeLeu]-4-cyclosporin |
| 1810 | O | (CH2)3-C(CH3)2-OH | [(R)-(4-Hydroxy-4-methylpentyloxy)methyl-Sar]-3-[(γ-allyloxy)-NMeLeu]-4-cyclosporin |
| 1811 | O | (CH2)4-N(CH3)2 | [(R)-(4-(N,N-Dimethylamino)butoxy)methyl-Sar]-3-[(γ-allyloxy)-NMeLeu]-4-cyclosporin |
| 1812 | O | (CH2)4-N(Et)2 | [(R)-(4-(N,N-Diethylamino)butoxy)methyl-Sar]-3-[(γ-allyloxy)-NMeLeu]-4-cyclosporin |
| 1813 | O | (CH2)4-NH-iBu | [(R)-(4-(N-Isobutylamino)butoxy)methyl-Sar]-3-[(γ-allyloxy)-NMeLeu]-4-cyclosporin |

TABLE 6-continued

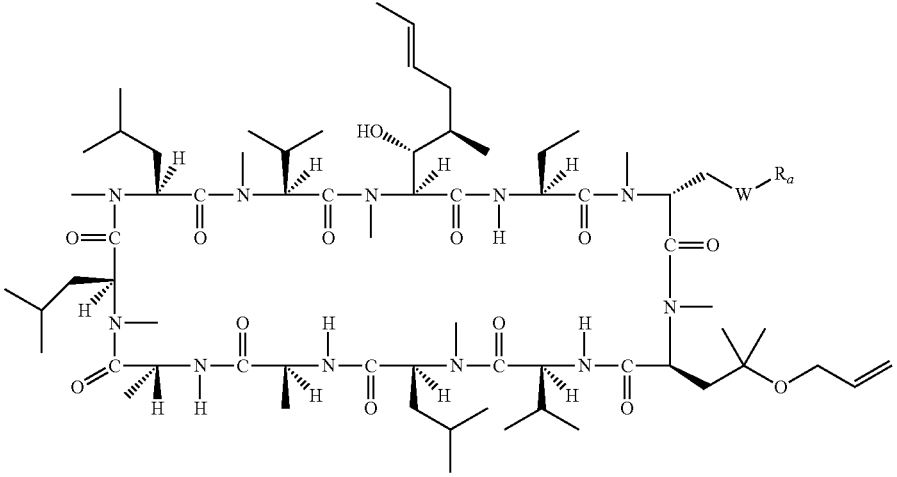

| Ex. No. | W | $R_a$ | Name |
|---|---|---|---|
| 1814 | O | 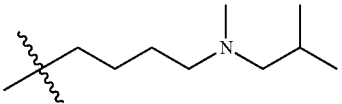 [SMILES: *CCCCN(C)CC(C)C] | [(R)-(4-(N-Isobutyl-N-methylamino)butoxy)methyl-Sar]-3-[(γ-allyloxy)-NMeLeu]-4-cyclosporin |
| 1815 | O | 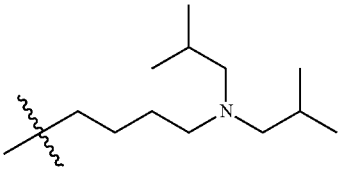 [SMILES: *CCCCN(CC(C)C)CC(C)C] | [(R)-(4-(N,N-Diisobutylamino)butoxy)methyl-Sar]-3-[(γ-allyloxy)-NMeLeu]-4-cyclosporin |
| 1816 | O | 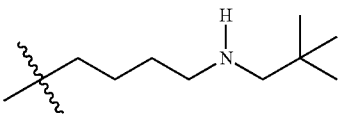 [SMILES: *CCCCNCC(C)(C)C] | [(R)-(4-(N-Neopentylamino)butoxy)methyl-Sar]-3-[(γ-allyloxy)-NMeLeu]-4-cyclosporin |
| 1817 | O | 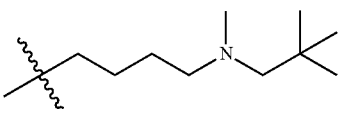 [SMILES: *CCCCN(C)CC(C)(C)C] | [(R)-(4-(N-Methyl-N-neopentylamino)butoxy)methyl-Sar]-3-[(γ-allyloxy)-NMeLeu]-4-cyclosporin |
| 1818 | O | 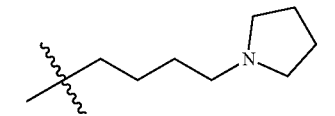 [SMILES: *CCCCN1CCCC1] | [(R)-(4-(N-Pyrrolidinyl)butoxy)methyl-Sar]-3-[(γ-allyloxy)-NMeLeu]-4-cyclosporin |
| 1819 | O | 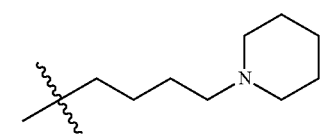 [SMILES: *CCCCN1CCCCC1] | [(R)-(4-(N-Piperidinyl)butoxy)methyl-Sar]-3-[(γ-allyloxy)-NMeLeu]-4-cyclosporin |
| 1820 | O | 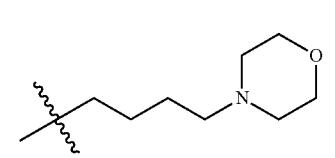 [SMILES: *CCCCN1CCOCC1] | [(R)-(4-(N-Morpholino)butoxy)methyl-Sar]-3-[(γ-allyloxy)-NMeLeu]-4-cyclosporin |

TABLE 6-continued

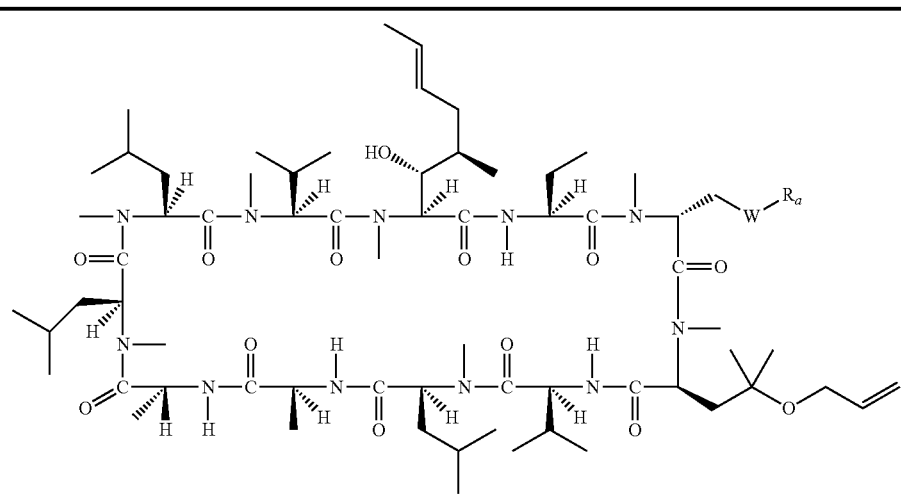

| Ex. No. | W | $R_a$ | Name |
|---|---|---|---|
| 1821 | O | 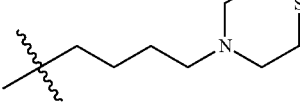 | [(R)-(4-(N-Thiomorpholino)butoxy)methyl-Sar]-3-[(γ-allyloxy)-NMeLeu]-4-cyclosporin |
| 1822 | O | 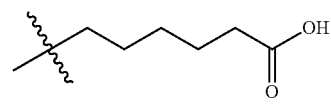 [SMILES: *CCCCCC(=O)O] | [(R)-(4-Carboxypentyloxy)methyl-Sar]-3-[(γ-allyloxy)-NMeLeu]-4-cyclosporin |
| 1823 | O | 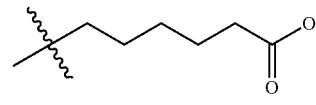 | [(R)-(4-Carboxypentyloxy)methyl-Sar]-3-[(γ-allyloxy)-NMeLeu]-4-cycloporin-potassium salt |
| 1824 | O | 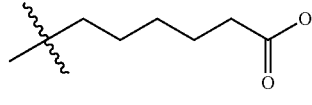 | [(R)-(4-Carboxypentyloxy)methyl-Sar]-3-[(γ-allyloxy)-NMeLeu]-4-cyclosporin-sodium salt |
| 1825 | O | 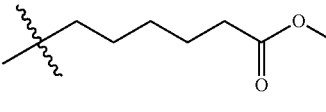 | [(R)-(4-Ethoxycarbonylpentyloxy)methyl-Sar]-3-[(γ-allyloxy)-NMeLeu]-4-cyclosporin |
| 1826 | O | 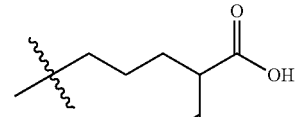 | [(R)-((4,4'-Dicarboxy)butoxy)methyl-Sar]-3-[(γ-allyloxy)-NMeLeu]-4-cyclosporin |
| 1827 | O | 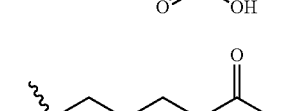 | [(R)-((4,4'-Dicarboxy)butoxy)methyl-Sar]-3-[(γ-allyloxy)-NMeLeu]-4-cyclosporin-dipotassium salt |
| 1828 | O | 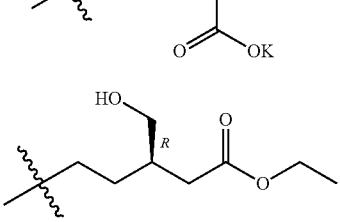 | [(R)-((R)-3-Hydroxymethyl-4-ethoxycarbonybutoxy)methyl-Sar]-3-[(γ-allyloxy)-NMeLeu]-4-cyclosporin |

TABLE 6-continued

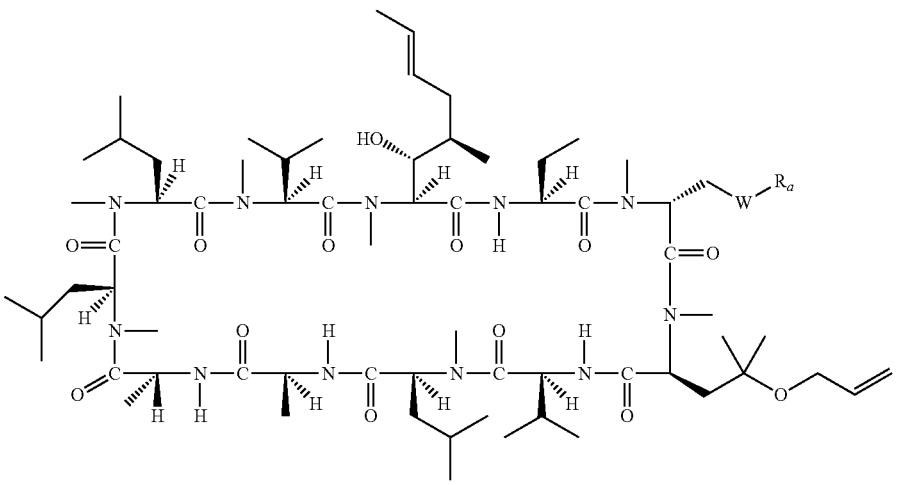

| Ex. No. | W | $R_a$ | Name |
|---|---|---|---|
| 1829 | O | 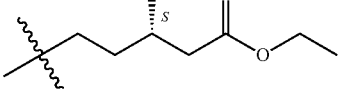 | [(R)-((S)-3-Hydroxymethyl-4-ethoxycarbonybutoxy)methyl-Sar]-3-[(γ-allyloxy)-NMeLeu]-4-cyclosporin |
| 1830 | $CH_2$ | —$NO_2$ | [(R)-2-Nitroethyl-Sar]-3-[(γ-allyloxy)-NMeLeu]-4-cyclosporin |
| 1831 | $CH_2$ | —$NH_2$ | [(R)-2-Aminoethyl-Sar]-3-[(γ-allyloxy)-NMeLeu]-4-cyclosporin |
| 1832 | $CH_2$ | —$N(CH_3)_2$ | [(R)-2-(N,N-Dimethylamino)ethyl-Sar]-3-[(γ-allyloxy)-NMeLeu]-4-cyclosporin |
| 1833 | $CH_2$ | —$N(CH2CH_3)_2$ | [(R)-2-(N,N-Diethylamino)ethyl-Sar]-3-[(γ-allyloxy)-NMeLeu]-4-cyclosporin |
| 1834 | $CH_2$ | —$CH_2N(CH_3)_2$ | [(R)-2-(N,N-Dimethylamino)propyl-Sar]-3-[(γ-allyloxy)-NMeLeu]-4-cycloporin |
| 1835 | $CH_2$ | —$(COOEt)_2$ | [(R)-2,2-Di(ethoxycarbonyl)ethyl)-Sar]-3-[(γ-allyloxy)-NMeLeu]-4-cyclosporin |
| 1836 | $CH_2$ | —$(CH_2OH)_2$ | [(R)-2,2-Di(hydroxylmethyl)ethyl)-Sar]-3-[(γ-allyloxy)-NMeLeu]-4-cycloporin |

Example 1837

Stability Testing of [(R)-3-(N,N-Dimethylamino)ethylthio-Sar]-3-[(γ-Hydroxy)-NMeLeu]-4-cyclosporin (SCY-635) and Cyclosporin Derivatives Stability of Cyclosporin derivatives was evaluated in methanol at 65° C. and 50° C., and HPLC was used to monitor possible isomerization of these compounds. It was found that SCY-635 is not stable and can easily convert to its corresponding epimer, which is expected to have low or no anti-viral activity.

Epimerization of SCY-635* in MeOH at 65° C.

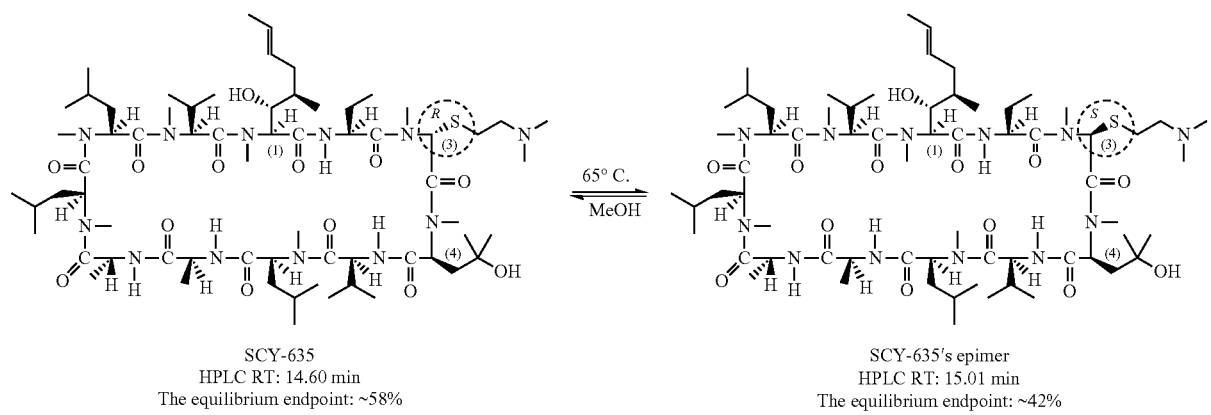

SCY-635
HPLC RT: 14.60 min
The equilibrium endpoint: ~58%

SCY-635's epimer
HPLC RT: 15.01 min
The equilibrium endpoint: ~42%

| Epimerization | SCY-635's epimer % | | | | |
|---|---|---|---|---|---|
| | 2 hours | 4 hours | 6 hours | 8 hours | 10 hours |
| SCY-635 ⇌ SCY-635's epimer | 24% | 35% | 39% | 41% | 43% |

*SCY-635 was prepared according to a method described by: Evans M, et al., 2003, *Bioorg. Med. Chem. Lett.*, 4, 4415-4419; Carry J, et al., 2004, *Synlett*. 2, 316-320; or U.S. Pat. No. 5,994,299 (each of which is incorporated herein by reference).

Epimerization of SCY-635's epimer* in MeOH at 65° C.

| Epimerization | SCY-635% | | |
|---|---|---|---|
| | 3 hours | 6 hours | 10 hours |
| SCY-635's epimer ⇌ SCY-635 | 51% | 58% | 58% |

\* During the stability study, it was found that SCY-635 transformed into its epimer, which was separated as a pure compound. HPLC RT: 14.60 minutes (SCY-635) and: 15.01 minutes (its epimer) (C8 reverse phase column, 250 mm, acetonitrile/0.077% $NH_4OAc$ in water, operation temperature: 64° C.; Detector: 210 nm).

When the epimer was treated with MeOH at 65° C., it also was found that it partially transformed to SCY-635. At the endpoint of the equilibrium, this solution contained about 58% of SCY-635 and about 42% of epimer.

TABLE 7

Epimerization of [(R)-2-(N, N-dimethylamino)ethylthio-Sar]-3-cyclosporin in MeOH at 65° C.

| Compound | Epimerization % | | |
|---|---|---|---|
| | 2 hours | 4 hours | 6 hours |
| [(R)-2-(N, N-Dimethylamino)ethylthio-Sar]-3-cyclosporin | ~12% | ~19% | ~23% |

TABLE 8

Epimerization of [(R)-3-(N-Morpholino)propylthio-Sar]-3-[(γ-hydroxy)-NMeLeu]-4-cyclosporin in MeOH at 65° C.

| Compound | Epimerization % in MeOH at 65° C. | | | | |
|---|---|---|---|---|---|
| | 2 hours | 4 hours | 6 hours | 8 hours | 10 hours |
| [(R)-3-(Morpholino)propylthio-Sar]-3-[(γ-hydroxy)-NMeLeu]-4-cyclosporin | 0% | 0% | 0% | Less than 1% | ~10% |

TABLE 9

Epimerization of [(R)-3-(N-Morpholino)propylthio-Sar]-3-[(γ-Methoxy)-NMeLeu]-4-cyclosporin in MeOH at 65° C.

| Compound | Epimerization % in MeOH at 65° C. | | | | | |
|---|---|---|---|---|---|---|
| | 2 hours | 4 hours | 10 hours | 22 hours | 30 hours | 38 hours |
| [(R)-3-(N-Morpholino)propylthio-Sar]-3-[(γ-methoxy)-NMeLeu]-4-cyclosporin | 0% | 0% | 0% | 0% | 0% | 0% |

TABLE 10
Epimerization of Cyclosporin Derivatives in MeOH at 50° C.
| Compounds | Epimerization % | | |
|---|---|---|---|
| | 29 hours | 77 hours | 125 hours |
| 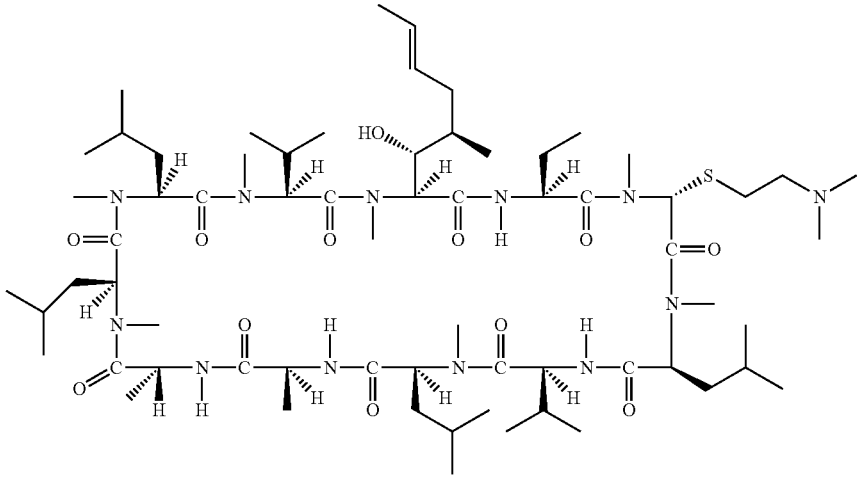<br>[(R)-2-(N, N-Dimethylamino)ethylthio-Sar]-3-cyclosporin | ~26% | ~32% | ~35% |
| 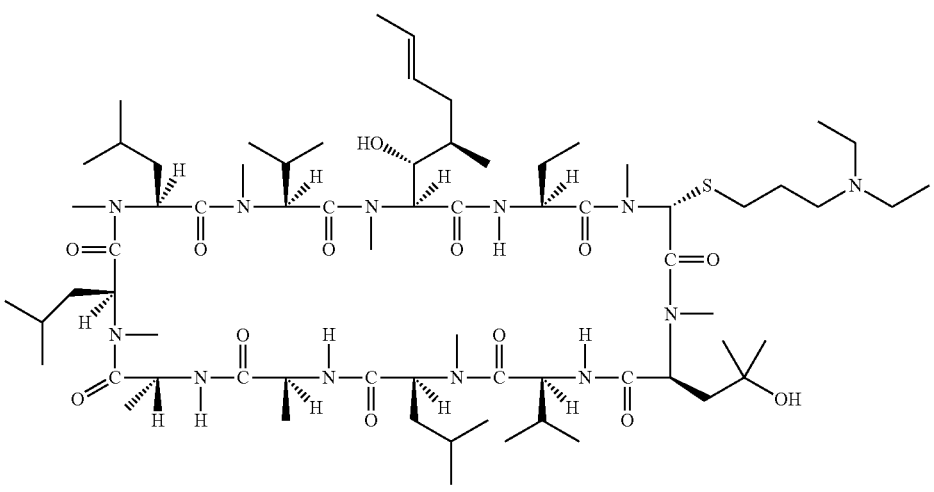<br>[(R)-3-(N, N Diethylamino)propylthio-Sar]-3-[(γ-hydroxy)-NMeLeu]-4-cyclosporin | 0% | Less than 1% | ~12% |

TABLE 10-continued

Epimerization of Cyclosporin Derivatives in MeOH at 50° C.

| Compounds | Epimerization % | | |
|---|---|---|---|
| | 29 hours | 77 hours | 125 hours |
| [(R)-3-(N, N-Diethylamino)propylthio-Sar]-3-[(γ-methoxy)-NMeLeu]-4-cyclosporin | 0% | 0% | 0% |
| [(R)-3-(N-Morpholino)propylthio-Sar]-3-[(γ-hydroxy)-NMeLeu]-4-cyclosporin | 0% | 0% | 0% |

TABLE 10-continued
Epimerization of Cyclosporin Derivatives in MeOH at 50° C.
| Compounds | Epimerization % | | |
|---|---|---|---|
| | 29 hours | 77 hours | 125 hours |
| | 0% | 0% | 0% |
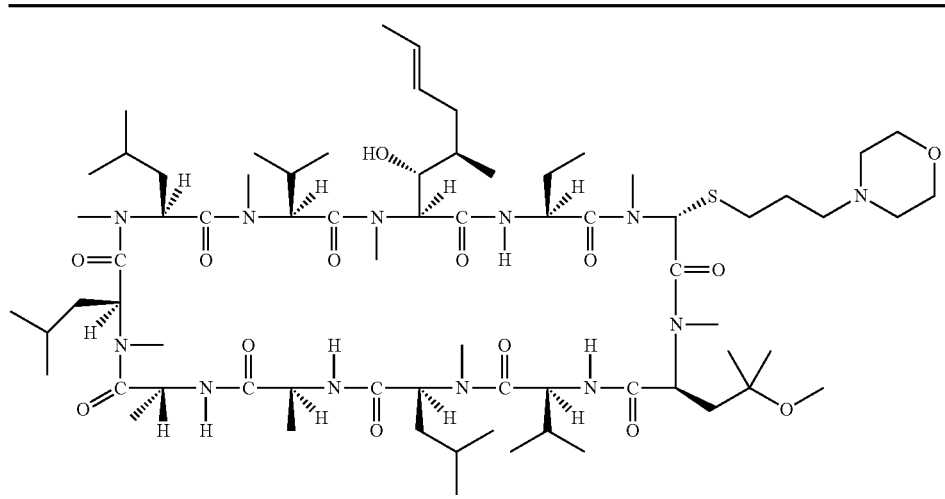
[(R)-3-(N-Morpholino)propylthio-Sar]-3-[(γ-methoxy)-NMeLeu]-4-cyclosporin
~4%  ~10%  ~16%
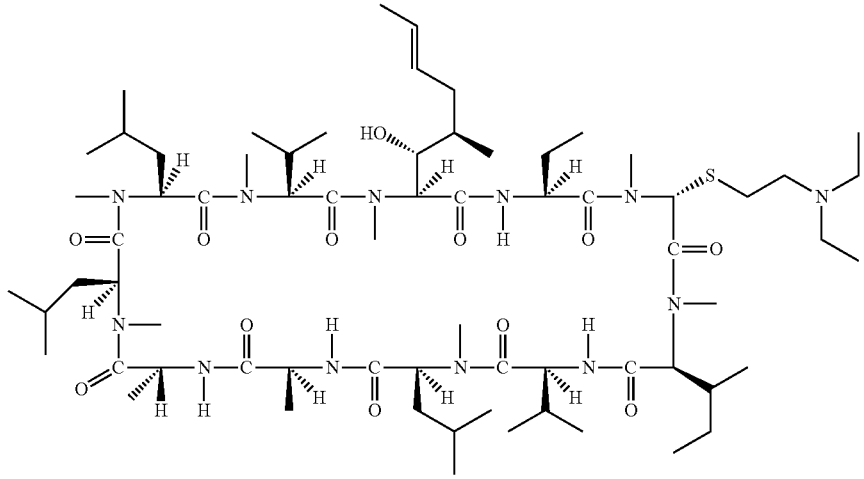
[(R)-2-(N,N-Diethylamino)ethylthio-Sar]-3-[NMeIle]-4-cyclosporin

TABLE 10-continued
Epimerization of Cyclosporin Derivatives in MeOH at 50° C.
| Compounds | Epimerization % | | |
|---|---|---|---|
| | 29 hours | 77 hours | 125 hours |
| | 0% | 0% | 0% |
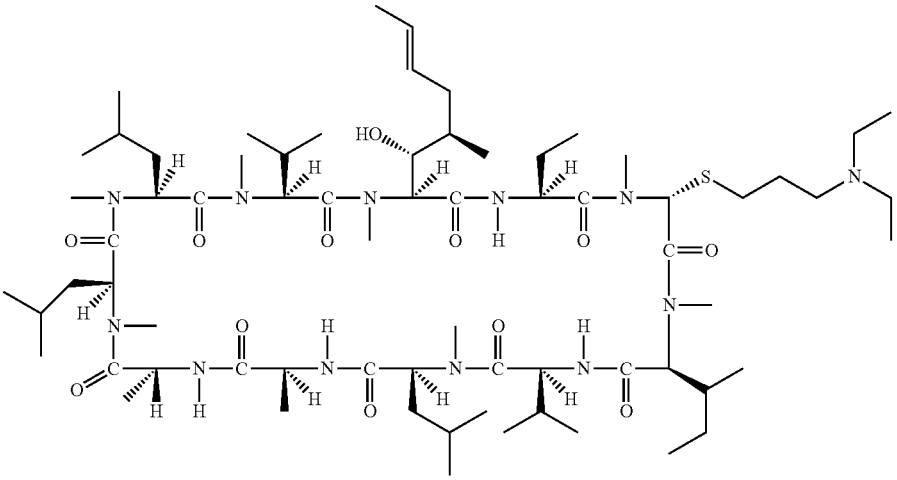
[(R)-3-(N,N-Diethylamino)propylthio-Sar]-3-[NMeIle]-4-cyclosporin
| | 0% | 0% | 0% |
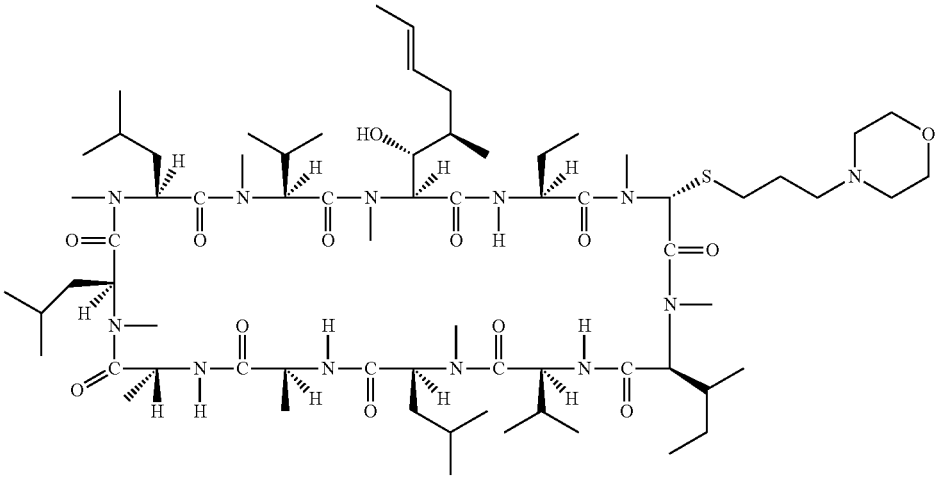
[(R)-3-(N-Morpholino)propylthio-Sar]-3-[NMeIle]-4-cyclosporin TABLE 10-continued
Epimerization of Cyclosporin Derivatives in MeOH at 50° C.
| Compounds | Epimerization % | | |
|---|---|---|---|
| | 29 hours | 77 hours | 125 hours |
| | 0% | 0% | 0% |
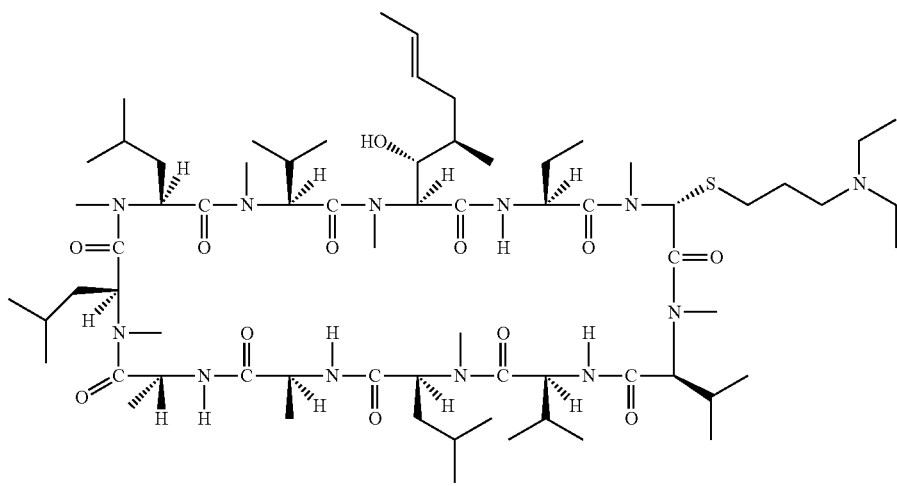
[(R)-3-(N,N-Diethylamino)propylthio-Sar]-3-[N-MeVal]-4-cyclosporin
| | 0% | 0% | 0% |
|---|---|---|---|
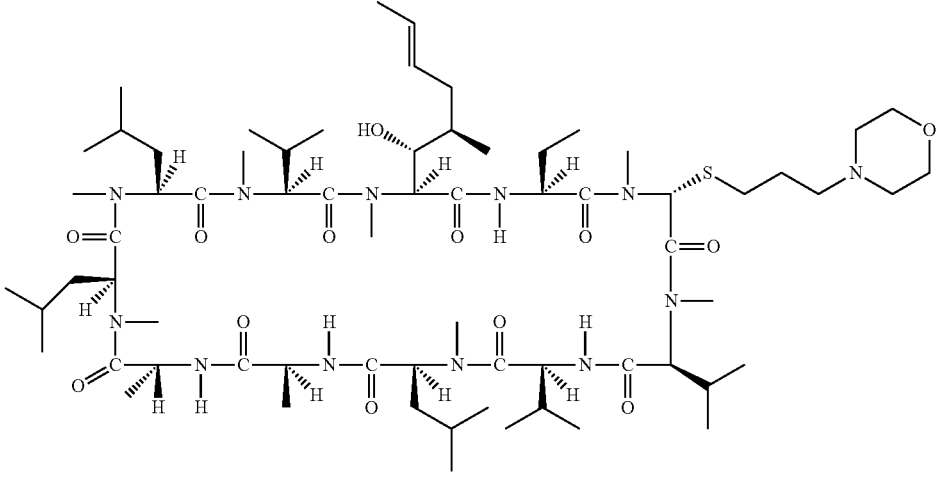
[(R)-3-(N-Morpholino)propylthio-Sar]-3-[NMeVal]-4-cyclosporin

TABLE 11

Epimerization of Cyclosporin Derivatives in MeOH at 50° C.-58° C.

| Compound | Epimerization % after 168 hours |
|---|---|
| [(S)-(2-(N,N-Diethylamino)ethylthio)methyl-Sar]-3-[(γ-hydroxy)-NMeLeu]-4-cyclosporin (Example 32, isomer B) | 0% |
| [(R)-(2-(N,N-Diethylamino)ethoxy)methyl-Sar]-3-[(γ-hydroxy)-NMeLeu]-4-cyclosporin (Example 105) | 0% |
| [(R)-(2-(N,N-Diethylamino)ethoxy)methyl-Sar]-3-cyclosporin (Example 8) | 0% |

TABLE 11-continued
Epimerization of Cyclosporin Derivatives in MeOH at 50° C.-58° C.
| Compound | Epimerization % after 168 hours |
|---|---|
| 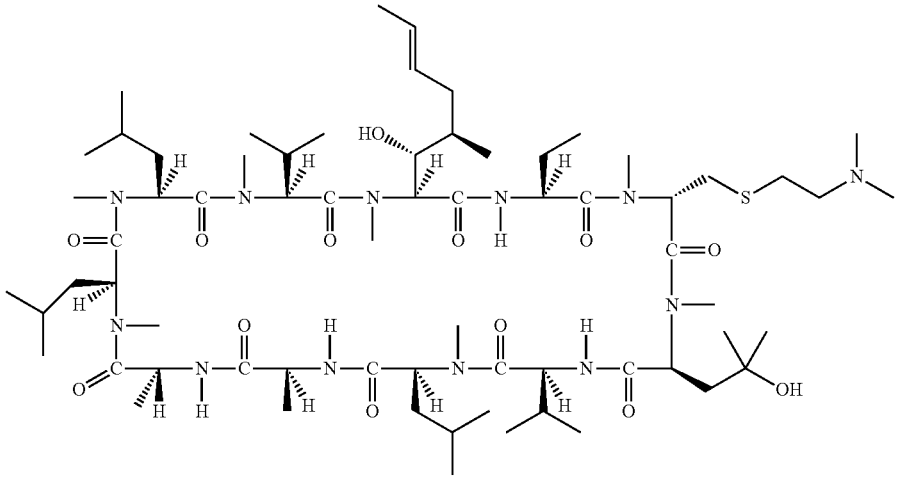 [(S)-(2-(N,N-Dimethylamino)ethylthio)methyl-Sar]-3-[(γ-hydroxy)-NMeLeu]-4-cyclosporin (Example 31, isomer B) | 0% |
| 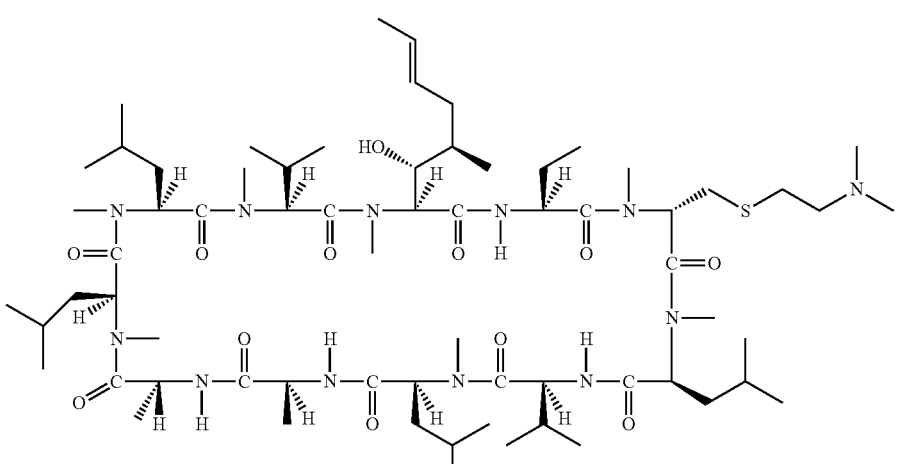 [(S)-(2-(N,N-Dimethylamino)ethylthio)methyl-Sar]-3-cyclosporin (Example 6, isomer B) | 0% |
| 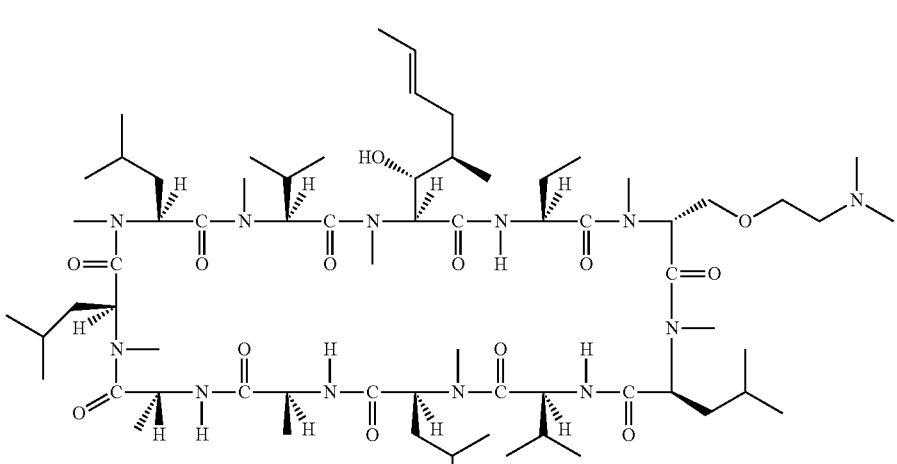 [(R)-(2-(N,N-Dimethylamino)ethoxy)methyl-Sar]-3-cyclosporin (Example 14) | 0% |

TABLE 11-continued

Epimerization of Cyclosporin Derivatives in MeOH at 50° C.-58° C.

| Compound | Epimerization % after 168 hours |
|---|---|
| [(S)-(2-(N,N-Diethylamino)ethylthio)methyl-Sar]-3-cyclosporin (Example 7, isomer B) | 0% |
| [(S)-(3-(N-Morpholino)propylthio)methyl-Sar]-3-[(γ-hydroxy)-NMeLeu]-4-cyclosporin (Example 65)) | 0% |
| [(S)-(3-(N,N-Dimethylamino)propylthio)methyl-Sar]-3-[(γ-hydroxy)-NMeLeu]-4-cyclosporin (Example 56) | 0% |

TABLE 11-continued

Epimerization of Cyclosporin Derivatives in MeOH at 50° C.-58° C.

| Compound | Epimerization % after 168 hours |
|---|---|
| [(S)-(3-(N-Piperidinyl)propylthio)methyl-Sar]-3-[(γ-hydroxy)-NMeLeu]-4-cyclosporin (Example 63) | 0% |
| [(S)-(3-(N,N-Diethylamino)propylthio)methyl-Sar]-3-[(γ-hydroxy)-N-MeLeu]-4-cyclosporin (Example 57) | 0% |

Based on the isomerization data, the inventors suggest that the epimerization of SCY-635 occurs through the following reaction mechanism:

group on leucine at position 4, elongating side carbon chain (e.g., with 3 carbons or higher), and/or substituting the amine terminal at position 3 with a bulky side chain can

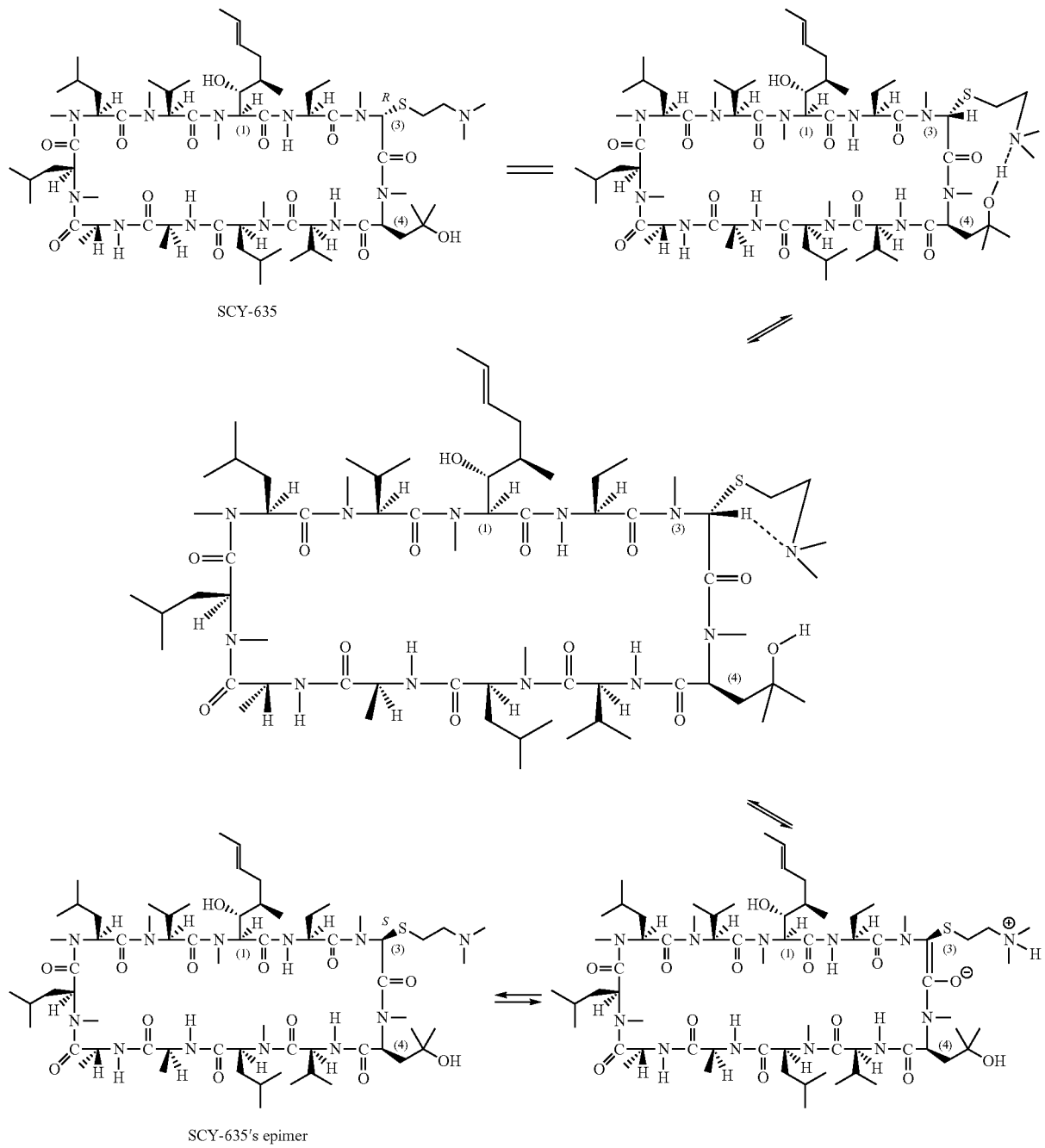

SCY-635

SCY-635's epimer

Thus, the two carbon side chain at position 3 of the sarcosine of cyclosporine contributes to the instability, because it can form a six-membered ring transition state, and stimulate the epimerization. Additionally, the epimerization is accelerated by the γ-hydroxyl group at the 4-position of leucine.

Accordingly, the inventors envisioned novel cyclosporine derivatives having enhanced stability while maintaining good cyclophilin binding activity. In particular, the inventors have surprisingly found that the masking the γ-hydroxyl prevent or minimize the epimerization. Specially, when the methylene substituents are introduced on position-3, those analogs are very stable, and can prevent the epimerization.

Example 1838

Anti HCV Activity of Cyclosporin Derivatives

Anti-HCV activity of cyclosporine derivatives were evaluated in the HCV subgenomic replicon assay. The assay use the cell line ET (luc-ubi-neo/ET), which is a Huh7 human hepatoma cell line harboring an HCV replicon with a stable luciferase (Luc) reporter. HCV RNA replication was assessed by quantifying HCV replicon-derived luciferase activity. The antiviral activity of cyclosporine analogs were evaluated after drug treatment to derive $EC_{50}$ and $EC_{90}$ values by using the luciferase end point (Krieger, N., et al., 2001, *J Virol.* 75, 4614-4624; Pietschmann, T., et al., 2002, *J Virol.* 76, 4008-4021; each of which is incorporated herein by reference). Cytotoxicity was assessed in parallel.

TABLE 12

Testing results of certain representative compounds

| Compound | Antiviral activity $EC_{50}$ (µM) |
|---|---|
| Cyclosporine A | 0.41 |
| [N-MeIle]-4-cyclosporin (SDZ-NIM-811) | 0.15 |
| [N-MeVal]-4-cyclosporin (SDZ 220-384) | 0.17 |
| (S)-2-(N,N-Diethylamino)ethylthio-Sar]-3-[N-MeIle]-4-cyclosporin | 0.04 |
| (R)-2-(N,N-Diethylamino)ethylthio-Sar]-3-[N-MeIle]-4-cyclosporin | 1.87 |
| (S)-2-(N,N-Diethylamino)ethylthio-Sar]-3-[N-MeVal]-4-cyclosporin | 0.04 |
| (R)-2-(N,N-Diethylamino)ethylthio-Sar]-3-[N-MeVal]-4-cyclosporin | 3.66 |
| (S)-2-(N,N-Dimethylamino)ethylthio-Sar]-3-[N-MeVal]-4-cyclosporin | 0.13 |
| (S)-2-(N-neo-Pentylamino)ethylthio-Sar]-3-cyclosporin | 0.23 |
| (R)-2-(N-neo-Pentylamino)ethylthio-Sar]-3-cyclosporin | 3.09 |
| (S)-2-(N-iso-Butyl-N-iso-propylamino)ethylthio-Sar]-3-cyclosporin | 0.48 |
| (R)-2-(N-iso-Butyl-N-iso-propylamino)ethylthio-Sar]-3-cyclosporin | 4.65 |
| (S)-2-(N-Diethylamino)ethylthio-Sar]-3-cyclosporin | 0.16 |
| [(S)-2-(N,N-Diethylamino)ethylthio-Sar]-3-[(γ-Methylthio)methoxy-NMeLeu]-4-cyclosporin | 0.11 |

TABLE 13

Testing results of certain representative compounds

| Compound | Antiviral activity $EC_{50}$ (µM) |
|---|---|
| [N-MeVal]-4-cyclosporin (SDZ 220-384) | 0.12 |
| [(S)-2-(N,N-Dimethylamino)ethylthio-Sar]-3-[(γ-hydroxy)-N-MeLeu]-4-cyclosporin (SCY-635) | 0.08 |
| [(S)-3-(N-Morpholino)propylthio-Sar]-3-[(γ-hydroxy)-N-MeLeu]-4-cyclosporin | 0.05 |
| [(R)-3-(N-Morpholino)propylthio-Sar]-3-[(γ-hydroxy)-N-MeLeu]-4-dihydrocyclosporin | 0.15 |
| [(S)-3-(N-Morpholino)propylthio-Sar]-3-[(γ-methoxy)-N-MeLeu]-4-cyclosporin | 0.06 |
| (S)-3-(N,N-Diethylamino)propylthio-Sar]-3-[(γ-hydroxy)-N-MeLeu]-4-cyclosporin | 0.07 |
| [(S)-(3-(N-Morpholino)propylthio-Sar]-3-[(γ-ethoxy)methoxy-N-MeLeu]-4-cyclosporin | 0.16 |
| [(S)-2-(N,N-Diethylamino)ethylthio-Sar]-3-[(γ-methylthio)methoxy-N-MeLeu]-4-cyclosporin | 0.13 |
| [(S)-(3-(N-Morpholino)propylthio-Sar]-3-[(γ-methylthio)methoxy-N-MeLeu]-4-cyclosporin | 0.16 |
| [(S)-(3-(N-Morpholino)propylthio-Sar]-3-[(γ-benzyloxy)-N-MeLeu]-4-cyclosporin | 0.28 |
| [(S)-3-(N-Morpholino)propylthio-Sar]-3-[(γ-(4-Methoxy)-benzyloxy)-N-MeLeu]-4-cyclosporin | 0.28 |
| [(S)-3-(N-Morpholino)propylthio-Sar]-3-[(γ-allyloxy)-N-MeLeu]-4-cyclosporin | 0.15 |
| [(S)-(2-(N,N-Diethylamino)ethylthio)methyl-Sar]-3-[(γ-hydroxy)-N-MeLeu]-4-cyclosporin (isomer B) | 0.03 |
| [(R)-(2-(N,N-Diethylamino)ethylthio)methyl-Sar]-3-[(γ-Hydroxy)-N-MeLeu]-4-cyclosporin (isomer A) | 2.12 |

TABLE 13-continued

Testing results of certain representative compounds

| Compound | Antiviral activity $EC_{50}$ (µM) |
|---|---|
| [(γ-Methoxy)-N-MeLeu]-4-cyclosporin | 0.18 |
| [(γ-Methoxy)-N-MeLeu]-4-dihydrocyclosporin | 0.35 |
| [(γ-Methylthio)methoxy-N-MeLeu]-4-cyclospori | 0.40 |
| [γ-(2-Hydroxyethoxy)-N-MeLeu]-4-dihydrocyclosporin | 0.43 |
| [N-MeSer]-4-cyclosporin | 0.56 |

TABLE 14

Testing results of certain representative compounds

| Compound | Antiviral activity $EC_{50}$ (µM) |
|---|---|
| [(S)-(2-(N,N-Dimethylamino)ethylthio)methyl-Sar]-3-[γ-(Hydroxy)-N-MeLeu]-4-cyclosporin (isomer B) | 0.05 |
| [(R)-(2-(N,N-Diethylamino)ethylthio)methyl-Sar]-3-[γ-(Hydroxy)-N-MeLeu]-4-cyclosporin (isomer A) | 2.12 |
| [(S)-(2-(N,N-Diethylamino)ethylthio)methyl-Sar]-3-[(γ-hydroxy)-NMeLeu]-4-cyclosporin (isomer B) | 0.03 |
| [(S)-(2-(N-Morpholino)ethylthio)methyl-Sar]-3-[(γ-hydroxy)-NMeLeu]-4-cyclosporin | 0.02 |
| [(S)-(2-(N-Piperidinyl)ethylthio)methyl-Sar]-3-[(γ-hydroxy)-NMeLeu]-4-cyclosporin | 0.04 |
| [(S)-(2-(4-Methyl-N-piperazinyl)ethylthio)methyl-Sar]-3-[(γ-hydroxy)-NMeLeu]-4-cyclosporin | 0.03 |
| [(S)-(3-(N-Morpholino)propylthio)methyl-Sar]-3-[(γ-hydroxy)-NMeLeu]-4-cyclosporin | 0.02 |
| [(S)-(3-(N,N-Dimethylamino)propylthio)methyl-Sar]-3-[(γ-hydroxy)-NMeLeu]-4-cyclosporin | 0.05 |
| [(S)-(3-(N,N-Diethylamino)propylthio)methyl-Sar]-3-[(γ-hydroxy)-NMeLeu]-4-cyclosporin | 0.03 |
| [(S)-(2-(N,N-Diethylamino)ethoxy)methyl-Sar]-3-[(γ-hydroxy)-NMeLeu]-4-cyclosporin | 0.05 |
| [(S)-(2-(N-Isopropyl-N-methylamino)ethylthio)methyl-Sar]-3-[(γ-hydroxy)-NMeLeu]-4-cyclosporin | 0.04 |
| [(R)-(2-(N,N-Diethylamino)ethoxy)methyl-Sar]-3-[(γ-methoxy)-NMeLeu]-4-cyclosporin | 0.02 |
| [(R)-(3-(N-Morpholino)propoxy)methyl-Sar]-3-[(γ-hydroxy)-NMeLeu]-4-cyclosporin | 0.04 |
| [(S)-(2-(N,N-Diethylamino)ethylthio)methyl-Sar]-3-[(γ-Methylthio)methoxy-NMeLeu]-4-cyclosporin | 0.02 |
| [(S)-(2-(N,N-Diethylamino)ethylthio)methyl-Sar]-3-[(γ-Ethoxy)methoxy-NMeLeu]-4-cyclosporin | 0.02 |
| [(R)-(3-(N-Pyrrolidinyl)propoxy)methyl-Sar]-3-[(γ-hydroxy)-N-MeLeu]-4-cyclosporin | 0.12 |

TABLE 15

Testing results of certain representative compounds

| Compound | Antiviral activity $EC_{50}$ (µM) |
|---|---|
| [N-MeIle]-4-cyclosporin (SDZ-NIM-811) | 0.14 |
| [N-MeVal]-4-cyclosporin (SDZ 220-384) | 0.14 |
| [(R)-2-(N,N-Dimethylamino)ethylthio-Sar]-3-[(γ-hydroxy)-N-MeLeu]-4-cyclosporin (SCY-635) | 0.12 |
| [D-N-MeAla]-3-[N-EtVal]-4-cyclosporin (Debio-025) | 0.07 |
| [(S)-(2-(N,N-Diethylamino)ethylthio)methyl-Sar]-3-[(γ-hydroxy)-N-MeLeu]-4-cyclosporin (isomer B) | 0.09 |
| (S)-(2-(N,N-Dimethylamino)ethylthio)methyl-Sar]-3-[γ-(Hydroxy)-N-MeLeu]-4-cyclosporin (isomer B) | 0.13 |
| [(S)-(2-(N-Morpholino)ethylthio)methyl-Sar]-3-[(γ-hydroxy)-N-MeLeu]-4-cyclosporin | 0.06 |
| [(S)-(3-(N-Piperidinyl)propylthio)methyl-Sar]-3-[(γ-hydroxy)-N-MeLeu]-4-cyclosporin | 0.05 |

TABLE 15-continued

Testing results of certain representative compounds

| Compound | Antiviral activity EC$_{50}$ (μM) |
|---|---|
| [(S)-(2-(N-Piperidino)ethylthio)methyl-Sar]-3-[(γ-hydroxy)-N-MeLeu]-4-cyclosporin | 0.08 |
| [(S)-(2-(4-Methylpiperazino)ethylthio)methyl-Sar]-3-[(γ-hydroxy)-N-MeLeu]-4-cyclosporin | 0.09 |
| [(S)-(2-(N-Pyrrolidinyl)ethylthio)methyl-Sar]-3-[(γ-hydroxy)-N-MeLeu]-4-cyclosporin | 0.11 |
| [(S)-(3-(N-Pyrrolidinyl)propylthio)methyl-Sar]-3-[(γ-hydroxy)-N-MeLeu]-4-cyclosporin | 0.10 |
| [(S)-(3-(N-Morpholino)propylthio)methyl-Sar]-3-[(γ-hydroxy)-N-MeLeu]-4-cyclosporin | 0.05 |
| [(S)-(3-(4-Methyl-N-piperazinyl)propylthio)methyl-Sar]-3-[(γ-hydroxy)-N-MeLeu]-4-cyclosporin | 0.09 |
| [(S)-(3-(N,N-Dimethylamino)propylthio)methyl-Sar]-3-[(γ-hydroxy)-N-MeLeu]-4-cyclosporin | 0.11 |
| [(S)-(3-(N,N-Diethylamino)propylthio)methyl-Sar]-3-[(γ-hydroxy)-N-MeLeu]-4-cyclosporin | 0.08 |
| [(S)-(3-(N-Ethyl-N-isopropylamino)propylthio)methyl-Sar]-3-[(γ-hydroxy)-N-MeLeu]-4-cyclosporin | 0.06 |
| [(S)-(2-(N-Ethyl-N-isopropylamino)ethylthio)methyl-Sar]-3-[(γ-hydroxy)-N-MeLeu]-4-cyclosporin | 0.07 |
| [(R)-(2-(N,N-Diethylamino)ethoxy)methyl-Sar]-3-[(γ-hydroxy)-N-MeLeu]-4-cyclosporin | 0.12 |
| [(S)-(2-(N-Methyl-N-iso-propylamino)ethylthio)methyl-Sar]-3-[(γ-hydroxy)-N-MeLeu]-4-cyclosporin | 0.10 |
| [(S)-(2-(N-Isopropylamino)ethylthio)methyl-Sar]-3-[(γ-hydroxy)-N-MeLeu]-4-cyclosporin | 0.19 |
| [(S)-(2-(N,N-Diisobutylamino)ethylthio)methyl-Sar]-3-[(γ-hydroxy)-N-MeLeu]-4-cyclosporin | 0.12 |
| [(S)-(2-(N-Neopentylamino)ethylthio)methyl-Sar]-3-[(γ-hydroxy)-N-MeLeu]-4-cyclosporin | 0.06 |
| [(S)-(2-(N-Ethyl-N-neopentylamino)ethylthio)methyl-Sar]-3-[(γ-hydroxy)-N-MeLeu]-4-cyclosporin | 0.06 |
| [(S)-(2-(N-Methyl-N-neopentylamino)ethylthio)methyl-Sar]-3-[(γ-hydroxy)-N-MeLeu]-4-cyclosporin | 0.07 |
| [(R)-(Ethoxycarbonylmethoxy)methyl-Sar]-3-cyclosporin | 0.18 |
| [(R)-(3-(N,N-Diethylamino)propoxy)methyl-Sar]-3-cyclosporin | 0.12 |
| [(R)-(3-(N,N-Dimethylamino)propoxy)methyl-Sar]-3-cyclosporin | 0.13 |
| [(R)-(2-(N,N-Diethylamino)ethoxy)methyl-Sar]-3-[(γ-methoxy)-N-MeLeu]-4-cyclosporin | 0.06 |
| [(R)-(3-(N-Morpholino)propoxy)methyl-Sar]-3-[(γ-hydroxy)-N-MeLeu]-4-cyclosporin | 0.09 |
| [(S)-3-(N,N-Diethylamino)propylthio-Sar]-3-[N-MeIle]-4-cyclosporin | 0.08 |
| [(R)-(3-(N-Pyrrolidinyl)propoxy)methyl-Sar]-3-[(γ-hydroxy)-N-MeLeu]-4-cyclosporin | 0.22 |
| [(S)-3-(N,N-Diethylamino)propylthio-Sar]-3-[N-MeVal]-4-cyclosporin | 0.07 |
| [(S)-(3-(N-Morpholino)propylthio-Sar]-3-[N-MeVal]-4-cyclosporin | 0.11 |
| [(S)-(2-(N,N-Diethylamino)ethylthio)methyl-Sar]-3-[N-MeVal]-4-cyclosporin | 0.14 |
| [(S)-(2-(N,N-Diethylamino)ethylthio)methyl-Sar]-3-[N-MeIle]-4-cyclosporin | 0.10 |
| [(R)-(2-(N,N-Diethylamino)ethoxy)methyl-Sar]-3-[N-MeIle]-4-cyclosporin | 0.16 |
| [(R)-(3-(N-Piperidinyl)propoxy)methyl-Sar]-3-[(γ-hydroxy)-N-MeLeu]-4-cyclosporin | 0.15 |
| [(R)-(2-(N,N-Dimethylamino)ethoxy)methyl-Sar]-3-cyclosporin | 0.15 |
| [(S)-(2-(N,N-Dimethylamino)ethylthio)methyl-Sar]-3-cyclosporin (isomer B) | 0.17 |
| [(S)-(2-(N,N-Diethylamino)ethylthio)methyl-Sar]-3-cyclosporin (isomer B) | 0.16 |
| [(R)-(2-(N-Piperidinyl)ethoxy)methyl-Sar]-3-[(γ-hydroxy)-N-MeLeu]-4-cyclosporin | 0.14 |
| [(R)-(2-(N-Pyrrolidino)ethoxy)methyl-Sar]-3-[(γ-hydroxy)-N-MeLeu]-4-cyclosporin | 0.20 |
| [(S)-(2-(N,N-Dimethylamino)ethylthio)methyl-Sar]-3-[(γ-methoxy)-N-MeLeu]-4-cyclosporin | 0.10 |
| [(S)-(3-(N,N-Dimethylamino)propylthio)methyl-Sar]-3-[(γ-methoxy)-N-MeLeu]-4-cyclosporin | 0.09 |
| [(S)-(3-(N,N-Diethylamino)propylthio)methyl-Sar]-3-[(γ-methoxy)-N-MeLeu]-4-cyclosporin | 0.07 |
| [(S)-(2-(N,N-Diethylamino)ethylthio)methyl-Sar]-3-[(γ-methoxy)-N-MeLeu]-4-cyclosporin | 0.09 |
| [(S)-(2-(N-Pyrrolidinyl)ethylthio)methyl-Sar]-3-[(γ-methoxy)-N-MeLeu]-4-cyclosporin | 0.09 |
| [(S)-(2-(N-Morpholino)ethylthio)methyl-Sar]-3-[(γ-methoxy)-N-MeLeu]-4-cyclosporin | 0.11 |
| [(R)-(2-(N,N-Dimethylamino)ethoxy)methyl-Sar]-3-[(γ-methoxy)-N-MeLeu]-4-cyclosporin | 0.15 |
| [(S)-(3-(N-Morpholino)propylthio)methyl-Sar]-3-[(γ-methoxy)-N-MeLeu]-4-cyclosporin | 0.10 |
| [(R)-(3-(N,N-Diethylamino)propoxy)methyl-Sar]-3-[(γ-hydroxy)-N-MeLeu]-4-cyclosporin | 0.18 |
| [(S)-(3-(N-Pyrrolidinyl)propylthio)methyl-Sar]-3-[(γ-methoxy)-N-MeLeu]-4-cyclosporin | 0.10 |
| [(S)-[(3-(N-piperidino)propylthio)methyl-Sar]-3-[(γ-methoxy)-N-MeLeu]-4-cyclosporin | 0.06 |
| [(R)-(2-(N,N-Dimethylamino)ethoxy)methyl-Sar]-3-[(γ-methoxy)-N-MeLeu]-4-cyclosporin | 0.24 |
| [(R)-(3-(N,N-Dimethylamino)propoxy)methyl-Sar]-3-[(γ-methoxy)-N-MeLeu]-4-cyclosporin | 0.26 |
| [(R)-(3-(N,N-Diethylamino)propoxy)methyl-Sar]-3-[(γ-methoxy)-N-MeLeu]-4-cyclosporine | 0.10 |
| [(R)-(2-(N-Morpholino)ethoxy)methyl-Sar]-3-[(γ-methoxy)-N-MeLeu]-4-cyclosporin | 0.15 |

TABLE 16

Testing results of certain representative compounds

| Compound | Antiviral activity EC$_{50}$ (μM) |
|---|---|
| [(R)-2-(N,N-Dimethylamino)ethylthio-Sar]-3-[(γ-hydroxy)-N-MeLeu]-4-cyclosporin (SCY-635) | 0.11 |
| [D-N-MeAla]-3-[N-EtVal]-4-cyclosporin (Debio-025) | 0.05 |
| [(S)-(2-(N-Neopentylamino)ethylthio)methyl-Sar]-3-[(γ-hydroxy)-N-MeLeu]-4-cyclosporin | 0.05 |
| [(S)-(2-(4-Ethyl-N-piperazinyl)ethylthio)methyl-Sar]-3-[(γ-hydroxy)-N-MeLeu]-4-cyclosporin | 0.06 |
| [(S)-(3-(N,N-Diisobutylamino)propylthio)methyl-Sar]-3-[(γ-hydroxy)-N-MeLeu]-4-cyclosporin | 0.04 |
| [(S)-(3-(N-Neopentylamino)propylthio)methyl-Sar]-3-[γ-hydroxy)-N-MeLeu]-4-cyclosporin | 0.05 |
| [(S)-(3-(N-Morpholino)propylthio)methyl-Sar]-3-[(γ-hydroxy)-N-MeLeu]-4-cyclosporin | 0.04 |
| [(S)-(3-(N-Thiomorpholino)propylthio)methyl-Sar]-3-[(γ-hydroxy)-N-MeLeu]-4-cyclosporin | 0.05 |
| [(S)-(3-(4-Methyl-N-piperazinyl)propylthio)methyl-Sar]-3-[(γ-hydroxy)-N-MeLeu]-4-cyclosporin | 0.04 |
| [(S)-(3-(4-Ethyl-N-piperazinyl)propylthio)methyl-Sar]-3-[(γ-hydroxy)-N-MeLeu]-4-cyclosporin | 0.05 |
| [(S)-(3-(4-N-n-Propyl-N-piperazinyl)propylthio)methyl-Sar]-3-[(γ-hydroxy)-N-MeLeu]-4-cyclosporin | 0.05 |
| [(S)-(3-(4-N-Isopropyl-N-piperazinyl)propylthio)methyl-Sar]-3-[(γ-hydroxy)-N-MeLeu]-4-cyclosporin | 0.05 |
| [(S)-(3-(4-N-Isobutyl-N-piperazinyl)propylthio)methyl-Sar]-3-[(γ-hydroxy)-N-MeLeu]-4-cyclosporin | 0.05 |
| [(S)-(3-(4-N-Neopentyl-N-piperazinyl)propylthio)methyl-Sar]-3-[(γ-hydroxy)-N-MeLeu]-4-cyclosporin | 0.06 |
| [(S)-(4-(N,N-Diethylamino)butylthio)methyl-Sar]-3-[(γ-hydroxy)-N-MeLeu]-4-cyclosporin | 0.07 |
| [(S)-(4-(N,N-Diisobutylamino)butylthio)methyl-Sar]-3-[(γ-hydroxy)-N-MeLeu]-4-cyclosporin | 0.04 |
| [(S)-(4-(N-Neopentylamino)butylthio)methyl-Sar]-3-[(γ-hydroxy)-N-MeLeu]-4-cyclosporin | 0.04 |
| [(S)-(4-hydroxylbutylthio)methyl-Sar]-3-[(γ-hydroxy)-N-MeLeu]-4-cyclosporin | 0.02 |

TABLE 16-continued

Testing results of certain representative compounds

| Compound | Antiviral activity EC$_{50}$ (μM) |
|---|---|
| [(S)-(4-(2-(Diethylamino)ethoxy)butylthio)methyl-Sar]-3-[(γ-hydroxy)-N-MeLeu]-4-cyclosporin | 0.05 |

Example 1839

Anti HIV Activity of Cyclosporin Derivatives

Anti-HIV activity of cyclosporine derivatives were evaluated by cytoprotection assay in an acute infection model using CEM-SS cells and either HIV-1$_{IIIB}$ or HIV-1 RF. Antiviral activity was determined as a reduction in virus-caused cytopathic effects when compounds prevent virus replication. Cytoprotection and compound cytotoxicity were evaluated using the tetrazollium dye MTS (Promega) to calculate cell viability following virus infection after 6-day incubation (Zhou G., et al., 2011, *J. Med. Chem.* 27, 7220-31; which is incorporated herein by reference).

TABLE 17

Testing results of certain representative compounds against HIV-1IIIB in CEM-SS cells (MTS Endpoint)

| Compound | Antiviral activity EC$_{50}$ (nM) |
|---|---|
| AZT | 9.0 |
| [(S)-(2-(N,N-Dimethylamino)ethylthio)methyl-Sar]-3-[(γ-Hydroxy)-NMeLeu]-4-cyclosporin (isomer B) | 118.0 |
| [(S)-(2-(N-Morpholino)ethylthio)methyl-Sar]-3-[(γ-hydroxy)-NMeLeu]-4-cyclosporin | 94.9 |

Examples 1840

Inhibition of Mitochondrial Permeability Transition (MPT)

The effect of cyclosporine analogs on mitochondrial permeability transition (MPT) was determined by a modified mitochondrial swelling assay measured as an influx of Ca$^{2+}$, published by J. Blattner et al., 2001, *Analytical Biochem,* 295, 220-226. Briefly, rat neuronal mitochondria in an ice-cold sucrose buffer were obtained after rat whole-body perfusion and a series of centrifugation. The total protein concentration in each sample batch was determined for standardization between assays. The mitochondrial swelling was induced by 100 micromolar of Calcium Chloride. Each compound (100 nM) was added to mitochondria 5 minutes before the addition of Ca$^{2+}$. The value of absorbance at the certain wavelength (620nm) reflected the degree of mitochondrial swelling. The percentage of the swelling was calculated by comparing the absorbance in the present or absent compound of the interests.

TABLE 18

Inhibition of Mitochondrial Swelling

| Compounds | Mitochondrial Swelling Relative % |
|---|---|
| Control | 100 |
| Cyclosporin A | 68.7 |
| [(S)-2-(N-Diethylamino)ethylthio-Sar]-3-[(γ-methylthio)methoxy-N-MeLeu]-4-cyclosporin | 52.4 |
| [(S)-(2-(N-Diethylamino)ethylthio)methyl-Sar]-3-[(γ-hydroxy)-N-MeLeu]-4-cyclosporin | 55.7 |

In above assay, the results in mitochondrial swelling strongly indicate that cyclosporine analogs can penetrate the mitochondrial membrane and inhibit mitochondrial swelling.

We claim:
1. A compound of Formula (I):

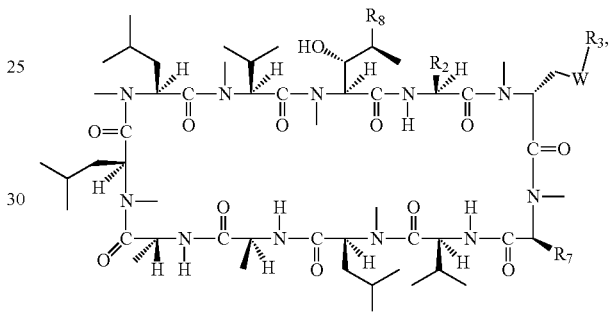

or pharmaceutically acceptable salt thereof, wherein:
R$_8$ is n-butyl, (E)-but-2-enyl,
R$_2$ is ethyl;
W is O, S, or CH$_2$;
R$_3$ is

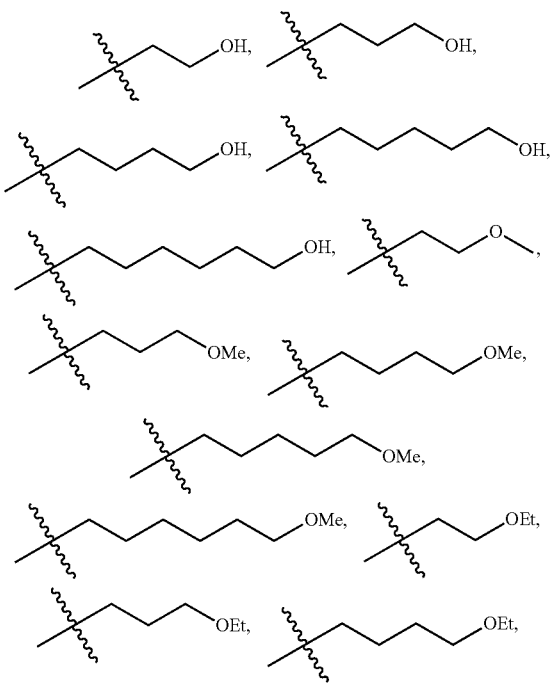

-continued

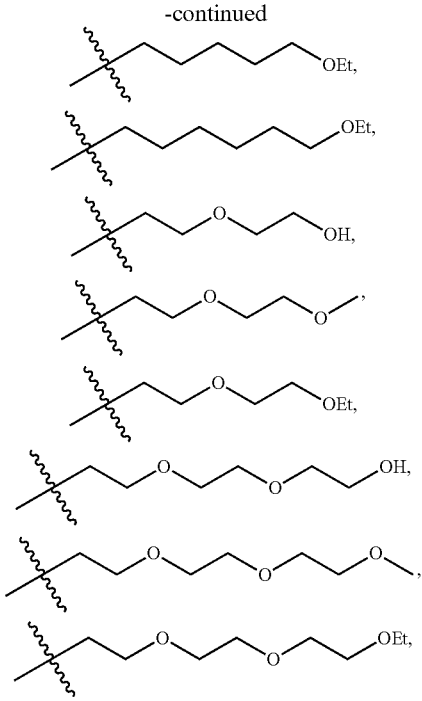

—(CH$_2$)$_5$—NR$_A$R$_B$, or —(CH$_2$)$_6$—NR$_A$R$_B$, wherein NR$_A$R$_B$ is selected from the group consisting of NH$_2$, NMe$_2$, NEt$_2$, NH(iso-butyl), NMe(iso-butyl), NEt(iso-butyl), N(iso-butyl)$_2$, NH(neopentyl), NMe(neopentyl), NEt(neopentyl), N(iso-butyl)(neopentyl), N(neopentyl)$_2$,

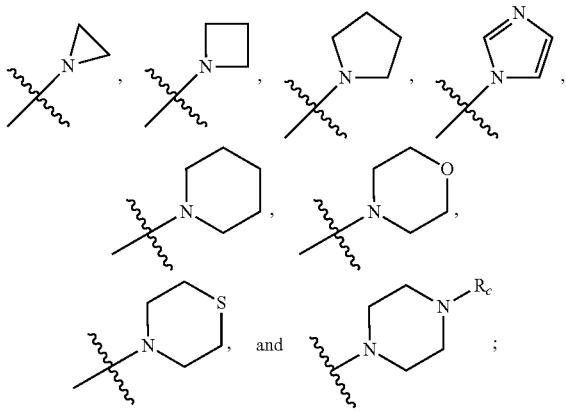

in which
R$_C$ is H, Me, Et, n-Pr, i-Pr, n-Bu, i-Bu, t-Bu, or CH$_2$CMe$_3$;
R$_7$ is

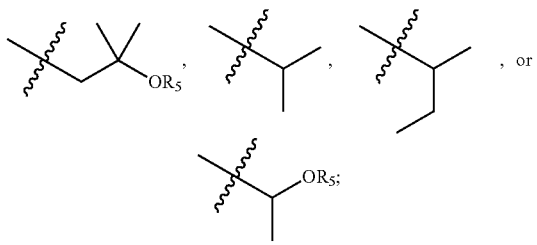

and
R$_5$ is H, (C$_1$-C$_6$)alkyl, (C$_2$-C$_6$)alkenyl, phenyl, benzyl, CH$_2$—S—(C$_1$-C$_6$)alky, CH$_2$—O—(C$_1$-C$_6$)alkyl, (C$_2$-C$_6$)alkylOH, or (C$_2$-C$_6$)alkylO(C$_1$-C$_6$)alkyl.

2. The compound of claim 1, wherein R$_8$ is n-butyl.
3. The compound of claim 1, wherein R$_8$ is (E)-but-2-enyl.
4. The compound of claim 1, wherein R$_7$ is

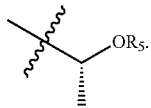

5. The compound of claim 1, wherein R$_7$ is

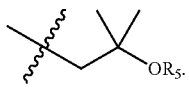

6. The compound of claim 1, wherein W is O.
7. The compound of claim 1, wherein W is S.
8. The compound of claim 1, wherein W is CH$_2$.
9. The compound of claim 1, wherein R$_3$ is —(CH$_2$)$_5$—NR$_A$R$_B$.
10. The compound of claim 1, wherein R$_3$ is —(CH$_2$)$_6$—NR$_A$R$_B$.
11. The compound of claim 1, wherein NR$_A$R$_B$ is selected from the group consisting of NH$_2$, NMe$_2$, NEt$_2$, NH(iso-butyl), NMe(iso-butyl), NEt(iso-butyl), N(iso-butyl)$_2$, NH(neopentyl), NMe(neopentyl), NEt(neopentyl), N(iso-butyl)(neopentyl), and N(neopentyl)$_2$.
12. The compound of claim 1, wherein NR$_A$R$_B$ is selected from the group consisting of

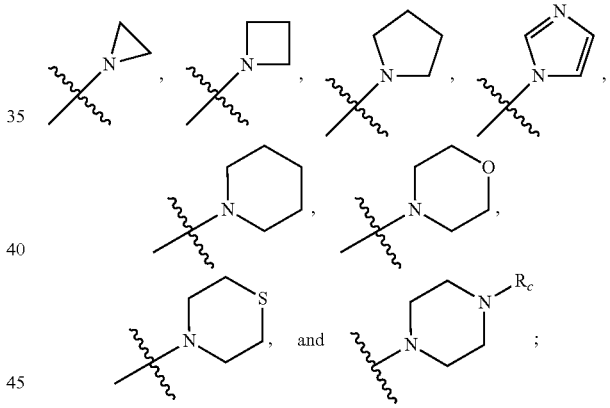

wherein
R$_C$ is H, Me, Et, n-Pr, i-Pr, n-Bu, i-Bu, t-Bu, or CH$_2$CMe$_3$.
13. The compound of claim 12, wherein NR$_A$R$_B$ is selected from the group consisting of

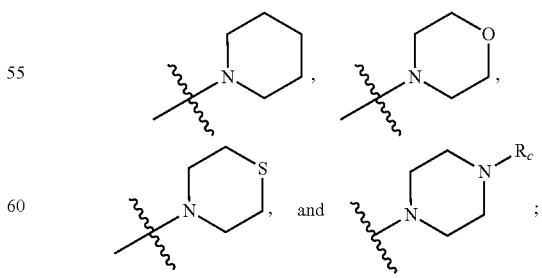

wherein R$_C$ is H, Me, Et, n-Pr, i-Pr, n-Bu, or i-Bu.
14. The compound of claim 1, wherein R$_5$ is H, (C$_1$-C$_6$)alkyl, (C$_2$-C$_6$)alkenyl, phenyl, benzyl, CH$_2$—S—(C$_1$-C$_6$)alky, or CH$_2$—O—(C$_1$-C$_6$)alkyl.

15. The compound of claim 14, wherein $R_5$ is H or $(C_1-C_6)$alkyl.
16. The compound of claim 15, wherein $R_5$ is H or Me.
17. The compound of claim 16, wherein $R_5$ is H.
18. The compound of claim 16, wherein $R_5$ is Me.
19. The compound of claim 1 selected from the group consisting of:
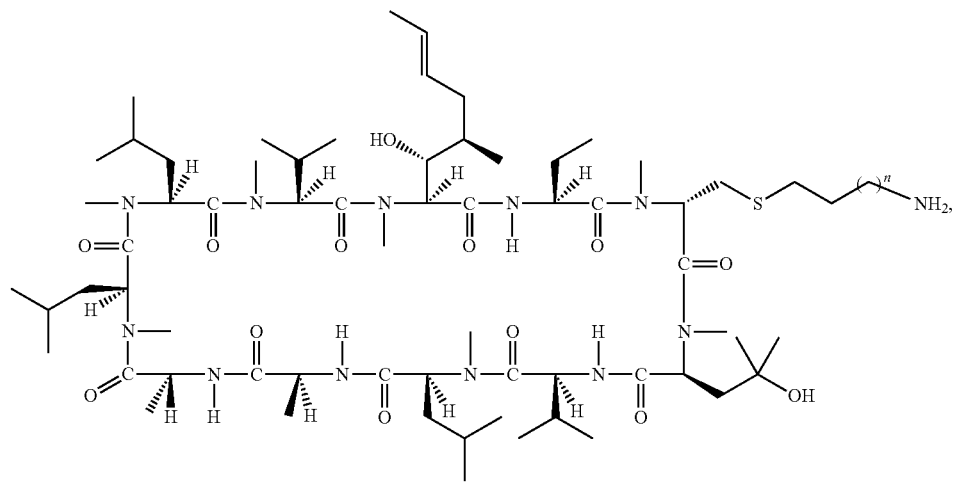
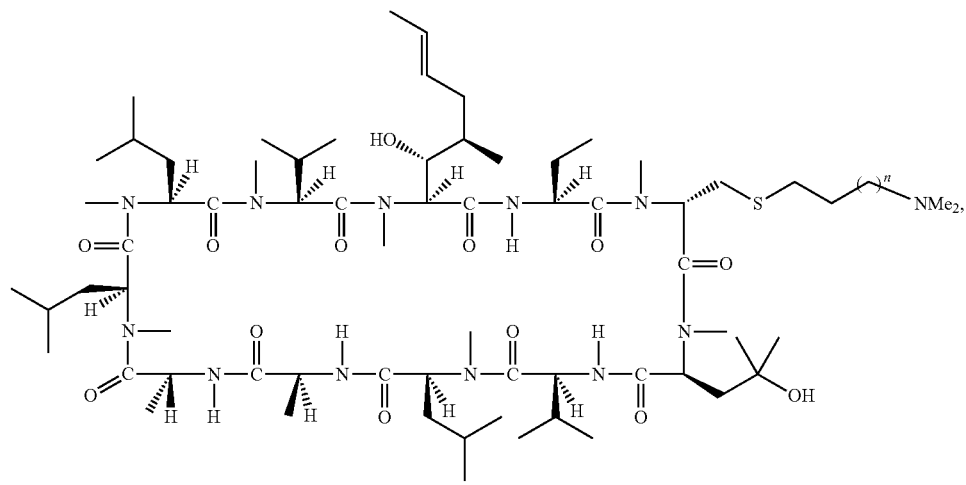
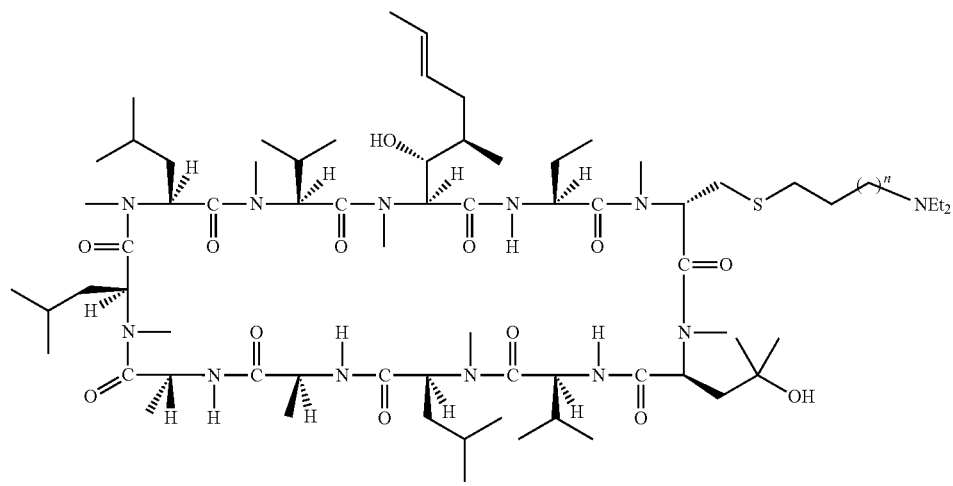

-continued
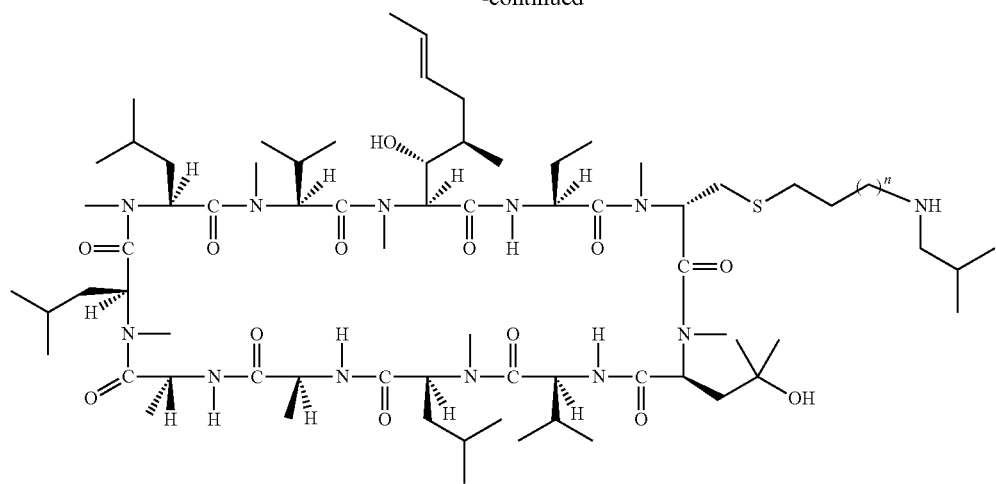
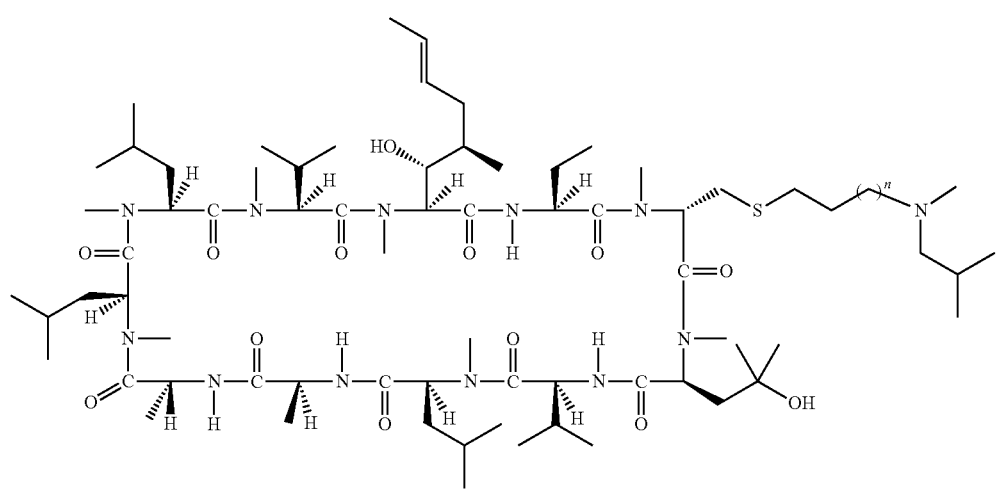
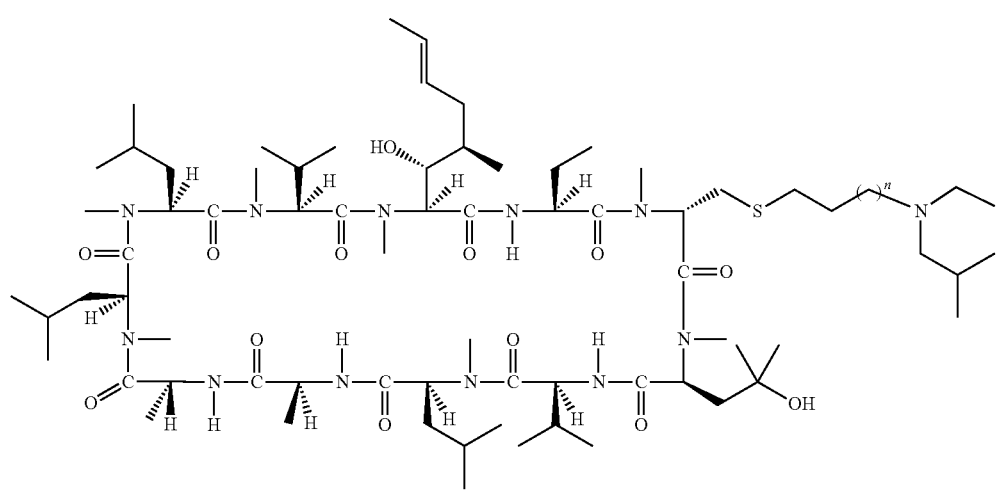

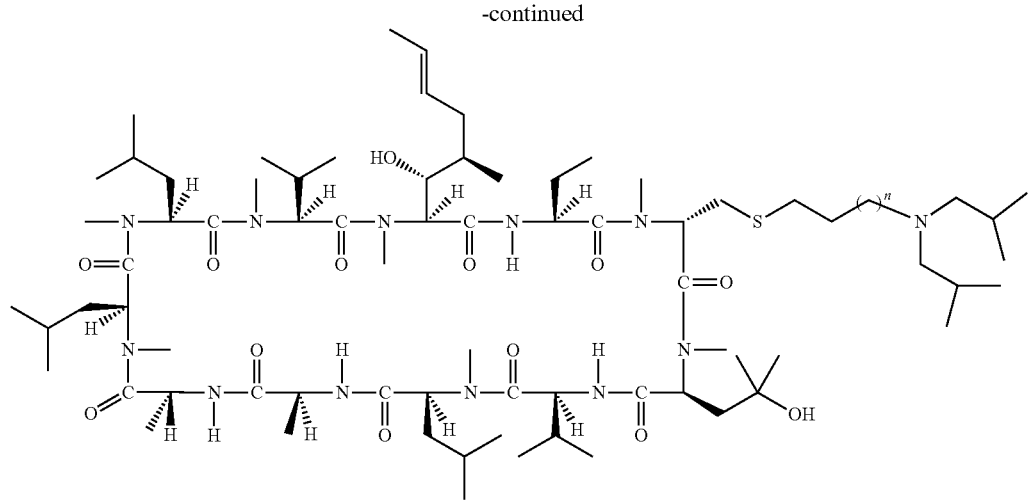
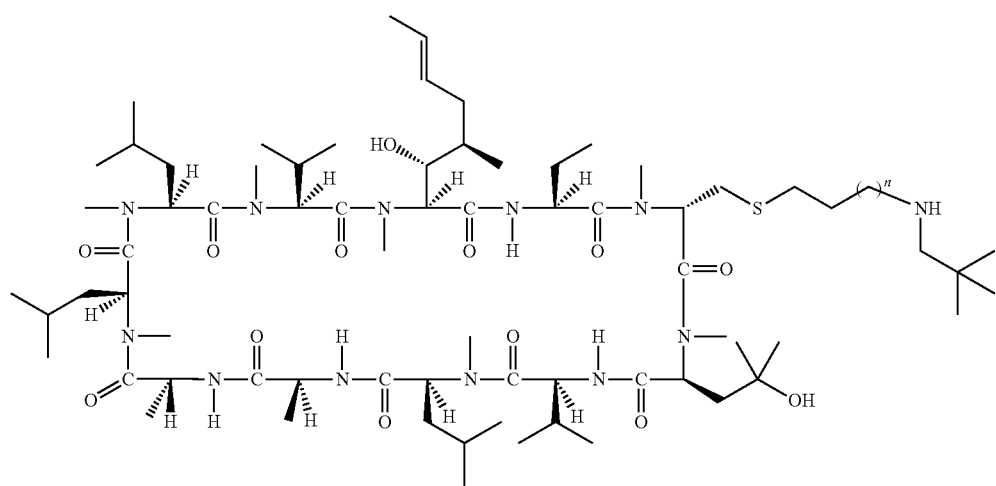
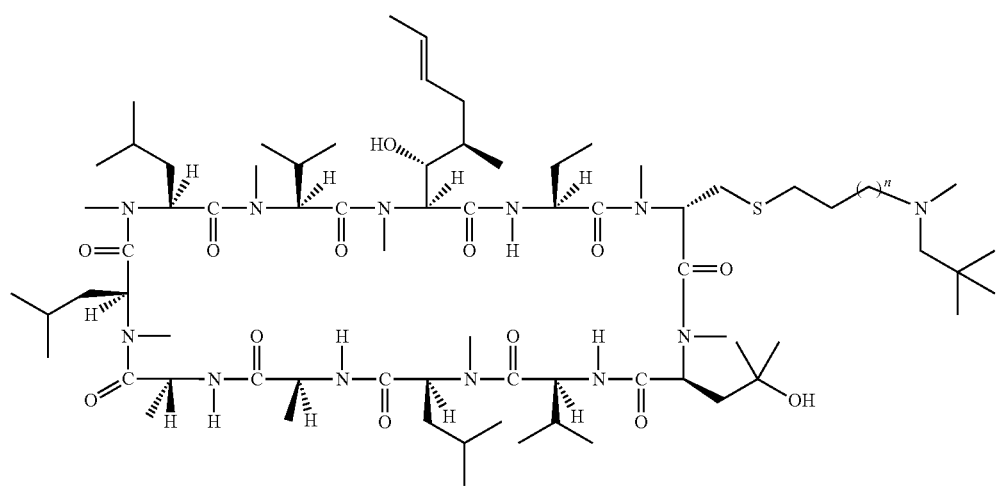

-continued

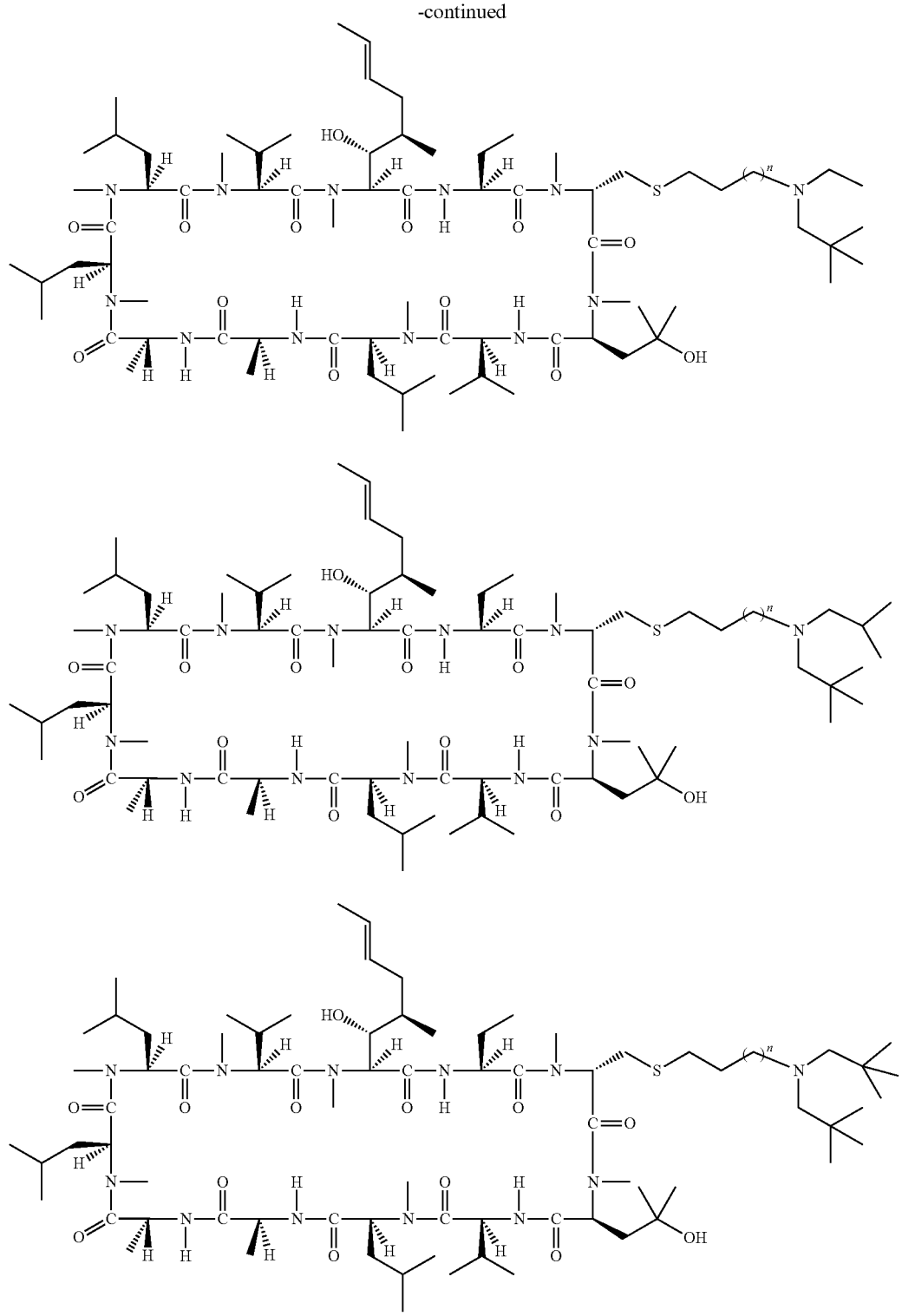

and a pharmaceutically acceptable salt thereof; wherein n is 3, or 4.

20. The compound of claim 19, wherein n is 3.

21. The compound of claim 19, wherein n is 4.

22. A pharmaceutical composition comprising at least one compound according to claim 1 and a pharmaceutically-acceptable carrier or diluent.

23. A method for treating a virus infection selected from the group consisting of hepatitis C virus infection, hepatitis B virus infection, and HIV infection in a mammalian species in need thereof, the method comprising administering to the mammalian species a therapeutically effective amount of at least one compound according to claim 1.

24. The method of claim 23, wherein the virus infection is hepatitis C virus infection.

25. The method of claim 23, wherein the virus infection is hepatitis B virus infection.

26. The method of claim 23, wherein the virus infection is HIV infection.

27. A method for inhibiting a cyclophilin in a subject in need thereof, the method comprising administrating to said subject an effective cyclophilin-inhibiting amount of at least one compound according to claim 1.

28. A method for treating a disease mediated by cyclophilin in a mammalian species in need thereof, the method comprising administering to the mammalian species a therapeutically effective amount of at least one compound according to claim 1.

29. The method of claim 28, wherein the cyclophilin is cyclophilin A, B, or C.

30. The method of claim 29, wherein the cyclophilin is cyclophilin A.

31. The method of claim 29, wherein the cyclophilin is cyclophilin B.

32. The method of claim 29, wherein the cyclophilin is cyclophilin C.

33. The compound of claim 1, having the structure of

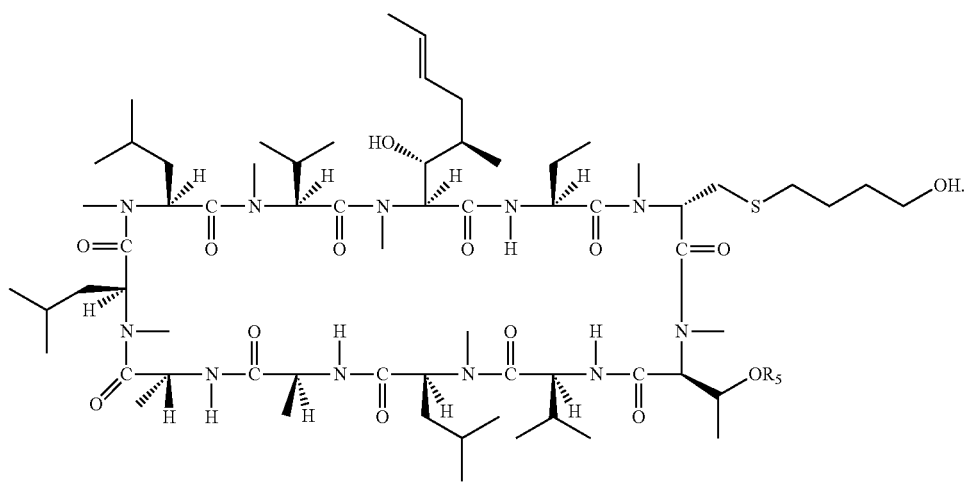

34. The compound of claim 1 selected from the group consisting of:

[(S)-(4-(Hydroxybutylthio)methyl-Sar]-3-[N-MeVal]-4-cyclosporin

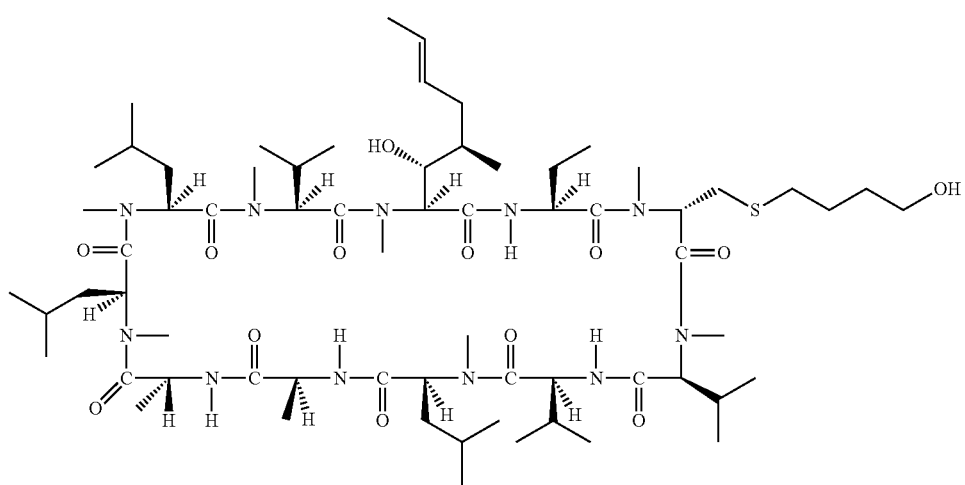

(                                                                              ),

[(S)-(4-(Hydroxybutylthio)methyl-Sar]-3-[N-MeIle]-4-cyclosporin
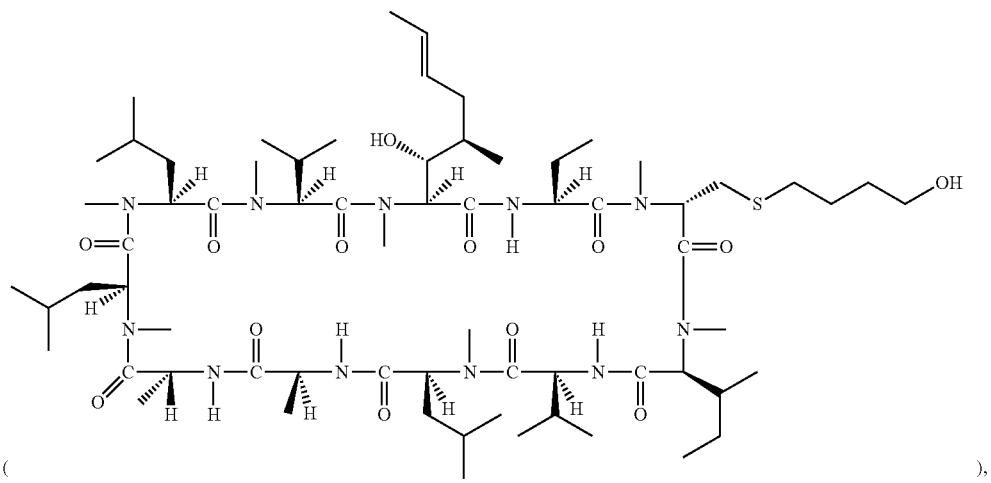 [SMILES: C/C=C/C[C@@H](C)[C@@H](O)[C@H]1C(=O)N[C@@H](CC)C(=O)N(C)[C@H](CSCCCCO)C(=O)N(C)[C@@H](C(C)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( ),
[(S)-(4-(Hydroxybutylthio)methyl-Sar]-3-[N-MeThr]-4-cyclosporin
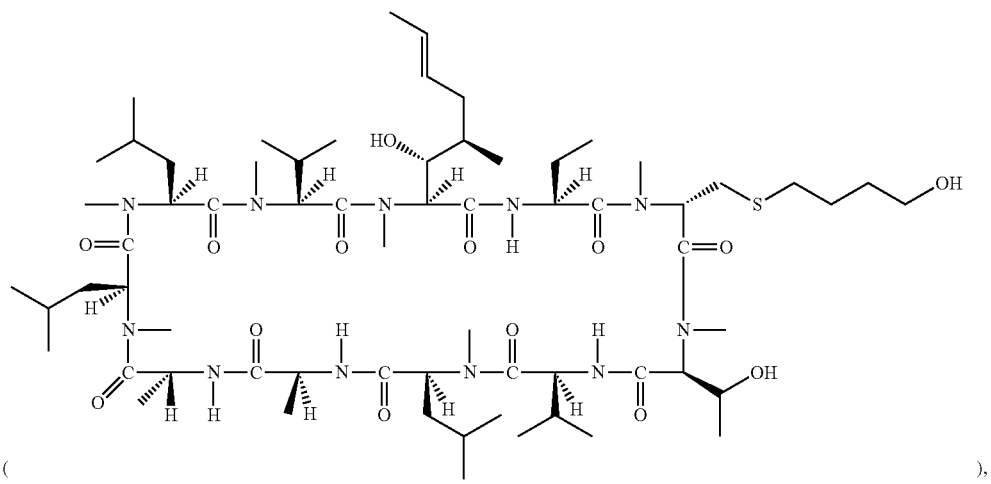
( ),
[(S)-(4-(Methoxybutylthio)methyl-Sar]-3-[N-MeVal]-4-cyclosporin
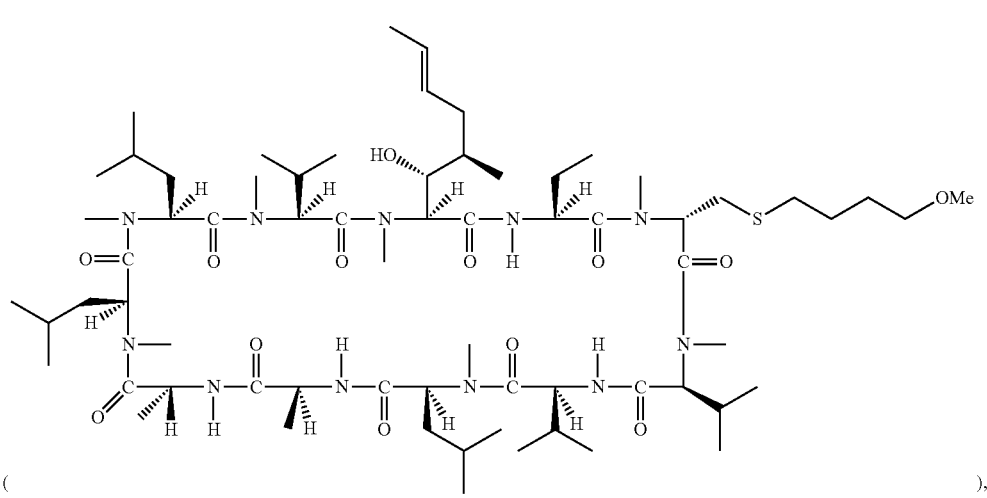 [SMILES: C/C=C/C[C@@H](C)[C@@H](O)[C@H]1C(=O)N[C@@H](CC)C(=O)N(C)[C@H](CSCCCCOC)C(=O)N(C)[C@@H](C(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( ),

[(S)-(4-(N-Methoxybutylthio)methyl-Sar]-3-[N-MeIle]-
   4-cyclosporin
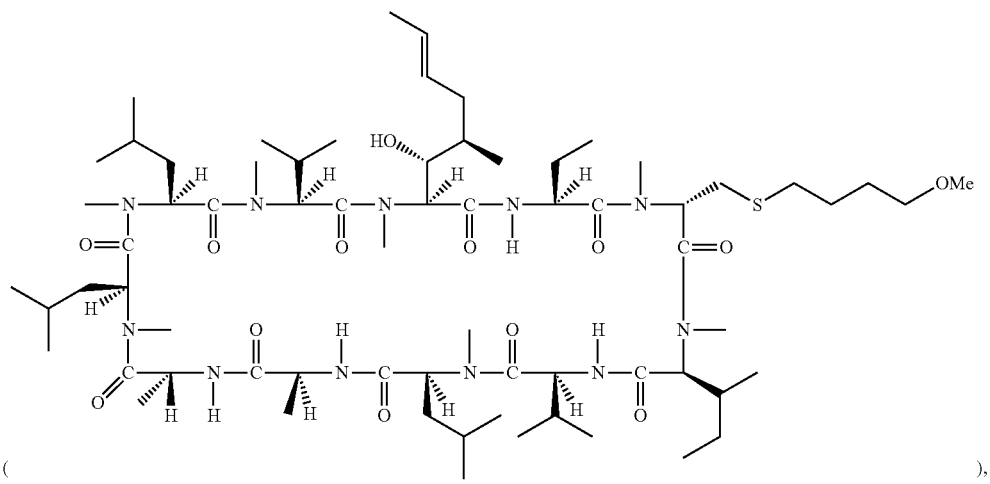
[(S)-(4-(N-Methoxybutylthio)methyl-Sar]-3-[N-MeThr]-
   4-cyclosporin
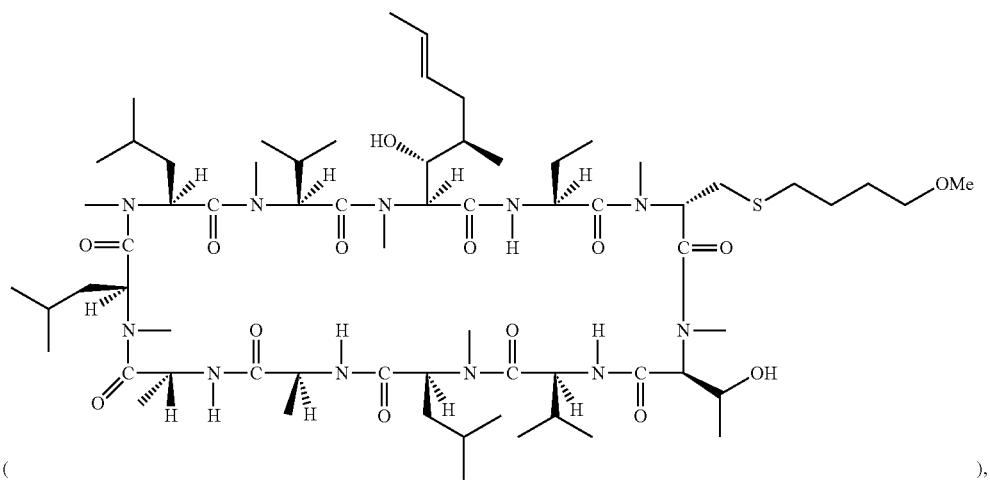
and
   a pharmaceutically acceptable salt thereof.
* * * * *